(12) United States Patent
Miyaji et al.

(10) Patent No.: US 8,552,031 B2
(45) Date of Patent: Oct. 8, 2013

(54) 3-ETHYLIDENEHYDRAZINO SUBSTITUTED HETEROCYCLIC COMPOUNDS AS THROMBOPOIETIN RECEPTOR ACTIVATORS

(75) Inventors: Katsuaki Miyaji, Funabashi (JP);
Yukihiro Shigeta, Funabashi (JP);
Satoshi Nakano, Funabashi (JP);
Shunuske Iwamoto, Funabashi (JP);
Yutaka Hirokawa, Funabashi (JP);
Hirofumi Ota, Funabashi (JP);
Kazufumi Yanagihara, Funabashi (JP);
Shingo Owada, Funabashi (JP);
Norihisa Ishiwata, Minami-Saitama-gun (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 1280 days.

(21) Appl. No.: 11/721,252

(22) PCT Filed: Dec. 7, 2005

(86) PCT No.: PCT/JP2005/022907
§ 371 (c)(1),
(2), (4) Date: Jun. 8, 2007

(87) PCT Pub. No.: WO2006/062240
PCT Pub. Date: Jun. 15, 2006

(65) Prior Publication Data
US 2009/0281317 A1  Nov. 12, 2009

(30) Foreign Application Priority Data

Dec. 8, 2004 (JP) .................. 2004-355195
Nov. 15, 2005 (JP) .................. 2005-330891

(51) Int. Cl.
*A01N 43/40* (2006.01)
*A61K 31/445* (2006.01)
*C07D 211/68* (2006.01)
*C07D 211/80* (2006.01)
*C07D 213/02* (2006.01)
*C07D 401/00* (2006.01)
*C07D 409/00* (2006.01)

(52) U.S. Cl.
USPC ........... 514/318; 514/326; 546/194; 546/211; 546/213

(58) Field of Classification Search
USPC .................. 514/318, 326; 546/194, 211, 213
See application file for complete search history.

(56) References Cited

U.S. PATENT DOCUMENTS

| | | |
|---|---|---|
| 2003/0195231 A1 | 10/2003 | Takemoto et al. |
| 2004/0063764 A1 | 4/2004 | Takemoto et al. |
| 2004/0077697 A1 | 4/2004 | Koshio et al. |
| 2004/0082626 A1 | 4/2004 | Takemoto et al. |
| 2005/0153977 A1 | 7/2005 | Sugasawa et al. |
| 2005/0282730 A1 | 12/2005 | Miyaji et al. |
| 2006/0069140 A1 | 3/2006 | Miyaji et al. |
| 2006/0094694 A1 | 5/2006 | Owada et al. |
| 2009/0131659 A1* | 5/2009 | Miyaji et al. .................. 544/105 |

FOREIGN PATENT DOCUMENTS

| | | |
|---|---|---|
| EP | 1 207 155 | 5/2002 |
| EP | 1 466 912 | 10/2004 |
| JP | 10-72492 | 3/1998 |
| JP | 11-1477 | 1/1999 |
| JP | 11-152276 | 6/1999 |
| JP | 2001-097948 | 4/2001 |
| JP | 2003-238565 | 8/2003 |
| WO | WO 96/40189 | 12/1996 |
| WO | WO 96/40750 | 12/1996 |
| WO | WO 98/25965 | 6/1998 |
| WO | WO 99/11262 | 3/1999 |
| WO | WO 00/35446 | 6/2000 |
| WO | WO 00/66112 | 11/2000 |
| WO | WO 01/07423 A1 | 2/2001 |
| WO | WO 01/17349 A1 | 3/2001 |
| WO | WO 01/21180 A1 | 3/2001 |
| WO | WO 01/34585 A1 | 5/2001 |
| WO | WO 01/39773 A1 | 6/2001 |
| WO | WO 01/53267 A1 | 7/2001 |
| WO | WO 01/89457 A2 | 11/2001 |

(Continued)

OTHER PUBLICATIONS

Wolff, Manfred E., Burger's Medicinal Chemistry and Drug Discovery, Fifth Ed., vol. 1: Principles and Practice, John Wiley & Sons, 1995, 975.*

(Continued)

*Primary Examiner* — Erich A Leeser

(74) *Attorney, Agent, or Firm* — Oblon, Spivak, McClelland, Maier & Neustadt, L.L.P.

(57) ABSTRACT

A compound represented by the formula (1): wherein A, B, $R^1$, $L^1$, $R^2$, $L^2$, $L^3$, Y, $L^4$, $R^3$ and X are the same as defined in the description, a tautomer, prodrug or pharmaceutically acceptable salt of the compound or a solvate thereof.

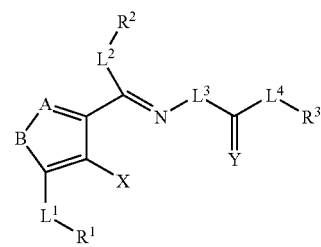

(1)

21 Claims, 1 Drawing Sheet

(56) References Cited

FOREIGN PATENT DOCUMENTS

| WO | WO 02/49413 | A2 | 6/2002 |
|---|---|---|---|
| WO | WO 02/059099 | A1 | 8/2002 |
| WO | WO 02/059100 | A1 | 8/2002 |
| WO | WO 02/062775 | A1 | 8/2002 |
| WO | 02 085343 | | 10/2002 |
| WO | WO 03/062233 | A1 | 7/2003 |
| WO | 2004 033433 | | 4/2004 |
| WO | WO 2004/033433 | A1 | 4/2004 |
| WO | 2004 108683 | | 12/2004 |
| WO | WO 2004/108683 | * | 12/2004 |
| WO | WO 2004/108683 | A1 | 12/2004 |

OTHER PUBLICATIONS

Banker, Gilbert S. et al., Modern Pharmaceutics, Marcel Dekker, New York (1996).*
Revised Utility and Written Description Guidelines, 66 FR 1092-1099 (2001).*
J. E. Cardier, "Effects of Megakaryocyte Growth and Development Factor (Thrombopoietin) on Liver Endothelial Cells in Vitro", Microvascular Reasearch, vol. 58, 1999, pp. 108-113.
M. F. Brizzi, et al., "Thrombopoietin Stimulates Endothelial Cell Motility and Neoangiogenesis by a Platelet-Activating Factor-Dependent Mechanism", Circulation Research, vol. 84, 1999, pp. 785-796.
"Blood", Journal of the American Society of Hematology vol. 98, No. 11, Nov. 16, 2001, pp. 71-72.
U.S. Appl. No. 11/721,786, filed Jun. 14, 2007, Miyaji et al.
U.S. Appl. No. 11/837,659, filed Aug. 13, 2007, Owada et al.
U.S. Appl. No. 12/303,436, filed Dec. 4, 2008, Miyaji et al.
U.S. Appl. No. 12/492,435, filed Jun. 26, 2009, Owada et al.
M. D. Mashkovsky "Medicaments,", Moscow, 1993, part 1, p. 8.
Chemical encyclopedic dictionary, Moscow, "Sovetskaya entsiclopedia," 1983, 1 front page, pp. 130-131.
U.S. Appl. No. 13/503,560, filed Apr. 23, 2012, Shigeta et al.
U.S. Appl. No. 13/613,195, filed Sep. 13, 2012, Owada et al.

* cited by examiner

3-ETHYLIDENEHYDRAZINO SUBSTITUTED HETEROCYCLIC COMPOUNDS AS THROMBOPOIETIN RECEPTOR ACTIVATORS

BACKGROUND OF THE INVENTION

1. Technical Field

The present invention relates to preventive, therapeutic and improving agents having affinity for and agonistic action on the thrombopoietin receptor for diseases against which activation of the thrombopoietin receptor is effective. Specifically, it relates to pharmaceutical compositions comprising compounds which increase platelets through stimulation of differentiation and proliferation of hematopoietic stem cells, megakaryocytic progenitor cells and megakaryocytes or compounds for therapeutic angiogenesis or with anti-arteriosclerosis action that stimulate differentiation and proliferation of vascular endothelial cells and endothelial progenitor cells.

2. Background Art

Thrombopoietin is a cytokine consisting of 332 amino acids that increases platelet production by stimulating differentiation and proliferation of hematopoietic stem cells, megakaryocytic progenitor cells and megakaryocytes mediated by its receptor and therefore is promising as a drug for hematological disorders. Recent reports that it stimulates differentiation and proliferation of vascular endothelial cells and endothelial progenitor cells have raised expectations of therapeutic angiogenesis, anti-arteriosclerosis and prevention of cardiovascular events (for example, non-patent document 1, non-patent document 2 and non-patent document 3).

Biologically active substances which have been known so far to regulate platelet production through the thrombopoietin receptor include, in addition to thrombopoietin itself, low molecular weight peptides having affinity for the thrombopoietin receptor (for example, patent document 1, patent document 2, patent document 3 and patent document 4).

As a result of search for nonpeptidic low molecular weight compounds that increase platelet production mediated by the thrombopoietin receptor, low molecular weight compounds having affinity for the thrombopoietin receptor have been reported (for example, patent document 5 to patent document 26).

1) Applications filed by Hokuriku Seiyaku Co., Ltd. relating to 1,4-benzodiazepine derivatives (patent documents 5 and 6)
2) International Laid-open Patent Applications filed by Shionogi & Co., Ltd. (patent documents 7-10)
3) International Laid-open Patent Applications filed by SmithKline Beecham Corp (patent documents 11-19)
4) Japanese Laid-open Patent Application filed by Torii Pharmaceutical Co., Ltd. (patent document 20)
5) International Laid-open Patent Application, filed by Roche Diagnostics GMBH (patent document 21)
6) International Laid-open Patent Application filed by Yamanouchi Pharmaceutical Co., Ltd. (patent document 22 and 23)
7) Japanese Laid-open Patent Application filed by Japan Tabacco Inc. (patent document 24)
8) Japanese Laid-open Patent Applications filed by Nissan Chemical Industries, Ltd. (patent documents 25 and 26)

Patent document 1 JP-A-10-72492
Patent document 2 WO96/40750
Patent document 3 WO96/40189
Patent document 4 WO98/25965
Patent document 5 JP-A-11-1477
Patent document 6 JP-A-11-152276
Patent document 7 WO01/07423
Patent document 8 WO01/53267
Patent document 9 WO02/059099
Patent document 10 WO02/059100
Patent document 11 WO00/35446
Patent document 12 WO00/66112
Patent document 13 WO01/34585
Patent document 14 WO01/17349
Patent document 15 WO01/39773
Patent document 16 WO01/21180
Patent document 17 WO01/89457
Patent document 18 WO02/49413
Patent document 19 WO02/085343
Patent document 20 JP-A-2001-97948
Patent document 21 WO99/11262
Patent document 22 WO02/062775
Patent document 23 WO03/062233
Patent document 24 JP-A-2003-238565
Patent document 25 WO04/033433
Patent document 26 WO04/108683
Non-patent document 1 Microvasc. Res., 1999: 58, p. 108-113
Non-patent document 2 Circ. Res., 1999: 84, p. 785-796
Non-patent document 3 Blood 2001:98, p. 71a-72a

DISCLOSURE OF THE INVENTION

Thrombopoietin and low molecular weight peptides having affinity for the thrombopoietin receptor are likely to be easily degraded in the gastrointestinal tract and are usually difficult to orally administer. As to thrombopoietin itself, the appearance of anti-thrombopoietin antibodies have been reported.

Besides, though it is probably possible to orally administer nonpeptidic low molecular weight compounds, no practical drugs have been put on the market.

Therefore, orally administrable low molecular weight compounds having excellent affinity for and agonistic action on the thrombopoietin receptor as preventive, therapeutic and improving agents for diseases against which activation of the thrombopoietin receptor is effective have been demanded. Specifically, low molecular, weight compounds which can serve as platelet increasing agents or increasing agents for other blood cells by stimulating differentiation and proliferation of hematopoietic stem cells, megakaryocytic progenitor cells and megakaryocytes or low molecular weight compounds which can be used for therapeutic angiogenesis or as preventive and therapeutic agents for arteriosclerosis by stimulating endothelial cells and endothelial progenitor cells have been demanded.

The present inventors conducted extensive research to find low molecular weight compounds having affinity for and agonistic action on the thrombopoietin receptor, and as a result, found that the compounds of the present invention have high affinity and agonistic action which enable them to show potent platelet increasing action by stimulating differentiation and proliferation of megakaryocytic progenitor cells and megakaryocytes. The present invention was accomplished on the basis of this discovery.

Namely, the present invention relates to:
1. A compound represented by the formula (1)

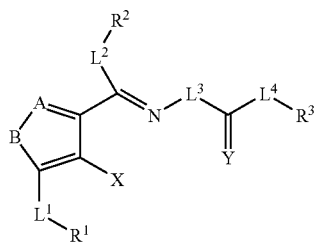

(1)

wherein A is a nitrogen atom or CR$^4$ (wherein R$^4$ is a hydrogen atom, a hydroxyl group (the hydroxyl group may be substituted with a C$_{2-6}$ alkenyl group or a C$_{2-6}$ alkynyl group), a thiol group (the thiol group may be substituted with a C$_{1-10}$ alkyl group, a C$_{2-6}$ alkenyl group, a C$_{2-6}$ alkynyl group or a C$_{1-10}$ alkylcarbonyl group), an amino group (the amino group may be substituted with one or two C$_{2-6}$ alkenyl groups or one or two C$_{2-6}$ alkynyl groups), a formyl group, a halogen atom, a nitro group, a cyano group, a C$_{1-10}$ alkyl group, a C$_{2-6}$ alkenyl group, a C$_{2-6}$ alkynyl group, a C$_{1-10}$ alkylcarbonylamino group, a mono- or di-C$_{1-10}$ alkylamino group, a C$_{1-10}$ alkoxy group (the C$_{1-10}$ alkyl group, the C$_{2-6}$ alkenyl group, the C$_{2-6}$ alkynyl group, the C$_{1-10}$ alkylcarbonylamino group, the mono- or di-C$_{1-10}$ alkylamino group and the C$_{1-10}$ alkoxy group may be optionally substituted with one or more substituents selected from the group consisting of carboxyl groups, nitro groups, cyano groups, halogen atoms, C$_{1-10}$ alkoxy groups, C$_{1-10}$ alkylcarbonyl groups, C$_{1-10}$ alkylcarbonyloxy groups, C$_{1-10}$ alkoxycarbonyl groups, C$_{1-10}$ alkylcarbonylamino groups, amino groups, mono- or di-C$_{1-10}$ alkylamino groups, hydroxyl groups, protected hydroxyl groups, C$_{2-14}$ aryl groups and C$_{2-14}$ aryloxy groups (the C$_{2-14}$ aryl groups and the C$_{2-14}$ aryloxy groups may be substituted with one or more C$_{1-6}$ alkyl groups (the C$_{1-6}$ alkyl groups may be substituted with one or more halogen atoms) or one or more halogen atoms)), a C$_{2-14}$ aryl group (the C$_{2-14}$ aryl group may be optionally substituted with one or more substituents selected from the group consisting of C$_{1-10}$ alkyl groups (the C$_{1-10}$ alkyl groups may be substituted with one or more halogen atoms), C$_{2-6}$ alkenyl groups, C$_{2-6}$ alkynyl groups, carboxyl groups, nitro groups, cyano groups, halogen atoms, C$_{1-10}$ alkoxy groups, C$_{1-10}$ alkylcarbonyl groups, C$_{1-10}$ alkylcarbonyloxy groups, C$_{1-10}$ alkoxycarbonyl groups, C$_{1-10}$ alkylcarbonylamino groups, amino groups, mono- or di-C$_{1-10}$ alkylamino groups, hydroxyl groups, protected hydroxyl groups, C$_{2-14}$ aryl groups and C$_{2-14}$ aryloxy groups), a C$_{2-14}$ aryloxy group (the C$_{2-14}$ aryloxy group may be optionally substituted with one or more substituents selected from the group consisting of C$_{1-10}$ alkyl groups (the C$_{1-10}$ alkyl groups may be substituted with one or more halogen atoms), C$_{2-6}$ alkenyl groups, C$_{2-6}$ alkynyl groups, carboxyl groups, nitro groups, cyano groups, halogen atoms, C$_{1-10}$ alkoxy groups, C$_{1-10}$ alkylcarbonyl groups, C$_{1-10}$ alkylcarbonyloxy groups, C$_{1-10}$ alkoxycarbonyl groups, C$_{1-10}$ alkylcarbonylamino groups, amino groups, mono- or di-C$_{1-10}$ alkylamino groups, hydroxyl groups, protected hydroxyl groups, C$_{2-14}$ aryl groups and C$_{2-14}$ aryloxy groups), SO$_2$R$^5$, SOR$^5$ or COR$^5$ (wherein R$^5$ is a hydroxyl group, a C$_{1-10}$ alkyl group, a C$_{2-6}$ alkenyl group, a C$_{2-6}$ alkynyl group, a C$_{2-9}$ heterocyclic group, a C$_{1-10}$ alkoxy group (the C$_{1-10}$ alkyl group, the C$_{2-6}$ alkenyl group, the C$_{2-6}$ alkynyl group, the C$_{2-9}$ heterocyclic group and the C$_{1-10}$ alkoxy group may be optionally substituted with one or more substituents selected from the group consisting of carboxyl groups, nitro groups, cyano groups, halogen atoms, C$_{1-10}$ alkoxy groups, C$_{1-10}$ alkylcarbonyl groups, C$_{1-10}$ alkylcarbonyloxy groups, C$_{1-10}$ alkoxycarbonyl groups, C$_{1-10}$ alkylcarbonylamino groups, amino groups, mono- or di-C$_{1-10}$ alkylamino groups, hydroxyl groups, protected hydroxyl groups, C$_{2-14}$ aryl groups and C$_{2-14}$ aryloxy groups (the C$_{2-14}$ aryl groups and the C$_{2-14}$ aryloxy groups may be substituted with one or more C$_{1-6}$ alkyl groups (the C$_{1-6}$ alkyl groups may be substituted with one or more halogen atoms) or one or more halogen atoms)), a C$_{2-14}$ aryl group (the C$_{2-14}$ aryl group may be optionally substituted with one or more substituents selected from the group consisting of C$_{1-10}$ alkyl groups (the C$_{1-10}$ alkyl groups may be substituted with one or more halogen atoms), C$_{2-6}$ alkenyl groups, C$_{2-6}$ alkynyl groups, carboxyl groups, nitro groups, cyano groups, halogen atoms, C$_{1-10}$ alkoxy groups, C$_{1-10}$ alkylcarbonyl groups, C$_{1-10}$ alkylcarbonyloxy groups, C$_{1-10}$ alkoxycarbonyl groups, C$_{1-10}$ alkylcarbonylamino groups, amino groups, mono- or di-C$_{1-10}$ alkylamino groups, hydroxyl groups, protected hydroxyl groups, C$_{2-14}$ aryl groups and C$_{2-14}$ aryloxy groups), a C$_{2-14}$ aryloxy group (the C$_{2-14}$ aryloxy group may be optionally substituted with one or more substituents selected from the group consisting of C$_{1-10}$ alkyl groups (the C$_{1-10}$ alkyl groups may be substituted with one or more halogen atoms), C$_{2-6}$ alkenyl groups, C$_{2-6}$ alkynyl groups, carboxyl groups, nitro groups, cyano groups, halogen atoms, C$_{1-10}$ alkoxy groups, C$_{1-10}$ alkylcarbonyl groups, C$_{1-10}$ alkylcarbonyloxy groups, C$_{1-10}$ alkoxycarbonyl groups, C$_{1-10}$ alkylcarbonylamino groups, amino groups, mono- or di-C$_{1-10}$ alkylamino groups, hydroxyl groups, protected hydroxyl groups, C$_{2-14}$ aryl groups and C$_{2-14}$ aryloxy groups) or NR$^6$R$^7$ (wherein each of R$^6$ and R$^7$ is independently a hydrogen atom, a hydroxyl group, a formyl group, a C$_{1-10}$ alkyl group, a C$_{2-6}$ alkenyl group, a C$_{2-6}$ alkynyl group, a C$_{1-10}$ alkylcarbonyloxy group, a C$_{1-10}$ alkoxycarbonyl group, a C$_{1-10}$ alkylcarbonyl group (the C$_{1-10}$ alkyl group, the C$_{2-6}$ alkenyl group, the C$_{2-6}$ alkynyl group, the C$_{1-10}$ alkylcarbonyloxy group, the C$_{1-10}$ alkoxycarbonyl group and the C$_{1-10}$ alkylcarbonyl group may be optionally substituted with one or more substituents selected from the group consisting of carboxyl groups, nitro groups, cyano groups, halogen atoms, C$_{1-10}$ alkoxy groups, C$_{1-10}$ alkylcarbonyl groups, C$_{1-10}$ alkylcarbonyloxy groups, C$_{1-10}$ alkoxycarbonyl groups, C$_{1-10}$ alkylcarbonylamino groups, amino groups, mono- or di-C$_{1-10}$ alkylamino groups, hydroxyl groups, protected hydroxyl groups, C$_{2-14}$ aryl groups and C$_{2-14}$ aryloxy groups (the C$_{2-14}$ aryl groups and the C$_{2-14}$ aryloxy groups may be substituted with one or more C$_{1-6}$ alkyl groups (the C$_{1-6}$ alkyl groups may be substituted with one or more halogen atoms) or one or more halogen atoms)) or a C$_{2-14}$ aryl group (the C$_{2-14}$ aryl group may be optionally substituted with one or more substituents selected from the group consisting of C$_{1-10}$ alkyl groups (the C$_{1-10}$ alkyl groups may be substituted with one or more halogen atoms), C$_{2-6}$ alkenyl groups, C$_{2-6}$ alkynyl groups, carboxyl groups, nitro groups, cyano groups, halogen atoms, C$_{1-10}$ alkoxy groups, C$_{1-10}$ alkylcarbonyl groups, C$_{1-10}$ alkylcarbonyloxy groups, C$_{1-10}$ alkoxycarbonyl groups, C$_{1-10}$ alkylcarbonylamino groups, amino groups, mono- or di-C$_{1-10}$ alkylamino groups, hydroxyl groups, protected hydroxyl groups, C$_{2-14}$ aryl groups and C$_{2-14}$ aryloxy groups), or R$^6$ and R$^7$ mean, together with each other, —(CH$_2$)$_{m1}$-E-(CH$_2$)$_{m2}$— (wherein E is an oxygen atom, a sulfur atom, CR$^{26}$R$^{27}$ (wherein each of R$^{26}$ and R$^{27}$ is independently a hydrogen atom, a C$_{1-10}$ alkyl group, a C$_{2-14}$ aryl group, a C$_{1-10}$ alkoxy group, a C$_{2-14}$ aryloxy group, a hydroxyl group or a protected hydroxyl group) or $NR^8$ (wherein $R^8$ is a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group, the $C_{1-10}$ alkylcarbonyloxy group, the $C_{1-10}$ alkoxycarbonyl group and the $C_{1-10}$ alkylcarbonyl group may be optionally substituted with one or more substituents selected from the group consisting of carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)) or a $C_{2-14}$ aryl group (the $C_{2-14}$ aryl group may be optionally substituted with one or more substituents selected from the group consisting of $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups)), and each of m1 and m2 is independently an integer of from 0 to 5 provided that m1+m2 is 3, 4 or 5)))), B is an oxygen atom, a sulfur atom or $NR^9$ (wherein $R^9$ is a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group, the $C_{1-10}$ alkylcarbonyloxy group, the $C_{1-10}$ alkoxycarbonyl group and the $C_{1-10}$ alkylcarbonyl group may be optionally substituted with one or more substituents selected from the group consisting of carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms), or one or more halogen atoms)), a $C_{2-14}$ aryl group (the $C_{2-14}$ aryl group may be optionally substituted with one or more substituents selected from the group consisting of $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups) or a $C_{2-14}$ aryloxy group (the $C_{2-14}$ aryloxy group may be optionally substituted with one or more substituents selected from the group consisting of $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups)) (provided that when A is a nitrogen atom, B is not NH), $R^1$ is a $C_{2-14}$ aryl group (the $C_{2-14}$ aryl group may be substituted with one or more substituents selected from the group consisting of halogen atoms, carboxyl groups, nitro groups, formyl groups, cyano groups, hydroxyl groups, protected hydroxyl groups, $C_{1-10}$ alkyl groups, $C_{2-6}$ alkenyl groups, $C_{2-6}$ alkynyl groups, $C_{1-10}$ alkoxy groups, $C_{1-10}$ alkylcarbonyl groups, $C_{1-10}$ alkylcarbonyloxy groups, $C_{1-10}$ alkoxycarbonyl groups (the $C_{1-10}$ alkyl groups, the $C_{2-6}$ alkenyl groups, the $C_{2-6}$ alkynyl groups, the $C_{1-10}$ alkoxy groups, the $C_{1-10}$ alkylcarbonyl groups, the $C_{1-10}$ alkylcarbonyloxy groups and the $C_{1-10}$ alkoxycarbonyl groups may be optionally substituted with one or more substituents selected from the group consisting of carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), $C_{2-14}$ aryl groups (the $C_{2-14}$ aryl groups may be optionally substituted with one or more substituents selected from the group consisting of $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups), thiol groups and amino groups (the thiol groups and the amino groups may be optionally substituted with one or two substituents selected from the group consisting of formyl groups, $C_{1-10}$ alkyl groups, $C_{2-6}$ alkenyl groups, $C_{2-6}$ alkynyl groups and $C_{1-10}$ alkylcarbonyl groups (the $C_{1-10}$ alkyl groups, the $C_{2-6}$ alkenyl groups, the $C_{2-6}$ alkynyl groups and the $C_{1-10}$ alkylcarbonyl groups may be optionally substituted with one or more substituents selected from the group consisting of carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)))), $L^1$ is a bond, $CR^{10}R^{11}$ (wherein each of $R^{10}$ and $R^{11}$ is independently a hydrogen atom or a $C_{1-6}$ alkyl group (the $C_{1-6}$ alkyl group may be substituted with one or more halogen atoms)), an oxygen atom, a sulfur atom or $NR^{12}$ (wherein $R^{12}$ is a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group, the $C_{1-10}$ alkylcarbonyloxy group, the $C_{1-10}$ alkoxycarbonyl group and the $C_{1-10}$ alkylcarbonyl group may be optionally substituted with one or more substituents selected from the group consisting of carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)) or a $C_{2-14}$ aryl group (the $C_{2-14}$ aryl group may be optionally substituted with one or more substituents selected from the group consisting of $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups)), X is $OR^{13}$, $SR^{13}$ or $NR^{14}R^{15}$ (wherein $R^{13}$ is a hydrogen atom, a $C_{1-10}$ alkyl group, a $C_{2-6}$ alkenyl group, a $C_{2-6}$ alkynyl group or a $C_{1-10}$ alkylcarbonyl group (the $C_{1-10}$ alkyl group, the $C_{2-6}$ alkenyl group, the $C_{2-6}$ alkynyl group and the $C_{1-10}$ alkylcarbonyl group may be optionally substituted with one or more substituents selected from the group consisting of carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), and each of $R^{14}$ and $R^{15}$ is independently a hydrogen atom, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group and the $C_{1-10}$ alkylcarbonyl group may be optionally substituted with one or more substituents selected from the group consisting of carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)) or a $C_{2-14}$ aryl group (the $C_{2-14}$ aryl group may be optionally substituted with one or more substituents selected from the group consisting of $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups)), $R^2$ is a hydrogen atom, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group and the $C_{1-10}$ alkylcarbonyl group may be optionally substituted with one or more substituents selected from the group consisting of carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)) or a $C_{2-14}$ aryl group (the $C_{2-14}$ aryl group may be optionally substituted with one or more substituents selected from the group consisting of $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups), $L^2$ is a bond, $CR^{34}R^{35}$ (wherein each of $R^{34}$ and $R^{35}$ is independently a hydrogen atom or a $C_{1-6}$ alkyl group (the $C_{1-6}$ alkyl group may be substituted with one or more halogen atoms)), an oxygen atom, a sulfur atom or $NR^{16}$ (wherein $R^{16}$ is a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group, the $C_{1-10}$ alkylcarbonyloxy group, the $C_{1-10}$ alkoxycarbonyl group and the $C_{1-10}$ alkylcarbonyl group may be optionally substituted with one or more substituents selected from the group consisting of carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)) or a $C_{2-14}$ aryl group (the $C_{2-14}$ aryl group may be optionally substituted with one or more substituents selected from the group consisting of $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups)), $L^3$ is a bond, $CR^{17}R^{18}$ (wherein each of $R^{17}$ and $R^{18}$ is independently a hydrogen atom, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group and the $C_{1-10}$ alkylcarbonyl group may be optionally substituted with one or more substituents selected from the group consisting of carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)) or a $C_{2-14}$ aryl group (the $C_{2-14}$ aryl group may be optionally substituted with one or more substituents selected from the group consisting of $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups)), an oxygen atom, a sulfur atom or $NR^{19}$ (wherein $R^{19}$ is a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkylcarbonyloxy group, the $C_{1-10}$ alkoxycarbonyl group, the $C_{1-10}$ alkoxy group and the $C_{1-10}$ alkylcarbonyl group may be optionally substituted with one or more substituents selected from the group consisting of carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)) or a $C_{2-14}$ aryl group (the $C_{2-14}$ aryl group may be optionally substituted with one or more substituents selected from the group consisting of $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups)), Y is an oxygen atom, a sulfur atom or $NR^{23}$ (wherein $R^{23}$ is a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group, the $C_{1-10}$ alkylcarbonyloxy group, the $C_{1-10}$ alkoxycarbonyl group and the $C_{1-10}$ alkylcarbonyl group may be optionally substituted with one or more substituents selected from the group consisting of carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)) or a $C_{2-14}$ aryl group (the $C_{2-14}$ aryl group may be substituted with one or more substituents selected from the group consisting of $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups)), $L^4$ is a bond, $CR^{20}R^{21}$ (wherein each of $R^{20}$ and $R^{21}$ is independently a hydrogen atom, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group and the $C_{1-10}$ alkylcarbonyl group may be optionally substituted with one or more substituents selected from the group consisting of carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)) or a $C_{2-14}$ aryl group (the $C_{2-14}$ aryl group may be optionally substituted with one or more substituents selected from the group consisting of $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms))), an oxygen atom, a sulfur atom or $NR^{22}$ (wherein $R^{22}$ is a hydrogen atom, a hydroxyl group, a protected hydroxyl group, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group, the $C_{1-10}$ alkylcarbonyloxy group, the $C_{1-10}$ alkoxycarbonyl group and the $C_{1-10}$ alkylcarbonyl group may be optionally substituted with one or more substituents selected from the group consisting of carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)) or a $C_{2-14}$ aryl group (the $C_{2-14}$ aryl group may be optionally substituted with one or more substituents selected from the group consisting of $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms))), and When $L^4$ is a bond, $R^3$ is a methyl group (the methyl group may be optionally substituted with one or more substituents selected from the group consisting of $C_{1-10}$ alkyl groups, $C_{2-10}$ alkenyl groups, $C_{2-10}$ alkynyl groups, $C_{2-9}$ heterocyclic groups, $C_{1-10}$ alkoxy groups, $C_{1-10}$ thioalkyl groups, $C_{1-10}$ alkylcarbonyl groups, mono- or di-$C_{1-10}$ alkylamino groups, $C_{1-10}$ alkylcarbonyloxy groups, $C_{1-10}$ alkoxycarbonyl groups, $C_{1-10}$ alkylcarbonylamino groups (the $C_{1-10}$ alkyl groups, the $C_{2-10}$ alkenyl groups, the $C_{2-10}$ alkynyl groups, the $C_{2-9}$ heterocyclic groups, the $C_{1-10}$ alkoxy groups, the $C_{1-10}$ thioalkyl groups, the $C_{1-10}$ alkylcarbonyl groups, the mono- or di-$C_{1-10}$ alkylamino groups, the $C_{1-10}$ alkylcarbonyloxy groups, the $C_{1-10}$ alkoxycarbonyl groups and the $C_{1-10}$ alkylcarbonylamino groups may be optionally substituted with one or more $C_{2-14}$ aryl groups (the $C_{2-14}$ aryl groups may be optionally substituted with one or more substituents independently represented by —$W^1$ ($CW^2W^3)_mW^4$ (wherein $W^1$ is ($CR^{24}R^{25})_n$ (wherein each of $R^{24}$ and $R^{25}$ is independently a hydrogen atom or a $C_{1-6}$ alkyl group (the $C_{1-6}$ alkyl group may be substituted with one or more halogen atoms), or $R^{24}$ and $R^{25}$ mean, together with each other, O= or S=, and n is 0, 1, 2 or 3), an oxygen atom, a sulfur atom or $NR^{36}$ (wherein $R^{36}$ is a hydrogen atom, a $C_{1-6}$ alkyl group, a formyl group or a $C_{1-6}$ alkylcarbonyl group), each of $W^2$ and $W^3$ is independently a hydrogen atom or a $C_{1-3}$ alkyl group (the $C_{1-3}$ alkyl group may be substituted with one or more halogen atoms), m is 0, 1, 2 or 3, and $W^4$ is a hydroxyl group, a protected hydroxyl group, a thiol group, an amino group, a formyl group, a halogen atom, a nitro group, a cyano group, a $C_{1-10}$ alkyl group, a $C_{2-6}$ alkenyl group, a $C_{2-6}$ alkynyl group, a $C_{2-9}$ heterocyclic group, a $C_{1-10}$ alkoxy group, a $C_{1-10}$ alkylcarbonyloxy group, a $C_{1-10}$ alkylcarbonylamino group, a mono- or di-$C_{1-10}$ alkylamino group (the $C_{1-10}$ alkyl group, the $C_{2-6}$ alkenyl group, the $C_{2-6}$ alkynyl group, the $C_{2-9}$ heterocyclic group, the $C_{1-10}$ alkoxy group, the $C_{1-10}$ alkylcarbonyloxy group, the $C_{1-10}$ alkylcarbonylamino group and the mono- or di-$C_{1-10}$ alkylamino group may be optionally substituted with one or more substituents selected from the group consisting of carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), a $C_{2-14}$ aryl group (the $C_{2-14}$ aryl group may be optionally substituted with one or more substituents selected from the group consisting of $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, thiol groups, phosphonic acid groups, sulfonic acid groups, tetrazole groups, $C_{2-14}$ aryl groups and $C_{2-14}$ aryloxy groups (the $C_{2-14}$ aryl groups and the $C_{2-14}$ aryloxy groups may be substituted with one or more $C_{1-10}$ alkyl groups (the $C_{1-10}$ alkyl groups may be substituted with one or more halogen atoms) or one or more halogen atoms)), $SO_2R^{28}$, $SOR^{28}$, $COR^{28}$ (wherein $R^{28}$ is a hydroxyl group, a protected hydroxyl group, a $C_{1-10}$ alkyl group, a $C_{2-6}$ alkenyl group, a $C_{2-6}$ alkynyl group, a $C_{2-9}$ heterocyclic group, a $C_{1-10}$ alkoxy group (the $C_{1-10}$ alkyl group, the $C_{2-6}$ alkenyl group, the $C_{2-6}$ alkynyl group, the $C_{2-9}$ heterocyclic group and the $C_{1-10}$ alkoxy group may be optionally substituted with one or more substituents selected from the group consisting of carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)) or $NR^{29}R^{30}$ (wherein each of $R^{29}$ and $R^{30}$ is independently a hydrogen atom, a hydroxyl group, a protected hydroxyl group, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylsulfonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group, the $C_{1-10}$ alkylcarbonyloxy group, the $C_{1-10}$ alkoxycarbonyl group, the $C_{1-10}$ alkylsulfonyl group and the $C_{1-10}$ alkylcarbonyl group may be optionally substituted with one or more substituents selected from the group consisting of carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be optionally substituted with one or more substituents selected from the group consisting of $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl group, sulfonyl groups, sulfamoyl groups, sulfo groups, nitro groups, cyano groups, halogen atoms, $C_{1-10}$ alkoxy groups (the $C_{1-10}$ alkoxy groups may be substituted with one or more halogen atoms), $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms))) or a $C_{2-14}$ aryl group (the $C_{2-14}$ aryl group may be optionally substituted with one or more substituents selected from the group consisting of $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl group, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), or $R^{29}$ and $R^{30}$, together with each other means —$(CH_2)_{m3}$-G-$(CH_2)_{m4}$— (wherein G is an oxygen atom, a sulfur atom, $CR^{31}R^{32}$ (wherein each of $R^{31}$ and $R^{32}$ is independently a hydrogen atom, a $C_{1-10}$ alkyl group, a $C_{2-14}$ aryl group, a $C_{1-10}$ alkoxy group, a $C_{2-14}$ aryloxy group, a hydroxyl group or a protected hydroxyl group) or $NR^{33}$ (wherein $R^{33}$ is a hydrogen atom, a hydroxyl group, a formyl group, a $C_{1-10}$ alkyl group, a $C_{2-6}$ alkenyl group, $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group, the $C_{1-10}$ alkylcarbonyloxy group, the $C_{1-10}$ alkoxycarbonyl group and the $C_{1-10}$ alkylcarbonyl group may be optionally substituted with one or more substituents selected from the group consisting of carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)) or a $C_{2-14}$ aryl group (the $C_{2-14}$ aryl group may be optionally substituted with one or more substituents selected from the group consisting of $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms))), and each of m3 and m4 is independently an integer of from 0 to 5, provided that m3+m4 is 3, 4 or 5))), a tetrazole group or a phosphonic acid group)) or one or more substituents independently represented by —$W^5$ $(CW^6W^7)_{m10}W^8$ (wherein $W^5$, $W^6$, $W^7$ and m10 are the same as $W^1$, $W^2$, $W^3$ and m, respectively, $W^1$, $W^2$, $W^3$ and m are the same as defined above, and $W^8$ is a hydroxyl group, a protected hydroxyl group, a thiol group, an amino group, a formyl group, a halogen atom, a nitro group, a cyano group, a $C_{1-10}$ alkyl group, a $C_{2-6}$ alkenyl group, a $C_{2-6}$ alkynyl group, a $C_{2-9}$ heterocyclic group, a $C_{1-10}$ alkoxy group, a $C_{1-10}$ alkylcarbonyloxy group, a $C_{1-10}$ alkylcarbonylamino group, a mono- or di-$C_{1-10}$ alkylamino group (the $C_{1-10}$ alkyl group, the $C_{2-6}$ alkenyl group, the $C_{2-6}$ alkynyl group, the $C_{2-9}$ heterocyclic group, the $C_{1-10}$ alkoxy group, the $C_{1-10}$ alkylcarbonyloxy group, the $C_{1-10}$ alkylcarbonylamino group and the mono- or di-$C_{1-10}$ alkylamino group may be optionally substituted with one or more substituents selected from the group consisting of carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), $SO_2R^{28a}$, $SOR^{28a}$, $COR^{28a}$ (wherein $R^{28a}$ is the same as $R^{28}$, and $R^{28}$ is the same as defined above), a tetrazole group or a phosphonic acid group)) and substituents independently represented by —$W^9$ $(CW^{10}W^{11})_{m11}W^{12}$ (wherein $W^9$, $W^{10}$, $W^{11}$, $W^{12}$ and m11 are the same as $W^1$, $W^2$, $W^3$, $W^8$ and m, respectively, and $W^1$, $W^2$, $W^3$, $W^8$ and m are the same as defined above)), a $C_{2-10}$ alkyl group, a $C_{2-10}$ alkenyl group, a $C_{2-10}$ alkynyl group or a $C_{2-9}$ heterocyclic group (the $C_{2-10}$ alkyl group, the $C_{2-10}$ alkenyl group, the $C_{2-10}$ alkynyl group and the $C_{2-9}$ heterocyclic group may be optionally substituted with one or more substituents selected from the group consisting of $C_{1-10}$ alkyl groups, $C_{2-10}$ alkenyl groups, $C_{2-10}$ alkynyl groups, $C_{2-9}$ heterocyclic groups, $C_{1-10}$ alkoxy groups, $C_{1-10}$ thioalkyl groups, $C_{1-10}$ alkylcarbonyl groups, mono- or di-$C_{1-10}$ alkylamino groups, $C_{1-10}$ alkylcarbonyloxy groups, $C_{1-10}$ alkoxycarbonyl groups, $C_{1-10}$ alkylsulfonyl groups, $C_{1-10}$ alkylaminocarbonyl groups, $C_{1-10}$ alkylaminosulfonyl groups, $C_{1-10}$ dialkylaminocarbonyl groups, $C_{1-10}$ alkylcarbonylamino groups (the $C_{1-10}$ alkyl groups, the $C_{2-10}$ alkenyl groups, the $C_{2-10}$ alkynyl groups, the $C_{2-9}$ heterocyclic groups, the $C_{1-10}$ alkoxy groups, the $C_{1-10}$ thioalkyl groups, the $C_{1-10}$ alkylcarbonyl groups, the mono- or di-$C_{1-10}$ alkylamino groups, the $C_{1-10}$ alkylcarbonyloxy groups, the $C_{1-10}$ alkoxycarbonyl groups, the $C_{1-10}$ alkylsulfonyl groups, the $C_{1-10}$ alkylaminocarbonyl groups, the $C_{1-10}$ alkylaminosulfonyl groups, the $C_{1-10}$ dialkylaminocarbonyl groups and the $C_{1-10}$ alkylcarbonylamino groups may be optionally substituted with one or more $C_{2-14}$ aryl groups (the $C_{2-14}$ aryl groups may be optionally substituted with one or more substituents independently represented by —$W^1$ $(CW^2W^3)_mW^4$ (wherein $W^1$, $W^2$, $W^3$, $W^4$ and m are the same as defined above)) or one or more substituents independently represented by —$W^5$ $(CW^6W^7)_{m10}W^8$ (wherein $W^5$, $W^6$, $W^7$, $W^8$ and m10 are the same as defined above)), substituents independently represented by $W^9(CW^{10}W^{11})_{m11}W^{12}$ (wherein $W^9$, $W^{10}$, $W^{11}$, $W^{12}$ and m11 are the same as defined above) and $C_{2-14}$ aryl groups (the $C_{2-14}$ aryl groups may be optionally substituted with one or more substituents independently represented by —$W^{13}(CW^{14}W^{15})_{m12}W^{16}$ (wherein $W^{13}$, $W^{14}$, $W^{15}$, $W^{16}$ and m12 are the same as $W^1$, $W^2$, $W^3$, $W^4$ and m, respectively, and $W^1$, $W^2$, $W^3$, $W^4$ and m are the same as defined above))), or when $L^4$ is $CR^{20}R^{21}$ (wherein each of $R^{20}$ and $R^{21}$ is independently a hydrogen atom, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyl group, (the $C_{1-10}$ alkyl group, the $C_{2-6}$ alkenyl group, the $C_{2-6}$ alkynyl group, the $C_{1-10}$ alkoxy group and the $C_{1-10}$ alkylcarbonyl group may be optionally substituted with one or more substituents selected from the group consisting of carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)) or a $C_{2-14}$ aryl group (the $C_{2-14}$ aryl group may be optionally substituted with one or more substituents selected from the group consisting of $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms))), an oxygen atom, a sulfur atom or $NR^{22}$ (wherein $R^{22}$ is a hydrogen atom, a hydroxyl group, a protected hydroxyl group, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group, the $C_{1-10}$ alkylcarbonyloxy group, the $C_{1-10}$ alkoxycarbonyl group and the $C_{1-10}$ alkylcarbonyl group may be optionally substituted with one or more substituents selected from the group consisting of carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)) or a $C_{2-14}$ aryl group (the $C_{2-14}$ aryl group may be optionally substituted with one or more substituents selected from the group consisting of $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms))), $R^3$ is a $C_{1-10}$ alkyl group, a $C_{2-10}$ alkenyl group, a $C_{2-10}$ alkynyl group, a $C_{2-9}$ heterocyclic group, a $C_{1-10}$ alkoxy group, a $C_{1-10}$ thioalkyl group, a $C_{1-10}$ alkylcarbonyl group, a mono- or di-$C_{1-10}$ alkylamino group, a $C_{1-10}$ alkylcarbonyloxy group, a $C_{1-10}$ alkoxycarbonyl group or a $C_{1-10}$ alkylcarbonylamino group (the $C_{1-10}$ alkyl group, the $C_{2-10}$ alkenyl group, the $C_{2-10}$ alkynyl group, the $C_{2-9}$ heterocyclic group, the $C_{1-10}$ alkoxy group, the $C_{1-10}$ thioalkyl group, the $C_{1-10}$ alkylcarbonyl group, the mono- or di-$C_{1-10}$ alkylamino group, the $C_{1-10}$ alkylcarbonyloxy group, the $C_{1-10}$ alkoxycarbonyl group and the $C_{1-10}$ alkylcarbonylamino group may be optionally substituted with one or more substituents selected from the group consisting of $C_{1-10}$ alkyl groups, $C_{2-10}$ alkenyl groups, $C_{2-10}$ alkynyl groups, $C_{2-9}$ heterocyclic groups, $C_{1-10}$ alkoxy groups, $C_{1-10}$ thioalkyl groups, $C_{1-10}$ alkylcarbonyl groups, mono- or di-$C_{1-10}$ alkylamino groups, $C_{1-10}$ alkylcarbonyloxy groups, $C_{1-10}$ alkoxycarbonyl groups, $C_{1-10}$ alkylcarbonylamino groups (the $C_{1-10}$ alkyl groups, the $C_{2-10}$ alkenyl groups, the $C_{2-10}$ alkynyl groups, the $C_{2-9}$ heterocyclic groups, the $C_{1-10}$ alkoxy groups, the $C_{1-10}$ thioalkyl groups, the $C_{1-10}$ alkylcarbonyl groups, the mono- or di-$C_{1-10}$ alkylamino groups, the $C_{1-10}$ alkylcarbonyloxy groups, the $C_{1-10}$ alkoxycarbonyl groups and the $C_{1-10}$ alkylcarbonylamino groups may be optionally substituted with one or more $C_{2-14}$ aryl groups (the $C_{2-14}$ aryl groups may be optionally substituted with one or more substituents independently represented by $—W^1(CW^2W^3)_mW^4$ (wherein $W^1$, $W^2$, $W^3$, $W^4$ and m are the same as defined above)) or one or more substituents independently represented by $—W^5(CW^6W^7)_{m10}W^8$ (wherein $W^5$, $W^6$, $W^7$, $W^8$ and m10 are the same as defined above)), substituents independently represented by $—W^9(CW^{10}W^{11})_{m11}W^{12}$ (wherein $W^9$, $W^{10}$, $W^{11}$, $W^{12}$ and m11 are the same as defined above) and $C_{2-14}$ aryl groups (the $C_{2-14}$ aryl groups may be optionally substituted with one or more substituents independently represented by $—W^{13}(CW^{14}W^{15})_{m12}W^{16}$ (wherein $W^{13}$, $W^{14}$, $W^{15}$, $W^{16}$ and m12 are the same as defined above))), a tautomer, prodrug or pharmaceutically acceptable salt of the compound or a solvate thereof.

2. The compound according to 1, wherein $L^4$ is a bond, $R^3$ is a methyl group (the methyl group may be optionally substituted with one or more substituents selected from the group consisting of $C_{1-10}$ alkyl groups, $C_{2-10}$ alkenyl groups, $C_{2-10}$ alkynyl groups, $C_{2-9}$ heterocyclic groups, $C_{1-10}$ alkoxy groups, $C_{1-10}$ thioalkyl groups, $C_{1-10}$ alkylcarbonyl groups, mono- or di-$C_{1-10}$ alkylamino groups, $C_{1-10}$ alkylcarbonyloxy groups, $C_{1-10}$ alkoxycarbonyl groups, $C_{1-10}$ alkylcarbonylamino groups (the $C_{1-10}$ alkyl groups, the $C_{2-10}$ alkenyl groups, the $C_{2-10}$ alkynyl groups, the $C_{2-9}$ heterocyclic groups, the $C_{1-10}$ alkoxy groups, the $C_{1-10}$ thioalkyl groups, the $C_{1-10}$ alkylcarbonyl groups, the mono- or di-$C_{1-10}$ alkylamino groups, the $C_{1-10}$ alkylcarbonyloxy groups, the $C_{1-10}$ alkoxycarbonyl groups and the $C_{1-10}$ alkylcarbonylamino groups may be optionally substituted with one or more $C_{2-14}$ aryl groups (the $C_{2-14}$ aryl groups may be optionally substituted with one or more substituents independently represented by $—W^1(CW^2W^3)_mW^4$ (wherein $W^1$ is $(CR^{24}R^{25})_n$ (wherein each of $R^{24}$ and $R^{25}$ is independently a hydrogen atom or a $C_{1-6}$ alkyl group (the $C_{1-6}$ alkyl group may be substituted with one or more halogen atoms), or $R^{24}$ and $R^{25}$ mean, together with each other, O= or S=, and n is 0, 1, 2 or 3), an oxygen atom, a sulfur atom or $NR^{36}$ (wherein $R^{36}$ is a hydrogen atom, a $C_{1-6}$ alkyl group, a formyl group or a $C_{1-6}$ alkylcarbonyl group), each of $W^2$ and $W^3$ is independently a hydrogen atom or a $C_{1-3}$ alkyl group (the $C_{1-3}$ alkyl group may be substituted with one or more halogen atoms), m is 0, 1, 2 or 3, and $W^4$ is a hydroxyl group, a protected hydroxyl group, a thiol group, an amino group, a formyl group, a halogen atom, a nitro group, a cyano group, a $C_{1-10}$ alkyl group, a $C_{2-6}$ alkenyl group, a $C_{2-6}$ alkynyl group, a $C_{2-9}$ heterocyclic group, a $C_{1-10}$ alkoxy group, a $C_{1-10}$ alkylcarbonyloxy group, a $C_{1-10}$ alkylcarbonylamino group, a mono- or di-$C_{1-10}$ alkylamino group (the $C_{1-10}$ alkyl group, the $C_{2-6}$ alkenyl group, the $C_{2-6}$ alkynyl group, the $C_{2-9}$ heterocyclic group, the $C_{1-10}$ alkoxy group, the $C_{1-10}$ alkylcarbonyloxy group, the $C_{1-10}$ alkylcarbonylamino group and the mono- or di-$C_{1-10}$ alkylamino group may be optionally substituted with one or more substituents selected from the group consisting of carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), a $C_{2-14}$ aryl group (the $C_{2-14}$ aryl group may be optionally substituted with one or more substituents selected from the group consisting of $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, thiol groups, phosphonic acid groups, sulfonic acid groups, tetrazole groups, $C_{2-14}$ aryl groups and $C_{2-14}$ aryloxy groups (the $C_{2-14}$ aryl groups and the $C_{2-14}$ aryloxy groups may be substituted with one or more $C_{1-10}$ alkyl groups (the $C_{1-10}$ alkyl groups may be substituted with one or more halogen atoms) or one or more halogen atoms)), $SO_2R^{28}$, $SOR^{28}$, $COR^{28}$ (wherein $R^{28}$ is a hydroxyl group, a protected hydroxyl group, a $C_{1-10}$ alkyl group, a $C_{2-6}$ alkenyl group, a $C_{2-6}$ alkynyl group, a $C_{2-9}$ heterocyclic group, a $C_{1-10}$ alkoxy group (the $C_{1-10}$ alkyl group, the $C_{2-6}$ alkenyl group, the $C_{2-6}$ alkynyl group, the $C_{2-9}$ heterocyclic group and the $C_{1-10}$ alkoxy group may be optionally substituted with one or more substituents selected from the group consisting of carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), a $C_{2-14}$ aryl group, a $C_{2-14}$ aryloxy group (the $C_{2-14}$ aryl group and the $C_{2-14}$ aryloxy group may be optionally substituted with one or more substituents selected from the group consisting of $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)) or $NR^{29}R^{30}$ (wherein each of $R^{29}$ and $R^{30}$ is independently a hydrogen atom, a hydroxyl group, a protected hydroxyl group, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylsulfonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group, the $C_{1-10}$ alkylcarbonyloxy group, the $C_{1-10}$ alkoxycarbonyl group, the $C_{1-10}$ alkylsulfonyl group and the $C_{1-10}$ alkylcarbonyl group may be optionally substituted with one or more substituents selected from the group consisting of carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be optionally substituted with one or more substituents selected from the group consisting of $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl group, sulfonyl groups, sulfamoyl groups, sulfo groups, nitro groups, cyano groups, halogen atoms, $C_{1-10}$ alkoxy groups (the $C_{1-10}$ alkoxy groups may be substituted with one or more halogen atoms), $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms))) or a $C_{2-14}$ aryl group (the $C_{2-14}$ aryl group may be optionally substituted with one or more substituents selected from the group consisting of $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl group, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), or $R^{29}$ and $R^{30}$, together with each other means —$(CH_2)_{m3}$-G-$(CH_2)_{m4}$— (wherein G is an oxygen atom, a sulfur atom, $CR^{31}R^{32}$ (wherein each of $R^{31}$ and $R^{32}$ is independently a hydrogen atom, a $C_{1-10}$ alkyl group, a $C_{2-14}$ aryl group, a $C_{1-10}$ alkoxy group, a $C_{2-14}$ aryloxy group, a hydroxyl group or a protected hydroxyl group) or $NR^{33}$ (wherein $R^{33}$ is a hydrogen atom, a hydroxyl group, a formyl group, a $C_{1-10}$ alkyl group, a $C_{2-6}$ alkenyl group, $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group, the $C_{1-10}$ alkylcarbonyloxy group, the $C_{1-10}$ alkoxycarbonyl group and the $C_{1-10}$ alkylcarbonyl group may be optionally substituted with one or more substituents selected from the group consisting of carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)) or a $C_{2-14}$ aryl group (the $C_{2-14}$ aryl group may be optionally substituted with one or more substituents selected from the group consisting of $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms))), and each of m3 and m4 is independently an integer of from 0 to 5, provided that m3+m4 is 3, 4 or 5))), a tetrazole group or a phosphonic acid group)) or one or more substituents independently represented by —$W^5$ $(CW^6W^7)_{m10}W^8$ (wherein $W^5$, $W^6$, $W^7$ and m10 are the same as $W^1$, $W^2$, $W^3$ and m, respectively, $W^1$, $W^2$, $W^3$ and m are the same as defined above, and $W^8$ is a hydroxyl group, a protected hydroxyl group, a thiol group, an amino group, a formyl group, a halogen atom, a nitro group, a cyano group, a $C_{1-10}$ alkyl group, a $C_{2-6}$ alkenyl group, a $C_{2-6}$ alkynyl group, a $C_{2-9}$ heterocyclic group, a $C_{1-10}$ alkoxy group, a $C_{1-10}$ alkylcarbonyloxy group, a $C_{1-10}$ alkylcarbonylamino group, a mono- or di-$C_{1-10}$ alkylamino group (the $C_{1-10}$ alkyl group, the $C_{2-6}$ alkenyl group, the $C_{2-6}$ alkynyl group, the $C_{2-9}$ heterocyclic group, the $C_{1-10}$ alkoxy group, the $C_{1-10}$ alkylcarbonyloxy group, the $C_{1-10}$ alkylcarbonylamino group and the mono- or di-$C_{1-10}$ alkylamino group may be optionally substituted with one or more substituents selected from the group consisting of carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), $SO_2R^{28a}$, $SOR^{28a}$, $COR^{28a}$ (wherein $R^{28a}$ is the same as $R^{28}$, and $R^{28}$ is the same as defined above), a tetrazole group or a phosphonic acid group)) and substituents independently represented by —$W^9(CW^{10}W^{11})_{m11}W^{12}$ (wherein $W^9$, $W^{10}$, $W^{11}$, $W^{12}$ and m11 are the same as $W^1$, $W^2$, $W^3$, $W^8$ and m, respectively, and $W^1$, $W^2$, $W^3$, $W^8$ and m are the same as defined above)), a $C_{2-10}$ alkyl group, a $C_{2-10}$ alkenyl group, a $C_{2-10}$ alkynyl group or a $C_{2-9}$ heterocyclic group (the $C_{2-10}$ alkyl group, the $C_{2-10}$ alkenyl group, the $C_{2-10}$ alkynyl group and the $C_{2-9}$ heterocyclic group may be optionally substituted with one or more substituents selected from the group consisting of $C_{1-10}$ alkyl groups, $C_{2-10}$ alkenyl groups, $C_{2-10}$ alkynyl groups, $C_{2-9}$ heterocyclic groups, $C_{1-10}$ alkoxy groups, $C_{1-10}$ thioalkyl groups, $C_{1-10}$ alkylcarbonyl groups, mono- or di-$C_{1-10}$ alkylamino groups, $C_{1-10}$ alkylcarbonyloxy groups, $C_{1-10}$ alkoxycarbonyl groups, $C_{1-10}$ alkylaminocarbonyl groups, $C_{1-10}$ dialkylaminocarbonyl groups, $C_{1-10}$ alkylcarbonylamino groups (the $C_{1-10}$ alkyl groups, the $C_{2-10}$ alkenyl groups, the $C_{2-10}$ alkynyl groups, the $C_{2-9}$ heterocyclic groups, the $C_{1-10}$ alkoxy groups, the $C_{1-10}$ thioalkyl groups, the $C_{1-10}$ alkylcarbonyl groups, the mono- or di-$C_{1-10}$ alkylamino groups, the $C_{1-10}$ alkylcarbonyloxy groups, the $C_{1-10}$ alkoxycarbonyl groups, the $C_{1-10}$ alkylaminocarbonyl groups, the $C_{1-10}$ dialkylaminocarbonyl groups and the $C_{1-10}$ alkylcarbonylamino groups may be optionally substituted with one or more $C_{2-14}$ aryl groups (the $C_{2-14}$ aryl groups may be optionally substituted with one or more substituents independently represented by —$W^1$ $(CW^2W^3)_mW^4$ (wherein $W^1$, $W^2$, $W^3$, $W^4$ and m are the same as defined above)) or one or more substituents independently represented by —$W^5$ $(CW^6W^7)_{m10}W^8$ (wherein $W^5$, $W^6$, $W^7$, $W^8$ and m10 are the same as defined above)), substituents independently represented by $W^9(CW^{10}W^{11})_{m11}W^{12}$ (wherein $W^9$, $W^{10}$, $W^{11}$, $W^{12}$ and m11 are the same as defined above) and $C_{2-14}$ aryl groups (the $C_{2-14}$ aryl groups may be optionally substituted with one or more substituents independently represented by —$W^{13}(CW^{14}W^{15})_{m12}W^{16}$ (wherein $W^{13}$, $W^{14}$, $W^{15}$, $W^{16}$ and m12 are the same as $W^1$, $W^2$, $W^3$, $W^4$ and m, respectively, and $W^1$, $W^2$, $W^3$, $W^4$ and m are the same as defined above))), a tautomer, prodrug or pharmaceutically acceptable salt of the compound or a solvate thereof.

3. The compound according to 1, wherein $L^4$ is $CR^{20}R^{21}$ (wherein each of $R^{20}$ and $R^{21}$ is independently a hydrogen atom, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group and the $C_{1-10}$ alkylcarbonyl group may be optionally substituted with one or more substituents selected from the group consisting of carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)) or a $C_{2-14}$ aryl group (the $C_{2-14}$ aryl group may be optionally substituted with one or more substituents selected from the group consisting of $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms))), an oxygen atom, a sulfur atom or $NR^{22}$ (wherein $R^{22}$ is a hydrogen atom, a hydroxyl group, a protected hydroxyl group, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group, the $C_{1-10}$ alkylcarbonyloxy group, the $C_{1-10}$ alkoxycarbonyl group and the $C_{1-10}$ alkylcarbonyl group may be optionally substituted with one or more substituents selected from the group consisting of carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)) or a $C_{2-14}$ aryl group (the $C_{2-14}$ aryl group may be optionally substituted with one or more substituents selected from the group consisting of $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms))), and $R^3$ is a $C_{1-10}$ alkyl group, a $C_{2-10}$ alkenyl group, a $C_{2-10}$ alkynyl group, a $C_{2-9}$ heterocyclic group, a $C_{1-10}$ alkoxy group, a $C_{1-10}$ thioalkyl group, a $C_{1-10}$ alkylcarbonyl group, a mono- or di-$C_{1-10}$ alkylamino group, a $C_{1-10}$ alkylcarbonyloxy group, a $C_{1-10}$ alkoxycarbonyl group or a $C_{1-10}$ alkylcarbonylamino group (the $C_{1-10}$ alkyl group, the $C_{2-10}$ alkenyl group, the $C_{2-10}$ alkynyl group, the $C_{2-9}$ heterocyclic group, the $C_{1-10}$ alkoxy group, the $C_{1-10}$ thioalkyl group, the $C_{1-10}$ alkylcarbonyl group, the mono- or di-$C_{1-10}$ alkylamino group, the $C_{1-10}$ alkylcarbonyloxy group, the $C_{1-10}$ alkoxycarbonyl group and the $C_{1-10}$ alkylcarbonylamino group may be optionally substituted with one or more substituents selected from the group consisting of $C_{1-10}$ alkyl groups, $C_{2-10}$ alkenyl groups, $C_{2-10}$ alkynyl groups, $C_{2-9}$ heterocyclic groups, $C_{1-10}$ alkoxy groups, $C_{1-10}$ thioalkyl groups, $C_{1-10}$ alkylcarbonyl groups, mono- or di-$C_{1-10}$ alkylamino groups, $C_{1-10}$ alkylcarbonyloxy groups, $C_{1-10}$ alkoxycarbonyl groups, $C_{1-10}$ alkylcarbonylamino groups (the $C_{1-10}$ alkyl groups, the $C_{2-10}$ alkenyl groups, the $C_{2-10}$ alkynyl groups, the $C_{2-9}$ heterocyclic groups, the $C_{1-10}$ alkoxy groups, the $C_{1-10}$ thioalkyl groups, the $C_{1-10}$ alkylcarbonyl groups, the mono- or di-$C_{1-10}$ alkylamino groups, the $C_{1-10}$ alkylcarbonyloxy groups, the $C_{1-10}$ alkoxycarbonyl groups and the $C_{1-10}$ alkylcarbonylamino groups may be optionally substituted with one or more $C_{2-14}$ aryl groups (the $C_{2-14}$ aryl groups may be optionally substituted with one or more substituents independently represented by —$W^1(CW^2W^3)_mW^4$ (wherein $W^1$ is $(CR^{24}R^{25})_n$ (wherein each of $R^{24}$ and $R^{25}$ is independently a hydrogen atom or a $C_{1-6}$ alkyl group (the $C_{1-6}$ alkyl group may be substituted with one or more halogen atoms), or $R^{24}$ and $R^{25}$ mean, together with each other, O= or S=, and n is 0, 1, 2 or 3), an oxygen atom, a sulfur atom or $NR^{36}$ (wherein $R^{36}$ is a hydrogen atom, a $C_{1-6}$ alkyl group, a formyl group or a $C_{1-6}$ alkylcarbonyl group), each of $W^2$ and $W^3$ is independently a hydrogen atom or a $C_{1-3}$ alkyl group (the $C_{1-3}$ alkyl group may be substituted with one or more halogen atoms), m is 0, 1, 2 or 3, and $W^4$ is a hydroxyl group, a protected hydroxyl group, a thiol group, an amino group, a formyl group, a halogen atom, a nitro group, a cyano group, a $C_{1-10}$ alkyl group, a $C_{2-6}$ alkenyl group, a $C_{2-6}$ alkynyl group, a $C_{2-9}$ heterocyclic group, a $C_{1-10}$ alkoxy group, a $C_{1-10}$ alkylcarbonyloxy group, a $C_{1-10}$ alkylcarbonylamino group, a mono- or di-$C_{1-10}$ alkylamino group (the $C_{1-10}$ alkyl group, the $C_{2-6}$ alkenyl group, the $C_{2-6}$ alkynyl group, the $C_{2-9}$ heterocyclic group, the $C_{1-10}$ alkoxy group, the $C_{1-10}$ alkylcarbonyloxy group, the $C_{1-10}$ alkylcarbonylamino group and the mono- or di-$C_{1-10}$ alkylamino group may be optionally substituted with one or more substituents selected from the group consisting of carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), a $C_{2-14}$ aryl group (the $C_{2-14}$ aryl group may be optionally substituted with one or more substituents selected from the group consisting of $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, thiol groups, phosphonic acid groups, sulfonic acid groups, tetrazole groups, $C_{2-14}$ aryl groups and $C_{2-14}$ aryloxy groups (the $C_{2-14}$ aryl groups and the $C_{2-14}$ aryloxy groups may be substituted with one or more $C_{1-10}$ alkyl groups (the $C_{1-10}$ alkyl groups may be substituted with one or more halogen atoms) or one or more halogen atoms)), $SO_2R^{28}$, $SOR^{28}$, $COR^{28}$ (wherein $R^{28}$ is a hydroxyl group, a protected hydroxyl group, a $C_{1-10}$ alkyl group, a $C_{2-6}$ alkenyl group, a $C_{2-6}$ alkynyl group, a $C_{2-9}$ heterocyclic group, a $C_{1-10}$ alkoxy group (the $C_{1-10}$ alkyl group, the $C_{2-6}$ alkenyl group, the $C_{2-6}$ alkynyl group, the $C_{2-9}$ heterocyclic group and the $C_{1-10}$ alkoxy group may be optionally substituted with one or more substituents selected from the group, consisting of carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)) or $NR^{29}R^{30}$ (wherein each of $R^{29}$ and $R^{30}$ is independently a hydrogen atom, a hydroxyl group, a protected hydroxyl group, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylsulfonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group, the $C_{1-10}$ alkylcarbonyloxy group, the $C_{1-10}$ alkoxycarbonyl group, the $C_{1-10}$ alkylsulfonyl group and the $C_{1-10}$ alkylcarbonyl group may be optionally substituted with one or more substituents selected from the group consisting of carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)) or a $C_{2-14}$ aryl group (the $C_{2-14}$ aryl group may be optionally substituted with one or more substituents selected from the group consisting of $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl group, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), or $R^{29}$ and $R^{30}$, together with each other means —$(CH_2)_{m3}$-G-$(CH_2)_{m4}$— (wherein G is an oxygen atom, a sulfur atom, $CR^{31}R^{32}$ (wherein each of $R^{31}$ and $R^{32}$ is independently a hydrogen atom, a $C_{1-10}$ alkyl group, a $C_{2-14}$ aryl group, a $C_{1-10}$ alkoxy group, a $C_{2-14}$ aryloxy group, a hydroxyl group or a protected hydroxyl group) or $NR^{33}$ (wherein $R^{33}$ is a hydrogen atom, a hydroxyl group, a formyl group, a $C_{1-10}$ alkyl group, a $C_{2-6}$ alkenyl group, $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group, the $C_{1-10}$ alkylcarbonyloxy group, the $C_{1-10}$ alkoxycarbonyl group and the $C_{1-10}$ alkylcarbonyl group may be optionally substituted with one or more substituents selected from the group consisting of carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)) or a $C_{2-14}$ aryl group (the $C_{2-14}$ aryl group may be optionally substituted with one or more substituents selected from the group consisting of $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms))), and each of m3 and m4 is independently an integer of from 0 to 5, provided that m3+m4 is 3, 4 or 5))), a tetrazole group or a phosphonic acid group)) or one or more substituents independently represented by —$W^5$ $(CW^6W^7)_{m10}W^8$ (wherein $W^5$, $W^6$, $W^7$ and m10 are the same as $W^1$, $W^2$, $W^3$ and m, respectively, $W^1$, $W^2$, $W^3$ and m are the same as defined above, and W is a hydroxyl group, a protected hydroxyl group, a thiol group, an amino group, a formyl group, a halogen atom, a nitro group, a cyano group, a $C_{1-10}$ alkyl group, a $C_{2-6}$ alkenyl group, a $C_{2-6}$ alkynyl group, a $C_{2-9}$ heterocyclic group, a $C_{1-10}$ alkoxy group, a $C_{1-10}$ alkylcarbonyloxy group, a $C_{1-10}$ alkylcarbonylamino group, a mono- or di-$C_{1-10}$ alkylamino group (the $C_{1-10}$ alkyl group, the $C_{2-6}$ alkenyl group, the $C_{2-6}$ alkynyl group, the $C_{2-9}$ heterocyclic group, the $C_{1-10}$ alkoxy group, the $C_{1-10}$ alkylcarbonyloxy group, the $C_{1-10}$ alkylcarbonylamino group and the mono- or di-$C_{1-10}$ alkylamino group may be optionally substituted with one or more substituents selected from the group consisting of carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), $SO_2R^{28a}$, $SOR^{28a}$, $COR^{28a}$ (wherein $R^{28a}$ is the same as $R^{28}$, and $R^{28}$ is the same as defined above), a tetrazole group or a phosphonic acid group)), substituents independently represented by —$W^9$ $(CW^{10}W^{11})_{m11}W^{12}$ (wherein $W^9$, $W^{10}$, $W^{11}$, $W^{12}$ and m11 are the same as $W^1$, $W^2$, $W^3$, $W^8$ and m, respectively, and $W^1$, $W^2$, $W^3$, $W^8$ and m are the same as defined above) and $C_{2-14}$ aryl groups (the $C_{2-14}$ aryl groups may be optionally substituted with one or more substituents independently represented by —$W^{13}(CW^{14}W^{15})_{m12}W^{16}$ (wherein $W^{13}$, $W^{14}$, $W^{15}$, $W^{16}$ and m12 are the same as $W^1$, $W^2$, $W^3$, $W^4$ and m, respectively, and $W^1$, $W^2$, $W^3$, $W^4$ and m are the same as defined above))), a tautomer, prodrug or pharmaceutically acceptable salt of the compound or a solvate thereof.

4. The compound according to any one of 1 to 3, wherein A is a nitrogen atom, and B is a sulfur atom, a tautomer, prodrug or pharmaceutically acceptable salt of the compound or a solvate thereof.

5. The compound according to any one of 1 to 3, wherein A is a nitrogen atom, and B is an oxygen atom, a tautomer, prodrug or pharmaceutically acceptable salt of the compound or a solvate thereof.

6. The compound according to any one of 1 to 3, wherein A is a nitrogen atom, and B is $NR^9$ other than NH (wherein $R^9$ is a hydrogen, atom, a hydroxyl group, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group, the $C_{1-10}$ alkylcarbonyloxy group, the $C_{1-10}$ alkoxycarbonyl group and the $C_{1-10}$ alkylcarbonyl group may be optionally substituted with one or more substituents selected from the group consisting of carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more alkyl groups (the $C_{1-6}$ alkyl groups may be substituted with one or more halogen atoms) or one or more halogen atoms)), a $C_{2-14}$ aryl group (the $C_{2-14}$ aryl group may be optionally substituted with one or more substituents selected from the group consisting of $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups) or a $C_{2-14}$ aryloxy group (the $C_{2-14}$ aryloxy group may be optionally substituted with one or more substituents selected from the group consisting of $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups)), a tautomer, prodrug or pharmaceutically acceptable salt of the compound or a solvate thereof.

7. The compound according to any one of 1 to 3, wherein A is $CR^4$ (wherein $R^4$ is a hydrogen atom, a hydroxyl group (the hydroxyl group may be substituted with a $C_{2-6}$ alkenyl group or a $C_{2-6}$ alkynyl group), a thiol group (the thiol group may be substituted with a $C_{1-10}$ alkyl group, a $C_{2-6}$ alkenyl group, a $C_{2-6}$ alkynyl group or a $C_{1-10}$ alkylcarbonyl group), an amino group (the amino group may be substituted with one or two $C_{2-6}$ alkenyl groups or one or two $C_{2-6}$ alkynyl groups), a formyl group, a halogen atom, a nitro group, a cyano group, a $C_{1-10}$ alkyl group, a $C_{2-6}$ alkenyl group, a $C_{2-6}$ alkynyl group, a $C_{1-10}$ alkylcarbonylamino group, a mono- or di-$C_{1-10}$ alkylamino group, a $C_{1-10}$ alkoxy group (the $C_{1-10}$ alkyl group, the $C_{2-6}$ alkenyl group, the $C_{2-6}$ alkynyl group, the $C_{1-10}$ alkylcarbonylamino group, the mono- or di-$C_{1-10}$ alkylamino group and the $C_{1-10}$ alkoxy group may be optionally substituted with one or more substituents selected from the group consisting of carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), a $C_{2-14}$ aryl group (the $C_{2-14}$ aryl group may be optionally substituted with one or more substituents selected from the group consisting of $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups), a $C_{2-14}$ aryloxy group (the $C_{2-14}$ aryloxy group may be optionally substituted with one or more substituents selected from the group consisting of $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups), $SO_2R^5$, $SOR^5$ or $COR^5$ (wherein $R^5$ is a hydroxyl group, a $C_{1-10}$ alkyl group, a $C_{2-6}$ alkenyl group, a $C_{2-6}$ alkynyl group, a $C_{2-9}$ heterocyclic group, a $C_{1-10}$ alkoxy group (the $C_{1-10}$ alkyl group, the $C_{2-6}$ alkenyl group, the $C_{2-6}$ alkynyl group, the $C_{2-9}$ heterocyclic group and the $C_{1-10}$ alkoxy group may be optionally substituted with one or more substituents selected from the group consisting of carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), a $C_{2-14}$ aryl group (the $C_{2-14}$ aryl group may be optionally substituted with one or more substituents selected from the group consisting of $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups), a $C_{2-14}$ aryloxy group (the $C_{2-14}$ aryloxy group may be optionally substituted with one or more substituents selected from the group consisting of $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups) or $NR^6R^7$ (wherein each of $R^6$ and $R^7$ is independently a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkylcarbonyloxy group, the $C_{1-10}$ alkoxycarbonyl group and the $C_{1-10}$ alkylcarbonyl group may be optionally substituted with one or more substituents selected from the group consisting of carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)) or a $C_{2-14}$ aryl group (the $C_{2-14}$ aryl group may be optionally substituted with one or more substituents selected from the group consisting of $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups), or $R^6$ and $R^7$ mean, together with each other, —$(CH_2)_{m1}$-E-$(CH_2)_{m2}$— (wherein E is an oxygen atom, a sulfur atom, $CR^{26}R^{27}$ (wherein each of $R^{26}$ and $R^{27}$ is independently a hydrogen atom, a $C_{1-10}$ alkyl group, a $C_{2-14}$ aryl group, a $C_{1-10}$ alkoxy group, a $C_{2-14}$ aryloxy group, a hydroxyl group or a protected hydroxyl group) or $NR^8$ (wherein $R^8$ is a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group, the $C_{1-10}$ alkylcarbonyloxy group, the $C_{1-10}$ alkoxycarbonyl group and the $C_{1-10}$ alkylcarbonyl group may be optionally substituted with one or more substituents selected from the group consisting of carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)) or a $C_{2-14}$ aryl group (the $C_{2-14}$ aryl group may be optionally substituted with one or more substituents selected from the group consisting of $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups)), and each of m1 and m2 is independently an integer of from 0 to 5 provided that m1+m2 is 3, 4 or 5)))), and B is an oxygen atom, a tautomer, prodrug or pharmaceutically acceptable salt of the compound or a solvate thereof.

8. The compound according to any one of 1 to 3, wherein A is $CR^4$ (wherein $R^4$ is a hydrogen atom, a hydroxyl group (the hydroxyl group may be substituted with a $C_{2-6}$ alkenyl group or a $C_{2-6}$ alkynyl group), a thiol group (the thiol group may be substituted with a $C_{1-10}$ alkyl group, a $C_{2-6}$ alkenyl group, a $C_{2-6}$ alkynyl group or a $C_{1-10}$ alkylcarbonyl group), an amino group (the amino group may be substituted with one or two $C_{2-6}$ alkenyl groups or one or two $C_{2-6}$ alkynyl groups), a formyl group, a halogen atom, a nitro group, a cyano group, a $C_{1-10}$ alkyl group, a $C_{2-6}$ alkenyl group, a $C_{2-6}$ alkynyl group, a $C_{1-10}$ alkylcarbonylamino group, a mono- or di-$C_{1-10}$ alkylamino group, a $C_{1-10}$ alkoxy group (the $C_{1-10}$ alkyl group, the $C_{2-6}$ alkenyl group, the $C_{2-6}$ alkynyl group, the $C_{1-10}$ alkylcarbonylamino group, the mono- or di-$C_{1-10}$ alkylamino group and the $C_{1-10}$ alkoxy group may be optionally substituted with one or more substituents selected from the group consisting of carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), a $C_{2-14}$ aryl group (the $C_{2-14}$ aryl group may be optionally substituted with one or more substituents selected from the group consisting of $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups), a $C_{2-14}$ aryloxy group may be optionally substituted with one or more substituents selected from the group consisting of $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonyl groups), $SO_2R^5$, $SOR^5$ or $COR^5$ (wherein $R^5$ is a hydroxyl group, a $C_{1-10}$ alkyl group, a $C_{2-6}$ alkenyl group, a $C_{2-6}$ alkynyl group, a $C_{2-9}$ heterocyclic group, a $C_{1-10}$ alkoxy group (the $C_{1-10}$ alkyl group, the $C_{2-6}$ alkenyl group, the $C_{2-6}$ alkynyl group, the $C_{2-9}$ heterocyclic group and the $C_{1-10}$ alkoxy group may be optionally substituted with one or more substituents selected from the group consisting of carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), a $C_{2-14}$ aryl group (the $C_{2-14}$ aryl group may be optionally substituted with one or more substituents selected from the group consisting of $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups) or $NR^6R^7$ (wherein each of $R^6$ and $R^7$ is independently a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkylcarbonyloxy group, the $C_{1-10}$ alkoxycarbonyl group and the $C_{1-10}$ alkylcarbonyl group may be optionally substituted with one or more substituents selected from the group consisting of carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)) or a $C_{2-14}$ aryl group (the $C_{2-14}$ aryl group may be optionally substituted with one or more substituents selected from the group consisting of $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups), or $R^6$ and $R^7$ mean, together with each other, —$(CH_2)_{m1}$-E-$(CH_2)_{m2}$— (wherein E is an oxygen atom, a sulfur atom, $CR^{26}R^{27}$ (wherein each of $R^{26}$ and $R^{27}$ is independently a hydrogen atom, a $C_{1-10}$ alkyl group, a $C_{2-14}$ aryl group, a $C_{1-10}$ alkoxy group, a $C_{2-14}$ aryloxy group, a hydroxyl group or a protected hydroxyl group) or $NR^8$ (wherein $R^8$ is a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group, the $C_{1-10}$ alkylcarbonyloxy group, the $C_{1-10}$ alkoxycarbonyl group and the $C_{1-10}$ alkylcarbonyl group may be optionally substituted with one or more substituents selected from the group consisting of carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)) or a $C_{2-14}$ aryl group (the $C_{2-14}$ aryl group may be optionally substituted with one or more substituents selected from the group consisting of $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups)), and each of m1 and m2 is independently an integer of from 0 to 5 provided that m1+m2 is 3, 4 or 5)))), and B is a sulfur atom, a tautomer, prodrug or pharmaceutically acceptable salt of the compound or a solvate thereof.

9. The compound according to any one of 1 to 3, wherein A is $CR^4$ (wherein $R^4$ is a hydrogen atom, a hydroxyl group (the hydroxyl group may be substituted with a $C_{2-6}$ alkenyl group or a $C_{2-6}$ alkynyl group), a thiol group (the thiol group may be substituted with a $C_{1-10}$ alkyl group, a $C_{2-6}$ alkenyl group, a $C_{2-6}$ alkynyl group or a $C_{1-10}$ alkylcarbonyl group), an amino group (the amino group may be substituted with one or two $C_{2-6}$ alkenyl groups or one or two $C_{2-6}$ alkynyl groups), a formyl group, a halogen atom, a nitro group, a cyano group, a $C_{1-10}$ alkyl group, a $C_{2-6}$ alkenyl group, a $C_{2-6}$ alkynyl group, a $C_{1-10}$ alkylcarbonylamino group, a mono- or di-$C_{1-10}$ alkylamino group, a $C_{1-10}$ alkoxy group (the $C_{1-10}$ alkyl group, the $C_{2-6}$ alkenyl group, the $C_{2-6}$ alkynyl group, the $C_{1-10}$ alkylcarbonylamino group, the mono- or di-$C_{1-10}$ alkylamino group and the $C_{1-10}$ alkoxy group may be optionally substituted with one or more substituents selected from the group consisting of carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), a $C_{2-14}$ aryl group (the $C_{2-14}$ aryl group may be optionally substituted with one or more substituents selected from the group consisting of $C_{2-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups), a $C_{2-14}$ aryloxy group (the $C_{2-14}$ aryloxy group may be optionally substituted with one or more substituents selected from the group consisting of $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups), $SO_2R^5$, $SOR^5$ or $COR^5$ (wherein $R^5$ is a hydroxyl group, a $C_{1-10}$ alkyl group, a $C_{2-6}$ alkenyl group, a $C_{2-6}$ alkynyl group, a $C_{2-9}$ heterocyclic group, a $C_{1-10}$ alkoxy group (the $C_{1-10}$ alkyl group, the $C_{2-6}$ alkenyl group, the $C_{2-6}$ alkynyl group, the $C_{2-9}$ heterocyclic group and the $C_{1-10}$ alkoxy group may be optionally substituted with one or more substituents selected from the group consisting of carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), a $C_{2-14}$ aryl group (the $C_{2-14}$ aryl group may be optionally substituted with one or more substituents selected from the group consisting of $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups) or $NR^6R^7$ (wherein each of $R^6$ and $R^7$ is independently a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkylcarbonyloxy group, the $C_{1-10}$ alkoxycarbonyl group and the $C_{1-10}$ alkylcarbonyl group may be optionally substituted with one or more substituents selected from the group consisting of carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)) or a $C_{2-14}$ aryl group (the $C_{2-14}$ aryl group may be optionally substituted with one or more substituents selected from the group consisting of $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups), or $R^6$ and $R^7$ mean, together with each other, —$(CH_2)_{m1}$-E-$(CH_2)_{m2}$— (wherein E is an oxygen atom, a sulfur atom, $CR^{26}R^{27}$ (wherein each of $R^{26}$ and $R^{27}$ is independently a hydrogen atom, a $C_{1-10}$ alkyl group, a $C_{2-14}$ aryl group, a $C_{1-10}$ alkoxy group, a $C_{2-14}$ aryloxy group, a hydroxyl group or a protected hydroxyl group) or $NR^8$ (wherein $R^8$ is a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group, the $C_{1-10}$ alkylcarbonyloxy group, the $C_{1-10}$ alkoxycarbonyl group and the $C_{1-10}$ alkylcarbonyl group may be optionally substituted with one or more substituents selected from the group consisting of carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)) or a $C_{2-14}$ aryl group (the $C_{2-14}$ aryl group may be optionally substituted with one or more substituents selected from the group consisting of $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups)), and each of m1 and m2 is independently an integer of from 0 to 5 provided that m1+m2 is 3, 4 or 5)))), and B is $NR^9$ (wherein $R^9$ is a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group, the $C_{1-10}$ alkylcarbonyloxy group, the $C_{1-10}$ alkoxycarbonyl group and the $C_{1-10}$ alkylcarbonyl group may be optionally substituted with one or more substituents selected from the group consisting of carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)) or a $C_{2-14}$ aryl group (the $C_{2-14}$ aryl group may be optionally substituted with one or more substituents selected from the group consisting of $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups)) or a $C_{2-14}$ aryloxy group (the $C_{2-14}$ aryloxy group may be optionally substituted with one or more substituents selected from the group consisting of $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups)), a tautomer, prodrug or pharmaceutically acceptable salt of the compound or a solvate thereof.

10. The compound according to any one of 1 to 9, wherein $L^1$ is a bond, a tautomer, prodrug or pharmaceutically acceptable salt of the compound or a solvate thereof.

11. The compound according to any one of 1 to 10, wherein $L^2$ is a bond, a tautomer, prodrug or pharmaceutically acceptable salt of the compound or a solvate thereof.

12. The compound according to any one of 1 to 11, wherein $L^3$ is $NR^{19}$ (wherein $R^{19}$ is a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkylcarbonyloxy group, the $C_{1-10}$ alkoxycarbonyl group, the $C_{1-10}$ alkoxy group and the $C_{1-10}$ alkylcarbonyl group may be optionally substituted with one or more substituents selected from the group consisting of carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)) or a $C_{2-14}$ aryl group (the $C_{2-14}$ aryl group may be optionally substituted with one or more substituents selected from the group consisting of $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups)), a tautomer, prodrug or pharmaceutically acceptable salt of the compound or a solvate thereof.

13. The compound according to any one of 1 to 11, wherein $L^3$ is NH, a tautomer, prodrug or pharmaceutically acceptable salt of the compound or a solvate thereof.

14. The compound according to any one of 3 to 11, wherein $L^3$ is the same as defined in 12, and $L^4$ is $NR^{22}$ (wherein $R^{22}$ is a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group, the $C_{1-10}$ alkylcarbonyloxy group, the $C_{1-10}$ alkoxycarbonyl group and the $C_{1-10}$ alkylcarbonyl group may be optionally substituted with one or more substituents selected from the group consisting of carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)) or a $C_{2-14}$ aryl group (the $C_{2-14}$ aryl group may be optionally substituted with one or more substituents selected from the group consisting of $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups)), a tautomer, prodrug or pharmaceutically acceptable salt of the compound or a solvate thereof.

15. The compound according to any one of 3 to 11, wherein $L^3$ is the same as defined in 13, and $L^4$ is $NR^{22}$ (wherein $R^{22}$ is a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group, the $C_{1-10}$ alkylcarbonyloxy group, the $C_{1-10}$ alkoxycarbonyl group and the $C_{1-10}$ alkylcarbonyl group may be optionally substituted with one or more substituents selected from the group consisting of carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)) or a $C_{2-14}$ aryl group (the $C_{2-14}$ aryl group may be optionally substituted with one or more substituents selected from the group consisting of $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups)), a tautomer, prodrug or pharmaceutically acceptable salt of the compound or a solvate thereof.

16. The compound according to 14 or 15, wherein $L^4$ is NH, a tautomer, prodrug or pharmaceutically acceptable salt of the compound or a solvate thereof.

17. The compound according to any one of 2 and 4 to 11, wherein $L^3$ is the same as defined in 12, and $L^4$ is a bond, a tautomer, prodrug or pharmaceutically acceptable salt of the compound or a solvate thereof.

18. The compound according to any one of 2 and 4 to 11, wherein $L^3$ is the same as defined in 13, and $L^4$ is a bond, a tautomer, prodrug or pharmaceutically acceptable salt of the compound or a solvate thereof.

19. The compound according to any one of 14 to 18, wherein Y is an oxygen atom, a tautomer, prodrug or pharmaceutically acceptable salt of the compound or a solvate thereof.

20. The compound according to any one of 14 to 18, wherein Y is a sulfur atom, a tautomer, prodrug or pharmaceutically acceptable salt of the compound or a solvate thereof.

21. The compound according to 19 or 20, wherein X is a hydroxyl group, a tautomer, prodrug or pharmaceutically acceptable salt of the compound or a solvate thereof.

22. The compound according to any one of 19 to 21, wherein $R^3$ is a $C_{2-9}$ heterocyclic group (the $C_{2-9}$ heterocyclic group may be optionally substituted with one or more substituents selected from the group consisting of hydroxyl groups, amino groups, carboxyl groups, phosphonic acid groups, sulfonic acid groups, carbamoyl groups, sulfamoyl groups, tetrazole groups, $C_{1-10}$ alkoxycarbonyl groups, $C_{1-10}$ alkoxy groups, $C_{1-10}$ thioalkyl groups, $C_{1-10}$ alkylcarbonyl groups, $C_{1-10}$ alkylcarbonyloxy groups, $C_{1-10}$ alkylcarbonylamino groups and mono- or di-$C_{1-10}$ alkylamino groups), a tautomer, prodrug or pharmaceutically acceptable salt of the compound or a solvate thereof.

23. The compound according to any one of 19 to 21, wherein $R^3$ is a $C_{2-9}$ heterocyclic group (the $C_{2-9}$ heterocyclic group is substituted with a substituent selected from the group consisting of a hydroxyl group, an amino group, a carboxyl group, a phosphonic acid group, a sulfonic acid group, a carbamoyl group, a sulfamoyl group, a tetrazole group and a $C_{1-10}$ alkoxycarbonyl group and with a substituent selected from the group consisting of a hydroxyl group, an amino group, a carboxyl group, a phosphonic acid group, a sulfonic acid group, a carbamoyl group, a sulfamoyl group, a tetrazole group, a $C_{1-10}$ alkoxycarbonyl group, a nitro group, a cyano group, a halogen atom, a $C_{1-10}$ alkyl group, a $C_{1-10}$ alkyl group substituted with one or more fluorine atoms, a sulfamoyl group substituted with a $C_{1-10}$ alkyl group, a carbamoyl group substituted with a $C_{1-10}$ alkyl group and a $C_{1-10}$ alkylcarbonylamino group), a tautomer, prodrug or pharmaceutically acceptable salt of the compound or a solvate thereof.

24. The compound according to any one of 19 to 21, wherein $R^3$ is a $C_{1-10}$ alkyl group or a $C_{2-10}$ alkenyl group (the $C_{1-10}$ alkyl group and the $C_{2-10}$ alkenyl group may be optionally substituted with one or more substituents selected from the group consisting of $C_{1-10}$ alkyl groups, $C_{2-10}$ alkenyl groups, $C_{1-10}$ alkoxy groups, $C_{1-10}$ thioalkyl groups, $C_{1-10}$ alkylcarbonyl groups, mono- or di-$C_{1-10}$ alkylamino groups, $C_{1-10}$ alkylcarbonyloxy groups, $C_{1-10}$ alkoxycarbonyl groups, $C_{1-10}$ alkylcarbonylamino groups (the $C_{1-10}$ alkyl groups, the $C_{2-10}$ alkenyl groups, the $C_{1-10}$ alkoxy groups, the $C_{1-10}$ thioalkyl groups, the $C_{1-10}$ alkylcarbonyl groups, the mono- or di-$C_{1-10}$ alkylamino groups, the $C_{1-10}$ alkylcarbonyloxy groups, the $C_{1-10}$ alkoxycarbonyl groups and the $C_{1-10}$ alkylcarbonylamino groups may be optionally substituted with one or more substituents selected from the group consisting of hydroxyl groups, amino groups, carboxyl groups, phosphonic acid groups, sulfonic acid groups, carbamoyl groups, sulfamoyl groups, tetrazole groups, $C_{1-10}$ alkoxycarbonyl groups, $C_{1-10}$ alkoxy groups, $C_{1-10}$ thioalkyl groups, $C_{1-10}$ alkylcarbonyl groups, $C_{1-10}$ alkylcarbonyloxy groups, $C_{1-10}$ alkylcarbonylamino groups and mono- or di-$C_{1-10}$ alkylamino groups), nitro group, halogen atoms, hydroxyl groups, amino groups, carboxyl groups, phosphonic acid groups, sulfonic acid groups, carbamoyl groups, sulfamoyl groups and tetrazole groups), a tautomer, prodrug or pharmaceutically acceptable salt of the compound or a solvate thereof.

25. The compound according to any one of 19 to 21, wherein $R^3$ is a $C_{1-10}$ alkyl group or a $C_{2-10}$ alkenyl group (the $C_{1-10}$ alkyl group and the $C_{2-10}$ alkenyl group may be optionally substituted with one or more substituents selected from the group consisting of $C_{1-10}$ alkyl groups, $C_{2-6}$ alkenyl groups, $C_{1-10}$ alkoxy groups, $C_{1-10}$ thioalkyl groups, $C_{1-10}$ alkylcarbonyl groups, mono- or di-$C_{1-10}$ alkylamino groups, $C_{1-10}$ alkylcarbonyloxy groups, $C_{1-10}$ alkoxycarbonyl groups, $C_{1-10}$ alkylcarbonylamino groups (the $C_{1-10}$ alkyl groups, the $C_{2-6}$ alkenyl groups, the $C_{1-10}$ alkoxy groups, the $C_{1-10}$ thioalkyl groups, the $C_{1-10}$ alkylcarbonyl groups, the mono- or di-$C_{1-10}$ alkylamino groups, the $C_{1-10}$ alkylcarbonyloxyl groups, the $C_{1-10}$ alkoxycarbonyl groups and the $C_{1-10}$ alkylcarbonylamino groups may be optionally substituted with one or more substituents selected from the group consisting of hydroxyl groups, amino groups, carboxyl groups, phosphonic acid groups, sulfonic acid groups, carbamoyl groups, sulfamoyl groups and tetrazole groups), halogen atoms, nitro groups, hydroxyl groups, amino groups, carboxyl groups, phosphonic acid groups, sulfonic acid groups, carbamoyl groups, sulfamoyl groups and tetrazole groups), a tautomer, prodrug or pharmaceutically acceptable salt of the compound or a solvate thereof.

26. The compound according to any one of 19 to 21, wherein $R^3$ is a $C_{2-9}$ heterocyclic group (the $C_{2-9}$ heterocyclic group is substituted with one or more substituents selected from the group consisting of hydroxyl groups, amino groups, halogen atoms, carboxyl groups, sulfonic acid groups, carbamoyl groups, hydroxycarbamoyl groups, cyanocarbamoyl groups, sulfamoyl groups, hydroxysulfamoyl groups, cyanosulfamoyl groups, thiocarbamoyl groups, —CH$_2$COOH, —OCH$_2$COOH, —NHCH$_2$COOH, —CH$_2$OH, —OCH$_2$OH, —NHCH$_2$OH, —CH$_2$CH$_2$OH, —(C=O) COOH, —CH$_2$(C=O)COOH, —NH(C=O)COOH, —NHSO$_2$NH$_2$, $C_{1-10}$ alkyl groups, $C_{1-10}$ alkylsulfonyl groups, $C_{1-10}$ alkylaminosulfonyl groups, $C_{1-10}$ alkylcarbonyl groups, $C_{1-10}$ alkylaminocarbonyl groups and $C_{1-10}$ dialkylaminocarbonyl groups (the $C_{1-10}$ alkyl groups, the $C_{1-10}$ alkylsulfonyl groups, the $C_{1-10}$ alkylaminosulfonyl groups, the $C_{1-10}$ alkylcarbonyl groups, the $C_{1-10}$ alkylaminocarbonyl groups and the $C_{1-10}$ dialkylaminocarbonyl groups may be substituted with one or more substituents selected from the group consisting of phenyl groups, thienyl groups, furyl groups, pyridyl groups, nitro groups, cyano groups, hydroxyl groups, amino groups, carboxyl groups, phosphonic acid groups, sulfonic acid groups, carbamoyl groups, sulfamoyl groups and tetrazole groups)), a tautomer, prodrug or pharmaceutically acceptable salt of the compound or a solvate thereof.

27. The thrombopoietin receptor activator according to any one of 1 to 26.

28. A preventive, therapeutic or improving agent for diseases against which activation of the thrombopoietin receptor is effective, which contains the thrombopoietin receptor activator according to 27, a tautomer, prodrug or pharmaceutically acceptable salt of the activator or a solvate thereof, as an active ingredient.

29. A platelet increasing agent containing the thrombopoietin receptor activator according to 27, a tautomer, prodrug or pharmaceutically acceptable salt of the activator or a solvate thereof, as an active ingredient.

30. Medicament containing the compound according to any one of 1 to 26, a tautomer, prodrug or pharmaceutically acceptable salt of the compound or a solvate thereof, as an active ingredient.

The present invention provides pharmaceutical compositions comprising compounds which increase platelets through stimulation of differentiation and proliferation of hematopoietic stem cells, megakaryocytic progenitor cells and megakaryocytes or compounds for therapeutic angiogenesis or with anti-arteriosclerosis action that stimulate differentiation and proliferation of vascular endothelial cells and endothelial progenitor cells.

BEST MODE FOR CARRYING OUT THE INVENTION

Figure 1:
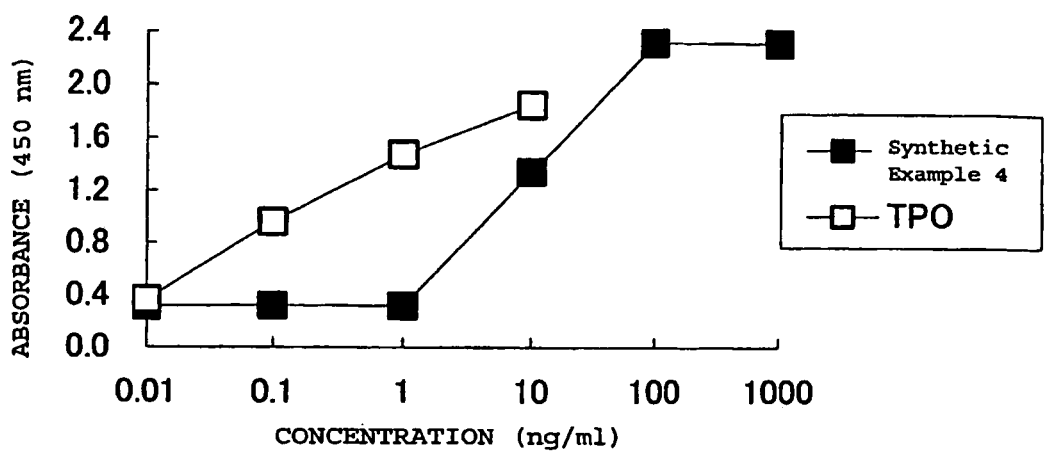
FIG. 1 shows the proliferation of UT7/EPO-mpl cells when stimulated by the compound of the present invention (Synthetic Example 4).

Now, the present invention will be described in detail.

In the present invention, "n" denotes normal, "i" denotes iso, "s" denotes secondary, "t" denotes tertiary, "c" denotes cyclo, "o" denotes ortho, "m" denotes meta, "p" denotes para, "Ph" denotes phenyl, "Py" denotes pyridyl, "Naphthyl" denotes naphthyl, "Me" denotes methyl, "Et" denotes ethyl, "Pr" denotes propyl, "Bu" denotes butyl and "Ac" denotes acetyl.

First, the terms, in the respective substituents $R^1$ to $R^{36}$ will be explained.

As a halogen atom, a fluorine atom, a chlorine atom, a bromine atom or an iodine atom may be mentioned.

A $C_{1-3}$ alkyl group may be linear, branched or a $C_3$ cycloalkyl group, and methyl, ethyl, n-propyl, i-propyl and c-propyl and the like may be mentioned.

A $C_{1-6}$ alkyl group may be linear, branched or a $C_{3-6}$ cycloalkyl group, and in addition to those mentioned above, n-butyl, i-butyl, s-butyl, t-butyl, c-butyl, 1-methyl-c-propyl, 2-methyl-c-propyl, n-pentyl, 1-methyl-n-butyl, 2-methyl-n-butyl, 3-methyl-n-butyl, 1,1-dimethyl-n-propyl, 1,2-dimethyl-n-propyl, 2,2-dimethyl-n-propyl, 1-ethyl-n-propyl, c-pentyl, 1-methyl-c-butyl, 2-methyl-c-butyl, 3-methyl-c-butyl, 1,2-dimethyl-c-propyl, 2,3-dimethyl-c-propyl, 1-ethyl-c-propyl, 2-ethyl-c-propyl, n-hexyl, 1-methyl-n-pentyl, 2-methyl-n-pentyl, 3-methyl-n-pentyl, 4-methyl-n-pentyl, 1,1-dimethyl-n-butyl, 1,2-dimethyl-n-butyl, 1,3-dimethyl-n-butyl, 2,2-dimethyl-n-butyl, 2,3-dimethyl-n-butyl, 3,3-dimethyl-n-butyl, 1-ethyl-n-butyl, 2-ethyl-n-butyl, 1,1,2-trimethyl-n-propyl, 1,2,2-trimethyl-n-propyl, 1-ethyl-1-methyl-n-propyl, 1-ethyl-2-methyl-n-propyl, c-hexyl, 1-methyl-c-pentyl, 2-methyl-c-pentyl, 3-methyl-c-pentyl, 1-ethyl-c-butyl, 2-ethyl-c-butyl, 3-ethyl-c-butyl, 1,2-dimethyl-c-butyl, 1,3-dimethyl-c-butyl, 2,2-dimethyl-c-butyl, 2,3-dimethyl-c-butyl, 2,4-dimethyl-c-butyl, 3,3-dimethyl-c-butyl, 1-n-propyl-c-propyl, 2-n-propyl-c-propyl, 1-i-propyl-c-propyl, 2-i-propyl-c-propyl, 1,2,2-trimethyl-c-propyl, 1,2,3-trimethyl-c-propyl, 2,2,3-trimethyl-c-propyl, 1-ethyl-2-methyl-c-propyl, 2-ethyl-1-methyl-c-propyl, 2-ethyl-2-methyl-c-propyl, 2-ethyl-3-methyl-c-propyl and the like may be mentioned.

A $C_{1-10}$ alkyl group may be linear, branched or a $C_{3-10}$ cycloalkyl group, and in addition to those mentioned above, 1-methyl-1-ethyl-n-pentyl, 1-heptyl, 2-heptyl, 1-ethyl-1,2-dimethyl-n-propyl, 1-ethyl-2,2-dimethyl-n-propyl, 1-octyl, 3-octyl, 4-methyl-3-n-heptyl, 6-methyl-2-n-heptyl, 2-propyl-1-n-heptyl, 2,4,4-trimethyl-1-n-pentyl, 1-nonyl, 2-nonyl, 2,6-dimethyl-4-n-heptyl, 3-ethyl-2,2-dimethyl-3-n-pentyl, 3,5,5-trimethyl-1-n-hexyl, 1-decyl, 2-decyl, 4-decyl, 3,7-dimethyl-1-n-octyl, 3,7-dimethyl-3-n-octyl, c-heptyl, c-octyl, 1-methyl-c-hexyl, 2-methyl-c-hexyl, 3-methyl-c-hexyl, 1,2-dimethyl-c-hexyl, 1-ethyl-c-hexyl, 1-methyl-c-pentyl, 2-methyl-c-pentyl, 3-methyl-c-pentyl and the like may be mentioned.

A $C_{2-10}$ alkyl group may be linear, branched or a $C_{3-10}$ cycloalkyl group, and those mentioned above as $C_{1-10}$ alkyl groups except for a methyl group may be mentioned.

As a $C_{2-6}$ alkynyl group, ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 2-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 1-n-propyl-2-propynyl, 2-ethyl-3-butynyl, 1-methyl-1-ethyl-2-propynyl, 1-i-propyl-2-propynyl and the like may be mentioned.

A $C_{2-10}$ alkynyl group may be linear or branched, and in addition to those mentioned above, 1-methyl-n-hexynyl, 1,2-dimethyl-n-hexynyl, 1-ethyl-n-hexynyl, 1-n-heptynyl, 2-n-heptynyl, 3-n-heptynyl, 4-n-heptynyl, 1-n-octynyl, 2-n-octynyl, 3-n-octynyl and the like may be mentioned.

A $C_{2-6}$ alkenyl group may be linear, branched or a $C_{3-6}$ cycloalkenyl group, and ethenyl, 1-propenyl, 2-propenyl, 1-methyl-1-ethenyl, 1-butenyl, 2-butenyl, 3-butenyl, 2-methyl-1-propenyl, 2-methyl-2-propenyl, 1-ethylethenyl, 1-methyl-1-propenyl, 1-methyl-2-propenyl, 1-pentenyl, 2-pentenyl, 3-pentenyl, 4-pentenyl, 1-n-propylethenyl, 1-methyl-1-butenyl, 1-methyl-2-butenyl, 1-methyl-3-butenyl, 2-ethyl-2-propenyl, 2-methyl-1-butenyl, 2-methyl-2-butenyl, 2-methyl-3-butenyl, 3-methyl-1-butenyl, 3-methyl-2-butenyl, 3-methyl-3-butenyl, 1,1-dimethyl-2-propenyl, 1-i-propylethenyl, 1,2-dimethyl-1-propenyl, 1,2-dimethyl-2-propenyl, 1-c-pentenyl, 2-c-pentenyl, 3-c-pentenyl, 1-hexenyl, 2-hexenyl, 3-hexenyl, 4-hexenyl, 5-hexenyl, 1-methyl-1-pentenyl, 1-methyl-2-pentenyl, 1-methyl-3-pentenyl, 1-methyl-4-pentenyl, 1-n-butylethenyl, 2-methyl-1-pentenyl, 2-methyl-2-pentenyl, 2-methyl-3-pentenyl, 2-methyl-4-pentenyl, 2-n-propyl-2-propenyl, 3-methyl-1-pentenyl, 3-methyl-2-pentenyl, 3-methyl-3-pentenyl, 3-methyl-4-pentenyl, 3-ethyl-3-butenyl, 4-methyl-1-pentenyl, 4-methyl-2-pentenyl, 4-methyl-3-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1-methyl-2-ethyl-2-propenyl, 1-s-butylethenyl, 1,3-dimethyl-1-butenyl, 1,3-dimethyl-2-butenyl, 1,3-dimethyl-3-butenyl, 1-i-butylethenyl, 2,2-dimethyl-3-butenyl, 2,3-dimethyl-1-butenyl, 2,3-dimethyl-2-butenyl, 2,3-dimethyl-3-butenyl, 2-i-propyl-2-propenyl, 3,3-dimethyl-1-butenyl, 1-ethyl-1-butenyl, 1-ethyl-2-butenyl, 1-ethyl-3-butenyl, 1-n-propyl-1-propenyl, 1-n-propyl-2-propenyl, 2-ethyl-1-butenyl, 2-ethyl-2-butenyl, 2-ethyl-3-butenyl, 1,1,2-trimethyl-2-propenyl, 1-t-butylethenyl, 1-methyl-1-ethyl-2-propenyl, 1-ethyl-2-methyl-1-propenyl, 1-ethyl-2-methyl-2-propenyl, 1-i-propyl-1-propenyl, 1-i-propyl-2-propenyl, 1-methyl-2-c-pentenyl, 1-methyl-3-c-pentenyl, 2-methyl-1-c-pentenyl, 2-methyl-2-c-pentenyl, 2-methyl-3-c-pentenyl, 2-methyl-4-c-pentenyl, 2-methyl-5-c-pentenyl, 2-methylene-c-pentyl, 3-methyl-1-c-pentenyl, 3-methyl-2-c-pentenyl, 3-methyl-3-c-pentenyl, 3-methyl-4-c-pentenyl, 3-methyl-5-c-pentenyl, 3-methylene-c-pentyl, 1-c-hexenyl, 2-c-hexenyl, 3-c-hexenyl and the like may be mentioned.

A $C_{2-10}$ alkenyl group may be linear, branched or a $C_{3-10}$ cycloalkenyl group, and in addition to those mentioned above, 1-methyl-n-hexenyl, 1,2-dimethyl-n-hexenyl, 1-ethyl-n-hexenyl, 1-n-heptenyl, 2-n-heptenyl, 3-n-heptenyl, 4-n-heptenyl, 1-n-octenyl, 2-n-octenyl, 3-n-octenyl, 1-methyl-c-hexenyl, 1,2-dimethyl-c-hexenyl, 1-ethyl-c-hexenyl, 1-c-heptenyl, 2-c-heptenyl, 3-c-heptenyl, 4-c-heptenyl, 1-c-octenyl, 2-c-octenyl, 3-c-octenyl, 4-c-octenyl and the like may be mentioned.

A $C_{2-9}$ heterocyclic group may be a heteromonocyclic or fused heterobicyclic group consisting of at least one atom optionally selected from nitrogen atoms, oxygen atoms and sulfur atoms and from 2 to 9 carbon atoms, and specifically, the following structures may be mentioned.

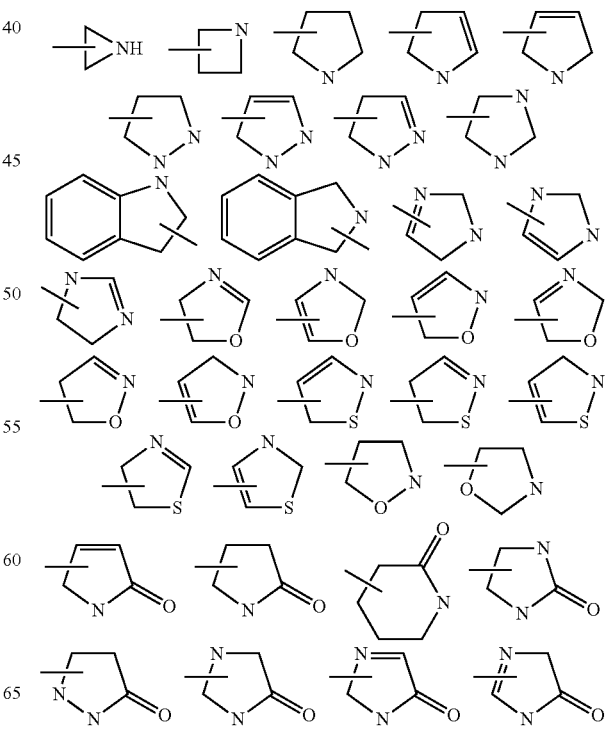

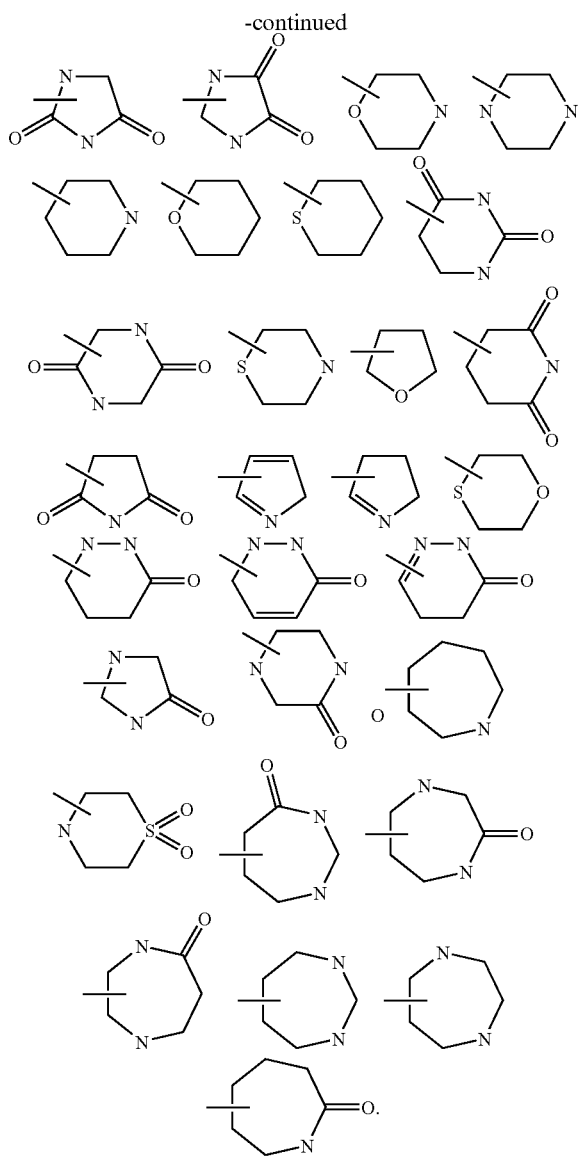

A C$_{2-14}$ aryl group may be a C$_{6-14}$ aryl group containing no hetero atoms as ring constituting atoms or a C$_{2-9}$ aromatic heterocyclic group, and a C$_{2-6}$ aromatic heterocyclic group may be a 5 to 7-membered C$_{2-6}$ heteromonocyclic group or 8 to 10-membered C$_{5-9}$ fused heterobicyclic group containing from 1 to 3 oxygen atoms, nitrogen atoms or sulfur atoms singly or in combination.

As a C$_{6-14}$ aryl group containing no hetero atoms, a phenyl group, a 1-indenyl group, a 2-indenyl group, a 3-indenyl group, a 4-indenyl group, a 5-indenyl group, a 6-indenyl group, a 7-indenyl group, an α-naphthyl group, a β-naphthyl group, a 1-tetrahydronaphthyl group, a 2-tetrahydronaphthyl group, a 5-tetrahydronaphthyl group, a 6-tetrahydronaphthyl group, an o-biphenylyl group, a m-biphenylyl group, a p-biphenylyl group, a 1-anthryl group, a 2-anthryl group, a 9-anthryl group, a 1-phenanthryl group, a 2-phenanthryl group, a 3-phenanthryl group, a 4-phenanthryl group, a 9-phenanthryl group or the like may be mentioned.

A 5 to 7-membered C$_{2-6}$ heteromonocyclic group may be a 2-thienyl group, a 3-thienyl group, a 2-furyl group, a 3-furyl group, a 2-pyranyl group, a 3-pyranyl group, a 4-pyranyl group, a 1-pyrrolyl group, a 2-pyrrolyl group, a 3-pyrrolyl group, a 1-imidazolyl group, a 2-imidazolyl group, a 4-imidazolyl group, a 1-pyrazolyl group, a 3-pyrazolyl group, a 4-pyrazolyl group, a 2-thiazolyl group, a 4-thiazolyl group, a 5-thiazolyl group, a 3-isothiazolyl group, a 4-isothiazolyl group, a 5-isothiazolyl group, a 2-oxazolyl group, a 4-oxazolyl group, a 5-oxazolyl group, a 3-isoxazolyl group, a 4-isoxazolyl group, a 5-isoxazolyl group, a 2-pyridyl group, a 3-pyridyl group, a 4-pyridyl group, a 2-pyrazinyl group, a 2-pyrimidinyl group, a 4-pyrimidinyl group, a 5-pyrimidinyl group, a 3-pyridazinyl group, a 4-pyridazinyl group, a 2-1,3,4-oxadiazolyl group, a 2-1,3,4-thiadiazolyl group, a 3-1,2,4-oxadiazolyl group, a 5-1,2,4-oxadiazolyl group, a 3-1,2,4-thiadiazolyl group, a 5-1,2,4-thiadiazolyl group, a 3-1,2,5-oxadiazolyl group, a 3-1,2,5-thiadiazolyl group or the like.

A 8 to 10-membered C$_{5-9}$ fused heterocyclic group may be a 2-benzofuranyl group, a 3-benzofuranyl group, a 4-benzofuranyl group, a 5-benzofuranyl group, a 6-benzofuranyl group, a 7-benzofuranyl group, a 1-isobenzofuranyl group, a 4-isobenzofuranyl group, a 5-isobenzofuranyl group, a 2-benzothienyl group, a 3-benzothienyl group, a 4-benzothienyl group, a 5-benzothienyl group, a 6-benzothienyl group, a 7-benzothienyl group, a 1-isobenzothienyl group, a 4-isobenzothienyl group, a 5-isobenzothienyl group, a 2-chromenyl group, a 3-chromenyl group, a 4-chromenyl group, a 5-chromenyl group, a 6-chromenyl group, a 7-chromenyl group, a 8-chromenyl group, a 1-indolizinyl group, a 2-indolizinyl group, a 3-indolizinyl group, a 5-indolizinyl group, a 6-indolizinyl group, a 7-indolizinyl group, a 8-indolizinyl group, a 1-isoindolyl group, a 2-isoindolyl group, a 4-isoindolyl group, a 5-isoindolyl group, a 1-indolyl group, a 2-indolyl group, a 3-indolyl group, a 4-indolyl group, a 5-indolyl group, a 6-indolyl group, a 7-indolyl group, 1-indazolyl group, a 2-indazolyl group, a 3-indazolyl group, a 4-indazolyl group, a 5-indazolyl group, a 6-indazolyl group, a 7-indazolyl group, a 1-purinyl group, a 2-purinyl group, a 3-purinyl group, a 6-purinyl group, a 7-purinyl group, a 8-purinyl group, a 2-quinolyl group, a 3-quinolyl group, a 4-quinolyl group, a 5-quinolyl group, a 6-quinolyl group, a 7-quinolyl group, a 8-quinolyl group, a 1-isoquinolyl group, a 3-isoquinolyl group, a 4-isoquinolyl group, a 5-isoquinolyl group, a 6-isoquinolyl group, a 7-isoquinolyl group, a 8-isoquinolyl group, a 1-phthalazinyl group, a 5-phthalazinyl group, a 6-phthalazinyl group, a 1-2,7-naphthyridinyl group, a 3-2,7-naphthyridinyl group, a 4-2,7-naphthyridinyl group, a 1-2,6-naphthyridinyl group, a 2-2,6-naphthyridinyl group, a 3-2,6-naphthyridinyl group, a 4-2,6-naphthyridinyl group, a 2-1,8-naphthyridinyl group, a 3-1,8-naphthyridinyl group, a 4-1,8-naphthyridinyl group, a 2-1,7-naphthyridinyl group, a 3-1,7-naphthyridinyl group, a 4-1,7-naphthyridinyl group, a 5-1,7-naphthyridinyl group, a 6-1,7-naphthyridinyl group, a 8-1,7-naphthyridinyl group, 2-1,6-naphthyridinyl group, a 3-1,6-naphthyridinyl group, a 4-1,6-naphthyridinyl group, a 5-1,6-naphthyridinyl group, a 7-1,6-naphthyridinyl group, a 8-1,6-naphthyridinyl group, a 2-1,5-naphthyridinyl group, a 3-1,5-naphthyridinyl group, a 4-1,5-naphthyridinyl group, a 6-1,5-naphthyridinyl group, a 7-1,5-naphthyridinyl group, a 8-1,5-naphthyridinyl group, a 2-quinoxalinyl group, a 5-quinoxalinyl group, a 6-quinoxalinyl group, a 2-quinazolinyl group, a 4-quinazolinyl group, a 5-quinazolinyl group, a 6-quinazolinyl group, a 7-quinazolinyl group, a 8-quinazolinyl group, a 3-cinnolinyl group, a 4-cinnolinyl group, a 5-cinnolinyl group, a 6-cinnolinyl group, a 7-cinnolinyl group, a 8-cinnolinyl group, a 2-pterdinyl group, a 4-pterdinyl group, a 6-pterdinyl group, a 7-pterdinyl group or the like.

A C$_{2-14}$ aryloxy group may be a C$_{6-14}$ aryloxy group containing no hetero atoms as ring constituting atoms or a C$_{2-9}$ aromatic heterocyclic oxy group, and a C$_{2-9}$ aromatic heterocyclic oxy group may be a 5 to 7-membered $C_{2-6}$ heteromonocyclic oxy group or 8 to 10-membered $C_{5-9}$ fused heterobicyclic oxy group containing from 1 to 3 oxygen atoms, nitrogen atoms or sulfur atoms singly or in combination.

As a $C_{6-14}$ aryloxy group containing no hetero atoms, a phenyloxy group, a 1-indenyloxy group, a 2-indenyloxy group, a 3-indenyloxy group, a 4-indenyloxy group, a 5-indenyloxy group, a 6-indenyloxy group, a 7-indenyloxy group, an α-naphthyloxy group, a β-naphthyloxy group, a 1-tetrahydronaphthyloxy group, a 2-tetrahydronaphthyloxy group, a 5-tetrahydronaphthyloxy group, a 6-tetrahydronaphthyloxy group, an o-biphenylyloxy group, a m-biphenylyloxy group, a p-biphenylyloxy group, a 1-anthryloxy group, a 2-anthryloxy group, a 9-anthryloxy group, a 1-phenanthryloxy group, a 2-phenanthryloxy group, a 3-phenanthryloxy group, a 4-phenanthryloxy group, a 9-phenanthryloxy group or the like may be mentioned.

A 5 to 7-membered $C_{2-6}$ heteromonocyclic oxy group may be a 2-thienyloxy group, a 3-thienyloxy group, a 2-furyloxy group, a 3-furyloxy group, a 2-pyranyloxy group, a 3-pyranyloxy group, a 4-pyranyloxy group, a 1-pyrrolyloxy group, a 2-pyrrolyloxy group, a 3-pyrrolyloxy group, a 1-imidazolyloxy group, a 2-imidazolyloxy group, a 4-imidazolyloxy group, a 1-pyrazolyloxy group, a 3-pyrazolyloxy group, a 4-pyrazolyloxy group, a 2-thiazolyloxy group, a 4-thiazolyloxy group, a 5-thiazolyloxy group, a 3-isothiazolyloxy group, a 4-isothiazolyloxy group, a 5-isothiazolyloxy group, a 2-oxazolyloxy group, a 4-oxazolyloxy group, a 5-oxazolyloxy group, a 3-isoxazolyloxy group, a 4-isoxazolyloxy group, a 5-isoxazolyloxy group, a 2-pyridyloxy group, a 3-pyridyloxy group, a 4-pyridyloxy group, a 2-pyrazinyloxy group, a 2-pyrimidinyloxy group, a 4-pyrimidinyloxy group, a 5-pyrimidinyloxy group, a 3-pyridazinyloxy group, a 4-pyridazinyloxy group, a 2-1,3,4-oxadiazolyloxy group, a 2-1,3,4-thiadiazolyloxy group, a 3-1,2,4-oxadiazolyloxy group, a 5-1,2,4-oxadiazolyloxy group, a 3-1,2,4-thiadiazolyloxy group, a 5-1,2,4-thiadiazolyloxy group, a 3-1,2,5-oxadiazolyloxy group, a 3-1,2,5-thiadiazolyloxy group or the like.

A 8 to 10-membered $C_{5-9}$ fused heterobicyclic oxy group may be a 2-benzofuranyloxy group, a 3-benzofuranyloxy group, a 4-benzofuranyloxy group, a 5-benzofuranyloxy group, a 6-benzofuranyloxy group, a 7-benzofuranyloxy group, a 1-isobenzofuranyloxy group, a 4-isobenzofuranyloxy group, a 5-isobenzofuranyloxy group, a 2-benzothienyloxy group, a 3-benzothienyloxy group, a 4-benzothienyloxy group, a 5-benzothienyloxy group, a 6-benzothienyloxy group, a 7-benzothienyloxy group, a 1-isobenzothienyloxy group, a 4-isobenzothienyloxy group, a 5-isobenzothienyloxy group, a 2-chromenyloxy group, a 3-chromenyloxy group, a 4-chromenyloxy group, a 5-chromenyloxy group, a 6-chromenyloxy group, a 7-chromenyloxy group, a 8-chromenyloxy group, a 1-indolizinyloxy group, a 2-indolizinyloxy group, a 3-indolizinyloxy group, a 5-indolizinyloxy group, a 6-indolizinyloxy group, a 7-indolizinyloxy group, a 8-indolizinyloxy group, a 1-isoindolyloxy group, a 2-isoindolyloxy group, a 4-isoindolyloxy group, a 5-isoindolyloxy group, a 1-indolyloxy group, a 2-indolyloxy group, a 3-indolyloxy group, a 4-indolyloxy group, a 5-indolyloxy group, a 6-indolyloxy group, a 7-indolyloxy group, 1-indazolyloxy group, a 2-indazolyloxy group, a 3-indazolyloxy group, a 4-indazolyloxy group, a 5-indazolyloxy group, a 6-indazolyloxy group, a 7-indazolyloxy group, a 1-purinyloxy group, a 2-purinyloxy group, a 3-purinyloxy group, a 6-purinyloxy group, a 7-purinyloxy group, a 8-purinyloxy group, a 2-quinolyloxy group, a 3-quinolyloxy group, a 4-quinolyloxy group, a 5-quinolyloxy group, a 6-quinolyloxy group, a 7-quinolyloxy group, a 8-quinolyloxy group, a 1-isoquinolyloxy group, a 3-isoquinolyloxy group, a 4-isoquinolyloxy group, a 5-isoquinolyloxy group, a 6-isoquinolyloxy group, a 7-isoquinolyloxy group, a 8-isoquinolyloxy group, a 1-phthalazinyloxy group, a 5-phthalazinyloxy group, a 6-phthalazinyloxy group, a 1-2,7-naphthyridinyloxy group, a 3-2,7-naphthyridinyloxy group, a 4-2,7-naphthyridinyloxy group, a 1-2,6-naphthyridinyloxy group, a 3-2,6-naphthyridinyloxy group, a 4-2,6-naphthyridinyloxy group, a 2-1,8-naphthyridinyloxy group, a 3-1,8-naphthyridinyloxy group, a 4-1,8-naphthyridinyloxy group, a 2-1,7-naphthyridinyloxy group, a 3-1,7-naphthyridinyloxy group, a 4-1,7-naphthyridinyloxy group, a 5-1,7-naphthyridinyloxy group, a 6-1,7-naphthyridinyloxy group, a 8-1,7-naphthyridinyloxy group, 2-1,6-naphthyridinyloxy group, a 3-1,6-naphthyridinyloxy group, a 4-1,6-naphthyridinyloxy group, a 5-1,6-naphthyridinyloxy group, a 7-1,6-naphthyridinyloxy group, a 8-1,6-naphthyridinyloxy group, a 2-1,5-naphthyridinyloxy group, a 3-1,5-naphthyridinyloxy group, a 4-1,5-naphthyridinyloxy group, a 6-1,5-naphthyridinyloxy group, a 7-1,5-naphthyridinyloxy group, a 8-1,5-naphthyridinyloxy group, a 2-quinoxalinyloxy group, a 5-quinoxalinyloxy group, a 6-quinoxalinyloxy group, a 2-quinazolinyloxy group, a 4-quinazolinyloxy group, a 5-quinazolinyloxy group, a 6-quinazolinyloxy group, a 7-quinazolinyloxy group, a 8-quinazolinyloxy group, a 3-cinnolinyloxy group, a 4-cinnolinyloxy group, a 5-cinnolinyloxy group, a 6-cinnolinyloxy group, a 7-cinnolinyloxy group, a 8-cinnolinyloxy group, a 2-pterdinyloxy group, a 4-pterdinyloxy group, a 6-pterdinyloxy group, a 7-pterdinyloxy group or the like.

A $C_{1-6}$ alkylcarbonyl group may linear, branched or a $C_{3-6}$ cycloalkylcarbonyl group, and be methylcarbonyl, ethylcarbonyl, n-propylcarbonyl, i-propylcarbonyl, c-propylcarbonyl, n-butylcarbonyl, i-butylcarbonyl, s-butylcarbonyl, t-butylcarbonyl, c-butylcarbonyl, 1-methyl-c-propylcarbonyl, 2-methyl-c-propylcarbonyl, n-pentylcarbonyl, 1-methyl-n-butylcarbonyl, 2-methyl-n-butylcarbonyl, 3-methyl-n-butylcarbonyl, 1,1-dimethyl-n-propylcarbonyl, 1,2-dimethyl-n-propylcarbonyl, 2,2-dimethyl-n-propylcarbonyl, 1-ethyl-n-propylcarbonyl, c-pentylcarbonyl, 1-methyl-c-butylcarbonyl, 2-methyl-c-butylcarbonyl, 3-methyl-c-butylcarbonyl, 1,2-dimethyl-c-propylcarbonyl, 2,3-dimethyl-c-propylcarbonyl, 1-ethyl-c-propylcarbonyl, 2-ethyl-c-propylcarbonyl, n-hexylcarbonyl, 1-methyl-n-pentylcarbonyl, 2-methyl-n-pentylcarbonyl, 3-methyl-n-pentylcarbonyl, 4-methyl-n-pentylcarbonyl, 1,1-dimethyl-n-butylcarbonyl, 1,2-dimethyl-n-butylcarbonyl, 1,3-dimethyl-n-butylcarbonyl, 2,2-dimethyl-n-butylcarbonyl, 2,3-dimethyl-n-butylcarbonyl, 3,3-dimethyl-n-butylcarbonyl, 1-ethyl-n-butylcarbonyl, 2-ethyl-n-butylcarbonyl, 1,1,2-trimethyl-n-propylcarbonyl, 1,2,2-trimethyl-n-propylcarbonyl, 1-ethyl-1-methyl-n-propylcarbonyl, 1-ethyl-2-methyl-n-propylcarbonyl, c-hexylcarbonyl, 1-methyl-c-pentylcarbonyl, 2-methyl-c-pentylcarbonyl, 3-methyl-c-pentylcarbonyl, 1-ethyl-c-butylcarbonyl, 2-ethyl-c-butylcarbonyl, 3-ethyl-c-butylcarbonyl, 1,2-dimethyl-c-butylcarbonyl, 1,3-dimethyl-c-butylcarbonyl, 2,2-dimethyl-c-butylcarbonyl, 2,3-dimethyl-c-butylcarbonyl, 2,4-dimethyl-c-butylcarbonyl, 3,3-dimethyl-c-butylcarbonyl, 1-n-propyl-c-propylcarbonyl, 2-n-propyl-c-propylcarbonyl, 1-i-propyl-c-propylcarbonyl, 2-i-propyl-c-propylcarbonyl, 1,2,2-trimethyl-c-propylcarbonyl, 1,2,3-trimethyl-c-propylcarbonyl, 2,2,3-trimethyl-c-propylcarbonyl, 1-ethyl-2-methyl-c-propylcarbonyl, 2-ethyl-1-methyl-c-propylcarbonyl, 2-ethyl-2-methyl-c-propylcarbonyl, 2-ethyl-3-methyl-c-propylcarbonyl or the like may be mentioned.

A $C_{1-10}$ alkylcarbonyl may be linear, branched or a $C_{3-10}$ cycloalkylcarbonyl group, and in addition to those mentioned above, 1-methyl-1-ethyl-n-pentylcarbonyl, 1-heptylcarbonyl, 2-heptylcarbonyl, 1-ethyl-1,2-dimethyl-n-propylcarbonyl, 1-ethyl-2,2-dimethyl-n-propylcarbonyl, 1-octylcarbonyl, 3-octylcarbonyl, 4-methyl-3-n-heptylcarbonyl, 6-methyl-2-n-heptylcarbonyl, 2-propyl-1-n-heptylcarbonyl, 2,4,4-trimethyl-1-n-pentylcarbonyl, 1-nonylcarbonyl, 2-nonylcarbonyl, 2,6-dimethyl-4-n-heptylcarbonyl, 3-ethyl-2,2-dimethyl-3-n-pentylcarbonyl, 3,5,5-trimethyl-1-n-hexylcarbonyl, 1-decylcarbonyl, 2-decylcarbonyl, 4-decylcarbonyl, 3,7-dimethyl-1-n-octylcarbonyl, 3,7-dimethyl-3-n-octylcarbonyl or the like may be mentioned.

A $C_{1-6}$ alkylaminosulfonyl group may be linear, branched or a $C_{3-6}$ cycloalkylaminosulfonyl group, and methylaminosulfonyl, ethylaminosulfonyl, n-propylaminosulfonyl, i-propylaminosulfonyl, c-propylaminosulfonyl, n-butylaminosulfonyl, i-butylaminosulfonyl, s-butylaminosulfonyl, t-butylaminosulfonyl, c-butylaminosulfonyl, 1-methyl-c-propylaminosulfonyl, 2-methyl-c-propylaminosulfonyl, n-pentylaminosulfonyl, 1-methyl-n-butylaminosulfonyl, 2-methyl-n-butylaminosulfonyl, 3-methyl-n-butylaminosulfonyl, 1,1-dimethyl-n-propylaminosulfonyl, 1,2-dimethyln-propylaminosulfonyl, 2,2-dimethyln-propylaminosulfonyl, 1-ethyl-n-propylaminosulfonyl, c-pentylaminosulfonyl, 1-methyl-c-butylaminosulfonyl, 2-methyl-c-butylaminosulfonyl, 3-methyl-c-butylaminosulfonyl, 1,2-dimethyl-c-propylaminosulfonyl, 2,3-dimethyl-c-propylaminosulfonyl, 1-ethyl-c-propylaminosulfonyl, 2-ethyl-c-propylaminosulfonyl, n-hexylaminosulfonyl, 1-methyl-n-pentylaminosulfonyl, 2-methyl-n-pentylaminosulfonyl, 3-methyl-n-pentylaminosulfonyl, 4-methyl-n-pentylaminosulfonyl, 1,1-dimethyl-n-butylaminosulfonyl, 1,2-dimethyl-n-butylaminosulfonyl, 1,3-dimethyl-n-butylaminosulfonyl, 2,2-dimethyl-n-butylaminosulfonyl, 2,3-dimethyl-n-butylaminosulfonyl, 3,3-dimethyl-n-butylaminosulfonyl, 1-ethyl-n-butylaminosulfonyl, 2-ethyl-n-butylaminosulfonyl, 1,1,2-trimethyl-n-propylaminosulfonyl, 1,2,2-trimethyl-n-propylaminosulfonyl, 1-ethyl-1-methyl-n-propylaminosulfonyl, 1-ethyl-2-methyl-n-propylaminosulfonyl, c-hexylaminosulfonyl, 1-methyl-c-pentylaminosulfonyl, 2-methyl-c-pentylaminosulfonyl, 3-methyl-c-pentylaminosulfonyl, 1-ethyl-c-butylaminosulfonyl, 2-ethyl-c-butylaminosulfonyl, 3-ethyl-c-butylaminosulfonyl, 1,2-dimethyl-c-butylaminosulfonyl, 1,3-dimethyl-c-butylaminosulfonyl, 2,2-dimethyl-c-butylaminosulfonyl, 2,3-dimethyl-c-butylaminosulfonyl, 2,4-dimethyl-c-butylaminosulfonyl, 3,3-dimethyl-c-butylaminosulfonyl, 1-n-propyl-c-propylaminosulfonyl, 2-n-propyl-c-propylaminosulfonyl, 1-i-propyl-c-propylaminosulfonyl, 2-i-propyl-c-propylaminosulfonyl, 1,2,2-trimethyl-c-propylaminosulfonyl, 1,2,3-trimethyl-c-propylaminosulfonyl, 2,2,3-trimethyl-c-propylaminosulfonyl, 1-ethyl-2-methyl-c-propylaminosulfonyl, 2-ethyl-1-methyl-c-propylaminosulfonyl, 2-ethyl-2-methyl-c-propylaminosulfonyl, 2-ethyl-3-methyl-c-propylaminosulfonyl or the like may be mentioned.

A $C_{1-10}$ alkylaminosulfonyl group may be linear, branched or a $C_{3-10}$ cycloalkylsulfonylamino group, and in addition to those mentioned above, 1-methyl-1-ethyl-n-pentylaminosulfonyl, 1-heptylaminosulfonyl, 2-heptylaminosulfonyl, 1-ethyl-1,2-dimethyl-n-propylaminosulfonyl, 1-ethyl-2,2-dimethyl-n-propylaminosulfonyl, 1-octylaminosulfonyl, 3-octylaminosulfonyl, 4-methyl-3-n-heptylaminosulfonyl, 6-methyl-2-n-heptylaminosulfonyl, 2-propyl-1-n-heptylaminosulfonyl, 2,4,4-trimethyl-1-n-pentylaminosulfonyl, 1-nonylaminosulfonyl, 2-nonylaminosulfonyl, 2,6-dimethyl-4-n-heptylaminosulfonyl, 3-ethyl-2,2-dimethyl-3-n-pentylaminosulfonyl, 3,5,5-trimethyl-1-n-hexylaminosulfonyl, 1-decylaminosulfonyl, 2-decylaminosulfonyl, 4-decylaminosulfonyl, 3,7-dimethyl-1-n-octylaminosulfonyl, 3,7-dimethyl-3-n-octylaminosulfonyl, c-heptylaminosulfonyl, c-octylaminosulfonyl, 1-methyl-c-hexylaminosulfonyl, 2-methyl-c-hexylaminosulfonyl, 3-methyl-c-hexylaminosulfonyl, 1,2-dimethyl-c-hexylaminosulfonyl, 1-ethyl-c-hexylaminosulfonyl, 1-methyl-c-pentylaminosulfonyl, 2-methyl-c-pentylaminosulfonyl, 3-methyl-c-pentylaminosulfonyl or the like may be mentioned.

A $C_{1-6}$ alkylsulfonyl group may be linear, branched or a $C_{3-6}$ cycloalkylsulfonyl group, and methylsulfonyl, ethylsulfonyl, n-propylsulfonyl, i-propylsulfonyl, c-propylsulfonyl, n-butylsulfonyl, i-butylsulfonyl, s-butylsulfonyl, t-butylsulfonyl, c-butylsulfonyl, 1-methyl-c-propylsulfonyl, 2-methyl-c-propylsulfonyl, n-pentylsulfonyl, 1-methyl-n-butylsulfonyl, 2-methyl-n-butylsulfonyl, 3-methyl-n-butylsulfonyl, 1,1-dimethyl-n-propylsulfonyl, 1,2-dimethyl-n-propylsulfonyl, 2,2-dimethyl-n-propylsulfonyl, 1-ethyl-n-propylsulfonyl, c-pentylsulfonyl, 1-methyl-c-butylsulfonyl, 2-methyl-c-butylsulfonyl, 3-methyl-c-butylsulfonyl, 1,2-dimethyl-c-propylsulfonyl, 2,3-dimethyl-c-propylsulfonyl, 1-ethyl-c-propylsulfonyl, 2-ethyl-c-propylsulfonyl, n-hexylsulfonyl, 1-methyl-n-pentylsulfonyl, 2-methyl-n-pentylsulfonyl, 3-methyl-n-pentylsulfonyl, 4-methyl-n-pentylsulfonyl, 1,1-dimethyl-n-butylsulfonyl, 1,2-dimethyl-n-butylsulfonyl, 1,3-dimethyl-n-butylsulfonyl, 2,2-dimethyl-n-butylsulfonyl, 2,3-dimethyl-n-butylsulfonyl, 3,3-dimethyl-n-butylsulfonyl, 1-ethyl-n-butylsulfonyl, 2-ethyl-n-butylsulfonyl, 1,1,2-trimethyl-n-propylsulfonyl, 1,2,2-trimethyl-n-propylsulfonyl, 1-ethyl-1-methyl-n-propylsulfonyl, 1-ethyl-2-methyl-n-propylsulfonyl, c-hexylsulfonyl, 1-methyl-c-pentylsulfonyl, 2-methyl-c-pentylsulfonyl, 3-methyl-c-pentylsulfonyl, 1-ethyl-c-butylsulfonyl, 2-ethyl-c-butylsulfonyl, 3-ethyl-c-butylsulfonyl, 1,2-dimethyl-c-butylsulfonyl, 1,3-dimethyl-c-butylsulfonyl, 2,2-dimethyl-c-butylsulfonyl, 2,3-dimethyl-c-butylsulfonyl, 2,4-dimethyl-c-butylsulfonyl, 3,3-dimethyl-c-butylsulfonyl, 1-n-propyl-c-propylsulfonyl, 2-n-propyl-c-propylsulfonyl, 1-i-propyl-c-propylsulfonyl, 2-i-propyl-c-propylsulfonyl, 1,2,2-trimethyl-c-propylsulfonyl, 1,2,3-trimethyl-c-propylsulfonyl, 2,2,3-trimethyl-c-propylsulfonyl, 1-ethyl-2-methyl-c-propylsulfonyl, 2-ethyl-1-methyl-c-propylsulfonyl, 2-ethyl-2-methyl-c-propylsulfonyl, 2-ethyl-3-methyl-c-propylsulfonyl or the like may be mentioned.

A $C_{1-10}$ alkylsulfonyl group may be linear, branched or a $C_{3-10}$ cycloalkylsulfonyl group, and in addition to those mentioned above, 1-methyl-1-ethyl-n-pentylsulfonyl, 1-heptylsulfonyl, 2-heptylsulfonyl, 1-ethyl-1,2-dimethyl-n-propylsulfonyl, 1-ethyl-2,2-dimethyl-n-propylsulfonyl, 1-octylsulfonyl, 3-octylsulfonyl, 4-methyl-3-n-heptylsulfonyl, 6-methyl-2-n-heptylsulfonyl, 2-propyl-1-n-n-heptylsulfonyl, 2,4,4-trimethyl-1-n-pentylsulfonyl, 1-nonylsulfonyl, 2-nonylsulfonyl, 2,6-dimethyl-4-n-heptylsulfonyl, 3-ethyl-2,2-dimethyl-3-n-pentylsulfonyl, 3,5,5-trimethyl-1-n-hexylsulfonyl, 1-decylsulfonyl, 2-decylsulfonyl, 4-decylsulfonyl, 3,7-dimethyl-1-n-octylsulfonyl, 3,7-dimethyl-3-n-octylsulfonyl, c-heptylsulfonyl, c-octylsulfonyl, 1-methyl-c-hexylsulfonyl, 2-methyl-c-hexylsulfonyl, 3-methyl-c-hexylsulfonyl, 1,2-dimethyl-c-hexylsulfonyl, 1-ethyl-c-hexylsulfonyl, 1-methyl-c-pentylsulfonyl, 2-methyl-c-pentylsulfonyl, 3-methyl-c-pentylsulfonyl or the like may be mentioned.

A $C_{1-10}$ alkoxy group may be linear, branched or a $C_{3-10}$ cycloalkoxy group, and methoxy, ethoxy, n-propoxy, i-propoxy, c-propoxy, n-butoxy, i-butoxy, s-butoxy, t-butoxy, c-butoxy, 1-methyl-c-propoxy, 2-methyl-c-propoxy, n-pentyloxy, 1-methyl-n-butoxy, 2-methyl-n-butoxy, 3-methyl-n-butoxy, 1,1-dimethyl-n-propoxy, 1,2-dimethyl-n-propoxy, 2,2-dimethyl-n-propoxy, 1-ethyl-n-propoxy, c-pentyloxy, 1-methyl-c-butoxy, 2-methyl-c-butoxy, 3-methyl-c-butoxy, 1,2-dimethyl-c-propoxy, 2,3-dimethyl-c-propoxy, 1-ethyl-c-propoxy, 2-ethyl-c-propoxy, n-hexyloxy, 1-methyl-n-pentyloxy, 2-methyl-n-pentyloxy, 3-methyl-n-pentyloxy, 4-methyl-n-pentyloxy, 1,1-dimethyl-n-butoxy, 1,2-dimethyl-n-butoxy, 1,3-dimethyl-n-butoxy, 2,2-dimethyl-n-butoxy, 2,3-dimethyl-n-butoxy, 3,3-dimethyl-n-butoxy, 1-ethyl-n-butoxy, 2-ethyl-n-butoxy, 1,1,2-trimethyl-n-propoxy, 1,2,2-trimethyl-n-propoxy, 1-ethyl-1-methyl-n-propoxy, 1-ethyl-2-methyl-n-propoxy, c-hexyloxy, 1-methyl-c-pentyloxy, 2-methyl-c-pentyloxy, 3-methyl-c-pentyloxy, 1-ethyl-c-butoxy, 2-ethyl-c-butoxy, 3-ethyl-c-butoxy, 1,2-dimethyl-c-butoxy, 1,3-dimethyl-c-butoxy, 2,2-dimethyl-c-butoxy, 2,3-dimethyl-c-butoxy, 2,4-dimethyl-c-butoxy, 3,3-dimethyl-c-butoxy, 1-n-propyl-c-propoxy, 2-n-propyl-c-propoxy, 1-i-propyl-c-propoxy, 2-i-propyl-c-propoxy, 1,2,2-trimethyl-c-propoxy, 1,2,3-trimethyl-c-propoxy, 2,2,3-trimethyl-c-propoxy, 1-ethyl-2-methyl-c-propoxy, 2-ethyl-1-methyl-c-propoxy, 2-ethyl-2-methyl-c-propoxy, 2-ethyl-3-methyl-c-propoxy, 1-methyl-1-ethyl-n-pentyloxy, 1-heptyloxy, 2-heptyloxy, 1-ethyl-1,2-dimethyl-n-propyloxy, 1-ethyl-2,2-dimethyl-n-propyloxy, 1-octyloxy, 3-octyloxy, 4-methyl-3-n-heptyloxy, 6-methyl-2-n-heptyloxy, 2-propyl-1-n-heptyloxy, 2,4,4-trimethyl-1-n-pentyloxy, 1-nonyloxy, 2-nonyloxy, 2,6-dimethyl-4-n-heptyloxy, 3-ethyl-2,2-dimethyl-3-n-pentyloxy, 3,5,5-trimethyl-1-n-hexyloxy, 1-decyloxy, 2-decyloxy, 4-decyloxy, 3,7-dimethyl-1-n-octyloxy, 3,7-dimethyl-3-n-octyloxy or the like may be mentioned.

A $C_{1-10}$ thioalkyl group may linear, branched or a $C_{3-10}$ cyclothioalkyl group, and be methylthio, ethylthio, n-propylthio, i-propylthio, c-propylthio, n-butylthio, i-butylthio, s-butylthio, t-butylthio, c-butylthio, 1-methyl-c-propylthio, 2-methyl-c-propylthio, n-pentylthio, 1-methyl-n-butylthio, 2-methyl-n-butylthio, 3-methyl-n-butylthio, 1,1-dimethyl-n-propylthio, 1,2-dimethyl-n-propylthio, 2,2-dimethyl-n-propylthio, 1-ethyl-n-propylthio, c-pentylthio, 1-methyl-c-butylthio, 2-methyl-c-butylthio, 3-methyl-c-butylthio, 1,2-dimethyl-c-propylthio, 2,3-dimethyl-c-propylthio, 1-ethyl-c-propylthio, 2-ethyl-c-propylthio, n-hexylthio, 1-methyl-n-pentylthio, 2-methyl-n-pentylthio, 3-methyl-n-pentylthio, 4-methyl-n-pentylthio, 1,1-dimethyl-n-butylthio, 1,2-dimethyl-n-butylthio, 1,3-dimethyl-n-butylthio, 2,2-dimethyl-n-butylthio, 2,3-dimethyl-n-butylthio, 3,3-dimethyl-n-butylthio, 1-ethyl-n-butylthio, 2-ethyl-n-butylthio, 1,1,2-trimethyl-n-propylthio, 1,2,2-trimethyl-n-propylthio, 1-ethyl-1-methyl-n-propylthio, 1-ethyl-2-methyl-n-propylthio, c-hexylthio, 1-methyl-c-pentylthio, 2-methyl-c-pentylthio, 3-methyl-c-pentylthio, 1-ethyl-c-butylthio, 2-ethyl-c-butylthio, 3-ethyl-c-butylthio, 1,2-dimethyl-c-butylthio, 1,3-dimethyl-c-butylthio, 2,2-dimethyl-c-butylthio, 2,3-dimethyl-c-butylthio, 2,4-dimethyl-c-butylthio, 3,3-dimethyl-c-butylthio, 1-n-propyl-c-propylthio, 2-n-propyl-c-propylthio, 1-i-propyl-c-propylthio, 2-i-propyl-c-propylthio, 1,2,2-trimethyl-c-propylthio, 1,2,3-trimethyl-c-propylthio, 2,2,3-trimethyl-c-propylthio, 1-ethyl-2-methyl-c-propylthio, 2-ethyl-1-methyl-c-propylthio, 2-ethyl-2-methyl-c-propylthio, 2-ethyl-3-methyl-c-propylthio, 1-methyl-1-ethyl-n-pentyl thio, 1-heptylthio, 2-heptylthio, 1-ethyl-1,2-dimethyl-n-propylthio, 1-ethyl-2,2-dimethyl-n-propylthio, 1-octylthio, 3-octylthio, 4-methyl-3-n-heptylthio, 6-methyl-2-n-heptylthio, 2-propyl-1-n-heptylthio, 2,4,4-trimethyl-1-n-pentylthio, 1-nonylthio, 2-nonylthio, 2,6-dimethyl-4-n-heptylthio, 3,5,5-trimethyl-1-n-hexylthio, 1-decylthio, 2-decylthio, 4-decylthio, 3,7-dimethyl-1-n-octylthio, 3,7-dimethyl-3-n-octylthio or the like may be mentioned.

A $C_{1-6}$ alkoxycarbonyl group may be linear, branched or a $C_{3-6}$ cycloalkoxycarbonyl group, and methoxycarbonyl, ethoxycarbonyl, n-propoxycarbonyl, i-propoxycarbonyl, c-propoxycarbonyl, n-butoxycarbonyl, i-butoxycarbonyl, s-butoxycarbonyl, t-butoxycarbonyl, c-butoxycarbonyl, 1-methyl-c-propoxycarbonyl, 2-methyl-c-propoxycarbonyl, n-pentyloxycarbonyl, 1-methyl-n-butoxycarbonyl, 2-methyl-n-butoxycarbonyl, 3-methyl-n-butoxycarbonyl, 1,1-dimethyl-n-propoxycarbonyl, 1,2-dimethyl-n-propoxycarbonyl, 2,2-dimethyl-n-propoxycarbonyl, 1-ethyl-n-propoxycarbonyl, c-pentyloxycarbonyl, 1-methyl-c-butoxycarbonyl, 2-methyl-c-butoxycarbonyl, 3-methyl-c-butoxycarbonyl, 1,2-dimethyl-c-propoxycarbonyl, 2,3-dimethyl-c-propoxycarbonyl, 1-ethyl-c-propoxycarbonyl, 2-ethyl-c-propoxycarbonyl, n-hexyloxycarbonyl, 1-methyl-n-pentyloxycarbonyl, 2-methyl-n-pentyloxycarbonyl, 3-methyl-n-pentyloxycarbonyl, 4-methyl-n-pentyloxycarbonyl, 1,1-dimethyl-n-butoxycarbonyl, 1,2-dimethyl-n-butoxycarbonyl, 1,3-dimethyl-n-butoxycarbonyl, 2,2-dimethyl-n-butoxycarbonyl, 2,3-dimethyl-n-butoxycarbonyl, 3,3-dimethyl-n-butoxycarbonyl, 1-ethyl-n-butoxycarbonyl, 2-ethyl-n-butoxycarbonyl, 1,1,2-trimethyl-n-propoxycarbonyl, 1,2,2-trimethyl-n-propoxycarbonyl, 1-ethyl-1-methyl-n-propoxycarbonyl, 1-ethyl-2-methyl-n-propoxycarbonyl, c-hexyloxycarbonyl, 1-methyl-c-pentyloxycarbonyl, 2-methyl-c-pentyloxycarbonyl, 3-methyl-c-pentyloxycarbonyl, 1-ethyl-c-butoxycarbonyl, 2-ethyl-c-butoxycarbonyl, 3-ethyl-c-butoxycarbonyl, 1,2-dimethyl-c-butoxycarbonyl, 1,3-dimethyl-c-butoxycarbonyl, 2,2-dimethyl-c-butoxycarbonyl, 2,3-dimethyl-c-butoxycarbonyl, 2,4-dimethyl-c-butoxycarbonyl, 3,3-dimethyl-c-butoxycarbonyl, 1-n-propyl-c-propoxycarbonyl, 2-n-propyl-c-propoxycarbonyl, 1-i-propyl-c-propoxycarbonyl, 2-i-propyl-c-propoxycarbonyl, 1,2,2-trimethyl-c-propoxycarbonyl, 1,2,3-trimethyl-c-propoxycarbonyl, 2,2,3-trimethyl-c-propoxycarbonyl, 1-ethyl-2-methyl-c-propoxycarbonyl, 2-ethyl-1-methyl-c-propoxycarbonyl, 2-ethyl-2-methyl-c-propoxycarbonyl, 2-ethyl-3-methyl-c-propoxycarbonyl or the like may be mentioned.

A $C_{1-10}$ alkoxycarbonyl group may be linear, branched or a $C_{3-10}$ cycloalkoxycarbonyl group, and in addition to those mentioned above, 1-methyl-1-ethyl-n-pentyloxycarbonyl, 1-heptyloxycarbonyl, 2-heptyloxycarbonyl, 1-ethyl-1,2-dimethyl-n-propyloxycarbonyl, 1-ethyl-2,2-dimethyl-n-propyloxycarbonyl, 1-octyloxycarbonyl, 3-octyloxycarbonyl, 4-methyl-3-n-heptyloxycarbonyl, 6-methyl-2-n-heptyloxycarbonyl, 2-propyl-1-n-heptyloxycarbonyl, 2,4,4-trimethyl-1-n-pentyloxycarbonyl, 1-nonyloxycarbonyl, 2-nonyloxycarbonyl, 2,6-dimethyl-4-n-heptyloxycarbonyl, 3-ethyl-2,2-dimethyl-3-n-pentyloxycarbonyl, 3,5,5-trimethyl-1-n-hexyloxycarbonyl, 1-decyloxycarbonyl, 2-decyloxycarbonyl, 4-decyloxycarbonyl, 3,7-dimethyl-1-n-octyloxycarbonyl, 3,7-dimethyl-3-n-octyloxycarbonyl or the like may be mentioned.

A $C_{1-10}$ alkylcarbonyloxy group may be linear, branched or a $C_{3-10}$ cycloalkylcarbonyloxy group, and methylcarbonyloxy, ethylcarbonyloxy, n-propylcarbonyloxy, i-propylcarbonyloxy, c-propylcarbonyloxy, n-butylcarbonyloxy, i-butylcarbonyloxy, s-butylcarbonyloxy, t-butylcarbonyloxy, c-butylcarbonyloxy, 1-methyl-c-propylcarbonyloxy, 2-methyl-c-propylcarbonyloxy, n-pentylcarbonyloxy, 1-methyl-n-butylcarbonyloxy, 2-methyl-n-butylcarbonyloxy, 3-methyl-n-butylcarbonyloxy, 1,1-dimethyl-n-propylcarbonyloxy, 1,2-dimethyl-n-propylcarbonyloxy, 2,2-dimethyl-n-propylcarbonyloxy, 1-ethyl-n-propylcarbonyloxy, c-pentylcarbonyloxy, 1-methyl-c-butylcarbonyloxy, 2-methyl-c-butylcarbonyloxy, 3-methyl-c-butylcarbonyloxy, 1,2-dimethyl-c-propylcarbonyloxy, 2,3- dimethyl-c-propylcarbonyloxy, 1-ethyl-c-propylcarbonyloxy, 2-ethyl-c-propylcarbonyloxy, n-hexylcarbonyloxy, 1-methyl-n-pentylcarbonyloxy, 2-methyl-n-pentylcarbonyloxy, 3-methyl-n-pentylcarbonyloxy, 4-methyl-n-pentylcarbonyloxy, 1,1-dimethyl-n-butylcarbonyloxy, 1,2-dimethyl-n-butylcarbonyloxy, 1,3-dimethyl-n-butylcarbonyloxy, 2,2-dimethyl-n-butylcarbonyloxy, 2,3-dimethyl-n-butylcarbonyloxy, 3,3-dimethyl-n-butylcarbonyloxy, 1-ethyl-n-butylcarbonyloxy, 2-ethyl-n-butylcarbonyloxy, 1,1,2-trimethyl-n-propylcarbonyloxy, 1,2,2-trimethyl-n-propylcarbonyloxy, 1-ethyl-1-methyl-n-propylcarbonyloxy, 1-ethyl-2-methyl-n-propylcarbonyloxy, c-hexylcarbonyloxy, 1-methyl-c-pentylcarbonyloxy, 2-methyl-c-pentylcarbonyloxy, 3-methyl-c-pentylcarbonyloxy, 1-ethyl-c-butylcarbonyloxy, 2-ethyl-c-butylcarbonyloxy, 3-ethyl-c-butylcarbonyloxy, 1,2-dimethyl-c-butylcarbonyloxy, 1,3-dimethyl-c-butylcarbonyloxy, 2,2-dimethyl-c-butylcarbonyloxy, 2,3-dimethyl-c-butylcarbonyloxy, 2,4-dimethyl-c-butylcarbonyloxy, 3,3-dimethyl-c-butylcarbonyloxy, 1-n-propyl-c-propylcarbonyloxy, 2-n-propyl-c-propyl carbonyl oxy, 1-i-propyl-c-propylcarbonyloxy, 2-i-propyl-c-propylcarbonyloxy, 1,2,2-trimethyl-c-propylcarbonyloxy, 1,2,3-trimethyl-c-propylcarbonyloxy, 2,2,3-trimethyl-c-propylcarbonyloxy, 1-ethyl-2-methyl-c-propylcarbonyloxy, 2-ethyl-1-methyl-c-propylcarbonyloxy, 2-ethyl-2-methyl-c-propylcarbonyloxy, 2-ethyl-3-methyl-c-propylcarbonyloxy, 1-methyl-1-ethyl-n-pentylcarbonyloxy, 1-heptylcarbonyloxy, 2-heptylcarbonyloxy, 1-ethyl-1,2-dimethyl-n-propylcarbonyloxy, 1-ethyl-2,2-dimethyl-n-propylcarbonyloxy, 1-octyl carbonyl oxy, 3-octylcarbonyloxy, 4-methyl-3-n-heptylcarbonyloxy, 6-methyl-2-n-heptylcarbonyloxy, 2-propyl-1-n-heptylcarbonyloxy, 2,4,4-trimethyl-1-n-pentylcarbonyloxy, 1-nonylcarbonyloxy, 2-nonylcarbohyloxy, 2,6-dimethyl-4-n-heptylcarbonyloxy, 3-ethyl-2,2-dimethyl-3-n-pentylcarbonyloxy, 3,5,5-trimethyl-1-n-hexylcarbonyloxy, 1-decylcarbonyloxy, 2-decylcarbonyloxy, 4-decylcarbonyloxy, 3,7-dimethyl-1-n-octylcarbonyloxy, 3,7-dimethyl-3-n-octylcarbonyloxy or the like may be mentioned.

A $C_{1-10}$ alkylcarbonylamino group may be linear, branched or a $C_{3-10}$ cycloalkylcarbonylamino group, and methylcarbonylamino, ethylcarbonylamino, n-propylcarbonylamino, i-propylcarbonylamino, c-propylcarbonylamino, n-butylcarbonylamino, i-butylcarbonylamino, s-butylcarbonylamino, t-butylcarbonylamino, c-butylcarbonylamino, 1-methyl-c-propylcarbonylamino, 2-methyl-c-propylcarbonylamino, n-pentylcarbonylamino, 1-methyl-n-butylcarbonylamino, 2-methyl-n-butylcarbonylamino, 3-methyl-n-butylcarbonylamino, 1,1-dimethyl-n-propylcarbonylamino, 1,2-dimethyl-n-propylcarbonylamino, 2,2-dimethyl-n-propylcarbonylamino, 1-ethyl-n-propylcarbonylamino, c-pentylcarbonylamino, 1-methyl-c-butylcarbonylamino, 2-methyl-c-butylcarbonylamino, 3-methyl-c-butylcarbonylamino, 1,2-dimethyl-c-propylcarbonylamino, 2,3-dimethyl-c-propylcarbonylamino, 1-ethyl-c-propylcarbonylamino, 2-ethyl-c-propylcarbonylamino, n-hexylcarbonylamino, 1-methyl-n-pentylcarbonylamino, 2-methyl-n-pentylcarbonylamino, 3-methyl-n-pentylcarbonylamino, 4-methyl-n-pentylcarbonylamino, 1,1-dimethyl-n-butylcarbonylamino, 1,2-dimethyl-n-butylcarbonylamino, 1,3-dimethyl-n-butylcarbonylamino, 2,2-dimethyl-n-butylcarbonylamino, 2,3-dimethyl-n-butylcarbonylamino, 3,3-dimethyl-n-butylcarbonylamino, 1-ethyl-n-butylcarbonylamino, 2-ethyl-n-butylcarbonylamino, 1,1,2-trimethyl-n-propylcarbonylamino, 1,2,2-trimethyl-n-propylcarbonylamino, 1-ethyl-1-methyl-n-propylcarbonylamino, 1-ethyl-2-methyl-n-propylcarbonylamino, c-hexylcarbonylamino, 1-methyl-c-pentylcarbonylamino, 2-methyl-c-pentylcarbonylamino, 3-methyl-c-pentylcarbonylamino, 1-ethyl-c-butylcarbonylamino, 2-ethyl-c-butylcarbonylamino, 3-ethyl-c-butylcarbonylamino, 1,2-dimethyl-c-butylcarbonylamino, 1,3-dimethyl-c-butylcarbonylamino, 2,2-dimethyl-c-butylcarbonylamino, 2,3-dimethyl-c-butylcarbonylamino, 2,4-dimethyl-c-butylcarbonylamino, 3,3-dimethyl-c-butylcarbonylamino, 1-n-propyl-c-propylcarbonylamino, 2-n-propyl-c-propylcarbonylamino, 1-i-propyl-c-propylcarbonylamino, 2-i-propyl-c-propylcarbonylamino, 1,2,2-trimethyl-c-propyl-carbonylamino, 1,2,3-trimethyl-c-propylcarbonylamino, 2,2,3-trimethyl-c-propylcarbonylamino, 1-ethyl-2-methyl-c-propylcarbonylamino, 2-ethyl-1-methyl-c-propylcarbonylamino, 2-ethyl-2-methyl-c-propylcarbonylamino, 2-ethyl-3-methyl-c-propylcarbonylamino, 1-methyl-1-ethyl-n-pentylcarbonylamino, 1-heptylcarbonylamino, 2-heptylcarbonylamino, 1-ethyl-1,2-dimethyl-n-propylcarbonylamino, 1-ethyl-2,2-dimethyl-n-propylcarbonylamino, 1-octylcarbonylamino, 3-octylcarbonylamino, 4-methyl-3-n-heptylcarbonylamino, 6-methyl-2-n-heptylcarbonylamino, 2-propyl-1-n-heptylcarbonylamino, 2,4,4-trimethyl-1-n-pentylcarbonylamino, 1-nonylcarbonylamino, 2-nonylcarbonylamino, 2,6-dimethyl-4-n-heptylcarbonylamino, 3-ethyl-2,2-dimethyl-3-n-pentylcarbonylamino, 3,5,5-trimethyl-1-n-hexylcarbonylamino, 1-decylcarbonylamino, 2-decylcarbonylamino, 4-decylcarbonylamino, 3,7-dimethyl-1-n-octylcarbonylamino, 3,7-dimethyl-3-n-octylcarbonylamino or the like may be mentioned.

A $C_{1-10}$ alkylaminocarbonyl group may be a $C_{1-10}$ monoalkylaminocarbonyl group or a $C_{1-10}$ dialkylaminocarbonyl group. A $C_{1-10}$ monoalkylaminocarbonyl group may be linear, branched or a $C_{3-10}$ cycloalkylaminocarbonyl group, and methylaminocarbonyl, ethylaminocarbonyl, n-propylaminocarbonyl, i-propylaminocarbonyl, c-propylaminocarbonyl, n-butylaminocarbonyl, i-butylaminocarbonyl, s-butylaminocarbonyl, t-butylaminocarbonyl, c-butylaminocarbonyl, 1-methyl-c-propylaminocarbonyl, 2-methyl-c-propylaminocarbonyl, n-pentylaminocarbonyl, 1-methyl-n-butylaminocarbonyl, 2-methyl-n-butylaminocarbonyl, 3-methyl-n-butylaminocarbonyl, 1,1-dimethyl-n-propylaminocarbonyl, 1,2-dimethyl-n-propylaminocarbonyl, 2,2-dimethyl-n-propylaminocarbonyl, 1-ethyl-n-propylaminocarbonyl, c-pentylaminocarbonyl, 1-methyl-c-butylaminocarbonyl, 2-methyl-c-butylaminocarbonyl, 3-methyl-c-butylaminocarbonyl, 1,2-dimethyl-c-propylaminocarbonyl, 2,3-dimethyl-c-propylaminocarbonyl, 1-ethyl-c-propylaminocarbonyl, 2-ethyl-c-propylaminocarbonyl, n-hexylaminocarbonyl, 1-methyl-n-pentylaminocarbonyl, 2-methyl-n-pentylaminocarbonyl, 3-methyl-n-pentylaminocarbonyl, 4-methyl-n-pentylaminocarbonyl, 1,1-dimethyl-n-butylaminocarbonyl, 1,2-dimethyl-n-butylaminocarbonyl, 1,3-dimethyl-n-butylaminocarbonyl, 2,2-dimethyl-n-butylaminocarbonyl, 2,3-dimethyl-n-butylaminocarbonyl, 3,3-dimethyl-n-butylaminocarbonyl, 1-ethyl-n-butylaminocarbonyl, 2-ethyl-n-butylaminocarbonyl, 1,1,2-trimethyl-n-propylaminocarbonyl, 1,2,2-trimethyl-n-propylaminocarbonyl, 1-ethyl-1-methyl-n-propylaminocarbonyl, 1-ethyl-2-methyl-n-propylaminocarbonyl, c-hexylaminocarbonyl, 1-methyl-c-pentylaminocarbonyl, 2-methyl-c-pentylaminocarbonyl, 3-methyl-c-pentylaminocarbonyl, 1-ethyl-c-butylaminocarbonyl, 2-ethyl-c-butylaminocarbonyl, 3-ethyl-c-butylaminocarbonyl, 1,2-dimethyl-c-butylaminocarbonyl, 1,3-dimethyl-c-butylaminocarbonyl, 2,2-dimethyl-c-butylaminocarbonyl, 2,3-dimethyl-c-butylaminocarbonyl, 2,4- dimethyl-c-butylaminocarbonyl, 3,3-dimethyl-c-butylaminocarbonyl, 1-n-propyl-c-propylaminocarbonyl, 2-n-propyl-c-propylaminocarbonyl, 1-i-propyl-c-propylaminocarbonyl, 2-i-propyl-c-propylaminocarbonyl, 1,2,2-trimethyl-c-propylaminocarbonyl, 1,2,3-trimethyl-c-propylaminocarbonyl, 2,2,3-trimethyl-c-propylaminocarbonyl, 1-ethyl-2-methyl-c-propylaminocarbonyl, 2-ethyl-1-methyl-c-propylaminocarbonyl, 2-ethyl-2-methyl-c-propylaminocarbonyl, 2-ethyl-3-methyl-c-propylaminocarbonyl, 1-methyl-1-ethyl-n-pentylaminocarbonyl, 1-heptylaminocarbonyl, 2-heptylaminocarbonyl, 1-ethyl-1,2-dimethyl-n-propylaminocarbonyl, 1-ethyl-2,2-dimethyl-n-propylaminocarbonyl, 1-octylaminocarbonyl, 3-octylaminocarbonyl, 4-methyl-3-n-heptylaminocarbonyl, 6-methyl-2-n-heptylaminocarbonyl, 2-propyl-1-n-heptylaminocarbonyl, 2,4,4-trimethyl-1-n-pentylaminocarbonyl, 1-nonylaminocarbonyl, 2-nonylaminocarbonyl, 2,6-dimethyl-4-n-heptylaminocarbonyl, 3-ethyl-2,2-dimethyl-3-n-pentylaminocarbonyl, 3,5,5-trimethyl-1-n-hexylaminocarbonyl, 1-decylaminocarbonyl, 2-decylaminocarbonyl, 4-decylaminocarbonyl, 3,7-dimethyl-1-n-octylaminocarbonyl, 3,7-dimethyl-3-n-octylaminocarbonyl or the like may be mentioned.

A $C_{1-10}$ dialkylaminocarbonyl group may be symmetric or asymmetric. A symmetric $C_{1-10}$ dialkylaminocarbonyl group may be linear, branched or a $C_{3-10}$ cycloalkylaminocarbonyl group, and dimethylaminocarbonyl, diethylaminocarbonyl, di-n-propylaminocarbonyl, di-i-propylaminocarbonyl, di-c-propylaminocarbonyl, di-n-butylaminocarbonyl, di-i-butylaminocarbonyl, di-s-butylaminocarbonyl, di-t-butylaminocarbonyl, di-c-butylaminocarbonyl, di-(1-methyl-c-propyl)aminocarbonyl, di-(2-methyl-c-propyl)aminocarbonyl, di-n-pentylaminocarbonyl, di-(1-methyl-n-butyl)aminocarbonyl, di-(2-methyl-n-butyl)aminocarbonyl, di-(3-methyl-n-butyl)aminocarbonyl, di-(1,1-dimethyl-n-propyl)aminocarbonyl, di-(1,2-dimethyl-n-propyl)aminocarbonyl, di-(2,2-dimethyl-n-propyl)aminocarbonyl, di-(1-ethyl-n-propyl)aminocarbonyl, di-c-pentylaminocarbonyl, di-(1-methyl-c-butyl)aminocarbonyl, di-(2-methyl-c-butyl)aminocarbonyl, di-(3-methyl-c-butyl)aminocarbonyl, di-(1,2-dimethyl-c-propyl)aminocarbonyl, di-(2,3-dimethyl-c-propyl)aminocarbonyl, di-(1-ethyl-c-propyl)aminocarbonyl, di-(2-ethyl-c-propyl)aminocarbonyl, di-n-hexylaminocarbonyl, di-(1-methyl-n-pentyl)aminocarbonyl, di-(2-methyl-n-pentyl)aminocarbonyl, di-(3-methyl-n-pentyl)aminocarbonyl, di-(4-methyl-n-pentyl)aminocarbonyl, di-(1,1-dimethyl-n-butyl)aminocarbonyl, di-(1,2-dimethyl-n-butyl)aminocarbonyl, di-(1,3-dimethyl-n-butyl)aminocarbonyl, di-(2,2-dimethyl-n-butyl)aminocarbonyl, di-(2,3-dimethyl-n-butyl)aminocarbonyl, di-(3,3-dimethyl-n-butyl)aminocarbonyl, di-(1-ethyl-n-butyl)aminocarbonyl, di-(2-ethyl-n-butyl)aminocarbonyl, di-(1,1,2-trimethyl-n-propyl)aminocarbonyl, di-(1,2,2-trimethyl-n-propyl)aminocarbonyl, di-(1-ethyl-1-methyl-n-propyl)aminocarbonyl, di-(1-ethyl-2-methyl-n-propyl)aminocarbonyl, di-c-hexylaminocarbonyl, di-(1-methyl-c-pentyl)aminocarbonyl, di-(2-methyl-c-pentyl)aminocarbonyl, di-(3-methyl-c-pentyl)aminocarbonyl, di-(1-ethyl-c-butyl)aminocarbonyl, di-(2-ethyl-c-butyl)aminocarbonyl, di-(3-ethyl-c-butyl)aminocarbonyl, di-(1,2-dimethyl-c-butyl)aminocarbonyl, di-(1,3-dimethyl-c-butyl)aminocarbonyl, di-(2,2-dimethyl-c-butyl)aminocarbonyl, di-(2,3-dimethyl-c-butyl)aminocarbonyl, di-(2,4-dimethyl-c-butyl)aminocarbonyl, di-(3,3-dimethyl-c-butyl)aminocarbonyl, di-(1-n-propyl-c-propyl)aminocarbonyl, di-(2-n-propyl-c-propyl)aminocarbonyl, di-(1-i-propyl-c-propyl)aminocarbonyl, di-(2-i-propyl-c-propyl)aminocarbonyl, di-(1,2,2-trimethyl-c-propyl)aminocarbonyl, di-(1,2,3-trimethyl-c-propyl)aminocarbonyl, di-(2,2,3-trimethyl-c-propyl)aminocarbonyl, di-(1-ethyl-2-methyl-c-propyl)aminocarbonyl, di-(2-ethyl-1-methyl-c-propyl)aminocarbonyl, di-(2-ethyl-2-methyl-c-propyl)aminocarbonyl, di-(2-ethyl-3-methyl-c-propyl)aminocarbonyl, di-(1-methyl-1-ethyl-n-pentyl)aminocarbonyl, di-(1-heptyl)aminocarbonyl, di-(2-heptyl)aminocarbonyl, di-(1-ethyl-1,2-dimethyl-n-propyl)aminocarbonyl, di-(1-ethyl-2,2-dimethyl-n-propyl)aminocarbonyl, di-(1-octyl)aminocarbonyl, di-(3-octyl)aminocarbonyl, di-(4-methyl-3-n-heptyl)aminocarbonyl, di-(6-methyl-2-n-heptyl)aminocarbonyl, di-(2-propyl-1-n-heptyl)aminocarbonyl, di-(2,4,4-trimethyl-1-n-pentyl)aminocarbonyl, di-(1-nonyl)aminocarbonyl, di-(2-nonyl)aminocarbonyl, di-(2,6-dimethyl-4-n-heptyl)aminocarbonyl, di-(3-ethyl-2,2-dimethyl-3-n-pentyl)aminocarbonyl, di-(3,5,5-trimethyl-1-n-hexyl)aminocarbonyl, di-(1-decyl)aminocarbonyl, di-(2-decyl)aminocarbonyl, di-(4-decyl)aminocarbonyl, di-(3,7-dimethyl-1-n-octyl)aminocarbonyl, di-(3,7-dimethyl-3-n-octyl)aminocarbonyl or the like may be mentioned.

An asymmetric $C_{1-10}$ dialkylaminocarbonyl group may be linear, branched or a $C_{3-10}$ cycloalkyl aminocarbonyl group, and (methyl, ethyl)aminocarbonyl, (methyl, n-propyl)aminocarbonyl, (methyl, i-propyl)aminocarbonyl, (methyl, c-propyl)aminocarbonyl, (methyl, n-butyl)aminocarbonyl, (methyl, i-butyl)aminocarbonyl, (methyl, s-butyl)aminocarbonyl, (methyl, t-butyl)aminocarbonyl, (methyl, n-pentyl)aminocarbonyl, (methyl, c-pentyl)aminocarbonyl, (methyl, n-hexyl)aminocarbonyl, (methyl, c-hexyl)aminocarbonyl, (ethyl, n-propyl)aminocarbonyl, (ethyl, i-propyl)aminocarbonyl, (ethyl, c-propyl)aminocarbonyl, (ethyl, n-butyl)aminocarbonyl, (ethyl, i-butyl)aminocarbonyl, (ethyl, s-butyl)aminocarbonyl, (ethyl, t-butyl)aminocarbonyl, (ethyl, n-pentyl)aminocarbonyl, (ethyl, c-pentyl)aminocarbonyl, (ethyl, n-hexyl)aminocarbonyl, (ethyl, c-hexyl)aminocarbonyl, (n-propyl, i-propyl)aminocarbonyl, (n-propyl, c-propyl)aminocarbonyl, (n-propyl, n-butyl)aminocarbonyl, (n-propyl, i-butyl)aminocarbonyl, (n-propyl, s-butyl)aminocarbonyl, (n-propyl, t-butyl)aminocarbonyl, (n-propyl, n-pentyl)aminocarbonyl, (n-propyl, c-pentyl)aminocarbonyl, (n-propyl, n-hexyl)aminocarbonyl, (n-propyl, c-hexyl)aminocarbonyl, (i-propyl, c-propyl)aminocarbonyl, (i-propyl, n-butyl)aminocarbonyl, (i-propyl, i-butyl)aminocarbonyl, (i-propyl, s-butyl)aminocarbonyl, (i-propyl, t-butyl)aminocarbonyl, (i-propyl, n-pentyl)aminocarbonyl, (i-propyl, c-pentyl)aminocarbonyl, (i-propyl, n-hexyl)aminocarbonyl, (i-propyl, c-hexyl)aminocarbonyl, (c-propyl, n-butyl)aminocarbonyl, (c-propyl, i-butyl)aminocarbonyl, (c-propyl, s-butyl)aminocarbonyl, (c-propyl, t-butyl)aminocarbonyl, (c-propyl, n-pentyl)aminocarbonyl, (c-propyl, c-pentyl)aminocarbonyl, (c-propyl, n-hexyl)aminocarbonyl, (c-propyl, c-hexyl)aminocarbonyl, (n-butyl, i-butyl)aminocarbonyl, (n-butyl, s-butyl)aminocarbonyl, (n-butyl, t-butyl)aminocarbonyl, (n-butyl, n-pentyl)aminocarbonyl, (n-butyl, c-pentyl)aminocarbonyl, (n-butyl, n-hexyl)aminocarbonyl, (n-butyl, c-hexyl)aminocarbonyl, (i-butyl, s-butyl)aminocarbonyl, (i-butyl, t-butyl)aminocarbonyl, (i-butyl, n-pentyl)aminocarbonyl, (i-butyl, c-pentyl)aminocarbonyl, (i-butyl, n-hexyl)aminocarbonyl, (i-butyl, c-hexyl)aminocarbonyl, (s-butyl, t-butyl)aminocarbonyl, (s-butyl, n-pentyl)aminocarbonyl, (s-butyl, c-pentyl)aminocarbonyl, (s-butyl, n-hexyl)aminocarbonyl, (s-butyl, c-hexyl)aminocarbonyl, (t-butyl, n-pentyl)aminocarbonyl, (t-butyl, c-pentyl)aminocarbonyl, (t-butyl, n-hexyl)aminocarbonyl, (t-butyl, c-hexyl)aminocarbonyl, (n-pentyl, c-pentyl)aminocarbonyl, (n-pentyl, n-hexyl)aminocarbonyl, (n-pentyl, c-hexyl)aminocarbonyl, (c-pentyl, n-hexyl)aminocarbonyl, (c-pentyl, c-hexyl)aminocarbonyl, (n-hexyl, c-hexyl)aminocarbonyl, (methyl, n-heptyl)aminocarbonyl, (methyl, n-octyl)aminocarbonyl, (methyl, n-nonyl)aminocarbonyl, (methyl, n-decyl)aminocarbonyl, (methyl, n-heptyl)aminocarbonyl, (ethyl, n-octyl)aminocarbonyl, (ethyl, n-nonyl)aminocarbonyl, (ethyl, n-decyl)aminocarbonyl or the like may be mentioned.

A $C_{1-10}$ monoalkylamino group may be linear, branched or a $C_{3-10}$ cycloalkylamino group, and methylamino, ethylamino, n-propylamino, i-propylamino, c-propylamino, n-butylamino, i-butylamino, s-butylamino, t-butylamino, c-butylamino, 1-methyl-c-propylamino, 2-methyl-c-propylamino, n-pentylamino, 1-methyl-n-butylamino, 2-methyl-n-butylamino, 3-methyl-n-butylamino, 1,1-dimethyl-n-propylamino, 1,2-dimethyl-n-propylamino, 2,2-dimethyl-n-propylamino, 1-ethyl-n-propylamino, c-pentylamino, 1-methyl-c-butylamino, 2-methyl-c-butylamino, 3-methyl-c-butylamino, 1,2-dimethyl-c-propylamino, 2,3-dimethyl-c-propylamino, 1-ethyl-c-propylamino, 2-ethyl-c-propylamino, n-hexylamino, 1-methyl-n-pentylamino, 2-methyl-n-pentylamino, 3-methyl-n-pentylamino, 4-methyl-n-pentylamino, 1,1-dimethyl-n-butylamino, 1,2-dimethyl-n-butylamino, 1,3-dimethyl-n-butylamino, 2,2-dimethyl-n-butylamino, 2,3-dimethyl-n-butylamino, 3,3-dimethyl-n-butylamino, 1-ethyl-n-butylamino, 2-ethyl-n-butylamino, 1,1,2-trimethyl-n-propylamino, 1,2,2-trimethyl-n-propylamino, 1-ethyl-1-methyl-n-propylamino, 1-ethyl-2-methyl-n-propylamino, c-hexylamino, 1-methyl-c-pentylamino, 2-methyl-c-pentylamino, 3-methyl-c-pentylamino, 1-ethyl-c-butylamino, 2-ethyl-c-butylamino, 3-ethyl-c-butylamino, 1,2-dimethyl-c-butylamino, 1,3-dimethyl-c-butylamino, 2,2-dimethyl-c-butylamino, 2,3-dimethyl-c-butylamino, 2,4-dimethyl-c-butylamino, 3,3-dimethyl-c-butylamino, 1-n-propyl-c-propylamino, 2-n-propyl-c-propylamino, 1-i-propyl-c-propylamino, 2-i-propyl-c-propylamino, 1,2,2-trimethyl-c-propylamino, 1,2,3-trimethyl-c-propylamino, 2,2,3-trimethyl-c-propylamino, 1-ethyl-2-methyl-c-propylamino, 2-ethyl-1-methyl-c-propylamino, 2-ethyl-2-methyl-c-propylamino, 2-ethyl-3-methyl-c-propylamino, 1-methyl-1-ethyl-n-pentylamino, 1-heptylamino, 2-heptylamino, 1-ethyl-1,2-dimethyl-n-propylamino, 1-ethyl-2,2-dimethyl-n-propylamino, 1-octylamino, 3-octylamino, 4-methyl-3-n-heptylamino, 6-methyl-2-n-heptylamino, 2-propyl-1-n-heptylamino, 2,4,4-trimethyl-1-n-pentylamino, 1-nonylamino, 2-nonylamino, 2,6-dimethyl-4-n-heptylamino, 3-ethyl-2,2-dimethyl-3-n-pentylamino, 3,5,5-trimethyl-1-n-hexylamino, 1-decylamino, 2-decylamino, 4-decylamino, 3,7-dimethyl-1-n-octylamino, 3,7-dimethyl-3-n-octylamino or the like may be mentioned.

A $C_{1-10}$ dialkylamino group may be symmetric or asymmetric. A symmetric $C_{1-10}$ dialkylamino group may be linear, branched or a $C_{3-10}$ cycloalkylamino group, and dimethylamino, diethylamino, di-n-propylamino, di-i-propylamino, di-c-propylamino, di-n-butylamino, di-i-butylamino, di-s-butylamino, di-t-butylamino, di-c-butylamino, di-(1-methyl-c-propyl)amino, di-(2-methyl-c-propyl)amino, di-n-pentylamino, di-(1-methyl-n-butyl)amino, di-(2-methyl-n-butyl)amino, di-(3-methyl-n-butyl)amino, di-(1,1-dimethyl-n-propyl)amino, di-(1,2-dimethyl-n-propyl)amino, di-(2,2-dimethyl-n-propyl)amino, di-(1-ethyl-n-propyl)amino, di-c-pentylamino, di-ti-methyl-c-butyl)amino, di-(2-methyl-c-butyl)amino, di-(3-methyl-c-butyl)amino, di-(1,2-dimethyl-c-propyl)amino, di-(2,3-dimethyl-c-propyl)amino, di-(1-ethyl-c-propyl)amino, di-(2-ethyl-c-propyl)amino, di-n-hexylamino, di-(1-methyl-n-pentyl)amino, di-(2-methyl-n-pentyl)amino, di-(3-methyl-n-pentyl)amino, di-(4-methyl-n-pentyl)amino, di-(1,1-dimethyl-n-butyl)amino, di-(1,2-dimethyl-n-butyl)amino, di-(1,3-dimethyl-n-butyl)amino, di-(2,2-dimethyl-n-butyl)amino, di-(2,3-dimethyl-n-butyl)amino, di-(3,3-dimethyl-n-butyl)amino, di-(1-ethyl-n-butyl)amino, di-(2-ethyl-n-butyl)amino, di-(1,1,2-trimethyl-n-propyl)amino, di-(1,2,2-trimethyl-n-propyl)amino, di-(1-ethyl-1-methyl-n-propyl)amino, di-(1-ethyl-2-methyl-n-propyl)amino, di-c-hexylamino, di-(1-methyl-c-pentyl)amino, di-(2-methyl-c-pentyl)amino, di-(3-methyl-c-pentyl)amino, di-(1-ethyl-c-butyl)amino, di-(2-ethyl-c-butyl)amino, di-(3-ethyl-c-butyl)amino, di-(1,2-dimethyl-c-butyl)amino, di-(1,3-dimethyl-c-butyl)amino, di-(2,2-dimethyl-c-butyl)amino, di-(2,3-dimethyl-c-butyl)amino, di-(2,4-dimethyl-c-butyl)amino, di-(3,3-dimethyl-c-butyl)amino, di-(1-n-propyl-c-propyl)amino, di-(2-n-propyl-c-propyl)amino, di-(1-i-propyl-c-propyl)amino, di-(2-i-propyl-c-propyl)amino, di-(1,2,2-trimethyl-c-propyl)amino, di-(1,2,3-trimethyl-c-propyl)amino, di-(2,2,3-trimethyl-c-propyl)amino, di-(1-ethyl-2-methyl-c-propyl)amino, di-(2-ethyl-1-methyl-c-propyl)amino, di-(2-ethyl-2-methyl-c-propyl)amino, di-(2-ethyl-3-methyl-c-propyl)amino, di-(1-methyl-1-ethyl-n-pentyl)amino, di-(1-heptyl)amino, di-(2-heptyl)amino, di-(1-ethyl-1,2-dimethyl-n-propyl)amino, di-(1-ethyl-2,2-dimethyl-n-propyl)amino, di-(1-octyl)amino, di-(3-octyl)amino, di-(4-methyl-3-n-heptyl)amino, di-(6-methyl-2-n-heptyl)amino, di-(2-propyl-1-n-heptyl)amino, di-(2,4,4-trimethyl-1-n-pentyl)amino, di-(1-nonyl)amino, di-(2-nonyl)amino, di-(2,6-dimethyl-4-n-heptyl)amino, di-(3-ethyl-2,2-dimethyl-3-n-pentyl)amino, di-(3,5,5-trimethyl-1-n-hexyl)amino, di-(1-decyl)amino, di-(2-decyl)amino, di-(4-decyl)amino, di-(3,7-dimethyl-1-n-octyl)amino, di-(3,7-dimethyl-3-n-octyl)amino or the like may be mentioned.

An asymmetric $C_{1-10}$ dialkylamino group may be linear, branched or a $C_{3-10}$ cycloalkylamino group, and (methyl, ethyl)amino, (methyl, n-propyl)amino, (methyl, i-propyl)amino, (methyl, c-propyl)amino, (methyl, n-butyl)amino, (methyl, i-butyl)amino, (methyl, s-butyl)amino, (methyl, t-butyl)amino, (methyl, n-pentyl)amino, (methyl, c-pentyl)amino, (methyl, n-hexyl)amino, (methyl, c-hexyl)amino, (ethyl, n-propyl)amino, (ethyl, i-propyl)amino, (ethyl, c-propyl)amino, (ethyl, n-butyl)amino, (ethyl, i-butyl)amino, (ethyl, s-butyl)amino, (ethyl, t-butyl)amino, (ethyl, n-pentyl)amino, (ethyl, c-pentyl)amino, (ethyl, n-hexyl)amino, (ethyl, c-hexyl)amino, (n-propyl, i-propyl)amino, (n-propyl, c-propyl)amino, (n-propyl, n-butyl)amino, (n-propyl, i-butyl)amino, (n-propyl, s-butyl)amino, (n-propyl, t-butyl)amino, (n-propyl, n-pentyl)amino, (n-propyl, c-pentyl)amino, (n-propyl, n-hexyl)amino, (n-propyl, c-hexyl)amino, (i-propyl, c-propyl)amino, (i-propyl, n-butyl)amino, (i-propyl, i-butyl)amino, (i-propyl, s-butyl)amino, (i-propyl, t-butyl)amino, (i-propyl, n-pentyl)amino, (i-propyl, c-pentyl)amino, (i-propyl, n-hexyl)amino, (i-propyl, c-hexyl)amino, (c-propyl, n-butyl)amino, (c-propyl, i-butyl)amino, (c-propyl, s-butyl)amino, (c-propyl, t-butyl)amino, (c-propyl, n-pentyl)amino, (c-propyl, c-pentyl)amino, (c-propyl, n-hexyl)amino, (c-propyl, c-hexyl)amino, (n-butyl, i-butyl)amino, (n-butyl, s-butyl)amino, (n-butyl, t-butyl)amino, (n-butyl, n-pentyl)amino, (n-butyl, c-pentyl)amino, (n-butyl, n-hexyl)amino, (n-butyl, c-hexyl)amino, (i-butyl, s-butyl)amino, (i-butyl, t-butyl)amino, (i-butyl, n-pentyl)amino, (i-butyl, c-pentyl)amino, (i-butyl, n-hexyl)amino, (i-butyl, c-hexyl)amino, (s-butyl, t-butyl)amino, (s-butyl, n-pentyl)amino, (s-butyl, c-pentyl)amino, (s-butyl, n-hexyl)amino, (s-butyl, c-hexyl)amino, (t-butyl, n-pentyl)amino, (t-butyl, c-pentyl)amino, (t-butyl, n-hexyl)amino, (t-butyl, c-hexyl)amino, (n-pentyl, c-pentyl)amino, (n-pentyl, n-hexyl)amino, (n-pentyl, c-hexyl)amino, (c-pentyl, n-hexyl)amino, (c-pentyl, c-hexyl)

amino, (n-hexyl, c-hexyl)amino, (methyl, n-heptyl)amino, (methyl, n-octyl)amino, (methyl, n-nonyl)amino, (methyl, n-decyl)amino, (methyl, n-heptyl)amino, (ethyl, n-octyl) amino, (ethyl, n-nonyl)amino, (ethyl, n-decyl)amino or the like may be mentioned.

The protecting group in a protected hydroxyl group may be a $C_{1-4}$ alkoxymethyl group (such as MOM: methoxymethyl, MEM: 2-methoxyethoxymethyl, ethoxymethyl, n-propoxymethyl, i-propoxymethyl, n-butoxymethyl, iBM: isobutyloxymethyl, BUM: t-butoxymethyl, POM: pivaloyloxymethyl, SEM: trimethylsilylethoxymethyl and the like, preferably a $C_{1-2}$ alkoxymethyl or the like), an aryloxymethyl (such as BOM: benzyloxymethyl, PMBM: p-methoxybenzyloxymethyl, p-AOM: p-anisyloxymethyl and the like), a $C_{1-4}$ alkylaminomethyl group (such as dimethylaminomethyl), a substituted acetamidomethyl group (such as Acm: acetamidomethyl, Tacm: trimethylacetamidomethyl and the like), a substituted thiomethyl group (such as MTM: methylthiomethyl, PTM: phenylthiomethyl, Btm: benzylthiomethyl and the like), a carboxyl group, a $C_{1-7}$ acyl group (such as formyl, acetyl, fluoroacetyl, difluoroacetyl, trifluoroacetyl, chloroacetyl, dichloroacetyl, trichloroacetyl, propionyl, Pv: pivaloyl, tigloyl and the like), an arylcarbonyl group (such as benzoyl, benzoylformyl, benzoylpropionyl, phenylpropionyl and the like), a $C_{1-4}$ alkoxycarbonyl group (such as methoxycarbonyl, ethoxycarbonyl, n-propoxycarbonyl, i-propoxycarbonyl, n-butoxycarbonyl, i-butoxycarbonyl, BOC: t-butoxycarbonyl, AOC: t-amyloxycarbonyl, VOC: vinyloxycarbonyl, AOC: allyloxycarbonyl, Teoc: 2-(trimethylsilyl)ethoxycarbonyl, Troc: 2,2,2-trichloroethoxycarbonyl and the like, preferably BOC and the like), an aryloxycarbonyl group (such as Z: benzyloxycarbonyl, p-nitrobenzyloxycarbonyl, MOZ: p-methoxybenzyloxycarbonyl and the like), a $C_{1-4}$ alkylaminocarbonyl group (such as methylcarbamoyl, Ec: ethylcarbamoyl, n-propylcarbamoyl, and the like), an arylaminocarbonyl group (such as phenyl carbamoyl and the like), a trialkylsilyl group (such as TMS: trimethylsilyl, TES: triethylsilyl, TIPS: triisopropylsilyl, DEIPS: diethylisopropylsilyl, DMIPS: dimethylisopropylsilyl, DTBMS: di-t-butylmethylsilyl, IPDMS: isopropyldimethylsilyl, TBDMS: t-butyldimethylsilyl, TDS: thexyldimethylsilyl and the like, preferably t-butyldimethylsilyl and the like), a trialkylarylsilyl group (such as DPMS: diphenylmethylsilyl, TBDPS: t-butyldiphenylsilyl, TBMPS: t-butyldimethoxyphenylsilyl, TPS: triphenylsilyl and the like), an alkylsulfonyl group, (such as Ms: methanesulfonyl, ethanesulfonyl and the like) or an arylsulfonyl group (such as benzenesulfonyl, Ts: p-toluenesulfonyl, p-chlorobenzenesulfonyl, MBS: p-methoxybenzenesulfonyl, m-nitrobenzenesulfonyl, iMds: 2,6-dimethoxy-4-methylbenzenesulfonyl, Mds: 2,6-dimethyl-4-methoxybenzenesulfonyl, Mtb: 2,4,6-trimethoxybenzenesulfonyl, Mte: 2,3,5,6-tetramethyl-4-methoxybenzenesulfonyl, Mtr: 2,3,6-trimethyl-4-methoxybenzenesulfonyl, Mts: 2,4,6-trimethylbenzenesulfonyl, Pme: pentamethylbenzenesulfonyl and the like).

Specific preferred examples of the substituent $R^1$ are a phenyl group, thienyl groups (a 2-thienyl group and a 3-thienyl group), furyl groups (a 2-furyl group and a 3-furyl group), pyridazinyl groups (a 3-pyridazinyl group and a 4-pyridazinyl group), pyridyl groups (a 2-pyridyl group, a 3-pyridyl group and a 4-pyridyl group), quinolyl groups (a 2-quinolyl group, a 3-quinolyl group, a 4-quinolyl group, a 5-quinolyl group, a 6-quinolyl group, a 7-quinolyl group and a 8-quinolyl group) and isoquinolyl groups (a 1-isoquinolyl group, a 3-isoquinolyl group, a 4-isoquinolyl group, a 5-isoquinolyl group, a 6-isoquinolyl group, a 7-isoquinolyl group and a 8-isoquinolyl group) optionally substituted with one or more of the following substituents.

Substituents: a $C_{1-10}$ alkyl group, a halogen atom, a $C_{1-10}$ alkyl group substituted with one or more halogen atoms, a $C_{1-10}$ alkoxy group substituted with one or more halogen atoms, a nitro group, an amino group, an amino group substituted with one or two $C_{1-10}$ alkyl groups, an amino group substituted with a $C_{1-10}$ alkylcarbonyl group, a thiol group substituted with a $C_{1-10}$ alkyl group, a thiol group substituted with a $C_{1-10}$ alkylcarbonyl group, a hydroxyl group, a alkoxy group, a $C_{1-10}$ alkylcarbonyloxy group, a $C_{1-10}$ alkoxycarbonyl group and a $C_{1-10}$ alkylcarbonyl group.

Particularly preferred examples of the substituent $R^1$ are a phenyl group, thienyl groups (a 2-thienyl group and a 3-thienyl group), furyl groups (a 2-furyl group and a 3-furyl group), pyridazinyl groups (a 3-pyridazinyl group and a 4-pyridazinyl group), pyridyl groups (a 2-pyridyl group, a 3-pyridyl group and a 4-pyridyl group), quinolyl groups (a 2-quinolyl group, a 3-quinolyl group, a 4-guinolyl group, a 5-quinolyl group, a 6-quinolyl group, a 7-quinolyl group and a 8-quinolyl group) and isoquinolyl groups (a 1-isoquinolyl group, a 3-isoquinolyl group, a 4-isoquinolyl group, a 5-isoquinolyl group, a 6-isoquinolyl group, a 7-isoquinolyl group and a 8-isoquinolyl group) optionally substituted with one or more of the following substituents.

Substituents: a methyl group, a t-butyl group, a trifluoromethyl group, a trifluoromethoxy group, a chlorine atom, a bromine atom, a fluorine atom, a methoxy group, a methylamino group, a dimethylamino group, a t-butyloxy group and a t-butylamino group.

Still further preferred specific examples of the substituent are a 3-methyl-phenyl group, a 4-methyl-phenyl group, a 3,4-dimethyl-phenyl group, a 3-t-butyl-phenyl group, a 4-t-butyl-phenyl group, a 3-trifluoromethyl-phenyl group, a 4-trifluoromethoxy-phenyl group, a 4-trifluoromethyl-phenyl group, a 3,4-ditrifluoromethyl-phenyl group, a 3-chloro-phenyl group, a 4-chloro-phenyl group, a 4-bromo-phenyl group, a 3-fluoro-phenyl group, a 4-fluoro-phenyl group, a 3,4-dichloro-phenyl group, a 4-methoxy-phenyl group, a 4-methylamino-phenyl group, a 3-methyl-thienyl group, a 4-methyl-thienyl group, a 3,4-dimethyl-thienyl group, a 3-t-butyl-thienyl group, a 4-t-butyl-thienyl group, a 3-trifluoromethyl-thienyl group, a 4-trifluoromethyl-thienyl group, a 3,4-ditrifluoromethyl-thienyl group, a 3-chloro-thienyl group, a 4-chloro-thienyl group, a 3-fluoro-thienyl group, a 4-fluoro-thienyl group, a 3,4-dichloro-thienyl group, a 4-methoxy-thienyl group, a 4-methylamino-thienyl group, a 3-methyl-furyl group, a 4-methyl-furyl group, a 3,4-dimethyl-furyl group, a 3-t-butyl-furyl group, a 4-t-butyl-furyl group, a 3-trifluoromethyl-furyl group, a 4-trifluoromethyl-furyl group, a 3,4-ditrifluoromethyl-furyl group, a 3-chloro-furyl group, a 4-chloro-furyl group, a 3-fluoro-furyl group, a 4-fluoro-furyl group, a 3,4-dichloro-furyl group, a 4-methoxy-furyl group, a 4-methyl-furyl group, a 5-chloro-pyridazinyl group, a 5-methyl-pyridazinyl group, a 5-methoxy-pyridazinyl group, a 4-chloro-pyridazinyl group, a 4-methylpyridazinyl group, a 4-methoxy-pyridazinyl group, a 4-t-butoxy-pyridazinyl group and the like.

Specific preferable examples of $L^1$ are a bond, $CH_2$, an oxygen atom, a sulfur atom, NH, N-Me, N—CHO, CHMe, $CMe_2$, N—$CH_2$Ph and the like, and particularly preferable examples are a bond, $CH_2$, an oxygen atom, a sulfur atom, NH, NMe and the like.

Specific preferable examples of the substituent $R^2$ are a hydrogen atom, a methyl group, an ethyl group, a n-propyl group, an i-propyl group, a t-butyl group, and a phenyl group (the methyl group, the ethyl group, the n-propyl group, the i-propyl group, the t-butyl group and the phenyl group may be optionally substituted with an amino group, a monomethylamino group, a dimethylamino group, a monoethylamino group, a diethylamino group, a methoxy group, an ethoxy group, a methoxycarbonyl group, an ethoxycarbonyl group, a methylcarbonyloxy group, an ethylcarbonyloxy group, a methylcarbonylamino group or an ethylcarbonylamino group and the like), and particularly preferable examples are a hydrogen atom, a methyl group, an ethyl group, a n-propyl group, an i-propyl group, a t-butyl group, a phenyl group and the like.

Specific preferable examples of $L^2$ are a bond, $CH_2$, an oxygen atom, a sulfur atom, NH, N-Me, N—CHO, CHMe, $CMe_2$, N—$CH_2$Ph and the like, and particularly preferable examples are a bond, $CH_2$, an oxygen atom, a sulfur atom, NH, NMe and the like.

Specific preferable examples of $L^3$ are a bond, $CH_2$, an oxygen atom, a sulfur atom, NH, NH—OH, N-Me, N—CHO, CHMe, $CMe_2$, N—$CH_2$PH and the like, and particularly preferred examples are a bond, $CH_2$, an oxygen atom, a sulfur atom, NH, NMe and the like.

Specific preferable examples of X are OH, SH, $NH_2$, OMe, SMe, NHMe, NHEt, NH—CHO, NH—$CH_2$Ph, $OCH_2$Ph, $SCH_2$Ph, OC(=O)$CH_3$, SC(=O)$CH_3$, NHC(=O)$CH_3$ and the like, and particularly preferable examples are OH, SH, $NH_2$ and the like.

Specific preferable examples of Y are an oxygen atom, a sulfur atom, NH, N—OH, N—CHO, N-Me, N—$CH_2$Ph, N-OMe, N—$OCH_2$Ph an the like, and particularly preferred examples are an oxygen atom, a sulfur atom, NH, N—OH and the like.

Specific preferable examples of $L^4$ are a bond, $CH_2$, an oxygen atom, a sulfur atom, NH, N-Me, N—CHO, CHMe, $CMe_2$, N—$CH_2$Ph and the like, and particularly preferred examples are a bond, $CH_2$, an oxygen atom, a sulfur atom, NH, NMe and the like.

Specific preferable examples of the substituent $R^3$ are a methyl group, an ethyl group, a n-propyl group, an i-propyl group, a n-butyl group, a s-butyl group, a t-butyl group, a c-propyl group, a c-butyl group, a c-pentyl group, a c-hexyl group, an ethynyl group, a 1-propynyl group, a 2-propynyl group, a 1-butynyl group, a 2-butynyl group, a 3-butynyl group, a 1-pentynyl group, a 2-pentynyl group, a 4-pentynyl group, a 1-methyl-2-butynyl group, a 1-methyl-3-butynyl group, a 2-methyl-3-butynyl group, a 3-methyl-1-butynyl group and the following heterocyclic groups optionally substituted with one or more of the following substituents.

Heterocyclic Groups

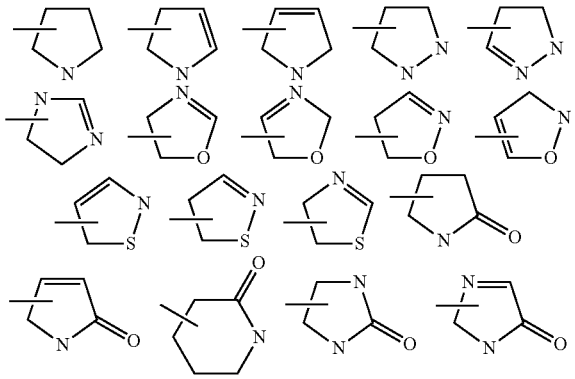

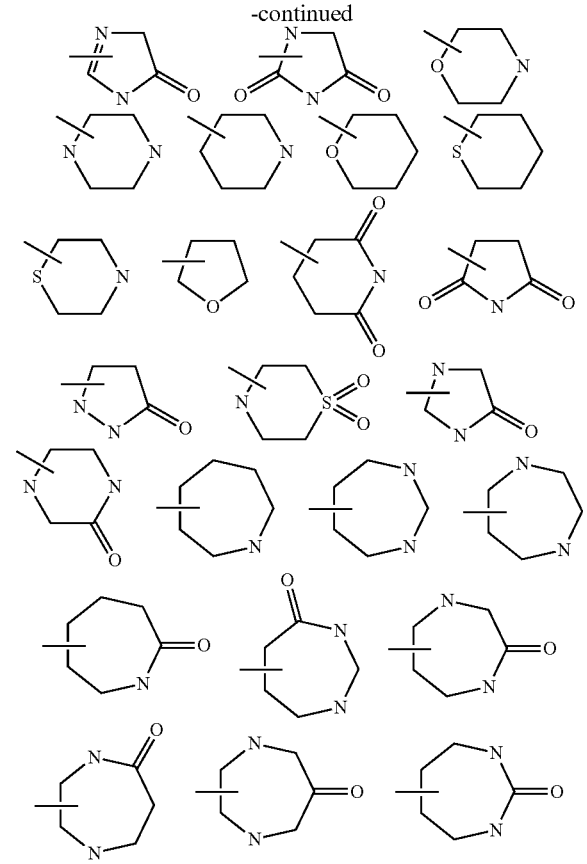

Substituents: a hydrogen atom, a hydroxyl group, an amino group, a halogen atom, a nitro group, a thiol group, a carboxyl group, a phosphonic acid group, a sulfonic acid group, a carbamoyl group, a hydroxylcarbamoyl group, a cyanocarbamoyl group, a sulfamoyl group, a hydroxysulfamoyl group, a cyanosulfamoyl group, a tetrazole group, a phenyl group, a thienyl group, a pyridyl group, a furyl group, —$CH_2CO_2H$, —$OCH_2CO_2H$, —$NHCH_2CO_2H$, —$CH_2CH_2CO_2H$, —$CH_2OH$, —$OCH_2OH$, —$NHCH_2OH$, —$CH_2CH_2OH$, —(C=O) $CO_2H$, —$CH_2$(C=O)$CO_2H$, —NH(C=O) $CO_2H$, —NHS(=O)$_2NH_2$, a $C_{1-10}$ alkyl group (the $C_{1-10}$ alkyl group may be substituted with one or more substituents selected from the group consisting of hydroxyl groups, carboxyl groups, the following aryl groups, the following heterocyclic groups and $C_{1-10}$ alkylamino groups (the $C_{1-10}$ alkylamino groups may be substituted with one or more of the following aryl groups or one or more of the heterocyclic groups)), a $C_{2-10}$ alkenyl group, a $C_{2-10}$ alkynyl group, a $C_{2-9}$ heterocyclic group, a $C_{1-10}$ thioalkyl group, a $C_{1-10}$ alkoxy group, a $C_{1-10}$ alkylcarbonyl group; a $C_{1-10}$ alkylaminocarbonyl group, a $C_{1-10}$ dialkylaminocarbonyl group, a mono- or di-$C_{1-10}$ alkylamino group, a $C_{1-10}$ alkylcarbonyloxy group, a $C_{1-10}$ alkoxycarbonyl group, an aminocarbonyl group, a $C_{1-10}$ alkylcarbonylamino group (the $C_{1-10}$ alkoxy group, the $C_{1-10}$ alkylcarbonyl group, the $C_{1-10}$ alkylaminocarbonyl group, the $C_{1-10}$ dialkylaminocarbonyl group, the mono- or di-$C_{1-10}$ alkylamino group, the $C_{1-10}$ alkylcarbonyloxy group, the $C_{1-10}$ alkoxycarbonyl group, the aminocarbonyl group and the $C_{1-10}$ alkylcarbonylamino group may be substituted with one or more substituents selected from the group consisting of carboxyl groups, carbamoyl groups, sulfamoyl groups, sulfo groups, amino groups, the following aryl groups and the following heterocyclic groups), the following aryl groups and the following heterocyclic groups.

Aryl groups: a phenyl group, thienyl groups (a 2-thienyl group and a 3-thienyl group), furyl groups (a 2-furyl group and a 3-furyl group), pyridazinyl groups (a 3-pyridazinyl group and a 4-pyridazinyl group), pyridyl groups (a 2-pyridyl group, a 3-pyridyl group and 4-pyridyl group), pyrimidinyl groups (a 2-pyrimidinyl group, a 4-pyrimidinyl group and a 5-pyrimidinyl group), quinolyl groups (a 2-quinolyl group, a 3-quinolyl group, a 4-quinolyl group, a 5-quinolyl group, a 6-quinolyl group, a 7-quinolyl group and a 8-quinolyl group) and isoquinolyl groups (a 1-isoquinolyl group, a 3-isoquinolyl group, a 4-isoquinolyl group, a 5-isoquinolyl group, a 6-isoquinolyl group, a 7-isoquinolyl group and a 8-isoquinolyl group).

Heterocyclic groups: a 1,3,4-oxadiazole group, a 1,3,4-thiadiazole group, a 1,2,4-oxadiazole group, a 1,2,4-thiadiazole group, a 1,2,5-oxadiazole group, a 1,2,5-thiadiazole group, a 1,2-oxazole group and a 1,2-thiazole group.

Still further specific preferable examples of the substituent $R^3$ are a methyl group, an ethyl group, a n-propyl group, an i-propyl group, a n-butyl group, a s-butyl group, a t-butyl group, a c-propyl group, a c-butyl group, a c-pentyl group, a c-hexyl group, an ethynyl group, a 1-propynyl group, a 2-propynyl group, a 1-butynyl group, a 2-butynyl group, a 3-butynyl group, a 1-pentynyl group, a 2-pentynyl group, a 4-pentynyl group, a 1-methyl-2-butynyl group, a 1-methyl-3-butynyl group, a 2-methyl-3-butynyl group, a 3-methyl-1-butynyl group and the following heterocyclic groups optionally substituted with one or more substituents optionally selected from substituent set A and with one or more substituents optionally selected from substituent set B.

Heterocyclic Groups

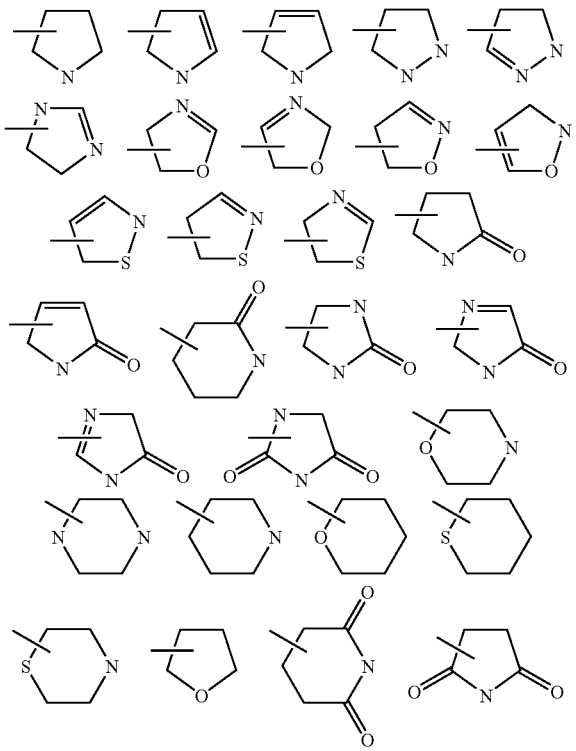

-continued

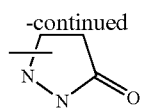

Substituent set A: a hydroxyl group, an amino group, a carboxyl group, a phosphonic acid group, a sulfonic acid group, a carbamoyl group, a hydroxycarbamoyl group, a cyanocarbamoyl group, a sulfamoyl group, a hydroxysulfamoyl group, a cyanosulfamoyl group, a tetrazole group, $-CH_2CO_2H$, $-OCH_2CO_2H$, $-NHCH_2CO_2H$, $-CH_2CH_2CO_2H$ and an alkoxycarbonyl group.

Substituent set B: a hydroxyl group, an amino group, a carboxyl group, a phosphonic acid group, a sulfonic acid group, a carbamoyl group, a hydroxycarbamoyl group, a cyanocarbamoyl group, a sulfamoyl group, a nitro group, a cyano group, a halogen atom, a $C_{1-10}$ alkyl group, a $C_{1-10}$ alkyl group substituted with one or more fluorine atoms, a sulfamoyl group substituted with a $C_{1-10}$ alkyl group, a carbamoyl group substituted with a $C_{1-10}$ alkyl group, a $C_{1-10}$ alkylcarbonylamino group and a $C_{1-10}$ alkylaminocarbonyl group (the $C_{1-10}$ alkylcarbonylamino group and the $C_{1-10}$ alkylaminocarbonyl group may be substituted with one or more substituents selected from the group consisting of phenyl groups, pyridyl groups, thienyl groups and furyl groups).

Favorable compounds as the thrombopoietin receptor activator, the preventive, therapeutic or improving agent for diseases against which activation of the thrombopoietin receptor is effective and the platelet increasing agent of the present invention are as follows.

1) Compounds represented by the formula (1) wherein A is a nitrogen atom, and B is a sulfur atom, tautomers, prodrugs or pharmaceutically acceptable salts of the compounds or solvates thereof.

2) Compounds represented by the formula (1) wherein A is a nitrogen atom, and B is an oxygen atom, tautomers, prodrugs or pharmaceutically acceptable salts of the compounds or solvates thereof.

3) Compounds represented by the formula (1) wherein A is a nitrogen atom, and B is $NR^9$ other than NH (wherein $R^9$ is a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group, the $C_{1-10}$ alkylcarbonyloxy group, the $C_{1-10}$ alkoxycarbonyl group and the $C_{1-10}$ alkylcarbonyl group may be optionally substituted with one or more substituents selected from the group consisting of carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), a $C_{2-14}$ aryl group (the $C_{2-14}$ aryl group may be optionally substituted with one or more substituents selected from the group consisting of $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups) or a $C_{2-14}$ aryloxy group (the $C_{2-14}$ aryloxy group may be optionally substituted with one or more substituents selected from the group consisting of $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups)), tautomers, prodrugs or pharmaceutically acceptable salts of the compounds or solvates thereof.

4) Compounds represented by the formula (1) wherein A is $CR^4$ (wherein $R^4$ is a hydrogen atom, a hydroxyl group (the hydroxyl group may be substituted with a $C_{2-6}$ alkenyl or a $C_{2-6}$ alkynyl group), a thiol group (the thiol group may be substituted with a $C_{1-10}$ alkyl group, a $C_{2-6}$ alkenyl group, a $C_{2-6}$ alkynyl group or a $C_{1-10}$ alkylcarbonyl group), an amino group (the amino group may be substituted with one or two $C_{2-6}$ alkenyl groups or one or two $C_{2-6}$ alkynyl groups), a formyl group, a halogen atom, a nitro group, a cyano group, a $C_{1-10}$ alkyl group, a $C_{2-6}$ alkenyl group, a $C_{2-6}$ alkynyl group, a $C_{1-10}$ alkylcarbonylamino group, a mono- or di-$C_{1-10}$ alkylamino group, a $C_{1-10}$ alkoxy group (the $C_{1-10}$ alkyl group, the $C_{2-6}$ alkenyl group, the $C_{2-6}$ alkynyl group, the $C_{1-10}$ alkylcarbonylamino group, the mono- or di-$C_{1-10}$ alkylamino group and the $C_{1-10}$ alkoxy group may be optionally substituted with one or more substituents selected from the group consisting of carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), a $C_{2-14}$ aryl group (the $C_{2-14}$ aryl group may be optionally substituted with one or more substituents selected from the group consisting of $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups), a $C_{2-14}$ aryloxy group (the $C_{2-14}$ aryloxy group may be optionally substituted with one or more substituents selected from the group consisting of $C_{1-10}$ alkyl groups (the $C_{1-10}$ alkyl groups may be substituted with one or more halogen atoms), $C_{2-6}$ alkenyls group, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups), $SO_2R^5$, $SOR^5$ or $COR^5$ (wherein $R^5$ is a hydroxyl group, a $C_{1-10}$ alkyl group, a $C_{2-6}$ alkenyl group, a $C_{2-6}$ alkynyl group, a $C_{1-10}$ alkoxy group (the $C_{1-10}$ alkyl group, the $C_{2-6}$ alkenyl group, the $C_{2-6}$ alkynyl group and the $C_{1-10}$ alkoxy group may be optionally substituted with one or more substituents selected from the group consisting of carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl group may be substituted with one or more halogen atoms) or one or more halogen atoms)), a $C_{2-14}$ aryl group (the $C_{2-14}$ aryl group may be optionally substituted with one or more substituents selected from the group consisting of $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups), a $C_{2-14}$ aryloxy group (the $C_{2-14}$ aryloxy group may be optionally substituted with one or more substituents selected from the group consisting of $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups) or $NR^6R^7$ (wherein each of $R^6$ and $R^7$ is independently a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkylcarbonyloxy group, the $C_{1-10}$ alkoxycarbonyl group and the $C_{1-10}$ alkylcarbonyl group may be optionally substituted with one or more substituents selected from the group consisting of carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)) or a $C_{2-14}$ aryl group (the $C_{2-14}$ aryl group may be optionally substituted with one or more substituents selected from the group consisting of $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups), or $R^6$ and $R^7$ mean, together with each other, —$(CH_2)_{m1}$-E-$(CH_2)_{m2}$— (wherein E is an oxygen atom, a sulfur atom, $CR^{26}R^{27}$ (wherein each of $R^{26}$ and $R^{27}$ is independently a hydrogen atom, a $C_{1-10}$ alkyl group, a $C_{2-14}$ aryl group, a $C_{1-10}$ alkoxy group, a $C_{2-14}$ aryloxy group, a hydroxyl group or a protected hydroxyl group) or NR$^8$ (wherein R$^8$ is a hydrogen atom, a hydroxyl group, a formyl group, a C$_{1-10}$ alkyl group, a C$_{2-6}$ alkenyl group, a C$_{2-6}$ alkynyl group, a C$_{1-10}$ alkoxy group, a C$_{1-10}$ alkylcarbonyloxy group, a C$_{1-10}$ alkoxycarbonyl group, a C$_{1-10}$ alkylcarbonyl group (the C$_{1-10}$ alkyl group, the C$_{2-6}$ alkenyl group, the C$_{2-6}$ alkynyl group, the C$_{1-10}$ alkoxy group, the C$_{1-10}$ alkylcarbonyloxy group, the C$_{1-10}$ alkoxycarbonyl group and the C$_{1-10}$ alkylcarbonyl group may be optionally substituted with one or more substituents selected from the group consisting of carboxyl groups, nitro groups, cyano groups, halogen atoms, C$_{1-10}$ alkoxy groups, C$_{1-10}$ alkylcarbonyl groups, C$_{1-10}$ alkylcarbonyloxy groups, C$_{1-10}$ alkoxycarbonyl groups, C$_{1-10}$ alkylcarbonylamino groups, amino groups, mono- or di-C$_{1-10}$ alkylamino groups, hydroxyl groups, protected hydroxyl groups, C$_{2-14}$ aryl groups and C$_{2-14}$ aryloxy groups (the C$_{2-14}$ aryl groups and the C$_{2-14}$ aryloxy groups may be substituted with one or more C$_{1-6}$ alkyl groups (the C$_{1-6}$ alkyl groups may be substituted with one or more halogen atoms) or one or more halogen atoms)) or a C$_{2-14}$ aryl group (the C$_{2-14}$ aryl group may be optionally substituted with one or more substituents selected from the group consisting of C$_{1-10}$ alkyl groups (the C$_{1-10}$ alkyl groups may be substituted with one or more halogen atoms), C$_{2-6}$ alkenyl groups, C$_{2-6}$ alkynyl groups, carboxyl groups, nitro groups, cyano groups, halogen atoms, C$_{1-10}$ alkoxy groups, C$_{1-10}$ alkylcarbonyl groups, C$_{1-10}$ alkylcarbonyloxy groups, C$_{1-10}$ alkoxycarbonyl groups, C$_{1-10}$ alkylcarbonylamino groups, amino groups, mono- or di-C$_{1-10}$ alkylamino groups, hydroxyl groups, protected hydroxyl groups, C$_{2-14}$ aryl groups and C$_{2-14}$ aryloxy groups)), and each of m1 and m2 is independently an integer of from 0 to 5 provided that m1+m2 is 3, 4 or 5)))), and B is a oxygen atom, tautomers, prodrugs or pharmaceutically acceptable salts of the compounds or solvates thereof.

5) Compounds represented by the formula (1) wherein A is CR$^4$ (wherein R$^4$ is a hydrogen atom, a hydroxyl group (the hydroxyl group may be substituted with a C$_{2-6}$ alkenyl or a C$_{2-6}$ alkynyl group), a thiol group (the thiol group may be substituted with a C$_{1-10}$ alkyl group, a C$_{2-6}$ alkenyl group, a C$_{2-6}$ alkynyl group or a C$_{1-10}$ alkylcarbonyl group), an amino group (the amino group may be substituted with one or two C$_{2-6}$ alkenyl groups or one or two C$_{2-6}$ alkynyl groups), a formyl group, a halogen atom, a nitro group, a cyano group, a C$_{1-10}$ alkyl group, a C$_{2-6}$ alkenyl group, a C$_{2-6}$ alkynyl group, a C$_{1-10}$ alkylcarbonylamino group, a mono- or di-C$_{1-10}$ alkylamino group, a C$_{1-10}$ alkoxy group (the C$_{1-10}$ alkyl group, the C$_{2-6}$ alkenyl group, the C$_{2-6}$ alkynyl group, the C$_{1-10}$ alkylcarbonylamino group, the mono- or di-C$_{1-10}$ alkylamino group and the C$_{1-10}$ alkoxy group may be optionally substituted with one or more substituents selected from the group consisting of carboxyl groups, nitro groups, cyano groups, halogen atoms, C$_{1-10}$ alkoxy groups, C$_{1-10}$ alkylcarbonyl groups, C$_{1-10}$ alkylcarbonyloxy groups, C$_{1-10}$ alkoxycarbonyl groups, C$_{1-10}$ alkylcarbonylamino groups, amino groups, mono- or di-C$_{1-10}$ alkylamino groups, hydroxyl groups, protected hydroxyl groups, C$_{2-14}$ aryl groups and C$_{2-14}$ aryloxy groups (the C$_{2-14}$ aryl group and the C$_{2-14}$ aryloxy group may be substituted with one or more C$_{1-6}$ alkyl groups (the C$_{1-6}$ alkyl groups may be substituted with one or more halogen atoms) or one or more halogen atoms)), a C$_{2-14}$ aryl group (the C$_{2-14}$ aryl group may be optionally substituted with one or more substituents selected from the group consisting of C$_{1-10}$ alkyl groups (the C$_{1-10}$ alkyl groups may be substituted with one or more halogen atoms), C$_{2-6}$ alkenyl groups, C$_{2-6}$ alkynyl groups, carboxyl groups, nitro groups, cyano groups, halogen atoms, C$_{1-10}$ alkoxy groups, C$_{1-10}$ alkylcarbonyl groups, C$_{1-10}$ alkylcarbonyloxy groups, C$_{1-10}$ alkoxycarbonyl groups, C$_{1-10}$ alkylcarbonylamino groups, amino groups, mono- or di-C$_{1-10}$ alkylamino groups, hydroxyl groups, protected hydroxyl groups, C$_{2-14}$ aryl groups and C$_{2-14}$ aryloxy groups), a C$_{2-14}$ aryloxy group (the C$_{2-14}$ aryloxy group may be optionally substituted with one or more substituents selected from the group consisting of C$_{1-10}$ alkyl groups (the C$_{1-10}$ alkyl groups may be substituted with one or more halogen atoms), C$_{2-6}$ alkenyl groups, C$_{2-6}$ alkynyl groups, carboxyl groups, nitro groups, cyano groups, halogen atoms, C$_{1-10}$ alkoxy groups, C$_{1-10}$ alkylcarbonyl groups, C$_{1-10}$ alkylcarbonyloxy groups, C$_{1-10}$ alkoxycarbonyl groups, C$_{1-10}$ alkylcarbonylamino groups, amino groups, mono- or di-C$_{1-10}$ alkylamino groups, hydroxyl groups, protected hydroxyl groups, C$_{2-14}$ aryl groups and C$_{2-14}$ aryloxy groups), SO$_2$R$^5$, SOR$^5$ or COR$^5$ (wherein R$^5$ is a hydroxyl group, a C$_{1-10}$ alkyl group, a C$_{2-6}$ alkenyl group, a C$_{2-6}$ alkynyl group, a C$_{1-10}$ alkoxy group (the C$_{1-10}$ alkyl group, the C$_{2-6}$ alkenyl group, the C$_{2-6}$ alkynyl group and the C$_{1-10}$ alkoxy group may be optionally substituted with one or more substituents selected from the group consisting of carboxyl groups, nitro groups, cyano groups, halogen atoms, C$_{1-10}$ alkoxy groups, C$_{1-10}$ alkylcarbonyl groups, C$_{1-10}$ alkylcarbonyloxy groups, C$_{1-10}$ alkoxycarbonyl groups, C$_{1-10}$ alkylcarbonylamino groups, amino groups, mono- or di-C$_{1-10}$ alkylamino groups, hydroxyl groups, protected hydroxyl groups, C$_{2-14}$ aryl groups and C$_{2-14}$ aryloxy groups (the C$_{2-14}$ aryl groups and the C$_{2-14}$ aryloxy groups may be substituted with one or more C$_{1-6}$ alkyl groups (the C$_{1-6}$ alkyl groups may be substituted with one or more halogen atoms) or one or more halogen atoms)), a C$_{2-14}$ aryl group (the C$_{2-14}$ aryl group, may be optionally substituted with one or more substituents selected from the group consisting of C$_{1-10}$ alkyl groups (the C$_{1-10}$ alkyl groups may be substituted with one or more halogen atoms), C$_{2-6}$ alkenyl groups, C$_{2-6}$ alkynyl groups, carboxyl groups, nitro groups, cyano groups, halogen atoms, C$_{1-10}$ alkoxy groups, C$_{1-10}$ alkylcarbonyl groups, C$_{1-10}$ alkylcarbonyloxy groups, C$_{1-10}$ alkoxycarbonyl groups, C$_{1-10}$ alkylcarbonylamino groups, amino groups, mono- or di-C$_{1-10}$ alkylamino groups, hydroxyl groups, protected hydroxyl groups, C$_{2-14}$ aryl groups and C$_{2-14}$ aryloxy groups), a C$_{2-14}$ aryloxy group (the C$_{2-14}$ aryloxy group may be optionally substituted with one or more substituents selected from the group consisting of C$_{1-10}$ alkyl groups (the C$_{1-10}$ alkyl groups may be substituted with one or more halogen atoms), C$_{2-6}$ alkenyl groups, C$_{2-6}$ alkynyl groups, carboxyl groups, nitro groups, cyano groups, halogen atoms, C$_{1-10}$ alkoxy groups, C$_{1-10}$ alkylcarbonyl groups, C$_{1-10}$ alkylcarbonyloxy groups, C$_{1-10}$ alkoxycarbonyl groups, C$_{1-10}$ alkylcarbonylamino groups, amino groups, mono- or di-C$_{1-10}$ alkylamino groups, hydroxyl groups, protected hydroxyl groups, C$_{2-14}$ aryl groups and C$_{2-14}$ aryloxy groups) or NR$^6$R$^7$ (wherein each of R$^6$ and R$^7$ is independently a hydrogen atom, a hydroxyl group, a formyl group, a C$_{1-10}$ alkyl group, a C$_{2-6}$ alkenyl group, a C$_{2-6}$ alkynyl group, a C$_{1-10}$ alkylcarbonyloxy group, a C$_{1-10}$ alkoxycarbonyl group, a C$_{1-10}$ alkylcarbonyl group (the C$_{1-10}$ alkyl group, the C$_{2-6}$ alkenyl group, the C$_{2-6}$ alkynyl group, the C$_{1-10}$ alkylcarbonyloxy group, the C$_{1-10}$ alkoxycarbonyl group and the C$_{1-10}$ alkylcarbonyl group may be optionally substituted with one or more substituents selected from the group consisting of carboxyl groups, nitro groups, cyano groups, halogen atoms, C$_{1-10}$ alkoxy groups, C$_{1-10}$ alkylcarbonyl groups, C$_{1-10}$ alkylcarbonyloxy groups, C$_{1-10}$ alkoxycarbonyl groups, C$_{1-10}$ alkylcarbonylamino groups, amino groups, mono- or di-C$_{1-10}$ alkylamino groups, hydroxyl groups, protected hydroxyl groups, C$_{2-14}$ aryl groups and C$_{2-14}$ aryloxy groups (the C$_{2-14}$ aryl groups and the C$_{2-14}$ aryloxy groups may be substituted with one or more $C_{1-6}$ alkyl groups (the $C_{1-6}$ alkyl groups may be substituted with one or more halogen atoms) or one or more halogen atoms)) or a $C_{2-14}$ aryl group (the $C_{2-14}$ aryl group may be optionally substituted with one or more substituents selected from the group consisting of $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups), or $R^6$ and $R^7$ mean, together with each other, —$(CH_2)_{m1}$-E-$(CH_2)_{m2}$— (wherein E is an oxygen atom, a sulfur atom, $CR^{26}R^{27}$ (wherein each of $R^{26}$ and $R^{27}$ is independently a hydrogen atom, a $C_{1-10}$ alkyl group, a $C_{2-14}$ aryl group, a $C_{1-10}$ alkoxy group, a $C_{2-14}$ aryloxy group, a hydroxyl group or a protected hydroxyl group) or $NR^8$ (wherein $R^8$ is a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group, the $C_{1-10}$ alkylcarbonyloxy group, the $C_{1-10}$ alkoxycarbonyl group and the $C_{1-10}$ alkylcarbonyl group may be optionally substituted with one or more substituents selected from the group consisting of carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)) or a $C_{2-14}$ aryl group (the $C_{2-14}$ aryl group may be optionally substituted with one or more substituents selected from the group consisting of $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups)), and each of m1 and m2 is independently an integer of from 0 to 5 provided that m1+m2 is 3, 4 or 5)))), and B is a sulfur atom, tautomers, prodrugs or pharmaceutically acceptable salts of the compounds or solvates thereof.

6) Compounds represented by the formula (1) wherein A is $CR^4$ (wherein $R^4$ is a hydrogen atom, a hydroxyl group (the hydroxyl group may be substituted with a $C_{2-6}$ alkenyl or a $C_{2-6}$ alkynyl group), a thiol group (the thiol group may be substituted with a $C_{1-10}$ alkyl group, a $C_{2-6}$ alkenyl group, a $C_{2-6}$ alkynyl group or a $C_{1-10}$ alkylcarbonyl group), an amino group (the amino group may be substituted with one or two $C_{2-6}$ alkenyl groups or one or two $C_{2-6}$ alkynyl groups), a formyl group, a halogen atom, a nitro group, a cyano group, a $C_{1-10}$ alkyl group, a $C_{2-6}$ alkenyl group, a $C_{2-6}$ alkynyl group, a $C_{1-10}$ alkylcarbonylamino group, a mono- or di-$C_{1-10}$ alkylamino group, a $C_{1-10}$ alkoxy group (the $C_{1-10}$ alkyl group, the $C_{2-6}$ alkenyl group, the $C_{2-6}$ alkynyl group, the $C_{1-10}$ alkylcarbonylamino group, the mono- or di-$C_{1-10}$ alkylamino group and the $C_{1-10}$ alkoxy group may be optionally substituted with one or more substituents selected from the group consisting of carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), a $C_{2-14}$ aryl group (the $C_{2-14}$ aryl group may be optionally substituted with one or more substituents selected from the group consisting of $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups), a $C_{2-14}$ aryloxy group (the $C_{2-14}$ aryloxy group may be optionally substituted with one or more substituents selected from the group consisting of $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups), $SO_2R^5$, $SOR^5$ or $COR^5$ (wherein $R^5$ is a hydroxyl group, a $C_{1-10}$ alkyl group, a $C_{2-6}$ alkenyl group, a $C_{2-6}$ alkynyl group, a $C_{1-10}$ alkoxy group (the $C_{1-10}$ alkyl group, the $C_{2-6}$ alkenyl group, the $C_{2-6}$ alkynyl group and the $C_{1-10}$ alkoxy group may be optionally substituted with one or more substituents selected from the group consisting of carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, an amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), a $C_{2-14}$ aryl group (the $C_{2-14}$ aryl group may be optionally substituted with one or more substituents selected from the group consisting of $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups), a $C_{2-14}$ aryloxy group (the $C_{2-14}$ aryloxy group may be optionally substituted with one or more substituents selected from the group consisting of $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups) or $NR^6R^7$ (wherein each of $R^6$ and $R^7$ is independently a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkylcarbonyloxy group, the $C_{1-10}$ alkoxycarbonyl group and the $C_{1-10}$ alkylcarbonyl group may be optionally substituted with one or more substituents selected from the group consisting of carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)) or a $C_{2-14}$ aryl group (the $C_{2-14}$ aryl group may be optionally substituted with one or more substituents selected from the group consisting of $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups), or $R^6$ and $R^7$ mean, together with each other, —$(CH_2)_{m1}$-E-$(CH_2)_{m2}$— (wherein E is an oxygen atom, a sulfur atom, $CR^{26}R^{27}$ (wherein each of $R^{26}$ and $R^{27}$ is independently a hydrogen atom, a $C_{1-10}$ alkyl group, a $C_{2-14}$ aryl group, a $C_{1-10}$ alkoxy group, a $C_{2-14}$ aryloxy group, a hydroxyl group or a protected hydroxyl group) or $NR^8$ (wherein $R^8$ is a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group, the $C_{1-10}$ alkylcarbonyloxy group, the $C_{1-10}$ alkoxycarbonyl group and the $C_{1-10}$ alkylcarbonyl group may be optionally substituted with one or more substituents selected from the group consisting of carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)) or a $C_{2-14}$ aryl group (the $C_{2-14}$ aryl group may be optionally substituted with one or more substituents selected from the group consisting of $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups)), and each of m1 and m2 is independently an integer of from 0 to 5 provided that m1+m2 is 3, 4 or 5)))), and B is $NR^9$ (wherein $R^9$ is a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group, the $C_{1-10}$ alkylcarbonyloxy group, the $C_{1-10}$ alkoxycarbonyl group and the $C_{1-10}$ alkylcarbonyl group may be optionally substituted with one or more substituents selected from the group consisting of carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), a $C_{2-14}$ aryl group (the $C_{2-14}$ aryl group may be optionally substituted with one or more substituents selected from the group consisting of $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups) or a $C_{2-14}$ aryloxy group (the $C_{2-14}$ aryloxy group may be optionally substituted with one or more substituents selected from the group consisting of $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups)), tautomers, prodrugs or pharmaceutically acceptable salts of the compounds or solvates thereof.

7) Compounds represented by the formula (1) according to 4), 5) or 6) wherein A is $CR^{37}$ (wherein $R^{37}$ is a hydrogen atom, a hydroxyl group (the hydroxyl group may be substituted with a $C_{2-6}$ alkenyl or a $C_{2-6}$ alkynyl group), a thiol group (the thiol group may be substituted with a $C_{1-10}$ alkyl group, a $C_{2-6}$ alkenyl group, a $C_{2-6}$ alkynyl group or a $C_{1-10}$ alkylcarbonyl group), an amino group (the amino group may be substituted with one or two $C_{2-6}$ alkenyl groups or one or two $C_{2-6}$ alkynyl groups), a formyl group, a halogen atom, a nitro group, a cyano group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonylamino group, a mono- or di-$C_{1-10}$ alkylamino group (the $C_{1-10}$ alkyl group, the $C_{2-6}$ alkenyl group, the $C_{2-6}$ alkynyl group, the $C_{1-10}$ alkoxy group, the $C_{1-10}$ alkylcarbonylamino group and the mono- or di-$C_{1-10}$ alkylamino group may be substituted with one or more substituents selected from the group consisting of halogen atoms, carboxyl groups, nitro groups and cyano groups), $SO_2R^{38}$, $SOR^{38}$ or $COR^{38}$ (wherein $R^{38}$ is a hydroxyl group, a $C_{1-10}$ alkyl group, a $C_{2-6}$ alkenyl group, a $C_{2-6}$ alkynyl group, a $C_{1-10}$ alkoxy group (the $C_{1-10}$ alkyl group, the $C_{2-6}$ alkenyl group, the $C_{2-6}$ alkynyl group and the $C_{1-10}$ alkoxy group may be substituted with one or more substituents selected from the group consisting of halogen atoms, carboxyl groups, nitro groups and cyano groups), a $C_{2-14}$ aryl group or a $C_{2-14}$ aryloxy group (the $C_{2-14}$ aryl group and the $C_{2-14}$ aryloxy group may be substituted with one or more $C_{1-6}$ alkyl groups (the $C_{1-6}$ alkyl groups may be substituted with one or more halogen atoms) or one or more halogen atoms))), tautomers, prodrugs or pharmaceutically acceptable salts of the compounds or solvates thereof. The terms in the respective substituents $R^{37}$ and $R^{38}$ are the same as those in the respective substituents $R^1$ to $R^{36}$.

8) Compounds represented by the formula (1) according to 3) or 6) wherein B is $NR^{39}$ (wherein $R^{39}$ is a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group, the $C_{1-10}$ alkylcarbonyloxy group, the $C_{1-10}$ alkoxycarbonyl group and the $C_{1-10}$ alkylcarbonyl group may be substituted with one or more substituents selected from the group consisting of carboxyl groups, halogen atoms, nitro groups and cyano groups), a $C_{2-14}$ aryl group or a $C_{2-14}$ aryloxy group (the $C_{2-14}$ aryl group and the $C_{2-14}$ aryloxy group may be substituted with one or more substituents selected from the group consisting of $C_{1-6}$ alkyl groups (the $C_{1-6}$ alkyl groups may be substituted with one or more halogen atoms), $C_{2-6}$ alkenyl groups, $C_{2-6}$ alkynyl groups, carboxyl groups, nitro groups, cyano groups and halogen atoms)), tautomers prodrugs or pharmaceutically acceptable salts of the compounds or solvates thereof. The terms in the substituent $R^{39}$ are the same as those in the respective substituents $R^1$ to $R^{36}$.

9) Compounds represented by the formula (1) according to 1), 2), 3), 4), 5), 6), 7) or 8) wherein $L^1$ is a bond, tautomers prodrugs or pharmaceutically acceptable salts of the compounds or solvates thereof.

10) Compounds represented by the formula (1) according to 1), 2), 3), 4), 5), 6), 7), 8) or 9) wherein $L^2$ is a bond, tautomers, prodrugs or pharmaceutically acceptable salts of the compounds or solvates thereof.

11) Compounds represented by the formula (1) according to 1), 2), 3), 4), 5), 6), 7), 8), 9) or 10) wherein $L^3$ is $NR^{19}$ (wherein $R^{19}$ is a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group, the $C_{1-10}$ alkylcarbonyloxy group, the $C_{1-10}$ alkoxycarbonyl group and the $C_{1-10}$ alkylcarbonyl group may be optionally substituted with one or more substituents selected from the group consisting of carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)) or a $C_{2-14}$ aryl group (the $C_{2-14}$ aryl group may be optionally substituted with one or more substituents selected from the group consisting of $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups)), tautomers, prodrugs or pharmaceutically acceptable salts of the compounds or solvates thereof.

12) The compounds according to 1), 2), 3), 4), 5), 6), 7), 8), 9) or 10) wherein $L^3$ is NH, tautomers, prodrugs or pharmaceutically acceptable salts of the compounds or solvates thereof.

13) The compounds according to 1), 2), 3), 4), 5), 6), 7), 8), 9) or 10) wherein $L^3$ is $CH_2$, tautomers, prodrugs or pharmaceutically acceptable salts of the compounds or solvates thereof.

14) The compounds according to 11), 12) or 13) wherein $R^2$ is a hydrogen atom, a $C_{1-10}$ alkyl group, a $C_{2-6}$ alkenyl group, a $C_{2-6}$ alkynyl group, a $C_{1-10}$ alkoxy group (the $C_{1-10}$ alkyl group, the $C_{2-6}$ alkenyl group, the $C_{2-6}$ alkynyl group and the $C_{1-10}$ alkoxy group may be optionally substituted with one or more substituents selected from the group consisting of carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), a $C_{2-14}$ aryl group or a $C_{2-14}$ aryloxy group (the $C_{2-14}$ aryl group and the $C_{2-14}$ aryloxy group may be substituted with one or more $C_{1-6}$ alkyl groups (the alkyl groups may be substituted with one or more halogen atoms) or one or more halogen atoms), tautomers, prodrugs or pharmaceutically acceptable salts of the compounds or solvates thereof.

15) The compounds according to 11), 12) or 13) wherein $R^2$ is a hydrogen atom, a $C_{1-10}$ alkyl group, a $C_{2-6}$ alkenyl group, a $C_{2-6}$ alkynyl group, a $C_{1-3}$ alkoxy group (the $C_{1-10}$ alkyl group, the $C_{2-6}$ alkenyl group, the $C_{2-6}$ alkynyl group and the $C_{1-3}$ alkoxy group may be optionally substituted with one or more substituents selected from the group consisting, of carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, phenyl groups and phenyloxyl groups (the phenyl groups and the phenyloxyl groups may be substituted with one or more $C_{1-6}$ alkyl groups (the $C_{1-6}$ alkyl groups may be substituted with one or more halogen atoms) or one or more halogen atoms), a phenyl group or a phenyloxy group (the phenyl group and the phenyloxy group may be substituted with one or more $C_{1-6}$ alkyl groups (the $C_{1-6}$ alkyl groups may be substituted with one or more halogen atoms) or one or more halogen atoms), tautomers, prodrugs or pharmaceutically acceptable salts of the compounds or solvates thereof.

16) The compounds according to 11), 12) or 13) wherein $R^2$ is a hydrogen atom, a $C_{1-10}$ alkyl group, a $C_{2-6}$ alkenyl group or a $C_{2-6}$ alkynyl group (the $C_{1-10}$ alkyl group, the $C_{2-6}$ alkenyl group and the $C_{2-6}$ alkynyl group may be optionally substituted with one or more substituents selected from the group consisting of carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups and protected hydroxyl groups), tautomers, prodrugs or pharmaceutically acceptable salts of the compounds or solvates thereof.

17) The compounds according to 11), 12) or 13) wherein $R^2$ is a hydrogen atom or a $C_{1-6}$ alkyl group (the $C_{2-6}$ alkyl group may be optionally substituted with one or more substituents selected from the group consisting of carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups and protected hydroxyl groups), tautomers, prodrugs or pharmaceutically acceptable salts of the compounds or solvates thereof.

18) The compounds according to 11), 12) or 13) wherein $R^2$ is a hydrogen atom or a $C_{1-3}$ alkyl group (the $C_{1-3}$ alkyl group may be optionally substituted with one or more substituents selected from the group consisting of halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups and protected hydroxyl groups), tautomers, prodrugs or pharmaceutically acceptable salts of the compounds or solvates thereof.

19) The compounds according to 14), 15), 16), 17) or 18) wherein $R^1$ is a $C_{2-14}$ aryl group (the $C_{2-14}$ aryl group may be optionally substituted with one or more substituents selected from the group consisting of halogen atoms, carboxyl groups, nitro groups, formyl groups, cyano groups, hydroxyl groups, protected hydroxyl groups, $C_{1-10}$ alkyl groups, $C_{2-6}$ alkenyl groups, $C_{2-6}$ alkynyl groups, $C_{1-10}$ alkoxy groups, $C_{1-10}$ alkylcarbonyl groups, $C_{1-10}$ alkoxycarbonyl groups, $C_{1-10}$ alkylcarbonyloxy groups (the $C_{1-10}$ alkyl groups, the $C_{2-6}$ alkenyl groups, the $C_{2-6}$ alkynyl groups and the $C_{1-10}$ alkylcarbonyl groups may be optionally substituted with one or more substituents selected from the group consisting of carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), $C_{2-14}$ aryl groups, $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms), thiol groups and amino groups (the thiol groups and the amino groups may be optionally substituted with one or more substituents selected from the group consisting of formyl groups, $C_{1-10}$ alkyl groups, $C_{2-6}$ alkenyl groups, $C_{2-6}$ alkynyl groups and $C_{1-10}$ alkylcarbonyl groups (the $C_{1-10}$ alkyl groups, the $C_{2-6}$ alkenyl groups, the $C_{2-6}$ alkynyl groups and the $C_{1-10}$ alkylcarbonyl groups may be optionally substituted with one or more substituents selected from the group consisting of carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)))), tautomers, prodrugs or pharmaceutically acceptable salts of the compounds or solvates thereof.

20) The compounds according to 14), 15), 16), 17) or 18) wherein $R^1$ is a phenyl group, a thienyl group, a furyl group, a pyridazinyl group, a pyridyl group, a quinolyl group or an isoquinolyl group (the phenyl group, the thienyl group, the furyl group, the pyridazinyl group, the pyridyl group, the quinolyl group and the isoquinolyl group may be optionally substituted with one or more substituents selected from the group consisting of halogen atoms, carboxyl groups, nitro groups, formyl groups, cyano groups, hydroxyl groups, protected hydroxyl groups, $C_{1-10}$ alkyl groups, $C_{2-6}$ alkenyl groups, $C_{2-6}$ alkynyl groups, $C_{1-10}$ alkoxy groups, $C_{1-10}$ alkylcarbonyl groups, $C_{1-10}$ alkoxycarbonyl groups, $C_{1-10}$ alkylcarbonyloxy groups (the $C_{1-10}$ alkyl groups, the $C_{2-6}$ alkenyl groups, the $C_{2-6}$ alkynyl groups, the $C_{1-10}$ alkoxy groups, the $C_{1-10}$ alkylcarbonyl groups, the $C_{1-10}$ alkylcarbonyloxy groups and the $C_{1-10}$ alkoxycarbonyl groups may be optionally substituted with one or more substituents selected from the group consisting of carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)))), tautomers, prodrugs or pharmaceutically acceptable salts of the compounds or solvates thereof.

21) The compounds according to 14), 15), 16), 17) or 18) wherein $R^1$ is a phenyl group, a thienyl group, a furyl group, a pyridazinyl group, a pyridyl group, a quinolyl group or an isoquinolyl group (the phenyl group, the thienyl group, the furyl group, the pyridazinyl group, the pyridyl group, the quinolyl group and the isoquinolyl group may be optionally substituted with one or more substituents selected from the group consisting of halogen atoms, carboxyl groups, nitro groups, formyl groups, cyano groups, hydroxyl groups, protected hydroxyl groups, $C_{1-10}$ alkyl groups, $C_{2-6}$ alkenyl groups, $C_{2-6}$ alkynyl groups, $C_{1-10}$ alkoxy groups, $C_{1-10}$ alkylcarbonyl groups, $C_{1-10}$ alkoxycarbonyl groups, $C_{1-10}$ alkylcarbonyloxy groups (the $C_{1-10}$ alkyl groups, the $C_{2-6}$ alkenyl groups, the $C_{2-6}$ alkynyl groups, the $C_{1-10}$ alkoxy groups, the $C_{1-10}$ alkylcarbonyl groups, the $C_{1-10}$ alkoxycarbonyl groups and the $C_{1-10}$ alkylcarbonyloxy groups may be optionally substituted with one or more substituents selected from the group consisting of halogen atoms, carboxyl groups, nitro groups and cyano groups), $C_{2-14}$ aryl groups, $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms), thiol groups and amino groups (the thiol groups and the amino groups may be optionally substituted with one or more substituents selected from the group consisting of formyl groups, $C_{1-10}$ alkyl groups, $C_{2-6}$ alkenyl groups, $C_{2-6}$ alkynyl groups and $C_{1-10}$ alkylcarbonyl groups (the $C_{1-10}$ alkyl groups, the $C_{2-6}$ alkenyl groups, the $C_{2-6}$ alkynyl groups and the $C_{1-10}$ alkylcarbonyl groups may be optionally substituted with one or more substituents selected from the group consisting of halogen atoms, carboxyl groups, nitro groups, cyano groups, hydroxyl groups and protected hydroxyl groups))), tautomers, prodrugs or pharmaceutically acceptable salts of the compounds or solvates thereof.

22) The compounds according to 14), 15), 16), 17) or 18) wherein $R^1$ is a phenyl group (the phenyl group may be optionally substituted with one or more substituents selected from the group consisting of halogen atoms, carboxyl groups, nitro groups, formyl groups, cyano groups, hydroxyl groups, protected hydroxyl groups, $C_{1-10}$ alkyl groups, $C_{2-6}$ alkenyl groups, $C_{2-6}$ alkynyl groups, $C_{1-10}$ alkoxy groups, $C_{1-10}$ alkylcarbonyl groups, $C_{1-10}$ alkoxycarbonyl groups, $C_{1-10}$ alkylcarbonyloxy groups (the $C_{1-10}$ alkyl groups, the $C_{2-6}$ alkenyl groups, the $C_{2-6}$ alkynyl groups, the $C_{1-10}$ alkoxy groups, the $C_{1-10}$ alkylcarbonyl groups, the alkoxycarbonyl groups and the $C_{1-10}$ alkylcarbonyloxy groups may be optionally substituted with one or more substituents selected from the group consisting of carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), thiol groups and amino groups (the thiol groups and the amino groups may be optionally substituted with one or more substituents selected from the group consisting of formyl groups, $C_{1-10}$ alkyl groups, $C_{2-6}$ alkenyl groups, $C_{2-6}$ alkynyl groups and $C_{1-10}$ alkylcarbonyl groups, (the $C_{1-10}$ alkyl groups, the $C_{2-6}$ alkenyl groups, the $C_{2-6}$ alkynyl groups and the $C_{1-10}$ alkylcarbonyl groups may be optionally substituted with one or more substituents selected from the group consisting of carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl group and the $C_{2-14}$ aryloxy group may be substituted with one or more $C_{1-6}$ alkyl groups (the $C_{1-6}$ alkyl group may be substituted with one or more halogen atoms) or one or more halogen atoms)))), tautomers, prodrugs or pharmaceutically acceptable salts of the compounds or solvates thereof.

23) The compounds according to 14), 15), 16), 17) or 18) wherein $R^1$ is a phenyl group (the phenyl group may be optionally substituted with one or more substituents selected from the group consisting of halogen atoms, carboxyl groups, nitro groups, formyl groups, cyano groups, hydroxyl groups, protected hydroxyl groups, $C_{1-10}$ alkyl groups, $C_{2-6}$ alkenyl groups, $C_{2-6}$ alkynyl groups, $C_{1-10}$ alkoxy groups, $C_{1-10}$ alkylcarbonyl groups, $C_{1-10}$ alkoxycarbonyl groups, $C_{1-10}$ alkylcarbonyloxy groups (the $C_{1-10}$ alkyl groups, the $C_{2-6}$ alkenyl groups, the $C_{2-6}$ alkynyl groups, the $C_{1-10}$ alkoxy groups, the $C_{1-10}$ alkylcarbonyl groups, the $C_{1-10}$ alkoxycarbonyl groups and the $C_{1-10}$ alkylcarbonyloxy groups may be optionally substituted with one or more substituents selected from the group consisting of halogen atoms, carboxyl groups, nitro groups and cyano groups), $C_{2-14}$ aryl groups, $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms), thiol groups and amino groups (the thiol groups and the amino groups may be optionally substituted with one or more substituents selected from the group consisting of formyl groups, $C_{1-10}$ alkyl groups, $C_{2-6}$ alkenyl groups, $C_{2-6}$ alkynyl groups and $C_{1-10}$ alkylcarbonyl groups (the $C_{1-10}$ alkyl groups, the $C_{2-6}$ alkenyl groups, the $C_{2-6}$ alkynyl groups and the $C_{1-10}$ alkylcarbonyl groups may be optionally substituted with one or more substituents selected from the group consisting of halogen atoms, carboxyl groups, nitro groups, cyano groups, hydroxyl groups and protected hydroxyl groups))), tautomers, prodrugs or pharmaceutically acceptable salts of the compounds or solvates thereof.

24) The compounds according to 19), 20), 21), 22) or 23) wherein Y is an oxygen atom, tautomers, prodrugs or pharmaceutically acceptable salts of the compounds or solvates thereof.

25) The compounds according to 19), 20), 21), 22) or 23) wherein Y is a sulfur atom, tautomers, prodrugs or pharmaceutically acceptable salts of the compounds or solvates thereof.

26) The compounds according to 24) or 25) wherein X is a hydroxyl group, tautomers, prodrugs or pharmaceutically acceptable salts of the compounds or solvates thereof.

27) The compounds according to 24), 25) or 26) wherein $L^4$ is a bond, and $R^3$ is an ethyl group, a n-propyl group, an i-propyl group, a n-butyl group, a s-butyl group, a t-butyl group, a c-propyl group, a c-butyl group, a c-pentyl group, a c-hexyl group, an ethynyl group, a 1-propynyl group, a 2-propynyl group, a 1-butynyl group, a 2-butynyl group, a 3-butynyl group, a 1-pentynyl group, a 2-pentynyl group, a 4-pentynyl group, a 1-methyl-2-butynyl group, a 1-methyl-3-butynyl group, a 2-methyl-3-butynyl group, a 3-methyl-1-butynyl group or any one of the following heterocyclic groups:

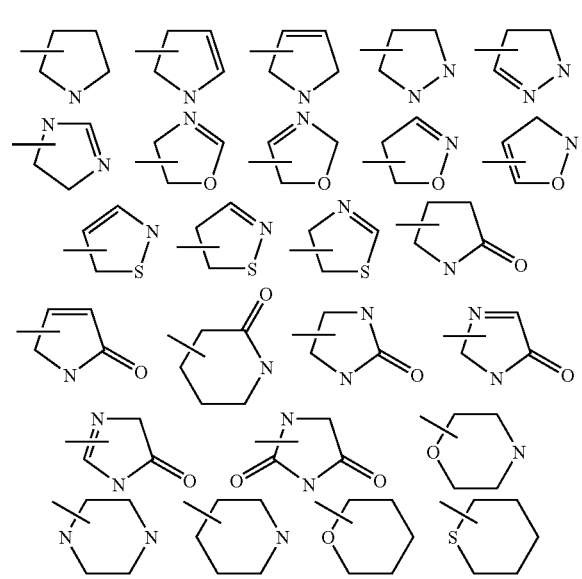

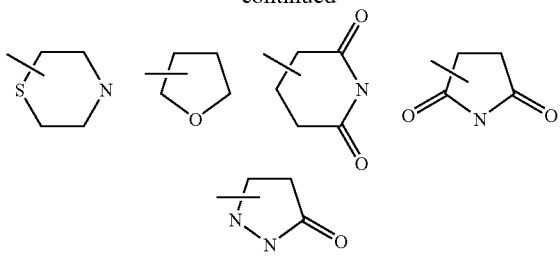

(the ethyl group, the n-propyl group, the i-propyl group, the n-butyl group, the s-butyl group, the t-butyl group, the c-propyl group, the c-butyl group, the c-pentyl group, the c-hexyl group, the ethynyl group, the 1-propynyl group, the 2-propynyl group, the 1-butynyl group, the 2-butynyl group, the 3-butynyl group, the 1-pentynyl group, the 2-pentynyl group, the 4-pentynyl group, the 1-methyl-2-butynyl group, the 1-methyl-3-butynyl group, the 2-methyl-3-butynyl group, the 3-methyl-1-butynyl group and the above heterocyclic groups may be optionally substituted with one or more substituents selected from the groups consisting of hydroxyl groups, amino groups, thiol groups, carboxyl group, phosphonic acid groups, sulfonic acid groups, carbamoyl groups, hydroxycarbamoyl groups, cyanocarbamoyl groups, sulfamoyl groups, hydroxysulfamoyl groups, cyanosulfamoyl groups, tetrazole groups, —CH$_2$CO$_2$H, groups (a 2-quinolyl group, a 3-quinolyl group, a 4-quinolyl group, a 5-quinolyl group, a 6-quinolyl group, a 7-quinolyl group and a 8-quinolyl group) and isoquinolyl groups (a 1-isoquinolyl group, a 3-isoquinolyl group, a 4-isoquinolyl group, a 5-isoquinolyl group, a 6-isoquinolyl group, a 7-isoquinolyl group and a 8-isoquinolyl group);

Heterocyclic groups: a 1,3,4-oxadiazole group, a 1,3,4-thiadiazole group, a 1,2,4-oxadiazole group, a 1,2,4-thiadiazole group, a 1,2,5-oxadiazole group, a 1,2,5-thiadiazole group, a 1,2-oxazole group, a 1,2-thiazole group, a 1,3-oxazole group, a 1,3-thiazole group, a pyrrole group, an imidazole group and a pyrazole group), tautomers, prodrugs or pharmaceutically acceptable salts of the compounds or solvates thereof.

28) The compounds according to 24), 25) or 26) wherein L$^4$ is a bond, and R$^3$ is a methyl group, an ethyl group, a n-propyl group, an i-propyl group, a n-butyl group, a s-butyl group, a t-butyl group, a c-propyl group, a c-butyl group, a c-pentyl group, a c-hexyl group, an ethynyl group, a 1-propynyl group, a 2-propynyl group, a 1-butynyl group, a 2-butynyl group, a 3-butynyl group, a 1-pentynyl group, a 2-pentynyl group, a 4-pentynyl group, a 1-methyl-2-butynyl group, a 1-methyl-3-butynyl group, a 2-methyl-3-butynyl group, a 3-methyl-1-butynyl group or any one of the following heterocyclic groups:
—OCH$_2$CO$_2$H,   —NHCH$_2$CO$_2$H,   —CH$_2$CH$_2$CO$_2$H, —CH$_2$OH, —OCH$_2$OH, —NHCH$_2$OH, —CH$_2$CH$_2$OH, C$_{1-10}$ alkoxycarbonyl groups, C$_{1-10}$ alkyl groups, C$_{2-10}$ alkenyl groups, C$_{2-10}$ alkynyl groups, C$_{2-9}$ heterocyclic groups, C$_{1-10}$ alkoxy groups, C$_{1-10}$ thioalkyl groups, C$_{1-10}$ alkylcarbonyl groups, mono- or di-C$_{1-10}$ alkylamino groups, C$_{1-10}$ alkylcarbonyloxy groups, C$_{1-10}$ alkoxycarbonyl groups, C$_{1-10}$ alkylcarbonylamino groups and the following aryl groups and heterocyclic groups (the C$_{1-10}$ alkyl groups, the C$_{2-10}$ alkenyl groups, the C$_{2-10}$ alkynyl groups, the C$_{2-9}$ heterocyclic groups, the C$_{1-10}$ alkoxy groups, the C$_{1-10}$ thioalkyl groups, the C$_{1-10}$ alkylcarbonyl groups, the mono- or di-C$_{1-10}$ alkylamino groups, the C$_{1-10}$ alkylcarbonyloxy groups, the C$_{3-10}$ alkoxycarbonyl groups, the C$_{1-10}$ alkylcarbonylamino groups and the following aryl groups and heterocyclic groups may be optionally substituted with one or more substituents selected from the group consisting of hydroxyl groups, carboxyl groups, carbamoyl groups, sulfonic acid groups and sulfamoyl groups):

Aryl groups: a phenyl group, thienyl groups (a thienyl groups (a 2-thienyl group and a 3-thienyl group), furyl groups (a 2-furyl group and a 3-furyl group), pyridazinyl groups (a 3-pyridazinyl group and a 4-pyridazinyl group), pyridyl groups (a 2-pyridyl group, a 3-pyridyl group and a 4-pyridyl group), a pyrazinyl group, pyrimidinyl group (a 2-pyrimidinyl group, a 4-pyrimidinyl group and a 5-pyrimidinyl group), quinolyl

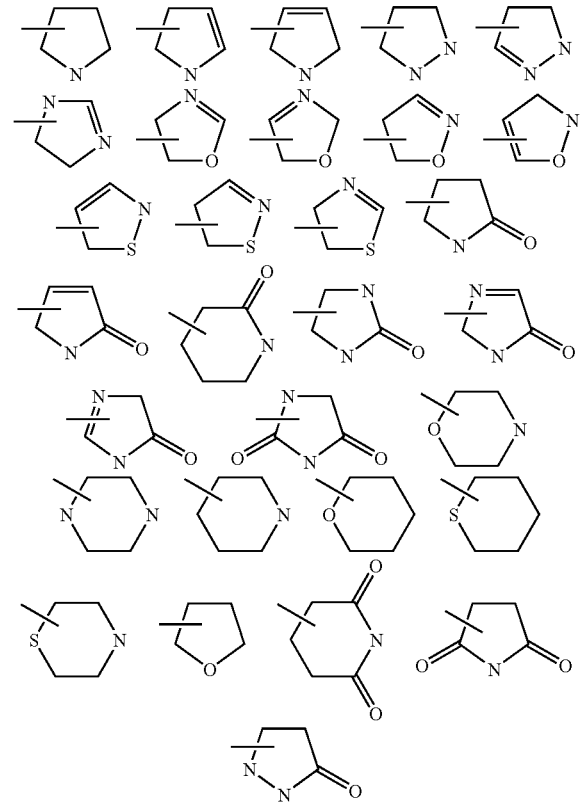

(the methyl group, the ethyl group, the n-propyl group, the i-propyl group, the n-butyl group, the s-butyl group, the t-butyl group, the c-propyl group, the c-butyl group, the c-pentyl group, the c-hexyl group, the ethynyl group, the 1-propynyl group, the 2-propynyl group, the 1-butynyl group, the 2-butynyl group, the 3-butynyl group, the 1-pentynyl group, the 2-pentynyl group, the 4-pentynyl group, the 1-methyl-2-butynyl group, the 1-methyl-3-butynyl group, the 2-methyl-3-butynyl group, the 3-methyl-1-butynyl group and the above heterocyclic groups may be optionally substituted with one or more substituents selected from the groups consisting of hydroxyl groups, amino groups, thiol groups, carboxyl group, phosphonic acid groups, sulfonic acid groups, carbamoyl groups, hydroxycarbamoyl groups, cyanocarbamoyl groups, sulfamoyl groups, hydroxysulfamoyl groups, cyanosulfamoyl groups, tetrazole groups, —CH$_2$CO$_2$H, —OCH$_2$CO$_2$H, —NHCH$_2$CO$_2$H,   —CH$_2$CH$_2$CO$_2$H,   —CH$_2$OH, —OCH$_2$OH, —NHCH$_2$OH, —CH$_2$CH$_2$OH, C$_{1-10}$ alkoxycarbonyl groups, C$_{1-10}$ alkyl groups, C$_{2-10}$ alkenyl groups, C$_{2-10}$ alkynyl groups, C$_{2-9}$ heterocyclic groups, C$_{1-10}$ alkoxy groups, $C_{1-10}$ thioalkyl groups, $C_{1-10}$ alkylcarbonyl groups, mono- or di-$C_{1-10}$ alkylamino groups, $C_{1-10}$ alkylcarbonyloxy groups, $C_{1-10}$ alkoxycarbonyl groups, $C_{1-10}$ alkylaminocarbonyl groups and $C_{1-10}$ alkylcarbonylamino groups (the $C_{1-10}$ alkyl groups, the $C_{2-10}$ alkenyl groups, the $C_{2-10}$ alkynyl groups, the $C_{2-9}$ heterocyclic groups, the $C_{1-10}$ alkoxy groups, the $C_{1-10}$ thioalkyl groups, the $C_{1-10}$ alkylcarbonyl groups, the mono- or di-$C_{1-10}$ alkylamino groups, the $C_{1-10}$ alkylcarbonyloxy groups, the $C_{1-10}$ alkoxycarbonyl groups, the $C_{1-10}$ alkylaminocarbonyl groups and the $C_{1-10}$ alkylcarbonylamino groups may be optionally substituted with one or more substituents selected from the group consisting of $C_{2-14}$ aryl groups, hydroxyl groups, carboxyl groups, carbamoyl groups, sulfonic acid groups and sulfamoyl groups), tautomers, prodrugs or pharmaceutically acceptable salts of the compounds or solvates thereof.

29) The compounds according to 24), 25) or 26) wherein $L^4$ is a bond, and $R^3$ is a methyl group, an ethyl group, a n-propyl group, an i-propyl group, a n-butyl group, a c-propyl group, a c-hexyl group, an ethynyl group, a 1-propynyl group, a 2-propynyl group or a 1-butynyl group (the methyl group, the ethyl group, the n-propyl group, the i-propyl group, the n-butyl group, the c-propyl group, the c-hexyl group, the ethynyl group, the 1-propynyl group, the 2-propynyl group and the 1-butynyl group may be optionally substituted with one or more substituents selected from the groups consisting of hydroxyl groups, amino groups, thiol groups, carboxyl group, phosphonic acid groups, sulfonic acid groups, carbamoyl groups, hydroxycarbamoyl groups, cyanocarbamoyl groups, sulfamoyl groups, hydroxysulfamoyl groups, cyanosulfamoyl groups, tetrazole groups, —CH$_2$CO$_2$H, —OCH$_2$CO$_2$H, —NHCH$_2$CO$_2$H, —CH$_2$CH$_2$CO$_2$H, —CH$_2$OH, —OCH$_2$OH, —NHCH$_2$OH, —CH$_2$CH$_2$OH, $C_{1-10}$ alkoxycarbonyl groups, $C_{1-10}$ alkyl groups, $C_{2-10}$ alkenyl groups, $C_{2-10}$ alkynyl groups, $C_{2-9}$ heterocyclic groups, $C_{1-10}$ alkoxy groups, $C_{1-10}$ thioalkyl groups, $C_{1-10}$ alkylcarbonyl groups, mono- or di-$C_{1-10}$ alkylamino groups, $C_{1-10}$ alkylcarbonyloxy groups, $C_{1-10}$ alkoxycarbonyl groups and $C_{1-10}$ alkylcarbonylamino groups (the $C_{1-10}$ alkyl groups, the $C_{2-10}$ alkenyl groups, the $C_{2-10}$ alkynyl groups, the $C_{2-9}$ heterocyclic groups, the $C_{1-10}$ alkoxy groups, the $C_{1-10}$ thioalkyl groups, the $C_{1-10}$ alkylcarbonyl groups, the mono- or di-$C_{1-10}$ alkylamino groups, the $C_{1-10}$ alkylcarbonyloxy groups, the $C_{1-10}$ alkoxycarbonyl groups and the $C_{1-10}$ alkylcarbonylamino groups may be optionally substituted with one or more substituents selected from the group consisting of hydroxyl groups, carboxyl groups, carbamoyl groups, sulfonic acid groups and sulfamoyl groups)), tautomers, prodrugs or pharmaceutically acceptable salts of the compounds or solvates thereof.

30) The compounds according to 24), 25) or 26) wherein $L^4$ is a bond, and $R^3$ is a methyl group, an ethyl group, a n-propyl group, an i-propyl group, a n-butyl group, a c-propyl group, a c-hexyl group, an ethynyl group, a 1-propynyl group, a 2-propynyl group or a 1-butynyl group (the methyl group, the ethyl group, the n-propyl group, the i-propyl group, the n-butyl group, the c-propyl group, the c-hexyl group, the ethynyl group, the 1-propynyl group, the 2-propynyl group and the 1-butynyl group may be optionally substituted with one or more substituents selected from the groups consisting of hydroxyl groups, amino groups, thiol groups, carboxyl group, phosphonic acid groups, sulfonic acid groups, carbamoyl groups, hydroxycarbamoyl groups, cyanocarbamoyl groups, sulfamoyl groups, hydroxysulfamoyl groups, cyanosulfamoyl groups, tetrazole groups, —CH$_2$CO$_2$H, —OCH$_2$CO$_2$H, —NHCH$_2$CO$_2$H, —CH$_2$CH$_2$CO$_2$H, —CH$_2$OH, —OCH$_2$OH, —NHCH$_2$OH, —CH$_2$CH$_2$OH and $C_{1-10}$ alkoxycarbonyl groups), tautomers, prodrugs or pharmaceutically acceptable salts of the compounds or solvates thereof.

31) The compounds according to 24), 25) or 26) wherein $L^4$ is a bond, and $R^3$ is any one of the following heterocyclic groups:

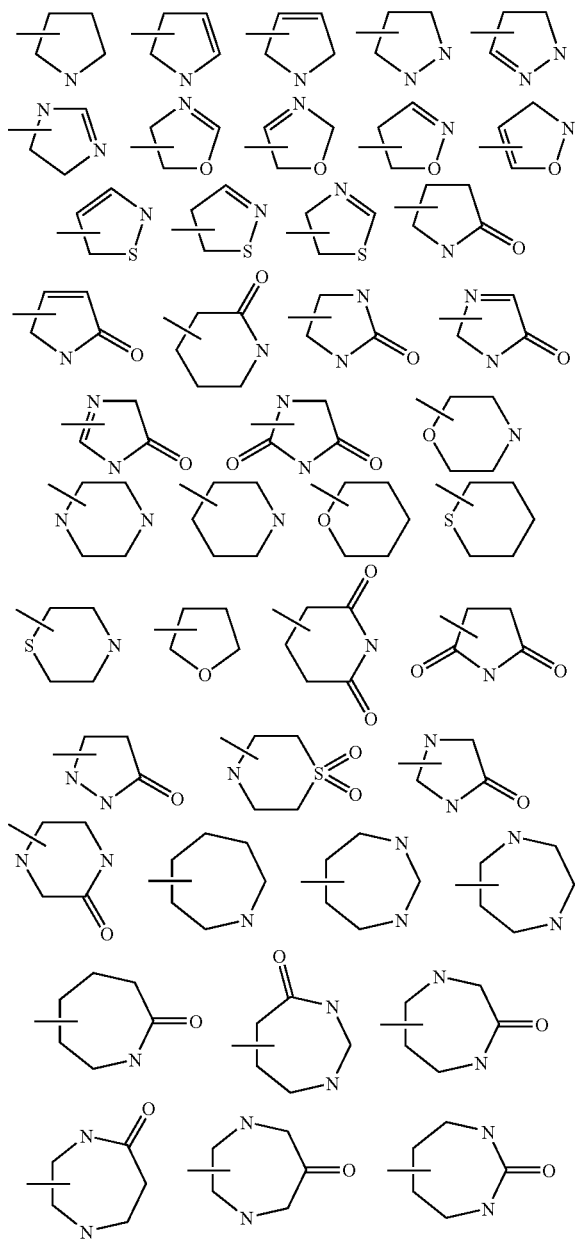

(the above heterocyclic groups may be optionally substituted with one or more substituents selected from the group consisting of hydrogen atoms, hydroxyl groups, amino groups, halogen atoms, nitro groups, thiol groups, carboxyl group, phosphonic acid groups, sulfonic acid groups, carbamoyl groups, hydroxycarbamoyl groups, cyanocarbamoyl groups, sulfamoyl groups, hydroxysulfamoyl groups, cyanosulfamoyl groups, tetrazole groups, phenyl groups, thienyl groups, pyridyl groups, furyl groups, —CH$_2$CO$_2$H, —OCH$_2$CO$_2$H, —NHCH$_2$CO$_2$H, —CH$_2$CH$_2$CO$_2$H, —CH$_2$OH, —OCH$_2$OH, —NHCH$_2$OH, —CH$_2$CH$_2$OH, —(C═O)CO$_2$H, —CH$_2$(C═O)CO$_2$H, —NH(C═O)CO$_2$H, —NHS (=O)₂NH₂, C$_{1-10}$ alkoxycarbonyl groups, C$_{1-10}$ alkyl groups (the C$_{1-10}$ alkyl groups may be substituted with one or more substituents selected from the group consisting of hydroxyl groups, carboxyl groups, phenyl groups, 2-thienyl groups, 3-thienyl groups, 2-furyl groups, 3-furyl groups, 3-pyridazinyl groups, 4-pyridazinyl groups, 2-pyridyl groups, 3-pyridyl groups, 4-pyridyl groups, pyrazinyl groups, 2-pyrimidinyl groups, 4-pyrimidinyl groups, 5-pyrimidinyl groups, 1,3-oxazolyl groups, 1,3-thiazolyl groups, pyrrolyl groups, imidazolyl groups, pyrazolyl groups, 2-quinolyl groups, 3-quinolyl groups, 4-quinolyl groups, 5-quinolyl groups, 6-quinolyl groups, 7-quinolyl groups, 8-quinolyl groups, 1-isoquinolyly groups, 3-isoquinolyly groups, 4-isoquinolyly groups, 5-isoquinolyly groups, 6-isoquinolyly groups, 7-isoquinolyly groups, 8-isoquinolyly groups, 1,3,4-oxadiazole groups, 1,3,4-thiadiazole groups, 1,2,4-oxadiazole groups, 1,2,4-thiadiazole groups, 1,2,5-oxadiazole groups, 1,2,5-thiadiazole groups, 1,2-oxazole groups, 1,2-thiazole groups and C$_{1-10}$ alkylaminocarbonyl groups (the C$_{1-10}$ alkylaminocarbonyl groups may be substituted with one or more substituents selected from the group consisting of phenyl groups, 2-thienyl groups, 3-thienyl groups, 2-furyl groups, 3-furyl groups, 3-pyridazinyl groups, 4-pyridazinyl groups, 2-pyridyl groups, 3-pyridyl groups, 4-pyridyl groups, 2-quinolyl groups, 3-quinolyl groups, 4-quinolyl groups, 5-quinolyl groups, 6-quinolyl groups, 7-quinolyl groups, 8-quinolyl groups, 1-isoquinolyly groups, 3-isoquinolyly groups, 4-isoquinolyly groups, 5-isoquinolyly groups, 6-isoquinolyly groups, 7-isoquinolyly groups, 8-isoquinolyly groups, 1,3,4-oxadiazole groups, 1,3,4-thiadiazole groups, 1,2,4-oxadiazole groups, 1,2,4-thiadiazole groups, 1,2,5-oxadiazole groups, 1,2,5-thiadiazole groups, 1,2-oxazole groups, 1,2-thiazole groups, 1,3-oxazole groups, 1,3-thiazole groups, pyrrole groups, imidazole groups and pyrazole groups)), C$_{2-10}$ alkenyl groups, C$_{2-10}$ alkynyl groups, C$_{2-9}$ heterocyclic groups, C$_{1-10}$ thioalkyl groups, C$_{1-10}$ alkoxy groups, C$_{1-10}$ alkylcarbonyl groups, C$_{1-10}$ alkylaminocarbonyl groups, C$_{1-10}$ dialkylaminocarbonyl groups, mono- or di-C$_{1-10}$ alkylamino groups, C$_{1-10}$ alkylcarbonyloxy groups, C$_{1-10}$ alkoxycarbonyl groups, C$_{1-10}$ alkylcarbonylamino groups (the C$_{1-10}$ alkoxy groups, the C$_{1-10}$ alkylcarbonyl groups, the C$_{1-10}$ alkylaminocarbonyl groups, the C$_{1-10}$ dialkylaminocarbonyl groups, the mono- or di-C$_{1-10}$ alkylamino groups, the C$_{1-10}$ alkylcarbonyloxy groups, the C$_{1-10}$ alkoxycarbonyl groups and the C$_{1-10}$ alkylcarbonylamino groups may be substituted with one or more substituents selected from the group consisting of carboxyl groups, carbamoyl groups, sulfamoyl groups, sulfo groups, phenyl groups, 2-thienyl groups, 3-thienyl groups, 2-furyl groups, 3-furyl groups, 3-pyridazinyl groups, 4-pyridazinyl groups, 2-pyridyl groups, 3-pyridyl groups, 4-pyridyl groups, 2-quinolyl groups, 3-quinolyl groups, 4-quinolyl groups, 5-quinolyl groups, 6-quinolyl groups, 7-quinolyl groups, 8-quinolyl groups, 1-isoquinolyly groups, 3-isoquinolyly groups, 4-isoquinolyly groups, 5-isoquinolyly groups, 6-isoquinolyly groups, 7-isoquinolyly groups, 8-isoquinolyly groups, 1,3,4-oxadiazole groups, 1,3,4-thiadiazole groups, 1,2,4-oxadiazole groups, 1,2,4-thiadiazole groups, 1,2,5-oxadiazole groups, 1,2,5-thiadiazole groups, 1,2-oxazole groups, 1,2-thiazole groups, 1,3-oxazole groups, 1,3-thiazole groups, pyrrole groups, imidazole groups and pyrazole groups), pyridylaminocarbonyl groups, phenyl groups, 2-thienyl groups, 3-thienyl groups, 2-furyl groups, 3-furyl groups, 3-pyridazinyl groups, 4-pyridazinyl groups, 2-pyridyl groups, 3-pyridyl groups; 4-pyridyl groups, 2-quinolyl groups, 3-quinolyl groups, 4-quinolyl groups, 5-quinolyl groups, 6-quinolyl groups, 7-quinolyl groups, 8-quinolyl groups, 1-isoquinolyly groups, 3-isoquinolyly groups, 4-isoquinolyly groups, 5-isoquinolyly groups, 6-isoquinolyly groups, 7-isoquinolyly groups, 8-isoquinolyly groups, 1,3,4-oxadiazole groups, 1,3,4-thiadiazole groups, 1,2,4-oxadiazole groups, 1,2,4-thiadiazole groups, 1,2,5-oxadiazole groups, 1,2,5-thiadiazole groups, 1,2-oxazole groups, 1,2-thiazole groups, 1,3-oxazole groups, 1,3-thiazole groups, pyrrole groups, imidazole groups and pyrazole groups), tautomers, prodrugs or pharmaceutically acceptable salts of the compounds or solvates thereof.

32) The compounds according to 24), 25) or 26) wherein L$^4$ is a bond, and R$^3$ is any one of the following heterocyclic groups:

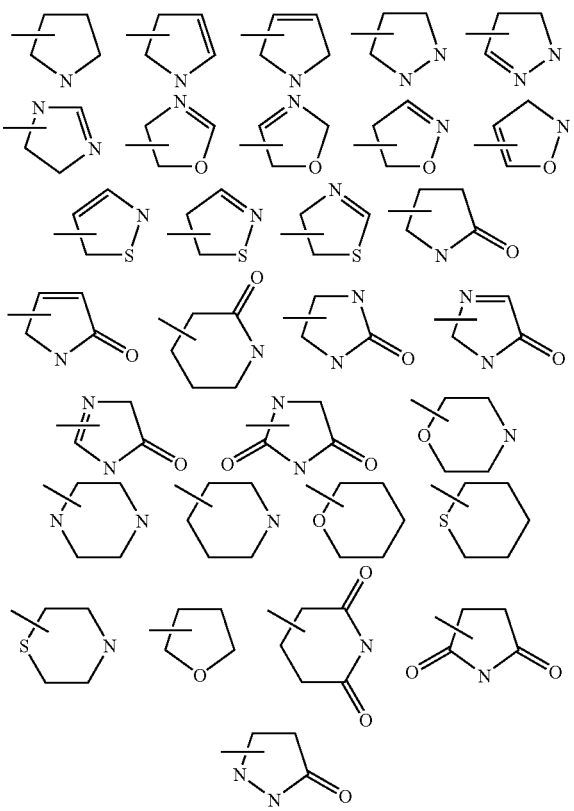

(the above heterocyclic groups may be optionally substituted with one or more substituents selected from the group consisting of hydroxyl groups, amino groups, thiol groups, carboxyl group, phosphonic acid groups, sulfonic acid groups, carbamoyl groups, hydroxycarbamoyl groups, cyanocarbamoyl groups, sulfamoyl groups, hydroxysulfamoyl groups, cyanosulfamoyl groups, tetrazole groups, —CH$_2$CO$_2$H, —OCH$_2$CO$_2$H, —NHCH$_2$CO$_2$H, —CH$_2$CH$_2$CO$_2$H, —CH$_2$OH, —OCH$_2$OH, —NHCH$_2$OH, —CH$_2$CH$_2$OH, C$_{1-10}$ alkoxycarbonyl groups, C$_{1-10}$ alkyl groups, C$_{1-10}$ alkylcarbonyl groups, C$_{1-10}$ alkylsulfonyl groups, C$_{1-10}$ alkylaminosulfonyl groups, C$_{1-10}$ alkylaminocarbonyl groups and C$_{1-10}$ dialkylaminocarbonyl groups (the C$_{1-10}$ alkyl groups, the C$_{1-10}$ alkylcarbonyl groups, the C$_{1-10}$ alkylsulfonyl groups, the C$_{1-10}$ alkylaminosulfonyl groups, the C$_{1-10}$ alkylaminocarbonyl groups and the C$_{1-10}$ dialkylaminocarbonyl groups may be substituted with one or more substituents selected from the group consisting of phenyl groups, thienyl groups, furyl groups, pyridyl groups, nitro groups, cyano groups, hydroxyl groups, amino groups, carboxyl groups, phosphonic acid groups, sulfonic acid groups, carbamoyl groups, sulfamoyl groups and tetrazole groups)), tautomers, prodrugs or pharmaceutically acceptable salts of the compounds or solvates thereof.

33) The compounds according to 24), 25) or 26) wherein $L^4$ is a bond, and $R^3$ is any one of the following heterocyclic groups:

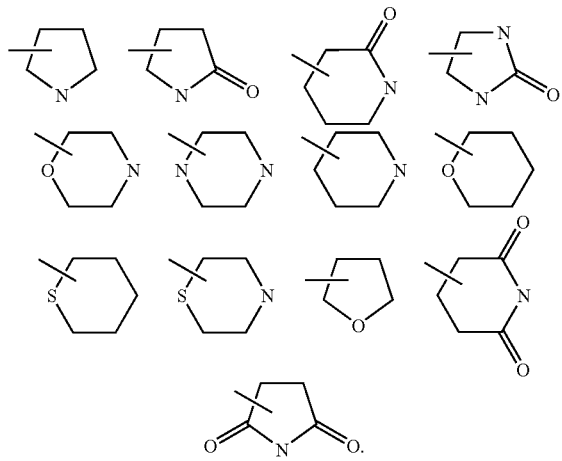

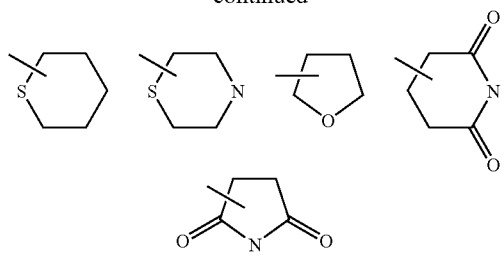

(the above heterocyclic groups may be optionally substituted with one or more substituents selected from the group consisting of hydroxyl groups, amino groups, thiol groups, carboxyl group, phosphonic acid groups, sulfonic acid groups, carbamoyl groups, hydroxycarbamoyl groups, cyanocarbamoyl groups, sulfamoyl groups, hydroxysulfamoyl groups, cyanosulfamoyl groups, tetrazole groups, —$CH_2CO_2H$, —$OCH_2CO_2H$, —$NHCH_2CO_2H$, —$CH_2CH_2CO_2H$, —$CH_2OH$, —$OCH_2OH$, —$NHCH_2OH$, —$CH_2CH_2OH$, $C_{1-10}$ alkoxycarbonyl groups, $C_{1-10}$ alkyl groups, $C_{2-10}$ alkenyl groups, $C_{2-10}$ alkynyl groups, $C_{2-9}$ heterocyclic groups, $C_{1-10}$ alkoxy groups, $C_{1-10}$ thioalkyl groups, $C_{1-10}$ alkylcarbonyl groups, mono- or di-$C_{1-10}$ alkylamino groups, $C_{1-10}$ alkylcarbonyloxy groups, $C_{1-10}$ alkoxycarbonyl groups and $C_{1-10}$ alkylcarbonylamino groups (the $C_{1-10}$ alkyl groups, the $C_{2-10}$ alkenyl groups, the $C_{2-10}$ alkynyl groups, the $C_{2-9}$ heterocyclic groups, the $C_{1-10}$ alkoxy groups, the $C_{1-10}$ thioalkyl groups, the $C_{1-10}$ alkylcarbonyl groups, the mono- or di-$C_{1-10}$ alkylamino groups, the $C_{1-10}$ alkylcarbonyloxy groups, the $C_{1-10}$ alkoxycarbonyl groups and the $C_{1-10}$ alkylcarbonylamino groups may be optionally substituted with one or more substituents selected from the group consisting of hydroxyl groups, carboxyl groups, carbamoyl groups, sulfonic acid groups and sulfamoyl groups)), tautomers, prodrugs or pharmaceutically acceptable salts of the compounds or solvates thereof.

34) The compounds according to 24), 25) or 26) wherein $L^4$ is a bond, and $R^3$ is any one of the following heterocyclic groups:

(the above heterocyclic groups are optionally substituted with one or more substituents selected from the group consisting of hydroxyl groups, amino groups, thiol groups, carboxyl group, phosphonic acid groups, sulfonic acid groups, carbamoyl groups, hydroxycarbamoyl groups, cyanocarbamoyl groups, sulfamoyl groups, hydroxysulfamoyl groups, cyanosulfamoyl groups, tetrazole groups, —$CH_2CO_2H$, —$OCH_2CO_2H$, —$NHCH_2CO_2H$, —$CH_2CH_2CO_2H$, —$CH_2OH$, —$OCH_2OH$, —$NHCH_2OH$, —$CH_2CH_2OH$, $C_{1-10}$ alkoxycarbonyl groups, methyl groups, ethyl groups, n-propyl groups, i-propyl groups, methylcarbonyl groups, ethylcarbonyl groups, n-propylcarbonyl groups, methylsulfonyl groups, ethylsulfonyl groups, n-propylsulfonyl groups, i-propyl sulfonyl groups, methylaminosulfonyl groups, ethylaminosulfonyl groups, n-propylaminosulfonyl groups, i-propylaminosulfonyl groups, methylaminocarbonyl groups, ethylaminocarbonyl groups, n-propylaminocarbonyl groups, i-propylaminocarbonyl groups, c-propylaminocarbonyl groups and n-butylaminocarbonyl groups (the methyl groups, the ethyl groups, the n-propyl groups, the i-propyl groups, the methylcarbonyl groups, the ethylcarbonyl groups, the n-propylcarbonyl groups, the methylsulfonyl groups, the ethylsulfonyl groups, the n-propylsulfonyl groups, the i-propylsulfonyl groups, the methylaminosulfonyl groups, the ethylaminosulfonyl groups, the n-propylaminosulfonyl groups, the i-propylaminosulfonyl groups, the methylaminocarbonyl groups, the ethylaminocarbonyl groups, the n-propylaminocarbonyl groups, the i-propylaminocarbonyl groups, the c-propylaminocarbonyl groups and the n-butylaminocarbonyl groups may be substituted with one or more substituents selected from the group consisting of phenyl groups, thienyl groups, pyridyl groups and furyl groups)), tautomers, prodrugs or pharmaceutically acceptable salts of the compounds or solvates thereof.

35) The compounds according to 24), 25) or 26) wherein $L^4$ is $NR^{22}$ (wherein $R^{22}$ is a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group, the $C_{1-10}$ alkylcarbonyloxy group, the $C_{1-10}$ alkoxycarbonyl group and the $C_{1-10}$ alkylcarbonyl group may be optionally substituted with one or more substituents selected from the group consisting of carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)) or a $C_{2-14}$ aryl group (the $C_{2-14}$ aryl group may be optionally substituted with one or more substituents selected from the group consisting of $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups)), and $R^3$ is an ethyl group, a n-propyl group, an i-propyl group, a n-butyl group, a s-butyl group, a t-butyl group, a c-propyl group, a c-butyl group, a c-pentyl group, a c-hexyl group, an ethynyl group, a 1-propynyl group, a 2-propynyl group, a 1-butynyl group, a 2-butynyl group, a 3-butynyl group, a 1-pentynyl group, a 2-pentynyl group, a 4-pentynyl group, a 1-methyl-2-butynyl group, a 1-methyl-3-butynyl group, a 2-methyl-3-butynyl group, a 3-methyl-1-butynyl group or any one of the following heterocyclic groups:

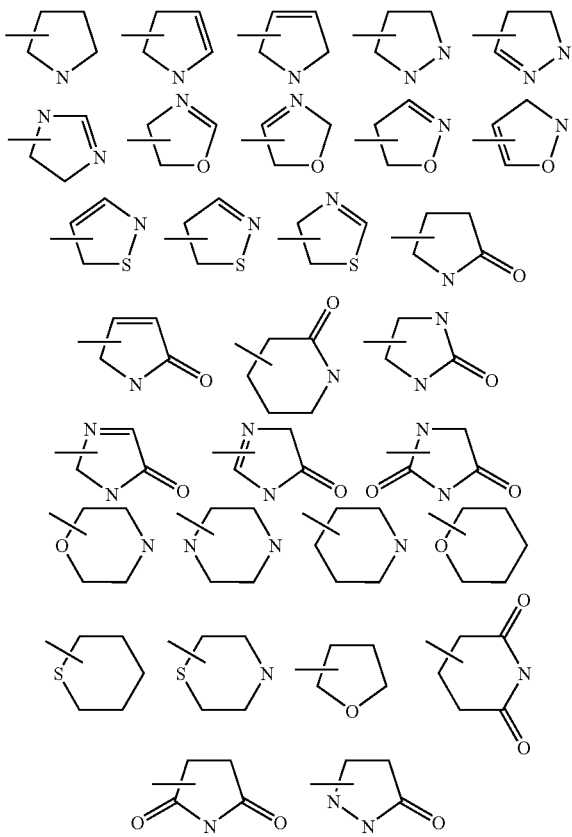

(the ethyl group, the n-propyl group, the i-propyl group, the n-butyl group, the s-butyl group, the t-butyl group, the c-propyl group, the c-butyl group, the c-pentyl group, the c-hexyl group, the ethynyl group, the 1-propynyl group, the 2-propynyl group, the 1-butynyl group, the 2-butynyl group, the 3-butynyl group, the 1-pentynyl group, the 2-pentynyl group, the 4-pentynyl group, the 1-methyl-2-butynyl group, the 1-methyl-3-butynyl group, the 2-methyl-3-butynyl group, the 3-methyl-1-butynyl group and the above heterocyclic groups may be optionally substituted with one or more substituents selected from the groups consisting of hydroxyl groups, amino groups, thiol groups, carboxyl group, phosphonic acid groups, sulfonic acid groups, carbamoyl groups, hydroxycarbamoyl groups, cyanocarbamoyl groups, sulfamoyl groups, hydroxysulfamoyl groups, cyanosulfamoyl groups, tetrazole groups, —$CH_2CO_2H$, —$OCH_2CO_2H$, —$NHCH_2CO_2H$, —$CH_2CH_2CO_2H$, —$CH_2OH$, —$OCH_2OH$, —$NHCH_2OH$, —$CH_2CH_2OH$, $C_{1-10}$ alkoxycarbonyl groups, $C_{1-10}$ alkyl groups, $C_{2-10}$ alkenyl groups, $C_{2-10}$ alkynyl groups, $C_{2-9}$ heterocyclic groups, $C_{1-10}$ alkoxy groups, $C_{1-10}$ thioalkyl groups, $C_{1-10}$ alkylcarbonyl groups, mono- or di-$C_{1-10}$ alkylamino groups, $C_{1-10}$ alkylcarbonyloxy groups, $C_{1-10}$ alkoxycarbonyl groups and $C_{1-10}$ alkylcarbonylamino groups (the $C_{1-10}$ alkyl groups, the $C_{2-10}$ alkenyl groups, the $C_{2-10}$ alkynyl groups, the $C_{2-9}$ heterocyclic groups, the $C_{1-10}$ alkoxy groups, the $C_{1-10}$ thioalkyl groups, the $C_{1-10}$ alkylcarbonyl groups, the mono- or di-$C_{1-10}$ alkylamino groups, the $C_{1-10}$ alkylcarbonyloxy groups, the $C_{1-10}$ alkoxycarbonyl groups and the $C_{1-10}$ alkylcarbonylamino groups may be optionally substituted with one or more substituents selected from the group consisting of hydroxyl groups, carboxyl groups, carbamoyl groups, sulfonic acid groups and sulfamoyl groups):

Aryl groups: a phenyl group, thienyl groups (a 2-thienyl group and a 3-thienyl group), furyl groups (a 2-furyl group and a 3-furyl group), pyridazinyl groups (a 3-pyridazinyl group and a 4-pyridazinyl group), pyridyl groups (a 2-pyridyl group, a 3-pyridyl group and a 4-pyridyl group), quinolyl groups (a 2-quinolyl group, a 3-quinolyl group, a 4-quinolyl group, a 5-quinolyl group, a 6-quinolyl group, a 7-quinolyl group and a 8-quinolyl group) and isoquinolyl groups (a 1-isoquinolyl group, a 3-isoquinolyl group, a 4-isoquinolyl group, a 5-isoquinolyl group, a 6-isoquinolyl group, a 7-isoquinolyl group and a 8-isoquinolyl group);

Heterocyclic groups: a 1,3,4-oxadiazole group, a 1,3,4-thiadiazole group, a 1,2,4-oxadiazole group, a 1,2,4-thiadiazole group, a 1,2,5-oxadiazole group, a 1,2,5-thiadiazole group, a 1,2-oxazole group and a 1,2-thiazole group), tautomers, prodrugs or pharmaceutically acceptable salts of the compounds or solvates thereof.

36) The compounds according to 24), 25) or 26) wherein $L^4$ is $NR^{22}$ (wherein $R^{22}$ is a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group, the $C_{1-10}$ alkylcarbonyloxy group, the $C_{1-10}$ alkoxycarbonyl group and the $C_{1-10}$ alkylcarbonyl group may be optionally substituted with one or more substituents selected from the group consisting of carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)) or a $C_{2-14}$ aryl group (the $C_{2-14}$ aryl group may be optionally substituted with one or more substituents selected from the group consisting of $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups)), and $R^3$ is a methyl group, an ethyl group, a n-propyl group, an i-propyl group, a n-butyl group, a s-butyl group, a t-butyl group, a c-propyl group, a c-butyl group, a c-pentyl group, a c-hexyl group, an ethynyl group, a 1-propynyl group, a 2-propynyl group, a 1-butynyl group, a 2-butynyl group, a 3-butynyl group, a 1-pentynyl group, a 2-pentynyl group, a 4-pentynyl group, a 1-methyl-2-butynyl group, a 1-methyl-3-butynyl group, a 2-methyl-3-butynyl group, a 3-methyl-1-butynyl group or any one of the following heterocyclic groups:

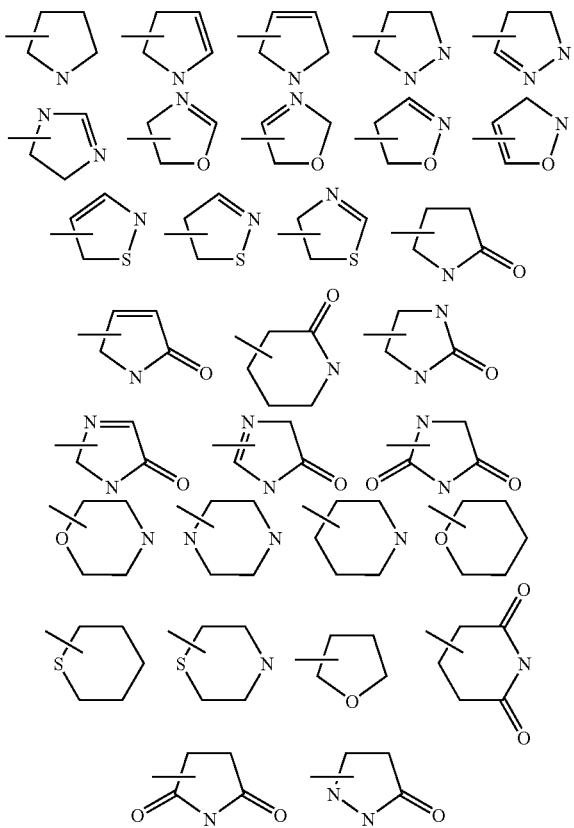

(the methyl group, the ethyl group, the n-propyl group, the i-propyl group, the n-butyl group, the s-butyl group, the t-butyl group, the c-propyl group, the c-butyl group, the c-pentyl group, the c-hexyl group, the ethynyl group, the 1-propynyl group, the 2-propynyl group, the 1-butynyl group, the 2-butynyl group, the 3-butynyl group, the 1-pentynyl group, the 2-pentynyl group, the 4-pentynyl group, the 1-methyl-2-butynyl group, the 1-methyl-3-butynyl group, the 2-methyl-3-butynyl group, the 3-methyl-1-butynyl group and the above heterocyclic groups may be optionally substituted with one or more substituents selected from the groups consisting of hydroxyl groups, amino groups, thiol groups, carboxyl group, phosphonic acid groups, sulfonic acid groups, carbamoyl groups, hydroxycarbamoyl groups, cyanocarbamoyl groups, sulfamoyl groups, hydroxysulfamoyl groups, cyanosulfamoyl groups, tetrazole groups, —$CH_2CO_2H$, —$OCH_2CO_2H$, —$NHCH_2CO_2H$, —$CH_2CH_2CO_2H$, —$CH_2OH$, —$OCH_2OH$, —$NHCH_2OH$, —$CH_2CH_2OH$, $C_{1-10}$ alkoxycarbonyl groups, $C_{1-10}$ alkyl groups, $C_{2-10}$ alkenyl groups, $C_{2-10}$ alkynyl groups, $C_{2-9}$ heterocyclic groups, $C_{1-10}$ alkoxy groups, $C_{1-10}$ thioalkyl groups, $C_{1-10}$ alkylcarbonyl groups, mono- or di-$C_{1-10}$ alkylamino groups, $C_{1-10}$ alkylcarbonyloxy groups, $C_{1-10}$ alkoxycarbonyl groups and $C_{1-10}$ alkylcarbonylamino groups (the $C_{1-10}$ alkyl groups, the $C_{2-10}$ alkenyl groups, the $C_{2-10}$ alkynyl groups, the $C_{2-9}$ heterocyclic groups, the $C_{1-10}$ alkoxy groups, the $C_{1-10}$ thioalkyl groups, the $C_{1-10}$ alkylcarbonyl groups, the mono- or di-$C_{1-10}$ alkylamino groups, the $C_{1-10}$ alkylcarbonyloxy groups, the $C_{1-10}$ alkoxycarbonyl groups and the $C_{1-10}$ alkylcarbonylamino groups may be optionally substituted with one or more substituents selected from the group consisting of hydroxyl groups, carboxyl groups, carbamoyl groups, sulfonic acid groups and sulfamoyl groups)), tautomers, prodrugs or pharmaceutically acceptable salts of the compounds or solvates thereof.

37) The compounds according to 24), 25) or 26) wherein $L^4$ is $NR^{22}$ (wherein $R^{22}$ is a hydrogen atom, a hydroxyl group, a formyl group, a $C_{1-10}$ alkyl group, a $C_{2-10}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group, the $C_{1-10}$ alkylcarbonyloxy group, the $C_{1-10}$ alkoxycarbonyl group and the $C_{1-10}$ alkylcarbonyl group may be optionally substituted with one or more substituents selected from the group consisting of carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)) or a $C_{2-14}$ aryl group (the $C_{2-14}$ aryl group may be optionally substituted with one or more substituents selected from the group consisting of $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups)), and $R^3$ is a methyl group, an ethyl group, a n-propyl group, an i-propyl group, a n-butyl group, a c-propyl group, a c-hexyl group, an ethynyl group, a 1-propynyl group, a 2-propynyl group or a 1-butynyl group (the methyl group, the ethyl group, the n-propyl group, the i-propyl group, the n-butyl group, the c-propyl group, the c-hexyl group, the ethynyl group, the 1-propynyl group, the 2-propynyl group and the 1-butynyl group may be optionally substituted with one or more substituents selected from the groups consisting of hydroxyl groups, amino groups, thiol groups, carboxyl group, phosphonic acid groups, sulfonic acid groups, carbamoyl groups, hydroxycarbamoyl groups, cyanocarbamoyl groups, sulfamoyl groups, hydroxysulfamoyl groups, cyanosulfamoyl groups, tetrazole groups, —$CH_2CO_2H$, —$OCH_2CO_2H$, —$NHCH_2CO_2H$, —$CH_2CH_2CO_2H$, —$CH_2OH$, —$OCH_2OH$, —$NHCH_2OH$, —$CH_2CH_2OH$, $C_{1-10}$ alkoxycarbonyl groups, $C_{1-10}$ alkyl groups, $C_{2-10}$ alkenyl groups, $C_{2-10}$ alkynyl groups, $C_{2-9}$ heterocyclic groups, $C_{1-10}$ alkoxy groups, $C_{1-10}$ thioalkyl groups, $C_{1-10}$ alkylcarbonyl groups, mono- or di-$C_{1-10}$ alkylamino groups, $C_{1-10}$ alkylcarbonyloxy groups, $C_{1-10}$ alkoxycarbonyl groups and $C_{1-10}$ alkylcarbonylamino groups (the $C_{1-10}$ alkyl groups, the $C_{2-10}$ alkenyl groups, the $C_{2-10}$ alkynyl groups, the $C_{2-9}$ heterocyclic groups, the $C_{1-10}$ alkoxy groups, the $C_{1-10}$ thioalkyl groups, the $C_{1-10}$ alkylcarbonyl groups, the mono- or di-$C_{1-10}$ alkylamino groups, the $C_{1-10}$ alkylcarbonyloxy groups, the $C_{1-10}$ alkoxycarbonyl groups and the $C_{1-10}$ alkylcarbonylamino groups may be optionally substituted with one or more substituents selected from the group consisting of hydroxyl groups, carboxyl groups, carbamoyl groups, sulfonic acid groups and sulfamoyl groups)), tautomers, prodrugs or pharmaceutically acceptable salts of the compounds or solvates thereof.

38) The compounds according to 24), 25) or 26) wherein $L^4$ is $NR^{22}$ (wherein $R^{22}$ is a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group, the $C_{1-10}$ alkylcarbonyloxy group, the $C_{1-10}$ alkoxycarbonyl group and the $C_{1-10}$ alkylcarbonyl group may be optionally substituted with one or more substituents selected from the group consisting of carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)) or a $C_{2-14}$ aryl group (the $C_{2-14}$ aryl group may be optionally substituted with one or more substituents selected from the group consisting of $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups)), and $R^3$ is a methyl group, an ethyl group, a n-propyl group, an i-propyl group, a n-butyl group, a c-propyl group, a c-hexyl group, an ethynyl group, a 1-propynyl group, a 2-propynyl group or a 1-butynyl group (the methyl group, the ethyl group, the n-propyl group, the i-propyl group, the n-butyl group, the c-propyl group, the c-hexyl group, the ethynyl group, the 1-propynyl group, the 2-propynyl group and the 1-butynyl group may be optionally substituted with one or more substituents selected from the groups consisting of hydroxyl groups, amino groups, thiol groups, carboxyl group, phosphonic acid groups, sulfonic acid groups, carbamoyl groups, hydroxycarbamoyl groups, cyanocarbamoyl groups, sulfamoyl groups, hydroxysulfamoyl groups, cyanosulfamoyl groups, tetrazole groups, —$CH_2CO_2H$, —$OCH_2CO_2H$, —$NHCH_2CO_2H$, —$CH_2CH_2CO_2H$, —$CH_2OH$, —$OCH_2OH$, —$NHCH_2OH$, —$CH_2CH_2OH$ and $C_{1-10}$ alkoxycarbonyl groups), tautomers, prodrugs or pharmaceutically acceptable salts of the compounds or solvates thereof.

39) The compounds according to 24), 25) or 26) wherein $L^4$ is $NR^{22}$ (wherein $R^{22}$ is a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group, the $C_{1-10}$ alkylcarbonyloxy group, the $C_{1-10}$ alkoxycarbonyl group and the $C_{1-10}$ alkylcarbonyl group may be optionally substituted with one or more substituents selected from the group consisting of carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)) or a $C_{2-14}$ aryl group (the $C_{2-14}$ aryl group may be optionally substituted with one or more substituents selected from the group consisting of $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups)), and $R^3$ is any one of the following heterocyclic groups:

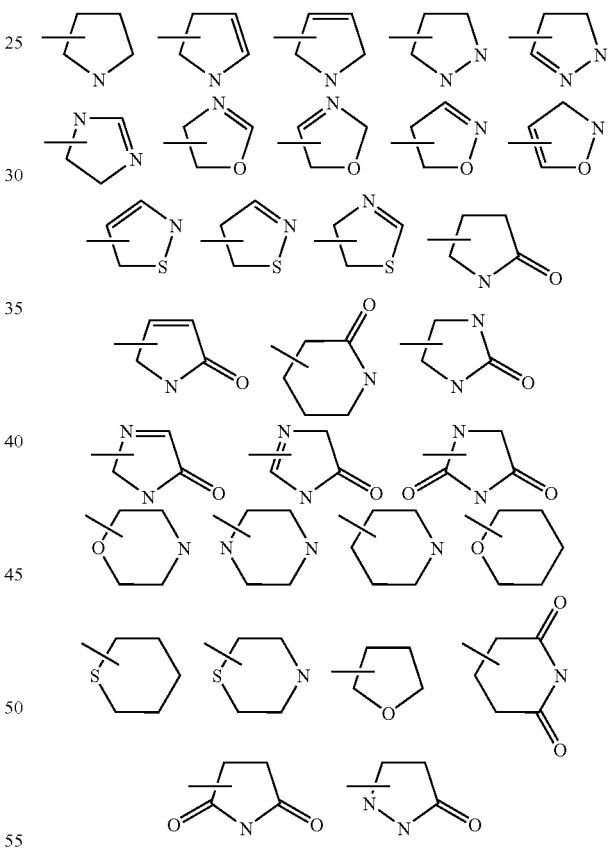

(the above heterocyclic groups may be optionally substituted with one or more substituents selected from the group consisting of hydroxyl groups, amino groups, thiol groups, carboxyl group, phosphonic acid groups, sulfonic acid groups, carbamoyl groups, hydroxycarbamoyl groups, cyanocarbamoyl groups, sulfamoyl groups, hydroxysulfamoyl groups, cyanosulfamoyl groups, tetrazole groups, —$CH_2CO_2H$, —$OCH_2CO_2H$, —$NHCH_2CO_2H$, —$CH_2CH_2CO_2H$, —$CH_2OH$, —$OCH_2OH$, —$NHCH_2OH$, —$CH_2CH_2OH$, $C_{1-10}$ alkoxycarbonyl groups, $C_{1-10}$ alkyl groups, $C_{2-10}$ alkenyl groups, $C_{2-10}$ alkynyl groups, $C_{2-9}$ heterocyclic groups, $C_{1-10}$ alkoxy groups, $C_{1-10}$ thioalkyl groups, $C_{1-10}$ alkylcarbonyl groups, mono- or di-$C_{1-10}$ alkylamino groups, $C_{1-10}$ alkylcarbonyloxy groups, $C_{1-10}$ alkoxycarbonyl groups and $C_{1-10}$ alkylcarbonylamino groups (the $C_{1-10}$ alkyl groups, the $C_{2-10}$ alkenyl groups, the $C_{2-10}$ alkynyl groups, the $C_{2-9}$ heterocyclic groups, the $C_{1-10}$ alkoxy groups, the $C_{1-10}$ thioalkyl groups, the $C_{1-10}$ alkylcarbonyl groups, the mono- or di-$C_{1-10}$ alkylamino groups, the $C_{1-10}$ alkylcarbonyloxy groups, the $C_{1-10}$ alkoxycarbonyl groups and the $C_{1-10}$ alkylcarbonylamino groups may be optionally substituted with one or more substituents selected from the group consisting of hydroxyl groups, carboxyl groups, carbamoyl groups, sulfonic acid groups and sulfamoyl groups)), tautomers, prodrugs or pharmaceutically acceptable salts of the compounds or solvates thereof.

40) The compounds according to 24), 25) or 26) wherein $L^4$ is $NR^{22}$ (wherein $R^{22}$ is a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group, the $C_{1-10}$ alkylcarbonyloxy group, the $C_{1-10}$ alkoxycarbonyl group and the $C_{1-10}$ alkylcarbonyl group may be optionally substituted with one or more substituents selected from the group consisting of carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)) or a $C_{2-14}$ aryl group (the $C_{2-14}$ aryl group may be optionally substituted with one or more substituents selected from the group consisting of $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups)), and $R^3$ is any one of the following heterocyclic groups:

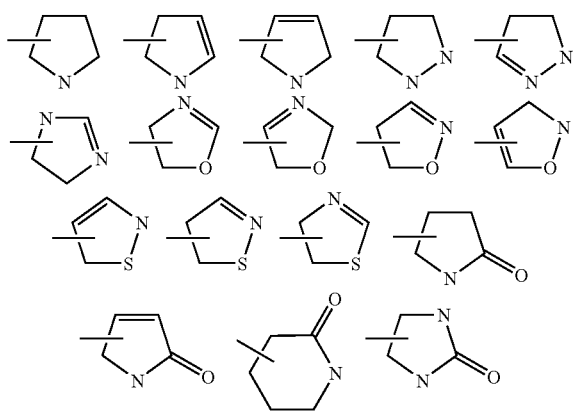

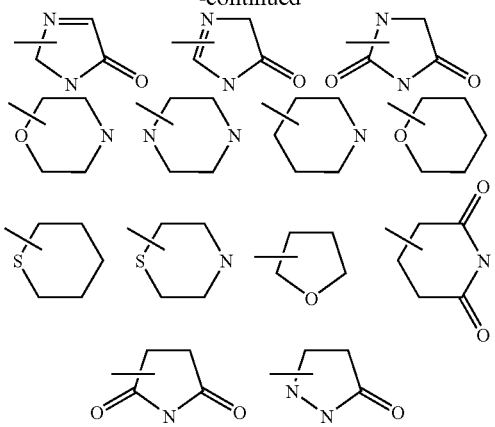

(the above heterocyclic groups may be optionally substituted with one or more substituents selected from the groups consisting of hydroxyl groups, amino groups, thiol groups, carboxyl group, phosphonic acid groups, sulfonic acid groups, carbamoyl groups, hydroxycarbamoyl groups, cyanocarbamoyl groups, sulfamoyl groups, hydroxysulfamoyl groups, cyanosulfamoyl groups, tetrazole groups, $-CH_2CO_2H$, $-OCH_2CO_2H$, $-NHCH_2CO_2H$, $-CH_2CH_2CO_2H$, $-CH_2OH$, $-OCH_2OH$, $-NHCH_2OH$, $-CH_2CH_2OH$ and $C_{1-10}$ alkoxycarbonyl groups), tautomers, prodrugs or pharmaceutically acceptable salts of the compounds or solvates thereof.

41) The compounds according to 24), 25) or 26) wherein $L^4$ is $NR^{22}$ (wherein $R^{22}$ is a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group, the $C_{1-10}$ alkylcarbonyloxy group, the $C_{1-10}$ alkoxycarbonyl group and the $C_{1-10}$ alkylcarbonyl group may be optionally substituted with one or more substituents selected from the group consisting of carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)) or a $C_{2-14}$ aryl group (the $C_{2-14}$ aryl group may be optionally substituted with one or more substituents selected from the group consisting of $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups)), and $R^3$ is any one of the following heterocyclic groups:

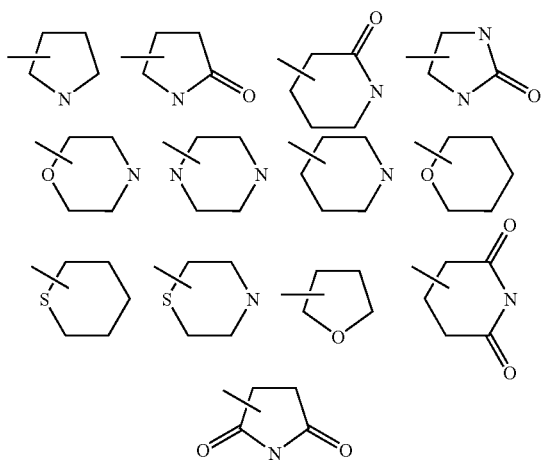

(the above heterocyclic groups may be optionally substituted with one or more substituents selected from the groups consisting of hydroxyl groups, amino groups, thiol groups, carboxyl group, phosphonic acid groups, sulfonic acid groups, carbamoyl groups, hydroxycarbamoyl groups, cyanocarbamoyl groups, sulfamoyl groups, hydroxysulfamoyl groups, cyanosulfamoyl groups, tetrazole groups, —$CH_2CO_2H$, —$OCH_2CO_2H$, —$NHCH_2CO_2H$, —$CH_2CH_2CO_2H$, —$CH_2OH$, —$OCH_2OH$, —$NHCH_2OH$, —$CH_2CH_2OH$, $C_{1-10}$ alkoxycarbonyl groups, $C_{1-10}$ alkyl groups, $C_{2-10}$ alkenyl groups, $C_{2-10}$ alkynyl groups, $C_{2-9}$ heterocyclic groups, $C_{1-10}$ alkoxy groups, $C_{1-10}$ thioalkyl groups, $C_{1-10}$ alkylcarbonyl groups, mono- or di-$C_{1-10}$ alkylamino groups, $C_{1-10}$ alkylcarbonyloxy groups, $C_{1-10}$ alkoxycarbonyl groups and $C_{1-10}$ alkylcarbonylamino groups (the $C_{1-10}$ alkyl groups, the $C_{2-10}$ alkenyl groups, the $C_{2-10}$ alkynyl groups, the $C_{2-9}$ heterocyclic groups, the $C_{1-10}$ alkoxy groups, the $C_{1-10}$ thioalkyl groups, the $C_{1-10}$ alkylcarbonyl groups, the mono- or di-$C_{1-10}$ alkylamino groups, the $C_{1-10}$ alkylcarbonyloxy groups, the $C_{1-10}$ alkoxycarbonyl groups and the $C_{1-10}$ alkylcarbonylamino groups may be optionally substituted with one or more substituents selected from the group consisting of hydroxyl groups, carboxyl groups, carbamoyl groups, sulfonic acid groups and sulfamoyl groups)), tautomers, prodrugs or pharmaceutically acceptable salts of the compounds or solvates thereof.

42) The compounds according to 24), 25) or 26) wherein $L^4$ is $NR^{22}$ (wherein $R^{22}$ is a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group, the $C_{1-10}$ alkylcarbonyloxy group, the $C_{1-10}$ alkoxycarbonyl group and the $C_{1-10}$ alkylcarbonyl group may be optionally substituted with one or more substituents selected from the group consisting of carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)) or a $C_{2-14}$ aryl group (the $C_{2-14}$ aryl group may be optionally substituted with one or more substituents selected from the group consisting of $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups)), and $R^3$ is any one of the following heterocyclic groups:

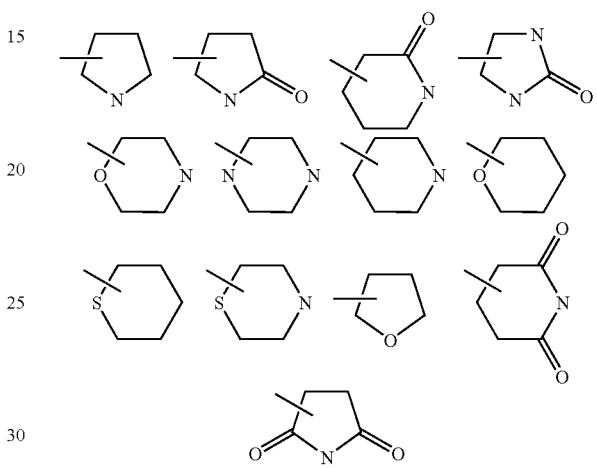

(the above heterocyclic groups may be optionally substituted with one or more substituents selected from the groups consisting of hydroxyl groups, amino groups, thiol groups, carboxyl group, phosphonic acid groups, sulfonic acid groups, carbamoyl groups, hydroxycarbamoyl groups, cyanocarbamoyl groups, sulfamoyl groups, hydroxysulfamoyl groups, cyanosulfamoyl groups, tetrazole groups, —$CH_2CO_2H$, —$OCH_2CO_2H$, —$NHCH_2CO_2H$, —$CH_2CH_2CO_2H$, —$CH_2OH$, —$OCH_2OH$, —$NHCH_2OH$, —$CH_2CH_2OH$ and $C_{1-10}$ alkoxycarbonyl groups), tautomers, prodrugs or pharmaceutically acceptable salts of the compounds or solvates thereof.

43) The compounds according to 24), 25) or 26) wherein $L^4$ is NH, and $R^3$ is an ethyl group, a n-propyl group, an i-propyl group, a n-butyl group, a s-butyl group, a t-butyl group, a c-propyl group, a c-butyl group, a c-pentyl group, a c-hexyl group, an ethynyl group, a 1-propynyl group, a 2-propynyl group, a 1-butynyl group, a 2-butynyl group, a 3-butynyl group, a 1-pentynyl group, a 2-pentynyl group, a 4-pentynyl group, a 1-methyl-2-butynyl group, a 1-methyl-3-butynyl group, a 2-methyl-3-butynyl group, a 3-methyl-1-butynyl group or any one of the following heterocyclic groups:

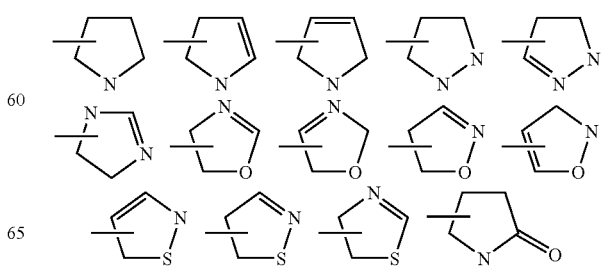

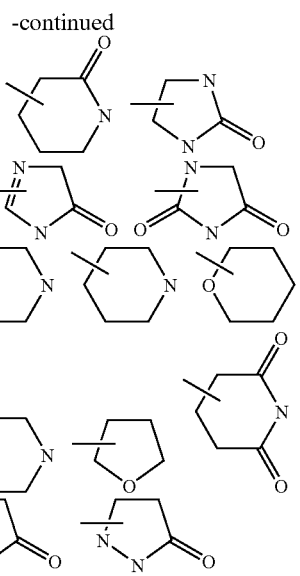

(the ethyl group, the n-propyl group, the i-propyl group, the n-butyl group, the s-butyl group, the t-butyl group, the c-propyl group, the c-butyl group, the c-pentyl group, the c-hexyl group, the ethynyl group, the 1-propynyl group, the 2-propynyl group, the 1-butynyl group, the 2-butynyl group, the 3-butynyl group, the 1-pentynyl group, the 2-pentynyl group, the 4-pentynyl group, the 1-methyl-2-butynyl group, the 1-methyl-3-butynyl group, the 2-methyl-3-butynyl group, the 3-methyl-1-butynyl group and the above heterocyclic groups may be optionally substituted with one or more substituents selected from the groups consisting of hydroxyl groups, amino groups, thiol groups, carboxyl group, phosphonic acid groups, sulfonic acid groups, carbamoyl groups, hydroxycarbamoyl groups, cyanocarbamoyl groups, sulfamoyl groups, hydroxysulfamoyl groups, cyanosulfamoyl groups, tetrazole groups, —$CH_2CO_2H$, —$OCH_2CO_2H$, —$NHCH_2CO_2H$, —$CH_2CH_2CO_2H$, —$CH_2OH$, —$OCH_2OH$, —$NHCH_2OH$, —$CH_2CH_2OH$, $C_{1-10}$ alkoxycarbonyl groups, $C_{1-10}$ alkyl groups, $C_{2-10}$ alkenyl groups, $C_{2-10}$ alkynyl groups, $C_{2-9}$ heterocyclic groups, $C_{1-10}$ alkoxy groups, $C_{1-10}$ thioalkyl groups, $C_{1-10}$ alkylcarbonyl groups, mono- or di-$C_{1-10}$ alkylamino groups, $C_{1-10}$ alkylcarbonyloxy groups, $C_{1-10}$ alkoxycarbonyl groups, $C_{1-10}$ alkylcarbonylamino groups and the following aryl groups and heterocyclic groups (the $C_{1-10}$ alkyl groups, the $C_{2-10}$ alkenyl groups, the $C_{2-10}$ alkynyl groups, the $C_{2-9}$ heterocyclic groups, the $C_{1-10}$ alkoxy groups, the $C_{1-10}$ thioalkyl groups, the $C_{1-10}$ alkylcarbonyl groups, the mono- or di-$C_{1-10}$ alkylamino groups, the $C_{1-10}$ alkylcarbonyloxy groups, the $C_{1-10}$ alkoxycarbonyl groups, the $C_{1-10}$ alkylcarbonylamino groups and the following aryl groups and heterocyclic groups may be optionally substituted with one or more substituents selected from the group consisting of hydroxyl groups, carboxyl groups, carbamoyl groups, sulfonic acid groups and sulfamoyl groups):

Aryl groups: a phenyl group, thienyl groups (a 2-thienyl group and a 3-thienyl group), furyl groups (a 2-furyl group and a 3-furyl group), pyridazinyl groups (a 3-pyridazinyl group and a 4-pyridazinyl group), pyridyl groups (a 2-pyridyl group, a 3-pyridyl group and a 4-pyridyl group), quinolyl groups (a 2-quinolyl group, a 3-quinolyl group, a 4-quinolyl group, a 5-quinolyl group, a 6-quinolyl group, a 7-quinolyl group and a 8-quinolyl group) and isoquinolyl groups (a 1-isoquinolyl group, a 3-isoquinolyl group, a 4-isoquinolyl group, a 5-isoquinolyl group, a 6-isoquinolyl group, a 7-isoquinolyl group and a 8-isoquinolyl group);

Heterocyclic groups: a 1,3,4-oxadiazole group, a 1,3,4-thiadiazole group, a 1,2,4-oxadiazole group, a 1,2,4-thiadiazole group, a 1,2,5-oxadiazole group, a 1,2,5-thiadiazole group, a 1,2-oxazole group and a 1,2-thiazole group),
tautomers, prodrugs or pharmaceutically acceptable salts of the compounds or solvates thereof.

44) The compounds according to 24), 25) or 26) wherein $L^4$ is NH, and $R^3$ is a methyl group, an ethyl group, a n-propyl group, an i-propyl group, a n-butyl group, a s-butyl group, a t-butyl group, a c-propyl group, a c-butyl group, a c-pentyl group, a c-hexyl group, an ethynyl group, a 1-propynyl group, a 2-propynyl group, a 1-butynyl group, a 2-butynyl group, a 3-butynyl group, a 1-pentynyl group, a 2-pentynyl group, a 4-pentynyl group, a 1-methyl-2-butynyl group, a 1-methyl-3-butynyl group, a 2-methyl-3-butynyl group, a 3-methyl-1-butynyl group or any one of the following heterocyclic groups:

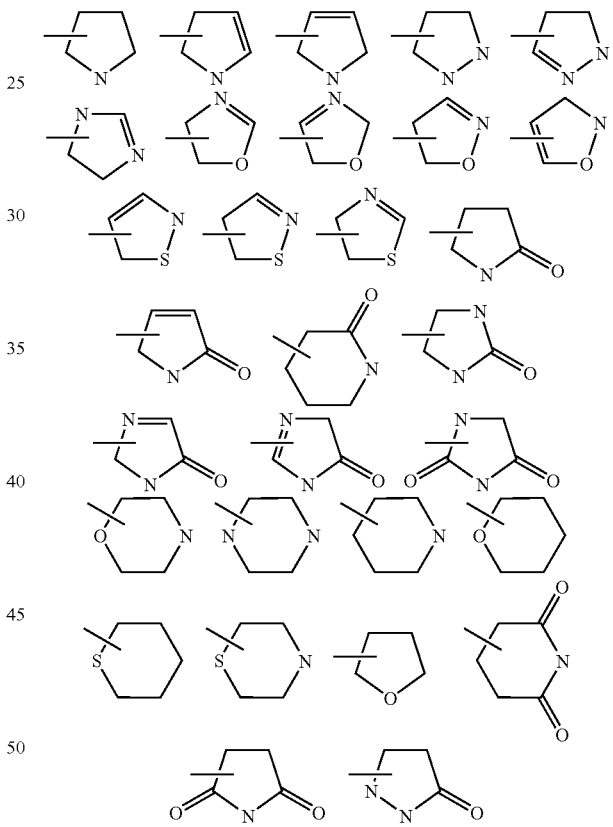

(the methyl group, the ethyl group, the n-propyl group, the i-propyl group, the n-butyl group, the s-butyl group, the t-butyl group, the c-propyl group, the c-butyl group, the c-pentyl group, the c-hexyl group, the ethynyl group, the 1-propynyl group, the 2-propynyl group, the 1-butynyl group, the 2-butynyl group, the 3-butynyl group, the 1-pentynyl group, the 2-pentynyl group, the 4-pentynyl group, the 1-methyl-2-butynyl group, the 1-methyl-3-butynyl group, the 2-methyl-3-butynyl group, the 3-methyl-1-butynyl group and the above heterocyclic groups may be optionally substituted with one or more substituents selected from the groups consisting of hydroxyl groups, amino groups, thiol groups, carboxyl group, phosphonic acid groups, sulfonic acid groups, carbamoyl groups, hydroxycarbamoyl groups, cyanocarbamoyl groups, sulfamoyl groups, hydroxysulfamoyl groups, cyanosulfamoyl groups, tetrazole groups, —CH$_2$CO$_2$H, —OCH$_2$CO$_2$H, —NHCH$_2$CO$_2$H, —CH$_2$CH$_2$CO$_2$H, —CH$_2$OH, —OCH$_2$OH, —NHCH$_2$OH, —CH$_2$CH$_2$OH, C$_{1-10}$ alkoxycarbonyl groups, C$_{1-10}$ alkyl groups, C$_{2-10}$ alkenyl groups, C$_{2-10}$ alkynyl groups, C$_{2-9}$ heterocyclic groups, C$_{1-10}$ alkoxy groups, C$_{1-10}$ thioalkyl groups, C$_{1-10}$ alkylcarbonyl groups, mono- or di-C$_{1-10}$ alkylamino groups, C$_{1-10}$ alkylcarbonyloxy groups, C$_{1-10}$ alkoxycarbonyl groups and C$_{1-10}$ alkylcarbonylamino groups (the C$_{1-10}$ alkyl groups, the C$_{2-10}$ alkenyl groups, the C$_{2-10}$ alkynyl groups, the C$_{2-9}$ heterocyclic groups, the C$_{1-10}$ alkoxy groups, the C$_{1-10}$ thioalkyl groups, the C$_{1-10}$ alkylcarbonyl groups, the mono- or di-C$_{1-10}$ alkylamino groups, the C$_{1-10}$ alkylcarbonyloxy groups, the C$_{1-10}$ alkoxycarbonyl groups and the C$_{1-10}$ alkylcarbonylamino groups may be optionally substituted with one or more substituents selected from the group consisting of hydroxyl groups, carboxyl groups, carbamoyl groups, sulfonic acid groups and sulfamoyl groups)), tautomers, prodrugs or pharmaceutically acceptable salts of the compounds or solvates thereof.

45) The compounds according to 24), 25) or 26) wherein L$^4$ is NH, and R$^3$ is a methyl group, an ethyl group, a n-propyl group, an i-propyl group, a n-butyl group, a c-propyl group, a c-hexyl group, an ethynyl group, a 1-propynyl group, a 2-propynyl group or a 1-butynyl group (the methyl group, the ethyl group, the n-propyl group, the i-propyl group, the n-butyl group, the c-propyl group, the c-hexyl group, the ethynyl group, the 1-propynyl group, the 2-propynyl group and the 1-butynyl group may be optionally substituted with one or more substituents selected from the groups consisting of hydroxyl groups, amino groups, thiol groups, carboxyl group, phosphonic acid groups, sulfonic acid groups, carbamoyl groups, hydroxycarbamoyl groups, cyanocarbamoyl groups, sulfamoyl groups, hydroxysulfamoyl groups, cyanosulfamoyl groups, tetrazole groups, —CH$_2$CO$_2$H, —OCH$_2$CO$_2$H, —NHCH$_2$CO$_2$H, —CH$_2$CH$_2$CO$_2$H, —CH$_2$OH, —OCH$_2$OH, —NHCH$_2$OH, —CH$_2$CH$_2$OH, C$_{1-10}$ alkoxycarbonyl groups, C$_{1-10}$ alkyl groups, C$_{2-10}$ alkenyl groups, C$_{1-10}$ alkynyl groups, C$_{2-9}$ heterocyclic groups, C$_{1-10}$ alkoxy groups, C$_{1-10}$ thioalkyl groups, C$_{1-10}$ alkylcarbonyl groups, mono- or di-C$_{1-10}$ alkylamino groups, C$_{1-10}$ alkylcarbonyloxy groups, C$_{1-10}$ alkoxycarbonyl groups and C$_{1-10}$ alkylcarbonylamino groups (the C$_{1-10}$ alkyl groups, the C$_{2-10}$ alkenyl groups, the C$_{2-10}$ alkynyl groups, the C$_{2-9}$ heterocyclic groups, the C$_{1-10}$ alkoxy groups, the C$_{1-10}$ thioalkyl groups, the C$_{1-10}$ alkylcarbonyl groups, the mono- or di-C$_{1-10}$ alkylamino groups, the C$_{1-10}$ alkylcarbonyloxy groups, the C$_{1-10}$ alkoxycarbonyl groups and the C$_{1-10}$ alkylcarbonylamino groups may be optionally substituted with one or more substituents selected from the group consisting of hydroxyl groups, carboxyl groups, carbamoyl groups, sulfonic acid groups and sulfamoyl groups)), tautomers, prodrugs or pharmaceutically acceptable salts of the compounds or solvates thereof.

46) The compounds according to 24), 25) or 26) wherein L$^4$ is NH, and R$^3$ is a methyl group, an ethyl group, a n-propyl group, an i-propyl group, a n-butyl group, a c-propyl group, a c-hexyl group, an ethynyl group, a 1-propynyl group, a 2-propynyl group or a 1-butynyl group (the methyl group, the ethyl group, the n-propyl group, the i-propyl group, the n-butyl group, the c-propyl group, the c-hexyl group, the ethynyl group, the 1-propynyl group, the 2-propynyl group and the 1-butynyl group may be optionally substituted with one or more substituents selected from the groups consisting of hydroxyl groups, amino groups, thiol groups, carboxyl group, phosphonic acid groups, sulfonic acid groups, carbamoyl groups, hydroxycarbamoyl groups, cyanocarbamoyl groups, sulfamoyl groups, hydroxysulfamoyl groups, cyanosulfamoyl groups, tetrazole groups, —CH$_2$CO$_2$H, —OCH$_2$CO$_2$H, —NHCH$_2$CO$_2$H, —CH$_2$CH$_2$CO$_2$H, —CH$_2$OH, —OCH$_2$OH, —NHCH$_2$OH, —CH$_2$CH$_2$OH and C$_{1-10}$ alkoxycarbonyl groups), tautomers, prodrugs or pharmaceutically acceptable salts of the compounds or solvates thereof.

47) The compounds according to 24), 25) or 26) wherein L$^4$ is NH, and R$^3$ is any one of the following heterocyclic groups:

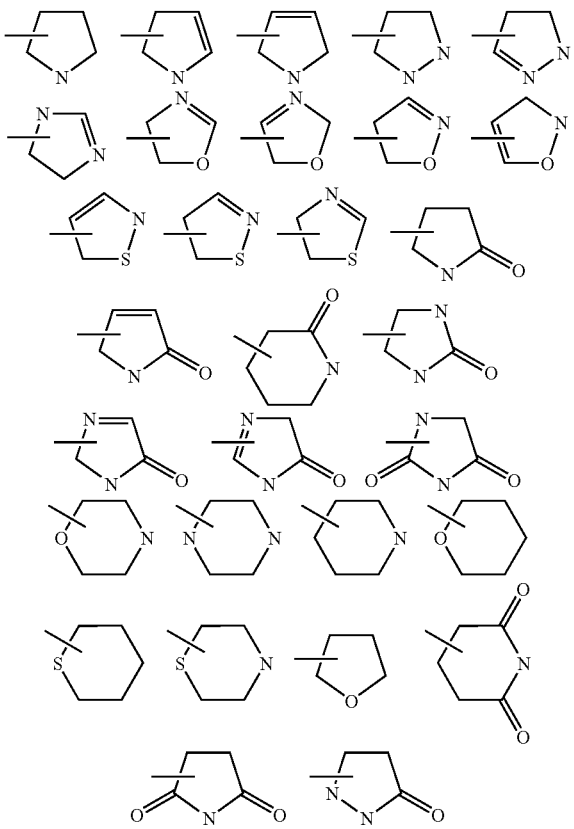

(the above heterocyclic groups may be optionally substituted with one or more substituents selected from the group consisting of hydroxyl groups, amino groups, thiol groups, carboxyl group, phosphonic acid groups, sulfonic acid groups, carbamoyl groups, hydroxycarbamoyl groups, cyanocarbamoyl groups, sulfamoyl groups, hydroxysulfamoyl groups, cyanosulfamoyl groups, tetrazole groups, —CH$_2$CO$_2$H, —OCH$_2$CO$_2$H, —NHCH$_2$CO$_2$H, —CH$_2$CH$_2$CO$_2$H, —CH$_2$OH, —OCH$_2$OH, —NHCH$_2$OH, —CH$_2$CH$_2$OH, C$_{1-10}$ alkoxycarbonyl groups, C$_{1-10}$ alkyl groups, C$_{2-10}$ alkenyl groups, C$_{2-10}$ alkynyl groups, C$_{2-9}$ heterocyclic groups, C$_{1-10}$ alkoxy groups, C$_{1-10}$ thioalkyl groups, C$_{1-10}$ alkylcarbonyl groups, mono- or di-C$_{1-10}$ alkylamino groups, C$_{1-10}$ alkylcarbonyloxy groups, C$_{1-10}$ alkoxycarbonyl groups and C$_{1-10}$ alkylcarbonylamino groups (the C$_{1-10}$ alkyl groups, the C$_{2-10}$ alkenyl groups, the C$_{2-10}$ alkynyl groups, the C$_{2-9}$ heterocyclic groups, the C$_{1-10}$ alkoxy groups, the C$_{1-10}$ thioalkyl groups, the C$_{1-10}$ alkylcarbonyl groups, the mono- or di-C$_{1-10}$ alkylamino groups, the C$_{1-10}$ alkylcarbonyloxy groups, the C$_{1-10}$ alkoxycarbonyl groups and the C$_{1-10}$ alkylcarbonylamino groups may be optionally substituted with one or more substituents selected from the group consisting of hydroxyl groups, carboxyl groups, carbamoyl groups, sulfonic acid groups and sulfamoyl groups)), tautomers, prodrugs or pharmaceutically acceptable salts of the compounds or solvates thereof.

48) The compounds according to 24), 25) or 26) wherein $L^4$ is NH, and $R^3$ is any one of the following heterocyclic groups:

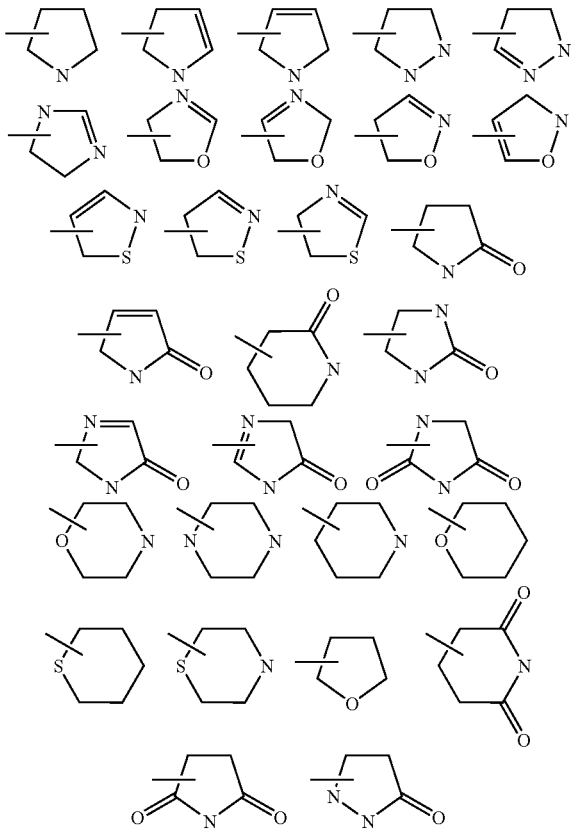

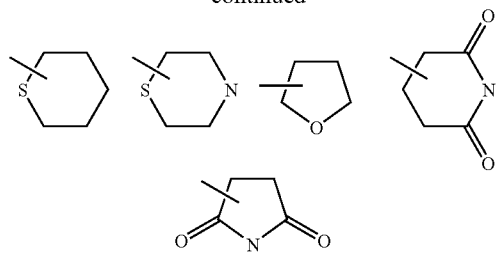

(the above heterocyclic groups may be optionally substituted with one or more substituents selected from the group consisting of hydroxyl groups, amino groups, thiol groups, carboxyl group, phosphonic acid groups, sulfonic acid groups, carbamoyl groups, hydroxycarbamoyl groups, cyanocarbamoyl groups, sulfamoyl groups, hydroxysulfamoyl groups, cyanosulfamoyl groups, tetrazole groups, —$CH_2CO_2H$, —$OCH_2CO_2H$, —$NHCH_2CO_2H$, —$CH_2CH_2CO_2H$, —$CH_2OH$, —$OCH_2OH$, —$NHCH_2OH$, —$CH_2CH_2OH$, $C_{1-10}$ alkoxycarbonyl groups, $C_{1-10}$ alkyl groups, $C_{2-10}$ alkenyl groups, $C_{2-10}$ alkynyl groups, $C_{2-9}$ heterocyclic groups, $C_{1-10}$ alkoxy groups, $C_{1-10}$ thioalkyl groups, $C_{1-10}$ alkylcarbonyl groups, mono- or di-$C_{1-10}$ alkylamino groups, $C_{1-10}$ alkylcarbonyloxy groups, $C_{1-10}$ alkoxycarbonyl groups and $C_{1-10}$ alkylcarbonylamino groups (the $C_{1-10}$ alkyl groups, the $C_{2-10}$ alkenyl groups, the $C_{2-10}$ alkynyl groups, the $C_{2-9}$ heterocyclic groups, the $C_{1-10}$ alkoxy groups, the $C_{1-10}$ thioalkyl groups, the $C_{1-10}$ alkylcarbonyl groups, the mono- or di-$C_{1-10}$ alkylamino groups, the $C_{1-10}$ alkylcarbonyloxy groups, the $C_{1-10}$ alkoxycarbonyl groups and the $C_{1-10}$ alkylcarbonylamino groups may be optionally substituted with one or more substituents selected from the group consisting of hydroxyl groups, carboxyl groups, carbamoyl groups, sulfonic acid groups and sulfamoyl groups)), tautomers, prodrugs or pharmaceutically acceptable salts of the compounds or solvates thereof.

50) The compounds according to 24), 25) or 26) wherein $L^4$ is NH, and $R^3$ is any one of the following heterocyclic groups:

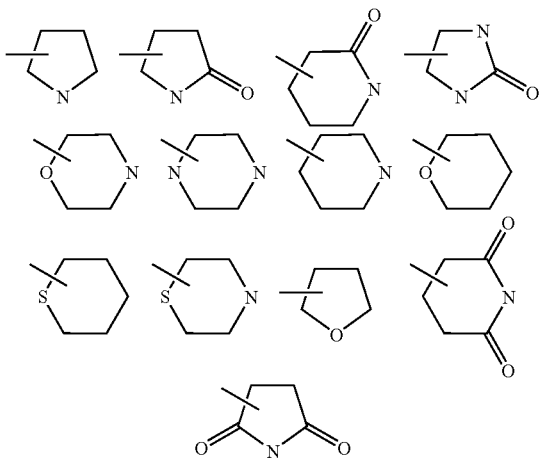

(the above heterocyclic groups may be optionally substituted with one or more substituents selected from the group consisting of hydroxyl groups, amino groups, thiol groups, carboxyl group, phosphonic acid groups, sulfonic acid groups, carbamoyl groups, hydroxycarbamoyl groups, cyanocarbamoyl groups, sulfamoyl groups, hydroxysulfamoyl groups, (the above heterocyclic groups may be optionally substituted with one or more substituents selected from the group consisting of hydroxyl groups, amino groups, thiol groups, carboxyl group, phosphonic acid groups, sulfonic acid groups, carbamoyl groups, hydroxycarbamoyl groups, cyanocarbamoyl groups, sulfamoyl groups, hydroxysulfamoyl groups, cyanosulfamoyl groups, tetrazole groups, —$CH_2CO_2H$, —$OCH_2CO_2H$, —$NHCH_2CO_2H$, —$CH_2CH_2CO_2H$, —$CH_2OH$, —$OCH_2OH$, —$NHCH_2OH$, —$CH_2CH_2OH$ and $C_{1-10}$ alkoxycarbonyl groups), tautomers, prodrugs or pharmaceutically acceptable salts of the compounds or solvates thereof.

49) The compounds according to 24), 25) or 26) wherein $L^4$ is NH, and $R^3$ is any one of the following heterocyclic groups:

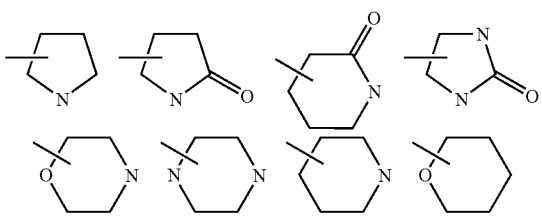

cyanosulfamoyl groups, tetrazole groups, —CH$_2$CO$_2$H, —OCH$_2$CO$_2$H, —NHCH$_2$CO$_2$H, —CH$_2$CH$_2$CO$_2$H, —CH$_2$OH, —OCH$_2$OH, —NHCH$_2$OH, —CH$_2$CH$_2$OH and C$_{1-10}$ alkoxycarbonyl groups), tautomers, prodrugs or pharmaceutically acceptable salts of the compounds or solvates thereof.

51) The compounds according to 24), 25) or 26) wherein L$^4$ is an oxygen atom or a sulfur atom, and R$^3$ is an ethyl group, a n-propyl group, an i-propyl group, a n-butyl group, a s-butyl group, a t-butyl group, a c-propyl group, a c-butyl group, a c-pentyl group, a c-hexyl group, an ethynyl group, a 1-propynyl group, a 2-propynyl group, a 1-butynyl group, a 2-butynyl group, a 3-butynyl group, a 1-pentynyl group, a 2-pentynyl group, a 4-pentynyl group, a 1-methyl-2-butynyl group, a 1-methyl-3-butynyl group, a 2-methyl-3-butynyl group, a 3-methyl-1-butynyl group or any one of the following heterocyclic groups:

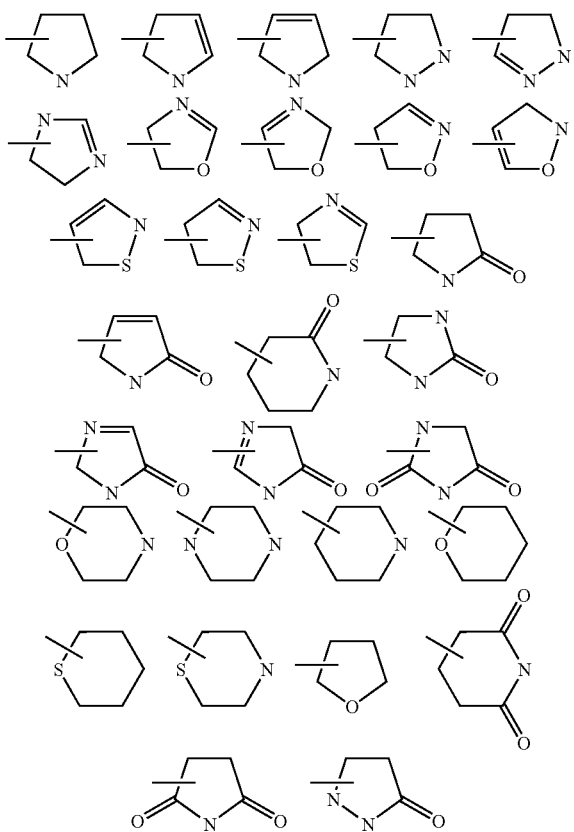

(the ethyl group, the n-propyl group, the i-propyl group, the n-butyl group, the s-butyl group, the t-butyl group, the c-propyl group, the c-butyl group, the c-pentyl group, the c-hexyl group, the ethynyl group, the 1-propynyl group, the 2-propynyl group, the 1-butynyl group, the 2-butynyl group, the 3-butynyl group, the 1-pentynyl group, the 2-pentynyl group, the 4-pentynyl group, the 1-methyl-2-butynyl group, the 1-methyl-3-butynyl group, the 2-methyl-3-butynyl group, the 3-methyl-1-butynyl group and the above heterocyclic groups may be optionally substituted with one or more substituents selected from the groups consisting of hydroxyl groups; amino groups, thiol groups, carboxyl group, phosphonic acid groups, sulfonic acid groups, carbamoyl groups, hydroxycarbamoyl groups, cyanocarbamoyl groups, sulfamoyl groups, hydroxysulfamoyl groups, cyanosulfamoyl groups, tetrazole groups, —CH$_2$CO$_2$H, —OCH$_2$CO$_2$H, —NHCH$_2$CO$_2$H, —CH$_2$CH$_2$CO$_2$H, —CH$_2$OH, —OCH$_2$OH, —NHCH$_2$OH, —CH$_2$CH$_2$OH, C$_{1-10}$ alkoxycarbonyl groups, C$_{1-10}$ alkyl groups, C$_{2-10}$ alkenyl groups, C$_{2-10}$ alkynyl groups, C$_{2-9}$ heterocyclic groups, C$_{1-10}$ alkoxy groups, C$_{1-10}$ thioalkyl groups, C$_{1-10}$ alkylcarbonyl groups, mono- or di-C$_{1-10}$ alkylamino groups, C$_{1-10}$ alkylcarbonyloxy groups, C$_{1-10}$ alkoxycarbonyl groups, C$_{1-10}$ alkylcarbonylamino groups and the following aryl groups and heterocyclic groups (the C$_{1-10}$ alkyl groups, the C$_{2-10}$ alkenyl groups, the C$_{2-10}$ alkynyl groups, the C$_{2-10}$ heterocyclic groups, the C$_{1-10}$ alkoxy groups, the C$_{1-10}$ thioalkyl groups, the C$_{1-10}$ alkylcarbonyl groups, the mono- or di-C$_{1-10}$ alkylamino groups, the C$_{1-10}$ alkylcarbonyloxy groups, the C$_{1-10}$ alkoxycarbonyl groups, the C$_{1-10}$ alkylcarbonylamino groups and the following aryl groups and heterocyclic groups may be optionally substituted with one or more substituents selected from the group consisting of hydroxyl groups, carboxyl groups, carbamoyl groups, sulfonic acid groups and sulfamoyl groups):

Aryl groups: a phenyl group, thienyl groups (a 2-thienyl group and a 3-thienyl group), furyl groups (a 2-furyl group and a 3-furyl group), pyridazinyl groups (a 3-pyridazinyl group and a 4-pyridazinyl group), pyridyl groups (a 2-pyridyl group, a 3-pyridyl group and a 4-pyridyl group), quinolyl groups (a 2-quinolyl group, a 3-quinolyl group, a 4-quinolyl group, a 5-quinolyl group, a 6-quinolyl group, a 7-quinolyl group and a 8-quinolyl group) and isoquinolyl groups (a 1-isoquinolyl group, a 3-isoquinolyl group, a 4-isoquinolyl group, a 5-isoquinolyl group, a 6-isoquinolyl group, a 7-isoquinolyl group and a 8-isoquinolyl group);

Heterocyclic groups: a 1,3,4-oxadiazole group, a 1,3,4-thiadiazole group, a 1,2,4-oxadiazole group, a 1,2,4-thiadiazole group, a 1,2,5-oxadiazole group, a 1,2,5-thiadiazole group, a 1,2-oxazole group and a 1,2-thiazole group), tautomers, prodrugs or pharmaceutically acceptable salts of the compounds or solvates thereof.

52) The compounds according to 24), 25) or 26) wherein L$^4$ is an oxygen atom or a sulfur atom, and R$^3$ is a methyl group, an ethyl group, a n-propyl group, an i-propyl group, a n-butyl group, a s-butyl group, a t-butyl group, a c-propyl group, a c-butyl group, a c-pentyl group, a c-hexyl group, an ethynyl group, a 1-propynyl group, a 2-propynyl group, a 1-butynyl group, a 2-butynyl group, a 3-butynyl group, a 1-pentynyl group, a 2-pentynyl group, a 4-pentynyl group, a 1-methyl-2-butynyl group, a 1-methyl-3-butynyl group, a 2-methyl-3-butynyl group, a 3-methyl-1-butynyl group or any one of the following heterocyclic groups:

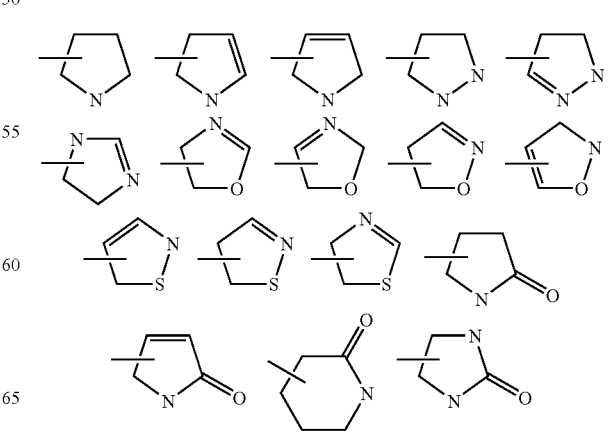

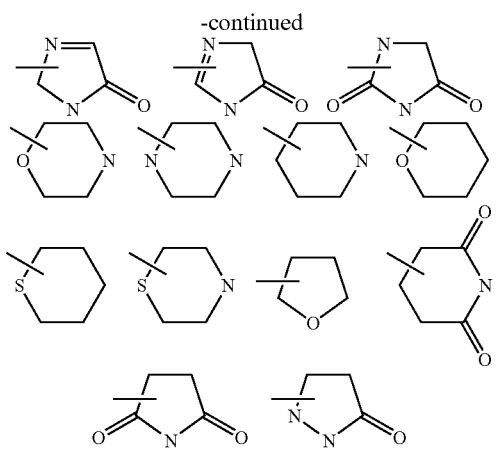

(the methyl group, the ethyl group, the n-propyl group, the i-propyl group, the n-butyl group, the s-butyl group, the t-butyl group, the c-propyl group, the c-butyl group, the c-pentyl group, the c-hexyl group, the ethynyl group, the 1-propynyl group, the 2-propynyl group, the 1-butynyl group, the 2-butynyl group, the 3-butynyl group, the 1-pentynyl group, the 2-pentynyl group, the 4-pentynyl group, the 1-methyl-2-butynyl group, the 1-methyl-3-butynyl group, the 2-methyl-3-butynyl group, the 3-methyl-1-butynyl group and the above heterocyclic groups may be optionally substituted with one or more substituents selected from the groups consisting of hydroxyl groups, amino groups, thiol groups, carboxyl group, phosphonic acid groups, sulfonic acid groups, carbamoyl groups, hydroxycarbamoyl groups, cyanocarbamoyl groups, sulfamoyl groups, hydroxysulfamoyl groups, cyanosulfamoyl groups, tetrazole groups, —$CH_2CO_2H$, —$OCH_2CO_2H$, —$NHCH_2CO_2H$, —$CH_2CH_2CO_2H$, —$CH_2OH$, —$OCH_2OH$, —$NHCH_2OH$, —$CH_2CH_2OH$, $C_{1-10}$ alkoxycarbonyl groups, $C_{1-10}$ alkyl groups, $C_{2-10}$ alkenyl groups, $C_{2-10}$ alkynyl groups, $C_{2-9}$ heterocyclic groups, $C_{1-10}$ alkoxy groups, $C_{1-10}$ thioalkyl groups, $C_{1-10}$ alkylcarbonyl groups, mono- or di-$C_{1-10}$ alkylamino groups, $C_{1-10}$ alkylcarbonyloxy groups, $C_{1-10}$ alkoxycarbonyl groups and $C_{1-10}$ alkylcarbonylamino groups (the $C_{1-10}$ alkyl groups, the $C_{2-10}$ alkenyl groups, the $C_{2-10}$ alkynyl groups, the $C_{2-9}$ heterocyclic groups, the $C_{1-10}$ alkoxy groups, the $C_{1-10}$ thioalkyl groups, the $C_{1-10}$ alkylcarbonyl groups, the mono- or di-$C_{1-10}$ alkylamino groups, the $C_{1-10}$ alkylcarbonyloxy groups, the $C_{1-10}$ alkoxycarbonyl groups and the $C_{1-10}$ alkylcarbonylamino groups may be optionally substituted with one or more substituents selected from the group consisting of hydroxyl groups, carboxyl groups, carbamoyl groups, sulfonic acid groups and sulfamoyl groups)), tautomers, prodrugs or pharmaceutically acceptable salts of the compounds or solvates thereof.

53) The compounds according to 24), 25) or 26) wherein $L^4$ is an oxygen atom or a sulfur atom, and $R^3$ is a methyl group, an ethyl group, a n-propyl group, an i-propyl group, a n-butyl group, a c-propyl group, a c-hexyl group, an ethynyl group, a 1-propynyl group, a 2-propynyl group or a 1-butynyl group (the methyl group, the ethyl group, the n-propyl group, the i-propyl group, the n-butyl group, the c-propyl group, the c-hexyl group, the ethynyl group, the 1-propynyl group, the 2-propynyl group and the 1-butynyl group may be optionally substituted with one or more substituents selected from the groups consisting of hydroxyl groups, amino groups, thiol groups, carboxyl group, phosphonic acid groups, sulfonic acid groups, carbamoyl groups, hydroxycarbamoyl groups, cyanocarbamoyl groups, sulfamoyl groups, hydroxysulfamoyl groups, cyanosulfamoyl groups, tetrazole groups, —$CH_2CO_2H$, —$OCH_2CO_2H$, —$NHCH_2CO_2H$, —$CH_2CH_2CO_2H$, —$CH_2OH$, —$OCH_2OH$, —$NHCH_2OH$, —$CH_2CH_2OH$, $C_{1-10}$ alkoxycarbonyl groups, $C_{1-10}$ alkyl groups, $C_{2-10}$ alkenyl groups, $C_{2-10}$ alkynyl groups, $C_{2-9}$ heterocyclic groups, $C_{1-10}$ alkoxy groups, $C_{1-10}$ thioalkyl groups, $C_{1-10}$ alkylcarbonyl groups, mono- or di-$C_{1-10}$ alkylamino groups, $C_{1-10}$ alkylcarbonyloxy groups, $C_{1-10}$ alkoxycarbonyl groups and $C_{1-10}$ alkylcarbonylamino groups (the $C_{1-10}$ alkyl groups, the $C_{2-10}$ alkenyl groups, the $C_{2-10}$ alkynyl groups, the $C_{2-9}$ heterocyclic groups, the $C_{1-10}$ alkoxy groups, the $C_{1-10}$ thioalkyl groups, the $C_{1-10}$ alkylcarbonyl groups, the mono- or di-$C_{1-10}$ alkylamino groups, the $C_{1-10}$ alkylcarbonyloxy groups, the $C_{1-10}$ alkoxycarbonyl groups and the $C_{1-10}$ alkylcarbonylamino groups may be optionally substituted with one or more substituents selected from the group consisting of hydroxyl groups, carboxyl groups, carbamoyl groups, sulfonic acid groups and sulfamoyl groups)), tautomers, prodrugs or pharmaceutically acceptable salts of the compounds or solvates thereof.

54) The compounds according to 24), 25) or 26) wherein $L^4$ is an oxygen atom or a sulfur atom, and $R^3$ is a methyl group, an ethyl group, a n-propyl group, an i-propyl group, a n-butyl group, a c-propyl group, a c-hexyl group, an ethynyl group, a 1-propynyl group, a 2-propynyl group or a 1-butynyl group (the methyl group, the ethyl group, the n-propyl group, the i-propyl group, the n-butyl group, the c-propyl group, the c-hexyl group, the ethynyl group, the 1-propynyl group, the 2-propynyl group and the 1-butynyl group may be optionally substituted with one or more substituents selected from the groups consisting of hydroxyl groups, amino groups, thiol groups, carboxyl group, phosphonic acid groups, sulfonic acid groups, carbamoyl groups, hydroxycarbamoyl groups, cyanocarbamoyl groups, sulfamoyl groups, hydroxysulfamoyl groups, cyanosulfamoyl groups, tetrazole groups, —$CH_2CO_2H$, —$OCH_2CO_2H$, —$NHCH_2CO_2H$, —$CH_2CH_2CO_2H$, —$CH_2OH$, —$OCH_2OH$, —$NHCH_2OH$, —$CH_2CH_2OH$ and $C_{1-10}$ alkoxycarbonyl groups), tautomers, prodrugs or pharmaceutically acceptable salts of the compounds or solvates thereof.

55) The compounds according to 24), 25) or 26) wherein $L^4$ is an oxygen atom or a sulfur atom, and $R^3$ is any one of the following heterocyclic groups:

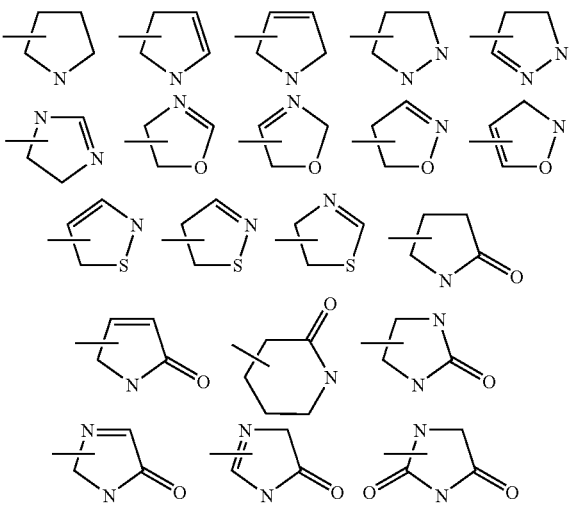

-continued

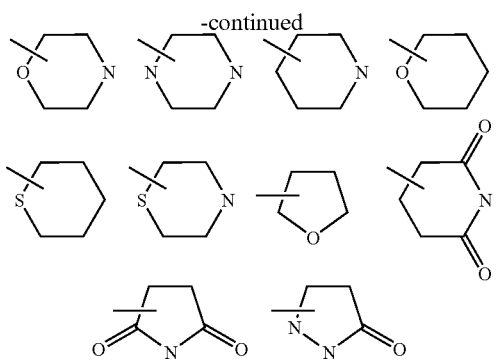

(the above heterocyclic groups may be optionally substituted with one or more substituents selected from the groups consisting of hydroxyl groups, amino groups, thiol groups, carboxyl group, phosphonic acid groups, sulfonic acid groups, carbamoyl groups, hydroxycarbamoyl groups, cyanocarbamoyl groups, sulfamoyl groups, hydroxysulfamoyl groups, cyanosulfamoyl groups, tetrazole groups, —$CH_2CO_2H$, —$OCH_2CO_2H$, —$NHCH_2CO_2H$, —$CH_2CH_2CO_2H$, —$CH_2OH$, —$OCH_2OH$, —$NHCH_2OH$, —$CH_2CH_2OH$, $C_{1-10}$ alkoxycarbonyl groups, $C_{1-10}$ alkyl groups, $C_{2-10}$ alkenyl groups, $C_{2-10}$ alkynyl groups, $C_{2-9}$ heterocyclic groups, $C_{1-10}$ alkoxy groups, $C_{1-10}$ thioalkyl groups, $C_{1-10}$ alkylcarbonyl groups, mono- or di-$C_{1-10}$ alkylamino groups, $C_{1-10}$ alkylcarbonyloxy groups, $C_{1-10}$ alkoxycarbonyl groups and $C_{1-10}$ alkylcarbonylamino groups (the $C_{1-10}$ alkyl groups, the $C_{2-10}$ alkenyl groups, the $C_{2-10}$ alkynyl groups, the $C_{2-6}$ heterocyclic groups, the $C_{1-10}$ alkoxy groups, the $C_{1-10}$ thioalkyl groups, the $C_{1-10}$ alkylcarbonyl groups, the mono- or di-$C_{1-10}$ alkylamino groups, the $C_{1-10}$ alkylcarbonyloxy groups, the $C_{1-10}$ alkoxycarbonyl groups and the $C_{1-10}$ alkylcarbonylamino groups may be optionally substituted with one or more substituents selected from the group consisting of hydroxyl groups, carboxyl groups, carbamoyl groups, sulfonic acid groups and sulfamoyl groups)), tautomers, prodrugs or pharmaceutically acceptable salts of the compounds or solvates thereof.

56) The compounds according to 24), 25) or 26) wherein $L^4$ is an oxygen atom or a sulfur atom, and $R^3$ is any one of the following heterocyclic groups:

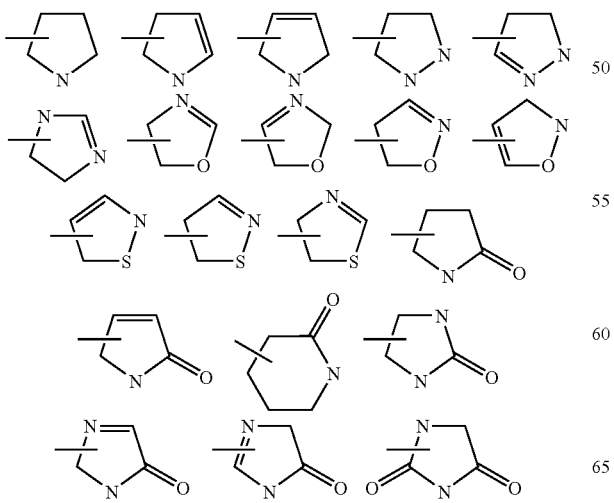

-continued

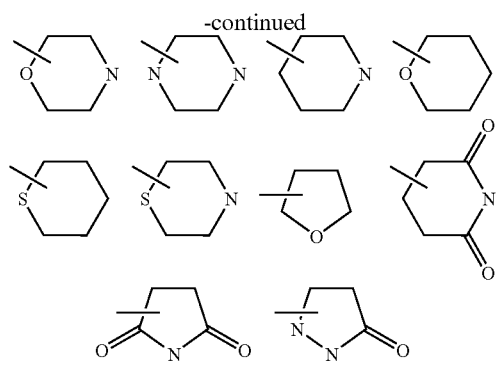

(the above heterocyclic groups may be optionally substituted with one or more substituents selected from the groups consisting of hydroxyl groups, amino groups, thiol groups, carboxyl group, phosphonic acid groups, sulfonic acid groups, carbamoyl groups, hydroxycarbamoyl groups, cyanocarbamoyl groups, sulfamoyl groups, hydroxysulfamoyl groups, cyanosulfamoyl groups, tetrazole groups, —$CH_2CO_2H$, —$OCH_2CO_2H$, —$NHCH_2CO_2H$, —$CH_2CH_2CO_2H$, —$CH_2OH$, —$OCH_2OH$, —$NHCH_2OH$, —$CH_2CH_2OH$ and $C_{1-10}$ alkoxycarbonyl groups), tautomers, prodrugs or pharmaceutically acceptable salts of the compounds or solvates thereof.

57) The compounds according to 24), 25) or 26) wherein $L^4$ is an oxygen atom or a sulfur atom, and $R^3$ is any one of the following heterocyclic groups:

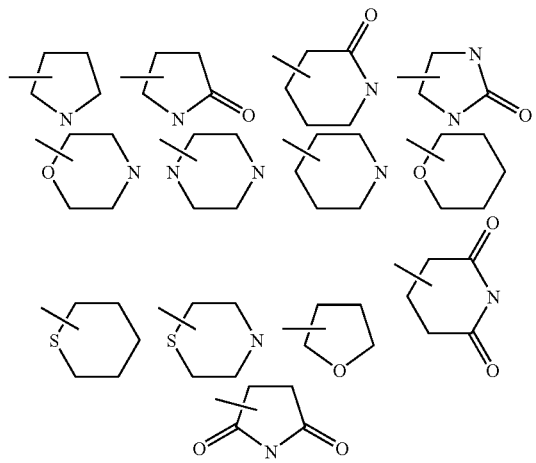

(the above heterocyclic groups may be optionally substituted with one or more substituents selected from the groups consisting of hydroxyl groups, amino groups, thiol groups, carboxyl group, phosphonic acid groups, sulfonic acid groups, carbamoyl groups, hydroxycarbamoyl groups, cyanocarbamoyl groups, sulfamoyl groups, hydroxysulfamoyl groups, cyanosulfamoyl groups, tetrazole groups, —$CH_2CO_2H$, —$OCH_2CO_2H$, —$NHCH_2CO_2H$, —$CH_2CH_2CO_2H$, —$CH_2OH$, —$OCH_2OH$, —$NHCH_2OH$, —$CH_2CH_2OH$, $C_{1-10}$ alkoxycarbonyl groups, $C_{1-10}$ alkyl groups, $C_{2-10}$ alkenyl groups, $C_{2-10}$ alkynyl groups, $C_{2-9}$ heterocyclic groups, $C_{1-10}$ alkoxy groups, $C_{1-10}$ thioalkyl groups, $C_{1-10}$ alkylcarbonyl groups, mono- or di-$C_{1-10}$ alkylamino groups, $C_{1-10}$ alkylcarbonyloxy groups, $C_{1-10}$ alkoxycarbonyl groups and $C_{1-10}$ alkylcarbonylamino groups (the $C_{1-10}$ alkyl groups, the $C_{2-10}$ alkenyl groups, the $C_{2-10}$ alkynyl groups, the $C_{2-9}$ heterocyclic groups, the $C_{1-10}$ alkoxy groups, the $C_{1-10}$ thioalkyl groups, the $C_{1-10}$ alkylcarbonyl groups, the mono- or di-$C_{1-10}$ alkylamino groups, the $C_{1-10}$ alkylcarbonyloxy groups, the $C_{1-10}$ alkoxycarbonyl groups and the $C_{1-10}$ alkylcarbonylamino groups may be optionally substituted with one or more substituents selected from the group consisting of hydroxyl groups, carboxyl groups, carbamoyl groups, sulfonic acid groups and sulfamoyl groups)), tautomers, prodrugs or pharmaceutically acceptable salts of the compounds or solvates thereof.

58) The compounds according to 24), 25) or 26) wherein $L^4$ is an oxygen atom or a sulfur atom, and $R^3$ is any one of the following heterocyclic groups:

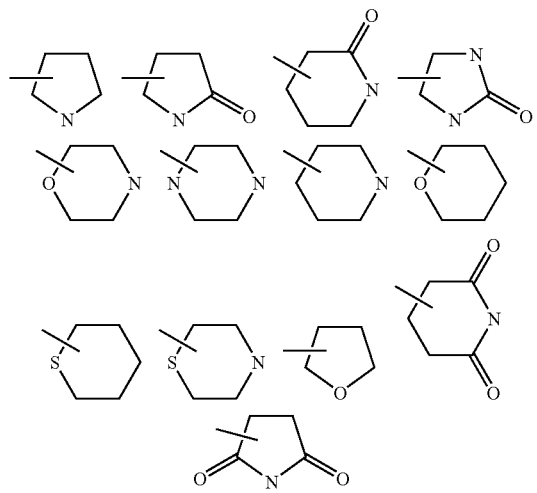

(the above heterocyclic groups may be optionally substituted with one or more substituents selected from the groups consisting of hydroxyl groups, amino groups, thiol groups, carboxyl group, phosphonic acid groups, sulfonic acid groups, carbamoyl groups, hydroxycarbamoyl groups, cyanocarbamoyl groups, sulfamoyl groups, hydroxysulfamoyl groups, cyanosulfamoyl groups, tetrazole groups, —CH$_2$CO$_2$H, —OCH$_2$CO$_2$H, —NHCH$_2$CO$_2$H, —CH$_2$CH$_2$CO$_2$H, —CH$_2$OH, —OCH$_2$OH, —NHCH$_2$OH, —CH$_2$CH$_2$OH and $C_{1-10}$ alkoxycarbonyl groups), tautomers, prodrugs or pharmaceutically acceptable salts of the compounds or solvates thereof.

59) The compounds wherein A, B, $R^1$, $L^1$, $R^2$, $L^2$, $L^3$, Y, $L^4$, $R^3$ and X are any of the following combinations in Table 1, tautomers, prodrugs or pharmaceutically acceptable salts of the compounds or solvates thereof. The symbols in Table 1 denote the flowing substituents.

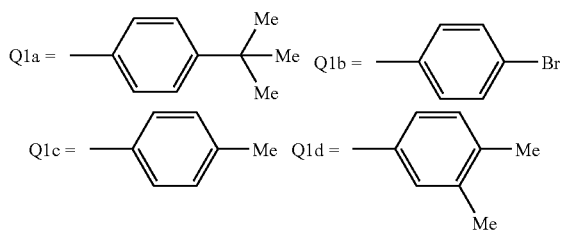

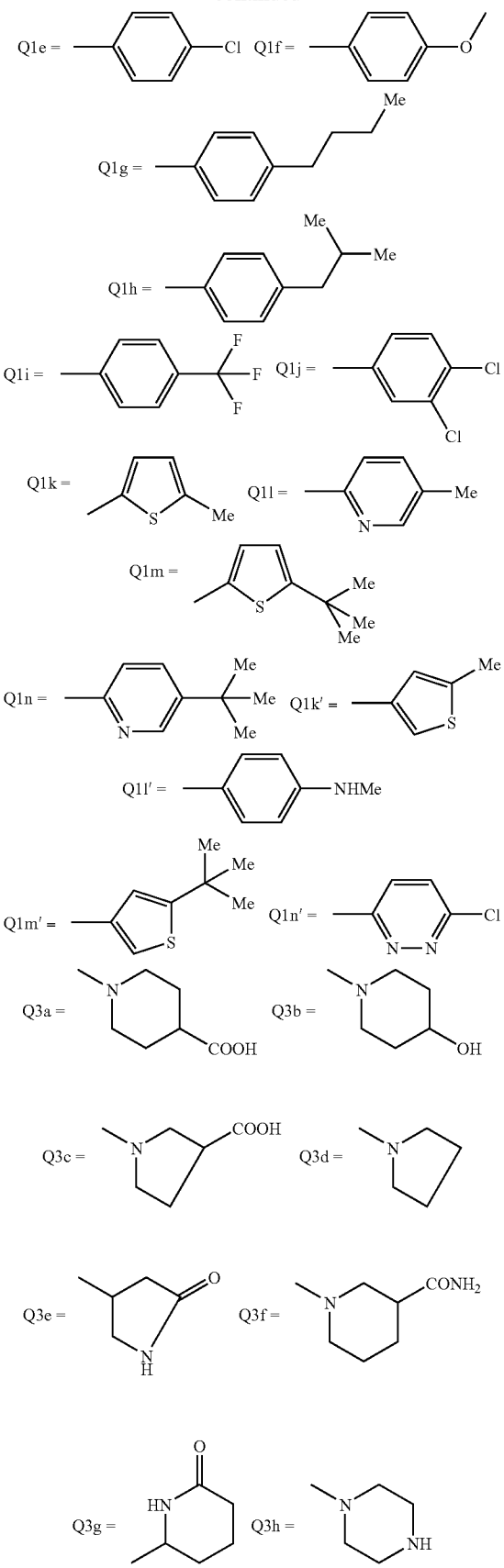

TABLE 1

| No | A | B | R¹ | L¹ | R² | L² | L³ | Y | L⁴ | R³ | X |
|---|---|---|---|---|---|---|---|---|---|---|---|
| 1 | N | NMe | Q1a | a bond | Me | a bond | NH | S | NH | Q3a | OH |
| 2 | N | NMe | Q1a | a bond | Me | a bond | NH | S | NH | Q3b | OH |
| 3 | N | NMe | Q1a | a bond | Me | a bond | NH | S | NH | Q3c | OH |
| 4 | N | NMe | Q1a | a bond | Me | a bond | NH | S | a bond | Q3a | OH |
| 5 | N | NMe | Q1a | a bond | Me | a bond | NH | S | a bond | Q3b | OH |
| 6 | N | NMe | Q1a | a bond | Me | a bond | NH | S | a bond | Q3c | OH |
| 7 | N | NMe | Q1a | a bond | Me | a bond | NH | O | NH | Q3a | OH |
| 8 | N | NMe | Q1a | a bond | Me | a bond | NH | O | NH | Q3b | OH |
| 9 | N | NMe | Q1a | a bond | Me | a bond | NH | O | NH | Q3c | OH |
| 10 | N | NMe | Q1a | a bond | Me | a bond | NH | O | a bond | Q3a | OH |
| 11 | N | NMe | Q1a | a bond | Me | a bond | NH | O | a bond | Q3b | OH |
| 12 | N | NMe | Q1a | a bond | Me | a bond | NH | O | a bond | Q3c | OH |
| 13 | N | NMe | Q1a | a bond | H | a bond | NH | S | NH | Q3a | OH |
| 14 | N | NMe | Q1a | a bond | H | a bond | NH | S | NH | Q3b | OH |
| 15 | N | NMe | Q1a | a bond | H | a bond | NH | S | NH | Q3c | OH |
| 16 | N | NMe | Q1a | a bond | H | a bond | NH | S | a bond | Q3a | OH |
| 17 | N | NMe | Q1a | a bond | H | a bond | NH | S | a bond | Q3b | OH |
| 18 | N | NMe | Q1a | a bond | H | a bond | NH | S | a bond | Q3c | OH |
| 19 | N | NMe | Q1a | a bond | H | a bond | NH | O | NH | Q3a | OH |
| 20 | N | NMe | Q1a | a bond | H | a bond | NH | O | NH | Q3b | OH |
| 21 | N | NMe | Q1a | a bond | H | a bond | NH | O | NH | Q3c | OH |
| 22 | N | NMe | Q1a | a bond | H | a bond | NH | O | a bond | Q3a | OH |
| 23 | N | NMe | Q1a | a bond | H | a bond | NH | O | a bond | Q3b | OH |
| 24 | N | NMe | Q1a | a bond | H | a bond | NH | O | a bond | Q3c | OH |
| 25 | N | NMe | Q1b | a bond | Me | a bond | NH | S | NH | Q3a | OH |
| 26 | N | NMe | Q1b | a bond | Me | a bond | NH | S | NH | Q3b | OH |
| 27 | N | NMe | Q1b | a bond | Me | a bond | NH | S | NH | Q3c | OH |
| 28 | N | NMe | Q1b | a bond | Me | a bond | NH | S | a bond | Q3a | OH |
| 29 | N | NMe | Q1b | a bond | Me | a bond | NH | S | a bond | Q3b | OH |
| 30 | N | NMe | Q1b | a bond | Me | a bond | NH | S | a bond | Q3c | OH |
| 31 | N | NMe | Q1b | a bond | Me | a bond | NH | O | NH | Q3a | OH |
| 32 | N | NMe | Q1b | a bond | Me | a bond | NH | O | NH | Q3b | OH |
| 33 | N | NMe | Q1b | a bond | Me | a bond | NH | O | NH | Q3c | OH |
| 34 | N | NMe | Q1b | a bond | Me | a bond | NH | O | a bond | Q3a | OH |
| 35 | N | NMe | Q1b | a bond | Me | a bond | NH | O | a bond | Q3b | OH |
| 36 | N | NMe | Q1b | a bond | Me | a bond | NH | O | a bond | Q3c | OH |
| 37 | N | NMe | Q1b | a bond | H | a bond | NH | S | NH | Q3a | OH |
| 38 | N | NMe | Q1b | a bond | H | a bond | NH | S | NH | Q3b | OH |
| 39 | N | NMe | Q1b | a bond | H | a bond | NH | S | NH | Q3c | OH |
| 40 | N | NMe | Q1b | a bond | H | a bond | NH | S | a bond | Q3a | OH |
| 41 | N | NMe | Q1b | a bond | H | a bond | NH | S | a bond | Q3b | OH |
| 42 | N | NMe | Q1b | a bond | H | a bond | NH | S | a bond | Q3c | OH |
| 43 | N | NMe | Q1b | a bond | H | a bond | NH | O | NH | Q3a | OH |
| 44 | N | NMe | Q1b | a bond | H | a bond | NH | O | NH | Q3b | OH |
| 45 | N | NMe | Q1b | a bond | H | a bond | NH | O | NH | Q3c | OH |
| 46 | N | NMe | Q1b | a bond | H | a bond | NH | O | a bond | Q3a | OH |
| 47 | N | NMe | Q1b | a bond | H | a bond | NH | O | a bond | Q3b | OH |
| 48 | N | NMe | Q1b | a bond | H | a bond | NH | O | a bond | Q3c | OH |
| 49 | N | NMe | Q1c | a bond | Me | a bond | NH | S | NH | Q3a | OH |
| 50 | N | NMe | Q1c | a bond | Me | a bond | NH | S | NH | Q3b | OH |
| 51 | N | NMe | Q1c | a bond | Me | a bond | NH | S | NH | Q3c | OH |
| 52 | N | NMe | Q1c | a bond | Me | a bond | NH | S | a bond | Q3a | OH |
| 53 | N | NMe | Q1c | a bond | Me | a bond | NH | S | a bond | Q3b | OH |
| 54 | N | NMe | Q1c | a bond | Me | a bond | NH | S | a bond | Q3c | OH |
| 55 | N | NMe | Q1c | a bond | Me | a bond | NH | O | NH | Q3a | OH |
| 56 | N | NMe | Q1c | a bond | Me | a bond | NH | O | NH | Q3b | OH |
| 57 | N | NMe | Q1c | a bond | Me | a bond | NH | O | NH | Q3c | OH |
| 58 | N | NMe | Q1c | a bond | Me | a bond | NH | O | a bond | Q3a | OH |
| 59 | N | NMe | Q1c | a bond | Me | a bond | NH | O | a bond | Q3b | OH |
| 60 | N | NMe | Q1c | a bond | Me | a bond | NH | O | a bond | Q3c | OH |
| 61 | N | NMe | Q1c | a bond | H | a bond | NH | S | NH | Q3a | OH |
| 62 | N | NMe | Q1c | a bond | H | a bond | NH | S | NH | Q3b | OH |
| 63 | N | NMe | Q1c | a bond | H | a bond | NH | S | NH | Q3c | OH |
| 64 | N | NMe | Q1c | a bond | H | a bond | NH | S | a bond | Q3a | OH |
| 65 | N | NMe | Q1c | a bond | H | a bond | NH | S | a bond | Q3b | OH |
| 66 | N | NMe | Q1c | a bond | H | a bond | NH | S | a bond | Q3c | OH |
| 67 | N | NMe | Q1c | a bond | H | a bond | NH | O | NH | Q3a | OH |
| 68 | N | NMe | Q1c | a bond | H | a bond | NH | O | NH | Q3b | OH |
| 69 | N | NMe | Q1c | a bond | H | a bond | NH | O | NH | Q3c | OH |
| 70 | N | NMe | Q1c | a bond | H | a bond | NH | O | a bond | Q3a | OH |
| 71 | N | NMe | Q1c | a bond | H | a bond | NH | O | a bond | Q3b | OH |
| 72 | N | NMe | Q1c | a bond | H | a bond | NH | O | a bond | Q3c | OH |
| 73 | N | NMe | Q1d | a bond | Me | a bond | NH | S | NH | Q3a | OH |
| 74 | N | NMe | Q1d | a bond | Me | a bond | NH | S | NH | Q3b | OH |
| 75 | N | NMe | Q1d | a bond | Me | a bond | NH | S | NH | Q3c | OH |
| 76 | N | NMe | Q1d | a bond | Me | a bond | NH | S | a bond | Q3a | OH |
| 77 | N | NMe | Q1d | a bond | Me | a bond | NH | S | a bond | Q3b | OH |
| 78 | N | NMe | Q1d | a bond | Me | a bond | NH | S | a bond | Q3c | OH |

TABLE 1-continued

| No | A | B | R¹ | L¹ | R² | L² | L³ | Y | L⁴ | R³ | X |
|---|---|---|---|---|---|---|---|---|---|---|---|
| 79 | N | NMe | Q1d | a bond | Me | a bond | NH | O | NH | Q3a | OH |
| 80 | N | NMe | Q1d | a bond | Me | a bond | NH | O | NH | Q3b | OH |
| 81 | N | NMe | Q1d | a bond | Me | a bond | NH | O | NH | Q3c | OH |
| 82 | N | NMe | Q1d | a bond | Me | a bond | NH | O | a bond | Q3a | OH |
| 83 | N | NMe | Q1d | a bond | Me | a bond | NH | O | a bond | Q3b | OH |
| 84 | N | NMe | Q1d | a bond | Me | a bond | NH | O | a bond | Q3c | OH |
| 85 | N | NMe | Q1d | a bond | H | a bond | NH | S | NH | Q3a | OH |
| 86 | N | NMe | Q1d | a bond | H | a bond | NH | S | NH | Q3b | OH |
| 87 | N | NMe | Q1d | a bond | H | a bond | NH | S | NH | Q3c | OH |
| 88 | N | NMe | Q1d | a bond | H | a bond | NH | S | a bond | Q3a | OH |
| 89 | N | NMe | Q1d | a bond | H | a bond | NH | S | a bond | Q3b | OH |
| 90 | N | NMe | Q1d | a bond | H | a bond | NH | S | a bond | Q3c | OH |
| 91 | N | NMe | Q1d | a bond | H | a bond | NH | O | NH | Q3a | OH |
| 92 | N | NMe | Q1d | a bond | H | a bond | NH | O | NH | Q3b | OH |
| 93 | N | NMe | Q1d | a bond | H | a bond | NH | O | NH | Q3c | OH |
| 94 | N | NMe | Q1d | a bond | H | a bond | NH | O | a bond | Q3a | OH |
| 95 | N | NMe | Q1d | a bond | H | a bond | NH | O | a bond | Q3b | OH |
| 96 | N | NMe | Q1d | a bond | H | a bond | NH | O | a bond | Q3c | OH |
| 97 | N | NMe | Q1e | a bond | Me | a bond | NH | S | NH | Q3a | OH |
| 98 | N | NMe | Q1e | a bond | Me | a bond | NH | S | NH | Q3b | OH |
| 99 | N | NMe | Q1e | a bond | Me | a bond | NH | S | NH | Q3c | OH |
| 100 | N | NMe | Q1e | a bond | Me | a bond | NH | S | a bond | Q3a | OH |
| 101 | N | NMe | Q1e | a bond | Me | a bond | NH | S | a bond | Q3b | OH |
| 102 | N | NMe | Q1e | a bond | Me | a bond | NH | S | a bond | Q3c | OH |
| 103 | N | NMe | Q1e | a bond | Me | a bond | NH | O | NH | Q3a | OH |
| 104 | N | NMe | Q1e | a bond | Me | a bond | NH | O | NH | Q3b | OH |
| 105 | N | NMe | Q1e | a bond | Me | a bond | NH | O | NH | Q3c | OH |
| 106 | N | NMe | Q1e | a bond | Me | a bond | NH | O | a bond | Q3a | OH |
| 107 | N | NMe | Q1e | a bond | Me | a bond | NH | O | a bond | Q3b | OH |
| 108 | N | NMe | Q1e | a bond | Me | a bond | NH | O | a bond | Q3c | OH |
| 109 | N | NMe | Q1e | a bond | H | a bond | NH | S | NH | Q3a | OH |
| 110 | N | NMe | Q1e | a bond | H | a bond | NH | S | NH | Q3b | OH |
| 111 | N | NMe | Q1e | a bond | H | a bond | NH | S | NH | Q3c | OH |
| 112 | N | NMe | Q1e | a bond | H | a bond | NH | S | a bond | Q3a | OH |
| 113 | N | NMe | Q1e | a bond | H | a bond | NH | S | a bond | Q3b | OH |
| 114 | N | NMe | Q1e | a bond | H | a bond | NH | S | a bond | Q3c | OH |
| 115 | N | NMe | Q1e | a bond | H | a bond | NH | O | NH | Q3a | OH |
| 116 | N | NMe | Q1e | a bond | H | a bond | NH | O | NH | Q3b | OH |
| 117 | N | NMe | Q1e | a bond | H | a bond | NH | O | NH | Q3c | OH |
| 118 | N | NMe | Q1e | a bond | H | a bond | NH | O | a bond | Q3a | OH |
| 119 | N | NMe | Q1e | a bond | H | a bond | NH | O | a bond | Q3b | OH |
| 120 | N | NMe | Q1e | a bond | H | a bond | NH | O | a bond | Q3c | OH |
| 121 | N | NMe | Q1f | a bond | Me | a bond | NH | S | NH | Q3a | OH |
| 122 | N | NMe | Q1f | a bond | Me | a bond | NH | S | NH | Q3b | OH |
| 123 | N | NMe | Q1f | a bond | Me | a bond | NH | S | NH | Q3c | OH |
| 124 | N | NMe | Q1f | a bond | Me | a bond | NH | S | a bond | Q3a | OH |
| 125 | N | NMe | Q1f | a bond | Me | a bond | NH | S | a bond | Q3b | OH |
| 126 | N | NMe | Q1f | a bond | Me | a bond | NH | S | a bond | Q3c | OH |
| 127 | N | NMe | Q1f | a bond | Me | a bond | NH | O | NH | Q3a | OH |
| 128 | N | NMe | Q1f | a bond | Me | a bond | NH | O | NH | Q3b | OH |
| 129 | N | NMe | Q1f | a bond | Me | a bond | NH | O | NH | Q3c | OH |
| 130 | N | NMe | Q1f | a bond | Me | a bond | NH | O | a bond | Q3a | OH |
| 131 | N | NMe | Q1f | a bond | Me | a bond | NH | O | a bond | Q3b | OH |
| 132 | N | NMe | Q1f | a bond | Me | a bond | NH | O | a bond | Q3c | OH |
| 133 | N | NMe | Q1f | a bond | H | a bond | NH | S | NH | Q3a | OH |
| 134 | N | NMe | Q1f | a bond | H | a bond | NH | S | NH | Q3b | OH |
| 135 | N | NMe | Q1f | a bond | H | a bond | NH | S | NH | Q3c | OH |
| 136 | N | NMe | Q1f | a bond | H | a bond | NH | S | a bond | Q3a | OH |
| 137 | N | NMe | Q1f | a bond | H | a bond | NH | S | a bond | Q3b | OH |
| 138 | N | NMe | Q1f | a bond | H | a bond | NH | S | a bond | Q3c | OH |
| 139 | N | NMe | Q1f | a bond | H | a bond | NH | O | NH | Q3a | OH |
| 140 | N | NMe | Q1f | a bond | H | a bond | NH | O | NH | Q3b | OH |
| 141 | N | NMe | Q1f | a bond | H | a bond | NH | O | NH | Q3c | OH |
| 142 | N | NMe | Q1f | a bond | H | a bond | NH | O | a bond | Q3a | OH |
| 143 | N | NMe | Q1f | a bond | H | a bond | NH | O | a bond | Q3b | OH |
| 144 | N | NMe | Q1f | a bond | H | a bond | NH | O | a bond | Q3c | OH |
| 145 | N | NMe | Q1g | a bond | Me | a bond | NH | S | NH | Q3a | OH |
| 146 | N | NMe | Q1g | a bond | Me | a bond | NH | S | NH | Q3b | OH |
| 147 | N | NMe | Q1g | a bond | Me | a bond | NH | S | NH | Q3c | OH |
| 148 | N | NMe | Q1g | a bond | Me | a bond | NH | S | a bond | Q3a | OH |
| 149 | N | NMe | Q1g | a bond | Me | a bond | NH | S | a bond | Q3b | OH |
| 150 | N | NMe | Q1g | a bond | Me | a bond | NH | S | a bond | Q3c | OH |
| 151 | N | NMe | Q1g | a bond | Me | a bond | NH | O | NH | Q3a | OH |
| 152 | N | NMe | Q1g | a bond | Me | a bond | NH | O | NH | Q3b | OH |
| 153 | N | NMe | Q1g | a bond | Me | a bond | NH | O | NH | Q3c | OH |
| 154 | N | NMe | Q1g | a bond | Me | a bond | NH | O | a bond | Q3a | OH |
| 155 | N | NMe | Q1g | a bond | Me | a bond | NH | O | a bond | Q3b | OH |
| 156 | N | NMe | Q1g | a bond | Me | a bond | NH | O | a bond | Q3c | OH |

TABLE 1-continued

| No | A | B | R¹ | L¹ | R² | L² | L³ | Y | L⁴ | R³ | X |
|---|---|---|---|---|---|---|---|---|---|---|---|
| 157 | N | NMe | Q1g | a bond | H | a bond | NH | S | NH | Q3a | OH |
| 158 | N | NMe | Q1g | a bond | H | a bond | NH | S | NH | Q3b | OH |
| 159 | N | NMe | Q1g | a bond | H | a bond | NH | S | NH | Q3c | OH |
| 160 | N | NMe | Q1g | a bond | H | a bond | NH | S | a bond | Q3a | OH |
| 161 | N | NMe | Q1g | a bond | H | a bond | NH | S | a bond | Q3b | OH |
| 162 | N | NMe | Q1g | a bond | H | a bond | NH | S | a bond | Q3c | OH |
| 163 | N | NMe | Q1g | a bond | H | a bond | NH | O | NH | Q3a | OH |
| 164 | N | NMe | Q1g | a bond | H | a bond | NH | O | NH | Q3b | OH |
| 165 | N | NMe | Q1g | a bond | H | a bond | NH | O | NH | Q3c | OH |
| 166 | N | NMe | Q1g | a bond | H | a bond | NH | O | a bond | Q3a | OH |
| 167 | N | NMe | Q1g | a bond | H | a bond | NH | O | a bond | Q3b | OH |
| 168 | N | NMe | Q1g | a bond | H | a bond | NH | O | a bond | Q3c | OH |
| 169 | N | NMe | Q1h | a bond | Me | a bond | NH | S | NH | Q3a | OH |
| 170 | N | NMe | Q1h | a bond | Me | a bond | NH | S | NH | Q3b | OH |
| 171 | N | NMe | Q1h | a bond | Me | a bond | NH | S | NH | Q3c | OH |
| 172 | N | NMe | Q1h | a bond | Me | a bond | NH | S | a bond | Q3a | OH |
| 173 | N | NMe | Q1h | a bond | Me | a bond | NH | S | a bond | Q3b | OH |
| 174 | N | NMe | Q1h | a bond | Me | a bond | NH | S | a bond | Q3c | OH |
| 175 | N | NMe | Q1h | a bond | Me | a bond | NH | O | NH | Q3a | OH |
| 176 | N | NMe | Q1h | a bond | Me | a bond | NH | O | NH | Q3b | OH |
| 177 | N | NMe | Q1h | a bond | Me | a bond | NH | O | NH | Q3c | OH |
| 178 | N | NMe | Q1h | a bond | Me | a bond | NH | O | a bond | Q3a | OH |
| 179 | N | NMe | Q1h | a bond | Me | a bond | NH | O | a bond | Q3b | OH |
| 180 | N | NMe | Q1h | a bond | Me | a bond | NH | O | a bond | Q3c | OH |
| 181 | N | NMe | Q1h | a bond | H | a bond | NH | S | NH | Q3a | OH |
| 182 | N | NMe | Q1h | a bond | H | a bond | NH | S | NH | Q3b | OH |
| 183 | N | NMe | Q1h | a bond | H | a bond | NH | S | NH | Q3c | OH |
| 184 | N | NMe | Q1h | a bond | H | a bond | NH | S | a bond | Q3a | OH |
| 185 | N | NMe | Q1h | a bond | H | a bond | NH | S | a bond | Q3b | OH |
| 186 | N | NMe | Q1h | a bond | H | a bond | NH | S | a bond | Q3c | OH |
| 187 | N | NMe | Q1h | a bond | H | a bond | NH | O | NH | Q3a | OH |
| 188 | N | NMe | Q1h | a bond | H | a bond | NH | O | NH | Q3b | OH |
| 189 | N | NMe | Q1h | a bond | H | a bond | NH | O | NH | Q3c | OH |
| 190 | N | NMe | Q1h | a bond | H | a bond | NH | O | a bond | Q3a | OH |
| 191 | N | NMe | Q1h | a bond | H | a bond | NH | O | a bond | Q3b | OH |
| 192 | N | NMe | Q1h | a bond | H | a bond | NH | O | a bond | Q3c | OH |
| 193 | N | NMe | Q1i | a bond | Me | a bond | NH | S | NH | Q3a | OH |
| 194 | N | NMe | Q1i | a bond | Me | a bond | NH | S | NH | Q3b | OH |
| 195 | N | NMe | Q1i | a bond | Me | a bond | NH | S | NH | Q3c | OH |
| 196 | N | NMe | Q1i | a bond | Me | a bond | NH | S | a bond | Q3a | OH |
| 197 | N | NMe | Q1i | a bond | Me | a bond | NH | S | a bond | Q3b | OH |
| 198 | N | NMe | Q1i | a bond | Me | a bond | NH | S | a bond | Q3c | OH |
| 199 | N | NMe | Q1i | a bond | Me | a bond | NH | O | NH | Q3a | OH |
| 200 | N | NMe | Q1i | a bond | Me | a bond | NH | O | NH | Q3b | OH |
| 201 | N | NMe | Q1i | a bond | Me | a bond | NH | O | NH | Q3c | OH |
| 202 | N | NMe | Q1i | a bond | Me | a bond | NH | O | a bond | Q3a | OH |
| 203 | N | NMe | Q1i | a bond | Me | a bond | NH | O | a bond | Q3b | OH |
| 204 | N | NMe | Q1i | a bond | Me | a bond | NH | O | a bond | Q3c | OH |
| 205 | N | NMe | Q1i | a bond | H | a bond | NH | S | NH | Q3a | OH |
| 206 | N | NMe | Q1i | a bond | H | a bond | NH | S | NH | Q3b | OH |
| 207 | N | NMe | Q1i | a bond | H | a bond | NH | S | NH | Q3c | OH |
| 208 | N | NMe | Q1i | a bond | H | a bond | NH | S | a bond | Q3a | OH |
| 209 | N | NMe | Q1i | a bond | H | a bond | NH | S | a bond | Q3b | OH |
| 210 | N | NMe | Q1i | a bond | H | a bond | NH | S | a bond | Q3c | OH |
| 211 | N | NMe | Q1i | a bond | H | a bond | NH | O | NH | Q3a | OH |
| 212 | N | NMe | Q1i | a bond | H | a bond | NH | O | NH | Q3b | OH |
| 213 | N | NMe | Q1i | a bond | H | a bond | NH | O | NH | Q3c | OH |
| 214 | N | NMe | Q1i | a bond | H | a bond | NH | O | a bond | Q3a | OH |
| 215 | N | NMe | Q1i | a bond | H | a bond | NH | O | a bond | Q3b | OH |
| 216 | N | NMe | Q1i | a bond | H | a bond | NH | O | a bond | Q3c | OH |
| 217 | N | NMe | Q1j | a bond | Me | a bond | NH | S | NH | Q3a | OH |
| 218 | N | NMe | Q1j | a bond | Me | a bond | NH | S | NH | Q3b | OH |
| 219 | N | NMe | Q1j | a bond | Me | a bond | NH | S | NH | Q3c | OH |
| 220 | N | NMe | Q1j | a bond | Me | a bond | NH | S | a bond | Q3a | OH |
| 221 | N | NMe | Q1j | a bond | Me | a bond | NH | S | a bond | Q3b | OH |
| 222 | N | NMe | Q1j | a bond | Me | a bond | NH | S | a bond | Q3c | OH |
| 223 | N | NMe | Q1j | a bond | Me | a bond | NH | O | NH | Q3a | OH |
| 224 | N | NMe | Q1j | a bond | Me | a bond | NH | O | NH | Q3b | OH |
| 225 | N | NMe | Q1j | a bond | Me | a bond | NH | O | NH | Q3c | OH |
| 226 | N | NMe | Q1j | a bond | Me | a bond | NH | O | a bond | Q3a | OH |
| 227 | N | NMe | Q1j | a bond | Me | a bond | NH | O | a bond | Q3b | OH |
| 228 | N | NMe | Q1j | a bond | Me | a bond | NH | O | a bond | Q3c | OH |
| 229 | N | NMe | Q1j | a bond | H | a bond | NH | S | NH | Q3a | OH |
| 230 | N | NMe | Q1j | a bond | H | a bond | NH | S | NH | Q3b | OH |
| 231 | N | NMe | Q1j | a bond | H | a bond | NH | S | NH | Q3c | OH |
| 232 | N | NMe | Q1j | a bond | H | a bond | NH | S | a bond | Q3a | OH |
| 233 | N | NMe | Q1j | a bond | H | a bond | NH | S | a bond | Q3b | OH |
| 234 | N | NMe | Q1j | a bond | H | a bond | NH | S | a bond | Q3c | OH |

TABLE 1-continued

| No | A | B | R¹ | L¹ | R² | L² | L³ | Y | L⁴ | R³ | X |
|---|---|---|---|---|---|---|---|---|---|---|---|
| 235 | N | NMe | Q1j | a bond | H | a bond | NH | O | NH | Q3a | OH |
| 236 | N | NMe | Q1j | a bond | H | a bond | NH | O | NH | Q3b | OH |
| 237 | N | NMe | Q1j | a bond | H | a bond | NH | O | NH | Q3c | OH |
| 238 | N | NMe | Q1j | a bond | H | a bond | NH | O | a bond | Q3a | OH |
| 239 | N | NMe | Q1j | a bond | H | a bond | NH | O | a bond | Q3b | OH |
| 240 | N | NMe | Q1j | a bond | H | a bond | NH | O | a bond | Q3c | OH |
| 241 | N | NEt | Q1a | a bond | Me | a bond | NH | S | NH | Q3a | OH |
| 242 | N | NEt | Q1a | a bond | Me | a bond | NH | S | NH | Q3b | OH |
| 243 | N | NEt | Q1a | a bond | Me | a bond | NH | S | NH | Q3c | OH |
| 244 | N | NEt | Q1a | a bond | Me | a bond | NH | S | a bond | Q3a | OH |
| 245 | N | NEt | Q1a | a bond | Me | a bond | NH | S | a bond | Q3b | OH |
| 246 | N | NEt | Q1a | a bond | Me | a bond | NH | S | a bond | Q3c | OH |
| 247 | N | NEt | Q1a | a bond | Me | a bond | NH | O | NH | Q3a | OH |
| 248 | N | NEt | Q1a | a bond | Me | a bond | NH | O | NH | Q3b | OH |
| 249 | N | NEt | Q1a | a bond | Me | a bond | NH | O | NH | Q3c | OH |
| 250 | N | NEt | Q1a | a bond | Me | a bond | NH | O | a bond | Q3a | OH |
| 251 | N | NEt | Q1a | a bond | Me | a bond | NH | O | a bond | Q3b | OH |
| 252 | N | NEt | Q1a | a bond | Me | a bond | NH | O | a bond | Q3c | OH |
| 253 | N | NEt | Q1a | a bond | H | a bond | NH | S | NH | Q3a | OH |
| 254 | N | NEt | Q1a | a bond | H | a bond | NH | S | NH | Q3b | OH |
| 255 | N | NEt | Q1a | a bond | H | a bond | NH | S | NH | Q3c | OH |
| 256 | N | NEt | Q1a | a bond | H | a bond | NH | S | a bond | Q3a | OH |
| 257 | N | NEt | Q1a | a bond | H | a bond | NH | S | a bond | Q3b | OH |
| 258 | N | NEt | Q1a | a bond | H | a bond | NH | S | a bond | Q3c | OH |
| 259 | N | NEt | Q1a | a bond | H | a bond | NH | O | NH | Q3a | OH |
| 260 | N | NEt | Q1a | a bond | H | a bond | NH | O | NH | Q3b | OH |
| 261 | N | NEt | Q1a | a bond | H | a bond | NH | O | NH | Q3c | OH |
| 262 | N | NEt | Q1a | a bond | H | a bond | NH | O | a bond | Q3a | OH |
| 263 | N | NEt | Q1a | a bond | H | a bond | NH | O | a bond | Q3b | OH |
| 264 | N | NEt | Q1a | a bond | H | a bond | NH | O | a bond | Q3c | OH |
| 265 | N | NEt | Q1b | a bond | Me | a bond | NH | S | NH | Q3a | OH |
| 266 | N | NEt | Q1b | a bond | Me | a bond | NH | S | NH | Q3b | OH |
| 267 | N | NEt | Q1b | a bond | Me | a bond | NH | S | NH | Q3c | OH |
| 268 | N | NEt | Q1b | a bond | Me | a bond | NH | S | a bond | Q3a | OH |
| 269 | N | NEt | Q1b | a bond | Me | a bond | NH | S | a bond | Q3b | OH |
| 270 | N | NEt | Q1b | a bond | Me | a bond | NH | S | a bond | Q3c | OH |
| 271 | N | NEt | Q1b | a bond | Me | a bond | NH | O | NH | Q3a | OH |
| 272 | N | NEt | Q1b | a bond | Me | a bond | NH | O | NH | Q3b | OH |
| 273 | N | NEt | Q1b | a bond | Me | a bond | NH | O | NH | Q3c | OH |
| 274 | N | NEt | Q1b | a bond | Me | a bond | NH | O | a bond | Q3a | OH |
| 275 | N | NEt | Q1b | a bond | Me | a bond | NH | O | a bond | Q3b | OH |
| 276 | N | NEt | Q1b | a bond | Me | a bond | NH | O | a bond | Q3c | OH |
| 277 | N | NEt | Q1b | a bond | H | a bond | NH | S | NH | Q3a | OH |
| 278 | N | NEt | Q1b | a bond | H | a bond | NH | S | NH | Q3b | OH |
| 279 | N | NEt | Q1b | a bond | H | a bond | NH | S | NH | Q3c | OH |
| 280 | N | NEt | Q1b | a bond | H | a bond | NH | S | a bond | Q3a | OH |
| 281 | N | NEt | Q1b | a bond | H | a bond | NH | S | a bond | Q3b | OH |
| 282 | N | NEt | Q1b | a bond | H | a bond | NH | S | a bond | Q3c | OH |
| 283 | N | NEt | Q1b | a bond | H | a bond | NH | O | NH | Q3a | OH |
| 284 | N | NEt | Q1b | a bond | H | a bond | NH | O | NH | Q3b | OH |
| 285 | N | NEt | Q1b | a bond | H | a bond | NH | O | NH | Q3c | OH |
| 286 | N | NEt | Q1b | a bond | H | a bond | NH | O | a bond | Q3a | OH |
| 287 | N | NEt | Q1b | a bond | H | a bond | NH | O | a bond | Q3b | OH |
| 288 | N | NEt | Q1b | a bond | H | a bond | NH | O | a bond | Q3c | OH |
| 289 | N | NEt | Q1c | a bond | Me | a bond | NH | S | NH | Q3a | OH |
| 290 | N | NEt | Q1c | a bond | Me | a bond | NH | S | NH | Q3b | OH |
| 291 | N | NEt | Q1c | a bond | Me | a bond | NH | S | NH | Q3c | OH |
| 292 | N | NEt | Q1c | a bond | Me | a bond | NH | S | a bond | Q3a | OH |
| 293 | N | NEt | Q1c | a bond | Me | a bond | NH | S | a bond | Q3b | OH |
| 294 | N | NEt | Q1c | a bond | Me | a bond | NH | S | a bond | Q3c | OH |
| 295 | N | NEt | Q1c | a bond | Me | a bond | NH | O | NH | Q3a | OH |
| 296 | N | NEt | Q1c | a bond | Me | a bond | NH | O | NH | Q3b | OH |
| 297 | N | NEt | Q1c | a bond | Me | a bond | NH | O | NH | Q3c | OH |
| 298 | N | NEt | Q1c | a bond | Me | a bond | NH | O | a bond | Q3a | OH |
| 299 | N | NEt | Q1c | a bond | Me | a bond | NH | O | a bond | Q3b | OH |
| 300 | N | NEt | Q1c | a bond | Me | a bond | NH | O | a bond | Q3c | OH |
| 301 | N | NEt | Q1c | a bond | H | a bond | NH | S | NH | Q3a | OH |
| 302 | N | NEt | Q1c | a bond | H | a bond | NH | S | NH | Q3b | OH |
| 303 | N | NEt | Q1c | a bond | H | a bond | NH | S | NH | Q3c | OH |
| 304 | N | NEt | Q1c | a bond | H | a bond | NH | S | a bond | Q3a | OH |
| 305 | N | NEt | Q1c | a bond | H | a bond | NH | S | a bond | Q3b | OH |
| 306 | N | NEt | Q1c | a bond | H | a bond | NH | S | a bond | Q3c | OH |
| 307 | N | NEt | Q1c | a bond | H | a bond | NH | O | NH | Q3a | OH |
| 308 | N | NEt | Q1c | a bond | H | a bond | NH | O | NH | Q3b | OH |
| 309 | N | NEt | Q1c | a bond | H | a bond | NH | O | NH | Q3c | OH |
| 310 | N | NEt | Q1c | a bond | H | a bond | NH | O | a bond | Q3a | OH |
| 311 | N | NEt | Q1c | a bond | H | a bond | NH | O | a bond | Q3b | OH |
| 312 | N | NEt | Q1c | a bond | H | a bond | NH | O | a bond | Q3c | OH |

TABLE 1-continued

| No | A | B | R¹ | L¹ | R² | L² | L³ | Y | L⁴ | R³ | X |
|---|---|---|---|---|---|---|---|---|---|---|---|
| 313 | N | NEt | Q1d | a bond | Me | a bond | NH | S | NH | Q3a | OH |
| 314 | N | NEt | Q1d | a bond | Me | a bond | NH | S | NH | Q3b | OH |
| 315 | N | NEt | Q1d | a bond | Me | a bond | NH | S | NH | Q3c | OH |
| 316 | N | NEt | Q1d | a bond | Me | a bond | NH | S | a bond | Q3a | OH |
| 317 | N | NEt | Q1d | a bond | Me | a bond | NH | S | a bond | Q3b | OH |
| 318 | N | NEt | Q1d | a bond | Me | a bond | NH | S | a bond | Q3c | OH |
| 319 | N | NEt | Q1d | a bond | Me | a bond | NH | O | NH | Q3a | OH |
| 320 | N | NEt | Q1d | a bond | Me | a bond | NH | O | NH | Q3b | OH |
| 321 | N | NEt | Q1d | a bond | Me | a bond | NH | O | NH | Q3c | OH |
| 322 | N | NEt | Q1d | a bond | Me | a bond | NH | O | a bond | Q3a | OH |
| 323 | N | NEt | Q1d | a bond | Me | a bond | NH | O | a bond | Q3b | OH |
| 324 | N | NEt | Q1d | a bond | Me | a bond | NH | O | a bond | Q3c | OH |
| 325 | N | NEt | Q1d | a bond | H | a bond | NH | S | NH | Q3a | OH |
| 326 | N | NEt | Q1d | a bond | H | a bond | NH | S | NH | Q3b | OH |
| 327 | N | NEt | Q1d | a bond | H | a bond | NH | S | NH | Q3c | OH |
| 328 | N | NEt | Q1d | a bond | H | a bond | NH | S | a bond | Q3a | OH |
| 329 | N | NEt | Q1d | a bond | H | a bond | NH | S | a bond | Q3b | OH |
| 330 | N | NEt | Q1d | a bond | H | a bond | NH | S | a bond | Q3c | OH |
| 331 | N | NEt | Q1d | a bond | H | a bond | NH | O | NH | Q3a | OH |
| 332 | N | NEt | Q1d | a bond | H | a bond | NH | O | NH | Q3b | OH |
| 333 | N | NEt | Q1d | a bond | H | a bond | NH | O | NH | Q3c | OH |
| 334 | N | NEt | Q1d | a bond | H | a bond | NH | O | a bond | Q3a | OH |
| 335 | N | NEt | Q1d | a bond | H | a bond | NH | O | a bond | Q3b | OH |
| 336 | N | NEt | Q1d | a bond | H | a bond | NH | O | a bond | Q3c | OH |
| 337 | N | NEt | Q1e | a bond | Me | a bond | NH | S | NH | Q3a | OH |
| 338 | N | NEt | Q1e | a bond | Me | a bond | NH | S | NH | Q3b | OH |
| 339 | N | NEt | Q1e | a bond | Me | a bond | NH | S | NH | Q3c | OH |
| 340 | N | NEt | Q1e | a bond | Me | a bond | NH | S | a bond | Q3a | OH |
| 341 | N | NEt | Q1e | a bond | Me | a bond | NH | S | a bond | Q3b | OH |
| 342 | N | NEt | Q1e | a bond | Me | a bond | NH | S | a bond | Q3c | OH |
| 343 | N | NEt | Q1e | a bond | Me | a bond | NH | O | NH | Q3a | OH |
| 344 | N | NEt | Q1e | a bond | Me | a bond | NH | O | NH | Q3b | OH |
| 345 | N | NEt | Q1e | a bond | Me | a bond | NH | O | NH | Q3c | OH |
| 346 | N | NEt | Q1e | a bond | Me | a bond | NH | O | a bond | Q3a | OH |
| 347 | N | NEt | Q1e | a bond | Me | a bond | NH | O | a bond | Q3b | OH |
| 348 | N | NEt | Q1e | a bond | Me | a bond | NH | O | a bond | Q3c | OH |
| 349 | N | NEt | Q1e | a bond | H | a bond | NH | S | NH | Q3a | OH |
| 350 | N | NEt | Q1e | a bond | H | a bond | NH | S | NH | Q3b | OH |
| 351 | N | NEt | Q1e | a bond | H | a bond | NH | S | NH | Q3c | OH |
| 352 | N | NEt | Q1e | a bond | H | a bond | NH | S | a bond | Q3a | OH |
| 353 | N | NEt | Q1e | a bond | H | a bond | NH | S | a bond | Q3b | OH |
| 354 | N | NEt | Q1e | a bond | H | a bond | NH | S | a bond | Q3c | OH |
| 355 | N | NEt | Q1e | a bond | H | a bond | NH | O | NH | Q3a | OH |
| 356 | N | NEt | Q1e | a bond | H | a bond | NH | O | NH | Q3b | OH |
| 357 | N | NEt | Q1e | a bond | H | a bond | NH | O | NH | Q3c | OH |
| 358 | N | NEt | Q1e | a bond | H | a bond | NH | O | a bond | Q3a | OH |
| 359 | N | NEt | Q1e | a bond | H | a bond | NH | O | a bond | Q3b | OH |
| 360 | N | NEt | Q1e | a bond | H | a bond | NH | O | a bond | Q3c | OH |
| 361 | N | NEt | Q1f | a bond | Me | a bond | NH | S | NH | Q3a | OH |
| 362 | N | NEt | Q1f | a bond | Me | a bond | NH | S | NH | Q3b | OH |
| 363 | N | NEt | Q1f | a bond | Me | a bond | NH | S | NH | Q3c | OH |
| 364 | N | NEt | Q1f | a bond | Me | a bond | NH | S | a bond | Q3a | OH |
| 365 | N | NEt | Q1f | a bond | Me | a bond | NH | S | a bond | Q3b | OH |
| 366 | N | NEt | Q1f | a bond | Me | a bond | NH | S | a bond | Q3c | OH |
| 367 | N | NEt | Q1f | a bond | Me | a bond | NH | O | NH | Q3a | OH |
| 368 | N | NEt | Q1f | a bond | Me | a bond | NH | O | NH | Q3b | OH |
| 369 | N | NEt | Q1f | a bond | Me | a bond | NH | O | NH | Q3c | OH |
| 370 | N | NEt | Q1f | a bond | Me | a bond | NH | O | a bond | Q3a | OH |
| 371 | N | NEt | Q1f | a bond | Me | a bond | NH | O | a bond | Q3b | OH |
| 372 | N | NEt | Q1f | a bond | Me | a bond | NH | O | a bond | Q3c | OH |
| 373 | N | NEt | Q1f | a bond | H | a bond | NH | S | NH | Q3a | OH |
| 374 | N | NEt | Q1f | a bond | H | a bond | NH | S | NH | Q3b | OH |
| 375 | N | NEt | Q1f | a bond | H | a bond | NH | S | NH | Q3c | OH |
| 376 | N | NEt | Q1f | a bond | H | a bond | NH | S | a bond | Q3a | OH |
| 377 | N | NEt | Q1f | a bond | H | a bond | NH | S | a bond | Q3b | OH |
| 378 | N | NEt | Q1f | a bond | H | a bond | NH | S | a bond | Q3c | OH |
| 379 | N | NEt | Q1f | a bond | H | a bond | NH | O | NH | Q3a | OH |
| 380 | N | NEt | Q1f | a bond | H | a bond | NH | O | NH | Q3b | OH |
| 381 | N | NEt | Q1f | a bond | H | a bond | NH | O | NH | Q3c | OH |
| 382 | N | NEt | Q1f | a bond | H | a bond | NH | O | a bond | Q3a | OH |
| 383 | N | NEt | Q1f | a bond | H | a bond | NH | O | a bond | Q3b | OH |
| 384 | N | NEt | Q1f | a bond | H | a bond | NH | O | a bond | Q3c | OH |
| 385 | N | NEt | Q1g | a bond | Me | a bond | NH | S | NH | Q3a | OH |
| 386 | N | NEt | Q1g | a bond | Me | a bond | NH | S | NH | Q3b | OH |
| 387 | N | NEt | Q1g | a bond | Me | a bond | NH | S | NH | Q3c | OH |
| 388 | N | NEt | Q1g | a bond | Me | a bond | NH | S | a bond | Q3a | OH |
| 389 | N | NEt | Q1g | a bond | Me | a bond | NH | S | a bond | Q3b | OH |
| 390 | N | NEt | Q1g | a bond | Me | a bond | NH | S | a bond | Q3c | OH |

TABLE 1-continued

| No | A | B | R¹ | L¹ | R² | L² | L³ | Y | L⁴ | R³ | X |
|---|---|---|---|---|---|---|---|---|---|---|---|
| 391 | N | NEt | Q1g | a bond | Me | a bond | NH | O | NH | Q3a | OH |
| 392 | N | NEt | Q1g | a bond | Me | a bond | NH | O | NH | Q3b | OH |
| 393 | N | NEt | Q1g | a bond | Me | a bond | NH | O | NH | Q3c | OH |
| 394 | N | NEt | Q1g | a bond | Me | a bond | NH | O | a bond | Q3a | OH |
| 395 | N | NEt | Q1g | a bond | Me | a bond | NH | O | a bond | Q3b | OH |
| 396 | N | NEt | Q1g | a bond | Me | a bond | NH | O | a bond | Q3c | OH |
| 397 | N | NEt | Q1g | a bond | H | a bond | NH | S | NH | Q3a | OH |
| 398 | N | NEt | Q1g | a bond | H | a bond | NH | S | NH | Q3b | OH |
| 399 | N | NEt | Q1g | a bond | H | a bond | NH | S | NH | Q3c | OH |
| 400 | N | NEt | Q1g | a bond | H | a bond | NH | S | a bond | Q3a | OH |
| 401 | N | NEt | Q1g | a bond | H | a bond | NH | S | a bond | Q3b | OH |
| 402 | N | NEt | Q1g | a bond | H | a bond | NH | S | a bond | Q3c | OH |
| 403 | N | NEt | Q1g | a bond | H | a bond | NH | O | NH | Q3a | OH |
| 404 | N | NEt | Q1g | a bond | H | a bond | NH | O | NH | Q3b | OH |
| 405 | N | NEt | Q1g | a bond | H | a bond | NH | O | NH | Q3c | OH |
| 406 | N | NEt | Q1g | a bond | H | a bond | NH | O | a bond | Q3a | OH |
| 407 | N | NEt | Q1g | a bond | H | a bond | NH | O | a bond | Q3b | OH |
| 408 | N | NEt | Q1g | a bond | H | a bond | NH | O | a bond | Q3c | OH |
| 409 | N | NEt | Q1h | a bond | Me | a bond | NH | S | NH | Q3a | OH |
| 410 | N | NEt | Q1h | a bond | Me | a bond | NH | S | NH | Q3b | OH |
| 411 | N | NEt | Q1h | a bond | Me | a bond | NH | S | NH | Q3c | OH |
| 412 | N | NEt | Q1h | a bond | Me | a bond | NH | S | a bond | Q3a | OH |
| 413 | N | NEt | Q1h | a bond | Me | a bond | NH | S | a bond | Q3b | OH |
| 414 | N | NEt | Q1h | a bond | Me | a bond | NH | S | a bond | Q3c | OH |
| 415 | N | NEt | Q1h | a bond | Me | a bond | NH | O | NH | Q3a | OH |
| 416 | N | NEt | Q1h | a bond | Me | a bond | NH | O | NH | Q3b | OH |
| 417 | N | NEt | Q1h | a bond | Me | a bond | NH | O | NH | Q3c | OH |
| 418 | N | NEt | Q1h | a bond | Me | a bond | NH | O | a bond | Q3a | OH |
| 419 | N | NEt | Q1h | a bond | Me | a bond | NH | O | a bond | Q3b | OH |
| 420 | N | NEt | Q1h | a bond | Me | a bond | NH | O | a bond | Q3c | OH |
| 421 | N | NEt | Q1h | a bond | H | a bond | NH | S | NH | Q3a | OH |
| 422 | N | NEt | Q1h | a bond | H | a bond | NH | S | NH | Q3b | OH |
| 423 | N | NEt | Q1h | a bond | H | a bond | NH | S | NH | Q3c | OH |
| 424 | N | NEt | Q1h | a bond | H | a bond | NH | S | a bond | Q3a | OH |
| 425 | N | NEt | Q1h | a bond | H | a bond | NH | S | a bond | Q3b | OH |
| 426 | N | NEt | Q1h | a bond | H | a bond | NH | S | a bond | Q3c | OH |
| 427 | N | NEt | Q1h | a bond | H | a bond | NH | O | NH | Q3a | OH |
| 428 | N | NEt | Q1h | a bond | H | a bond | NH | O | NH | Q3b | OH |
| 429 | N | NEt | Q1h | a bond | H | a bond | NH | O | NH | Q3c | OH |
| 430 | N | NEt | Q1h | a bond | H | a bond | NH | O | a bond | Q3a | OH |
| 431 | N | NEt | Q1h | a bond | H | a bond | NH | O | a bond | Q3b | OH |
| 432 | N | NEt | Q1h | a bond | H | a bond | NH | O | a bond | Q3c | OH |
| 433 | N | NEt | Q1i | a bond | Me | a bond | NH | S | NH | Q3a | OH |
| 434 | N | NEt | Q1i | a bond | Me | a bond | NH | S | NH | Q3b | OH |
| 435 | N | NEt | Q1i | a bond | Me | a bond | NH | S | NH | Q3c | OH |
| 436 | N | NEt | Q1i | a bond | Me | a bond | NH | S | a bond | Q3a | OH |
| 437 | N | NEt | Q1i | a bond | Me | a bond | NH | S | a bond | Q3b | OH |
| 438 | N | NEt | Q1i | a bond | Me | a bond | NH | S | a bond | Q3c | OH |
| 439 | N | NEt | Q1i | a bond | Me | a bond | NH | O | NH | Q3a | OH |
| 440 | N | NEt | Q1i | a bond | Me | a bond | NH | O | NH | Q3b | OH |
| 441 | N | NEt | Q1i | a bond | Me | a bond | NH | O | NH | Q3c | OH |
| 442 | N | NEt | Q1i | a bond | Me | a bond | NH | O | a bond | Q3a | OH |
| 443 | N | NEt | Q1i | a bond | Me | a bond | NH | O | a bond | Q3b | OH |
| 444 | N | NEt | Q1i | a bond | Me | a bond | NH | O | a bond | Q3c | OH |
| 445 | N | NEt | Q1i | a bond | H | a bond | NH | S | NH | Q3a | OH |
| 446 | N | NEt | Q1i | a bond | H | a bond | NH | S | NH | Q3b | OH |
| 447 | N | NEt | Q1i | a bond | H | a bond | NH | S | NH | Q3c | OH |
| 448 | N | NEt | Q1i | a bond | H | a bond | NH | S | a bond | Q3a | OH |
| 449 | N | NEt | Q1i | a bond | H | a bond | NH | S | a bond | Q3b | OH |
| 450 | N | NEt | Q1i | a bond | H | a bond | NH | S | a bond | Q3c | OH |
| 451 | N | NEt | Q1i | a bond | H | a bond | NH | O | NH | Q3a | OH |
| 452 | N | NEt | Q1i | a bond | H | a bond | NH | O | NH | Q3b | OH |
| 453 | N | NEt | Q1i | a bond | H | a bond | NH | O | NH | Q3c | OH |
| 454 | N | NEt | Q1i | a bond | H | a bond | NH | O | a bond | Q3a | OH |
| 455 | N | NEt | Q1i | a bond | H | a bond | NH | O | a bond | Q3b | OH |
| 456 | N | NEt | Q1i | a bond | H | a bond | NH | O | a bond | Q3c | OH |
| 457 | N | NEt | Q1j | a bond | Me | a bond | NH | S | NH | Q3a | OH |
| 458 | N | NEt | Q1j | a bond | Me | a bond | NH | S | NH | Q3b | OH |
| 459 | N | NEt | Q1j | a bond | Me | a bond | NH | S | NH | Q3c | OH |
| 460 | N | NEt | Q1j | a bond | Me | a bond | NH | S | a bond | Q3a | OH |
| 461 | N | NEt | Q1j | a bond | Me | a bond | NH | S | a bond | Q3b | OH |
| 462 | N | NEt | Q1j | a bond | Me | a bond | NH | S | a bond | Q3c | OH |
| 463 | N | NEt | Q1j | a bond | Me | a bond | NH | O | NH | Q3a | OH |
| 464 | N | NEt | Q1j | a bond | Me | a bond | NH | O | NH | Q3b | OH |
| 465 | N | NEt | Q1j | a bond | Me | a bond | NH | O | NH | Q3c | OH |
| 466 | N | NEt | Q1j | a bond | Me | a bond | NH | O | a bond | Q3a | OH |
| 467 | N | NEt | Q1j | a bond | Me | a bond | NH | O | a bond | Q3b | OH |
| 468 | N | NEt | Q1j | a bond | Me | a bond | NH | O | a bond | Q3c | OH |

TABLE 1-continued

| No | A | B | R¹ | L¹ | R² | L² | L³ | Y | L⁴ | R³ | X |
|---|---|---|---|---|---|---|---|---|---|---|---|
| 469 | N | NEt | Q1j | a bond | H | a bond | NH | S | NH | Q3a | OH |
| 470 | N | NEt | Q1j | a bond | H | a bond | NH | S | NH | Q3b | OH |
| 471 | N | NEt | Q1j | a bond | H | a bond | NH | S | NH | Q3c | OH |
| 472 | N | NEt | Q1j | a bond | H | a bond | NH | S | a bond | Q3a | OH |
| 473 | N | NEt | Q1j | a bond | H | a bond | NH | S | a bond | Q3b | OH |
| 474 | N | NEt | Q1j | a bond | H | a bond | NH | S | a bond | Q3c | OH |
| 475 | N | NEt | Q1j | a bond | H | a bond | NH | O | NH | Q3a | OH |
| 476 | N | NEt | Q1j | a bond | H | a bond | NH | O | NH | Q3b | OH |
| 477 | N | NEt | Q1j | a bond | H | a bond | NH | O | NH | Q3c | OH |
| 478 | N | NEt | Q1j | a bond | H | a bond | NH | O | a bond | Q3a | OH |
| 479 | N | NEt | Q1j | a bond | H | a bond | NH | O | a bond | Q3b | OH |
| 480 | N | NEt | Q1j | a bond | H | a bond | NH | O | a bond | Q3c | OH |
| 481 | N | S | Q1a | a bond | Me | a bond | NH | S | NH | Q3a | OH |
| 482 | N | S | Q1a | a bond | Me | a bond | NH | S | NH | Q3b | OH |
| 483 | N | S | Q1a | a bond | Me | a bond | NH | S | NH | Q3c | OH |
| 484 | N | S | Q1a | a bond | Me | a bond | NH | S | a bond | Q3a | OH |
| 485 | N | S | Q1a | a bond | Me | a bond | NH | S | a bond | Q3b | OH |
| 486 | N | S | Q1a | a bond | Me | a bond | NH | S | a bond | Q3c | OH |
| 487 | N | S | Q1a | a bond | Me | a bond | NH | O | NH | Q3a | OH |
| 488 | N | S | Q1a | a bond | Me | a bond | NH | O | NH | Q3b | OH |
| 489 | N | S | Q1a | a bond | Me | a bond | NH | O | NH | Q3c | OH |
| 490 | N | S | Q1a | a bond | Me | a bond | NH | O | a bond | Q3a | OH |
| 491 | N | S | Q1a | a bond | Me | a bond | NH | O | a bond | Q3b | OH |
| 492 | N | S | Q1a | a bond | Me | a bond | NH | O | a bond | Q3c | OH |
| 493 | N | S | Q1a | a bond | H | a bond | NH | S | NH | Q3a | OH |
| 494 | N | S | Q1a | a bond | H | a bond | NH | S | NH | Q3b | OH |
| 495 | N | S | Q1a | a bond | H | a bond | NH | S | NH | Q3c | OH |
| 496 | N | S | Q1a | a bond | H | a bond | NH | S | a bond | Q3a | OH |
| 497 | N | S | Q1a | a bond | H | a bond | NH | S | a bond | Q3b | OH |
| 498 | N | S | Q1a | a bond | H | a bond | NH | S | a bond | Q3c | OH |
| 499 | N | S | Q1a | a bond | H | a bond | NH | O | NH | Q3a | OH |
| 500 | N | S | Q1a | a bond | H | a bond | NH | O | NH | Q3b | OH |
| 501 | N | S | Q1a | a bond | H | a bond | NH | O | NH | Q3c | OH |
| 502 | N | S | Q1a | a bond | H | a bond | NH | O | a bond | Q3a | OH |
| 503 | N | S | Q1a | a bond | H | a bond | NH | O | a bond | Q3b | OH |
| 504 | N | S | Q1a | a bond | H | a bond | NH | O | a bond | Q3c | OH |
| 505 | N | S | Q1b | a bond | Me | a bond | NH | S | NH | Q3a | OH |
| 506 | N | S | Q1b | a bond | Me | a bond | NH | S | NH | Q3b | OH |
| 507 | N | S | Q1b | a bond | Me | a bond | NH | S | NH | Q3c | OH |
| 508 | N | S | Q1b | a bond | Me | a bond | NH | S | a bond | Q3a | OH |
| 509 | N | S | Q1b | a bond | Me | a bond | NH | S | a bond | Q3b | OH |
| 510 | N | S | Q1b | a bond | Me | a bond | NH | S | a bond | Q3c | OH |
| 511 | N | S | Q1b | a bond | Me | a bond | NH | O | NH | Q3a | OH |
| 512 | N | S | Q1b | a bond | Me | a bond | NH | O | NH | Q3b | OH |
| 513 | N | S | Q1b | a bond | Me | a bond | NH | O | NH | Q3c | OH |
| 514 | N | S | Q1b | a bond | Me | a bond | NH | O | a bond | Q3a | OH |
| 515 | N | S | Q1b | a bond | Me | a bond | NH | O | a bond | Q3b | OH |
| 516 | N | S | Q1b | a bond | Me | a bond | NH | O | a bond | Q3c | OH |
| 517 | N | S | Q1b | a bond | H | a bond | NH | S | NH | Q3a | OH |
| 518 | N | S | Q1b | a bond | H | a bond | NH | S | NH | Q3b | OH |
| 519 | N | S | Q1b | a bond | H | a bond | NH | S | NH | Q3c | OH |
| 520 | N | S | Q1b | a bond | H | a bond | NH | S | a bond | Q3a | OH |
| 521 | N | S | Q1b | a bond | H | a bond | NH | S | a bond | Q3b | OH |
| 522 | N | S | Q1b | a bond | H | a bond | NH | S | a bond | Q3c | OH |
| 523 | N | S | Q1b | a bond | H | a bond | NH | O | NH | Q3a | OH |
| 524 | N | S | Q1b | a bond | H | a bond | NH | O | NH | Q3b | OH |
| 525 | N | S | Q1b | a bond | H | a bond | NH | O | NH | Q3c | OH |
| 526 | N | S | Q1b | a bond | H | a bond | NH | O | a bond | Q3a | OH |
| 527 | N | S | Q1b | a bond | H | a bond | NH | O | a bond | Q3b | OH |
| 528 | N | S | Q1b | a bond | H | a bond | NH | O | a bond | Q3c | OH |
| 529 | N | S | Q1c | a bond | Me | a bond | NH | S | NH | Q3a | OH |
| 530 | N | S | Q1c | a bond | Me | a bond | NH | S | NH | Q3b | OH |
| 531 | N | S | Q1c | a bond | Me | a bond | NH | S | NH | Q3c | OH |
| 532 | N | S | Q1c | a bond | Me | a bond | NH | S | a bond | Q3a | OH |
| 533 | N | S | Q1c | a bond | Me | a bond | NH | S | a bond | Q3b | OH |
| 534 | N | S | Q1c | a bond | Me | a bond | NH | S | a bond | Q3c | OH |
| 535 | N | S | Q1c | a bond | Me | a bond | NH | O | NH | Q3a | OH |
| 536 | N | S | Q1c | a bond | Me | a bond | NH | O | NH | Q3b | OH |
| 537 | N | S | Q1c | a bond | Me | a bond | NH | O | NH | Q3c | OH |
| 538 | N | S | Q1c | a bond | Me | a bond | NH | O | a bond | Q3a | OH |
| 539 | N | S | Q1c | a bond | Me | a bond | NH | O | a bond | Q3b | OH |
| 540 | N | S | Q1c | a bond | Me | a bond | NH | O | a bond | Q3c | OH |
| 541 | N | S | Q1c | a bond | H | a bond | NH | S | NH | Q3a | OH |
| 542 | N | S | Q1c | a bond | H | a bond | NH | S | NH | Q3b | OH |
| 543 | N | S | Q1c | a bond | H | a bond | NH | S | NH | Q3c | OH |
| 544 | N | S | Q1c | a bond | H | a bond | NH | S | a bond | Q3a | OH |
| 545 | N | S | Q1c | a bond | H | a bond | NH | S | a bond | Q3b | OH |
| 546 | N | S | Q1c | a bond | H | a bond | NH | S | a bond | Q3c | OH |

TABLE 1-continued

| No | A | B | R¹ | L¹ | R² | L² | L³ | Y | L⁴ | R³ | X |
|---|---|---|---|---|---|---|---|---|---|---|---|
| 547 | N | S | Q1c | a bond | H | a bond | NH | O | NH | Q3a | OH |
| 548 | N | S | Q1c | a bond | H | a bond | NH | O | NH | Q3b | OH |
| 549 | N | S | Q1c | a bond | H | a bond | NH | O | NH | Q3c | OH |
| 550 | N | S | Q1c | a bond | H | a bond | NH | O | a bond | Q3a | OH |
| 551 | N | S | Q1c | a bond | H | a bond | NH | O | a bond | Q3b | OH |
| 552 | N | S | Q1c | a bond | H | a bond | NH | O | a bond | Q3c | OH |
| 553 | N | S | Q1d | a bond | Me | a bond | NH | S | NH | Q3a | OH |
| 554 | N | S | Q1d | a bond | Me | a bond | NH | S | NH | Q3b | OH |
| 555 | N | S | Q1d | a bond | Me | a bond | NH | S | NH | Q3c | OH |
| 556 | N | S | Q1d | a bond | Me | a bond | NH | S | a bond | Q3a | OH |
| 557 | N | S | Q1d | a bond | Me | a bond | NH | S | a bond | Q3b | OH |
| 558 | N | S | Q1d | a bond | Me | a bond | NH | S | a bond | Q3c | OH |
| 559 | N | S | Q1d | a bond | Me | a bond | NH | O | NH | Q3a | OH |
| 560 | N | S | Q1d | a bond | Me | a bond | NH | O | NH | Q3b | OH |
| 561 | N | S | Q1d | a bond | Me | a bond | NH | O | NH | Q3c | OH |
| 562 | N | S | Q1d | a bond | Me | a bond | NH | O | a bond | Q3a | OH |
| 563 | N | S | Q1d | a bond | Me | a bond | NH | O | a bond | Q3b | OH |
| 564 | N | S | Q1d | a bond | Me | a bond | NH | O | a bond | Q3c | OH |
| 565 | N | S | Q1d | a bond | H | a bond | NH | S | NH | Q3a | OH |
| 566 | N | S | Q1d | a bond | H | a bond | NH | S | NH | Q3b | OH |
| 567 | N | S | Q1d | a bond | H | a bond | NH | S | NH | Q3c | OH |
| 568 | N | S | Q1d | a bond | H | a bond | NH | S | a bond | Q3a | OH |
| 569 | N | S | Q1d | a bond | H | a bond | NH | S | a bond | Q3b | OH |
| 570 | N | S | Q1d | a bond | H | a bond | NH | S | a bond | Q3c | OH |
| 571 | N | S | Q1d | a bond | H | a bond | NH | O | NH | Q3a | OH |
| 572 | N | S | Q1d | a bond | H | a bond | NH | O | NH | Q3b | OH |
| 573 | N | S | Q1d | a bond | H | a bond | NH | O | NH | Q3c | OH |
| 574 | N | S | Q1d | a bond | H | a bond | NH | O | a bond | Q3a | OH |
| 575 | N | S | Q1d | a bond | H | a bond | NH | O | a bond | Q3b | OH |
| 576 | N | S | Q1d | a bond | H | a bond | NH | O | a bond | Q3c | OH |
| 577 | N | S | Q1e | a bond | Me | a bond | NH | S | NH | Q3a | OH |
| 578 | N | S | Q1e | a bond | Me | a bond | NH | S | NH | Q3b | OH |
| 579 | N | S | Q1e | a bond | Me | a bond | NH | S | NH | Q3c | OH |
| 580 | N | S | Q1e | a bond | Me | a bond | NH | S | a bond | Q3a | OH |
| 581 | N | S | Q1e | a bond | Me | a bond | NH | S | a bond | Q3b | OH |
| 582 | N | S | Q1e | a bond | Me | a bond | NH | S | a bond | Q3c | OH |
| 583 | N | S | Q1e | a bond | Me | a bond | NH | O | NH | Q3a | OH |
| 584 | N | S | Q1e | a bond | Me | a bond | NH | O | NH | Q3b | OH |
| 585 | N | S | Q1e | a bond | Me | a bond | NH | O | NH | Q3c | OH |
| 586 | N | S | Q1e | a bond | Me | a bond | NH | O | a bond | Q3a | OH |
| 587 | N | S | Q1e | a bond | Me | a bond | NH | O | a bond | Q3b | OH |
| 588 | N | S | Q1e | a bond | Me | a bond | NH | O | a bond | Q3c | OH |
| 589 | N | S | Q1e | a bond | H | a bond | NH | S | NH | Q3a | OH |
| 590 | N | S | Q1e | a bond | H | a bond | NH | S | NH | Q3b | OH |
| 591 | N | S | Q1e | a bond | H | a bond | NH | S | NH | Q3c | OH |
| 592 | N | S | Q1e | a bond | H | a bond | NH | S | a bond | Q3a | OH |
| 593 | N | S | Q1e | a bond | H | a bond | NH | S | a bond | Q3b | OH |
| 594 | N | S | Q1e | a bond | H | a bond | NH | S | a bond | Q3c | OH |
| 595 | N | S | Q1e | a bond | H | a bond | NH | O | NH | Q3a | OH |
| 596 | N | S | Q1e | a bond | H | a bond | NH | O | NH | Q3b | OH |
| 597 | N | S | Q1e | a bond | H | a bond | NH | O | NH | Q3c | OH |
| 598 | N | S | Q1e | a bond | H | a bond | NH | O | a bond | Q3a | OH |
| 599 | N | S | Q1e | a bond | H | a bond | NH | O | a bond | Q3b | OH |
| 600 | N | S | Q1e | a bond | H | a bond | NH | O | a bond | Q3c | OH |
| 601 | N | S | Q1f | a bond | Me | a bond | NH | S | NH | Q3a | OH |
| 602 | N | S | Q1f | a bond | Me | a bond | NH | S | NH | Q3b | OH |
| 603 | N | S | Q1f | a bond | Me | a bond | NH | S | NH | Q3c | OH |
| 604 | N | S | Q1f | a bond | Me | a bond | NH | S | a bond | Q3a | OH |
| 605 | N | S | Q1f | a bond | Me | a bond | NH | S | a bond | Q3b | OH |
| 606 | N | S | Q1f | a bond | Me | a bond | NH | S | a bond | Q3c | OH |
| 607 | N | S | Q1f | a bond | Me | a bond | NH | O | NH | Q3a | OH |
| 608 | N | S | Q1f | a bond | Me | a bond | NH | O | NH | Q3b | OH |
| 609 | N | S | Q1f | a bond | Me | a bond | NH | O | NH | Q3c | OH |
| 610 | N | S | Q1f | a bond | Me | a bond | NH | O | a bond | Q3a | OH |
| 611 | N | S | Q1f | a bond | Me | a bond | NH | O | a bond | Q3b | OH |
| 612 | N | S | Q1f | a bond | Me | a bond | NH | O | a bond | Q3c | OH |
| 613 | N | S | Q1f | a bond | H | a bond | NH | S | NH | Q3a | OH |
| 614 | N | S | Q1f | a bond | H | a bond | NH | S | NH | Q3b | OH |
| 615 | N | S | Q1f | a bond | H | a bond | NH | S | NH | Q3c | OH |
| 616 | N | S | Q1f | a bond | H | a bond | NH | S | a bond | Q3a | OH |
| 617 | N | S | Q1f | a bond | H | a bond | NH | S | a bond | Q3b | OH |
| 618 | N | S | Q1f | a bond | H | a bond | NH | S | a bond | Q3c | OH |
| 619 | N | S | Q1f | a bond | H | a bond | NH | O | NH | Q3a | OH |
| 620 | N | S | Q1f | a bond | H | a bond | NH | O | NH | Q3b | OH |
| 621 | N | S | Q1f | a bond | H | a bond | NH | O | NH | Q3c | OH |
| 622 | N | S | Q1f | a bond | H | a bond | NH | O | a bond | Q3a | OH |
| 623 | N | S | Q1f | a bond | H | a bond | NH | O | a bond | Q3b | OH |
| 624 | N | S | Q1f | a bond | H | a bond | NH | O | a bond | Q3c | OH |

TABLE 1-continued

| No | A | B | R¹ | L¹ | R² | L² | L³ | Y | L⁴ | R³ | X |
|---|---|---|---|---|---|---|---|---|---|---|---|
| 625 | N | S | Q1g | a bond | Me | a bond | NH | S | NH | Q3a | OH |
| 626 | N | S | Q1g | a bond | Me | a bond | NH | S | NH | Q3b | OH |
| 627 | N | S | Q1g | a bond | Me | a bond | NH | S | NH | Q3c | OH |
| 628 | N | S | Q1g | a bond | Me | a bond | NH | S | a bond | Q3a | OH |
| 629 | N | S | Q1g | a bond | Me | a bond | NH | S | a bond | Q3b | OH |
| 630 | N | S | Q1g | a bond | Me | a bond | NH | S | a bond | Q3c | OH |
| 631 | N | S | Q1g | a bond | Me | a bond | NH | O | NH | Q3a | OH |
| 632 | N | S | Q1g | a bond | Me | a bond | NH | O | NH | Q3b | OH |
| 633 | N | S | Q1g | a bond | Me | a bond | NH | O | NH | Q3c | OH |
| 634 | N | S | Q1g | a bond | Me | a bond | NH | O | a bond | Q3a | OH |
| 635 | N | S | Q1g | a bond | Me | a bond | NH | O | a bond | Q3b | OH |
| 636 | N | S | Q1g | a bond | Me | a bond | NH |  | a bond | Q3c | OH |
| 637 | N | S | Q1g | a bond | H | a bond | NH |  | NH | Q3a | OH |
| 638 | N | S | Q1g | a bond | H | a bond | NH | S | NH | Q3b | OH |
| 639 | N | S | Q1g | a bond | H | a bond | NH | S | NH | Q3c | OH |
| 640 | N | S | Q1g | a bond | H | a bond | NH | S | a bond | Q3a | OH |
| 641 | N | S | Q1g | a bond | H | a bond | NH | S | a bond | Q3b | OH |
| 642 | N | S | Q1g | a bond | H | a bond | NH | S | a bond | Q3c | OH |
| 643 | N | S | Q1g | a bond | H | a bond | NH | O | NH | Q3a | OH |
| 644 | N | S | Q1g | a bond | H | a bond | NH | O | NH | Q3b | OH |
| 645 | N | S | Q1g | a bond | H | a bond | NH | O | NH | Q3c | OH |
| 646 | N | S | Q1g | a bond | H | a bond | NH | O | a bond | Q3a | OH |
| 647 | N | S | Q1g | a bond | H | a bond | NH | O | a bond | Q3b | OH |
| 648 | N | S | Q1g | a bond | H | a bond | NH | O | a bond | Q3c | OH |
| 649 | N | S | Q1h | a bond | Me | a bond | NH | S | NH | Q3a | OH |
| 650 | N | S | Q1h | a bond | Me | a bond | NH | S | NH | Q3b | OH |
| 651 | N | S | Q1h | a bond | Me | a bond | NH | S | NH | Q3c | OH |
| 652 | N | S | Q1h | a bond | Me | a bond | NH | S | a bond | Q3a | OH |
| 653 | N | S | Q1h | a bond | Me | a bond | NH | S | a bond | Q3b | OH |
| 654 | N | S | Q1h | a bond | Me | a bond | NH | S | a bond | Q3c | OH |
| 655 | N | S | Q1h | a bond | Me | a bond | NH | O | NH | Q3a | OH |
| 656 | N | S | Q1h | a bond | Me | a bond | NH | O | NH | Q3b | OH |
| 657 | N | S | Q1h | a bond | Me | a bond | NH | O | NH | Q3c | OH |
| 658 | N | S | Q1h | a bond | Me | a bond | NH | O | a bond | Q3a | OH |
| 659 | N | S | Q1h | a bond | Me | a bond | NH | O | a bond | Q3b | OH |
| 660 | N | S | Q1h | a bond | Me | a bond | NH | O | a bond | Q3c | OH |
| 661 | N | S | Q1h | a bond | H | a bond | NH | S | NH | Q3a | OH |
| 662 | N | S | Q1h | a bond | H | a bond | NH | S | NH | Q3b | OH |
| 663 | N | S | Q1h | a bond | H | a bond | NH | S | NH | Q3c | OH |
| 664 | N | S | Q1h | a bond | H | a bond | NH | S | a bond | Q3a | OH |
| 665 | N | S | Q1h | a bond | H | a bond | NH | S | a bond | Q3b | OH |
| 666 | N | S | Q1h | a bond | H | a bond | NH | S | a bond | Q3c | OH |
| 667 | N | S | Q1h | a bond | H | a bond | NH | O | NH | Q3a | OH |
| 668 | N | S | Q1h | a bond | H | a bond | NH | O | NH | Q3b | OH |
| 669 | N | S | Q1h | a bond | H | a bond | NH | O | NH | Q3c | OH |
| 670 | N | S | Q1h | a bond | H | a bond | NH | O | a bond | Q3a | OH |
| 671 | N | S | Q1h | a bond | H | a bond | NH | O | a bond | Q3b | OH |
| 672 | N | S | Q1h | a bond | H | a bond | NH | O | a bond | Q3c | OH |
| 673 | N | S | Q1i | a bond | Me | a bond | NH | S | NH | Q3a | OH |
| 674 | N | S | Q1i | a bond | Me | a bond | NH | S | NH | Q3b | OH |
| 675 | N | S | Q1i | a bond | Me | a bond | NH | S | NH | Q3c | OH |
| 676 | N | S | Q1i | a bond | Me | a bond | NH | S | a bond | Q3a | OH |
| 677 | N | S | Q1i | a bond | Me | a bond | NH | S | a bond | Q3b | OH |
| 678 | N | S | Q1i | a bond | Me | a bond | NH | S | a bond | Q3c | OH |
| 679 | N | S | Q1i | a bond | Me | a bond | NH | O | NH | Q3a | OH |
| 680 | N | S | Q1i | a bond | Me | a bond | NH | O | NH | Q3b | OH |
| 681 | N | S | Q1i | a bond | Me | a bond | NH | O | NH | Q3c | OH |
| 682 | N | S | Q1i | a bond | Me | a bond | NH | O | a bond | Q3a | OH |
| 683 | N | S | Q1i | a bond | Me | a bond | NH | O | a bond | Q3b | OH |
| 684 | N | S | Q1i | a bond | Me | a bond | NH | O | a bond | Q3c | OH |
| 685 | N | S | Q1i | a bond | H | a bond | NH | S | NH | Q3a | OH |
| 686 | N | S | Q1i | a bond | H | a bond | NH | S | NH | Q3b | OH |
| 687 | N | S | Q1i | a bond | H | a bond | NH | S | NH | Q3c | OH |
| 688 | N | S | Q1i | a bond | H | a bond | NH | S | a bond | Q3a | OH |
| 689 | N | S | Q1i | a bond | H | a bond | NH | S | a bond | Q3b | OH |
| 690 | N | S | Q1i | a bond | H | a bond | NH | S | a bond | Q3c | OH |
| 691 | N | S | Q1i | a bond | H | a bond | NH | O | NH | Q3a | OH |
| 692 | N | S | Q1i | a bond | H | a bond | NH | O | NH | Q3b | OH |
| 693 | N | S | Q1i | a bond | H | a bond | NH | O | NH | Q3c | OH |
| 694 | N | S | Q1i | a bond | H | a bond | NH | O | a bond | Q3a | OH |
| 695 | N | S | Q1i | a bond | H | a bond | NH | O | a bond | Q3b | OH |
| 696 | N | S | Q1i | a bond | H | a bond | NH | O | a bond | Q3c | OH |
| 697 | N | S | Q1j | a bond | Me | a bond | NH | S | NH | Q3a | OH |
| 698 | N | S | Q1j | a bond | Me | a bond | NH | S | NH | Q3b | OH |
| 699 | N | S | Q1j | a bond | Me | a bond | NH | S | NH | Q3c | OH |
| 700 | N | S | Q1j | a bond | Me | a bond | NH | S | a bond | Q3a | OH |
| 701 | N | S | Q1j | a bond | Me | a bond | NH | S | a bond | Q3b | OH |
| 702 | N | S | Q1j | a bond | Me | a bond | NH | S | a bond | Q3c | OH |

TABLE 1-continued

| No | A | B | R¹ | L¹ | R² | L² | L³ | Y | L⁴ | R³ | X |
|---|---|---|---|---|---|---|---|---|---|---|---|
| 703 | N | S | Q1j | a bond | Me | a bond | NH | O | NH | Q3a | OH |
| 704 | N | S | Q1j | a bond | Me | a bond | NH | O | NH | Q3b | OH |
| 705 | N | S | Q1j | a bond | Me | a bond | NH | O | NH | Q3c | OH |
| 706 | N | S | Q1j | a bond | Me | a bond | NH | O | a bond | Q3a | OH |
| 707 | N | S | Q1j | a bond | Me | a bond | NH | O | a bond | Q3b | OH |
| 708 | N | S | Q1j | a bond | Me | a bond | NH | O | a bond | Q3c | OH |
| 709 | N | S | Q1j | a bond | H | a bond | NH | S | NH | Q3a | OH |
| 710 | N | S | Q1j | a bond | H | a bond | NH | S | NH | Q3b | OH |
| 711 | N | S | Q1j | a bond | H | a bond | NH | S | NH | Q3c | OH |
| 712 | N | S | Q1j | a bond | H | a bond | NH | S | a bond | Q3a | OH |
| 713 | N | S | Q1j | a bond | H | a bond | NH | S | a bond | Q3b | OH |
| 714 | N | S | Q1j | a bond | H | a bond | NH | S | a bond | Q3c | OH |
| 715 | N | S | Q1j | a bond | H | a bond | NH | O | NH | Q3a | OH |
| 716 | N | S | Q1j | a bond | H | a bond | NH | O | NH | Q3b | OH |
| 717 | N | S | Q1j | a bond | H | a bond | NH | O | NH | Q3c | OH |
| 718 | N | S | Q1j | a bond | H | a bond | NH | O | a bond | Q3a | OH |
| 719 | N | S | Q1j | a bond | H | a bond | NH | O | a bond | Q3b | OH |
| 720 | N | S | Q1j | a bond | H | a bond | NH | O | a bond | Q3c | OH |
| 721 | N | O | Q1a | a bond | Me | a bond | NH | S | NH | Q3a | OH |
| 722 | N | O | Q1a | a bond | Me | a bond | NH | S | NH | Q3b | OH |
| 723 | N | O | Q1a | a bond | Me | a bond | NH | S | NH | Q3c | OH |
| 724 | N | O | Q1a | a bond | Me | a bond | NH | S | a bond | Q3a | OH |
| 725 | N | O | Q1a | a bond | Me | a bond | NH | S | a bond | Q3b | OH |
| 726 | N | O | Q1a | a bond | Me | a bond | NH | S | a bond | Q3c | OH |
| 727 | N | O | Q1a | a bond | Me | a bond | NH | O | NH | Q3a | OH |
| 728 | N | O | Q1a | a bond | Me | a bond | NH | O | NH | Q3b | OH |
| 729 | N | O | Q1a | a bond | Me | a bond | NH | O | NH | Q3c | OH |
| 730 | N | O | Q1a | a bond | Me | a bond | NH | O | a bond | Q3a | OH |
| 731 | N | O | Q1a | a bond | Me | a bond | NH | O | a bond | Q3b | OH |
| 732 | N | O | Q1a | a bond | Me | a bond | NH | O | a bond | Q3c | OH |
| 733 | N | O | Q1a | a bond | H | a bond | NH | S | NH | Q3a | OH |
| 734 | N | O | Q1a | a bond | H | a bond | NH | S | NH | Q3b | OH |
| 735 | N | O | Q1a | a bond | H | a bond | NH | S | NH | Q3c | OH |
| 736 | N | O | Q1a | a bond | H | a bond | NH | S | a bond | Q3a | OH |
| 737 | N | O | Q1a | a bond | H | a bond | NH | S | a bond | Q3b | OH |
| 738 | N | O | Q1a | a bond | H | a bond | NH | S | a bond | Q3c | OH |
| 739 | N | O | Q1a | a bond | H | a bond | NH | O | NH | Q3a | OH |
| 740 | N | O | Q1a | a bond | H | a bond | NH | O | NH | Q3b | OH |
| 741 | N | O | Q1a | a bond | H | a bond | NH | O | NH | Q3c | OH |
| 742 | N | O | Q1a | a bond | H | a bond | NH | O | a bond | Q3a | OH |
| 743 | N | O | Q1a | a bond | H | a bond | NH | O | a bond | Q3b | OH |
| 744 | N | O | Q1a | a bond | H | a bond | NH | O | a bond | Q3c | OH |
| 745 | N | O | Q1b | a bond | Me | a bond | NH | S | NH | Q3a | OH |
| 746 | N | O | Q1b | a bond | Me | a bond | NH | S | NH | Q3b | OH |
| 747 | N | O | Q1b | a bond | Me | a bond | NH | S | NH | Q3c | OH |
| 748 | N | O | Q1b | a bond | Me | a bond | NH | S | a bond | Q3a | OH |
| 749 | N | O | Q1b | a bond | Me | a bond | NH | S | a bond | Q3b | OH |
| 750 | N | O | Q1b | a bond | Me | a bond | NH | S | a bond | Q3c | OH |
| 751 | N | O | Q1b | a bond | Me | a bond | NH | O | NH | Q3a | OH |
| 752 | N | O | Q1b | a bond | Me | a bond | NH | O | NH | Q3b | OH |
| 753 | N | O | Q1b | a bond | Me | a bond | NH | O | NH | Q3c | OH |
| 754 | N | O | Q1b | a bond | Me | a bond | NH | O | a bond | Q3a | OH |
| 755 | N | O | Q1b | a bond | Me | a bond | NH | O | a bond | Q3b | OH |
| 756 | N | O | Q1b | a bond | Me | a bond | NH | O | a bond | Q3c | OH |
| 757 | N | O | Q1b | a bond | H | a bond | NH | S | NH | Q3a | OH |
| 758 | N | O | Q1b | a bond | H | a bond | NH | S | NH | Q3b | OH |
| 759 | N | O | Q1b | a bond | H | a bond | NH | S | NH | Q3c | OH |
| 760 | N | O | Q1b | a bond | H | a bond | NH | S | a bond | Q3a | OH |
| 761 | N | O | Q1b | a bond | H | a bond | NH | S | a bond | Q3b | OH |
| 762 | N | O | Q1b | a bond | H | a bond | NH | S | a bond | Q3c | OH |
| 763 | N | O | Q1b | a bond | H | a bond | NH | O | NH | Q3a | OH |
| 764 | N | O | Q1b | a bond | H | a bond | NH | O | NH | Q3b | OH |
| 765 | N | O | Q1b | a bond | H | a bond | NH | O | NH | Q3c | OH |
| 766 | N | O | Q1b | a bond | H | a bond | NH | O | a bond | Q3a | OH |
| 767 | N | O | Q1b | a bond | H | a bond | NH | O | a bond | Q3b | OH |
| 768 | N | O | Q1b | a bond | H | a bond | NH | O | a bond | Q3c | OH |
| 769 | N | O | Q1c | a bond | Me | a bond | NH | S | NH | Q3a | OH |
| 770 | N | O | Q1c | a bond | Me | a bond | NH | S | NH | Q3b | OH |
| 771 | N | O | Q1c | a bond | Me | a bond | NH | S | NH | Q3c | OH |
| 772 | N | O | Q1c | a bond | Me | a bond | NH | S | a bond | Q3a | OH |
| 773 | N | O | Q1c | a bond | Me | a bond | NH | S | a bond | Q3b | OH |
| 774 | N | O | Q1c | a bond | Me | a bond | NH | S | a bond | Q3c | OH |
| 775 | N | O | Q1c | a bond | Me | a bond | NH | O | NH | Q3a | OH |
| 776 | N | O | Q1c | a bond | Me | a bond | NH | O | NH | Q3b | OH |
| 777 | N | O | Q1c | a bond | Me | a bond | NH | O | NH | Q3c | OH |
| 778 | N | O | Q1c | a bond | Me | a bond | NH | O | a bond | Q3a | OH |
| 779 | N | O | Q1c | a bond | Me | a bond | NH | O | a bond | Q3b | OH |
| 780 | N | O | Q1c | a bond | Me | a bond | NH | O | a bond | Q3c | OH |

TABLE 1-continued

| No | A | B | R¹ | L¹ | R² | L² | L³ | Y | L⁴ | R³ | X |
|---|---|---|---|---|---|---|---|---|---|---|---|
| 781 | N | O | Q1c | a bond | H | a bond | NH | S | NH | Q3a | OH |
| 782 | N | O | Q1c | a bond | H | a bond | NH | S | NH | Q3b | OH |
| 783 | N | O | Q1c | a bond | H | a bond | NH | S | NH | Q3c | OH |
| 784 | N | O | Q1c | a bond | H | a bond | NH | S | a bond | Q3a | OH |
| 785 | N | O | Q1c | a bond | H | a bond | NH | S | a bond | Q3b | OH |
| 786 | N | O | Q1c | a bond | H | a bond | NH | S | a bond | Q3c | OH |
| 787 | N | O | Q1c | a bond | H | a bond | NH | O | NH | Q3a | OH |
| 788 | N | O | Q1c | a bond | H | a bond | NH | O | NH | Q3b | OH |
| 789 | N | O | Q1c | a bond | H | a bond | NH | O | NH | Q3c | OH |
| 790 | N | O | Q1c | a bond | H | a bond | NH | O | a bond | Q3a | OH |
| 791 | N | O | Q1c | a bond | H | a bond | NH | O | a bond | Q3b | OH |
| 792 | N | O | Q1c | a bond | H | a bond | NH | O | a bond | Q3c | OH |
| 793 | N | O | Q1d | a bond | Me | a bond | NH | S | NH | Q3a | OH |
| 794 | N | O | Q1d | a bond | Me | a bond | NH | S | NH | Q3b | OH |
| 795 | N | O | Q1d | a bond | Me | a bond | NH | S | NH | Q3c | OH |
| 796 | N | O | Q1d | a bond | Me | a bond | NH | S | a bond | Q3a | OH |
| 797 | N | O | Q1d | a bond | Me | a bond | NH | S | a bond | Q3b | OH |
| 798 | N | O | Q1d | a bond | Me | a bond | NH | S | a bond | Q3c | OH |
| 799 | N | O | Q1d | a bond | Me | a bond | NH | O | NH | Q3a | OH |
| 800 | N | O | Q1d | a bond | Me | a bond | NH | O | NH | Q3b | OH |
| 801 | N | O | Q1d | a bond | Me | a bond | NH | O | NH | Q3c | OH |
| 802 | N | O | Q1d | a bond | Me | a bond | NH | O | a bond | Q3a | OH |
| 803 | N | O | Q1d | a bond | Me | a bond | NH | O | a bond | Q3b | OH |
| 804 | N | O | Q1d | a bond | Me | a bond | NH | O | a bond | Q3c | OH |
| 805 | N | O | Q1d | a bond | H | a bond | NH | S | NH | Q3a | OH |
| 806 | N | O | Q1d | a bond | H | a bond | NH | S | NH | Q3b | OH |
| 807 | N | O | Q1d | a bond | H | a bond | NH | S | NH | Q3c | OH |
| 808 | N | O | Q1d | a bond | H | a bond | NH | S | a bond | Q3a | OH |
| 809 | N | O | Q1d | a bond | H | a bond | NH | S | a bond | Q3b | OH |
| 810 | N | O | Q1d | a bond | H | a bond | NH | S | a bond | Q3c | OH |
| 811 | N | O | Q1d | a bond | H | a bond | NH | O | NH | Q3a | OH |
| 812 | N | O | Q1d | a bond | H | a bond | NH | O | NH | Q3b | OH |
| 813 | N | O | Q1d | a bond | H | a bond | NH | O | NH | Q3c | OH |
| 814 | N | O | Q1d | a bond | H | a bond | NH | O | a bond | Q3a | OH |
| 815 | N | O | Q1d | a bond | H | a bond | NH | O | a bond | Q3b | OH |
| 816 | N | O | Q1d | a bond | H | a bond | NH | O | a bond | Q3c | OH |
| 817 | N | O | Q1e | a bond | Me | a bond | NH | S | NH | Q3a | OH |
| 818 | N | O | Q1e | a bond | Me | a bond | NH | S | NH | Q3b | OH |
| 819 | N | O | Q1e | a bond | Me | a bond | NH | S | NH | Q3c | OH |
| 820 | N | O | Q1e | a bond | Me | a bond | NH | S | a bond | Q3a | OH |
| 821 | N | O | Q1e | a bond | Me | a bond | NH | S | a bond | Q3b | OH |
| 822 | N | O | Q1e | a bond | Me | a bond | NH | S | a bond | Q3c | OH |
| 823 | N | O | Q1e | a bond | Me | a bond | NH | O | NH | Q3a | OH |
| 824 | N | O | Q1e | a bond | Me | a bond | NH | O | NH | Q3b | OH |
| 825 | N | O | Q1e | a bond | Me | a bond | NH | O | NH | Q3c | OH |
| 826 | N | O | Q1e | a bond | Me | a bond | NH | O | a bond | Q3a | OH |
| 827 | N | O | Q1e | a bond | Me | a bond | NH | O | a bond | Q3b | OH |
| 828 | N | O | Q1e | a bond | Me | a bond | NH | O | a bond | Q3c | OH |
| 829 | N | O | Q1e | a bond | H | a bond | NH | S | NH | Q3a | OH |
| 830 | N | O | Q1e | a bond | H | a bond | NH | S | NH | Q3b | OH |
| 831 | N | O | Q1e | a bond | H | a bond | NH | S | NH | Q3c | OH |
| 832 | N | O | Q1e | a bond | H | a bond | NH | S | a bond | Q3a | OH |
| 833 | N | O | Q1e | a bond | H | a bond | NH | S | a bond | Q3b | OH |
| 834 | N | O | Q1e | a bond | H | a bond | NH | S | a bond | Q3c | OH |
| 835 | N | O | Q1e | a bond | H | a bond | NH | O | NH | Q3a | OH |
| 836 | N | O | Q1e | a bond | H | a bond | NH | O | NH | Q3b | OH |
| 837 | N | O | Q1e | a bond | H | a bond | NH | O | NH | Q3c | OH |
| 838 | N | O | Q1e | a bond | H | a bond | NH | O | a bond | Q3a | OH |
| 839 | N | O | Q1e | a bond | H | a bond | NH | O | a bond | Q3b | OH |
| 840 | N | O | Q1e | a bond | H | a bond | NH | O | a bond | Q3c | OH |
| 841 | N | O | Q1f | a bond | Me | a bond | NH | S | NH | Q3a | OH |
| 842 | N | O | Q1f | a bond | Me | a bond | NH | S | NH | Q3b | OH |
| 843 | N | O | Q1f | a bond | Me | a bond | NH | S | NH | Q3c | OH |
| 844 | N | O | Q1f | a bond | Me | a bond | NH | S | a bond | Q3a | OH |
| 845 | N | O | Q1f | a bond | Me | a bond | NH | S | a bond | Q3b | OH |
| 846 | N | O | Q1f | a bond | Me | a bond | NH | S | a bond | Q3c | OH |
| 847 | N | O | Q1f | a bond | Me | a bond | NH | O | NH | Q3a | OH |
| 848 | N | O | Q1f | a bond | Me | a bond | NH | O | NH | Q3b | OH |
| 849 | N | O | Q1f | a bond | Me | a bond | NH | O | NH | Q3c | OH |
| 850 | N | O | Q1f | a bond | Me | a bond | NH | O | a bond | Q3a | OH |
| 851 | N | O | Q1f | a bond | Me | a bond | NH | O | a bond | Q3b | OH |
| 852 | N | O | Q1f | a bond | Me | a bond | NH | O | a bond | Q3c | OH |
| 853 | N | O | Q1f | a bond | H | a bond | NH | S | NH | Q3a | OH |
| 854 | N | O | Q1f | a bond | H | a bond | NH | S | NH | Q3b | OH |
| 855 | N | O | Q1f | a bond | H | a bond | NH | S | NH | Q3c | OH |
| 856 | N | O | Q1f | a bond | H | a bond | NH | S | a bond | Q3a | OH |
| 857 | N | O | Q1f | a bond | H | a bond | NH | S | a bond | Q3b | OH |
| 858 | N | O | Q1f | a bond | H | a bond | NH | S | a bond | Q3c | OH |

TABLE 1-continued

| No | A | B | R¹ | L¹ | R² | L² | L³ | Y | L⁴ | R³ | X |
|---|---|---|---|---|---|---|---|---|---|---|---|
| 859 | N | O | Q1f | a bond | H | a bond | NH | O | NH | Q3a | OH |
| 860 | N | O | Q1f | a bond | H | a bond | NH | O | NH | Q3b | OH |
| 861 | N | O | Q1f | a bond | H | a bond | NH | O | NH | Q3c | OH |
| 862 | N | O | Q1f | a bond | H | a bond | NH | O | a bond | Q3a | OH |
| 863 | N | O | Q1f | a bond | H | a bond | NH | O | a bond | Q3b | OH |
| 864 | N | O | Q1f | a bond | H | a bond | NH | O | a bond | Q3c | OH |
| 865 | N | O | Q1g | a bond | Me | a bond | NH | S | NH | Q3a | OH |
| 866 | N | O | Q1g | a bond | Me | a bond | NH | S | NH | Q3b | OH |
| 867 | N | O | Q1g | a bond | Me | a bond | NH | S | NH | Q3c | OH |
| 868 | N | O | Q1g | a bond | Me | a bond | NH | S | a bond | Q3a | OH |
| 869 | N | O | Q1g | a bond | Me | a bond | NH | S | a bond | Q3b | OH |
| 870 | N | O | Q1g | a bond | Me | a bond | NH | S | a bond | Q3c | OH |
| 871 | N | O | Q1g | a bond | Me | a bond | NH | O | NH | Q3a | OH |
| 872 | N | O | Q1g | a bond | Me | a bond | NH | O | NH | Q3b | OH |
| 873 | N | O | Q1g | a bond | Me | a bond | NH | O | NH | Q3c | OH |
| 874 | N | O | Q1g | a bond | Me | a bond | NH | O | a bond | Q3a | OH |
| 875 | N | O | Q1g | a bond | Me | a bond | NH | O | a bond | Q3b | OH |
| 876 | N | O | Q1g | a bond | Me | a bond | NH | O | a bond | Q3c | OH |
| 877 | N | O | Q1g | a bond | H | a bond | NH | S | NH | Q3a | OH |
| 878 | N | O | Q1g | a bond | H | a bond | NH | S | NH | Q3b | OH |
| 879 | N | O | Q1g | a bond | H | a bond | NH | S | NH | Q3c | OH |
| 880 | N | O | Q1g | a bond | H | a bond | NH | S | a bond | Q3a | OH |
| 881 | N | O | Q1g | a bond | H | a bond | NH | S | a bond | Q3b | OH |
| 882 | N | O | Q1g | a bond | H | a bond | NH | S | a bond | Q3c | OH |
| 883 | N | O | Q1g | a bond | H | a bond | NH | O | NH | Q3a | OH |
| 884 | N | O | Q1g | a bond | H | a bond | NH | O | NH | Q3b | OH |
| 885 | N | O | Q1g | a bond | H | a bond | NH | O | NH | Q3c | OH |
| 886 | N | O | Q1g | a bond | H | a bond | NH | O | a bond | Q3a | OH |
| 887 | N | O | Q1g | a bond | H | a bond | NH | O | a bond | Q3b | OH |
| 888 | N | O | Q1g | a bond | H | a bond | NH | O | a bond | Q3c | OH |
| 889 | N | O | Q1h | a bond | Me | a bond | NH | S | NH | Q3a | OH |
| 890 | N | O | Q1h | a bond | Me | a bond | NH | S | NH | Q3b | OH |
| 891 | N | O | Q1h | a bond | Me | a bond | NH | S | NH | Q3c | OH |
| 892 | N | O | Q1h | a bond | Me | a bond | NH | S | a bond | Q3a | OH |
| 893 | N | O | Q1h | a bond | Me | a bond | NH | S | a bond | Q3b | OH |
| 894 | N | O | Q1h | a bond | Me | a bond | NH | S | a bond | Q3c | OH |
| 895 | N | O | Q1h | a bond | Me | a bond | NH | O | NH | Q3a | OH |
| 896 | N | O | Q1h | a bond | Me | a bond | NH | O | NH | Q3b | OH |
| 897 | N | O | Q1h | a bond | Me | a bond | NH | O | NH | Q3c | OH |
| 898 | N | O | Q1h | a bond | Me | a bond | NH | O | a bond | Q3a | OH |
| 899 | N | O | Q1h | a bond | Me | a bond | NH | O | a bond | Q3b | OH |
| 900 | N | O | Q1h | a bond | Me | a bond | NH | O | a bond | Q3c | OH |
| 901 | N | O | Q1h | a bond | H | a bond | NH | S | NH | Q3a | OH |
| 902 | N | O | Q1h | a bond | H | a bond | NH | S | NH | Q3b | OH |
| 903 | N | O | Q1h | a bond | H | a bond | NH | S | NH | Q3c | OH |
| 904 | N | O | Q1h | a bond | H | a bond | NH | S | a bond | Q3a | OH |
| 905 | N | O | Q1h | a bond | H | a bond | NH | S | a bond | Q3b | OH |
| 906 | N | O | Q1h | a bond | H | a bond | NH | S | a bond | Q3c | OH |
| 907 | N | O | Q1h | a bond | H | a bond | NH | O | NH | Q3a | OH |
| 908 | N | O | Q1h | a bond | H | a bond | NH | O | NH | Q3b | OH |
| 909 | N | O | Q1h | a bond | H | a bond | NH | O | NH | Q3c | OH |
| 910 | N | O | Q1h | a bond | H | a bond | NH | O | a bond | Q3a | OH |
| 911 | N | O | Q1h | a bond | H | a bond | NH | O | a bond | Q3b | OH |
| 912 | N | O | Q1h | a bond | H | a bond | NH | O | a bond | Q3c | OH |
| 913 | N | O | Q1i | a bond | Me | a bond | NH | S | NH | Q3a | OH |
| 914 | N | O | Q1i | a bond | Me | a bond | NH | S | NH | Q3b | OH |
| 915 | N | O | Q1i | a bond | Me | a bond | NH | S | NH | Q3c | OH |
| 916 | N | O | Q1i | a bond | Me | a bond | NH | S | a bond | Q3a | OH |
| 917 | N | O | Q1i | a bond | Me | a bond | NH | S | a bond | Q3b | OH |
| 918 | N | O | Q1i | a bond | Me | a bond | NH | S | a bond | Q3c | OH |
| 919 | N | O | Q1i | a bond | Me | a bond | NH | O | NH | Q3a | OH |
| 920 | N | O | Q1i | a bond | Me | a bond | NH | O | NH | Q3b | OH |
| 921 | N | O | Q1i | a bond | Me | a bond | NH | O | NH | Q3c | OH |
| 922 | N | O | Q1i | a bond | Me | a bond | NH | O | a bond | Q3a | OH |
| 923 | N | O | Q1i | a bond | Me | a bond | NH | O | a bond | Q3b | OH |
| 924 | N | O | Q1i | a bond | Me | a bond | NH | O | a bond | Q3c | OH |
| 925 | N | O | Q1i | a bond | H | a bond | NH | S | NH | Q3a | OH |
| 926 | N | O | Q1i | a bond | H | a bond | NH | S | NH | Q3b | OH |
| 927 | N | O | Q1i | a bond | H | a bond | NH | S | NH | Q3c | OH |
| 928 | N | O | Q1i | a bond | H | a bond | NH | S | a bond | Q3a | OH |
| 929 | N | O | Q1i | a bond | H | a bond | NH | S | a bond | Q3b | OH |
| 930 | N | O | Q1i | a bond | H | a bond | NH | S | a bond | Q3c | OH |
| 931 | N | O | Q1i | a bond | H | a bond | NH | O | NH | Q3a | OH |
| 932 | N | O | Q1i | a bond | H | a bond | NH | O | NH | Q3b | OH |
| 933 | N | O | Q1i | a bond | H | a bond | NH | O | NH | Q3c | OH |
| 934 | N | O | Q1i | a bond | H | a bond | NH | O | a bond | Q3a | OH |
| 935 | N | O | Q1i | a bond | H | a bond | NH | O | a bond | Q3b | OH |
| 936 | N | O | Q1i | a bond | H | a bond | NH | O | a bond | Q3c | OH |

TABLE 1-continued

| No | A | B | R¹ | L¹ | R² | L² | L³ | Y | L⁴ | R³ | X |
|---|---|---|---|---|---|---|---|---|---|---|---|
| 937 | N | O | Q1j | a bond | Me | a bond | NH | S | NH | Q3a | OH |
| 938 | N | O | Q1j | a bond | Me | a bond | NH | S | NH | Q3b | OH |
| 939 | N | O | Q1j | a bond | Me | a bond | NH | S | NH | Q3c | OH |
| 940 | N | O | Q1j | a bond | Me | a bond | NH | S | a bond | Q3a | OH |
| 941 | N | O | Q1j | a bond | Me | a bond | NH | S | a bond | Q3b | OH |
| 942 | N | O | Q1j | a bond | Me | a bond | NH | S | a bond | Q3c | OH |
| 943 | N | O | Q1j | a bond | Me | a bond | NH | O | NH | Q3a | OH |
| 944 | N | O | Q1j | a bond | Me | a bond | NH | O | NH | Q3b | OH |
| 945 | N | O | Q1j | a bond | Me | a bond | NH | O | NH | Q3c | OH |
| 946 | N | O | Q1j | a bond | Me | a bond | NH | O | a bond | Q3a | OH |
| 947 | N | O | Q1j | a bond | Me | a bond | NH | O | a bond | Q3b | OH |
| 948 | N | O | Q1j | a bond | Me | a bond | NH | O | a bond | Q3c | OH |
| 949 | N | O | Q1j | a bond | H | a bond | NH | S | NH | Q3a | OH |
| 950 | N | O | Q1j | a bond | H | a bond | NH | S | NH | Q3b | OH |
| 951 | N | O | Q1j | a bond | H | a bond | NH | S | NH | Q3c | OH |
| 952 | N | O | Q1j | a bond | H | a bond | NH | S | a bond | Q3a | OH |
| 953 | N | O | Q1j | a bond | H | a bond | NH | S | a bond | Q3b | OH |
| 954 | N | O | Q1j | a bond | H | a bond | NH | S | a bond | Q3c | OH |
| 955 | N | O | Q1j | a bond | H | a bond | NH | O | NH | Q3a | OH |
| 956 | N | O | Q1j | a bond | H | a bond | NH | O | NH | Q3b | OH |
| 957 | N | O | Q1j | a bond | H | a bond | NH | O | NH | Q3c | OH |
| 958 | N | O | Q1j | a bond | H | a bond | NH | O | a bond | Q3a | OH |
| 959 | N | O | Q1j | a bond | H | a bond | NH | O | a bond | Q3b | OH |
| 960 | N | O | Q1j | a bond | H | a bond | NH | O | a bond | Q3c | OH |
| 961 | CH | NMe | Q1a | a bond | Me | a bond | NH | S | NH | Q3a | OH |
| 962 | CH | NMe | Q1a | a bond | Me | a bond | NH | S | NH | Q3b | OH |
| 963 | CH | NMe | Q1a | a bond | Me | a bond | NH | S | NH | Q3c | OH |
| 964 | CH | NMe | Q1a | a bond | Me | a bond | NH | S | a bond | Q3a | OH |
| 965 | CH | NMe | Q1a | a bond | Me | a bond | NH | S | a bond | Q3b | OH |
| 966 | CH | NMe | Q1a | a bond | Me | a bond | NH | S | a bond | Q3c | OH |
| 967 | CH | NMe | Q1a | a bond | Me | a bond | NH | O | NH | Q3a | OH |
| 968 | CH | NMe | Q1a | a bond | Me | a bond | NH | O | NH | Q3b | OH |
| 969 | CH | NMe | Q1a | a bond | Me | a bond | NH | O | NH | Q3c | OH |
| 970 | CH | NMe | Q1a | a bond | Me | a bond | NH | O | a bond | Q3a | OH |
| 971 | CH | NMe | Q1a | a bond | Me | a bond | NH | O | a bond | Q3b | OH |
| 972 | CH | NMe | Q1a | a bond | Me | a bond | NH | O | a bond | Q3c | OH |
| 973 | CH | NMe | Q1a | a bond | H | a bond | NH | S | NH | Q3a | OH |
| 974 | CH | NMe | Q1a | a bond | H | a bond | NH | S | NH | Q3b | OH |
| 975 | CH | NMe | Q1a | a bond | H | a bond | NH | S | NH | Q3c | OH |
| 976 | CH | NMe | Q1a | a bond | H | a bond | NH | S | a bond | Q3a | OH |
| 977 | CH | NMe | Q1a | a bond | H | a bond | NH | S | a bond | Q3b | OH |
| 978 | CH | NMe | Q1a | a bond | H | a bond | NH | S | a bond | Q3c | OH |
| 979 | CH | NMe | Q1a | a bond | H | a bond | NH | O | NH | Q3a | OH |
| 980 | CH | NMe | Q1a | a bond | H | a bond | NH | O | NH | Q3b | OH |
| 981 | CH | NMe | Q1a | a bond | H | a bond | NH | O | NH | Q3c | OH |
| 982 | CH | NMe | Q1a | a bond | H | a bond | NH | O | a bond | Q3a | OH |
| 983 | CH | NMe | Q1a | a bond | H | a bond | NH | O | a bond | Q3b | OH |
| 984 | CH | NMe | Q1a | a bond | H | a bond | NH | O | a bond | Q3c | OH |
| 985 | CH | NMe | Q1b | a bond | Me | a bond | NH | S | NH | Q3a | OH |
| 986 | CH | NMe | Q1b | a bond | Me | a bond | NH | S | NH | Q3b | OH |
| 987 | CH | NMe | Q1b | a bond | Me | a bond | NH | S | NH | Q3c | OH |
| 988 | CH | NMe | Q1b | a bond | Me | a bond | NH | S | a bond | Q3a | OH |
| 989 | CH | NMe | Q1b | a bond | Me | a bond | NH | S | a bond | Q3b | OH |
| 990 | CH | NMe | Q1b | a bond | Me | a bond | NH | S | a bond | Q3c | OH |
| 991 | CH | NMe | Q1b | a bond | Me | a bond | NH | O | NH | Q3a | OH |
| 992 | CH | NMe | Q1b | a bond | Me | a bond | NH | O | NH | Q3b | OH |
| 993 | CH | NMe | Q1b | a bond | Me | a bond | NH | O | NH | Q3c | OH |
| 994 | CH | NMe | Q1b | a bond | Me | a bond | NH | O | a bond | Q3a | OH |
| 995 | CH | NMe | Q1b | a bond | Me | a bond | NH | O | a bond | Q3b | OH |
| 996 | CH | NMe | Q1b | a bond | Me | a bond | NH | O | a bond | Q3c | OH |
| 997 | CH | NMe | Q1b | a bond | H | a bond | NH | S | NH | Q3a | OH |
| 998 | CH | NMe | Q1b | a bond | H | a bond | NH | S | NH | Q3b | OH |
| 999 | CH | NMe | Q1b | a bond | H | a bond | NH | S | NH | Q3c | OH |
| 1000 | CH | NMe | Q1b | a bond | H | a bond | NH | S | a bond | Q3a | OH |
| 1001 | CH | NMe | Q1b | a bond | H | a bond | NH | S | a bond | Q3b | OH |
| 1002 | CH | NMe | Q1b | a bond | H | a bond | NH | S | a bond | Q3c | OH |
| 1003 | CH | NMe | Q1b | a bond | H | a bond | NH | O | NH | Q3a | OH |
| 1004 | CH | NMe | Q1b | a bond | H | a bond | NH | O | NH | Q3b | OH |
| 1005 | CH | NMe | Q1b | a bond | H | a bond | NH | O | NH | Q3c | OH |
| 1006 | CH | NMe | Q1b | a bond | H | a bond | NH | O | a bond | Q3a | OH |
| 1007 | CH | NMe | Q1b | a bond | H | a bond | NH | O | a bond | Q3b | OH |
| 1008 | CH | NMe | Q1b | a bond | H | a bond | NH | O | a bond | Q3c | OH |
| 1009 | CH | NMe | Q1c | a bond | Me | a bond | NH | S | NH | Q3a | OH |
| 1010 | CH | NMe | Q1c | a bond | Me | a bond | NH | S | NH | Q3b | OH |
| 1011 | CH | NMe | Q1c | a bond | Me | a bond | NH | S | NH | Q3c | OH |
| 1012 | CH | NMe | Q1c | a bond | Me | a bond | NH | S | a bond | Q3a | OH |
| 1013 | CH | NMe | Q1c | a bond | Me | a bond | NH | S | a bond | Q3b | OH |
| 1014 | CH | NMe | Q1c | a bond | Me | a bond | NH | S | a bond | Q3c | OH |

TABLE 1-continued

| No | A | B | R¹ | L¹ | R² | L² | L³ | Y | L⁴ | R³ | X |
|---|---|---|---|---|---|---|---|---|---|---|---|
| 1015 | CH | NMe | Q1c | a bond | Me | a bond | NH | O | NH | Q3a | OH |
| 1016 | CH | NMe | Q1c | a bond | Me | a bond | NH | O | NH | Q3b | OH |
| 1017 | CH | NMe | Q1c | a bond | Me | a bond | NH | O | NH | Q3c | OH |
| 1018 | CH | NMe | Q1c | a bond | Me | a bond | NH | O | a bond | Q3a | OH |
| 1019 | CH | NMe | Q1c | a bond | Me | a bond | NH | O | a bond | Q3b | OH |
| 1020 | CH | NMe | Q1c | a bond | Me | a bond | NH | O | a bond | Q3c | OH |
| 1021 | CH | NMe | Q1c | a bond | H | a bond | NH | S | NH | Q3a | OH |
| 1022 | CH | NMe | Q1c | a bond | H | a bond | NH | S | NH | Q3b | OH |
| 1023 | CH | NMe | Q1c | a bond | H | a bond | NH | S | NH | Q3c | OH |
| 1024 | CH | NMe | Q1c | a bond | H | a bond | NH | S | a bond | Q3a | OH |
| 1025 | CH | NMe | Q1c | a bond | H | a bond | NH | S | a bond | Q3b | OH |
| 1026 | CH | NMe | Q1c | a bond | H | a bond | NH | S | a bond | Q3c | OH |
| 1027 | CH | NMe | Q1c | a bond | H | a bond | NH | O | NH | Q3a | OH |
| 1028 | CH | NMe | Q1c | a bond | H | a bond | NH | O | NH | Q3b | OH |
| 1029 | CH | NMe | Q1c | a bond | H | a bond | NH | O | NH | Q3c | OH |
| 1030 | CH | NMe | Q1c | a bond | H | a bond | NH | O | a bond | Q3a | OH |
| 1031 | CH | NMe | Q1c | a bond | H | a bond | NH | O | a bond | Q3b | OH |
| 1032 | CH | NMe | Q1c | a bond | H | a bond | NH | O | a bond | Q3c | OH |
| 1033 | CH | NMe | Q1d | a bond | Me | a bond | NH | S | NH | Q3a | OH |
| 1034 | CH | NMe | Q1d | a bond | Me | a bond | NH | S | NH | Q3b | OH |
| 1035 | CH | NMe | Q1d | a bond | Me | a bond | NH | S | NH | Q3c | OH |
| 1036 | CH | NMe | Q1d | a bond | Me | a bond | NH | S | a bond | Q3a | OH |
| 1037 | CH | NMe | Q1d | a bond | Me | a bond | NH | S | a bond | Q3b | OH |
| 1038 | CH | NMe | Q1d | a bond | Me | a bond | NH | S | a bond | Q3c | OH |
| 1039 | CH | NMe | Q1d | a bond | Me | a bond | NH | O | NH | Q3a | OH |
| 1040 | CH | NMe | Q1d | a bond | Me | a bond | NH | O | NH | Q3b | OH |
| 1041 | CH | NMe | Q1d | a bond | Me | a bond | NH | O | NH | Q3c | OH |
| 1042 | CH | NMe | Q1d | a bond | Me | a bond | NH | O | a bond | Q3a | OH |
| 1043 | CH | NMe | Q1d | a bond | Me | a bond | NH | O | a bond | Q3b | OH |
| 1044 | CH | NMe | Q1d | a bond | Me | a bond | NH | O | a bond | Q3c | OH |
| 1045 | CH | NMe | Q1d | a bond | H | a bond | NH | S | NH | Q3a | OH |
| 1046 | CH | NMe | Q1d | a bond | H | a bond | NH | S | NH | Q3b | OH |
| 1047 | CH | NMe | Q1d | a bond | H | a bond | NH | S | NH | Q3c | OH |
| 1048 | CH | NMe | Q1d | a bond | H | a bond | NH | S | a bond | Q3a | OH |
| 1049 | CH | NMe | Q1d | a bond | H | a bond | NH | S | a bond | Q3b | OH |
| 1050 | CH | NMe | Q1d | a bond | H | a bond | NH | S | a bond | Q3c | OH |
| 1051 | CH | NMe | Q1d | a bond | H | a bond | NH | O | NH | Q3a | OH |
| 1052 | CH | NMe | Q1d | a bond | H | a bond | NH | O | NH | Q3b | OH |
| 1053 | CH | NMe | Q1d | a bond | H | a bond | NH | O | NH | Q3c | OH |
| 1054 | CH | NMe | Q1d | a bond | H | a bond | NH | O | a bond | Q3a | OH |
| 1055 | CH | NMe | Q1d | a bond | H | a bond | NH | O | a bond | Q3b | OH |
| 1056 | CH | NMe | Q1d | a bond | H | a bond | NH | O | a bond | Q3c | OH |
| 1057 | CH | NMe | Q1e | a bond | Me | a bond | NH | S | NH | Q3a | OH |
| 1058 | CH | NMe | Q1e | a bond | Me | a bond | NH | S | NH | Q3b | OH |
| 1059 | CH | NMe | Q1e | a bond | Me | a bond | NH | S | NH | Q3c | OH |
| 1060 | CH | NMe | Q1e | a bond | Me | a bond | NH | S | a bond | Q3a | OH |
| 1061 | CH | NMe | Q1e | a bond | Me | a bond | NH | S | a bond | Q3b | OH |
| 1062 | CH | NMe | Q1e | a bond | Me | a bond | NH | S | a bond | Q3c | OH |
| 1063 | CH | NMe | Q1e | a bond | Me | a bond | NH | O | NH | Q3a | OH |
| 1064 | CH | NMe | Q1e | a bond | Me | a bond | NH | O | NH | Q3b | OH |
| 1065 | CH | NMe | Q1e | a bond | Me | a bond | NH | O | NH | Q3c | OH |
| 1066 | CH | NMe | Q1e | a bond | Me | a bond | NH | O | a bond | Q3a | OH |
| 1067 | CH | NMe | Q1e | a bond | Me | a bond | NH | O | a bond | Q3b | OH |
| 1068 | CH | NMe | Q1e | a bond | Me | a bond | NH | O | a bond | Q3c | OH |
| 1069 | CH | NMe | Q1e | a bond | H | a bond | NH | S | NH | Q3a | OH |
| 1070 | CH | NMe | Q1e | a bond | H | a bond | NH | S | NH | Q3b | OH |
| 1071 | CH | NMe | Q1e | a bond | H | a bond | NH | S | NH | Q3c | OH |
| 1072 | CH | NMe | Q1e | a bond | H | a bond | NH | S | a bond | Q3a | OH |
| 1073 | CH | NMe | Q1e | a bond | H | a bond | NH | S | a bond | Q3b | OH |
| 1074 | CH | NMe | Q1e | a bond | H | a bond | NH | S | a bond | Q3c | OH |
| 1075 | CH | NMe | Q1e | a bond | H | a bond | NH | O | NH | Q3a | OH |
| 1076 | CH | NMe | Q1e | a bond | H | a bond | NH | O | NH | Q3b | OH |
| 1077 | CH | NMe | Q1e | a bond | H | a bond | NH | O | NH | Q3c | OH |
| 1078 | CH | NMe | Q1e | a bond | H | a bond | NH | O | a bond | Q3a | OH |
| 1079 | CH | NMe | Q1e | a bond | H | a bond | NH | O | a bond | Q3b | OH |
| 1080 | CH | NMe | Q1e | a bond | H | a bond | NH | O | a bond | Q3c | OH |
| 1081 | CH | NMe | Q1f | a bond | Me | a bond | NH | S | NH | Q3a | OH |
| 1082 | CH | NMe | Q1f | a bond | Me | a bond | NH | S | NH | Q3b | OH |
| 1083 | CH | NMe | Q1f | a bond | Me | a bond | NH | S | NH | Q3c | OH |
| 1084 | CH | NMe | Q1f | a bond | Me | a bond | NH | S | a bond | Q3a | OH |
| 1085 | CH | NMe | Q1f | a bond | Me | a bond | NH | S | a bond | Q3b | OH |
| 1086 | CH | NMe | Q1f | a bond | Me | a bond | NH | S | a bond | Q3c | OH |
| 1087 | CH | NMe | Q1f | a bond | Me | a bond | NH | O | NH | Q3a | OH |
| 1088 | CH | NMe | Q1f | a bond | Me | a bond | NH | O | NH | Q3b | OH |
| 1089 | CH | NMe | Q1f | a bond | Me | a bond | NH | O | NH | Q3c | OH |
| 1090 | CH | NMe | Q1f | a bond | Me | a bond | NH | O | a bond | Q3a | OH |
| 1091 | CH | NMe | Q1f | a bond | Me | a bond | NH | O | a bond | Q3b | OH |
| 1092 | CH | NMe | Q1f | a bond | Me | a bond | NH | O | a bond | Q3c | OH |

TABLE 1-continued

| No | A | B | R¹ | L¹ | R² | L² | L³ | Y | L⁴ | R³ | X |
|---|---|---|---|---|---|---|---|---|---|---|---|
| 1093 | CH | NMe | Q1f | a bond | H | a bond | NH | S | NH | Q3a | OH |
| 1094 | CH | NMe | Q1f | a bond | H | a bond | NH | S | NH | Q3b | OH |
| 1095 | CH | NMe | Q1f | a bond | H | a bond | NH | S | NH | Q3c | OH |
| 1096 | CH | NMe | Q1f | a bond | H | a bond | NH | S | a bond | Q3a | OH |
| 1097 | CH | NMe | Q1f | a bond | H | a bond | NH | S | a bond | Q3b | OH |
| 1098 | CH | NMe | Q1f | a bond | H | a bond | NH | S | a bond | Q3c | OH |
| 1099 | CH | NMe | Q1f | a bond | H | a bond | NH | O | NH | Q3a | OH |
| 1100 | CH | NMe | Q1f | a bond | H | a bond | NH | O | NH | Q3b | OH |
| 1101 | CH | NMe | Q1f | a bond | H | a bond | NH | O | NH | Q3c | OH |
| 1102 | CH | NMe | Q1f | a bond | H | a bond | NH | O | a bond | Q3a | OH |
| 1103 | CH | NMe | Q1f | a bond | H | a bond | NH | O | a bond | Q3b | OH |
| 1104 | CH | NMe | Q1f | a bond | H | a bond | NH | O | a bond | Q3c | OH |
| 1105 | CH | NMe | Q1g | a bond | Me | a bond | NH | S | NH | Q3a | OH |
| 1106 | CH | NMe | Q1g | a bond | Me | a bond | NH | S | NH | Q3b | OH |
| 1107 | CH | NMe | Q1g | a bond | Me | a bond | NH | S | NH | Q3c | OH |
| 1108 | CH | NMe | Q1g | a bond | Me | a bond | NH | S | a bond | Q3a | OH |
| 1109 | CH | NMe | Q1g | a bond | Me | a bond | NH | S | a bond | Q3b | OH |
| 1110 | CH | NMe | Q1g | a bond | Me | a bond | NH | S | a bond | Q3c | OH |
| 1111 | CH | NMe | Q1g | a bond | Me | a bond | NH | O | NH | Q3a | OH |
| 1112 | CH | NMe | Q1g | a bond | Me | a bond | NH | O | NH | Q3b | OH |
| 1113 | CH | NMe | Q1g | a bond | Me | a bond | NH | O | NH | Q3c | OH |
| 1114 | CH | NMe | Q1g | a bond | Me | a bond | NH | O | a bond | Q3a | OH |
| 1115 | CH | NMe | Q1g | a bond | Me | a bond | NH | O | a bond | Q3b | OH |
| 1116 | CH | NMe | Q1g | a bond | Me | a bond | NH | O | a bond | Q3c | OH |
| 1117 | CH | NMe | Q1g | a bond | H | a bond | NH | S | NH | Q3a | OH |
| 1118 | CH | NMe | Q1g | a bond | H | a bond | NH | S | NH | Q3b | OH |
| 1119 | CH | NMe | Q1g | a bond | H | a bond | NH | S | NH | Q3c | OH |
| 1120 | CH | NMe | Q1g | a bond | H | a bond | NH | S | a bond | Q3a | OH |
| 1121 | CH | NMe | Q1g | a bond | H | a bond | NH | S | a bond | Q3b | OH |
| 1122 | CH | NMe | Q1g | a bond | H | a bond | NH | S | a bond | Q3c | OH |
| 1123 | CH | NMe | Q1g | a bond | H | a bond | NH | O | NH | Q3a | OH |
| 1124 | CH | NMe | Q1g | a bond | H | a bond | NH | O | NH | Q3b | OH |
| 1125 | CH | NMe | Q1g | a bond | H | a bond | NH | O | NH | Q3c | OH |
| 1126 | CH | NMe | Q1g | a bond | H | a bond | NH | O | a bond | Q3a | OH |
| 1127 | CH | NMe | Q1g | a bond | H | a bond | NH | O | a bond | Q3b | OH |
| 1128 | CH | NMe | Q1g | a bond | H | a bond | NH | O | a bond | Q3c | OH |
| 1129 | CH | NMe | Q1h | a bond | Me | a bond | NH | S | NH | Q3a | OH |
| 1130 | CH | NMe | Q1h | a bond | Me | a bond | NH | S | NH | Q3b | OH |
| 1131 | CH | NMe | Q1h | a bond | Me | a bond | NH | S | NH | Q3c | OH |
| 1132 | CH | NMe | Q1h | a bond | Me | a bond | NH | S | a bond | Q3a | OH |
| 1133 | CH | NMe | Q1h | a bond | Me | a bond | NH | S | a bond | Q3b | OH |
| 1134 | CH | NMe | Q1h | a bond | Me | a bond | NH | S | a bond | Q3c | OH |
| 1135 | CH | NMe | Q1h | a bond | Me | a bond | NH | O | NH | Q3a | OH |
| 1136 | CH | NMe | Q1h | a bond | Me | a bond | NH | O | NH | Q3b | OH |
| 1137 | CH | NMe | Q1h | a bond | Me | a bond | NH | O | NH | Q3c | OH |
| 1138 | CH | NMe | Q1h | a bond | Me | a bond | NH | O | a bond | Q3a | OH |
| 1139 | CH | NMe | Q1h | a bond | Me | a bond | NH | O | a bond | Q3b | OH |
| 1140 | CH | NMe | Q1h | a bond | Me | a bond | NH | O | a bond | Q3c | OH |
| 1141 | CH | NMe | Q1h | a bond | H | a bond | NH | S | NH | Q3a | OH |
| 1142 | CH | NMe | Q1h | a bond | H | a bond | NH | S | NH | Q3b | OH |
| 1143 | CH | NMe | Q1h | a bond | H | a bond | NH | S | NH | Q3c | OH |
| 1144 | CH | NMe | Q1h | a bond | H | a bond | NH | S | a bond | Q3a | OH |
| 1145 | CH | NMe | Q1h | a bond | H | a bond | NH | S | a bond | Q3b | OH |
| 1146 | CH | NMe | Q1h | a bond | H | a bond | NH | S | a bond | Q3c | OH |
| 1147 | CH | NMe | Q1h | a bond | H | a bond | NH | O | NH | Q3a | OH |
| 1148 | CH | NMe | Q1h | a bond | H | a bond | NH | O | NH | Q3b | OH |
| 1149 | CH | NMe | Q1h | a bond | H | a bond | NH | O | NH | Q3c | OH |
| 1150 | CH | NMe | Q1h | a bond | H | a bond | NH | O | a bond | Q3a | OH |
| 1151 | CH | NMe | Q1h | a bond | H | a bond | NH | O | a bond | Q3b | OH |
| 1152 | CH | NMe | Q1h | a bond | H | a bond | NH | O | a bond | Q3c | OH |
| 1153 | CH | NMe | Q1i | a bond | Me | a bond | NH | S | NH | Q3a | OH |
| 1154 | CH | NMe | Q1i | a bond | Me | a bond | NH | S | NH | Q3b | OH |
| 1155 | CH | NMe | Q1i | a bond | Me | a bond | NH | S | NH | Q3c | OH |
| 1156 | CH | NMe | Q1i | a bond | Me | a bond | NH | S | a bond | Q3a | OH |
| 1157 | CH | NMe | Q1i | a bond | Me | a bond | NH | S | a bond | Q3b | OH |
| 1158 | CH | NMe | Q1i | a bond | Me | a bond | NH | S | a bond | Q3c | OH |
| 1159 | CH | NMe | Q1i | a bond | Me | a bond | NH | O | NH | Q3a | OH |
| 1160 | CH | NMe | Q1i | a bond | Me | a bond | NH | O | NH | Q3b | OH |
| 1161 | CH | NMe | Q1i | a bond | Me | a bond | NH | O | NH | Q3c | OH |
| 1162 | CH | NMe | Q1i | a bond | Me | a bond | NH | O | a bond | Q3a | OH |
| 1163 | CH | NMe | Q1i | a bond | Me | a bond | NH | O | a bond | Q3b | OH |
| 1164 | CH | NMe | Q1i | a bond | Me | a bond | NH | O | a bond | Q3c | OH |
| 1165 | CH | NMe | Q1i | a bond | H | a bond | NH | S | NH | Q3a | OH |
| 1166 | CH | NMe | Q1i | a bond | H | a bond | NH | S | NH | Q3b | OH |
| 1167 | CH | NMe | Q1i | a bond | H | a bond | NH | S | NH | Q3c | OH |
| 1168 | CH | NMe | Q1i | a bond | H | a bond | NH | S | a bond | Q3a | OH |
| 1169 | CH | NMe | Q1i | a bond | H | a bond | NH | S | a bond | Q3b | OH |
| 1170 | CH | NMe | Q1i | a bond | H | a bond | NH | S | a bond | Q3c | OH |

TABLE 1-continued

| No | A | B | R¹ | L¹ | R² | L² | L³ | Y | L⁴ | R³ | X |
|---|---|---|---|---|---|---|---|---|---|---|---|
| 1171 | CH | NMe | Q1i | a bond | H | a bond | NH | O | NH | Q3a | OH |
| 1172 | CH | NMe | Q1i | a bond | H | a bond | NH | O | NH | Q3b | OH |
| 1173 | CH | NMe | Q1i | a bond | H | a bond | NH | O | NH | Q3c | OH |
| 1174 | CH | NMe | Q1i | a bond | H | a bond | NH | O | a bond | Q3a | OH |
| 1175 | CH | NMe | Q1i | a bond | H | a bond | NH | O | a bond | Q3b | OH |
| 1176 | CH | NMe | Q1i | a bond | H | a bond | NH | O | a bond | Q3c | OH |
| 1177 | CH | NMe | Q1j | a bond | Me | a bond | NH | S | NH | Q3a | OH |
| 1178 | CH | NMe | Q1j | a bond | Me | a bond | NH | S | NH | Q3b | OH |
| 1179 | CH | NMe | Q1j | a bond | Me | a bond | NH | S | NH | Q3c | OH |
| 1180 | CH | NMe | Q1j | a bond | Me | a bond | NH | S | a bond | Q3a | OH |
| 1181 | CH | NMe | Q1j | a bond | Me | a bond | NH | S | a bond | Q3b | OH |
| 1182 | CH | NMe | Q1j | a bond | Me | a bond | NH | S | a bond | Q3c | OH |
| 1183 | CH | NMe | Q1j | a bond | Me | a bond | NH | O | NH | Q3a | OH |
| 1184 | CH | NMe | Q1j | a bond | Me | a bond | NH | O | NH | Q3b | OH |
| 1185 | CH | NMe | Q1j | a bond | Me | a bond | NH | O | NH | Q3c | OH |
| 1186 | CH | NMe | Q1j | a bond | Me | a bond | NH | O | a bond | Q3a | OH |
| 1187 | CH | NMe | Q1j | a bond | Me | a bond | NH | O | a bond | Q3b | OH |
| 1188 | CH | NMe | Q1j | a bond | Me | a bond | NH | O | a bond | Q3c | OH |
| 1189 | CH | NMe | Q1j | a bond | H | a bond | NH | S | NH | Q3a | OH |
| 1190 | CH | NMe | Q1j | a bond | H | a bond | NH | S | NH | Q3b | OH |
| 1191 | CH | NMe | Q1j | a bond | H | a bond | NH | S | NH | Q3c | OH |
| 1192 | CH | NMe | Q1j | a bond | H | a bond | NH | S | a bond | Q3a | OH |
| 1193 | CH | NMe | Q1j | a bond | H | a bond | NH | S | a bond | Q3b | OH |
| 1194 | CH | NMe | Q1j | a bond | H | a bond | NH | S | a bond | Q3c | OH |
| 1195 | CH | NMe | Q1j | a bond | H | a bond | NH | O | NH | Q3a | OH |
| 1196 | CH | NMe | Q1j | a bond | H | a bond | NH | O | NH | Q3b | OH |
| 1197 | CH | NMe | Q1j | a bond | H | a bond | NH | O | NH | Q3c | OH |
| 1198 | CH | NMe | Q1j | a bond | H | a bond | NH | O | a bond | Q3a | OH |
| 1199 | CH | NMe | Q1j | a bond | H | a bond | NH | O | a bond | Q3b | OH |
| 1200 | CH | NMe | Q1j | a bond | H | a bond | NH | O | a bond | Q3c | OH |
| 1201 | CH | NEt | Q1a | a bond | Me | a bond | NH | S | NH | Q3a | OH |
| 1202 | CH | NEt | Q1a | a bond | Me | a bond | NH | S | NH | Q3b | OH |
| 1203 | CH | NEt | Q1a | a bond | Me | a bond | NH | S | NH | Q3c | OH |
| 1204 | CH | NEt | Q1a | a bond | Me | a bond | NH | S | a bond | Q3a | OH |
| 1205 | CH | NEt | Q1a | a bond | Me | a bond | NH | S | a bond | Q3b | OH |
| 1206 | CH | NEt | Q1a | a bond | Me | a bond | NH | S | a bond | Q3c | OH |
| 1207 | CH | NEt | Q1a | a bond | Me | a bond | NH | O | NH | Q3a | OH |
| 1208 | CH | NEt | Q1a | a bond | Me | a bond | NH | O | NH | Q3b | OH |
| 1209 | CH | NEt | Q1a | a bond | Me | a bond | NH | O | NH | Q3c | OH |
| 1210 | CH | NEt | Q1a | a bond | Me | a bond | NH | O | a bond | Q3a | OH |
| 1211 | CH | NEt | Q1a | a bond | Me | a bond | NH | O | a bond | Q3b | OH |
| 1212 | CH | NEt | Q1a | a bond | Me | a bond | NH | O | a bond | Q3c | OH |
| 1213 | CH | NEt | Q1a | a bond | H | a bond | NH | S | NH | Q3a | OH |
| 1214 | CH | NEt | Q1a | a bond | H | a bond | NH | S | NH | Q3b | OH |
| 1215 | CH | NEt | Q1a | a bond | H | a bond | NH | S | NH | Q3c | OH |
| 1216 | CH | NEt | Q1a | a bond | H | a bond | NH | S | a bond | Q3a | OH |
| 1217 | CH | NEt | Q1a | a bond | H | a bond | NH | S | a bond | Q3b | OH |
| 1218 | CH | NEt | Q1a | a bond | H | a bond | NH | S | a bond | Q3c | OH |
| 1219 | CH | NEt | Q1a | a bond | H | a bond | NH | O | NH | Q3a | OH |
| 1220 | CH | NEt | Q1a | a bond | H | a bond | NH | O | NH | Q3b | OH |
| 1221 | CH | NEt | Q1a | a bond | H | a bond | NH | O | NH | Q3c | OH |
| 1222 | CH | NEt | Q1a | a bond | H | a bond | NH | O | a bond | Q3a | OH |
| 1223 | CH | NEt | Q1a | a bond | H | a bond | NH | O | a bond | Q3b | OH |
| 1224 | CH | NEt | Q1a | a bond | H | a bond | NH | O | a bond | Q3c | OH |
| 1225 | CH | NEt | Q1b | a bond | Me | a bond | NH | S | NH | Q3a | OH |
| 1226 | CH | NEt | Q1b | a bond | Me | a bond | NH | S | NH | Q3b | OH |
| 1227 | CH | NEt | Q1b | a bond | Me | a bond | NH | S | NH | Q3c | OH |
| 1228 | CH | NEt | Q1b | a bond | Me | a bond | NH | S | a bond | Q3a | OH |
| 1229 | CH | NEt | Q1b | a bond | Me | a bond | NH | S | a bond | Q3b | OH |
| 1230 | CH | NEt | Q1b | a bond | Me | a bond | NH | S | a bond | Q3c | OH |
| 1231 | CH | NEt | Q1b | a bond | Me | a bond | NH | O | NH | Q3a | OH |
| 1232 | CH | NEt | Q1b | a bond | Me | a bond | NH | O | NH | Q3b | OH |
| 1233 | CH | NEt | Q1b | a bond | Me | a bond | NH | O | NH | Q3c | OH |
| 1234 | CH | NEt | Q1b | a bond | Me | a bond | NH | O | a bond | Q3a | OH |
| 1235 | CH | NEt | Q1b | a bond | Me | a bond | NH | O | a bond | Q3b | OH |
| 1236 | CH | NEt | Q1b | a bond | Me | a bond | NH | O | a bond | Q3c | OH |
| 1237 | CH | NEt | Q1b | a bond | H | a bond | NH | S | NH | Q3a | OH |
| 1238 | CH | NEt | Q1b | a bond | H | a bond | NH | S | NH | Q3b | OH |
| 1239 | CH | NEt | Q1b | a bond | H | a bond | NH | S | NH | Q3c | OH |
| 1240 | CH | NEt | Q1b | a bond | H | a bond | NH | S | a bond | Q3a | OH |
| 1241 | CH | NEt | Q1b | a bond | H | a bond | NH | S | a bond | Q3b | OH |
| 1242 | CH | NEt | Q1b | a bond | H | a bond | NH | S | a bond | Q3c | OH |
| 1243 | CH | NEt | Q1b | a bond | H | a bond | NH | O | NH | Q3a | OH |
| 1244 | CH | NEt | Q1b | a bond | H | a bond | NH | O | NH | Q3b | OH |
| 1245 | CH | NEt | Q1b | a bond | H | a bond | NH | O | NH | Q3c | OH |
| 1246 | CH | NEt | Q1b | a bond | H | a bond | NH | O | a bond | Q3a | OH |
| 1247 | CH | NEt | Q1b | a bond | H | a bond | NH | O | a bond | Q3b | OH |
| 1248 | CH | NEt | Q1b | a bond | H | a bond | NH | O | a bond | Q3c | OH |

TABLE 1-continued

| No | A | B | R¹ | L¹ | R² | L² | L³ | Y | L⁴ | R³ | X |
|---|---|---|---|---|---|---|---|---|---|---|---|
| 1249 | CH | NEt | Q1c | a bond | Me | a bond | NH | S | NH | Q3a | OH |
| 1250 | CH | NEt | Q1c | a bond | Me | a bond | NH | S | NH | Q3b | OH |
| 1251 | CH | NEt | Q1c | a bond | Me | a bond | NH | S | NH | Q3c | OH |
| 1252 | CH | NEt | Q1c | a bond | Me | a bond | NH | S | a bond | Q3a | OH |
| 1253 | CH | NEt | Q1c | a bond | Me | a bond | NH | S | a bond | Q3b | OH |
| 1254 | CH | NEt | Q1c | a bond | Me | a bond | NH | S | a bond | Q3c | OH |
| 1255 | CH | NEt | Q1c | a bond | Me | a bond | NH | O | NH | Q3a | OH |
| 1256 | CH | NEt | Q1c | a bond | Me | a bond | NH | O | NH | Q3b | OH |
| 1257 | CH | NEt | Q1c | a bond | Me | a bond | NH | O | NH | Q3c | OH |
| 1258 | CH | NEt | Q1c | a bond | Me | a bond | NH | O | a bond | Q3a | OH |
| 1259 | CH | NEt | Q1c | a bond | Me | a bond | NH | O | a bond | Q3b | OH |
| 1260 | CH | NEt | Q1c | a bond | Me | a bond | NH | O | a bond | Q3c | OH |
| 1261 | CH | NEt | Q1c | a bond | H | a bond | NH | S | NH | Q3a | OH |
| 1262 | CH | NEt | Q1c | a bond | H | a bond | NH | S | NH | Q3b | OH |
| 1263 | CH | NEt | Q1c | a bond | H | a bond | NH | S | NH | Q3c | OH |
| 1264 | CH | NEt | Q1c | a bond | H | a bond | NH | S | a bond | Q3a | OH |
| 1265 | CH | NEt | Q1c | a bond | H | a bond | NH | S | a bond | Q3b | OH |
| 1266 | CH | NEt | Q1c | a bond | H | a bond | NH | S | a bond | Q3c | OH |
| 1267 | CH | NEt | Q1c | a bond | H | a bond | NH | O | NH | Q3a | OH |
| 1268 | CH | NEt | Q1c | a bond | H | a bond | NH | O | NH | Q3b | OH |
| 1269 | CH | NEt | Q1c | a bond | H | a bond | NH | O | NH | Q3c | OH |
| 1270 | CH | NEt | Q1c | a bond | H | a bond | NH | O | a bond | Q3a | OH |
| 1271 | CH | NEt | Q1c | a bond | H | a bond | NH | O | a bond | Q3b | OH |
| 1272 | CH | NEt | Q1c | a bond | H | a bond | NH | O | a bond | Q3c | OH |
| 1273 | CH | NEt | Q1d | a bond | Me | a bond | NH | S | NH | Q3a | OH |
| 1274 | CH | NEt | Q1d | a bond | Me | a bond | NH | S | NH | Q3b | OH |
| 1275 | CH | NEt | Q1d | a bond | Me | a bond | NH | S | NH | Q3c | OH |
| 1276 | CH | NEt | Q1d | a bond | Me | a bond | NH | S | a bond | Q3a | OH |
| 1277 | CH | NEt | Q1d | a bond | Me | a bond | NH | S | a bond | Q3b | OH |
| 1278 | CH | NEt | Q1d | a bond | Me | a bond | NH | S | a bond | Q3c | OH |
| 1279 | CH | NEt | Q1d | a bond | Me | a bond | NH | O | NH | Q3a | OH |
| 1280 | CH | NEt | Q1d | a bond | Me | a bond | NH | O | NH | Q3b | OH |
| 1281 | CH | NEt | Q1d | a bond | Me | a bond | NH | O | NH | Q3c | OH |
| 1282 | CH | NEt | Q1d | a bond | Me | a bond | NH | O | a bond | Q3a | OH |
| 1283 | CH | NEt | Q1d | a bond | Me | a bond | NH | O | a bond | Q3b | OH |
| 1284 | CH | NEt | Q1d | a bond | Me | a bond | NH | O | a bond | Q3c | OH |
| 1285 | CH | NEt | Q1d | a bond | H | a bond | NH | S | NH | Q3a | OH |
| 1286 | CH | NEt | Q1d | a bond | H | a bond | NH | S | NH | Q3b | OH |
| 1287 | CH | NEt | Q1d | a bond | H | a bond | NH | S | NH | Q3c | OH |
| 1288 | CH | NEt | Q1d | a bond | H | a bond | NH | S | a bond | Q3a | OH |
| 1289 | CH | NEt | Q1d | a bond | H | a bond | NH | S | a bond | Q3b | OH |
| 1290 | CH | NEt | Q1d | a bond | H | a bond | NH | S | a bond | Q3c | OH |
| 1291 | CH | NEt | Q1d | a bond | H | a bond | NH | O | NH | Q3a | OH |
| 1292 | CH | NEt | Q1d | a bond | H | a bond | NH | O | NH | Q3b | OH |
| 1293 | CH | NEt | Q1d | a bond | H | a bond | NH | O | NH | Q3c | OH |
| 1294 | CH | NEt | Q1d | a bond | H | a bond | NH | O | a bond | Q3a | OH |
| 1295 | CH | NEt | Q1d | a bond | H | a bond | NH | O | a bond | Q3b | OH |
| 1296 | CH | NEt | Q1d | a bond | H | a bond | NH | O | a bond | Q3c | OH |
| 1297 | CH | NEt | Q1e | a bond | Me | a bond | NH | S | NH | Q3a | OH |
| 1298 | CH | NEt | Q1e | a bond | Me | a bond | NH | S | NH | Q3b | OH |
| 1299 | CH | NEt | Q1e | a bond | Me | a bond | NH | S | NH | Q3c | OH |
| 1300 | CH | NEt | Q1e | a bond | Me | a bond | NH | S | a bond | Q3a | OH |
| 1301 | CH | NEt | Q1e | a bond | Me | a bond | NH | S | a bond | Q3b | OH |
| 1302 | CH | NEt | Q1e | a bond | Me | a bond | NH | S | a bond | Q3c | OH |
| 1303 | CH | NEt | Q1e | a bond | Me | a bond | NH | O | NH | Q3a | OH |
| 1304 | CH | NEt | Q1e | a bond | Me | a bond | NH | O | NH | Q3b | OH |
| 1305 | CH | NEt | Q1e | a bond | Me | a bond | NH | O | NH | Q3c | OH |
| 1306 | CH | NEt | Q1e | a bond | Me | a bond | NH | O | a bond | Q3a | OH |
| 1307 | CH | NEt | Q1e | a bond | Me | a bond | NH | O | a bond | Q3b | OH |
| 1308 | CH | NEt | Q1e | a bond | Me | a bond | NH | O | a bond | Q3c | OH |
| 1309 | CH | NEt | Q1e | a bond | H | a bond | NH | S | NH | Q3a | OH |
| 1310 | CH | NEt | Q1e | a bond | H | a bond | NH | S | NH | Q3b | OH |
| 1311 | CH | NEt | Q1e | a bond | H | a bond | NH | S | NH | Q3c | OH |
| 1312 | CH | NEt | Q1e | a bond | H | a bond | NH | S | a bond | Q3a | OH |
| 1313 | CH | NEt | Q1e | a bond | H | a bond | NH | S | a bond | Q3b | OH |
| 1314 | CH | NEt | Q1e | a bond | H | a bond | NH | S | a bond | Q3c | OH |
| 1315 | CH | NEt | Q1e | a bond | H | a bond | NH | O | NH | Q3a | OH |
| 1316 | CH | NEt | Q1e | a bond | H | a bond | NH | O | NH | Q3b | OH |
| 1317 | CH | NEt | Q1e | a bond | H | a bond | NH | O | NH | Q3c | OH |
| 1318 | CH | NEt | Q1e | a bond | H | a bond | NH | O | a bond | Q3a | OH |
| 1319 | CH | NEt | Q1e | a bond | H | a bond | NH | O | a bond | Q3b | OH |
| 1320 | CH | NEt | Q1e | a bond | H | a bond | NH | O | a bond | Q3c | OH |
| 1321 | CH | NEt | Q1f | a bond | Me | a bond | NH | S | NH | Q3a | OH |
| 1322 | CH | NEt | Q1f | a bond | Me | a bond | NH | S | NH | Q3b | OH |
| 1323 | CH | NEt | Q1f | a bond | Me | a bond | NH | S | NH | Q3c | OH |
| 1324 | CH | NEt | Q1f | a bond | Me | a bond | NH | S | a bond | Q3a | OH |
| 1325 | CH | NEt | Q1f | a bond | Me | a bond | NH | S | a bond | Q3b | OH |
| 1326 | CH | NEt | Q1f | a bond | Me | a bond | NH | S | a bond | Q3c | OH |

TABLE 1-continued

| No | A | B | R¹ | L¹ | R² | L² | L³ | Y | L⁴ | R³ | X |
|---|---|---|---|---|---|---|---|---|---|---|---|
| 1327 | CH | NEt | Q1f | a bond | Me | a bond | NH | O | NH | Q3a | OH |
| 1328 | CH | NEt | Q1f | a bond | Me | a bond | NH | O | NH | Q3b | OH |
| 1329 | CH | NEt | Q1f | a bond | Me | a bond | NH | O | NH | Q3c | OH |
| 1330 | CH | NEt | Q1f | a bond | Me | a bond | NH | O | a bond | Q3a | OH |
| 1331 | CH | NEt | Q1f | a bond | Me | a bond | NH | O | a bond | Q3b | OH |
| 1332 | CH | NEt | Q1f | a bond | Me | a bond | NH | O | a bond | Q3c | OH |
| 1333 | CH | NEt | Q1f | a bond | H | a bond | NH | S | NH | Q3a | OH |
| 1334 | CH | NEt | Q1f | a bond | H | a bond | NH | S | NH | Q3b | OH |
| 1335 | CH | NEt | Q1f | a bond | H | a bond | NH | S | NH | Q3c | OH |
| 1336 | CH | NEt | Q1f | a bond | H | a bond | NH | S | a bond | Q3a | OH |
| 1337 | CH | NEt | Q1f | a bond | H | a bond | NH | S | a bond | Q3b | OH |
| 1338 | CH | NEt | Q1f | a bond | H | a bond | NH | S | a bond | Q3c | OH |
| 1339 | CH | NEt | Q1f | a bond | H | a bond | NH | O | NH | Q3a | OH |
| 1340 | CH | NEt | Q1f | a bond | H | a bond | NH | O | NH | Q3b | OH |
| 1341 | CH | NEt | Q1f | a bond | H | a bond | NH | O | NH | Q3c | OH |
| 1342 | CH | NEt | Q1f | a bond | H | a bond | NH | O | a bond | Q3a | OH |
| 1343 | CH | NEt | Q1f | a bond | H | a bond | NH | O | a bond | Q3b | OH |
| 1344 | CH | NEt | Q1f | a bond | H | a bond | NH | O | a bond | Q3c | OH |
| 1345 | CH | NEt | Q1g | a bond | Me | a bond | NH | S | NH | Q3a | OH |
| 1346 | CH | NEt | Q1g | a bond | Me | a bond | NH | S | NH | Q3b | OH |
| 1347 | CH | NEt | Q1g | a bond | Me | a bond | NH | S | NH | Q3c | OH |
| 1348 | CH | NEt | Q1g | a bond | Me | a bond | NH | S | a bond | Q3a | OH |
| 1349 | CH | NEt | Q1g | a bond | Me | a bond | NH | S | a bond | Q3b | OH |
| 1350 | CH | NEt | Q1g | a bond | Me | a bond | NH | S | a bond | Q3c | OH |
| 1351 | CH | NEt | Q1g | a bond | Me | a bond | NH | O | NH | Q3a | OH |
| 1352 | CH | NEt | Q1g | a bond | Me | a bond | NH | O | NH | Q3b | OH |
| 1353 | CH | NEt | Q1g | a bond | Me | a bond | NH | O | NH | Q3c | OH |
| 1354 | CH | NEt | Q1g | a bond | Me | a bond | NH | O | a bond | Q3a | OH |
| 1355 | CH | NEt | Q1g | a bond | Me | a bond | NH | O | a bond | Q3b | OH |
| 1356 | CH | NEt | Q1g | a bond | Me | a bond | NH | O | a bond | Q3c | OH |
| 1357 | CH | NEt | Q1g | a bond | H | a bond | NH | S | NH | Q3a | OH |
| 1358 | CH | NEt | Q1g | a bond | H | a bond | NH | S | NH | Q3b | OH |
| 1359 | CH | NEt | Q1g | a bond | H | a bond | NH | S | NH | Q3c | OH |
| 1360 | CH | NEt | Q1g | a bond | H | a bond | NH | S | a bond | Q3a | OH |
| 1361 | CH | NEt | Q1g | a bond | H | a bond | NH | S | a bond | Q3b | OH |
| 1362 | CH | NEt | Q1g | a bond | H | a bond | NH | S | a bond | Q3c | OH |
| 1363 | CH | NEt | Q1g | a bond | H | a bond | NH | O | NH | Q3a | OH |
| 1364 | CH | NEt | Q1g | a bond | H | a bond | NH | O | NH | Q3b | OH |
| 1365 | CH | NEt | Q1g | a bond | H | a bond | NH | O | NH | Q3c | OH |
| 1366 | CH | NEt | Q1g | a bond | H | a bond | NH | O | a bond | Q3a | OH |
| 1367 | CH | NEt | Q1g | a bond | H | a bond | NH | O | a bond | Q3b | OH |
| 1368 | CH | NEt | Q1g | a bond | H | a bond | NH | O | a bond | Q3c | OH |
| 1369 | CH | NEt | Q1h | a bond | Me | a bond | NH | S | NH | Q3a | OH |
| 1370 | CH | NEt | Q1h | a bond | Me | a bond | NH | S | NH | Q3b | OH |
| 1371 | CH | NEt | Q1h | a bond | Me | a bond | NH | S | NH | Q3c | OH |
| 1372 | CH | NEt | Q1h | a bond | Me | a bond | NH | S | a bond | Q3a | OH |
| 1373 | CH | NEt | Q1h | a bond | Me | a bond | NH | S | a bond | Q3b | OH |
| 1374 | CH | NEt | Q1h | a bond | Me | a bond | NH | S | a bond | Q3c | OH |
| 1375 | CH | NEt | Q1h | a bond | Me | a bond | NH | O | NH | Q3a | OH |
| 1376 | CH | NEt | Q1h | a bond | Me | a bond | NH | O | NH | Q3b | OH |
| 1377 | CH | NEt | Q1h | a bond | Me | a bond | NH | O | NH | Q3c | OH |
| 1378 | CH | NEt | Q1h | a bond | Me | a bond | NH | O | a bond | Q3a | OH |
| 1379 | CH | NEt | Q1h | a bond | Me | a bond | NH | O | a bond | Q3b | OH |
| 1380 | CH | NEt | Q1h | a bond | Me | a bond | NH | O | a bond | Q3c | OH |
| 1381 | CH | NEt | Q1h | a bond | H | a bond | NH | S | NH | Q3a | OH |
| 1382 | CH | NEt | Q1h | a bond | H | a bond | NH | S | NH | Q3b | OH |
| 1383 | CH | NEt | Q1h | a bond | H | a bond | NH | S | NH | Q3c | OH |
| 1384 | CH | NEt | Q1h | a bond | H | a bond | NH | S | a bond | Q3a | OH |
| 1385 | CH | NEt | Q1h | a bond | H | a bond | NH | S | a bond | Q3b | OH |
| 1386 | CH | NEt | Q1h | a bond | H | a bond | NH | S | a bond | Q3c | OH |
| 1387 | CH | NEt | Q1h | a bond | H | a bond | NH | O | NH | Q3a | OH |
| 1388 | CH | NEt | Q1h | a bond | H | a bond | NH | O | NH | Q3b | OH |
| 1389 | CH | NEt | Q1h | a bond | H | a bond | NH | O | NH | Q3c | OH |
| 1390 | CH | NEt | Q1h | a bond | H | a bond | NH | O | a bond | Q3a | OH |
| 1391 | CH | NEt | Q1h | a bond | H | a bond | NH | O | a bond | Q3b | OH |
| 1392 | CH | NEt | Q1h | a bond | H | a bond | NH | O | a bond | Q3c | OH |
| 1393 | CH | NEt | Q1i | a bond | Me | a bond | NH | S | NH | Q3a | OH |
| 1394 | CH | NEt | Q1i | a bond | Me | a bond | NH | S | NH | Q3b | OH |
| 1395 | CH | NEt | Q1i | a bond | Me | a bond | NH | S | NH | Q3c | OH |
| 1396 | CH | NEt | Q1i | a bond | Me | a bond | NH | S | a bond | Q3a | OH |
| 1397 | CH | NEt | Q1i | a bond | Me | a bond | NH | S | a bond | Q3b | OH |
| 1398 | CH | NEt | Q1i | a bond | Me | a bond | NH | S | a bond | Q3c | OH |
| 1399 | CH | NEt | Q1i | a bond | Me | a bond | NH | O | NH | Q3a | OH |
| 1400 | CH | NEt | Q1i | a bond | Me | a bond | NH | O | NH | Q3b | OH |
| 1401 | CH | NEt | Q1i | a bond | Me | a bond | NH | O | NH | Q3c | OH |
| 1402 | CH | NEt | Q1i | a bond | Me | a bond | NH | O | a bond | Q3a | OH |
| 1403 | CH | NEt | Q1i | a bond | Me | a bond | NH | O | a bond | Q3b | OH |
| 1404 | CH | NEt | Q1i | a bond | Me | a bond | NH | O | a bond | Q3c | OH |

TABLE 1-continued

| No | A | B | R¹ | L¹ | R² | L² | L³ | Y | L⁴ | R³ | X |
|---|---|---|---|---|---|---|---|---|---|---|---|
| 1405 | CH | NEt | Q1i | a bond | H | a bond | NH | S | NH | Q3a | OH |
| 1406 | CH | NEt | Q1i | a bond | H | a bond | NH | S | NH | Q3b | OH |
| 1407 | CH | NEt | Q1i | a bond | H | a bond | NH | S | NH | Q3c | OH |
| 1408 | CH | NEt | Q1i | a bond | H | a bond | NH | S | a bond | Q3a | OH |
| 1409 | CH | NEt | Q1i | a bond | H | a bond | NH | S | a bond | Q3b | OH |
| 1410 | CH | NEt | Q1i | a bond | H | a bond | NH | S | a bond | Q3c | OH |
| 1411 | CH | NEt | Q1i | a bond | H | a bond | NH | O | NH | Q3a | OH |
| 1412 | CH | NEt | Q1i | a bond | H | a bond | NH | O | NH | Q3b | OH |
| 1413 | CH | NEt | Q1i | a bond | H | a bond | NH | O | NH | Q3c | OH |
| 1414 | CH | NEt | Q1i | a bond | H | a bond | NH | O | a bond | Q3a | OH |
| 1415 | CH | NEt | Q1i | a bond | H | a bond | NH | O | a bond | Q3b | OH |
| 1416 | CH | NEt | Q1i | a bond | H | a bond | NH | O | a bond | Q3c | OH |
| 1417 | CH | NEt | Q1j | a bond | Me | a bond | NH | S | NH | Q3a | OH |
| 1418 | CH | NEt | Q1j | a bond | Me | a bond | NH | S | NH | Q3b | OH |
| 1419 | CH | NEt | Q1j | a bond | Me | a bond | NH | S | NH | Q3c | OH |
| 1420 | CH | NEt | Q1j | a bond | Me | a bond | NH | S | a bond | Q3a | OH |
| 1421 | CH | NEt | Q1j | a bond | Me | a bond | NH | S | a bond | Q3b | OH |
| 1422 | CH | NEt | Q1j | a bond | Me | a bond | NH | S | a bond | Q3c | OH |
| 1423 | CH | NEt | Q1j | a bond | Me | a bond | NH | O | NH | Q3a | OH |
| 1424 | CH | NEt | Q1j | a bond | Me | a bond | NH | O | NH | Q3b | OH |
| 1425 | CH | NEt | Q1j | a bond | Me | a bond | NH | O | NH | Q3c | OH |
| 1426 | CH | NEt | Q1j | a bond | Me | a bond | NH | O | a bond | Q3a | OH |
| 1427 | CH | NEt | Q1j | a bond | Me | a bond | NH | O | a bond | Q3b | OH |
| 1428 | CH | NEt | Q1j | a bond | Me | a bond | NH | O | a bond | Q3c | OH |
| 1429 | CH | NEt | Q1j | a bond | H | a bond | NH | S | NH | Q3a | OH |
| 1430 | CH | NEt | Q1j | a bond | H | a bond | NH | S | NH | Q3b | OH |
| 1431 | CH | NEt | Q1j | a bond | H | a bond | NH | S | NH | Q3c | OH |
| 1432 | CH | NEt | Q1j | a bond | H | a bond | NH | S | a bond | Q3a | OH |
| 1433 | CH | NEt | Q1j | a bond | H | a bond | NH | S | a bond | Q3b | OH |
| 1434 | CH | NEt | Q1j | a bond | H | a bond | NH | S | a bond | Q3c | OH |
| 1435 | CH | NEt | Q1j | a bond | H | a bond | NH | O | NH | Q3a | OH |
| 1436 | CH | NEt | Q1j | a bond | H | a bond | NH | O | NH | Q3b | OH |
| 1437 | CH | NEt | Q1j | a bond | H | a bond | NH | O | NH | Q3c | OH |
| 1438 | CH | NEt | Q1j | a bond | H | a bond | NH | O | a bond | Q3a | OH |
| 1439 | CH | NEt | Q1j | a bond | H | a bond | NH | O | a bond | Q3b | OH |
| 1440 | CH | NEt | Q1j | a bond | H | a bond | NH | O | a bond | Q3c | OH |
| 1441 | CH | S | Q1a | a bond | Me | a bond | NH | S | NH | Q3a | OH |
| 1442 | CH | S | Q1a | a bond | Me | a bond | NH | S | NH | Q3b | OH |
| 1443 | CH | S | Q1a | a bond | Me | a bond | NH | S | NH | Q3c | OH |
| 1444 | CH | S | Q1a | a bond | Me | a bond | NH | S | a bond | Q3a | OH |
| 1445 | CH | S | Q1a | a bond | Me | a bond | NH | S | a bond | Q3b | OH |
| 1446 | CH | S | Q1a | a bond | Me | a bond | NH | S | a bond | Q3c | OH |
| 1447 | CH | S | Q1a | a bond | Me | a bond | NH | O | NH | Q3a | OH |
| 1448 | CH | S | Q1a | a bond | Me | a bond | NH | O | NH | Q3b | OH |
| 1449 | CH | S | Q1a | a bond | Me | a bond | NH | O | NH | Q3c | OH |
| 1450 | CH | S | Q1a | a bond | Me | a bond | NH | O | a bond | Q3a | OH |
| 1451 | CH | S | Q1a | a bond | Me | a bond | NH | O | a bond | Q3b | OH |
| 1452 | CH | S | Q1a | a bond | Me | a bond | NH | O | a bond | Q3c | OH |
| 1453 | CH | S | Q1a | a bond | H | a bond | NH | S | NH | Q3a | OH |
| 1454 | CH | S | Q1a | a bond | H | a bond | NH | S | NH | Q3b | OH |
| 1455 | CH | S | Q1a | a bond | H | a bond | NH | S | NH | Q3c | OH |
| 1456 | CH | S | Q1a | a bond | H | a bond | NH | S | a bond | Q3a | OH |
| 1457 | CH | S | Q1a | a bond | H | a bond | NH | S | a bond | Q3b | OH |
| 1458 | CH | S | Q1a | a bond | H | a bond | NH | S | a bond | Q3c | OH |
| 1459 | CH | S | Q1a | a bond | H | a bond | NH | O | NH | Q3a | OH |
| 1460 | CH | S | Q1a | a bond | H | a bond | NH | O | NH | Q3b | OH |
| 1461 | CH | S | Q1a | a bond | H | a bond | NH | O | NH | Q3c | OH |
| 1462 | CH | S | Q1a | a bond | H | a bond | NH | O | a bond | Q3a | OH |
| 1463 | CH | S | Q1a | a bond | H | a bond | NH | O | a bond | Q3b | OH |
| 1464 | CH | S | Q1a | a bond | H | a bond | NH | O | a bond | Q3c | OH |
| 1465 | CH | S | Q1b | a bond | Me | a bond | NH | S | NH | Q3a | OH |
| 1466 | CH | S | Q1b | a bond | Me | a bond | NH | S | NH | Q3b | OH |
| 1467 | CH | S | Q1b | a bond | Me | a bond | NH | S | NH | Q3c | OH |
| 1468 | CH | S | Q1b | a bond | Me | a bond | NH | S | a bond | Q3a | OH |
| 1469 | CH | S | Q1b | a bond | Me | a bond | NH | S | a bond | Q3b | OH |
| 1470 | CH | S | Q1b | a bond | Me | a bond | NH | S | a bond | Q3c | OH |
| 1471 | CH | S | Q1b | a bond | Me | a bond | NH | O | NH | Q3a | OH |
| 1472 | CH | S | Q1b | a bond | Me | a bond | NH | O | NH | Q3b | OH |
| 1473 | CH | S | Q1b | a bond | Me | a bond | NH | O | NH | Q3c | OH |
| 1474 | CH | S | Q1b | a bond | Me | a bond | NH | O | a bond | Q3a | OH |
| 1475 | CH | S | Q1b | a bond | Me | a bond | NH | O | a bond | Q3b | OH |
| 1476 | CH | S | Q1b | a bond | Me | a bond | NH | O | a bond | Q3c | OH |
| 1477 | CH | S | Q1b | a bond | H | a bond | NH | S | NH | Q3a | OH |
| 1478 | CH | S | Q1b | a bond | H | a bond | NH | S | NH | Q3b | OH |
| 1479 | CH | S | Q1b | a bond | H | a bond | NH | S | NH | Q3c | OH |
| 1480 | CH | S | Q1b | a bond | H | a bond | NH | S | a bond | Q3a | OH |
| 1481 | CH | S | Q1b | a bond | H | a bond | NH | S | a bond | Q3b | OH |
| 1482 | CH | S | Q1b | a bond | H | a bond | NH | S | a bond | Q3c | OH |

TABLE 1-continued

| No | A | B | R¹ | L¹ | R² | L² | L³ | Y | L⁴ | R³ | X |
|---|---|---|---|---|---|---|---|---|---|---|---|
| 1483 | CH | S | Q1b | a bond | H | a bond | NH | O | NH | Q3a | OH |
| 1484 | CH | S | Q1b | a bond | H | a bond | NH | O | NH | Q3b | OH |
| 1485 | CH | S | Q1b | a bond | H | a bond | NH | O | NH | Q3c | OH |
| 1486 | CH | S | Q1b | a bond | H | a bond | NH | O | a bond | Q3a | OH |
| 1487 | CH | S | Q1b | a bond | H | a bond | NH | O | a bond | Q3b | OH |
| 1488 | CH | S | Q1b | a bond | H | a bond | NH | O | a bond | Q3c | OH |
| 1489 | CH | S | Q1c | a bond | Me | a bond | NH | S | NH | Q3a | OH |
| 1490 | CH | S | Q1c | a bond | Me | a bond | NH | S | NH | Q3b | OH |
| 1491 | CH | S | Q1c | a bond | Me | a bond | NH | S | NH | Q3c | OH |
| 1492 | CH | S | Q1c | a bond | Me | a bond | NH | S | a bond | Q3a | OH |
| 1493 | CH | S | Q1c | a bond | Me | a bond | NH | S | a bond | Q3b | OH |
| 1494 | CH | S | Q1c | a bond | Me | a bond | NH | S | a bond | Q3c | OH |
| 1495 | CH | S | Q1c | a bond | Me | a bond | NH | O | NH | Q3a | OH |
| 1496 | CH | S | Q1c | a bond | Me | a bond | NH | O | NH | Q3b | OH |
| 1497 | CH | S | Q1c | a bond | Me | a bond | NH | O | NH | Q3c | OH |
| 1498 | CH | S | Q1c | a bond | Me | a bond | NH | O | a bond | Q3a | OH |
| 1499 | CH | S | Q1c | a bond | Me | a bond | NH | O | a bond | Q3b | OH |
| 1500 | CH | S | Q1c | a bond | Me | a bond | NH | O | a bond | Q3c | OH |
| 1501 | CH | S | Q1c | a bond | H | a bond | NH | S | NH | Q3a | OH |
| 1502 | CH | S | Q1c | a bond | H | a bond | NH | S | NH | Q3b | OH |
| 1503 | CH | S | Q1c | a bond | H | a bond | NH | S | NH | Q3c | OH |
| 1504 | CH | S | Q1c | a bond | H | a bond | NH | S | a bond | Q3a | OH |
| 1505 | CH | S | Q1c | a bond | H | a bond | NH | S | a bond | Q3b | OH |
| 1506 | CH | S | Q1c | a bond | H | a bond | NH | S | a bond | Q3c | OH |
| 1507 | CH | S | Q1c | a bond | H | a bond | NH | O | NH | Q3a | OH |
| 1508 | CH | S | Q1c | a bond | H | a bond | NH | O | NH | Q3b | OH |
| 1509 | CH | S | Q1c | a bond | H | a bond | NH | O | NH | Q3c | OH |
| 1510 | CH | S | Q1c | a bond | H | a bond | NH | O | a bond | Q3a | OH |
| 1511 | CH | S | Q1c | a bond | H | a bond | NH | O | a bond | Q3b | OH |
| 1512 | CH | S | Q1c | a bond | H | a bond | NH | O | a bond | Q3c | OH |
| 1513 | CH | S | Q1d | a bond | Me | a bond | NH | S | NH | Q3a | OH |
| 1514 | CH | S | Q1d | a bond | Me | a bond | NH | S | NH | Q3b | OH |
| 1515 | CH | S | Q1d | a bond | Me | a bond | NH | S | NH | Q3c | OH |
| 1516 | CH | S | Q1d | a bond | Me | a bond | NH | S | a bond | Q3a | OH |
| 1517 | CH | S | Q1d | a bond | Me | a bond | NH | S | a bond | Q3b | OH |
| 1518 | CH | S | Q1d | a bond | Me | a bond | NH | S | a bond | Q3c | OH |
| 1519 | CH | S | Q1d | a bond | Me | a bond | NH | O | NH | Q3a | OH |
| 1520 | CH | S | Q1d | a bond | Me | a bond | NH | O | NH | Q3b | OH |
| 1521 | CH | S | Q1d | a bond | Me | a bond | NH | O | NH | Q3c | OH |
| 1522 | CH | S | Q1d | a bond | Me | a bond | NH | O | a bond | Q3a | OH |
| 1523 | CH | S | Q1d | a bond | Me | a bond | NH | O | a bond | Q3b | OH |
| 1524 | CH | S | Q1d | a bond | Me | a bond | NH | O | a bond | Q3c | OH |
| 1525 | CH | S | Q1d | a bond | H | a bond | NH | S | NH | Q3a | OH |
| 1526 | CH | S | Q1d | a bond | H | a bond | NH | S | NH | Q3b | OH |
| 1527 | CH | S | Q1d | a bond | H | a bond | NH | S | NH | Q3c | OH |
| 1528 | CH | S | Q1d | a bond | H | a bond | NH | S | a bond | Q3a | OH |
| 1529 | CH | S | Q1d | a bond | H | a bond | NH | S | a bond | Q3b | OH |
| 1530 | CH | S | Q1d | a bond | H | a bond | NH | S | a bond | Q3c | OH |
| 1531 | CH | S | Q1d | a bond | H | a bond | NH | O | NH | Q3a | OH |
| 1532 | CH | S | Q1d | a bond | H | a bond | NH | O | NH | Q3b | OH |
| 1533 | CH | S | Q1d | a bond | H | a bond | NH | O | NH | Q3c | OH |
| 1534 | CH | S | Q1d | a bond | H | a bond | NH | O | a bond | Q3a | OH |
| 1535 | CH | S | Q1d | a bond | H | a bond | NH | O | a bond | Q3b | OH |
| 1536 | CH | S | Q1d | a bond | H | a bond | NH | O | a bond | Q3c | OH |
| 1537 | CH | S | Q1e | a bond | Me | a bond | NH | S | NH | Q3a | OH |
| 1538 | CH | S | Q1e | a bond | Me | a bond | NH | S | NH | Q3b | OH |
| 1539 | CH | S | Q1e | a bond | Me | a bond | NH | S | NH | Q3c | OH |
| 1540 | CH | S | Q1e | a bond | Me | a bond | NH | S | a bond | Q3a | OH |
| 1541 | CH | S | Q1e | a bond | Me | a bond | NH | S | a bond | Q3b | OH |
| 1542 | CH | S | Q1e | a bond | Me | a bond | NH | S | a bond | Q3c | OH |
| 1543 | CH | S | Q1e | a bond | Me | a bond | NH | O | NH | Q3a | OH |
| 1544 | CH | S | Q1e | a bond | Me | a bond | NH | O | NH | Q3b | OH |
| 1545 | CH | S | Q1e | a bond | Me | a bond | NH | O | NH | Q3c | OH |
| 1546 | CH | S | Q1e | a bond | Me | a bond | NH | O | a bond | Q3a | OH |
| 1547 | CH | S | Q1e | a bond | Me | a bond | NH | O | a bond | Q3b | OH |
| 1548 | CH | S | Q1e | a bond | Me | a bond | NH | O | a bond | Q3c | OH |
| 1549 | CH | S | Q1e | a bond | H | a bond | NH | S | NH | Q3a | OH |
| 1550 | CH | S | Q1e | a bond | H | a bond | NH | S | NH | Q3b | OH |
| 1551 | CH | S | Q1e | a bond | H | a bond | NH | S | NH | Q3c | OH |
| 1552 | CH | S | Q1e | a bond | H | a bond | NH | S | a bond | Q3a | OH |
| 1553 | CH | S | Q1e | a bond | H | a bond | NH | S | a bond | Q3b | OH |
| 1554 | CH | S | Q1e | a bond | H | a bond | NH | S | a bond | Q3c | OH |
| 1555 | CH | S | Q1e | a bond | H | a bond | NH | O | NH | Q3a | OH |
| 1556 | CH | S | Q1e | a bond | H | a bond | NH | O | NH | Q3b | OH |
| 1557 | CH | S | Q1e | a bond | H | a bond | NH | O | NH | Q3c | OH |
| 1558 | CH | S | Q1e | a bond | H | a bond | NH | O | a bond | Q3a | OH |
| 1559 | CH | S | Q1e | a bond | H | a bond | NH | O | a bond | Q3b | OH |
| 1560 | CH | S | Q1e | a bond | H | a bond | NH | O | a bond | Q3c | OH |

TABLE 1-continued

| No | A | B | R¹ | L¹ | R² | L² | L³ | Y | L⁴ | R³ | X |
|---|---|---|---|---|---|---|---|---|---|---|---|
| 1561 | CH | S | Q1f | a bond | Me | a bond | NH | S | NH | Q3a | OH |
| 1562 | CH | S | Q1f | a bond | Me | a bond | NH | S | NH | Q3b | OH |
| 1563 | CH | S | Q1f | a bond | Me | a bond | NH | S | NH | Q3c | OH |
| 1564 | CH | S | Q1f | a bond | Me | a bond | NH | S | a bond | Q3a | OH |
| 1565 | CH | S | Q1f | a bond | Me | a bond | NH | S | a bond | Q3b | OH |
| 1566 | CH | S | Q1f | a bond | Me | a bond | NH | S | a bond | Q3c | OH |
| 1567 | CH | S | Q1f | a bond | Me | a bond | NH | O | NH | Q3a | OH |
| 1568 | CH | S | Q1f | a bond | Me | a bond | NH | O | NH | Q3b | OH |
| 1569 | CH | S | Q1f | a bond | Me | a bond | NH | O | NH | Q3c | OH |
| 1570 | CH | S | Q1f | a bond | Me | a bond | NH | O | a bond | Q3a | OH |
| 1571 | CH | S | Q1f | a bond | Me | a bond | NH | O | a bond | Q3b | OH |
| 1572 | CH | S | Q1f | a bond | Me | a bond | NH | O | a bond | Q3c | OH |
| 1573 | CH | S | Q1f | a bond | H | a bond | NH | S | NH | Q3a | OH |
| 1574 | CH | S | Q1f | a bond | H | a bond | NH | S | NH | Q3b | OH |
| 1575 | CH | S | Q1f | a bond | H | a bond | NH | S | NH | Q3c | OH |
| 1576 | CH | S | Q1f | a bond | H | a bond | NH | S | a bond | Q3a | OH |
| 1577 | CH | S | Q1f | a bond | H | a bond | NH | S | a bond | Q3b | OH |
| 1578 | CH | S | Q1f | a bond | H | a bond | NH | S | a bond | Q3c | OH |
| 1579 | CH | S | Q1f | a bond | H | a bond | NH | O | NH | Q3a | OH |
| 1580 | CH | S | Q1f | a bond | H | a bond | NH | O | NH | Q3b | OH |
| 1581 | CH | S | Q1f | a bond | H | a bond | NH | O | NH | Q3c | OH |
| 1582 | CH | S | Q1f | a bond | H | a bond | NH | O | a bond | Q3a | OH |
| 1583 | CH | S | Q1f | a bond | H | a bond | NH | O | a bond | Q3b | OH |
| 1584 | CH | S | Q1f | a bond | H | a bond | NH | O | a bond | Q3c | OH |
| 1585 | CH | S | Q1g | a bond | Me | a bond | NH | S | NH | Q3a | OH |
| 1586 | CH | S | Q1g | a bond | Me | a bond | NH | S | NH | Q3b | OH |
| 1587 | CH | S | Q1g | a bond | Me | a bond | NH | S | NH | Q3c | OH |
| 1588 | CH | S | Q1g | a bond | Me | a bond | NH | S | a bond | Q3a | OH |
| 1589 | CH | S | Q1g | a bond | Me | a bond | NH | S | a bond | Q3b | OH |
| 1590 | CH | S | Q1g | a bond | Me | a bond | NH | S | a bond | Q3c | OH |
| 1591 | CH | S | Q1g | a bond | Me | a bond | NH | O | NH | Q3a | OH |
| 1592 | CH | S | Q1g | a bond | Me | a bond | NH | O | NH | Q3b | OH |
| 1593 | CH | S | Q1g | a bond | Me | a bond | NH | O | NH | Q3c | OH |
| 1594 | CH | S | Q1g | a bond | Me | a bond | NH | O | a bond | Q3a | OH |
| 1595 | CH | S | Q1g | a bond | Me | a bond | NH | O | a bond | Q3b | OH |
| 1596 | CH | S | Q1g | a bond | Me | a bond | NH | O | a bond | Q3c | OH |
| 1597 | CH | S | Q1g | a bond | H | a bond | NH | S | NH | Q3a | OH |
| 1598 | CH | S | Q1g | a bond | H | a bond | NH | S | NH | Q3b | OH |
| 1599 | CH | S | Q1g | a bond | H | a bond | NH | S | NH | Q3c | OH |
| 1600 | CH | S | Q1g | a bond | H | a bond | NH | S | a bond | Q3a | OH |
| 1601 | CH | S | Q1g | a bond | H | a bond | NH | S | a bond | Q3b | OH |
| 1602 | CH | S | Q1g | a bond | H | a bond | NH | S | a bond | Q3c | OH |
| 1603 | CH | S | Q1g | a bond | H | a bond | NH | O | NH | Q3a | OH |
| 1604 | CH | S | Q1g | a bond | H | a bond | NH | O | NH | Q3b | OH |
| 1605 | CH | S | Q1g | a bond | H | a bond | NH | O | NH | Q3c | OH |
| 1606 | CH | S | Q1g | a bond | H | a bond | NH | O | a bond | Q3a | OH |
| 1607 | CH | S | Q1g | a bond | H | a bond | NH | O | a bond | Q3b | OH |
| 1608 | CH | S | Q1g | a bond | H | a bond | NH | O | a bond | Q3c | OH |
| 1609 | CH | S | Q1h | a bond | Me | a bond | NH | S | NH | Q3a | OH |
| 1610 | CH | S | Q1h | a bond | Me | a bond | NH | S | NH | Q3b | OH |
| 1611 | CH | S | Q1h | a bond | Me | a bond | NH | S | NH | Q3c | OH |
| 1612 | CH | S | Q1h | a bond | Me | a bond | NH | S | a bond | Q3a | OH |
| 1613 | CH | S | Q1h | a bond | Me | a bond | NH | S | a bond | Q3b | OH |
| 1614 | CH | S | Q1h | a bond | Me | a bond | NH | S | a bond | Q3c | OH |
| 1615 | CH | S | Q1h | a bond | Me | a bond | NH | O | NH | Q3a | OH |
| 1616 | CH | S | Q1h | a bond | Me | a bond | NH | O | NH | Q3b | OH |
| 1617 | CH | S | Q1h | a bond | Me | a bond | NH | O | NH | Q3c | OH |
| 1618 | CH | S | Q1h | a bond | Me | a bond | NH | O | a bond | Q3a | OH |
| 1619 | CH | S | Q1h | a bond | Me | a bond | NH | O | a bond | Q3b | OH |
| 1620 | CH | S | Q1h | a bond | Me | a bond | NH | O | a bond | Q3c | OH |
| 1621 | CH | S | Q1h | a bond | H | a bond | NH | S | NH | Q3a | OH |
| 1622 | CH | S | Q1h | a bond | H | a bond | NH | S | NH | Q3b | OH |
| 1623 | CH | S | Q1h | a bond | H | a bond | NH | S | NH | Q3c | OH |
| 1624 | CH | S | Q1h | a bond | H | a bond | NH | S | a bond | Q3a | OH |
| 1625 | CH | S | Q1h | a bond | H | a bond | NH | S | a bond | Q3b | OH |
| 1626 | CH | S | Q1h | a bond | H | a bond | NH | S | a bond | Q3c | OH |
| 1627 | CH | S | Q1h | a bond | H | a bond | NH | O | NH | Q3a | OH |
| 1628 | CH | S | Q1h | a bond | H | a bond | NH | O | NH | Q3b | OH |
| 1629 | CH | S | Q1h | a bond | H | a bond | NH | O | NH | Q3c | OH |
| 1630 | CH | S | Q1h | a bond | H | a bond | NH | O | a bond | Q3a | OH |
| 1631 | CH | S | Q1h | a bond | H | a bond | NH | O | a bond | Q3b | OH |
| 1632 | CH | S | Q1h | a bond | H | a bond | NH | O | a bond | Q3c | OH |
| 1633 | CH | S | Q1i | a bond | Me | a bond | NH | S | NH | Q3a | OH |
| 1634 | CH | S | Q1i | a bond | Me | a bond | NH | S | NH | Q3b | OH |
| 1635 | CH | S | Q1i | a bond | Me | a bond | NH | S | NH | Q3c | OH |
| 1636 | CH | S | Q1i | a bond | Me | a bond | NH | S | a bond | Q3a | OH |
| 1637 | CH | S | Q1i | a bond | Me | a bond | NH | S | a bond | Q3b | OH |
| 1638 | CH | S | Q1i | a bond | Me | a bond | NH | S | a bond | Q3c | OH |

TABLE 1-continued

| No | A | B | R¹ | L¹ | R² | L² | L³ | Y | L⁴ | R³ | X |
|---|---|---|---|---|---|---|---|---|---|---|---|
| 1639 | CH | S | Q1i | a bond | Me | a bond | NH | O | NH | Q3a | OH |
| 1640 | CH | S | Q1i | a bond | Me | a bond | NH | O | NH | Q3b | OH |
| 1641 | CH | S | Q1i | a bond | Me | a bond | NH | O | NH | Q3c | OH |
| 1642 | CH | S | Q1i | a bond | Me | a bond | NH | O | a bond | Q3a | OH |
| 1643 | CH | S | Q1i | a bond | Me | a bond | NH | O | a bond | Q3b | OH |
| 1644 | CH | S | Q1i | a bond | Me | a bond | NH | O | a bond | Q3c | OH |
| 1645 | CH | S | Q1i | a bond | H | a bond | NH | S | NH | Q3a | OH |
| 1646 | CH | S | Q1i | a bond | H | a bond | NH | S | NH | Q3b | OH |
| 1647 | CH | S | Q1i | a bond | H | a bond | NH | S | NH | Q3c | OH |
| 1648 | CH | S | Q1i | a bond | H | a bond | NH | S | a bond | Q3a | OH |
| 1649 | CH | S | Q1i | a bond | H | a bond | NH | S | a bond | Q3b | OH |
| 1650 | CH | S | Q1i | a bond | H | a bond | NH | S | a bond | Q3c | OH |
| 1651 | CH | S | Q1i | a bond | H | a bond | NH | O | NH | Q3a | OH |
| 1652 | CH | S | Q1i | a bond | H | a bond | NH | O | NH | Q3b | OH |
| 1653 | CH | S | Q1i | a bond | H | a bond | NH | O | NH | Q3c | OH |
| 1654 | CH | S | Q1i | a bond | H | a bond | NH | O | a bond | Q3a | OH |
| 1655 | CH | S | Q1i | a bond | H | a bond | NH | O | a bond | Q3b | OH |
| 1656 | CH | S | Q1i | a bond | H | a bond | NH | O | a bond | Q3c | OH |
| 1657 | CH | S | Q1j | a bond | Me | a bond | NH | S | NH | Q3a | OH |
| 1658 | CH | S | Q1j | a bond | Me | a bond | NH | S | NH | Q3b | OH |
| 1659 | CH | S | Q1j | a bond | Me | a bond | NH | S | NH | Q3c | OH |
| 1660 | CH | S | Q1j | a bond | Me | a bond | NH | S | a bond | Q3a | OH |
| 1661 | CH | S | Q1j | a bond | Me | a bond | NH | S | a bond | Q3b | OH |
| 1662 | CH | S | Q1j | a bond | Me | a bond | NH | S | a bond | Q3c | OH |
| 1663 | CH | S | Q1j | a bond | Me | a bond | NH | O | NH | Q3a | OH |
| 1664 | CH | S | Q1j | a bond | Me | a bond | NH | O | NH | Q3b | OH |
| 1665 | CH | S | Q1j | a bond | Me | a bond | NH | O | NH | Q3c | OH |
| 1666 | CH | S | Q1j | a bond | Me | a bond | NH | O | a bond | Q3a | OH |
| 1667 | CH | S | Q1j | a bond | Me | a bond | NH | O | a bond | Q3b | OH |
| 1668 | CH | S | Q1j | a bond | Me | a bond | NH | O | a bond | Q3c | OH |
| 1669 | CH | S | Q1j | a bond | H | a bond | NH | S | NH | Q3a | OH |
| 1670 | CH | S | Q1j | a bond | H | a bond | NH | S | NH | Q3b | OH |
| 1671 | CH | S | Q1j | a bond | H | a bond | NH | S | NH | Q3c | OH |
| 1672 | CH | S | Q1j | a bond | H | a bond | NH | S | a bond | Q3a | OH |
| 1673 | CH | S | Q1j | a bond | H | a bond | NH | S | a bond | Q3b | OH |
| 1674 | CH | S | Q1j | a bond | H | a bond | NH | S | a bond | Q3c | OH |
| 1675 | CH | S | Q1j | a bond | H | a bond | NH | O | NH | Q3a | OH |
| 1676 | CH | S | Q1j | a bond | H | a bond | NH | O | NH | Q3b | OH |
| 1677 | CH | S | Q1j | a bond | H | a bond | NH | O | NH | Q3c | OH |
| 1678 | CH | S | Q1j | a bond | H | a bond | NH | O | a bond | Q3a | OH |
| 1679 | CH | S | Q1j | a bond | H | a bond | NH | O | a bond | Q3b | OH |
| 1680 | CH | S | Q1j | a bond | H | a bond | NH | O | a bond | Q3c | OH |
| 1681 | CH | O | Q1a | a bond | Me | a bond | NH | S | NH | Q3a | OH |
| 1682 | CH | O | Q1a | a bond | Me | a bond | NH | S | NH | Q3b | OH |
| 1683 | CH | O | Q1a | a bond | Me | a bond | NH | S | NH | Q3c | OH |
| 1684 | CH | O | Q1a | a bond | Me | a bond | NH | S | a bond | Q3a | OH |
| 1685 | CH | O | Q1a | a bond | Me | a bond | NH | S | a bond | Q3b | OH |
| 1686 | CH | O | Q1a | a bond | Me | a bond | NH | S | a bond | Q3c | OH |
| 1687 | CH | O | Q1a | a bond | Me | a bond | NH | O | NH | Q3a | OH |
| 1688 | CH | O | Q1a | a bond | Me | a bond | NH | O | NH | Q3b | OH |
| 1689 | CH | O | Q1a | a bond | Me | a bond | NH | O | NH | Q3c | OH |
| 1690 | CH | O | Q1a | a bond | Me | a bond | NH | O | a bond | Q3a | OH |
| 1691 | CH | O | Q1a | a bond | Me | a bond | NH | O | a bond | Q3b | OH |
| 1692 | CH | O | Q1a | a bond | Me | a bond | NH | O | a bond | Q3c | OH |
| 1693 | CH | O | Q1a | a bond | H | a bond | NH | S | NH | Q3a | OH |
| 1694 | CH | O | Q1a | a bond | H | a bond | NH | S | NH | Q3b | OH |
| 1695 | CH | O | Q1a | a bond | H | a bond | NH | S | NH | Q3c | OH |
| 1696 | CH | O | Q1a | a bond | H | a bond | NH | S | a bond | Q3a | OH |
| 1697 | CH | O | Q1a | a bond | H | a bond | NH | S | a bond | Q3b | OH |
| 1698 | CH | O | Q1a | a bond | H | a bond | NH | S | a bond | Q3c | OH |
| 1699 | CH | O | Q1a | a bond | H | a bond | NH | O | NH | Q3a | OH |
| 1700 | CH | O | Q1a | a bond | H | a bond | NH | O | NH | Q3b | OH |
| 1701 | CH | O | Q1a | a bond | H | a bond | NH | O | NH | Q3c | OH |
| 1702 | CH | O | Q1a | a bond | H | a bond | NH | O | a bond | Q3a | OH |
| 1703 | CH | O | Q1a | a bond | H | a bond | NH | O | a bond | Q3b | OH |
| 1704 | CH | O | Q1a | a bond | H | a bond | NH | O | a bond | Q3c | OH |
| 1705 | CH | O | Q1b | a bond | Me | a bond | NH | S | NH | Q3a | OH |
| 1706 | CH | O | Q1b | a bond | Me | a bond | NH | S | NH | Q3b | OH |
| 1707 | CH | O | Q1b | a bond | Me | a bond | NH | S | NH | Q3c | OH |
| 1708 | CH | O | Q1b | a bond | Me | a bond | NH | S | a bond | Q3a | OH |
| 1709 | CH | O | Q1b | a bond | Me | a bond | NH | S | a bond | Q3b | OH |
| 1710 | CH | O | Q1b | a bond | Me | a bond | NH | S | a bond | Q3c | OH |
| 1711 | CH | O | Q1b | a bond | Me | a bond | NH | O | NH | Q3a | OH |
| 1712 | CH | O | Q1b | a bond | Me | a bond | NH | O | NH | Q3b | OH |
| 1713 | CH | O | Q1b | a bond | Me | a bond | NH | O | NH | Q3c | OH |
| 1714 | CH | O | Q1b | a bond | Me | a bond | NH | O | a bond | Q3a | OH |
| 1715 | CH | O | Q1b | a bond | Me | a bond | NH | O | a bond | Q3b | OH |
| 1716 | CH | O | Q1b | a bond | Me | a bond | NH | O | a bond | Q3c | OH |

TABLE 1-continued

| No | A | B | R¹ | L¹ | R² | L² | L³ | Y | L⁴ | R³ | X |
|---|---|---|---|---|---|---|---|---|---|---|---|
| 1717 | CH | O | Q1b | a bond | H | a bond | NH | S | NH | Q3a | OH |
| 1718 | CH | O | Q1b | a bond | H | a bond | NH | S | NH | Q3b | OH |
| 1719 | CH | O | Q1b | a bond | H | a bond | NH | S | NH | Q3c | OH |
| 1720 | CH | O | Q1b | a bond | H | a bond | NH | S | a bond | Q3a | OH |
| 1721 | CH | O | Q1b | a bond | H | a bond | NH | S | a bond | Q3b | OH |
| 1722 | CH | O | Q1b | a bond | H | a bond | NH | S | a bond | Q3c | OH |
| 1723 | CH | O | Q1b | a bond | H | a bond | NH | O | NH | Q3a | OH |
| 1724 | CH | O | Q1b | a bond | H | a bond | NH | O | NH | Q3b | OH |
| 1725 | CH | O | Q1b | a bond | H | a bond | NH | O | NH | Q3c | OH |
| 1726 | CH | O | Q1b | a bond | H | a bond | NH | O | a bond | Q3a | OH |
| 1727 | CH | O | Q1b | a bond | H | a bond | NH | O | a bond | Q3b | OH |
| 1728 | CH | O | Q1b | a bond | H | a bond | NH | O | a bond | Q3c | OH |
| 1729 | CH | O | Q1c | a bond | Me | a bond | NH | S | NH | Q3a | OH |
| 1730 | CH | O | Q1c | a bond | Me | a bond | NH | S | NH | Q3b | OH |
| 1731 | CH | O | Q1c | a bond | Me | a bond | NH | S | NH | Q3c | OH |
| 1732 | CH | O | Q1c | a bond | Me | a bond | NH | S | a bond | Q3a | OH |
| 1733 | CH | O | Q1c | a bond | Me | a bond | NH | S | a bond | Q3b | OH |
| 1734 | CH | O | Q1c | a bond | Me | a bond | NH | S | a bond | Q3c | OH |
| 1735 | CH | O | Q1c | a bond | Me | a bond | NH | O | NH | Q3a | OH |
| 1736 | CH | O | Q1c | a bond | Me | a bond | NH | O | NH | Q3b | OH |
| 1737 | CH | O | Q1c | a bond | Me | a bond | NH | O | NH | Q3c | OH |
| 1738 | CH | O | Q1c | a bond | Me | a bond | NH | O | a bond | Q3a | OH |
| 1739 | CH | O | Q1c | a bond | Me | a bond | NH | O | a bond | Q3b | OH |
| 1740 | CH | O | Q1c | a bond | Me | a bond | NH | O | a bond | Q3c | OH |
| 1741 | CH | O | Q1c | a bond | H | a bond | NH | S | NH | Q3a | OH |
| 1742 | CH | O | Q1c | a bond | H | a bond | NH | S | NH | Q3b | OH |
| 1743 | CH | O | Q1c | a bond | H | a bond | NH | S | NH | Q3c | OH |
| 1744 | CH | O | Q1c | a bond | H | a bond | NH | S | a bond | Q3a | OH |
| 1745 | CH | O | Q1c | a bond | H | a bond | NH | S | a bond | Q3b | OH |
| 1746 | CH | O | Q1c | a bond | H | a bond | NH | S | a bond | Q3c | OH |
| 1747 | CH | O | Q1c | a bond | H | a bond | NH | O | NH | Q3a | OH |
| 1748 | CH | O | Q1c | a bond | H | a bond | NH | O | NH | Q3b | OH |
| 1749 | CH | O | Q1c | a bond | H | a bond | NH | O | NH | Q3c | OH |
| 1750 | CH | O | Q1c | a bond | H | a bond | NH | O | a bond | Q3a | OH |
| 1751 | CH | O | Q1c | a bond | H | a bond | NH | O | a bond | Q3b | OH |
| 1752 | CH | O | Q1c | a bond | H | a bond | NH | O | a bond | Q3c | OH |
| 1753 | CH | O | Q1d | a bond | Me | a bond | NH | S | NH | Q3a | OH |
| 1754 | CH | O | Q1d | a bond | Me | a bond | NH | S | NH | Q3b | OH |
| 1755 | CH | O | Q1d | a bond | Me | a bond | NH | S | NH | Q3c | OH |
| 1756 | CH | O | Q1d | a bond | Me | a bond | NH | S | a bond | Q3a | OH |
| 1757 | CH | O | Q1d | a bond | Me | a bond | NH | S | a bond | Q3b | OH |
| 1758 | CH | O | Q1d | a bond | Me | a bond | NH | S | a bond | Q3c | OH |
| 1759 | CH | O | Q1d | a bond | Me | a bond | NH | O | NH | Q3a | OH |
| 1760 | CH | O | Q1d | a bond | Me | a bond | NH | O | NH | Q3b | OH |
| 1761 | CH | O | Q1d | a bond | Me | a bond | NH | O | NH | Q3c | OH |
| 1762 | CH | O | Q1d | a bond | Me | a bond | NH | O | a bond | Q3a | OH |
| 1763 | CH | O | Q1d | a bond | Me | a bond | NH | O | a bond | Q3b | OH |
| 1764 | CH | O | Q1d | a bond | Me | a bond | NH | O | a bond | Q3c | OH |
| 1765 | CH | O | Q1d | a bond | H | a bond | NH | S | NH | Q3a | OH |
| 1766 | CH | O | Q1d | a bond | H | a bond | NH | S | NH | Q3b | OH |
| 1767 | CH | O | Q1d | a bond | H | a bond | NH | S | NH | Q3c | OH |
| 1768 | CH | O | Q1d | a bond | H | a bond | NH | S | a bond | Q3a | OH |
| 1769 | CH | O | Q1d | a bond | H | a bond | NH | S | a bond | Q3b | OH |
| 1770 | CH | O | Q1d | a bond | H | a bond | NH | S | a bond | Q3c | OH |
| 1771 | CH | O | Q1d | a bond | H | a bond | NH | O | NH | Q3a | OH |
| 1772 | CH | O | Q1d | a bond | H | a bond | NH | O | NH | Q3b | OH |
| 1773 | CH | O | Q1d | a bond | H | a bond | NH | O | NH | Q3c | OH |
| 1774 | CH | O | Q1d | a bond | H | a bond | NH | O | a bond | Q3a | OH |
| 1775 | CH | O | Q1d | a bond | H | a bond | NH | O | a bond | Q3b | OH |
| 1776 | CH | O | Q1d | a bond | H | a bond | NH | O | a bond | Q3c | OH |
| 1777 | CH | O | Q1e | a bond | Me | a bond | NH | S | NH | Q3a | OH |
| 1778 | CH | O | Q1e | a bond | Me | a bond | NH | S | NH | Q3b | OH |
| 1779 | CH | O | Q1e | a bond | Me | a bond | NH | S | NH | Q3c | OH |
| 1780 | CH | O | Q1e | a bond | Me | a bond | NH | S | a bond | Q3a | OH |
| 1781 | CH | O | Q1e | a bond | Me | a bond | NH | S | a bond | Q3b | OH |
| 1782 | CH | O | Q1e | a bond | Me | a bond | NH | S | a bond | Q3c | OH |
| 1783 | CH | O | Q1e | a bond | Me | a bond | NH | O | NH | Q3a | OH |
| 1784 | CH | O | Q1e | a bond | Me | a bond | NH | O | NH | Q3b | OH |
| 1785 | CH | O | Q1e | a bond | Me | a bond | NH | O | NH | Q3c | OH |
| 1786 | CH | O | Q1e | a bond | Me | a bond | NH | O | a bond | Q3a | OH |
| 1787 | CH | O | Q1e | a bond | Me | a bond | NH | O | a bond | Q3b | OH |
| 1788 | CH | O | Q1e | a bond | Me | a bond | NH | O | a bond | Q3c | OH |
| 1789 | CH | O | Q1e | a bond | H | a bond | NH | S | NH | Q3a | OH |
| 1790 | CH | O | Q1e | a bond | H | a bond | NH | S | NH | Q3b | OH |
| 1791 | CH | O | Q1e | a bond | H | a bond | NH | S | NH | Q3c | OH |
| 1792 | CH | O | Q1e | a bond | H | a bond | NH | S | a bond | Q3a | OH |
| 1793 | CH | O | Q1e | a bond | H | a bond | NH | S | a bond | Q3b | OH |
| 1794 | CH | O | Q1e | a bond | H | a bond | NH | S | a bond | Q3c | OH |

TABLE 1-continued

| No | A | B | R¹ | L¹ | R² | L² | L³ | Y | L⁴ | R³ | X |
|---|---|---|---|---|---|---|---|---|---|---|---|
| 1795 | CH | O | Q1e | a bond | H | a bond | NH | O | NH | Q3a | OH |
| 1796 | CH | O | Q1e | a bond | H | a bond | NH | O | NH | Q3b | OH |
| 1797 | CH | O | Q1e | a bond | H | a bond | NH | O | NH | Q3c | OH |
| 1798 | CH | O | Q1e | a bond | H | a bond | NH | O | a bond | Q3a | OH |
| 1799 | CH | O | Q1e | a bond | H | a bond | NH | O | a bond | Q3b | OH |
| 1800 | CH | O | Q1e | a bond | H | a bond | NH | O | a bond | Q3c | OH |
| 1801 | CH | O | Q1f | a bond | Me | a bond | NH | S | NH | Q3a | OH |
| 1802 | CH | O | Q1f | a bond | Me | a bond | NH | S | NH | Q3b | OH |
| 1803 | CH | O | Q1f | a bond | Me | a bond | NH | S | NH | Q3c | OH |
| 1804 | CH | O | Q1f | a bond | Me | a bond | NH | S | a bond | Q3a | OH |
| 1805 | CH | O | Q1f | a bond | Me | a bond | NH | S | a bond | Q3b | OH |
| 1806 | CH | O | Q1f | a bond | Me | a bond | NH | S | a bond | Q3c | OH |
| 1807 | CH | O | Q1f | a bond | Me | a bond | NH | O | NH | Q3a | OH |
| 1808 | CH | O | Q1f | a bond | Me | a bond | NH | O | NH | Q3b | OH |
| 1809 | CH | O | Q1f | a bond | Me | a bond | NH | O | NH | Q3c | OH |
| 1810 | CH | O | Q1f | a bond | Me | a bond | NH | O | a bond | Q3a | OH |
| 1811 | CH | O | Q1f | a bond | Me | a bond | NH | O | a bond | Q3b | OH |
| 1812 | CH | O | Q1f | a bond | Me | a bond | NH | O | a bond | Q3c | OH |
| 1813 | CH | O | Q1f | a bond | H | a bond | NH | S | NH | Q3a | OH |
| 1814 | CH | O | Q1f | a bond | H | a bond | NH | S | NH | Q3b | OH |
| 1815 | CH | O | Q1f | a bond | H | a bond | NH | S | NH | Q3c | OH |
| 1816 | CH | O | Q1f | a bond | H | a bond | NH | S | a bond | Q3a | OH |
| 1817 | CH | O | Q1f | a bond | H | a bond | NH | S | a bond | Q3b | OH |
| 1818 | CH | O | Q1f | a bond | H | a bond | NH | S | a bond | Q3c | OH |
| 1819 | CH | O | Q1f | a bond | H | a bond | NH | O | NH | Q3a | OH |
| 1820 | CH | O | Q1f | a bond | H | a bond | NH | O | NH | Q3b | OH |
| 1821 | CH | O | Q1f | a bond | H | a bond | NH | O | NH | Q3c | OH |
| 1822 | CH | O | Q1f | a bond | H | a bond | NH | O | a bond | Q3a | OH |
| 1823 | CH | O | Q1f | a bond | H | a bond | NH | O | a bond | Q3b | OH |
| 1824 | CH | O | Q1f | a bond | H | a bond | NH | O | a bond | Q3c | OH |
| 1825 | CH | O | Q1g | a bond | Me | a bond | NH | S | NH | Q3a | OH |
| 1826 | CH | O | Q1g | a bond | Me | a bond | NH | S | NH | Q3b | OH |
| 1827 | CH | O | Q1g | a bond | Me | a bond | NH | S | NH | Q3c | OH |
| 1828 | CH | O | Q1g | a bond | Me | a bond | NH | S | a bond | Q3a | OH |
| 1829 | CH | O | Q1g | a bond | Me | a bond | NH | S | a bond | Q3b | OH |
| 1830 | CH | O | Q1g | a bond | Me | a bond | NH | S | a bond | Q3c | OH |
| 1831 | CH | O | Q1g | a bond | Me | a bond | NH | O | NH | Q3a | OH |
| 1832 | CH | O | Q1g | a bond | Me | a bond | NH | O | NH | Q3b | OH |
| 1833 | CH | O | Q1g | a bond | Me | a bond | NH | O | NH | Q3c | OH |
| 1834 | CH | O | Q1g | a bond | Me | a bond | NH | O | a bond | Q3a | OH |
| 1835 | CH | O | Q1g | a bond | Me | a bond | NH | O | a bond | Q3b | OH |
| 1836 | CH | O | Q1g | a bond | Me | a bond | NH | O | a bond | Q3c | OH |
| 1837 | CH | O | Q1g | a bond | H | a bond | NH | S | NH | Q3a | OH |
| 1838 | CH | O | Q1g | a bond | H | a bond | NH | S | NH | Q3b | OH |
| 1839 | CH | O | Q1g | a bond | H | a bond | NH | S | NH | Q3c | OH |
| 1840 | CH | O | Q1g | a bond | H | a bond | NH | S | a bond | Q3a | OH |
| 1841 | CH | O | Q1g | a bond | H | a bond | NH | S | a bond | Q3b | OH |
| 1842 | CH | O | Q1g | a bond | H | a bond | NH | S | a bond | Q3c | OH |
| 1843 | CH | O | Q1g | a bond | H | a bond | NH | O | NH | Q3a | OH |
| 1844 | CH | O | Q1g | a bond | H | a bond | NH | O | NH | Q3b | OH |
| 1845 | CH | O | Q1g | a bond | H | a bond | NH | O | NH | Q3c | OH |
| 1846 | CH | O | Q1g | a bond | H | a bond | NH | O | a bond | Q3a | OH |
| 1847 | CH | O | Q1g | a bond | H | a bond | NH | O | a bond | Q3b | OH |
| 1848 | CH | O | Q1g | a bond | H | a bond | NH | O | a bond | Q3c | OH |
| 1849 | CH | O | Q1h | a bond | Me | a bond | NH | S | NH | Q3a | OH |
| 1850 | CH | O | Q1h | a bond | Me | a bond | NH | S | NH | Q3b | OH |
| 1851 | CH | O | Q1h | a bond | Me | a bond | NH | S | NH | Q3c | OH |
| 1852 | CH | O | Q1h | a bond | Me | a bond | NH | S | a bond | Q3a | OH |
| 1853 | CH | O | Q1h | a bond | Me | a bond | NH | S | a bond | Q3b | OH |
| 1854 | CH | O | Q1h | a bond | Me | a bond | NH | S | a bond | Q3c | OH |
| 1855 | CH | O | Q1h | a bond | Me | a bond | NH | O | NH | Q3a | OH |
| 1856 | CH | O | Q1h | a bond | Me | a bond | NH | O | NH | Q3b | OH |
| 1857 | CH | O | Q1h | a bond | Me | a bond | NH | O | NH | Q3c | OH |
| 1858 | CH | O | Q1h | a bond | Me | a bond | NH | O | a bond | Q3a | OH |
| 1859 | CH | O | Q1h | a bond | Me | a bond | NH | O | a bond | Q3b | OH |
| 1860 | CH | O | Q1h | a bond | Me | a bond | NH | O | a bond | Q3c | OH |
| 1861 | CH | O | Q1h | a bond | H | a bond | NH | S | NH | Q3a | OH |
| 1862 | CH | O | Q1h | a bond | H | a bond | NH | S | NH | Q3b | OH |
| 1863 | CH | O | Q1h | a bond | H | a bond | NH | S | NH | Q3c | OH |
| 1864 | CH | O | Q1h | a bond | H | a bond | NH | S | a bond | Q3a | OH |
| 1865 | CH | O | Q1h | a bond | H | a bond | NH | S | a bond | Q3b | OH |
| 1866 | CH | O | Q1h | a bond | H | a bond | NH | S | a bond | Q3c | OH |
| 1867 | CH | O | Q1h | a bond | H | a bond | NH | O | NH | Q3a | OH |
| 1868 | CH | O | Q1h | a bond | H | a bond | NH | O | NH | Q3b | OH |
| 1869 | CH | O | Q1h | a bond | H | a bond | NH | O | NH | Q3c | OH |
| 1870 | CH | O | Q1h | a bond | H | a bond | NH | O | a bond | Q3a | OH |
| 1871 | CH | O | Q1h | a bond | H | a bond | NH | O | a bond | Q3b | OH |
| 1872 | CH | O | Q1h | a bond | H | a bond | NH | O | a bond | Q3c | OH |

TABLE 1-continued

| No | A | B | R¹ | L¹ | R² | L² | L³ | Y | L⁴ | R³ | X |
|---|---|---|---|---|---|---|---|---|---|---|---|
| 1873 | CH | O | Q1i | a bond | Me | a bond | NH | S | NH | Q3a | OH |
| 1874 | CH | O | Q1i | a bond | Me | a bond | NH | S | NH | Q3b | OH |
| 1875 | CH | O | Q1i | a bond | Me | a bond | NH | S | NH | Q3c | OH |
| 1876 | CH | O | Q1i | a bond | Me | a bond | NH | S | a bond | Q3a | OH |
| 1877 | CH | O | Q1i | a bond | Me | a bond | NH | S | a bond | Q3b | OH |
| 1878 | CH | O | Q1i | a bond | Me | a bond | NH | S | a bond | Q3c | OH |
| 1879 | CH | O | Q1i | a bond | Me | a bond | NH | O | NH | Q3a | OH |
| 1880 | CH | O | Q1i | a bond | Me | a bond | NH | O | NH | Q3b | OH |
| 1881 | CH | O | Q1i | a bond | Me | a bond | NH | O | NH | Q3c | OH |
| 1882 | CH | O | Q1i | a bond | Me | a bond | NH | O | a bond | Q3a | OH |
| 1883 | CH | O | Q1i | a bond | Me | a bond | NH | O | a bond | Q3b | OH |
| 1884 | CH | O | Q1i | a bond | Me | a bond | NH | O | a bond | Q3c | OH |
| 1885 | CH | O | Q1i | a bond | H | a bond | NH | S | NH | Q3a | OH |
| 1886 | CH | O | Q1i | a bond | H | a bond | NH | S | NH | Q3b | OH |
| 1887 | CH | O | Q1i | a bond | H | a bond | NH | S | NH | Q3c | OH |
| 1888 | CH | O | Q1i | a bond | H | a bond | NH | S | a bond | Q3a | OH |
| 1889 | CH | O | Q1i | a bond | H | a bond | NH | S | a bond | Q3b | OH |
| 1890 | CH | O | Q1i | a bond | H | a bond | NH | S | a bond | Q3c | OH |
| 1891 | CH | O | Q1i | a bond | H | a bond | NH | O | NH | Q3a | OH |
| 1892 | CH | O | Q1i | a bond | H | a bond | NH | O | NH | Q3b | OH |
| 1893 | CH | O | Q1i | a bond | H | a bond | NH | O | NH | Q3c | OH |
| 1894 | CH | O | Q1i | a bond | H | a bond | NH | O | a bond | Q3a | OH |
| 1895 | CH | O | Q1i | a bond | H | a bond | NH | O | a bond | Q3b | OH |
| 1896 | CH | O | Q1i | a bond | H | a bond | NH | O | a bond | Q3c | OH |
| 1897 | CH | O | Q1j | a bond | Me | a bond | NH | S | NH | Q3a | OH |
| 1898 | CH | O | Q1j | a bond | Me | a bond | NH | S | NH | Q3b | OH |
| 1899 | CH | O | Q1j | a bond | Me | a bond | NH | S | NH | Q3c | OH |
| 1900 | CH | O | Q1j | a bond | Me | a bond | NH | S | a bond | Q3a | OH |
| 1901 | CH | O | Q1j | a bond | Me | a bond | NH | S | a bond | Q3b | OH |
| 1902 | CH | O | Q1j | a bond | Me | a bond | NH | S | a bond | Q3c | OH |
| 1903 | CH | O | Q1j | a bond | Me | a bond | NH | O | NH | Q3a | OH |
| 1904 | CH | O | Q1j | a bond | Me | a bond | NH | O | NH | Q3b | OH |
| 1905 | CH | O | Q1j | a bond | Me | a bond | NH | O | NH | Q3c | OH |
| 1906 | CH | O | Q1j | a bond | Me | a bond | NH | O | a bond | Q3a | OH |
| 1907 | CH | O | Q1j | a bond | Me | a bond | NH | O | a bond | Q3b | OH |
| 1908 | CH | O | Q1j | a bond | Me | a bond | NH | O | a bond | Q3c | OH |
| 1909 | CH | O | Q1j | a bond | H | a bond | NH | S | NH | Q3a | OH |
| 1910 | CH | O | Q1j | a bond | H | a bond | NH | S | NH | Q3b | OH |
| 1911 | CH | O | Q1j | a bond | H | a bond | NH | S | NH | Q3c | OH |
| 1912 | CH | O | Q1j | a bond | H | a bond | NH | S | a bond | Q3a | OH |
| 1913 | CH | O | Q1j | a bond | H | a bond | NH | S | a bond | Q3b | OH |
| 1914 | CH | O | Q1j | a bond | H | a bond | NH | S | a bond | Q3c | OH |
| 1915 | CH | O | Q1j | a bond | H | a bond | NH | O | NH | Q3a | OH |
| 1916 | CH | O | Q1j | a bond | H | a bond | NH | O | NH | Q3b | OH |
| 1917 | CH | O | Q1j | a bond | H | a bond | NH | O | NH | Q3c | OH |
| 1918 | CH | O | Q1j | a bond | H | a bond | NH | O | a bond | Q3a | OH |
| 1919 | CH | O | Q1j | a bond | H | a bond | NH | O | a bond | Q3b | OH |
| 1920 | CH | O | Q1j | a bond | H | a bond | NH | O | a bond | Q3c | OH |
| 1921 | CMe | NMe | Q1a | a bond | Me | a bond | NH | S | NH | Q3a | OH |
| 1922 | CMe | NMe | Q1a | a bond | Me | a bond | NH | S | NH | Q3b | OH |
| 1923 | CMe | NMe | Q1a | a bond | Me | a bond | NH | S | NH | Q3c | OH |
| 1924 | CMe | NMe | Q1a | a bond | Me | a bond | NH | S | a bond | Q3a | OH |
| 1925 | CMe | NMe | Q1a | a bond | Me | a bond | NH | S | a bond | Q3b | OH |
| 1926 | CMe | NMe | Q1a | a bond | Me | a bond | NH | S | a bond | Q3c | OH |
| 1927 | CMe | NMe | Q1a | a bond | Me | a bond | NH | O | NH | Q3a | OH |
| 1928 | CMe | NMe | Q1a | a bond | Me | a bond | NH | O | NH | Q3b | OH |
| 1929 | CMe | NMe | Q1a | a bond | Me | a bond | NH | O | NH | Q3c | OH |
| 1930 | CMe | NMe | Q1a | a bond | Me | a bond | NH | O | a bond | Q3a | OH |
| 1931 | CMe | NMe | Q1a | a bond | Me | a bond | NH | O | a bond | Q3b | OH |
| 1932 | CMe | NMe | Q1a | a bond | Me | a bond | NH | O | a bond | Q3c | OH |
| 1933 | CMe | NMe | Q1a | a bond | H | a bond | NH | S | NH | Q3a | OH |
| 1934 | CMe | NMe | Q1a | a bond | H | a bond | NH | S | NH | Q3b | OH |
| 1935 | CMe | NMe | Q1a | a bond | H | a bond | NH | S | NH | Q3c | OH |
| 1936 | CMe | NMe | Q1a | a bond | H | a bond | NH | S | a bond | Q3a | OH |
| 1937 | CMe | NMe | Q1a | a bond | H | a bond | NH | S | a bond | Q3b | OH |
| 1938 | CMe | NMe | Q1a | a bond | H | a bond | NH | S | a bond | Q3c | OH |
| 1939 | CMe | NMe | Q1a | a bond | H | a bond | NH | O | NH | Q3a | OH |
| 1940 | CMe | NMe | Q1a | a bond | H | a bond | NH | O | NH | Q3b | OH |
| 1941 | CMe | NMe | Q1a | a bond | H | a bond | NH | O | NH | Q3c | OH |
| 1942 | CMe | NMe | Q1a | a bond | H | a bond | NH | O | a bond | Q3a | OH |
| 1943 | CMe | NMe | Q1a | a bond | H | a bond | NH | O | a bond | Q3b | OH |
| 1944 | CMe | NMe | Q1a | a bond | H | a bond | NH | O | a bond | Q3c | OH |
| 1945 | CMe | NMe | Q1b | a bond | Me | a bond | NH | S | NH | Q3a | OH |
| 1946 | CMe | NMe | Q1b | a bond | Me | a bond | NH | S | NH | Q3b | OH |
| 1947 | CMe | NMe | Q1b | a bond | Me | a bond | NH | S | NH | Q3c | OH |
| 1948 | CMe | NMe | Q1b | a bond | Me | a bond | NH | S | a bond | Q3a | OH |
| 1949 | CMe | NMe | Q1b | a bond | Me | a bond | NH | S | a bond | Q3b | OH |
| 1950 | CMe | NMe | Q1b | a bond | Me | a bond | NH | S | a bond | Q3c | OH |

TABLE 1-continued

| No | A | B | R¹ | L¹ | R² | L² | L³ | Y | L⁴ | R³ | X |
|---|---|---|---|---|---|---|---|---|---|---|---|
| 1951 | CMe | NMe | Q1b | a bond | Me | a bond | NH | O | NH | Q3a | OH |
| 1952 | CMe | NMe | Q1b | a bond | Me | a bond | NH | O | NH | Q3b | OH |
| 1953 | CMe | NMe | Q1b | a bond | Me | a bond | NH | O | NH | Q3c | OH |
| 1954 | CMe | NMe | Q1b | a bond | Me | a bond | NH | O | a bond | Q3a | OH |
| 1955 | CMe | NMe | Q1b | a bond | Me | a bond | NH | O | a bond | Q3b | OH |
| 1956 | CMe | NMe | Q1b | a bond | Me | a bond | NH | O | a bond | Q3c | OH |
| 1957 | CMe | NMe | Q1b | a bond | H | a bond | NH | S | NH | Q3a | OH |
| 1958 | CMe | NMe | Q1b | a bond | H | a bond | NH | S | NH | Q3b | OH |
| 1959 | CMe | NMe | Q1b | a bond | H | a bond | NH | S | NH | Q3c | OH |
| 1960 | CMe | NMe | Q1b | a bond | H | a bond | NH | S | a bond | Q3a | OH |
| 1961 | CMe | NMe | Q1b | a bond | H | a bond | NH | S | a bond | Q3b | OH |
| 1962 | CMe | NMe | Q1b | a bond | H | a bond | NH | S | a bond | Q3c | OH |
| 1963 | CMe | NMe | Q1b | a bond | H | a bond | NH | O | NH | Q3a | OH |
| 1964 | CMe | NMe | Q1b | a bond | H | a bond | NH | O | NH | Q3b | OH |
| 1965 | CMe | NMe | Q1b | a bond | H | a bond | NH | O | NH | Q3c | OH |
| 1966 | CMe | NMe | Q1b | a bond | H | a bond | NH | O | a bond | Q3a | OH |
| 1967 | CMe | NMe | Q1b | a bond | H | a bond | NH | O | a bond | Q3b | OH |
| 1968 | CMe | NMe | Q1b | a bond | H | a bond | NH | O | a bond | Q3c | OH |
| 1969 | CMe | NMe | Q1c | a bond | Me | a bond | NH | S | NH | Q3a | OH |
| 1970 | CMe | NMe | Q1c | a bond | Me | a bond | NH | S | NH | Q3b | OH |
| 1971 | CMe | NMe | Q1c | a bond | Me | a bond | NH | S | NH | Q3c | OH |
| 1972 | CMe | NMe | Q1c | a bond | Me | a bond | NH | S | a bond | Q3a | OH |
| 1973 | CMe | NMe | Q1c | a bond | Me | a bond | NH | S | a bond | Q3b | OH |
| 1974 | CMe | NMe | Q1c | a bond | Me | a bond | NH | S | a bond | Q3c | OH |
| 1975 | CMe | NMe | Q1c | a bond | Me | a bond | NH | O | NH | Q3a | OH |
| 1976 | CMe | NMe | Q1c | a bond | Me | a bond | NH | O | NH | Q3b | OH |
| 1977 | CMe | NMe | Q1c | a bond | Me | a bond | NH | O | NH | Q3c | OH |
| 1978 | CMe | NMe | Q1c | a bond | Me | a bond | NH | O | a bond | Q3a | OH |
| 1979 | CMe | NMe | Q1c | a bond | Me | a bond | NH | O | a bond | Q3b | OH |
| 1980 | CMe | NMe | Q1c | a bond | Me | a bond | NH | O | a bond | Q3c | OH |
| 1981 | CMe | NMe | Q1c | a bond | H | a bond | NH | S | NH | Q3a | OH |
| 1982 | CMe | NMe | Q1c | a bond | H | a bond | NH | S | NH | Q3b | OH |
| 1983 | CMe | NMe | Q1c | a bond | H | a bond | NH | S | NH | Q3c | OH |
| 1984 | CMe | NMe | Q1c | a bond | H | a bond | NH | S | a bond | Q3a | OH |
| 1985 | CMe | NMe | Q1c | a bond | H | a bond | NH | S | a bond | Q3b | OH |
| 1986 | CMe | NMe | Q1c | a bond | H | a bond | NH | S | a bond | Q3c | OH |
| 1987 | CMe | NMe | Q1c | a bond | H | a bond | NH | O | NH | Q3a | OH |
| 1988 | CMe | NMe | Q1c | a bond | H | a bond | NH | O | NH | Q3b | OH |
| 1989 | CMe | NMe | Q1c | a bond | H | a bond | NH | O | NH | Q3c | OH |
| 1990 | CMe | NMe | Q1c | a bond | H | a bond | NH | O | a bond | Q3a | OH |
| 1991 | CMe | NMe | Q1c | a bond | H | a bond | NH | O | a bond | Q3b | OH |
| 1992 | CMe | NMe | Q1c | a bond | H | a bond | NH | O | a bond | Q3c | OH |
| 1993 | CMe | NMe | Q1d | a bond | Me | a bond | NH | S | NH | Q3a | OH |
| 1994 | CMe | NMe | Q1d | a bond | Me | a bond | NH | S | NH | Q3b | OH |
| 1995 | CMe | NMe | Q1d | a bond | Me | a bond | NH | S | NH | Q3c | OH |
| 1996 | CMe | NMe | Q1d | a bond | Me | a bond | NH | S | a bond | Q3a | OH |
| 1997 | CMe | NMe | Q1d | a bond | Me | a bond | NH | S | a bond | Q3b | OH |
| 1998 | CMe | NMe | Q1d | a bond | Me | a bond | NH | S | a bond | Q3c | OH |
| 1999 | CMe | NMe | Q1d | a bond | Me | a bond | NH | O | NH | Q3a | OH |
| 2000 | CMe | NMe | Q1d | a bond | Me | a bond | NH | O | NH | Q3b | OH |
| 2001 | CMe | NMe | Q1d | a bond | Me | a bond | NH | O | NH | Q3c | OH |
| 2002 | CMe | NMe | Q1d | a bond | Me | a bond | NH | O | a bond | Q3a | OH |
| 2003 | CMe | NMe | Q1d | a bond | Me | a bond | NH | O | a bond | Q3b | OH |
| 2004 | CMe | NMe | Q1d | a bond | Me | a bond | NH | O | a bond | Q3c | OH |
| 2005 | CMe | NMe | Q1d | a bond | H | a bond | NH | S | NH | Q3a | OH |
| 2006 | CMe | NMe | Q1d | a bond | H | a bond | NH | S | NH | Q3b | OH |
| 2007 | CMe | NMe | Q1d | a bond | H | a bond | NH | S | NH | Q3c | OH |
| 2008 | CMe | NMe | Q1d | a bond | H | a bond | NH | S | a bond | Q3a | OH |
| 2009 | CMe | NMe | Q1d | a bond | H | a bond | NH | S | a bond | Q3b | OH |
| 2010 | CMe | NMe | Q1d | a bond | H | a bond | NH | S | a bond | Q3c | OH |
| 2011 | CMe | NMe | Q1d | a bond | H | a bond | NH | O | NH | Q3a | OH |
| 2012 | CMe | NMe | Q1d | a bond | H | a bond | NH | O | NH | Q3b | OH |
| 2013 | CMe | NMe | Q1d | a bond | H | a bond | NH | O | NH | Q3c | OH |
| 2014 | CMe | NMe | Q1d | a bond | H | a bond | NH | O | a bond | Q3a | OH |
| 2015 | CMe | NMe | Q1d | a bond | H | a bond | NH | O | a bond | Q3b | OH |
| 2016 | CMe | NMe | Q1d | a bond | H | a bond | NH | O | a bond | Q3c | OH |
| 2017 | CMe | NMe | Q1e | a bond | Me | a bond | NH | S | NH | Q3a | OH |
| 2018 | CMe | NMe | Q1e | a bond | Me | a bond | NH | S | NH | Q3b | OH |
| 2019 | CMe | NMe | Q1e | a bond | Me | a bond | NH | S | NH | Q3c | OH |
| 2020 | CMe | NMe | Q1e | a bond | Me | a bond | NH | S | a bond | Q3a | OH |
| 2021 | CMe | NMe | Q1e | a bond | Me | a bond | NH | S | a bond | Q3b | OH |
| 2022 | CMe | NMe | Q1e | a bond | Me | a bond | NH | S | a bond | Q3c | OH |
| 2023 | CMe | NMe | Q1e | a bond | Me | a bond | NH | O | NH | Q3a | OH |
| 2024 | CMe | NMe | Q1e | a bond | Me | a bond | NH | O | NH | Q3b | OH |
| 2025 | CMe | NMe | Q1e | a bond | Me | a bond | NH | O | NH | Q3c | OH |
| 2026 | CMe | NMe | Q1e | a bond | Me | a bond | NH | O | a bond | Q3a | OH |
| 2027 | CMe | NMe | Q1e | a bond | Me | a bond | NH | O | a bond | Q3b | OH |
| 2028 | CMe | NMe | Q1e | a bond | Me | a bond | NH | O | a bond | Q3c | OH |

TABLE 1-continued

| No | A | B | R¹ | L¹ | R² | L² | L³ | Y | L⁴ | R³ | X |
|---|---|---|---|---|---|---|---|---|---|---|---|
| 2029 | CMe | NMe | Q1e | a bond | H | a bond | NH | S | NH | Q3a | OH |
| 2030 | CMe | NMe | Q1e | a bond | H | a bond | NH | S | NH | Q3b | OH |
| 2031 | CMe | NMe | Q1e | a bond | H | a bond | NH | S | NH | Q3c | OH |
| 2032 | CMe | NMe | Q1e | a bond | H | a bond | NH | S | a bond | Q3a | OH |
| 2033 | CMe | NMe | Q1e | a bond | H | a bond | NH | S | a bond | Q3b | OH |
| 2034 | CMe | NMe | Q1e | a bond | H | a bond | NH | S | a bond | Q3c | OH |
| 2035 | CMe | NMe | Q1e | a bond | H | a bond | NH | O | NH | Q3a | OH |
| 2036 | CMe | NMe | Q1e | a bond | H | a bond | NH | O | NH | Q3b | OH |
| 2037 | CMe | NMe | Q1e | a bond | H | a bond | NH | O | NH | Q3c | OH |
| 2038 | CMe | NMe | Q1e | a bond | H | a bond | NH | O | a bond | Q3a | OH |
| 2039 | CMe | NMe | Q1e | a bond | H | a bond | NH | O | a bond | Q3b | OH |
| 2040 | CMe | NMe | Q1e | a bond | H | a bond | NH | O | a bond | Q3c | OH |
| 2041 | CMe | NMe | Q1f | a bond | Me | a bond | NH | S | NH | Q3a | OH |
| 2042 | CMe | NMe | Q1f | a bond | Me | a bond | NH | S | NH | Q3b | OH |
| 2043 | CMe | NMe | Q1f | a bond | Me | a bond | NH | S | NH | Q3c | OH |
| 2044 | CMe | NMe | Q1f | a bond | Me | a bond | NH | S | a bond | Q3a | OH |
| 2045 | CMe | NMe | Q1f | a bond | Me | a bond | NH | S | a bond | Q3b | OH |
| 2046 | CMe | NMe | Q1f | a bond | Me | a bond | NH | S | a bond | Q3c | OH |
| 2047 | CMe | NMe | Q1f | a bond | Me | a bond | NH | O | NH | Q3a | OH |
| 2048 | CMe | NMe | Q1f | a bond | Me | a bond | NH | O | NH | Q3b | OH |
| 2049 | CMe | NMe | Q1f | a bond | Me | a bond | NH | O | NH | Q3c | OH |
| 2050 | CMe | NMe | Q1f | a bond | Me | a bond | NH | O | a bond | Q3a | OH |
| 2051 | CMe | NMe | Q1f | a bond | Me | a bond | NH | O | a bond | Q3b | OH |
| 2052 | CMe | NMe | Q1f | a bond | Me | a bond | NH | O | a bond | Q3c | OH |
| 2053 | CMe | NMe | Q1f | a bond | H | a bond | NH | S | NH | Q3a | OH |
| 2054 | CMe | NMe | Q1f | a bond | H | a bond | NH | S | NH | Q3b | OH |
| 2055 | CMe | NMe | Q1f | a bond | H | a bond | NH | S | NH | Q3c | OH |
| 2056 | CMe | NMe | Q1f | a bond | H | a bond | NH | S | a bond | Q3a | OH |
| 2057 | CMe | NMe | Q1f | a bond | H | a bond | NH | S | a bond | Q3b | OH |
| 2058 | CMe | NMe | Q1f | a bond | H | a bond | NH | S | a bond | Q3c | OH |
| 2059 | CMe | NMe | Q1f | a bond | H | a bond | NH | O | NH | Q3a | OH |
| 2060 | CMe | NMe | Q1f | a bond | H | a bond | NH | O | NH | Q3b | OH |
| 2061 | CMe | NMe | Q1f | a bond | H | a bond | NH | O | NH | Q3c | OH |
| 2062 | CMe | NMe | Q1f | a bond | H | a bond | NH | O | a bond | Q3a | OH |
| 2063 | CMe | NMe | Q1f | a bond | H | a bond | NH | O | a bond | Q3b | OH |
| 2064 | CMe | NMe | Q1f | a bond | H | a bond | NH | O | a bond | Q3c | OH |
| 2065 | CMe | NMe | Q1g | a bond | Me | a bond | NH | S | NH | Q3a | OH |
| 2066 | CMe | NMe | Q1g | a bond | Me | a bond | NH | S | NH | Q3b | OH |
| 2067 | CMe | NMe | Q1g | a bond | Me | a bond | NH | S | NH | Q3c | OH |
| 2068 | CMe | NMe | Q1g | a bond | Me | a bond | NH | S | a bond | Q3a | OH |
| 2069 | CMe | NMe | Q1g | a bond | Me | a bond | NH | S | a bond | Q3b | OH |
| 2070 | CMe | NMe | Q1g | a bond | Me | a bond | NH | S | a bond | Q3c | OH |
| 2071 | CMe | NMe | Q1g | a bond | Me | a bond | NH | O | NH | Q3a | OH |
| 2072 | CMe | NMe | Q1g | a bond | Me | a bond | NH | O | NH | Q3b | OH |
| 2073 | CMe | NMe | Q1g | a bond | Me | a bond | NH | O | NH | Q3c | OH |
| 2074 | CMe | NMe | Q1g | a bond | Me | a bond | NH | O | a bond | Q3a | OH |
| 2075 | CMe | NMe | Q1g | a bond | Me | a bond | NH | O | a bond | Q3b | OH |
| 2076 | CMe | NMe | Q1g | a bond | Me | a bond | NH | O | a bond | Q3c | OH |
| 2077 | CMe | NMe | Q1g | a bond | H | a bond | NH | S | NH | Q3a | OH |
| 2078 | CMe | NMe | Q1g | a bond | H | a bond | NH | S | NH | Q3b | OH |
| 2079 | CMe | NMe | Q1g | a bond | H | a bond | NH | S | NH | Q3c | OH |
| 2080 | CMe | NMe | Q1g | a bond | H | a bond | NH | S | a bond | Q3a | OH |
| 2081 | CMe | NMe | Q1g | a bond | H | a bond | NH | S | a bond | Q3b | OH |
| 2082 | CMe | NMe | Q1g | a bond | H | a bond | NH | S | a bond | Q3c | OH |
| 2083 | CMe | NMe | Q1g | a bond | H | a bond | NH | O | NH | Q3a | OH |
| 2084 | CMe | NMe | Q1g | a bond | H | a bond | NH | O | NH | Q3b | OH |
| 2085 | CMe | NMe | Q1g | a bond | H | a bond | NH | O | NH | Q3c | OH |
| 2086 | CMe | NMe | Q1g | a bond | H | a bond | NH | O | a bond | Q3a | OH |
| 2087 | CMe | NMe | Q1g | a bond | H | a bond | NH | O | a bond | Q3b | OH |
| 2088 | CMe | NMe | Q1g | a bond | H | a bond | NH | O | a bond | Q3c | OH |
| 2089 | CMe | NMe | Q1h | a bond | Me | a bond | NH | S | NH | Q3a | OH |
| 2090 | CMe | NMe | Q1h | a bond | Me | a bond | NH | S | NH | Q3b | OH |
| 2091 | CMe | NMe | Q1h | a bond | Me | a bond | NH | S | NH | Q3c | OH |
| 2092 | CMe | NMe | Q1h | a bond | Me | a bond | NH | S | a bond | Q3a | OH |
| 2093 | CMe | NMe | Q1h | a bond | Me | a bond | NH | S | a bond | Q3b | OH |
| 2094 | CMe | NMe | Q1h | a bond | Me | a bond | NH | S | a bond | Q3c | OH |
| 2095 | CMe | NMe | Q1h | a bond | Me | a bond | NH | O | NH | Q3a | OH |
| 2096 | CMe | NMe | Q1h | a bond | Me | a bond | NH | O | NH | Q3b | OH |
| 2097 | CMe | NMe | Q1b | a bond | Me | a bond | NH | O | NH | Q3c | OH |
| 2098 | CMe | NMe | Q1h | a bond | Me | a bond | NH | O | a bond | Q3a | OH |
| 2099 | CMe | NMe | Q1h | a bond | Me | a bond | NH | O | a bond | Q3b | OH |
| 2100 | CMe | NMe | Q1h | a bond | Me | a bond | NH | O | a bond | Q3c | OH |
| 2101 | CMe | NMe | Q1h | a bond | H | a bond | NH | S | NH | Q3a | OH |
| 2102 | CMe | NMe | Q1h | a bond | H | a bond | NH | S | NH | Q3b | OH |
| 2103 | CMe | NMe | Q1h | a bond | H | a bond | NH | S | NH | Q3c | OH |
| 2104 | CMe | NMe | Q1h | a bond | H | a bond | NH | S | a bond | Q3a | OH |
| 2105 | CMe | NMe | Q1h | a bond | H | a bond | NH | S | a bond | Q3b | OH |
| 2106 | CMe | NMe | Q1h | a bond | H | a bond | NH | S | a bond | Q3c | OH |

TABLE 1-continued

| No | A | B | R¹ | L¹ | R² | L² | L³ | Y | L⁴ | R³ | X |
|---|---|---|---|---|---|---|---|---|---|---|---|
| 2107 | CMe | NMe | Q1h | a bond | H | a bond | NH | O | NH | Q3a | OH |
| 2108 | CMe | NMe | Q1h | a bond | H | a bond | NH | O | NH | Q3b | OH |
| 2109 | CMe | NMe | Q1h | a bond | H | a bond | NH | O | NH | Q3c | OH |
| 2110 | CMe | NMe | Q1h | a bond | H | a bond | NH | O | a bond | Q3a | OH |
| 2111 | CMe | NMe | Q1h | a bond | H | a bond | NH | O | a bond | Q3b | OH |
| 2112 | CMe | NMe | Q1h | a bond | H | a bond | NH | O | a bond | Q3c | OH |
| 2113 | CMe | NMe | Q1i | a bond | Me | a bond | NH | S | NH | Q3a | OH |
| 2114 | CMe | NMe | Q1i | a bond | Me | a bond | NH | S | NH | Q3b | OH |
| 2115 | CMe | NMe | Q1i | a bond | Me | a bond | NH | S | NH | Q3c | OH |
| 2116 | CMe | NMe | Q1i | a bond | Me | a bond | NH | S | a bond | Q3a | OH |
| 2117 | CMe | NMe | Q1i | a bond | Me | a bond | NH | S | a bond | Q3b | OH |
| 2118 | CMe | NMe | Q1i | a bond | Me | a bond | NH | S | a bond | Q3c | OH |
| 2119 | CMe | NMe | Q1i | a bond | Me | a bond | NH | O | NH | Q3a | OH |
| 2120 | CMe | NMe | Q1i | a bond | Me | a bond | NH | O | NH | Q3b | OH |
| 2121 | CMe | NMe | Q1i | a bond | Me | a bond | NH | O | NH | Q3c | OH |
| 2122 | CMe | NMe | Q1i | a bond | Me | a bond | NH | O | a bond | Q3a | OH |
| 2123 | CMe | NMe | Q1i | a bond | Me | a bond | NH | O | a bond | Q3b | OH |
| 2124 | CMe | NMe | Q1i | a bond | Me | a bond | NH | O | a bond | Q3c | OH |
| 2125 | CMe | NMe | Q1i | a bond | H | a bond | NH | S | NH | Q3a | OH |
| 2126 | CMe | NMe | Q1i | a bond | H | a bond | NH | S | NH | Q3b | OH |
| 2127 | CMe | NMe | Q1i | a bond | H | a bond | NH | S | NH | Q3c | OH |
| 2128 | CMe | NMe | Q1i | a bond | H | a bond | NH | S | a bond | Q3a | OH |
| 2129 | CMe | NMe | Q1i | a bond | H | a bond | NH | S | a bond | Q3b | OH |
| 2130 | CMe | NMe | Q1i | a bond | H | a bond | NH | S | a bond | Q3c | OH |
| 2131 | CMe | NMe | Q1i | a bond | H | a bond | NH | O | NH | Q3a | OH |
| 2132 | CMe | NMe | Q1i | a bond | H | a bond | NH | O | NH | Q3b | OH |
| 2133 | CMe | NMe | Q1i | a bond | H | a bond | NH | O | NH | Q3c | OH |
| 2134 | CMe | NMe | Q1i | a bond | H | a bond | NH | O | a bond | Q3a | OH |
| 2135 | CMe | NMe | Q1i | a bond | H | a bond | NH | O | a bond | Q3b | OH |
| 2136 | CMe | NMe | Q1i | a bond | H | a bond | NH | O | a bond | Q3c | OH |
| 2137 | CMe | NMe | Q1j | a bond | Me | a bond | NH | S | NH | Q3a | OH |
| 2138 | CMe | NMe | Q1j | a bond | Me | a bond | NH | S | NH | Q3b | OH |
| 2139 | CMe | NMe | Q1j | a bond | Me | a bond | NH | S | NH | Q3c | OH |
| 2140 | CMe | NMe | Q1j | a bond | Me | a bond | NH | S | a bond | Q3a | OH |
| 2141 | CMe | NMe | Q1j | a bond | Me | a bond | NH | S | a bond | Q3b | OH |
| 2142 | CMe | NMe | Q1j | a bond | Me | a bond | NH | S | a bond | Q3c | OH |
| 2143 | CMe | NMe | Q1j | a bond | Me | a bond | NH | O | NH | Q3a | OH |
| 2144 | CMe | NMe | Q1j | a bond | Me | a bond | NH | O | NH | Q3b | OH |
| 2145 | CMe | NMe | Q1j | a bond | Me | a bond | NH | O | NH | Q3c | OH |
| 2146 | CMe | NMe | Q1j | a bond | Me | a bond | NH | O | a bond | Q3a | OH |
| 2147 | CMe | NMe | Q1j | a bond | Me | a bond | NH | O | a bond | Q3b | OH |
| 2148 | CMe | NMe | Q1j | a bond | Me | a bond | NH | O | a bond | Q3c | OH |
| 2149 | CMe | NMe | Q1j | a bond | H | a bond | NH | S | NH | Q3a | OH |
| 2150 | CMe | NMe | Q1j | a bond | H | a bond | NH | S | NH | Q3b | OH |
| 2151 | CMe | NMe | Q1j | a bond | H | a bond | NH | S | NH | Q3c | OH |
| 2152 | CMe | NMe | Q1j | a bond | H | a bond | NH | S | a bond | Q3a | OH |
| 2153 | CMe | NMe | Q1j | a bond | H | a bond | NH | S | a bond | Q3b | OH |
| 2154 | CMe | NMe | Q1j | a bond | H | a bond | NH | S | a bond | Q3c | OH |
| 2155 | CMe | NMe | Q1j | a bond | H | a bond | NH | O | NH | Q3a | OH |
| 2156 | CMe | NMe | Q1j | a bond | H | a bond | NH | O | NH | Q3b | OH |
| 2157 | CMe | NMe | Q1j | a bond | H | a bond | NH | O | NH | Q3c | OH |
| 2158 | CMe | NMe | Q1j | a bond | H | a bond | NH | O | a bond | Q3a | OH |
| 2159 | CMe | NMe | Q1j | a bond | H | a bond | NH | O | a bond | Q3b | OH |
| 2160 | CMe | NMe | Q1j | a bond | H | a bond | NH | O | a bond | Q3c | OH |
| 2161 | CMe | NEt | Q1a | a bond | Me | a bond | NH | S | NH | Q3a | OH |
| 2162 | CMe | NEt | Q1a | a bond | Me | a bond | NH | S | NH | Q3b | OH |
| 2163 | CMe | NEt | Q1a | a bond | Me | a bond | NH | S | NH | Q3c | OH |
| 2164 | CMe | NEt | Q1a | a bond | Me | a bond | NH | S | a bond | Q3a | OH |
| 2165 | CMe | NEt | Q1a | a bond | Me | a bond | NH | S | a bond | Q3b | OH |
| 2166 | CMe | NEt | Q1a | a bond | Me | a bond | NH | S | a bond | Q3c | OH |
| 2167 | CMe | NEt | Q1a | a bond | Me | a bond | NH | O | NH | Q3a | OH |
| 2168 | CMe | NEt | Q1a | a bond | Me | a bond | NH | O | NH | Q3b | OH |
| 2169 | CMe | NEt | Q1a | a bond | Me | a bond | NH | O | NH | Q3c | OH |
| 2170 | CMe | NEt | Q1a | a bond | Me | a bond | NH | O | a bond | Q3a | OH |
| 2171 | CMe | NEt | Q1a | a bond | Me | a bond | NH | O | a bond | Q3b | OH |
| 2172 | CMe | NEt | Q1a | a bond | Me | a bond | NH | O | a bond | Q3c | OH |
| 2173 | CMe | NEt | Q1a | a bond | H | a bond | NH | S | NH | Q3a | OH |
| 2174 | CMe | NEt | Q1a | a bond | H | a bond | NH | S | NH | Q3b | OH |
| 2175 | CMe | NEt | Q1a | a bond | H | a bond | NH | S | NH | Q3c | OH |
| 2176 | CMe | NEt | Q1a | a bond | H | a bond | NH | S | a bond | Q3a | OH |
| 2177 | CMe | NEt | Q1a | a bond | H | a bond | NH | S | a bond | Q3b | OH |
| 2178 | CMe | NEt | Q1a | a bond | H | a bond | NH | S | a bond | Q3c | OH |
| 2179 | CMe | NEt | Q1a | a bond | H | a bond | NH | O | NH | Q3a | OH |
| 2180 | CMe | NEt | Q1a | a bond | H | a bond | NH | O | NH | Q3b | OH |
| 2181 | CMe | NEt | Q1a | a bond | H | a bond | NH | O | NH | Q3c | OH |
| 2182 | CMe | NEt | Q1a | a bond | H | a bond | NH | O | a bond | Q3a | OH |
| 2183 | CMe | NEt | Q1a | a bond | H | a bond | NH | O | a bond | Q3b | OH |
| 2184 | CMe | NEt | Q1a | a bond | H | a bond | NH | O | a bond | Q3c | OH |

TABLE 1-continued

| No | A | B | R¹ | L¹ | R² | L² | L³ | Y | L⁴ | R³ | X |
|---|---|---|---|---|---|---|---|---|---|---|---|
| 2185 | CMe | NEt | Q1b | a bond | Me | a bond | NH | S | NH | Q3a | OH |
| 2186 | CMe | NEt | Q1b | a bond | Me | a bond | NH | S | NH | Q3b | OH |
| 2187 | CMe | NEt | Q1b | a bond | Me | a bond | NH | S | NH | Q3c | OH |
| 2188 | CMe | NEt | Q1b | a bond | Me | a bond | NH | S | a bond | Q3a | OH |
| 2189 | CMe | NEt | Q1b | a bond | Me | a bond | NH | S | a bond | Q3b | OH |
| 2190 | CMe | NEt | Q1b | a bond | Me | a bond | NH | S | a bond | Q3c | OH |
| 2191 | CMe | NEt | Q1b | a bond | Me | a bond | NH | O | NH | Q3a | OH |
| 2192 | CMe | NEt | Q1b | a bond | Me | a bond | NH | O | NH | Q3b | OH |
| 2193 | CMe | NEt | Q1b | a bond | Me | a bond | NH | O | NH | Q3c | OH |
| 2194 | CMe | NEt | Q1b | a bond | Me | a bond | NH | O | a bond | Q3a | OH |
| 2195 | CMe | NEt | Q1b | a bond | Me | a bond | NH | O | a bond | Q3b | OH |
| 2196 | CMe | NEt | Q1b | a bond | Me | a bond | NH | O | a bond | Q3c | OH |
| 2197 | CMe | NEt | Q1b | a bond | H | a bond | NH | S | NH | Q3a | OH |
| 2198 | CMe | NEt | Q1b | a bond | H | a bond | NH | S | NH | Q3b | OH |
| 2199 | CMe | NEt | Q1b | a bond | H | a bond | NH | S | NH | Q3c | OH |
| 2200 | CMe | NEt | Q1b | a bond | H | a bond | NH | S | a bond | Q3a | OH |
| 2201 | CMe | NEt | Q1b | a bond | H | a bond | NH | S | a bond | Q3b | OH |
| 2202 | CMe | NEt | Q1b | a bond | H | a bond | NH | S | a bond | Q3c | OH |
| 2203 | CMe | NEt | Q1b | a bond | H | a bond | NH | O | NH | Q3a | OH |
| 2204 | CMe | NEt | Q1b | a bond | H | a bond | NH | O | NH | Q3b | OH |
| 2205 | CMe | NEt | Q1b | a bond | H | a bond | NH | O | NH | Q3c | OH |
| 2206 | CMe | NEt | Q1b | a bond | H | a bond | NH | O | a bond | Q3a | OH |
| 2207 | CMe | NEt | Q1b | a bond | H | a bond | NH | O | a bond | Q3b | OH |
| 2208 | CMe | NEt | Q1b | a bond | H | a bond | NH | O | a bond | Q3c | OH |
| 2209 | CMe | NEt | Q1c | a bond | Me | a bond | NH | S | NH | Q3a | OH |
| 2210 | CMe | NEt | Q1c | a bond | Me | a bond | NH | S | NH | Q3b | OH |
| 2211 | CMe | NEt | Q1c | a bond | Me | a bond | NH | S | NH | Q3c | OH |
| 2212 | CMe | NEt | Q1c | a bond | Me | a bond | NH | S | a bond | Q3a | OH |
| 2213 | CMe | NEt | Q1c | a bond | Me | a bond | NH | S | a bond | Q3b | OH |
| 2214 | CMe | NEt | Q1c | a bond | Me | a bond | NH | S | a bond | Q3c | OH |
| 2215 | CMe | NEt | Q1c | a bond | Me | a bond | NH | O | NH | Q3a | OH |
| 2216 | CMe | NEt | Q1c | a bond | Me | a bond | NH | O | NH | Q3b | OH |
| 2217 | CMe | NEt | Q1c | a bond | Me | a bond | NH | O | NH | Q3c | OH |
| 2218 | CMe | NEt | Q1c | a bond | Me | a bond | NH | O | a bond | Q3a | OH |
| 2219 | CMe | NEt | Q1c | a bond | Me | a bond | NH | O | a bond | Q3b | OH |
| 2220 | CMe | NEt | Q1c | a bond | Me | a bond | NH | O | a bond | Q3c | OH |
| 2221 | CMe | NEt | Q1c | a bond | H | a bond | NH | S | NH | Q3a | OH |
| 2222 | CMe | NEt | Q1c | a bond | H | a bond | NH | S | NH | Q3b | OH |
| 2223 | CMe | NEt | Q1c | a bond | H | a bond | NH | S | NH | Q3c | OH |
| 2224 | CMe | NEt | Q1c | a bond | H | a bond | NH | S | a bond | Q3a | OH |
| 2225 | CMe | NEt | Q1c | a bond | H | a bond | NH | S | a bond | Q3b | OH |
| 2226 | CMe | NEt | Q1c | a bond | H | a bond | NH | S | a bond | Q3c | OH |
| 2227 | CMe | NEt | Q1c | a bond | H | a bond | NH | O | NH | Q3a | OH |
| 2228 | CMe | NEt | Q1c | a bond | H | a bond | NH | O | NH | Q3b | OH |
| 2229 | CMe | NEt | Q1c | a bond | H | a bond | NH | O | NH | Q3c | OH |
| 2230 | CMe | NEt | Q1c | a bond | H | a bond | NH | O | a bond | Q3a | OH |
| 2231 | CMe | NEt | Q1c | a bond | H | a bond | NH | O | a bond | Q3b | OH |
| 2232 | CMe | NEt | Q1c | a bond | H | a bond | NH | O | a bond | Q3c | OH |
| 2233 | CMe | NEt | Q1d | a bond | Me | a bond | NH | S | NH | Q3a | OH |
| 2234 | CMe | NEt | Q1d | a bond | Me | a bond | NH | S | NH | Q3b | OH |
| 2235 | CMe | NEt | Q1d | a bond | Me | a bond | NH | S | NH | Q3c | OH |
| 2236 | CMe | NEt | Q1d | a bond | Me | a bond | NH | S | a bond | Q3a | OH |
| 2237 | CMe | NEt | Q1d | a bond | Me | a bond | NH | S | a bond | Q3b | OH |
| 2238 | CMe | NEt | Q1d | a bond | Me | a bond | NH | S | a bond | Q3c | OH |
| 2239 | CMe | NEt | Q1d | a bond | Me | a bond | NH | O | NH | Q3a | OH |
| 2240 | CMe | NEt | Q1d | a bond | Me | a bond | NH | O | NH | Q3b | OH |
| 2241 | CMe | NEt | Q1d | a bond | Me | a bond | NH | O | NH | Q3c | OH |
| 2242 | CMe | NEt | Q1d | a bond | Me | a bond | NH | O | a bond | Q3a | OH |
| 2243 | CMe | NEt | Q1d | a bond | Me | a bond | NH | O | a bond | Q3b | OH |
| 2244 | CMe | NEt | Q1d | a bond | Me | a bond | NH | O | a bond | Q3c | OH |
| 2245 | CMe | NEt | Q1d | a bond | H | a bond | NH | S | NH | Q3a | OH |
| 2246 | CMe | NEt | Q1d | a bond | H | a bond | NH | S | NH | Q3b | OH |
| 2247 | CMe | NEt | Q1d | a bond | H | a bond | NH | S | NH | Q3c | OH |
| 2248 | CMe | NEt | Q1d | a bond | H | a bond | NH | S | a bond | Q3a | OH |
| 2249 | CMe | NEt | Q1d | a bond | H | a bond | NH | S | a bond | Q3b | OH |
| 2250 | CMe | NEt | Q1d | a bond | H | a bond | NH | S | a bond | Q3c | OH |
| 2251 | CMe | NEt | Q1d | a bond | H | a bond | NH | O | NH | Q3a | OH |
| 2252 | CMe | NEt | Q1d | a bond | H | a bond | NH | O | NH | Q3b | OH |
| 2253 | CMe | NEt | Q1d | a bond | H | a bond | NH | O | NH | Q3c | OH |
| 2254 | CMe | NEt | Q1d | a bond | H | a bond | NH | O | a bond | Q3a | OH |
| 2255 | CMe | NEt | Q1d | a bond | H | a bond | NH | O | a bond | Q3b | OH |
| 2256 | CMe | NEt | Q1d | a bond | H | a bond | NH | O | a bond | Q3c | OH |
| 2257 | CMe | NEt | Q1e | a bond | Me | a bond | NH | S | NH | Q3a | OH |
| 2258 | CMe | NEt | Q1e | a bond | Me | a bond | NH | S | NH | Q3b | OH |
| 2259 | CMe | NEt | Q1e | a bond | Me | a bond | NH | S | NH | Q3c | OH |
| 2260 | CMe | NEt | Q1e | a bond | Me | a bond | NH | S | a bond | Q3a | OH |
| 2261 | CMe | NEt | Q1e | a bond | Me | a bond | NH | S | a bond | Q3b | OH |
| 2262 | CMe | NEt | Q1e | a bond | Me | a bond | NH | S | a bond | Q3c | OH |

TABLE 1-continued

| No | A | B | R¹ | L¹ | R² | L² | L³ | Y | L⁴ | R³ | X |
|---|---|---|---|---|---|---|---|---|---|---|---|
| 2263 | CMe | NEt | Q1e | a bond | Me | a bond | NH | O | NH | Q3a | OH |
| 2264 | CMe | NEt | Q1e | a bond | Me | a bond | NH | O | NH | Q3b | OH |
| 2265 | CMe | NEt | Q1e | a bond | Me | a bond | NH | O | NH | Q3c | OH |
| 2266 | CMe | NEt | Q1e | a bond | Me | a bond | NH | O | a bond | Q3a | OH |
| 2267 | CMe | NEt | Q1e | a bond | Me | a bond | NH | O | a bond | Q3b | OH |
| 2268 | CMe | NEt | Q1e | a bond | Me | a bond | NH | O | a bond | Q3c | OH |
| 2269 | CMe | NEt | Q1e | a bond | H | a bond | NH | S | NH | Q3a | OH |
| 2270 | CMe | NEt | Q1e | a bond | H | a bond | NH | S | NH | Q3b | OH |
| 2271 | CMe | NEt | Q1e | a bond | H | a bond | NH | S | NH | Q3c | OH |
| 2272 | CMe | NEt | Q1e | a bond | H | a bond | NH | S | a bond | Q3a | OH |
| 2273 | CMe | NEt | Q1e | a bond | H | a bond | NH | S | a bond | Q3b | OH |
| 2274 | CMe | NEt | Q1e | a bond | H | a bond | NH | S | a bond | Q3c | OH |
| 2275 | CMe | NEt | Q1e | a bond | H | a bond | NH | O | NH | Q3a | OH |
| 2276 | CMe | NEt | Q1e | a bond | H | a bond | NH | O | NH | Q3b | OH |
| 2277 | CMe | NEt | Q1e | a bond | H | a bond | NH | O | NH | Q3c | OH |
| 2278 | CMe | NEt | Q1e | a bond | H | a bond | NH | O | a bond | Q3a | OH |
| 2279 | CMe | NEt | Q1e | a bond | H | a bond | NH | O | a bond | Q3b | OH |
| 2280 | CMe | NEt | Q1e | a bond | H | a bond | NH | O | a bond | Q3c | OH |
| 2281 | CMe | NEt | Q1f | a bond | Me | a bond | NH | S | NH | Q3a | OH |
| 2282 | CMe | NEt | Q1f | a bond | Me | a bond | NH | S | NH | Q3b | OH |
| 2283 | CMe | NEt | Q1f | a bond | Me | a bond | NH | S | NH | Q3c | OH |
| 2284 | CMe | NEt | Q1f | a bond | Me | a bond | NH | S | a bond | Q3a | OH |
| 2285 | CMe | NEt | Q1f | a bond | Me | a bond | NH | S | a bond | Q3b | OH |
| 2286 | CMe | NEt | Q1f | a bond | Me | a bond | NH | S | a bond | Q3c | OH |
| 2287 | CMe | NEt | Q1f | a bond | Me | a bond | NH | O | NH | Q3a | OH |
| 2288 | CMe | NEt | Q1f | a bond | Me | a bond | NH | O | NH | Q3b | OH |
| 2289 | CMe | NEt | Q1f | a bond | Me | a bond | NH | O | NH | Q3c | OH |
| 2290 | CMe | NEt | Q1f | a bond | Me | a bond | NH | O | a bond | Q3a | OH |
| 2291 | CMe | NEt | Q1f | a bond | Me | a bond | NH | O | a bond | Q3b | OH |
| 2292 | CMe | NEt | Q1f | a bond | Me | a bond | NH | O | a bond | Q3c | OH |
| 2293 | CMe | NEt | Q1f | a bond | H | a bond | NH | S | NH | Q3a | OH |
| 2294 | CMe | NEt | Q1f | a bond | H | a bond | NH | S | NH | Q3b | OH |
| 2295 | CMe | NEt | Q1f | a bond | H | a bond | NH | S | NH | Q3c | OH |
| 2296 | CMe | NEt | Q1f | a bond | H | a bond | NH | S | a bond | Q3a | OH |
| 2297 | CMe | NEt | Q1f | a bond | H | a bond | NH | S | a bond | Q3b | OH |
| 2298 | CMe | NEt | Q1f | a bond | H | a bond | NH | S | a bond | Q3c | OH |
| 2299 | CMe | NEt | Q1f | a bond | H | a bond | NH | O | NH | Q3a | OH |
| 2300 | CMe | NEt | Q1f | a bond | H | a bond | NH | O | NH | Q3b | OH |
| 2301 | CMe | NEt | Q1f | a bond | H | a bond | NH | O | NH | Q3c | OH |
| 2302 | CMe | NEt | Q1f | a bond | H | a bond | NH | O | a bond | Q3a | OH |
| 2303 | CMe | NEt | Q1f | a bond | H | a bond | NH | O | a bond | Q3b | OH |
| 2304 | CMe | NEt | Q1f | a bond | H | a bond | NH | O | a bond | Q3c | OH |
| 2305 | CMe | NEt | Q1g | a bond | Me | a bond | NH | S | NH | Q3a | OH |
| 2306 | CMe | NEt | Q1g | a bond | Me | a bond | NH | S | NH | Q3b | OH |
| 2307 | CMe | NEt | Q1g | a bond | Me | a bond | NH | S | NH | Q3c | OH |
| 2308 | CMe | NEt | Q1g | a bond | Me | a bond | NH | S | a bond | Q3a | OH |
| 2309 | CMe | NEt | Q1g | a bond | Me | a bond | NH | S | a bond | Q3b | OH |
| 2310 | CMe | NEt | Q1g | a bond | Me | a bond | NH | S | a bond | Q3c | OH |
| 2311 | CMe | NEt | Q1g | a bond | Me | a bond | NH | O | NH | Q3a | OH |
| 2312 | CMe | NEt | Q1g | a bond | Me | a bond | NH | O | NH | Q3b | OH |
| 2313 | CMe | NEt | Q1g | a bond | Me | a bond | NH | O | NH | Q3c | OH |
| 2314 | CMe | NEt | Q1g | a bond | Me | a bond | NH | O | a bond | Q3a | OH |
| 2315 | CMe | NEt | Q1g | a bond | Me | a bond | NH | O | a bond | Q3b | OH |
| 2316 | CMe | NEt | Q1g | a bond | Me | a bond | NH | O | a bond | Q3c | OH |
| 2317 | CMe | NEt | Q1g | a bond | H | a bond | NH | S | NH | Q3a | OH |
| 2318 | CMe | NEt | Q1g | a bond | H | a bond | NH | S | NH | Q3b | OH |
| 2319 | CMe | NEt | Q1g | a bond | H | a bond | NH | S | NH | Q3c | OH |
| 2320 | CMe | NEt | Q1g | a bond | H | a bond | NH | S | a bond | Q3a | OH |
| 2321 | CMe | NEt | Q1g | a bond | H | a bond | NH | S | a bond | Q3b | OH |
| 2322 | CMe | NEt | Q1g | a bond | H | a bond | NH | S | a bond | Q3c | OH |
| 2323 | CMe | NEt | Q1g | a bond | H | a bond | NH | O | NH | Q3a | OH |
| 2324 | CMe | NEt | Q1g | a bond | H | a bond | NH | O | NH | Q3b | OH |
| 2325 | CMe | NEt | Q1g | a bond | H | a bond | NH | O | NH | Q3c | OH |
| 2326 | CMe | NEt | Q1g | a bond | H | a bond | NH | O | a bond | Q3a | OH |
| 2327 | CMe | NEt | Q1g | a bond | H | a bond | NH | O | a bond | Q3b | OH |
| 2328 | CMe | NEt | Q1g | a bond | H | a bond | NH | O | a bond | Q3c | OH |
| 2329 | CMe | NEt | Q1h | a bond | Me | a bond | NH | S | NH | Q3a | OH |
| 2330 | CMe | NEt | Q1h | a bond | Me | a bond | NH | S | NH | Q3b | OH |
| 2331 | CMe | NEt | Q1h | a bond | Me | a bond | NH | S | NH | Q3c | OH |
| 2332 | CMe | NEt | Q1h | a bond | Me | a bond | NH | S | a bond | Q3a | OH |
| 2333 | CMe | NEt | Q1h | a bond | Me | a bond | NH | S | a bond | Q3b | OH |
| 2334 | CMe | NEt | Q1h | a bond | Me | a bond | NH | S | a bond | Q3c | OH |
| 2335 | CMe | NEt | Q1h | a bond | Me | a bond | NH | O | NH | Q3a | OH |
| 2336 | CMe | NEt | Q1h | a bond | Me | a bond | NH | O | NH | Q3b | OH |
| 2337 | CMe | NEt | Q1h | a bond | Me | a bond | NH | O | NH | Q3c | OH |
| 2338 | CMe | NEt | Q1h | a bond | Me | a bond | NH | O | a bond | Q3a | OH |
| 2339 | CMe | NEt | Q1h | a bond | Me | a bond | NH | O | a bond | Q3b | OH |
| 2340 | CMe | NEt | Q1h | a bond | Me | a bond | NH | O | a bond | Q3c | OH |

TABLE 1-continued

| No | A | B | R¹ | L¹ | R² | L² | L³ | Y | L⁴ | R³ | X |
|---|---|---|---|---|---|---|---|---|---|---|---|
| 2341 | CMe | NEt | Q1h | a bond | H | a bond | NH | S | NH | Q3a | OH |
| 2342 | CMe | NEt | Q1h | a bond | H | a bond | NH | S | NH | Q3b | OH |
| 2343 | CMe | NEt | Q1h | a bond | H | a bond | NH | S | NH | Q3c | OH |
| 2344 | CMe | NEt | Q1h | a bond | H | a bond | NH | S | a bond | Q3a | OH |
| 2345 | CMe | NEt | Q1h | a bond | H | a bond | NH | S | a bond | Q3b | OH |
| 2346 | CMe | NEt | Q1h | a bond | H | a bond | NH | S | a bond | Q3c | OH |
| 2347 | CMe | NEt | Q1h | a bond | H | a bond | NH | O | NH | Q3a | OH |
| 2348 | CMe | NEt | Q1h | a bond | H | a bond | NH | O | NH | Q3b | OH |
| 2349 | CMe | NEt | Q1h | a bond | H | a bond | NH | O | NH | Q3c | OH |
| 2350 | CMe | NEt | Q1h | a bond | H | a bond | NH | O | a bond | Q3a | OH |
| 2351 | CMe | NEt | Q1h | a bond | H | a bond | NH | O | a bond | Q3b | OH |
| 2352 | CMe | NEt | Q1h | a bond | H | a bond | NH | O | a bond | Q3c | OH |
| 2353 | CMe | NEt | Q1i | a bond | Me | a bond | NH | S | NH | Q3a | OH |
| 2354 | CMe | NEt | Q1i | a bond | Me | a bond | NH | S | NH | Q3b | OH |
| 2355 | CMe | NEt | Q1i | a bond | Me | a bond | NH | S | NH | Q3c | OH |
| 2356 | CMe | NEt | Q1i | a bond | Me | a bond | NH | S | a bond | Q3a | OH |
| 2357 | CMe | NEt | Q1i | a bond | Me | a bond | NH | S | a bond | Q3b | OH |
| 2358 | CMe | NEt | Q1i | a bond | Me | a bond | NH | S | a bond | Q3c | OH |
| 2359 | CMe | NEt | Q1i | a bond | Me | a bond | NH | O | NH | Q3a | OH |
| 2360 | CMe | NEt | Q1i | a bond | Me | a bond | NH | O | NH | Q3b | OH |
| 2361 | CMe | NEt | Q1i | a bond | Me | a bond | NH | O | NH | Q3c | OH |
| 2362 | CMe | NEt | Q1i | a bond | Me | a bond | NH | O | a bond | Q3a | OH |
| 2363 | CMe | NEt | Q1i | a bond | Me | a bond | NH | O | a bond | Q3b | OH |
| 2364 | CMe | NEt | Q1i | a bond | Me | a bond | NH | O | a bond | Q3c | OH |
| 2365 | CMe | NEt | Q1i | a bond | H | a bond | NH | S | NH | Q3a | OH |
| 2366 | CMe | NEt | Q1i | a bond | H | a bond | NH | S | NH | Q3b | OH |
| 2367 | CMe | NEt | Q1i | a bond | H | a bond | NH | S | NH | Q3c | OH |
| 2368 | CMe | NEt | Q1i | a bond | H | a bond | NH | S | a bond | Q3a | OH |
| 2369 | CMe | NEt | Q1i | a bond | H | a bond | NH | S | a bond | Q3b | OH |
| 2370 | CMe | NEt | Q1i | a bond | H | a bond | NH | S | a bond | Q3c | OH |
| 2371 | CMe | NEt | Q1i | a bond | H | a bond | NH | O | NH | Q3a | OH |
| 2372 | CMe | NEt | Q1i | a bond | H | a bond | NH | O | NH | Q3b | OH |
| 2373 | CMe | NEt | Q1i | a bond | H | a bond | NH | O | NH | Q3c | OH |
| 2374 | CMe | NEt | Q1i | a bond | H | a bond | NH | O | a bond | Q3a | OH |
| 2375 | CMe | NEt | Q1i | a bond | H | a bond | NH | O | a bond | Q3b | OH |
| 2376 | CMe | NEt | Q1i | a bond | H | a bond | NH | O | a bond | Q3c | OH |
| 2377 | CMe | NEt | Q1j | a bond | Me | a bond | NH | S | NH | Q3a | OH |
| 2378 | CMe | NEt | Q1j | a bond | Me | a bond | NH | S | NH | Q3b | OH |
| 2379 | CMe | NEt | Q1j | a bond | Me | a bond | NH | S | NH | Q3c | OH |
| 2380 | CMe | NEt | Q1j | a bond | Me | a bond | NH | S | a bond | Q3a | OH |
| 2381 | CMe | NEt | Q1j | a bond | Me | a bond | NH | S | a bond | Q3b | OH |
| 2382 | CMe | NEt | Q1j | a bond | Me | a bond | NH | S | a bond | Q3c | OH |
| 2383 | CMe | NEt | Q1j | a bond | Me | a bond | NH | O | NH | Q3a | OH |
| 2384 | CMe | NEt | Q1j | a bond | Me | a bond | NH | O | NH | Q3b | OH |
| 2385 | CMe | NEt | Q1j | a bond | Me | a bond | NH | O | NH | Q3c | OH |
| 2386 | CMe | NEt | Q1j | a bond | Me | a bond | NH | O | a bond | Q3a | OH |
| 2387 | CMe | NEt | Q1j | a bond | Me | a bond | NH | O | a bond | Q3b | OH |
| 2388 | CMe | NEt | Q1j | a bond | Me | a bond | NH | O | a bond | Q3c | OH |
| 2389 | CMe | NEt | Q1j | a bond | H | a bond | NH | S | NH | Q3a | OH |
| 2390 | CMe | NEt | Q1j | a bond | H | a bond | NH | S | NH | Q3b | OH |
| 2391 | CMe | NEt | Q1j | a bond | H | a bond | NH | S | NH | Q3c | OH |
| 2392 | CMe | NEt | Q1j | a bond | H | a bond | NH | S | a bond | Q3a | OH |
| 2393 | CMe | NEt | Q1j | a bond | H | a bond | NH | S | a bond | Q3b | OH |
| 2394 | CMe | NEt | Q1j | a bond | H | a bond | NH | S | a bond | Q3c | OH |
| 2395 | CMe | NEt | Q1j | a bond | H | a bond | NH | O | NH | Q3a | OH |
| 2396 | CMe | NEt | Q1j | a bond | H | a bond | NH | O | NH | Q3b | OH |
| 2397 | CMe | NEt | Q1j | a bond | H | a bond | NH | O | NH | Q3c | OH |
| 2398 | CMe | NEt | Q1j | a bond | H | a bond | NH | O | a bond | Q3a | OH |
| 2399 | CMe | NEt | Q1j | a bond | H | a bond | NH | O | a bond | Q3b | OH |
| 2400 | CMe | NEt | Q1j | a bond | H | a bond | NH | O | a bond | Q3c | OH |
| 2401 | CMe | S | Q1a | a bond | Me | a bond | NH | S | NH | Q3a | OH |
| 2402 | CMe | S | Q1a | a bond | Me | a bond | NH | S | NH | Q3b | OH |
| 2403 | CMe | S | Q1a | a bond | Me | a bond | NH | S | NH | Q3c | OH |
| 2404 | CMe | S | Q1a | a bond | Me | a bond | NH | S | a bond | Q3a | OH |
| 2405 | CMe | S | Q1a | a bond | Me | a bond | NH | S | a bond | Q3b | OH |
| 2406 | CMe | S | Q1a | a bond | Me | a bond | NH | S | a bond | Q3c | OH |
| 2407 | CMe | S | Q1a | a bond | Me | a bond | NH | O | NH | Q3a | OH |
| 2408 | CMe | S | Q1a | a bond | Me | a bond | NH | O | NH | Q3b | OH |
| 2409 | CMe | S | Q1a | a bond | Me | a bond | NH | O | NH | Q3c | OH |
| 2410 | CMe | S | Q1a | a bond | Me | a bond | NH | O | a bond | Q3a | OH |
| 2411 | CMe | S | Q1a | a bond | Me | a bond | NH | O | a bond | Q3b | OH |
| 2412 | CMe | S | Q1a | a bond | Me | a bond | NH | O | a bond | Q3c | OH |
| 2413 | CMe | S | Q1a | a bond | H | a bond | NH | S | NH | Q3a | OH |
| 2414 | CMe | S | Q1a | a bond | H | a bond | NH | S | NH | Q3b | OH |
| 2415 | CMe | S | Q1a | a bond | H | a bond | NH | S | NH | Q3c | OH |
| 2416 | CMe | S | Q1a | a bond | H | a bond | NH | S | a bond | Q3a | OH |
| 2417 | CMe | S | Q1a | a bond | H | a bond | NH | S | a bond | Q3b | OH |
| 2418 | CMe | S | Q1a | a bond | H | a bond | NH | S | a bond | Q3c | OH |

TABLE 1-continued

| No | A | B | R¹ | L¹ | R² | L² | L³ | Y | L⁴ | R³ | X |
|---|---|---|---|---|---|---|---|---|---|---|---|
| 2419 | CMe | S | Q1a | a bond | H | a bond | NH | O | NH | Q3a | OH |
| 2420 | CMe | S | Q1a | a bond | H | a bond | NH | O | NH | Q3b | OH |
| 2421 | CMe | S | Q1a | a bond | H | a bond | NH | O | NH | Q3c | OH |
| 2422 | CMe | S | Q1a | a bond | H | a bond | NH | O | a bond | Q3a | OH |
| 2423 | CMe | S | Q1a | a bond | H | a bond | NH | O | a bond | Q3b | OH |
| 2424 | CMe | S | Q1a | a bond | H | a bond | NH | O | a bond | Q3c | OH |
| 2425 | CMe | S | Q1b | a bond | Me | a bond | NH | S | NH | Q3a | OH |
| 2426 | CMe | S | Q1b | a bond | Me | a bond | NH | S | NH | Q3b | OH |
| 2427 | CMe | S | Q1b | a bond | Me | a bond | NH | S | NH | Q3c | OH |
| 2428 | CMe | S | Q1b | a bond | Me | a bond | NH | S | a bond | Q3a | OH |
| 2429 | CMe | S | Q1b | a bond | Me | a bond | NH | S | a bond | Q3b | OH |
| 2430 | CMe | S | Q1b | a bond | Me | a bond | NH | S | a bond | Q3c | OH |
| 2431 | CMe | S | Q1b | a bond | Me | a bond | NH | O | NH | Q3a | OH |
| 2432 | CMe | S | Q1b | a bond | Me | a bond | NH | O | NH | Q3b | OH |
| 2433 | CMe | S | Q1b | a bond | Me | a bond | NH | O | NH | Q3c | OH |
| 2434 | CMe | S | Q1b | a bond | Me | a bond | NH | O | a bond | Q3a | OH |
| 2435 | CMe | S | Q1b | a bond | Me | a bond | NH | O | a bond | Q3b | OH |
| 2436 | CMe | S | Q1b | a bond | Me | a bond | NH | O | a bond | Q3c | OH |
| 2437 | CMe | S | Q1b | a bond | H | a bond | NH | S | NH | Q3a | OH |
| 2438 | CMe | S | Q1b | a bond | H | a bond | NH | S | NH | Q3b | OH |
| 2439 | CMe | S | Q1b | a bond | H | a bond | NH | S | NH | Q3c | OH |
| 2440 | CMe | S | Q1b | a bond | H | a bond | NH | S | a bond | Q3a | OH |
| 2441 | CMe | S | Q1b | a bond | H | a bond | NH | S | a bond | Q3b | OH |
| 2442 | CMe | S | Q1b | a bond | H | a bond | NH | S | a bond | Q3c | OH |
| 2443 | CMe | S | Q1b | a bond | H | a bond | NH | O | NH | Q3a | OH |
| 2444 | CMe | S | Q1b | a bond | H | a bond | NH | O | NH | Q3b | OH |
| 2445 | CMe | S | Q1b | a bond | H | a bond | NH | O | NH | Q3c | OH |
| 2446 | CMe | S | Q1b | a bond | H | a bond | NH | O | a bond | Q3a | OH |
| 2447 | CMe | S | Q1b | a bond | H | a bond | NH | O | a bond | Q3b | OH |
| 2448 | CMe | S | Q1b | a bond | H | a bond | NH | O | a bond | Q3c | OH |
| 2449 | CMe | S | Q1c | a bond | Me | a bond | NH | S | NH | Q3a | OH |
| 2450 | CMe | S | Q1c | a bond | Me | a bond | NH | S | NH | Q3b | OH |
| 2451 | CMe | S | Q1c | a bond | Me | a bond | NH | S | NH | Q3c | OH |
| 2452 | CMe | S | Q1c | a bond | Me | a bond | NH | S | a bond | Q3a | OH |
| 2453 | CMe | S | Q1c | a bond | Me | a bond | NH | S | a bond | Q3b | OH |
| 2454 | CMe | S | Q1c | a bond | Me | a bond | NH | S | a bond | Q3c | OH |
| 2455 | CMe | S | Q1c | a bond | Me | a bond | NH | O | NH | Q3a | OH |
| 2456 | CMe | S | Q1c | a bond | Me | a bond | NH | O | NH | Q3b | OH |
| 2457 | CMe | S | Q1c | a bond | Me | a bond | NH | O | NH | Q3c | OH |
| 2458 | CMe | S | Q1c | a bond | Me | a bond | NH | O | a bond | Q3a | OH |
| 2459 | CMe | S | Q1c | a bond | Me | a bond | NH | O | a bond | Q3b | OH |
| 2460 | CMe | S | Q1c | a bond | Me | a bond | NH | O | a bond | Q3c | OH |
| 2461 | CMe | S | Q1c | a bond | H | a bond | NH | S | NH | Q3a | OH |
| 2462 | CMe | S | Q1c | a bond | H | a bond | NH | S | NH | Q3b | OH |
| 2463 | CMe | S | Q1c | a bond | H | a bond | NH | S | NH | Q3c | OH |
| 2464 | CMe | S | Q1c | a bond | H | a bond | NH | S | a bond | Q3a | OH |
| 2465 | CMe | S | Q1c | a bond | H | a bond | NH | S | a bond | Q3b | OH |
| 2466 | CMe | S | Q1c | a bond | H | a bond | NH | S | a bond | Q3c | OH |
| 2467 | CMe | S | Q1c | a bond | H | a bond | NH | O | NH | Q3a | OH |
| 2468 | CMe | S | Q1c | a bond | H | a bond | NH | O | NH | Q3b | OH |
| 2469 | CMe | S | Q1c | a bond | H | a bond | NH | O | NH | Q3c | OH |
| 2470 | CMe | S | Q1c | a bond | H | a bond | NH | O | a bond | Q3a | OH |
| 2471 | CMe | S | Q1c | a bond | H | a bond | NH | O | a bond | Q3b | OH |
| 2472 | CMe | S | Q1c | a bond | H | a bond | NH | O | a bond | Q3c | OH |
| 2473 | CMe | S | Q1d | a bond | Me | a bond | NH | S | NH | Q3a | OH |
| 2474 | CMe | S | Q1d | a bond | Me | a bond | NH | S | NH | Q3b | OH |
| 2475 | CMe | S | Q1d | a bond | Me | a bond | NH | S | NH | Q3c | OH |
| 2476 | CMe | S | Q1d | a bond | Me | a bond | NH | S | a bond | Q3a | OH |
| 2477 | CMe | S | Q1d | a bond | Me | a bond | NH | S | a bond | Q3b | OH |
| 2478 | CMe | S | Q1d | a bond | Me | a bond | NH | S | a bond | Q3c | OH |
| 2479 | CMe | S | Q1d | a bond | Me | a bond | NH | O | NH | Q3a | OH |
| 2480 | CMe | S | Q1d | a bond | Me | a bond | NH | O | NH | Q3b | OH |
| 2481 | CMe | S | Q1d | a bond | Me | a bond | NH | O | NH | Q3c | OH |
| 2482 | CMe | S | Q1d | a bond | Me | a bond | NH | O | a bond | Q3a | OH |
| 2483 | CMe | S | Q1d | a bond | Me | a bond | NH | O | a bond | Q3b | OH |
| 2484 | CMe | S | Q1d | a bond | Me | a bond | NH | O | a bond | Q3c | OH |
| 2485 | CMe | S | Q1d | a bond | H | a bond | NH | S | NH | Q3a | OH |
| 2486 | CMe | S | Q1d | a bond | H | a bond | NH | S | NH | Q3b | OH |
| 2487 | CMe | S | Q1d | a bond | H | a bond | NH | S | NH | Q3c | OH |
| 2488 | CMe | S | Q1d | a bond | H | a bond | NH | S | a bond | Q3a | OH |
| 2489 | CMe | S | Q1d | a bond | H | a bond | NH | S | a bond | Q3b | OH |
| 2490 | CMe | S | Q1d | a bond | H | a bond | NH | S | a bond | Q3c | OH |
| 2491 | CMe | S | Q1d | a bond | H | a bond | NH | O | NH | Q3a | OH |
| 2492 | CMe | S | Q1d | a bond | H | a bond | NH | O | NH | Q3b | OH |
| 2493 | CMe | S | Q1d | a bond | H | a bond | NH | O | NH | Q3c | OH |
| 2494 | CMe | S | Q1d | a bond | H | a bond | NH | O | a bond | Q3a | OH |
| 2495 | CMe | S | Q1d | a bond | H | a bond | NH | O | a bond | Q3b | OH |
| 2496 | CMe | S | Q1d | a bond | H | a bond | NH | O | a bond | Q3c | OH |

TABLE 1-continued

| No | A | B | R¹ | L¹ | R² | L² | L³ | Y | L⁴ | R³ | X |
|---|---|---|---|---|---|---|---|---|---|---|---|
| 2497 | CMe | S | Q1e | a bond | Me | a bond | NH | S | NH | Q3a | OH |
| 2498 | CMe | S | Q1e | a bond | Me | a bond | NH | S | NH | Q3b | OH |
| 2499 | CMe | S | Q1e | a bond | Me | a bond | NH | S | NH | Q3c | OH |
| 2500 | CMe | S | Q1e | a bond | Me | a bond | NH | S | a bond | Q3a | OH |
| 2501 | CMe | S | Q1e | a bond | Me | a bond | NH | S | a bond | Q3b | OH |
| 2502 | CMe | S | Q1e | a bond | Me | a bond | NH | S | a bond | Q3c | OH |
| 2503 | CMe | S | Q1e | a bond | Me | a bond | NH | O | NH | Q3a | OH |
| 2504 | CMe | S | Q1e | a bond | Me | a bond | NH | O | NH | Q3b | OH |
| 2505 | CMe | S | Q1e | a bond | Me | a bond | NH | O | NH | Q3c | OH |
| 2506 | CMe | S | Q1e | a bond | Me | a bond | NH | O | a bond | Q3a | OH |
| 2507 | CMe | S | Q1e | a bond | Me | a bond | NH | O | a bond | Q3b | OH |
| 2508 | CMe | S | Q1e | a bond | Me | a bond | NH | O | a bond | Q3c | OH |
| 2509 | CMe | S | Q1e | a bond | H | a bond | NH | S | NH | Q3a | OH |
| 2510 | CMe | S | Q1e | a bond | H | a bond | NH | S | NH | Q3b | OH |
| 2511 | CMe | S | Q1e | a bond | H | a bond | NH | S | NH | Q3c | OH |
| 2512 | CMe | S | Q1e | a bond | H | a bond | NH | S | a bond | Q3a | OH |
| 2513 | CMe | S | Q1e | a bond | H | a bond | NH | S | a bond | Q3b | OH |
| 2514 | CMe | S | Q1e | a bond | H | a bond | NH | S | a bond | Q3c | OH |
| 2515 | CMe | S | Q1e | a bond | H | a bond | NH | O | NH | Q3a | OH |
| 2516 | CMe | S | Q1e | a bond | H | a bond | NH | O | NH | Q3b | OH |
| 2517 | CMe | S | Q1e | a bond | H | a bond | NH | O | NH | Q3c | OH |
| 2518 | CMe | S | Q1e | a bond | H | a bond | NH | O | a bond | Q3a | OH |
| 2519 | CMe | S | Q1e | a bond | H | a bond | NH | O | a bond | Q3b | OH |
| 2520 | CMe | S | Q1e | a bond | H | a bond | NH | O | a bond | Q3c | OH |
| 2521 | CMe | S | Q1f | a bond | Me | a bond | NH | S | NH | Q3a | OH |
| 2522 | CMe | S | Q1f | a bond | Me | a bond | NH | S | NH | Q3b | OH |
| 2523 | CMe | S | Q1f | a bond | Me | a bond | NH | S | NH | Q3c | OH |
| 2524 | CMe | S | Q1f | a bond | Me | a bond | NH | S | a bond | Q3a | OH |
| 2525 | CMe | S | Q1f | a bond | Me | a bond | NH | S | a bond | Q3b | OH |
| 2526 | CMe | S | Q1f | a bond | Me | a bond | NH | S | a bond | Q3c | OH |
| 2527 | CMe | S | Q1f | a bond | Me | a bond | NH | O | NH | Q3a | OH |
| 2528 | CMe | S | Q1f | a bond | Me | a bond | NH | O | NH | Q3b | OH |
| 2529 | CMe | S | Q1f | a bond | Me | a bond | NH | O | NH | Q3c | OH |
| 2530 | CMe | S | Q1f | a bond | Me | a bond | NH | O | a bond | Q3a | OH |
| 2531 | CMe | S | Q1f | a bond | Me | a bond | NH | O | a bond | Q3b | OH |
| 2532 | CMe | S | Q1f | a bond | Me | a bond | NH | O | a bond | Q3c | OH |
| 2533 | CMe | S | Q1f | a bond | H | a bond | NH | S | NH | Q3a | OH |
| 2534 | CMe | S | Q1f | a bond | H | a bond | NH | S | NH | Q3b | OH |
| 2535 | CMe | S | Q1f | a bond | H | a bond | NH | S | NH | Q3c | OH |
| 2536 | CMe | S | Q1f | a bond | H | a bond | NH | S | a bond | Q3a | OH |
| 2537 | CMe | S | Q1f | a bond | H | a bond | NH | S | a bond | Q3b | OH |
| 2538 | CMe | S | Q1f | a bond | H | a bond | NH | S | a bond | Q3c | OH |
| 2539 | CMe | S | Q1f | a bond | H | a bond | NH | O | NH | Q3a | OH |
| 2540 | CMe | S | Q1f | a bond | H | a bond | NH | O | NH | Q3b | OH |
| 2541 | CMe | S | Q1f | a bond | H | a bond | NH | O | NH | Q3c | OH |
| 2542 | CMe | S | Q1f | a bond | H | a bond | NH | O | a bond | Q3a | OH |
| 2543 | CMe | S | Q1f | a bond | H | a bond | NH | O | a bond | Q3b | OH |
| 2544 | CMe | S | Q1f | a bond | H | a bond | NH | O | a bond | Q3c | OH |
| 2545 | CMe | S | Q1g | a bond | Me | a bond | NH | S | NH | Q3a | OH |
| 2546 | CMe | S | Q1g | a bond | Me | a bond | NH | S | NH | Q3b | OH |
| 2547 | CMe | S | Q1g | a bond | Me | a bond | NH | S | NH | Q3c | OH |
| 2548 | CMe | S | Q1g | a bond | Me | a bond | NH | S | a bond | Q3a | OH |
| 2549 | CMe | S | Q1g | a bond | Me | a bond | NH | S | a bond | Q3b | OH |
| 2550 | CMe | S | Q1g | a bond | Me | a bond | NH | S | a bond | Q3c | OH |
| 2551 | CMe | S | Q1g | a bond | Me | a bond | NH | O | NH | Q3a | OH |
| 2552 | CMe | S | Q1g | a bond | Me | a bond | NH | O | NH | Q3b | OH |
| 2553 | CMe | S | Q1g | a bond | Me | a bond | NH | O | NH | Q3c | OH |
| 2554 | CMe | S | Q1g | a bond | Me | a bond | NH | O | a bond | Q3a | OH |
| 2555 | CMe | S | Q1g | a bond | Me | a bond | NH | O | a bond | Q3b | OH |
| 2556 | CMe | S | Q1g | a bond | Me | a bond | NH | O | a bond | Q3c | OH |
| 2557 | CMe | S | Q1g | a bond | H | a bond | NH | S | NH | Q3a | OH |
| 2558 | CMe | S | Q1g | a bond | H | a bond | NH | S | NH | Q3b | OH |
| 2559 | CMe | S | Q1g | a bond | H | a bond | NH | S | NH | Q3c | OH |
| 2560 | CMe | S | Q1g | a bond | H | a bond | NH | S | a bond | Q3a | OH |
| 2561 | CMe | S | Q1g | a bond | H | a bond | NH | S | a bond | Q3b | OH |
| 2562 | CMe | S | Q1g | a bond | H | a bond | NH | S | a bond | Q3c | OH |
| 2563 | CMe | S | Q1g | a bond | H | a bond | NH | O | NH | Q3a | OH |
| 2564 | CMe | S | Q1g | a bond | H | a bond | NH | O | NH | Q3b | OH |
| 2565 | CMe | S | Q1g | a bond | H | a bond | NH | O | NH | Q3c | OH |
| 2566 | CMe | S | Q1g | a bond | H | a bond | NH | O | a bond | Q3a | OH |
| 2567 | CMe | S | Q1g | a bond | H | a bond | NH | O | a bond | Q3b | OH |
| 2568 | CMe | S | Q1g | a bond | H | a bond | NH | O | a bond | Q3c | OH |
| 2569 | CMe | S | Q1h | a bond | Me | a bond | NH | S | NH | Q3a | OH |
| 2570 | CMe | S | Q1h | a bond | Me | a bond | NH | S | NH | Q3b | OH |
| 2571 | CMe | S | Q1h | a bond | Me | a bond | NH | S | NH | Q3c | OH |
| 2572 | CMe | S | Q1h | a bond | Me | a bond | NH | S | a bond | Q3a | OH |
| 2573 | CMe | S | Q1h | a bond | Me | a bond | NH | S | a bond | Q3b | OH |
| 2574 | CMe | S | Q1h | a bond | Me | a bond | NH | S | a bond | Q3c | OH |

TABLE 1-continued

| No | A | B | R¹ | L¹ | R² | L² | L³ | Y | L⁴ | R³ | X |
|---|---|---|---|---|---|---|---|---|---|---|---|
| 2575 | CMe | S | Q1h | a bond | Me | a bond | NH | O | NH | Q3a | OH |
| 2576 | CMe | S | Q1h | a bond | Me | a bond | NH | O | NH | Q3b | OH |
| 2577 | CMe | S | Q1h | a bond | Me | a bond | NH | O | NH | Q3c | OH |
| 2578 | CMe | S | Q1h | a bond | Me | a bond | NH | O | a bond | Q3a | OH |
| 2579 | CMe | S | Q1h | a bond | Me | a bond | NH | O | a bond | Q3b | OH |
| 2580 | CMe | S | Q1h | a bond | Me | a bond | NH | O | a bond | Q3c | OH |
| 2581 | CMe | S | Q1h | a bond | H | a bond | NH | S | NH | Q3a | OH |
| 2582 | CMe | S | Q1h | a bond | H | a bond | NH | S | NH | Q3b | OH |
| 2583 | CMe | S | Q1h | a bond | H | a bond | NH | S | NH | Q3c | OH |
| 2584 | CMe | S | Q1h | a bond | H | a bond | NH | S | a bond | Q3a | OH |
| 2585 | CMe | S | Q1h | a bond | H | a bond | NH | S | a bond | Q3b | OH |
| 2586 | CMe | S | Q1h | a bond | H | a bond | NH | S | a bond | Q3c | OH |
| 2587 | CMe | S | Q1h | a bond | H | a bond | NH | O | NH | Q3a | OH |
| 2588 | CMe | S | Q1h | a bond | H | a bond | NH | O | NH | Q3b | OH |
| 2589 | CMe | S | Q1h | a bond | H | a bond | NH | O | NH | Q3c | OH |
| 2590 | CMe | S | Q1h | a bond | H | a bond | NH | O | a bond | Q3a | OH |
| 2591 | CMe | S | Q1h | a bond | H | a bond | NH | O | a bond | Q3b | OH |
| 2592 | CMe | S | Q1h | a bond | H | a bond | NH | O | a bond | Q3c | OH |
| 2593 | CMe | S | Q1i | a bond | Me | a bond | NH | S | NH | Q3a | OH |
| 2594 | CMe | S | Q1i | a bond | Me | a bond | NH | S | NH | Q3b | OH |
| 2595 | CMe | S | Q1i | a bond | Me | a bond | NH | S | NH | Q3c | OH |
| 2596 | CMe | S | Q1i | a bond | Me | a bond | NH | S | a bond | Q3a | OH |
| 2597 | CMe | S | Q1i | a bond | Me | a bond | NH | S | a bond | Q3b | OH |
| 2598 | CMe | S | Q1i | a bond | Me | a bond | NH | S | a bond | Q3c | OH |
| 2599 | CMe | S | Q1i | a bond | Me | a bond | NH | O | NH | Q3a | OH |
| 2600 | CMe | S | Q1i | a bond | Me | a bond | NH | O | NH | Q3b | OH |
| 2601 | CMe | S | Q1i | a bond | Me | a bond | NH | O | NH | Q3c | OH |
| 2602 | CMe | S | Q1i | a bond | Me | a bond | NH | O | a bond | Q3a | OH |
| 2603 | CMe | S | Q1i | a bond | Me | a bond | NH | O | a bond | Q3b | OH |
| 2604 | CMe | S | Q1i | a bond | Me | a bond | NH | O | a bond | Q3c | OH |
| 2605 | CMe | S | Q1i | a bond | H | a bond | NH | S | NH | Q3a | OH |
| 2606 | CMe | S | Q1i | a bond | H | a bond | NH | S | NH | Q3b | OH |
| 2607 | CMe | S | Q1i | a bond | H | a bond | NH | S | NH | Q3c | OH |
| 2608 | CMe | S | Q1i | a bond | H | a bond | NH | S | a bond | Q3a | OH |
| 2609 | CMe | S | Q1i | a bond | H | a bond | NH | S | a bond | Q3b | OH |
| 2610 | CMe | S | Q1i | a bond | H | a bond | NH | S | a bond | Q3c | OH |
| 2611 | CMe | S | Q1i | a bond | H | a bond | NH | O | NH | Q3a | OH |
| 2612 | CMe | S | Q1i | a bond | H | a bond | NH | O | NH | Q3b | OH |
| 2613 | CMe | S | Q1i | a bond | H | a bond | NH | O | NH | Q3c | OH |
| 2614 | CMe | S | Q1i | a bond | H | a bond | NH | O | a bond | Q3a | OH |
| 2615 | CMe | S | Q1i | a bond | H | a bond | NH | O | a bond | Q3b | OH |
| 2616 | CMe | S | Q1i | a bond | H | a bond | NH | O | a bond | Q3c | OH |
| 2617 | CMe | S | Q1j | a bond | Me | a bond | NH | S | NH | Q3a | OH |
| 2618 | CMe | S | Q1j | a bond | Me | a bond | NH | S | NH | Q3b | OH |
| 2619 | CMe | S | Q1j | a bond | Me | a bond | NH | S | NH | Q3c | OH |
| 2620 | CMe | S | Q1j | a bond | Me | a bond | NH | S | a bond | Q3a | OH |
| 2621 | CMe | S | Q1j | a bond | Me | a bond | NH | S | a bond | Q3b | OH |
| 2622 | CMe | S | Q1j | a bond | Me | a bond | NH | S | a bond | Q3c | OH |
| 2623 | CMe | S | Q1j | a bond | Me | a bond | NH | O | NH | Q3a | OH |
| 2624 | CMe | S | Q1j | a bond | Me | a bond | NH | O | NH | Q3b | OH |
| 2625 | CMe | S | Q1j | a bond | Me | a bond | NH | O | NH | Q3c | OH |
| 2626 | CMe | S | Q1j | a bond | Me | a bond | NH | O | a bond | Q3a | OH |
| 2627 | CMe | S | Q1j | a bond | Me | a bond | NH | O | a bond | Q3b | OH |
| 2628 | CMe | S | Q1j | a bond | Me | a bond | NH | O | a bond | Q3c | OH |
| 2629 | CMe | S | Q1j | a bond | H | a bond | NH | S | NH | Q3a | OH |
| 2630 | CMe | S | Q1j | a bond | H | a bond | NH | S | NH | Q3b | OH |
| 2631 | CMe | S | Q1j | a bond | H | a bond | NH | S | NH | Q3c | OH |
| 2632 | CMe | S | Q1j | a bond | H | a bond | NH | S | a bond | Q3a | OH |
| 2633 | CMe | S | Q1j | a bond | H | a bond | NH | S | a bond | Q3b | OH |
| 2634 | CMe | S | Q1j | a bond | H | a bond | NH | S | a bond | Q3c | OH |
| 2635 | CMe | S | Q1j | a bond | H | a bond | NH | O | NH | Q3a | OH |
| 2636 | CMe | S | Q1j | a bond | H | a bond | NH | O | NH | Q3b | OH |
| 2637 | CMe | S | Q1j | a bond | H | a bond | NH | O | NH | Q3c | OH |
| 2638 | CMe | S | Q1j | a bond | H | a bond | NH | O | a bond | Q3a | OH |
| 2639 | CMe | S | Q1j | a bond | H | a bond | NH | O | a bond | Q3b | OH |
| 2640 | CMe | S | Q1j | a bond | H | a bond | NH | O | a bond | Q3c | OH |
| 2641 | CMe | O | Q1a | a bond | Me | a bond | NH | S | NH | Q3a | OH |
| 2642 | CMe | O | Q1a | a bond | Me | a bond | NH | S | NH | Q3b | OH |
| 2643 | CMe | O | Q1a | a bond | Me | a bond | NH | S | NH | Q3c | OH |
| 2644 | CMe | O | Q1a | a bond | Me | a bond | NH | S | a bond | Q3a | OH |
| 2645 | CMe | O | Q1a | a bond | Me | a bond | NH | S | a bond | Q3b | OH |
| 2646 | CMe | O | Q1a | a bond | Me | a bond | NH | S | a bond | Q3c | OH |
| 2647 | CMe | O | Q1a | a bond | Me | a bond | NH | O | NH | Q3a | OH |
| 2648 | CMe | O | Q1a | a bond | Me | a bond | NH | O | NH | Q3b | OH |
| 2649 | CMe | O | Q1a | a bond | Me | a bond | NH | O | NH | Q3c | OH |
| 2650 | CMe | O | Q1a | a bond | Me | a bond | NH | O | a bond | Q3a | OH |
| 2651 | CMe | O | Q1a | a bond | Me | a bond | NH | O | a bond | Q3b | OH |
| 2652 | CMe | O | Q1a | a bond | Me | a bond | NH | O | a bond | Q3c | OH |

TABLE 1-continued

| No | A | B | R¹ | L¹ | R² | L² | L³ | Y | L⁴ | R³ | X |
|---|---|---|---|---|---|---|---|---|---|---|---|
| 2653 | CMe | O | Q1a | a bond | H | a bond | NH | S | NH | Q3a | OH |
| 2654 | CMe | O | Q1a | a bond | H | a bond | NH | S | NH | Q3b | OH |
| 2655 | CMe | O | Q1a | a bond | H | a bond | NH | S | NH | Q3c | OH |
| 2656 | CMe | O | Q1a | a bond | H | a bond | NH | S | a bond | Q3a | OH |
| 2657 | CMe | O | Q1a | a bond | H | a bond | NH | S | a bond | Q3b | OH |
| 2658 | CMe | O | Q1a | a bond | H | a bond | NH | S | a bond | Q3c | OH |
| 2659 | CMe | O | Q1a | a bond | H | a bond | NH | O | NH | Q3a | OH |
| 2660 | CMe | O | Q1a | a bond | H | a bond | NH | O | NH | Q3b | OH |
| 2661 | CMe | O | Q1a | a bond | H | a bond | NH | O | NH | Q3c | OH |
| 2662 | CMe | O | Q1a | a bond | H | a bond | NH | O | a bond | Q3a | OH |
| 2663 | CMe | O | Q1a | a bond | H | a bond | NH | O | a bond | Q3b | OH |
| 2664 | CMe | O | Q1a | a bond | H | a bond | NH | O | a bond | Q3c | OH |
| 2665 | CMe | O | Q1b | a bond | Me | a bond | NH | S | NH | Q3a | OH |
| 2666 | CMe | O | Q1b | a bond | Me | a bond | NH | S | NH | Q3b | OH |
| 2667 | CMe | O | Q1b | a bond | Me | a bond | NH | S | NH | Q3c | OH |
| 2668 | CMe | O | Q1b | a bond | Me | a bond | NH | S | a bond | Q3a | OH |
| 2669 | CMe | O | Q1b | a bond | Me | a bond | NH | S | a bond | Q3b | OH |
| 2670 | CMe | O | Q1b | a bond | Me | a bond | NH | S | a bond | Q3c | OH |
| 2671 | CMe | O | Q1b | a bond | Me | a bond | NH | O | NH | Q3a | OH |
| 2672 | CMe | O | Q1b | a bond | Me | a bond | NH | O | NH | Q3b | OH |
| 2673 | CMe | O | Q1b | a bond | Me | a bond | NH | O | NH | Q3c | OH |
| 2674 | CMe | O | Q1b | a bond | Me | a bond | NH | O | a bond | Q3a | OH |
| 2675 | CMe | O | Q1b | a bond | Me | a bond | NH | O | a bond | Q3b | OH |
| 2676 | CMe | O | Q1b | a bond | Me | a bond | NH | O | a bond | Q3c | OH |
| 2677 | CMe | O | Q1b | a bond | H | a bond | NH | S | NH | Q3a | OH |
| 2678 | CMe | O | Q1b | a bond | H | a bond | NH | S | NH | Q3b | OH |
| 2679 | CMe | O | Q1b | a bond | H | a bond | NH | S | NH | Q3c | OH |
| 2680 | CMe | O | Q1b | a bond | H | a bond | NH | S | a bond | Q3a | OH |
| 2681 | CMe | O | Q1b | a bond | H | a bond | NH | S | a bond | Q3b | OH |
| 2682 | CMe | O | Q1b | a bond | H | a bond | NH | S | a bond | Q3c | OH |
| 2683 | CMe | O | Q1b | a bond | H | a bond | NH | O | NH | Q3a | OH |
| 2684 | CMe | O | Q1b | a bond | H | a bond | NH | O | NH | Q3b | OH |
| 2685 | CMe | O | Q1b | a bond | H | a bond | NH | O | NH | Q3c | OH |
| 2686 | CMe | O | Q1b | a bond | H | a bond | NH | O | a bond | Q3a | OH |
| 2687 | CMe | O | Q1b | a bond | H | a bond | NH | O | a bond | Q3b | OH |
| 2688 | CMe | O | Q1b | a bond | H | a bond | NH | O | a bond | Q3c | OH |
| 2689 | CMe | O | Q1c | a bond | Me | a bond | NH | S | NH | Q3a | OH |
| 2690 | CMe | O | Q1c | a bond | Me | a bond | NH | S | NH | Q3b | OH |
| 2691 | CMe | O | Q1c | a bond | Me | a bond | NH | S | NH | Q3c | OH |
| 2692 | CMe | O | Q1c | a bond | Me | a bond | NH | S | a bond | Q3a | OH |
| 2693 | CMe | O | Q1c | a bond | Me | a bond | NH | S | a bond | Q3b | OH |
| 2694 | CMe | O | Q1c | a bond | Me | a bond | NH | S | a bond | Q3c | OH |
| 2695 | CMe | O | Q1c | a bond | Me | a bond | NH | O | NH | Q3a | OH |
| 2696 | CMe | O | Q1c | a bond | Me | a bond | NH | O | NH | Q3b | OH |
| 2697 | CMe | O | Q1c | a bond | Me | a bond | NH | O | NH | Q3c | OH |
| 2698 | CMe | O | Q1c | a bond | Me | a bond | NH | O | a bond | Q3a | OH |
| 2699 | CMe | O | Q1c | a bond | Me | a bond | NH | O | a bond | Q3b | OH |
| 2700 | CMe | O | Q1c | a bond | Me | a bond | NH | O | a bond | Q3c | OH |
| 2701 | CMe | O | Q1c | a bond | H | a bond | NH | S | NH | Q3a | OH |
| 2702 | CMe | O | Q1c | a bond | H | a bond | NH | S | NH | Q3b | OH |
| 2703 | CMe | O | Q1c | a bond | H | a bond | NH | S | NH | Q3c | OH |
| 2704 | CMe | O | Q1c | a bond | H | a bond | NH | S | a bond | Q3a | OH |
| 2705 | CMe | O | Q1c | a bond | H | a bond | NH | S | a bond | Q3b | OH |
| 2706 | CMe | O | Q1c | a bond | H | a bond | NH | S | a bond | Q3c | OH |
| 2707 | CMe | O | Q1c | a bond | H | a bond | NH | O | NH | Q3a | OH |
| 2708 | CMe | O | Q1c | a bond | H | a bond | NH | O | NH | Q3b | OH |
| 2709 | CMe | O | Q1c | a bond | H | a bond | NH | O | NH | Q3c | OH |
| 2710 | CMe | O | Q1c | a bond | H | a bond | NH | O | a bond | Q3a | OH |
| 2711 | CMe | O | Q1c | a bond | H | a bond | NH | O | a bond | Q3b | OH |
| 2712 | CMe | O | Q1c | a bond | H | a bond | NH | O | a bond | Q3c | OH |
| 2713 | CMe | O | Q1d | a bond | Me | a bond | NH | S | NH | Q3a | OH |
| 2714 | CMe | O | Q1d | a bond | Me | a bond | NH | S | NH | Q3b | OH |
| 2715 | CMe | O | Q1d | a bond | Me | a bond | NH | S | NH | Q3c | OH |
| 2716 | CMe | O | Q1d | a bond | Me | a bond | NH | S | a bond | Q3a | OH |
| 2717 | CMe | O | Q1d | a bond | Me | a bond | NH | S | a bond | Q3b | OH |
| 2718 | CMe | O | Q1d | a bond | Me | a bond | NH | S | a bond | Q3c | OH |
| 2719 | CMe | O | Q1d | a bond | Me | a bond | NH | O | NH | Q3a | OH |
| 2720 | CMe | O | Q1d | a bond | Me | a bond | NH | O | NH | Q3b | OH |
| 2721 | CMe | O | Q1d | a bond | Me | a bond | NH | O | NH | Q3c | OH |
| 2722 | CMe | O | Q1d | a bond | Me | a bond | NH | O | a bond | Q3a | OH |
| 2723 | CMe | O | Q1d | a bond | Me | a bond | NH | O | a bond | Q3b | OH |
| 2724 | CMe | O | Q1d | a bond | Me | a bond | NH | O | a bond | Q3c | OH |
| 2725 | CMe | O | Q1d | a bond | H | a bond | NH | S | NH | Q3a | OH |
| 2726 | CMe | O | Q1d | a bond | H | a bond | NH | S | NH | Q3b | OH |
| 2727 | CMe | O | Q1d | a bond | H | a bond | NH | S | NH | Q3c | OH |
| 2728 | CMe | O | Q1d | a bond | H | a bond | NH | S | a bond | Q3a | OH |
| 2729 | CMe | O | Q1d | a bond | H | a bond | NH | S | a bond | Q3b | OH |
| 2730 | CMe | O | Q1d | a bond | H | a bond | NH | S | a bond | Q3c | OH |

TABLE 1-continued

| No | A | B | R¹ | L¹ | R² | L² | L³ | Y | L⁴ | R³ | X |
|---|---|---|---|---|---|---|---|---|---|---|---|
| 2731 | CMe | O | Q1d | a bond | H | a bond | NH | O | NH | Q3a | OH |
| 2732 | CMe | O | Q1d | a bond | H | a bond | NH | O | NH | Q3b | OH |
| 2733 | CMe | O | Q1d | a bond | H | a bond | NH | O | NH | Q3c | OH |
| 2734 | CMe | O | Q1d | a bond | H | a bond | NH | O | a bond | Q3a | OH |
| 2735 | CMe | O | Q1d | a bond | H | a bond | NH | O | a bond | Q3b | OH |
| 2736 | CMe | O | Q1d | a bond | H | a bond | NH | O | a bond | Q3c | OH |
| 2737 | CMe | O | Q1e | a bond | Me | a bond | NH | S | NH | Q3a | OH |
| 2738 | CMe | O | Q1e | a bond | Me | a bond | NH | S | NH | Q3b | OH |
| 2739 | CMe | O | Q1e | a bond | Me | a bond | NH | S | NH | Q3c | OH |
| 2740 | CMe | O | Q1e | a bond | Me | a bond | NH | S | a bond | Q3a | OH |
| 2741 | CMe | O | Q1e | a bond | Me | a bond | NH | S | a bond | Q3b | OH |
| 2742 | CMe | O | Q1e | a bond | Me | a bond | NH | S | a bond | Q3c | OH |
| 2743 | CMe | O | Q1e | a bond | Me | a bond | NH | O | NH | Q3a | OH |
| 2744 | CMe | O | Q1e | a bond | Me | a bond | NH | O | NH | Q3b | OH |
| 2745 | CMe | O | Q1e | a bond | Me | a bond | NH | O | NH | Q3c | OH |
| 2746 | CMe | O | Q1e | a bond | Me | a bond | NH | O | a bond | Q3a | OH |
| 2747 | CMe | O | Q1e | a bond | Me | a bond | NH | O | a bond | Q3b | OH |
| 2748 | CMe | O | Q1e | a bond | Me | a bond | NH | O | a bond | Q3c | OH |
| 2749 | CMe | O | Q1e | a bond | H | a bond | NH | S | NH | Q3a | OH |
| 2750 | CMe | O | Q1e | a bond | H | a bond | NH | S | NH | Q3b | OH |
| 2751 | CMe | O | Q1e | a bond | H | a bond | NH | S | NH | Q3c | OH |
| 2752 | CMe | O | Q1e | a bond | H | a bond | NH | S | a bond | Q3a | OH |
| 2753 | CMe | O | Q1e | a bond | H | a bond | NH | S | a bond | Q3b | OH |
| 2754 | CMe | O | Q1e | a bond | H | a bond | NH | S | a bond | Q3c | OH |
| 2755 | CMe | O | Q1e | a bond | H | a bond | NH | O | NH | Q3a | OH |
| 2756 | CMe | O | Q1e | a bond | H | a bond | NH | O | NH | Q3b | OH |
| 2757 | CMe | O | Q1e | a bond | H | a bond | NH | O | NH | Q3c | OH |
| 2758 | CMe | O | Q1e | a bond | H | a bond | NH | O | a bond | Q3a | OH |
| 2759 | CMe | O | Q1e | a bond | H | a bond | NH | O | a bond | Q3b | OH |
| 2760 | CMe | O | Q1e | a bond | H | a bond | NH | O | a bond | Q3c | OH |
| 2761 | CMe | O | Q1f | a bond | Me | a bond | NH | S | NH | Q3a | OH |
| 2762 | CMe | O | Q1f | a bond | Me | a bond | NH | S | NH | Q3b | OH |
| 2763 | CMe | O | Q1f | a bond | Me | a bond | NH | S | NH | Q3c | OH |
| 2764 | CMe | O | Q1f | a bond | Me | a bond | NH | S | a bond | Q3a | OH |
| 2765 | CMe | O | Q1f | a bond | Me | a bond | NH | S | a bond | Q3b | OH |
| 2766 | CMe | O | Q1f | a bond | Me | a bond | NH | S | a bond | Q3c | OH |
| 2767 | CMe | O | Q1f | a bond | Me | a bond | NH | O | NH | Q3a | OH |
| 2768 | CMe | O | Q1f | a bond | Me | a bond | NH | O | NH | Q3b | OH |
| 2769 | CMe | O | Q1f | a bond | Me | a bond | NH | O | NH | Q3c | OH |
| 2770 | CMe | O | Q1f | a bond | Me | a bond | NH | O | a bond | Q3a | OH |
| 2771 | CMe | O | Q1f | a bond | Me | a bond | NH | O | a bond | Q3b | OH |
| 2772 | CMe | O | Q1f | a bond | Me | a bond | NH | O | a bond | Q3c | OH |
| 2773 | CMe | O | Q1f | a bond | H | a bond | NH | S | NH | Q3a | OH |
| 2774 | CMe | O | Q1f | a bond | H | a bond | NH | S | NH | Q3b | OH |
| 2775 | CMe | O | Q1f | a bond | H | a bond | NH | S | NH | Q3c | OH |
| 2776 | CMe | O | Q1f | a bond | H | a bond | NH | S | a bond | Q3a | OH |
| 2777 | CMe | O | Q1f | a bond | H | a bond | NH | S | a bond | Q3b | OH |
| 2778 | CMe | O | Q1f | a bond | H | a bond | NH | S | a bond | Q3c | OH |
| 2779 | CMe | O | Q1f | a bond | H | a bond | NH | O | NH | Q3a | OH |
| 2780 | CMe | O | Q1f | a bond | H | a bond | NH | O | NH | Q3b | OH |
| 2781 | CMe | O | Q1f | a bond | H | a bond | NH | O | NH | Q3c | OH |
| 2782 | CMe | O | Q1f | a bond | H | a bond | NH | O | a bond | Q3a | OH |
| 2783 | CMe | O | Q1f | a bond | H | a bond | NH | O | a bond | Q3b | OH |
| 2784 | CMe | O | Q1f | a bond | H | a bond | NH | O | a bond | Q3c | OH |
| 2785 | CMe | O | Q1g | a bond | Me | a bond | NH | S | NH | Q3a | OH |
| 2786 | CMe | O | Q1g | a bond | Me | a bond | NH | S | NH | Q3b | OH |
| 2787 | CMe | O | Q1g | a bond | Me | a bond | NH | S | NH | Q3c | OH |
| 2788 | CMe | O | Q1g | a bond | Me | a bond | NH | S | a bond | Q3a | OH |
| 2789 | CMe | O | Q1g | a bond | Me | a bond | NH | S | a bond | Q3b | OH |
| 2790 | CMe | O | Q1g | a bond | Me | a bond | NH | S | a bond | Q3c | OH |
| 2791 | CMe | O | Q1g | a bond | Me | a bond | NH | O | NH | Q3a | OH |
| 2792 | CMe | O | Q1g | a bond | Me | a bond | NH | O | NH | Q3b | OH |
| 2793 | CMe | O | Q1g | a bond | Me | a bond | NH | O | NH | Q3c | OH |
| 2794 | CMe | O | Q1g | a bond | Me | a bond | NH | O | a bond | Q3a | OH |
| 2795 | CMe | O | Q1g | a bond | Me | a bond | NH | O | a bond | Q3b | OH |
| 2796 | CMe | O | Q1g | a bond | Me | a bond | NH | O | a bond | Q3c | OH |
| 2797 | CMe | O | Q1g | a bond | H | a bond | NH | S | NH | Q3a | OH |
| 2798 | CMe | O | Q1g | a bond | H | a bond | NH | S | NH | Q3b | OH |
| 2799 | CMe | O | Q1g | a bond | H | a bond | NH | S | NH | Q3c | OH |
| 2800 | CMe | O | Q1g | a bond | H | a bond | NH | S | a bond | Q3a | OH |
| 2801 | CMe | O | Q1g | a bond | H | a bond | NH | S | a bond | Q3b | OH |
| 2802 | CMe | O | Q1g | a bond | H | a bond | NH | S | a bond | Q3c | OH |
| 2803 | CMe | O | Q1g | a bond | H | a bond | NH | O | NH | Q3a | OH |
| 2804 | CMe | O | Q1g | a bond | H | a bond | NH | O | NH | Q3b | OH |
| 2805 | CMe | O | Q1g | a bond | H | a bond | NH | O | NH | Q3c | OH |
| 2806 | CMe | O | Q1g | a bond | H | a bond | NH | O | a bond | Q3a | OH |
| 2807 | CMe | O | Q1g | a bond | H | a bond | NH | O | a bond | Q3b | OH |
| 2808 | CMe | O | Q1g | a bond | H | a bond | NH | O | a bond | Q3c | OH |

TABLE 1-continued

| No | A | B | R¹ | L¹ | R² | L² | L³ | Y | L⁴ | R³ | X |
|---|---|---|---|---|---|---|---|---|---|---|---|
| 2809 | CMe | O | Q1h | a bond | Me | a bond | NH | S | NH | Q3a | OH |
| 2810 | CMe | O | Q1h | a bond | Me | a bond | NH | S | NH | Q3b | OH |
| 2811 | CMe | O | Q1h | a bond | Me | a bond | NH | S | NH | Q3c | OH |
| 2812 | CMe | O | Q1h | a bond | Me | a bond | NH | S | a bond | Q3a | OH |
| 2813 | CMe | O | Q1h | a bond | Me | a bond | NH | S | a bond | Q3b | OH |
| 2814 | CMe | O | Q1h | a bond | Me | a bond | NH | S | a bond | Q3c | OH |
| 2815 | CMe | O | Q1h | a bond | Me | a bond | NH | O | NH | Q3a | OH |
| 2816 | CMe | O | Q1h | a bond | Me | a bond | NH | O | NH | Q3b | OH |
| 2817 | CMe | O | Q1h | a bond | Me | a bond | NH | O | NH | Q3c | OH |
| 2818 | CMe | O | Q1h | a bond | Me | a bond | NH | O | a bond | Q3a | OH |
| 2819 | CMe | O | Q1h | a bond | Me | a bond | NH | O | a bond | Q3b | OH |
| 2820 | CMe | O | Q1h | a bond | Me | a bond | NH | O | a bond | Q3c | OH |
| 2821 | CMe | O | Q1h | a bond | H | a bond | NH | S | NH | Q3a | OH |
| 2822 | CMe | O | Q1h | a bond | H | a bond | NH | S | NH | Q3b | OH |
| 2823 | CMe | O | Q1h | a bond | H | a bond | NH | S | NH | Q3c | OH |
| 2824 | CMe | O | Q1h | a bond | H | a bond | NH | S | a bond | Q3a | OH |
| 2825 | CMe | O | Q1h | a bond | H | a bond | NH | S | a bond | Q3b | OH |
| 2826 | CMe | O | Q1h | a bond | H | a bond | NH | S | a bond | Q3c | OH |
| 2827 | CMe | O | Q1h | a bond | H | a bond | NH | O | NH | Q3a | OH |
| 2828 | CMe | O | Q1h | a bond | H | a bond | NH | O | NH | Q3b | OH |
| 2829 | CMe | O | Q1h | a bond | H | a bond | NH | O | NH | Q3c | OH |
| 2830 | CMe | O | Q1h | a bond | H | a bond | NH | O | a bond | Q3a | OH |
| 2831 | CMe | O | Q1h | a bond | H | a bond | NH | O | a bond | Q3b | OH |
| 2832 | CMe | O | Q1h | a bond | H | a bond | NH | O | a bond | Q3c | OH |
| 2833 | CMe | O | Q1i | a bond | Me | a bond | NH | S | NH | Q3a | OH |
| 2834 | CMe | O | Q1i | a bond | Me | a bond | NH | S | NH | Q3b | OH |
| 2835 | CMe | O | Q1i | a bond | Me | a bond | NH | S | NH | Q3c | OH |
| 2836 | CMe | O | Q1i | a bond | Me | a bond | NH | S | a bond | Q3a | OH |
| 2837 | CMe | O | Q1i | a bond | Me | a bond | NH | S | a bond | Q3b | OH |
| 2838 | CMe | O | Q1i | a bond | Me | a bond | NH | S | a bond | Q3c | OH |
| 2839 | CMe | O | Q1i | a bond | Me | a bond | NH | O | NH | Q3a | OH |
| 2840 | CMe | O | Q1i | a bond | Me | a bond | NH | O | NH | Q3b | OH |
| 2841 | CMe | O | Q1i | a bond | Me | a bond | NH | O | NH | Q3c | OH |
| 2842 | CMe | O | Q1i | a bond | Me | a bond | NH | O | a bond | Q3a | OH |
| 2843 | CMe | O | Q1i | a bond | Me | a bond | NH | O | a bond | Q3b | OH |
| 2844 | CMe | O | Q1i | a bond | Me | a bond | NH | O | a bond | Q3c | OH |
| 2845 | CMe | O | Q1i | a bond | H | a bond | NH | S | NH | Q3a | OH |
| 2846 | CMe | O | Q1i | a bond | H | a bond | NH | S | NH | Q3b | OH |
| 2847 | CMe | O | Q1i | a bond | H | a bond | NH | S | NH | Q3c | OH |
| 2848 | CMe | O | Q1i | a bond | H | a bond | NH | S | a bond | Q3a | OH |
| 2849 | CMe | O | Q1i | a bond | H | a bond | NH | S | a bond | Q3b | OH |
| 2850 | CMe | O | Q1i | a bond | H | a bond | NH | S | a bond | Q3c | OH |
| 2851 | CMe | O | Q1i | a bond | H | a bond | NH | O | NH | Q3a | OH |
| 2852 | CMe | O | Q1i | a bond | H | a bond | NH | O | NH | Q3b | OH |
| 2853 | CMe | O | Q1i | a bond | H | a bond | NH | O | NH | Q3c | OH |
| 2854 | CMe | O | Q1i | a bond | H | a bond | NH | O | a bond | Q3a | OH |
| 2855 | CMe | O | Q1i | a bond | H | a bond | NH | O | a bond | Q3b | OH |
| 2856 | CMe | O | Q1i | a bond | H | a bond | NH | O | a bond | Q3c | OH |
| 2857 | CMe | O | Q1j | a bond | Me | a bond | NH | S | NH | Q3a | OH |
| 2858 | CMe | O | Q1j | a bond | Me | a bond | NH | S | NH | Q3b | OH |
| 2859 | CMe | O | Q1j | a bond | Me | a bond | NH | S | NH | Q3c | OH |
| 2860 | CMe | O | Q1j | a bond | Me | a bond | NH | S | a bond | Q3a | OH |
| 2861 | CMe | O | Q1j | a bond | Me | a bond | NH | S | a bond | Q3b | OH |
| 2862 | CMe | O | Q1j | a bond | Me | a bond | NH | S | a bond | Q3c | OH |
| 2863 | CMe | O | Q1j | a bond | Me | a bond | NH | O | NH | Q3a | OH |
| 2864 | CMe | O | Q1j | a bond | Me | a bond | NH | O | NH | Q3b | OH |
| 2865 | CMe | O | Q1j | a bond | Me | a bond | NH | O | NH | Q3c | OH |
| 2866 | CMe | O | Q1j | a bond | Me | a bond | NH | O | a bond | Q3a | OH |
| 2867 | CMe | O | Q1j | a bond | Me | a bond | NH | O | a bond | Q3b | OH |
| 2868 | CMe | O | Q1j | a bond | Me | a bond | NH | O | a bond | Q3c | OH |
| 2869 | CMe | O | Q1j | a bond | H | a bond | NH | S | NH | Q3a | OH |
| 2870 | CMe | O | Q1j | a bond | H | a bond | NH | S | NH | Q3b | OH |
| 2871 | CMe | O | Q1j | a bond | H | a bond | NH | S | NH | Q3c | OH |
| 2872 | CMe | O | Q1j | a bond | H | a bond | NH | S | a bond | Q3a | OH |
| 2873 | CMe | O | Q1j | a bond | H | a bond | NH | S | a bond | Q3b | OH |
| 2874 | CMe | O | Q1j | a bond | H | a bond | NH | S | a bond | Q3c | OH |
| 2875 | CMe | O | Q1j | a bond | H | a bond | NH | O | NH | Q3a | OH |
| 2876 | CMe | O | Q1j | a bond | H | a bond | NH | O | NH | Q3b | OH |
| 2877 | CMe | O | Q1j | a bond | H | a bond | NH | O | NH | Q3c | OH |
| 2878 | CMe | O | Q1j | a bond | H | a bond | NH | O | a bond | Q3a | OH |
| 2879 | CMe | O | Q1j | a bond | H | a bond | NH | O | a bond | Q3b | OH |
| 2880 | CMe | O | Q1j | a bond | H | a bond | NH | O | a bond | Q3c | OH |
| 2881 | N | NMe | Q1k | a bond | Me | a bond | NH | O | a bond | Q3d | OH |
| 2882 | N | NMe | Q1k | a bond | Me | a bond | NH | O | a bond | Q3e | OH |
| 2883 | N | NMe | Q1k | a bond | Me | a bond | NH | O | a bond | Q3f | OH |
| 2884 | N | NMe | Q1k | a bond | Me | a bond | NH | O | a bond | Q3f | OH |
| 2885 | N | NMe | Q1k | a bond | Me | a bond | NH | O | NH | Q3a | OH |
| 2886 | N | NMe | Q1k | a bond | Me | a bond | NH | O | NH | Q3d | OH |

TABLE 1-continued

| No | A | B | R¹ | L¹ | R² | L² | L³ | Y | L⁴ | R³ | X |
|---|---|---|---|---|---|---|---|---|---|---|---|
| 2887 | N | NMe | Q1k | a bond | Me | a bond | NH | O | NH | Q3e | OH |
| 2888 | N | NMe | Q1k | a bond | Me | a bond | NH | O | NH | Q3f | OH |
| 2889 | N | NMe | Q1k | a bond | Me | a bond | NH | S | a bond | Q3a | OH |
| 2890 | N | NMe | Q1k | a bond | Me | a bond | NH | S | a bond | Q3d | OH |
| 2891 | N | NMe | Q1k | a bond | Me | a bond | NH | S | a bond | Q3e | OH |
| 2892 | N | NMe | Q1k | a bond | Me | a bond | NH | S | a bond | Q3f | OH |
| 2893 | N | NMe | Q1k | a bond | Me | a bond | NH | S | NH | Q3a | OH |
| 2894 | N | NMe | Q1k | a bond | Me | a bond | NH | S | NH | Q3d | OH |
| 2895 | N | NMe | Q1k | a bond | Me | a bond | NH | S | NH | Q3e | OH |
| 2896 | N | NMe | Q1k | a bond | Me | a bond | NH | S | NH | Q3f | OH |
| 2897 | N | NMe | Q1l | a bond | Me | a bond | NH | O | a bond | Q3a | OH |
| 2898 | N | NMe | Q1l | a bond | Me | a bond | NH | O | a bond | Q3d | OH |
| 2899 | N | NMe | Q1l | a bond | Me | a bond | NH | O | a bond | Q3e | OH |
| 2900 | N | NMe | Q1l | a bond | Me | a bond | NH | O | a bond | Q3f | OH |
| 2901 | N | NMe | Q1l | a bond | Me | a bond | NH | O | NH | Q3a | OH |
| 2902 | N | NMe | Q1l | a bond | Me | a bond | NH | O | NH | Q3d | OH |
| 2903 | N | NMe | Q1l | a bond | Me | a bond | NH | O | NH | Q3e | OH |
| 2904 | N | NMe | Q1l | a bond | Me | a bond | NH | O | NH | Q3f | OH |
| 2905 | N | NMe | Q1l | a bond | Me | a bond | NH | S | a bond | Q3a | OH |
| 2906 | N | NMe | Q1l | a bond | Me | a bond | NH | S | a bond | Q3d | OH |
| 2907 | N | NMe | Q1l | a bond | Me | a bond | NH | S | a bond | Q3e | OH |
| 2908 | N | NMe | Q1l | a bond | Me | a bond | NH | S | a bond | Q3f | OH |
| 2909 | N | NMe | Q1l | a bond | Me | a bond | NH | S | NH | Q3a | OH |
| 2910 | N | NMe | Q1l | a bond | Me | a bond | NH | S | NH | Q3d | OH |
| 2911 | N | NMe | Q1l | a bond | Me | a bond | NH | S | NH | Q3e | OH |
| 2912 | N | NMe | Q1l | a bond | Me | a bond | NH | S | NH | Q3f | OH |
| 2913 | N | NMe | Q1m | a bond | Me | a bond | NH | O | a bond | Q3a | OH |
| 2914 | N | NMe | Q1m | a bond | Me | a bond | NH | O | a bond | Q3d | OH |
| 2915 | N | NMe | Q1m | a bond | Me | a bond | NH | O | a bond | Q3e | OH |
| 2916 | N | NMe | Q1m | a bond | Me | a bond | NH | O | a bond | Q3f | OH |
| 2917 | N | NMe | Q1m | a bond | Me | a bond | NH | O | NH | Q3a | OH |
| 2918 | N | NMe | Q1m | a bond | Me | a bond | NH | O | NH | Q3d | OH |
| 2919 | N | NMe | Q1m | a bond | Me | a bond | NH | O | NH | Q3e | OH |
| 2920 | N | NMe | Q1m | a bond | Me | a bond | NH | O | NH | Q3f | OH |
| 2921 | N | NMe | Q1m | a bond | Me | a bond | NH | S | a bond | Q3a | OH |
| 2922 | N | NMe | Q1m | a bond | Me | a bond | NH | S | a bond | Q3d | OH |
| 2923 | N | NMe | Q1m | a bond | Me | a bond | NH | S | a bond | Q3e | OH |
| 2924 | N | NMe | Q1m | a bond | Me | a bond | NH | S | a bond | Q3f | OH |
| 2925 | N | NMe | Q1m | a bond | Me | a bond | NH | S | NH | Q3a | OH |
| 2926 | N | NMe | Q1m | a bond | Me | a bond | NH | S | NH | Q3d | OH |
| 2927 | N | NMe | Q1m | a bond | Me | a bond | NH | S | NH | Q3e | OH |
| 2928 | N | NMe | Q1m | a bond | Me | a bond | NH | S | NH | Q3f | OH |
| 2929 | N | NMe | Q1n | a bond | Me | a bond | NH | O | a bond | Q3a | OH |
| 2930 | N | NMe | Q1n | a bond | Me | a bond | NH | O | a bond | Q3d | OH |
| 2931 | N | NMe | Q1n | a bond | Me | a bond | NH | O | a bond | Q3e | OH |
| 2932 | N | NMe | Q1n | a bond | Me | a bond | NH | O | a bond | Q3f | OH |
| 2933 | N | NMe | Q1n | a bond | Me | a bond | NH | O | NH | Q3a | OH |
| 2934 | N | NMe | Q1n | a bond | Me | a bond | NH | O | NH | Q3d | OH |
| 2935 | N | NMe | Q1n | a bond | Me | a bond | NH | O | NH | Q3e | OH |
| 2936 | N | NMe | Q1n | a bond | Me | a bond | NH | O | NH | Q3f | OH |
| 2937 | N | NMe | Q1n | a bond | Me | a bond | NH | S | a bond | Q3a | OH |
| 2938 | N | NMe | Q1n | a bond | Me | a bond | NH | S | a bond | Q3d | OH |
| 2939 | N | NMe | Q1n | a bond | Me | a bond | NH | S | a bond | Q3e | OH |
| 2940 | N | NMe | Q1n | a bond | Me | a bond | NH | S | a bond | Q3f | OH |
| 2941 | N | NMe | Q1n | a bond | Me | a bond | NH | S | NH | Q3a | OH |
| 2942 | N | NMe | Q1n | a bond | Me | a bond | NH | S | NH | Q3d | OH |
| 2943 | N | NMe | Q1n | a bond | Me | a bond | NH | S | NH | Q3e | OH |
| 2944 | N | NMe | Q1n | a bond | Me | a bond | NH | S | NH | Q3f | OH |
| 2945 | N | NEt | Q1k | a bond | Me | a bond | NH | O | a bond | Q3a | OH |
| 2946 | N | NEt | Q1k | a bond | Me | a bond | NH | O | a bond | Q3d | OH |
| 2947 | N | NEt | Q1k | a bond | Me | a bond | NH | O | a bond | Q3e | OH |
| 2948 | N | NEt | Q1k | a bond | Me | a bond | NH | O | a bond | Q3f | OH |
| 2949 | N | NEt | Q1k | a bond | Me | a bond | NH | O | NH | Q3a | OH |
| 2950 | N | NEt | Q1k | a bond | Me | a bond | NH | O | NH | Q3d | OH |
| 2951 | N | NEt | Q1k | a bond | Me | a bond | NH | O | NH | Q3e | OH |
| 2952 | N | NEt | Q1k | a bond | Me | a bond | NH | O | NH | Q3f | OH |
| 2953 | N | NEt | Q1k | a bond | Me | a bond | NH | S | a bond | Q3a | OH |
| 2954 | N | NEt | Q1k | a bond | Me | a bond | NH | S | a bond | Q3d | OH |
| 2955 | N | NEt | Q1k | a bond | Me | a bond | NH | S | a bond | Q3e | OH |
| 2956 | N | NEt | Q1k | a bond | Me | a bond | NH | S | a bond | Q3f | OH |
| 2957 | N | NEt | Q1k | a bond | Me | a bond | NH | S | NH | Q3a | OH |
| 2958 | N | NEt | Q1k | a bond | Me | a bond | NH | S | NH | Q3d | OH |
| 2959 | N | NEt | Q1k | a bond | Me | a bond | NH | S | NH | Q3e | OH |
| 2960 | N | NEt | Q1k | a bond | Me | a bond | NH | S | NH | Q3f | OH |
| 2961 | N | NEt | Q1l | a bond | Me | a bond | NH | O | a bond | Q3a | OH |
| 2962 | N | NEt | Q1l | a bond | Me | a bond | NH | O | a bond | Q3d | OH |
| 2963 | N | NEt | Q1l | a bond | Me | a bond | NH | O | a bond | Q3e | OH |
| 2964 | N | NEt | Q1l | a bond | Me | a bond | NH | O | a bond | Q3f | OH |

TABLE 1-continued

| No | A | B | R¹ | L¹ | R² | L² | L³ | Y | L⁴ | R³ | X |
|---|---|---|---|---|---|---|---|---|---|---|---|
| 2965 | N | NEt | Q1l | a bond | Me | a bond | NH | O | NH | Q3a | OH |
| 2966 | N | NEt | Q1l | a bond | Me | a bond | NH | O | NH | Q3d | OH |
| 2967 | N | NEt | Q1l | a bond | Me | a bond | NH | O | NH | Q3e | OH |
| 2968 | N | NEt | Q1l | a bond | Me | a bond | NH | O | NH | Q3f | OH |
| 2969 | N | NEt | Q1l | a bond | Me | a bond | NH | S | a bond | Q3a | OH |
| 2970 | N | NEt | Q1l | a bond | Me | a bond | NH | S | a bond | Q3d | OH |
| 2971 | N | NEt | Q1l | a bond | Me | a bond | NH | S | a bond | Q3e | OH |
| 2972 | N | NEt | Q1l | a bond | Me | a bond | NH | S | a bond | Q3f | OH |
| 2973 | N | NEt | Q1l | a bond | Me | a bond | NH | S | NH | Q3a | OH |
| 2974 | N | NEt | Q1l | a bond | Me | a bond | NH | S | NH | Q3d | OH |
| 2975 | N | NEt | Q1l | a bond | Me | a bond | NH | S | NH | Q3e | OH |
| 2976 | N | NEt | Q1l | a bond | Me | a bond | NH | S | NH | Q3f | OH |
| 2977 | N | NEt | Q1m | a bond | Me | a bond | NH | O | a bond | Q3a | OH |
| 2978 | N | NEt | Q1m | a bond | Me | a bond | NH | O | a bond | Q3d | OH |
| 2979 | N | NEt | Q1m | a bond | Me | a bond | NH | O | a bond | Q3e | OH |
| 2980 | N | NEt | Q1m | a bond | Me | a bond | NH | O | a bond | Q3f | OH |
| 2981 | N | NEt | Q1m | a bond | Me | a bond | NH | O | NH | Q3a | OH |
| 2982 | N | NEt | Q1m | a bond | Me | a bond | NH | O | NH | Q3d | OH |
| 2983 | N | NEt | Q1m | a bond | Me | a bond | NH | O | NH | Q3e | OH |
| 2984 | N | NEt | Q1m | a bond | Me | a bond | NH | O | NH | Q3f | OH |
| 2985 | N | NEt | Q1m | a bond | Me | a bond | NH | S | a bond | Q3a | OH |
| 2986 | N | NEt | Q1m | a bond | Me | a bond | NH | S | a bond | Q3d | OH |
| 2987 | N | NEt | Q1m | a bond | Me | a bond | NH | S | a bond | Q3e | OH |
| 2988 | N | NEt | Q1m | a bond | Me | a bond | NH | S | a bond | Q3f | OH |
| 2989 | N | NEt | Q1m | a bond | Me | a bond | NH | S | NH | Q3a | OH |
| 2990 | N | NEt | Q1m | a bond | Me | a bond | NH | S | NH | Q3d | OH |
| 2991 | N | NEt | Q1m | a bond | Me | a bond | NH | S | NH | Q3e | OH |
| 2992 | N | NEt | Q1m | a bond | Me | a bond | NH | S | NH | Q3f | OH |
| 2993 | N | NEt | Q1n | a bond | Me | a bond | NH | O | a bond | Q3a | OH |
| 2994 | N | NEt | Q1n | a bond | Me | a bond | NH | O | a bond | Q3d | OH |
| 2995 | N | NEt | Q1n | a bond | Me | a bond | NH | O | a bond | Q3e | OH |
| 2996 | N | NEt | Q1n | a bond | Me | a bond | NH | O | a bond | Q3f | OH |
| 2997 | N | NEt | Q1n | a bond | Me | a bond | NH | O | NH | Q3a | OH |
| 2998 | N | NEt | Q1n | a bond | Me | a bond | NH | O | NH | Q3d | OH |
| 2999 | N | NEt | Q1n | a bond | Me | a bond | NH | O | NH | Q3e | OH |
| 3000 | N | NEt | Q1n | a bond | Me | a bond | NH | O | NH | Q3f | OH |
| 3001 | N | NEt | Q1n | a bond | Me | a bond | NH | S | a bond | Q3a | OH |
| 3002 | N | NEt | Q1n | a bond | Me | a bond | NH | S | a bond | Q3d | OH |
| 3003 | N | NEt | Q1n | a bond | Me | a bond | NH | S | a bond | Q3e | OH |
| 3004 | N | NEt | Q1n | a bond | Me | a bond | NH | S | a bond | Q3f | OH |
| 3005 | N | NEt | Q1n | a bond | Me | a bond | NH | S | NH | Q3a | OH |
| 3006 | N | NEt | Q1n | a bond | Me | a bond | NH | S | NH | Q3d | OH |
| 3007 | N | NEt | Q1n | a bond | Me | a bond | NH | S | NH | Q3e | OH |
| 3008 | N | NEt | Q1n | a bond | Me | a bond | NH | S | NH | Q3f | OH |
| 3009 | N | S | Q1k | a bond | Me | a bond | NH | O | a bond | Q3a | OH |
| 3010 | N | S | Q1k | a bond | Me | a bond | NH | O | a bond | Q3d | OH |
| 3011 | N | S | Q1k | a bond | Me | a bond | NH | O | a bond | Q3e | OH |
| 3012 | N | S | Q1k | a bond | Me | a bond | NH | O | a bond | Q3f | OH |
| 3013 | N | S | Q1k | a bond | Me | a bond | NH | O | NH | Q3a | OH |
| 3014 | N | S | Q1k | a bond | Me | a bond | NH | O | NH | Q3d | OH |
| 3015 | N | S | Q1k | a bond | Me | a bond | NH | O | NH | Q3e | OH |
| 3016 | N | S | Q1k | a bond | Me | a bond | NH | O | NH | Q3f | OH |
| 3017 | N | S | Q1k | a bond | Me | a bond | NH | S | a bond | Q3a | OH |
| 3018 | N | S | Q1k | a bond | Me | a bond | NH | S | a bond | Q3d | OH |
| 3019 | N | S | Q1k | a bond | Me | a bond | NH | S | a bond | Q3e | OH |
| 3020 | N | S | Q1k | a bond | Me | a bond | NH | S | a bond | Q3f | OH |
| 3021 | N | S | Q1k | a bond | Me | a bond | NH | S | NH | Q3a | OH |
| 3022 | N | S | Q1k | a bond | Me | a bond | NH | S | NH | Q3d | OH |
| 3023 | N | S | Q1k | a bond | Me | a bond | NH | S | NH | Q3e | OH |
| 3024 | N | S | Q1k | a bond | Me | a bond | NH | S | NH | Q3f | OH |
| 3025 | N | S | Q1l | a bond | Me | a bond | NH | O | a bond | Q3a | OH |
| 3026 | N | S | Q1l | a bond | Me | a bond | NH | O | a bond | Q3d | OH |
| 3027 | N | S | Q1l | a bond | Me | a bond | NH | O | a bond | Q3e | OH |
| 3028 | N | S | Q1l | a bond | Me | a bond | NH | O | a bond | Q3f | OH |
| 3029 | N | S | Q1l | a bond | Me | a bond | NH | O | NH | Q3a | OH |
| 3030 | N | S | Q1l | a bond | Me | a bond | NH | O | NH | Q3d | OH |
| 3031 | N | S | Q1l | a bond | Me | a bond | NH | O | NH | Q3e | OH |
| 3032 | N | S | Q1l | a bond | Me | a bond | NH | O | NH | Q3f | OH |
| 3033 | N | S | Q1l | a bond | Me | a bond | NH | S | a bond | Q3a | OH |
| 3034 | N | S | Q1l | a bond | Me | a bond | NH | S | a bond | Q3d | OH |
| 3035 | N | S | Q1l | a bond | Me | a bond | NH | S | a bond | Q3e | OH |
| 3036 | N | S | Q1l | a bond | Me | a bond | NH | S | a bond | Q3f | OH |
| 3037 | N | S | Q1l | a bond | Me | a bond | NH | S | NH | Q3a | OH |
| 3038 | N | S | Q1l | a bond | Me | a bond | NH | S | NH | Q3d | OH |
| 3039 | N | S | Q1l | a bond | Me | a bond | NH | S | NH | Q3e | OH |
| 3040 | N | S | Q1l | a bond | Me | a bond | NH | S | NH | Q3f | OH |
| 3041 | N | S | Q1m | a bond | Me | a bond | NH | O | a bond | Q3a | OH |
| 3042 | N | S | Q1m | a bond | Me | a bond | NH | O | a bond | Q3d | OH |

TABLE 1-continued

| No | A | B | R¹ | L¹ | R² | L² | L³ | Y | L⁴ | R³ | X |
|---|---|---|---|---|---|---|---|---|---|---|---|
| 3043 | N | S | Q1m | a bond | Me | a bond | NH | O | a bond | Q3e | OH |
| 3044 | N | S | Q1m | a bond | Me | a bond | NH | O | a bond | Q3f | OH |
| 3045 | N | S | Q1m | a bond | Me | a bond | NH | O | NH | Q3a | OH |
| 3046 | N | S | Q1m | a bond | Me | a bond | NH | O | NH | Q3d | OH |
| 3047 | N | S | Q1m | a bond | Me | a bond | NH | O | NH | Q3e | OH |
| 3048 | N | S | Q1m | a bond | Me | a bond | NH | O | NH | Q3f | OH |
| 3049 | N | S | Q1m | a bond | Me | a bond | NH | S | a bond | Q3a | OH |
| 3050 | N | S | Q1m | a bond | Me | a bond | NH | S | a bond | Q3d | OH |
| 3051 | N | S | Q1m | a bond | Me | a bond | NH | S | a bond | Q3e | OH |
| 3052 | N | S | Q1m | a bond | Me | a bond | NH | S | a bond | Q3f | OH |
| 3053 | N | S | Q1m | a bond | Me | a bond | NH | S | NH | Q3a | OH |
| 3054 | N | S | Q1m | a bond | Me | a bond | NH | S | NH | Q3d | OH |
| 3055 | N | S | Q1m | a bond | Me | a bond | NH | S | NH | Q3e | OH |
| 3056 | N | S | Q1m | a bond | Me | a bond | NH | S | NH | Q3f | OH |
| 3057 | N | S | Q1n | a bond | Me | a bond | NH | O | a bond | Q3a | OH |
| 3058 | N | S | Q1n | a bond | Me | a bond | NH | O | a bond | Q3d | OH |
| 3059 | N | S | Q1n | a bond | Me | a bond | NH | O | a bond | Q3e | OH |
| 3060 | N | S | Q1n | a bond | Me | a bond | NH | O | a bond | Q3f | OH |
| 3061 | N | S | Q1n | a bond | Me | a bond | NH | O | NH | Q3a | OH |
| 3062 | N | S | Q1n | a bond | Me | a bond | NH | O | NH | Q3d | OH |
| 3063 | N | S | Q1n | a bond | Me | a bond | NH | O | NH | Q3e | OH |
| 3064 | N | S | Q1n | a bond | Me | a bond | NH | O | NH | Q3f | OH |
| 3065 | N | S | Q1n | a bond | Me | a bond | NH | S | a bond | Q3a | OH |
| 3066 | N | S | Q1n | a bond | Me | a bond | NH | S | a bond | Q3d | OH |
| 3067 | N | S | Q1n | a bond | Me | a bond | NH | S | a bond | Q3e | OH |
| 3068 | N | S | Q1n | a bond | Me | a bond | NH | S | a bond | Q3f | OH |
| 3069 | N | S | Q1n | a bond | Me | a bond | NH | S | NH | Q3a | OH |
| 3070 | N | S | Q1n | a bond | Me | a bond | NH | S | NH | Q3d | OH |
| 3071 | N | S | Q1n | a bond | Me | a bond | NH | S | NH | Q3e | OH |
| 3072 | N | S | Q1n | a bond | Me | a bond | NH | S | NH | Q3f | OH |
| 3073 | N | O | Q1k | a bond | Me | a bond | NH | O | a bond | Q3a | OH |
| 3074 | N | O | Q1k | a bond | Me | a bond | NH | O | a bond | Q3d | OH |
| 3075 | N | O | Q1k | a bond | Me | a bond | NH | O | a bond | Q3e | OH |
| 3076 | N | O | Q1k | a bond | Me | a bond | NH | O | a bond | Q3f | OH |
| 3077 | N | O | Q1k | a bond | Me | a bond | NH | O | NH | Q3a | OH |
| 3078 | N | O | Q1k | a bond | Me | a bond | NH | O | NH | Q3d | OH |
| 3079 | N | O | Q1k | a bond | Me | a bond | NH | O | NH | Q3e | OH |
| 3080 | N | O | Q1k | a bond | Me | a bond | NH | O | NH | Q3f | OH |
| 3081 | N | O | Q1k | a bond | Me | a bond | NH | S | a bond | Q3a | OH |
| 3082 | N | O | Q1k | a bond | Me | a bond | NH | S | a bond | Q3d | OH |
| 3083 | N | O | Q1k | a bond | Me | a bond | NH | S | a bond | Q3e | OH |
| 3084 | N | O | Q1k | a bond | Me | a bond | NH | S | a bond | Q3f | OH |
| 3085 | N | O | Q1k | a bond | Me | a bond | NH | S | NH | Q3a | OH |
| 3086 | N | O | Q1k | a bond | Me | a bond | NH | S | NH | Q3d | OH |
| 3087 | N | O | Q1k | a bond | Me | a bond | NH | S | NH | Q3e | OH |
| 3088 | N | O | Q1k | a bond | Me | a bond | NH | S | NH | Q3f | OH |
| 3089 | N | O | Q1l | a bond | Me | a bond | NH | O | a bond | Q3a | OH |
| 3090 | N | O | Q1l | a bond | Me | a bond | NH | O | a bond | Q3d | OH |
| 3091 | N | O | Q1l | a bond | Me | a bond | NH | O | a bond | Q3e | OH |
| 3092 | N | O | Q1l | a bond | Me | a bond | NH | O | a bond | Q3f | OH |
| 3093 | N | O | Q1l | a bond | Me | a bond | NH | O | NH | Q3a | OH |
| 3094 | N | O | Q1l | a bond | Me | a bond | NH | O | NH | Q3d | OH |
| 3095 | N | O | Q1l | a bond | Me | a bond | NH | O | NH | Q3e | OH |
| 3096 | N | O | Q1l | a bond | Me | a bond | NH | O | NH | Q3f | OH |
| 3097 | N | O | Q1l | a bond | Me | a bond | NH | S | a bond | Q3a | OH |
| 3098 | N | O | Q1l | a bond | Me | a bond | NH | S | a bond | Q3d | OH |
| 3099 | N | O | Q1l | a bond | Me | a bond | NH | S | a bond | Q3e | OH |
| 3100 | N | O | Q1l | a bond | Me | a bond | NH | S | a bond | Q3f | OH |
| 3101 | N | O | Q1l | a bond | Me | a bond | NH | S | NH | Q3a | OH |
| 3102 | N | O | Q1l | a bond | Me | a bond | NH | S | NH | Q3d | OH |
| 3103 | N | O | Q1l | a bond | Me | a bond | NH | S | NH | Q3e | OH |
| 3104 | N | O | Q1l | a bond | Me | a bond | NH | S | NH | Q3f | OH |
| 3105 | N | O | Q1m | a bond | Me | a bond | NH | O | a bond | Q3a | OH |
| 3106 | N | O | Q1m | a bond | Me | a bond | NH | O | a bond | Q3d | OH |
| 3107 | N | O | Q1m | a bond | Me | a bond | NH | O | a bond | Q3e | OH |
| 3108 | N | O | Q1m | a bond | Me | a bond | NH | O | a bond | Q3f | OH |
| 3109 | N | O | Q1m | a bond | Me | a bond | NH | O | NH | Q3a | OH |
| 3110 | N | O | Q1m | a bond | Me | a bond | NH | O | NH | Q3d | OH |
| 3111 | N | O | Q1m | a bond | Me | a bond | NH | O | NH | Q3e | OH |
| 3112 | N | O | Q1m | a bond | Me | a bond | NH | O | NH | Q3f | OH |
| 3113 | N | O | Q1m | a bond | Me | a bond | NH | S | a bond | Q3a | OH |
| 3114 | N | O | Q1m | a bond | Me | a bond | NH | S | a bond | Q3d | OH |
| 3115 | N | O | Q1m | a bond | Me | a bond | NH | S | a bond | Q3e | OH |
| 3116 | N | O | Q1m | a bond | Me | a bond | NH | S | a bond | Q3f | OH |
| 3117 | N | O | Q1m | a bond | Me | a bond | NH | S | NH | Q3a | OH |
| 3118 | N | O | Q1m | a bond | Me | a bond | NH | S | NH | Q3d | OH |
| 3119 | N | O | Q1m | a bond | Me | a bond | NH | S | NH | Q3e | OH |
| 3120 | N | O | Q1m | a bond | Me | a bond | NH | S | NH | Q3f | OH |

TABLE 1-continued

| No | A | B | R¹ | L¹ | R² | L² | L³ | Y | L⁴ | R³ | X |
|---|---|---|---|---|---|---|---|---|---|---|---|
| 3121 | N | O | Q1n | a bond | Me | a bond | NH | O | a bond | Q3a | OH |
| 3122 | N | O | Q1n | a bond | Me | a bond | NH | O | a bond | Q3d | OH |
| 3123 | N | O | Q1n | a bond | Me | a bond | NH | O | a bond | Q3e | OH |
| 3124 | N | O | Q1n | a bond | Me | a bond | NH | O | a bond | Q3f | OH |
| 3125 | N | O | Q1n | a bond | Me | a bond | NH | O | NH | Q3a | OH |
| 3126 | N | O | Q1n | a bond | Me | a bond | NH | O | NH | Q3d | OH |
| 3127 | N | O | Q1n | a bond | Me | a bond | NH | O | NH | Q3e | OH |
| 3128 | N | O | Q1n | a bond | Me | a bond | NH | O | NH | Q3f | OH |
| 3129 | N | O | Q1n | a bond | Me | a bond | NH | S | a bond | Q3a | OH |
| 3130 | N | O | Q1n | a bond | Me | a bond | NH | S | a bond | Q3d | OH |
| 3131 | N | O | Q1n | a bond | Me | a bond | NH | S | a bond | Q3e | OH |
| 3132 | N | O | Q1n | a bond | Me | a bond | NH | S | a bond | Q3f | OH |
| 3133 | N | O | Q1n | a bond | Me | a bond | NH | S | NH | Q3a | OH |
| 3134 | N | O | Q1n | a bond | Me | a bond | NH | S | NH | Q3d | OH |
| 3135 | N | O | Q1n | a bond | Me | a bond | NH | S | NH | Q3e | OH |
| 3136 | N | O | Q1n | a bond | Me | a bond | NH | S | NH | Q3f | OH |
| 3137 | CH | NMe | Q1k | a bond | Me | a bond | NH | O | a bond | Q3a | OH |
| 3138 | CH | NMe | Q1k | a bond | Me | a bond | NH | O | a bond | Q3d | OH |
| 3139 | CH | NMe | Q1k | a bond | Me | a bond | NH | O | a bond | Q3e | OH |
| 3140 | CH | NMe | Q1k | a bond | Me | a bond | NH | O | a bond | Q3f | OH |
| 3141 | CH | NMe | Q1k | a bond | Me | a bond | NH | O | NH | Q3a | OH |
| 3142 | CH | NMe | Q1k | a bond | Me | a bond | NH | O | NH | Q3d | OH |
| 3143 | CH | NMe | Q1k | a bond | Me | a bond | NH | O | NH | Q3e | OH |
| 3144 | CH | NMe | Q1k | a bond | Me | a bond | NH | O | NH | Q3f | OH |
| 3145 | CH | NMe | Q1k | a bond | Me | a bond | NH | S | a bond | Q3a | OH |
| 3146 | CH | NMe | Q1k | a bond | Me | a bond | NH | S | a bond | Q3d | OH |
| 3147 | CH | NMe | Q1k | a bond | Me | a bond | NH | S | a bond | Q3e | OH |
| 3148 | CH | NMe | Q1k | a bond | Me | a bond | NH | S | a bond | Q3f | OH |
| 3149 | CH | NMe | Q1k | a bond | Me | a bond | NH | S | NH | Q3a | OH |
| 3150 | CH | NMe | Q1k | a bond | Me | a bond | NH | S | NH | Q3d | OH |
| 3151 | CH | NMe | Q1k | a bond | Me | a bond | NH | S | NH | Q3e | OH |
| 3152 | CH | NMe | Q1k | a bond | Me | a bond | NH | S | NH | Q3f | OH |
| 3153 | CH | NMe | Q1l | a bond | Me | a bond | NH | O | a bond | Q3a | OH |
| 3154 | CH | NMe | Q1l | a bond | Me | a bond | NH | O | a bond | Q3d | OH |
| 3155 | CH | NMe | Q1l | a bond | Me | a bond | NH | O | a bond | Q3e | OH |
| 3156 | CH | NMe | Q1l | a bond | Me | a bond | NH | O | a bond | Q3f | OH |
| 3157 | CH | NMe | Q1l | a bond | Me | a bond | NH | O | NH | Q3a | OH |
| 3158 | CH | NMe | Q1l | a bond | Me | a bond | NH | O | NH | Q3d | OH |
| 3159 | CH | NMe | Q1l | a bond | Me | a bond | NH | O | NH | Q3e | OH |
| 3160 | CH | NMe | Q1l | a bond | Me | a bond | NH | O | NH | Q3f | OH |
| 3161 | CH | NMe | Q1l | a bond | Me | a bond | NH | S | a bond | Q3a | OH |
| 3162 | CH | NMe | Q1l | a bond | Me | a bond | NH | S | a bond | Q3d | OH |
| 3163 | CH | NMe | Q1l | a bond | Me | a bond | NH | S | a bond | Q3e | OH |
| 3164 | CH | NMe | Q1l | a bond | Me | a bond | NH | S | a bond | Q3f | OH |
| 3165 | CH | NMe | Q1l | a bond | Me | a bond | NH | S | NH | Q3a | OH |
| 3166 | CH | NMe | Q1l | a bond | Me | a bond | NH | S | NH | Q3d | OH |
| 3167 | CH | NMe | Q1l | a bond | Me | a bond | NH | S | NH | Q3e | OH |
| 3168 | CH | NMe | Q1l | a bond | Me | a bond | NH | S | NH | Q3f | OH |
| 3169 | CH | NMe | Q1m | a bond | Me | a bond | NH | O | a bond | Q3a | OH |
| 3170 | CH | NMe | Q1m | a bond | Me | a bond | NH | O | a bond | Q3d | OH |
| 3171 | CH | NMe | Q1m | a bond | Me | a bond | NH | O | a bond | Q3e | OH |
| 3172 | CH | NMe | Q1m | a bond | Me | a bond | NH | O | a bond | Q3f | OH |
| 3173 | CH | NMe | Q1m | a bond | Me | a bond | NH | O | NH | Q3a | OH |
| 3174 | CH | NMe | Q1m | a bond | Me | a bond | NH | O | NH | Q3d | OH |
| 3175 | CH | NMe | Q1m | a bond | Me | a bond | NH | O | NH | Q3e | OH |
| 3176 | CH | NMe | Q1m | a bond | Me | a bond | NH | O | NH | Q3f | OH |
| 3177 | CH | NMe | Q1m | a bond | Me | a bond | NH | S | a bond | Q3a | OH |
| 3178 | CH | NMe | Q1m | a bond | Me | a bond | NH | S | a bond | Q3d | OH |
| 3179 | CH | NMe | Q1m | a bond | Me | a bond | NH | S | a bond | Q3e | OH |
| 3180 | CH | NMe | Q1m | a bond | Me | a bond | NH | S | a bond | Q3f | OH |
| 3181 | CH | NMe | Q1m | a bond | Me | a bond | NH | S | NH | Q3a | OH |
| 3182 | CH | NMe | Q1m | a bond | Me | a bond | NH | S | NH | Q3d | OH |
| 3183 | CH | NMe | Q1m | a bond | Me | a bond | NH | S | NH | Q3e | OH |
| 3184 | CH | NMe | Q1m | a bond | Me | a bond | NH | S | NH | Q3f | OH |
| 3185 | CH | NMe | Q1n | a bond | Me | a bond | NH | O | a bond | Q3a | OH |
| 3186 | CH | NMe | Q1n | a bond | Me | a bond | NH | O | a bond | Q3d | OH |
| 3187 | CH | NMe | Q1n | a bond | Me | a bond | NH | O | a bond | Q3e | OH |
| 3188 | CH | NMe | Q1n | a bond | Me | a bond | NH | O | a bond | Q3f | OH |
| 3189 | CH | NMe | Q1n | a bond | Me | a bond | NH | O | NH | Q3a | OH |
| 3190 | CH | NMe | Q1n | a bond | Me | a bond | NH | O | NH | Q3d | OH |
| 3191 | CH | NMe | Q1n | a bond | Me | a bond | NH | O | NH | Q3e | OH |
| 3192 | CH | NMe | Q1n | a bond | Me | a bond | NH | O | NH | Q3f | OH |
| 3193 | CH | NMe | Q1n | a bond | Me | a bond | NH | S | a bond | Q3a | OH |
| 3194 | CH | NMe | Q1n | a bond | Me | a bond | NH | S | a bond | Q3d | OH |
| 3195 | CH | NMe | Q1n | a bond | Me | a bond | NH | S | a bond | Q3e | OH |
| 3196 | CH | NMe | Q1n | a bond | Me | a bond | NH | S | a bond | Q3f | OH |
| 3197 | CH | NMe | Q1n | a bond | Me | a bond | NH | S | NH | Q3a | OH |
| 3198 | CH | NMe | Q1n | a bond | Me | a bond | NH | S | NH | Q3d | OH |

TABLE 1-continued

| No | A | B | R¹ | L¹ | R² | L² | L³ | Y | L⁴ | R³ | X |
|---|---|---|---|---|---|---|---|---|---|---|---|
| 3199 | CH | NMe | Q1n | a bond | Me | a bond | NH | S | NH | Q3e | OH |
| 3200 | CH | NMe | Q1n | a bond | Me | a bond | NH | S | NH | Q3f | OH |
| 3201 | CH | NEt | Q1k | a bond | Me | a bond | NH | O | a bond | Q3a | OH |
| 3202 | CH | NEt | Q1k | a bond | Me | a bond | NH | O | a bond | Q3d | OH |
| 3203 | CH | NEt | Q1k | a bond | Me | a bond | NH | O | a bond | Q3e | OH |
| 3204 | CH | NEt | Q1k | a bond | Me | a bond | NH | O | a bond | Q3f | OH |
| 3205 | CH | NEt | Q1k | a bond | Me | a bond | NH | O | NH | Q3a | OH |
| 3206 | CH | NEt | Q1k | a bond | Me | a bond | NH | O | NH | Q3d | OH |
| 3207 | CH | NEt | Q1k | a bond | Me | a bond | NH | O | NH | Q3e | OH |
| 3208 | CH | NEt | Q1k | a bond | Me | a bond | NH | O | NH | Q3f | OH |
| 3209 | CH | NEt | Q1k | a bond | Me | a bond | NH | S | a bond | Q3a | OH |
| 3210 | CH | NEt | Q1k | a bond | Me | a bond | NH | S | a bond | Q3d | OH |
| 3211 | CH | NEt | Q1k | a bond | Me | a bond | NH | S | a bond | Q3e | OH |
| 3212 | CH | NEt | Q1k | a bond | Me | a bond | NH | S | a bond | Q3f | OH |
| 3213 | CH | NEt | Q1k | a bond | Me | a bond | NH | S | NH | Q3a | OH |
| 3214 | CH | NEt | Q1k | a bond | Me | a bond | NH | S | NH | Q3d | OH |
| 3215 | CH | NEt | Q1k | a bond | Me | a bond | NH | S | NH | Q3e | OH |
| 3216 | CH | NEt | Q1k | a bond | Me | a bond | NH | S | NH | Q3f | OH |
| 3217 | CH | NEt | Q1l | a bond | Me | a bond | NH | O | a bond | Q3a | OH |
| 3218 | CH | NEt | Q1l | a bond | Me | a bond | NH | O | a bond | Q3d | OH |
| 3219 | CH | NEt | Q1l | a bond | Me | a bond | NH | O | a bond | Q3e | OH |
| 3220 | CH | NEt | Q1l | a bond | Me | a bond | NH | O | a bond | Q3f | OH |
| 3221 | CH | NEt | Q1l | a bond | Me | a bond | NH | O | NH | Q3a | OH |
| 3222 | CH | NEt | Q1l | a bond | Me | a bond | NH | O | NH | Q3d | OH |
| 3223 | CH | NEt | Q1l | a bond | Me | a bond | NH | O | NH | Q3e | OH |
| 3224 | CH | NEt | Q1l | a bond | Me | a bond | NH | O | NH | Q3f | OH |
| 3225 | CH | NEt | Q1l | a bond | Me | a bond | NH | S | a bond | Q3a | OH |
| 3226 | CH | NEt | Q1l | a bond | Me | a bond | NH | S | a bond | Q3d | OH |
| 3227 | CH | NEt | Q1l | a bond | Me | a bond | NH | S | a bond | Q3e | OH |
| 3228 | CH | NEt | Q1l | a bond | Me | a bond | NH | S | a bond | Q3f | OH |
| 3229 | CH | NEt | Q1l | a bond | Me | a bond | NH | S | NH | Q3a | OH |
| 3230 | CH | NEt | Q1l | a bond | Me | a bond | NH | S | NH | Q3d | OH |
| 3231 | CH | NEt | Q1l | a bond | Me | a bond | NH | S | NH | Q3e | OH |
| 3232 | CH | NEt | Q1l | a bond | Me | a bond | NH | S | NH | Q3f | OH |
| 3233 | CH | NEt | Q1m | a bond | Me | a bond | NH | O | a bond | Q3a | OH |
| 3234 | CH | NEt | Q1m | a bond | Me | a bond | NH | O | a bond | Q3d | OH |
| 3235 | CH | NEt | Q1m | a bond | Me | a bond | NH | O | a bond | Q3e | OH |
| 3236 | CH | NEt | Q1m | a bond | Me | a bond | NH | O | a bond | Q3f | OH |
| 3237 | CH | NEt | Q1m | a bond | Me | a bond | NH | O | NH | Q3a | OH |
| 3238 | CH | NEt | Q1m | a bond | Me | a bond | NH | O | NH | Q3d | OH |
| 3239 | CH | NEt | Q1m | a bond | Me | a bond | NH | O | NH | Q3e | OH |
| 3240 | CH | NEt | Q1m | a bond | Me | a bond | NH | O | NH | Q3f | OH |
| 3241 | CH | NEt | Q1m | a bond | Me | a bond | NH | S | a bond | Q3a | OH |
| 3242 | CH | NEt | Q1m | a bond | Me | a bond | NH | S | a bond | Q3d | OH |
| 3243 | CH | NEt | Q1m | a bond | Me | a bond | NH | S | a bond | Q3e | OH |
| 3244 | CH | NEt | Q1m | a bond | Me | a bond | NH | S | a bond | Q3f | OH |
| 3245 | CH | NEt | Q1m | a bond | Me | a bond | NH | S | NH | Q3a | OH |
| 3246 | CH | NEt | Q1m | a bond | Me | a bond | NH | S | NH | Q3d | OH |
| 3247 | CH | NEt | Q1m | a bond | Me | a bond | NH | S | NH | Q3e | OH |
| 3248 | CH | NEt | Q1m | a bond | Me | a bond | NH | S | NH | Q3f | OH |
| 3249 | CH | NEt | Q1n | a bond | Me | a bond | NH | O | a bond | Q3a | OH |
| 3250 | CH | NEt | Q1n | a bond | Me | a bond | NH | O | a bond | Q3d | OH |
| 3251 | CH | NEt | Q1n | a bond | Me | a bond | NH | O | a bond | Q3e | OH |
| 3252 | CH | NEt | Q1n | a bond | Me | a bond | NH | O | a bond | Q3f | OH |
| 3253 | CH | NEt | Q1n | a bond | Me | a bond | NH | O | NH | Q3a | OH |
| 3254 | CH | NEt | Q1n | a bond | Me | a bond | NH | O | NH | Q3d | OH |
| 3255 | CH | NEt | Q1n | a bond | Me | a bond | NH | O | NH | Q3e | OH |
| 3256 | CH | NEt | Q1n | a bond | Me | a bond | NH | O | NH | Q3f | OH |
| 3257 | CH | NEt | Q1n | a bond | Me | a bond | NH | S | a bond | Q3a | OH |
| 3258 | CH | NEt | Q1n | a bond | Me | a bond | NH | S | a bond | Q3d | OH |
| 3259 | CH | NEt | Q1n | a bond | Me | a bond | NH | S | a bond | Q3e | OH |
| 3260 | CH | NEt | Q1n | a bond | Me | a bond | NH | S | a bond | Q3f | OH |
| 3261 | CH | NEt | Q1n | a bond | Me | a bond | NH | S | NH | Q3a | OH |
| 3262 | CH | NEt | Q1n | a bond | Me | a bond | NH | S | NH | Q3d | OH |
| 3263 | CH | NEt | Q1n | a bond | Me | a bond | NH | S | NH | Q3e | OH |
| 3264 | CH | NEt | Q1n | a bond | Me | a bond | NH | S | NH | Q3f | OH |
| 3265 | CH | S | Q1k | a bond | Me | a bond | NH | O | a bond | Q3a | OH |
| 3266 | CH | S | Q1k | a bond | Me | a bond | NH | O | a bond | Q3d | OH |
| 3267 | CH | S | Q1k | a bond | Me | a bond | NH | O | a bond | Q3e | OH |
| 3268 | CH | S | Q1k | a bond | Me | a bond | NH | O | a bond | Q3f | OH |
| 3269 | CH | S | Q1k | a bond | Me | a bond | NH | O | NH | Q3a | OH |
| 3270 | CH | S | Q1k | a bond | Me | a bond | NH | O | NH | Q3d | OH |
| 3271 | CH | S | Q1k | a bond | Me | a bond | NH | O | NH | Q3e | OH |
| 3272 | CH | S | Q1k | a bond | Me | a bond | NH | O | NH | Q3f | OH |
| 3273 | CH | S | Q1k | a bond | Me | a bond | NH | S | a bond | Q3a | OH |
| 3274 | CH | S | Q1k | a bond | Me | a bond | NH | S | a bond | Q3d | OH |
| 3275 | CH | S | Q1k | a bond | Me | a bond | NH | S | a bond | Q3e | OH |
| 3276 | CH | S | Q1k | a bond | Me | a bond | NH | S | a bond | Q3f | OH |

TABLE 1-continued

| No | A | B | R¹ | L¹ | R² | L² | L³ | Y | L⁴ | R³ | X |
|---|---|---|---|---|---|---|---|---|---|---|---|
| 3277 | CH | S | Q1k | a bond | Me | a bond | NH | S | NH | Q3a | OH |
| 3278 | CH | S | Q1k | a bond | Me | a bond | NH | S | NH | Q3d | OH |
| 3279 | CH | S | Q1k | a bond | Me | a bond | NH | S | NH | Q3e | OH |
| 3280 | CH | S | Q1k | a bond | Me | a bond | NH | S | NH | Q3f | OH |
| 3281 | CH | S | Q1l | a bond | Me | a bond | NH | O | a bond | Q3a | OH |
| 3282 | CH | S | Q1l | a bond | Me | a bond | NH | O | a bond | Q3d | OH |
| 3283 | CH | S | Q1l | a bond | Me | a bond | NH | O | a bond | Q3e | OH |
| 3284 | CH | S | Q1l | a bond | Me | a bond | NH | O | a bond | Q3f | OH |
| 3285 | CH | S | Q1l | a bond | Me | a bond | NH | O | NH | Q3a | OH |
| 3286 | CH | S | Q1l | a bond | Me | a bond | NH | O | NH | Q3d | OH |
| 3287 | CH | S | Q1l | a bond | Me | a bond | NH | O | NH | Q3e | OH |
| 3288 | CH | S | Q1l | a bond | Me | a bond | NH | O | NH | Q3f | OH |
| 3289 | CH | S | Q1l | a bond | Me | a bond | NH | S | a bond | Q3a | OH |
| 3290 | CH | S | Q1l | a bond | Me | a bond | NH | S | a bond | Q3d | OH |
| 3291 | CH | S | Q1l | a bond | Me | a bond | NH | S | a bond | Q3e | OH |
| 3292 | CH | S | Q1l | a bond | Me | a bond | NH | S | a bond | Q3f | OH |
| 3293 | CH | S | Q1l | a bond | Me | a bond | NH | S | NH | Q3a | OH |
| 3294 | CH | S | Q1l | a bond | Me | a bond | NH | S | NH | Q3d | OH |
| 3295 | CH | S | Q1l | a bond | Me | a bond | NH | S | NH | Q3e | OH |
| 3296 | CH | S | Q1l | a bond | Me | a bond | NH | S | NH | Q3f | OH |
| 3297 | CH | S | Q1m | a bond | Me | a bond | NH | O | a bond | Q3a | OH |
| 3298 | CH | S | Q1m | a bond | Me | a bond | NH | O | a bond | Q3d | OH |
| 3299 | CH | S | Q1m | a bond | Me | a bond | NH | O | a bond | Q3e | OH |
| 3300 | CH | S | Q1m | a bond | Me | a bond | NH | O | a bond | Q3f | OH |
| 3301 | CH | S | Q1m | a bond | Me | a bond | NH | O | NH | Q3a | OH |
| 3302 | CH | S | Q1m | a bond | Me | a bond | NH | O | NH | Q3d | OH |
| 3303 | CH | S | Q1m | a bond | Me | a bond | NH | O | NH | Q3e | OH |
| 3304 | CH | S | Q1m | a bond | Me | a bond | NH | O | NH | Q3f | OH |
| 3305 | CH | S | Q1m | a bond | Me | a bond | NH | S | a bond | Q3a | OH |
| 3306 | CH | S | Q1m | a bond | Me | a bond | NH | S | a bond | Q3d | OH |
| 3307 | CH | S | Q1m | a bond | Me | a bond | NH | S | a bond | Q3e | OH |
| 3308 | CH | S | Q1m | a bond | Me | a bond | NH | S | a bond | Q3f | OH |
| 3309 | CH | S | Q1m | a bond | Me | a bond | NH | S | NH | Q3a | OH |
| 3310 | CH | S | Q1m | a bond | Me | a bond | NH | S | NH | Q3d | OH |
| 3311 | CH | S | Q1m | a bond | Me | a bond | NH | S | NH | Q3e | OH |
| 3312 | CH | S | Q1m | a bond | Me | a bond | NH | S | NH | Q3f | OH |
| 3313 | CH | S | Q1n | a bond | Me | a bond | NH | O | a bond | Q3a | OH |
| 3314 | CH | S | Q1n | a bond | Me | a bond | NH | O | a bond | Q3d | OH |
| 3315 | CH | S | Q1n | a bond | Me | a bond | NH | O | a bond | Q3e | OH |
| 3316 | CH | S | Q1n | a bond | Me | a bond | NH | O | a bond | Q3f | OH |
| 3317 | CH | S | Q1n | a bond | Me | a bond | NH | O | NH | Q3a | OH |
| 3318 | CH | S | Q1n | a bond | Me | a bond | NH | O | NH | Q3d | OH |
| 3319 | CH | S | Q1n | a bond | Me | a bond | NH | O | NH | Q3e | OH |
| 3320 | CH | S | Q1n | a bond | Me | a bond | NH | O | NH | Q3f | OH |
| 3321 | CH | S | Q1n | a bond | Me | a bond | NH | S | a bond | Q3a | OH |
| 3322 | CH | S | Q1n | a bond | Me | a bond | NH | S | a bond | Q3d | OH |
| 3323 | CH | S | Q1n | a bond | Me | a bond | NH | S | a bond | Q3e | OH |
| 3324 | CH | S | Q1n | a bond | Me | a bond | NH | S | a bond | Q3f | OH |
| 3325 | CH | S | Q1n | a bond | Me | a bond | NH | S | NH | Q3a | OH |
| 3326 | CH | S | Q1n | a bond | Me | a bond | NH | S | NH | Q3d | OH |
| 3327 | CH | S | Q1n | a bond | Me | a bond | NH | S | NH | Q3e | OH |
| 3328 | CH | S | Q1n | a bond | Me | a bond | NH | S | NH | Q3f | OH |
| 3329 | CH | O | Q1k | a bond | Me | a bond | NH | O | a bond | Q3a | OH |
| 3330 | CH | O | Q1k | a bond | Me | a bond | NH | O | a bond | Q3d | OH |
| 3331 | CH | O | Q1k | a bond | Me | a bond | NH | O | a bond | Q3e | OH |
| 3332 | CH | O | Q1k | a bond | Me | a bond | NH | O | a bond | Q3f | OH |
| 3333 | CH | O | Q1k | a bond | Me | a bond | NH | O | NH | Q3a | OH |
| 3334 | CH | O | Q1k | a bond | Me | a bond | NH | O | NH | Q3d | OH |
| 3335 | CH | O | Q1k | a bond | Me | a bond | NH | O | NH | Q3e | OH |
| 3336 | CH | O | Q1k | a bond | Me | a bond | NH | O | NH | Q3f | OH |
| 3337 | CH | O | Q1k | a bond | Me | a bond | NH | S | a bond | Q3a | OH |
| 3338 | CH | O | Q1k | a bond | Me | a bond | NH | S | a bond | Q3d | OH |
| 3339 | CH | O | Q1k | a bond | Me | a bond | NH | S | a bond | Q3e | OH |
| 3340 | CH | O | Q1k | a bond | Me | a bond | NH | S | a bond | Q3f | OH |
| 3341 | CH | O | Q1k | a bond | Me | a bond | NH | S | NH | Q3a | OH |
| 3342 | CH | O | Q1k | a bond | Me | a bond | NH | S | NH | Q3d | OH |
| 3343 | CH | O | Q1k | a bond | Me | a bond | NH | S | NH | Q3e | OH |
| 3344 | CH | O | Q1k | a bond | Me | a bond | NH | S | NH | Q3f | OH |
| 3345 | CH | O | Q1l | a bond | Me | a bond | NH | O | a bond | Q3a | OH |
| 3346 | CH | O | Q1l | a bond | Me | a bond | NH | O | a bond | Q3d | OH |
| 3347 | CH | O | Q1l | a bond | Me | a bond | NH | O | a bond | Q3e | OH |
| 3348 | CH | O | Q1l | a bond | Me | a bond | NH | O | a bond | Q3f | OH |
| 3349 | CH | O | Q1l | a bond | Me | a bond | NH | O | NH | Q3a | OH |
| 3350 | CH | O | Q1l | a bond | Me | a bond | NH | O | NH | Q3d | OH |
| 3351 | CH | O | Q1l | a bond | Me | a bond | NH | O | NH | Q3e | OH |
| 3352 | CH | O | Q1l | a bond | Me | a bond | NH | O | NH | Q3f | OH |
| 3353 | CH | O | Q1l | a bond | Me | a bond | NH | S | a bond | Q3a | OH |
| 3354 | CH | O | Q1l | a bond | Me | a bond | NH | S | a bond | Q3d | OH |

TABLE 1-continued

| No | A | B | R¹ | L¹ | R² | L² | L³ | Y | L⁴ | R³ | X |
|---|---|---|---|---|---|---|---|---|---|---|---|
| 3355 | CH | O | Q1l | a bond | Me | a bond | NH | S | a bond | Q3e | OH |
| 3356 | CH | O | Q1l | a bond | Me | a bond | NH | S | a bond | Q3f | OH |
| 3357 | CH | O | Q1l | a bond | Me | a bond | NH | S | NH | Q3a | OH |
| 3358 | CH | O | Q1l | a bond | Me | a bond | NH | S | NH | Q3d | OH |
| 3359 | CH | O | Q1l | a bond | Me | a bond | NH | S | NH | Q3e | OH |
| 3360 | CH | O | Q1l | a bond | Me | a bond | NH | S | NH | Q3f | OH |
| 3361 | CH | O | Q1m | a bond | Me | a bond | NH | O | a bond | Q3a | OH |
| 3362 | CH | O | Q1m | a bond | Me | a bond | NH | O | a bond | Q3d | OH |
| 3363 | CH | O | Q1m | a bond | Me | a bond | NH | O | a bond | Q3e | OH |
| 3364 | CH | O | Q1m | a bond | Me | a bond | NH | O | a bond | Q3f | OH |
| 3365 | CH | O | Q1m | a bond | Me | a bond | NH | O | NH | Q3a | OH |
| 3366 | CH | O | Q1m | a bond | Me | a bond | NH | O | NH | Q3d | OH |
| 3367 | CH | O | Q1m | a bond | Me | a bond | NH | O | NH | Q3e | OH |
| 3368 | CH | O | Q1m | a bond | Me | a bond | NH | O | NH | Q3f | OH |
| 3369 | CH | O | Q1m | a bond | Me | a bond | NH | S | a bond | Q3a | OH |
| 3370 | CH | O | Q1m | a bond | Me | a bond | NH | S | a bond | Q3d | OH |
| 3371 | CH | O | Q1m | a bond | Me | a bond | NH | S | a bond | Q3e | OH |
| 3372 | CH | O | Q1m | a bond | Me | a bond | NH | S | a bond | Q3f | OH |
| 3373 | CH | O | Q1m | a bond | Me | a bond | NH | S | NH | Q3a | OH |
| 3374 | CH | O | Q1m | a bond | Me | a bond | NH | S | NH | Q3d | OH |
| 3375 | CH | O | Q1m | a bond | Me | a bond | NH | S | NH | Q3e | OH |
| 3376 | CH | O | Q1m | a bond | Me | a bond | NH | S | NH | Q3f | OH |
| 3377 | CH | O | Q1n | a bond | Me | a bond | NH | O | a bond | Q3a | OH |
| 3378 | CH | O | Q1n | a bond | Me | a bond | NH | O | a bond | Q3d | OH |
| 3379 | CH | O | Q1n | a bond | Me | a bond | NH | O | a bond | Q3e | OH |
| 3380 | CH | O | Q1n | a bond | Me | a bond | NH | O | a bond | Q3f | OH |
| 3381 | CH | O | Q1n | a bond | Me | a bond | NH | O | NH | Q3a | OH |
| 3382 | CH | O | Q1n | a bond | Me | a bond | NH | O | NH | Q3d | OH |
| 3383 | CH | O | Q1n | a bond | Me | a bond | NH | O | NH | Q3e | OH |
| 3384 | CH | O | Q1n | a bond | Me | a bond | NH | O | NH | Q3f | OH |
| 3385 | CH | O | Q1n | a bond | Me | a bond | NH | S | a bond | Q3a | OH |
| 3386 | CH | O | Q1n | a bond | Me | a bond | NH | S | a bond | Q3d | OH |
| 3387 | CH | O | Q1n | a bond | Me | a bond | NH | S | a bond | Q3e | OH |
| 3388 | CH | O | Q1n | a bond | Me | a bond | NH | S | a bond | Q3f | OH |
| 3389 | CH | O | Q1n | a bond | Me | a bond | NH | S | NH | Q3a | OH |
| 3390 | CH | O | Q1n | a bond | Me | a bond | NH | S | NH | Q3d | OH |
| 3391 | CH | O | Q1n | a bond | Me | a bond | NH | S | NH | Q3e | OH |
| 3392 | CH | O | Q1n | a bond | Me | a bond | NH | S | NH | Q3f | OH |
| 3393 | CMe | NMe | Q1k | a bond | Me | a bond | NH | O | a bond | Q3a | OH |
| 3394 | CMe | NMe | Q1k | a bond | Me | a bond | NH | O | a bond | Q3d | OH |
| 3395 | CMe | NMe | Q1k | a bond | Me | a bond | NH | O | a bond | Q3e | OH |
| 3396 | CMe | NMe | Q1k | a bond | Me | a bond | NH | O | a bond | Q3f | OH |
| 3397 | CMe | NMe | Q1k | a bond | Me | a bond | NH | O | NH | Q3a | OH |
| 3398 | CMe | NMe | Q1k | a bond | Me | a bond | NH | O | NH | Q3d | OH |
| 3399 | CMe | NMe | Q1k | a bond | Me | a bond | NH | O | NH | Q3e | OH |
| 3400 | CMe | NMe | Q1k | a bond | Me | a bond | NH | O | NH | Q3f | OH |
| 3401 | CMe | NMe | Q1k | a bond | Me | a bond | NH | S | a bond | Q3a | OH |
| 3402 | CMe | NMe | Q1k | a bond | Me | a bond | NH | S | a bond | Q3d | OH |
| 3403 | CMe | NMe | Q1k | a bond | Me | a bond | NH | S | a bond | Q3e | OH |
| 3404 | CMe | NMe | Q1k | a bond | Me | a bond | NH | S | a bond | Q3f | OH |
| 3405 | CMe | NMe | Q1k | a bond | Me | a bond | NH | S | NH | Q3a | OH |
| 3406 | CMe | NMe | Q1k | a bond | Me | a bond | NH | S | NH | Q3d | OH |
| 3407 | CMe | NMe | Q1k | a bond | Me | a bond | NH | S | NH | Q3e | OH |
| 3408 | CMe | NMe | Q1k | a bond | Me | a bond | NH | S | NH | Q3f | OH |
| 3409 | CMe | NMe | Q1l | a bond | Me | a bond | NH | O | a bond | Q3a | OH |
| 3410 | CMe | NMe | Q1l | a bond | Me | a bond | NH | O | a bond | Q3d | OH |
| 3411 | CMe | NMe | Q1l | a bond | Me | a bond | NH | O | a bond | Q3e | OH |
| 3412 | CMe | NMe | Q1l | a bond | Me | a bond | NH | O | a bond | Q3f | OH |
| 3413 | CMe | NMe | Q1l | a bond | Me | a bond | NH | O | NH | Q3a | OH |
| 3414 | CMe | NMe | Q1l | a bond | Me | a bond | NH | O | NH | Q3d | OH |
| 3415 | CMe | NMe | Q1l | a bond | Me | a bond | NH | O | NH | Q3e | OH |
| 3416 | CMe | NMe | Q1l | a bond | Me | a bond | NH | O | NH | Q3f | OH |
| 3417 | CMe | NMe | Q1l | a bond | Me | a bond | NH | S | a bond | Q3a | OH |
| 3418 | CMe | NMe | Q1l | a bond | Me | a bond | NH | S | a bond | Q3d | OH |
| 3419 | CMe | NMe | Q1l | a bond | Me | a bond | NH | S | a bond | Q3e | OH |
| 3420 | CMe | NMe | Q1l | a bond | Me | a bond | NH | S | a bond | Q3f | OH |
| 3421 | CMe | NMe | Q1l | a bond | Me | a bond | NH | S | NH | Q3a | OH |
| 3422 | CMe | NMe | Q1l | a bond | Me | a bond | NH | S | NH | Q3d | OH |
| 3423 | CMe | NMe | Q1l | a bond | Me | a bond | NH | S | NH | Q3e | OH |
| 3424 | CMe | NMe | Q1l | a bond | Me | a bond | NH | S | NH | Q3f | OH |
| 3425 | CMe | NMe | Q1m | a bond | Me | a bond | NH | O | a bond | Q3a | OH |
| 3426 | CMe | NMe | Q1m | a bond | Me | a bond | NH | O | a bond | Q3d | OH |
| 3427 | CMe | NMe | Q1m | a bond | Me | a bond | NH | O | a bond | Q3e | OH |
| 3428 | CMe | NMe | Q1m | a bond | Me | a bond | NH | O | a bond | Q3f | OH |
| 3429 | CMe | NMe | Q1m | a bond | Me | a bond | NH | O | NH | Q3a | OH |
| 3430 | CMe | NMe | Q1m | a bond | Me | a bond | NH | O | NH | Q3d | OH |
| 3431 | CMe | NMe | Q1m | a bond | Me | a bond | NH | O | NH | Q3e | OH |
| 3432 | CMe | NMe | Q1m | a bond | Me | a bond | NH | O | NH | Q3f | OH |

TABLE 1-continued

| No | A | B | R¹ | L¹ | R² | L² | L³ | Y | L⁴ | R³ | X |
|---|---|---|---|---|---|---|---|---|---|---|---|
| 3433 | CMe | NMe | Q1m | a bond | Me | a bond | NH | S | a bond | Q3a | OH |
| 3434 | CMe | NMe | Q1m | a bond | Me | a bond | NH | S | a bond | Q3d | OH |
| 3435 | CMe | NMe | Q1m | a bond | Me | a bond | NH | S | a bond | Q3e | OH |
| 3436 | CMe | NMe | Q1m | a bond | Me | a bond | NH | S | a bond | Q3f | OH |
| 3437 | CMe | NMe | Q1m | a bond | Me | a bond | NH | S | NH | Q3a | OH |
| 3438 | CMe | NMe | Q1m | a bond | Me | a bond | NH | S | NH | Q3d | OH |
| 3439 | CMe | NMe | Q1m | a bond | Me | a bond | NH | S | NH | Q3e | OH |
| 3440 | CMe | NMe | Q1m | a bond | Me | a bond | NH | S | NH | Q3f | OH |
| 3441 | CMe | NMe | Q1n | a bond | Me | a bond | NH | O | a bond | Q3a | OH |
| 3442 | CMe | NMe | Q1n | a bond | Me | a bond | NH | O | a bond | Q3d | OH |
| 3443 | CMe | NMe | Q1n | a bond | Me | a bond | NH | O | a bond | Q3e | OH |
| 3444 | CMe | NMe | Q1n | a bond | Me | a bond | NH | O | a bond | Q3f | OH |
| 3445 | CMe | NMe | Q1n | a bond | Me | a bond | NH | O | NH | Q3a | OH |
| 3446 | CMe | NMe | Q1n | a bond | Me | a bond | NH | O | NH | Q3d | OH |
| 3447 | CMe | NMe | Q1n | a bond | Me | a bond | NH | O | NH | Q3e | OH |
| 3448 | CMe | NMe | Q1n | a bond | Me | a bond | NH | O | NH | Q3f | OH |
| 3449 | CMe | NMe | Q1n | a bond | Me | a bond | NH | S | a bond | Q3a | OH |
| 3450 | CMe | NMe | Q1n | a bond | Me | a bond | NH | S | a bond | Q3d | OH |
| 3451 | CMe | NMe | Q1n | a bond | Me | a bond | NH | S | a bond | Q3e | OH |
| 3452 | CMe | NMe | Q1n | a bond | Me | a bond | NH | S | a bond | Q3f | OH |
| 3453 | CMe | NMe | Q1n | a bond | Me | a bond | NH | S | NH | Q3a | OH |
| 3454 | CMe | NMe | Q1n | a bond | Me | a bond | NH | S | NH | Q3d | OH |
| 3455 | CMe | NMe | Q1n | a bond | Me | a bond | NH | S | NH | Q3e | OH |
| 3456 | CMe | NMe | Q1n | a bond | Me | a bond | NH | S | NH | Q3f | OH |
| 3457 | CMe | NEt | Q1k | a bond | Me | a bond | NH | O | a bond | Q3a | OH |
| 3458 | CMe | NEt | Q1k | a bond | Me | a bond | NH | O | a bond | Q3d | OH |
| 3459 | CMe | NEt | Q1k | a bond | Me | a bond | NH | O | a bond | Q3e | OH |
| 3460 | CMe | NEt | Q1k | a bond | Me | a bond | NH | O | a bond | Q3f | OH |
| 3461 | CMe | NEt | Q1k | a bond | Me | a bond | NH | O | NH | Q3a | OH |
| 3462 | CMe | NEt | Q1k | a bond | Me | a bond | NH | O | NH | Q3d | OH |
| 3463 | CMe | NEt | Q1k | a bond | Me | a bond | NH | O | NH | Q3e | OH |
| 3464 | CMe | NEt | Q1k | a bond | Me | a bond | NH | O | NH | Q3f | OH |
| 3465 | CMe | NEt | Q1k | a bond | Me | a bond | NH | S | a bond | Q3a | OH |
| 3466 | CMe | NEt | Q1k | a bond | Me | a bond | NH | S | a bond | Q3d | OH |
| 3467 | CMe | NEt | Q1k | a bond | Me | a bond | NH | S | a bond | Q3e | OH |
| 3468 | CMe | NEt | Q1k | a bond | Me | a bond | NH | S | a bond | Q3f | OH |
| 3469 | CMe | NEt | Q1k | a bond | Me | a bond | NH | S | NH | Q3a | OH |
| 3470 | CMe | NEt | Q1k | a bond | Me | a bond | NH | S | NH | Q3d | OH |
| 3471 | CMe | NEt | Q1k | a bond | Me | a bond | NH | S | NH | Q3e | OH |
| 3472 | CMe | NEt | Q1k | a bond | Me | a bond | NH | S | NH | Q3f | OH |
| 3473 | CMe | NEt | Q1l | a bond | Me | a bond | NH | O | a bond | Q3a | OH |
| 3474 | CMe | NEt | Q1l | a bond | Me | a bond | NH | O | a bond | Q3d | OH |
| 3475 | CMe | NEt | Q1l | a bond | Me | a bond | NH | O | a bond | Q3e | OH |
| 3476 | CMe | NEt | Q1l | a bond | Me | a bond | NH | O | a bond | Q3f | OH |
| 3477 | CMe | NEt | Q1l | a bond | Me | a bond | NH | O | NH | Q3a | OH |
| 3478 | CMe | NEt | Q1l | a bond | Me | a bond | NH | O | NH | Q3d | OH |
| 3479 | CMe | NEt | Q1l | a bond | Me | a bond | NH | O | NH | Q3e | OH |
| 3480 | CMe | NEt | Q1l | a bond | Me | a bond | NH | O | NH | Q3f | OH |
| 3481 | CMe | NEt | Q1l | a bond | Me | a bond | NH | S | a bond | Q3a | OH |
| 3482 | CMe | NEt | Q1l | a bond | Me | a bond | NH | S | a bond | Q3d | OH |
| 3483 | CMe | NEt | Q1l | a bond | Me | a bond | NH | S | a bond | Q3e | OH |
| 3484 | CMe | NEt | Q1l | a bond | Me | a bond | NH | S | a bond | Q3f | OH |
| 3485 | CMe | NEt | Q1l | a bond | Me | a bond | NH | S | NH | Q3a | OH |
| 3486 | CMe | NEt | Q1l | a bond | Me | a bond | NH | S | NH | Q3d | OH |
| 3487 | CMe | NEt | Q1l | a bond | Me | a bond | NH | S | NH | Q3e | OH |
| 3488 | CMe | NEt | Q1l | a bond | Me | a bond | NH | S | NH | Q3f | OH |
| 3489 | CMe | NEt | Q1m | a bond | Me | a bond | NH | O | a bond | Q3a | OH |
| 3490 | CMe | NEt | Q1m | a bond | Me | a bond | NH | O | a bond | Q3d | OH |
| 3491 | CMe | NEt | Q1m | a bond | Me | a bond | NH | O | a bond | Q3e | OH |
| 3492 | CMe | NEt | Q1m | a bond | Me | a bond | NH | O | a bond | Q3f | OH |
| 3493 | CMe | NEt | Q1m | a bond | Me | a bond | NH | O | NH | Q3a | OH |
| 3494 | CMe | NEt | Q1m | a bond | Me | a bond | NH | O | NH | Q3d | OH |
| 3495 | CMe | NEt | Q1m | a bond | Me | a bond | NH | O | NH | Q3e | OH |
| 3496 | CMe | NEt | Q1m | a bond | Me | a bond | NH | O | NH | Q3f | OH |
| 3497 | CMe | NEt | Q1m | a bond | Me | a bond | NH | S | a bond | Q3a | OH |
| 3498 | CMe | NEt | Q1m | a bond | Me | a bond | NH | S | a bond | Q3d | OH |
| 3499 | CMe | NEt | Q1m | a bond | Me | a bond | NH | S | a bond | Q3e | OH |
| 3500 | CMe | NEt | Q1m | a bond | Me | a bond | NH | S | a bond | Q3f | OH |
| 3501 | CMe | NEt | Q1m | a bond | Me | a bond | NH | S | NH | Q3a | OH |
| 3502 | CMe | NEt | Q1m | a bond | Me | a bond | NH | S | NH | Q3d | OH |
| 3503 | CMe | NEt | Q1m | a bond | Me | a bond | NH | S | NH | Q3e | OH |
| 3504 | CMe | NEt | Q1m | a bond | Me | a bond | NH | S | NH | Q3f | OH |
| 3505 | CMe | NEt | Q1n | a bond | Me | a bond | NH | O | a bond | Q3a | OH |
| 3506 | CMe | NEt | Q1n | a bond | Me | a bond | NH | O | a bond | Q3d | OH |
| 3507 | CMe | NEt | Q1n | a bond | Me | a bond | NH | O | a bond | Q3e | OH |
| 3508 | CMe | NEt | Q1n | a bond | Me | a bond | NH | O | a bond | Q3f | OH |
| 3509 | CMe | NEt | Q1n | a bond | Me | a bond | NH | O | NH | Q3a | OH |
| 3510 | CMe | NEt | Q1n | a bond | Me | a bond | NH | O | NH | Q3d | OH |

TABLE 1-continued

| No | A | B | R¹ | L¹ | R² | L² | L³ | Y | L⁴ | R³ | X |
|---|---|---|---|---|---|---|---|---|---|---|---|
| 3511 | CMe | NEt | Q1n | a bond | Me | a bond | NH | O | NH | Q3e | OH |
| 3512 | CMe | NEt | Q1n | a bond | Me | a bond | NH | O | NH | Q3f | OH |
| 3513 | CMe | NEt | Q1n | a bond | Me | a bond | NH | S | a bond | Q3a | OH |
| 3514 | CMe | NEt | Q1n | a bond | Me | a bond | NH | S | a bond | Q3d | OH |
| 3515 | CMe | NEt | Q1n | a bond | Me | a bond | NH | S | a bond | Q3e | OH |
| 3516 | CMe | NEt | Q1n | a bond | Me | a bond | NH | S | a bond | Q3f | OH |
| 3517 | CMe | NEt | Q1n | a bond | Me | a bond | NH | S | NH | Q3a | OH |
| 3518 | CMe | NEt | Q1n | a bond | Me | a bond | NH | S | NH | Q3d | OH |
| 3519 | CMe | NEt | Q1n | a bond | Me | a bond | NH | S | NH | Q3e | OH |
| 3520 | CMe | NEt | Q1n | a bond | Me | a bond | NH | S | NH | Q3f | OH |
| 3521 | CMe | S | Q1k | a bond | Me | a bond | NH | O | a bond | Q3a | OH |
| 3522 | CMe | S | Q1k | a bond | Me | a bond | NH | O | a bond | Q3d | OH |
| 3523 | CMe | S | Q1k | a bond | Me | a bond | NH | O | a bond | Q3e | OH |
| 3524 | CMe | S | Q1k | a bond | Me | a bond | NH | O | a bond | Q3f | OH |
| 3525 | CMe | S | Q1k | a bond | Me | a bond | NH | O | NH | Q3a | OH |
| 3526 | CMe | S | Q1k | a bond | Me | a bond | NH | O | NH | Q3d | OH |
| 3527 | CMe | S | Q1k | a bond | Me | a bond | NH | O | NH | Q3e | OH |
| 3528 | CMe | S | Q1k | a bond | Me | a bond | NH | O | NH | Q3f | OH |
| 3529 | CMe | S | Q1k | a bond | Me | a bond | NH | S | a bond | Q3a | OH |
| 3530 | CMe | S | Q1k | a bond | Me | a bond | NH | S | a bond | Q3d | OH |
| 3531 | CMe | S | Q1k | a bond | Me | a bond | NH | S | a bond | Q3e | OH |
| 3532 | CMe | S | Q1k | a bond | Me | a bond | NH | S | a bond | Q3f | OH |
| 3533 | CMe | S | Q1k | a bond | Me | a bond | NH | S | NH | Q3a | OH |
| 3534 | CMe | S | Q1k | a bond | Me | a bond | NH | S | NH | Q3d | OH |
| 3535 | CMe | S | Q1k | a bond | Me | a bond | NH | S | NH | Q3e | OH |
| 3536 | CMe | S | Q1k | a bond | Me | a bond | NH | S | NH | Q3f | OH |
| 3537 | CMe | S | Q1l | a bond | Me | a bond | NH | O | a bond | Q3a | OH |
| 3538 | CMe | S | Q1l | a bond | Me | a bond | NH | O | a bond | Q3d | OH |
| 3539 | CMe | S | Q1l | a bond | Me | a bond | NH | O | a bond | Q3e | OH |
| 3540 | CMe | S | Q1l | a bond | Me | a bond | NH | O | a bond | Q3f | OH |
| 3541 | CMe | S | Q1l | a bond | Me | a bond | NH | O | NH | Q3a | OH |
| 3542 | CMe | S | Q1l | a bond | Me | a bond | NH | O | NH | Q3d | OH |
| 3543 | CMe | S | Q1l | a bond | Me | a bond | NH | O | NH | Q3e | OH |
| 3544 | CMe | S | Q1l | a bond | Me | a bond | NH | O | NH | Q3f | OH |
| 3545 | CMe | S | Q1l | a bond | Me | a bond | NH | S | a bond | Q3a | OH |
| 3546 | CMe | S | Q1l | a bond | Me | a bond | NH | S | a bond | Q3d | OH |
| 3547 | CMe | S | Q1l | a bond | Me | a bond | NH | S | a bond | Q3e | OH |
| 3548 | CMe | S | Q1l | a bond | Me | a bond | NH | S | a bond | Q3f | OH |
| 3549 | CMe | S | Q1l | a bond | Me | a bond | NH | S | NH | Q3a | OH |
| 3550 | CMe | S | Q1l | a bond | Me | a bond | NH | S | NH | Q3d | OH |
| 3551 | CMe | S | Q1l | a bond | Me | a bond | NH | S | NH | Q3e | OH |
| 3552 | CMe | S | Q1l | a bond | Me | a bond | NH | S | NH | Q3f | OH |
| 3553 | CMe | S | Q1m | a bond | Me | a bond | NH | O | a bond | Q3a | OH |
| 3554 | CMe | S | Q1m | a bond | Me | a bond | NH | O | a bond | Q3d | OH |
| 3555 | CMe | S | Q1m | a bond | Me | a bond | NH | O | a bond | Q3e | OH |
| 3556 | CMe | S | Q1m | a bond | Me | a bond | NH | O | a bond | Q3f | OH |
| 3557 | CMe | S | Q1m | a bond | Me | a bond | NH | O | NH | Q3a | OH |
| 3558 | CMe | S | Q1m | a bond | Me | a bond | NH | O | NH | Q3d | OH |
| 3559 | CMe | S | Q1m | a bond | Me | a bond | NH | O | NH | Q3e | OH |
| 3560 | CMe | S | Q1m | a bond | Me | a bond | NH | O | NH | Q3f | OH |
| 3561 | CMe | S | Q1m | a bond | Me | a bond | NH | S | a bond | Q3a | OH |
| 3562 | CMe | S | Q1m | a bond | Me | a bond | NH | S | a bond | Q3d | OH |
| 3563 | CMe | S | Q1m | a bond | Me | a bond | NH | S | a bond | Q3e | OH |
| 3564 | CMe | S | Q1m | a bond | Me | a bond | NH | S | a bond | Q3f | OH |
| 3565 | CMe | S | Q1m | a bond | Me | a bond | NH | S | NH | Q3a | OH |
| 3566 | CMe | S | Q1m | a bond | Me | a bond | NH | S | NH | Q3d | OH |
| 3567 | CMe | S | Q1m | a bond | Me | a bond | NH | S | NH | Q3e | OH |
| 3568 | CMe | S | Q1m | a bond | Me | a bond | NH | S | NH | Q3f | OH |
| 3569 | CMe | S | Q1n | a bond | Me | a bond | NH | O | a bond | Q3a | OH |
| 3570 | CMe | S | Q1n | a bond | Me | a bond | NH | O | a bond | Q3d | OH |
| 3571 | CMe | S | Q1n | a bond | Me | a bond | NH | O | a bond | Q3e | OH |
| 3572 | CMe | S | Q1n | a bond | Me | a bond | NH | O | a bond | Q3f | OH |
| 3573 | CMe | S | Q1n | a bond | Me | a bond | NH | O | NH | Q3a | OH |
| 3574 | CMe | S | Q1n | a bond | Me | a bond | NH | O | NH | Q3d | OH |
| 3575 | CMe | S | Q1n | a bond | Me | a bond | NH | O | NH | Q3e | OH |
| 3576 | CMe | S | Q1n | a bond | Me | a bond | NH | O | NH | Q3f | OH |
| 3577 | CMe | S | Q1n | a bond | Me | a bond | NH | S | a bond | Q3a | OH |
| 3578 | CMe | S | Q1n | a bond | Me | a bond | NH | S | a bond | Q3d | OH |
| 3579 | CMe | S | Q1n | a bond | Me | a bond | NH | S | a bond | Q3e | OH |
| 3580 | CMe | S | Q1n | a bond | Me | a bond | NH | S | a bond | Q3f | OH |
| 3581 | CMe | S | Q1n | a bond | Me | a bond | NH | S | NH | Q3a | OH |
| 3582 | CMe | S | Q1n | a bond | Me | a bond | NH | S | NH | Q3d | OH |
| 3583 | CMe | S | Q1n | a bond | Me | a bond | NH | S | NH | Q3e | OH |
| 3584 | CMe | S | Q1n | a bond | Me | a bond | NH | S | NH | Q3f | OH |
| 3585 | CMe | O | Q1k | a bond | Me | a bond | NH | O | a bond | Q3a | OH |
| 3586 | CMe | O | Q1k | a bond | Me | a bond | NH | O | a bond | Q3d | OH |
| 3587 | CMe | O | Q1k | a bond | Me | a bond | NH | O | a bond | Q3e | OH |
| 3588 | CMe | O | Q1k | a bond | Me | a bond | NH | O | a bond | Q3f | OH |

TABLE 1-continued

| No | A | B | R¹ | L¹ | R² | L² | L³ | Y | L⁴ | R³ | X |
|---|---|---|---|---|---|---|---|---|---|---|---|
| 3589 | CMe | O | Q1k | a bond | Me | a bond | NH | O | NH | Q3a | OH |
| 3590 | CMe | O | Q1k | a bond | Me | a bond | NH | O | NH | Q3d | OH |
| 3591 | CMe | O | Q1k | a bond | Me | a bond | NH | O | NH | Q3e | OH |
| 3592 | CMe | O | Q1k | a bond | Me | a bond | NH | O | NH | Q3f | OH |
| 3593 | CMe | O | Q1k | a bond | Me | a bond | NH | S | a bond | Q3a | OH |
| 3594 | CMe | O | Q1k | a bond | Me | a bond | NH | S | a bond | Q3d | OH |
| 3595 | CMe | O | Q1k | a bond | Me | a bond | NH | S | a bond | Q3e | OH |
| 3596 | CMe | O | Q1k | a bond | Me | a bond | NH | S | a bond | Q3f | OH |
| 3597 | CMe | O | Q1k | a bond | Me | a bond | NH | S | NH | Q3a | OH |
| 3598 | CMe | O | Q1k | a bond | Me | a bond | NH | S | NH | Q3d | OH |
| 3599 | CMe | O | Q1k | a bond | Me | a bond | NH | S | NH | Q3e | OH |
| 3600 | CMe | O | Q1k | a bond | Me | a bond | NH | S | NH | Q3f | OH |
| 3601 | CMe | O | Q1l | a bond | Me | a bond | NH | O | a bond | Q3a | OH |
| 3602 | CMe | O | Q1l | a bond | Me | a bond | NH | O | a bond | Q3d | OH |
| 3603 | CMe | O | Q1l | a bond | Me | a bond | NH | O | a bond | Q3e | OH |
| 3604 | CMe | O | Q1l | a bond | Me | a bond | NH | O | a bond | Q3f | OH |
| 3605 | CMe | O | Q1l | a bond | Me | a bond | NH | O | NH | Q3a | OH |
| 3606 | CMe | O | Q1l | a bond | Me | a bond | NH | O | NH | Q3d | OH |
| 3607 | CMe | O | Q1l | a bond | Me | a bond | NH | O | NH | Q3e | OH |
| 3608 | CMe | O | Q1l | a bond | Me | a bond | NH | O | NH | Q3f | OH |
| 3609 | CMe | O | Q1l | a bond | Me | a bond | NH | S | a bond | Q3a | OH |
| 3610 | CMe | O | Q1l | a bond | Me | a bond | NH | S | a bond | Q3d | OH |
| 3611 | CMe | O | Q1l | a bond | Me | a bond | NH | S | a bond | Q3e | OH |
| 3612 | CMe | O | Q1l | a bond | Me | a bond | NH | S | a bond | Q3f | OH |
| 3613 | CMe | O | Q1l | a bond | Me | a bond | NH | S | NH | Q3a | OH |
| 3614 | CMe | O | Q1l | a bond | Me | a bond | NH | S | NH | Q3d | OH |
| 3615 | CMe | O | Q1l | a bond | Me | a bond | NH | S | NH | Q3e | OH |
| 3616 | CMe | O | Q1l | a bond | Me | a bond | NH | S | NH | Q3f | OH |
| 3617 | CMe | O | Q1m | a bond | Me | a bond | NH | O | a bond | Q3a | OH |
| 3618 | CMe | O | Q1m | a bond | Me | a bond | NH | O | a bond | Q3d | OH |
| 3619 | CMe | O | Q1m | a bond | Me | a bond | NH | O | a bond | Q3e | OH |
| 3620 | CMe | O | Q1m | a bond | Me | a bond | NH | O | a bond | Q3f | OH |
| 3621 | CMe | O | Q1m | a bond | Me | a bond | NH | O | NH | Q3a | OH |
| 3622 | CMe | O | Q1m | a bond | Me | a bond | NH | O | NH | Q3d | OH |
| 3623 | CMe | O | Q1m | a bond | Me | a bond | NH | O | NH | Q3e | OH |
| 3624 | CMe | O | Q1m | a bond | Me | a bond | NH | O | NH | Q3f | OH |
| 3625 | CMe | O | Q1m | a bond | Me | a bond | NH | S | a bond | Q3a | OH |
| 3626 | CMe | O | Q1m | a bond | Me | a bond | NH | S | a bond | Q3d | OH |
| 3627 | CMe | O | Q1m | a bond | Me | a bond | NH | S | a bond | Q3e | OH |
| 3628 | CMe | O | Q1m | a bond | Me | a bond | NH | S | a bond | Q3f | OH |
| 3629 | CMe | O | Q1m | a bond | Me | a bond | NH | S | NH | Q3a | OH |
| 3630 | CMe | O | Q1m | a bond | Me | a bond | NH | S | NH | Q3d | OH |
| 3631 | CMe | O | Q1m | a bond | Me | a bond | NH | S | NH | Q3e | OH |
| 3632 | CMe | O | Q1n | a bond | Me | a bond | NH | S | NH | Q3f | OH |
| 3633 | CMe | O | Q1n | a bond | Me | a bond | NH | O | a bond | Q3a | OH |
| 3634 | CMe | O | Q1n | a bond | Me | a bond | NH | O | a bond | Q3d | OH |
| 3635 | CMe | O | Q1n | a bond | Me | a bond | NH | O | a bond | Q3e | OH |
| 3636 | CMe | O | Q1n | a bond | Me | a bond | NH | O | a bond | Q3f | OH |
| 3637 | CMe | O | Q1n | a bond | Me | a bond | NH | O | NH | Q3a | OH |
| 3638 | CMe | O | Q1n | a bond | Me | a bond | NH | O | NH | Q3d | OH |
| 3639 | CMe | O | Q1n | a bond | Me | a bond | NH | O | NH | Q3e | OH |
| 3640 | CMe | O | Q1n | a bond | Me | a bond | NH | O | NH | Q3f | OH |
| 3641 | CMe | O | Q1n | a bond | Me | a bond | NH | S | a bond | Q3a | OH |
| 3642 | CMe | O | Q1n | a bond | Me | a bond | NH | S | a bond | Q3d | OH |
| 3643 | CMe | O | Q1n | a bond | Me | a bond | NH | S | a bond | Q3e | OH |
| 3644 | CMe | O | Q1n | a bond | Me | a bond | NH | S | a bond | Q3f | OH |
| 3645 | CMe | O | Q1n | a bond | Me | a bond | NH | S | NH | Q3a | OH |
| 3646 | CMe | O | Q1n | a bond | Me | a bond | NH | S | NH | Q3d | OH |
| 3647 | CMe | O | Q1n | a bond | Me | a bond | NH | S | NH | Q3e | OH |
| 3648 | CMe | O | Q1n | a bond | Me | a bond | NH | S | NH | Q3f | OH |
| 3649 | N | NMe | Q1k' | a bond | Me | a bond | NH | O | a bond | Q3a | OH |
| 3650 | N | NMe | Q1k' | a bond | Me | a bond | NH | O | a bond | Q3d | OH |
| 3651 | N | NMe | Q1k' | a bond | Me | a bond | NH | O | a bond | Q3e | OH |
| 3652 | N | NMe | Q1k' | a bond | Me | a bond | NH | O | a bond | Q3f | OH |
| 3653 | N | NMe | Q1k' | a bond | Me | a bond | NH | O | NH | Q3a | OH |
| 3654 | N | NMe | Q1k' | a bond | Me | a bond | NH | O | NH | Q3d | OH |
| 3655 | N | NMe | Q1k' | a bond | Me | a bond | NH | O | NH | Q3e | OH |
| 3656 | N | NMe | Q1k' | a bond | Me | a bond | NH | O | NH | Q3f | OH |
| 3657 | N | NMe | Q1k' | a bond | Me | a bond | NH | S | a bond | Q3a | OH |
| 3658 | N | NMe | Q1k' | a bond | Me | a bond | NH | S | a bond | Q3d | OH |
| 3659 | N | NMe | Q1k' | a bond | Me | a bond | NH | S | a bond | Q3e | OH |
| 3660 | N | NMe | Q1k' | a bond | Me | a bond | NH | S | a bond | Q3f | OH |
| 3661 | N | NMe | Q1k' | a bond | Me | a bond | NH | S | NH | Q3a | OH |
| 3662 | N | NMe | Q1k' | a bond | Me | a bond | NH | S | NH | Q3d | OH |
| 3663 | N | NMe | Q1k' | a bond | Me | a bond | NH | S | NH | Q3e | OH |
| 3664 | N | NMe | Q1k' | a bond | Me | a bond | NH | S | NH | Q3f | OH |
| 3665 | N | NMe | Q1l' | a bond | Me | a bond | NH | O | a bond | Q3a | OH |
| 3666 | N | NMe | Q1l' | a bond | Me | a bond | NH | O | a bond | Q3d | OH |

TABLE 1-continued

| No | A | B | R¹ | L¹ | R² | L² | L³ | Y | L⁴ | R³ | X |
|---|---|---|---|---|---|---|---|---|---|---|---|
| 3667 | N | NMe | Q1l' | a bond | Me | a bond | NH | O | a bond | Q3e | OH |
| 3668 | N | NMe | Q1l' | a bond | Me | a bond | NH | O | a bond | Q3f | OH |
| 3669 | N | NMe | Q1l' | a bond | Me | a bond | NH | O | NH | Q3a | OH |
| 3670 | N | NMe | Q1l' | a bond | Me | a bond | NH | O | NH | Q3d | OH |
| 3671 | N | NMe | Q1l' | a bond | Me | a bond | NH | O | NH | Q3e | OH |
| 3672 | N | NMe | Q1l' | a bond | Me | a bond | NH | O | NH | Q3f | OH |
| 3673 | N | NMe | Q1l' | a bond | Me | a bond | NH | S | a bond | Q3a | OH |
| 3674 | N | NMe | Q1l' | a bond | Me | a bond | NH | S | a bond | Q3d | OH |
| 3675 | N | NMe | Q1l' | a bond | Me | a bond | NH | S | a bond | Q3e | OH |
| 3676 | N | NMe | Q1l' | a bond | Me | a bond | NH | S | a bond | Q3f | OH |
| 3677 | N | NMe | Q1l' | a bond | Me | a bond | NH | S | NH | Q3a | OH |
| 3678 | N | NMe | Q1l' | a bond | Me | a bond | NH | S | NH | Q3d | OH |
| 3679 | N | NMe | Q1l' | a bond | Me | a bond | NH | S | NH | Q3e | OH |
| 3680 | N | NMe | Q1l' | a bond | Me | a bond | NH | S | NH | Q3f | OH |
| 3681 | N | NMe | Q1m' | a bond | Me | a bond | NH | O | a bond | Q3a | OH |
| 3682 | N | NMe | Q1m' | a bond | Me | a bond | NH | O | a bond | Q3d | OH |
| 3683 | N | NMe | Q1m' | a bond | Me | a bond | NH | O | a bond | Q3e | OH |
| 3684 | N | NMe | Q1m' | a bond | Me | a bond | NH | O | a bond | Q3f | OH |
| 3685 | N | NMe | Q1m' | a bond | Me | a bond | NH | O | NH | Q3a | OH |
| 3686 | N | NMe | Q1m' | a bond | Me | a bond | NH | O | NH | Q3d | OH |
| 3687 | N | NMe | Q1m' | a bond | Me | a bond | NH | O | NH | Q3e | OH |
| 3688 | N | NMe | Q1m' | a bond | Me | a bond | NH | O | NH | Q3f | OH |
| 3689 | N | NMe | Q1m' | a bond | Me | a bond | NH | S | a bond | Q3a | OH |
| 3690 | N | NMe | Q1m' | a bond | Me | a bond | NH | S | a bond | Q3d | OH |
| 3691 | N | NMe | Q1m' | a bond | Me | a bond | NH | S | a bond | Q3e | OH |
| 3692 | N | NMe | Q1m' | a bond | Me | a bond | NH | S | a bond | Q3f | OH |
| 3693 | N | NMe | Q1m' | a bond | Me | a bond | NH | S | NH | Q3a | OH |
| 3694 | N | NMe | Q1m' | a bond | Me | a bond | NH | S | NH | Q3d | OH |
| 3695 | N | NMe | Q1m' | a bond | Me | a bond | NH | S | NH | Q3e | OH |
| 3696 | N | NMe | Q1m' | a bond | Me | a bond | NH | S | NH | Q3f | OH |
| 3697 | N | NMe | Q1n' | a bond | Me | a bond | NH | O | a bond | Q3a | OH |
| 3698 | N | NMe | Q1n' | a bond | Me | a bond | NH | O | a bond | Q3d | OH |
| 3699 | N | NMe | Q1n' | a bond | Me | a bond | NH | O | a bond | Q3e | OH |
| 3700 | N | NMe | Q1n' | a bond | Me | a bond | NH | O | a bond | Q3f | OH |
| 3701 | N | NMe | Q1n' | a bond | Me | a bond | NH | O | NH | Q3a | OH |
| 3702 | N | NMe | Q1n' | a bond | Me | a bond | NH | O | NH | Q3d | OH |
| 3703 | N | NMe | Q1n' | a bond | Me | a bond | NH | O | NH | Q3e | OH |
| 3704 | N | NMe | Q1n' | a bond | Me | a bond | NH | O | NH | Q3f | OH |
| 3705 | N | NMe | Q1n' | a bond | Me | a bond | NH | S | a bond | Q3a | OH |
| 3706 | N | NMe | Q1n' | a bond | Me | a bond | NH | S | a bond | Q3d | OH |
| 3707 | N | NMe | Q1n' | a bond | Me | a bond | NH | S | a bond | Q3e | OH |
| 3708 | N | NMe | Q1n' | a bond | Me | a bond | NH | S | a bond | Q3f | OH |
| 3709 | N | NMe | Q1n' | a bond | Me | a bond | NH | S | NH | Q3a | OH |
| 3710 | N | NMe | Q1n' | a bond | Me | a bond | NH | S | NH | Q3d | OH |
| 3711 | N | NMe | Q1n' | a bond | Me | a bond | NH | S | NH | Q3e | OH |
| 3712 | N | NMe | Q1n' | a bond | Me | a bond | NH | S | NH | Q3f | OH |
| 3713 | N | NEt | Q1k' | a bond | Me | a bond | NH | O | a bond | Q3a | OH |
| 3714 | N | NEt | Q1k' | a bond | Me | a bond | NH | O | a bond | Q3d | OH |
| 3715 | N | NEt | Q1k' | a bond | Me | a bond | NH | O | a bond | Q3e | OH |
| 3716 | N | NEt | Q1k' | a bond | Me | a bond | NH | O | a bond | Q3f | OH |
| 3717 | N | NEt | Q1k' | a bond | Me | a bond | NH | O | NH | Q3a | OH |
| 3718 | N | NEt | Q1k' | a bond | Me | a bond | NH | O | NH | Q3d | OH |
| 3719 | N | NEt | Q1k' | a bond | Me | a bond | NH | O | NH | Q3e | OH |
| 3720 | N | NEt | Q1k' | a bond | Me | a bond | NH | O | NH | Q3f | OH |
| 3721 | N | NEt | Q1k' | a bond | Me | a bond | NH | S | a bond | Q3a | OH |
| 3722 | N | NEt | Q1k' | a bond | Me | a bond | NH | S | a bond | Q3d | OH |
| 3723 | N | NEt | Q1k' | a bond | Me | a bond | NH | S | a bond | Q3e | OH |
| 3724 | N | NEt | Q1k' | a bond | Me | a bond | NH | S | a bond | Q3f | OH |
| 3725 | N | NEt | Q1k' | a bond | Me | a bond | NH | S | NH | Q3a | OH |
| 3726 | N | NEt | Q1k' | a bond | Me | a bond | NH | S | NH | Q3d | OH |
| 3727 | N | NEt | Q1k' | a bond | Me | a bond | NH | S | NH | Q3e | OH |
| 3728 | N | NEt | Q1k' | a bond | Me | a bond | NH | S | NH | Q3f | OH |
| 3729 | N | NEt | Q1l' | a bond | Me | a bond | NH | O | a bond | Q3a | OH |
| 3730 | N | NEt | Q1l' | a bond | Me | a bond | NH | O | a bond | Q3d | OH |
| 3731 | N | NEt | Q1l' | a bond | Me | a bond | NH | O | a bond | Q3e | OH |
| 3732 | N | NEt | Q1l' | a bond | Me | a bond | NH | O | a bond | Q3f | OH |
| 3733 | N | NEt | Q1l' | a bond | Me | a bond | NH | O | NH | Q3a | OH |
| 3734 | N | NEt | Q1l' | a bond | Me | a bond | NH | O | NH | Q3d | OH |
| 3735 | N | NEt | Q1l' | a bond | Me | a bond | NH | O | NH | Q3e | OH |
| 3736 | N | NEt | Q1l' | a bond | Me | a bond | NH | O | NH | Q3f | OH |
| 3737 | N | NEt | Q1l' | a bond | Me | a bond | NH | S | a bond | Q3a | OH |
| 3738 | N | NEt | Q1l' | a bond | Me | a bond | NH | S | a bond | Q3d | OH |
| 3739 | N | NEt | Q1l' | a bond | Me | a bond | NH | S | a bond | Q3e | OH |
| 3740 | N | NEt | Q1l' | a bond | Me | a bond | NH | S | a bond | Q3f | OH |
| 3741 | N | NEt | Q1l' | a bond | Me | a bond | NH | S | NH | Q3a | OH |
| 3742 | N | NEt | Q1l' | a bond | Me | a bond | NH | S | NH | Q3d | OH |
| 3743 | N | NEt | Q1l' | a bond | Me | a bond | NH | S | NH | Q3e | OH |
| 3744 | N | NEt | Q1l' | a bond | Me | a bond | NH | S | NH | Q3f | OH |

TABLE 1-continued

| No | A | B | R¹ | L¹ | R² | L² | L³ | Y | L⁴ | R³ | X |
|---|---|---|---|---|---|---|---|---|---|---|---|
| 3745 | N | NEt | Q1m' | a bond | Me | a bond | NH | O | a bond | Q3a | OH |
| 3746 | N | NEt | Q1m' | a bond | Me | a bond | NH | O | a bond | Q3d | OH |
| 3747 | N | NEt | Q1m' | a bond | Me | a bond | NH | O | a bond | Q3e | OH |
| 3748 | N | NEt | Q1m' | a bond | Me | a bond | NH | O | a bond | Q3f | OH |
| 3749 | N | NEt | Q1m' | a bond | Me | a bond | NH | O | NH | Q3a | OH |
| 3750 | N | NEt | Q1m' | a bond | Me | a bond | NH | O | NH | Q3d | OH |
| 3751 | N | NEt | Q1m' | a bond | Me | a bond | NH | O | NH | Q3e | OH |
| 3752 | N | NEt | Q1m' | a bond | Me | a bond | NH | O | NH | Q3f | OH |
| 3753 | N | NEt | Q1m' | a bond | Me | a bond | NH | S | a bond | Q3a | OH |
| 3754 | N | NEt | Q1m' | a bond | Me | a bond | NH | S | a bond | Q3d | OH |
| 3755 | N | NEt | Q1m' | a bond | Me | a bond | NH | S | a bond | Q3e | OH |
| 3756 | N | NEt | Q1m' | a bond | Me | a bond | NH | S | a bond | Q3f | OH |
| 3757 | N | NEt | Q1m' | a bond | Me | a bond | NH | S | NH | Q3a | OH |
| 3758 | N | NEt | Q1m' | a bond | Me | a bond | NH | S | NH | Q3d | OH |
| 3759 | N | NEt | Q1m' | a bond | Me | a bond | NH | S | NH | Q3e | OH |
| 3760 | N | NEt | Q1m' | a bond | Me | a bond | NH | S | NH | Q3f | OH |
| 3761 | N | NEt | Q1n' | a bond | Me | a bond | NH | O | a bond | Q3a | OH |
| 3762 | N | NEt | Q1n' | a bond | Me | a bond | NH | O | a bond | Q3d | OH |
| 3763 | N | NEt | Q1n' | a bond | Me | a bond | NH | O | a bond | Q3e | OH |
| 3764 | N | NEt | Q1n' | a bond | Me | a bond | NH | O | a bond | Q3f | OH |
| 3765 | N | NEt | Q1n' | a bond | Me | a bond | NH | O | NH | Q3a | OH |
| 3766 | N | NEt | Q1n' | a bond | Me | a bond | NH | O | NH | Q3d | OH |
| 3767 | N | NEt | Q1n' | a bond | Me | a bond | NH | O | NH | Q3e | OH |
| 3768 | N | NEt | Q1n' | a bond | Me | a bond | NH | O | NH | Q3f | OH |
| 3769 | N | NEt | Q1n' | a bond | Me | a bond | NH | S | a bond | Q3a | OH |
| 3770 | N | NEt | Q1n' | a bond | Me | a bond | NH | S | a bond | Q3d | OH |
| 3771 | N | NEt | Q1n' | a bond | Me | a bond | NH | S | a bond | Q3e | OH |
| 3772 | N | NEt | Q1n' | a bond | Me | a bond | NH | S | a bond | Q3f | OH |
| 3773 | N | NEt | Q1n' | a bond | Me | a bond | NH | S | NH | Q3a | OH |
| 3774 | N | NEt | Q1n' | a bond | Me | a bond | NH | S | NH | Q3d | OH |
| 3775 | N | NEt | Q1n' | a bond | Me | a bond | NH | S | NH | Q3e | OH |
| 3776 | N | NEt | Q1n' | a bond | Me | a bond | NH | S | NH | Q3f | OH |
| 3777 | N | S | Q1k' | a bond | Me | a bond | NH | O | a bond | Q3a | OH |
| 3778 | N | S | Q1k' | a bond | Me | a bond | NH | O | a bond | Q3d | OH |
| 3779 | N | S | Q1k' | a bond | Me | a bond | NH | O | a bond | Q3e | OH |
| 3780 | N | S | Q1k' | a bond | Me | a bond | NH | O | a bond | Q3f | OH |
| 3781 | N | S | Q1k' | a bond | Me | a bond | NH | O | NH | Q3a | OH |
| 3782 | N | S | Q1k' | a bond | Me | a bond | NH | O | NH | Q3d | OH |
| 3783 | N | S | Q1k' | a bond | Me | a bond | NH | O | NH | Q3e | OH |
| 3784 | N | S | Q1k' | a bond | Me | a bond | NH | O | NH | Q3f | OH |
| 3785 | N | S | Q1k' | a bond | Me | a bond | NH | S | a bond | Q3a | OH |
| 3786 | N | S | Q1k' | a bond | Me | a bond | NH | S | a bond | Q3d | OH |
| 3787 | N | S | Q1k' | a bond | Me | a bond | NH | S | a bond | Q3e | OH |
| 3788 | N | S | Q1k' | a bond | Me | a bond | NH | S | a bond | Q3f | OH |
| 3789 | N | S | Q1k' | a bond | Me | a bond | NH | S | NH | Q3a | OH |
| 3790 | N | S | Q1k' | a bond | Me | a bond | NH | S | NH | Q3d | OH |
| 3791 | N | S | Q1k' | a bond | Me | a bond | NH | S | NH | Q3e | OH |
| 3792 | N | S | Q1k' | a bond | Me | a bond | NH | S | NH | Q3f | OH |
| 3793 | N | S | Q1l' | a bond | Me | a bond | NH | O | a bond | Q3a | OH |
| 3794 | N | S | Q1l' | a bond | Me | a bond | NH | O | a bond | Q3d | OH |
| 3795 | N | S | Q1l' | a bond | Me | a bond | NH | O | a bond | Q3e | OH |
| 3796 | N | S | Q1l' | a bond | Me | a bond | NH | O | a bond | Q3f | OH |
| 3797 | N | S | Q1l' | a bond | Me | a bond | NH | O | NH | Q3a | OH |
| 3798 | N | S | Q1l' | a bond | Me | a bond | NH | O | NH | Q3d | OH |
| 3799 | N | S | Q1l' | a bond | Me | a bond | NH | O | NH | Q3e | OH |
| 3800 | N | S | Q1l' | a bond | Me | a bond | NH | O | NH | Q3f | OH |
| 3801 | N | S | Q1l' | a bond | Me | a bond | NH | S | a bond | Q3a | OH |
| 3802 | N | S | Q1l' | a bond | Me | a bond | NH | S | a bond | Q3d | OH |
| 3803 | N | S | Q1l' | a bond | Me | a bond | NH | S | a bond | Q3e | OH |
| 3804 | N | S | Q1l' | a bond | Me | a bond | NH | S | a bond | Q3f | OH |
| 3805 | N | S | Q1l' | a bond | Me | a bond | NH | S | NH | Q3a | OH |
| 3806 | N | S | Q1l' | a bond | Me | a bond | NH | S | NH | Q3d | OH |
| 3807 | N | S | Q1l' | a bond | Me | a bond | NH | S | NH | Q3e | OH |
| 3808 | N | S | Q1l' | a bond | Me | a bond | NH | S | NH | Q3f | OH |
| 3809 | N | S | Q1m' | a bond | Me | a bond | NH | O | a bond | Q3a | OH |
| 3810 | N | S | Q1m' | a bond | Me | a bond | NH | O | a bond | Q3d | OH |
| 3811 | N | S | Q1m' | a bond | Me | a bond | NH | O | a bond | Q3e | OH |
| 3812 | N | S | Q1m' | a bond | Me | a bond | NH | O | a bond | Q3f | OH |
| 3813 | N | S | Q1m' | a bond | Me | a bond | NH | O | NH | Q3a | OH |
| 3814 | N | S | Q1m' | a bond | Me | a bond | NH | O | NH | Q3d | OH |
| 3815 | N | S | Q1m' | a bond | Me | a bond | NH | O | NH | Q3e | OH |
| 3816 | N | S | Q1m' | a bond | Me | a bond | NH | O | NH | Q3f | OH |
| 3817 | N | S | Q1m' | a bond | Me | a bond | NH | S | a bond | Q3a | OH |
| 3818 | N | S | Q1m' | a bond | Me | a bond | NH | S | a bond | Q3d | OH |
| 3819 | N | S | Q1m' | a bond | Me | a bond | NH | S | a bond | Q3e | OH |
| 3820 | N | S | Q1m' | a bond | Me | a bond | NH | S | a bond | Q3f | OH |
| 3821 | N | S | Q1m' | a bond | Me | a bond | NH | S | NH | Q3a | OH |
| 3822 | N | S | Q1m' | a bond | Me | a bond | NH | S | NH | Q3d | OH |

TABLE 1-continued

| No | A | B | R¹ | L¹ | R² | L² | L³ | Y | L⁴ | R³ | X |
|---|---|---|---|---|---|---|---|---|---|---|---|
| 3823 | N | S | Q1m' | a bond | Me | a bond | NH | S | NH | Q3e | OH |
| 3824 | N | S | Q1m' | a bond | Me | a bond | NH | S | NH | Q3f | OH |
| 3825 | N | S | Q1n' | a bond | Me | a bond | NH | O | a bond | Q3a | OH |
| 3826 | N | S | Q1n' | a bond | Me | a bond | NH | O | a bond | Q3d | OH |
| 3827 | N | S | Q1n' | a bond | Me | a bond | NH | O | a bond | Q3e | OH |
| 3828 | N | S | Q1n' | a bond | Me | a bond | NH | O | a bond | Q3f | OH |
| 3829 | N | S | Q1n' | a bond | Me | a bond | NH | O | NH | Q3a | OH |
| 3830 | N | S | Q1n' | a bond | Me | a bond | NH | O | NH | Q3d | OH |
| 3831 | N | S | Q1n' | a bond | Me | a bond | NH | O | NH | Q3e | OH |
| 3832 | N | S | Q1n' | a bond | Me | a bond | NH | O | NH | Q3f | OH |
| 3833 | N | S | Q1n' | a bond | Me | a bond | NH | S | a bond | Q3a | OH |
| 3834 | N | S | Q1n' | a bond | Me | a bond | NH | S | a bond | Q3d | OH |
| 3835 | N | S | Q1n' | a bond | Me | a bond | NH | S | a bond | Q3e | OH |
| 3836 | N | S | Q1n' | a bond | Me | a bond | NH | S | a bond | Q3f | OH |
| 3837 | N | S | Q1n' | a bond | Me | a bond | NH | S | NH | Q3a | OH |
| 3838 | N | S | Q1n' | a bond | Me | a bond | NH | S | NH | Q3d | OH |
| 3839 | N | S | Q1n' | a bond | Me | a bond | NH | S | NH | Q3e | OH |
| 3840 | N | S | Q1n' | a bond | Me | a bond | NH | S | NH | Q3f | OH |
| 3841 | N | O | Q1k' | a bond | Me | a bond | NH | O | a bond | Q3a | OH |
| 3842 | N | O | Q1k' | a bond | Me | a bond | NH | O | a bond | Q3d | OH |
| 3843 | N | O | Q1k' | a bond | Me | a bond | NH | O | a bond | Q3e | OH |
| 3844 | N | O | Q1k' | a bond | Me | a bond | NH | O | a bond | Q3f | OH |
| 3845 | N | O | Q1k' | a bond | Me | a bond | NH | O | NH | Q3a | OH |
| 3846 | N | O | Q1k' | a bond | Me | a bond | NH | O | NH | Q3d | OH |
| 3847 | N | O | Q1k' | a bond | Me | a bond | NH | O | NH | Q3e | OH |
| 3848 | N | O | Q1k' | a bond | Me | a bond | NH | O | NH | Q3f | OH |
| 3849 | N | O | Q1k' | a bond | Me | a bond | NH | S | a bond | Q3a | OH |
| 3850 | N | O | Q1k' | a bond | Me | a bond | NH | S | a bond | Q3d | OH |
| 3851 | N | O | Q1k' | a bond | Me | a bond | NH | S | a bond | Q3e | OH |
| 3852 | N | O | Q1k' | a bond | Me | a bond | NH | S | a bond | Q3f | OH |
| 3853 | N | O | Q1k' | a bond | Me | a bond | NH | S | NH | Q3a | OH |
| 3854 | N | O | Q1k' | a bond | Me | a bond | NH | S | NH | Q3d | OH |
| 3855 | N | O | Q1k' | a bond | Me | a bond | NH | S | NH | Q3e | OH |
| 3856 | N | O | Q1k' | a bond | Me | a bond | NH | S | NH | Q3f | OH |
| 3857 | N | O | Q1l' | a bond | Me | a bond | NH | O | a bond | Q3a | OH |
| 3858 | N | O | Q1l' | a bond | Me | a bond | NH | O | a bond | Q3d | OH |
| 3859 | N | O | Q1l' | a bond | Me | a bond | NH | O | a bond | Q3e | OH |
| 3860 | N | O | Q1l' | a bond | Me | a bond | NH | O | a bond | Q3f | OH |
| 3861 | N | O | Q1l' | a bond | Me | a bond | NH | O | NH | Q3a | OH |
| 3862 | N | O | Q1l' | a bond | Me | a bond | NH | O | NH | Q3d | OH |
| 3863 | N | O | Q1l' | a bond | Me | a bond | NH | O | NH | Q3e | OH |
| 3864 | N | O | Q1l' | a bond | Me | a bond | NH | O | NH | Q3f | OH |
| 3865 | N | O | Q1l' | a bond | Me | a bond | NH | S | a bond | Q3a | OH |
| 3866 | N | O | Q1l' | a bond | Me | a bond | NH | S | a bond | Q3d | OH |
| 3867 | N | O | Q1l' | a bond | Me | a bond | NH | S | a bond | Q3e | OH |
| 3868 | N | O | Q1l' | a bond | Me | a bond | NH | S | a bond | Q3f | OH |
| 3869 | N | O | Q1l' | a bond | Me | a bond | NH | S | NH | Q3a | OH |
| 3870 | N | O | Q1l' | a bond | Me | a bond | NH | S | NH | Q3d | OH |
| 3871 | N | O | Q1l' | a bond | Me | a bond | NH | S | NH | Q3e | OH |
| 3872 | N | O | Q1l' | a bond | Me | a bond | NH | S | NH | Q3f | OH |
| 3873 | N | O | Q1m' | a bond | Me | a bond | NH | O | a bond | Q3a | OH |
| 3874 | N | O | Q1m' | a bond | Me | a bond | NH | O | a bond | Q3d | OH |
| 3875 | N | O | Q1m' | a bond | Me | a bond | NH | O | a bond | Q3e | OH |
| 3876 | N | O | Q1m' | a bond | Me | a bond | NH | O | a bond | Q3f | OH |
| 3877 | N | O | Q1m' | a bond | Me | a bond | NH | O | NH | Q3a | OH |
| 3878 | N | O | Q1m' | a bond | Me | a bond | NH | O | NH | Q3d | OH |
| 3879 | N | O | Q1m' | a bond | Me | a bond | NH | O | NH | Q3e | OH |
| 3880 | N | O | Q1m' | a bond | Me | a bond | NH | O | NH | Q3f | OH |
| 3881 | N | O | Q1m' | a bond | Me | a bond | NH | S | a bond | Q3a | OH |
| 3882 | N | O | Q1m' | a bond | Me | a bond | NH | S | a bond | Q3d | OH |
| 3883 | N | O | Q1m' | a bond | Me | a bond | NH | S | a bond | Q3e | OH |
| 3884 | N | O | Q1m' | a bond | Me | a bond | NH | S | a bond | Q3f | OH |
| 3885 | N | O | Q1m' | a bond | Me | a bond | NH | S | NH | Q3a | OH |
| 3886 | N | O | Q1m' | a bond | Me | a bond | NH | S | NH | Q3d | OH |
| 3887 | N | O | Q1m' | a bond | Me | a bond | NH | S | NH | Q3e | OH |
| 3888 | N | O | Q1m' | a bond | Me | a bond | NH | S | NH | Q3f | OH |
| 3889 | N | O | Q1n' | a bond | Me | a bond | NH | O | a bond | Q3a | OH |
| 3890 | N | O | Q1n' | a bond | Me | a bond | NH | O | a bond | Q3d | OH |
| 3891 | N | O | Q1n' | a bond | Me | a bond | NH | O | a bond | Q3e | OH |
| 3892 | N | O | Q1n' | a bond | Me | a bond | NH | O | a bond | Q3f | OH |
| 3893 | N | O | Q1n' | a bond | Me | a bond | NH | O | NH | Q3a | OH |
| 3894 | N | O | Q1n' | a bond | Me | a bond | NH | O | NH | Q3d | OH |
| 3895 | N | O | Q1n' | a bond | Me | a bond | NH | O | NH | Q3e | OH |
| 3896 | N | O | Q1n' | a bond | Me | a bond | NH | O | NH | Q3f | OH |
| 3897 | N | O | Q1n' | a bond | Me | a bond | NH | S | a bond | Q3a | OH |
| 3898 | N | O | Q1n' | a bond | Me | a bond | NH | S | a bond | Q3d | OH |
| 3899 | N | O | Q1n' | a bond | Me | a bond | NH | S | a bond | Q3e | OH |
| 3900 | N | O | Q1n' | a bond | Me | a bond | NH | S | a bond | Q3f | OH |

TABLE 1-continued

| No | A | B | R¹ | L¹ | R² | L² | L³ | Y | L⁴ | R³ | X |
|---|---|---|---|---|---|---|---|---|---|---|---|
| 3901 | N | O | Q1n' | a bond | Me | a bond | NH | S | NH | Q3a | OH |
| 3902 | N | O | Q1n' | a bond | Me | a bond | NH | S | NH | Q3d | OH |
| 3903 | N | O | Q1n' | a bond | Me | a bond | NH | S | NH | Q3e | OH |
| 3904 | N | O | Q1n' | a bond | Me | a bond | NH | S | NH | Q3f | OH |
| 3905 | CH | NMe | Q1k' | a bond | Me | a bond | NH | O | a bond | Q3a | OH |
| 3906 | CH | NMe | Q1k' | a bond | Me | a bond | NH | O | a bond | Q3d | OH |
| 3907 | CH | NMe | Q1k' | a bond | Me | a bond | NH | O | a bond | Q3e | OH |
| 3908 | CH | NMe | Q1k' | a bond | Me | a bond | NH | O | a bond | Q3f | OH |
| 3909 | CH | NMe | Q1k' | a bond | Me | a bond | NH | O | NH | Q3a | OH |
| 3910 | CH | NMe | Q1k' | a bond | Me | a bond | NH | O | NH | Q3d | OH |
| 3911 | CH | NMe | Q1k' | a bond | Me | a bond | NH | O | NH | Q3e | OH |
| 3912 | CH | NMe | Q1k' | a bond | Me | a bond | NH | O | NH | Q3f | OH |
| 3913 | CH | NMe | Q1k' | a bond | Me | a bond | NH | S | a bond | Q3a | OH |
| 3914 | CH | NMe | Q1k' | a bond | Me | a bond | NH | S | a bond | Q3d | OH |
| 3915 | CH | NMe | Q1k' | a bond | Me | a bond | NH | S | a bond | Q3e | OH |
| 3916 | CH | NMe | Q1k' | a bond | Me | a bond | NH | S | a bond | Q3f | OH |
| 3917 | CH | NMe | Q1k' | a bond | Me | a bond | NH | S | NH | Q3a | OH |
| 3918 | CH | NMe | Q1k' | a bond | Me | a bond | NH | S | NH | Q3d | OH |
| 3919 | CH | NMe | Q1k' | a bond | Me | a bond | NH | S | NH | Q3e | OH |
| 3920 | CH | NMe | Q1k' | a bond | Me | a bond | NH | S | NH | Q3f | OH |
| 3921 | CH | NMe | Q1l' | a bond | Me | a bond | NH | O | a bond | Q3a | OH |
| 3922 | CH | NMe | Q1l' | a bond | Me | a bond | NH | O | a bond | Q3d | OH |
| 3923 | CH | NMe | Q1l' | a bond | Me | a bond | NH | O | a bond | Q3e | OH |
| 3924 | CH | NMe | Q1l' | a bond | Me | a bond | NH | O | a bond | Q3f | OH |
| 3925 | CH | NMe | Q1l' | a bond | Me | a bond | NH | O | NH | Q3a | OH |
| 3926 | CH | NMe | Q1l' | a bond | Me | a bond | NH | O | NH | Q3d | OH |
| 3927 | CH | NMe | Q1l' | a bond | Me | a bond | NH | O | NH | Q3e | OH |
| 3928 | CH | NMe | Q1l' | a bond | Me | a bond | NH | O | NH | Q3f | OH |
| 3929 | CH | NMe | Q1l' | a bond | Me | a bond | NH | S | a bond | Q3a | OH |
| 3930 | CH | NMe | Q1l' | a bond | Me | a bond | NH | S | a bond | Q3d | OH |
| 3931 | CH | NMe | Q1l' | a bond | Me | a bond | NH | S | a bond | Q3e | OH |
| 3932 | CH | NMe | Q1l' | a bond | Me | a bond | NH | S | a bond | Q3f | OH |
| 3933 | CH | NMe | Q1l' | a bond | Me | a bond | NH | S | NH | Q3a | OH |
| 3934 | CH | NMe | Q1l' | a bond | Me | a bond | NH | S | NH | Q3d | OH |
| 3935 | CH | NMe | Q1l' | a bond | Me | a bond | NH | S | NH | Q3e | OH |
| 3936 | CH | NMe | Q1l' | a bond | Me | a bond | NH | S | NH | Q3f | OH |
| 3937 | CH | NMe | Q1m' | a bond | Me | a bond | NH | O | a bond | Q3a | OH |
| 3938 | CH | NMe | Q1m' | a bond | Me | a bond | NH | O | a bond | Q3d | OH |
| 3939 | CH | NMe | Q1m' | a bond | Me | a bond | NH | O | a bond | Q3e | OH |
| 3940 | CH | NMe | Q1m' | a bond | Me | a bond | NH | O | a bond | Q3f | OH |
| 3941 | CH | NMe | Q1m' | a bond | Me | a bond | NH | O | NH | Q3a | OH |
| 3942 | CH | NMe | Q1m' | a bond | Me | a bond | NH | O | NH | Q3d | OH |
| 3943 | CH | NMe | Q1m' | a bond | Me | a bond | NH | O | NH | Q3e | OH |
| 3944 | CH | NMe | Q1m' | a bond | Me | a bond | NH | O | NH | Q3f | OH |
| 3945 | CH | NMe | Q1m' | a bond | Me | a bond | NH | S | a bond | Q3a | OH |
| 3946 | CH | NMe | Q1m' | a bond | Me | a bond | NH | S | a bond | Q3d | OH |
| 3947 | CH | NMe | Q1m' | a bond | Me | a bond | NH | S | a bond | Q3e | OH |
| 3948 | CH | NMe | Q1m' | a bond | Me | a bond | NH | S | a bond | Q3f | OH |
| 3949 | CH | NMe | Q1m' | a bond | Me | a bond | NH | S | NH | Q3a | OH |
| 3950 | CH | NMe | Q1m' | a bond | Me | a bond | NH | S | NH | Q3d | OH |
| 3951 | CH | NMe | Q1m' | a bond | Me | a bond | NH | S | NH | Q3e | OH |
| 3952 | CH | NMe | Q1m' | a bond | Me | a bond | NH | S | NH | Q3f | OH |
| 3953 | CH | NMe | Q1n' | a bond | Me | a bond | NH | O | a bond | Q3a | OH |
| 3954 | CH | NMe | Q1n' | a bond | Me | a bond | NH | O | a bond | Q3d | OH |
| 3955 | CH | NMe | Q1n' | a bond | Me | a bond | NH | O | a bond | Q3e | OH |
| 3956 | CH | NMe | Q1n' | a bond | Me | a bond | NH | O | a bond | Q3f | OH |
| 3957 | CH | NMe | Q1n' | a bond | Me | a bond | NH | O | NH | Q3a | OH |
| 3958 | CH | NMe | Q1n' | a bond | Me | a bond | NH | O | NH | Q3d | OH |
| 3959 | CH | NMe | Q1n' | a bond | Me | a bond | NH | O | NH | Q3e | OH |
| 3960 | CH | NMe | Q1n' | a bond | Me | a bond | NH | O | NH | Q3f | OH |
| 3961 | CH | NMe | Q1n' | a bond | Me | a bond | NH | S | a bond | Q3a | OH |
| 3962 | CH | NMe | Q1n' | a bond | Me | a bond | NH | S | a bond | Q3d | OH |
| 3963 | CH | NMe | Q1n' | a bond | Me | a bond | NH | S | a bond | Q3e | OH |
| 3964 | CH | NMe | Q1n' | a bond | Me | a bond | NH | S | a bond | Q3f | OH |
| 3965 | CH | NMe | Q1n' | a bond | Me | a bond | NH | S | NH | Q3a | OH |
| 3966 | CH | NMe | Q1n' | a bond | Me | a bond | NH | S | NH | Q3d | OH |
| 3967 | CH | NMe | Q1n' | a bond | Me | a bond | NH | S | NH | Q3e | OH |
| 3968 | CH | NMe | Q1n' | a bond | Me | a bond | NH | S | NH | Q3f | OH |
| 3969 | CH | NEt | Q1k' | a bond | Me | a bond | NH | O | a bond | Q3a | OH |
| 3970 | CH | NEt | Q1k' | a bond | Me | a bond | NH | O | a bond | Q3d | OH |
| 3971 | CH | NEt | Q1k' | a bond | Me | a bond | NH | O | a bond | Q3e | OH |
| 3972 | CH | NEt | Q1k' | a bond | Me | a bond | NH | O | a bond | Q3f | OH |
| 3973 | CH | NEt | Q1k' | a bond | Me | a bond | NH | O | NH | Q3a | OH |
| 3974 | CH | NEt | Q1k' | a bond | Me | a bond | NH | O | NH | Q3d | OH |
| 3975 | CH | NEt | Q1k' | a bond | Me | a bond | NH | O | NH | Q3e | OH |
| 3976 | CH | NEt | Q1k' | a bond | Me | a bond | NH | O | NH | Q3f | OH |
| 3977 | CH | NEt | Q1k' | a bond | Me | a bond | NH | S | a bond | Q3a | OH |
| 3978 | CH | NEt | Q1k' | a bond | Me | a bond | NH | S | a bond | Q3d | OH |

TABLE 1-continued

| No | A | B | R¹ | L¹ | R² | L² | L³ | Y | L⁴ | R³ | X |
|---|---|---|---|---|---|---|---|---|---|---|---|
| 3979 | CH | NEt | Q1k' | a bond | Me | a bond | NH | S | a bond | Q3e | OH |
| 3980 | CH | NEt | Q1k' | a bond | Me | a bond | NH | S | a bond | Q3f | OH |
| 3981 | CH | NEt | Q1k' | a bond | Me | a bond | NH | S | NH | Q3a | OH |
| 3982 | CH | NEt | Q1k' | a bond | Me | a bond | NH | S | NH | Q3d | OH |
| 3983 | CH | NEt | Q1k' | a bond | Me | a bond | NH | S | NH | Q3e | OH |
| 3984 | CH | NEt | Q1k' | a bond | Me | a bond | NH | S | NH | Q3f | OH |
| 3985 | CH | NEt | Q1l' | a bond | Me | a bond | NH | O | a bond | Q3a | OH |
| 3986 | CH | NEt | Q1l' | a bond | Me | a bond | NH | O | a bond | Q3d | OH |
| 3987 | CH | NEt | Q1l' | a bond | Me | a bond | NH | O | a bond | Q3e | OH |
| 3988 | CH | NEt | Q1l' | a bond | Me | a bond | NH | O | a bond | Q3f | OH |
| 3989 | CH | NEt | Q1l' | a bond | Me | a bond | NH | O | NH | Q3a | OH |
| 3990 | CH | NEt | Q1l' | a bond | Me | a bond | NH | O | NH | Q3d | OH |
| 3991 | CH | NEt | Q1l' | a bond | Me | a bond | NH | O | NH | Q3e | OH |
| 3992 | CH | NEt | Q1l' | a bond | Me | a bond | NH | O | NH | Q3f | OH |
| 3993 | CH | NEt | Q1l' | a bond | Me | a bond | NH | S | a bond | Q3a | OH |
| 3994 | CH | NEt | Q1l' | a bond | Me | a bond | NH | S | a bond | Q3d | OH |
| 3995 | CH | NEt | Q1l' | a bond | Me | a bond | NH | S | a bond | Q3e | OH |
| 3996 | CH | NEt | Q1l' | a bond | Me | a bond | NH | S | a bond | Q3f | OH |
| 3997 | CH | NEt | Q1l' | a bond | Me | a bond | NH | S | NH | Q3a | OH |
| 3998 | CH | NEt | Q1l' | a bond | Me | a bond | NH | S | NH | Q3d | OH |
| 3999 | CH | NEt | Q1l' | a bond | Me | a bond | NH | S | NH | Q3e | OH |
| 4000 | CH | NEt | Q1l' | a bond | Me | a bond | NH | S | NH | Q3f | OH |
| 4001 | CH | NEt | Q1m' | a bond | Me | a bond | NH | O | a bond | Q3a | OH |
| 4002 | CH | NEt | Q1m' | a bond | Me | a bond | NH | O | a bond | Q3d | OH |
| 4003 | CH | NEt | Q1m' | a bond | Me | a bond | NH | O | a bond | Q3e | OH |
| 4004 | CH | NEt | Q1m' | a bond | Me | a bond | NH | O | a bond | Q3f | OH |
| 4005 | CH | NEt | Q1m' | a bond | Me | a bond | NH | O | NH | Q3a | OH |
| 4006 | CH | NEt | Q1m' | a bond | Me | a bond | NH | O | NH | Q3d | OH |
| 4007 | CH | NEt | Q1m' | a bond | Me | a bond | NH | O | NH | Q3e | OH |
| 4008 | CH | NEt | Q1m' | a bond | Me | a bond | NH | O | NH | Q3f | OH |
| 4009 | CH | NEt | Q1m' | a bond | Me | a bond | NH | S | a bond | Q3a | OH |
| 4010 | CH | NEt | Q1m' | a bond | Me | a bond | NH | S | a bond | Q3d | OH |
| 4011 | CH | NEt | Q1m' | a bond | Me | a bond | NH | S | a bond | Q3e | OH |
| 4012 | CH | NEt | Q1m' | a bond | Me | a bond | NH | S | a bond | Q3f | OH |
| 4013 | CH | NEt | Q1m' | a bond | Me | a bond | NH | S | NH | Q3a | OH |
| 4014 | CH | NEt | Q1m' | a bond | Me | a bond | NH | S | NH | Q3d | OH |
| 4015 | CH | NEt | Q1m' | a bond | Me | a bond | NH | S | NH | Q3e | OH |
| 4016 | CH | NEt | Q1m' | a bond | Me | a bond | NH | S | NH | Q3f | OH |
| 4017 | CH | NEt | Q1n' | a bond | Me | a bond | NH | O | a bond | Q3a | OH |
| 4018 | CH | NEt | Q1n' | a bond | Me | a bond | NH | O | a bond | Q3d | OH |
| 4019 | CH | NEt | Q1n' | a bond | Me | a bond | NH | O | a bond | Q3e | OH |
| 4020 | CH | NEt | Q1n' | a bond | Me | a bond | NH | O | a bond | Q3f | OH |
| 4021 | CH | NEt | Q1n' | a bond | Me | a bond | NH | O | NH | Q3a | OH |
| 4022 | CH | NEt | Q1n' | a bond | Me | a bond | NH | O | NH | Q3d | OH |
| 4023 | CH | NEt | Q1n' | a bond | Me | a bond | NH | O | NH | Q3e | OH |
| 4024 | CH | NEt | Q1n' | a bond | Me | a bond | NH | O | NH | Q3f | OH |
| 4025 | CH | NEt | Q1n' | a bond | Me | a bond | NH | S | a bond | Q3a | OH |
| 4026 | CH | NEt | Q1n' | a bond | Me | a bond | NH | S | a bond | Q3d | OH |
| 4027 | CH | NEt | Q1n' | a bond | Me | a bond | NH | S | a bond | Q3e | OH |
| 4028 | CH | NEt | Q1n' | a bond | Me | a bond | NH | S | a bond | Q3f | OH |
| 4029 | CH | NEt | Q1n' | a bond | Me | a bond | NH | S | NH | Q3a | OH |
| 4030 | CH | NEt | Q1n' | a bond | Me | a bond | NH | S | NH | Q3d | OH |
| 4031 | CH | NEt | Q1n' | a bond | Me | a bond | NH | S | NH | Q3e | OH |
| 4032 | CH | NEt | Q1n' | a bond | Me | a bond | NH | S | NH | Q3f | OH |
| 4033 | CH | S | Q1k' | a bond | Me | a bond | NH | O | a bond | Q3a | OH |
| 4034 | CH | S | Q1k' | a bond | Me | a bond | NH | O | a bond | Q3d | OH |
| 4035 | CH | S | Q1k' | a bond | Me | a bond | NH | O | a bond | Q3e | OH |
| 4036 | CH | S | Q1k' | a bond | Me | a bond | NH | O | a bond | Q3f | OH |
| 4037 | CH | S | Q1k' | a bond | Me | a bond | NH | O | NH | Q3a | OH |
| 4038 | CH | S | Q1k' | a bond | Me | a bond | NH | O | NH | Q3d | OH |
| 4039 | CH | S | Q1k' | a bond | Me | a bond | NH | O | NH | Q3e | OH |
| 4040 | CH | S | Q1k' | a bond | Me | a bond | NH | O | NH | Q3f | OH |
| 4041 | CH | S | Q1k' | a bond | Me | a bond | NH | S | a bond | Q3a | OH |
| 4042 | CH | S | Q1k' | a bond | Me | a bond | NH | S | a bond | Q3d | OH |
| 4043 | CH | S | Q1k' | a bond | Me | a bond | NH | S | a bond | Q3e | OH |
| 4044 | CH | S | Q1k' | a bond | Me | a bond | NH | S | a bond | Q3f | OH |
| 4045 | CH | S | Q1k' | a bond | Me | a bond | NH | S | NH | Q3a | OH |
| 4046 | CH | S | Q1k' | a bond | Me | a bond | NH | S | NH | Q3d | OH |
| 4047 | CH | S | Q1k' | a bond | Me | a bond | NH | S | NH | Q3e | OH |
| 4048 | CH | S | Q1k' | a bond | Me | a bond | NH | S | NH | Q3f | OH |
| 4049 | CH | S | Q1l' | a bond | Me | a bond | NH | O | a bond | Q3a | OH |
| 4050 | CH | S | Q1l' | a bond | Me | a bond | NH | O | a bond | Q3d | OH |
| 4051 | CH | S | Q1l' | a bond | Me | a bond | NH | O | a bond | Q3e | OH |
| 4052 | CH | S | Q1l' | a bond | Me | a bond | NH | O | a bond | Q3f | OH |
| 4053 | CH | S | Q1l' | a bond | Me | a bond | NH | O | NH | Q3a | OH |
| 4054 | CH | S | Q1l' | a bond | Me | a bond | NH | O | NH | Q3d | OH |
| 4055 | CH | S | Q1l' | a bond | Me | a bond | NH | O | NH | Q3e | OH |
| 4056 | CH | S | Q1l' | a bond | Me | a bond | NH | O | NH | Q3f | OH |

TABLE 1-continued

| No | A | B | R¹ | L¹ | R² | L² | L³ | Y | L⁴ | R³ | X |
|---|---|---|---|---|---|---|---|---|---|---|---|
| 4057 | CH | S | Q1l' | a bond | Me | a bond | NH | S | a bond | Q3a | OH |
| 4058 | CH | S | Q1l' | a bond | Me | a bond | NH | S | a bond | Q3d | OH |
| 4059 | CH | S | Q1l' | a bond | Me | a bond | NH | S | a bond | Q3e | OH |
| 4060 | CH | S | Q1l' | a bond | Me | a bond | NH | S | a bond | Q3f | OH |
| 4061 | CH | S | Q1l' | a bond | Me | a bond | NH | S | NH | Q3a | OH |
| 4062 | CH | S | Q1l' | a bond | Me | a bond | NH | S | NH | Q3d | OH |
| 4063 | CH | S | Q1l' | a bond | Me | a bond | NH | S | NH | Q3e | OH |
| 4064 | CH | S | Q1l' | a bond | Me | a bond | NH | S | NH | Q3f | OH |
| 4065 | CH | S | Q1m' | a bond | Me | a bond | NH | O | a bond | Q3a | OH |
| 4066 | CH | S | Q1m' | a bond | Me | a bond | NH | O | a bond | Q3d | OH |
| 4067 | CH | S | Q1m' | a bond | Me | a bond | NH | O | a bond | Q3e | OH |
| 4068 | CH | S | Q1m' | a bond | Me | a bond | NH | O | a bond | Q3f | OH |
| 4069 | CH | S | Q1m' | a bond | Me | a bond | NH | O | NH | Q3a | OH |
| 4070 | CH | S | Q1m' | a bond | Me | a bond | NH | O | NH | Q3d | OH |
| 4071 | CH | S | Q1m' | a bond | Me | a bond | NH | O | NH | Q3e | OH |
| 4072 | CH | S | Q1m' | a bond | Me | a bond | NH | O | NH | Q3f | OH |
| 4073 | CH | S | Q1m' | a bond | Me | a bond | NH | S | a bond | Q3a | OH |
| 4074 | CH | S | Q1m' | a bond | Me | a bond | NH | S | a bond | Q3d | OH |
| 4075 | CH | S | Q1m' | a bond | Me | a bond | NH | S | a bond | Q3e | OH |
| 4076 | CH | S | Q1m' | a bond | Me | a bond | NH | S | a bond | Q3f | OH |
| 4077 | CH | S | Q1m' | a bond | Me | a bond | NH | S | NH | Q3a | OH |
| 4078 | CH | S | Q1m' | a bond | Me | a bond | NH | S | NH | Q3d | OH |
| 4079 | CH | S | Q1m' | a bond | Me | a bond | NH | S | NH | Q3e | OH |
| 4080 | CH | S | Q1m' | a bond | Me | a bond | NH | S | NH | Q3f | OH |
| 4081 | CH | S | Q1n' | a bond | Me | a bond | NH | O | a bond | Q3a | OH |
| 4082 | CH | S | Q1n' | a bond | Me | a bond | NH | O | a bond | Q3d | OH |
| 4083 | CH | S | Q1n' | a bond | Me | a bond | NH | O | a bond | Q3e | OH |
| 4084 | CH | S | Q1n' | a bond | Me | a bond | NH | O | a bond | Q3f | OH |
| 4085 | CH | S | Q1n' | a bond | Me | a bond | NH | O | NH | Q3a | OH |
| 4086 | CH | S | Q1n' | a bond | Me | a bond | NH | O | NH | Q3d | OH |
| 4087 | CH | S | Q1n' | a bond | Me | a bond | NH | O | NH | Q3e | OH |
| 4088 | CH | S | Q1n' | a bond | Me | a bond | NH | O | NH | Q3f | OH |
| 4089 | CH | S | Q1n' | a bond | Me | a bond | NH | S | a bond | Q3a | OH |
| 4090 | CH | S | Q1n' | a bond | Me | a bond | NH | S | a bond | Q3d | OH |
| 4091 | CH | S | Q1n' | a bond | Me | a bond | NH | S | a bond | Q3e | OH |
| 4092 | CH | S | Q1n' | a bond | Me | a bond | NH | S | a bond | Q3f | OH |
| 4093 | CH | S | Q1n' | a bond | Me | a bond | NH | S | NH | Q3a | OH |
| 4094 | CH | S | Q1n' | a bond | Me | a bond | NH | S | NH | Q3d | OH |
| 4095 | CH | S | Q1n' | a bond | Me | a bond | NH | S | NH | Q3e | OH |
| 4096 | CH | S | Q1n' | a bond | Me | a bond | NH | S | NH | Q3f | OH |
| 4097 | CH | O | Q1k' | a bond | Me | a bond | NH | O | a bond | Q3a | OH |
| 4098 | CH | O | Q1k' | a bond | Me | a bond | NH | O | a bond | Q3d | OH |
| 4099 | CH | O | Q1k' | a bond | Me | a bond | NH | O | a bond | Q3e | OH |
| 4100 | CH | O | Q1k' | a bond | Me | a bond | NH | O | a bond | Q3f | OH |
| 4101 | CH | O | Q1k' | a bond | Me | a bond | NH | O | NH | Q3a | OH |
| 4102 | CH | O | Q1k' | a bond | Me | a bond | NH | O | NH | Q3d | OH |
| 4103 | CH | O | Q1k' | a bond | Me | a bond | NH | O | NH | Q3e | OH |
| 4104 | CH | O | Q1k' | a bond | Me | a bond | NH | O | NH | Q3f | OH |
| 4105 | CH | O | Q1k' | a bond | Me | a bond | NH | S | a bond | Q3a | OH |
| 4106 | CH | O | Q1k' | a bond | Me | a bond | NH | S | a bond | Q3d | OH |
| 4107 | CH | O | Q1k' | a bond | Me | a bond | NH | S | a bond | Q3e | OH |
| 4108 | CH | O | Q1k' | a bond | Me | a bond | NH | S | a bond | Q3f | OH |
| 4109 | CH | O | Q1k' | a bond | Me | a bond | NH | S | NH | Q3a | OH |
| 4110 | CH | O | Q1k' | a bond | Me | a bond | NH | S | NH | Q3d | OH |
| 4111 | CH | O | Q1k' | a bond | Me | a bond | NH | S | NH | Q3e | OH |
| 4112 | CH | O | Q1k' | a bond | Me | a bond | NH | S | NH | Q3f | OH |
| 4113 | CH | O | Q1l' | a bond | Me | a bond | NH | O | a bond | Q3a | OH |
| 4114 | CH | O | Q1l' | a bond | Me | a bond | NH | O | a bond | Q3d | OH |
| 4115 | CH | O | Q1l' | a bond | Me | a bond | NH | O | a bond | Q3e | OH |
| 4116 | CH | O | Q1l' | a bond | Me | a bond | NH | O | a bond | Q3f | OH |
| 4117 | CH | O | Q1l' | a bond | Me | a bond | NH | O | NH | Q3a | OH |
| 4118 | CH | O | Q1l' | a bond | Me | a bond | NH | O | NH | Q3d | OH |
| 4119 | CH | O | Q1l' | a bond | Me | a bond | NH | O | NH | Q3e | OH |
| 4120 | CH | O | Q1l' | a bond | Me | a bond | NH | O | NH | Q3f | OH |
| 4121 | CH | O | Q1l' | a bond | Me | a bond | NH | S | a bond | Q3a | OH |
| 4122 | CH | O | Q1l' | a bond | Me | a bond | NH | S | a bond | Q3d | OH |
| 4123 | CH | O | Q1l' | a bond | Me | a bond | NH | S | a bond | Q3e | OH |
| 4124 | CH | O | Q1l' | a bond | Me | a bond | NH | S | a bond | Q3f | OH |
| 4125 | CH | O | Q1l' | a bond | Me | a bond | NH | S | NH | Q3a | OH |
| 4126 | CH | O | Q1l' | a bond | Me | a bond | NH | S | NH | Q3d | OH |
| 4127 | CH | O | Q1l' | a bond | Me | a bond | NH | S | NH | Q3e | OH |
| 4128 | CH | O | Q1l' | a bond | Me | a bond | NH | S | NH | Q3f | OH |
| 4129 | CH | O | Q1m' | a bond | Me | a bond | NH | O | a bond | Q3a | OH |
| 4130 | CH | O | Q1m' | a bond | Me | a bond | NH | O | a bond | Q3d | OH |
| 4131 | CH | O | Q1m' | a bond | Me | a bond | NH | O | a bond | Q3e | OH |
| 4132 | CH | O | Q1m' | a bond | Me | a bond | NH | O | a bond | Q3f | OH |
| 4133 | CH | O | Q1m' | a bond | Me | a bond | NH | O | NH | Q3a | OH |
| 4134 | CH | O | Q1m' | a bond | Me | a bond | NH | O | NH | Q3d | OH |

TABLE 1-continued

| No | A | B | R¹ | L¹ | R² | L² | L³ | Y | L⁴ | R³ | X |
|---|---|---|---|---|---|---|---|---|---|---|---|
| 4135 | CH | O | Q1m' | a bond | Me | a bond | NH | O | NH | Q3e | OH |
| 4136 | CH | O | Q1m' | a bond | Me | a bond | NH | O | NH | Q3f | OH |
| 4137 | CH | O | Q1m' | a bond | Me | a bond | NH | S | a bond | Q3a | OH |
| 4138 | CH | O | Q1m' | a bond | Me | a bond | NH | S | a bond | Q3d | OH |
| 4139 | CH | O | Q1m' | a bond | Me | a bond | NH | S | a bond | Q3e | OH |
| 4140 | CH | O | Q1m' | a bond | Me | a bond | NH | S | a bond | Q3f | OH |
| 4141 | CH | O | Q1m' | a bond | Me | a bond | NH | S | NH | Q3a | OH |
| 4142 | CH | O | Q1m' | a bond | Me | a bond | NH | S | NH | Q3d | OH |
| 4143 | CH | O | Q1m' | a bond | Me | a bond | NH | S | NH | Q3e | OH |
| 4144 | CH | O | Q1m' | a band | Me | a bond | NH | S | NH | Q3f | OH |
| 4145 | CH | O | Q1n' | a bond | Me | a bond | NH | O | a bond | Q3a | OH |
| 4146 | CH | O | Q1n' | a bond | Me | a bond | NH | O | a bond | Q3d | OH |
| 4147 | CH | O | Q1n' | a bond | Me | a bond | NH | O | a bond | Q3e | OH |
| 4148 | CH | O | Q1n' | a bond | Me | a bond | NH | O | a bond | Q3f | OH |
| 4149 | CH | O | Q1n' | a bond | Me | a bond | NH | O | NH | Q3a | OH |
| 4150 | CH | O | Q1n' | a bond | Me | a bond | NH | O | NH | Q3d | OH |
| 4151 | CH | O | Q1n' | a bond | Me | a bond | NH | O | NH | Q3e | OH |
| 4152 | CH | O | Q1n' | a bond | Me | a bond | NH | O | NH | Q3f | OH |
| 4153 | CH | O | Q1n' | a bond | Me | a bond | NH | S | a bond | Q3a | OH |
| 4154 | CH | O | Q1n' | a bond | Me | a bond | NH | S | a bond | Q3d | OH |
| 4155 | CH | O | Q1n' | a bond | Me | a bond | NH | S | a bond | Q3e | OH |
| 4156 | CH | O | Q1n' | a bond | Me | a bond | NH | S | a bond | Q3f | OH |
| 4157 | CH | O | Q1n' | a bond | Me | a bond | NH | S | NH | Q3a | OH |
| 4158 | CH | O | Q1n' | a bond | Me | a bond | NH | S | NH | Q3d | OH |
| 4159 | CH | O | Q1n' | a bond | Me | a bond | NH | S | NH | Q3e | OH |
| 4160 | CH | O | Q1n' | a bond | Me | a bond | NH | S | NH | Q3f | OH |
| 4161 | CMe | NMe | Q1k' | a bond | Me | a bond | NH | O | a bond | Q3a | OH |
| 4162 | CMe | NMe | Q1k' | a bond | Me | a bond | NH | O | a bond | Q3d | OH |
| 4163 | CMe | NMe | Q1k' | a bond | Me | a bond | NH | O | a bond | Q3e | OH |
| 4164 | CMe | NMe | Q1k' | a bond | Me | a bond | NH | O | a bond | Q3f | OH |
| 4165 | CMe | NMe | Q1k' | a bond | Me | a bond | NH | O | NH | Q3a | OH |
| 4166 | CMe | NMe | Q1k' | a bond | Me | a bond | NH | O | NH | Q3d | OH |
| 4167 | CMe | NMe | Q1k' | a bond | Me | a bond | NH | O | NH | Q3e | OH |
| 4168 | CMe | NMe | Q1k' | a bond | Me | a bond | NH | O | NH | Q3f | OH |
| 4169 | CMe | NMe | Q1k' | a bond | Me | a bond | NH | S | a bond | Q3a | OH |
| 4170 | CMe | NMe | Q1k' | a bond | Me | a bond | NH | S | a bond | Q3d | OH |
| 4171 | CMe | NMe | Q1k' | a bond | Me | a bond | NH | S | a bond | Q3e | OH |
| 4172 | CMe | NMe | Q1k' | a bond | Me | a bond | NH | S | a bond | Q3f | OH |
| 4173 | CMe | NMe | Q1k' | a bond | Me | a bond | NH | S | NH | Q3a | OH |
| 4174 | CMe | NMe | Q1k' | a bond | Me | a bond | NH | S | NH | Q3d | OH |
| 4175 | CMe | NMe | Q1k' | a bond | Me | a bond | NH | S | NH | Q3e | OH |
| 4176 | CMe | NMe | Q1k' | a bond | Me | a bond | NH | S | NH | Q3f | OH |
| 4177 | CMe | NMe | Q1l' | a bond | Me | a bond | NH | O | a bond | Q3a | OH |
| 4178 | CMe | NMe | Q1l' | a bond | Me | a bond | NH | O | a bond | Q3d | OH |
| 4179 | CMe | NMe | Q1l' | a bond | Me | a bond | NH | O | a bond | Q3e | OH |
| 4180 | CMe | NMe | Q1l' | a bond | Me | a bond | NH | O | a bond | Q3f | OH |
| 4181 | CMe | NMe | Q1l' | a bond | Me | a bond | NH | O | NH | Q3a | OH |
| 4182 | CMe | NMe | Q1l' | a bond | Me | a bond | NH | O | NH | Q3d | OH |
| 4183 | CMe | NMe | Q1l' | a bond | Me | a bond | NH | O | NH | Q3e | OH |
| 4184 | CMe | NMe | Q1l' | a bond | Me | a bond | NH | O | NH | Q3f | OH |
| 4185 | CMe | NMe | Q1l' | a bond | Me | a bond | NH | S | a bond | Q3a | OH |
| 4186 | CMe | NMe | Q1l' | a bond | Me | a bond | NH | S | a bond | Q3d | OH |
| 4187 | CMe | NMe | Q1l' | a bond | Me | a bond | NH | S | a bond | Q3e | OH |
| 4188 | CMe | NMe | Q1l' | a bond | Me | a bond | NH | S | a bond | Q3f | OH |
| 4189 | CMe | NMe | Q1l' | a bond | Me | a bond | NH | S | NH | Q3a | OH |
| 4190 | CMe | NMe | Q1l' | a bond | Me | a bond | NH | S | NH | Q3d | OH |
| 4191 | CMe | NMe | Q1l' | a bond | Me | a bond | NH | S | NH | Q3e | OH |
| 4192 | CMe | NMe | Q1l' | a bond | Me | a bond | NH | S | NH | Q3f | OH |
| 4193 | CMe | NMe | Q1m' | a bond | Me | a bond | NH | O | a bond | Q3a | OH |
| 4194 | CMe | NMe | Q1m' | a bond | Me | a bond | NH | O | a bond | Q3d | OH |
| 4195 | CMe | NMe | Q1m' | a bond | Me | a bond | NH | O | a bond | Q3e | OH |
| 4196 | CMe | NMe | Q1m' | a bond | Me | a bond | NH | O | a bond | Q3f | OH |
| 4197 | CMe | NMe | Q1m' | a bond | Me | a bond | NH | O | NH | Q3a | OH |
| 4198 | CMe | NMe | Q1m' | a bond | Me | a bond | NH | O | NH | Q3d | OH |
| 4199 | CMe | NMe | Q1m' | a bond | Me | a bond | NH | O | NH | Q3e | OH |
| 4200 | CMe | NMe | Q1m' | a bond | Me | a bond | NH | O | NH | Q3f | OH |
| 4201 | CMe | NMe | Q1m' | a bond | Me | a bond | NH | S | a bond | Q3a | OH |
| 4202 | CMe | NMe | Q1m' | a bond | Me | a bond | NH | S | a bond | Q3d | OH |
| 4203 | CMe | NMe | Q1m' | a bond | Me | a bond | NH | S | a bond | Q3e | OH |
| 4204 | CMe | NMe | Q1m' | a bond | Me | a bond | NH | S | a bond | Q3f | OH |
| 4205 | CMe | NMe | Q1m' | a bond | Me | a bond | NH | S | NH | Q3a | OH |
| 4206 | CMe | NMe | Q1m' | a bond | Me | a bond | NH | S | NH | Q3d | OH |
| 4207 | CMe | NMe | Q1m' | a bond | Me | a bond | NH | S | NH | Q3e | OH |
| 4208 | CMe | NMe | Q1m' | a bond | Me | a bond | NH | S | NH | Q3f | OH |
| 4209 | CMe | NMe | Q1n' | a bond | Me | a bond | NH | O | a bond | Q3a | OH |
| 4210 | CMe | NMe | Q1n' | a bond | Me | a bond | NH | O | a bond | Q3d | OH |
| 4211 | CMe | NMe | Q1n' | a bond | Me | a bond | NH | O | a bond | Q3e | OH |
| 4212 | CMe | NMe | Q1n' | a bond | Me | a bond | NH | O | a bond | Q3f | OH |

TABLE 1-continued

| No | A | B | R¹ | L¹ | R² | L² | L³ | Y | L⁴ | R³ | X |
|---|---|---|---|---|---|---|---|---|---|---|---|
| 4213 | CMe | NMe | Q1n' | a bond | Me | a bond | NH | O | NH | Q3a | OH |
| 4214 | CMe | NMe | Q1n' | a bond | Me | a bond | NH | O | NH | Q3d | OH |
| 4215 | CMe | NMe | Q1n' | a bond | Me | a bond | NH | O | NH | Q3e | OH |
| 4216 | CMe | NMe | Q1n' | a bond | Me | a bond | NH | O | NH | Q3f | OH |
| 4217 | CMe | NMe | Q1n' | a bond | Me | a bond | NH | S | a bond | Q3a | OH |
| 4218 | CMe | NMe | Q1n' | a bond | Me | a bond | NH | S | a bond | Q3d | OH |
| 4219 | CMe | NMe | Q1n' | a bond | Me | a bond | NH | S | a bond | Q3e | OH |
| 4220 | CMe | NMe | Q1n' | a bond | Me | a bond | NH | S | a bond | Q3f | OH |
| 4221 | CMe | NMe | Q1n' | a bond | Me | a bond | NH | S | NH | Q3a | OH |
| 4222 | CMe | NMe | Q1n' | a bond | Me | a bond | NH | S | NH | Q3d | OH |
| 4223 | CMe | NMe | Q1n' | a bond | Me | a bond | NH | S | NH | Q3e | OH |
| 4224 | CMe | NMe | Q1n' | a bond | Me | a bond | NH | S | NH | Q3f | OH |
| 4225 | CMe | NEt | Q1k' | a bond | Me | a bond | NH | O | a bond | Q3a | OH |
| 4226 | CMe | NEt | Q1k' | a bond | Me | a bond | NH | O | a bond | Q3d | OH |
| 4227 | CMe | NEt | Q1k' | a bond | Me | a bond | NH | O | a bond | Q3e | OH |
| 4228 | CMe | NEt | Q1k' | a bond | Me | a bond | NH | O | a bond | Q3f | OH |
| 4229 | CMe | NEt | Q1k' | a bond | Me | a bond | NH | O | NH | Q3a | OH |
| 4230 | CMe | NEt | Q1k' | a bond | Me | a bond | NH | O | NH | Q3d | OH |
| 4231 | CMe | NEt | Q1k' | a bond | Me | a bond | NH | O | NH | Q3e | OH |
| 4232 | CMe | NEt | Q1k' | a bond | Me | a bond | NH | O | NH | Q3f | OH |
| 4233 | CMe | NEt | Q1k' | a bond | Me | a bond | NH | S | a bond | Q3a | OH |
| 4234 | CMe | NEt | Q1k' | a bond | Me | a bond | NH | S | a bond | Q3d | OH |
| 4235 | CMe | NEt | Q1k' | a bond | Me | a bond | NH | S | a bond | Q3e | OH |
| 4236 | CMe | NEt | Q1k' | a bond | Me | a bond | NH | S | a bond | Q3f | OH |
| 4237 | CMe | NEt | Q1k' | a bond | Me | a bond | NH | S | NH | Q3a | OH |
| 4238 | CMe | NEt | Q1k' | a bond | Me | a bond | NH | S | NH | Q3d | OH |
| 4239 | CMe | NEt | Q1k' | a bond | Me | a bond | NH | S | NH | Q3e | OH |
| 4240 | CMe | NEt | Q1k' | a bond | Me | a bond | NH | S | NH | Q3f | OH |
| 4241 | CMe | NEt | Q1l' | a bond | Me | a bond | NH | O | a bond | Q3a | OH |
| 4242 | CMe | NEt | Q1l' | a bond | Me | a bond | NH | O | a bond | Q3d | OH |
| 4243 | CMe | NEt | Q1l' | a bond | Me | a bond | NH | O | a bond | Q3e | OH |
| 4244 | CMe | NEt | Q1l' | a bond | Me | a bond | NH | O | a bond | Q3f | OH |
| 4245 | CMe | NEt | Q1l' | a bond | Me | a bond | NH | O | NH | Q3a | OH |
| 4246 | CMe | NEt | Q1l' | a bond | Me | a bond | NH | O | NH | Q3d | OH |
| 4247 | CMe | NEt | Q1l' | a bond | Me | a bond | NH | O | NH | Q3e | OH |
| 4248 | CMe | NEt | Q1l' | a bond | Me | a bond | NH | O | NH | Q3f | OH |
| 4249 | CMe | NEt | Q1l' | a bond | Me | a bond | NH | S | a bond | Q3a | OH |
| 4250 | CMe | NEt | Q1l' | a bond | Me | a bond | NH | S | a bond | Q3d | OH |
| 4251 | CMe | NEt | Q1l' | a bond | Me | a bond | NH | S | a bond | Q3e | OH |
| 4252 | CMe | NEt | Q1l' | a bond | Me | a bond | NH | S | a bond | Q3f | OH |
| 4253 | CMe | NEt | Q1l' | a bond | Me | a bond | NH | S | NH | Q3a | OH |
| 4254 | CMe | NEt | Q1l' | a bond | Me | a bond | NH | S | NH | Q3d | OH |
| 4255 | CMe | NEt | Q1l' | a bond | Me | a bond | NH | S | NH | Q3e | OH |
| 4256 | CMe | NEt | Q1l' | a bond | Me | a bond | NH | S | NH | Q3f | OH |
| 4257 | CMe | NEt | Q1m' | a bond | Me | a bond | NH | O | a bond | Q3a | OH |
| 4258 | CMe | NEt | Q1m' | a bond | Me | a bond | NH | O | a bond | Q3d | OH |
| 4259 | CMe | NEt | Q1m' | a bond | Me | a bond | NH | O | a bond | Q3e | OH |
| 4260 | CMe | NEt | Q1m' | a bond | Me | a bond | NH | O | a bond | Q3f | OH |
| 4261 | CMe | NEt | Q1m' | a bond | Me | a bond | NH | O | NH | Q3a | OH |
| 4262 | CMe | NEt | Q1m' | a bond | Me | a bond | NH | O | NH | Q3d | OH |
| 4263 | CMe | NEt | Q1m' | a bond | Me | a bond | NH | O | NH | Q3e | OH |
| 4264 | CMe | NEt | Q1m' | a bond | Me | a bond | NH | O | NH | Q3f | OH |
| 4265 | CMe | NEt | Q1m' | a bond | Me | a bond | NH | S | a bond | Q3a | OH |
| 4266 | CMe | NEt | Q1m' | a bond | Me | a bond | NH | S | a bond | Q3d | OH |
| 4267 | CMe | NEt | Q1m' | a bond | Me | a bond | NH | S | a bond | Q3e | OH |
| 4268 | CMe | NEt | Q1m' | a bond | Me | a bond | NH | S | a bond | Q3f | OH |
| 4269 | CMe | NEt | Q1m' | a bond | Me | a bond | NH | S | NH | Q3a | OH |
| 4270 | CMe | NEt | Q1m' | a bond | Me | a bond | NH | S | NH | Q3d | OH |
| 4271 | CMe | NEt | Q1m' | a bond | Me | a bond | NH | S | NH | Q3e | OH |
| 4272 | CMe | NEt | Q1m' | a bond | Me | a bond | NH | S | NH | Q3f | OH |
| 4273 | CMe | NEt | Q1n' | a bond | Me | a bond | NH | O | a bond | Q3a | OH |
| 4274 | CMe | NEt | Q1n' | a bond | Me | a bond | NH | O | a bond | Q3d | OH |
| 4275 | CMe | NEt | Q1n' | a bond | Me | a bond | NH | O | a bond | Q3e | OH |
| 4276 | CMe | Net | Q1n' | a bond | Me | a bond | NH | O | a bond | Q3f | OH |
| 4277 | CMe | NEt | Q1n' | a bond | Me | a bond | NH | O | NH | Q3a | OH |
| 4278 | CMe | NEt | Q1n' | a bond | Me | a bond | NH | O | NH | Q3d | OH |
| 4279 | CMe | NEt | Q1n' | a bond | Me | a bond | NH | O | NH | Q3e | OH |
| 4280 | CMe | NEt | Q1n' | a bond | Me | a bond | NH | O | NH | Q3f | OH |
| 4281 | CMe | NEt | Q1n' | a bond | Me | a bond | NH | S | a bond | Q3a | OH |
| 4282 | CMe | NEt | Q1n' | a bond | Me | a bond | NH | S | a bond | Q3d | OH |
| 4283 | CMe | NEt | Q1n' | a bond | Me | a bond | NH | S | a bond | Q3e | OH |
| 4284 | CMe | NEt | Q1n' | a bond | Me | a bond | NH | S | a bond | Q3f | OH |
| 4285 | CMe | NEt | Q1n' | a bond | Me | a bond | NH | S | NH | Q3a | OH |
| 4286 | CMe | NEt | Q1n' | a bond | Me | a bond | NH | S | NH | Q3d | OH |
| 4287 | CMe | NEt | Q1n' | a bond | Me | a bond | NH | S | NH | Q3e | OH |
| 4288 | CMe | NEt | Q1n' | a bond | Me | a bond | NH | S | NH | Q3f | OH |
| 4289 | CMe | S | Q1k' | a bond | Me | a bond | NH | O | a bond | Q3a | OH |
| 4290 | CMe | S | Q1k' | a bond | Me | a bond | NH | O | a bond | Q3d | OH |

TABLE 1-continued

| No | A | B | R¹ | L¹ | R² | L² | L³ | Y | L⁴ | R³ | X |
|---|---|---|---|---|---|---|---|---|---|---|---|
| 4291 | CMe | S | Q1k' | a bond | Me | a bond | NH | O | a bond | Q3e | OH |
| 4292 | CMe | S | Q1k' | a bond | Me | a bond | NH | O | a bond | Q3f | OH |
| 4293 | CMe | S | Q1k' | a bond | Me | a bond | NH | O | NH | Q3a | OH |
| 4294 | CMe | S | Q1k' | a bond | Me | a bond | NH | O | NH | Q3d | OH |
| 4295 | CMe | S | Q1k' | a bond | Me | a bond | NH | O | NH | Q3e | OH |
| 4296 | CMe | S | Q1k' | a bond | Me | a bond | NH | O | NH | Q3f | OH |
| 4297 | CMe | S | Q1k' | a bond | Me | a bond | NH | S | a bond | Q3a | OH |
| 4298 | CMe | S | Q1k' | a bond | Me | a bond | NH | S | a bond | Q3d | OH |
| 4299 | CMe | S | Q1k' | a bond | Me | a bond | NH | S | a bond | Q3e | OH |
| 4300 | CMe | S | Q1k' | a bond | Me | a bond | NH | S | a bond | Q3f | OH |
| 4301 | CMe | S | Q1k' | a bond | Me | a bond | NH | S | NH | Q3a | OH |
| 4302 | CMe | S | Q1k' | a bond | Me | a bond | NH | S | NH | Q3d | OH |
| 4303 | CMe | S | Q1k' | a bond | Me | a bond | NH | S | NH | Q3e | OH |
| 4304 | CMe | S | Q1k' | a bond | Me | a bond | NH | S | NH | Q3f | OH |
| 4305 | CMe | S | Q1l' | a bond | Me | a bond | NH | O | a bond | Q3a | OH |
| 4306 | CMe | S | Q1l' | a bond | Me | a bond | NH | O | a bond | Q3d | OH |
| 4307 | CMe | S | Q1l' | a bond | Me | a bond | NH | O | a bond | Q3e | OH |
| 4308 | CMe | S | Q1l' | a bond | Me | a bond | NH | O | a bond | Q3f | OH |
| 4309 | CMe | S | Q1l' | a bond | Me | a bond | NH | O | NH | Q3a | OH |
| 4310 | CMe | S | Q1l' | a bond | Me | a bond | NH | O | NH | Q3d | OH |
| 4311 | CMe | S | Q1l' | a bond | Me | a bond | NH | O | NH | Q3e | OH |
| 4312 | CMe | S | Q1l' | a bond | Me | a bond | NH | O | NH | Q3f | OH |
| 4313 | CMe | S | Q1l' | a bond | Me | a bond | NH | S | a bond | Q3a | OH |
| 4314 | CMe | S | Q1l' | a bond | Me | a bond | NH | S | a bond | Q3d | OH |
| 4315 | CMe | S | Q1l' | a bond | Me | a bond | NH | S | a bond | Q3e | OH |
| 4316 | CMe | S | Q1l' | a bond | Me | a bond | NH | S | a bond | Q3f | OH |
| 4317 | CMe | S | Q1l' | a bond | Me | a bond | NH | S | NH | Q3a | OH |
| 4318 | CMe | S | Q1l' | a bond | Me | a bond | NH | S | NH | Q3d | OH |
| 4319 | CMe | S | Q1l' | a bond | Me | a bond | NH | S | NH | Q3e | OH |
| 4320 | CMe | S | Q1l' | a bond | Me | a bond | NH | S | NH | Q3f | OH |
| 4321 | CMe | S | Q1m' | a bond | Me | a bond | NH | O | a bond | Q3a | OH |
| 4322 | CMe | S | Q1m' | a bond | Me | a bond | NH | O | a bond | Q3d | OH |
| 4323 | CMe | S | Q1m' | a bond | Me | a bond | NH | O | a bond | Q3e | OH |
| 4324 | CMe | S | Q1m' | a bond | Me | a bond | NH | O | a bond | Q3f | OH |
| 4325 | CMe | S | Q1m' | a bond | Me | a bond | NH | O | NH | Q3a | OH |
| 4326 | CMe | S | Q1m' | a bond | Me | a bond | NH | O | NH | Q3d | OH |
| 4327 | CMe | S | Q1m' | a bond | Me | a bond | NH | O | NH | Q3e | OH |
| 4328 | CMe | S | Q1m' | a bond | Me | a bond | NH | O | NH | Q3f | OH |
| 4329 | CMe | S | Q1m' | a bond | Me | a bond | NH | S | a bond | Q3a | OH |
| 4330 | CMe | S | Q1m' | a bond | Me | a bond | NH | S | a bond | Q3d | OH |
| 4331 | CMe | S | Q1m' | a bond | Me | a bond | NH | S | a bond | Q3e | OH |
| 4332 | CMe | S | Q1m' | a bond | Me | a bond | NH | S | a bond | Q3f | OH |
| 4333 | CMe | S | Q1m' | a bond | Me | a bond | NH | S | NH | Q3a | OH |
| 4334 | CMe | S | Q1m' | a bond | Me | a bond | NH | S | NH | Q3d | OH |
| 4335 | CMe | S | Q1m' | a bond | Me | a bond | NH | S | NH | Q3e | OH |
| 4336 | CMe | S | Q1m' | a bond | Me | a bond | NH | S | NH | Q3f | OH |
| 4337 | CMe | S | Q1n' | a bond | Me | a bond | NH | O | a bond | Q3a | OH |
| 4338 | CMe | S | Q1n' | a bond | Me | a bond | NH | O | a bond | Q3d | OH |
| 4339 | CMe | S | Q1n' | a bond | Me | a bond | NH | O | a bond | Q3e | OH |
| 4340 | CMe | S | Q1n' | a bond | Me | a bond | NH | O | a bond | Q3f | OH |
| 4341 | CMe | S | Q1n' | a bond | Me | a bond | NH | O | NH | Q3a | OH |
| 4342 | CMe | S | Q1n' | a bond | Me | a bond | NH | O | NH | Q3d | OH |
| 4343 | CMe | S | Q1n' | a bond | Me | a bond | NH | O | NH | Q3e | OH |
| 4344 | CMe | S | Q1n' | a bond | Me | a bond | NH | O | NH | Q3f | OH |
| 4345 | CMe | S | Q1n' | a bond | Me | a bond | NH | S | a bond | Q3a | OH |
| 4346 | CMe | S | Q1n' | a bond | Me | a bond | NH | S | a bond | Q3d | OH |
| 4347 | CMe | S | Q1n' | a bond | Me | a bond | NH | S | a bond | Q3e | OH |
| 4348 | CMe | S | Q1n' | a bond | Me | a bond | NH | S | a bond | Q3f | OH |
| 4349 | CMe | S | Q1n' | a bond | Me | a bond | NH | S | NH | Q3a | OH |
| 4350 | CMe | S | Q1n' | a bond | Me | a bond | NH | S | NH | Q3d | OH |
| 4351 | CMe | S | Q1n' | a bond | Me | a bond | NH | S | NH | Q3e | OH |
| 4352 | CMe | S | Q1n' | a bond | Me | a bond | NH | S | NH | Q3f | OH |
| 4353 | CMe | O | Q1k' | a bond | Me | a bond | NH | O | a bond | Q3a | OH |
| 4354 | CMe | O | Q1k' | a bond | Me | a bond | NH | O | a bond | Q3d | OH |
| 4355 | CMe | O | Q1k' | a bond | Me | a bond | NH | O | a bond | Q3e | OH |
| 4356 | CMe | O | Q1k' | a bond | Me | a bond | NH | O | a bond | Q3f | OH |
| 4357 | CMe | O | Q1k' | a bond | Me | a bond | NH | O | NH | Q3a | OH |
| 4358 | CMe | O | Q1k' | a bond | Me | a bond | NH | O | NH | Q3d | OH |
| 4359 | CMe | O | Q1k' | a bond | Me | a bond | NH | O | NH | Q3e | OH |
| 4360 | CMe | O | Q1k' | a bond | Me | a bond | NH | O | NH | Q3f | OH |
| 4361 | CMe | O | Q1k' | a bond | Me | a bond | NH | S | a bond | Q3a | OH |
| 4362 | CMe | O | Q1k' | a bond | Me | a bond | NH | S | a bond | Q3d | OH |
| 4363 | CMe | O | Q1k' | a bond | Me | a bond | NH | S | a bond | Q3e | OH |
| 4364 | CMe | O | Q1k' | a bond | Me | a bond | NH | S | a bond | Q3f | OH |
| 4365 | CMe | O | Q1k' | a bond | Me | a bond | NH | S | NH | Q3a | OH |
| 4366 | CMe | O | Q1k' | a bond | Me | a bond | NH | S | NH | Q3d | OH |
| 4367 | CMe | O | Q1k' | a bond | Me | a bond | NH | S | NH | Q3e | OH |
| 4368 | CMe | O | Q1k' | a bond | Me | a bond | NH | S | NH | Q3f | OH |

TABLE 1-continued

| No | A | B | R¹ | L¹ | R² | L² | L³ | Y | L⁴ | R³ | X |
|---|---|---|---|---|---|---|---|---|---|---|---|
| 4369 | CMe | O | Q1l' | a bond | Me | a bond | NH | O | a bond | Q3a | OH |
| 4370 | CMe | O | Q1l' | a bond | Me | a bond | NH | O | a bond | Q3d | OH |
| 4371 | CMe | O | Q1l' | a bond | Me | a bond | NH | O | a bond | Q3e | OH |
| 4372 | CMe | O | Q1l' | a bond | Me | a bond | NH | O | a bond | Q3f | OH |
| 4373 | CMe | O | Q1l' | a bond | Me | a bond | NH | O | NH | Q3a | OH |
| 4374 | CMe | O | Q1l' | a bond | Me | a bond | NH | O | NH | Q3d | OH |
| 4375 | CMe | O | Q1l' | a bond | Me | a bond | NH | O | NH | Q3e | OH |
| 4376 | CMe | O | Q1l' | a bond | Me | a bond | NH | O | NH | Q3f | OH |
| 4377 | CMe | O | Q1l' | a bond | Me | a bond | NH | S | a bond | Q3a | OH |
| 4378 | CMe | O | Q1l' | a bond | Me | a bond | NH | S | a bond | Q3d | OH |
| 4379 | CMe | O | Q1l' | a bond | Me | a bond | NH | S | a bond | Q3e | OH |
| 4380 | CMe | O | Q1l' | a bond | Me | a bond | NH | S | a bond | Q3f | OH |
| 4381 | CMe | O | Q1l' | a bond | Me | a bond | NH | S | NH | Q3a | OH |
| 4382 | CMe | O | Q1l' | a bond | Me | a bond | NH | S | NH | Q3d | OH |
| 4383 | CMe | O | Q1l' | a bond | Me | a bond | NH | S | NH | Q3e | OH |
| 4384 | CMe | O | Q1l' | a bond | Me | a bond | NH | S | NH | Q3f | OH |
| 4385 | CMe | O | Q1m' | a bond | Me | a bond | NH | O | a bond | Q3a | OH |
| 4386 | CMe | O | Q1m' | a bond | Me | a bond | NH | O | a bond | Q3d | OH |
| 4387 | CMe | O | Q1m' | a bond | Me | a bond | NH | O | a bond | Q3e | OH |
| 4388 | CMe | O | Q1m' | a bond | Me | a bond | NH | O | a bond | Q3f | OH |
| 4389 | CMe | O | Q1m' | a bond | Me | a bond | NH | O | NH | Q3a | OH |
| 4390 | CMe | O | Q1m' | a bond | Me | a bond | NH | O | NH | Q3d | OH |
| 4391 | CMe | O | Q1m' | a bond | Me | a bond | NH | O | NH | Q3e | OH |
| 4392 | CMe | O | Q1m' | a bond | Me | a bond | NH | O | NH | Q3f | OH |
| 4393 | CMe | O | Q1m' | a bond | Me | a bond | NH | S | a bond | Q3a | OH |
| 4394 | CMe | O | Q1m' | a bond | Me | a bond | NH | S | a bond | Q3d | OH |
| 4395 | CMe | O | Q1m' | a bond | Me | a bond | NH | S | a bond | Q3e | OH |
| 4396 | CMe | O | Q1m' | a bond | Me | a bond | NH | S | a bond | Q3f | OH |
| 4397 | CMe | O | Q1m' | a bond | Me | a bond | NH | S | NH | Q3a | OH |
| 4398 | CMe | O | Q1m' | a bond | Me | a bond | NH | S | NH | Q3d | OH |
| 4399 | CMe | O | Q1m' | a bond | Me | a bond | NH | S | NH | Q3e | OH |
| 4400 | CMe | O | Q1m' | a bond | Me | a bond | NH | S | NH | Q3f | OH |
| 4401 | CMe | O | Q1n' | a bond | Me | a bond | NH | O | a bond | Q3a | OH |
| 4402 | CMe | O | Q1n' | a bond | Me | a bond | NH | O | a bond | Q3d | OH |
| 4403 | CMe | O | Q1n' | a bond | Me | a bond | NH | O | a bond | Q3e | OH |
| 4404 | CMe | O | Q1n' | a bond | Me | a bond | NH | O | a bond | Q3f | OH |
| 4405 | CMe | O | Q1n' | a bond | Me | a bond | NH | O | NH | Q3a | OH |
| 4406 | CMe | O | Q1n' | a bond | Me | a bond | NH | O | NH | Q3d | OH |
| 4407 | CMe | O | Q1n' | a bond | Me | a bond | NH | O | NH | Q3e | OH |
| 4408 | CMe | O | Q1n' | a bond | Me | a bond | NH | O | NH | Q3f | OH |
| 4409 | CMe | O | Q1n' | a bond | Me | a bond | NH | S | a bond | Q3a | OH |
| 4410 | CMe | O | Q1n' | a bond | Me | a bond | NH | S | a bond | Q3d | OH |
| 4411 | CMe | O | Q1n' | a bond | Me | a bond | NH | S | a bond | Q3e | OH |
| 4412 | CMe | O | Q1n' | a bond | Me | a bond | NH | S | a bond | Q3f | OH |
| 4413 | CMe | O | Q1n' | a bond | Me | a bond | NH | S | NH | Q3a | OH |
| 4414 | CMe | O | Q1n' | a bond | Me | a bond | NH | S | NH | Q3d | OH |
| 4415 | CMe | O | Q1n' | a bond | Me | a bond | NH | S | NH | Q3e | OH |
| 4416 | CMe | O | Q1n' | a bond | Me | a bond | NH | S | NH | Q3f | OH |
| 4417 | N | NMe | Q1a | a bond | Me | a bond | NH | O | a bond | Q3d | OH |
| 4418 | N | NMe | Q1a | a bond | Me | a bond | NH | O | a bond | Q3e | OH |
| 4419 | N | NMe | Q1a | a bond | Me | a bond | NH | O | a bond | Q3f | OH |
| 4420 | N | NMe | Q1a | a bond | Me | a bond | NH | O | NH | Q3d | OH |
| 4421 | N | NMe | Q1a | a bond | Me | a bond | NH | O | NH | Q3e | OH |
| 4422 | N | NMe | Q1a | a bond | Me | a bond | NH | O | NH | Q3f | OH |
| 4423 | N | NMe | Q1a | a bond | Me | a bond | NH | S | a bond | Q3d | OH |
| 4424 | N | NMe | Q1a | a bond | Me | a bond | NH | S | a bond | Q3e | OH |
| 4425 | N | NMe | Q1a | a bond | Me | a bond | NH | S | a bond | Q3f | OH |
| 4426 | N | NMe | Q1a | a bond | Me | a bond | NH | S | NH | Q3d | OH |
| 4427 | N | NMe | Q1a | a bond | Me | a bond | NH | S | NH | Q3e | OH |
| 4428 | N | NMe | Q1a | a bond | Me | a bond | NH | S | NH | Q3f | OH |
| 4429 | N | NMe | Q1b | a bond | Me | a bond | NH | O | a bond | Q3d | OH |
| 4430 | N | NMe | Q1b | a bond | Me | a bond | NH | O | a bond | Q3e | OH |
| 4431 | N | NMe | Q1b | a bond | Me | a bond | NH | O | a bond | Q3f | OH |
| 4432 | N | NMe | Q1b | a bond | Me | a bond | NH | O | NH | Q3d | OH |
| 4433 | N | NMe | Q1b | a bond | Me | a bond | NH | O | NH | Q3e | OH |
| 4434 | N | NMe | Q1b | a bond | Me | a bond | NH | O | NH | Q3f | OH |
| 4435 | N | NMe | Q1b | a bond | Me | a bond | NH | S | a bond | Q3d | OH |
| 4436 | N | NMe | Q1b | a bond | Me | a bond | NH | S | a bond | Q3e | OH |
| 4437 | N | NMe | Q1b | a bond | Me | a bond | NH | S | a bond | Q3f | OH |
| 4438 | N | NMe | Q1b | a bond | Me | a bond | NH | S | NH | Q3d | OH |
| 4439 | N | NMe | Q1b | a bond | Me | a bond | NH | S | NH | Q3e | OH |
| 4440 | N | NMe | Q1b | a bond | Me | a bond | NH | S | NH | Q3f | OH |
| 4441 | N | NMe | Q1c | a bond | Me | a bond | NH | O | a bond | Q3d | OH |
| 4442 | N | NMe | Q1c | a bond | Me | a bond | NH | O | a bond | Q3e | OH |
| 4443 | N | NMe | Q1c | a bond | Me | a bond | NH | O | a bond | Q3f | OH |
| 4444 | N | NMe | Q1c | a bond | Me | a bond | NH | O | NH | Q3d | OH |
| 4445 | N | NMe | Q1c | a bond | Me | a bond | NH | O | NH | Q3e | OH |
| 4446 | N | NMe | Q1c | a bond | Me | a bond | NH | O | NH | Q3f | OH |

TABLE 1-continued

| No | A | B | R¹ | L¹ | R² | L² | L³ | Y | L⁴ | R³ | X |
|---|---|---|---|---|---|---|---|---|---|---|---|
| 4447 | N | NMe | Q1c | a bond | Me | a bond | NH | S | a bond | Q3d | OH |
| 4448 | N | NMe | Q1c | a bond | Me | a bond | NH | S | a bond | Q3e | OH |
| 4449 | N | NMe | Q1c | a bond | Me | a bond | NH | S | a bond | Q3f | OH |
| 4450 | N | NMe | Q1c | a bond | Me | a bond | NH | S | NH | Q3d | OH |
| 4451 | N | NMe | Q1c | a bond | Me | a bond | NH | S | NH | Q3e | OH |
| 4452 | N | NMe | Q1c | a bond | Me | a bond | NH | S | NH | Q3f | OH |
| 4453 | N | NEt | Q1a | a bond | Me | a bond | NH | O | a bond | Q3d | OH |
| 4454 | N | NEt | Q1a | a bond | Me | a bond | NH | O | a bond | Q3e | OH |
| 4455 | N | NEt | Q1a | a bond | Me | a bond | NH | O | a bond | Q3f | OH |
| 4456 | N | NEt | Q1a | a bond | Me | a bond | NH | O | NH | Q3d | OH |
| 4457 | N | NEt | Q1a | a bond | Me | a bond | NH | O | NH | Q3e | OH |
| 4458 | N | NEt | Q1a | a bond | Me | a bond | NH | O | NH | Q3f | OH |
| 4459 | N | NEt | Q1a | a bond | Me | a bond | NH | S | a bond | Q3d | OH |
| 4460 | N | NEt | Q1a | a bond | Me | a bond | NH | S | a bond | Q3e | OH |
| 4461 | N | NEt | Q1a | a bond | Me | a bond | NH | S | a bond | Q3f | OH |
| 4462 | N | NEt | Q1a | a bond | Me | a bond | NH | S | NH | Q3d | OH |
| 4463 | N | NEt | Q1a | a bond | Me | a bond | NH | S | NH | Q3e | OH |
| 4464 | N | NEt | Q1a | a bond | Me | a bond | NH | S | NH | Q3f | OH |
| 4465 | N | NEt | Q1b | a bond | Me | a bond | NH | O | a bond | Q3d | OH |
| 4466 | N | NEt | Q1b | a bond | Me | a bond | NH | O | a bond | Q3e | OH |
| 4467 | N | NEt | Q1b | a bond | Me | a bond | NH | O | a bond | Q3f | OH |
| 4468 | N | NEt | Q1b | a bond | Me | a bond | NH | O | NH | Q3d | OH |
| 4469 | N | NEt | Q1b | a bond | Me | a bond | NH | O | NH | Q3e | OH |
| 4470 | N | NEt | Q1b | a bond | Me | a bond | NH | O | NH | Q3f | OH |
| 4471 | N | NEt | Q1b | a bond | Me | a bond | NH | S | a bond | Q3d | OH |
| 4472 | N | NEt | Q1b | a bond | Me | a bond | NH | S | a bond | Q3e | OH |
| 4473 | N | NEt | Q1b | a bond | Me | a bond | NH | S | a bond | Q3f | OH |
| 4474 | N | NEt | Q1b | a bond | Me | a bond | NH | S | NH | Q3d | OH |
| 4475 | N | NEt | Q1b | a bond | Me | a bond | NH | S | NH | Q3e | OH |
| 4476 | N | NEt | Q1b | a bond | Me | a bond | NH | S | NH | Q3f | OH |
| 4477 | N | NEt | Q1c | a bond | Me | a bond | NH | O | a bond | Q3d | OH |
| 4478 | N | NEt | Q1c | a bond | Me | a bond | NH | O | a bond | Q3e | OH |
| 4479 | N | NEt | Q1c | a bond | Me | a bond | NH | O | a bond | Q3f | OH |
| 4480 | N | NEt | Q1c | a bond | Me | a bond | NH | O | NH | Q3d | OH |
| 4481 | N | NEt | Q1c | a bond | Me | a bond | NH | O | NH | Q3e | OH |
| 4482 | N | NEt | Q1c | a bond | Me | a bond | NH | O | NH | Q3f | OH |
| 4483 | N | NEt | Q1c | a bond | Me | a bond | NH | S | a bond | Q3d | OH |
| 4484 | N | NEt | Q1c | a bond | Me | a bond | NH | S | a bond | Q3e | OH |
| 4485 | N | NEt | Q1c | a bond | Me | a bond | NH | S | a bond | Q3f | OH |
| 4486 | N | NEt | Q1c | a bond | Me | a bond | NH | S | NH | Q3d | OH |
| 4487 | N | NEt | Q1c | a bond | Me | a bond | NH | S | NH | Q3e | OH |
| 4488 | N | NEt | Q1c | a bond | Me | a bond | NH | S | NH | Q3f | OH |
| 4489 | N | S | Q1a | a bond | Me | a bond | NH | O | a bond | Q3d | OH |
| 4490 | N | S | Q1a | a bond | Me | a bond | NH | O | a bond | Q3e | OH |
| 4491 | N | S | Q1a | a bond | Me | a bond | NH | O | a bond | Q3f | OH |
| 4492 | N | S | Q1a | a bond | Me | a bond | NH | O | NH | Q3d | OH |
| 4493 | N | S | Q1a | a bond | Me | a bond | NH | O | NH | Q3e | OH |
| 4494 | N | S | Q1a | a bond | Me | a bond | NH | O | NH | Q3f | OH |
| 4495 | N | S | Q1a | a bond | Me | a bond | NH | S | a bond | Q3d | OH |
| 4496 | N | S | Q1a | a bond | Me | a bond | NH | S | a bond | Q3e | OH |
| 4497 | N | S | Q1a | a bond | Me | a bond | NH | S | a bond | Q3f | OH |
| 4498 | N | S | Q1a | a bond | Me | a bond | NH | S | NH | Q3d | OH |
| 4499 | N | S | Q1a | a bond | Me | a bond | NH | S | NH | Q3e | OH |
| 4500 | N | S | Q1a | a bond | Me | a bond | NH | S | NH | Q3f | OH |
| 4501 | N | S | Q1b | a bond | Me | a bond | NH | O | a bond | Q3d | OH |
| 4502 | N | S | Q1b | a bond | Me | a bond | NH | O | a bond | Q3e | OH |
| 4503 | N | S | Q1b | a bond | Me | a bond | NH | O | a bond | Q3f | OH |
| 4504 | N | S | Q1b | a bond | Me | a bond | NH | O | NH | Q3d | OH |
| 4505 | N | S | Q1b | a bond | Me | a bond | NH | O | NH | Q3e | OH |
| 4506 | N | S | Q1b | a bond | Me | a bond | NH | O | NH | Q3f | OH |
| 4507 | N | S | Q1b | a bond | Me | a bond | NH | S | a bond | Q3d | OH |
| 4508 | N | S | Q1b | a bond | Me | a bond | NH | S | a bond | Q3e | OH |
| 4509 | N | S | Q1b | a bond | Me | a bond | NH | S | a bond | Q3f | OH |
| 4510 | N | S | Q1b | a bond | Me | a bond | NH | S | NH | Q3d | OH |
| 4511 | N | S | Q1b | a bond | Me | a bond | NH | S | NH | Q3e | OH |
| 4512 | N | S | Q1b | a bond | Me | a bond | NH | S | NH | Q3f | OH |
| 4513 | N | S | Q1c | a bond | Me | a bond | NH | O | a bond | Q3d | OH |
| 4514 | N | S | Q1c | a bond | Me | a bond | NH | O | a bond | Q3e | OH |
| 4515 | N | S | Q1c | a bond | Me | a bond | NH | O | a bond | Q3f | OH |
| 4516 | N | S | Q1c | a bond | Me | a bond | NH | O | NH | Q3d | OH |
| 4517 | N | S | Q1c | a bond | Me | a bond | NH | O | NH | Q3e | OH |
| 4518 | N | S | Q1c | a bond | Me | a bond | NH | O | NH | Q3f | OH |
| 4519 | N | S | Q1c | a bond | Me | a bond | NH | S | a bond | Q3d | OH |
| 4520 | N | S | Q1c | a bond | Me | a bond | NH | S | a bond | Q3e | OH |
| 4521 | N | S | Q1c | a bond | Me | a bond | NH | S | a bond | Q3f | OH |
| 4522 | N | S | Q1c | a bond | Me | a bond | NH | S | NH | Q3d | OH |
| 4523 | N | S | Q1c | a bond | Me | a bond | NH | S | NH | Q3e | OH |
| 4524 | N | S | Q1c | a bond | Me | a bond | NH | S | NH | Q3f | OH |

TABLE 1-continued

| No | A | B | R¹ | L¹ | R² | L² | L³ | Y | L⁴ | R³ | X |
|---|---|---|---|---|---|---|---|---|---|---|---|
| 4525 | N | O | Q1a | a bond | Me | a bond | NH | O | a bond | Q3d | OH |
| 4526 | N | O | Q1a | a bond | Me | a bond | NH | O | a bond | Q3e | OH |
| 4527 | N | O | Q1a | a bond | Me | a bond | NH | O | a bond | Q3f | OH |
| 4528 | N | O | Q1a | a bond | Me | a bond | NH | O | NH | Q3d | OH |
| 4529 | N | O | Q1a | a bond | Me | a bond | NH | O | NH | Q3e | OH |
| 4530 | N | O | Q1a | a bond | Me | a bond | NH | O | NH | Q3f | OH |
| 4531 | N | O | Q1a | a bond | Me | a bond | NH | S | a bond | Q3d | OH |
| 4532 | N | O | Q1a | a bond | Me | a bond | NH | S | a bond | Q3e | OH |
| 4533 | N | O | Q1a | a bond | Me | a bond | NH | S | a bond | Q3f | OH |
| 4534 | N | O | Q1a | a bond | Me | a bond | NH | S | NH | Q3d | OH |
| 4535 | N | O | Q1a | a bond | Me | a bond | NH | S | NH | Q3e | OH |
| 4536 | N | O | Q1a | a bond | Me | a bond | NH | S | NH | Q3f | OH |
| 4537 | N | O | Q1b | a bond | Me | a bond | NH | O | a bond | Q3d | OH |
| 4538 | N | O | Q1b | a bond | Me | a bond | NH | O | a bond | Q3e | OH |
| 4539 | N | O | Q1b | a bond | Me | a bond | NH | O | a bond | Q3f | OH |
| 4540 | N | O | Q1b | a bond | Me | a bond | NH | O | NH | Q3d | OH |
| 4541 | N | O | Q1b | a bond | Me | a bond | NH | O | NH | Q3e | OH |
| 4542 | N | O | Q1b | a bond | Me | a bond | NH | O | NH | Q3f | OH |
| 4543 | N | O | Q1b | a bond | Me | a bond | NH | S | a bond | Q3d | OH |
| 4544 | N | O | Q1b | a bond | Me | a bond | NH | S | a bond | Q3e | OH |
| 4545 | N | O | Q1b | a bond | Me | a bond | NH | S | a bond | Q3f | OH |
| 4546 | N | O | Q1b | a bond | Me | a bond | NH | S | NH | Q3d | OH |
| 4547 | N | O | Q1b | a bond | Me | a bond | NH | S | NH | Q3e | OH |
| 4548 | N | O | Q1b | a bond | Me | a bond | NH | S | NH | Q3f | OH |
| 4549 | N | O | Q1c | a bond | Me | a bond | NH | O | a bond | Q3d | OH |
| 4550 | N | O | Q1c | a bond | Me | a bond | NH | O | a bond | Q3e | OH |
| 4551 | N | O | Q1c | a bond | Me | a bond | NH | O | a bond | Q3f | OH |
| 4552 | N | O | Q1c | a bond | Me | a bond | NH | O | NH | Q3d | OH |
| 4553 | N | O | Q1c | a bond | Me | a bond | NH | O | NH | Q3e | OH |
| 4554 | N | O | Q1c | a bond | Me | a bond | NH | O | NH | Q3f | OH |
| 4555 | N | O | Q1c | a bond | Me | a bond | NH | S | a bond | Q3d | OH |
| 4556 | N | O | Q1c | a bond | Me | a bond | NH | S | a bond | Q3e | OH |
| 4557 | N | O | Q1c | a bond | Me | a bond | NH | S | a bond | Q3f | OH |
| 4558 | N | O | Q1c | a bond | Me | a bond | NH | S | NH | Q3d | OH |
| 4559 | N | O | Q1c | a bond | Me | a bond | NH | S | NH | Q3e | OH |
| 4560 | N | O | Q1c | a bond | Me | a bond | NH | S | NH | Q3f | OH |
| 4561 | CH | NMe | Q1a | a bond | Me | a bond | NH | O | a bond | Q3d | OH |
| 4562 | CH | NMe | Q1a | a bond | Me | a bond | NH | O | a bond | Q3e | OH |
| 4563 | CH | NMe | Q1a | a bond | Me | a bond | NH | O | a bond | Q3f | OH |
| 4564 | CH | NMe | Q1a | a bond | Me | a bond | NH | O | NH | Q3d | OH |
| 4565 | CH | NMe | Q1a | a bond | Me | a bond | NH | O | NH | Q3e | OH |
| 4566 | CH | NMe | Q1a | a bond | Me | a bond | NH | O | NH | Q3f | OH |
| 4567 | CH | NMe | Q1a | a bond | Me | a bond | NH | S | a bond | Q3d | OH |
| 4568 | CH | NMe | Q1a | a bond | Me | a bond | NH | S | a bond | Q3e | OH |
| 4569 | CH | NMe | Q1a | a bond | Me | a bond | NH | S | a bond | Q3f | OH |
| 4570 | CH | NMe | Q1a | a bond | Me | a bond | NH | S | NH | Q3d | OH |
| 4571 | CH | NMe | Q1a | a bond | Me | a bond | NH | S | NH | Q3e | OH |
| 4572 | CH | NMe | Q1a | a bond | Me | a bond | NH | S | NH | Q3f | OH |
| 4573 | CH | NMe | Q1b | a bond | Me | a bond | NH | O | a bond | Q3d | OH |
| 4574 | CH | NMe | Q1b | a bond | Me | a bond | NH | O | a bond | Q3e | OH |
| 4575 | CH | NMe | Q1b | a bond | Me | a bond | NH | O | a bond | Q3f | OH |
| 4576 | CH | NMe | Q1b | a bond | Me | a bond | NH | O | NH | Q3d | OH |
| 4577 | CH | NMe | Q1b | a bond | Me | a bond | NH | O | NH | Q3e | OH |
| 4578 | CH | NMe | Q1b | a bond | Me | a bond | NH | O | NH | Q3f | OH |
| 4579 | CH | NMe | Q1b | a bond | Me | a bond | NH | S | a bond | Q3d | OH |
| 4580 | CH | NMe | Q1b | a bond | Me | a bond | NH | S | a bond | Q3e | OH |
| 4581 | CH | NMe | Q1b | a bond | Me | a bond | NH | S | a bond | Q3f | OH |
| 4582 | CH | NMe | Q1b | a bond | Me | a bond | NH | S | NH | Q3d | OH |
| 4583 | CH | NMe | Q1b | a bond | Me | a bond | NH | S | NH | Q3e | OH |
| 4584 | CH | NMe | Q1b | a bond | Me | a bond | NH | S | NH | Q3f | OH |
| 4585 | CH | NMe | Q1c | a bond | Me | a bond | NH | O | a bond | Q3d | OH |
| 4586 | CH | NMe | Q1c | a bond | Me | a bond | NH | O | a bond | Q3e | OH |
| 4587 | CH | NMe | Q1c | a bond | Me | a bond | NH | O | a bond | Q3f | OH |
| 4588 | CH | NMe | Q1c | a bond | Me | a bond | NH | O | NH | Q3d | OH |
| 4589 | CH | NMe | Q1c | a bond | Me | a bond | NH | O | NH | Q3e | OH |
| 4590 | CH | NMe | Q1c | a bond | Me | a bond | NH | O | NH | Q3f | OH |
| 4591 | CH | NMe | Q1c | a bond | Me | a bond | NH | S | a bond | Q3d | OH |
| 4592 | CH | NMe | Q1c | a bond | Me | a bond | NH | S | a bond | Q3e | OH |
| 4593 | CH | NMe | Q1c | a bond | Me | a bond | NH | S | a bond | Q3f | OH |
| 4594 | CH | NMe | Q1c | a bond | Me | a bond | NH | S | NH | Q3d | OH |
| 4595 | CH | NMe | Q1c | a bond | Me | a bond | NH | S | NH | Q3e | OH |
| 4596 | CH | NMe | Q1c | a bond | Me | a bond | NH | S | NH | Q3f | OH |
| 4597 | CH | NEt | Q1a | a bond | Me | a bond | NH | O | a bond | Q3d | OH |
| 4598 | CH | NEt | Q1a | a bond | Me | a bond | NH | O | a bond | Q3e | OH |
| 4599 | CH | NEt | Q1a | a bond | Me | a bond | NH | O | a bond | Q3f | OH |
| 4600 | CH | NEt | Q1a | a bond | Me | a bond | NH | O | NH | Q3d | OH |
| 4601 | CH | NEt | Q1a | a bond | Me | a bond | NH | O | NH | Q3e | OH |
| 4602 | CH | NEt | Q1a | a bond | Me | a bond | NH | O | NH | Q3f | OH |

TABLE 1-continued

| No | A | B | R¹ | L¹ | R² | L² | L³ | Y | L⁴ | R³ | X |
|---|---|---|---|---|---|---|---|---|---|---|---|
| 4603 | CH | NEt | Q1a | a bond | Me | a bond | NH | S | a bond | Q3d | OH |
| 4604 | CH | NEt | Q1a | a bond | Me | a bond | NH | S | a bond | Q3e | OH |
| 4605 | CH | NEt | Q1a | a bond | Me | a bond | NH | S | a bond | Q3f | OH |
| 4606 | CH | NEt | Q1a | a bond | Me | a bond | NH | S | NH | Q3d | OH |
| 4607 | CH | NEt | Q1a | a bond | Me | a bond | NH | S | NH | Q3e | OH |
| 4608 | CH | NEt | Q1a | a bond | Me | a bond | NH | S | NH | Q3f | OH |
| 4609 | CH | NEt | Q1b | a bond | Me | a bond | NH | O | a bond | Q3d | OH |
| 4610 | CH | NEt | Q1b | a bond | Me | a bond | NH | O | a bond | Q3e | OH |
| 4611 | CH | NEt | Q1b | a bond | Me | a bond | NH | O | a bond | Q3f | OH |
| 4612 | CH | NEt | Q1b | a bond | Me | a bond | NH | O | NH | Q3d | OH |
| 4613 | CH | NEt | Q1b | a bond | Me | a bond | NH | O | NH | Q3e | OH |
| 4614 | CH | NEt | Q1b | a bond | Me | a bond | NH | O | NH | Q3f | OH |
| 4615 | CH | NEt | Q1b | a bond | Me | a bond | NH | S | a bond | Q3d | OH |
| 4616 | CH | NEt | Q1b | a bond | Me | a bond | NH | S | a bond | Q3e | OH |
| 4617 | CH | NEt | Q1b | a bond | Me | a bond | NH | S | a bond | Q3f | OH |
| 4618 | CH | NEt | Q1b | a bond | Me | a bond | NH | S | NH | Q3d | OH |
| 4619 | CH | NEt | Q1b | a bond | Me | a bond | NH | S | NH | Q3e | OH |
| 4620 | CH | NEt | Q1b | a bond | Me | a bond | NH | S | NH | Q3f | OH |
| 4621 | CH | NEt | Q1c | a bond | Me | a bond | NH | O | a bond | Q3d | OH |
| 4622 | CH | NEt | Q1c | a bond | Me | a bond | NH | O | a bond | Q3e | OH |
| 4623 | CH | NEt | Q1c | a bond | Me | a bond | NH | O | a bond | Q3f | OH |
| 4624 | CH | NEt | Q1c | a bond | Me | a bond | NH | O | NH | Q3d | OH |
| 4625 | CH | NEt | Q1c | a bond | Me | a bond | NH | O | NH | Q3e | OH |
| 4626 | CH | NEt | Q1c | a bond | Me | a bond | NH | O | NH | Q3f | OH |
| 4627 | CH | NEt | Q1c | a bond | Me | a bond | NH | S | a bond | Q3d | OH |
| 4628 | CH | NEt | Q1c | a bond | Me | a bond | NH | S | a bond | Q3e | OH |
| 4629 | CH | NEt | Q1c | a bond | Me | a bond | NH | S | a bond | Q3f | OH |
| 4630 | CH | NEt | Q1c | a bond | Me | a bond | NH | S | NH | Q3d | OH |
| 4631 | CH | NEt | Q1c | a bond | Me | a bond | NH | S | NH | Q3e | OH |
| 4632 | CH | NEt | Q1c | a bond | Me | a bond | NH | S | NH | Q3f | OH |
| 4633 | CH | S | Q1a | a bond | Me | a bond | NH | O | a bond | Q3d | OH |
| 4634 | CH | S | Q1a | a bond | Me | a bond | NH | O | a bond | Q3e | OH |
| 4635 | CH | S | Q1a | a bond | Me | a bond | NH | O | a bond | Q3f | OH |
| 4636 | CH | S | Q1a | a bond | Me | a bond | NH | O | NH | Q3d | OH |
| 4637 | CH | S | Q1a | a bond | Me | a bond | NH | O | NH | Q3e | OH |
| 4638 | CH | S | Q1a | a bond | Me | a bond | NH | O | NH | Q3f | OH |
| 4639 | CH | S | Q1a | a bond | Me | a bond | NH | S | a bond | Q3d | OH |
| 4640 | CH | S | Q1a | a bond | Me | a bond | NH | S | a bond | Q3e | OH |
| 4641 | CH | S | Q1a | a bond | Me | a bond | NH | S | a bond | Q3f | OH |
| 4642 | CH | S | Q1a | a bond | Me | a bond | NH | S | NH | Q3d | OH |
| 4643 | CH | S | Q1a | a bond | Me | a bond | NH | S | NH | Q3e | OH |
| 4644 | CH | S | Q1a | a bond | Me | a bond | NH | S | NH | Q3f | OH |
| 4645 | CH | S | Q1b | a bond | Me | a bond | NH | O | a bond | Q3d | OH |
| 4646 | CH | S | Q1b | a bond | Me | a bond | NH | O | a bond | Q3e | OH |
| 4647 | CH | S | Q1b | a bond | Me | a bond | NH | O | a bond | Q3f | OH |
| 4648 | CH | S | Q1b | a bond | Me | a bond | NH | O | NH | Q3d | OH |
| 4649 | CH | S | Q1b | a bond | Me | a bond | NH | O | NH | Q3e | OH |
| 4650 | CH | S | Q1b | a bond | Me | a bond | NH | O | NH | Q3f | OH |
| 4651 | CH | S | Q1b | a bond | Me | a bond | NH | S | a bond | Q3d | OH |
| 4652 | CH | S | Q1b | a bond | Me | a bond | NH | S | a bond | Q3e | OH |
| 4653 | CH | S | Q1b | a bond | Me | a bond | NH | S | a bond | Q3f | OH |
| 4654 | CH | S | Q1b | a bond | Me | a bond | NH | S | NH | Q3d | OH |
| 4655 | CH | S | Q1b | a bond | Me | a bond | NH | S | NH | Q3e | OH |
| 4656 | CH | S | Q1b | a bond | Me | a bond | NH | S | NH | Q3f | OH |
| 4657 | CH | S | Q1c | a bond | Me | a bond | NH | O | a bond | Q3d | OH |
| 4658 | CH | S | Q1c | a bond | Me | a bond | NH | O | a bond | Q3e | OH |
| 4659 | CH | S | Q1c | a bond | Me | a bond | NH | O | a bond | Q3f | OH |
| 4660 | CH | S | Q1c | a bond | Me | a bond | NH | O | NH | Q3d | OH |
| 4661 | CH | S | Q1c | a bond | Me | a bond | NH | O | NH | Q3e | OH |
| 4662 | CH | S | Q1c | a bond | Me | a bond | NH | O | NH | Q3f | OH |
| 4663 | CH | S | Q1c | a bond | Me | a bond | NH | S | a bond | Q3d | OH |
| 4664 | CH | S | Q1c | a bond | Me | a bond | NH | S | a bond | Q3e | OH |
| 4665 | CH | S | Q1c | a bond | Me | a bond | NH | S | a bond | Q3f | OH |
| 4666 | CH | S | Q1c | a bond | Me | a bond | NH | S | NH | Q3d | OH |
| 4667 | CH | S | Q1c | a bond | Me | a bond | NH | S | NH | Q3e | OH |
| 4668 | CH | S | Q1c | a bond | Me | a bond | NH | S | NH | Q3f | OH |
| 4669 | CH | O | Q1a | a bond | Me | a bond | NH | O | a bond | Q3d | OH |
| 4670 | CH | O | Q1a | a bond | Me | a bond | NH | O | a bond | Q3e | OH |
| 4671 | CH | O | Q1a | a bond | Me | a bond | NH | O | a bond | Q3f | OH |
| 4672 | CH | O | Q1a | a bond | Me | a bond | NH | O | NH | Q3d | OH |
| 4673 | CH | O | Q1a | a bond | Me | a bond | NH | O | NH | Q3e | OH |
| 4674 | CH | O | Q1a | a bond | Me | a bond | NH | O | NH | Q3f | OH |
| 4675 | CH | O | Q1a | a bond | Me | a bond | NH | S | a bond | Q3d | OH |
| 4676 | CH | O | Q1a | a bond | Me | a bond | NH | S | a bond | Q3e | OH |
| 4677 | CH | O | Q1a | a bond | Me | a bond | NH | S | a bond | Q3f | OH |
| 4678 | CH | O | Q1a | a bond | Me | a bond | NH | S | NH | Q3d | OH |
| 4679 | CH | O | Q1a | a bond | Me | a bond | NH | S | NH | Q3e | OH |
| 4680 | CH | O | Q1a | a bond | Me | a bond | NH | S | NH | Q3f | OH |

TABLE 1-continued

| No | A | B | R¹ | L¹ | R² | L² | L³ | Y | L⁴ | R³ | X |
|---|---|---|---|---|---|---|---|---|---|---|---|
| 4681 | CH | O | Q1b | a bond | Me | a bond | NH | O | a bond | Q3d | OH |
| 4682 | CH | O | Q1b | a bond | Me | a bond | NH | O | a bond | Q3e | OH |
| 4683 | CH | O | Q1b | a bond | Me | a bond | NH | O | a bond | Q3f | OH |
| 4684 | CH | O | Q1b | a bond | Me | a bond | NH | O | NH | Q3d | OH |
| 4685 | CH | O | Q1b | a bond | Me | a bond | NH | O | NH | Q3e | OH |
| 4686 | CH | O | Q1b | a bond | Me | a bond | NH | O | NH | Q3f | OH |
| 4687 | CH | O | Q1b | a bond | Me | a bond | NH | S | a bond | Q3d | OH |
| 4688 | CH | O | Q1b | a bond | Me | a bond | NH | S | a bond | Q3e | OH |
| 4689 | CH | O | Q1b | a bond | Me | a bond | NH | S | a bond | Q3f | OH |
| 4690 | CH | O | Q1b | a bond | Me | a bond | NH | S | NH | Q3d | OH |
| 4691 | CH | O | Q1b | a bond | Me | a bond | NH | S | NH | Q3e | OH |
| 4692 | CH | O | Q1b | a bond | Me | a bond | NH | S | NH | Q3f | OH |
| 4693 | CH | O | Q1c | a bond | Me | a bond | NH | O | a bond | Q3d | OH |
| 4694 | CH | O | Q1c | a bond | Me | a bond | NH | O | a bond | Q3e | OH |
| 4695 | CH | O | Q1c | a bond | Me | a bond | NH | O | a bond | Q3f | OH |
| 4696 | CH | O | Q1c | a bond | Me | a bond | NH | O | NH | Q3d | OH |
| 4697 | CH | O | Q1c | a bond | Me | a bond | NH | O | NH | Q3e | OH |
| 4698 | CH | O | Q1c | a bond | Me | a bond | NH | O | NH | Q3f | OH |
| 4699 | CH | O | Q1c | a bond | Me | a bond | NH | S | a bond | Q3d | OH |
| 4700 | CH | O | Q1c | a bond | Me | a bond | NH | S | a bond | Q3e | OH |
| 4701 | CH | O | Q1c | a bond | Me | a bond | NH | S | a bond | Q3f | OH |
| 4702 | CH | O | Q1c | a bond | Me | a bond | NH | S | NH | Q3d | OH |
| 4703 | CH | O | Q1c | a bond | Me | a bond | NH | S | NH | Q3e | OH |
| 4704 | CH | O | Q1c | a bond | Me | a bond | NH | S | NH | Q3f | OH |
| 4705 | CMe | NMe | Q1a | a bond | Me | a bond | NH | O | a bond | Q3d | OH |
| 4706 | CMe | NMe | Q1a | a bond | Me | a bond | NH | O | a bond | Q3e | OH |
| 4707 | CMe | NMe | Q1a | a bond | Me | a bond | NH | O | a bond | Q3f | OH |
| 4708 | CMe | NMe | Q1a | a bond | Me | a bond | NH | O | NH | Q3d | OH |
| 4709 | CMe | NMe | Q1a | a bond | Me | a bond | NH | O | NH | Q3e | OH |
| 4710 | CMe | NMe | Q1a | a bond | Me | a bond | NH | O | NH | Q3f | OH |
| 4711 | CMe | NMe | Q1a | a bond | Me | a bond | NH | S | a bond | Q3d | OH |
| 4712 | CMe | NMe | Q1a | a bond | Me | a bond | NH | S | a bond | Q3e | OH |
| 4713 | CMe | NMe | Q1a | a bond | Me | a bond | NH | S | a bond | Q3f | OH |
| 4714 | CMe | NMe | Q1a | a bond | Me | a bond | NH | S | NH | Q3d | OH |
| 4715 | CMe | NMe | Q1a | a bond | Me | a bond | NH | S | NH | Q3e | OH |
| 4716 | CMe | NMe | Q1a | a bond | Me | a bond | NH | S | NH | Q3f | OH |
| 4717 | CMe | NMe | Q1b | a bond | Me | a bond | NH | O | a bond | Q3d | OH |
| 4718 | CMe | NMe | Q1b | a bond | Me | a bond | NH | O | a bond | Q3e | OH |
| 4719 | CMe | NMe | Q1b | a bond | Me | a bond | NH | O | a bond | Q3f | OH |
| 4720 | CMe | NMe | Q1b | a bond | Me | a bond | NH | O | NH | Q3d | OH |
| 4721 | CMe | NMe | Q1b | a bond | Me | a bond | NH | O | NH | Q3e | OH |
| 4722 | CMe | NMe | Q1b | a bond | Me | a bond | NH | O | NH | Q3f | OH |
| 4723 | CMe | NMe | Q1b | a bond | Me | a bond | NH | S | a bond | Q3d | OH |
| 4724 | CMe | NMe | Q1b | a bond | Me | a bond | NH | S | a bond | Q3e | OH |
| 4725 | CMe | NMe | Q1b | a bond | Me | a bond | NH | S | a bond | Q3f | OH |
| 4726 | CMe | NMe | Q1b | a bond | Me | a bond | NH | S | NH | Q3d | OH |
| 4727 | CMe | NMe | Q1b | a bond | Me | a bond | NH | S | NH | Q3e | OH |
| 4728 | CMe | NMe | Q1b | a bond | Me | a bond | NH | S | NH | Q3f | OH |
| 4729 | CMe | NMe | Q1c | a bond | Me | a bond | NH | O | a bond | Q3d | OH |
| 4730 | CMe | NMe | Q1c | a bond | Me | a bond | NH | O | a bond | Q3e | OH |
| 4731 | CMe | NMe | Q1c | a bond | Me | a bond | NH | O | a bond | Q3f | OH |
| 4732 | CMe | NMe | Q1c | a bond | Me | a bond | NH | O | NH | Q3d | OH |
| 4733 | CMe | NMe | Q1c | a bond | Me | a bond | NH | O | NH | Q3e | OH |
| 4734 | CMe | NMe | Q1c | a bond | Me | a bond | NH | O | NH | Q3f | OH |
| 4735 | CMe | NMe | Q1c | a bond | Me | a bond | NH | S | a bond | Q3d | OH |
| 4736 | CMe | NMe | Q1c | a bond | Me | a bond | NH | S | a bond | Q3e | OH |
| 4737 | CMe | NMe | Q1c | a bond | Me | a bond | NH | S | a bond | Q3f | OH |
| 4738 | CMe | NMe | Q1c | a bond | Me | a bond | NH | S | NH | Q3d | OH |
| 4739 | CMe | NMe | Q1c | a bond | Me | a bond | NH | S | NH | Q3e | OH |
| 4740 | CMe | NMe | Q1c | a bond | Me | a bond | NH | S | NH | Q3f | OH |
| 4741 | CMe | NEt | Q1a | a bond | Me | a bond | NH | O | a bond | Q3d | OH |
| 4742 | CMe | NEt | Q1a | a bond | Me | a bond | NH | O | a bond | Q3e | OH |
| 4743 | CMe | NEt | Q1a | a bond | Me | a bond | NH | O | a bond | Q3f | OH |
| 4744 | CMe | NEt | Q1a | a bond | Me | a bond | NH | O | NH | Q3d | OH |
| 4745 | CMe | NEt | Q1a | a bond | Me | a bond | NH | O | NH | Q3e | OH |
| 4746 | CMe | NEt | Q1a | a bond | Me | a bond | NH | O | NH | Q3f | OH |
| 4747 | CMe | NEt | Q1a | a bond | Me | a bond | NH | S | a bond | Q3d | OH |
| 4748 | CMe | NEt | Q1a | a bond | Me | a bond | NH | S | a bond | Q3e | OH |
| 4749 | CMe | NEt | Q1a | a bond | Me | a bond | NH | S | a bond | Q3f | OH |
| 4750 | CMe | NEt | Q1a | a bond | Me | a bond | NH | S | NH | Q3d | OH |
| 4751 | CMe | NEt | Q1a | a bond | Me | a bond | NH | S | NH | Q3e | OH |
| 4752 | CMe | NEt | Q1a | a bond | Me | a bond | NH | S | NH | Q3f | OH |
| 4753 | CMe | NEt | Q1b | a bond | Me | a bond | NH | O | a bond | Q3d | OH |
| 4754 | CMe | NEt | Q1b | a bond | Me | a bond | NH | O | a bond | Q3e | OH |
| 4755 | CMe | NEt | Q1b | a bond | Me | a bond | NH | O | a bond | Q3f | OH |
| 4756 | CMe | NEt | Q1b | a bond | Me | a bond | NH | O | NH | Q3d | OH |
| 4757 | CMe | NEt | Q1b | a bond | Me | a bond | NH | O | NH | Q3e | OH |
| 4758 | CMe | NEt | Q1b | a bond | Me | a bond | NH | O | NH | Q3f | OH |

TABLE 1-continued

| No | A | B | R¹ | L¹ | R² | L² | L³ | Y | L⁴ | R³ | X |
|---|---|---|---|---|---|---|---|---|---|---|---|
| 4759 | CMe | NEt | Q1b | a bond | Me | a bond | NH | S | a bond | Q3d | OH |
| 4760 | CMe | NEt | Q1b | a bond | Me | a bond | NH | S | a bond | Q3e | OH |
| 4761 | CMe | NEt | Q1b | a bond | Me | a bond | NH | S | a bond | Q3f | OH |
| 4762 | CMe | NEt | Q1b | a bond | Me | a bond | NH | S | NH | Q3d | OH |
| 4763 | CMe | NEt | Q1b | a bond | Me | a bond | NH | S | NH | Q3e | OH |
| 4764 | CMe | NEt | Q1b | a bond | Me | a bond | NH | S | NH | Q3f | OH |
| 4765 | CMe | NEt | Q1c | a bond | Me | a bond | NH | O | a bond | Q3d | OH |
| 4766 | CMe | NEt | Q1c | a bond | Me | a bond | NH | O | a bond | Q3e | OH |
| 4767 | CMe | NEt | Q1c | a bond | Me | a bond | NH | O | a bond | Q3f | OH |
| 4768 | CMe | NEt | Q1c | a bond | Me | a bond | NH | O | NH | Q3d | OH |
| 4769 | CMe | NEt | Q1c | a bond | Me | a bond | NH | O | NH | Q3e | OH |
| 4770 | CMe | NEt | Q1c | a bond | Me | a bond | NH | O | NH | Q3f | OH |
| 4771 | CMe | NEt | Q1c | a bond | Me | a bond | NH | S | a bond | Q3d | OH |
| 4772 | CMe | NEt | Q1c | a bond | Me | a bond | NH | S | a bond | Q3e | OH |
| 4773 | CMe | NEt | Q1c | a bond | Me | a bond | NH | S | a bond | Q3f | OH |
| 4774 | CMe | NEt | Q1c | a bond | Me | a bond | NH | S | NH | Q3d | OH |
| 4775 | CMe | NEt | Q1c | a bond | Me | a bond | NH | S | NH | Q3e | OH |
| 4776 | CMe | NEt | Q1c | a bond | Me | a bond | NH | S | NH | Q3f | OH |
| 4777 | CMe | S | Q1a | a bond | Me | a bond | NH | O | a bond | Q3d | OH |
| 4778 | CMe | S | Q1a | a bond | Me | a bond | NH | O | a bond | Q3e | OH |
| 4779 | CMe | S | Q1a | a bond | Me | a bond | NH | O | a bond | Q3f | OH |
| 4780 | CMe | S | Q1a | a bond | Me | a bond | NH | O | NH | Q3d | OH |
| 4781 | CMe | S | Q1a | a bond | Me | a bond | NH | O | NH | Q3e | OH |
| 4782 | CMe | S | Q1a | a bond | Me | a bond | NH | O | NH | Q3f | OH |
| 4783 | CMe | S | Q1a | a bond | Me | a bond | NH | S | a bond | Q3d | OH |
| 4784 | CMe | S | Q1a | a bond | Me | a bond | NH | S | a bond | Q3e | OH |
| 4785 | CMe | S | Q1a | a bond | Me | a bond | NH | S | a bond | Q3f | OH |
| 4786 | CMe | S | Q1a | a bond | Me | a bond | NH | S | NH | Q3d | OH |
| 4787 | CMe | S | Q1a | a bond | Me | a bond | NH | S | NH | Q3e | OH |
| 4788 | CMe | S | Q1a | a bond | Me | a bond | NH | S | NH | Q3f | OH |
| 4789 | CMe | S | Q1b | a bond | Me | a bond | NH | O | a bond | Q3d | OH |
| 4790 | CMe | S | Q1b | a bond | Me | a bond | NH | O | a bond | Q3e | OH |
| 4791 | CMe | S | Q1b | a bond | Me | a bond | NH | O | a bond | Q3f | OH |
| 4792 | CMe | S | Q1b | a bond | Me | a bond | NH | O | NH | Q3d | OH |
| 4793 | CMe | S | Q1b | a bond | Me | a bond | NH | O | NH | Q3e | OH |
| 4794 | CMe | S | Q1b | a bond | Me | a bond | NH | O | NH | Q3f | OH |
| 4795 | CMe | S | Q1b | a bond | Me | a bond | NH | S | a bond | Q3d | OH |
| 4796 | CMe | S | Q1b | a bond | Me | a bond | NH | S | a bond | Q3e | OH |
| 4797 | CMe | S | Q1b | a bond | Me | a bond | NH | S | a bond | Q3f | OH |
| 4798 | CMe | S | Q1b | a bond | Me | a bond | NH | S | NH | Q3d | OH |
| 4799 | CMe | S | Q1b | a bond | Me | a bond | NH | S | NH | Q3e | OH |
| 4800 | CMe | S | Q1b | a bond | Me | a bond | NH | S | NH | Q3f | OH |
| 4801 | CMe | S | Q1c | a bond | Me | a bond | NH | O | a bond | Q3d | OH |
| 4802 | CMe | S | Q1c | a bond | Me | a bond | NH | O | a bond | Q3e | OH |
| 4803 | CMe | S | Q1c | a bond | Me | a bond | NH | O | a bond | Q3f | OH |
| 4804 | CMe | S | Q1c | a bond | Me | a bond | NH | O | NH | Q3d | OH |
| 4805 | CMe | S | Q1c | a bond | Me | a bond | NH | O | NH | Q3e | OH |
| 4806 | CMe | S | Q1c | a bond | Me | a bond | NH | O | NH | Q3f | OH |
| 4807 | CMe | S | Q1c | a bond | Me | a bond | NH | S | a bond | Q3d | OH |
| 4808 | CMe | S | Q1c | a bond | Me | a bond | NH | S | a bond | Q3e | OH |
| 4809 | CMe | S | Q1c | a bond | Me | a bond | NH | S | a bond | Q3f | OH |
| 4810 | CMe | S | Q1c | a bond | Me | a bond | NH | S | NH | Q3d | OH |
| 4811 | CMe | S | Q1c | a bond | Me | a bond | NH | S | NH | Q3e | OH |
| 4812 | CMe | S | Q1c | a bond | Me | a bond | NH | S | NH | Q3f | OH |
| 4813 | CMe | O | Q1a | a bond | Me | a bond | NH | O | a bond | Q3d | OH |
| 4814 | CMe | O | Q1a | a bond | Me | a bond | NH | O | a bond | Q3e | OH |
| 4815 | CMe | O | Q1a | a bond | Me | a bond | NH | O | a bond | Q3f | OH |
| 4816 | CMe | O | Q1a | a bond | Me | a bond | NH | O | NH | Q3d | OH |
| 4817 | CMe | O | Q1a | a bond | Me | a bond | NH | O | NH | Q3e | OH |
| 4818 | CMe | O | Q1a | a bond | Me | a bond | NH | O | NH | Q3f | OH |
| 4819 | CMe | O | Q1a | a bond | Me | a bond | NH | S | a bond | Q3d | OH |
| 4820 | CMe | O | Q1a | a bond | Me | a bond | NH | S | a bond | Q3e | OH |
| 4821 | CMe | O | Q1a | a bond | Me | a bond | NH | S | a bond | Q3f | OH |
| 4822 | CMe | O | Q1a | a bond | Me | a bond | NH | S | NH | Q3d | OH |
| 4823 | CMe | O | Q1a | a bond | Me | a bond | NH | S | NH | Q3e | OH |
| 4824 | CMe | O | Q1a | a bond | Me | a bond | NH | S | NH | Q3f | OH |
| 4825 | CMe | O | Q1b | a bond | Me | a bond | NH | O | a bond | Q3d | OH |
| 4826 | CMe | O | Q1b | a bond | Me | a bond | NH | O | a bond | Q3e | OH |
| 4827 | CMe | O | Q1b | a bond | Me | a bond | NH | O | a bond | Q3f | OH |
| 4828 | CMe | O | Q1b | a bond | Me | a bond | NH | O | NH | Q3d | OH |
| 4829 | CMe | O | Q1b | a bond | Me | a bond | NH | O | NH | Q3e | OH |
| 4830 | CMe | O | Q1b | a bond | Me | a bond | NH | O | NH | Q3f | OH |
| 4831 | CMe | O | Q1b | a bond | Me | a bond | NH | S | a bond | Q3d | OH |
| 4832 | CMe | O | Q1b | a bond | Me | a bond | NH | S | a bond | Q3e | OH |
| 4833 | CMe | O | Q1b | a bond | Me | a bond | NH | S | a bond | Q3f | OH |
| 4834 | CMe | O | Q1b | a bond | Me | a bond | NH | S | NH | Q3d | OH |
| 4835 | CMe | O | Q1b | a bond | Me | a bond | NH | S | NH | Q3e | OH |
| 4836 | CMe | O | Q1b | a bond | Me | a bond | NH | S | NH | Q3f | OH |

TABLE 1-continued

| No | A | B | R¹ | L¹ | R² | L² | L³ | Y | L⁴ | R³ | X |
|---|---|---|---|---|---|---|---|---|---|---|---|
| 4837 | CMe | O | Q1c | a bond | Me | a bond | NH | O | a bond | Q3d | OH |
| 4838 | CMe | O | Q1c | a bond | Me | a bond | NH | O | a bond | Q3e | OH |
| 4839 | CMe | O | Q1c | a bond | Me | a bond | NH | O | a bond | Q3f | OH |
| 4840 | CMe | O | Q1c | a bond | Me | a bond | NH | O | NH | Q3d | OH |
| 4841 | CMe | O | Q1c | a bond | Me | a bond | NH | O | NH | Q3e | OH |
| 4842 | CMe | O | Q1c | a bond | Me | a bond | NH | O | NH | Q3f | OH |
| 4843 | CMe | O | Q1c | a bond | Me | a bond | NH | S | a bond | Q3d | OH |
| 4844 | CMe | O | Q1c | a bond | Me | a bond | NH | S | a bond | Q3e | OH |
| 4845 | CMe | O | Q1c | a bond | Me | a bond | NH | S | a bond | Q3f | OH |
| 4846 | CMe | O | Q1c | a bond | Me | a bond | NH | S | NH | Q3d | OH |
| 4847 | CMe | O | Q1c | a bond | Me | a bond | NH | S | NH | Q3e | OH |
| 4848 | CMe | O | Q1c | a bond | Me | a bond | NH | S | NH | Q3f | OH |
| 4849 | N | NMe | Q1a | a bond | Me | a bond | NH | S | NH | Q3g | OH |
| 4850 | N | NMe | Q1a | a bond | Me | a bond | NH | S | NH | Q3h | OH |
| 4851 | N | NMe | Q1b | a bond | Me | a bond | NH | S | NH | Q3g | OH |
| 4852 | N | NMe | Q1b | a bond | Me | a bond | NH | S | NH | Q3h | OH |
| 4853 | N | NMe | Q1c | a bond | Me | a bond | NH | S | NH | Q3g | OH |
| 4854 | N | NMe | Q1c | a bond | Me | a bond | NH | S | NH | Q3h | OH |
| 4855 | N | NEt | Q1a | a bond | Me | a bond | NH | S | NH | Q3g | OH |
| 4856 | N | NEt | Q1a | a bond | Me | a bond | NH | S | NH | Q3h | OH |
| 4857 | N | NEt | Q1b | a bond | Me | a bond | NH | S | NH | Q3g | OH |
| 4858 | N | NEt | Q1b | a bond | Me | a bond | NH | S | NH | Q3h | OH |
| 4859 | N | NEt | Q1c | a bond | Me | a bond | NH | S | NH | Q3g | OH |
| 4860 | N | NEt | Q1c | a bond | Me | a bond | NH | S | NH | Q3h | OH |
| 4861 | N | S | Q1a | a bond | Me | a bond | NH | S | NH | Q3g | OH |
| 4862 | N | S | Q1a | a bond | Me | a bond | NH | S | NH | Q3h | OH |
| 4863 | N | S | Q1b | a bond | Me | a bond | NH | S | NH | Q3g | OH |
| 4864 | N | S | Q1b | a bond | Me | a bond | NH | S | NH | Q3h | OH |
| 4865 | N | S | Q1c | a bond | Me | a bond | NH | S | NH | Q3g | OH |
| 4866 | N | S | Q1c | a bond | Me | a bond | NH | S | NH | Q3h | OH |
| 4867 | N | O | Q1a | a bond | Me | a bond | NH | S | NH | Q3g | OH |
| 4868 | N | O | Q1a | a bond | Me | a bond | NH | S | NH | Q3h | OH |
| 4869 | N | O | Q1b | a bond | Me | a bond | NH | S | NH | Q3g | OH |
| 4870 | N | O | Q1b | a bond | Me | a bond | NH | S | NH | Q3h | OH |
| 4871 | N | O | Q1c | a bond | Me | a bond | NH | S | NH | Q3g | OH |
| 4872 | N | O | Q1c | a bond | Me | a bond | NH | S | NH | Q3h | OH |
| 4873 | CH | NMe | Q1a | a bond | Me | a bond | NH | S | NH | Q3g | OH |
| 4874 | CH | NMe | Q1a | a bond | Me | a bond | NH | S | NH | Q3h | OH |
| 4875 | CH | NMe | Q1b | a bond | Me | a bond | NH | S | NH | Q3g | OH |
| 4876 | CH | NMe | Q1b | a bond | Me | a bond | NH | S | NH | Q3h | OH |
| 4877 | CH | NMe | Q1c | a bond | Me | a bond | NH | S | NH | Q3g | OH |
| 4878 | CH | NMe | Q1c | a bond | Me | a bond | NH | S | NH | Q3h | OH |
| 4879 | CH | NEt | Q1a | a bond | Me | a bond | NH | S | NH | Q3g | OH |
| 4880 | CH | NEt | Q1a | a bond | Me | a bond | NH | S | NH | Q3h | OH |
| 4881 | CH | NEt | Q1b | a bond | Me | a bond | NH | S | NH | Q3g | OH |
| 4882 | CH | NEt | Q1b | a bond | Me | a bond | NH | S | NH | Q3h | OH |
| 4883 | CH | NEt | Q1c | a bond | Me | a bond | NH | S | NH | Q3g | OH |
| 4884 | CH | NEt | Q1c | a bond | Me | a bond | NH | S | NH | Q3h | OH |
| 4885 | CH | S | Q1a | a bond | Me | a bond | NH | S | NH | Q3g | OH |
| 4886 | CH | S | Q1a | a bond | Me | a bond | NH | S | NH | Q3h | OH |
| 4887 | CH | S | Q1b | a bond | Me | a bond | NH | S | NH | Q3g | OH |
| 4888 | CH | S | Q1b | a bond | Me | a bond | NH | S | NH | Q3h | OH |
| 4889 | CH | S | Q1c | a bond | Me | a bond | NH | S | NH | Q3g | OH |
| 4890 | CH | S | Q1c | a bond | Me | a bond | NH | S | NH | Q3h | OH |
| 4891 | CH | O | Q1a | a bond | Me | a bond | NH | S | NH | Q3g | OH |
| 4892 | CH | O | Q1a | a bond | Me | a bond | NH | S | NH | Q3h | OH |
| 4893 | CH | O | Q1b | a bond | Me | a bond | NH | S | NH | Q3g | OH |
| 4894 | CH | O | Q1b | a bond | Me | a bond | NH | S | NH | Q3h | OH |
| 4895 | CH | O | Q1c | a bond | Me | a bond | NH | S | NH | Q3g | OH |
| 4896 | CH | O | Q1c | a bond | Me | a bond | NH | S | NH | Q3h | OH |
| 4897 | CMe | NMe | Q1a | a bond | Me | a bond | NH | S | NH | Q3g | OH |
| 4898 | CMe | NMe | Q1a | a bond | Me | a bond | NH | S | NH | Q3h | OH |
| 4899 | CMe | NMe | Q1b | a bond | Me | a bond | NH | S | NH | Q3g | OH |
| 4900 | CMe | NMe | Q1b | a bond | Me | a bond | NH | S | NH | Q3h | OH |
| 4901 | CMe | NMe | Q1c | a bond | Me | a bond | NH | S | NH | Q3g | OH |
| 4902 | CMe | NMe | Q1c | a bond | Me | a bond | NH | S | NH | Q3h | OH |
| 4903 | CMe | NEt | Q1a | a bond | Me | a bond | NH | S | NH | Q3g | OH |
| 4904 | CMe | NEt | Q1a | a bond | Me | a bond | NH | S | NH | Q3h | OH |
| 4905 | CMe | NEt | Q1b | a bond | Me | a bond | NH | S | NH | Q3g | OH |
| 4906 | CMe | NEt | Q1b | a bond | Me | a bond | NH | S | NH | Q3h | OH |
| 4907 | CMe | NEt | Q1c | a bond | Me | a bond | NH | S | NH | Q3g | OH |
| 4908 | CMe | NEt | Q1c | a bond | Me | a bond | NH | S | NH | Q3h | OH |
| 4909 | CMe | S | Q1a | a bond | Me | a bond | NH | S | NH | Q3g | OH |
| 4910 | CMe | S | Q1a | a bond | Me | a bond | NH | S | NH | Q3h | OH |
| 4911 | CMe | S | Q1b | a bond | Me | a bond | NH | S | NH | Q3g | OH |
| 4912 | CMe | S | Q1b | a bond | Me | a bond | NH | S | NH | Q3h | OH |
| 4913 | CMe | S | Q1c | a bond | Me | a bond | NH | S | NH | Q3g | OH |
| 4914 | CMe | S | Q1c | a bond | Me | a bond | NH | S | NH | Q3h | OH |

TABLE 1-continued

| No | A | B | R¹ | L¹ | R² | L² | L³ | Y | L⁴ | R³ | X |
|---|---|---|---|---|---|---|---|---|---|---|---|
| 4915 | CMe | O | Q1a | a bond | Me | a bond | NH | S | NH | Q3g | OH |
| 4916 | CMe | O | Q1a | a bond | Me | a bond | NH | S | NH | Q3h | OH |
| 4917 | CMe | O | Q1b | a bond | Me | a bond | NH | S | NH | Q3g | OH |
| 4918 | CMe | O | Q1b | a bond | Me | a bond | NH | S | NH | Q3h | OH |
| 4919 | CMe | O | Q1c | a bond | Me | a bond | NH | S | NH | Q3g | OH |
| 4920 | CMe | O | Q1c | a bond | Me | a bond | NH | S | NH | Q3h | OH |
| 4921 | N | NMe | Q1a | a bond | Me | a bond | NH | O | a bond | Q3g | OH |
| 4922 | N | NMe | Q1a | a bond | Me | a bond | NH | O | a bond | Q3h | OH |
| 4923 | N | NMe | Q1b | a bond | Me | a bond | NH | O | a bond | Q3g | OH |
| 4924 | N | NMe | Q1b | a bond | Me | a bond | NH | O | a bond | Q3h | OH |
| 4925 | N | NMe | Q1c | a bond | Me | a bond | NH | O | a bond | Q3g | OH |
| 4926 | N | NMe | Q1c | a bond | Me | a bond | NH | O | a bond | Q3h | OH |
| 4927 | N | NEt | Q1a | a bond | Me | a bond | NH | O | a bond | Q3g | OH |
| 4928 | N | NEt | Q1a | a bond | Me | a bond | NH | O | a bond | Q3h | OH |
| 4929 | N | NEt | Q1b | a bond | Me | a bond | NH | O | a bond | Q3g | OH |
| 4930 | N | NEt | Q1b | a bond | Me | a bond | NH | O | a bond | Q3h | OH |
| 4931 | N | NEt | Q1c | a bond | Me | a bond | NH | O | a bond | Q3g | OH |
| 4932 | N | NEt | Q1c | a bond | Me | a bond | NH | O | a bond | Q3h | OH |
| 4933 | N | S | Q1a | a bond | Me | a bond | NH | O | a bond | Q3g | OH |
| 4934 | N | S | Q1a | a bond | Me | a bond | NH | O | a bond | Q3h | OH |
| 4935 | N | S | Q1b | a bond | Me | a bond | NH | O | a bond | Q3g | OH |
| 4936 | N | S | Q1b | a bond | Me | a bond | NH | O | a bond | Q3h | OH |
| 4937 | N | S | Q1c | a bond | Me | a bond | NH | O | a bond | Q3g | OH |
| 4938 | N | S | Q1c | a bond | Me | a bond | NH | O | a bond | Q3h | OH |
| 4939 | N | O | Q1a | a bond | Me | a bond | NH | O | a bond | Q3g | OH |
| 4940 | N | O | Q1a | a bond | Me | a bond | NH | O | a bond | Q3h | OH |
| 4941 | N | O | Q1b | a bond | Me | a bond | NH | O | a bond | Q3g | OH |
| 4942 | N | O | Q1b | a bond | Me | a bond | NH | O | a bond | Q3h | OH |
| 4943 | N | O | Q1c | a bond | Me | a bond | NH | O | a bond | Q3g | OH |
| 4944 | N | O | Q1c | a bond | Me | a bond | NH | O | a bond | Q3h | OH |
| 4945 | CH | NMe | Q1a | a bond | Me | a bond | NH | O | a bond | Q3g | OH |
| 4946 | CH | NMe | Q1a | a bond | Me | a bond | NH | O | a bond | Q3h | OH |
| 4947 | CH | NMe | Q1b | a bond | Me | a bond | NH | O | a bond | Q3g | OH |
| 4948 | CH | NMe | Q1b | a bond | Me | a bond | NH | O | a bond | Q3h | OH |
| 4949 | CH | NMe | Q1c | a bond | Me | a bond | NH | O | a bond | Q3g | OH |
| 4950 | CH | NMe | Q1c | a bond | Me | a bond | NH | O | a bond | Q3h | OH |
| 4951 | CH | NEt | Q1a | a bond | Me | a bond | NH | O | a bond | Q3g | OH |
| 4952 | CH | NEt | Q1a | a bond | Me | a bond | NH | O | a bond | Q3h | OH |
| 4953 | CH | NEt | Q1b | a bond | Me | a bond | NH | O | a bond | Q3g | OH |
| 4954 | CH | NEt | Q1b | a bond | Me | a bond | NH | O | a bond | Q3h | OH |
| 4955 | CH | NEt | Q1c | a bond | Me | a bond | NH | O | a bond | Q3g | OH |
| 4956 | CH | NEt | Q1c | a bond | Me | a bond | NH | O | a bond | Q3h | OH |
| 4957 | CH | S | Q1a | a bond | Me | a bond | NH | O | a bond | Q3g | OH |
| 4958 | CH | S | Q1a | a bond | Me | a bond | NH | O | a bond | Q3h | OH |
| 4959 | CH | S | Q1b | a bond | Me | a bond | NH | O | a bond | Q3g | OH |
| 4960 | CH | S | Q1b | a bond | Me | a bond | NH | O | a bond | Q3h | OH |
| 4961 | CH | S | Q1c | a bond | Me | a bond | NH | O | a bond | Q3g | OH |
| 4962 | CH | S | Q1c | a bond | Me | a bond | NH | O | a bond | Q3h | OH |
| 4963 | CH | O | Q1a | a bond | Me | a bond | NH | O | a bond | Q3g | OH |
| 4964 | CH | O | Q1a | a bond | Me | a bond | NH | O | a bond | Q3h | OH |
| 4965 | CH | O | Q1b | a bond | Me | a bond | NH | O | a bond | Q3g | OH |
| 4966 | CH | O | Q1b | a bond | Me | a bond | NH | O | a bond | Q3h | OH |
| 4967 | CH | O | Q1c | a bond | Me | a bond | NH | O | a bond | Q3g | OH |
| 4968 | CH | O | Q1c | a bond | Me | a bond | NH | O | a bond | Q3h | OH |
| 4969 | CMe | NMe | Q1a | a bond | Me | a bond | NH | O | a bond | Q3g | OH |
| 4970 | CMe | NMe | Q1a | a bond | Me | a bond | NH | O | a bond | Q3h | OH |
| 4971 | CMe | NMe | Q1b | a bond | Me | a bond | NH | O | a bond | Q3g | OH |
| 4972 | CMe | NMe | Q1b | a bond | Me | a bond | NH | O | a bond | Q3h | OH |
| 4973 | CMe | NMe | Q1c | a bond | Me | a bond | NH | O | a bond | Q3g | OH |
| 4974 | CMe | NMe | Q1c | a bond | Me | a bond | NH | O | a bond | Q3h | OH |
| 4975 | CMe | NEt | Q1a | a bond | Me | a bond | NH | O | a bond | Q3g | OH |
| 4976 | CMe | NEt | Q1a | a bond | Me | a bond | NH | O | a bond | Q3h | OH |
| 4977 | CMe | NEt | Q1b | a bond | Me | a bond | NH | O | a bond | Q3g | OH |
| 4978 | CMe | NEt | Q1b | a bond | Me | a bond | NH | O | a bond | Q3h | OH |
| 4979 | CMe | NEt | Q1c | a bond | Me | a bond | NH | O | a bond | Q3g | OH |
| 4980 | CMe | NEt | Q1c | a bond | Me | a bond | NH | O | a bond | Q3h | OH |
| 4981 | CMe | S | Q1a | a bond | Me | a bond | NH | O | a bond | Q3g | OH |
| 4982 | CMe | S | Q1a | a bond | Me | a bond | NH | O | a bond | Q3h | OH |
| 4983 | CMe | S | Q1b | a bond | Me | a bond | NH | O | a bond | Q3g | OH |
| 4984 | CMe | S | Q1b | a bond | Me | a bond | NH | O | a bond | Q3h | OH |
| 4985 | CMe | S | Q1c | a bond | Me | a bond | NH | O | a bond | Q3g | OH |
| 4986 | CMe | S | Q1c | a bond | Me | a bond | NH | O | a bond | Q3h | OH |
| 4987 | CMe | O | Q1a | a bond | Me | a bond | NH | O | a bond | Q3g | OH |
| 4988 | CMe | O | Q1a | a bond | Me | a bond | NH | O | a bond | Q3h | OH |
| 4989 | CMe | O | Q1b | a bond | Me | a bond | NH | O | a bond | Q3g | OH |
| 4990 | CMe | O | Q1b | a bond | Me | a bond | NH | O | a bond | Q3h | OH |
| 4991 | CMe | O | Q1c | a bond | Me | a bond | NH | O | a bond | Q3g | OH |
| 4992 | CMe | O | Q1c | a bond | Me | a bond | NH | O | a bond | Q3h | OH |

TABLE 1-continued

| No | A | B | R¹ | L¹ | R² | L² | L³ | Y | L⁴ | R³ | X |
|---|---|---|---|---|---|---|---|---|---|---|---|
| 4992 | CMe | O | Q1c | a bond | Me | a bond | NH | O | a bond | Q3h | OH |
| 4993 | CH | NH | Q1a | a bond | Me | a bond | NH | S | NH | Q3a | OH |
| 4994 | CH | NH | Q1a | a bond | Me | a bond | NH | S | NH | Q3b | OH |
| 4995 | CH | NH | Q1a | a bond | Me | a bond | NH | S | NH | Q3c | OH |
| 4996 | CH | NH | Q1a | a bond | Me | a bond | NH | S | a bond | Q3a | OH |
| 4997 | CH | NH | Q1a | a bond | Me | a bond | NH | S | a bond | Q3b | OH |
| 4998 | CH | NH | Q1a | a bond | Me | a bond | NH | S | a bond | Q3c | OH |
| 4999 | CH | NH | Q1a | a bond | Me | a bond | NH | O | NH | Q3a | OH |
| 5000 | CH | NH | Q1a | a bond | Me | a bond | NH | O | NH | Q3b | OH |
| 5001 | CH | NH | Q1a | a bond | Me | a bond | NH | O | NH | Q3c | OH |
| 5002 | CH | NH | Q1a | a bond | Me | a bond | NH | O | a bond | Q3a | OH |
| 5003 | CH | NH | Q1a | a bond | Me | a bond | NH | O | a bond | Q3b | OH |
| 5004 | CH | NH | Q1a | a bond | Me | a bond | NH | O | a bond | Q3c | OH |
| 5005 | CH | NH | Q1a | a bond | H | a bond | NH | S | NH | Q3a | OH |
| 5006 | CH | NH | Q1a | a bond | H | a bond | NH | S | NH | Q3b | OH |
| 5007 | CH | NH | Q1a | a bond | H | a bond | NH | S | NH | Q3c | OH |
| 5008 | CH | NH | Q1a | a bond | H | a bond | NH | S | a bond | Q3a | OH |
| 5009 | CH | NH | Q1a | a bond | H | a bond | NH | S | a bond | Q3b | OH |
| 5010 | CH | NH | Q1a | a bond | H | a bond | NH | S | a bond | Q3c | OH |
| 5011 | CH | NH | Q1a | a bond | H | a bond | NH | O | NH | Q3a | OH |
| 5012 | CH | NH | Q1a | a bond | H | a bond | NH | O | NH | Q3b | OH |
| 5013 | CH | NH | Q1a | a bond | H | a bond | NH | O | NH | Q3c | OH |
| 5014 | CH | NH | Q1a | a bond | H | a bond | NH | O | a bond | Q3a | OH |
| 5015 | CH | NH | Q1a | a bond | H | a bond | NH | O | a bond | Q3b | OH |
| 5016 | CH | NH | Q1a | a bond | H | a bond | NH | O | a bond | Q3c | OH |
| 5017 | CH | NH | Q1b | a bond | Me | a bond | NH | S | NH | Q3a | OH |
| 5018 | CH | NH | Q1b | a bond | Me | a bond | NH | S | NH | Q3b | OH |
| 5019 | CH | NH | Q1b | a bond | Me | a bond | NH | S | NH | Q3c | OH |
| 5020 | CH | NH | Q1b | a bond | Me | a bond | NH | S | a bond | Q3a | OH |
| 5021 | CH | NH | Q1b | a bond | Me | a bond | NH | S | a bond | Q3b | OH |
| 5022 | CH | NH | Q1b | a bond | Me | a bond | NH | S | a bond | Q3c | OH |
| 5023 | CH | NH | Q1b | a bond | Me | a bond | NH | O | NH | Q3a | OH |
| 5024 | CH | NH | Q1b | a bond | Me | a bond | NH | O | NH | Q3b | OH |
| 5025 | CH | NH | Q1b | a bond | Me | a bond | NH | O | NH | Q3c | OH |
| 5026 | CH | NH | Q1b | a bond | Me | a bond | NH | O | a bond | Q3a | OH |
| 5027 | CH | NH | Q1b | a bond | Me | a bond | NH | O | a bond | Q3b | OH |
| 5028 | CH | NH | Q1b | a bond | Me | a bond | NH | O | a bond | Q3c | OH |
| 5029 | CH | NH | Q1b | a bond | H | a bond | NH | S | NH | Q3a | OH |
| 5030 | CH | NH | Q1b | a bond | H | a bond | NH | S | NH | Q3b | OH |
| 5031 | CH | NH | Q1b | a bond | H | a bond | NH | S | NH | Q3c | OH |
| 5032 | CH | NH | Q1b | a bond | H | a bond | NH | S | a bond | Q3a | OH |
| 5033 | CH | NH | Q1b | a bond | H | a bond | NH | S | a bond | Q3b | OH |
| 5034 | CH | NH | Q1b | a bond | H | a bond | NH | S | a bond | Q3c | OH |
| 5035 | CH | NH | Q1b | a bond | H | a bond | NH | O | NH | Q3a | OH |
| 5036 | CH | NH | Q1b | a bond | H | a bond | NH | O | NH | Q3b | OH |
| 5037 | CH | NH | Q1b | a bond | H | a bond | NH | O | NH | Q3c | OH |
| 5038 | CH | NH | Q1b | a bond | H | a bond | NH | O | a bond | Q3a | OH |
| 5039 | CH | NH | Q1b | a bond | H | a bond | NH | O | a bond | Q3b | OH |
| 5040 | CH | NH | Q1b | a bond | H | a bond | NH | O | a bond | Q3c | OH |
| 5041 | CH | NH | Q1c | a bond | Me | a bond | NH | S | NH | Q3a | OH |
| 5042 | CH | NH | Q1c | a bond | Me | a bond | NH | S | NH | Q3b | OH |
| 5043 | CH | NH | Q1c | a bond | Me | a bond | NH | S | NH | Q3c | OH |
| 5044 | CH | NH | Q1c | a bond | Me | a bond | NH | S | a bond | Q3a | OH |
| 5045 | CH | NH | Q1c | a bond | Me | a bond | NH | S | a bond | Q3b | OH |
| 5046 | CH | NH | Q1c | a bond | Me | a bond | NH | S | a bond | Q3c | OH |
| 5047 | CH | NH | Q1c | a bond | Me | a bond | NH | O | NH | Q3a | OH |
| 5048 | CH | NH | Q1c | a bond | Me | a bond | NH | O | NH | Q3b | OH |
| 5049 | CH | NH | Q1c | a bond | Me | a bond | NH | O | NH | Q3c | OH |
| 5050 | CH | NH | Q1c | a bond | Me | a bond | NH | O | a bond | Q3a | OH |
| 5051 | CH | NH | Q1c | a bond | Me | a bond | NH | O | a bond | Q3b | OH |
| 5052 | CH | NH | Q1c | a bond | Me | a bond | NH | O | a bond | Q3c | OH |
| 5053 | CH | NH | Q1c | a bond | H | a bond | NH | S | NH | Q3a | OH |
| 5054 | CH | NH | Q1c | a bond | H | a bond | NH | S | NH | Q3b | OH |
| 5055 | CH | NH | Q1c | a bond | H | a bond | NH | S | NH | Q3c | OH |
| 5056 | CH | NH | Q1c | a bond | H | a bond | NH | S | a bond | Q3a | OH |
| 5057 | CH | NH | Q1c | a bond | H | a bond | NH | S | a bond | Q3b | OH |
| 5058 | CH | NH | Q1c | a bond | H | a bond | NH | S | a bond | Q3c | OH |
| 5059 | CH | NH | Q1c | a bond | H | a bond | NH | O | NH | Q3a | OH |
| 5060 | CH | NH | Q1c | a bond | H | a bond | NH | O | NH | Q3b | OH |
| 5061 | CH | NH | Q1c | a bond | H | a bond | NH | O | NH | Q3c | OH |
| 5062 | CH | NH | Q1c | a bond | H | a bond | NH | O | a bond | Q3a | OH |
| 5063 | CH | NH | Q1c | a bond | H | a bond | NH | O | a bond | Q3b | OH |
| 5064 | CH | NH | Q1c | a bond | H | a bond | NH | O | a bond | Q3c | OH |
| 5065 | CH | NH | Q1d | a bond | Me | a bond | NH | S | NH | Q3a | OH |
| 5066 | CH | NH | Q1d | a bond | Me | a bond | NH | S | NH | Q3b | OH |
| 5067 | CH | NH | Q1d | a bond | Me | a bond | NH | S | NH | Q3c | OH |
| 5068 | CH | NH | Q1d | a bond | Me | a bond | NH | S | a bond | Q3a | OH |
| 5069 | CH | NH | Q1d | a bond | Me | a bond | NH | S | a bond | Q3b | OH |

TABLE 1-continued

| No | A | B | R¹ | L¹ | R² | L² | L³ | Y | L⁴ | R³ | X |
|---|---|---|---|---|---|---|---|---|---|---|---|
| 5070 | CH | NH | Q1d | a bond | Me | a bond | NH | S | a bond | Q3c | OH |
| 5071 | CH | NH | Q1d | a bond | Me | a bond | NH | O | NH | Q3a | OH |
| 5072 | CH | NH | Q1d | a bond | Me | a bond | NH | O | NH | Q3b | OH |
| 5073 | CH | NH | Q1d | a bond | Me | a bond | NH | O | NH | Q3c | OH |
| 5074 | CH | NH | Q1d | a bond | Me | a bond | NH | O | a bond | Q3a | OH |
| 5075 | CH | NH | Q1d | a bond | Me | a bond | NH | O | a bond | Q3b | OH |
| 5076 | CH | NH | Q1d | a bond | Me | a bond | NH | O | a bond | Q3c | OH |
| 5077 | CH | NH | Q1d | a bond | H | a bond | NH | S | NH | Q3a | OH |
| 5078 | CH | NH | Q1d | a bond | H | a bond | NH | S | NH | Q3b | OH |
| 5079 | CH | NH | Q1d | a bond | H | a bond | NH | S | NH | Q3c | OH |
| 5080 | CH | NH | Q1d | a bond | H | a bond | NH | S | a bond | Q3a | OH |
| 5081 | CH | NH | Q1d | a bond | H | a bond | NH | S | a bond | Q3b | OH |
| 5082 | CH | NH | Q1d | a bond | H | a bond | NH | S | a bond | Q3c | OH |
| 5083 | CH | NH | Q1d | a bond | H | a bond | NH | O | NH | Q3a | OH |
| 5084 | CH | NH | Q1d | a bond | H | a bond | NH | O | NH | Q3b | OH |
| 5085 | CH | NH | Q1d | a bond | H | a bond | NH | O | NH | Q3c | OH |
| 5086 | CH | NH | Q1d | a bond | H | a bond | NH | O | a bond | Q3a | OH |
| 5087 | CH | NH | Q1d | a bond | H | a bond | NH | O | a bond | Q3b | OH |
| 5088 | CH | NH | Q1d | a bond | H | a bond | NH | O | a bond | Q3c | OH |
| 5089 | CH | NH | Q1e | a bond | Me | a bond | NH | S | NH | Q3a | OH |
| 5090 | CH | NH | Q1e | a bond | Me | a bond | NH | S | NH | Q3b | OH |
| 5091 | CH | NH | Q1e | a bond | Me | a bond | NH | S | NH | Q3c | OH |
| 5092 | CH | NH | Q1e | a bond | Me | a bond | NH | S | a bond | Q3a | OH |
| 5093 | CH | NH | Q1e | a bond | Me | a bond | NH | S | a bond | Q3b | OH |
| 5094 | CH | NH | Q1e | a bond | Me | a bond | NH | S | a bond | Q3c | OH |
| 5095 | CH | NH | Q1e | a bond | Me | a bond | NH | O | NH | Q3a | OH |
| 5096 | CH | NH | Q1e | a bond | Me | a bond | NH | O | NH | Q3b | OH |
| 5097 | CH | NH | Q1e | a bond | Me | a bond | NH | O | NH | Q3c | OH |
| 5098 | CH | NH | Q1e | a bond | Me | a bond | NH | O | a bond | Q3a | OH |
| 5099 | CH | NH | Q1e | a bond | Me | a bond | NH | O | a bond | Q3b | OH |
| 5100 | CH | NH | Q1e | a bond | Me | a bond | NH | O | a bond | Q3c | OH |
| 5101 | CH | NH | Q1e | a bond | H | a bond | NH | S | NH | Q3a | OH |
| 5102 | CH | NH | Q1e | a bond | H | a bond | NH | S | NH | Q3b | OH |
| 5103 | CH | NH | Q1e | a bond | H | a bond | NH | S | NH | Q3c | OH |
| 5104 | CH | NH | Q1e | a bond | H | a bond | NH | S | a bond | Q3a | OH |
| 5105 | CH | NH | Q1e | a bond | H | a bond | NH | S | a bond | Q3b | OH |
| 5106 | CH | NH | Q1e | a bond | H | a bond | NH | S | a bond | Q3c | OH |
| 5107 | CH | NH | Q1e | a bond | H | a bond | NH | O | NH | Q3a | OH |
| 5108 | CH | NH | Q1e | a bond | H | a bond | NH | O | NH | Q3b | OH |
| 5109 | CH | NH | Q1e | a bond | H | a bond | NH | O | NH | Q3c | OH |
| 5110 | CH | NH | Q1e | a bond | H | a bond | NH | O | a bond | Q3a | OH |
| 5111 | CH | NH | Q1e | a bond | H | a bond | NH | O | a bond | Q3b | OH |
| 5112 | CH | NH | Q1e | a bond | H | a bond | NH | O | a bond | Q3c | OH |
| 5113 | CH | NH | Q1f | a bond | Me | a bond | NH | S | NH | Q3a | OH |
| 5114 | CH | NH | Q1f | a bond | Me | a bond | NH | S | NH | Q3b | OH |
| 5115 | CH | NH | Q1f | a bond | Me | a bond | NH | S | NH | Q3c | OH |
| 5116 | CH | NH | Q1f | a bond | Me | a bond | NH | S | a bond | Q3a | OH |
| 5117 | CH | NH | Q1f | a bond | Me | a bond | NH | S | a bond | Q3b | OH |
| 5118 | CH | NH | Q1f | a bond | Me | a bond | NH | S | a bond | Q3c | OH |
| 5119 | CH | NH | Q1f | a bond | Me | a bond | NH | O | NH | Q3a | OH |
| 5120 | CH | NH | Q1f | a bond | Me | a bond | NH | O | NH | Q3b | OH |
| 5121 | CH | NH | Q1f | a bond | Me | a bond | NH | O | NH | Q3c | OH |
| 5122 | CH | NH | Q1f | a bond | Me | a bond | NH | O | a bond | Q3a | OH |
| 5123 | CH | NH | Q1f | a bond | Me | a bond | NH | O | a bond | Q3b | OH |
| 5124 | CH | NH | Q1f | a bond | Me | a bond | NH | O | a bond | Q3c | OH |
| 5125 | CH | NH | Q1f | a bond | H | a bond | NH | S | NH | Q3a | OH |
| 5126 | CH | NH | Q1f | a bond | H | a bond | NH | S | NH | Q3b | OH |
| 5127 | CH | NH | Q1f | a bond | H | a bond | NH | S | NH | Q3c | OH |
| 5128 | CH | NH | Q1f | a bond | H | a bond | NH | S | a bond | Q3a | OH |
| 5129 | CH | NH | Q1f | a bond | H | a bond | NH | S | a bond | Q3b | OH |
| 5130 | CH | NH | Q1f | a bond | H | a bond | NH | S | a bond | Q3c | OH |
| 5131 | CH | NH | Q1f | a bond | H | a bond | NH | O | NH | Q3a | OH |
| 5132 | CH | NH | Q1f | a bond | H | a bond | NH | O | NH | Q3b | OH |
| 5133 | CH | NH | Q1f | a bond | H | a bond | NH | O | NH | Q3c | OH |
| 5134 | CH | NH | Q1f | a bond | H | a bond | NH | O | a bond | Q3a | OH |
| 5135 | CH | NH | Q1f | a bond | H | a bond | NH | O | a bond | Q3b | OH |
| 5136 | CH | NH | Q1f | a bond | H | a bond | NH | O | a bond | Q3c | OH |
| 5137 | CH | NH | Q1g | a bond | Me | a bond | NH | S | NH | Q3a | OH |
| 5138 | CH | NH | Q1g | a bond | Me | a bond | NH | S | NH | Q3b | OH |
| 5139 | CH | NH | Q1g | a bond | Me | a bond | NH | S | NH | Q3c | OH |
| 5140 | CH | NH | Q1g | a bond | Me | a bond | NH | S | a bond | Q3a | OH |
| 5141 | CH | NH | Q1g | a bond | Me | a bond | NH | S | a bond | Q3b | OH |
| 5142 | CH | NH | Q1g | a bond | Me | a bond | NH | S | a bond | Q3c | OH |
| 5143 | CH | NH | Q1g | a bond | Me | a bond | NH | O | NH | Q3a | OH |
| 5144 | CH | NH | Q1g | a bond | Me | a bond | NH | O | NH | Q3b | OH |
| 5145 | CH | NH | Q1g | a bond | Me | a bond | NH | O | NH | Q3c | OH |
| 5146 | CH | NH | Q1g | a bond | Me | a bond | NH | O | a bond | Q3a | OH |
| 5147 | CH | NH | Q1g | a bond | Me | a bond | NH | O | a bond | Q3b | OH |

TABLE 1-continued

| No | A | B | R¹ | L¹ | R² | L² | L³ | Y | L⁴ | R³ | X |
|---|---|---|---|---|---|---|---|---|---|---|---|
| 5148 | CH | NH | Q1g | a bond | Me | a bond | NH | O | a bond | Q3c | OH |
| 5149 | CH | NH | Q1g | a bond | H | a bond | NH | S | NH | Q3a | OH |
| 5150 | CH | NH | Q1g | a bond | H | a bond | NH | S | NH | Q3b | OH |
| 5151 | CH | NH | Q1g | a bond | H | a bond | NH | S | NH | Q3c | OH |
| 5152 | CH | NH | Q1g | a bond | H | a bond | NH | S | a bond | Q3a | OH |
| 5153 | CH | NH | Q1g | a bond | H | a bond | NH | S | a bond | Q3b | OH |
| 5154 | CH | NH | Q1g | a bond | H | a bond | NH | S | a bond | Q3c | OH |
| 5155 | CH | NH | Q1g | a bond | H | a bond | NH | O | NH | Q3a | OH |
| 5156 | CH | NH | Q1g | a bond | H | a bond | NH | O | NH | Q3b | OH |
| 5157 | CH | NH | Q1g | a bond | H | a bond | NH | O | NH | Q3c | OH |
| 5158 | CH | NH | Q1g | a bond | H | a bond | NH | O | a bond | Q3a | OH |
| 5159 | CH | NH | Q1g | a bond | H | a bond | NH | O | a bond | Q3b | OH |
| 5160 | CH | NH | Q1g | a bond | H | a bond | NH | O | a bond | Q3c | OH |
| 5161 | CH | NH | Q1h | a bond | Me | a bond | NH | S | NH | Q3a | OH |
| 5162 | CH | NH | Q1h | a bond | Me | a bond | NH | S | NH | Q3b | OH |
| 5163 | CH | NH | Q1h | a bond | Me | a bond | NH | S | NH | Q3c | OH |
| 5164 | CH | NH | Q1h | a bond | Me | a bond | NH | S | a bond | Q3a | OH |
| 5165 | CH | NH | Q1h | a bond | Me | a bond | NH | S | a bond | Q3b | OH |
| 5166 | CH | NH | Q1h | a bond | Me | a bond | NH | S | a bond | Q3c | OH |
| 5167 | CH | NH | Q1h | a bond | Me | a bond | NH | O | NH | Q3a | OH |
| 5168 | CH | NH | Q1h | a bond | Me | a bond | NH | O | NH | Q3b | OH |
| 5169 | CH | NH | Q1h | a bond | Me | a bond | NH | O | NH | Q3c | OH |
| 5170 | CH | NH | Q1h | a bond | Me | a bond | NH | O | a bond | Q3a | OH |
| 5171 | CH | NH | Q1h | a bond | Me | a bond | NH | O | a bond | Q3b | OH |
| 5172 | CH | NH | Q1h | a bond | Me | a bond | NH | O | a bond | Q3c | OH |
| 5173 | CH | NH | Q1h | a bond | H | a bond | NH | S | NH | Q3a | OH |
| 5174 | CH | NH | Q1h | a bond | H | a bond | NH | S | NH | Q3b | OH |
| 5175 | CH | NH | Q1h | a bond | H | a bond | NH | S | NH | Q3c | OH |
| 5176 | CH | NH | Q1h | a bond | H | a bond | NH | S | a bond | Q3a | OH |
| 5177 | CH | NH | Q1h | a bond | H | a bond | NH | S | a bond | Q3b | OH |
| 5178 | CH | NH | Q1h | a bond | H | a bond | NH | S | a bond | Q3c | OH |
| 5179 | CH | NH | Q1h | a bond | H | a bond | NH | O | NH | Q3a | OH |
| 5180 | CH | NH | Q1h | a bond | H | a bond | NH | O | NH | Q3b | OH |
| 5181 | CH | NH | Q1h | a bond | H | a bond | NH | O | NH | Q3c | OH |
| 5182 | CH | NH | Q1h | a bond | H | a bond | NH | O | a bond | Q3a | OH |
| 5183 | CH | NH | Q1h | a bond | H | a bond | NH | O | a bond | Q3b | OH |
| 5184 | CH | NH | Q1h | a bond | H | a bond | NH | O | a bond | Q3c | OH |
| 5185 | CH | NH | Q1i | a bond | Me | a bond | NH | S | NH | Q3a | OH |
| 5186 | CH | NH | Q1i | a bond | Me | a bond | NH | S | NH | Q3b | OH |
| 5187 | CH | NH | Q1i | a bond | Me | a bond | NH | S | NH | Q3c | OH |
| 5188 | CH | NH | Q1i | a bond | Me | a bond | NH | S | a bond | Q3a | OH |
| 5189 | CH | NH | Q1i | a bond | Me | a bond | NH | S | a bond | Q3b | OH |
| 5190 | CH | NH | Q1i | a bond | Me | a bond | NH | S | a bond | Q3c | OH |
| 5191 | CH | NH | Q1i | a bond | Me | a bond | NH | O | NH | Q3a | OH |
| 5192 | CH | NH | Q1i | a bond | Me | a bond | NH | O | NH | Q3b | OH |
| 5193 | CH | NH | Q1i | a bond | Me | a bond | NH | O | NH | Q3c | OH |
| 5194 | CH | NH | Q1i | a bond | Me | a bond | NH | O | a bond | Q3a | OH |
| 5195 | CH | NH | Q1i | a bond | Me | a bond | NH | O | a bond | Q3b | OH |
| 5196 | CH | NH | Q1i | a bond | Me | a bond | NH | O | a bond | Q3c | OH |
| 5197 | CH | NH | Q1i | a bond | H | a bond | NH | S | NH | Q3a | OH |
| 5198 | CH | NH | Q1i | a bond | H | a bond | NH | S | NH | Q3b | OH |
| 5199 | CH | NH | Q1i | a bond | H | a bond | NH | S | NH | Q3c | OH |
| 5200 | CH | NH | Q1i | a bond | H | a bond | NH | S | a bond | Q3a | OH |
| 5201 | CH | NH | Q1i | a bond | H | a bond | NH | S | a bond | Q3b | OH |
| 5202 | CH | NH | Q1i | a bond | H | a bond | NH | S | a bond | Q3c | OH |
| 5203 | CH | NH | Q1i | a bond | H | a bond | NH | O | NH | Q3a | OH |
| 5204 | CH | NH | Q1i | a bond | H | a bond | NH | O | NH | Q3b | OH |
| 5205 | CH | NH | Q1i | a bond | H | a bond | NH | O | NH | Q3c | OH |
| 5206 | CH | NH | Q1i | a bond | H | a bond | NH | O | a bond | Q3a | OH |
| 5207 | CH | NH | Q1i | a bond | H | a bond | NH | O | a bond | Q3b | OH |
| 5208 | CH | NH | Q1i | a bond | H | a bond | NH | O | a bond | Q3c | OH |
| 5209 | CH | NH | Q1j | a bond | Me | a bond | NH | S | NH | Q3a | OH |
| 5210 | CH | NH | Q1j | a bond | Me | a bond | NH | S | NH | Q3b | OH |
| 5211 | CH | NH | Q1j | a bond | Me | a bond | NH | S | NH | Q3c | OH |
| 5212 | CH | NH | Q1j | a bond | Me | a bond | NH | S | a bond | Q3a | OH |
| 5213 | CH | NH | Q1j | a bond | Me | a bond | NH | S | a bond | Q3b | OH |
| 5214 | CH | NH | Q1j | a bond | Me | a bond | NH | S | a bond | Q3c | OH |
| 5215 | CH | NH | Q1j | a bond | Me | a bond | NH | O | NH | Q3a | OH |
| 5216 | CH | NH | Q1j | a bond | Me | a bond | NH | O | NH | Q3b | OH |
| 5217 | CH | NH | Q1j | a bond | Me | a bond | NH | O | NH | Q3c | OH |
| 5218 | CH | NH | Q1j | a bond | Me | a bond | NH | O | a bond | Q3a | OH |
| 5219 | CH | NH | Q1j | a bond | Me | a bond | NH | O | a bond | Q3b | OH |
| 5220 | CH | NH | Q1j | a bond | Me | a bond | NH | O | a bond | Q3c | OH |
| 5221 | CH | NH | Q1j | a bond | H | a bond | NH | S | NH | Q3a | OH |
| 5222 | CH | NH | Q1j | a bond | H | a bond | NH | S | NH | Q3b | OH |
| 5223 | CH | NH | Q1j | a bond | H | a bond | NH | S | NH | Q3c | OH |
| 5224 | CH | NH | Q1j | a bond | H | a bond | NH | S | a bond | Q3a | OH |
| 5225 | CH | NH | Q1j | a bond | H | a bond | NH | S | a bond | Q3b | OH |

TABLE 1-continued

| No | A | B | R¹ | L¹ | R² | L² | L³ | Y | L⁴ | R³ | X |
|---|---|---|---|---|---|---|---|---|---|---|---|
| 5226 | CH | NH | Q1j | a bond | H | a bond | NH | S | a bond | Q3c | OH |
| 5227 | CH | NH | Q1j | a bond | H | a bond | NH | O | NH | Q3a | OH |
| 5228 | CH | NH | Q1j | a bond | H | a bond | NH | O | NH | Q3b | OH |
| 5229 | CH | NH | Q1j | a bond | H | a bond | NH | O | NH | Q3c | OH |
| 5230 | CH | NH | Q1j | a bond | H | a bond | NH | O | a bond | Q3a | OH |
| 5231 | CH | NH | Q1j | a bond | H | a bond | NH | O | a bond | Q3b | OH |
| 5232 | CH | NH | Q1j | a bond | H | a bond | NH | O | a bond | Q3c | OH |
| 5233 | CMe | NH | Q1a | a bond | Me | a bond | NH | S | NH | Q3a | OH |
| 5234 | CMe | NH | Q1a | a bond | Me | a bond | NH | S | NH | Q3b | OH |
| 5235 | CMe | NH | Q1a | a bond | Me | a bond | NH | S | NH | Q3c | OH |
| 5236 | CMe | NH | Q1a | a bond | Me | a bond | NH | S | a bond | Q3a | OH |
| 5237 | CMe | NH | Q1a | a bond | Me | a bond | NH | S | a bond | Q3b | OH |
| 5238 | CMe | NH | Q1a | a bond | Me | a bond | NH | S | a bond | Q3c | OH |
| 5239 | CMe | NH | Q1a | a bond | Me | a bond | NH | O | NH | Q3a | OH |
| 5240 | CMe | NH | Q1a | a bond | Me | a bond | NH | O | NH | Q3b | OH |
| 5241 | CMe | NH | Q1a | a bond | Me | a bond | NH | O | NH | Q3c | OH |
| 5242 | CMe | NH | Q1a | a bond | Me | a bond | NH | O | a bond | Q3a | OH |
| 5243 | CMe | NH | Q1a | a bond | Me | a bond | NH | O | a bond | Q3b | OH |
| 5244 | CMe | NH | Q1a | a bond | Me | a bond | NH | O | a bond | Q3c | OH |
| 5245 | CMe | NH | Q1a | a bond | H | a bond | NH | S | NH | Q3a | OH |
| 5246 | CMe | NH | Q1a | a bond | H | a bond | NH | S | NH | Q3b | OH |
| 5247 | CMe | NH | Q1a | a bond | H | a bond | NH | S | NH | Q3c | OH |
| 5248 | CMe | NH | Q1a | a bond | H | a bond | NH | S | a bond | Q3a | OH |
| 5249 | CMe | NH | Q1a | a bond | H | a bond | NH | S | a bond | Q3b | OH |
| 5250 | CMe | NH | Q1a | a bond | H | a bond | NH | S | a bond | Q3c | OH |
| 5251 | CMe | NH | Q1a | a bond | H | a bond | NH | O | NH | Q3a | OH |
| 5252 | CMe | NH | Q1a | a bond | H | a bond | NH | O | NH | Q3b | OH |
| 5253 | CMe | NH | Q1a | a bond | H | a bond | NH | O | NH | Q3c | OH |
| 5254 | CMe | NH | Q1a | a bond | H | a bond | NH | O | a bond | Q3a | OH |
| 5255 | CMe | NH | Q1a | a bond | H | a bond | NH | O | a bond | Q3b | OH |
| 5256 | CMe | NH | Q1a | a bond | H | a bond | NH | O | a bond | Q3c | OH |
| 5257 | CMe | NH | Q1b | a bond | Me | a bond | NH | S | NH | Q3a | OH |
| 5258 | CMe | NH | Q1b | a bond | Me | a bond | NH | S | NH | Q3b | OH |
| 5259 | CMe | NH | Q1b | a bond | Me | a bond | NH | S | NH | Q3c | OH |
| 5260 | CMe | NH | Q1b | a bond | Me | a bond | NH | S | a bond | Q3a | OH |
| 5261 | CMe | NH | Q1b | a bond | Me | a bond | NH | S | a bond | Q3b | OH |
| 5262 | CMe | NH | Q1b | a bond | Me | a bond | NH | S | a bond | Q3c | OH |
| 5263 | CMe | NH | Q1b | a bond | Me | a bond | NH | O | NH | Q3a | OH |
| 5264 | CMe | NH | Q1b | a bond | Me | a bond | NH | O | NH | Q3b | OH |
| 5265 | CMe | NH | Q1b | a bond | Me | a bond | NH | O | NH | Q3c | OH |
| 5266 | CMe | NH | Q1b | a bond | Me | a bond | NH | O | a bond | Q3a | OH |
| 5267 | CMe | NH | Q1b | a bond | Me | a bond | NH | O | a bond | Q3b | OH |
| 5268 | CMe | NH | Q1b | a bond | Me | a bond | NH | O | a bond | Q3c | OH |
| 5269 | CMe | NH | Q1b | a bond | H | a bond | NH | S | NH | Q3a | OH |
| 5270 | CMe | NH | Q1b | a bond | H | a bond | NH | S | NH | Q3b | OH |
| 5271 | CMe | NH | Q1b | a bond | H | a bond | NH | S | NH | Q3c | OH |
| 5272 | CMe | NH | Q1b | a bond | H | a bond | NH | S | a bond | Q3a | OH |
| 5273 | CMe | NH | Q1b | a bond | H | a bond | NH | S | a bond | Q3b | OH |
| 5274 | CMe | NH | Q1b | a bond | H | a bond | NH | S | a bond | Q3c | OH |
| 5275 | CMe | NH | Q1b | a bond | H | a bond | NH | O | NH | Q3a | OH |
| 5276 | CMe | NH | Q1b | a bond | H | a bond | NH | O | NH | Q3b | OH |
| 5277 | CMe | NH | Q1b | a bond | H | a bond | NH | O | NH | Q3c | OH |
| 5278 | CMe | NH | Q1b | a bond | H | a bond | NH | O | a bond | Q3a | OH |
| 5279 | CMe | NH | Q1b | a bond | H | a bond | NH | O | a bond | Q3b | OH |
| 5280 | CMe | NH | Q1b | a bond | H | a bond | NH | O | a bond | Q3c | OH |
| 5281 | CMe | NH | Q1c | a bond | Me | a bond | NH | S | NH | Q3a | OH |
| 5282 | CMe | NH | Q1c | a bond | Me | a bond | NH | S | NH | Q3b | OH |
| 5283 | CMe | NH | Q1c | a bond | Me | a bond | NH | S | NH | Q3c | OH |
| 5284 | CMe | NH | Q1c | a bond | Me | a bond | NH | S | a bond | Q3a | OH |
| 5285 | CMe | NH | Q1c | a bond | Me | a bond | NH | S | a bond | Q3b | OH |
| 5286 | CMe | NH | Q1c | a bond | Me | a bond | NH | S | a bond | Q3c | OH |
| 5287 | CMe | NH | Q1c | a bond | Me | a bond | NH | O | NH | Q3a | OH |
| 5288 | CMe | NH | Q1c | a bond | Me | a bond | NH | O | NH | Q3b | OH |
| 5289 | CMe | NH | Q1c | a bond | Me | a bond | NH | O | NH | Q3c | OH |
| 5290 | CMe | NH | Q1c | a bond | Me | a bond | NH | O | a bond | Q3a | OH |
| 5291 | CMe | NH | Q1c | a bond | Me | a bond | NH | O | a bond | Q3b | OH |
| 5292 | CMe | NH | Q1c | a bond | Me | a bond | NH | O | a bond | Q3c | OH |
| 5293 | CMe | NH | Q1c | a bond | H | a bond | NH | S | NH | Q3a | OH |
| 5294 | CMe | NH | Q1c | a bond | H | a bond | NH | S | NH | Q3b | OH |
| 5295 | CMe | NH | Q1c | a bond | H | a bond | NH | S | NH | Q3c | OH |
| 5296 | CMe | NH | Q1c | a bond | H | a bond | NH | S | a bond | Q3a | OH |
| 5297 | CMe | NH | Q1c | a bond | H | a bond | NH | S | a bond | Q3b | OH |
| 5298 | CMe | NH | Q1c | a bond | H | a bond | NH | S | a bond | Q3c | OH |
| 5299 | CMe | NH | Q1c | a bond | H | a bond | NH | O | NH | Q3a | OH |
| 5300 | CMe | NH | Q1c | a bond | H | a bond | NH | O | NH | Q3b | OH |
| 5301 | CMe | NH | Q1c | a bond | H | a bond | NH | O | NH | Q3c | OH |
| 5302 | CMe | NH | Q1c | a bond | H | a bond | NH | O | a bond | Q3a | OH |
| 5303 | CMe | NH | Q1c | a bond | H | a bond | NH | O | a bond | Q3b | OH |

TABLE 1-continued

| No | A | B | R¹ | L¹ | R² | L² | L³ | Y | L⁴ | R³ | X |
|---|---|---|---|---|---|---|---|---|---|---|---|
| 5304 | CMe | NH | Q1c | a bond | H | a bond | NH | O | a bond | Q3c | OH |
| 5305 | CMe | NH | Q1d | a bond | Me | a bond | NH | S | NH | Q3a | OH |
| 5306 | CMe | NH | Q1d | a bond | Me | a bond | NH | S | NH | Q3b | OH |
| 5307 | CMe | NH | Q1d | a bond | Me | a bond | NH | S | NH | Q3c | OH |
| 5308 | CMe | NH | Q1d | a bond | Me | a bond | NH | S | a bond | Q3a | OH |
| 5309 | CMe | NH | Q1d | a bond | Me | a bond | NH | S | a bond | Q3b | OH |
| 5310 | CMe | NH | Q1d | a bond | Me | a bond | NH | S | a bond | Q3c | OH |
| 5311 | CMe | NH | Q1d | a bond | Me | a bond | NH | O | NH | Q3a | OH |
| 5312 | CMe | NH | Q1d | a bond | Me | a bond | NH | O | NH | Q3b | OH |
| 5313 | CMe | NH | Q1d | a bond | Me | a bond | NH | O | NH | Q3c | OH |
| 5314 | CMe | NH | Q1d | a bond | Me | a bond | NH | O | a bond | Q3a | OH |
| 5315 | CMe | NH | Q1d | a bond | Me | a bond | NH | O | a bond | Q3b | OH |
| 5316 | CMe | NH | Q1d | a bond | Me | a bond | NH | O | a bond | Q3c | OH |
| 5317 | CMe | NH | Q1d | a bond | H | a bond | NH | S | NH | Q3a | OH |
| 5318 | CMe | NH | Q1d | a bond | H | a bond | NH | S | NH | Q3b | OH |
| 5319 | CMe | NH | Q1d | a bond | H | a bond | NH | S | NH | Q3c | OH |
| 5320 | CMe | NH | Q1d | a bond | H | a bond | NH | S | a bond | Q3a | OH |
| 5321 | CMe | NH | Q1d | a bond | H | a bond | NH | S | a bond | Q3b | OH |
| 5322 | CMe | NH | Q1d | a bond | H | a bond | NH | S | a bond | Q3c | OH |
| 5323 | CMe | NH | Q1d | a bond | H | a bond | NH | O | NH | Q3a | OH |
| 5324 | CMe | NH | Q1d | a bond | H | a bond | NH | O | NH | Q3b | OH |
| 5325 | CMe | NH | Q1d | a bond | H | a bond | NH | O | NH | Q3c | OH |
| 5326 | CMe | NH | Q1d | a bond | H | a bond | NH | O | a bond | Q3a | OH |
| 5327 | CMe | NH | Q1d | a bond | H | a bond | NH | O | a bond | Q3b | OH |
| 5328 | CMe | NH | Q1d | a bond | H | a bond | NH | O | a bond | Q3c | OH |
| 5329 | CMe | NH | Q1e | a bond | Me | a bond | NH | S | NH | Q3a | OH |
| 5330 | CMe | NH | Q1e | a bond | Me | a bond | NH | S | NH | Q3b | OH |
| 5331 | CMe | NH | Q1e | a bond | Me | a bond | NH | S | NH | Q3c | OH |
| 5332 | CMe | NH | Q1e | a bond | Me | a bond | NH | S | a bond | Q3a | OH |
| 5333 | CMe | NH | Q1e | a bond | Me | a bond | NH | S | a bond | Q3b | OH |
| 5334 | CMe | NH | Q1e | a bond | Me | a bond | NH | S | a bond | Q3c | OH |
| 5335 | CMe | NH | Q1e | a bond | Me | a bond | NH | O | NH | Q3a | OH |
| 5336 | CMe | NH | Q1e | a bond | Me | a bond | NH | O | NH | Q3b | OH |
| 5337 | CMe | NH | Q1e | a bond | Me | a bond | NH | O | NH | Q3c | OH |
| 5338 | CMe | NH | Q1e | a bond | Me | a bond | NH | O | a bond | Q3a | OH |
| 5339 | CMe | NH | Q1e | a bond | Me | a bond | NH | O | a bond | Q3b | OH |
| 5340 | CMe | NH | Q1e | a bond | Me | a bond | NH | O | a bond | Q3c | OH |
| 5341 | CMe | NH | Q1e | a bond | H | a bond | NH | S | NH | Q3a | OH |
| 5342 | CMe | NH | Q1e | a bond | H | a bond | NH | S | NH | Q3b | OH |
| 5343 | CMe | NH | Q1e | a bond | H | a bond | NH | S | NH | Q3c | OH |
| 5344 | CMe | NH | Q1e | a bond | H | a bond | NH | S | a bond | Q3a | OH |
| 5345 | CMe | NH | Q1e | a bond | H | a bond | NH | S | a bond | Q3b | OH |
| 5346 | CMe | NH | Q1e | a bond | H | a bond | NH | S | a bond | Q3c | OH |
| 5347 | CMe | NH | Q1e | a bond | H | a bond | NH | O | NH | Q3a | OH |
| 5348 | CMe | NH | Q1e | a bond | H | a bond | NH | O | NH | Q3b | OH |
| 5349 | CMe | NH | Q1e | a bond | H | a bond | NH | O | NH | Q3c | OH |
| 5350 | CMe | NH | Q1e | a bond | H | a bond | NH | O | a bond | Q3a | OH |
| 5351 | CMe | NH | Q1e | a bond | H | a bond | NH | O | a bond | Q3b | OH |
| 5352 | CMe | NH | Q1e | a bond | H | a bond | NH | O | a bond | Q3c | OH |
| 5353 | CMe | NH | Q1f | a bond | Me | a bond | NH | S | NH | Q3a | OH |
| 5354 | CMe | NH | Q1f | a bond | Me | a bond | NH | S | NH | Q3b | OH |
| 5355 | CMe | NH | Q1f | a bond | Me | a bond | NH | S | NH | Q3c | OH |
| 5356 | CMe | NH | Q1f | a bond | Me | a bond | NH | S | a bond | Q3a | OH |
| 5357 | CMe | NH | Q1f | a bond | Me | a bond | NH | S | a bond | Q3b | OH |
| 5358 | CMe | NH | Q1f | a bond | Me | a bond | NH | S | a bond | Q3c | OH |
| 5359 | CMe | NH | Q1f | a bond | Me | a bond | NH | O | NH | Q3a | OH |
| 5360 | CMe | NH | Q1f | a bond | Me | a bond | NH | O | NH | Q3b | OH |
| 5361 | CMe | NH | Q1f | a bond | Me | a bond | NH | O | NH | Q3c | OH |
| 5362 | CMe | NH | Q1f | a bond | Me | a bond | NH | O | a bond | Q3a | OH |
| 5363 | CMe | NH | Q1f | a bond | Me | a bond | NH | O | a bond | Q3b | OH |
| 5364 | CMe | NH | Q1f | a bond | Me | a bond | NH | O | a bond | Q3c | OH |
| 5365 | CMe | NH | Q1f | a bond | H | a bond | NH | S | NH | Q3a | OH |
| 5366 | CMe | NH | Q1f | a bond | H | a bond | NH | S | NH | Q3b | OH |
| 5367 | CMe | NH | Q1f | a bond | H | a bond | NH | S | NH | Q3c | OH |
| 5368 | CMe | NH | Q1f | a bond | H | a bond | NH | S | a bond | Q3a | OH |
| 5369 | CMe | NH | Q1f | a bond | H | a bond | NH | S | a bond | Q3b | OH |
| 5370 | CMe | NH | Q1f | a bond | H | a bond | NH | S | a bond | Q3c | OH |
| 5371 | CMe | NH | Q1f | a bond | H | a bond | NH | O | NH | Q3a | OH |
| 5372 | CMe | NH | Q1f | a bond | H | a bond | NH | O | NH | Q3b | OH |
| 5373 | CMe | NH | Q1f | a bond | H | a bond | NH | O | NH | Q3c | OH |
| 5374 | CMe | NH | Q1f | a bond | H | a bond | NH | O | a bond | Q3a | OH |
| 5375 | CMe | NH | Q1f | a bond | H | a bond | NH | O | a bond | Q3b | OH |
| 5376 | CMe | NH | Q1f | a bond | H | a bond | NH | O | a bond | Q3c | OH |
| 5377 | CMe | NH | Q1g | a bond | Me | a bond | NH | S | NH | Q3a | OH |
| 5378 | CMe | NH | Q1g | a bond | Me | a bond | NH | S | NH | Q3b | OH |
| 5379 | CMe | NH | Q1g | a bond | Me | a bond | NH | S | NH | Q3c | OH |
| 5380 | CMe | NH | Q1g | a bond | Me | a bond | NH | S | a bond | Q3a | OH |
| 5381 | CMe | NH | Q1g | a bond | Me | a bond | NH | S | a bond | Q3b | OH |

TABLE 1-continued

| No | A | B | R¹ | L¹ | R² | L² | L³ | Y | L⁴ | R³ | X |
|---|---|---|---|---|---|---|---|---|---|---|---|
| 5382 | CMe | NH | Q1g | a bond | Me | a bond | NH | S | a bond | Q3c | OH |
| 5383 | CMe | NH | Q1g | a bond | Me | a bond | NH | O | NH | Q3a | OH |
| 5384 | CMe | NH | Q1g | a bond | Me | a bond | NH | O | NH | Q3b | OH |
| 5385 | CMe | NH | Q1g | a bond | Me | a bond | NH | O | NH | Q3c | OH |
| 5386 | CMe | NH | Q1g | a bond | Me | a bond | NH | O | a bond | Q3a | OH |
| 5387 | CMe | NH | Q1g | a bond | Me | a bond | NH | O | a bond | Q3b | OH |
| 5388 | CMe | NH | Q1g | a bond | Me | a bond | NH | O | a bond | Q3c | OH |
| 5389 | CMe | NH | Q1g | a bond | H | a bond | NH | S | NH | Q3a | OH |
| 5390 | CMe | NH | Q1g | a bond | H | a bond | NH | S | NH | Q3b | OH |
| 5391 | CMe | NH | Q1g | a bond | H | a bond | NH | S | NH | Q3c | OH |
| 5392 | CMe | NH | Q1g | a bond | H | a bond | NH | S | a bond | Q3a | OH |
| 5393 | CMe | NH | Q1g | a bond | H | a bond | NH | S | a bond | Q3b | OH |
| 5394 | CMe | NH | Q1g | a bond | H | a bond | NH | S | a bond | Q3c | OH |
| 5395 | CMe | NH | Q1g | a bond | H | a bond | NH | O | NH | Q3a | OH |
| 5396 | CMe | NH | Q1g | a bond | H | a bond | NH | O | NH | Q3b | OH |
| 5397 | CMe | NH | Q1g | a bond | H | a bond | NH | O | NH | Q3c | OH |
| 5398 | CMe | NH | Q1g | a bond | H | a bond | NH | O | a bond | Q3a | OH |
| 5399 | CMe | NH | Q1g | a bond | H | a bond | NH | O | a bond | Q3b | OH |
| 5400 | CMe | NH | Q1g | a bond | H | a bond | NH | O | a bond | Q3c | OH |
| 5401 | CMe | NH | Q1h | a bond | Me | a bond | NH | S | NH | Q3a | OH |
| 5402 | CMe | NH | Q1h | a bond | Me | a bond | NH | S | NH | Q3b | OH |
| 5403 | CMe | NH | Q1h | a bond | Me | a bond | NH | S | NH | Q3c | OH |
| 5404 | CMe | NH | Q1h | a bond | Me | a bond | NH | S | a bond | Q3a | OH |
| 5405 | CMe | NH | Q1h | a bond | Me | a bond | NH | S | a bond | Q3b | OH |
| 5406 | CMe | NH | Q1h | a bond | Me | a bond | NH | S | a bond | Q3c | OH |
| 5407 | CMe | NH | Q1h | a bond | Me | a bond | NH | O | NH | Q3a | OH |
| 5408 | CMe | NH | Q1h | a bond | Me | a bond | NH | O | NH | Q3b | OH |
| 5409 | CMe | NH | Q1h | a bond | Me | a bond | NH | O | NH | Q3c | OH |
| 5410 | CMe | NH | Q1h | a bond | Me | a bond | NH | O | a bond | Q3a | OH |
| 5411 | CMe | NH | Q1h | a bond | Me | a bond | NH | O | a bond | Q3b | OH |
| 5412 | CMe | NH | Q1h | a bond | Me | a bond | NH | O | a bond | Q3c | OH |
| 5413 | CMe | NH | Q1h | a bond | H | a bond | NH | S | NH | Q3a | OH |
| 5414 | CMe | NH | Q1h | a bond | H | a bond | NH | S | NH | Q3b | OH |
| 5415 | CMe | NH | Q1h | a bond | H | a bond | NH | S | NH | Q3c | OH |
| 5416 | CMe | NH | Q1h | a bond | H | a bond | NH | S | a bond | Q3a | OH |
| 5417 | CMe | NH | Q1h | a bond | H | a bond | NH | S | a bond | Q3b | OH |
| 5418 | CMe | NH | Q1h | a bond | H | a bond | NH | S | a bond | Q3c | OH |
| 5419 | CMe | NH | Q1h | a bond | H | a bond | NH | O | NH | Q3a | OH |
| 5420 | CMe | NH | Q1h | a bond | H | a bond | NH | O | NH | Q3b | OH |
| 5421 | CMe | NH | Q1h | a bond | H | a bond | NH | O | NH | Q3c | OH |
| 5422 | CMe | NH | Q1h | a bond | H | a bond | NH | O | a bond | Q3a | OH |
| 5423 | CMe | NH | Q1h | a bond | H | a bond | NH | O | a bond | Q3b | OH |
| 5424 | CMe | NH | Q1h | a bond | H | a bond | NH | O | a bond | Q3c | OH |
| 5425 | CMe | NH | Q1i | a bond | Me | a bond | NH | S | NH | Q3a | OH |
| 5426 | CMe | NH | Q1i | a bond | Me | a bond | NH | S | NH | Q3b | OH |
| 5427 | CMe | NH | Q1i | a bond | Me | a bond | NH | S | NH | Q3c | OH |
| 5428 | CMe | NH | Q1i | a bond | Me | a bond | NH | S | a bond | Q3a | OH |
| 5429 | CMe | NH | Q1i | a bond | Me | a bond | NH | S | a bond | Q3b | OH |
| 5430 | CMe | NH | Q1i | a bond | Me | a bond | NH | S | a bond | Q3c | OH |
| 5431 | CMe | NH | Q1i | a bond | Me | a bond | NH | O | NH | Q3a | OH |
| 5432 | CMe | NH | Q1i | a bond | Me | a bond | NH | O | NH | Q3b | OH |
| 5433 | CMe | NH | Q1i | a bond | Me | a bond | NH | O | NH | Q3c | OH |
| 5434 | CMe | NH | Q1i | a bond | Me | a bond | NH | O | a bond | Q3a | OH |
| 5435 | CMe | NH | Q1i | a bond | Me | a bond | NH | O | a bond | Q3b | OH |
| 5436 | CMe | NH | Q1i | a bond | Me | a bond | NH | O | a bond | Q3c | OH |
| 5437 | CMe | NH | Q1i | a bond | H | a bond | NH | S | NH | Q3a | OH |
| 5438 | CMe | NH | Q1i | a bond | H | a bond | NH | S | NH | Q3b | OH |
| 5439 | CMe | NH | Q1i | a bond | H | a bond | NH | S | NH | Q3c | OH |
| 5440 | CMe | NH | Q1i | a bond | H | a bond | NH | S | a bond | Q3a | OH |
| 5441 | CMe | NH | Q1i | a bond | H | a bond | NH | S | a bond | Q3b | OH |
| 5442 | CMe | NH | Q1i | a bond | H | a bond | NH | S | a bond | Q3c | OH |
| 5443 | CMe | NH | Q1i | a bond | H | a bond | NH | O | NH | Q3a | OH |
| 5444 | CMe | NH | Q1i | a bond | H | a bond | NH | O | NH | Q3b | OH |
| 5445 | CMe | NH | Q1i | a bond | H | a bond | NH | O | NH | Q3c | OH |
| 5446 | CMe | NH | Q1i | a bond | H | a bond | NH | O | a bond | Q3a | OH |
| 5447 | CMe | NH | Q1i | a bond | H | a bond | NH | O | a bond | Q3b | OH |
| 5448 | CMe | NH | Q1i | a bond | H | a bond | NH | O | a bond | Q3c | OH |
| 5449 | CMe | NH | Q1j | a bond | Me | a bond | NH | S | NH | Q3a | OH |
| 5450 | CMe | NH | Q1j | a bond | Me | a bond | NH | S | NH | Q3b | OH |
| 5451 | CMe | NH | Q1j | a bond | Me | a bond | NH | S | NH | Q3c | OH |
| 5452 | CMe | NH | Q1j | a bond | Me | a bond | NH | S | a bond | Q3a | OH |
| 5453 | CMe | NH | Q1j | a bond | Me | a bond | NH | S | a bond | Q3b | OH |
| 5454 | CMe | NH | Q1j | a bond | Me | a bond | NH | S | a bond | Q3c | OH |
| 5455 | CMe | NH | Q1j | a bond | Me | a bond | NH | O | NH | Q3a | OH |
| 5456 | CMe | NH | Q1j | a bond | Me | a bond | NH | O | NH | Q3b | OH |
| 5457 | CMe | NH | Q1j | a bond | Me | a bond | NH | O | NH | Q3c | OH |
| 5458 | CMe | NH | Q1j | a bond | Me | a bond | NH | O | a bond | Q3a | OH |
| 5459 | CMe | NH | Q1j | a bond | Me | a bond | NH | O | a bond | Q3b | OH |

TABLE 1-continued

| No | A | B | R¹ | L¹ | R² | L² | L³ | Y | L⁴ | R³ | X |
|---|---|---|---|---|---|---|---|---|---|---|---|
| 5460 | CMe | NH | Q1j | a bond | Me | a bond | NH | O | a bond | Q3c | OH |
| 5461 | CMe | NH | Q1j | a bond | H | a bond | NH | S | NH | Q3a | OH |
| 5462 | CMe | NH | Q1j | a bond | H | a bond | NH | S | NH | Q3b | OH |
| 5463 | CMe | NH | Q1j | a bond | H | a bond | NH | S | NH | Q3c | OH |
| 5464 | CMe | NH | Q1j | a bond | H | a bond | NH | S | a bond | Q3a | OH |
| 5465 | CMe | NH | Q1j | a bond | H | a bond | NH | S | a bond | Q3b | OH |
| 5466 | CMe | NH | Q1j | a bond | H | a bond | NH | S | a bond | Q3c | OH |
| 5467 | CMe | NH | Q1j | a bond | H | a bond | NH | O | NH | Q3a | OH |
| 5468 | CMe | NH | Q1j | a bond | H | a bond | NH | O | NH | Q3b | OH |
| 5469 | CMe | NH | Q1j | a bond | H | a bond | NH | O | NH | Q3c | OH |
| 5470 | CMe | NH | Q1j | a bond | H | a bond | NH | O | a bond | Q3a | OH |
| 5471 | CMe | NH | Q1j | a bond | H | a bond | NH | O | a bond | Q3b | OH |
| 5472 | CMe | NH | Q1j | a bond | H | a bond | NH | O | a bond | Q3c | OH |
| 5473 | N | NMe | Q1a | a bond | Me | a bond | NH | S | a bond | Q3g | OH |
| 5474 | N | NMe | Q1a | a bond | Me | a bond | NH | S | a bond | Q3h | OH |
| 5475 | N | NMe | Q1a | a bond | H | a bond | NH | S | a bond | Q3g | OH |
| 5476 | N | NMe | Q1a | a bond | H | a bond | NH | S | a bond | Q3h | OH |
| 5477 | N | NMe | Q1a | a bond | Me | a bond | NH | O | a bond | Q3g | OH |
| 5478 | N | NMe | Q1a | a bond | Me | a bond | NH | O | a bond | Q3h | OH |
| 5479 | N | NMe | Q1a | a bond | H | a bond | NH | O | a bond | Q3g | OH |
| 5480 | N | NMe | Q1a | a bond | H | a bond | NH | O | a bond | Q3h | OH |
| 5481 | N | NMe | Q1b | a bond | Me | a bond | NH | S | a bond | Q3g | OH |
| 5482 | N | NMe | Q1b | a bond | Me | a bond | NH | S | a bond | Q3h | OH |
| 5483 | N | NMe | Q1b | a bond | H | a bond | NH | S | a bond | Q3g | OH |
| 5484 | N | NMe | Q1b | a bond | H | a bond | NH | S | a bond | Q3h | OH |
| 5485 | N | NMe | Q1b | a bond | Me | a bond | NH | O | a bond | Q3g | OH |
| 5486 | N | NMe | Q1b | a bond | Me | a bond | NH | O | a bond | Q3h | OH |
| 5487 | N | NMe | Q1b | a bond | H | a bond | NH | O | a bond | Q3g | OH |
| 5488 | N | NMe | Q1b | a bond | H | a bond | NH | O | a bond | Q3h | OH |
| 5489 | N | NMe | Q1c | a bond | Me | a bond | NH | S | a bond | Q3g | OH |
| 5490 | N | NMe | Q1c | a bond | Me | a bond | NH | S | a bond | Q3h | OH |
| 5491 | N | NMe | Q1c | a bond | H | a bond | NH | S | a bond | Q3g | OH |
| 5492 | N | NMe | Q1c | a bond | H | a bond | NH | S | a bond | Q3h | OH |
| 5493 | N | NMe | Q1c | a bond | Me | a bond | NH | O | a bond | Q3g | OH |
| 5494 | N | NMe | Q1c | a bond | Me | a bond | NH | O | a bond | Q3h | OH |
| 5495 | N | NMe | Q1c | a bond | H | a bond | NH | O | a bond | Q3g | OH |
| 5496 | N | NMe | Q1c | a bond | H | a bond | NH | O | a bond | Q3h | OH |
| 5497 | CH | S | Q1a | a bond | Me | a bond | NH | S | a bond | Q3g | OH |
| 5498 | CH | S | Q1a | a bond | Me | a bond | NH | S | a bond | Q3h | OH |
| 5499 | CH | S | Q1a | a bond | H | a bond | NH | S | a bond | Q3g | OH |
| 5500 | CH | S | Q1a | a bond | H | a bond | NH | S | a bond | Q3h | OH |
| 5501 | CH | S | Q1a | a bond | Me | a bond | NH | O | a bond | Q3g | OH |
| 5502 | CH | S | Q1a | a bond | Me | a bond | NH | O | a bond | Q3h | OH |
| 5503 | CH | S | Q1a | a bond | H | a bond | NH | O | a bond | Q3g | OH |
| 5504 | N | NMe | Q1g | a bond | Me | a bond | NH | O | a bond | Q3d | OH |
| 5505 | N | NMe | Q1g | a bond | Me | a bond | NH | O | a bond | Q3e | OH |
| 5506 | N | NMe | Q1g | a bond | Me | a bond | NH | O | a bond | Q3f | OH |
| 5507 | N | NMe | Q1g | a bond | Me | a bond | NH | O | a bond | Q3g | OH |
| 5508 | N | NMe | Q1g | a bond | Me | a bond | NH | O | a bond | Q3h | OH |
| 5509 | N | NMe | Q1g | a bond | H | a bond | NH | O | a bond | Q3d | OH |
| 5510 | N | NMe | Q1g | a bond | H | a bond | NH | O | a bond | Q3e | OH |
| 5511 | N | NMe | Q1g | a bond | H | a bond | NH | O | a bond | Q3f | OH |
| 5512 | N | NMe | Q1g | a bond | H | a bond | NH | O | a bond | Q3g | OH |
| 5513 | N | NMe | Q1g | a bond | H | a bond | NH | O | a bond | Q3h | OH |
| 5514 | N | NMe | Q1h | a bond | Me | a bond | NH | S | a bond | Q3d | OH |
| 5515 | N | NMe | Q1h | a bond | Me | a bond | NH | S | a bond | Q3e | OH |
| 5516 | N | NMe | Q1h | a bond | Me | a bond | NH | S | a bond | Q3f | OH |
| 5517 | N | NMe | Q1h | a bond | Me | a bond | NH | S | a bond | Q3g | OH |
| 5518 | N | NMe | Q1h | a bond | Me | a bond | NH | S | a bond | Q3h | OH |
| 5519 | N | NMe | Q1h | a bond | H | a bond | NH | S | a bond | Q3d | OH |
| 5520 | N | NMe | Q1h | a bond | H | a bond | NH | S | a bond | Q3e | OH |
| 5521 | N | NMe | Q1h | a bond | H | a bond | NH | S | a bond | Q3f | OH |
| 5522 | N | NMe | Q1h | a bond | H | a bond | NH | S | a bond | Q3g | OH |
| 5523 | N | NMe | Q1h | a bond | H | a bond | NH | S | a bond | Q3h | OH |
| 5524 | N | NMe | Q1h | a bond | Me | a bond | NH | O | a bond | Q3d | OH |
| 5525 | N | NMe | Q1h | a bond | Me | a bond | NH | O | a bond | Q3e | OH |
| 5526 | N | NMe | Q1h | a bond | Me | a bond | NH | O | a bond | Q3f | OH |
| 5527 | N | NMe | Q1h | a bond | Me | a bond | NH | O | a bond | Q3g | OH |
| 5528 | N | NMe | Q1h | a bond | Me | a bond | NH | O | a bond | Q3h | OH |
| 5529 | N | NMe | Q1h | a bond | H | a bond | NH | O | a bond | Q3d | OH |
| 5530 | N | NMe | Q1h | a bond | H | a bond | NH | O | a bond | Q3e | OH |
| 5531 | N | NMe | Q1h | a bond | H | a bond | NH | O | a bond | Q3f | OH |
| 5532 | N | NMe | Q1h | a bond | H | a bond | NH | O | a bond | Q3g | OH |
| 5533 | N | NMe | Q1h | a bond | H | a bond | NH | O | a bond | Q3h | OH |
| 5534 | N | NMe | Q1i | a bond | Me | a bond | NH | S | a bond | Q3d | OH |
| 5535 | N | NMe | Q1i | a bond | Me | a bond | NH | S | a bond | Q3e | OH |
| 5536 | N | NMe | Q1i | a bond | Me | a bond | NH | S | a bond | Q3f | OH |
| 5537 | N | NMe | Q1i | a bond | Me | a bond | NH | S | a bond | Q3g | OH |

TABLE 1-continued

| No | A | B | R¹ | L¹ | R² | L² | L³ | Y | L⁴ | R³ | X |
|---|---|---|---|---|---|---|---|---|---|---|---|
| 5538 | N | NMe | Q1i | a bond | Me | a bond | NH | S | a bond | Q3h | OH |
| 5539 | N | NMe | Q1i | a bond | H | a bond | NH | S | a bond | Q3d | OH |
| 5540 | N | NMe | Q1i | a bond | H | a bond | NH | S | a bond | Q3e | OH |
| 5541 | N | NMe | Q1i | a bond | H | a bond | NH | S | a bond | Q3f | OH |
| 5542 | N | NMe | Q1i | a bond | H | a bond | NH | S | a bond | Q3g | OH |
| 5543 | N | NMe | Q1i | a bond | H | a bond | NH | S | a bond | Q3h | OH |
| 5544 | N | NMe | Q1i | a bond | Me | a bond | NH | O | a bond | Q3d | OH |
| 5545 | N | NMe | Q1i | a bond | Me | a bond | NH | O | a bond | Q3e | OH |
| 5546 | N | NMe | Q1i | a bond | Me | a bond | NH | O | a bond | Q3f | OH |
| 5547 | N | NMe | Q1i | a bond | Me | a bond | NH | O | a bond | Q3g | OH |
| 5548 | N | NMe | Q1i | a bond | Me | a bond | NH | O | a bond | Q3h | OH |
| 5549 | N | NMe | Q1i | a bond | H | a bond | NH | O | a bond | Q3d | OH |
| 5550 | N | NMe | Q1i | a bond | H | a bond | NH | O | a bond | Q3e | OH |
| 5551 | N | NMe | Q1i | a bond | H | a bond | NH | O | a bond | Q3f | OH |
| 5552 | N | NMe | Q1i | a bond | H | a bond | NH | O | a bond | Q3g | OH |
| 5553 | N | NMe | Q1i | a bond | H | a bond | NH | O | a bond | Q3h | OH |
| 5554 | N | NMe | Q1j | a bond | Me | a bond | NH | S | a bond | Q3d | OH |
| 5555 | N | NMe | Q1j | a bond | Me | a bond | NH | S | a bond | Q3e | OH |
| 5556 | N | NMe | Q1j | a bond | Me | a bond | NH | S | a bond | Q3f | OH |
| 5557 | N | NMe | Q1j | a bond | Me | a bond | NH | S | a bond | Q3g | OH |
| 5558 | N | NMe | Q1j | a bond | Me | a bond | NH | S | a bond | Q3h | OH |
| 5559 | N | NMe | Q1j | a bond | H | a bond | NH | S | a bond | Q3d | OH |
| 5560 | N | NMe | Q1j | a bond | H | a bond | NH | S | a bond | Q3e | OH |
| 5561 | N | NMe | Q1j | a bond | H | a bond | NH | S | a bond | Q3f | OH |
| 5562 | N | NMe | Q1j | a bond | H | a bond | NH | S | a bond | Q3g | OH |
| 5563 | N | NMe | Q1j | a bond | H | a bond | NH | S | a bond | Q3h | OH |
| 5564 | N | NMe | Q1j | a bond | Me | a bond | NH | O | a bond | Q3d | OH |
| 5565 | N | NMe | Q1j | a bond | Me | a bond | NH | O | a bond | Q3e | OH |
| 5566 | N | NMe | Q1j | a bond | Me | a bond | NH | O | a bond | Q3f | OH |
| 5567 | N | NMe | Q1j | a bond | Me | a bond | NH | O | a bond | Q3g | OH |
| 5568 | N | NMe | Q1j | a bond | Me | a bond | NH | O | a bond | Q3h | OH |
| 5569 | N | NMe | Q1j | a bond | H | a bond | NH | O | a bond | Q3d | OH |
| 5570 | N | NMe | Q1j | a bond | H | a bond | NH | O | a bond | Q3e | OH |
| 5571 | N | NMe | Q1j | a bond | H | a bond | NH | O | a bond | Q3f | OH |
| 5572 | N | NMe | Q1j | a bond | H | a bond | NH | O | a bond | Q3g | OH |
| 5573 | N | NMe | Q1j | a bond | H | a bond | NH | O | a bond | Q3h | OH |
| 5574 | CH | S | Q1f | a bond | Me | a bond | NH | S | a bond | Q3d | OH |
| 5575 | CH | S | Q1f | a bond | Me | a bond | NH | S | a bond | Q3e | OH |
| 5576 | CH | S | Q1f | a bond | Me | a bond | NH | S | a bond | Q3f | OH |
| 5577 | CH | S | Q1f | a bond | Me | a bond | NH | S | a bond | Q3g | OH |
| 5578 | CH | S | Q1f | a bond | Me | a bond | NH | S | a bond | Q3h | OH |
| 5579 | CH | S | Q1f | a bond | H | a bond | NH | S | a bond | Q3d | OH |
| 5580 | CH | S | Q1f | a bond | H | a bond | NH | S | a bond | Q3e | OH |
| 5581 | CH | S | Q1f | a bond | H | a bond | NH | S | a bond | Q3f | OH |
| 5582 | CH | S | Q1f | a bond | H | a bond | NH | S | a bond | Q3g | OH |
| 5583 | CH | S | Q1f | a bond | H | a bond | NH | S | a bond | Q3h | OH |
| 5584 | CH | S | Q1f | a bond | Me | a bond | NH | O | a bond | Q3d | OH |
| 5585 | CH | S | Q1f | a bond | Me | a bond | NH | O | a bond | Q3e | OH |
| 5586 | CH | S | Q1f | a bond | Me | a bond | NH | O | a bond | Q3f | OH |
| 5587 | CH | S | Q1f | a bond | Me | a bond | NH | O | a bond | Q3g | OH |
| 5588 | CH | S | Q1f | a bond | Me | a bond | NH | O | a bond | Q3h | OH |
| 5589 | CH | S | Q1f | a bond | H | a bond | NH | O | a bond | Q3d | OH |
| 5590 | CH | S | Q1f | a bond | H | a bond | NH | O | a bond | Q3e | OH |
| 5591 | CH | S | Q1f | a bond | H | a bond | NH | O | a bond | Q3f | OH |
| 5592 | CH | S | Q1f | a bond | H | a bond | NH | O | a bond | Q3g | OH |
| 5593 | CH | S | Q1f | a bond | H | a bond | NH | O | a bond | Q3h | OH |
| 5594 | CH | S | Q1g | a bond | Me | a bond | NH | S | a bond | Q3d | OH |
| 5595 | CH | S | Q1g | a bond | Me | a bond | NH | S | a bond | Q3e | OH |
| 5596 | CH | S | Q1g | a bond | Me | a bond | NH | S | a bond | Q3f | OH |
| 5597 | CH | S | Q1g | a bond | Me | a bond | NH | S | a bond | Q3g | OH |
| 5598 | CH | S | Q1g | a bond | Me | a bond | NH | S | a bond | Q3h | OH |
| 5599 | CH | S | Q1g | a bond | H | a bond | NH | S | a bond | Q3d | OH |
| 5600 | CH | S | Q1g | a bond | H | a bond | NH | S | a bond | Q3e | OH |
| 5601 | CH | S | Q1g | a bond | H | a bond | NH | S | a bond | Q3f | OH |
| 5602 | CH | S | Q1g | a bond | H | a bond | NH | S | a bond | Q3g | OH |
| 5603 | CH | S | Q1g | a bond | H | a bond | NH | S | a bond | Q3h | OH |
| 5604 | CH | S | Q1g | a bond | Me | a bond | NH | O | a bond | Q3d | OH |
| 5605 | CH | S | Q1g | a bond | Me | a bond | NH | O | a bond | Q3e | OH |
| 5606 | CH | S | Q1g | a bond | Me | a bond | NH | O | a bond | Q3f | OH |
| 5607 | CH | S | Q1g | a bond | Me | a bond | NH | O | a bond | Q3g | OH |
| 5608 | CH | S | Q1g | a bond | Me | a bond | NH | O | a bond | Q3h | OH |
| 5609 | CH | S | Q1g | a bond | H | a bond | NH | O | a bond | Q3d | OH |
| 5610 | CH | S | Q1g | a bond | H | a bond | NH | O | a bond | Q3e | OH |
| 5611 | CH | S | Q1g | a bond | H | a bond | NH | O | a bond | Q3f | OH |
| 5612 | CH | S | Q1g | a bond | H | a bond | NH | O | a bond | Q3g | OH |
| 5613 | CH | S | Q1g | a bond | H | a bond | NH | O | a bond | Q3h | OH |
| 5614 | CH | S | Q1h | a bond | Me | a bond | NH | S | a bond | Q3d | OH |
| 5615 | CH | S | Q1h | a bond | Me | a bond | NH | S | a bond | Q3e | OH |

TABLE 1-continued

| No | A | B | R¹ | L¹ | R² | L² | L³ | Y | L⁴ | R³ | X |
|---|---|---|---|---|---|---|---|---|---|---|---|
| 5616 | CH | S | Q1h | a bond | Me | a bond | NH | S | a bond | Q3f | OH |
| 5617 | CH | S | Q1h | a bond | Me | a bond | NH | S | a bond | Q3g | OH |
| 5618 | CH | S | Q1h | a bond | Me | a bond | NH | S | a bond | Q3h | OH |
| 5619 | CH | S | Q1h | a bond | H | a bond | NH | S | a bond | Q3d | OH |
| 5620 | CH | S | Q1h | a bond | H | a bond | NH | S | a bond | Q3e | OH |
| 5621 | CH | S | Q1h | a bond | H | a bond | NH | S | a bond | Q3f | OH |
| 5622 | CH | S | Q1h | a bond | H | a bond | NH | S | a bond | Q3g | OH |
| 5623 | CH | S | Q1h | a bond | H | a bond | NH | S | a bond | Q3h | OH |
| 5624 | CH | S | Q1h | a bond | Me | a bond | NH | O | a bond | Q3d | OH |
| 5625 | CH | S | Q1h | a bond | Me | a bond | NH | O | a bond | Q3e | OH |
| 5626 | CH | S | Q1h | a bond | Me | a bond | NH | O | a bond | Q3f | OH |
| 5627 | CH | S | Q1h | a bond | Me | a bond | NH | O | a bond | Q3g | OH |
| 5628 | CH | S | Q1h | a bond | Me | a bond | NH | O | a bond | Q3h | OH |
| 5629 | CH | S | Q1h | a bond | H | a bond | NH | O | a bond | Q3d | OH |
| 5630 | CH | S | Q1h | a bond | H | a bond | NH | O | a bond | Q3e | OH |
| 5631 | CH | S | Q1h | a bond | H | a bond | NH | O | a bond | Q3f | OH |
| 5632 | CH | S | Q1h | a bond | H | a bond | NH | O | a bond | Q3g | OH |
| 5633 | CH | S | Q1h | a bond | H | a bond | NH | O | a bond | Q3h | OH |
| 5634 | CH | S | Q1i | a bond | Me | a bond | NH | S | a bond | Q3d | OH |
| 5635 | CH | S | Q1i | a bond | Me | a bond | NH | S | a bond | Q3e | OH |
| 5636 | CH | S | Q1i | a bond | Me | a bond | NH | S | a bond | Q3f | OH |
| 5637 | CH | S | Q1i | a bond | Me | a bond | NH | S | a bond | Q3g | OH |
| 5638 | CH | S | Q1i | a bond | Me | a bond | NH | S | a bond | Q3h | OH |
| 5639 | CH | S | Q1i | a bond | H | a bond | NH | S | a bond | Q3d | OH |
| 5640 | CH | S | Q1i | a bond | H | a bond | NH | S | a bond | Q3e | OH |
| 5641 | CH | S | Q1i | a bond | H | a bond | NH | S | a bond | Q3f | OH |
| 5642 | CH | S | Q1i | a bond | H | a bond | NH | S | a bond | Q3g | OH |
| 5643 | CH | S | Q1i | a bond | H | a bond | NH | S | a bond | Q3h | OH |
| 5644 | CH | S | Q1i | a bond | Me | a bond | NH | O | a bond | Q3d | OH |
| 5645 | CH | S | Q1i | a bond | Me | a bond | NH | O | a bond | Q3e | OH |
| 5646 | CH | S | Q1i | a bond | Me | a bond | NH | O | a bond | Q3f | OH |
| 5647 | CH | S | Q1i | a bond | Me | a bond | NH | O | a bond | Q3g | OH |
| 5648 | CH | S | Q1i | a bond | Me | a bond | NH | O | a bond | Q3h | OH |
| 5649 | CH | S | Q1i | a bond | H | a bond | NH | O | a bond | Q3d | OH |
| 5650 | CH | S | Q1i | a bond | H | a bond | NH | O | a bond | Q3e | OH |
| 5651 | CH | S | Q1i | a bond | H | a bond | NH | O | a bond | Q3f | OH |
| 5652 | CH | S | Q1i | a bond | H | a bond | NH | O | a bond | Q3g | OH |
| 5653 | CH | S | Q1i | a bond | H | a bond | NH | O | a bond | Q3h | OH |
| 5654 | CH | S | Q1j | a bond | Me | a bond | NH | S | a bond | Q3d | OH |
| 5655 | CH | S | Q1j | a bond | Me | a bond | NH | S | a bond | Q3e | OH |
| 5656 | CH | S | Q1j | a bond | Me | a bond | NH | S | a bond | Q3f | OH |
| 5657 | CH | S | Q1j | a bond | Me | a bond | NH | S | a bond | Q3g | OH |
| 5658 | CH | S | Q1j | a bond | Me | a bond | NH | S | a bond | Q3h | OH |
| 5659 | CH | S | Q1j | a bond | H | a bond | NH | S | a bond | Q3d | OH |
| 5660 | CH | S | Q1j | a bond | H | a bond | NH | S | a bond | Q3e | OH |
| 5661 | CH | S | Q1j | a bond | H | a bond | NH | S | a bond | Q3f | OH |
| 5662 | CH | S | Q1j | a bond | H | a bond | NH | S | a bond | Q3g | OH |
| 5663 | CH | S | Q1j | a bond | H | a bond | NH | S | a bond | Q3h | OH |
| 5664 | CH | S | Q1j | a bond | Me | a bond | NH | O | a bond | Q3d | OH |
| 5665 | CH | S | Q1j | a bond | Me | a bond | NH | O | a bond | Q3e | OH |
| 5666 | CH | S | Q1j | a bond | Me | a bond | NH | O | a bond | Q3f | OH |
| 5667 | CH | S | Q1j | a bond | Me | a bond | NH | O | a bond | Q3g | OH |
| 5668 | CH | S | Q1j | a bond | Me | a bond | NH | O | a bond | Q3h | OH |
| 5669 | CH | S | Q1j | a bond | H | a bond | NH | O | a bond | Q3d | OH |
| 5670 | CH | S | Q1j | a bond | H | a bond | NH | O | a bond | Q3e | OH |
| 5671 | CH | S | Q1j | a bond | H | a bond | NH | O | a bond | Q3f | OH |
| 5672 | CH | S | Q1j | a bond | H | a bond | NH | O | a bond | Q3g | OH |
| 5673 | CH | S | Q1j | a bond | H | a bond | NH | O | a bond | Q3h | OH |
| 5674 | N | NMe | Q1k | a bond | Me | a bond | NH | S | a bond | Q3b | OH |
| 5675 | N | NMe | Q1k | a bond | Me | a bond | NH | S | a bond | Q3c | OH |
| 5676 | N | NMe | Q1k | a bond | Me | a bond | NH | S | a bond | Q3g | OH |
| 5677 | N | NMe | Q1k | a bond | Me | a bond | NH | S | a bond | Q3h | OH |
| 5678 | N | NMe | Q1k | a bond | H | a bond | NH | S | a bond | Q3b | OH |
| 5679 | N | NMe | Q1k | a bond | H | a bond | NH | S | a bond | Q3c | OH |
| 5680 | N | NMe | Q1k | a bond | H | a bond | NH | S | a bond | Q3g | OH |
| 5681 | N | NMe | Q1k | a bond | H | a bond | NH | S | a bond | Q3h | OH |
| 5682 | N | NMe | Q1k | a bond | Me | a bond | NH | O | a bond | Q3b | OH |
| 5683 | N | NMe | Q1k | a bond | Me | a bond | NH | O | a bond | Q3c | OH |
| 5684 | N | NMe | Q1k | a bond | Me | a bond | NH | O | a bond | Q3g | OH |
| 5685 | N | NMe | Q1k | a bond | Me | a bond | NH | O | a bond | Q3h | OH |
| 5686 | N | NMe | Q1k | a bond | H | a bond | NH | O | a bond | Q3b | OH |
| 5687 | N | NMe | Q1k | a bond | H | a bond | NH | O | a bond | Q3c | OH |
| 5688 | N | NMe | Q1k | a bond | H | a bond | NH | O | a bond | Q3g | OH |
| 5689 | N | NMe | Q1k | a bond | H | a bond | NH | O | a bond | Q3h | OH |
| 5690 | N | NMe | Q1l | a bond | Me | a bond | NH | S | a bond | Q3b | OH |
| 5691 | N | NMe | Q1l | a bond | Me | a bond | NH | S | a bond | Q3c | OH |
| 5692 | N | NMe | Q1l | a bond | Me | a bond | NH | S | a bond | Q3g | OH |
| 5693 | N | NMe | Q1l | a bond | Me | a bond | NH | S | a bond | Q3h | OH |

TABLE 1-continued

| No | A | B | R¹ | L¹ | R² | L² | L³ | Y | L⁴ | R³ | X |
|---|---|---|---|---|---|---|---|---|---|---|---|
| 5694 | N | NMe | Q1l | a bond | H | a bond | NH | S | a bond | Q3b | OH |
| 5695 | N | NMe | Q1l | a bond | H | a bond | NH | S | a bond | Q3c | OH |
| 5696 | N | NMe | Q1l | a bond | H | a bond | NH | S | a bond | Q3g | OH |
| 5697 | N | NMe | Q1l | a bond | H | a bond | NH | S | a bond | Q3h | OH |
| 5698 | N | NMe | Q1l | a bond | Me | a bond | NH | O | a bond | Q3b | OH |
| 5699 | N | NMe | Q1l | a bond | Me | a bond | NH | O | a bond | Q3c | OH |
| 5700 | N | NMe | Q1l | a bond | Me | a bond | NH | O | a bond | Q3g | OH |
| 5701 | N | NMe | Q1l | a bond | Me | a bond | NH | O | a bond | Q3h | OH |
| 5702 | N | NMe | Q1l | a bond | H | a bond | NH | O | a bond | Q3b | OH |
| 5703 | N | NMe | Q1l | a bond | H | a bond | NH | O | a bond | Q3c | OH |
| 5704 | N | NMe | Q1l | a bond | H | a bond | NH | O | a bond | Q3g | OH |
| 5705 | N | NMe | Q1l | a bond | H | a bond | NH | O | a bond | Q3h | OH |
| 5706 | N | NMe | Q1m | a bond | Me | a bond | NH | S | a bond | Q3b | OH |
| 5707 | N | NMe | Q1m | a bond | Me | a bond | NH | S | a bond | Q3c | OH |
| 5708 | N | NMe | Q1m | a bond | Me | a bond | NH | S | a bond | Q3g | OH |
| 5709 | N | NMe | Q1m | a bond | Me | a bond | NH | S | a bond | Q3h | OH |
| 5710 | N | NMe | Q1m | a bond | H | a bond | NH | S | a bond | Q3b | OH |
| 5711 | N | NMe | Q1m | a bond | H | a bond | NH | S | a bond | Q3c | OH |
| 5712 | N | NMe | Q1m | a bond | H | a bond | NH | S | a bond | Q3g | OH |
| 5713 | N | NMe | Q1m | a bond | H | a bond | NH | S | a bond | Q3h | OH |
| 5714 | N | NMe | Q1m | a bond | Me | a bond | NH | O | a bond | Q3b | OH |
| 5715 | N | NMe | Q1m | a bond | Me | a bond | NH | O | a bond | Q3c | OH |
| 5716 | N | NMe | Q1m | a bond | Me | a bond | NH | O | a bond | Q3g | OH |
| 5717 | N | NMe | Q1m | a bond | Me | a bond | NH | O | a bond | Q3h | OH |
| 5718 | N | NMe | Q1m | a bond | H | a bond | NH | O | a bond | Q3b | OH |
| 5719 | N | NMe | Q1m | a bond | H | a bond | NH | O | a bond | Q3c | OH |
| 5720 | N | NMe | Q1m | a bond | H | a bond | NH | O | a bond | Q3g | OH |
| 5721 | N | NMe | Q1m | a bond | H | a bond | NH | O | a bond | Q3h | OH |
| 5722 | N | NMe | Q1n | a bond | Me | a bond | NH | S | a bond | Q3b | OH |
| 5723 | N | NMe | Q1n | a bond | Me | a bond | NH | S | a bond | Q3c | OH |
| 5724 | N | NMe | Q1n | a bond | Me | a bond | NH | S | a bond | Q3g | OH |
| 5725 | N | NMe | Q1n | a bond | Me | a bond | NH | S | a bond | Q3h | OH |
| 5726 | N | NMe | Q1n | a bond | H | a bond | NH | S | a bond | Q3b | OH |
| 5727 | N | NMe | Q1n | a bond | H | a bond | NH | S | a bond | Q3c | OH |
| 5728 | N | NMe | Q1n | a bond | H | a bond | NH | S | a bond | Q3g | OH |
| 5729 | N | NMe | Q1n | a bond | H | a bond | NH | S | a bond | Q3h | OH |
| 5730 | N | NMe | Q1n | a bond | Me | a bond | NH | O | a bond | Q3b | OH |
| 5731 | N | NMe | Q1n | a bond | Me | a bond | NH | O | a bond | Q3c | OH |
| 5732 | N | NMe | Q1n | a bond | Me | a bond | NH | O | a bond | Q3g | OH |
| 5733 | N | NMe | Q1n | a bond | Me | a bond | NH | O | a bond | Q3h | OH |
| 5734 | N | NMe | Q1n | a bond | H | a bond | NH | O | a bond | Q3b | OH |
| 5735 | N | NMe | Q1n | a bond | H | a bond | NH | O | a bond | Q3c | OH |
| 5736 | N | NMe | Q1n | a bond | H | a bond | NH | O | a bond | Q3g | OH |
| 5737 | N | NMe | Q1n | a bond | H | a bond | NH | O | a bond | Q3h | OH |
| 5738 | N | NMe | Q1k' | a bond | Me | a bond | NH | S | a bond | Q3b | OH |
| 5739 | N | NMe | Q1k' | a bond | Me | a bond | NH | S | a bond | Q3c | OH |
| 5740 | N | NMe | Q1k' | a bond | Me | a bond | NH | S | a bond | Q3g | OH |
| 5741 | N | NMe | Q1k' | a bond | Me | a bond | NH | S | a bond | Q3h | OH |
| 5742 | N | NMe | Q1k' | a bond | H | a bond | NH | S | a bond | Q3b | OH |
| 5743 | N | NMe | Q1k' | a bond | H | a bond | NH | S | a bond | Q3c | OH |
| 5744 | N | NMe | Q1k' | a bond | H | a bond | NH | S | a bond | Q3g | OH |
| 5745 | N | NMe | Q1k' | a bond | H | a bond | NH | S | a bond | Q3h | OH |
| 5746 | N | NMe | Q1k' | a bond | Me | a bond | NH | O | a bond | Q3b | OH |
| 5747 | N | NMe | Q1k' | a bond | Me | a bond | NH | O | a bond | Q3c | OH |
| 5748 | N | NMe | Q1k' | a bond | Me | a bond | NH | O | a bond | Q3g | OH |
| 5749 | N | NMe | Q1k' | a bond | Me | a bond | NH | O | a bond | Q3h | OH |
| 5750 | N | NMe | Q1k' | a bond | H | a bond | NH | O | a bond | Q3b | OH |
| 5751 | N | NMe | Q1k' | a bond | H | a bond | NH | O | a bond | Q3c | OH |
| 5752 | N | NMe | Q1k' | a bond | H | a bond | NH | O | a bond | Q3g | OH |
| 5753 | N | NMe | Q1k' | a bond | H | a bond | NH | O | a bond | Q3h | OH |
| 5754 | N | NMe | Q1l' | a bond | Me | a bond | NH | S | a bond | Q3b | OH |
| 5755 | N | NMe | Q1l' | a bond | Me | a bond | NH | S | a bond | Q3c | OH |
| 5756 | N | NMe | Q1l' | a bond | Me | a bond | NH | S | a bond | Q3g | OH |
| 5757 | N | NMe | Q1l' | a bond | Me | a bond | NH | S | a bond | Q3h | OH |
| 5758 | N | NMe | Q1l' | a bond | H | a bond | NH | S | a bond | Q3b | OH |
| 5759 | N | NMe | Q1l' | a bond | H | a bond | NH | S | a bond | Q3c | OH |
| 5760 | N | NMe | Q1l' | a bond | H | a bond | NH | S | a bond | Q3g | OH |
| 5761 | N | NMe | Q1l' | a bond | H | a bond | NH | S | a bond | Q3h | OH |
| 5762 | N | NMe | Q1l' | a bond | Me | a bond | NH | O | a bond | Q3b | OH |
| 5763 | N | NMe | Q1l' | a bond | Me | a bond | NH | O | a bond | Q3c | OH |
| 5764 | N | NMe | Q1l' | a bond | Me | a bond | NH | O | a bond | Q3g | OH |
| 5765 | N | NMe | Q1l' | a bond | Me | a bond | NH | O | a bond | Q3h | OH |
| 5766 | N | NMe | Q1l' | a bond | H | a bond | NH | O | a bond | Q3b | OH |
| 5767 | N | NMe | Q1l' | a bond | H | a bond | NH | O | a bond | Q3c | OH |
| 5768 | N | NMe | Q1l' | a bond | H | a bond | NH | O | a bond | Q3g | OH |
| 5769 | N | NMe | Q1l' | a bond | H | a bond | NH | O | a bond | Q3h | OH |
| 5770 | N | NMe | Q1m' | a bond | Me | a bond | NH | S | a bond | Q3b | OH |
| 5771 | N | NMe | Q1m' | a bond | Me | a bond | NH | S | a bond | Q3c | OH |

TABLE 1-continued

| No | A | B | R¹ | L¹ | R² | L² | L³ | Y | L⁴ | R³ | X |
|---|---|---|---|---|---|---|---|---|---|---|---|
| 5772 | N | NMe | Q1m' | a bond | Me | a bond | NH | S | a bond | Q3g | OH |
| 5773 | N | NMe | Q1m' | a bond | Me | a bond | NH | S | a bond | Q3h | OH |
| 5774 | N | NMe | Q1m' | a bond | H | a bond | NH | S | a bond | Q3b | OH |
| 5775 | N | NMe | Q1m' | a bond | H | a bond | NH | S | a bond | Q3c | OH |
| 5776 | N | NMe | Q1m' | a bond | H | a bond | NH | S | a bond | Q3g | OH |
| 5777 | N | NMe | Q1m' | a bond | H | a bond | NH | S | a bond | Q3h | OH |
| 5778 | N | NMe | Q1m' | a bond | Me | a bond | NH | O | a bond | Q3b | OH |
| 5779 | N | NMe | Q1m' | a bond | Me | a bond | NH | O | a bond | Q3c | OH |
| 5780 | N | NMe | Q1m' | a bond | Me | a bond | NH | O | a bond | Q3g | OH |
| 5781 | N | NMe | Q1m' | a bond | Me | a bond | NH | O | a bond | Q3h | OH |
| 5782 | N | NMe | Q1m' | a bond | H | a bond | NH | O | a bond | Q3b | OH |
| 5783 | N | NMe | Q1m' | a bond | H | a bond | NH | O | a bond | Q3c | OH |
| 5784 | N | NMe | Q1m' | a bond | H | a bond | NH | O | a bond | Q3g | OH |
| 5785 | N | NMe | Q1m' | a bond | H | a bond | NH | O | a bond | Q3h | OH |
| 5786 | N | NMe | Q1n' | a bond | Me | a bond | NH | S | a bond | Q3b | OH |
| 5787 | N | NMe | Q1n' | a bond | Me | a bond | NH | S | a bond | Q3c | OH |
| 5788 | N | NMe | Q1n' | a bond | Me | a bond | NH | S | a bond | Q3g | OH |
| 5789 | N | NMe | Q1n' | a bond | Me | a bond | NH | S | a bond | Q3h | OH |
| 5790 | N | NMe | Q1n' | a bond | H | a bond | NH | S | a bond | Q3b | OH |
| 5791 | N | NMe | Q1n' | a bond | H | a bond | NH | S | a bond | Q3c | OH |
| 5792 | N | NMe | Q1n' | a bond | H | a bond | NH | S | a bond | Q3g | OH |
| 5793 | N | NMe | Q1n' | a bond | H | a bond | NH | S | a bond | Q3h | OH |
| 5794 | N | NMe | Q1n' | a bond | Me | a bond | NH | O | a bond | Q3b | OH |
| 5795 | N | NMe | Q1n' | a bond | Me | a bond | NH | O | a bond | Q3c | OH |
| 5796 | N | NMe | Q1n' | a bond | Me | a bond | NH | O | a bond | Q3g | OH |
| 5797 | N | NMe | Q1n' | a bond | Me | a bond | NH | O | a bond | Q3h | OH |
| 5798 | N | NMe | Q1n' | a bond | H | a bond | NH | O | a bond | Q3b | OH |
| 5799 | N | NMe | Q1n' | a bond | H | a bond | NH | O | a bond | Q3c | OH |
| 5800 | N | NMe | Q1n' | a bond | H | a bond | NH | O | a bond | Q3g | OH |
| 5801 | N | NMe | Q1n' | a bond | H | a bond | NH | O | a bond | Q3h | OH |
| 5802 | CH | S | Q1k | a bond | Me | a bond | NH | S | a bond | Q3b | OH |
| 5803 | CH | S | Q1k | a bond | Me | a bond | NH | S | a bond | Q3c | OH |
| 5804 | CH | S | Q1k | a bond | Me | a bond | NH | S | a bond | Q3g | OH |
| 5805 | CH | S | Q1k | a bond | Me | a bond | NH | S | a bond | Q3h | OH |
| 5806 | CH | S | Q1k | a bond | H | a bond | NH | S | a bond | Q3b | OH |
| 5807 | CH | S | Q1k | a bond | H | a bond | NH | S | a bond | Q3c | OH |
| 5808 | CH | S | Q1k | a bond | H | a bond | NH | S | a bond | Q3g | OH |
| 5809 | CH | S | Q1k | a bond | H | a bond | NH | S | a bond | Q3h | OH |
| 5810 | CH | S | Q1k | a bond | Me | a bond | NH | O | a bond | Q3b | OH |
| 5811 | CH | S | Q1k | a bond | Me | a bond | NH | O | a bond | Q3c | OH |
| 5812 | CH | S | Q1k | a bond | Me | a bond | NH | O | a bond | Q3g | OH |
| 5813 | CH | S | Q1k | a bond | Me | a bond | NH | O | a bond | Q3h | OH |
| 5814 | CH | S | Q1k | a bond | H | a bond | NH | O | a bond | Q3b | OH |
| 5815 | CH | S | Q1k | a bond | H | a bond | NH | O | a bond | Q3c | OH |
| 5816 | CH | S | Q1k | a bond | H | a bond | NH | O | a bond | Q3g | OH |
| 5817 | CH | S | Q1k | a bond | H | a bond | NH | O | a bond | Q3h | OH |
| 5818 | CH | S | Q1l | a bond | Me | a bond | NH | S | a bond | Q3b | OH |
| 5819 | CH | S | Q1l | a bond | Me | a bond | NH | S | a bond | Q3c | OH |
| 5820 | CH | S | Q1l | a bond | Me | a bond | NH | S | a bond | Q3g | OH |
| 5821 | CH | S | Q1l | a bond | Me | a bond | NH | S | a bond | Q3h | OH |
| 5822 | CH | S | Q1l | a bond | H | a bond | NH | S | a bond | Q3b | OH |
| 5823 | CH | S | Q1l | a bond | H | a bond | NH | S | a bond | Q3c | OH |
| 5824 | CH | S | Q1l | a bond | H | a bond | NH | S | a bond | Q3g | OH |
| 5825 | CH | S | Q1l | a bond | H | a bond | NH | S | a bond | Q3h | OH |
| 5826 | CH | S | Q1l | a bond | Me | a bond | NH | O | a bond | Q3b | OH |
| 5827 | CH | S | Q1l | a bond | Me | a bond | NH | O | a bond | Q3c | OH |
| 5828 | CH | S | Q1l | a bond | Me | a bond | NH | O | a bond | Q3g | OH |
| 5829 | CH | S | Q1l | a bond | Me | a bond | NH | O | a bond | Q3h | OH |
| 5830 | CH | S | Q1l | a bond | H | a bond | NH | O | a bond | Q3b | OH |
| 5831 | CH | S | Q1l | a bond | H | a bond | NH | O | a bond | Q3c | OH |
| 5832 | CH | S | Q1l | a bond | H | a bond | NH | O | a bond | Q3g | OH |
| 5833 | CH | S | Q1l | a bond | H | a bond | NH | O | a bond | Q3h | OH |
| 5834 | CH | S | Q1m | a bond | Me | a bond | NH | S | a bond | Q3b | OH |
| 5835 | CH | S | Q1m | a bond | Me | a bond | NH | S | a bond | Q3c | OH |
| 5836 | CH | S | Q1m | a bond | Me | a bond | NH | S | a bond | Q3g | OH |
| 5837 | CH | S | Q1m | a bond | Me | a bond | NH | S | a bond | Q3h | OH |
| 5838 | CH | S | Q1m | a bond | H | a bond | NH | S | a bond | Q3b | OH |
| 5839 | CH | S | Q1m | a bond | H | a bond | NH | S | a bond | Q3c | OH |
| 5840 | CH | S | Q1m | a bond | H | a bond | NH | S | a bond | Q3g | OH |
| 5841 | CH | S | Q1m | a bond | H | a bond | NH | S | a bond | Q3h | OH |
| 5842 | CH | S | Q1m | a bond | Me | a bond | NH | O | a bond | Q3b | OH |
| 5843 | CH | S | Q1m | a bond | Me | a bond | NH | O | a bond | Q3c | OH |
| 5844 | CH | S | Q1m | a bond | Me | a bond | NH | O | a bond | Q3g | OH |
| 5845 | CH | S | Q1m | a bond | Me | a bond | NH | O | a bond | Q3h | OH |
| 5846 | CH | S | Q1m | a bond | H | a bond | NH | O | a bond | Q3b | OH |
| 5847 | CH | S | Q1m | a bond | H | a bond | NH | O | a bond | Q3c | OH |
| 5848 | CH | S | Q1m | a bond | H | a bond | NH | O | a bond | Q3g | OH |
| 5849 | CH | S | Q1m | a bond | H | a bond | NH | O | a bond | Q3h | OH |

TABLE 1-continued

| No | A | B | R¹ | L¹ | R² | L² | L³ | Y | L⁴ | R³ | X |
|---|---|---|---|---|---|---|---|---|---|---|---|
| 5850 | CH | S | Q1n | a bond | Me | a bond | NH | S | a bond | Q3b | OH |
| 5851 | CH | S | Q1n | a bond | Me | a bond | NH | S | a bond | Q3c | OH |
| 5852 | CH | S | Q1n | a bond | Me | a bond | NH | S | a bond | Q3g | OH |
| 5853 | CH | S | Q1n | a bond | Me | a bond | NH | S | a bond | Q3h | OH |
| 5854 | CH | S | Q1n | a bond | H | a bond | NH | S | a bond | Q3b | OH |
| 5855 | CH | S | Q1n | a bond | H | a bond | NH | S | a bond | Q3c | OH |
| 5856 | CH | S | Q1n | a bond | H | a bond | NH | S | a bond | Q3g | OH |
| 5857 | CH | S | Q1n | a bond | H | a bond | NH | S | a bond | Q3h | OH |
| 5858 | CH | S | Q1n | a bond | Me | a bond | NH | O | a bond | Q3b | OH |
| 5859 | CH | S | Q1n | a bond | Me | a bond | NH | O | a bond | Q3c | OH |
| 5860 | CH | S | Q1n | a bond | Me | a bond | NH | O | a bond | Q3g | OH |
| 5861 | CH | S | Q1n | a bond | Me | a bond | NH | O | a bond | Q3h | OH |
| 5862 | CH | S | Q1n | a bond | H | a bond | NH | O | a bond | Q3b | OH |
| 5863 | CH | S | Q1n | a bond | H | a bond | NH | O | a bond | Q3c | OH |
| 5864 | CH | S | Q1n | a bond | H | a bond | NH | O | a bond | Q3g | OH |
| 5865 | CH | S | Q1n | a bond | H | a bond | NH | O | a bond | Q3h | OH |
| 5866 | CH | S | Q1k' | a bond | Me | a bond | NH | S | a bond | Q3b | OH |
| 5867 | CH | S | Q1k' | a bond | Me | a bond | NH | S | a bond | Q3c | OH |
| 5868 | CH | S | Q1k' | a bond | Me | a bond | NH | S | a bond | Q3g | OH |
| 5869 | CH | S | Q1k' | a bond | Me | a bond | NH | S | a bond | Q3h | OH |
| 5870 | CH | S | Q1k' | a bond | H | a bond | NH | S | a bond | Q3b | OH |
| 5871 | CH | S | Q1k' | a bond | H | a bond | NH | S | a bond | Q3c | OH |
| 5872 | CH | S | Q1k' | a bond | H | a bond | NH | S | a bond | Q3g | OH |
| 5873 | CH | S | Q1k' | a bond | H | a bond | NH | S | a bond | Q3h | OH |
| 5874 | CH | S | Q1k' | a bond | Me | a bond | NH | O | a bond | Q3b | OH |
| 5875 | CH | S | Q1k' | a bond | Me | a bond | NH | O | a bond | Q3c | OH |
| 5876 | CH | S | Q1k' | a bond | Me | a bond | NH | O | a bond | Q3g | OH |
| 5877 | CH | S | Q1k' | a bond | Me | a bond | NH | O | a bond | Q3h | OH |
| 5878 | CH | S | Q1k' | a bond | H | a bond | NH | O | a bond | Q3b | OH |
| 5879 | CH | S | Q1k' | a bond | H | a bond | NH | O | a bond | Q3c | OH |
| 5880 | CH | S | Q1k' | a bond | H | a bond | NH | O | a bond | Q3g | OH |
| 5881 | CH | S | Q1k' | a bond | H | a bond | NH | O | a bond | Q3h | OH |
| 5882 | CH | S | Q1l' | a bond | Me | a bond | NH | S | a bond | Q3b | OH |
| 5883 | CH | S | Q1l' | a bond | Me | a bond | NH | S | a bond | Q3c | OH |
| 5884 | CH | S | Q1l' | a bond | Me | a bond | NH | S | a bond | Q3g | OH |
| 5885 | CH | S | Q1l' | a bond | Me | a bond | NH | S | a bond | Q3h | OH |
| 5886 | CH | S | Q1l' | a bond | H | a bond | NH | S | a bond | Q3b | OH |
| 5887 | CH | S | Q1l' | a bond | H | a bond | NH | S | a bond | Q3c | OH |
| 5888 | CH | S | Q1l' | a bond | H | a bond | NH | S | a bond | Q3g | OH |
| 5889 | CH | S | Q1l' | a bond | H | a bond | NH | S | a bond | Q3h | OH |
| 5890 | CH | S | Q1l' | a bond | Me | a bond | NH | O | a bond | Q3b | OH |
| 5891 | CH | S | Q1l' | a bond | Me | a bond | NH | O | a bond | Q3c | OH |
| 5892 | CH | S | Q1l' | a bond | Me | a bond | NH | O | a bond | Q3g | OH |
| 5893 | CH | S | Q1l' | a bond | Me | a bond | NH | O | a bond | Q3h | OH |
| 5894 | CH | S | Q1l' | a bond | H | a bond | NH | O | a bond | Q3b | OH |
| 5895 | CH | S | Q1l' | a bond | H | a bond | NH | O | a bond | Q3c | OH |
| 5896 | CH | S | Q1l' | a bond | H | a bond | NH | O | a bond | Q3g | OH |
| 5897 | CH | S | Q1l' | a bond | H | a bond | NH | O | a bond | Q3h | OH |
| 5898 | CH | S | Q1m' | a bond | Me | a bond | NH | S | a bond | Q3b | OH |
| 5899 | CH | S | Q1m' | a bond | Me | a bond | NH | S | a bond | Q3c | OH |
| 5900 | CH | S | Q1m' | a bond | Me | a bond | NH | S | a bond | Q3g | OH |
| 5901 | CH | S | Q1m' | a bond | Me | a bond | NH | S | a bond | Q3h | OH |
| 5902 | CH | S | Q1m' | a bond | H | a bond | NH | S | a bond | Q3b | OH |
| 5903 | CH | S | Q1m' | a bond | H | a bond | NH | S | a bond | Q3c | OH |
| 5904 | CH | S | Q1m' | a bond | H | a bond | NH | S | a bond | Q3g | OH |
| 5905 | CH | S | Q1m' | a bond | H | a bond | NH | S | a bond | Q3h | OH |
| 5906 | CH | S | Q1m' | a bond | Me | a bond | NH | O | a bond | Q3b | OH |
| 5907 | CH | S | Q1m' | a bond | Me | a bond | NH | O | a bond | Q3c | OH |
| 5908 | CH | S | Q1m' | a bond | Me | a bond | NH | O | a bond | Q3g | OH |
| 5909 | CH | S | Q1m' | a bond | Me | a bond | NH | O | a bond | Q3h | OH |
| 5910 | CH | S | Q1m' | a bond | H | a bond | NH | O | a bond | Q3b | OH |
| 5911 | CH | S | Q1m' | a bond | H | a bond | NH | O | a bond | Q3c | OH |
| 5912 | CH | S | Q1m' | a bond | H | a bond | NH | O | a bond | Q3g | OH |
| 5913 | CH | S | Q1m' | a bond | H | a bond | NH | O | a bond | Q3h | OH |
| 5914 | CH | S | Q1n' | a bond | Me | a bond | NH | S | a bond | Q3b | OH |
| 5915 | CH | S | Q1n' | a bond | Me | a bond | NH | S | a bond | Q3c | OH |
| 5916 | CH | S | Q1n' | a bond | Me | a bond | NH | S | a bond | Q3g | OH |
| 5917 | CH | S | Q1n' | a bond | Me | a bond | NH | S | a bond | Q3h | OH |
| 5918 | CH | S | Q1n' | a bond | H | a bond | NH | S | a bond | Q3b | OH |
| 5919 | CH | S | Q1n' | a bond | H | a bond | NH | S | a bond | Q3c | OH |
| 5920 | CH | S | Q1n' | a bond | H | a bond | NH | S | a bond | Q3g | OH |
| 5921 | CH | S | Q1n' | a bond | H | a bond | NH | S | a bond | Q3h | OH |
| 5922 | CH | S | Q1n' | a bond | Me | a bond | NH | O | a bond | Q3b | OH |
| 5923 | CH | S | Q1n' | a bond | Me | a bond | NH | O | a bond | Q3c | OH |
| 5924 | CH | S | Q1n' | a bond | Me | a bond | NH | O | a bond | Q3g | OH |
| 5925 | CH | S | Q1n' | a bond | Me | a bond | NH | O | a bond | Q3h | OH |
| 5926 | CH | S | Q1n' | a bond | H | a bond | NH | O | a bond | Q3b | OH |
| 5927 | CH | S | Q1n' | a bond | H | a bond | NH | O | a bond | Q3c | OH |

TABLE 1-continued

| No | A | B | R¹ | L¹ | R² | L² | L³ | Y | L⁴ | R³ | X |
|---|---|---|---|---|---|---|---|---|---|---|---|
| 5928 | CH | S | Q1n' | a bond | H | a bond | NH | O | a bond | Q3g | OH |
| 5929 | CH | S | Q1n' | a bond | H | a bond | NH | O | a bond | Q3h | OH |
| 5930 | CH | S | Q1d | a bond | Me | a bond | NH | S | a bond | Q3d | OH |
| 5931 | CH | S | Q1d | a bond | Me | a bond | NH | S | a bond | Q3e | OH |
| 5932 | CH | S | Q1d | a bond | Me | a bond | NH | S | a bond | Q3f | OH |
| 5933 | CH | S | Q1d | a bond | Me | a bond | NH | S | a bond | Q3g | OH |
| 5934 | CH | S | Q1d | a bond | Me | a bond | NH | S | a bond | Q3h | OH |
| 5935 | CH | S | Q1d | a bond | H | a bond | NH | S | a bond | Q3d | OH |
| 5936 | CH | S | Q1d | a bond | H | a bond | NH | S | a bond | Q3e | OH |
| 5937 | CH | S | Q1d | a bond | H | a bond | NH | S | a bond | Q3f | OH |
| 5938 | CH | S | Q1d | a bond | H | a bond | NH | S | a bond | Q3g | OH |
| 5939 | CH | S | Q1d | a bond | H | a bond | NH | S | a bond | Q3h | OH |
| 5940 | CH | S | Q1d | a bond | Me | a bond | NH | O | a bond | Q3d | OH |
| 5941 | CH | S | Q1d | a bond | Me | a bond | NH | O | a bond | Q3e | OH |
| 5942 | CH | S | Q1d | a bond | Me | a bond | NH | O | a bond | Q3f | OH |
| 5943 | CH | S | Q1d | a bond | Me | a bond | NH | O | a bond | Q3g | OH |
| 5944 | CH | S | Q1d | a bond | Me | a bond | NH | O | a bond | Q3h | OH |
| 5945 | CH | S | Q1d | a bond | H | a bond | NH | O | a bond | Q3d | OH |
| 5946 | CH | S | Q1d | a bond | H | a bond | NH | O | a bond | Q3e | OH |
| 5947 | CH | S | Q1d | a bond | H | a bond | NH | O | a bond | Q3f | OH |
| 5948 | CH | S | Q1d | a bond | H | a bond | NH | O | a bond | Q3g | OH |
| 5949 | CH | S | Q1d | a bond | H | a bond | NH | O | a bond | Q3h | OH |
| 5950 | CH | S | Q1e | a bond | Me | a bond | NH | S | a bond | Q3d | OH |
| 5951 | CH | S | Q1e | a bond | Me | a bond | NH | S | a bond | Q3e | OH |
| 5952 | CH | S | Q1e | a bond | Me | a bond | NH | S | a bond | Q3f | OH |
| 5953 | CH | S | Q1e | a bond | Me | a bond | NH | S | a bond | Q3g | OH |
| 5954 | CH | S | Q1e | a bond | Me | a bond | NH | S | a bond | Q3h | OH |
| 5955 | CH | S | Q1e | a bond | H | a bond | NH | S | a bond | Q3d | OH |
| 5956 | CH | S | Q1e | a bond | H | a bond | NH | S | a bond | Q3e | OH |
| 5957 | CH | S | Q1e | a bond | H | a bond | NH | S | a bond | Q3f | OH |
| 5958 | CH | S | Q1e | a bond | H | a bond | NH | S | a bond | Q3g | OH |
| 5959 | CH | S | Q1e | a bond | H | a bond | NH | S | a bond | Q3h | OH |
| 5960 | CH | S | Q1e | a bond | Me | a bond | NH | O | a bond | Q3d | OH |
| 5961 | CH | S | Q1e | a bond | Me | a bond | NH | O | a bond | Q3e | OH |
| 5962 | CH | S | Q1e | a bond | Me | a bond | NH | O | a bond | Q3f | OH |
| 5963 | CH | S | Q1e | a bond | Me | a bond | NH | O | a bond | Q3g | OH |
| 5964 | CH | S | Q1e | a bond | Me | a bond | NH | O | a bond | Q3h | OH |
| 5965 | CH | S | Q1e | a bond | H | a bond | NH | O | a bond | Q3d | OH |
| 5966 | CH | S | Q1e | a bond | H | a bond | NH | O | a bond | Q3e | OH |
| 5967 | CH | S | Q1e | a bond | H | a bond | NH | O | a bond | Q3f | OH |
| 5968 | CH | S | Q1e | a bond | H | a bond | NH | O | a bond | Q3g | OH |
| 5969 | CH | S | Q1e | a bond | H | a bond | NH | O | a bond | Q3h | OH |
| 5970 | CH | S | Q1a | a bond | H | a bond | NH | O | a bond | Q3h | OH |
| 5971 | CH | S | Q1b | a bond | Me | a bond | NH | S | a bond | Q3g | OH |
| 5972 | CH | S | Q1b | a bond | Me | a bond | NH | S | a bond | Q3h | OH |
| 5973 | CH | S | Q1b | a bond | H | a bond | NH | S | a bond | Q3g | OH |
| 5974 | CH | S | Q1b | a bond | H | a bond | NH | S | a bond | Q3h | OH |
| 5975 | CH | S | Q1b | a bond | Me | a bond | NH | O | a bond | Q3g | OH |
| 5976 | CH | S | Q1b | a bond | Me | a bond | NH | O | a bond | Q3h | OH |
| 5977 | CH | S | Q1b | a bond | H | a bond | NH | O | a bond | Q3g | OH |
| 5978 | CH | S | Q1b | a bond | H | a bond | NH | O | a bond | Q3h | OH |
| 5979 | CH | S | Q1c | a bond | Me | a bond | NH | S | a bond | Q3g | OH |
| 5980 | CH | S | Q1c | a bond | Me | a bond | NH | S | a bond | Q3h | OH |
| 5981 | CH | S | Q1c | a bond | H | a bond | NH | S | a bond | Q3g | OH |
| 5982 | CH | S | Q1c | a bond | H | a bond | NH | S | a bond | Q3h | OH |
| 5983 | CH | S | Q1c | a bond | Me | a bond | NH | O | a bond | Q3g | OH |
| 5984 | CH | S | Q1c | a bond | Me | a bond | NH | O | a bond | Q3h | OH |
| 5985 | CH | S | Q1c | a bond | H | a bond | NH | O | a bond | Q3g | OH |
| 5986 | CH | S | Q1c | a bond | H | a bond | NH | O | a bond | Q3h | OH |
| 5987 | N | NMe | Q1d | a bond | Me | a bond | NH | S | a bond | Q3d | OH |
| 5988 | N | NMe | Q1d | a bond | Me | a bond | NH | S | a bond | Q3e | OH |
| 5989 | N | NMe | Q1d | a bond | Me | a bond | NH | S | a bond | Q3f | OH |
| 5990 | N | NMe | Q1d | a bond | Me | a bond | NH | S | a bond | Q3g | OH |
| 5991 | N | NMe | Q1d | a bond | Me | a bond | NH | S | a bond | Q3h | OH |
| 5992 | N | NMe | Q1d | a bond | H | a bond | NH | S | a bond | Q3d | OH |
| 5993 | N | NMe | Q1d | a bond | H | a bond | NH | S | a bond | Q3e | OH |
| 5994 | N | NMe | Q1d | a bond | H | a bond | NH | S | a bond | Q3f | OH |
| 5995 | N | NMe | Q1d | a bond | H | a bond | NH | S | a bond | Q3g | OH |
| 5996 | N | NMe | Q1d | a bond | H | a bond | NH | S | a bond | Q3h | OH |
| 5997 | N | NMe | Q1d | a bond | Me | a bond | NH | O | a bond | Q3d | OH |
| 5998 | N | NMe | Q1d | a bond | Me | a bond | NH | O | a bond | Q3e | OH |
| 5999 | N | NMe | Q1d | a bond | Me | a bond | NH | O | a bond | Q3f | OH |
| 6000 | N | NMe | Q1d | a bond | Me | a bond | NH | O | a bond | Q3g | OH |
| 6001 | N | NMe | Q1d | a bond | Me | a bond | NH | O | a bond | Q3h | OH |
| 6002 | N | NMe | Q1d | a bond | H | a bond | NH | O | a bond | Q3d | OH |
| 6003 | N | NMe | Q1d | a bond | H | a bond | NH | O | a bond | Q3e | OH |
| 6004 | N | NMe | Q1d | a bond | H | a bond | NH | O | a bond | Q3f | OH |
| 6005 | N | NMe | Q1d | a bond | H | a bond | NH | O | a bond | Q3g | OH |

TABLE 1-continued

| No | A | B | R¹ | L¹ | R² | L² | L³ | Y | L⁴ | R³ | X |
|---|---|---|---|---|---|---|---|---|---|---|---|
| 6006 | N | NMe | Q1d | a bond | H | a bond | NH | O | a bond | Q3h | OH |
| 6007 | N | NMe | Q1e | a bond | Me | a bond | NH | S | a bond | Q3d | OH |
| 6008 | N | NMe | Q1e | a bond | Me | a bond | NH | S | a bond | Q3e | OH |
| 6009 | N | NMe | Q1e | a bond | Me | a bond | NH | S | a bond | Q3f | OH |
| 6010 | N | NMe | Q1e | a bond | Me | a bond | NH | S | a bond | Q3g | OH |
| 6011 | N | NMe | Q1e | a bond | Me | a bond | NH | S | a bond | Q3h | OH |
| 6012 | N | NMe | Q1e | a bond | H | a bond | NH | S | a bond | Q3d | OH |
| 6013 | N | NMe | Q1e | a bond | H | a bond | NH | S | a bond | Q3e | OH |
| 6014 | N | NMe | Q1e | a bond | H | a bond | NH | S | a bond | Q3f | OH |
| 6015 | N | NMe | Q1e | a bond | H | a bond | NH | S | a bond | Q3g | OH |
| 6016 | N | NMe | Q1e | a bond | H | a bond | NH | S | a bond | Q3h | OH |
| 6017 | N | NMe | Q1e | a bond | Me | a bond | NH | O | a bond | Q3d | OH |
| 6018 | N | NMe | Q1e | a bond | Me | a bond | NH | O | a bond | Q3e | OH |
| 6019 | N | NMe | Q1e | a bond | Me | a bond | NH | O | a bond | Q3f | OH |
| 6020 | N | NMe | Q1e | a bond | Me | a bond | NH | O | a bond | Q3g | OH |
| 6021 | N | NMe | Q1e | a bond | Me | a bond | NH | O | a bond | Q3h | OH |
| 6022 | N | NMe | Q1e | a bond | H | a bond | NH | O | a bond | Q3d | OH |
| 6023 | N | NMe | Q1e | a bond | H | a bond | NH | O | a bond | Q3e | OH |
| 6024 | N | NMe | Q1e | a bond | H | a bond | NH | O | a bond | Q3f | OH |
| 6025 | N | NMe | Q1e | a bond | H | a bond | NH | O | a bond | Q3g | OH |
| 6026 | N | NMe | Q1e | a bond | H | a bond | NH | O | a bond | Q3h | OH |
| 6027 | N | NEt | Q1e | a bond | Me | a bond | NH | S | a bond | Q3d | OH |
| 6028 | CH | NMe | Q1e | a bond | Me | a bond | NH | S | a bond | Q3e | OH |
| 6029 | N | O | Q1e | a bond | Me | a bond | NH | S | a bond | Q3f | OH |
| 6030 | N | S | Q1e | a bond | Me | a bond | NH | S | a bond | Q3g | OH |
| 6031 | CH | NEt | Q1e | a bond | Me | a bond | NH | S | a bond | Q3h | OH |
| 6032 | CMe | S | Q1e | a bond | H | a bond | NH | S | a bond | Q3d | OH |
| 6033 | CH | O | Q1e | a bond | H | a bond | NH | S | a bond | Q3e | OH |
| 6034 | CMe | O | Q1e | a bond | H | a bond | NH | S | a bond | Q3f | OH |
| 6035 | CMe | NMe | Q1e | a bond | H | a bond | NH | S | a bond | Q3g | OH |
| 6036 | CMe | NEt | Q1e | a bond | H | a bond | NH | S | a bond | Q3h | OH |
| 6037 | CBr | S | Q1b | a bond | Me | a bond | NH | S | a bond | Q3a | OH |
| 6038 | CCl | S | Q1b | a bond | Me | a bond | NH | S | a bond | Q3a | OH |
| 6039 | CF | S | Q1b | a bond | Me | a bond | NH | S | a bond | Q3a | OH |
| 6040 | N | NMe | Q1f | a bond | Me | a bond | NH | S | a bond | Q3d | OH |
| 6041 | N | NMe | Q1f | a bond | Me | a bond | NH | S | a bond | Q3e | OH |
| 6042 | N | NMe | Q1f | a bond | Me | a bond | NH | S | a bond | Q3f | OH |
| 6043 | N | NMe | Q1f | a bond | Me | a bond | NH | S | a bond | Q3g | OH |
| 6044 | N | NMe | Q1f | a bond | Me | a bond | NH | S | a bond | Q3h | OH |
| 6045 | N | NMe | Q1f | a bond | H | a bond | NH | S | a bond | Q3d | OH |
| 6046 | N | NMe | Q1f | a bond | H | a bond | NH | S | a bond | Q3e | OH |
| 6047 | N | NMe | Q1f | a bond | H | a bond | NH | S | a bond | Q3f | OH |
| 6048 | N | NMe | Q1f | a bond | H | a bond | NH | S | a bond | Q3g | OH |
| 6049 | N | NMe | Q1f | a bond | H | a bond | NH | S | a bond | Q3h | OH |
| 6050 | N | NMe | Q1f | a bond | Me | a bond | NH | O | a bond | Q3d | OH |
| 6051 | N | NMe | Q1f | a bond | Me | a bond | NH | O | a bond | Q3e | OH |
| 6052 | N | NMe | Q1f | a bond | Me | a bond | NH | O | a bond | Q3f | OH |
| 6053 | N | NMe | Q1f | a bond | Me | a bond | NH | O | a bond | Q3g | OH |
| 6054 | N | NMe | Q1f | a bond | Me | a bond | NH | O | a bond | Q3h | OH |
| 6055 | N | NMe | Q1f | a bond | H | a bond | NH | O | a bond | Q3d | OH |
| 6056 | N | NMe | Q1f | a bond | H | a bond | NH | O | a bond | Q3e | OH |
| 6057 | N | NMe | Q1f | a bond | H | a bond | NH | O | a bond | Q3f | OH |
| 6058 | N | NMe | Q1f | a bond | H | a bond | NH | O | a bond | Q3g | OH |
| 6059 | N | NMe | Q1f | a bond | H | a bond | NH | O | a bond | Q3h | OH |
| 6060 | N | NMe | Q1g | a bond | Me | a bond | NH | S | a bond | Q3d | OH |
| 6061 | N | NMe | Q1g | a bond | Me | a bond | NH | S | a bond | Q3e | OH |
| 6062 | N | NMe | Q1g | a bond | Me | a bond | NH | S | a bond | Q3f | OH |
| 6063 | N | NMe | Q1g | a bond | Me | a bond | NH | S | a bond | Q3g | OH |
| 6064 | N | NMe | Q1g | a bond | Me | a bond | NH | S | a bond | Q3h | OH |
| 6065 | N | NMe | Q1g | a bond | H | a bond | NH | S | a bond | Q3d | OH |
| 6066 | N | NMe | Q1g | a bond | H | a bond | NH | S | a bond | Q3e | OH |
| 6067 | N | NMe | Q1g | a bond | H | a bond | NH | S | a bond | Q3f | OH |
| 6068 | N | NMe | Q1g | a bond | H | a bond | NH | S | a bond | Q3g | OH |
| 6069 | N | NMe | Q1g | a bond | H | a bond | NH | S | a bond | Q3h | OH |

60) The compounds wherein A, B, $R^1$, $L^1$, $R^2$, $L^2$, $L^3$, Y, $L^4$, $R^3$ and X are any of the following combinations in Table 2, tautomers, prodrugs or pharmaceutically acceptable salts of the compounds or solvates thereof. The symbols in Table 2 denote the flowing substituents.

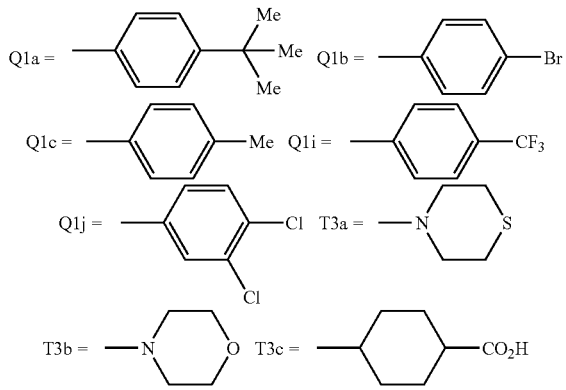

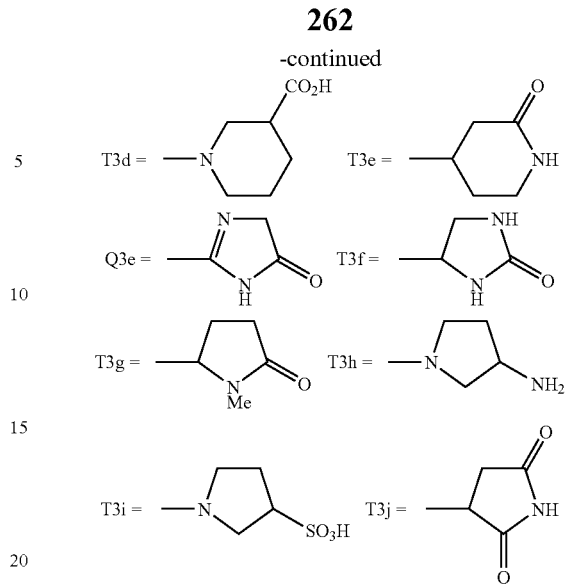

TABLE 2

| No | A | B | $R^1$ | $L^1$ | $R^2$ | $L^2$ | $L^3$ | Y | $L^4$ | $R^3$ | X |
|---|---|---|---|---|---|---|---|---|---|---|---|
| 1 | N | NMe | Q1a | a bond | Me | a bond | NH | S | NH | T3a | OH |
| 2 | N | NMe | Q1a | a bond | Me | a bond | NH | S | NH | T3b | OH |
| 3 | N | NMe | Q1a | a bond | Me | a bond | NH | S | NH | T3c | OH |
| 4 | N | NMe | Q1a | a bond | Me | a bond | NH | S | NH | T3d | OH |
| 5 | N | NMe | Q1a | a bond | Me | a bond | NH | S | NH | T3e | OH |
| 6 | N | NMe | Q1a | a bond | Me | a bond | NH | S | NH | T3f | OH |
| 7 | N | NMe | Q1a | a bond | Me | a bond | NH | S | NH | T3g | OH |
| 8 | N | NMe | Q1a | a bond | Me | a bond | NH | S | NH | T3h | OH |
| 9 | N | NMe | Q1a | a bond | Me | a bond | NH | S | NH | T3i | OH |
| 10 | N | NMe | Q1a | a bond | Me | a bond | NH | S | NH | T3j | OH |
| 11 | N | NMe | Q1a | a bond | Me | a bond | NH | S | a bond | T3a | OH |
| 12 | N | NMe | Q1a | a bond | Me | a bond | NH | S | a bond | T3b | OH |
| 13 | N | NMe | Q1a | a bond | Me | a bond | NH | S | a bond | T3c | OH |
| 14 | N | NMe | Q1a | a bond | Me | a bond | NH | S | a bond | T3d | OH |
| 15 | N | NMe | Q1a | a bond | Me | a bond | NH | S | a bond | T3e | OH |
| 16 | N | NMe | Q1a | a bond | Me | a bond | NH | S | a bond | T3f | OH |
| 17 | N | NMe | Q1a | a bond | Me | a bond | NH | S | a bond | T3g | OH |
| 18 | N | NMe | Q1a | a bond | Me | a bond | NH | S | a bond | T3h | OH |
| 19 | N | NMe | Q1a | a bond | Me | a bond | NH | S | a bond | T3i | OH |
| 20 | N | NMe | Q1a | a bond | Me | a bond | NH | S | a bond | T3j | OH |
| 21 | N | NMe | Q1a | a bond | Me | a bond | NH | O | NH | T3a | OH |
| 22 | N | NMe | Q1a | a bond | Me | a bond | NH | O | NH | T3b | OH |
| 23 | N | NMe | Q1a | a bond | Me | a bond | NH | O | NH | T3c | OH |
| 24 | N | NMe | Q1a | a bond | Me | a bond | NH | O | NH | T3d | OH |
| 25 | N | NMe | Q1a | a bond | Me | a bond | NH | O | NH | T3e | OH |
| 26 | N | NMe | Q1a | a bond | Me | a bond | NH | O | NH | T3f | OH |
| 27 | N | NMe | Q1a | a bond | Me | a bond | NH | O | NH | T3g | OH |
| 28 | N | NMe | Q1a | a bond | Me | a bond | NH | O | NH | T3h | OH |
| 29 | N | NMe | Q1a | a bond | Me | a bond | NH | O | NH | T3i | OH |
| 30 | N | NMe | Q1a | a bond | Me | a bond | NH | O | NH | T3j | OH |
| 31 | N | NMe | Q1a | a bond | Me | a bond | NH | O | a bond | T3a | OH |
| 32 | N | NMe | Q1a | a bond | Me | a bond | NH | O | a bond | T3b | OH |
| 33 | N | NMe | Q1a | a bond | Me | a bond | NH | O | a bond | T3c | OH |
| 34 | N | NMe | Q1a | a bond | Me | a bond | NH | O | a bond | T3d | OH |
| 35 | N | NMe | Q1a | a bond | Me | a bond | NH | O | a bond | T3e | OH |
| 36 | N | NMe | Q1a | a bond | Me | a bond | NH | O | a bond | T3f | OH |
| 37 | N | NMe | Q1a | a bond | Me | a bond | NH | O | a bond | T3g | OH |
| 38 | N | NMe | Q1a | a bond | Me | a bond | NH | O | a bond | T3h | OH |
| 39 | N | NMe | Q1a | a bond | Me | a bond | NH | O | a bond | T3i | OH |
| 40 | N | NMe | Q1a | a bond | Me | a bond | NH | O | a bond | T3j | OH |
| 41 | N | NMe | Q1a | a bond | H | a bond | NH | S | NH | T3a | OH |
| 42 | N | NMe | Q1a | a bond | H | a bond | NH | S | NH | T3b | OH |
| 43 | N | NMe | Q1a | a bond | H | a bond | NH | S | NH | T3c | OH |
| 44 | N | NMe | Q1a | a bond | H | a bond | NH | S | NH | T3d | OH |
| 45 | N | NMe | Q1a | a bond | H | a bond | NH | S | NH | T3e | OH |
| 46 | N | NMe | Q1a | a bond | H | a bond | NH | S | NH | T3f | OH |
| 47 | N | NMe | Q1a | a bond | H | a bond | NH | S | NH | T3g | OH |
| 48 | N | NMe | Q1a | a bond | H | a bond | NH | S | NH | T3h | OH |
| 49 | N | NMe | Q1a | a bond | H | a bond | NH | S | NH | T3i | OH |

TABLE 2-continued

| No | A | B | R¹ | L¹ | R² | L² | L³ | Y | L⁴ | R³ | X |
|---|---|---|---|---|---|---|---|---|---|---|---|
| 50 | N | NMe | Q1a | a bond | H | a bond | NH | S | NH | T3j | OH |
| 51 | N | NMe | Q1a | a bond | H | a bond | NH | S | a bond | T3a | OH |
| 52 | N | NMe | Q1a | a bond | H | a bond | NH | S | a bond | T3b | OH |
| 53 | N | NMe | Q1a | a bond | H | a bond | NH | S | a bond | T3c | OH |
| 54 | N | NMe | Q1a | a bond | H | a bond | NH | S | a bond | T3d | OH |
| 55 | N | NMe | Q1a | a bond | H | a bond | NH | S | a bond | T3e | OH |
| 56 | N | NMe | Q1a | a bond | H | a bond | NH | S | a bond | T3f | OH |
| 57 | N | NMe | Q1a | a bond | H | a bond | NH | S | a bond | T3g | OH |
| 58 | N | NMe | Q1a | a bond | H | a bond | NH | S | a bond | T3h | OH |
| 59 | N | NMe | Q1a | a bond | H | a bond | NH | S | a bond | T3i | OH |
| 60 | N | NMe | Q1a | a bond | H | a bond | NH | S | a bond | T3j | OH |
| 61 | N | NMe | Q1a | a bond | H | a bond | NH | O | NH | T3a | OH |
| 62 | N | NMe | Q1a | a bond | H | a bond | NH | O | NH | T3b | OH |
| 63 | N | NMe | Q1a | a bond | H | a bond | NH | O | NH | T3c | OH |
| 64 | N | NMe | Q1a | a bond | H | a bond | NH | O | NH | T3d | OH |
| 65 | N | NMe | Q1a | a bond | H | a bond | NH | O | NH | T3e | OH |
| 66 | N | NMe | Q1a | a bond | H | a bond | NH | O | NH | T3f | OH |
| 67 | N | NMe | Q1a | a bond | H | a bond | NH | O | NH | T3g | OH |
| 68 | N | NMe | Q1a | a bond | H | a bond | NH | O | NH | T3h | OH |
| 69 | N | NMe | Q1a | a bond | H | a bond | NH | O | NH | T3i | OH |
| 70 | N | NMe | Q1a | a bond | H | a bond | NH | O | NH | T3j | OH |
| 71 | N | NMe | Q1a | a bond | H | a bond | NH | O | a bond | T3a | OH |
| 72 | N | NMe | Q1a | a bond | H | a bond | NH | O | a bond | T3b | OH |
| 73 | N | NMe | Q1a | a bond | H | a bond | NH | O | a bond | T3c | OH |
| 74 | N | NMe | Q1a | a bond | H | a bond | NH | O | a bond | T3d | OH |
| 75 | N | NMe | Q1a | a bond | H | a bond | NH | O | a bond | T3e | OH |
| 76 | N | NMe | Q1a | a bond | H | a bond | NH | O | a bond | T3f | OH |
| 77 | N | NMe | Q1a | a bond | H | a bond | NH | O | a bond | T3g | OH |
| 78 | N | NMe | Q1a | a bond | H | a bond | NH | O | a bond | T3h | OH |
| 79 | N | NMe | Q1a | a bond | H | a bond | NH | O | a bond | T3i | OH |
| 80 | N | NMe | Q1a | a bond | H | a bond | NH | O | a bond | T3j | OH |
| 81 | N | NMe | Q1b | a bond | Me | a bond | NH | S | NH | T3a | OH |
| 82 | N | NMe | Q1b | a bond | Me | a bond | NH | S | NH | T3b | OH |
| 83 | N | NMe | Q1b | a bond | Me | a bond | NH | S | NH | T3c | OH |
| 84 | N | NMe | Q1b | a bond | Me | a bond | NH | S | NH | T3d | OH |
| 85 | N | NMe | Q1b | a bond | Me | a bond | NH | S | NH | T3e | OH |
| 86 | N | NMe | Q1b | a bond | Me | a bond | NH | S | NH | T3f | OH |
| 87 | N | NMe | Q1b | a bond | Me | a bond | NH | S | NH | T3g | OH |
| 88 | N | NMe | Q1b | a bond | Me | a bond | NH | S | NH | T3h | OH |
| 89 | N | NMe | Q1b | a bond | Me | a bond | NH | S | NH | T3i | OH |
| 90 | N | NMe | Q1b | a bond | Me | a bond | NH | S | NH | T3j | OH |
| 91 | N | NMe | Q1b | a bond | Me | a bond | NH | S | a bond | T3a | OH |
| 92 | N | NMe | Q1b | a bond | Me | a bond | NH | S | a bond | T3b | OH |
| 93 | N | NMe | Q1b | a bond | Me | a bond | NH | S | a bond | T3c | OH |
| 94 | N | NMe | Q1b | a bond | Me | a bond | NH | S | a bond | T3d | OH |
| 95 | N | NMe | Q1b | a bond | Me | a bond | NH | S | a bond | T3e | OH |
| 96 | N | NMe | Q1b | a bond | Me | a bond | NH | S | a bond | T3f | OH |
| 97 | N | NMe | Q1b | a bond | Me | a bond | NH | S | a bond | T3g | OH |
| 98 | N | NMe | Q1b | a bond | Me | a bond | NH | S | a bond | T3h | OH |
| 99 | N | NMe | Q1b | a bond | Me | a bond | NH | S | a bond | T3i | OH |
| 100 | N | NMe | Q1b | a bond | Me | a bond | NH | S | a bond | T3j | OH |
| 101 | N | NMe | Q1b | a bond | Me | a bond | NH | O | H | T3a | OH |
| 102 | N | NMe | Q1b | a bond | Me | a bond | NH | O | H | T3b | OH |
| 103 | N | NMe | Q1b | a bond | Me | a bond | NH | O | NH | T3c | OH |
| 104 | N | NMe | Q1b | a bond | Me | a bond | NH | O | NH | T3d | OH |
| 105 | N | NMe | Q1b | a bond | Me | a bond | NH | O | NH | T3e | OH |
| 106 | N | NMe | Q1b | a bond | Me | a bond | NH | O | NH | T3f | OH |
| 107 | N | NMe | Q1b | a bond | Me | a bond | NH | O | NH | T3g | OH |
| 108 | N | NMe | Q1b | a bond | Me | a bond | NH | O | NH | T3h | OH |
| 109 | N | NMe | Q1b | a bond | Me | a bond | NH | O | NH | T3i | OH |
| 110 | N | NMe | Q1b | a bond | Me | a bond | NH | O | NH | T3j | OH |
| 111 | N | NMe | Q1b | a bond | Me | a bond | NH | O | a bond | T3a | OH |
| 112 | N | NMe | Q1b | a bond | Me | a bond | NH | O | a bond | T3b | OH |
| 113 | N | NMe | Q1b | a bond | Me | a bond | NH | O | a bond | T3c | OH |
| 114 | N | NMe | Q1b | a bond | Me | a bond | NH | O | a bond | T3d | OH |
| 115 | N | NMe | Q1b | a bond | Me | a bond | NH | O | a bond | T3e | OH |
| 116 | N | NMe | Q1b | a bond | Me | a bond | NH | O | a bond | T3f | OH |
| 117 | N | NMe | Q1b | a bond | Me | a bond | NH | O | a bond | T3g | OH |
| 118 | N | NMe | Q1b | a bond | Me | a bond | NH | O | a bond | T3h | OH |
| 119 | N | NMe | Q1b | a bond | Me | a bond | NH | O | a bond | T3i | OH |
| 120 | N | NMe | Q1b | a bond | Me | a bond | NH | O | a bond | T3j | OH |
| 121 | N | NMe | Q1b | a bond | H | a bond | NH | S | H | T3a | OH |
| 122 | N | NMe | Q1b | a bond | H | a bond | NH | S | H | T3b | OH |
| 123 | N | NMe | Q1b | a bond | H | a bond | NH | S | H | T3c | OH |
| 124 | N | NMe | Q1b | a bond | H | a bond | NH | S | NH | T3d | OH |
| 125 | N | NMe | Q1b | a bond | H | a bond | NH | S | NH | T3e | OH |
| 126 | N | NMe | Q1b | a bond | H | a bond | NH | S | NH | T3f | OH |
| 127 | N | NMe | Q1b | a bond | H | a bond | NH | S | NH | T3g | OH |

TABLE 2-continued

| No | A | B | R¹ | L¹ | R² | L² | L³ | Y | L⁴ | R³ | X |
|---|---|---|---|---|---|---|---|---|---|---|---|
| 128 | N | NMe | Q1b | a bond | H | a bond | NH | S | NH | T3h | OH |
| 129 | N | NMe | Q1b | a bond | H | a bond | NH | S | NH | T3i | OH |
| 130 | N | NMe | Q1b | a bond | H | a bond | NH | S | NH | T3j | OH |
| 131 | N | NMe | Q1b | a bond | H | a bond | NH | S | a bond | T3a | OH |
| 132 | N | NMe | Q1b | a bond | H | a bond | NH | S | a bond | T3b | OH |
| 133 | N | NMe | Q1b | a bond | H | a bond | NH | S | a bond | T3c | OH |
| 134 | N | NMe | Q1b | a bond | H | a bond | NH | S | a bond | T3d | OH |
| 135 | N | NMe | Q1b | a bond | H | a bond | NH | S | a bond | T3e | OH |
| 136 | N | NMe | Q1b | a bond | H | a bond | NH | S | a bond | T3f | OH |
| 137 | N | NMe | Q1b | a bond | H | a bond | NH | S | a bond | T3g | OH |
| 138 | N | NMe | Q1b | a bond | H | a bond | NH | S | a bond | T3h | OH |
| 139 | N | NMe | Q1b | a bond | H | a bond | NH | S | a bond | T3i | OH |
| 140 | N | NMe | Q1b | a bond | H | a bond | NH | S | a bond | T3j | OH |
| 141 | N | NMe | Q1b | a bond | H | a bond | NH | O | NH | T3a | OH |
| 142 | N | NMe | Q1b | a bond | H | a bond | NH | O | NH | T3b | OH |
| 143 | N | NMe | Q1b | a bond | H | a bond | NH | O | NH | T3c | OH |
| 144 | N | NMe | Q1b | a bond | H | a bond | NH | O | NH | T3d | OH |
| 145 | N | NMe | Q1b | a bond | H | a bond | NH | O | NH | T3e | OH |
| 146 | N | NMe | Q1b | a bond | H | a bond | NH | O | NH | T3f | OH |
| 147 | N | NMe | Q1b | a bond | H | a bond | NH | O | NH | T3g | OH |
| 148 | N | NMe | Q1b | a bond | H | a bond | NH | O | NH | T3h | OH |
| 149 | N | NMe | Q1b | a bond | H | a bond | NH | O | NH | T3i | OH |
| 150 | N | NMe | Q1b | a bond | H | a bond | NH | O | NH | T3j | OH |
| 151 | N | NMe | Q1b | a bond | H | a bond | NH | O | a bond | T3a | OH |
| 152 | N | NMe | Q1b | a bond | H | a bond | NH | O | a bond | T3b | OH |
| 153 | N | NMe | Q1b | a bond | H | a bond | NH | O | a bond | T3c | OH |
| 154 | N | NMe | Q1b | a bond | H | a bond | NH | O | a bond | T3d | OH |
| 155 | N | NMe | Q1b | a bond | H | a bond | NH | O | a bond | T3e | OH |
| 156 | N | NMe | Q1b | a bond | H | a bond | NH | O | a bond | T3f | OH |
| 157 | N | NMe | Q1b | a bond | H | a bond | NH | O | a bond | T3g | OH |
| 158 | N | NMe | Q1b | a bond | H | a bond | NH | O | a bond | T3h | OH |
| 159 | N | NMe | Q1b | a bond | H | a bond | NH | O | a bond | T3i | OH |
| 160 | N | NMe | Q1b | a bond | H | a bond | NH | O | a bond | T3j | OH |
| 161 | N | NMe | Q1c | a bond | Me | a bond | NH | S | NH | T3a | OH |
| 162 | N | NMe | Q1c | a bond | Me | a bond | H | S | NH | T3b | OH |
| 163 | N | NMe | Q1c | a bond | Me | a bond | NH | S | NH | T3c | OH |
| 164 | N | NMe | Q1c | a bond | Me | a bond | NH | S | NH | T3d | OH |
| 165 | N | NMe | Q1c | a bond | Me | a bond | NH | S | NH | T3e | OH |
| 166 | N | NMe | Q1c | a bond | Me | a bond | NH | S | NH | T3f | OH |
| 167 | N | NMe | Q1c | a bond | Me | a bond | NH | S | NH | T3g | OH |
| 168 | N | NMe | Q1c | a bond | Me | a bond | NH | S | NH | T3h | OH |
| 169 | N | NMe | Q1c | a bond | Me | a bond | NH | S | NH | T3i | OH |
| 170 | N | NMe | Q1c | a bond | Me | a bond | NH | S | NH | T3j | OH |
| 171 | N | NMe | Q1c | a bond | Me | a bond | NH | S | a bond | T3a | OH |
| 172 | N | NMe | Q1c | a bond | Me | a bond | NH | S | a bond | T3b | OH |
| 173 | N | NMe | Q1c | a bond | Me | a bond | NH | S | a bond | T3c | OH |
| 174 | N | NMe | Q1c | a bond | Me | a bond | NH | S | a bond | T3d | OH |
| 175 | N | NMe | Q1c | a bond | Me | a bond | NH | S | a bond | T3e | OH |
| 176 | N | NMe | Q1c | a bond | Me | a bond | NH | S | a bond | T3f | OH |
| 177 | N | NMe | Q1c | a bond | Me | a bond | NH | S | a bond | T3g | OH |
| 178 | N | NMe | Q1c | a bond | Me | a bond | NH | S | a bond | T3h | OH |
| 179 | N | NMe | Q1c | a bond | Me | a bond | NH | S | a bond | T3i | OH |
| 180 | N | NMe | Q1c | a bond | Me | a bond | NH | S | a bond | T3j | OH |
| 181 | N | NMe | Q1c | a bond | Me | a bond | NH | O | NH | T3a | OH |
| 182 | N | NMe | Q1c | a bond | Me | a bond | NH | O | NH | T3b | OH |
| 183 | N | NMe | Q1c | a bond | Me | a bond | NH | O | NH | T3c | OH |
| 184 | N | NMe | Q1c | a bond | Me | a bond | NH | O | NH | T3d | OH |
| 185 | N | NMe | Q1c | a bond | Me | a bond | NH | O | NH | T3e | OH |
| 186 | N | NMe | Q1c | a bond | Me | a bond | NH | O | NH | T3f | OH |
| 187 | N | NMe | Q1c | a bond | Me | a bond | NH | O | NH | T3g | OH |
| 188 | N | NMe | Q1c | a bond | Me | a bond | NH | O | NH | T3h | OH |
| 189 | N | NMe | Q1c | a bond | Me | a bond | NH | O | NH | T3i | OH |
| 190 | N | NMe | Q1c | a bond | Me | a bond | NH | O | NH | T3j | OH |
| 191 | N | NMe | Q1c | a bond | Me | a bond | NH | O | a bond | T3a | OH |
| 192 | N | NMe | Q1c | a bond | Me | a bond | NH | O | a bond | T3b | OH |
| 193 | N | NMe | Q1c | a bond | Me | a bond | NH | O | a bond | T3c | OH |
| 194 | N | NMe | Q1c | a bond | Me | a bond | NH | O | a bond | T3d | OH |
| 195 | N | NMe | Q1c | a bond | Me | a bond | NH | O | a bond | T3e | OH |
| 196 | N | NMe | Q1c | a bond | Me | a bond | NH | O | a bond | T3f | OH |
| 197 | N | NMe | Q1c | a bond | Me | a bond | NH | O | a bond | T3g | OH |
| 198 | N | NMe | Q1c | a bond | Me | a bond | NH | O | a bond | T3h | OH |
| 199 | N | NMe | Q1c | a bond | Me | a bond | NH | O | a bond | T3i | OH |
| 200 | N | NMe | Q1c | a bond | Me | a bond | NH | O | a bond | T3j | OH |
| 201 | N | NMe | Q1c | a bond | H | a bond | NH | S | NH | T3a | OH |
| 202 | N | NMe | Q1c | a bond | H | a bond | NH | S | NH | T3b | OH |
| 203 | N | NMe | Q1c | a bond | H | a bond | NH | S | NH | T3c | OH |
| 204 | N | NMe | Q1c | a bond | H | a bond | NH | S | NH | T3d | OH |
| 205 | N | NMe | Q1c | a bond | H | a bond | NH | S | NH | T3e | OH |

TABLE 2-continued

| No | A | B | R¹ | L¹ | R² | L² | L³ | Y | L⁴ | R³ | X |
|---|---|---|---|---|---|---|---|---|---|---|---|
| 206 | N | NMe | Q1c | a bond | H | a bond | NH | S | NH | T3f | OH |
| 207 | N | NMe | Q1c | a bond | H | a bond | NH | S | NH | T3g | OH |
| 208 | N | NMe | Q1c | a bond | H | a bond | NH | S | H | T3h | OH |
| 209 | N | NMe | Q1c | a bond | H | a bond | NH | S | NH | T3i | OH |
| 210 | N | NMe | Q1c | a bond | H | a bond | NH | S | NH | T3j | OH |
| 211 | N | NMe | Q1c | a bond | H | a bond | NH | S | a bond | T3a | OH |
| 212 | N | NMe | Q1c | a bond | H | a bond | NH | S | a bond | T3b | OH |
| 213 | N | NMe | Q1c | a bond | H | a bond | NH | S | a bond | T3c | OH |
| 214 | N | NMe | Q1c | a bond | H | a bond | NH | S | a bond | T3d | OH |
| 215 | N | NMe | Q1c | a bond | H | a bond | NH | S | a bond | T3e | OH |
| 216 | N | NMe | Q1c | a bond | H | a bond | NH | S | a bond | T3f | OH |
| 217 | N | NMe | Q1c | a bond | H | a bond | NH | S | a bond | T3g | OH |
| 218 | N | NMe | Q1c | a bond | H | a bond | NH | S | a bond | T3h | OH |
| 219 | N | NMe | Q1c | a bond | H | a bond | NH | S | a bond | T3i | OH |
| 220 | N | NMe | Q1c | a bond | H | a bond | NH | S | a bond | T3j | OH |
| 221 | N | NMe | Q1c | a bond | H | a bond | NH | O | NH | T3a | OH |
| 222 | N | NMe | Q1c | a bond | H | a bond | NH | O | NH | T3b | OH |
| 223 | N | NMe | Q1c | a bond | H | a bond | NH | O | NH | T3c | OH |
| 224 | N | NMe | Q1c | a bond | H | a bond | NH | O | NH | T3d | OH |
| 225 | N | NMe | Q1c | a bond | H | a bond | NH | O | NH | T3e | OH |
| 226 | N | NMe | Q1c | a bond | H | a bond | NH | O | NH | T3f | OH |
| 227 | N | NMe | Q1c | a bond | H | a bond | NH | O | NH | T3g | OH |
| 228 | N | NMe | Q1c | a bond | H | a bond | NH | O | NH | T3h | OH |
| 229 | N | NMe | Q1c | a bond | H | a bond | NH | O | NH | T3i | OH |
| 230 | N | NMe | Q1c | a bond | H | a bond | NH | O | NH | T3j | OH |
| 231 | N | NMe | Q1c | a bond | H | a bond | NH | O | a bond | T3a | OH |
| 232 | N | NMe | Q1c | a bond | H | a bond | NH | O | a bond | T3b | OH |
| 233 | N | NMe | Q1c | a bond | H | a bond | NH | O | a bond | T3c | OH |
| 234 | N | NMe | Q1c | a bond | H | a bond | NH | O | a bond | T3d | OH |
| 235 | N | NMe | Q1c | a bond | H | a bond | NH | O | a bond | T3e | OH |
| 236 | N | NMe | Q1c | a bond | H | a bond | NH | O | a bond | T3f | OH |
| 237 | N | NMe | Q1c | a bond | H | a bond | NH | O | a bond | T3g | OH |
| 238 | N | NMe | Q1c | a bond | H | a bond | NH | O | a bond | T3h | OH |
| 239 | N | NMe | Q1c | a bond | H | a bond | NH | O | a bond | T3i | OH |
| 240 | N | NMe | Q1c | a bond | H | a bond | NH | O | a bond | T3j | OH |
| 241 | N | NMe | Q1i | a bond | Me | a bond | NH | S | NH | T3a | OH |
| 242 | N | NMe | Q1i | a bond | Me | a bond | NH | S | NH | T3b | OH |
| 243 | N | NMe | Q1i | a bond | Me | a bond | NH | S | NH | T3c | OH |
| 244 | N | NMe | Q1i | a bond | Me | a bond | NH | S | NH | T3d | OH |
| 245 | N | NMe | Q1i | a bond | Me | a bond | NH | S | NH | T3e | OH |
| 246 | N | NMe | Q1i | a bond | Me | a bond | NH | S | NH | T3f | OH |
| 247 | N | NMe | Q1i | a bond | Me | a bond | NH | S | NH | T3g | OH |
| 248 | N | NMe | Q1i | a bond | Me | a bond | NH | S | NH | T3h | OH |
| 249 | N | NMe | Q1i | a bond | Me | a bond | NH | S | NH | T3i | OH |
| 250 | N | NMe | Q1i | a bond | Me | a bond | NH | S | NH | T3j | OH |
| 251 | N | NMe | Q1i | a bond | Me | a bond | NH | S | a bond | T3a | OH |
| 252 | N | NMe | Q1i | a bond | Me | a bond | NH | S | a bond | T3b | OH |
| 253 | N | NMe | Q1i | a bond | Me | a bond | NH | S | a bond | T3c | OH |
| 254 | N | NMe | Q1i | a bond | Me | a bond | NH | S | a bond | T3d | OH |
| 255 | N | NMe | Q1i | a bond | Me | a bond | NH | S | a bond | T3e | OH |
| 256 | N | NMe | Q1i | a bond | Me | a bond | NH | S | a bond | T3f | OH |
| 257 | N | NMe | Q1i | a bond | Me | a bond | NH | S | a bond | T3g | OH |
| 258 | N | NMe | Q1i | a bond | Me | a bond | NH | S | a bond | T3h | OH |
| 259 | N | NMe | Q1i | a bond | Me | a bond | NH | S | a bond | T3i | OH |
| 260 | N | NMe | Q1i | a bond | Me | a bond | NH | S | a bond | T3j | OH |
| 261 | N | NMe | Q1i | a bond | Me | a bond | NH | O | NH | T3a | OH |
| 262 | N | NMe | Q1i | a bond | Me | a bond | NH | O | NH | T3b | OH |
| 263 | N | NMe | Q1i | a bond | Me | a bond | NH | O | NH | T3c | OH |
| 264 | N | NMe | Q1i | a bond | Me | a bond | NH | O | NH | T3d | OH |
| 265 | N | NMe | Q1i | a bond | Me | a bond | NH | O | NH | T3e | OH |
| 266 | N | NMe | Q1i | a bond | Me | a bond | NH | O | NH | T3f | OH |
| 267 | N | NMe | Q1i | a bond | Me | a bond | NH | O | NH | T3g | OH |
| 268 | N | NMe | Q1i | a bond | Me | a bond | NH | O | NH | T3h | OH |
| 269 | N | NMe | Q1i | a bond | Me | a bond | NH | O | NH | T3i | OH |
| 270 | N | NMe | Q1i | a bond | Me | a bond | NH | O | H | T3j | OH |
| 271 | N | NMe | Q1i | a bond | Me | a bond | NH | O | a bond | T3a | OH |
| 272 | N | NMe | Q1i | a bond | Me | a bond | NH | O | a bond | T3b | OH |
| 273 | N | NMe | Q1i | a bond | Me | a bond | NH | O | a bond | T3c | OH |
| 274 | N | NMe | Q1i | a bond | Me | a bond | NH | O | a bond | T3d | OH |
| 275 | N | NMe | Q1i | a bond | Me | a bond | NH | O | a bond | T3e | OH |
| 276 | N | NMe | Q1i | a bond | Me | a bond | NH | O | a bond | T3f | OH |
| 277 | N | NMe | Q1i | a bond | Me | a bond | NH | O | a bond | T3g | OH |
| 278 | N | NMe | Q1i | a bond | Me | a bond | NH | O | a bond | T3h | OH |
| 279 | N | NMe | Q1i | a bond | Me | a bond | NH | O | a bond | T3i | OH |
| 280 | N | NMe | Q1i | a bond | Me | a bond | NH | O | a bond | T3j | OH |
| 281 | N | NMe | Q1i | a bond | H | a bond | NH | S | NH | T3a | OH |
| 282 | N | NMe | Q1i | a bond | H | a bond | NH | S | NH | T3b | OH |
| 283 | N | NMe | Q1i | a bond | H | a bond | NH | S | NH | T3c | OH |

TABLE 2-continued

| No | A | B | R¹ | L¹ | R² | L² | L³ | Y | L⁴ | R³ | X |
|---|---|---|---|---|---|---|---|---|---|---|---|
| 284 | N | NMe | Q1i | a bond | H | a bond | NH | S | NH | T3d | OH |
| 285 | N | NMe | Q1i | a bond | H | a bond | NH | S | NH | T3e | OH |
| 286 | N | NMe | Q1i | a bond | H | a bond | NH | S | NH | T3f | OH |
| 287 | N | NMe | Q1i | a bond | H | a bond | NH | S | NH | T3g | OH |
| 288 | N | NMe | Q1i | a bond | H | a bond | NH | S | NH | T3h | OH |
| 289 | N | NMe | Q1i | a bond | H | a bond | NH | S | NH | T3i | OH |
| 290 | N | NMe | Q1i | a bond | H | a bond | NH | S | NH | T3j | OH |
| 291 | N | NMe | Q1i | a bond | H | a bond | NH | S | a bond | T3a | OH |
| 292 | N | NMe | Q1i | a bond | H | a bond | NH | S | a bond | T3b | OH |
| 293 | N | NMe | Q1i | a bond | H | a bond | NH | S | a bond | T3c | OH |
| 294 | N | NMe | Q1i | a bond | H | a bond | NH | S | a bond | T3d | OH |
| 295 | N | NMe | Q1i | a bond | H | a bond | NH | S | a bond | T3e | OH |
| 296 | N | NMe | Q1i | a bond | H | a bond | NH | S | a bond | T3f | OH |
| 297 | N | NMe | Q1i | a bond | H | a bond | NH | S | a bond | T3g | OH |
| 298 | N | NMe | Q1i | a bond | H | a bond | NH | S | a bond | T3h | OH |
| 299 | N | NMe | Q1i | a bond | H | a bond | NH | S | a bond | T3i | OH |
| 300 | N | NMe | Q1i | a bond | H | a bond | NH | S | a bond | T3j | OH |
| 301 | N | NMe | Q1i | a bond | H | a bond | NH | O | H | T3a | OH |
| 302 | N | NMe | Q1i | a bond | H | a bond | NH | O | NH | T3b | OH |
| 303 | N | NMe | Q1i | a bond | H | a bond | NH | O | NH | T3c | OH |
| 304 | N | NMe | Q1i | a bond | H | a bond | NH | O | NH | T3d | OH |
| 305 | N | NMe | Q1i | a bond | H | a bond | NH | O | NH | T3e | OH |
| 306 | N | NMe | Q1i | a bond | H | a bond | NH | O | NH | T3f | OH |
| 307 | N | NMe | Q1i | a bond | H | a bond | NH | O | NH | T3g | OH |
| 308 | N | NMe | Q1i | a bond | H | a bond | NH | O | NH | T3h | OH |
| 309 | N | NMe | Q1i | a bond | H | a bond | NH | O | NH | T3i | OH |
| 310 | N | NMe | Q1i | a bond | H | a bond | NH | O | NH | T3j | OH |
| 311 | N | NMe | Q1i | a bond | H | a bond | NH | O | a bond | T3a | OH |
| 312 | N | NMe | Q1i | a bond | H | a bond | NH | O | a bond | T3b | OH |
| 313 | N | NMe | Q1i | a bond | H | a bond | NH | O | a bond | T3c | OH |
| 314 | N | NMe | Q1i | a bond | H | a bond | NH | O | a bond | T3d | OH |
| 315 | N | NMe | Q1i | a bond | H | a bond | NH | O | a bond | T3e | OH |
| 316 | N | NMe | Q1i | a bond | H | a bond | NH | O | a bond | T3f | OH |
| 317 | N | NMe | Q1i | a bond | H | a bond | NH | O | a bond | T3g | OH |
| 318 | N | NMe | Q1i | a bond | H | a bond | NH | O | a bond | T3h | OH |
| 319 | N | NMe | Q1i | a bond | H | a bond | NH | O | a bond | T3i | OH |
| 320 | N | NMe | Q1i | a bond | H | a bond | NH | O | a bond | T3j | OH |
| 321 | N | NMe | Q1j | a bond | Me | a bond | NH | S | NH | T3a | OH |
| 322 | N | NMe | Q1j | a bond | Me | a bond | NH | S | NH | T3b | OH |
| 323 | N | NMe | Q1j | a bond | Me | a bond | NH | S | NH | T3c | OH |
| 324 | N | NMe | Q1j | a bond | Me | a bond | NH | S | NH | T3d | OH |
| 325 | N | NMe | Q1j | a bond | Me | a bond | NH | S | NH | T3e | OH |
| 326 | N | NMe | Q1j | a bond | Me | a bond | NH | S | NH | T3f | OH |
| 327 | N | NMe | Q1j | a bond | Me | a bond | NH | S | NH | T3g | OH |
| 328 | N | NMe | Q1j | a bond | Me | a bond | NH | S | NH | T3h | OH |
| 329 | N | NMe | Q1j | a bond | Me | a bond | NH | S | NH | T3i | OH |
| 330 | N | NMe | Q1j | a bond | Me | a bond | NH | S | NH | T3j | OH |
| 331 | N | NMe | Q1j | a bond | Me | a bond | NH | S | a bond | T3a | OH |
| 332 | N | NMe | Q1j | a bond | Me | a bond | NH | S | a bond | T3b | OH |
| 333 | N | NMe | Q1j | a bond | Me | a bond | NH | S | a bond | T3c | OH |
| 334 | N | NMe | Q1j | a bond | Me | a bond | NH | S | a bond | T3d | OH |
| 335 | N | NMe | Q1j | a bond | Me | a bond | NH | S | a bond | T3e | OH |
| 336 | N | NMe | Q1j | a bond | Me | a bond | NH | S | a bond | T3f | OH |
| 337 | N | NMe | Q1j | a bond | Me | a bond | NH | S | a bond | T3g | OH |
| 338 | N | NMe | Q1j | a bond | Me | a bond | NH | S | a bond | T3h | OH |
| 339 | N | NMe | Q1j | a bond | Me | a bond | NH | S | a bond | T3i | OH |
| 340 | N | NMe | Q1j | a bond | Me | a bond | NH | S | a bond | T3j | OH |
| 341 | N | NMe | Q1j | a bond | Me | a bond | NH | O | NH | T3a | OH |
| 342 | N | NMe | Q1j | a bond | Me | a bond | NH | O | NH | T3b | OH |
| 343 | N | NMe | Q1j | a bond | Me | a bond | NH | O | NH | T3c | OH |
| 344 | N | NMe | Q1j | a bond | Me | a bond | NH | O | NH | T3d | OH |
| 345 | N | NMe | Q1j | a bond | Me | a bond | NH | O | NH | T3e | OH |
| 346 | N | NMe | Q1j | a bond | Me | a bond | NH | O | NH | T3f | OH |
| 347 | N | NMe | Q1j | a bond | Me | a bond | NH | O | NH | T3g | OH |
| 348 | N | NMe | Q1j | a bond | Me | a bond | NH | O | NH | T3h | OH |
| 349 | N | NMe | Q1j | a bond | Me | a bond | NH | O | NH | T3i | OH |
| 350 | N | NMe | Q1j | a bond | Me | a bond | NH | O | NH | T3j | OH |
| 351 | N | NMe | Q1j | a bond | Me | a bond | NH | O | a bond | T3a | OH |
| 352 | N | NMe | Q1j | a bond | Me | a bond | NH | O | a bond | T3b | OH |
| 353 | N | NMe | Q1j | a bond | Me | a bond | NH | O | a bond | T3c | OH |
| 354 | N | NMe | Q1j | a bond | Me | a bond | NH | O | a bond | T3d | OH |
| 355 | N | NMe | Q1j | a bond | Me | a bond | NH | O | a bond | T3e | OH |
| 356 | N | NMe | Q1j | a bond | Me | a bond | NH | O | a bond | T3f | OH |
| 357 | N | NMe | Q1j | a bond | Me | a bond | NH | O | a bond | T3g | OH |
| 358 | N | NMe | Q1j | a bond | Me | a bond | NH | O | a bond | T3h | OH |
| 359 | N | NMe | Q1j | a bond | Me | a bond | NH | O | a bond | T3i | OH |
| 360 | N | NMe | Q1j | a bond | Me | a bond | NH | O | a bond | T3j | OH |
| 361 | N | NMe | Q1j | a bond | H | a bond | NH | S | NH | T3a | OH |

TABLE 2-continued

| No | A | B | R¹ | L¹ | R² | L² | L³ | Y | L⁴ | R³ | X |
|---|---|---|---|---|---|---|---|---|---|---|---|
| 362 | N | NMe | Q1j | a bond | H | a bond | NH | S | NH | T3b | OH |
| 363 | N | NMe | Q1j | a bond | H | a bond | NH | S | NH | T3c | OH |
| 364 | N | NMe | Q1j | a bond | H | a bond | NH | S | NH | T3d | OH |
| 365 | N | NMe | Q1j | a bond | H | a bond | NH | S | NH | T3e | OH |
| 366 | N | NMe | Q1j | a bond | H | a bond | NH | S | NH | T3f | OH |
| 367 | N | NMe | Q1j | a bond | H | a bond | NH | S | NH | T3g | OH |
| 368 | N | NMe | Q1j | a bond | H | a bond | NH | S | NH | T3h | OH |
| 369 | N | NMe | Q1j | a bond | H | a bond | NH | S | NH | T3i | OH |
| 370 | N | NMe | Q1j | a bond | H | a bond | NH | S | NH | T3j | OH |
| 371 | N | NMe | Q1j | a bond | H | a bond | NH | S | a bond | T3a | OH |
| 372 | N | NMe | Q1j | a bond | H | a bond | NH | S | a bond | T3b | OH |
| 373 | N | NMe | Q1j | a bond | H | a bond | NH | S | a bond | T3c | OH |
| 374 | N | NMe | Q1j | a bond | H | a bond | NH | S | a bond | T3d | OH |
| 375 | N | NMe | Q1j | a bond | H | a bond | NH | S | a bond | T3e | OH |
| 376 | N | NMe | Q1j | a bond | H | a bond | NH | S | a bond | T3f | OH |
| 377 | N | NMe | Q1j | a bond | H | a bond | NH | S | a bond | T3g | OH |
| 378 | N | NMe | Q1j | a bond | H | a bond | NH | S | a bond | T3h | OH |
| 379 | N | NMe | Q1j | a bond | H | a bond | NH | S | a bond | T3i | OH |
| 380 | N | NMe | Q1j | a bond | H | a bond | NH | S | a bond | T3j | OH |
| 381 | N | NMe | Q1j | a bond | H | a bond | NH | O | NH | T3a | OH |
| 382 | N | NMe | Q1j | a bond | H | a bond | NH | O | NH | T3b | OH |
| 383 | N | NMe | Q1j | a bond | H | a bond | NH | O | NH | T3c | OH |
| 384 | N | NMe | Q1j | a bond | H | a bond | NH | O | NH | T3d | OH |
| 385 | N | NMe | Q1j | a bond | H | a bond | NH | O | NH | T3e | OH |
| 386 | N | NMe | Q1j | a bond | H | a bond | NH | O | NH | T3f | OH |
| 387 | N | NMe | Q1j | a bond | H | a bond | NH | O | NH | T3g | OH |
| 388 | N | NMe | Q1j | a bond | H | a bond | NH | O | NH | T3h | OH |
| 389 | N | NMe | Q1j | a bond | H | a bond | NH | O | NH | T3i | OH |
| 390 | N | NMe | Q1j | a bond | H | a bond | NH | O | NH | T3j | OH |
| 391 | N | NMe | Q1j | a bond | H | a bond | NH | O | a bond | T3a | OH |
| 392 | N | NMe | Q1j | a bond | H | a bond | NH | O | a bond | T3b | OH |
| 393 | N | NMe | Q1j | a bond | H | a bond | NH | O | a bond | T3c | OH |
| 394 | N | NMe | Q1j | a bond | H | a bond | NH | O | a bond | T3d | OH |
| 395 | N | NMe | Q1j | a bond | H | a bond | NH | O | a bond | T3e | OH |
| 396 | N | NMe | Q1j | a bond | H | a bond | NH | O | a bond | T3f | OH |
| 397 | N | NMe | Q1j | a bond | H | a bond | NH | O | a bond | T3g | OH |
| 398 | N | NMe | Q1j | a bond | H | a bond | NH | O | a bond | T3h | OH |
| 399 | N | NMe | Q1j | a bond | H | a bond | NH | O | a bond | T3i | OH |
| 400 | N | NMe | Q1j | a bond | H | a bond | NH | O | a bond | T3j | OH |
| 401 | N | S | Q1a | a bond | Me | a bond | NH | S | NH | T3a | OH |
| 402 | N | S | Q1a | a bond | Me | a bond | NH | S | NH | T3b | OH |
| 403 | N | S | Q1a | a bond | Me | a bond | NH | S | NH | T3c | OH |
| 404 | N | S | Q1a | a bond | Me | a bond | NH | S | NH | T3d | OH |
| 405 | N | S | Q1a | a bond | Me | a bond | NH | S | NH | T3e | OH |
| 406 | N | S | Q1a | a bond | Me | a bond | NH | S | NH | T3f | OH |
| 407 | N | S | Q1a | a bond | Me | a bond | NH | S | NH | T3g | OH |
| 408 | N | S | Q1a | a bond | Me | a bond | NH | S | NH | T3h | OH |
| 409 | N | S | Q1a | a bond | Me | a bond | NH | S | NH | T3i | OH |
| 410 | N | S | Q1a | a bond | Me | a bond | NH | S | NH | T3j | OH |
| 411 | N | S | Q1a | a bond | Me | a bond | NH | S | a bond | T3a | OH |
| 412 | N | S | Q1a | a bond | Me | a bond | NH | S | a bond | T3b | OH |
| 413 | N | S | Q1a | a bond | Me | a bond | NH | S | a bond | T3c | OH |
| 414 | N | S | Q1a | a bond | Me | a bond | NH | S | a bond | T3d | OH |
| 415 | N | S | Q1a | a bond | Me | a bond | NH | S | a bond | T3e | OH |
| 416 | N | S | Q1a | a bond | Me | a bond | NH | S | a bond | T3f | OH |
| 417 | N | S | Q1a | a bond | Me | a bond | NH | S | a bond | T3g | OH |
| 418 | N | S | Q1a | a bond | Me | a bond | NH | S | a bond | T3h | OH |
| 419 | N | S | Q1a | a bond | Me | a bond | NH | S | a bond | T3i | OH |
| 420 | N | S | Q1a | a bond | Me | a bond | NH | S | a bond | T3j | OH |
| 421 | N | S | Q1a | a bond | Me | a bond | NH | O | NH | T3a | OH |
| 422 | N | S | Q1a | a bond | Me | a bond | NH | O | NH | T3b | OH |
| 423 | N | S | Q1a | a bond | Me | a bond | NH | O | NH | T3c | OH |
| 424 | N | S | Q1a | a bond | Me | a bond | NH | O | NH | T3d | OH |
| 425 | N | S | Q1a | a bond | Me | a bond | NH | O | NH | T3e | OH |
| 426 | N | S | Q1a | a bond | Me | a bond | NH | O | NH | T3f | OH |
| 427 | N | S | Q1a | a bond | Me | a bond | NH | O | NH | T3g | OH |
| 428 | N | S | Q1a | a bond | Me | a bond | NH | O | NH | T3h | OH |
| 429 | N | S | Q1a | a bond | Me | a bond | NH | O | NH | T3i | OH |
| 430 | N | S | Q1a | a bond | Me | a bond | NH | O | NH | T3j | OH |
| 431 | N | S | Q1a | a bond | Me | a bond | NH | O | a bond | T3a | OH |
| 432 | N | S | Q1a | a bond | Me | a bond | NH | O | a bond | T3b | OH |
| 433 | N | S | Q1a | a bond | Me | a bond | NH | O | a bond | T3c | OH |
| 434 | N | S | Q1a | a bond | Me | a bond | NH | O | a bond | T3d | OH |
| 435 | N | S | Q1a | a bond | Me | a bond | NH | O | a bond | T3e | OH |
| 436 | N | S | Q1a | a bond | Me | a bond | NH | O | a bond | T3f | OH |
| 437 | N | S | Q1a | a bond | Me | a bond | NH | O | a bond | T3g | OH |
| 438 | N | S | Q1a | a bond | Me | a bond | NH | O | a bond | T3h | OH |
| 439 | N | S | Q1a | a bond | Me | a bond | NH | O | a bond | T3i | OH |

TABLE 2-continued

| No | A | B | R¹ | L¹ | R² | L² | L³ | Y | L⁴ | R³ | X |
|---|---|---|---|---|---|---|---|---|---|---|---|
| 440 | N | S | Q1a | a bond | Me | a bond | NH | O | a bond | T3j | OH |
| 441 | N | S | Q1a | a bond | H | a bond | NH | S | NH | T3a | OH |
| 442 | N | S | Q1a | a bond | H | a bond | NH | S | NH | T3b | OH |
| 443 | N | S | Q1a | a bond | H | a bond | NH | S | NH | T3c | OH |
| 444 | N | S | Q1a | a bond | H | a bond | NH | S | NH | T3d | OH |
| 445 | N | S | Q1a | a bond | H | a bond | NH | S | NH | T3e | OH |
| 446 | N | S | Q1a | a bond | H | a bond | NH | S | NH | T3f | OH |
| 447 | N | S | Q1a | a bond | H | a bond | NH | S | NH | T3g | OH |
| 448 | N | S | Q1a | a bond | H | a bond | NH | S | NH | T3h | OH |
| 449 | N | S | Q1a | a bond | H | a bond | NH | S | NH | T3i | OH |
| 450 | N | S | Q1a | a bond | H | a bond | NH | S | NH | T3j | OH |
| 451 | N | S | Q1a | a bond | H | a bond | NH | S | a bond | T3a | OH |
| 452 | N | S | Q1a | a bond | H | a bond | NH | S | a bond | T3b | OH |
| 453 | N | S | Q1a | a bond | H | a bond | NH | S | a bond | T3c | OH |
| 454 | N | S | Q1a | a bond | H | a bond | NH | S | a bond | T3d | OH |
| 455 | N | S | Q1a | a bond | H | a bond | NH | S | a bond | T3e | OH |
| 456 | N | S | Q1a | a bond | H | a bond | NH | S | a bond | T3f | OH |
| 457 | N | S | Q1a | a bond | H | a bond | NH | S | a bond | T3g | OH |
| 458 | N | S | Q1a | a bond | H | a bond | NH | S | a bond | T3h | OH |
| 459 | N | S | Q1a | a bond | H | a bond | NH | S | a bond | T3i | OH |
| 460 | N | S | Q1a | a bond | H | a bond | NH | S | a bond | T3j | OH |
| 461 | N | S | Q1a | a bond | H | a bond | NH | O | NH | T3a | OH |
| 462 | N | S | Q1a | a bond | H | a bond | NH | O | NH | T3b | OH |
| 463 | N | S | Q1a | a bond | H | a bond | NH | O | NH | T3c | OH |
| 464 | N | S | Q1a | a bond | H | a bond | NH | O | NH | T3d | OH |
| 465 | N | S | Q1a | a bond | H | a bond | NH | O | NH | T3e | OH |
| 466 | N | S | Q1a | a bond | H | a bond | NH | O | NH | T3f | OH |
| 467 | N | S | Q1a | a bond | H | a bond | NH | O | NH | T3g | OH |
| 468 | N | S | Q1a | a bond | H | a bond | NH | O | NH | T3h | OH |
| 469 | N | S | Q1a | a bond | H | a bond | NH | O | NH | T3i | OH |
| 470 | N | S | Q1a | a bond | H | a bond | NH | O | NH | T3j | OH |
| 471 | N | S | Q1a | a bond | H | a bond | NH | O | a bond | T3a | OH |
| 472 | N | S | Q1a | a bond | H | a bond | NH | O | a bond | T3b | OH |
| 473 | N | S | Q1a | a bond | H | a bond | NH | O | a bond | T3c | OH |
| 474 | N | S | Q1a | a bond | H | a bond | NH | O | a bond | T3d | OH |
| 475 | N | S | Q1a | a bond | H | a bond | NH | O | a bond | T3e | OH |
| 476 | N | S | Q1a | a bond | H | a bond | NH | O | a bond | T3f | OH |
| 477 | N | S | Q1a | a bond | H | a bond | NH | O | a bond | T3g | OH |
| 478 | N | S | Q1a | a bond | H | a bond | NH | O | a bond | T3h | OH |
| 479 | N | S | Q1a | a bond | H | a bond | NH | O | a bond | T3i | OH |
| 480 | N | S | Q1a | a bond | H | a bond | NH | O | a bond | T3j | OH |
| 481 | N | S | Q1b | a bond | Me | a bond | NH | S | NH | T3a | OH |
| 482 | N | S | Q1b | a bond | Me | a bond | NH | S | NH | T3b | OH |
| 483 | N | S | Q1b | a bond | Me | a bond | NH | S | NH | T3c | OH |
| 484 | N | S | Q1b | a bond | Me | a bond | NH | S | NH | T3d | OH |
| 485 | N | S | Q1b | a bond | Me | a bond | NH | S | NH | T3e | OH |
| 486 | N | S | Q1b | a bond | Me | a bond | NH | S | NH | T3f | OH |
| 487 | N | S | Q1b | a bond | Me | a bond | NH | S | NH | T3g | OH |
| 488 | N | S | Q1b | a bond | Me | a bond | NH | S | NH | T3h | OH |
| 489 | N | S | Q1b | a bond | Me | a bond | NH | S | NH | T3i | OH |
| 490 | N | S | Q1b | a bond | Me | a bond | NH | S | NH | T3j | OH |
| 491 | N | S | Q1b | a bond | Me | a bond | NH | S | a bond | T3a | OH |
| 492 | N | S | Q1b | a bond | Me | a bond | NH | S | a bond | T3b | OH |
| 493 | N | S | Q1b | a bond | Me | a bond | NH | S | a bond | T3c | OH |
| 494 | N | S | Q1b | a bond | Me | a bond | NH | S | a bond | T3d | OH |
| 495 | N | S | Q1b | a bond | Me | a bond | NH | S | a bond | T3e | OH |
| 496 | N | S | Q1b | a bond | Me | a bond | NH | S | a bond | T3f | OH |
| 497 | N | S | Q1b | a bond | Me | a bond | NH | S | a bond | T3g | OH |
| 498 | N | S | Q1b | a bond | Me | a bond | NH | S | a bond | T3h | OH |
| 499 | N | S | Q1b | a bond | Me | a bond | NH | S | a bond | T3i | OH |
| 500 | N | S | Q1b | a bond | Me | a bond | NH | S | a bond | T3j | OH |
| 501 | N | S | Q1b | a bond | Me | a bond | NH | O | NH | T3a | OH |
| 502 | N | S | Q1b | a bond | Me | a bond | NH | O | NH | T3b | OH |
| 503 | N | S | Q1b | a bond | Me | a bond | NH | O | NH | T3c | OH |
| 504 | N | S | Q1b | a bond | Me | a bond | NH | O | NH | T3d | OH |
| 505 | N | S | Q1b | a bond | Me | a bond | NH | O | NH | T3e | OH |
| 506 | N | S | Q1b | a bond | Me | a bond | NH | O | NH | T3f | OH |
| 507 | N | S | Q1b | a bond | Me | a bond | NH | O | NH | T3g | OH |
| 508 | N | S | Q1b | a bond | Me | a bond | NH | O | NH | T3h | OH |
| 509 | N | S | Q1b | a bond | Me | a bond | NH | O | NH | T3i | OH |
| 510 | N | S | Q1b | a bond | Me | a bond | NH | O | NH | T3j | OH |
| 511 | N | S | Q1b | a bond | Me | a bond | NH | O | a bond | T3a | OH |
| 512 | N | S | Q1b | a bond | Me | a bond | NH | O | a bond | T3b | OH |
| 513 | N | S | Q1b | a bond | Me | a bond | NH | O | a bond | T3c | OH |
| 514 | N | S | Q1b | a bond | Me | a bond | NH | O | a bond | T3d | OH |
| 515 | N | S | Q1b | a bond | Me | a bond | NH | O | a bond | T3e | OH |
| 516 | N | S | Q1b | a bond | Me | a bond | NH | O | a bond | T3f | OH |
| 517 | N | S | Q1b | a bond | Me | a bond | NH | O | a bond | T3g | OH |

TABLE 2-continued

| No | A | B | R¹ | L¹ | R² | L² | L³ | Y | L⁴ | R³ | X |
|---|---|---|---|---|---|---|---|---|---|---|---|
| 518 | N | S | Q1b | a bond | Me | a bond | NH | O | a bond | T3h | OH |
| 519 | N | S | Q1b | a bond | Me | a bond | NH | O | a bond | T3i | OH |
| 520 | N | S | Q1b | a bond | Me | a bond | NH | O | a bond | T3j | OH |
| 521 | N | S | Q1b | a bond | H | a bond | NH | S | NH | T3a | OH |
| 522 | N | S | Q1b | a bond | H | a bond | NH | S | NH | T3b | OH |
| 523 | N | S | Q1b | a bond | H | a bond | NH | S | NH | T3c | OH |
| 524 | N | S | Q1b | a bond | H | a bond | NH | S | NH | T3d | OH |
| 525 | N | S | Q1b | a bond | H | a bond | NH | S | NH | T3e | OH |
| 526 | N | S | Q1b | a bond | H | a bond | NH | S | NH | T3f | OH |
| 527 | N | S | Q1b | a bond | H | a bond | NH | S | NH | T3g | OH |
| 528 | N | S | Q1b | a bond | H | a bond | NH | S | NH | T3h | OH |
| 529 | N | S | Q1b | a bond | H | a bond | NH | S | NH | T3i | OH |
| 530 | N | S | Q1b | a bond | H | a bond | NH | S | NH | T3j | OH |
| 531 | N | S | Q1b | a bond | H | a bond | NH | S | a bond | T3a | OH |
| 532 | N | S | Q1b | a bond | H | a bond | NH | S | a bond | T3b | OH |
| 533 | N | S | Q1b | a bond | H | a bond | NH | S | a bond | T3c | OH |
| 534 | N | S | Q1b | a bond | H | a bond | NH | S | a bond | T3d | OH |
| 535 | N | S | Q1b | a bond | H | a bond | NH | S | a bond | T3e | OH |
| 536 | N | S | Q1b | a bond | H | a bond | NH | S | a bond | T3f | OH |
| 537 | N | S | Q1b | a bond | H | a bond | NH | S | a bond | T3g | OH |
| 538 | N | S | Q1b | a bond | H | a bond | NH | S | a bond | T3h | OH |
| 539 | N | S | Q1b | a bond | H | a bond | NH | S | a bond | T3i | OH |
| 540 | N | S | Q1b | a bond | H | a bond | NH | S | a bond | T3j | OH |
| 541 | N | S | Q1b | a bond | H | a bond | NH | O | NH | T3a | OH |
| 542 | N | S | Q1b | a bond | H | a bond | NH | O | NH | T3b | OH |
| 543 | N | S | Q1b | a bond | H | a bond | NH | O | NH | T3c | OH |
| 544 | N | S | Q1b | a bond | H | a bond | NH | O | NH | T3d | OH |
| 545 | N | S | Q1b | a bond | H | a bond | NH | O | NH | T3e | OH |
| 546 | N | S | Q1b | a bond | H | a bond | NH | O | NH | T3f | OH |
| 547 | N | S | Q1b | a bond | H | a bond | NH | O | NH | T3g | OH |
| 548 | N | S | Q1b | a bond | H | a bond | NH | O | NH | T3h | OH |
| 549 | N | S | Q1b | a bond | H | a bond | NH | O | NH | T3i | OH |
| 550 | N | S | Q1b | a bond | H | a bond | NH | O | NH | T3j | OH |
| 551 | N | S | Q1b | a bond | H | a bond | NH | O | a bond | T3a | OH |
| 552 | N | S | Q1b | a bond | H | a bond | NH | O | a bond | T3b | OH |
| 553 | N | S | Q1b | a bond | H | a bond | NH | O | a bond | T3c | OH |
| 554 | N | S | Q1b | a bond | H | a bond | NH | O | a bond | T3d | OH |
| 555 | N | S | Q1b | a bond | H | a bond | NH | O | a bond | T3e | OH |
| 556 | N | S | Q1b | a bond | H | a bond | NH | O | a bond | T3f | OH |
| 557 | N | S | Q1b | a bond | H | a bond | NH | O | a bond | T3g | OH |
| 558 | N | S | Q1b | a bond | H | a bond | NH | O | a bond | T3h | OH |
| 559 | N | S | Q1b | a bond | H | a bond | NH | O | a bond | T3i | OH |
| 560 | N | S | Q1b | a bond | H | a bond | NH | O | a bond | T3j | OH |
| 561 | N | S | Q1c | a bond | Me | a bond | NH | S | NH | T3a | OH |
| 562 | N | S | Q1c | a bond | Me | a bond | NH | S | NH | T3b | OH |
| 563 | N | S | Q1c | a bond | Me | a bond | NH | S | NH | T3c | OH |
| 564 | N | S | Q1c | a bond | Me | a bond | NH | S | NH | T3d | OH |
| 565 | N | S | Q1c | a bond | Me | a bond | NH | S | NH | T3e | OH |
| 566 | N | S | Q1c | a bond | Me | a bond | NH | S | NH | T3f | OH |
| 567 | N | S | Q1c | a bond | Me | a bond | NH | S | NH | T3g | OH |
| 568 | N | S | Q1c | a bond | Me | a bond | NH | S | NH | T3h | OH |
| 569 | N | S | Q1c | a bond | Me | a bond | NH | S | NH | T3i | OH |
| 570 | N | S | Q1c | a bond | Me | a bond | NH | S | NH | T3j | OH |
| 571 | N | S | Q1c | a bond | Me | a bond | NH | S | a bond | T3a | OH |
| 572 | N | S | Q1c | a bond | Me | a bond | NH | S | a bond | T3b | OH |
| 573 | N | S | Q1c | a bond | Me | a bond | NH | S | a bond | T3c | OH |
| 574 | N | S | Q1c | a bond | Me | a bond | NH | S | a bond | T3d | OH |
| 575 | N | S | Q1c | a bond | Me | a bond | NH | S | a bond | T3e | OH |
| 576 | N | S | Q1c | a bond | Me | a bond | NH | S | a bond | T3f | OH |
| 577 | N | S | Q1c | a bond | Me | a bond | NH | S | a bond | T3g | OH |
| 578 | N | S | Q1c | a bond | Me | a bond | NH | S | a bond | T3h | OH |
| 579 | N | S | Q1c | a bond | Me | a bond | NH | S | a bond | T3i | OH |
| 580 | N | S | Q1c | a bond | Me | a bond | NH | S | a bond | T3j | OH |
| 581 | N | S | Q1c | a bond | Me | a bond | NH | O | NH | T3a | OH |
| 582 | N | S | Q1c | a bond | Me | a bond | NH | O | NH | T3b | OH |
| 583 | N | S | Q1c | a bond | Me | a bond | NH | O | NH | T3c | OH |
| 584 | N | S | Q1c | a bond | Me | a bond | NH | O | NH | T3d | OH |
| 585 | N | S | Q1c | a bond | Me | a bond | NH | O | NH | T3e | OH |
| 586 | N | S | Q1c | a bond | Me | a bond | NH | O | NH | T3f | OH |
| 587 | N | S | Q1c | a bond | Me | a bond | NH | O | NH | T3g | OH |
| 588 | N | S | Q1c | a bond | Me | a bond | NH | O | NH | T3h | OH |
| 589 | N | S | Q1c | a bond | Me | a bond | NH | O | NH | T3i | OH |
| 590 | N | S | Q1c | a bond | Me | a bond | NH | O | NH | T3j | OH |
| 591 | N | S | Q1c | a bond | Me | a bond | NH | O | a bond | T3a | OH |
| 592 | N | S | Q1c | a bond | Me | a bond | NH | O | a bond | T3b | OH |
| 593 | N | S | Q1c | a bond | Me | a bond | NH | O | a bond | T3c | OH |
| 594 | N | S | Q1c | a bond | Me | a bond | NH | O | a bond | T3d | OH |
| 595 | N | S | Q1c | a bond | Me | a bond | NH | O | a bond | T3e | OH |

TABLE 2-continued

| No | A | B | R¹ | L¹ | R² | L² | L³ | Y | L⁴ | R³ | X |
|---|---|---|---|---|---|---|---|---|---|---|---|
| 596 | N | S | Q1c | a bond | Me | a bond | NH | O | a bond | T3f | OH |
| 597 | N | S | Q1c | a bond | Me | a bond | NH | O | a bond | T3g | OH |
| 598 | N | S | Q1c | a bond | Me | a bond | NH | O | a bond | T3h | OH |
| 599 | N | S | Q1c | a bond | Me | a bond | NH | O | a bond | T3i | OH |
| 600 | N | S | Q1c | a bond | Me | a bond | NH | O | a bond | T3j | OH |
| 601 | N | S | Q1c | a bond | H | a bond | NH | S | NH | T3a | OH |
| 602 | N | S | Q1c | a bond | H | a bond | NH | S | NH | T3b | OH |
| 603 | N | S | Q1c | a bond | H | a bond | NH | S | NH | T3c | OH |
| 604 | N | S | Q1c | a bond | H | a bond | NH | S | NH | T3d | OH |
| 605 | N | S | Q1c | a bond | H | a bond | NH | S | NH | T3e | OH |
| 606 | N | S | Q1c | a bond | H | a bond | NH | S | NH | T3f | OH |
| 607 | N | S | Q1c | a bond | H | a bond | NH | S | NH | T3g | OH |
| 608 | N | S | Q1c | a bond | H | a bond | NH | S | NH | T3h | OH |
| 609 | N | S | Q1c | a bond | H | a bond | NH | S | NH | T3i | OH |
| 610 | N | S | Q1c | a bond | H | a bond | NH | S | NH | T3j | OH |
| 611 | N | S | Q1c | a bond | H | a bond | NH | S | a bond | T3a | OH |
| 612 | N | S | Q1c | a bond | H | a bond | NH | S | a bond | T3b | OH |
| 613 | N | S | Q1c | a bond | H | a bond | NH | S | a bond | T3c | OH |
| 614 | N | S | Q1c | a bond | H | a bond | NH | S | a bond | T3d | OH |
| 615 | N | S | Q1c | a bond | H | a bond | NH | S | a bond | T3e | OH |
| 616 | N | S | Q1c | a bond | H | a bond | NH | S | a bond | T3f | OH |
| 617 | N | S | Q1c | a bond | H | a bond | NH | S | a bond | T3g | OH |
| 618 | N | S | Q1c | a bond | H | a bond | NH | S | a bond | T3h | OH |
| 619 | N | S | Q1c | a bond | H | a bond | NH | S | a bond | T3i | OH |
| 620 | N | S | Q1c | a bond | H | a bond | NH | S | a bond | T3j | OH |
| 621 | N | S | Q1c | a bond | H | a bond | NH | O | NH | T3a | OH |
| 622 | N | S | Q1c | a bond | H | a bond | NH | O | NH | T3b | OH |
| 623 | N | S | Q1c | a bond | H | a bond | NH | O | NH | T3c | OH |
| 624 | N | S | Q1c | a bond | H | a bond | NH | O | NH | T3d | OH |
| 625 | N | S | Q1c | a bond | H | a bond | NH | O | NH | T3e | OH |
| 626 | N | S | Q1c | a bond | H | a bond | NH | O | NH | T3f | OH |
| 627 | N | S | Q1c | a bond | H | a bond | NH | O | NH | T3g | OH |
| 628 | N | S | Q1c | a bond | H | a bond | NH | O | NH | T3h | OH |
| 629 | N | S | Q1c | a bond | H | a bond | NH | O | NH | T3i | OH |
| 630 | N | S | Q1c | a bond | H | a bond | NH | O | NH | T3j | OH |
| 631 | N | S | Q1c | a bond | H | a bond | NH | O | a bond | T3a | OH |
| 632 | N | S | Q1c | a bond | H | a bond | NH | O | a bond | T3b | OH |
| 633 | N | S | Q1c | a bond | H | a bond | NH | O | a bond | T3c | OH |
| 634 | N | S | Q1c | a bond | H | a bond | NH | O | a bond | T3d | OH |
| 635 | N | S | Q1c | a bond | H | a bond | NH | O | a bond | T3e | OH |
| 636 | N | S | Q1c | a bond | H | a bond | NH | O | a bond | T3f | OH |
| 637 | N | S | Q1c | a bond | H | a bond | NH | O | a bond | T3g | OH |
| 638 | N | S | Q1c | a bond | H | a bond | NH | O | a bond | T3h | OH |
| 639 | N | S | Q1c | a bond | H | a bond | NH | O | a bond | T3i | OH |
| 640 | N | S | Q1c | a bond | H | a bond | NH | O | a bond | T3j | OH |
| 641 | N | S | Q1i | a bond | Me | a bond | NH | S | NH | T3a | OH |
| 642 | N | S | Q1i | a bond | Me | a bond | NH | S | NH | T3b | OH |
| 643 | N | S | Q1i | a bond | Me | a bond | NH | S | NH | T3c | OH |
| 644 | N | S | Q1i | a bond | Me | a bond | NH | S | NH | T3d | OH |
| 645 | N | S | Q1i | a bond | Me | a bond | NH | S | NH | T3e | OH |
| 646 | N | S | Q1i | a bond | Me | a bond | NH | S | NH | T3f | OH |
| 647 | N | S | Q1i | a bond | Me | a bond | NH | S | NH | T3g | OH |
| 648 | N | S | Q1i | a bond | Me | a bond | NH | S | NH | T3h | OH |
| 649 | N | S | Q1i | a bond | Me | a bond | NH | S | NH | T3i | OH |
| 650 | N | S | Q1i | a bond | Me | a bond | NH | S | NH | T3j | OH |
| 651 | N | S | Q1i | a bond | Me | a bond | NH | S | a bond | T3a | OH |
| 652 | N | S | Q1i | a bond | Me | a bond | NH | S | a bond | T3b | OH |
| 653 | N | S | Q1i | a bond | Me | a bond | NH | S | a bond | T3c | OH |
| 654 | N | S | Q1i | a bond | Me | a bond | NH | S | a bond | T3d | OH |
| 655 | N | S | Q1i | a bond | Me | a bond | NH | S | a bond | T3e | OH |
| 656 | N | S | Q1i | a bond | Me | a bond | NH | S | a bond | T3f | OH |
| 657 | N | S | Q1i | a bond | Me | a bond | NH | S | a bond | T3g | OH |
| 658 | N | S | Q1i | a bond | Me | a bond | NH | S | a bond | T3h | OH |
| 659 | N | S | Q1i | a bond | Me | a bond | NH | S | a bond | T3i | OH |
| 660 | N | S | Q1i | a bond | Me | a bond | NH | S | a bond | T3j | OH |
| 661 | N | S | Q1i | a bond | Me | a bond | NH | O | NH | T3a | OH |
| 662 | N | S | Q1i | a bond | Me | a bond | NH | O | NH | T3b | OH |
| 663 | N | S | Q1i | a bond | Me | a bond | NH | O | NH | T3c | OH |
| 664 | N | S | Q1i | a bond | Me | a bond | NH | O | NH | T3d | OH |
| 665 | N | S | Q1i | a bond | Me | a bond | NH | O | NH | T3e | OH |
| 666 | N | S | Q1i | a bond | Me | a bond | NH | O | NH | T3f | OH |
| 667 | N | S | Q1i | a bond | Me | a bond | NH | O | NH | T3g | OH |
| 668 | N | S | Q1i | a bond | Me | a bond | NH | O | NH | T3h | OH |
| 669 | N | S | Q1i | a bond | Me | a bond | NH | O | NH | T3i | OH |
| 670 | N | S | Q1i | a bond | Me | a bond | NH | O | NH | T3j | OH |
| 671 | N | S | Q1i | a bond | Me | a bond | NH | O | a bond | T3a | OH |
| 672 | N | S | Q1i | a bond | Me | a bond | NH | O | a bond | T3b | OH |
| 673 | N | S | Q1i | a bond | Me | a bond | NH | O | a bond | T3c | OH |

TABLE 2-continued

| No | A | B | R¹ | L¹ | R² | L² | L³ | Y | L⁴ | R³ | X |
|---|---|---|---|---|---|---|---|---|---|---|---|
| 674 | N | S | Q1i | a bond | Me | a bond | NH | O | a bond | T3d | OH |
| 675 | N | S | Q1i | a bond | Me | a bond | NH | O | a bond | T3e | OH |
| 676 | N | S | Q1i | a bond | Me | a bond | NH | O | a bond | T3f | OH |
| 677 | N | S | Q1i | a bond | Me | a bond | NH | O | a bond | T3g | OH |
| 678 | N | S | Q1i | a bond | Me | a bond | NH | O | a bond | T3h | OH |
| 679 | N | S | Q1i | a bond | Me | a bond | NH | O | a bond | T3i | OH |
| 680 | N | S | Q1i | a bond | Me | a bond | NH | O | a bond | T3j | OH |
| 681 | N | S | Q1i | a bond | H | a bond | NH | S | NH | T3a | OH |
| 682 | N | S | Q1i | a bond | H | a bond | NH | S | NH | T3b | OH |
| 683 | N | S | Q1i | a bond | H | a bond | NH | S | NH | T3c | OH |
| 684 | N | S | Q1i | a bond | H | a bond | NH | S | NH | T3d | OH |
| 685 | N | S | Q1i | a bond | H | a bond | NH | S | NH | T3e | OH |
| 686 | N | S | Q1i | a bond | H | a bond | NH | S | NH | T3f | OH |
| 687 | N | S | Q1i | a bond | H | a bond | NH | S | NH | T3g | OH |
| 688 | N | S | Q1i | a bond | H | a bond | NH | S | NH | T3h | OH |
| 689 | N | S | Q1i | a bond | H | a bond | NH | S | NH | T3i | OH |
| 690 | N | S | Q1i | a bond | H | a bond | NH | S | NH | T3j | OH |
| 691 | N | S | Q1i | a bond | H | a bond | NH | S | a bond | T3a | OH |
| 692 | N | S | Q1i | a bond | H | a bond | NH | S | a bond | T3b | OH |
| 693 | N | S | Q1i | a bond | H | a bond | NH | S | a bond | T3c | OH |
| 694 | N | S | Q1i | a bond | H | a bond | NH | S | a bond | T3d | OH |
| 695 | N | S | Q1i | a bond | H | a bond | NH | S | a bond | T3e | OH |
| 696 | N | S | Q1i | a bond | H | a bond | NH | S | a bond | T3f | OH |
| 697 | N | S | Q1i | a bond | H | a bond | NH | S | a bond | T3g | OH |
| 698 | N | S | Q1i | a bond | H | a bond | NH | S | a bond | T3h | OH |
| 699 | N | S | Q1i | a bond | H | a bond | NH | S | a bond | T3i | OH |
| 700 | N | S | Q1i | a bond | H | a bond | NH | S | a bond | T3j | OH |
| 701 | N | S | Q1i | a bond | H | a bond | NH | O | NH | T3a | OH |
| 702 | N | S | Q1i | a bond | H | a bond | NH | O | NH | T3b | OH |
| 703 | N | S | Q1i | a bond | H | a bond | NH | O | NH | T3c | OH |
| 704 | N | S | Q1i | a bond | H | a bond | NH | O | NH | T3d | OH |
| 705 | N | S | Q1i | a bond | H | a bond | NH | O | NH | T3e | OH |
| 706 | N | S | Q1i | a bond | H | a bond | NH | O | NH | T3f | OH |
| 707 | N | S | Q1i | a bond | H | a bond | NH | O | NH | T3g | OH |
| 708 | N | S | Q1i | a bond | H | a bond | NH | O | NH | T3h | OH |
| 709 | N | S | Q1i | a bond | H | a bond | NH | O | NH | T3i | OH |
| 710 | N | S | Q1i | a bond | H | a bond | NH | O | NH | T3j | OH |
| 711 | N | S | Q1i | a bond | H | a bond | NH | O | a bond | T3a | OH |
| 712 | N | S | Q1i | a bond | H | a bond | NH | O | a bond | T3b | OH |
| 713 | N | S | Q1i | a bond | H | a bond | NH | O | a bond | T3c | OH |
| 714 | N | S | Q1i | a bond | H | a bond | NH | O | a bond | T3d | OH |
| 715 | N | S | Q1i | a bond | H | a bond | NH | O | a bond | T3e | OH |
| 716 | N | S | Q1i | a bond | H | a bond | NH | O | a bond | T3f | OH |
| 717 | N | S | Q1i | a bond | H | a bond | NH | O | a bond | T3g | OH |
| 718 | N | S | Q1i | a bond | H | a bond | NH | O | a bond | T3h | OH |
| 719 | N | S | Q1i | a bond | H | a bond | NH | O | a bond | T3i | OH |
| 720 | N | S | Q1i | a bond | H | a bond | NH | O | a bond | T3j | OH |
| 721 | N | S | Q1j | a bond | Me | a bond | NH | S | NH | T3a | OH |
| 722 | N | S | Q1j | a bond | Me | a bond | NH | S | NH | T3b | OH |
| 723 | N | S | Q1j | a bond | Me | a bond | NH | S | NH | T3c | OH |
| 724 | N | S | Q1j | a bond | Me | a bond | NH | S | NH | T3d | OH |
| 725 | N | S | Q1j | a bond | Me | a bond | NH | S | NH | T3e | OH |
| 726 | N | S | Q1j | a bond | Me | a bond | NH | S | NH | T3f | OH |
| 727 | N | S | Q1j | a bond | Me | a bond | NH | S | NH | T3g | OH |
| 728 | N | S | Q1j | a bond | Me | a bond | NH | S | NH | T3h | OH |
| 729 | N | S | Q1j | a bond | Me | a bond | NH | S | NH | T3i | OH |
| 730 | N | S | Q1j | a bond | Me | a bond | NH | S | NH | T3j | OH |
| 731 | N | S | Q1j | a bond | Me | a bond | NH | S | a bond | T3a | OH |
| 732 | N | S | Q1j | a bond | Me | a bond | NH | S | a bond | T3b | OH |
| 733 | N | S | Q1j | a bond | Me | a bond | NH | S | a bond | T3c | OH |
| 734 | N | S | Q1j | a bond | Me | a bond | NH | S | a bond | T3d | OH |
| 735 | N | S | Q1j | a bond | Me | a bond | NH | S | a bond | T3e | OH |
| 736 | N | S | Q1j | a bond | Me | a bond | NH | S | a bond | T3f | OH |
| 737 | N | S | Q1j | a bond | Me | a bond | NH | S | a bond | T3g | OH |
| 738 | N | S | Q1j | a bond | Me | a bond | NH | S | a bond | T3h | OH |
| 739 | N | S | Q1j | a bond | Me | a bond | NH | S | a bond | T3i | OH |
| 740 | N | S | Q1j | a bond | Me | a bond | NH | S | a bond | T3j | OH |
| 741 | N | S | Q1j | a bond | Me | a bond | NH | O | NH | T3a | OH |
| 742 | N | S | Q1j | a bond | Me | a bond | NH | O | NH | T3b | OH |
| 743 | N | S | Q1j | a bond | Me | a bond | NH | O | NH | T3c | OH |
| 744 | N | S | Q1j | a bond | Me | a bond | NH | O | NH | T3d | OH |
| 745 | N | S | Q1j | a bond | Me | a bond | NH | O | NH | T3e | OH |
| 746 | N | S | Q1j | a bond | Me | a bond | NH | O | NH | T3f | OH |
| 747 | N | S | Q1j | a bond | Me | a bond | NH | O | NH | T3g | OH |
| 748 | N | S | Q1j | a bond | Me | a bond | NH | O | NH | T3h | OH |
| 749 | N | S | Q1j | a bond | Me | a bond | NH | O | NH | T3i | OH |
| 750 | N | S | Q1j | a bond | Me | a bond | NH | O | NH | T3j | OH |
| 751 | N | S | Q1j | a bond | Me | a bond | NH | O | a bond | T3a | OH |

TABLE 2-continued

| No | A | B | R¹ | L¹ | R² | L² | L³ | Y | L⁴ | R³ | X |
|---|---|---|---|---|---|---|---|---|---|---|---|
| 752 | N | S | Q1j | a bond | Me | a bond | NH | O | a bond | T3b | OH |
| 753 | N | S | Q1j | a bond | Me | a bond | NH | O | a bond | T3c | OH |
| 754 | N | S | Q1j | a bond | Me | a bond | NH | O | a bond | T3d | OH |
| 755 | N | S | Q1j | a bond | Me | a bond | NH | O | a bond | T3e | OH |
| 756 | N | S | Q1j | a bond | Me | a bond | NH | O | a bond | T3f | OH |
| 757 | N | S | Q1j | a bond | Me | a bond | NH | O | a bond | T3g | OH |
| 758 | N | S | Q1j | a bond | Me | a bond | NH | O | a bond | T3h | OH |
| 759 | N | S | Q1j | a bond | Me | a bond | NH | O | a bond | T3i | OH |
| 760 | N | S | Q1j | a bond | Me | a bond | NH | O | a bond | T3j | OH |
| 761 | N | S | Q1j | a bond | H | a bond | NH | S | NH | T3a | OH |
| 762 | N | S | Q1j | a bond | H | a bond | NH | S | NH | T3b | OH |
| 763 | N | S | Q1j | a bond | H | a bond | NH | S | NH | T3c | OH |
| 764 | N | S | Q1j | a bond | H | a bond | NH | S | NH | T3d | OH |
| 765 | N | S | Q1j | a bond | H | a bond | NH | S | NH | T3e | OH |
| 766 | N | S | Q1j | a bond | H | a bond | NH | S | NH | T3f | OH |
| 767 | N | S | Q1j | a bond | H | a bond | NH | S | NH | T3g | OH |
| 768 | N | S | Q1j | a bond | H | a bond | NH | S | NH | T3h | OH |
| 769 | N | S | Q1j | a bond | H | a bond | NH | S | NH | T3i | OH |
| 770 | N | S | Q1j | a bond | H | a bond | NH | S | NH | T3j | OH |
| 771 | N | S | Q1j | a bond | H | a bond | NH | S | a bond | T3a | OH |
| 772 | N | S | Q1j | a bond | H | a bond | NH | S | a bond | T3b | OH |
| 773 | N | S | Q1j | a bond | H | a bond | NH | S | a bond | T3c | OH |
| 774 | N | S | Q1j | a bond | H | a bond | NH | S | a bond | T3d | OH |
| 775 | N | S | Q1j | a bond | H | a bond | NH | S | a bond | T3e | OH |
| 776 | N | S | Q1j | a bond | H | a bond | NH | S | a bond | T3f | OH |
| 777 | N | S | Q1j | a bond | H | a bond | NH | S | a bond | T3g | OH |
| 778 | N | S | Q1j | a bond | H | a bond | NH | S | a bond | T3h | OH |
| 779 | N | S | Q1j | a bond | H | a bond | NH | S | a bond | T3i | OH |
| 780 | N | S | Q1j | a bond | H | a bond | NH | S | a bond | T3j | OH |
| 781 | N | S | Q1j | a bond | H | a bond | NH | O | NH | T3a | OH |
| 782 | N | S | Q1j | a bond | H | a bond | NH | O | NH | T3b | OH |
| 783 | N | S | Q1j | a bond | H | a bond | NH | O | NH | T3c | OH |
| 784 | N | S | Q1j | a bond | H | a bond | NH | O | NH | T3d | OH |
| 785 | N | S | Q1j | a bond | H | a bond | NH | O | NH | T3e | OH |
| 786 | N | S | Q1j | a bond | H | a bond | NH | O | NH | T3f | OH |
| 787 | N | S | Q1j | a bond | H | a bond | NH | O | NH | T3g | OH |
| 788 | N | S | Q1j | a bond | H | a bond | NH | O | NH | T3h | OH |
| 789 | N | S | Q1j | a bond | H | a bond | NH | O | NH | T3i | OH |
| 790 | N | S | Q1j | a bond | H | a bond | NH | O | NH | T3j | OH |
| 791 | N | S | Q1j | a bond | H | a bond | NH | O | a bond | T3a | OH |
| 792 | N | S | Q1j | a bond | H | a bond | NH | O | a bond | T3b | OH |
| 793 | N | S | Q1j | a bond | H | a bond | NH | O | a bond | T3c | OH |
| 794 | N | S | Q1j | a bond | H | a bond | NH | O | a bond | T3d | OH |
| 795 | N | S | Q1j | a bond | H | a bond | NH | O | a bond | T3e | OH |
| 796 | N | S | Q1j | a bond | H | a bond | NH | O | a bond | T3f | OH |
| 797 | N | S | Q1j | a bond | H | a bond | NH | O | a bond | T3g | OH |
| 798 | N | S | Q1j | a bond | H | a bond | NH | O | a bond | T3h | OH |
| 799 | N | S | Q1j | a bond | H | a bond | NH | O | a bond | T3i | OH |
| 800 | N | S | Q1j | a bond | H | a bond | NH | O | a bond | T3j | OH |
| 801 | N | O | Q1a | a bond | Me | a bond | NH | S | NH | T3a | OH |
| 802 | N | O | Q1a | a bond | Me | a bond | NH | S | NH | T3b | OH |
| 803 | N | O | Q1a | a bond | Me | a bond | NH | S | NH | T3c | OH |
| 804 | N | O | Q1a | a bond | Me | a bond | NH | S | NH | T3d | OH |
| 805 | N | O | Q1a | a bond | Me | a bond | NH | S | NH | T3e | OH |
| 806 | N | O | Q1a | a bond | Me | a bond | NH | S | NH | T3f | OH |
| 807 | N | O | Q1a | a bond | Me | a bond | NH | S | NH | T3g | OH |
| 808 | N | O | Q1a | a bond | Me | a bond | NH | S | NH | T3h | OH |
| 809 | N | O | Q1a | a bond | Me | a bond | NH | S | NH | T3i | OH |
| 810 | N | O | Q1a | a bond | Me | a bond | NH | S | NH | T3j | OH |
| 811 | N | O | Q1a | a bond | Me | a bond | NH | S | a bond | T3a | OH |
| 812 | N | O | Q1a | a bond | Me | a bond | NH | S | a bond | T3b | OH |
| 813 | N | O | Q1a | a bond | Me | a bond | NH | S | a bond | T3c | OH |
| 814 | N | O | Q1a | a bond | Me | a bond | NH | S | a bond | T3d | OH |
| 815 | N | O | Q1a | a bond | Me | a bond | NH | S | a bond | T3e | OH |
| 816 | N | O | Q1a | a bond | Me | a bond | NH | S | a bond | T3f | OH |
| 817 | N | O | Q1a | a bond | Me | a bond | NH | S | a bond | T3g | OH |
| 818 | N | O | Q1a | a bond | Me | a bond | NH | S | a bond | T3h | OH |
| 819 | N | O | Q1a | a bond | Me | a bond | NH | S | a bond | T3i | OH |
| 820 | N | O | Q1a | a bond | Me | a bond | NH | S | a bond | T3j | OH |
| 821 | N | O | Q1a | a bond | Me | a bond | NH | O | NH | T3a | OH |
| 822 | N | O | Q1a | a bond | Me | a bond | NH | O | NH | T3b | OH |
| 823 | N | O | Q1a | a bond | Me | a bond | NH | O | NH | T3c | OH |
| 824 | N | O | Q1a | a bond | Me | a bond | NH | O | NH | T3d | OH |
| 825 | N | O | Q1a | a bond | Me | a bond | NH | O | NH | T3e | OH |
| 826 | N | O | Q1a | a bond | Me | a bond | NH | O | NH | T3f | OH |
| 827 | N | O | Q1a | a bond | Me | a bond | NH | O | NH | T3g | OH |
| 828 | N | O | Q1a | a bond | Me | a bond | NH | O | NH | T3h | OH |
| 829 | N | O | Q1a | a bond | Me | a bond | NH | O | NH | T3i | OH |

TABLE 2-continued

| No | A | B | R¹ | L¹ | R² | L² | L³ | Y | L⁴ | R³ | X |
|---|---|---|---|---|---|---|---|---|---|---|---|
| 830 | N | O | Q1a | a bond | Me | a bond | NH | O | NH | T3j | OH |
| 831 | N | O | Q1a | a bond | Me | a bond | NH | O | a bond | T3a | OH |
| 832 | N | O | Q1a | a bond | Me | a bond | NH | O | a bond | T3b | OH |
| 833 | N | O | Q1a | a bond | Me | a bond | NH | O | a bond | T3c | OH |
| 834 | N | O | Q1a | a bond | Me | a bond | NH | O | a bond | T3d | OH |
| 835 | N | O | Q1a | a bond | Me | a bond | NH | O | a bond | T3e | OH |
| 836 | N | O | Q1a | a bond | Me | a bond | NH | O | a bond | T3f | OH |
| 837 | N | O | Q1a | a bond | Me | a bond | NH | O | a bond | T3g | OH |
| 838 | N | O | Q1a | a bond | Me | a bond | NH | O | a bond | T3h | OH |
| 839 | N | O | Q1a | a bond | Me | a bond | NH | O | a bond | T3i | OH |
| 840 | N | O | Q1a | a bond | Me | a bond | NH | O | a bond | T3j | OH |
| 841 | N | O | Q1a | a bond | H | a bond | NH | S | NH | T3a | OH |
| 842 | N | O | Q1a | a bond | H | a bond | NH | S | NH | T3b | OH |
| 843 | N | O | Q1a | a bond | H | a bond | NH | S | NH | T3c | OH |
| 844 | N | O | Q1a | a bond | H | a bond | NH | S | NH | T3d | OH |
| 845 | N | O | Q1a | a bond | H | a bond | NH | S | NH | T3e | OH |
| 846 | N | O | Q1a | a bond | H | a bond | NH | S | NH | T3f | OH |
| 847 | N | O | Q1a | a bond | H | a bond | NH | S | NH | T3g | OH |
| 848 | N | O | Q1a | a bond | H | a bond | NH | S | NH | T3h | OH |
| 849 | N | O | Q1a | a bond | H | a bond | NH | S | NH | T3i | OH |
| 850 | N | O | Q1a | a bond | H | a bond | NH | S | NH | T3j | OH |
| 851 | N | O | Q1a | a bond | H | a bond | NH | S | a bond | T3a | OH |
| 852 | N | O | Q1a | a bond | H | a bond | NH | S | a bond | T3b | OH |
| 853 | N | O | Q1a | a bond | H | a bond | NH | S | a bond | T3c | OH |
| 854 | N | O | Q1a | a bond | H | a bond | NH | S | a bond | T3d | OH |
| 855 | N | O | Q1a | a bond | H | a bond | NH | S | a bond | T3e | OH |
| 856 | N | O | Q1a | a bond | H | a bond | NH | S | a bond | T3f | OH |
| 857 | N | O | Q1a | a bond | H | a bond | NH | S | a bond | T3g | OH |
| 858 | N | O | Q1a | a bond | H | a bond | NH | S | a bond | T3h | OH |
| 859 | N | O | Q1a | a bond | H | a bond | NH | S | a bond | T3i | OH |
| 860 | N | O | Q1a | a bond | H | a bond | NH | S | a bond | T3j | OH |
| 861 | N | O | Q1a | a bond | H | a bond | NH | O | NH | T3a | OH |
| 862 | N | O | Q1a | a bond | H | a bond | NH | O | NH | T3b | OH |
| 863 | N | O | Q1a | a bond | H | a bond | NH | O | NH | T3c | OH |
| 864 | N | O | Q1a | a bond | H | a bond | NH | O | NH | T3d | OH |
| 865 | N | O | Q1a | a bond | H | a bond | NH | O | NH | T3e | OH |
| 866 | N | O | Q1a | a bond | H | a bond | NH | O | NH | T3f | OH |
| 867 | N | O | Q1a | a bond | H | a bond | NH | O | NH | T3g | OH |
| 868 | N | O | Q1a | a bond | H | a bond | NH | O | NH | T3h | OH |
| 869 | N | O | Q1a | a bond | H | a bond | NH | O | NH | T3i | OH |
| 870 | N | O | Q1a | a bond | H | a bond | NH | O | NH | T3j | OH |
| 871 | N | O | Q1a | a bond | H | a bond | NH | O | a bond | T3a | OH |
| 872 | N | O | Q1a | a bond | H | a bond | NH | O | a bond | T3b | OH |
| 873 | N | O | Q1a | a bond | H | a bond | NH | O | a bond | T3c | OH |
| 874 | N | O | Q1a | a bond | H | a bond | NH | O | a bond | T3d | OH |
| 875 | N | O | Q1a | a bond | H | a bond | NH | O | a bond | T3e | OH |
| 876 | N | O | Q1a | a bond | H | a bond | NH | O | a bond | T3f | OH |
| 877 | N | O | Q1a | a bond | H | a bond | NH | O | a bond | T3g | OH |
| 878 | N | O | Q1a | a bond | H | a bond | NH | O | a bond | T3h | OH |
| 879 | N | O | Q1a | a bond | H | a bond | NH | O | a bond | T3i | OH |
| 880 | N | O | Q1a | a bond | H | a bond | NH | O | a bond | T3j | OH |
| 881 | N | O | Q1b | a bond | Me | a bond | NH | S | NH | T3a | OH |
| 882 | N | O | Q1b | a bond | Me | a bond | NH | S | NH | T3b | OH |
| 883 | N | O | Q1b | a bond | Me | a bond | NH | S | NH | T3c | OH |
| 884 | N | O | Q1b | a bond | Me | a bond | NH | S | NH | T3d | OH |
| 885 | N | O | Q1b | a bond | Me | a bond | NH | S | NH | T3e | OH |
| 886 | N | O | Q1b | a bond | Me | a bond | NH | S | NH | T3f | OH |
| 887 | N | O | Q1b | a bond | Me | a bond | NH | S | NH | T3g | OH |
| 888 | N | O | Q1b | a bond | Me | a bond | NH | S | NH | T3h | OH |
| 889 | N | O | Q1b | a bond | Me | a bond | NH | S | NH | T3i | OH |
| 890 | N | O | Q1b | a bond | Me | a bond | NH | S | NH | T3j | OH |
| 891 | N | O | Q1b | a bond | Me | a bond | NH | S | a bond | T3a | OH |
| 892 | N | O | Q1b | a bond | Me | a bond | NH | S | a bond | T3b | OH |
| 893 | N | O | Q1b | a bond | Me | a bond | NH | S | a bond | T3c | OH |
| 894 | N | O | Q1b | a bond | Me | a bond | NH | S | a bond | T3d | OH |
| 895 | N | O | Q1b | a bond | Me | a bond | NH | S | a bond | T3e | OH |
| 896 | N | O | Q1b | a bond | Me | a bond | NH | S | a bond | T3f | OH |
| 897 | N | O | Q1b | a bond | Me | a bond | NH | S | a bond | T3g | OH |
| 898 | N | O | Q1b | a bond | Me | a bond | NH | S | a bond | T3h | OH |
| 899 | N | O | Q1b | a bond | Me | a bond | NH | S | a bond | T3i | OH |
| 900 | N | O | Q1b | a bond | Me | a bond | NH | S | a bond | T3j | OH |
| 901 | N | O | Q1b | a bond | Me | a bond | NH | O | NH | T3a | OH |
| 902 | N | O | Q1b | a bond | Me | a bond | NH | O | NH | T3b | OH |
| 903 | N | O | Q1b | a bond | Me | a bond | NH | O | NH | T3c | OH |
| 904 | N | O | Q1b | a bond | Me | a bond | NH | O | NH | T3d | OH |
| 905 | N | O | Q1b | a bond | Me | a bond | NH | O | NH | T3e | OH |
| 906 | N | O | Q1b | a bond | Me | a bond | NH | O | NH | T3f | OH |
| 907 | N | O | Q1b | a bond | Me | a bond | NH | O | NH | T3g | OH |

TABLE 2-continued

| No | A | B | R¹ | L¹ | R² | L² | L³ | Y | L⁴ | R³ | X |
|---|---|---|---|---|---|---|---|---|---|---|---|
| 908 | N | O | Q1b | a bond | Me | a bond | NH | O | NH | T3h | OH |
| 909 | N | O | Q1b | a bond | Me | a bond | NH | O | NH | T3i | OH |
| 910 | N | O | Q1b | a bond | Me | a bond | NH | O | NH | T3j | OH |
| 911 | N | O | Q1b | a bond | Me | a bond | NH | O | a bond | T3a | OH |
| 912 | N | O | Q1b | a bond | Me | a bond | NH | O | a bond | T3b | OH |
| 913 | N | O | Q1b | a bond | Me | a bond | NH | O | a bond | T3c | OH |
| 914 | N | O | Q1b | a bond | Me | a bond | NH | O | a bond | T3d | OH |
| 915 | N | O | Q1b | a bond | Me | a bond | NH | O | a bond | T3e | OH |
| 916 | N | O | Q1b | a bond | Me | a bond | NH | O | a bond | T3f | OH |
| 917 | N | O | Q1b | a bond | Me | a bond | NH | O | a bond | T3g | OH |
| 918 | N | O | Q1b | a bond | Me | a bond | NH | O | a bond | T3h | OH |
| 919 | N | O | Q1b | a bond | Me | a bond | NH | O | a bond | T3i | OH |
| 920 | N | O | Q1b | a bond | Me | a bond | NH | O | a bond | T3j | OH |
| 921 | N | O | Q1b | a bond | H | a bond | NH | S | NH | T3a | OH |
| 922 | N | O | Q1b | a bond | H | a bond | NH | S | NH | T3b | OH |
| 923 | N | O | Q1b | a bond | H | a bond | NH | S | NH | T3c | OH |
| 924 | N | O | Q1b | a bond | H | a bond | NH | S | NH | T3d | OH |
| 925 | N | O | Q1b | a bond | H | a bond | NH | S | NH | T3e | OH |
| 926 | N | O | Q1b | a bond | H | a bond | NH | S | NH | T3f | OH |
| 927 | N | O | Q1b | a bond | H | a bond | NH | S | NH | T3g | OH |
| 928 | N | O | Q1b | a bond | H | a bond | NH | S | NH | T3h | OH |
| 929 | N | O | Q1b | a bond | H | a bond | NH | S | NH | T3i | OH |
| 930 | N | O | Q1b | a bond | H | a bond | NH | S | NH | T3j | OH |
| 931 | N | O | Q1b | a bond | H | a bond | NH | S | a bond | T3a | OH |
| 932 | N | O | Q1b | a bond | H | a bond | NH | S | a bond | T3b | OH |
| 933 | N | O | Q1b | a bond | H | a bond | NH | S | a bond | T3c | OH |
| 934 | N | O | Q1b | a bond | H | a bond | NH | S | a bond | T3d | OH |
| 935 | N | O | Q1b | a bond | H | a bond | NH | S | a bond | T3e | OH |
| 936 | N | O | Q1b | a bond | H | a bond | NH | S | a bond | T3f | OH |
| 937 | N | O | Q1b | a bond | H | a bond | NH | S | a bond | T3g | OH |
| 938 | N | O | Q1b | a bond | H | a bond | NH | S | a bond | T3h | OH |
| 939 | N | O | Q1b | a bond | H | a bond | NH | S | a bond | T3i | OH |
| 940 | N | O | Q1b | a bond | H | a bond | NH | S | a bond | T3j | OH |
| 941 | N | O | Q1b | a bond | H | a bond | NH | O | NH | T3a | OH |
| 942 | N | O | Q1b | a bond | H | a bond | NH | O | NH | T3b | OH |
| 943 | N | O | Q1b | a bond | H | a bond | NH | O | NH | T3c | OH |
| 944 | N | O | Q1b | a bond | H | a bond | NH | O | NH | T3d | OH |
| 945 | N | O | Q1b | a bond | H | a bond | NH | O | NH | T3e | OH |
| 946 | N | O | Q1b | a bond | H | a bond | NH | O | NH | T3f | OH |
| 947 | N | O | Q1b | a bond | H | a bond | NH | O | NH | T3g | OH |
| 948 | N | O | Q1b | a bond | H | a bond | NH | O | NH | T3h | OH |
| 949 | N | O | Q1b | a bond | H | a bond | NH | O | NH | T3i | OH |
| 950 | N | O | Q1b | a bond | H | a bond | NH | O | NH | T3j | OH |
| 951 | N | O | Q1b | a bond | H | a bond | NH | O | a bond | T3a | OH |
| 952 | N | O | Q1b | a bond | H | a bond | NH | O | a bond | T3b | OH |
| 953 | N | O | Q1b | a bond | H | a bond | NH | O | a bond | T3c | OH |
| 954 | N | O | Q1b | a bond | H | a bond | NH | O | a bond | T3d | OH |
| 955 | N | O | Q1b | a bond | H | a bond | NH | O | a bond | T3e | OH |
| 956 | N | O | Q1b | a bond | H | a bond | NH | O | a bond | T3f | OH |
| 957 | N | O | Q1b | a bond | H | a bond | NH | O | a bond | T3g | OH |
| 958 | N | O | Q1b | a bond | H | a bond | NH | O | a bond | T3h | OH |
| 959 | N | O | Q1b | a bond | H | a bond | NH | O | a bond | T3i | OH |
| 960 | N | O | Q1b | a bond | H | a bond | NH | O | a bond | T3j | OH |
| 961 | N | O | Q1c | a bond | Me | a bond | NH | S | NH | T3a | OH |
| 962 | N | O | Q1c | a bond | Me | a bond | NH | S | NH | T3b | OH |
| 963 | N | O | Q1c | a bond | Me | a bond | NH | S | NH | T3c | OH |
| 964 | N | O | Q1c | a bond | Me | a bond | NH | S | NH | T3d | OH |
| 965 | N | O | Q1c | a bond | Me | a bond | NH | S | NH | T3e | OH |
| 966 | N | O | Q1c | a bond | Me | a bond | NH | S | NH | T3f | OH |
| 967 | N | O | Q1c | a bond | Me | a bond | NH | S | NH | T3g | OH |
| 968 | N | O | Q1c | a bond | Me | a bond | NH | S | NH | T3h | OH |
| 969 | N | O | Q1c | a bond | Me | a bond | NH | S | NH | T3i | OH |
| 970 | N | O | Q1c | a bond | Me | a bond | NH | S | NH | T3j | OH |
| 971 | N | O | Q1c | a bond | Me | a bond | NH | S | a bond | T3a | OH |
| 972 | N | O | Q1c | a bond | Me | a bond | NH | S | a bond | T3b | OH |
| 973 | N | O | Q1c | a bond | Me | a bond | NH | S | a bond | T3c | OH |
| 974 | N | O | Q1c | a bond | Me | a bond | NH | S | a bond | T3d | OH |
| 975 | N | O | Q1c | a bond | Me | a bond | NH | S | a bond | T3e | OH |
| 976 | N | O | Q1c | a bond | Me | a bond | NH | S | a bond | T3f | OH |
| 977 | N | O | Q1c | a bond | Me | a bond | NH | S | a bond | T3g | OH |
| 978 | N | O | Q1c | a bond | Me | a bond | NH | S | a bond | T3h | OH |
| 979 | N | O | Q1c | a bond | Me | a bond | NH | S | a bond | T3i | OH |
| 980 | N | O | Q1c | a bond | Me | a bond | NH | S | a bond | T3j | OH |
| 981 | N | O | Q1c | a bond | Me | a bond | NH | O | NH | T3a | OH |
| 982 | N | O | Q1c | a bond | Me | a bond | NH | O | NH | T3b | OH |
| 983 | N | O | Q1c | a bond | Me | a bond | NH | O | NH | T3c | OH |
| 984 | N | O | Q1c | a bond | Me | a bond | NH | O | NH | T3d | OH |
| 985 | N | O | Q1c | a bond | Me | a bond | NH | O | NH | T3e | OH |

TABLE 2-continued

| No | A | B | R¹ | L¹ | R² | L² | L³ | Y | L⁴ | R³ | X |
|---|---|---|---|---|---|---|---|---|---|---|---|
| 986 | N | O | Q1c | a bond | Me | a bond | NH | O | NH | T3f | OH |
| 987 | N | O | Q1c | a bond | Me | a bond | NH | O | NH | T3g | OH |
| 988 | N | O | Q1c | a bond | Me | a bond | NH | O | NH | T3h | OH |
| 989 | N | O | Q1c | a bond | Me | a bond | NH | O | NH | T3i | OH |
| 990 | N | O | Q1c | a bond | Me | a bond | NH | O | NH | T3j | OH |
| 991 | N | O | Q1c | a bond | Me | a bond | NH | O | a bond | T3a | OH |
| 992 | N | O | Q1c | a bond | Me | a bond | NH | O | a bond | T3b | OH |
| 993 | N | O | Q1c | a bond | Me | a bond | NH | O | a bond | T3c | OH |
| 994 | N | O | Q1c | a bond | Me | a bond | NH | O | a bond | T3d | OH |
| 995 | N | O | Q1c | a bond | Me | a bond | NH | O | a bond | T3e | OH |
| 996 | N | O | Q1c | a bond | Me | a bond | NH | O | a bond | T3f | OH |
| 997 | N | O | Q1c | a bond | Me | a bond | NH | O | a bond | T3g | OH |
| 998 | N | O | Q1c | a bond | Me | a bond | NH | O | a bond | T3h | OH |
| 999 | N | O | Q1c | a bond | Me | a bond | NH | O | a bond | T3i | OH |
| 1000 | N | O | Q1c | a bond | Me | a bond | NH | O | a bond | T3j | OH |
| 1001 | N | O | Q1c | a bond | H | a bond | NH | S | NH | T3a | OH |
| 1002 | N | O | Q1c | a bond | H | a bond | NH | S | NH | T3b | OH |
| 1003 | N | O | Q1c | a bond | H | a bond | NH | S | NH | T3c | OH |
| 1004 | N | O | Q1c | a bond | H | a bond | NH | S | NH | T3d | OH |
| 1005 | N | O | Q1c | a bond | H | a bond | H | S | NH | T3e | OH |
| 1006 | N | O | Q1c | a bond | H | a bond | NH | S | NH | T3f | OH |
| 1007 | N | O | Q1c | a bond | H | a bond | NH | S | NH | T3g | OH |
| 1008 | N | O | Q1c | a bond | H | a bond | NH | S | NH | T3h | OH |
| 1009 | N | O | Q1c | a bond | H | a bond | NH | S | NH | T3i | OH |
| 1010 | N | O | Q1c | a bond | H | a bond | NH | S | NH | T3j | OH |
| 1011 | N | O | Q1c | a bond | H | a bond | NH | S | a bond | T3a | OH |
| 1012 | N | O | Q1c | a bond | H | a bond | NH | S | a bond | T3b | OH |
| 1013 | N | O | Q1c | a bond | H | a bond | NH | S | a bond | T3c | OH |
| 1014 | N | O | Q1c | a bond | H | a bond | NH | S | a bond | T3d | OH |
| 1015 | N | O | Q1c | a bond | H | a bond | NH | S | a bond | T3e | OH |
| 1016 | N | O | Q1c | a bond | H | a bond | NH | S | a bond | T3f | OH |
| 1017 | N | O | Q1c | a bond | H | a bond | NH | S | a bond | T3g | OH |
| 1018 | N | O | Q1c | a bond | H | a bond | NH | S | a bond | T3h | OH |
| 1019 | N | O | Q1c | a bond | H | a bond | NH | S | a bond | T3i | OH |
| 1020 | N | O | Q1c | a bond | H | a bond | NH | S | a bond | T3j | OH |
| 1021 | N | O | Q1c | a bond | H | a bond | NH | O | H | T3a | OH |
| 1022 | N | O | Q1c | a bond | H | a bond | NH | O | NH | T3b | OH |
| 1023 | N | O | Q1c | a bond | H | a bond | NH | O | NH | T3c | OH |
| 1024 | N | O | Q1c | a bond | H | a bond | NH | O | NH | T3d | OH |
| 1025 | N | O | Q1c | a bond | H | a bond | NH | O | NH | T3e | OH |
| 1026 | N | O | Q1c | a bond | H | a bond | NH | O | NH | T3f | OH |
| 1027 | N | O | Q1c | a bond | H | a bond | NH | O | NH | T3g | OH |
| 1028 | N | O | Q1c | a bond | H | a bond | NH | O | NH | T3h | OH |
| 1029 | N | O | Q1c | a bond | H | a bond | NH | O | NH | T3i | OH |
| 1030 | N | O | Q1c | a bond | H | a bond | NH | O | NH | T3j | OH |
| 1031 | N | O | Q1c | a bond | H | a bond | NH | O | a bond | T3a | OH |
| 1032 | N | O | Q1c | a bond | H | a bond | NH | O | a bond | T3b | OH |
| 1033 | N | O | Q1c | a bond | H | a bond | NH | O | a bond | T3c | OH |
| 1034 | N | O | Q1c | a bond | H | a bond | NH | O | a bond | T3d | OH |
| 1035 | N | O | Q1c | a bond | H | a bond | NH | O | a bond | T3e | OH |
| 1036 | N | O | Q1c | a bond | H | a bond | NH | O | a bond | T3f | OH |
| 1037 | N | O | Q1c | a bond | H | a bond | NH | O | a bond | T3g | OH |
| 1038 | N | O | Q1c | a bond | H | a bond | NH | O | a bond | T3h | OH |
| 1039 | N | O | Q1c | a bond | H | a bond | NH | O | a bond | T3i | OH |
| 1040 | N | O | Q1c | a bond | H | a bond | NH | O | a bond | T3j | OH |
| 1041 | N | O | Q1i | a bond | Me | a bond | NH | S | NH | T3a | OH |
| 1042 | N | O | Q1i | a bond | Me | a bond | NH | S | NH | T3b | OH |
| 1043 | N | O | Q1i | a bond | Me | a bond | NH | S | NH | T3c | OH |
| 1044 | N | O | Q1i | a bond | Me | a bond | NH | S | NH | T3d | OH |
| 1045 | N | O | Q1i | a bond | Me | a bond | NH | S | NH | T3e | OH |
| 1046 | N | O | Q1i | a bond | Me | a bond | NH | S | NH | T3f | OH |
| 1047 | N | O | Q1i | a bond | Me | a bond | NH | S | NH | T3g | OH |
| 1048 | N | O | Q1i | a bond | Me | a bond | NH | S | NH | T3h | OH |
| 1049 | N | O | Q1i | a bond | Me | a bond | NH | S | NH | T3i | OH |
| 1050 | N | O | Q1i | a bond | Me | a bond | NH | S | NH | T3j | OH |
| 1051 | N | O | Q1i | a bond | Me | a bond | NH | S | a bond | T3a | OH |
| 1052 | N | O | Q1i | a bond | Me | a bond | NH | S | a bond | T3b | OH |
| 1053 | N | O | Q1i | a bond | Me | a bond | NH | S | a bond | T3c | OH |
| 1054 | N | O | Q1i | a bond | Me | a bond | NH | S | a bond | T3d | OH |
| 1055 | N | O | Q1i | a bond | Me | a bond | NH | S | a bond | T3e | OH |
| 1056 | N | O | Q1i | a bond | Me | a bond | NH | S | a bond | T3f | OH |
| 1057 | N | O | Q1i | a bond | Me | a bond | NH | S | a bond | T3g | OH |
| 1058 | N | O | Q1i | a bond | Me | a bond | NH | S | a bond | T3h | OH |
| 1059 | N | O | Q1i | a bond | Me | a bond | NH | S | a bond | T3i | OH |
| 1060 | N | O | Q1i | a bond | Me | a bond | NH | S | a bond | T3j | OH |
| 1061 | N | O | Q1i | a bond | Me | a bond | NH | O | NH | T3a | OH |
| 1062 | N | O | Q1i | a bond | Me | a bond | NH | O | NH | T3b | OH |
| 1063 | N | O | Q1i | a bond | Me | a bond | NH | O | NH | T3c | OH |

TABLE 2-continued

| No | A | B | R¹ | L¹ | R² | L² | L³ | Y | L⁴ | R³ | X |
|---|---|---|---|---|---|---|---|---|---|---|---|
| 1064 | N | O | Q1i | a bond | Me | a bond | NH | O | NH | T3d | OH |
| 1065 | N | O | Q1i | a bond | Me | a bond | NH | O | NH | T3e | OH |
| 1066 | N | O | Q1i | a bond | Me | a bond | NH | O | NH | T3f | OH |
| 1067 | N | O | Q1i | a bond | Me | a bond | NH | O | NH | T3g | OH |
| 1068 | N | O | Q1i | a bond | Me | a bond | NH | O | NH | T3h | OH |
| 1069 | N | O | Q1i | a bond | Me | a bond | NH | O | NH | T3i | OH |
| 1070 | N | O | Q1i | a bond | Me | a bond | NH | O | NH | T3j | OH |
| 1071 | N | O | Q1i | a bond | Me | a bond | NH | O | a bond | T3a | OH |
| 1072 | N | O | Q1i | a bond | Me | a bond | NH | O | a bond | T3b | OH |
| 1073 | N | O | Q1i | a bond | Me | a bond | NH | O | a bond | T3c | OH |
| 1074 | N | O | Q1i | a bond | Me | a bond | NH | O | a bond | T3d | OH |
| 1075 | N | O | Q1i | a bond | Me | a bond | NH | O | a bond | T3e | OH |
| 1076 | N | O | Q1i | a bond | Me | a bond | NH | O | a bond | T3f | OH |
| 1077 | N | O | Q1i | a bond | Me | a bond | NH | O | a bond | T3g | OH |
| 1078 | N | O | Q1i | a bond | Me | a bond | NH | O | a bond | T3h | OH |
| 1079 | N | O | Q1i | a bond | Me | a bond | NH | O | a bond | T3i | OH |
| 1080 | N | O | Q1i | a bond | Me | a bond | NH | O | a bond | T3j | OH |
| 1081 | N | O | Q1i | a bond | H | a bond | NH | S | NH | T3a | OH |
| 1082 | N | O | Q1i | a bond | H | a bond | NH | S | NH | T3b | OH |
| 1083 | N | O | Q1i | a bond | H | a bond | NH | S | NH | T3c | OH |
| 1084 | N | O | Q1i | a bond | H | a bond | NH | S | NH | T3d | OH |
| 1085 | N | O | Q1i | a bond | H | a bond | NH | S | NH | T3e | OH |
| 1086 | N | O | Q1i | a bond | H | a bond | NH | S | NH | T3f | OH |
| 1087 | N | O | Q1i | a bond | H | a bond | NH | S | NH | T3g | OH |
| 1088 | N | O | Q1i | a bond | H | a bond | NH | S | NH | T3h | OH |
| 1089 | N | O | Q1i | a bond | H | a bond | NH | S | NH | T3i | OH |
| 1090 | N | O | Q1i | a bond | H | a bond | NH | S | NH | T3j | OH |
| 1091 | N | O | Q1i | a bond | H | a bond | NH | S | a bond | T3a | OH |
| 1092 | N | O | Q1i | a bond | H | a bond | NH | S | a bond | T3b | OH |
| 1093 | N | O | Q1i | a bond | H | a bond | NH | S | a bond | T3c | OH |
| 1094 | N | O | Q1i | a bond | H | a bond | NH | S | a bond | T3d | OH |
| 1095 | N | O | Q1i | a bond | H | a bond | NH | S | a bond | T3e | OH |
| 1096 | N | O | Q1i | a bond | H | a bond | NH | S | a bond | T3f | OH |
| 1097 | N | O | Q1i | a bond | H | a bond | NH | S | a bond | T3g | OH |
| 1098 | N | O | Q1i | a bond | H | a bond | NH | S | a bond | T3h | OH |
| 1099 | N | O | Q1i | a bond | H | a bond | NH | S | a bond | T3i | OH |
| 1100 | N | O | Q1i | a bond | H | a bond | NH | S | a bond | T3j | OH |
| 1101 | N | O | Q1i | a bond | H | a bond | NH | O | NH | T3a | OH |
| 1102 | N | O | Q1i | a bond | H | a bond | NH | O | NH | T3b | OH |
| 1103 | N | O | Q1i | a bond | H | a bond | NH | O | NH | T3c | OH |
| 1104 | N | O | Q1i | a bond | H | a bond | NH | O | NH | T3d | OH |
| 1105 | N | O | Q1i | a bond | H | a bond | NH | O | NH | T3e | OH |
| 1106 | N | O | Q1i | a bond | H | a bond | NH | O | NH | T3f | OH |
| 1107 | N | O | Q1i | a bond | H | a bond | NH | O | NH | T3g | OH |
| 1108 | N | O | Q1i | a bond | H | a bond | NH | O | NH | T3h | OH |
| 1109 | N | O | Q1i | a bond | H | a bond | NH | O | NH | T3i | OH |
| 1110 | N | O | Q1i | a bond | H | a bond | NH | O | NH | T3j | OH |
| 1111 | N | O | Q1i | a bond | H | a bond | NH | O | a bond | T3a | OH |
| 1112 | N | O | Q1i | a bond | H | a bond | NH | O | a bond | T3b | OH |
| 1113 | N | O | Q1i | a bond | H | a bond | NH | O | a bond | T3c | OH |
| 1114 | N | O | Q1i | a bond | H | a bond | NH | O | a bond | T3d | OH |
| 1115 | N | O | Q1i | a bond | H | a bond | NH | O | a bond | T3e | OH |
| 1116 | N | O | Q1i | a bond | H | a bond | NH | O | a bond | T3f | OH |
| 1117 | N | O | Q1i | a bond | H | a bond | NH | O | a bond | T3g | OH |
| 1118 | N | O | Q1i | a bond | H | a bond | NH | O | a bond | T3h | OH |
| 1119 | N | O | Q1i | a bond | H | a bond | NH | O | a bond | T3i | OH |
| 1120 | N | O | Q1i | a bond | H | a bond | NH | O | a bond | T3j | OH |
| 1121 | N | O | Q1j | a bond | Me | a bond | NH | S | NH | T3a | OH |
| 1122 | N | O | Q1j | a bond | Me | a bond | NH | S | NH | T3b | OH |
| 1123 | N | O | Q1j | a bond | Me | a bond | NH | S | NH | T3c | OH |
| 1124 | N | O | Q1j | a bond | Me | a bond | NH | S | NH | T3d | OH |
| 1125 | N | O | Q1j | a bond | Me | a bond | NH | S | NH | T3e | OH |
| 1126 | N | O | Q1j | a bond | Me | a bond | NH | S | NH | T3f | OH |
| 1127 | N | O | Q1j | a bond | Me | a bond | NH | S | NH | T3g | OH |
| 1128 | N | O | Q1j | a bond | Me | a bond | NH | S | NH | T3h | OH |
| 1129 | N | O | Q1j | a bond | Me | a bond | NH | S | NH | T3i | OH |
| 1130 | N | O | Q1j | a bond | Me | a bond | NH | S | NH | T3j | OH |
| 1131 | N | O | Q1j | a bond | Me | a bond | NH | S | a bond | T3a | OH |
| 1132 | N | O | Q1j | a bond | Me | a bond | NH | S | a bond | T3b | OH |
| 1133 | N | O | Q1j | a bond | Me | a bond | NH | S | a bond | T3c | OH |
| 1134 | N | O | Q1j | a bond | Me | a bond | NH | S | a bond | T3d | OH |
| 1135 | N | O | Q1j | a bond | Me | a bond | NH | S | a bond | T3e | OH |
| 1136 | N | O | Q1j | a bond | Me | a bond | NH | S | a bond | T3f | OH |
| 1137 | N | O | Q1j | a bond | Me | a bond | NH | S | a bond | T3g | OH |
| 1138 | N | O | Q1j | a bond | Me | a bond | NH | S | a bond | T3h | OH |
| 1139 | N | O | Q1j | a bond | Me | a bond | NH | S | a bond | T3i | OH |
| 1140 | N | O | Q1j | a bond | Me | a bond | NH | S | a bond | T3j | OH |
| 1141 | N | O | Q1j | a bond | Me | a bond | NH | O | NH | T3a | OH |

TABLE 2-continued

| No | A | B | R¹ | L¹ | R² | L² | L³ | Y | L⁴ | R³ | X |
|---|---|---|---|---|---|---|---|---|---|---|---|
| 1142 | N | O | Q1j | a bond | Me | a bond | NH | O | NH | T3b | OH |
| 1143 | N | O | Q1j | a bond | Me | a bond | NH | O | NH | T3c | OH |
| 1144 | N | O | Q1j | a bond | Me | a bond | NH | O | NH | T3d | OH |
| 1145 | N | O | Q1j | a bond | Me | a bond | NH | O | NH | T3e | OH |
| 1146 | N | O | Q1j | a bond | Me | a bond | NH | O | NH | T3f | OH |
| 1147 | N | O | Q1j | a bond | Me | a bond | NH | O | NH | T3g | OH |
| 1148 | N | O | Q1j | a bond | Me | a bond | NH | O | NH | T3h | OH |
| 1149 | N | O | Q1j | a bond | Me | a bond | NH | O | NH | T3i | OH |
| 1150 | N | O | Q1i | a bond | Me | a bond | NH | O | NH | T3j | OH |
| 1151 | N | O | Q1j | a bond | Me | a bond | NH | O | a bond | T3a | OH |
| 1152 | N | O | Q1j | a bond | Me | a bond | NH | O | a bond | T3b | OH |
| 1153 | N | O | Q1j | a bond | Me | a bond | NH | O | a bond | T3c | OH |
| 1154 | N | O | Q1j | a bond | Me | a bond | NH | O | a bond | T3d | OH |
| 1155 | N | O | Q1j | a bond | Me | a bond | NH | O | a bond | T3e | OH |
| 1156 | N | O | Q1j | a bond | Me | a bond | NH | O | a bond | T3f | OH |
| 1157 | N | O | Q1j | a bond | Me | a bond | NH | O | a bond | T3g | OH |
| 1158 | N | O | Q1j | a bond | Me | a bond | NH | O | a bond | T3h | OH |
| 1159 | N | O | Q1j | a bond | Me | a bond | NH | O | a bond | T3i | OH |
| 1160 | N | O | Q1j | a bond | Me | a bond | NH | O | a bond | T3j | OH |
| 1161 | N | O | Q1j | a bond | H | a bond | NH | S | NH | T3a | OH |
| 1162 | N | O | Q1j | a bond | H | a bond | NH | S | NH | T3b | OH |
| 1163 | N | O | Q1j | a bond | H | a bond | NH | S | NH | T3c | OH |
| 1164 | N | O | Q1j | a bond | H | a bond | NH | S | NH | T3d | OH |
| 1165 | N | O | Q1j | a bond | H | a bond | NH | S | NH | T3e | OH |
| 1166 | N | O | Q1j | a bond | H | a bond | NH | S | NH | T3f | OH |
| 1167 | N | O | Q1j | a bond | H | a bond | NH | S | NH | T3g | OH |
| 1168 | N | O | Q1j | a bond | H | a bond | NH | S | NH | T3h | OH |
| 1169 | N | O | Q1j | a bond | H | a bond | NH | S | NH | T3i | OH |
| 1170 | N | O | Q1j | a bond | H | a bond | NH | S | NH | T3j | OH |
| 1171 | N | O | Q1j | a bond | H | a bond | NH | S | a bond | T3a | OH |
| 1172 | N | O | Q1j | a bond | H | a bond | NH | S | a bond | T3b | OH |
| 1173 | N | O | Q1j | a bond | H | a bond | NH | S | a bond | T3c | OH |
| 1174 | N | O | Q1j | a bond | H | a bond | NH | S | a bond | T3d | OH |
| 1175 | N | O | Q1j | a bond | H | a bond | NH | S | a bond | T3e | OH |
| 1176 | N | O | Q1j | a bond | H | a bond | NH | S | a bond | T3f | OH |
| 1177 | N | O | Q1j | a bond | H | a bond | NH | S | a bond | T3g | OH |
| 1178 | N | O | Q1j | a bond | H | a bond | NH | S | a bond | T3h | OH |
| 1179 | N | O | Q1j | a bond | H | a bond | NH | S | a bond | T3i | OH |
| 1180 | N | O | Q1j | a bond | H | a bond | NH | S | a bond | T3j | OH |
| 1181 | N | O | Q1j | a bond | H | a bond | NH | O | NH | T3a | OH |
| 1182 | N | O | Q1j | a bond | H | a bond | NH | O | NH | T3b | OH |
| 1183 | N | O | Q1j | a bond | H | a bond | NH | O | NH | T3c | OH |
| 1184 | N | O | Q1j | a bond | H | a bond | NH | O | NH | T3d | OH |
| 1185 | N | O | Q1j | a bond | H | a bond | NH | O | NH | T3e | OH |
| 1186 | N | O | Q1j | a bond | H | a bond | NH | O | NH | T3f | OH |
| 1187 | N | O | Q1j | a bond | H | a bond | NH | O | NH | T3g | OH |
| 1188 | N | O | Q1j | a bond | H | a bond | NH | O | NH | T3h | OH |
| 1189 | N | O | Q1j | a bond | H | a bond | NH | O | NH | T3i | OH |
| 1190 | N | O | Q1j | a bond | H | a bond | NH | O | NH | T3j | OH |
| 1191 | N | O | Q1j | a bond | H | a bond | NH | O | a bond | T3a | OH |
| 1192 | N | O | Q1j | a bond | H | a bond | NH | O | a bond | T3b | OH |
| 1193 | N | O | Q1j | a bond | H | a bond | NH | O | a bond | T3c | OH |
| 1194 | N | O | Q1j | a bond | H | a bond | NH | O | a bond | T3d | OH |
| 1195 | N | O | Q1j | a bond | H | a bond | NH | O | a bond | T3e | OH |
| 1196 | N | O | Q1j | a bond | H | a bond | NH | O | a bond | T3f | OH |
| 1197 | N | O | Q1j | a bond | H | a bond | NH | O | a bond | T3g | OH |
| 1198 | N | O | Q1j | a bond | H | a bond | NH | O | a bond | T3h | OH |
| 1199 | N | O | Q1j | a bond | H | a bond | NH | O | a bond | T3i | OH |
| 1200 | N | O | Q1j | a bond | H | a bond | NH | O | a bond | T3j | OH |
| 1201 | CH | NMe | Q1a | a bond | Me | a bond | NH | S | NH | T3a | OH |
| 1202 | CH | NMe | Q1a | a bond | Me | a bond | NH | S | NH | T3b | OH |
| 1203 | CH | NMe | Q1a | a bond | Me | a bond | NH | S | NH | T3c | OH |
| 1204 | CH | NMe | Q1a | a bond | Me | a bond | NH | S | NH | T3d | OH |
| 1205 | CH | NMe | Q1a | a bond | Me | a bond | NH | S | NH | T3e | OH |
| 1206 | CH | NMe | Q1a | a bond | Me | a bond | NH | S | NH | T3f | OH |
| 1207 | CH | NMe | Q1a | a bond | Me | a bond | NH | S | NH | T3g | OH |
| 1208 | CH | NMe | Q1a | a bond | Me | a bond | NH | S | NH | T3h | OH |
| 1209 | CH | NMe | Q1a | a bond | Me | a bond | NH | S | NH | T3i | OH |
| 1210 | CH | NMe | Q1a | a bond | Me | a bond | NH | S | NH | T3j | OH |
| 1211 | CH | NMe | Q1a | a bond | Me | a bond | NH | S | a bond | T3a | OH |
| 1212 | CH | NMe | Q1a | a bond | Me | a bond | NH | S | a bond | T3b | OH |
| 1213 | CH | NMe | Q1a | a bond | Me | a bond | NH | S | a bond | T3c | OH |
| 1214 | CH | NMe | Q1a | a bond | Me | a bond | NH | S | a bond | T3d | OH |
| 1215 | CH | NMe | Q1a | a bond | Me | a bond | NH | S | a bond | T3e | OH |
| 1216 | CH | NMe | Q1a | a bond | Me | a bond | NH | S | a bond | T3f | OH |
| 1217 | CH | NMe | Q1a | a bond | Me | a bond | NH | S | a bond | T3g | OH |
| 1218 | CH | NMe | Q1a | a bond | Me | a bond | NH | S | a bond | T3h | OH |
| 1219 | CH | NMe | Q1a | a bond | Me | a bond | NH | S | a bond | T3i | OH |

TABLE 2-continued

| No | A | B | R¹ | L¹ | R² | L² | L³ | Y | L⁴ | R³ | X |
|---|---|---|---|---|---|---|---|---|---|---|---|
| 1220 | CH | NMe | Q1a | a bond | Me | a bond | NH | S | a bond | T3j | OH |
| 1221 | CH | NMe | Q1a | a bond | Me | a bond | NH | O | NH | T3a | OH |
| 1222 | CH | NMe | Q1a | a bond | Me | a bond | NH | O | NH | T3b | OH |
| 1223 | CH | NMe | Q1a | a bond | Me | a bond | NH | O | NH | T3c | OH |
| 1224 | CH | NMe | Q1a | a bond | Me | a bond | NH | O | NH | T3d | OH |
| 1225 | CH | NMe | Q1a | a bond | Me | a bond | NH | O | NH | T3e | OH |
| 1226 | CH | NMe | Q1a | a bond | Me | a bond | NH | O | NH | T3f | OH |
| 1227 | CH | NMe | Q1a | a bond | Me | a bond | NH | O | NH | T3g | OH |
| 1228 | CH | NMe | Q1a | a bond | Me | a bond | NH | O | NH | T3h | OH |
| 1229 | CH | NMe | Q1a | a bond | Me | a bond | NH | O | NH | T3i | OH |
| 1230 | CH | NMe | Q1a | a bond | Me | a bond | NH | O | NH | T3j | OH |
| 1231 | CH | NMe | Q1a | a bond | Me | a bond | NH | O | a bond | T3a | OH |
| 1232 | CH | NMe | Q1a | a bond | Me | a bond | NH | O | a bond | T3b | OH |
| 1233 | CH | NMe | Q1a | a bond | Me | a bond | NH | O | a bond | T3c | OH |
| 1234 | CH | NMe | Q1a | a bond | Me | a bond | NH | O | a bond | T3d | OH |
| 1235 | CH | NMe | Q1a | a bond | Me | a bond | NH | O | a bond | T3e | OH |
| 1236 | CH | NMe | Q1a | a bond | Me | a bond | NH | O | a bond | T3f | OH |
| 1237 | CH | NMe | Q1a | a bond | Me | a bond | NH | O | a bond | T3g | OH |
| 1238 | CH | NMe | Q1a | a bond | Me | a bond | NH | O | a bond | T3h | OH |
| 1239 | CH | NMe | Q1a | a bond | Me | a bond | NH | O | a bond | T3i | OH |
| 1240 | CH | NMe | Q1a | a bond | Me | a bond | NH | O | a bond | T3j | OH |
| 1241 | CH | NMe | Q1a | a bond | H | a bond | NH | S | NH | T3a | OH |
| 1242 | CH | NMe | Q1a | a bond | H | a bond | NH | S | NH | T3b | OH |
| 1243 | CH | NMe | Q1a | a bond | H | a bond | NH | S | NH | T3c | OH |
| 1244 | CH | NMe | Q1a | a bond | H | a bond | NH | S | NH | T3d | OH |
| 1245 | CH | NMe | Q1a | a bond | H | a bond | NH | S | NH | T3e | OH |
| 1246 | CH | NMe | Q1a | a bond | H | a bond | NH | S | NH | T3f | OH |
| 1247 | CH | NMe | Q1a | a bond | H | a bond | NH | S | NH | T3g | OH |
| 1248 | CH | NMe | Q1a | a bond | H | a bond | NH | S | NH | T3h | OH |
| 1249 | CH | NMe | Q1a | a bond | H | a bond | NH | S | NH | T3i | OH |
| 1250 | CH | NMe | Q1a | a bond | H | a bond | NH | S | NH | T3j | OH |
| 1251 | CH | NMe | Q1a | a bond | H | a bond | NH | S | a bond | T3a | OH |
| 1252 | CH | NMe | Q1a | a bond | H | a bond | NH | S | a bond | T3b | OH |
| 1253 | CH | NMe | Q1a | a bond | H | a bond | NH | S | a bond | T3c | OH |
| 1254 | CH | NMe | Q1a | a bond | H | a bond | NH | S | a bond | T3d | OH |
| 1255 | CH | NMe | Q1a | a bond | H | a bond | NH | S | a bond | T3e | OH |
| 1256 | CH | NMe | Q1a | a bond | H | a bond | NH | S | a bond | T3f | OH |
| 1257 | CH | NMe | Q1a | a bond | H | a bond | NH | S | a bond | T3g | OH |
| 1258 | CH | NMe | Q1a | a bond | H | a bond | NH | S | a bond | T3h | OH |
| 1259 | CH | NMe | Q1a | a bond | H | a bond | NH | S | a bond | T3i | OH |
| 1260 | CH | NMe | Q1a | a bond | H | a bond | NH | S | a bond | T3j | OH |
| 1261 | CH | NMe | Q1a | a bond | H | a bond | NH | O | NH | T3a | OH |
| 1262 | CH | NMe | Q1a | a bond | H | a bond | NH | O | NH | T3b | OH |
| 1263 | CH | NMe | Q1a | a bond | H | a bond | NH | O | NH | T3c | OH |
| 1264 | CH | NMe | Q1a | a bond | H | a bond | NH | O | NH | T3d | OH |
| 1265 | CH | NMe | Q1a | a bond | H | a bond | NH | O | NH | T3e | OH |
| 1266 | CH | NMe | Q1a | a bond | H | a bond | NH | O | NH | T3f | OH |
| 1267 | CH | NMe | Q1a | a bond | H | a bond | NH | O | NH | T3g | OH |
| 1268 | CH | NMe | Q1a | a bond | H | a bond | NH | O | NH | T3h | OH |
| 1269 | CH | NMe | Q1a | a bond | H | a bond | NH | O | NH | T3i | OH |
| 1270 | CH | NMe | Q1a | a bond | H | a bond | NH | O | NH | T3j | OH |
| 1271 | CH | NMe | Q1a | a bond | H | a bond | NH | O | a bond | T3a | OH |
| 1272 | CH | NMe | Q1a | a bond | H | a bond | NH | O | a bond | T3b | OH |
| 1273 | CH | NMe | Q1a | a bond | H | a bond | NH | O | a bond | T3c | OH |
| 1274 | CH | NMe | Q1a | a bond | H | a bond | NH | O | a bond | T3d | OH |
| 1275 | CH | NMe | Q1a | a bond | H | a bond | NH | O | a bond | T3e | OH |
| 1276 | CH | NMe | Q1a | a bond | H | a bond | NH | O | a bond | T3f | OH |
| 1277 | CH | NMe | Q1a | a bond | H | a bond | NH | O | a bond | T3g | OH |
| 1278 | CH | NMe | Q1a | a bond | H | a bond | NH | O | a bond | T3h | OH |
| 1279 | CH | NMe | Q1a | a bond | H | a bond | NH | O | a bond | T3i | OH |
| 1280 | CH | NMe | Q1a | a bond | H | a bond | NH | O | a bond | T3j | OH |
| 1281 | CH | NMe | Q1b | a bond | Me | a bond | NH | S | NH | T3a | OH |
| 1282 | CH | NMe | Q1b | a bond | Me | a bond | NH | S | NH | T3b | OH |
| 1283 | CH | NMe | Q1b | a bond | Me | a bond | NH | S | NH | T3c | OH |
| 1284 | CH | NMe | Q1b | a bond | Me | a bond | NH | S | NH | T3d | OH |
| 1285 | CH | NMe | Q1b | a bond | Me | a bond | NH | S | NH | T3e | OH |
| 1286 | CH | NMe | Q1b | a bond | Me | a bond | NH | S | NH | T3f | OH |
| 1287 | CH | NMe | Q1b | a bond | Me | a bond | NH | S | NH | T3g | OH |
| 1288 | CH | NMe | Q1b | a bond | Me | a bond | NH | S | NH | T3h | OH |
| 1289 | CH | NMe | Q1b | a bond | Me | a bond | NH | S | NH | T3i | OH |
| 1290 | CH | NMe | Q1b | a bond | Me | a bond | NH | S | NH | T3j | OH |
| 1291 | CH | NMe | Q1b | a bond | Me | a bond | NH | S | a bond | T3a | OH |
| 1292 | CH | NMe | Q1b | a bond | Me | a bond | NH | S | a bond | T3b | OH |
| 1293 | CH | NMe | Q1b | a bond | Me | a bond | NH | S | a bond | T3c | OH |
| 1294 | CH | NMe | Q1b | a bond | Me | a bond | NH | S | a bond | T3d | OH |
| 1295 | CH | NMe | Q1b | a bond | Me | a bond | NH | S | a bond | T3e | OH |
| 1296 | CH | NMe | Q1b | a bond | Me | a bond | NH | S | a bond | T3f | OH |
| 1297 | CH | NMe | Q1b | a bond | Me | a bond | NH | S | a bond | T3g | OH |

TABLE 2-continued

| No | A | B | R¹ | L¹ | R² | L² | L³ | Y | L⁴ | R³ | X |
|---|---|---|---|---|---|---|---|---|---|---|---|
| 1298 | CH | NMe | Q1b | a bond | Me | a bond | NH | S | a bond | T3h | OH |
| 1299 | CH | NMe | Q1b | a bond | Me | a bond | NH | S | a bond | T3i | OH |
| 1300 | CH | NMe | Q1b | a bond | Me | a bond | NH | S | a bond | T3j | OH |
| 1301 | CH | NMe | Q1b | a bond | Me | a bond | NH | O | NH | T3a | OH |
| 1302 | CH | NMe | Q1b | a bond | Me | a bond | NH | O | NH | T3b | OH |
| 1303 | CH | NMe | Q1b | a bond | Me | a bond | NH | O | NH | T3c | OH |
| 1304 | CH | NMe | Q1b | a bond | Me | a bond | NH | O | NH | T3d | OH |
| 1305 | CH | NMe | Q1b | a bond | Me | a bond | NH | O | NH | T3e | OH |
| 1306 | CH | NMe | Q1b | a bond | Me | a bond | NH | O | NH | T3f | OH |
| 1307 | CH | NMe | Q1b | a bond | Me | a bond | NH | O | NH | T3g | OH |
| 1308 | CH | NMe | Q1b | a bond | Me | a bond | NH | O | NH | T3h | OH |
| 1309 | CH | NMe | Q1b | a bond | Me | a bond | NH | O | NH | T3i | OH |
| 1310 | CH | NMe | Q1b | a bond | Me | a bond | NH | O | NH | T3j | OH |
| 1311 | CH | NMe | Q1b | a bond | Me | a bond | NH | O | a bond | T3a | OH |
| 1312 | CH | NMe | Q1b | a bond | Me | a bond | NH | O | a bond | T3b | OH |
| 1313 | CH | NMe | Q1b | a bond | Me | a bond | NH | O | a bond | T3c | OH |
| 1314 | CH | NMe | Q1b | a bond | Me | a bond | NH | O | a bond | T3d | OH |
| 1315 | CH | NMe | Q1b | a bond | Me | a bond | NH | O | a bond | T3e | OH |
| 1316 | CH | NMe | Q1b | a bond | Me | a bond | NH | O | a bond | T3f | OH |
| 1317 | CH | NMe | Q1b | a bond | Me | a bond | NH | O | a bond | T3g | OH |
| 1318 | CH | NMe | Q1b | a bond | Me | a bond | NH | O | a bond | T3h | OH |
| 1319 | CH | NMe | Q1b | a bond | Me | a bond | NH | O | a bond | T3i | OH |
| 1320 | CH | NMe | Q1b | a bond | Me | a bond | NH | O | a bond | T3j | OH |
| 1321 | CH | NMe | Q1b | a bond | H | a bond | NH | S | NH | T3a | OH |
| 1322 | CH | NMe | Q1b | a bond | H | a bond | NH | S | NH | T3b | OH |
| 1323 | CH | NMe | Q1b | a bond | H | a bond | NH | S | NH | T3c | OH |
| 1324 | CH | NMe | Q1b | a bond | H | a bond | NH | S | NH | T3d | OH |
| 1325 | CH | NMe | Q1b | a bond | H | a bond | NH | S | NH | T3e | OH |
| 1326 | CH | NMe | Q1b | a bond | H | a bond | NH | S | NH | T3f | OH |
| 1327 | CH | NMe | Q1b | a bond | H | a bond | NH | S | NH | T3g | OH |
| 1328 | CH | NMe | Q1b | a bond | H | a bond | NH | S | NH | T3h | OH |
| 1329 | CH | NMe | Q1b | a bond | H | a bond | NH | S | NH | T3i | OH |
| 1330 | CH | NMe | Q1b | a bond | H | a bond | NH | S | NH | T3j | OH |
| 1331 | CH | NMe | Q1b | a bond | H | a bond | NH | S | a bond | T3a | OH |
| 1332 | CH | NMe | Q1b | a bond | H | a bond | NH | S | a bond | T3b | OH |
| 1333 | CH | NMe | Q1b | a bond | H | a bond | NH | S | a bond | T3c | OH |
| 1334 | CH | NMe | Q1b | a bond | H | a bond | NH | S | a bond | T3d | OH |
| 1335 | CH | NMe | Q1b | a bond | H | a bond | NH | S | a bond | T3e | OH |
| 1336 | CH | NMe | Q1b | a bond | H | a bond | NH | S | a bond | T3f | OH |
| 1337 | CH | NMe | Q1b | a bond | H | a bond | NH | S | a bond | T3g | OH |
| 1338 | CH | NMe | Q1b | a bond | H | a bond | NH | S | a bond | T3h | OH |
| 1339 | CH | NMe | Q1b | a bond | H | a bond | NH | S | a bond | T3i | OH |
| 1340 | CH | NMe | Q1b | a bond | H | a bond | NH | S | a bond | T3j | OH |
| 1341 | CH | NMe | Q1b | a bond | H | a bond | NH | O | NH | T3a | OH |
| 1342 | CH | NMe | Q1b | a bond | H | a bond | NH | O | NH | T3b | OH |
| 1343 | CH | NMe | Q1b | a bond | H | a bond | NH | O | NH | T3c | OH |
| 1344 | CH | NMe | Q1b | a bond | H | a bond | NH | O | NH | T3d | OH |
| 1345 | CH | NMe | Q1b | a bond | H | a bond | NH | O | NH | T3e | OH |
| 1346 | CH | NMe | Q1b | a bond | H | a bond | NH | O | NH | T3f | OH |
| 1347 | CH | NMe | Q1b | a bond | H | a bond | NH | O | NH | T3g | OH |
| 1348 | CH | NMe | Q1b | a bond | H | a bond | NH | O | NH | T3h | OH |
| 1349 | CH | NMe | Q1b | a bond | H | a bond | NH | O | NH | T3i | OH |
| 1350 | CH | NMe | Q1b | a bond | H | a bond | NH | O | NH | T3j | OH |
| 1351 | CH | NMe | Q1b | a bond | H | a bond | NH | O | a bond | T3a | OH |
| 1352 | CH | NMe | Q1b | a bond | H | a bond | NH | O | a bond | T3b | OH |
| 1353 | CH | NMe | Q1b | a bond | H | a bond | NH | O | a bond | T3c | OH |
| 1354 | CH | NMe | Q1b | a bond | H | a bond | NH | O | a bond | T3d | OH |
| 1355 | CH | NMe | Q1b | a bond | H | a bond | NH | O | a bond | T3e | OH |
| 1356 | CH | NMe | Q1b | a bond | H | a bond | NH | O | a bond | T3f | OH |
| 1357 | CH | NMe | Q1b | a bond | H | a bond | NH | O | a bond | T3g | OH |
| 1358 | CH | NMe | Q1b | a bond | H | a bond | NH | O | a bond | T3h | OH |
| 1359 | CH | NMe | Q1b | a bond | H | a bond | NH | O | a bond | T3i | OH |
| 1360 | CH | NMe | Q1b | a bond | H | a bond | NH | O | a bond | T3j | OH |
| 1361 | CH | NMe | Q1c | a bond | Me | a bond | NH | S | NH | T3a | OH |
| 1362 | CH | NMe | Q1c | a bond | Me | a bond | NH | S | NH | T3b | OH |
| 1363 | CH | NMe | Q1c | a bond | Me | a bond | NH | S | NH | T3c | OH |
| 1364 | CH | NMe | Q1c | a bond | Me | a bond | NH | S | NH | T3d | OH |
| 1365 | CH | NMe | Q1c | a bond | Me | a bond | NH | S | NH | T3e | OH |
| 1366 | CH | NMe | Q1c | a bond | Me | a bond | NH | S | NH | T3f | OH |
| 1367 | CH | NMe | Q1c | a bond | Me | a bond | NH | S | NH | T3g | OH |
| 1368 | CH | NMe | Q1c | a bond | Me | a bond | NH | S | NH | T3h | OH |
| 1369 | CH | NMe | Q1c | a bond | Me | a bond | NH | S | NH | T3i | OH |
| 1370 | CH | NMe | Q1c | a bond | Me | a bond | NH | S | NH | T3j | OH |
| 1371 | CH | NMe | Q1c | a bond | Me | a bond | NH | S | a bond | T3a | OH |
| 1372 | CH | NMe | Q1c | a bond | Me | a bond | NH | S | a bond | T3b | OH |
| 1373 | CH | NMe | Q1c | a bond | Me | a bond | NH | S | a bond | T3c | OH |
| 1374 | CH | NMe | Q1c | a bond | Me | a bond | NH | S | a bond | T3d | OH |
| 1375 | CH | NMe | Q1c | a bond | Me | a bond | NH | S | a bond | T3e | OH |

TABLE 2-continued

| No | A | B | R¹ | L¹ | R² | L² | L³ | Y | L⁴ | R³ | X |
|---|---|---|---|---|---|---|---|---|---|---|---|
| 1376 | CH | NMe | Q1c | a bond | Me | a bond | NH | S | a bond | T3f | OH |
| 1377 | CH | NMe | Q1c | a bond | Me | a bond | NH | S | a bond | T3g | OH |
| 1378 | CH | NMe | Q1c | a bond | Me | a bond | NH | S | a bond | T3h | OH |
| 1379 | CH | NMe | Q1c | a bond | Me | a bond | NH | S | a bond | T3i | OH |
| 1380 | CH | NMe | Q1c | a bond | Me | a bond | NH | S | a bond | T3j | OH |
| 1381 | CH | NMe | Q1c | a bond | Me | a bond | NH | O | NH | T3a | OH |
| 1382 | CH | NMe | Q1c | a bond | Me | a bond | NH | O | NH | T3b | OH |
| 1383 | CH | NMe | Q1c | a bond | Me | a bond | NH | O | NH | T3c | OH |
| 1384 | CH | NMe | Q1c | a bond | Me | a bond | NH | O | NH | T3d | OH |
| 1385 | CH | NMe | Q1c | a bond | Me | a bond | NH | O | NH | T3e | OH |
| 1386 | CH | NMe | Q1c | a bond | Me | a bond | NH | O | NH | T3f | OH |
| 1387 | CH | NMe | Q1c | a bond | Me | a bond | NH | O | NH | T3g | OH |
| 1388 | CH | NMe | Q1c | a bond | Me | a bond | NH | O | NH | T3h | OH |
| 1389 | CH | NMe | Q1c | a bond | Me | a bond | NH | O | NH | T3i | OH |
| 1390 | CH | NMe | Q1c | a bond | Me | a bond | NH | O | NH | T3j | OH |
| 1391 | CH | NMe | Q1c | a bond | Me | a bond | NH | O | a bond | T3a | OH |
| 1392 | CH | NMe | Q1c | a bond | Me | a bond | NH | O | a bond | T3b | OH |
| 1393 | CH | NMe | Q1c | a bond | Me | a bond | NH | O | a bond | T3c | OH |
| 1394 | CH | NMe | Q1c | a bond | Me | a bond | NH | O | a bond | T3d | OH |
| 1395 | CH | NMe | Q1c | a bond | Me | a bond | NH | O | a bond | T3e | OH |
| 1396 | CH | NMe | Q1c | a bond | Me | a bond | NH | O | a bond | T3f | OH |
| 1397 | CH | NMe | Q1c | a bond | Me | a bond | NH | O | a bond | T3g | OH |
| 1398 | CH | NMe | Q1c | a bond | Me | a bond | NH | O | a bond | T3h | OH |
| 1399 | CH | NMe | Q1c | a bond | Me | a bond | NH | O | a bond | T3i | OH |
| 1400 | CH | NMe | Q1c | a bond | Me | a bond | NH | O | a bond | T3j | OH |
| 1401 | CH | NMe | Q1c | a bond | H | a bond | NH | S | NH | T3a | OH |
| 1402 | CH | NMe | Q1c | a bond | H | a bond | NH | S | NH | T3b | OH |
| 1403 | CH | NMe | Q1c | a bond | H | a bond | NH | S | NH | T3c | OH |
| 1404 | CH | NMe | Q1c | a bond | H | a bond | NH | S | NH | T3d | OH |
| 1405 | CH | NMe | Q1c | a bond | H | a bond | NH | S | NH | T3e | OH |
| 1406 | CH | NMe | Q1c | a bond | H | a bond | NH | S | NH | T3f | OH |
| 1407 | CH | NMe | Q1c | a bond | H | a bond | NH | S | NH | T3g | OH |
| 1408 | CH | NMe | Q1c | a bond | H | a bond | NH | S | NH | T3h | OH |
| 1409 | CH | NMe | Q1c | a bond | H | a bond | NH | S | NH | T3i | OH |
| 1410 | CH | NMe | Q1c | a bond | H | a bond | NH | S | NH | T3j | OH |
| 1411 | CH | NMe | Q1c | a bond | H | a bond | NH | S | a bond | T3a | OH |
| 1412 | CH | NMe | Q1c | a bond | H | a bond | NH | S | a bond | T3b | OH |
| 1413 | CH | NMe | Q1c | a bond | H | a bond | NH | S | a bond | T3c | OH |
| 1414 | CH | NMe | Q1c | a bond | H | a bond | NH | S | a bond | T3d | OH |
| 1415 | CH | NMe | Q1c | a bond | H | a bond | NH | S | a bond | T3e | OH |
| 1416 | CH | NMe | Q1c | a bond | H | a bond | NH | S | a bond | T3f | OH |
| 1417 | CH | NMe | Q1c | a bond | H | a bond | NH | S | a bond | T3g | OH |
| 1418 | CH | NMe | Q1c | a bond | H | a bond | NH | S | a bond | T3h | OH |
| 1419 | CH | NMe | Q1c | a bond | H | a bond | NH | S | a bond | T3i | OH |
| 1420 | CH | NMe | Q1c | a bond | H | a bond | NH | S | a bond | T3j | OH |
| 1421 | CH | NMe | Q1c | a bond | H | a bond | NH | O | NH | T3a | OH |
| 1422 | CH | NMe | Q1c | a bond | H | a bond | NH | O | NH | T3b | OH |
| 1423 | CH | NMe | Q1c | a bond | H | a bond | NH | O | NH | T3c | OH |
| 1424 | CH | NMe | Q1c | a bond | H | a bond | NH | O | NH | T3d | OH |
| 1425 | CH | NMe | Q1c | a bond | H | a bond | NH | O | NH | T3e | OH |
| 1426 | CH | NMe | Q1c | a bond | H | a bond | NH | O | NH | T3f | OH |
| 1427 | CH | NMe | Q1c | a bond | H | a bond | NH | O | NH | T3g | OH |
| 1428 | CH | NMe | Q1c | a bond | H | a bond | NH | O | NH | T3h | OH |
| 1429 | CH | NMe | Q1c | a bond | H | a bond | NH | O | NH | T3i | OH |
| 1430 | CH | NMe | Q1c | a bond | H | a bond | NH | O | NH | T3j | OH |
| 1431 | CH | NMe | Q1c | a bond | H | a bond | NH | O | a bond | T3a | OH |
| 1432 | CH | NMe | Q1c | a bond | H | a bond | NH | O | a bond | T3b | OH |
| 1433 | CH | NMe | Q1c | a bond | H | a bond | NH | O | a bond | T3c | OH |
| 1434 | CH | NMe | Q1c | a bond | H | a bond | NH | O | a bond | T3d | OH |
| 1435 | CH | NMe | Q1c | a bond | H | a bond | NH | O | a bond | T3e | OH |
| 1436 | CH | NMe | Q1c | a bond | H | a bond | NH | O | a bond | T3f | OH |
| 1437 | CH | NMe | Q1c | a bond | H | a bond | NH | O | a bond | T3g | OH |
| 1438 | CH | NMe | Q1c | a bond | H | a bond | NH | O | a bond | T3h | OH |
| 1439 | CH | NMe | Q1c | a bond | H | a bond | NH | O | a bond | T3i | OH |
| 1440 | CH | NMe | Q1c | a bond | H | a bond | NH | O | a bond | T3j | OH |
| 1441 | CH | NMe | Q1i | a bond | Me | a bond | NH | S | NH | T3a | OH |
| 1442 | CH | NMe | Q1i | a bond | Me | a bond | NH | S | NH | T3b | OH |
| 1443 | CH | NMe | Q1i | a bond | Me | a bond | NH | S | NH | T3c | OH |
| 1444 | CH | NMe | Q1i | a bond | Me | a bond | NH | S | NH | T3d | OH |
| 1445 | CH | NMe | Q1i | a bond | Me | a bond | NH | S | NH | T3e | OH |
| 1446 | CH | NMe | Q1i | a bond | Me | a bond | NH | S | NH | T3f | OH |
| 1447 | CH | NMe | Q1i | a bond | Me | a bond | NH | S | NH | T3g | OH |
| 1448 | CH | NMe | Q1i | a bond | Me | a bond | NH | S | NH | T3h | OH |
| 1449 | CH | NMe | Q1i | a bond | Me | a bond | NH | S | NH | T3i | OH |
| 1450 | CH | NMe | Q1i | a bond | Me | a bond | NH | S | NH | T3j | OH |
| 1451 | CH | NMe | Q1i | a bond | Me | a bond | NH | S | a bond | T3a | OH |
| 1452 | CH | NMe | Q1i | a bond | Me | a bond | NH | S | a bond | T3b | OH |
| 1453 | CH | NMe | Q1i | a bond | Me | a bond | NH | S | a bond | T3c | OH |

TABLE 2-continued

| No | A | B | R¹ | L¹ | R² | L² | L³ | Y | L⁴ | R³ | X |
|---|---|---|---|---|---|---|---|---|---|---|---|
| 1454 | CH | NMe | Q1i | a bond | Me | a bond | NH | S | a bond | T3d | OH |
| 1455 | CH | NMe | Q1i | a bond | Me | a bond | NH | S | a bond | T3e | OH |
| 1456 | CH | NMe | Q1i | a bond | Me | a bond | NH | S | a bond | T3f | OH |
| 1457 | CH | NMe | Q1i | a bond | Me | a bond | NH | S | a bond | T3g | OH |
| 1458 | CH | NMe | Q1i | a bond | Me | a bond | NH | S | a bond | T3h | OH |
| 1459 | CH | NMe | Q1i | a bond | Me | a bond | NH | S | a bond | T3i | OH |
| 1460 | CH | NMe | Q1i | a bond | Me | a bond | NH | S | a bond | T3j | OH |
| 1461 | CH | NMe | Q1i | a bond | Me | a bond | NH | O | NH | T3a | OH |
| 1462 | CH | NMe | Q1i | a bond | Me | a bond | NH | O | NH | T3b | OH |
| 1463 | CH | NMe | Q1i | a bond | Me | a bond | NH | O | NH | T3c | OH |
| 1464 | CH | NMe | Q1i | a bond | Me | a bond | NH | O | NH | T3d | OH |
| 1465 | CH | NMe | Q1i | a bond | Me | a bond | NH | O | NH | T3e | OH |
| 1466 | CH | NMe | Q1i | a bond | Me | a bond | NH | O | NH | T3f | OH |
| 1467 | CH | NMe | Q1i | a bond | Me | a bond | NH | O | NH | T3g | OH |
| 1468 | CH | NMe | Q1i | a bond | Me | a bond | NH | O | NH | T3h | OH |
| 1469 | CH | NMe | Q1i | a bond | Me | a bond | NH | O | NH | T3i | OH |
| 1470 | CH | NMe | Q1i | a bond | Me | a bond | NH | O | NH | T3j | OH |
| 1471 | CH | NMe | Q1i | a bond | Me | a bond | NH | O | a bond | T3a | OH |
| 1472 | CH | NMe | Q1i | a bond | Me | a bond | NH | O | a bond | T3b | OH |
| 1473 | CH | NMe | Q1i | a bond | Me | a bond | NH | O | a bond | T3c | OH |
| 1474 | CH | NMe | Q1i | a bond | Me | a bond | NH | O | a bond | T3d | OH |
| 1475 | CH | NMe | Q1i | a bond | Me | a bond | NH | O | a bond | T3e | OH |
| 1476 | CH | NMe | Q1i | a bond | Me | a bond | NH | O | a bond | T3f | OH |
| 1477 | CH | NMe | Q1i | a bond | Me | a bond | NH | O | a bond | T3g | OH |
| 1478 | CH | NMe | Q1i | a bond | Me | a bond | NH | O | a bond | T3h | OH |
| 1479 | CH | NMe | Q1i | a bond | Me | a bond | NH | O | a bond | T3i | OH |
| 1480 | CH | NMe | Q1i | a bond | Me | a bond | NH | O | a bond | T3j | OH |
| 1481 | CH | NMe | Q1i | a bond | H | a bond | NH | S | NH | T3a | OH |
| 1482 | CH | NMe | Q1i | a bond | H | a bond | NH | S | NH | T3b | OH |
| 1483 | CH | NMe | Q1i | a bond | H | a bond | NH | S | NH | T3c | OH |
| 1484 | CH | NMe | Q1i | a bond | H | a bond | NH | S | NH | T3d | OH |
| 1485 | CH | NMe | Q1i | a bond | H | a bond | NH | S | NH | T3e | OH |
| 1486 | CH | NMe | Q1i | a bond | H | a bond | NH | S | NH | T3f | OH |
| 1487 | CH | NMe | Q1i | a bond | H | a bond | NH | S | NH | T3g | OH |
| 1488 | CH | NMe | Q1i | a bond | H | a bond | NH | S | NH | T3h | OH |
| 1489 | CH | NMe | Q1i | a bond | H | a bond | NH | S | NH | T3i | OH |
| 1490 | CH | NMe | Q1i | a bond | H | a bond | NH | S | NH | T3j | OH |
| 1491 | CH | NMe | Q1i | a bond | H | a bond | NH | S | a bond | T3a | OH |
| 1492 | CH | NMe | Q1i | a bond | H | a bond | NH | S | a bond | T3b | OH |
| 1493 | CH | NMe | Q1i | a bond | H | a bond | NH | S | a bond | T3c | OH |
| 1494 | CH | NMe | Q1i | a bond | H | a bond | NH | S | a bond | T3d | OH |
| 1495 | CH | NMe | Q1i | a bond | H | a bond | NH | S | a bond | T3e | OH |
| 1496 | CH | NMe | Q1i | a bond | H | a bond | NH | S | a bond | T3f | OH |
| 1497 | CH | NMe | Q1i | a bond | H | a bond | NH | S | a bond | T3g | OH |
| 1498 | CH | NMe | Q1i | a bond | H | a bond | NH | S | a bond | T3h | OH |
| 1499 | CH | NMe | Q1i | a bond | H | a bond | NH | S | a bond | T3i | OH |
| 1500 | CH | NMe | Q1i | a bond | H | a bond | NH | S | a bond | T3j | OH |
| 1501 | CH | NMe | Q1i | a bond | H | a bond | NH | O | NH | T3a | OH |
| 1502 | CH | NMe | Q1i | a bond | H | a bond | NH | O | NH | T3b | OH |
| 1503 | CH | NMe | Q1i | a bond | H | a bond | NH | O | NH | T3c | OH |
| 1504 | CH | NMe | Q1i | a bond | H | a bond | NH | O | NH | T3d | OH |
| 1505 | CH | NMe | Q1i | a bond | H | a bond | NH | O | NH | T3e | OH |
| 1506 | CH | NMe | Q1i | a bond | H | a bond | NH | O | NH | T3f | OH |
| 1507 | CH | NMe | Q1i | a bond | H | a bond | NH | O | NH | T3g | OH |
| 1508 | CH | NMe | Q1i | a bond | H | a bond | NH | O | NH | T3h | OH |
| 1509 | CH | NMe | Q1i | a bond | H | a bond | NH | O | NH | T3i | OH |
| 1510 | CH | NMe | Q1i | a bond | H | a bond | NH | O | NH | T3j | OH |
| 1511 | CH | NMe | Q1i | a bond | H | a bond | NH | O | a bond | T3a | OH |
| 1512 | CH | NMe | Q1i | a bond | H | a bond | NH | O | a bond | T3b | OH |
| 1513 | CH | NMe | Q1i | a bond | H | a bond | NH | O | a bond | T3c | OH |
| 1514 | CH | NMe | Q1i | a bond | H | a bond | NH | O | a bond | T3d | OH |
| 1515 | CH | NMe | Q1i | a bond | H | a bond | NH | O | a bond | T3e | OH |
| 1516 | CH | NMe | Q1i | a bond | H | a bond | NH | O | a bond | T3f | OH |
| 1517 | CH | NMe | Q1i | a bond | H | a bond | NH | O | a bond | T3g | OH |
| 1518 | CH | NMe | Q1i | a bond | H | a bond | NH | O | a bond | T3h | OH |
| 1519 | CH | NMe | Q1i | a bond | H | a bond | NH | O | a bond | T3i | OH |
| 1520 | CH | NMe | Q1i | a bond | H | a bond | NH | O | a bond | T3j | OH |
| 1521 | CH | NMe | Q1j | a bond | Me | a bond | NH | S | NH | T3a | OH |
| 1522 | CH | NMe | Q1j | a bond | Me | a bond | NH | S | NH | T3b | OH |
| 1523 | CH | NMe | Q1j | a bond | Me | a bond | NH | S | NH | T3c | OH |
| 1524 | CH | NMe | Q1j | a bond | Me | a bond | NH | S | NH | T3d | OH |
| 1525 | CH | NMe | Q1j | a bond | Me | a bond | NH | S | NH | T3e | OH |
| 1526 | CH | NMe | Q1j | a bond | Me | a bond | NH | S | NH | T3f | OH |
| 1527 | CH | NMe | Q1j | a bond | Me | a bond | NH | S | NH | T3g | OH |
| 1528 | CH | NMe | Q1j | a bond | Me | a bond | NH | S | NH | T3h | OH |
| 1529 | CH | NMe | Q1j | a bond | Me | a bond | NH | S | NH | T3i | OH |
| 1530 | CH | NMe | Q1j | a bond | Me | a bond | NH | S | NH | T3j | OH |
| 1531 | CH | NMe | Q1j | a bond | Me | a bond | NH | S | a bond | T3a | OH |

TABLE 2-continued

| No | A | B | R¹ | L¹ | R² | L² | L³ | Y | L⁴ | R³ | X |
|---|---|---|---|---|---|---|---|---|---|---|---|
| 1532 | CH | NMe | Q1j | a bond | Me | a bond | NH | S | a bond | T3b | OH |
| 1533 | CH | NMe | Q1j | a bond | Me | a bond | NH | S | a bond | T3c | OH |
| 1534 | CH | NMe | Q1j | a bond | Me | a bond | NH | S | a bond | T3d | OH |
| 1535 | CH | NMe | Q1j | a bond | Me | a bond | NH | S | a bond | T3e | OH |
| 1536 | CH | NMe | Q1j | a bond | Me | a bond | NH | S | a bond | T3f | OH |
| 1537 | CH | NMe | Q1j | a bond | Me | a bond | NH | S | a bond | T3g | OH |
| 1538 | CH | NMe | Q1j | a bond | Me | a bond | NH | S | a bond | T3h | OH |
| 1539 | CH | NMe | Q1j | a bond | Me | a bond | NH | S | a bond | T3i | OH |
| 1540 | CH | NMe | Q1j | a bond | Me | a bond | NH | S | a bond | T3j | OH |
| 1541 | CH | NMe | Q1j | a bond | Me | a bond | NH | O | H | T3a | OH |
| 1542 | CH | NMe | Q1j | a bond | Me | a bond | NH | O | NH | T3b | OH |
| 1543 | CH | NMe | Q1j | a bond | Me | a bond | NH | O | NH | T3c | OH |
| 1544 | CH | NMe | Q1j | a bond | Me | a bond | NH | O | NH | T3d | OH |
| 1545 | CH | NMe | Q1j | a bond | Me | a bond | NH | O | NH | T3e | OH |
| 1546 | CH | NMe | Q1j | a bond | Me | a bond | NH | O | NH | T3f | OH |
| 1547 | CH | NMe | Q1j | a bond | Me | a bond | NH | O | NH | T3g | OH |
| 1548 | CH | NMe | Q1j | a bond | Me | a bond | NH | O | NH | T3h | OH |
| 1549 | CH | NMe | Q1j | a bond | Me | a bond | NH | O | NH | T3i | OH |
| 1550 | CH | NMe | Q1j | a bond | Me | a bond | NH | O | NH | T3j | OH |
| 1551 | CH | NMe | Q1j | a bond | Me | a bond | NH | O | a bond | T3a | OH |
| 1552 | CH | NMe | Q1j | a bond | Me | a bond | NH | O | a bond | T3b | OH |
| 1553 | CH | NMe | Q1j | a bond | Me | a bond | NH | O | a bond | T3c | OH |
| 1554 | CH | NMe | Q1j | a bond | Me | a bond | NH | O | a bond | T3d | OH |
| 1555 | CH | NMe | Q1j | a bond | Me | a bond | NH | O | a bond | T3e | OH |
| 1556 | CH | NMe | Q1j | a bond | Me | a bond | NH | O | a bond | T3f | OH |
| 1557 | CH | NMe | Q1j | a bond | Me | a bond | NH | O | a bond | T3g | OH |
| 1558 | CH | NMe | Q1j | a bond | Me | a bond | NH | O | a bond | T3h | OH |
| 1559 | CH | NMe | Q1j | a bond | Me | a bond | NH | O | a bond | T3i | OH |
| 1560 | CH | NMe | Q1j | a bond | Me | a bond | NH | O | a bond | T3j | OH |
| 1561 | CH | NMe | Q1j | a bond | H | a bond | NH | S | NH | T3a | OH |
| 1562 | CH | NMe | Q1j | a bond | H | a bond | NH | S | NH | T3b | OH |
| 1563 | CH | NMe | Q1j | a bond | H | a bond | NH | S | NH | T3c | OH |
| 1564 | CH | NMe | Q1j | a bond | H | a bond | NH | S | NH | T3d | OH |
| 1565 | CH | NMe | Q1j | a bond | H | a bond | NH | S | NH | T3e | OH |
| 1566 | CH | NMe | Q1j | a bond | H | a bond | NH | S | NH | T3f | OH |
| 1567 | CH | NMe | Q1j | a bond | H | a bond | NH | S | NH | T3g | OH |
| 1568 | CH | NMe | Q1j | a bond | H | a bond | NH | S | NH | T3h | OH |
| 1569 | CH | NMe | Q1j | a bond | H | a bond | NH | S | NH | T3i | OH |
| 1570 | CH | NMe | Q1j | a bond | H | a bond | NH | S | NH | T3j | OH |
| 1571 | CH | NMe | Q1j | a bond | H | a bond | NH | S | a bond | T3a | OH |
| 1572 | CH | NMe | Q1j | a bond | H | a bond | NH | S | a bond | T3b | OH |
| 1573 | CH | NMe | Q1j | a bond | H | a bond | NH | S | a bond | T3c | OH |
| 1574 | CH | NMe | Q1j | a bond | H | a bond | NH | S | a bond | T3d | OH |
| 1575 | CH | NMe | Q1j | a bond | H | a bond | NH | S | a bond | T3e | OH |
| 1576 | CH | NMe | Q1j | a bond | H | a bond | NH | S | a bond | T3f | OH |
| 1577 | CH | NMe | Q1j | a bond | H | a bond | NH | S | a bond | T3g | OH |
| 1578 | CH | NMe | Q1j | a bond | H | a bond | NH | S | a bond | T3h | OH |
| 1579 | CH | NMe | Q1j | a bond | H | a bond | NH | S | a bond | T3i | OH |
| 1580 | CH | NMe | Q1j | a bond | H | a bond | NH | S | a bond | T3j | OH |
| 1581 | CH | NMe | Q1j | a bond | H | a bond | NH | O | NH | T3a | OH |
| 1582 | CH | NMe | Q1j | a bond | H | a bond | NH | O | NH | T3b | OH |
| 1583 | CH | NMe | Q1j | a bond | H | a bond | NH | O | NH | T3c | OH |
| 1584 | CH | NMe | Q1j | a bond | H | a bond | NH | O | NH | T3d | OH |
| 1585 | CH | NMe | Q1j | a bond | H | a bond | NH | O | NH | T3e | OH |
| 1586 | CH | NMe | Q1j | a bond | H | a bond | NH | O | NH | T3f | OH |
| 1587 | CH | NMe | Q1j | a bond | H | a bond | NH | O | NH | T3g | OH |
| 1588 | CH | NMe | Q1j | a bond | H | a bond | NH | O | NH | T3h | OH |
| 1589 | CH | NMe | Q1j | a bond | H | a bond | NH | O | NH | T3i | OH |
| 1590 | CH | NMe | Q1j | a bond | H | a bond | NH | O | NH | T3j | OH |
| 1591 | CH | NMe | Q1j | a bond | H | a bond | NH | O | a bond | T3a | OH |
| 1592 | CH | NMe | Q1j | a bond | H | a bond | NH | O | a bond | T3b | OH |
| 1593 | CH | NMe | Q1j | a bond | H | a bond | NH | O | a bond | T3c | OH |
| 1594 | CH | NMe | Q1j | a bond | H | a bond | NH | O | a bond | T3d | OH |
| 1595 | CH | NMe | Q1j | a bond | H | a bond | NH | O | a bond | T3e | OH |
| 1596 | CH | NMe | Q1j | a bond | H | a bond | NH | O | a bond | T3f | OH |
| 1597 | CH | NMe | Q1j | a bond | H | a bond | NH | O | a bond | T3g | OH |
| 1598 | CH | NMe | Q1j | a bond | H | a bond | NH | O | a bond | T3h | OH |
| 1599 | CH | NMe | Q1j | a bond | H | a bond | NH | O | a bond | T3i | OH |
| 1600 | CH | NMe | Q1j | a bond | H | a bond | NH | O | a bond | T3j | OH |
| 1601 | CH | S | Q1a | a bond | Me | a bond | NH | S | NH | T3a | OH |
| 1602 | CH | S | Q1a | a bond | Me | a bond | NH | S | NH | T3b | OH |
| 1603 | CH | S | Q1a | a bond | Me | a bond | NH | S | NH | T3c | OH |
| 1604 | CH | S | Q1a | a bond | Me | a bond | NH | S | NH | T3d | OH |
| 1605 | CH | S | Q1a | a bond | Me | a bond | NH | S | NH | T3e | OH |
| 1606 | CH | S | Q1a | a bond | Me | a bond | NH | S | NH | T3f | OH |
| 1607 | CH | S | Q1a | a bond | Me | a bond | NH | S | NH | T3g | OH |
| 1608 | CH | S | Q1a | a bond | Me | a bond | NH | S | NH | T3h | OH |
| 1609 | CH | S | Q1a | a bond | Me | a bond | NH | S | NH | T3i | OH |

TABLE 2-continued

| No | A | B | R¹ | L¹ | R² | L² | L³ | Y | L⁴ | R³ | X |
|---|---|---|---|---|---|---|---|---|---|---|---|
| 1610 | CH | S | Q1a | a bond | Me | a bond | NH | S | NH | T3j | OH |
| 1611 | CH | S | Q1a | a bond | Me | a bond | NH | S | a bond | T3a | OH |
| 1612 | CH | S | Q1a | a bond | Me | a bond | NH | S | a bond | T3b | OH |
| 1613 | CH | S | Q1a | a bond | Me | a bond | NH | S | a bond | T3c | OH |
| 1614 | CH | S | Q1a | a bond | Me | a bond | NH | S | a bond | T3d | OH |
| 1615 | CH | S | Q1a | a bond | Me | a bond | NH | S | a bond | T3e | OH |
| 1616 | CH | S | Q1a | a bond | Me | a bond | NH | S | a bond | T3f | OH |
| 1617 | CH | S | Q1a | a bond | Me | a bond | NH | S | a bond | T3g | OH |
| 1618 | CH | S | Q1a | a bond | Me | a bond | NH | S | a bond | T3h | OH |
| 1619 | CH | S | Q1a | a bond | Me | a bond | NH | S | a bond | T3i | OH |
| 1620 | CH | S | Q1a | a bond | Me | a bond | NH | S | a bond | T3j | OH |
| 1621 | CH | S | Q1a | a bond | Me | a bond | NH | O | NH | T3a | OH |
| 1622 | CH | S | Q1a | a bond | Me | a bond | NH | O | NH | T3b | OH |
| 1623 | CH | S | Q1a | a bond | Me | a bond | NH | O | NH | T3c | OH |
| 1624 | CH | S | Q1a | a bond | Me | a bond | NH | O | NH | T3d | OH |
| 1625 | CH | S | Q1a | a bond | Me | a bond | NH | O | NH | T3e | OH |
| 1626 | CH | S | Q1a | a bond | Me | a bond | NH | O | NH | T3f | OH |
| 1627 | CH | S | Q1a | a bond | Me | a bond | NH | O | NH | T3g | OH |
| 1628 | CH | S | Q1a | a bond | Me | a bond | NH | O | NH | T3h | OH |
| 1629 | CH | S | Q1a | a bond | Me | a bond | NH | O | NH | T3i | OH |
| 1630 | CH | S | Q1a | a bond | Me | a bond | NH | O | NH | T3j | OH |
| 1631 | CH | S | Q1a | a bond | Me | a bond | NH | O | a bond | T3a | OH |
| 1632 | CH | S | Q1a | a bond | Me | a bond | NH | O | a bond | T3b | OH |
| 1633 | CH | S | Q1a | a bond | Me | a bond | NH | O | a bond | T3c | OH |
| 1634 | CH | S | Q1a | a bond | Me | a bond | NH | O | a bond | T3d | OH |
| 1635 | CH | S | Q1a | a bond | Me | a bond | NH | O | a bond | T3e | OH |
| 1636 | CH | S | Q1a | a bond | Me | a bond | NH | O | a bond | T3f | OH |
| 1637 | CH | S | Q1a | a bond | Me | a bond | NH | O | a bond | T3g | OH |
| 1638 | CH | S | Q1a | a bond | Me | a bond | NH | O | a bond | T3h | OH |
| 1639 | CH | S | Q1a | a bond | Me | a bond | NH | O | a bond | T3i | OH |
| 1640 | CH | S | Q1a | a bond | Me | a bond | NH | O | a bond | T3j | OH |
| 1641 | CH | S | Q1a | a bond | H | a bond | NH | S | NH | T3a | OH |
| 1642 | CH | S | Q1a | a bond | H | a bond | NH | S | NH | T3b | OH |
| 1643 | CH | S | Q1a | a bond | H | a bond | NH | S | NH | T3c | OH |
| 1644 | CH | S | Q1a | a bond | H | a bond | NH | S | NH | T3d | OH |
| 1645 | CH | S | Q1a | a bond | H | a bond | NH | S | NH | T3e | OH |
| 1646 | CH | S | Q1a | a bond | H | a bond | NH | S | NH | T3f | OH |
| 1647 | CH | S | Q1a | a bond | H | a bond | NH | S | NH | T3g | OH |
| 1648 | CH | S | Q1a | a bond | H | a bond | NH | S | NH | T3h | OH |
| 1649 | CH | S | Q1a | a bond | H | a bond | NH | S | NH | T3i | OH |
| 1650 | CH | S | Q1a | a bond | H | a bond | NH | S | NH | T3j | OH |
| 1651 | CH | S | Q1a | a bond | H | a bond | NH | S | a bond | T3a | OH |
| 1652 | CH | S | Q1a | a bond | H | a bond | NH | S | a bond | T3b | OH |
| 1653 | CH | S | Q1a | a bond | H | a bond | NH | S | a bond | T3c | OH |
| 1654 | CH | S | Q1a | a bond | H | a bond | NH | S | a bond | T3d | OH |
| 1655 | CH | S | Q1a | a bond | H | a bond | NH | S | a bond | T3e | OH |
| 1656 | CH | S | Q1a | a bond | H | a bond | NH | S | a bond | T3f | OH |
| 1657 | CH | S | Q1a | a bond | H | a bond | NH | S | a bond | T3g | OH |
| 1658 | CH | S | Q1a | a bond | H | a bond | NH | S | a bond | T3h | OH |
| 1659 | CH | S | Q1a | a bond | H | a bond | NH | S | a bond | T3i | OH |
| 1660 | CH | S | Q1a | a bond | H | a bond | NH | S | a bond | T3j | OH |
| 1661 | CH | S | Q1a | a bond | H | a bond | NH | O | NH | T3a | OH |
| 1662 | CH | S | Q1a | a bond | H | a bond | NH | O | NH | T3b | OH |
| 1663 | CH | S | Q1a | a bond | H | a bond | NH | O | NH | T3c | OH |
| 1664 | CH | S | Q1a | a bond | H | a bond | NH | O | NH | T3d | OH |
| 1665 | CH | S | Q1a | a bond | H | a bond | NH | O | NH | T3e | OH |
| 1666 | CH | S | Q1a | a bond | H | a bond | NH | O | NH | T3f | OH |
| 1667 | CH | S | Q1a | a bond | H | a bond | NH | O | NH | T3g | OH |
| 1668 | CH | S | Q1a | a bond | H | a bond | NH | O | NH | T3h | OH |
| 1669 | CH | S | Q1a | a bond | H | a bond | NH | O | NH | T3i | OH |
| 1670 | CH | S | Q1a | a bond | H | a bond | NH | O | NH | T3j | OH |
| 1671 | CH | S | Q1a | a bond | H | a bond | NH | O | a bond | T3a | OH |
| 1672 | CH | S | Q1a | a bond | H | a bond | NH | O | a bond | T3b | OH |
| 1673 | CH | S | Q1a | a bond | H | a bond | NH | O | a bond | T3c | OH |
| 1674 | CH | S | Q1a | a bond | H | a bond | NH | O | a bond | T3d | OH |
| 1675 | CH | S | Q1a | a bond | H | a bond | NH | O | a bond | T3e | OH |
| 1676 | CH | S | Q1a | a bond | H | a bond | NH | O | a bond | T3f | OH |
| 1677 | CH | S | Q1a | a bond | H | a bond | NH | O | a bond | T3g | OH |
| 1678 | CH | S | Q1a | a bond | H | a bond | NH | O | a bond | T3h | OH |
| 1679 | CH | S | Q1a | a bond | H | a bond | NH | O | a bond | T3i | OH |
| 1680 | CH | S | Q1a | a bond | H | a bond | NH | O | a bond | T3j | OH |
| 1681 | CH | S | Q1b | a bond | Me | a bond | NH | S | NH | T3a | OH |
| 1682 | CH | S | Q1b | a bond | Me | a bond | NH | S | NH | T3b | OH |
| 1683 | CH | S | Q1b | a bond | Me | a bond | NH | S | NH | T3c | OH |
| 1684 | CH | S | Q1b | a bond | Me | a bond | NH | S | NH | T3d | OH |
| 1685 | CH | S | Q1b | a bond | Me | a bond | NH | S | NH | T3e | OH |
| 1686 | CH | S | Q1b | a bond | Me | a bond | NH | S | NH | T3f | OH |
| 1687 | CH | S | Q1b | a bond | Me | a bond | NH | S | NH | T3g | OH |

TABLE 2-continued

| No | A | B | R¹ | L¹ | R² | L² | L³ | Y | L⁴ | R³ | X |
|---|---|---|---|---|---|---|---|---|---|---|---|
| 1688 | CH | S | Q1b | a bond | Me | a bond | NH | S | NH | T3h | OH |
| 1689 | CH | S | Q1b | a bond | Me | a bond | NH | S | NH | T3i | OH |
| 1690 | CH | S | Q1b | a bond | Me | a bond | NH | S | NH | T3j | OH |
| 1691 | CH | S | Q1b | a bond | Me | a bond | NH | S | a bond | T3a | OH |
| 1692 | CH | S | Q1b | a bond | Me | a bond | NH | S | a bond | T3b | OH |
| 1693 | CH | S | Q1b | a bond | Me | a bond | NH | S | a bond | T3c | OH |
| 1694 | CH | S | Q1b | a bond | Me | a bond | NH | S | a bond | T3d | OH |
| 1695 | CH | S | Q1b | a bond | Me | a bond | NH | S | a bond | T3e | OH |
| 1696 | CH | S | Q1b | a bond | Me | a bond | NH | S | a bond | T3f | OH |
| 1697 | CH | S | Q1b | a bond | Me | a bond | NH | S | a bond | T3g | OH |
| 1698 | CH | S | Q1b | a bond | Me | a bond | NH | S | a bond | T3h | OH |
| 1699 | CH | S | Q1b | a bond | Me | a bond | NH | S | a bond | T3i | OH |
| 1700 | CH | S | Q1b | a bond | Me | a bond | NH | S | a bond | T3j | OH |
| 1701 | CH | S | Q1b | a bond | Me | a bond | NH | O | NH | T3a | OH |
| 1702 | CH | S | Q1b | a bond | Me | a bond | NH | O | NH | T3b | OH |
| 1703 | CH | S | Q1b | a bond | Me | a bond | NH | O | NH | T3c | OH |
| 1704 | CH | S | Q1b | a bond | Me | a bond | NH | O | NH | T3d | OH |
| 1705 | CH | S | Q1b | a bond | Me | a bond | NH | O | NH | T3e | OH |
| 1706 | CH | S | Q1b | a bond | Me | a bond | NH | O | NH | T3f | OH |
| 1707 | CH | S | Q1b | a bond | Me | a bond | NH | O | NH | T3g | OH |
| 1708 | CH | S | Q1b | a bond | Me | a bond | NH | O | NH | T3h | OH |
| 1709 | CH | S | Q1b | a bond | Me | a bond | NH | O | NH | T3i | OH |
| 1710 | CH | S | Q1b | a bond | Me | a bond | NH | O | NH | T3j | OH |
| 1711 | CH | S | Q1b | a bond | Me | a bond | NH | O | a bond | T3a | OH |
| 1712 | CH | S | Q1b | a bond | Me | a bond | NH | O | a bond | T3b | OH |
| 1713 | CH | S | Q1b | a bond | Me | a bond | NH | O | a bond | T3c | OH |
| 1714 | CH | S | Q1b | a bond | Me | a bond | NH | O | a bond | T3d | OH |
| 1715 | CH | S | Q1b | a bond | Me | a bond | NH | O | a bond | T3e | OH |
| 1716 | CH | S | Q1b | a bond | Me | a bond | NH | O | a bond | T3f | OH |
| 1717 | CH | S | Q1b | a bond | Me | a bond | NH | O | a bond | T3g | OH |
| 1718 | CH | S | Q1b | a bond | Me | a bond | NH | O | a bond | T3h | OH |
| 1719 | CH | S | Q1b | a bond | Me | a bond | NH | O | a bond | T3i | OH |
| 1720 | CH | S | Q1b | a bond | Me | a bond | NH | O | a bond | T3j | OH |
| 1721 | CH | S | Q1b | a bond | H | a bond | NH | S | NH | T3a | OH |
| 1722 | CH | S | Q1b | a bond | H | a bond | NH | S | NH | T3b | OH |
| 1723 | CH | S | Q1b | a bond | H | a bond | NH | S | NH | T3c | OH |
| 1724 | CH | S | Q1b | a bond | H | a bond | NH | S | NH | T3d | OH |
| 1725 | CH | S | Q1b | a bond | H | a bond | NH | S | NH | T3e | OH |
| 1726 | CH | S | Q1b | a bond | H | a bond | NH | S | NH | T3f | OH |
| 1727 | CH | S | Q1b | a bond | H | a bond | NH | S | NH | T3g | OH |
| 1728 | CH | S | Q1b | a bond | H | a bond | NH | S | NH | T3h | OH |
| 1729 | CH | S | Q1b | a bond | H | a bond | NH | S | NH | T3i | OH |
| 1730 | CH | S | Q1b | a bond | H | a bond | NH | S | NH | T3j | OH |
| 1731 | CH | S | Q1b | a bond | H | a bond | NH | S | a bond | T3a | OH |
| 1732 | CH | S | Q1b | a bond | H | a bond | NH | S | a bond | T3b | OH |
| 1733 | CH | S | Q1b | a bond | H | a bond | NH | S | a bond | T3c | OH |
| 1734 | CH | S | Q1b | a bond | H | a bond | NH | S | a bond | T3d | OH |
| 1735 | CH | S | Q1b | a bond | H | a bond | NH | S | a bond | T3e | OH |
| 1736 | CH | S | Q1b | a bond | H | a bond | NH | S | a bond | T3f | OH |
| 1737 | CH | S | Q1b | a bond | H | a bond | NH | S | a bond | T3g | OH |
| 1738 | CH | S | Q1b | a bond | H | a bond | NH | S | a bond | T3h | OH |
| 1739 | CH | S | Q1b | a bond | H | a bond | NH | S | a bond | T3i | OH |
| 1740 | CH | S | Q1b | a bond | H | a bond | NH | S | a bond | T3j | OH |
| 1741 | CH | S | Q1b | a bond | H | a bond | NH | O | NH | T3a | OH |
| 1742 | CH | S | Q1b | a bond | H | a bond | NH | O | NH | T3b | OH |
| 1743 | CH | S | Q1b | a bond | H | a bond | NH | O | NH | T3c | OH |
| 1744 | CH | S | Q1b | a bond | H | a bond | NH | O | NH | T3d | OH |
| 1745 | CH | S | Q1b | a bond | H | a bond | NH | O | NH | T3e | OH |
| 1746 | CH | S | Q1b | a bond | H | a bond | NH | O | NH | T3f | OH |
| 1747 | CH | S | Q1b | a bond | H | a bond | NH | O | NH | T3g | OH |
| 1748 | CH | S | Q1b | a bond | H | a bond | NH | O | NH | T3h | OH |
| 1749 | CH | S | Q1b | a bond | H | a bond | NH | O | NH | T3i | OH |
| 1750 | CH | S | Q1b | a bond | H | a bond | NH | O | NH | T3j | OH |
| 1751 | CH | S | Q1b | a bond | H | a bond | NH | O | a bond | T3a | OH |
| 1752 | CH | S | Q1b | a bond | H | a bond | NH | O | a bond | T3b | OH |
| 1753 | CH | S | Q1b | a bond | H | a bond | NH | O | a bond | T3c | OH |
| 1754 | CH | S | Q1b | a bond | H | a bond | NH | O | a bond | T3d | OH |
| 1755 | CH | S | Q1b | a bond | H | a bond | NH | O | a bond | T3e | OH |
| 1756 | CH | S | Q1b | a bond | H | a bond | NH | O | a bond | T3f | OH |
| 1757 | CH | S | Q1b | a bond | H | a bond | NH | O | a bond | T3g | OH |
| 1758 | CH | S | Q1b | a bond | H | a bond | NH | O | a bond | T3h | OH |
| 1759 | CH | S | Q1b | a bond | H | a bond | NH | O | a bond | T3i | OH |
| 1760 | CH | S | Q1b | a bond | H | a bond | NH | O | a bond | T3j | OH |
| 1761 | CH | S | Q1c | a bond | Me | a bond | NH | S | NH | T3a | OH |
| 1762 | CH | S | Q1c | a bond | Me | a bond | NH | S | NH | T3b | OH |
| 1763 | CH | S | Q1c | a bond | Me | a bond | NH | S | NH | T3c | OH |
| 1764 | CH | S | Q1c | a bond | Me | a bond | NH | S | NH | T3d | OH |
| 1765 | CH | S | Q1c | a bond | Me | a bond | NH | S | NH | T3e | OH |

TABLE 2-continued

| No | A | B | R¹ | L¹ | R² | L² | L³ | Y | L⁴ | R³ | X |
|---|---|---|---|---|---|---|---|---|---|---|---|
| 1766 | CH | S | Q1c | a bond | Me | a bond | NH | S | NH | T3f | OH |
| 1767 | CH | S | Q1c | a bond | Me | a bond | NH | S | NH | T3g | OH |
| 1768 | CH | S | Q1c | a bond | Me | a bond | NH | S | NH | T3h | OH |
| 1769 | CH | S | Q1c | a bond | Me | a bond | NH | S | NH | T3i | OH |
| 1770 | CH | S | Q1c | a bond | Me | a bond | NH | S | NH | T3j | OH |
| 1771 | CH | S | Q1c | a bond | Me | a bond | NH | S | a bond | T3a | OH |
| 1772 | CH | S | Q1c | a bond | Me | a bond | NH | S | a bond | T3b | OH |
| 1773 | CH | S | Q1c | a bond | Me | a bond | NH | S | a bond | T3c | OH |
| 1774 | CH | S | Q1c | a bond | Me | a bond | NH | S | a bond | T3d | OH |
| 1775 | CH | S | Q1c | a bond | Me | a bond | NH | S | a bond | T3e | OH |
| 1776 | CH | S | Q1c | a bond | Me | a bond | NH | S | a bond | T3f | OH |
| 1777 | CH | S | Q1c | a bond | Me | a bond | NH | S | a bond | T3g | OH |
| 1778 | CH | S | Q1c | a bond | Me | a bond | NH | S | a bond | T3h | OH |
| 1779 | CH | S | Q1c | a bond | Me | a bond | NH | S | a bond | T3i | OH |
| 1780 | CH | S | Q1c | a bond | Me | a bond | NH | S | a bond | T3j | OH |
| 1781 | CH | S | Q1c | a bond | Me | a bond | NH | O | NH | T3a | OH |
| 1782 | CH | S | Q1c | a bond | Me | a bond | NH | O | NH | T3b | OH |
| 1783 | CH | S | Q1c | a bond | Me | a bond | NH | O | NH | T3c | OH |
| 1784 | CH | S | Q1c | a bond | Me | a bond | NH | O | NH | T3d | OH |
| 1785 | CH | S | Q1c | a bond | Me | a bond | NH | O | NH | T3e | OH |
| 1786 | CH | S | Q1c | a bond | Me | a bond | NH | O | NH | T3f | OH |
| 1787 | CH | S | Q1c | a bond | Me | a bond | NH | O | NH | T3g | OH |
| 1788 | CH | S | Q1c | a bond | Me | a bond | NH | O | NH | T3h | OH |
| 1789 | CH | S | Q1c | a bond | Me | a bond | NH | O | NH | T3i | OH |
| 1790 | CH | S | Q1c | a bond | Me | a bond | NH | O | NH | T3j | OH |
| 1791 | CH | S | Q1c | a bond | Me | a bond | NH | O | a bond | T3a | OH |
| 1792 | CH | S | Q1c | a bond | Me | a bond | NH | O | a bond | T3b | OH |
| 1793 | CH | S | Q1c | a bond | Me | a bond | NH | O | a bond | T3c | OH |
| 1794 | CH | S | Q1c | a bond | Me | a bond | NH | O | a bond | T3d | OH |
| 1795 | CH | S | Q1c | a bond | Me | a bond | NH | O | a bond | T3e | OH |
| 1796 | CH | S | Q1c | a bond | Me | a bond | NH | O | a bond | T3f | OH |
| 1797 | CH | S | Q1c | a bond | Me | a bond | NH | O | a bond | T3g | OH |
| 1798 | CH | S | Q1c | a bond | Me | a bond | NH | O | a bond | T3h | OH |
| 1799 | CH | S | Q1c | a bond | Me | a bond | NH | O | a bond | T3i | OH |
| 1800 | CH | S | Q1c | a bond | Me | a bond | NH | O | a bond | T3j | OH |
| 1801 | CH | S | Q1c | a bond | H | a bond | NH | S | NH | T3a | OH |
| 1802 | CH | S | Q1c | a bond | H | a bond | NH | S | NH | T3b | OH |
| 1803 | CH | S | Q1c | a bond | H | a bond | NH | S | NH | T3c | OH |
| 1804 | CH | S | Q1c | a bond | H | a bond | NH | S | NH | T3d | OH |
| 1805 | CH | S | Q1c | a bond | H | a bond | NH | S | NH | T3e | OH |
| 1806 | CH | S | Q1c | a bond | H | a bond | NH | S | NH | T3f | OH |
| 1807 | CH | S | Q1c | a bond | H | a bond | NH | S | NH | T3g | OH |
| 1808 | CH | S | Q1c | a bond | H | a bond | NH | S | NH | T3h | OH |
| 1809 | CH | S | Q1c | a bond | H | a bond | NH | S | NH | T3i | OH |
| 1810 | CH | S | Q1c | a bond | H | a bond | NH | S | NH | T3j | OH |
| 1811 | CH | S | Q1c | a bond | H | a bond | NH | S | a bond | T3a | OH |
| 1812 | CH | S | Q1c | a bond | H | a bond | NH | S | a bond | T3b | OH |
| 1813 | CH | S | Q1c | a bond | H | a bond | NH | S | a bond | T3c | OH |
| 1814 | CH | S | Q1c | a bond | H | a bond | NH | S | a bond | T3d | OH |
| 1815 | CH | S | Q1c | a bond | H | a bond | NH | S | a bond | T3e | OH |
| 1816 | CH | S | Q1c | a bond | H | a bond | NH | S | a bond | T3f | OH |
| 1817 | CH | S | Q1c | a bond | H | a bond | NH | S | a bond | T3g | OH |
| 1818 | CH | S | Q1c | a bond | H | a bond | NH | S | a bond | T3h | OH |
| 1819 | CH | S | Q1c | a bond | H | a bond | NH | S | a bond | T3i | OH |
| 1820 | CH | S | Q1c | a bond | H | a bond | NH | S | a bond | T3j | OH |
| 1821 | CH | S | Q1c | a bond | H | a bond | NH | O | NH | T3a | OH |
| 1822 | CH | S | Q1c | a bond | H | a bond | NH | O | NH | T3b | OH |
| 1823 | CH | S | Q1c | a bond | H | a bond | NH | O | NH | T3c | OH |
| 1824 | CH | S | Q1c | a bond | H | a bond | NH | O | NH | T3d | OH |
| 1825 | CH | S | Q1c | a bond | H | a bond | NH | O | NH | T3e | OH |
| 1826 | CH | S | Q1c | a bond | H | a bond | NH | O | NH | T3f | OH |
| 1827 | CH | S | Q1c | a bond | H | a bond | NH | O | NH | T3g | OH |
| 1828 | CH | S | Q1c | a bond | H | a bond | NH | O | NH | T3h | OH |
| 1829 | CH | S | Q1c | a bond | H | a bond | NH | O | NH | T3i | OH |
| 1830 | CH | S | Q1c | a bond | H | a bond | NH | O | NH | T3j | OH |
| 1831 | CH | S | Q1c | a bond | H | a bond | NH | O | a bond | T3a | OH |
| 1832 | CH | S | Q1c | a bond | H | a bond | NH | O | a bond | T3b | OH |
| 1833 | CH | S | Q1c | a bond | H | a bond | NH | O | a bond | T3c | OH |
| 1834 | CH | S | Q1c | a bond | H | a bond | NH | O | a bond | T3d | OH |
| 1835 | CH | S | Q1c | a bond | H | a bond | NH | O | a bond | T3e | OH |
| 1836 | CH | S | Q1c | a bond | H | a bond | NH | O | a bond | T3f | OH |
| 1837 | CH | S | Q1c | a bond | H | a bond | NH | O | a bond | T3g | OH |
| 1838 | CH | S | Q1c | a bond | H | a bond | NH | O | a bond | T3h | OH |
| 1839 | CH | S | Q1c | a bond | H | a bond | NH | O | a bond | T3i | OH |
| 1840 | CH | S | Q1c | a bond | H | a bond | NH | O | a bond | T3j | OH |
| 1841 | CH | S | Q1i | a bond | Me | a bond | NH | S | NH | T3a | OH |
| 1842 | CH | S | Q1i | a bond | Me | a bond | NH | S | NH | T3b | OH |
| 1843 | CH | S | Q1i | a bond | Me | a bond | NH | S | NH | T3c | OH |

TABLE 2-continued

| No | A | B | R¹ | L¹ | R² | L² | L³ | Y | L⁴ | R³ | X |
|---|---|---|---|---|---|---|---|---|---|---|---|
| 1844 | CH | S | Q1i | a bond | Me | a bond | NH | S | NH | T3d | OH |
| 1845 | CH | S | Q1i | a bond | Me | a bond | NH | S | NH | T3e | OH |
| 1846 | CH | S | Q1i | a bond | Me | a bond | NH | S | NH | T3f | OH |
| 1847 | CH | S | Q1i | a bond | Me | a bond | NH | S | NH | T3g | OH |
| 1848 | CH | S | Q1i | a bond | Me | a bond | NH | S | NH | T3h | OH |
| 1849 | CH | S | Q1i | a bond | Me | a bond | NH | S | NH | T3i | OH |
| 1850 | CH | S | Q1i | a bond | Me | a bond | NH | S | NH | T3j | OH |
| 1851 | CH | S | Q1i | a bond | Me | a bond | NH | S | a bond | T3a | OH |
| 1852 | CH | S | Q1i | a bond | Me | a bond | NH | S | a bond | T3b | OH |
| 1853 | CH | S | Q1i | a bond | Me | a bond | NH | S | a bond | T3c | OH |
| 1854 | CH | S | Q1i | a bond | Me | a bond | NH | S | a bond | T3d | OH |
| 1855 | CH | S | Q1i | a bond | Me | a bond | NH | S | a bond | T3e | OH |
| 1856 | CH | S | Q1i | a bond | Me | a bond | NH | S | a bond | T3f | OH |
| 1857 | CH | S | Q1i | a bond | Me | a bond | NH | S | a bond | T3g | OH |
| 1858 | CH | S | Q1i | a bond | Me | a bond | NH | S | a bond | T3h | OH |
| 1859 | CH | S | Q1i | a bond | Me | a bond | NH | S | a bond | T3i | OH |
| 1860 | CH | S | Q1i | a bond | Me | a bond | NH | S | a bond | T3j | OH |
| 1861 | CH | S | Q1i | a bond | Me | a bond | NH | O | NH | T3a | OH |
| 1862 | CH | S | Q1i | a bond | Me | a bond | NH | O | NH | T3b | OH |
| 1863 | CH | S | Q1i | a bond | Me | a bond | NH | O | NH | T3c | OH |
| 1864 | CH | S | Q1i | a bond | Me | a bond | NH | O | NH | T3d | OH |
| 1865 | CH | S | Q1i | a bond | Me | a bond | NH | O | NH | T3e | OH |
| 1866 | CH | S | Q1i | a bond | Me | a bond | NH | O | NH | T3f | OH |
| 1867 | CH | S | Q1i | a bond | Me | a bond | NH | O | NH | T3g | OH |
| 1868 | CH | S | Q1i | a bond | Me | a bond | NH | O | NH | T3h | OH |
| 1869 | CH | S | Q1i | a bond | Me | a bond | NH | O | NH | T3i | OH |
| 1870 | CH | S | Q1i | a bond | Me | a bond | NH | O | NH | T3j | OH |
| 1871 | CH | S | Q1i | a bond | Me | a bond | NH | O | a bond | T3a | OH |
| 1872 | CH | S | Q1i | a bond | Me | a bond | NH | O | a bond | T3b | OH |
| 1873 | CH | S | Q1i | a bond | Me | a bond | NH | O | a bond | T3c | OH |
| 1874 | CH | S | Q1i | a bond | Me | a bond | NH | O | a bond | T3d | OH |
| 1875 | CH | S | Q1i | a bond | Me | a bond | NH | O | a bond | T3e | OH |
| 1876 | CH | S | Q1i | a bond | Me | a bond | NH | O | a bond | T3f | OH |
| 1877 | CH | S | Q1i | a bond | Me | a bond | NH | O | a bond | T3g | OH |
| 1878 | CH | S | Q1i | a bond | Me | a bond | NH | O | a bond | T3h | OH |
| 1879 | CH | S | Q1i | a bond | Me | a bond | NH | O | a bond | T3i | OH |
| 1880 | CH | S | Q1i | a bond | Me | a bond | NH | O | a bond | T3j | OH |
| 1881 | CH | S | Q1i | a bond | H | a bond | NH | S | NH | T3a | OH |
| 1882 | CH | S | Q1i | a bond | H | a bond | NH | S | NH | T3b | OH |
| 1883 | CH | S | Q1i | a bond | H | a bond | NH | S | NH | T3c | OH |
| 1884 | CH | S | Q1i | a bond | H | a bond | NH | S | NH | T3d | OH |
| 1885 | CH | S | Q1i | a bond | H | a bond | NH | S | NH | T3e | OH |
| 1886 | CH | S | Q1i | a bond | H | a bond | NH | S | NH | T3f | OH |
| 1887 | CH | S | Q1i | a bond | H | a bond | NH | S | NH | T3g | OH |
| 1888 | CH | S | Q1i | a bond | H | a bond | NH | S | NH | T3h | OH |
| 1889 | CH | S | Q1i | a bond | H | a bond | NH | S | NH | T3i | OH |
| 1890 | CH | S | Q1i | a bond | H | a bond | NH | S | NH | T3j | OH |
| 1891 | CH | S | Q1i | a bond | H | a bond | NH | S | a bond | T3a | OH |
| 1892 | CH | S | Q1i | a bond | H | a bond | NH | S | a bond | T3b | OH |
| 1893 | CH | S | Q1i | a bond | H | a bond | NH | S | a bond | T3c | OH |
| 1894 | CH | S | Q1i | a bond | H | a bond | NH | S | a bond | T3d | OH |
| 1895 | CH | S | Q1i | a bond | H | a bond | NH | S | a bond | T3e | OH |
| 1896 | CH | S | Q1i | a bond | H | a bond | NH | S | a bond | T3f | OH |
| 1897 | CH | S | Q1i | a bond | H | a bond | NH | S | a bond | T3g | OH |
| 1898 | CH | S | Q1i | a bond | H | a bond | NH | S | a bond | T3h | OH |
| 1899 | CH | S | Q1i | a bond | H | a bond | NH | S | a bond | T3i | OH |
| 1900 | CH | S | Q1i | a bond | H | a bond | NH | S | a bond | T3j | OH |
| 1901 | CH | S | Q1i | a bond | H | a bond | NH | O | NH | T3a | OH |
| 1902 | CH | S | Q1i | a bond | H | a bond | NH | O | NH | T3b | OH |
| 1903 | CH | S | Q1i | a bond | H | a bond | NH | O | NH | T3c | OH |
| 1904 | CH | S | Q1i | a bond | H | a bond | NH | O | NH | T3d | OH |
| 1905 | CH | S | Q1i | a bond | H | a bond | NH | O | NH | T3e | OH |
| 1906 | CH | S | Q1i | a bond | H | a bond | NH | O | NH | T3f | OH |
| 1907 | CH | S | Q1i | a bond | H | a bond | NH | O | NH | T3g | OH |
| 1908 | CH | S | Q1i | a bond | H | a bond | NH | O | NH | T3h | OH |
| 1909 | CH | S | Q1i | a bond | H | a bond | NH | O | NH | T3i | OH |
| 1910 | CH | S | Q1i | a bond | H | a bond | NH | O | NH | T3j | OH |
| 1911 | CH | S | Q1i | a bond | H | a bond | NH | O | a bond | T3a | OH |
| 1912 | CH | S | Q1i | a bond | H | a bond | NH | O | a bond | T3b | OH |
| 1913 | CH | S | Q1i | a bond | H | a bond | NH | O | a bond | T3c | OH |
| 1914 | CH | S | Q1i | a bond | H | a bond | NH | O | a bond | T3d | OH |
| 1915 | CH | S | Q1i | a bond | H | a bond | NH | O | a bond | T3e | OH |
| 1916 | CH | S | Q1i | a bond | H | a bond | NH | O | a bond | T3f | OH |
| 1917 | CH | S | Q1i | a bond | H | a bond | NH | O | a bond | T3g | OH |
| 1918 | CH | S | Q1i | a bond | H | a bond | NH | O | a bond | T3h | OH |
| 1919 | CH | S | Q1i | a bond | H | a bond | NH | O | a bond | T3i | OH |
| 1920 | CH | S | Q1i | a bond | H | a bond | NH | O | a bond | T3j | OH |
| 1921 | CH | S | Q1j | a bond | Me | a bond | NH | S | NH | T3a | OH |

TABLE 2-continued

| No | A | B | R¹ | L¹ | R² | L² | L³ | Y | L⁴ | R³ | X |
|---|---|---|---|---|---|---|---|---|---|---|---|
| 1922 | CH | S | Q1j | a bond | Me | a bond | NH | S | NH | T3b | OH |
| 1923 | CH | S | Q1j | a bond | Me | a bond | NH | S | NH | T3c | OH |
| 1924 | CH | S | Q1j | a bond | Me | a bond | NH | S | NH | T3d | OH |
| 1925 | CH | S | Q1j | a bond | Me | a bond | NH | S | NH | T3e | OH |
| 1926 | CH | S | Q1j | a bond | Me | a bond | NH | S | NH | T3f | OH |
| 1927 | CH | S | Q1j | a bond | Me | a bond | NH | S | NH | T3g | OH |
| 1928 | CH | S | Q1j | a bond | Me | a bond | NH | S | NH | T3h | OH |
| 1929 | CH | S | Q1j | a bond | Me | a bond | NH | S | NH | T3i | OH |
| 1930 | CH | S | Q1j | a bond | Me | a bond | NH | S | NH | T3j | OH |
| 1931 | CH | S | Q1j | a bond | Me | a bond | NH | S | a bond | T3a | OH |
| 1932 | CH | S | Q1j | a bond | Me | a bond | NH | S | a bond | T3b | OH |
| 1933 | CH | S | Q1j | a bond | Me | a bond | NH | S | a bond | T3c | OH |
| 1934 | CH | S | Q1j | a bond | Me | a bond | NH | S | a bond | T3d | OH |
| 1935 | CH | S | Q1j | a bond | Me | a bond | NH | S | a bond | T3e | OH |
| 1936 | CH | S | Q1j | a bond | Me | a bond | NH | S | a bond | T3f | OH |
| 1937 | CH | S | Q1j | a bond | Me | a bond | NH | S | a bond | T3g | OH |
| 1938 | CH | S | Q1j | a bond | Me | a bond | NH | S | a bond | T3h | OH |
| 1939 | CH | S | Q1j | a bond | Me | a bond | NH | S | a bond | T3i | OH |
| 1940 | CH | S | Q1j | a bond | Me | a bond | NH | S | a bond | T3j | OH |
| 1941 | CH | S | Q1j | a bond | Me | a bond | NH | O | NH | T3a | OH |
| 1942 | CH | S | Q1j | a bond | Me | a bond | NH | O | NH | T3b | OH |
| 1943 | CH | S | Q1j | a bond | Me | a bond | NH | O | NH | T3c | OH |
| 1944 | CH | S | Q1j | a bond | Me | a bond | NH | O | NH | T3d | OH |
| 1945 | CH | S | Q1j | a bond | Me | a bond | NH | O | NH | T3e | OH |
| 1946 | CH | S | Q1j | a bond | Me | a bond | NH | O | NH | T3f | OH |
| 1947 | CH | S | Q1j | a bond | Me | a bond | NH | O | NH | T3g | OH |
| 1948 | CH | S | Q1j | a bond | Me | a bond | NH | O | NH | T3h | OH |
| 1949 | CH | S | Q1j | a bond | Me | a bond | NH | O | NH | T3i | OH |
| 1950 | CH | S | Q1j | a bond | Me | a bond | NH | O | NH | T3j | OH |
| 1951 | CH | S | Q1j | a bond | Me | a bond | NH | O | a bond | T3a | OH |
| 1952 | CH | S | Q1j | a bond | Me | a bond | NH | O | a bond | T3b | OH |
| 1953 | CH | S | Q1j | a bond | Me | a bond | NH | O | a bond | T3c | OH |
| 1954 | CH | S | Q1j | a bond | Me | a bond | NH | O | a bond | T3d | OH |
| 1955 | CH | S | Q1j | a bond | Me | a bond | NH | O | a bond | T3e | OH |
| 1956 | CH | S | Q1j | a bond | Me | a bond | NH | O | a bond | T3f | OH |
| 1957 | CH | S | Q1j | a bond | Me | a bond | NH | O | a bond | T3g | OH |
| 1958 | CH | S | Q1j | a bond | Me | a bond | NH | O | a bond | T3h | OH |
| 1959 | CH | S | Q1j | a bond | Me | a bond | NH | O | a bond | T3i | OH |
| 1960 | CH | S | Q1j | a bond | Me | a bond | NH | O | a bond | T3j | OH |
| 1961 | CH | S | Q1j | a bond | H | a bond | NH | S | NH | T3a | OH |
| 1962 | CH | S | Q1j | a bond | H | a bond | NH | S | NH | T3b | OH |
| 1963 | CH | S | Q1j | a bond | H | a bond | NH | S | NH | T3c | OH |
| 1964 | CH | S | Q1j | a bond | H | a bond | NH | S | NH | T3d | OH |
| 1965 | CH | S | Q1j | a bond | H | a bond | NH | S | NH | T3e | OH |
| 1966 | CH | S | Q1j | a bond | H | a bond | NH | S | NH | T3f | OH |
| 1967 | CH | S | Q1j | a bond | H | a bond | NH | S | NH | T3g | OH |
| 1968 | CH | S | Q1j | a bond | H | a bond | NH | S | NH | T3h | OH |
| 1969 | CH | S | Q1j | a bond | H | a bond | NH | S | NH | T3i | OH |
| 1970 | CH | S | Q1j | a bond | H | a bond | NH | S | NH | T3j | OH |
| 1971 | CH | S | Q1j | a bond | H | a bond | NH | S | a bond | T3a | OH |
| 1972 | CH | S | Q1j | a bond | H | a bond | NH | S | a bond | T3b | OH |
| 1973 | CH | S | Q1j | a bond | H | a bond | NH | S | a bond | T3c | OH |
| 1974 | CH | S | Q1j | a bond | H | a bond | NH | S | a bond | T3d | OH |
| 1975 | CH | S | Q1j | a bond | H | a bond | NH | S | a bond | T3e | OH |
| 1976 | CH | S | Q1j | a bond | H | a bond | NH | S | a bond | T3f | OH |
| 1977 | CH | S | Q1j | a bond | H | a bond | NH | S | a bond | T3g | OH |
| 1978 | CH | S | Q1j | a bond | H | a bond | NH | S | a bond | T3h | OH |
| 1979 | CH | S | Q1j | a bond | H | a bond | NH | S | a bond | T3i | OH |
| 1980 | CH | S | Q1j | a bond | H | a bond | NH | S | a bond | T3j | OH |
| 1981 | CH | S | Q1j | a bond | H | a bond | NH | O | NH | T3a | OH |
| 1982 | CH | S | Q1j | a bond | H | a bond | NH | O | NH | T3b | OH |
| 1983 | CH | S | Q1j | a bond | H | a bond | NH | O | NH | T3c | OH |
| 1984 | CH | S | Q1j | a bond | H | a bond | NH | O | NH | T3d | OH |
| 1985 | CH | S | Q1j | a bond | H | a bond | NH | O | NH | T3e | OH |
| 1986 | CH | S | Q1j | a bond | H | a bond | NH | O | NH | T3f | OH |
| 1987 | CH | S | Q1j | a bond | H | a bond | NH | O | NH | T3g | OH |
| 1988 | CH | S | Q1j | a bond | H | a bond | NH | O | NH | T3h | OH |
| 1989 | CH | S | Q1j | a bond | H | a bond | NH | O | NH | T3i | OH |
| 1990 | CH | S | Q1j | a bond | H | a bond | NH | O | NH | T3j | OH |
| 1991 | CH | S | Q1j | a bond | H | a bond | NH | O | a bond | T3a | OH |
| 1992 | CH | S | Q1j | a bond | H | a bond | NH | O | a bond | T3b | OH |
| 1993 | CH | S | Q1j | a bond | H | a bond | NH | O | a bond | T3c | OH |
| 1994 | CH | S | Q1j | a bond | H | a bond | NH | O | a bond | T3d | OH |
| 1995 | CH | S | Q1j | a bond | H | a bond | NH | O | a bond | T3e | OH |
| 1996 | CH | S | Q1j | a bond | H | a bond | NH | O | a bond | T3f | OH |
| 1997 | CH | S | Q1j | a bond | H | a bond | NH | O | a bond | T3g | OH |
| 1998 | CH | S | Q1j | a bond | H | a bond | NH | O | a bond | T3h | OH |
| 1999 | CH | S | Q1j | a bond | H | a bond | NH | O | a bond | T3i | OH |

TABLE 2-continued

| No | A | B | R¹ | L¹ | R² | L² | L³ | Y | L⁴ | R³ | X |
|---|---|---|---|---|---|---|---|---|---|---|---|
| 2000 | CH | S | Q1j | a bond | H | a bond | NH | O | a bond | T3j | OH |
| 2001 | CH | O | Q1a | a bond | Me | a bond | NH | S | NH | T3a | OH |
| 2002 | CH | O | Q1a | a bond | Me | a bond | NH | S | NH | T3b | OH |
| 2003 | CH | O | Q1a | a bond | Me | a bond | NH | S | NH | T3c | OH |
| 2004 | CH | O | Q1a | a bond | Me | a bond | NH | S | NH | T3d | OH |
| 2005 | CH | O | Q1a | a bond | Me | a bond | NH | S | NH | T3e | OH |
| 2006 | CH | O | Q1a | a bond | Me | a bond | NH | S | NH | T3f | OH |
| 2007 | CH | O | Q1a | a bond | Me | a bond | NH | S | NH | T3g | OH |
| 2008 | CH | O | Q1a | a bond | Me | a bond | NH | S | NH | T3h | OH |
| 2009 | CH | O | Q1a | a bond | Me | a bond | NH | S | NH | T3i | OH |
| 2010 | CH | O | Q1a | a bond | Me | a bond | NH | S | NH | T3j | OH |
| 2011 | CH | O | Q1a | a bond | Me | a bond | NH | S | a bond | T3a | OH |
| 2012 | CH | O | Q1a | a bond | Me | a bond | NH | S | a bond | T3b | OH |
| 2013 | CH | O | Q1a | a bond | Me | a bond | NH | S | a bond | T3c | OH |
| 2014 | CH | O | Q1a | a bond | Me | a bond | NH | S | a bond | T3d | OH |
| 2015 | CH | O | Q1a | a bond | Me | a bond | NH | S | a bond | T3e | OH |
| 2016 | CH | O | Q1a | a bond | Me | a bond | NH | S | a bond | T3f | OH |
| 2017 | CH | O | Q1a | a bond | Me | a bond | NH | S | a bond | T3g | OH |
| 2018 | CH | O | Q1a | a bond | Me | a bond | NH | S | a bond | T3h | OH |
| 2019 | CH | O | Q1a | a bond | Me | a bond | NH | S | a bond | T3i | OH |
| 2020 | CH | O | Q1a | a bond | Me | a bond | NH | S | a bond | T3j | OH |
| 2021 | CH | O | Q1a | a bond | Me | a bond | NH | O | NH | T3a | OH |
| 2022 | CH | O | Q1a | a bond | Me | a bond | NH | O | NH | T3b | OH |
| 2023 | CH | O | Q1a | a bond | Me | a bond | NH | O | NH | T3c | OH |
| 2024 | CH | O | Q1a | a bond | Me | a bond | NH | O | NH | T3d | OH |
| 2025 | CH | O | Q1a | a bond | Me | a bond | NH | O | NH | T3e | OH |
| 2026 | CH | O | Q1a | a bond | Me | a bond | NH | O | NH | T3f | OH |
| 2027 | CH | O | Q1a | a bond | Me | a bond | NH | O | NH | T3g | OH |
| 2028 | CH | O | Q1a | a bond | Me | a bond | NH | O | NH | T3h | OH |
| 2029 | CH | O | Q1a | a bond | Me | a bond | NH | O | NH | T3i | OH |
| 2030 | CH | O | Q1a | a bond | Me | a bond | NH | O | NH | T3j | OH |
| 2031 | CH | O | Q1a | a bond | Me | a bond | NH | O | a bond | T3a | OH |
| 2032 | CH | O | Q1a | a bond | Me | a bond | NH | O | a bond | T3b | OH |
| 2033 | CH | O | Q1a | a bond | Me | a bond | NH | O | a bond | T3c | OH |
| 2034 | CH | O | Q1a | a bond | Me | a bond | NH | O | a bond | T3d | OH |
| 2035 | CH | O | Q1a | a bond | Me | a bond | NH | O | a bond | T3e | OH |
| 2036 | CH | O | Q1a | a bond | Me | a bond | NH | O | a bond | T3f | OH |
| 2037 | CH | O | Q1a | a bond | Me | a bond | NH | O | a bond | T3g | OH |
| 2038 | CH | O | Q1a | a bond | Me | a bond | NH | O | a bond | T3h | OH |
| 2039 | CH | O | Q1a | a bond | Me | a bond | NH | O | a bond | T3i | OH |
| 2040 | CH | O | Q1a | a bond | Me | a bond | NH | O | a bond | T3j | OH |
| 2041 | CH | O | Q1a | a bond | H | a bond | NH | S | NH | T3a | OH |
| 2042 | CH | O | Q1a | a bond | H | a bond | NH | S | NH | T3b | OH |
| 2043 | CH | O | Q1a | a bond | H | a bond | NH | S | NH | T3c | OH |
| 2044 | CH | O | Q1a | a bond | H | a bond | NH | S | NH | T3d | OH |
| 2045 | CH | O | Q1a | a bond | H | a bond | NH | S | NH | T3e | OH |
| 2046 | CH | O | Q1a | a bond | H | a bond | NH | S | NH | T3f | OH |
| 2047 | CH | O | Q1a | a bond | H | a bond | NH | S | NH | T3g | OH |
| 2048 | CH | O | Q1a | a bond | H | a bond | NH | S | NH | T3h | OH |
| 2049 | CH | O | Q1a | a bond | H | a bond | NH | S | NH | T3i | OH |
| 2050 | CH | O | Q1a | a bond | H | a bond | NH | S | NH | T3j | OH |
| 2051 | CH | O | Q1a | a bond | H | a bond | NH | S | a bond | T3a | OH |
| 2052 | CH | O | Q1a | a bond | H | a bond | NH | S | a bond | T3b | OH |
| 2053 | CH | O | Q1a | a bond | H | a bond | NH | S | a bond | T3c | OH |
| 2054 | CH | O | Q1a | a bond | H | a bond | NH | S | a bond | T3d | OH |
| 2055 | CH | O | Q1a | a bond | H | a bond | NH | S | a bond | T3e | OH |
| 2056 | CH | O | Q1a | a bond | H | a bond | NH | S | a bond | T3f | OH |
| 2057 | CH | O | Q1a | a bond | H | a bond | NH | S | a bond | T3g | OH |
| 2058 | CH | O | Q1a | a bond | H | a bond | NH | S | a bond | T3h | OH |
| 2059 | CH | O | Q1a | a bond | H | a bond | NH | S | a bond | T3i | OH |
| 2060 | CH | O | Q1a | a bond | H | a bond | NH | S | a bond | T3j | OH |
| 2061 | CH | O | Q1a | a bond | H | a bond | NH | O | NH | T3a | OH |
| 2062 | CH | O | Q1a | a bond | H | a bond | NH | O | NH | T3b | OH |
| 2063 | CH | O | Q1a | a bond | H | a bond | NH | O | NH | T3c | OH |
| 2064 | CH | O | Q1a | a bond | H | a bond | NH | O | NH | T3d | OH |
| 2065 | CH | O | Q1a | a bond | H | a bond | NH | O | NH | T3e | OH |
| 2066 | CH | O | Q1a | a bond | H | a bond | NH | O | NH | T3f | OH |
| 2067 | CH | O | Q1a | a bond | H | a bond | NH | O | NH | T3g | OH |
| 2068 | CH | O | Q1a | a bond | H | a bond | NH | O | NH | T3h | OH |
| 2069 | CH | O | Q1a | a bond | H | a bond | NH | O | NH | T3i | OH |
| 2070 | CH | O | Q1a | a bond | H | a bond | NH | O | NH | T3j | OH |
| 2071 | CH | O | Q1a | a bond | H | a bond | NH | O | a bond | T3a | OH |
| 2072 | CH | O | Q1a | a bond | H | a bond | NH | O | a bond | T3b | OH |
| 2073 | CH | O | Q1a | a bond | H | a bond | NH | O | a bond | T3c | OH |
| 2074 | CH | O | Q1a | a bond | H | a bond | NH | O | a bond | T3d | OH |
| 2075 | CH | O | Q1a | a bond | H | a bond | NH | O | a bond | T3e | OH |
| 2076 | CH | O | Q1a | a bond | H | a bond | NH | O | a bond | T3f | OH |
| 2077 | CH | O | Q1a | a bond | H | a bond | NH | O | a bond | T3g | OH |

TABLE 2-continued

| No | A | B | R¹ | L¹ | R² | L² | L³ | Y | L⁴ | R³ | X |
|---|---|---|---|---|---|---|---|---|---|---|---|
| 2078 | CH | O | Q1a | a bond | H | a bond | NH | O | a bond | T3h | OH |
| 2079 | CH | O | Q1a | a bond | H | a bond | NH | O | a bond | T3i | OH |
| 2080 | CH | O | Q1a | a bond | H | a bond | NH | O | a bond | T3j | OH |
| 2081 | CH | O | Q1b | a bond | Me | a bond | NH | S | NH | T3a | OH |
| 2082 | CH | O | Q1b | a bond | Me | a bond | NH | S | NH | T3b | OH |
| 2083 | CH | O | Q1b | a bond | Me | a bond | NH | S | NH | T3c | OH |
| 2084 | CH | O | Q1b | a bond | Me | a bond | NH | S | NH | T3d | OH |
| 2085 | CH | O | Q1b | a bond | Me | a bond | NH | S | NH | T3e | OH |
| 2086 | CH | O | Q1b | a bond | Me | a bond | NH | S | NH | T3f | OH |
| 2087 | CH | O | Q1b | a bond | Me | a bond | NH | S | NH | T3g | OH |
| 2088 | CH | O | Q1b | a bond | Me | a bond | NH | S | NH | T3h | OH |
| 2089 | CH | O | Q1b | a bond | Me | a bond | NH | S | NH | T3i | OH |
| 2090 | CH | O | Q1b | a bond | Me | a bond | NH | S | NH | T3j | OH |
| 2091 | CH | O | Q1b | a bond | Me | a bond | NH | S | a bond | T3a | OH |
| 2092 | CH | O | Q1b | a bond | Me | a bond | NH | S | a bond | T3b | OH |
| 2093 | CH | O | Q1b | a bond | Me | a bond | NH | S | a bond | T3c | OH |
| 2094 | CH | O | Q1b | a bond | Me | a bond | NH | S | a bond | T3d | OH |
| 2095 | CH | O | Q1b | a bond | Me | a bond | NH | S | a bond | T3e | OH |
| 2096 | CH | O | Q1b | a bond | Me | a bond | NH | S | a bond | T3f | OH |
| 2097 | CH | O | Q1b | a bond | Me | a bond | NH | S | a bond | T3g | OH |
| 2098 | CH | O | Q1b | a bond | Me | a bond | NH | S | a bond | T3h | OH |
| 2099 | CH | O | Q1b | a bond | Me | a bond | NH | S | a bond | T3i | OH |
| 2100 | CH | O | Q1b | a bond | Me | a bond | NH | S | a bond | T3j | OH |
| 2101 | CH | O | Q1b | a bond | Me | a bond | NH | O | NH | T3a | OH |
| 2102 | CH | O | Q1b | a bond | Me | a bond | NH | O | NH | T3b | OH |
| 2103 | CH | O | Q1b | a bond | Me | a bond | NH | O | NH | T3c | OH |
| 2104 | CH | O | Q1b | a bond | Me | a bond | NH | O | NH | T3d | OH |
| 2105 | CH | O | Q1b | a bond | Me | a bond | NH | O | NH | T3e | OH |
| 2106 | CH | O | Q1b | a bond | Me | a bond | NH | O | NH | T3f | OH |
| 2107 | CH | O | Q1b | a bond | Me | a bond | NH | O | NH | T3g | OH |
| 2108 | CH | O | Q1b | a bond | Me | a bond | NH | O | NH | T3h | OH |
| 2109 | CH | O | Q1b | a bond | Me | a bond | NH | O | NH | T3i | OH |
| 2110 | CH | O | Q1b | a bond | Me | a bond | NH | O | NH | T3j | OH |
| 2111 | CH | O | Q1b | a bond | Me | a bond | NH | O | a bond | T3a | OH |
| 2112 | CH | O | Q1b | a bond | Me | a bond | NH | O | a bond | T3b | OH |
| 2113 | CH | O | Q1b | a bond | Me | a bond | NH | O | a bond | T3c | OH |
| 2114 | CH | O | Q1b | a bond | Me | a bond | NH | O | a bond | T3d | OH |
| 2115 | CH | O | Q1b | a bond | Me | a bond | NH | O | a bond | T3e | OH |
| 2116 | CH | O | Q1b | a bond | Me | a bond | NH | O | a bond | T3f | OH |
| 2117 | CH | O | Q1b | a bond | Me | a bond | NH | O | a bond | T3g | OH |
| 2118 | CH | O | Q1b | a bond | Me | a bond | NH | O | a bond | T3h | OH |
| 2119 | CH | O | Q1b | a bond | Me | a bond | NH | O | a bond | T3i | OH |
| 2120 | CH | O | Q1b | a bond | Me | a bond | NH | O | a bond | T3j | OH |
| 2121 | CH | O | Q1b | a bond | H | a bond | NH | S | NH | T3a | OH |
| 2122 | CH | O | Q1b | a bond | H | a bond | NH | S | NH | T3b | OH |
| 2123 | CH | O | Q1b | a bond | H | a bond | NH | S | NH | T3c | OH |
| 2124 | CH | O | Q1b | a bond | H | a bond | NH | S | NH | T3d | OH |
| 2125 | CH | O | Q1b | a bond | H | a bond | NH | S | NH | T3e | OH |
| 2126 | CH | O | Q1b | a bond | H | a bond | NH | S | NH | T3f | OH |
| 2127 | CH | O | Q1b | a bond | H | a bond | NH | S | NH | T3g | OH |
| 2128 | CH | O | Q1b | a bond | H | a bond | NH | S | NH | T3h | OH |
| 2129 | CH | O | Q1b | a bond | H | a bond | NH | S | NH | T3i | OH |
| 2130 | CH | O | Q1b | a bond | H | a bond | NH | S | NH | T3j | OH |
| 2131 | CH | O | Q1b | a bond | H | a bond | NH | S | a bond | T3a | OH |
| 2132 | CH | O | Q1b | a bond | H | a bond | NH | S | a bond | T3b | OH |
| 2133 | CH | O | Q1b | a bond | H | a bond | NH | S | a bond | T3c | OH |
| 2134 | CH | O | Q1b | a bond | H | a bond | NH | S | a bond | T3d | OH |
| 2135 | CH | O | Q1b | a bond | H | a bond | NH | S | a bond | T3e | OH |
| 2136 | CH | O | Q1b | a bond | H | a bond | NH | S | a bond | T3f | OH |
| 2137 | CH | O | Q1b | a bond | H | a bond | NH | S | a bond | T3g | OH |
| 2138 | CH | O | Q1b | a bond | H | a bond | NH | S | a bond | T3h | OH |
| 2139 | CH | O | Q1b | a bond | H | a bond | NH | S | a bond | T3i | OH |
| 2140 | CH | O | Q1b | a bond | H | a bond | NH | S | a bond | T3j | OH |
| 2141 | CH | O | Q1b | a bond | H | a bond | NH | O | NH | T3a | OH |
| 2142 | CH | O | Q1b | a bond | H | a bond | NH | O | NH | T3b | OH |
| 2143 | CH | O | Q1b | a bond | H | a bond | NH | O | NH | T3c | OH |
| 2144 | CH | O | Q1b | a bond | H | a bond | NH | O | NH | T3d | OH |
| 2145 | CH | O | Q1b | a bond | H | a bond | NH | O | NH | T3e | OH |
| 2146 | CH | O | Q1b | a bond | H | a bond | NH | O | NH | T3f | OH |
| 2147 | CH | O | Q1b | a bond | H | a bond | NH | O | NH | T3g | OH |
| 2148 | CH | O | Q1b | a bond | H | a bond | NH | O | NH | T3h | OH |
| 2149 | CH | O | Q1b | a bond | H | a bond | NH | O | NH | T3i | OH |
| 2150 | CH | O | Q1b | a bond | H | a bond | NH | O | NH | T3j | OH |
| 2151 | CH | O | Q1b | a bond | H | a bond | NH | O | a bond | T3a | OH |
| 2152 | CH | O | Q1b | a bond | H | a bond | NH | O | a bond | T3b | OH |
| 2153 | CH | O | Q1b | a bond | H | a bond | NH | O | a bond | T3c | OH |
| 2154 | CH | O | Q1b | a bond | H | a bond | NH | O | a bond | T3d | OH |
| 2155 | CH | O | Q1b | a bond | H | a bond | NH | O | a bond | T3e | OH |

TABLE 2-continued

| No | A | B | R¹ | L¹ | R² | L² | L³ | Y | L⁴ | R³ | X |
|---|---|---|---|---|---|---|---|---|---|---|---|
| 2156 | CH | O | Q1b | a bond | H | a bond | NH | O | a bond | T3f | OH |
| 2157 | CH | O | Q1b | a bond | H | a bond | NH | O | a bond | T3g | OH |
| 2158 | CH | O | Q1b | a bond | H | a bond | NH | O | a bond | T3h | OH |
| 2159 | CH | O | Q1b | a bond | H | a bond | NH | O | a bond | T3i | OH |
| 2160 | CH | O | Q1b | a bond | H | a bond | NH | O | a bond | T3j | OH |
| 2161 | CH | O | Q1c | a bond | Me | a bond | NH | S | NH | T3a | OH |
| 2162 | CH | O | Q1c | a bond | Me | a bond | NH | S | NH | T3b | OH |
| 2163 | CH | O | Q1c | a bond | Me | a bond | NH | S | NH | T3c | OH |
| 2164 | CH | O | Q1c | a bond | Me | a bond | NH | S | NH | T3d | OH |
| 2165 | CH | O | Q1c | a bond | Me | a bond | NH | S | NH | T3e | OH |
| 2166 | CH | O | Q1c | a bond | Me | a bond | NH | S | NH | T3f | OH |
| 2167 | CH | O | Q1c | a bond | Me | a bond | NH | S | NH | T3g | OH |
| 2168 | CH | O | Q1c | a bond | Me | a bond | NH | S | NH | T3h | OH |
| 2169 | CH | O | Q1c | a bond | Me | a bond | NH | S | NH | T3i | OH |
| 2170 | CH | O | Q1c | a bond | Me | a bond | NH | S | NH | T3j | OH |
| 2171 | CH | O | Q1c | a bond | Me | a bond | NH | S | a bond | T3a | OH |
| 2172 | CH | O | Q1c | a bond | Me | a bond | NH | S | a bond | T3b | OH |
| 2173 | CH | O | Q1c | a bond | Me | a bond | NH | S | a bond | T3c | OH |
| 2174 | CH | O | Q1c | a bond | Me | a bond | NH | S | a bond | T3d | OH |
| 2175 | CH | O | Q1c | a bond | Me | a bond | NH | S | a bond | T3e | OH |
| 2176 | CH | O | Q1c | a bond | Me | a bond | NH | S | a bond | T3f | OH |
| 2177 | CH | O | Q1c | a bond | Me | a bond | NH | S | a bond | T3g | OH |
| 2178 | CH | O | Q1c | a bond | Me | a bond | NH | S | a bond | T3h | OH |
| 2179 | CH | O | Q1c | a bond | Me | a bond | NH | S | a bond | T3i | OH |
| 2180 | CH | O | Q1c | a bond | Me | a bond | NH | S | a bond | T3j | OH |
| 2181 | CH | O | Q1c | a bond | Me | a bond | NH | O | NH | T3a | OH |
| 2182 | CH | O | Q1c | a bond | Me | a bond | NH | O | NH | T3b | OH |
| 2183 | CH | O | Q1c | a bond | Me | a bond | NH | O | NH | T3c | OH |
| 2184 | CH | O | Q1c | a bond | Me | a bond | NH | O | NH | T3d | OH |
| 2185 | CH | O | Q1c | a bond | Me | a bond | NH | O | NH | T3e | OH |
| 2186 | CH | O | Q1c | a bond | Me | a bond | NH | O | NH | T3f | OH |
| 2187 | CH | O | Q1c | a bond | Me | a bond | NH | O | NH | T3g | OH |
| 2188 | CH | O | Q1c | a bond | Me | a bond | NH | O | NH | T3h | OH |
| 2189 | CH | O | Q1c | a bond | Me | a bond | NH | O | NH | T3i | OH |
| 2190 | CH | O | Q1c | a bond | Me | a bond | NH | O | NH | T3j | OH |
| 2191 | CH | O | Q1c | a bond | Me | a bond | NH | O | a bond | T3a | OH |
| 2192 | CH | O | Q1c | a bond | Me | a bond | NH | O | a bond | T3b | OH |
| 2193 | CH | O | Q1c | a bond | Me | a bond | NH | O | a bond | T3c | OH |
| 2194 | CH | O | Q1c | a bond | Me | a bond | NH | O | a bond | T3d | OH |
| 2195 | CH | O | Q1c | a bond | Me | a bond | NH | O | a bond | T3e | OH |
| 2196 | CH | O | Q1c | a bond | Me | a bond | NH | O | a bond | T3f | OH |
| 2197 | CH | O | Q1c | a bond | Me | a bond | NH | O | a bond | T3g | OH |
| 2198 | CH | O | Q1c | a bond | Me | a bond | NH | O | a bond | T3h | OH |
| 2199 | CH | O | Q1c | a bond | Me | a bond | NH | O | a bond | T3i | OH |
| 2200 | CH | O | Q1c | a bond | Me | a bond | NH | O | a bond | T3j | OH |
| 2201 | CH | O | Q1c | a bond | H | a bond | NH | S | NH | T3a | OH |
| 2202 | CH | O | Q1c | a bond | H | a bond | NH | S | NH | T3b | OH |
| 2203 | CH | O | Q1c | a bond | H | a bond | NH | S | NH | T3c | OH |
| 2204 | CH | O | Q1c | a bond | H | a bond | NH | S | NH | T3d | OH |
| 2205 | CH | O | Q1c | a bond | H | a bond | NH | S | NH | T3e | OH |
| 2206 | CH | O | Q1c | a bond | H | a bond | NH | S | NH | T3f | OH |
| 2207 | CH | O | Q1c | a bond | H | a bond | NH | S | NH | T3g | OH |
| 2208 | CH | O | Q1c | a bond | H | a bond | NH | S | NH | T3h | OH |
| 2209 | CH | O | Q1c | a bond | H | a bond | NH | S | NH | T3i | OH |
| 2210 | CH | O | Q1c | a bond | H | a bond | NH | S | NH | T3j | OH |
| 2211 | CH | O | Q1c | a bond | H | a bond | NH | S | a bond | T3a | OH |
| 2212 | CH | O | Q1c | a bond | H | a bond | NH | S | a bond | T3b | OH |
| 2213 | CH | O | Q1c | a bond | H | a bond | NH | S | a bond | T3c | OH |
| 2214 | CH | O | Q1c | a bond | H | a bond | NH | S | a bond | T3d | OH |
| 2215 | CH | O | Q1c | a bond | H | a bond | NH | S | a bond | T3e | OH |
| 2216 | CH | O | Q1c | a bond | H | a bond | NH | S | a bond | T3f | OH |
| 2217 | CH | O | Q1c | a bond | H | a bond | NH | S | a bond | T3g | OH |
| 2218 | CH | O | Q1c | a bond | H | a bond | NH | S | a bond | T3h | OH |
| 2219 | CH | O | Q1c | a bond | H | a bond | NH | S | a bond | T3i | OH |
| 2220 | CH | O | Q1c | a bond | H | a bond | NH | S | a bond | T3j | OH |
| 2221 | CH | O | Q1c | a bond | H | a bond | NH | O | NH | T3a | OH |
| 2222 | CH | O | Q1c | a bond | H | a bond | NH | O | NH | T3b | OH |
| 2223 | CH | O | Q1c | a bond | H | a bond | NH | O | NH | T3c | OH |
| 2224 | CH | O | Q1c | a bond | H | a bond | NH | O | NH | T3d | OH |
| 2225 | CH | O | Q1c | a bond | H | a bond | NH | O | NH | T3e | OH |
| 2226 | CH | O | Q1c | a bond | H | a bond | NH | O | NH | T3f | OH |
| 2227 | CH | O | Q1c | a bond | H | a bond | NH | O | NH | T3g | OH |
| 2228 | CH | O | Q1c | a bond | H | a bond | NH | O | NH | T3h | OH |
| 2229 | CH | O | Q1c | a bond | H | a bond | NH | O | NH | T3i | OH |
| 2230 | CH | O | Q1c | a bond | H | a bond | NH | O | NH | T3j | OH |
| 2231 | CH | O | Q1c | a bond | H | a bond | NH | O | a bond | T3a | OH |
| 2232 | CH | O | Q1c | a bond | H | a bond | NH | O | a bond | T3b | OH |
| 2233 | CH | O | Q1c | a bond | H | a bond | NH | O | a bond | T3c | OH |

TABLE 2-continued

| No | A | B | R¹ | L¹ | R² | L² | L³ | Y | L⁴ | R³ | X |
|---|---|---|---|---|---|---|---|---|---|---|---|
| 2234 | CH | O | Q1c | a bond | H | a bond | NH | O | a bond | T3d | OH |
| 2235 | CH | O | Q1c | a bond | H | a bond | NH | O | a bond | T3e | OH |
| 2236 | CH | O | Q1c | a bond | H | a bond | NH | O | a bond | T3f | OH |
| 2237 | CH | O | Q1c | a bond | H | a bond | NH | O | a bond | T3g | OH |
| 2238 | CH | O | Q1c | a bond | H | a bond | NH | O | a bond | T3h | OH |
| 2239 | CH | O | Q1c | a bond | H | a bond | NH | O | a bond | T3i | OH |
| 2240 | CH | O | Q1c | a bond | H | a bond | NH | O | a bond | T3j | OH |
| 2241 | CH | O | Q1i | a bond | Me | a bond | NH | S | NH | T3a | OH |
| 2242 | CH | O | Q1i | a bond | Me | a bond | NH | S | NH | T3b | OH |
| 2243 | CH | O | Q1i | a bond | Me | a bond | NH | S | NH | T3c | OH |
| 2244 | CH | O | Q1i | a bond | Me | a bond | NH | S | NH | T3d | OH |
| 2245 | CH | O | Q1i | a bond | Me | a bond | NH | S | NH | T3e | OH |
| 2246 | CH | O | Q1i | a bond | Me | a bond | NH | S | NH | T3f | OH |
| 2247 | CH | O | Q1i | a bond | Me | a bond | NH | S | NH | T3g | OH |
| 2248 | CH | O | Q1i | a bond | Me | a bond | NH | S | NH | T3h | OH |
| 2249 | CH | O | Q1i | a bond | Me | a bond | NH | S | NH | T3i | OH |
| 2250 | CH | O | Q1i | a bond | Me | a bond | NH | S | NH | T3j | OH |
| 2251 | CH | O | Q1i | a bond | Me | a bond | NH | S | a bond | T3a | OH |
| 2252 | CH | O | Q1i | a bond | Me | a bond | NH | S | a bond | T3b | OH |
| 2253 | CH | O | Q1i | a bond | Me | a bond | NH | S | a bond | T3c | OH |
| 2254 | CH | O | Q1i | a bond | Me | a bond | NH | S | a bond | T3d | OH |
| 2255 | CH | O | Q1i | a bond | Me | a bond | NH | S | a bond | T3e | OH |
| 2256 | CH | O | Q1i | a bond | Me | a bond | NH | S | a bond | T3f | OH |
| 2257 | CH | O | Q1i | a bond | Me | a bond | NH | S | a bond | T3g | OH |
| 2258 | CH | O | Q1i | a bond | Me | a bond | NH | S | a bond | T3h | OH |
| 2259 | CH | O | Q1i | a bond | Me | a bond | NH | S | a bond | T3i | OH |
| 2260 | CH | O | Q1i | a bond | Me | a bond | NH | S | a bond | T3j | OH |
| 2261 | CH | O | Q1i | a bond | Me | a bond | NH | O | NH | T3a | OH |
| 2262 | CH | O | Q1i | a bond | Me | a bond | NH | O | NH | T3b | OH |
| 2263 | CH | O | Q1i | a bond | Me | a bond | NH | O | NH | T3c | OH |
| 2264 | CH | O | Q1i | a bond | Me | a bond | NH | O | NH | T3d | OH |
| 2265 | CH | O | Q1i | a bond | Me | a bond | NH | O | NH | T3e | OH |
| 2266 | CH | O | Q1i | a bond | Me | a bond | NH | O | NH | T3f | OH |
| 2267 | CH | O | Q1i | a bond | Me | a bond | NH | O | NH | T3g | OH |
| 2268 | CH | O | Q1i | a bond | Me | a bond | NH | O | NH | T3h | OH |
| 2269 | CH | O | Q1i | a bond | Me | a bond | NH | O | NH | T3i | OH |
| 2270 | CH | O | Q1i | a bond | Me | a bond | NH | O | NH | T3j | OH |
| 2271 | CH | O | Q1i | a bond | Me | a bond | NH | O | a bond | T3a | OH |
| 2272 | CH | O | Q1i | a bond | Me | a bond | NH | O | a bond | T3b | OH |
| 2273 | CH | O | Q1i | a bond | Me | a bond | NH | O | a bond | T3c | OH |
| 2274 | CH | O | Q1i | a bond | Me | a bond | NH | O | a bond | T3d | OH |
| 2275 | CH | O | Q1i | a bond | Me | a bond | NH | O | a bond | T3e | OH |
| 2276 | CH | O | Q1i | a bond | Me | a bond | NH | O | a bond | T3f | OH |
| 2277 | CH | O | Q1i | a bond | Me | a bond | NH | O | a bond | T3g | OH |
| 2278 | CH | O | Q1i | a bond | Me | a bond | NH | O | a bond | T3h | OH |
| 2279 | CH | O | Q1i | a bond | Me | a bond | NH | O | a bond | T3i | OH |
| 2280 | CH | O | Q1i | a bond | Me | a bond | NH | O | a bond | T3j | OH |
| 2281 | CH | O | Q1i | a bond | H | a bond | NH | S | NH | T3a | OH |
| 2282 | CH | O | Q1i | a bond | H | a bond | NH | S | NH | T3b | OH |
| 2283 | CH | O | Q1i | a bond | H | a bond | NH | S | NH | T3c | OH |
| 2284 | CH | O | Q1i | a bond | H | a bond | NH | S | NH | T3d | OH |
| 2285 | CH | O | Q1i | a bond | H | a bond | NH | S | NH | T3e | OH |
| 2286 | CH | O | Q1i | a bond | H | a bond | NH | S | NH | T3f | OH |
| 2287 | CH | O | Q1i | a bond | H | a bond | NH | S | NH | T3g | OH |
| 2288 | CH | O | Q1i | a bond | H | a bond | NH | S | NH | T3h | OH |
| 2289 | CH | O | Q1i | a bond | H | a bond | NH | S | NH | T3i | OH |
| 2290 | CH | O | Q1i | a bond | H | a bond | NH | S | NH | T3j | OH |
| 2291 | CH | O | Q1i | a bond | H | a bond | NH | S | a bond | T3a | OH |
| 2292 | CH | O | Q1i | a bond | H | a bond | NH | S | a bond | T3b | OH |
| 2293 | CH | O | Q1i | a bond | H | a bond | NH | S | a bond | T3c | OH |
| 2294 | CH | O | Q1i | a bond | H | a bond | NH | S | a bond | T3d | OH |
| 2295 | CH | O | Q1i | a bond | H | a bond | NH | S | a bond | T3e | OH |
| 2296 | CH | O | Q1i | a bond | H | a bond | NH | S | a bond | T3f | OH |
| 2297 | CH | O | Q1i | a bond | H | a bond | NH | S | a bond | T3g | OH |
| 2298 | CH | O | Q1i | a bond | H | a bond | NH | S | a bond | T3h | OH |
| 2299 | CH | O | Q1i | a bond | H | a bond | NH | S | a bond | T3i | OH |
| 2300 | CH | O | Q1i | a bond | H | a bond | NH | S | a bond | T3j | OH |
| 2301 | CH | O | Q1i | a bond | H | a bond | NH | O | NH | T3a | OH |
| 2302 | CH | O | Q1i | a bond | H | a bond | NH | O | NH | T3b | OH |
| 2303 | CH | O | Q1i | a bond | H | a bond | NH | O | NH | T3c | OH |
| 2304 | CH | O | Q1i | a bond | H | a bond | NH | O | NH | T3d | OH |
| 2305 | CH | O | Q1i | a bond | H | a bond | NH | O | NH | T3e | OH |
| 2306 | CH | O | Q1i | a bond | H | a bond | NH | O | NH | T3f | OH |
| 2307 | CH | O | Q1i | a bond | H | a bond | NH | O | NH | T3g | OH |
| 2308 | CH | O | Q1i | a bond | H | a bond | NH | O | NH | T3h | OH |
| 2309 | CH | O | Q1i | a bond | H | a bond | NH | O | NH | T3i | OH |
| 2310 | CH | O | Q1i | a bond | H | a bond | NH | O | NH | T3j | OH |
| 2311 | CH | O | Q1i | a bond | H | a bond | NH | O | a bond | T3a | OH |

TABLE 2-continued

| No | A | B | R¹ | L¹ | R² | L² | L³ | Y | L⁴ | R³ | X |
|---|---|---|---|---|---|---|---|---|---|---|---|
| 2312 | CH | O | Q1i | a bond | H | a bond | NH | O | a bond | T3b | OH |
| 2313 | CH | O | Q1i | a bond | H | a bond | NH | O | a bond | T3c | OH |
| 2314 | CH | O | Q1i | a bond | H | a bond | NH | O | a bond | T3d | OH |
| 2315 | CH | O | Q1i | a bond | H | a bond | NH | O | a bond | T3e | OH |
| 2316 | CH | O | Q1i | a bond | H | a bond | NH | O | a bond | T3f | OH |
| 2317 | CH | O | Q1i | a bond | H | a bond | NH | O | a bond | T3g | OH |
| 2318 | CH | O | Q1i | a bond | H | a bond | NH | O | a bond | T3h | OH |
| 2319 | CH | O | Q1i | a bond | H | a bond | NH | O | a bond | T3i | OH |
| 2320 | CH | O | Q1i | a bond | H | a bond | NH | O | a bond | T3j | OH |
| 2321 | CH | O | Q1j | a bond | Me | a bond | NH | S | NH | T3a | OH |
| 2322 | CH | O | Q1j | a bond | Me | a bond | NH | S | NH | T3b | OH |
| 2323 | CH | O | Q1j | a bond | Me | a bond | NH | S | NH | T3c | OH |
| 2324 | CH | O | Q1j | a bond | Me | a bond | NH | S | NH | T3d | OH |
| 2325 | CH | O | Q1j | a bond | Me | a bond | NH | S | NH | T3e | OH |
| 2326 | CH | O | Q1j | a bond | Me | a bond | NH | S | NH | T3f | OH |
| 2327 | CH | O | Q1j | a bond | Me | a bond | NH | S | NH | T3g | OH |
| 2328 | CH | O | Q1j | a bond | Me | a bond | NH | S | NH | T3h | OH |
| 2329 | CH | O | Q1j | a bond | Me | a bond | NH | S | NH | T3i | OH |
| 2330 | CH | O | Q1j | a bond | Me | a bond | NH | S | NH | T3j | OH |
| 2331 | CH | O | Q1j | a bond | Me | a bond | NH | S | a bond | T3a | OH |
| 2332 | CH | O | Q1j | a bond | Me | a bond | NH | S | a bond | T3b | OH |
| 2333 | CH | O | Q1j | a bond | Me | a bond | NH | S | a bond | T3c | OH |
| 2334 | CH | O | Q1j | a bond | Me | a bond | NH | S | a bond | T3d | OH |
| 2335 | CH | O | Q1j | a bond | Me | a bond | NH | S | a bond | T3e | OH |
| 2336 | CH | O | Q1j | a bond | Me | a bond | NH | S | a bond | T3f | OH |
| 2337 | CH | O | Q1j | a bond | Me | a bond | NH | S | a bond | T3g | OH |
| 2338 | CH | O | Q1j | a bond | Me | a bond | NH | S | a bond | T3h | OH |
| 2339 | CH | O | Q1j | a bond | Me | a bond | NH | S | a bond | T3i | OH |
| 2340 | CH | O | Q1j | a bond | Me | a bond | NH | S | a bond | T3j | OH |
| 2341 | CH | O | Q1j | a bond | Me | a bond | NH | O | NH | T3a | OH |
| 2342 | CH | O | Q1j | a bond | Me | a bond | NH | O | NH | T3b | OH |
| 2343 | CH | O | Q1j | a bond | Me | a bond | NH | O | NH | T3c | OH |
| 2344 | CH | O | Q1j | a bond | Me | a bond | NH | O | NH | T3d | OH |
| 2345 | CH | O | Q1j | a bond | Me | a bond | NH | O | NH | T3e | OH |
| 2346 | CH | O | Q1j | a bond | Me | a bond | NH | O | NH | T3f | OH |
| 2347 | CH | O | Q1j | a bond | Me | a bond | NH | O | NH | T3g | OH |
| 2348 | CH | O | Q1j | a bond | Me | a bond | NH | O | NH | T3h | OH |
| 2349 | CH | O | Q1j | a bond | Me | a bond | NH | O | NH | T3i | OH |
| 2350 | CH | O | Q1j | a bond | Me | a bond | NH | O | NH | T3j | OH |
| 2351 | CH | O | Q1j | a bond | Me | a bond | NH | O | a bond | T3a | OH |
| 2352 | CH | O | Q1j | a bond | Me | a bond | NH | O | a bond | T3b | OH |
| 2353 | CH | O | Q1j | a bond | Me | a bond | NH | O | a bond | T3c | OH |
| 2354 | CH | O | Q1j | a bond | Me | a bond | NH | O | a bond | T3d | OH |
| 2355 | CH | O | Q1j | a bond | Me | a bond | NH | O | a bond | T3e | OH |
| 2356 | CH | O | Q1j | a bond | Me | a bond | NH | O | a bond | T3f | OH |
| 2357 | CH | O | Q1j | a bond | Me | a bond | NH | O | a bond | T3g | OH |
| 2358 | CH | O | Q1j | a bond | Me | a bond | NH | O | a bond | T3h | OH |
| 2359 | CH | O | Q1j | a bond | Me | a bond | NH | O | a bond | T3i | OH |
| 2360 | CH | O | Q1j | a bond | Me | a bond | NH | O | a bond | T3j | OH |
| 2361 | CH | O | Q1j | a bond | H | a bond | NH | S | NH | T3a | OH |
| 2362 | CH | O | Q1j | a bond | H | a bond | NH | S | NH | T3b | OH |
| 2363 | CH | O | Q1j | a bond | H | a bond | NH | S | NH | T3c | OH |
| 2364 | CH | O | Q1j | a bond | H | a bond | NH | S | NH | T3d | OH |
| 2365 | CH | O | Q1j | a bond | H | a bond | NH | S | NH | T3e | OH |
| 2366 | CH | O | Q1j | a bond | H | a bond | NH | S | NH | T3f | OH |
| 2367 | CH | O | Q1j | a bond | H | a bond | NH | S | NH | T3g | OH |
| 2368 | CH | O | Q1j | a bond | H | a bond | NH | S | NH | T3h | OH |
| 2369 | CH | O | Q1j | a bond | H | a bond | NH | S | NH | T3i | OH |
| 2370 | CH | O | Q1j | a bond | H | a bond | NH | S | NH | T3j | OH |
| 2371 | CH | O | Q1j | a bond | H | a bond | NH | S | a bond | T3a | OH |
| 2372 | CH | O | Q1j | a bond | H | a bond | NH | S | a bond | T3b | OH |
| 2373 | CH | O | Q1j | a bond | H | a bond | NH | S | a bond | T3c | OH |
| 2374 | CH | O | Q1j | a bond | H | a bond | NH | S | a bond | T3d | OH |
| 2375 | CH | O | Q1j | a bond | H | a bond | NH | S | a bond | T3e | OH |
| 2376 | CH | O | Q1j | a bond | H | a bond | NH | S | a bond | T3f | OH |
| 2377 | CH | O | Q1j | a bond | H | a bond | NH | S | a bond | T3g | OH |
| 2378 | CH | O | Q1j | a bond | H | a bond | NH | S | a bond | T3h | OH |
| 2379 | CH | O | Q1j | a bond | H | a bond | NH | S | a bond | T3i | OH |
| 2380 | CH | O | Q1j | a bond | H | a bond | NH | S | a bond | T3j | OH |
| 2381 | CH | O | Q1j | a bond | H | a bond | NH | O | NH | T3a | OH |
| 2382 | CH | O | Q1j | a bond | H | a bond | NH | O | NH | T3b | OH |
| 2383 | CH | O | Q1j | a bond | H | a bond | NH | O | NH | T3c | OH |
| 2384 | CH | O | Q1j | a bond | H | a bond | NH | O | NH | T3d | OH |
| 2385 | CH | O | Q1j | a bond | H | a bond | NH | O | NH | T3e | OH |
| 2386 | CH | O | Q1j | a bond | H | a bond | NH | O | NH | T3f | OH |
| 2387 | CH | O | Q1j | a bond | H | a bond | NH | O | NH | T3g | OH |
| 2388 | CH | O | Q1j | a bond | H | a bond | NH | O | NH | T3h | OH |
| 2389 | CH | O | Q1j | a bond | H | a bond | NH | O | NH | T3i | OH |

TABLE 2-continued

| No | A | B | R¹ | L¹ | R² | L² | L³ | Y | L⁴ | R³ | X |
|---|---|---|---|---|---|---|---|---|---|---|---|
| 2390 | CH | O | Q1j | a bond | H | a bond | NH | O | NH | T3j | OH |
| 2391 | CH | O | Q1j | a bond | H | a bond | NH | O | a bond | T3a | OH |
| 2392 | CH | O | Q1j | a bond | H | a bond | NH | O | a bond | T3b | OH |
| 2393 | CH | O | Q1j | a bond | H | a bond | NH | O | a bond | T3c | OH |
| 2394 | CH | O | Q1j | a bond | H | a bond | NH | O | a bond | T3d | OH |
| 2395 | CH | O | Q1j | a bond | H | a bond | NH | O | a bond | T3e | OH |
| 2396 | CH | O | Q1j | a bond | H | a bond | NH | O | a bond | T3f | OH |
| 2397 | CH | O | Q1j | a bond | H | a bond | NH | O | a bond | T3g | OH |
| 2398 | CH | O | Q1j | a bond | H | a bond | NH | O | a bond | T3h | OH |
| 2399 | CH | O | Q1j | a bond | H | a bond | NH | O | a bond | T3i | OH |
| 2400 | CH | O | Q1j | a bond | H | a bond | NH | O | a bond | T3j | OH |
| 2401 | CMe | NMe | Q1a | a bond | Me | a bond | NH | S | NH | T3a | OH |
| 2402 | CMe | NMe | Q1a | a bond | Me | a bond | NH | S | NH | T3b | OH |
| 2403 | CMe | NMe | Q1a | a bond | Me | a bond | NH | S | NH | T3c | OH |
| 2404 | CMe | NMe | Q1a | a bond | Me | a bond | NH | S | NH | T3d | OH |
| 2405 | CMe | NMe | Q1a | a bond | Me | a bond | NH | S | NH | T3e | OH |
| 2406 | CMe | NMe | Q1a | a bond | Me | a bond | NH | S | NH | T3f | OH |
| 2407 | CMe | NMe | Q1a | a bond | Me | a bond | NH | S | NH | T3g | OH |
| 2408 | CMe | NMe | Q1a | a bond | Me | a bond | NH | S | NH | T3h | OH |
| 2409 | CMe | NMe | Q1a | a bond | Me | a bond | NH | S | NH | T3i | OH |
| 2410 | CMe | NMe | Q1a | a bond | Me | a bond | NH | S | NH | T3j | OH |
| 2411 | CMe | NMe | Q1a | a bond | Me | a bond | NH | S | a bond | T3a | OH |
| 2412 | CMe | NMe | Q1a | a bond | Me | a bond | NH | S | a bond | T3b | OH |
| 2413 | CMe | NMe | Q1a | a bond | Me | a bond | NH | S | a bond | T3c | OH |
| 2414 | CMe | NMe | Q1a | a bond | Me | a bond | NH | S | a bond | T3d | OH |
| 2415 | CMe | NMe | Q1a | a bond | Me | a bond | NH | S | a bond | T3e | OH |
| 2416 | CMe | NMe | Q1a | a bond | Me | a bond | NH | S | a bond | T3f | OH |
| 2417 | CMe | NMe | Q1a | a bond | Me | a bond | NH | S | a bond | T3g | OH |
| 2418 | CMe | NMe | Q1a | a bond | Me | a bond | NH | S | a bond | T3h | OH |
| 2419 | CMe | NMe | Q1a | a bond | Me | a bond | NH | S | a bond | T3i | OH |
| 2420 | CMe | NMe | Q1a | a bond | Me | a bond | NH | S | a bond | T3j | OH |
| 2421 | CMe | NMe | Q1a | a bond | Me | a bond | NH | O | NH | T3a | OH |
| 2422 | CMe | NMe | Q1a | a bond | Me | a bond | NH | O | NH | T3b | OH |
| 2423 | CMe | NMe | Q1a | a bond | Me | a bond | NH | O | NH | T3c | OH |
| 2424 | CMe | NMe | Q1a | a bond | Me | a bond | NH | O | NH | T3d | OH |
| 2425 | CMe | NMe | Q1a | a bond | Me | a bond | NH | O | NH | T3e | OH |
| 2426 | CMe | NMe | Q1a | a bond | Me | a bond | NH | O | NH | T3f | OH |
| 2427 | CMe | NMe | Q1a | a bond | Me | a bond | NH | O | NH | T3g | OH |
| 2428 | CMe | NMe | Q1a | a bond | Me | a bond | NH | O | NH | T3h | OH |
| 2429 | CMe | NMe | Q1a | a bond | Me | a bond | NH | O | NH | T3i | OH |
| 2430 | CMe | NMe | Q1a | a bond | Me | a bond | NH | O | NH | T3j | OH |
| 2431 | CMe | NMe | Q1a | a bond | Me | a bond | NH | O | a bond | T3a | OH |
| 2432 | CMe | NMe | Q1a | a bond | Me | a bond | NH | O | a bond | T3b | OH |
| 2433 | CMe | NMe | Q1a | a bond | Me | a bond | NH | O | a bond | T3c | OH |
| 2434 | CMe | NMe | Q1a | a bond | Me | a bond | NH | O | a bond | T3d | OH |
| 2435 | CMe | NMe | Q1a | a bond | Me | a bond | NH | O | a bond | T3e | OH |
| 2436 | CMe | NMe | Q1a | a bond | Me | a bond | NH | O | a bond | T3f | OH |
| 2437 | CMe | NMe | Q1a | a bond | Me | a bond | NH | O | a bond | T3g | OH |
| 2438 | CMe | NMe | Q1a | a bond | Me | a bond | NH | O | a bond | T3h | OH |
| 2439 | CMe | NMe | Q1a | a bond | Me | a bond | NH | O | a bond | T3i | OH |
| 2440 | CMe | NMe | Q1a | a bond | Me | a bond | NH | O | a bond | T3j | OH |
| 2441 | CMe | NMe | Q1a | a bond | H | a bond | NH | S | NH | T3a | OH |
| 2442 | CMe | NMe | Q1a | a bond | H | a bond | NH | S | NH | T3b | OH |
| 2443 | CMe | NMe | Q1a | a bond | H | a bond | NH | S | NH | T3c | OH |
| 2444 | CMe | NMe | Q1a | a bond | H | a bond | NH | S | NH | T3d | OH |
| 2445 | CMe | NMe | Q1a | a bond | H | a bond | NH | S | NH | T3e | OH |
| 2446 | CMe | NMe | Q1a | a bond | H | a bond | NH | S | NH | T3f | OH |
| 2447 | CMe | NMe | Q1a | a bond | H | a bond | NH | S | NH | T3g | OH |
| 2448 | CMe | NMe | Q1a | a bond | H | a bond | NH | S | NH | T3h | OH |
| 2449 | CMe | NMe | Q1a | a bond | H | a bond | NH | S | NH | T3i | OH |
| 2450 | CMe | NMe | Q1a | a bond | H | a bond | NH | S | NH | T3j | OH |
| 2451 | CMe | NMe | Q1a | a bond | H | a bond | NH | S | a bond | T3a | OH |
| 2452 | CMe | NMe | Q1a | a bond | H | a bond | NH | S | a bond | T3b | OH |
| 2453 | CMe | NMe | Q1a | a bond | H | a bond | NH | S | a bond | T3c | OH |
| 2454 | CMe | NMe | Q1a | a bond | H | a bond | NH | S | a bond | T3d | OH |
| 2455 | CMe | NMe | Q1a | a bond | H | a bond | NH | S | a bond | T3e | OH |
| 2456 | CMe | NMe | Q1a | a bond | H | a bond | NH | S | a bond | T3f | OH |
| 2457 | CMe | NMe | Q1a | a bond | H | a bond | NH | S | a bond | T3g | OH |
| 2458 | CMe | NMe | Q1a | a bond | H | a bond | NH | S | a bond | T3h | OH |
| 2459 | CMe | NMe | Q1a | a bond | H | a bond | NH | S | a bond | T3i | OH |
| 2460 | CHe | NMe | Q1a | a bond | H | a bond | NH | S | a bond | T3j | OH |
| 2461 | CMe | NMe | Q1a | a bond | H | a bond | NH | O | NH | T3a | OH |
| 2462 | CMe | NMe | Q1a | a bond | H | a bond | NH | O | NH | T3b | OH |
| 2463 | CMe | NMe | Q1a | a bond | H | a bond | NH | O | NH | T3c | OH |
| 2464 | CMe | NMe | Q1a | a bond | H | a bond | NH | O | NH | T3d | OH |
| 2465 | CMe | NMe | Q1a | a bond | H | a bond | NH | O | NH | T3e | OH |
| 2466 | CMe | NMe | Q1a | a bond | H | a bond | NH | O | NH | T3f | OH |
| 2467 | CMe | NMe | Q1a | a bond | H | a bond | NH | O | NH | T3g | OH |

TABLE 2-continued

| No | A | B | R¹ | L¹ | R² | L² | L³ | Y | L⁴ | R³ | X |
|---|---|---|---|---|---|---|---|---|---|---|---|
| 2468 | CMe | NMe | Q1a | a bond | H | a bond | NH | O | NH | T3h | OH |
| 2469 | CMe | NMe | Q1a | a bond | H | a bond | NH | O | NH | T3i | OH |
| 2470 | CMe | NMe | Q1a | a bond | H | a bond | NH | O | NH | T3j | OH |
| 2471 | CMe | NMe | Q1a | a bond | H | a bond | NH | O | a bond | T3a | OH |
| 2472 | CMe | NMe | Q1a | a bond | H | a bond | NH | O | a bond | T3b | OH |
| 2473 | CMe | NMe | Q1a | a bond | H | a bond | NH | O | a bond | T3c | OH |
| 2474 | CMe | NMe | Q1a | a bond | H | a bond | NH | O | a bond | T3d | OH |
| 2475 | CMe | NMe | Q1a | a bond | H | a bond | NH | O | a bond | T3e | OH |
| 2476 | CMe | NMe | Q1a | a bond | H | a bond | NH | O | a bond | T3f | OH |
| 2477 | CMe | NMe | Q1a | a bond | H | a bond | NH | O | a bond | T3g | OH |
| 2478 | CMe | NMe | Q1a | a bond | H | a bond | NH | O | a bond | T3h | OH |
| 2479 | CMe | NMe | Q1a | a bond | H | a bond | NH | O | a bond | T3i | OH |
| 2480 | CMe | NMe | Q1a | a bond | H | a bond | NH | O | a bond | T3j | OH |
| 2481 | CMe | NMe | Q1b | a bond | Me | a bond | NH | S | NH | T3a | OH |
| 2482 | CMe | NMe | Q1b | a bond | Me | a bond | NH | S | NH | T3b | OH |
| 2483 | CMe | NMe | Q1b | a bond | Me | a bond | NH | S | NH | T3c | OH |
| 2484 | CMe | NMe | Q1b | a bond | Me | a bond | NH | S | NH | T3d | OH |
| 2485 | CMe | NMe | Q1b | a bond | Me | a bond | NH | S | NH | T3e | OH |
| 2486 | CMe | NMe | Q1b | a bond | Me | a bond | NH | S | NH | T3f | OH |
| 2487 | CMe | NMe | Q1b | a bond | Me | a bond | NH | S | NH | T3g | OH |
| 2488 | CMe | NMe | Q1b | a bond | Me | a bond | NH | S | NH | T3h | OH |
| 2489 | CMe | NMe | Q1b | a bond | Me | a bond | NH | S | NH | T3i | OH |
| 2490 | CMe | NMe | Q1b | a bond | Me | a bond | NH | S | NH | T3j | OH |
| 2491 | CMe | NMe | Q1b | a bond | Me | a bond | NH | S | a bond | T3a | OH |
| 2492 | CMe | NMe | Q1b | a bond | Me | a bond | NH | S | a bond | T3b | OH |
| 2493 | CMe | NMe | Q1b | a bond | Me | a bond | NH | S | a bond | T3c | OH |
| 2494 | CMe | NMe | Q1b | a bond | Me | a bond | NH | S | a bond | T3d | OH |
| 2495 | CMe | NMe | Q1b | a bond | Me | a bond | NH | S | a bond | T3e | OH |
| 2496 | CMe | NMe | Q1b | a bond | Me | a bond | NH | S | a bond | T3f | OH |
| 2497 | CMe | NMe | Q1b | a bond | Me | a bond | NH | S | a bond | T3g | OH |
| 2498 | CMe | NMe | Q1b | a bond | Me | a bond | NH | S | a bond | T3h | OH |
| 2499 | CMe | NMe | Q1b | a bond | Me | a bond | NH | S | a bond | T3i | OH |
| 2500 | CMe | NMe | Q1b | a bond | Me | a bond | NH | S | a bond | T3j | OH |
| 2501 | CMe | NMe | Q1b | a bond | Me | a bond | NH | O | NH | T3a | OH |
| 2502 | CMe | NMe | Q1b | a bond | Me | a bond | NH | O | NH | T3b | OH |
| 2503 | CMe | NMe | Q1b | a bond | Me | a bond | NH | O | NH | T3c | OH |
| 2504 | CMe | NMe | Q1b | a bond | Me | a bond | NH | O | NH | T3d | OH |
| 2505 | CMe | NMe | Q1b | a bond | Me | a bond | NH | O | NH | T3e | OH |
| 2506 | CMe | NMe | Q1b | a bond | Me | a bond | NH | O | NH | T3f | OH |
| 2507 | CMe | NMe | Q1b | a bond | Me | a bond | NH | O | NH | T3g | OH |
| 2508 | CMe | NMe | Q1b | a bond | Me | a bond | NH | O | NH | T3h | OH |
| 2509 | CMe | NMe | Q1b | a bond | Me | a bond | NH | O | NH | T3i | OH |
| 2510 | CMe | NMe | Q1b | a bond | Me | a bond | NH | O | NH | T3j | OH |
| 2511 | CMe | NMe | Q1b | a bond | Me | a bond | NH | O | a bond | T3a | OH |
| 2512 | CMe | NMe | Q1b | a bond | Me | a bond | NH | O | a bond | T3b | OH |
| 2513 | CMe | NMe | Q1b | a bond | Me | a bond | NH | O | a bond | T3c | OH |
| 2514 | CMe | NMe | Q1b | a bond | Me | a bond | NH | O | a bond | T3d | OH |
| 2515 | CMe | NMe | Q1b | a bond | Me | a bond | NH | O | a bond | T3e | OH |
| 2516 | CMe | NMe | Q1b | a bond | Me | a bond | NH | O | a bond | T3f | OH |
| 2517 | CMe | NMe | Q1b | a bond | Me | a bond | NH | O | a bond | T3g | OH |
| 2518 | CMe | NMe | Q1b | a bond | Me | a bond | NH | O | a bond | T3h | OH |
| 2519 | CMe | NMe | Q1b | a bond | Me | a bond | NH | O | a bond | T3i | OH |
| 2520 | CMe | NMe | Q1b | a bond | Me | a bond | NH | O | a bond | T3j | OH |
| 2521 | CMe | NMe | Q1b | a bond | H | a bond | NH | S | NH | T3a | OH |
| 2522 | CMe | NMe | Q1b | a bond | H | a bond | NH | S | NH | T3b | OH |
| 2523 | CMe | NMe | Q1b | a bond | H | a bond | NH | S | NH | T3c | OH |
| 2524 | CMe | NMe | Q1b | a bond | H | a bond | NH | S | NH | T3d | OH |
| 2525 | CMe | NMe | Q1b | a bond | H | a bond | NH | S | NH | T3e | OH |
| 2526 | CMe | NMe | Q1b | a bond | H | a bond | NH | S | NH | T3f | OH |
| 2527 | CMe | NMe | Q1b | a bond | H | a bond | NH | S | NH | T3g | OH |
| 2528 | CMe | NMe | Q1b | a bond | H | a bond | NH | S | NH | T3h | OH |
| 2529 | CMe | NMe | Q1b | a bond | H | a bond | NH | S | NH | T3i | OH |
| 2530 | CMe | NMe | Q1b | a bond | H | a bond | NH | S | NH | T3j | OH |
| 2531 | CMe | NMe | Q1b | a bond | H | a bond | NH | S | a bond | T3a | OH |
| 2532 | CMe | NMe | Q1b | a bond | H | a bond | NH | S | a bond | T3b | OH |
| 2533 | CMe | NMe | Q1b | a bond | H | a bond | NH | S | a bond | T3c | OH |
| 2534 | CMe | NMe | Q1b | a bond | H | a bond | NH | S | a bond | T3d | OH |
| 2535 | CMe | NMe | Q1b | a bond | H | a bond | NH | S | a bond | T3e | OH |
| 2536 | CMe | NMe | Q1b | a bond | H | a bond | NH | S | a bond | T3f | OH |
| 2537 | CMe | NMe | Q1b | a bond | H | a bond | NH | S | a bond | T3g | OH |
| 2538 | CMe | NMe | Q1b | a bond | H | a bond | NH | S | a bond | T3h | OH |
| 2539 | CMe | NMe | Q1b | a bond | H | a bond | NH | S | a bond | T3i | OH |
| 2540 | CMe | NMe | Q1b | a bond | H | a bond | NH | S | a bond | T3j | OH |
| 2541 | CMe | NMe | Q1b | a bond | H | a bond | NH | O | NH | T3a | OH |
| 2542 | CMe | NMe | Q1b | a bond | H | a bond | NH | O | NH | T3b | OH |
| 2543 | CMe | NMe | Q1b | a bond | H | a bond | NH | O | NH | T3c | OH |
| 2544 | CMe | NMe | Q1b | a bond | H | a bond | NH | O | NH | T3d | OH |
| 2545 | CMe | NMe | Q1b | a bond | H | a bond | NH | O | NH | T3e | OH |

TABLE 2-continued

| No | A | B | R¹ | L¹ | R² | L² | L³ | Y | L⁴ | R³ | X |
|---|---|---|---|---|---|---|---|---|---|---|---|
| 2546 | CMe | NMe | Q1b | a bond | H | a bond | NH | O | NH | T3f | OH |
| 2547 | CMe | NMe | Q1b | a bond | H | a bond | NH | O | NH | T3g | OH |
| 2548 | CMe | NMe | Q1b | a bond | H | a bond | NH | O | NH | T3h | OH |
| 2549 | CMe | NMe | Q1b | a bond | H | a bond | NH | O | NH | T3i | OH |
| 2550 | CMe | NMe | Q1b | a bond | H | a bond | NH | O | NH | T3j | OH |
| 2551 | CMe | NMe | Q1b | a bond | H | a bond | NH | O | a bond | T3a | OH |
| 2552 | CMe | NMe | Q1b | a bond | H | a bond | NH | O | a bond | T3b | OH |
| 2553 | CMe | NMe | Q1b | a bond | H | a bond | NH | O | a bond | T3c | OH |
| 2554 | CMe | NMe | Q1b | a bond | H | a bond | NH | O | a bond | T3d | OH |
| 2555 | CMe | NMe | Q1b | a bond | H | a bond | NH | O | a bond | T3e | OH |
| 2556 | CMe | NMe | Q1b | a bond | H | a bond | NH | O | a bond | T3f | OH |
| 2557 | CMe | NMe | Q1b | a bond | H | a bond | NH | O | a bond | T3g | OH |
| 2558 | CMe | NMe | Q1b | a bond | H | a bond | NH | O | a bond | T3h | OH |
| 2559 | CMe | NMe | Q1b | a bond | H | a bond | NH | O | a bond | T3i | OH |
| 2560 | CMe | NMe | Q1b | a bond | H | a bond | NH | O | a bond | T3j | OH |
| 2561 | CMe | NMe | Q1c | a bond | Me | a bond | NH | S | NH | T3a | OH |
| 2562 | CMe | NMe | Q1c | a bond | Me | a bond | NH | S | NH | T3b | OH |
| 2563 | CMe | NMe | Q1c | a bond | Me | a bond | NH | S | NH | T3c | OH |
| 2564 | CMe | NMe | Q1c | a bond | Me | a bond | NH | S | NH | T3d | OH |
| 2565 | CMe | NMe | Q1c | a bond | Me | a bond | NH | S | NH | T3e | OH |
| 2566 | CMe | NMe | Q1c | a bond | Me | a bond | NH | S | NH | T3f | OH |
| 2567 | CMe | NMe | Q1c | a bond | Me | a bond | NH | S | NH | T3g | OH |
| 2568 | CMe | NMe | Q1c | a bond | Me | a bond | NH | S | NH | T3h | OH |
| 2569 | CMe | NMe | Q1c | a bond | Me | a bond | NH | S | NH | T3i | OH |
| 2570 | CMe | NMe | Q1c | a bond | Me | a bond | NH | S | NH | T3j | OH |
| 2571 | CMe | NMe | Q1c | a bond | Me | a bond | NH | S | a bond | T3a | OH |
| 2572 | CMe | NMe | Q1c | a bond | Me | a bond | NH | S | a bond | T3b | OH |
| 2573 | CMe | NMe | Q1c | a bond | Me | a bond | NH | S | a bond | T3c | OH |
| 2574 | CMe | NMe | Q1c | a bond | Me | a bond | NH | S | a bond | T3d | OH |
| 2575 | CMe | NMe | Q1c | a bond | Me | a bond | NH | S | a bond | T3e | OH |
| 2576 | CMe | NMe | Q1c | a bond | Me | a bond | NH | S | a bond | T3f | OH |
| 2577 | CMe | NMe | Q1c | a bond | Me | a bond | NH | S | a bond | T3g | OH |
| 2578 | CMe | NMe | Q1c | a bond | Me | a bond | NH | S | a bond | T3h | OH |
| 2579 | CMe | NMe | Q1c | a bond | Me | a bond | NH | S | a bond | T3i | OH |
| 2580 | CMe | NMe | Q1c | a bond | Me | a bond | NH | S | a bond | T3j | OH |
| 2581 | CMe | NMe | Q1c | a bond | Me | a bond | NH | O | NH | T3a | OH |
| 2582 | CMe | NMe | Q1c | a bond | Me | a bond | NH | O | NH | T3b | OH |
| 2583 | CMe | NMe | Q1c | a bond | Me | a bond | NH | O | NH | T3c | OH |
| 2584 | CMe | NMe | Q1c | a bond | Me | a bond | NH | O | NH | T3d | OH |
| 2585 | CMe | NMe | Q1c | a bond | Me | a bond | NH | O | NH | T3e | OH |
| 2586 | CMe | NMe | Q1c | a bond | Me | a bond | NH | O | NH | T3f | OH |
| 2587 | CMe | NMe | Q1c | a bond | Me | a bond | NH | O | NH | T3g | OH |
| 2588 | CMe | NMe | Q1c | a bond | Me | a bond | NH | O | NH | T3h | OH |
| 2589 | CMe | NMe | Q1c | a bond | Me | a bond | NH | O | NH | T3i | OH |
| 2590 | CMe | NMe | Q1c | a bond | Me | a bond | NH | O | NH | T3j | OH |
| 2591 | CMe | NMe | Q1c | a bond | Me | a bond | NH | O | a bond | T3a | OH |
| 2592 | CMe | NMe | Q1c | a bond | Me | a bond | NH | O | a bond | T3b | OH |
| 2593 | CMe | NMe | Q1c | a bond | Me | a bond | NH | O | a bond | T3c | OH |
| 2594 | CMe | NMe | Q1c | a bond | Me | a bond | NH | O | a bond | T3d | OH |
| 2595 | CMe | NMe | Q1c | a bond | Me | a bond | NH | O | a bond | T3e | OH |
| 2596 | CMe | NMe | Q1c | a bond | Me | a bond | NH | O | a bond | T3f | OH |
| 2597 | CMe | NMe | Q1c | a bond | Me | a bond | NH | O | a bond | T3g | OH |
| 2598 | CMe | NMe | Q1c | a bond | Me | a bond | NH | O | a bond | T3h | OH |
| 2599 | CMe | NMe | Q1c | a bond | Me | a bond | NH | O | a bond | T3i | OH |
| 2600 | CMe | NMe | Q1c | a bond | Me | a bond | NH | O | a bond | T3j | OH |
| 2601 | CMe | NMe | Q1c | a bond | H | a bond | NH | S | NH | T3a | OH |
| 2602 | CMe | NMe | Q1c | a bond | H | a bond | NH | S | NH | T3b | OH |
| 2603 | CMe | NMe | Q1c | a bond | H | a bond | NH | S | NH | T3c | OH |
| 2604 | CMe | NMe | Q1c | a bond | H | a bond | NH | S | NH | T3d | OH |
| 2605 | CMe | NMe | Q1c | a bond | H | a bond | NH | S | NH | T3e | OH |
| 2606 | CMe | NMe | Q1c | a bond | H | a bond | NH | S | NH | T3f | OH |
| 2607 | CMe | NMe | Q1c | a bond | H | a bond | NH | S | NH | T3g | OH |
| 2608 | CMe | NMe | Q1c | a bond | H | a bond | NH | S | NH | T3h | OH |
| 2609 | CMe | NMe | Q1c | a bond | H | a bond | NH | S | NH | T3i | OH |
| 2610 | CMe | NMe | Q1c | a bond | H | a bond | NH | S | NH | T3j | OH |
| 2611 | CMe | NMe | Q1c | a bond | H | a bond | NH | S | a bond | T3a | OH |
| 2612 | CMe | NMe | Q1c | a bond | H | a bond | NH | S | a bond | T3b | OH |
| 2613 | CMe | NMe | Q1c | a bond | H | a bond | NH | S | a bond | T3c | OH |
| 2614 | CMe | NMe | Q1c | a bond | H | a bond | NH | S | a bond | T3d | OH |
| 2615 | CMe | NMe | Q1c | a bond | H | a bond | NH | S | a bond | T3e | OH |
| 2616 | CMe | NMe | Q1c | a bond | H | a bond | NH | S | a bond | T3f | OH |
| 2617 | CMe | NMe | Q1c | a bond | H | a bond | NH | S | a bond | T3g | OH |
| 2618 | CMe | NMe | Q1c | a bond | H | a bond | NH | S | a bond | T3h | OH |
| 2619 | CMe | NMe | Q1c | a bond | H | a bond | NH | S | a bond | T3i | OH |
| 2620 | CMe | NMe | Q1c | a bond | H | a bond | NH | S | a bond | T3j | OH |
| 2621 | CMe | NMe | Q1c | a bond | H | a bond | NH | O | NH | T3a | OH |
| 2622 | CMe | NMe | Q1c | a bond | H | a bond | NH | O | NH | T3b | OH |
| 2623 | CMe | NMe | Q1c | a bond | H | a bond | NH | O | NH | T3c | OH |

TABLE 2-continued

| No | A | B | R¹ | L¹ | R² | L² | L³ | Y | L⁴ | R³ | X |
|---|---|---|---|---|---|---|---|---|---|---|---|
| 2624 | CMe | NMe | Q1c | a bond | H | a bond | NH | O | NH | T3d | OH |
| 2625 | CMe | NMe | Q1c | a bond | H | a bond | NH | O | NH | T3e | OH |
| 2626 | CMe | NMe | Q1c | a bond | H | a bond | NH | O | NH | T3f | OH |
| 2627 | CMe | NMe | Q1c | a bond | H | a bond | NH | O | NH | T3g | OH |
| 2628 | CMe | NMe | Q1c | a bond | H | a bond | NH | O | NH | T3h | OH |
| 2629 | CMe | NMe | Q1c | a bond | H | a bond | NH | O | NH | T3i | OH |
| 2630 | CMe | NMe | Q1c | a bond | H | a bond | NH | O | NH | T3j | OH |
| 2631 | CMe | NMe | Q1c | a bond | H | a bond | NH | O | a bond | T3a | OH |
| 2632 | CMe | NMe | Q1c | a bond | H | a bond | NH | O | a bond | T3b | OH |
| 2633 | CMe | NMe | Q1c | a bond | H | a bond | NH | O | a bond | T3c | OH |
| 2634 | CMe | NMe | Q1c | a bond | H | a bond | NH | O | a bond | T3d | OH |
| 2635 | CMe | NMe | Q1c | a bond | H | a bond | NH | O | a bond | T3e | OH |
| 2636 | CMe | NMe | Q1c | a bond | H | a bond | NH | O | a bond | T3f | OH |
| 2637 | CMe | NMe | Q1c | a bond | H | a bond | NH | O | a bond | T3g | OH |
| 2638 | CMe | NMe | Q1c | a bond | H | a bond | NH | O | a bond | T3h | OH |
| 2639 | CMe | NMe | Q1c | a bond | H | a bond | NH | O | a bond | T3i | OH |
| 2640 | CMe | NMe | Q1c | a bond | H | a bond | NH | O | a bond | T3j | OH |
| 2641 | CMe | NMe | Q1i | a bond | Me | a bond | NH | S | NH | T3a | OH |
| 2642 | CMe | NMe | Q1i | a bond | Me | a bond | NH | S | NH | T3b | OH |
| 2643 | CMe | NMe | Q1i | a bond | Me | a bond | NH | S | NH | T3c | OH |
| 2644 | CMe | NMe | Q1i | a bond | Me | a bond | NH | S | NH | T3d | OH |
| 2645 | CMe | NMe | Q1i | a bond | Me | a bond | NH | S | NH | T3e | OH |
| 2646 | CMe | NMe | Q1i | a bond | Me | a bond | NH | S | NH | T3f | OH |
| 2647 | CMe | NMe | Q1i | a bond | Me | a bond | NH | S | NH | T3g | OH |
| 2648 | CMe | NMe | Q1i | a bond | Me | a bond | NH | S | NH | T3h | OH |
| 2649 | CMe | NMe | Q1i | a bond | Me | a bond | NH | S | NH | T3i | OH |
| 2650 | CMe | NMe | Q1i | a bond | Me | a bond | NH | S | NH | T3j | OH |
| 2651 | CMe | NMe | Q1i | a bond | Me | a bond | NH | S | a bond | T3a | OH |
| 2652 | CMe | NMe | Q1i | a bond | Me | a bond | NH | S | a bond | T3b | OH |
| 2653 | CMe | NMe | Q1i | a bond | Me | a bond | NH | S | a bond | T3c | OH |
| 2654 | CMe | NMe | Q1i | a bond | Me | a bond | NH | S | a bond | T3d | OH |
| 2655 | CMe | NMe | Q1i | a bond | Me | a bond | NH | S | a bond | T3e | OH |
| 2656 | CMe | NMe | Q1i | a bond | Me | a bond | NH | S | a bond | T3f | OH |
| 2657 | CMe | NMe | Q1i | a bond | Me | a bond | NH | S | a bond | T3g | OH |
| 2658 | CMe | NMe | Q1i | a bond | Me | a bond | NH | S | a bond | T3h | OH |
| 2659 | CMe | NMe | Q1i | a bond | Me | a bond | NH | S | a bond | T3i | OH |
| 2660 | CMe | NMe | Q1i | a bond | Me | a bond | NH | S | a bond | T3j | OH |
| 2661 | CMe | NMe | Q1i | a bond | Me | a bond | NH | O | NH | T3a | OH |
| 2662 | CMe | NMe | Q1i | a bond | Me | a bond | NH | O | NH | T3b | OH |
| 2663 | CMe | NMe | Q1i | a bond | Me | a bond | NH | O | NH | T3c | OH |
| 2664 | CMe | NMe | Q1i | a bond | Me | a bond | NH | O | NH | T3d | OH |
| 2665 | CMe | NMe | Q1i | a bond | Me | a bond | NH | O | NH | T3e | OH |
| 2666 | CMe | NMe | Q1i | a bond | Me | a bond | NH | O | NH | T3f | OH |
| 2667 | CMe | NMe | Q1i | a bond | Me | a bond | NH | O | NH | T3g | OH |
| 2668 | CMe | NMe | Q1i | a bond | Me | a bond | NH | O | NH | T3h | OH |
| 2669 | CMe | NMe | Q1i | a bond | Me | a bond | NH | O | NH | T3i | OH |
| 2670 | CMe | NMe | Q1i | a bond | Me | a bond | NH | O | NH | T3j | OH |
| 2671 | CMe | NMe | Q1i | a bond | Me | a bond | NH | O | a bond | T3a | OH |
| 2672 | CMe | NMe | Q1i | a bond | Me | a bond | NH | O | a bond | T3b | OH |
| 2673 | CMe | NMe | Q1i | a bond | Me | a bond | NH | O | a bond | T3c | OH |
| 2674 | CMe | NMe | Q1i | a bond | Me | a bond | NH | O | a bond | T3d | OH |
| 2675 | CMe | NMe | Q1i | a bond | Me | a bond | NH | O | a bond | T3e | OH |
| 2676 | CMe | NMe | Q1i | a bond | Me | a bond | NH | O | a bond | T3f | OH |
| 2677 | CMe | NMe | Q1i | a bond | Me | a bond | NH | O | a bond | T3g | OH |
| 2678 | CMe | NMe | Q1i | a bond | Me | a bond | NH | O | a bond | T3h | OH |
| 2679 | CMe | NMe | Q1i | a bond | Me | a bond | NH | O | a bond | T3i | OH |
| 2680 | CMe | NMe | Q1i | a bond | Me | a bond | NH | O | a bond | T3j | OH |
| 2681 | CMe | NMe | Q1i | a bond | H | a bond | NH | S | NH | T3a | OH |
| 2682 | CMe | NMe | Q1i | a bond | H | a bond | NH | S | NH | T3b | OH |
| 2683 | CMe | NMe | Q1i | a bond | H | a bond | NH | S | NH | T3c | OH |
| 2684 | CMe | NMe | Q1i | a bond | H | a bond | NH | S | NH | T3d | OH |
| 2685 | CMe | NMe | Q1i | a bond | H | a bond | NH | S | NH | T3e | OH |
| 2686 | CMe | NMe | Q1i | a bond | H | a bond | NH | S | NH | T3f | OH |
| 2687 | CMe | NMe | Q1i | a bond | H | a bond | NH | S | NH | T3g | OH |
| 2688 | CMe | NMe | Q1i | a bond | H | a bond | NH | S | NH | T3h | OH |
| 2689 | CMe | NMe | Q1i | a bond | H | a bond | NH | S | NH | T3i | OH |
| 2690 | CMe | NMe | Q1i | a bond | H | a bond | NH | S | NH | T3j | OH |
| 2691 | CMe | NMe | Q1i | a bond | H | a bond | NH | S | a bond | T3a | OH |
| 2692 | CMe | NMe | Q1i | a bond | H | a bond | NH | S | a bond | T3b | OH |
| 2693 | CMe | NMe | Q1i | a bond | H | a bond | NH | S | a bond | T3c | OH |
| 2694 | CMe | NMe | Q1i | a bond | H | a bond | NH | S | a bond | T3d | OH |
| 2695 | CMe | NMe | Q1i | a bond | H | a bond | NH | S | a bond | T3e | OH |
| 2696 | CMe | NMe | Q1i | a bond | H | a bond | NH | S | a bond | T3f | OH |
| 2697 | CMe | NMe | Q1i | a bond | H | a bond | NH | S | a bond | T3g | OH |
| 2698 | CMe | NMe | Q1i | a bond | H | a bond | NH | S | a bond | T3h | OH |
| 2699 | CMe | NMe | Q1i | a bond | H | a bond | NH | S | a bond | T3i | OH |
| 2700 | CMe | NMe | Q1i | a bond | H | a bond | NH | S | a bond | T3j | OH |
| 2701 | CMe | NMe | Q1i | a bond | H | a bond | NH | O | NH | T3a | OH |

TABLE 2-continued

| No | A | B | R¹ | L¹ | R² | L² | L³ | Y | L⁴ | R³ | X |
|---|---|---|---|---|---|---|---|---|---|---|---|
| 2702 | CMe | NMe | Q1i | a bond | H | a bond | NH | O | NH | T3b | OH |
| 2703 | CMe | NMe | Q1i | a bond | H | a bond | NH | O | NH | T3c | OH |
| 2704 | CMe | NMe | Q1i | a bond | H | a bond | NH | O | NH | T3d | OH |
| 2705 | CMe | NMe | Q1i | a bond | H | a bond | NH | O | NH | T3e | OH |
| 2706 | CMe | NMe | Q1i | a bond | H | a bond | NH | O | NH | T3f | OH |
| 2707 | CMe | NMe | Q1i | a bond | H | a bond | NH | O | NH | T3g | OH |
| 2708 | CMe | NMe | Q1i | a bond | H | a bond | NH | O | NH | T3h | OH |
| 2709 | CMe | NMe | Q1i | a bond | H | a bond | NH | O | NH | T3i | OH |
| 2710 | CMe | NMe | Q1i | a bond | H | a bond | NH | O | NH | T3j | OH |
| 2711 | CMe | NMe | Q1i | a bond | H | a bond | NH | O | a bond | T3a | OH |
| 2712 | CMe | NMe | Q1i | a bond | H | a bond | NH | O | a bond | T3b | OH |
| 2713 | CMe | NMe | Q1i | a bond | H | a bond | NH | O | a bond | T3c | OH |
| 2714 | CMe | NMe | Q1i | a bond | H | a bond | NH | O | a bond | T3d | OH |
| 2715 | CMe | NMe | Q1i | a bond | H | a bond | NH | O | a bond | T3e | OH |
| 2716 | CMe | NMe | Q1i | a bond | H | a bond | NH | O | a bond | T3f | OH |
| 2717 | CMe | NMe | Q1i | a bond | H | a bond | NH | O | a bond | T3g | OH |
| 2718 | CMe | NMe | Q1i | a bond | H | a bond | NH | O | a bond | T3h | OH |
| 2719 | CMe | NMe | Q1i | a bond | H | a bond | NH | O | a bond | T3i | OH |
| 2720 | CMe | NMe | Q1i | a bond | H | a bond | NH | O | a bond | T3j | OH |
| 2721 | CMe | NMe | Q1j | a bond | Me | a bond | NH | S | NH | T3a | OH |
| 2722 | CMe | NMe | Q1j | a bond | Me | a bond | NH | S | NH | T3b | OH |
| 2723 | CMe | NMe | Q1j | a bond | Me | a bond | NH | S | NH | T3c | OH |
| 2724 | CMe | NMe | Q1j | a bond | Me | a bond | NH | S | NH | T3d | OH |
| 2725 | CMe | NMe | Q1j | a bond | Me | a bond | NH | S | NH | T3e | OH |
| 2726 | CMe | NMe | Q1j | a bond | Me | a bond | NH | S | NH | T3f | OH |
| 2727 | CMe | NMe | Q1j | a bond | Me | a bond | NH | S | NH | T3g | OH |
| 2728 | CMe | NMe | Q1j | a bond | Me | a bond | NH | S | NH | T3h | OH |
| 2729 | CMe | NMe | Q1j | a bond | Me | a bond | NH | S | NH | T3i | OH |
| 2730 | CMe | NMe | Q1j | a bond | Me | a bond | NH | S | NH | T3j | OH |
| 2731 | CMe | NMe | Q1j | a bond | Me | a bond | NH | S | a bond | T3a | OH |
| 2732 | CMe | NMe | Q1j | a bond | Me | a bond | NH | S | a bond | T3b | OH |
| 2733 | CMe | NMe | Q1j | a bond | Me | a bond | NH | S | a bond | T3c | OH |
| 2734 | CMe | NMe | Q1j | a bond | Me | a bond | NH | S | a bond | T3d | OH |
| 2735 | CMe | NMe | Q1j | a bond | Me | a bond | NH | S | a bond | T3e | OH |
| 2736 | CMe | NMe | Q1j | a bond | Me | a bond | NH | S | a bond | T3f | OH |
| 2737 | CMe | NMe | Q1j | a bond | Me | a bond | NH | S | a bond | T3g | OH |
| 2738 | CMe | NMe | Q1j | a bond | Me | a bond | NH | S | a bond | T3h | OH |
| 2739 | CMe | NMe | Q1j | a bond | Me | a bond | NH | S | a bond | T3i | OH |
| 2740 | CMe | NMe | Q1j | a bond | Me | a bond | NH | S | a bond | T3j | OH |
| 2741 | CMe | NMe | Q1j | a bond | Me | a bond | NH | O | NH | T3a | OH |
| 2742 | CMe | NMe | Q1j | a bond | Me | a bond | NH | O | NH | T3b | OH |
| 2743 | CMe | NMe | Q1j | a bond | Me | a bond | NH | O | NH | T3c | OH |
| 2744 | CMe | NMe | Q1j | a bond | Me | a bond | NH | O | NH | T3d | OH |
| 2745 | CMe | NMe | Q1j | a bond | Me | a bond | NH | O | NH | T3e | OH |
| 2746 | CMe | NMe | Q1j | a bond | Me | a bond | NH | O | NH | T3f | OH |
| 2747 | CMe | NMe | Q1j | a bond | Me | a bond | NH | O | NH | T3g | OH |
| 2748 | CMe | NMe | Q1j | a bond | Me | a bond | NH | O | NH | T3h | OH |
| 2749 | CMe | NMe | Q1j | a bond | Me | a bond | NH | O | NH | T3i | OH |
| 2750 | CMe | NMe | Q1j | a bond | Me | a bond | NH | O | NH | T3j | OH |
| 2751 | CMe | NMe | Q1j | a bond | Me | a bond | NH | O | a bond | T3a | OH |
| 2752 | CMe | NMe | Q1j | a bond | Me | a bond | NH | O | a bond | T3b | OH |
| 2753 | CMe | NMe | Q1j | a bond | Me | a bond | NH | O | a bond | T3c | OH |
| 2754 | CMe | NMe | Q1j | a bond | Me | a bond | NH | O | a bond | T3d | OH |
| 2755 | CMe | NMe | Q1j | a bond | Me | a bond | NH | O | a bond | T3e | OH |
| 2756 | CMe | NMe | Q1j | a bond | Me | a bond | NH | O | a bond | T3f | OH |
| 2757 | CMe | NMe | Q1j | a bond | Me | a bond | NH | O | a bond | T3g | OH |
| 2758 | CMe | NMe | Q1j | a bond | Me | a bond | NH | O | a bond | T3h | OH |
| 2759 | CMe | NMe | Q1j | a bond | Me | a bond | NH | O | a bond | T3i | OH |
| 2760 | CMe | NMe | Q1j | a bond | Me | a bond | NH | O | a bond | T3j | OH |
| 2761 | CMe | NMe | Q1j | a bond | H | a bond | NH | S | NH | T3a | OH |
| 2762 | CMe | NMe | Q1j | a bond | H | a bond | NH | S | NH | T3b | OH |
| 2763 | CMe | NMe | Q1j | a bond | H | a bond | NH | S | NH | T3c | OH |
| 2764 | CMe | NMe | Q1j | a bond | H | a bond | NH | S | NH | T3d | OH |
| 2765 | CMe | NMe | Q1j | a bond | H | a bond | NH | S | NH | T3e | OH |
| 2766 | CMe | NMe | Q1j | a bond | H | a bond | NH | S | NH | T3f | OH |
| 2767 | CMe | NMe | Q1j | a bond | H | a bond | NH | S | NH | T3g | OH |
| 2768 | CMe | NMe | Q1j | a bond | H | a bond | NH | S | NH | T3h | OH |
| 2769 | CMe | NMe | Q1j | a bond | H | a bond | NH | S | NH | T3i | OH |
| 2770 | CMe | NMe | Q1j | a bond | H | a bond | NH | S | NH | T3j | OH |
| 2771 | CMe | NMe | Q1j | a bond | H | a bond | NH | S | a bond | T3a | OH |
| 2772 | CMe | NMe | Q1j | a bond | H | a bond | NH | S | a bond | T3b | OH |
| 2773 | CMe | NMe | Q1j | a bond | H | a bond | NH | S | a bond | T3c | OH |
| 2774 | CMe | NMe | Q1j | a bond | H | a bond | NH | S | a bond | T3d | OH |
| 2775 | CMe | NMe | Q1j | a bond | H | a bond | NH | S | a bond | T3e | OH |
| 2776 | CMe | NMe | Q1j | a bond | H | a bond | NH | S | a bond | T3f | OH |
| 2777 | CMe | NMe | Q1j | a bond | H | a bond | NH | S | a bond | T3g | OH |
| 2778 | CMe | NMe | Q1j | a bond | H | a bond | NH | S | a bond | T3h | OH |
| 2779 | CMe | NMe | Q1j | a bond | H | a bond | NH | S | a bond | T3i | OH |

TABLE 2-continued

| No | A | B | R¹ | L¹ | R² | L² | L³ | Y | L⁴ | R³ | X |
|---|---|---|---|---|---|---|---|---|---|---|---|
| 2780 | CMe | NMe | Q1j | a bond | H | a bond | NH | S | a bond | T3j | OH |
| 2781 | CMe | NMe | Q1j | a bond | H | a bond | NH | O | NH | T3a | OH |
| 2782 | CMe | NMe | Q1j | a bond | H | a bond | NH | O | NH | T3b | OH |
| 2783 | CMe | NMe | Q1j | a bond | H | a bond | NH | O | NH | T3c | OH |
| 2784 | CMe | NMe | Q1j | a bond | H | a bond | NH | O | NH | T3d | OH |
| 2785 | CMe | NMe | Q1j | a bond | H | a bond | NH | O | NH | T3e | OH |
| 2786 | CMe | NMe | Q1j | a bond | H | a bond | NH | O | NH | T3f | OH |
| 2787 | CMe | NMe | Q1j | a bond | H | a bond | NH | O | NH | T3g | OH |
| 2788 | CMe | NMe | Q1j | a bond | H | a bond | NH | O | NH | T3h | OH |
| 2789 | CMe | NMe | Q1j | a bond | H | a bond | NH | O | NH | T3i | OH |
| 2790 | CMe | NMe | Q1j | a bond | H | a bond | NH | O | NH | T3j | OH |
| 2791 | CMe | NMe | Q1j | a bond | H | a bond | NH | O | a bond | T3a | OH |
| 2792 | CMe | NMe | Q1j | a bond | H | a bond | NH | O | a bond | T3b | OH |
| 2793 | CMe | NMe | Q1j | a bond | H | a bond | NH | O | a bond | T3c | OH |
| 2794 | CMe | NMe | Q1j | a bond | H | a bond | NH | O | a bond | T3d | OH |
| 2795 | CMe | NMe | Q1j | a bond | H | a bond | NH | O | a bond | T3e | OH |
| 2796 | CMe | NMe | Q1j | a bond | H | a bond | NH | O | a bond | T3f | OH |
| 2797 | CMe | NMe | Q1j | a bond | H | a bond | NH | O | a bond | T3g | OH |
| 2798 | CMe | NMe | Q1j | a bond | H | a bond | NH | O | a bond | T3h | OH |
| 2799 | CMe | NMe | Q1j | a bond | H | a bond | NH | O | a bond | T3i | OH |
| 2800 | CMe | NMe | Q1j | a bond | H | a bond | NH | O | a bond | T3j | OH |
| 2801 | CMe | S | Q1a | a bond | Me | a bond | NH | S | NH | T3a | OH |
| 2802 | CMe | S | Q1a | a bond | Me | a bond | NH | S | NH | T3b | OH |
| 2803 | CMe | S | Q1a | a bond | Me | a bond | NH | S | NH | T3c | OH |
| 2804 | CMe | S | Q1a | a bond | Me | a bond | NH | S | NH | T3d | OH |
| 2805 | CMe | S | Q1a | a bond | Me | a bond | NH | S | NH | T3e | OH |
| 2806 | CMe | S | Q1a | a bond | Me | a bond | NH | S | NH | T3f | OH |
| 2807 | CMe | S | Q1a | a bond | Me | a bond | NH | S | NH | T3g | OH |
| 2808 | CMe | S | Q1a | a bond | Me | a bond | NH | S | NH | T3h | OH |
| 2809 | CMe | S | Q1a | a bond | Me | a bond | NH | S | NH | T3i | OH |
| 2810 | CMe | S | Q1a | a bond | Me | a bond | NH | S | NH | T3j | OH |
| 2811 | CMe | S | Q1a | a bond | Me | a bond | NH | S | a bond | T3a | OH |
| 2812 | CMe | S | Q1a | a bond | Me | a bond | NH | S | a bond | T3b | OH |
| 2813 | CMe | S | Q1a | a bond | Me | a bond | NH | S | a bond | T3c | OH |
| 2814 | CMe | S | Q1a | a bond | Me | a bond | NH | S | a bond | T3d | OH |
| 2815 | CMe | S | Q1a | a bond | Me | a bond | NH | S | a bond | T3e | OH |
| 2816 | CMe | S | Q1a | a bond | Me | a bond | NH | S | a bond | T3f | OH |
| 2817 | CMe | S | Q1a | a bond | Me | a bond | NH | S | a bond | T3g | OH |
| 2818 | CMe | S | Q1a | a bond | Me | a bond | NH | S | a bond | T3h | OH |
| 2819 | CMe | S | Q1a | a bond | Me | a bond | NH | S | a bond | T3i | OH |
| 2820 | CMe | S | Q1a | a bond | Me | a bond | NH | S | a bond | T3j | OH |
| 2821 | CMe | S | Q1a | a bond | Me | a bond | NH | O | NH | T3a | OH |
| 2822 | CMe | S | Q1a | a bond | Me | a bond | NH | O | NH | T3b | OH |
| 2823 | CMe | S | Q1a | a bond | Me | a bond | NH | O | NH | T3c | OH |
| 2824 | CMe | S | Q1a | a bond | Me | a bond | NH | O | NH | T3d | OH |
| 2825 | CMe | S | Q1a | a bond | Me | a bond | NH | O | NH | T3e | OH |
| 2826 | CMe | S | Q1a | a bond | Me | a bond | NH | O | NH | T3f | OH |
| 2827 | CMe | S | Q1a | a bond | Me | a bond | NH | O | NH | T3g | OH |
| 2828 | CMe | S | Q1a | a bond | Me | a bond | NH | O | NH | T3h | OH |
| 2829 | CMe | S | Q1a | a bond | Me | a bond | NH | O | NH | T3i | OH |
| 2830 | CMe | S | Q1a | a bond | Me | a bond | NH | O | NH | T3j | OH |
| 2831 | CMe | S | Q1a | a bond | Me | a bond | NH | O | a bond | T3a | OH |
| 2832 | CMe | S | Q1a | a bond | Me | a bond | NH | O | a bond | T3b | OH |
| 2833 | CMe | S | Q1a | a bond | Me | a bond | NH | O | a bond | T3c | OH |
| 2834 | CMe | S | Q1a | a bond | Me | a bond | NH | O | a bond | T3d | OH |
| 2835 | CMe | S | Q1a | a bond | Me | a bond | NH | O | a bond | T3e | OH |
| 2836 | CMe | S | Q1a | a bond | Me | a bond | NH | O | a bond | T3f | OH |
| 2837 | CMe | S | Q1a | a bond | Me | a bond | NH | O | a bond | T3g | OH |
| 2838 | CMe | S | Q1a | a bond | Me | a bond | NH | O | a bond | T3h | OH |
| 2839 | CMe | S | Q1a | a bond | Me | a bond | NH | O | a bond | T3i | OH |
| 2840 | CMe | S | Q1a | a bond | Me | a bond | NH | O | a bond | T3j | OH |
| 2841 | CMe | S | Q1a | a bond | H | a bond | NH | S | NH | T3a | OH |
| 2842 | CMe | S | Q1a | a bond | H | a bond | NH | S | NH | T3b | OH |
| 2843 | CMe | S | Q1a | a bond | H | a bond | NH | S | NH | T3c | OH |
| 2844 | CMe | S | Q1a | a bond | H | a bond | NH | S | NH | T3d | OH |
| 2845 | CMe | S | Q1a | a bond | H | a bond | NH | S | NH | T3e | OH |
| 2846 | CMe | S | Q1a | a bond | H | a bond | NH | S | NH | T3f | OH |
| 2847 | CMe | S | Q1a | a bond | H | a bond | NH | S | NH | T3g | OH |
| 2848 | CMe | S | Q1a | a bond | H | a bond | NH | S | NH | T3h | OH |
| 2849 | CMe | S | Q1a | a bond | H | a bond | NH | S | NH | T3i | OH |
| 2850 | CMe | S | Q1a | a bond | H | a bond | NH | S | NH | T3j | OH |
| 2851 | CMe | S | Q1a | a bond | H | a bond | NH | S | a bond | T3a | OH |
| 2852 | CMe | S | Q1a | a bond | H | a bond | NH | S | a bond | T3b | OH |
| 2853 | CMe | S | Q1a | a bond | H | a bond | NH | S | a bond | T3c | OH |
| 2854 | CMe | S | Q1a | a bond | H | a bond | NH | S | a bond | T3d | OH |
| 2855 | CMe | S | Q1a | a bond | H | a bond | NH | S | a bond | T3e | OH |
| 2856 | CMe | S | Q1a | a bond | H | a bond | NH | S | a bond | T3f | OH |
| 2857 | CMe | S | Q1a | a bond | H | a bond | NH | S | a bond | T3g | OH |

TABLE 2-continued

| No | A | B | R¹ | L¹ | R² | L² | L³ | Y | L⁴ | R³ | X |
|---|---|---|---|---|---|---|---|---|---|---|---|
| 2858 | CMe | S | Q1a | a bond | H | a bond | NH | S | a bond | T3h | OH |
| 2859 | CMe | S | Q1a | a bond | H | a bond | NH | S | a bond | T3i | OH |
| 2860 | CMe | S | Q1a | a bond | H | a bond | NH | S | a bond | T3j | OH |
| 2861 | CMe | S | Q1a | a bond | H | a bond | NH | O | NH | T3a | OH |
| 2862 | CMe | S | Q1a | a bond | H | a bond | NH | O | NH | T3b | OH |
| 2863 | CMe | S | Q1a | a bond | H | a bond | NH | O | NH | T3c | OH |
| 2864 | CMe | S | Q1a | a bond | H | a bond | NH | O | NH | T3d | OH |
| 2865 | CMe | S | Q1a | a bond | H | a bond | NH | O | NH | T3e | OH |
| 2866 | CMe | S | Q1a | a bond | H | a bond | NH | O | NH | T3f | OH |
| 2867 | CMe | S | Q1a | a bond | H | a bond | NH | O | NH | T3g | OH |
| 2868 | CMe | S | Q1a | a bond | H | a bond | NH | O | NH | T3h | OH |
| 2869 | CMe | S | Q1a | a bond | H | a bond | NH | O | NH | T3i | OH |
| 2870 | CMe | S | Q1a | a bond | H | a bond | NH | O | NH | T3j | OH |
| 2871 | CMe | S | Q1a | a bond | H | a bond | NH | O | a bond | T3a | OH |
| 2872 | CMe | S | Q1a | a bond | H | a bond | NH | O | a bond | T3b | OH |
| 2873 | CMe | S | Q1a | a bond | H | a bond | NH | O | a bond | T3c | OH |
| 2874 | CMe | S | Q1a | a bond | H | a bond | NH | O | a bond | T3d | OH |
| 2875 | CMe | S | Q1a | a bond | H | a bond | NH | O | a bond | T3e | OH |
| 2876 | CMe | S | Q1a | a bond | H | a bond | NH | O | a bond | T3f | OH |
| 2877 | CMe | S | Q1a | a bond | H | a bond | NH | O | a bond | T3g | OH |
| 2878 | CMe | S | Q1a | a bond | H | a bond | NH | O | a bond | T3h | OH |
| 2879 | CMe | S | Q1a | a bond | H | a bond | NH | O | a bond | T3i | OH |
| 2880 | CMe | S | Q1a | a bond | H | a bond | NH | O | a bond | T3j | OH |
| 2881 | CMe | S | Q1b | a bond | Me | a bond | NH | S | NH | T3a | OH |
| 2882 | CMe | S | Q1b | a bond | Me | a bond | NH | S | NH | T3b | OH |
| 2883 | CMe | S | Q1b | a bond | Me | a bond | NH | S | NH | T3c | OH |
| 2884 | CMe | S | Q1b | a bond | Me | a bond | NH | S | NH | T3d | OH |
| 2885 | CMe | S | Q1b | a bond | Me | a bond | NH | S | NH | T3e | OH |
| 2886 | CMe | S | Q1b | a bond | Me | a bond | NH | S | NH | T3f | OH |
| 2887 | CMe | S | Q1b | a bond | Me | a bond | NH | S | NH | T3g | OH |
| 2888 | CMe | S | Q1b | a bond | Me | a bond | NH | S | NH | T3h | OH |
| 2889 | CMe | S | Q1b | a bond | Me | a bond | NH | S | NH | T3i | OH |
| 2890 | CMe | S | Q1b | a bond | Me | a bond | NH | S | NH | T3j | OH |
| 2891 | CMe | S | Q1b | a bond | Me | a bond | NH | S | a bond | T3a | OH |
| 2892 | CMe | S | Q1b | a bond | Me | a bond | NH | S | a bond | T3b | OH |
| 2893 | CMe | S | Q1b | a bond | Me | a bond | NH | S | a bond | T3c | OH |
| 2894 | CMe | S | Q1b | a bond | Me | a bond | NH | S | a bond | T3d | OH |
| 2895 | CMe | S | Q1b | a bond | Me | a bond | NH | S | a bond | T3e | OH |
| 2896 | CMe | S | Q1b | a bond | Me | a bond | NH | S | a bond | T3f | OH |
| 2897 | CMe | S | Q1b | a bond | Me | a bond | NH | S | a bond | T3g | OH |
| 2898 | CMe | S | Q1b | a bond | Me | a bond | NH | S | a bond | T3h | OH |
| 2899 | CMe | S | Q1b | a bond | Me | a bond | NH | S | a bond | T3i | OH |
| 2900 | CMe | S | Q1b | a bond | Me | a bond | NH | S | a bond | T3j | OH |
| 2901 | CMe | S | Q1b | a bond | Me | a bond | NH | O | NH | T3a | OH |
| 2902 | CMe | S | Q1b | a bond | Me | a bond | NH | O | NH | T3b | OH |
| 2903 | CMe | S | Q1b | a bond | Me | a bond | NH | O | NH | T3c | OH |
| 2904 | CMe | S | Q1b | a bond | Me | a bond | NH | O | NH | T3d | OH |
| 2905 | CMe | S | Q1b | a bond | Me | a bond | NH | O | NH | T3e | OH |
| 2906 | CMe | S | Q1b | a bond | Me | a bond | NH | O | NH | T3f | OH |
| 2907 | CMe | S | Q1b | a bond | Me | a bond | NH | O | NH | T3g | OH |
| 2908 | CMe | S | Q1b | a bond | Me | a bond | NH | O | NH | T3h | OH |
| 2909 | CMe | S | Q1b | a bond | Me | a bond | NH | O | NH | T3i | OH |
| 2910 | CMe | S | Q1b | a bond | Me | a bond | NH | O | NH | T3j | OH |
| 2911 | CMe | S | Q1b | a bond | Me | a bond | NH | O | a bond | T3a | OH |
| 2912 | CMe | S | Q1b | a bond | Me | a bond | NH | O | a bond | T3b | OH |
| 2913 | CMe | S | Q1b | a bond | Me | a bond | NH | O | a bond | T3c | OH |
| 2914 | CMe | S | Q1b | a bond | Me | a bond | NH | O | a bond | T3d | OH |
| 2915 | CMe | S | Q1b | a bond | Me | a bond | NH | O | a bond | T3e | OH |
| 2916 | CMe | S | Q1b | a bond | Me | a bond | NH | O | a bond | T3f | OH |
| 2917 | CMe | S | Q1b | a bond | Me | a bond | NH | O | a bond | T3g | OH |
| 2918 | CMe | S | Q1b | a bond | Me | a bond | NH | O | a bond | T3h | OH |
| 2919 | CMe | S | Q1b | a bond | Me | a bond | NH | O | a bond | T3i | OH |
| 2920 | CMe | S | Q1b | a bond | Me | a bond | NH | O | a bond | T3j | OH |
| 2921 | CMe | S | Q1b | a bond | H | a bond | NH | S | NH | T3a | OH |
| 2922 | CMe | S | Q1b | a bond | H | a bond | NH | S | NH | T3b | OH |
| 2923 | CMe | S | Q1b | a bond | H | a bond | NH | S | NH | T3c | OH |
| 2924 | CMe | S | Q1b | a bond | H | a bond | NH | S | NH | T3d | OH |
| 2925 | CMe | S | Q1b | a bond | H | a bond | NH | S | NH | T3e | OH |
| 2926 | CMe | S | Q1b | a bond | H | a bond | NH | S | NH | T3f | OH |
| 2927 | CMe | S | Q1b | a bond | H | a bond | NH | S | NH | T3g | OH |
| 2928 | CMe | S | Q1b | a bond | H | a bond | NH | S | NH | T3h | OH |
| 2929 | CMe | S | Q1b | a bond | H | a bond | NH | S | NH | T3i | OH |
| 2930 | CMe | S | Q1b | a bond | H | a bond | NH | S | NH | T3j | OH |
| 2931 | CMe | S | Q1b | a bond | H | a bond | NH | S | a bond | T3a | OH |
| 2932 | CMe | S | Q1b | a bond | H | a bond | NH | S | a bond | T3b | OH |
| 2933 | CMe | S | Q1b | a bond | H | a bond | NH | S | a bond | T3c | OH |
| 2934 | CMe | S | Q1b | a bond | H | a bond | NH | S | a bond | T3d | OH |
| 2935 | CMe | S | Q1b | a bond | H | a bond | NH | S | a bond | T3e | OH |

TABLE 2-continued

| No | A | B | R¹ | L¹ | R² | L² | L³ | Y | L⁴ | R³ | X |
|---|---|---|---|---|---|---|---|---|---|---|---|
| 2936 | CMe | S | Q1b | a bond | H | a bond | NH | S | a bond | T3f | OH |
| 2937 | CMe | S | Q1b | a bond | H | a bond | NH | S | a bond | T3g | OH |
| 2938 | CMe | S | Q1b | a bond | H | a bond | NH | S | a bond | T3h | OH |
| 2939 | CMe | S | Q1b | a bond | H | a bond | NH | S | a bond | T3i | OH |
| 2940 | CMe | S | Q1b | a bond | H | a bond | NH | S | a bond | T3j | OH |
| 2941 | CMe | S | Q1b | a bond | H | a bond | NH | O | NH | T3a | OH |
| 2942 | CMe | S | Q1b | a bond | H | a bond | NH | O | NH | T3b | OH |
| 2943 | CMe | S | Q1b | a bond | H | a bond | NH | O | NH | T3c | OH |
| 2944 | CMe | S | Q1b | a bond | H | a bond | NH | O | NH | T3d | OH |
| 2945 | CMe | S | Q1b | a bond | H | a bond | NH | O | NH | T3e | OH |
| 2946 | CMe | S | Q1b | a bond | H | a bond | NH | O | NH | T3f | OH |
| 2947 | CMe | S | Q1b | a bond | H | a bond | NH | O | NH | T3g | OH |
| 2948 | CMe | S | Q1b | a bond | H | a bond | NH | O | NH | T3h | OH |
| 2949 | CMe | S | Q1b | a bond | H | a bond | NH | O | NH | T3i | OH |
| 2950 | CMe | S | Q1b | a bond | H | a bond | NH | O | NH | T3j | OH |
| 2951 | CMe | S | Q1b | a bond | H | a bond | NH | O | a bond | T3a | OH |
| 2952 | CMe | S | Q1b | a bond | H | a bond | NH | O | a bond | T3b | OH |
| 2953 | CMe | S | Q1b | a bond | H | a bond | NH | O | a bond | T3c | OH |
| 2954 | CMe | S | Q1b | a bond | H | a bond | NH | O | a bond | T3d | OH |
| 2955 | CMe | S | Q1b | a bond | H | a bond | NH | O | a bond | T3e | OH |
| 2956 | CMe | S | Q1b | a bond | H | a bond | NH | O | a bond | T3f | OH |
| 2957 | CMe | S | Q1b | a bond | H | a bond | NH | O | a bond | T3g | OH |
| 2958 | CMe | S | Q1b | a bond | H | a bond | NH | O | a bond | T3h | OH |
| 2959 | CMe | S | Q1b | a bond | H | a bond | NH | O | a bond | T3i | OH |
| 2960 | CMe | S | Q1b | a bond | H | a bond | NH | O | a bond | T3j | OH |
| 2961 | CMe | S | Q1c | a bond | Me | a bond | NH | S | NH | T3a | OH |
| 2962 | CMe | S | Q1c | a bond | Me | a bond | NH | S | NH | T3b | OH |
| 2963 | CMe | S | Q1c | a bond | Me | a bond | NH | S | NH | T3c | OH |
| 2964 | CMe | S | Q1c | a bond | Me | a bond | NH | S | NH | T3d | OH |
| 2965 | CMe | S | Q1c | a bond | Me | a bond | NH | S | NH | T3e | OH |
| 2966 | CMe | S | Q1c | a bond | Me | a bond | NH | S | NH | T3f | OH |
| 2967 | CMe | S | Q1c | a bond | Me | a bond | NH | S | NH | T3g | OH |
| 2968 | CMe | S | Q1c | a bond | Me | a bond | NH | S | NH | T3h | OH |
| 2969 | CMe | S | Q1c | a bond | Me | a bond | NH | S | NH | T3i | OH |
| 2970 | CMe | S | Q1c | a bond | Me | a bond | NH | S | NH | T3j | OH |
| 2971 | CMe | S | Q1c | a bond | Me | a bond | NH | S | a bond | T3a | OH |
| 2972 | CMe | S | Q1c | a bond | Me | a bond | NH | S | a bond | T3b | OH |
| 2973 | CMe | S | Q1c | a bond | Me | a bond | NH | S | a bond | T3c | OH |
| 2974 | CMe | S | Q1c | a bond | Me | a bond | NH | S | a bond | T3d | OH |
| 2975 | CMe | S | Q1c | a bond | Me | a bond | NH | S | a bond | T3e | OH |
| 2976 | CMe | S | Q1c | a bond | Me | a bond | NH | S | a bond | T3f | OH |
| 2977 | CMe | S | Q1c | a bond | Me | a bond | NH | S | a bond | T3g | OH |
| 2978 | CMe | S | Q1c | a bond | Me | a bond | NH | S | a bond | T3h | OH |
| 2979 | CMe | S | Q1c | a bond | Me | a bond | NH | S | a bond | T3i | OH |
| 2980 | CMe | S | Q1c | a bond | Me | a bond | NH | S | a bond | T3j | OH |
| 2981 | CMe | S | Q1c | a bond | Me | a bond | NH | O | NH | T3a | OH |
| 2982 | CMe | S | Q1c | a bond | Me | a bond | NH | O | NH | T3b | OH |
| 2983 | CMe | S | Q1c | a bond | Me | a bond | NH | O | NH | T3c | OH |
| 2984 | CMe | S | Q1c | a bond | Me | a bond | NH | O | NH | T3d | OH |
| 2985 | CMe | S | Q1c | a bond | Me | a bond | NH | O | NH | T3e | OH |
| 2986 | CMe | S | Q1c | a bond | Me | a bond | NH | O | NH | T3f | OH |
| 2987 | CMe | S | Q1c | a bond | Me | a bond | NH | O | NH | T3g | OH |
| 2988 | CMe | S | Q1c | a bond | Me | a bond | NH | O | NH | T3h | OH |
| 2989 | CMe | S | Q1c | a bond | Me | a bond | NH | O | NH | T3i | OH |
| 2990 | CMe | S | Q1c | a bond | Me | a bond | NH | O | NH | T3j | OH |
| 2991 | CMe | S | Q1c | a bond | Me | a bond | NH | O | a bond | T3a | OH |
| 2992 | CMe | S | Q1c | a bond | Me | a bond | NH | O | a bond | T3b | OH |
| 2993 | CMe | S | Q1c | a bond | Me | a bond | NH | O | a bond | T3c | OH |
| 2994 | CMe | S | Q1c | a bond | Me | a bond | NH | O | a bond | T3d | OH |
| 2995 | CMe | S | Q1c | a bond | Me | a bond | NH | O | a bond | T3e | OH |
| 2996 | CMe | S | Q1c | a bond | Me | a bond | NH | O | a bond | T3f | OH |
| 2997 | CMe | S | Q1c | a bond | Me | a bond | NH | O | a bond | T3g | OH |
| 2998 | CMe | S | Q1c | a bond | Me | a bond | NH | O | a bond | T3h | OH |
| 2999 | CMe | S | Q1c | a bond | Me | a bond | NH | O | a bond | T3i | OH |
| 3000 | CMe | S | Q1c | a bond | Me | a bond | NH | O | a bond | T3j | OH |
| 3001 | CMe | S | Q1c | a bond | H | a bond | NH | S | NH | T3a | OH |
| 3002 | CMe | S | Q1c | a bond | H | a bond | NH | S | NH | T3b | OH |
| 3003 | CMe | S | Q1c | a bond | H | a bond | NH | S | NH | T3c | OH |
| 3004 | CMe | S | Q1c | a bond | H | a bond | NH | S | NH | T3d | OH |
| 3005 | CMe | S | Q1c | a bond | H | a bond | NH | S | NH | T3e | OH |
| 3006 | CMe | S | Q1c | a bond | H | a bond | NH | S | NH | T3f | OH |
| 3007 | CMe | S | Q1c | a bond | H | a bond | NH | S | NH | T3g | OH |
| 3008 | CMe | S | Q1c | a bond | H | a bond | NH | S | NH | T3h | OH |
| 3009 | CMe | S | Q1c | a bond | H | a bond | NH | S | NH | T3i | OH |
| 3010 | CMe | S | Q1c | a bond | H | a bond | NH | S | NH | T3j | OH |
| 3011 | CMe | S | Q1c | a bond | H | a bond | NH | S | a bond | T3a | OH |
| 3012 | CMe | S | Q1c | a bond | H | a bond | NH | S | a bond | T3b | OH |
| 3013 | CMe | S | Q1c | a bond | H | a bond | NH | S | a bond | T3c | OH |

TABLE 2-continued

| No | A | B | R¹ | L¹ | R² | L² | L³ | Y | L⁴ | R³ | X |
|---|---|---|---|---|---|---|---|---|---|---|---|
| 3014 | CMe | S | Q1c | a bond | H | a bond | NH | S | a bond | T3d | OH |
| 3015 | CMe | S | Q1c | a bond | H | a bond | NH | S | a bond | T3e | OH |
| 3016 | CMe | S | Q1c | a bond | H | a bond | NH | S | a bond | T3f | OH |
| 3017 | CMe | S | Q1c | a bond | H | a bond | NH | S | a bond | T3g | OH |
| 3018 | CMe | S | Q1c | a bond | H | a bond | NH | S | a bond | T3h | OH |
| 3019 | CMe | S | Q1c | a bond | H | a bond | NH | S | a bond | T3i | OH |
| 3020 | CMe | S | Q1c | a bond | H | a bond | NH | S | a bond | T3j | OH |
| 3021 | CMe | S | Q1c | a bond | H | a bond | NH | O | NH | T3a | OH |
| 3022 | CMe | S | Q1c | a bond | H | a bond | NH | O | NH | T3b | OH |
| 3023 | CMe | S | Q1c | a bond | H | a bond | NH | O | NH | T3c | OH |
| 3024 | CMe | S | Q1c | a bond | H | a bond | NH | O | NH | T3d | OH |
| 3025 | CMe | S | Q1c | a bond | H | a bond | NH | O | NH | T3e | OH |
| 3026 | CMe | S | Q1c | a bond | H | a bond | NH | O | NH | T3f | OH |
| 3027 | CMe | S | Q1c | a bond | H | a bond | NH | O | NH | T3g | OH |
| 3028 | CMe | S | Q1c | a bond | H | a bond | NH | O | NH | T3h | OH |
| 3029 | CMe | S | Q1c | a bond | H | a bond | NH | O | NH | T3i | OH |
| 3030 | CMe | S | Q1c | a bond | H | a bond | NH | O | NH | T3j | OH |
| 3031 | CMe | S | Q1c | a bond | H | a bond | NH | O | abond | T3a | OH |
| 3032 | CMe | S | Q1c | a bond | H | a bond | NH | O | a bond | T3b | OH |
| 3033 | CMe | S | Q1c | a bond | H | a bond | NH | O | a bond | T3c | OH |
| 3034 | CMe | S | Q1c | a bond | H | a bond | NH | O | a bond | T3d | OH |
| 3035 | CMe | S | Q1c | a bond | H | a bond | NH | O | a bond | T3e | OH |
| 3036 | CMe | S | Q1c | a bond | H | a bond | NH | O | a bond | T3f | OH |
| 3037 | CMe | S | Q1c | a bond | H | a bond | NH | O | a bond | T3g | OH |
| 3038 | CMe | S | Q1c | a bond | H | a bond | NH | O | a bond | T3h | OH |
| 3039 | CMe | S | Q1c | a bond | H | a bond | NH | O | a bond | T3i | OH |
| 3040 | CMe | S | Q1c | a bond | H | a bond | NH | O | a bond | T3j | OH |
| 3041 | CMe | S | Q1i | a bond | Me | a bond | NH | S | NH | T3a | OH |
| 3042 | CMe | S | Q1i | a bond | Me | a bond | NH | S | NH | T3b | OH |
| 3043 | CMe | S | Q1i | a bond | Me | a bond | NH | S | NH | T3c | OH |
| 3044 | CMe | S | Q1i | a bond | Me | a bond | NH | S | NH | T3d | OH |
| 3045 | CMe | S | Q1i | a bond | Me | a bond | NH | S | NH | T3e | OH |
| 3046 | CMe | S | Q1i | a bond | Me | a bond | NH | S | NH | T3f | OH |
| 3047 | CMe | S | Q1i | a bond | Me | a bond | NH | S | NH | T3g | OH |
| 3048 | CMe | S | Q1i | a bond | Me | a bond | NH | S | NH | T3h | OH |
| 3049 | CMe | S | Q1i | a bond | Me | a bond | NH | S | NH | T3i | OH |
| 3050 | CMe | S | Q1i | a bond | Me | a bond | NH | S | NH | T3j | OH |
| 3051 | CMe | S | Q1i | a bond | Me | a bond | NH | S | a bond | T3a | OH |
| 3052 | CMe | S | Q1i | a bond | Me | a bond | NH | S | a bond | T3b | OH |
| 3053 | CMe | S | Q1i | a bond | Me | a bond | NH | S | a bond | T3c | OH |
| 3054 | CMe | S | Q1i | a bond | Me | a bond | NH | S | a bond | T3d | OH |
| 3055 | CMe | S | Q1i | a bond | Me | a bond | NH | S | a bond | T3e | OH |
| 3056 | CMe | S | Q1i | a bond | Me | a bond | NH | S | a bond | T3f | OH |
| 3057 | CMe | S | Q1i | a bond | Me | a bond | NH | S | a bond | T3g | OH |
| 3058 | CMe | S | Q1i | a bond | Me | a bond | NH | S | a bond | T3h | OH |
| 3059 | CMe | S | Q1i | a bond | Me | a bond | NH | S | a bond | T3i | OH |
| 3060 | CMe | S | Q1i | a bond | Me | a bond | NH | S | a bond | T3j | OH |
| 3061 | CMe | S | Q1i | a bond | Me | a bond | NH | O | NH | T3a | OH |
| 3062 | CMe | S | Q1i | a bond | Me | a bond | NH | O | NH | T3b | OH |
| 3063 | CMe | S | Q1i | a bond | Me | a bond | NH | O | NH | T3c | OH |
| 3064 | CMe | S | Q1i | a bond | Me | a bond | NH | O | NH | T3d | OH |
| 3065 | CMe | S | Q1i | a bond | Me | a bond | NH | O | NH | T3e | OH |
| 3066 | CMe | S | Q1i | a bond | Me | a bond | NH | O | NH | T3f | OH |
| 3067 | CMe | S | Q1i | a bond | Me | a bond | NH | O | NH | T3g | OH |
| 3068 | CMe | S | Q1i | a bond | Me | a bond | NH | O | NH | T3h | OH |
| 3069 | CMe | S | Q1i | a bond | Me | a bond | NH | O | NH | T3i | OH |
| 3070 | CMe | S | Q1i | a bond | Me | a bond | NH | O | NH | T3j | OH |
| 3071 | CMe | S | Q1i | a bond | Me | a bond | NH | O | a bond | T3a | OH |
| 3072 | CMe | S | Q1i | a bond | Me | a bond | NH | O | a bond | T3b | OH |
| 3073 | CMe | S | Q1i | a bond | Me | a bond | NH | O | a bond | T3c | OH |
| 3074 | CMe | S | Q1i | a bond | Me | a bond | NH | O | a bond | T3d | OH |
| 3075 | CMe | S | Q1i | a bond | Me | a bond | NH | O | a bond | T3e | OH |
| 3076 | CMe | S | Q1i | a bond | Me | a bond | NH | O | a bond | T3f | OH |
| 3077 | CMe | S | Q1i | a bond | Me | a bond | NH | O | a bond | T3g | OH |
| 3078 | CMe | S | Q1i | a bond | Me | a bond | NH | O | a bond | T3h | OH |
| 3079 | CMe | S | Q1i | a bond | Me | a bond | NH | O | a bond | T3i | OH |
| 3080 | CMe | S | Q1i | a bond | Me | a bond | NH | O | a bond | T3j | OH |
| 3081 | CMe | S | Q1i | a bond | H | a bond | NH | S | NH | T3a | OH |
| 3082 | CMe | S | Q1i | a bond | H | a bond | NH | S | NH | T3b | OH |
| 3083 | CMe | S | Q1i | a bond | H | a bond | NH | S | NH | T3c | OH |
| 3084 | CMe | S | Q1i | a bond | H | a bond | NH | S | NH | T3d | OH |
| 3085 | CMe | S | Q1i | a bond | H | a bond | NH | S | NH | T3e | OH |
| 3086 | CMe | S | Q1i | a bond | H | a bond | NH | S | NH | T3f | OH |
| 3087 | CMe | S | Q1i | a bond | H | a bond | NH | S | NH | T3g | OH |
| 3088 | CMe | S | Q1i | a bond | H | a bond | NH | S | NH | T3h | OH |
| 3089 | CMe | S | Q1i | a bond | H | a bond | NH | S | NH | T3i | OH |
| 3090 | CMe | S | Q1i | a bond | H | a bond | NH | S | NH | T3j | OH |
| 3091 | CMe | S | Q1i | a bond | H | a bond | NH | S | a bond | T3a | OH |

TABLE 2-continued

| No | A | B | R¹ | L¹ | R² | L² | L³ | Y | L⁴ | R³ | X |
|---|---|---|---|---|---|---|---|---|---|---|---|
| 3092 | CMe | S | Q1i | a bond | H | a bond | NH | S | a bond | T3b | OH |
| 3093 | CMe | S | Q1i | a bond | H | a bond | NH | S | a bond | T3c | OH |
| 3094 | CMe | S | Q1i | a bond | H | a bond | NH | S | a bond | T3d | OH |
| 3095 | CMe | S | Q1i | a bond | H | a bond | NH | S | a bond | T3e | OH |
| 3096 | CMe | S | Q1i | a bond | H | a bond | NH | S | a bond | T3f | OH |
| 3097 | CMe | S | Q1i | a bond | H | a bond | NH | S | a bond | T3g | OH |
| 3098 | CMe | S | Q1i | a bond | H | a bond | NH | S | a bond | T3h | OH |
| 3099 | CMe | S | Q1i | a bond | H | a bond | NH | S | a bond | T3i | OH |
| 3100 | CMe | S | Q1i | a bond | H | a bond | NH | S | a bond | T3j | OH |
| 3101 | CMe | S | Q1i | a bond | H | a bond | NH | O | NH | T3a | OH |
| 3102 | CMe | S | Q1i | a bond | H | a bond | NH | O | NH | T3b | OH |
| 3103 | CMe | S | Q1i | a bond | H | a bond | NH | O | NH | T3c | OH |
| 3104 | CMe | S | Q1i | a bond | H | a bond | NH | O | NH | T3d | OH |
| 3105 | CMe | S | Q1i | a bond | H | a bond | NH | O | NH | T3e | OH |
| 3106 | CMe | S | Q1i | a bond | H | a bond | NH | O | NH | T3f | OH |
| 3107 | CMe | S | Q1i | a bond | H | a bond | NH | O | NH | T3g | OH |
| 3108 | CMe | S | Q1i | a bond | H | a bond | NH | O | NH | T3h | OH |
| 3109 | CMe | S | Q1i | a bond | H | a bond | NH | O | NH | T3i | OH |
| 3110 | CMe | S | Q1i | a bond | H | a bond | NH | O | NH | T3j | OH |
| 3111 | CMe | S | Q1i | a bond | H | a bond | NH | O | a bond | T3a | OH |
| 3112 | CMe | S | Q1i | a bond | H | a bond | NH | O | a bond | T3b | OH |
| 3113 | CMe | S | Q1i | a bond | H | a bond | NH | O | a bond | T3c | OH |
| 3114 | CMe | S | Q1i | a bond | H | a bond | NH | O | a bond | T3d | OH |
| 3115 | CMe | S | Q1i | a bond | H | a bond | NH | O | a bond | T3e | OH |
| 3116 | CMe | S | Q1i | a bond | H | a bond | NH | O | a bond | T3f | OH |
| 3117 | CMe | S | Q1i | a bond | H | a bond | NH | O | a bond | T3g | OH |
| 3118 | CMe | S | Q1i | a bond | H | a bond | NH | O | a bond | T3h | OH |
| 3119 | CMe | S | Q1i | a bond | H | a bond | NH | O | a bond | T3i | OH |
| 3120 | CMe | S | Q1i | a bond | H | a bond | NH | O | a bond | T3j | OH |
| 3121 | CMe | S | Q1j | a bond | Me | a bond | NH | S | NH | T3a | OH |
| 3122 | CMe | S | Q1j | a bond | Me | a bond | NH | S | NH | T3b | OH |
| 3123 | CMe | S | Q1j | a bond | Me | a bond | NH | S | NH | T3c | OH |
| 3124 | CMe | S | Q1j | a bond | Me | a bond | NH | S | NH | T3d | OH |
| 3125 | CMe | S | Q1j | a bond | Me | a bond | NH | S | NH | T3e | OH |
| 3126 | CMe | S | Q1j | a bond | Me | a bond | NH | S | NH | T3f | OH |
| 3127 | CMe | S | Q1j | a bond | Me | a bond | NH | S | NH | T3g | OH |
| 3128 | CMe | S | Q1j | a bond | Me | a bond | NH | S | NH | T3h | OH |
| 3129 | CMe | S | Q1j | a bond | Me | a bond | NH | S | NH | T3i | OH |
| 3130 | CMe | S | Q1j | a bond | Me | a bond | NH | S | NH | T3j | OH |
| 3131 | CMe | S | Q1j | a bond | Me | a bond | NH | S | a bond | T3a | OH |
| 3132 | CMe | S | Q1j | a bond | Me | a bond | NH | S | a bond | T3b | OH |
| 3133 | CMe | S | Q1j | a bond | Me | a bond | NH | S | a bond | T3c | OH |
| 3134 | CMe | S | Q1j | a bond | Me | a bond | NH | S | a bond | T3d | OH |
| 3135 | CMe | S | Q1j | a bond | Me | a bond | NH | S | a bond | T3e | OH |
| 3136 | CMe | S | Q1j | a bond | Me | a bond | NH | S | a bond | T3f | OH |
| 3137 | CMe | S | Q1j | a bond | Me | a bond | NH | S | a bond | T3g | OH |
| 3138 | CMe | S | Q1j | a bond | Me | a bond | NH | S | a bond | T3h | OH |
| 3139 | CMe | S | Q1j | a bond | Me | a bond | NH | S | a bond | T3i | OH |
| 3140 | CMe | S | Q1j | a bond | Me | a bond | NH | S | a bond | T3j | OH |
| 3141 | CMe | S | Q1j | a bond | Me | a bond | NH | O | NH | T3a | OH |
| 3142 | CMe | S | Q1j | a bond | Me | a bond | NH | O | NH | T3b | OH |
| 3143 | CMe | S | Q1j | a bond | Me | a bond | NH | O | NH | T3c | OH |
| 3144 | CMe | S | Q1j | a bond | Me | a bond | NH | O | NH | T3d | OH |
| 3145 | CMe | S | Q1j | a bond | Me | a bond | NH | O | NH | T3e | OH |
| 3146 | CMe | S | Q1j | a bond | Me | a bond | NH | O | NH | T3f | OH |
| 3147 | CMe | S | Q1j | a bond | Me | a bond | NH | O | NH | T3g | OH |
| 3148 | CMe | S | Q1j | a bond | Me | a bond | NH | O | NH | T3h | OH |
| 3149 | CMe | S | Q1j | a bond | Me | a bond | NH | O | NH | T3i | OH |
| 3150 | CMe | S | Q1j | a bond | Me | a bond | NH | O | NH | T3j | OH |
| 3151 | CMe | S | Q1j | a bond | Me | a bond | NH | O | a bond | T3a | OH |
| 3152 | CMe | S | Q1j | a bond | Me | a bond | NH | O | a bond | T3b | OH |
| 3153 | CMe | S | Q1j | a bond | Me | a bond | NH | O | a bond | T3c | OH |
| 3154 | CMe | S | Q1j | a bond | Me | a bond | NH | O | a bond | T3d | OH |
| 3155 | CMe | S | Q1j | a bond | Me | a bond | NH | O | a bond | T3e | OH |
| 3156 | CMe | S | Q1j | a bond | Me | a bond | NH | O | a bond | T3f | OH |
| 3157 | CMe | S | Q1j | a bond | Me | a bond | NH | O | a bond | T3g | OH |
| 3158 | CMe | S | Q1j | a bond | Me | a bond | NH | O | a bond | T3h | OH |
| 3159 | CMe | S | Q1j | a bond | Me | a bond | NH | O | a bond | T3i | OH |
| 3160 | CMe | S | Q1j | a bond | Me | a bond | NH | O | a bond | T3j | OH |
| 3161 | CMe | S | Q1j | a bond | H | a bond | NH | S | NH | T3a | OH |
| 3162 | CMe | S | Q1j | a bond | H | a bond | NH | S | NH | T3b | OH |
| 3163 | CMe | S | Q1j | a bond | H | a bond | NH | S | NH | T3c | OH |
| 3164 | CMe | S | Q1j | a bond | H | a bond | NH | S | NH | T3d | OH |
| 3165 | CMe | S | Q1j | a bond | H | a bond | NH | S | NH | T3e | OH |
| 3166 | CMe | S | Q1j | a bond | H | a bond | NH | S | NH | T3f | OH |
| 3167 | CMe | S | Q1j | a bond | H | a bond | NH | S | NH | T3g | OH |
| 3168 | CMe | S | Q1j | a bond | H | a bond | NH | S | NH | T3h | OH |
| 3169 | CMe | S | Q1j | a bond | H | a bond | NH | S | NH | T3i | OH |

TABLE 2-continued

| No | A | B | R¹ | L¹ | R² | L² | L³ | Y | L⁴ | R³ | X |
|---|---|---|---|---|---|---|---|---|---|---|---|
| 3170 | CMe | S | Q1j | a bond | H | a bond | NH | S | NH | T3j | OH |
| 3171 | CMe | S | Q1j | a bond | H | a bond | NH | S | a bond | T3a | OH |
| 3172 | CMe | S | Q1j | a bond | H | a bond | NH | S | a bond | T3b | OH |
| 3173 | CMe | S | Q1j | a bond | H | a bond | NH | S | a bond | T3c | OH |
| 3174 | CMe | S | Q1j | a bond | H | a bond | NH | S | a bond | T3d | OH |
| 3175 | CMe | S | Q1j | a bond | H | a bond | NH | S | a bond | T3e | OH |
| 3176 | CMe | S | Q1j | a bond | H | a bond | NH | S | a bond | T3f | OH |
| 3177 | CMe | S | Q1j | a bond | H | a bond | NH | S | a bond | T3g | OH |
| 3178 | CMe | S | Q1j | a bond | H | a bond | NH | S | a bond | T3h | OH |
| 3179 | CMe | S | Q1j | a bond | H | a bond | NH | S | a bond | T3i | OH |
| 3180 | CMe | S | Q1j | a bond | H | a bond | NH | S | a bond | T3j | OH |
| 3181 | CMe | S | Q1j | a bond | H | a bond | NH | O | NH | T3a | OH |
| 3182 | CMe | S | Q1j | a bond | H | a bond | NH | O | NH | T3b | OH |
| 3183 | CMe | S | Q1j | a bond | H | a bond | NH | O | NH | T3c | OH |
| 3184 | CMe | S | Q1j | a bond | H | a bond | NH | O | NH | T3d | OH |
| 3185 | CMe | S | Q1j | a bond | H | a bond | NH | O | NH | T3e | OH |
| 3186 | CMe | S | Q1j | a bond | H | a bond | NH | O | NH | T3f | OH |
| 3187 | CMe | S | Q1j | a bond | H | a bond | NH | O | NH | T3g | OH |
| 3188 | CMe | S | Q1j | a bond | H | a bond | NH | O | NH | T3h | OH |
| 3189 | CMe | S | Q1j | a bond | H | a bond | NH | O | NH | T3i | OH |
| 3190 | CMe | S | Q1j | a bond | H | a bond | NH | O | NH | T3j | OH |
| 3191 | CMe | S | Q1j | a bond | H | a bond | NH | O | a bond | T3a | OH |
| 3192 | CMe | S | Q1j | a bond | H | a bond | NH | O | a bond | T3b | OH |
| 3193 | CMe | S | Q1j | a bond | H | a bond | NH | O | a bond | T3c | OH |
| 3194 | CMe | S | Q1j | a bond | H | a bond | NH | O | a bond | T3d | OH |
| 3195 | CMe | S | Q1j | a bond | H | a bond | NH | O | a bond | T3e | OH |
| 3196 | CMe | S | Q1j | a bond | H | a bond | NH | O | a bond | T3f | OH |
| 3197 | CMe | S | Q1j | a bond | H | a bond | NH | O | a bond | T3g | OH |
| 3198 | CMe | S | Q1j | a bond | H | a bond | NH | O | a bond | T3h | OH |
| 3199 | CMe | S | Q1j | a bond | H | a bond | NH | O | a bond | T3i | OH |
| 3200 | CMe | S | Q1j | a bond | H | a bond | NH | O | a bond | T3j | OH |
| 3201 | CMe | O | Q1a | a bond | Me | a bond | NH | S | NH | T3a | OH |
| 3202 | CMe | O | Q1a | a bond | Me | a bond | NH | S | NH | T3b | OH |
| 3203 | CMe | O | Q1a | a bond | Me | a bond | NH | S | NH | T3c | OH |
| 3204 | CMe | O | Q1a | a bond | Me | a bond | NH | S | NH | T3d | OH |
| 3205 | CMe | O | Q1a | a bond | Me | a bond | NH | S | NH | T3e | OH |
| 3206 | CMe | O | Q1a | a bond | Me | a bond | NH | S | NH | T3f | OH |
| 3207 | CMe | O | Q1a | a bond | Me | a bond | NH | S | NH | T3g | OH |
| 3208 | CMe | O | Q1a | a bond | Me | a bond | NH | S | NH | T3h | OH |
| 3209 | CMe | O | Q1a | a bond | Me | a bond | NH | S | NH | T3i | OH |
| 3210 | CMe | O | Q1a | a bond | Me | a bond | NH | S | NH | T3j | OH |
| 3211 | CMe | O | Q1a | a bond | Me | a bond | NH | S | a bond | T3a | OH |
| 3212 | CMe | O | Q1a | a bond | Me | a bond | NH | S | a bond | T3b | OH |
| 3213 | CMe | O | Q1a | a bond | Me | a bond | NH | S | a bond | T3c | OH |
| 3214 | CMe | O | Q1a | a bond | Me | a bond | NH | S | a bond | T3d | OH |
| 3215 | CMe | O | Q1a | a bond | Me | a bond | NH | S | a bond | T3e | OH |
| 3216 | CMe | O | Q1a | a bond | Me | a bond | NH | S | a bond | T3f | OH |
| 3217 | CMe | O | Q1a | a bond | Me | a bond | NH | S | a bond | T3g | OH |
| 3218 | CMe | O | Q1a | a bond | Me | a bond | NH | S | a bond | T3h | OH |
| 3219 | CMe | O | Q1a | a bond | Me | a bond | NH | S | a bond | T3i | OH |
| 3220 | CMe | O | Q1a | a bond | Me | a bond | NH | S | a bond | T3j | OH |
| 3221 | CMe | O | Q1a | a bond | Me | a bond | NH | O | NH | T3a | OH |
| 3222 | CMe | O | Q1a | a bond | Me | a bond | NH | O | NH | T3b | OH |
| 3223 | CMe | O | Q1a | a bond | Me | a bond | NH | O | NH | T3c | OH |
| 3224 | CMe | O | Q1a | a bond | Me | a bond | NH | O | NH | T3d | OH |
| 3225 | CMe | O | Q1a | a bond | Me | a bond | NH | O | NH | T3e | OH |
| 3226 | CMe | O | Q1a | a bond | Me | a bond | NH | O | NH | T3f | OH |
| 3227 | CMe | O | Q1a | a bond | Me | a bond | NH | O | NH | T3g | OH |
| 3228 | CMe | O | Q1a | a bond | Me | a bond | NH | O | NH | T3h | OH |
| 3229 | CMe | O | Q1a | a bond | Me | a bond | NH | O | NH | T3i | OH |
| 3230 | CMe | O | Q1a | a bond | Me | a bond | NH | O | NH | T3j | OH |
| 3231 | CMe | O | Q1a | a bond | Me | a bond | NH | O | a bond | T3a | OH |
| 3232 | CMe | O | Q1a | a bond | Me | a bond | NH | O | a bond | T3b | OH |
| 3233 | CMe | O | Q1a | a bond | Me | a bond | NH | O | a bond | T3c | OH |
| 3234 | CMe | O | Q1a | a bond | Me | a bond | NH | O | a bond | T3d | OH |
| 3235 | CMe | O | Q1a | a bond | Me | a bond | NH | O | a bond | T3e | OH |
| 3236 | CMe | O | Q1a | a bond | Me | a bond | NH | O | a bond | T3f | OH |
| 3237 | CMe | O | Q1a | a bond | Me | a bond | NH | O | a bond | T3g | OH |
| 3238 | CMe | O | Q1a | a bond | Me | a bond | NH | O | a bond | T3h | OH |
| 3239 | CMe | O | Q1a | a bond | Me | a bond | NH | O | a bond | T3i | OH |
| 3240 | CMe | O | Q1a | a bond | Me | a bond | NH | O | a bond | T3j | OH |
| 3241 | CMe | O | Q1a | a bond | H | a bond | NH | S | NH | T3a | OH |
| 3242 | CMe | O | Q1a | a bond | H | a bond | NH | S | NH | T3b | OH |
| 3243 | CMe | O | Q1a | a bond | H | a bond | NH | S | NH | T3c | OH |
| 3244 | CMe | O | Q1a | a bond | H | a bond | NH | S | NH | T3d | OH |
| 3245 | CMe | O | Q1a | a bond | H | a bond | NH | S | NH | T3e | OH |
| 3246 | CMe | O | Q1a | a bond | H | a bond | NH | S | NH | T3f | OH |
| 3247 | CMe | O | Q1a | a bond | H | a bond | NH | S | NH | T3g | OH |

TABLE 2-continued

| No | A | B | R¹ | L¹ | R² | L² | L³ | Y | L⁴ | R³ | X |
|---|---|---|---|---|---|---|---|---|---|---|---|
| 3248 | CMe | O | Q1a | a bond | H | a bond | NH | S | NH | T3h | OH |
| 3249 | CMe | O | Q1a | a bond | H | a bond | NH | S | NH | T3i | OH |
| 3250 | CMe | O | Q1a | a bond | H | a bond | NH | S | NH | T3j | OH |
| 3251 | CMe | O | Q1a | a bond | H | a bond | NH | S | a bond | T3a | OH |
| 3252 | CMe | O | Q1a | a bond | H | a bond | NH | S | a bond | T3b | OH |
| 3253 | CMe | O | Q1a | a bond | H | a bond | NH | S | a bond | T3c | OH |
| 3254 | CMe | O | Q1a | a bond | H | a bond | NH | S | a bond | T3d | OH |
| 3255 | CMe | O | Q1a | a bond | H | a bond | NH | S | a bond | T3e | OH |
| 3256 | CMe | O | Q1a | a bond | H | a bond | NH | S | a bond | T3f | OH |
| 3257 | CMe | O | Q1a | a bond | H | a bond | NH | S | a bond | T3g | OH |
| 3258 | CMe | O | Q1a | a bond | H | a bond | NH | S | a bond | T3h | OH |
| 3259 | CMe | O | Q1a | a bond | H | a bond | NH | S | a bond | T3i | OH |
| 3260 | CMe | O | Q1a | a bond | H | a bond | NH | S | a bond | T3j | OH |
| 3261 | CMe | O | Q1a | a bond | H | a bond | NH | O | NH | T3a | OH |
| 3262 | CMe | O | Q1a | a bond | H | a bond | NH | O | NH | T3b | OH |
| 3263 | CMe | O | Q1a | a bond | H | a bond | NH | O | NH | T3c | OH |
| 3264 | CMe | O | Q1a | a bond | H | a bond | NH | O | NH | T3d | OH |
| 3265 | CMe | O | Q1a | a bond | H | a bond | NH | O | NH | T3e | OH |
| 3266 | CMe | O | Q1a | a bond | H | a bond | NH | O | NH | T3f | OH |
| 3267 | CMe | O | Q1a | a bond | H | a bond | NH | O | NH | T3g | OH |
| 3268 | CMe | O | Q1a | a bond | H | a bond | NH | O | NH | T3h | OH |
| 3269 | CMe | O | Q1a | a bond | H | a bond | NH | O | NH | T3i | OH |
| 3270 | CMe | O | Q1a | a bond | H | a bond | NH | O | NH | T3j | OH |
| 3271 | CMe | O | Q1a | a bond | H | a bond | NH | O | a bond | T3a | OH |
| 3272 | CMe | O | Q1a | a bond | H | a bond | NH | O | a bond | T3b | OH |
| 3273 | CMe | O | Q1a | a bond | H | a bond | NH | O | a bond | T3c | OH |
| 3274 | CMe | O | Q1a | a bond | H | a bond | NH | O | a bond | T3d | OH |
| 3275 | CMe | O | Q1a | a bond | H | a bond | NH | O | a bond | T3e | OH |
| 3276 | CMe | O | Q1a | a bond | H | a bond | NH | O | a bond | T3f | OH |
| 3277 | CMe | O | Q1a | a bond | H | a bond | NH | O | a bond | T3g | OH |
| 3278 | CMe | O | Q1a | a bond | H | a bond | NH | O | a bond | T3h | OH |
| 3279 | CMe | O | Q1a | a bond | H | a bond | NH | O | a bond | T3i | OH |
| 3280 | CMe | O | Q1a | a bond | H | a bond | NH | O | a bond | T3j | OH |
| 3281 | CMe | O | Q1b | a bond | Me | a bond | NH | S | NH | T3a | OH |
| 3282 | CMe | O | Q1b | a bond | Me | a bond | NH | S | NH | T3b | OH |
| 3283 | CMe | O | Q1b | a bond | Me | a bond | NH | S | NH | T3c | OH |
| 3284 | CMe | O | Q1b | a bond | Me | a bond | NH | S | NH | T3d | OH |
| 3285 | CMe | O | Q1b | a bond | Me | a bond | NH | S | NH | T3e | OH |
| 3286 | CMe | O | Q1b | a bond | Me | a bond | NH | S | NH | T3f | OH |
| 3287 | CMe | O | Q1b | a bond | Me | a bond | NH | S | NH | T3g | OH |
| 3288 | CMe | O | Q1b | a bond | Me | a bond | NH | S | NH | T3h | OH |
| 3289 | CMe | O | Q1b | a bond | Me | a bond | NH | S | NH | T3i | OH |
| 3290 | CMe | O | Q1b | a bond | Me | a bond | NH | S | NH | T3j | OH |
| 3291 | CMe | O | Q1b | a bond | Me | a bond | NH | S | a bond | T3a | OH |
| 3292 | CMe | O | Q1b | a bond | Me | a bond | NH | S | a bond | T3b | OH |
| 3293 | CMe | O | Q1b | a bond | Me | a bond | NH | S | a bond | T3c | OH |
| 3294 | CMe | O | Q1b | a bond | Me | a bond | NH | S | a bond | T3d | OH |
| 3295 | CMe | O | Q1b | a bond | Me | a bond | NH | S | a bond | T3e | OH |
| 3296 | CMe | O | Q1b | a bond | Me | a bond | NH | S | a bond | T3f | OH |
| 3297 | CMe | O | Q1b | a bond | Me | a bond | NH | S | a bond | T3g | OH |
| 3298 | CMe | O | Q1b | a bond | Me | a bond | NH | S | a bond | T3h | OH |
| 3299 | CMe | O | Q1b | a bond | Me | a bond | NH | S | a bond | T3i | OH |
| 3300 | CMe | O | Q1b | a bond | Me | a bond | NH | S | a bond | T3j | OH |
| 3301 | CMe | O | Q1b | a bond | Me | a bond | NH | O | NH | T3a | OH |
| 3302 | CMe | O | Q1b | a bond | Me | a bond | NH | O | NH | T3b | OH |
| 3303 | CMe | O | Q1b | a bond | Me | a bond | NH | O | NH | T3c | OH |
| 3304 | CMe | O | Q1b | a bond | Me | a bond | NH | O | NH | T3d | OH |
| 3305 | CMe | O | Q1b | a bond | Me | a bond | NH | O | NH | T3e | OH |
| 3306 | CMe | O | Q1b | a bond | Me | a bond | NH | O | NH | T3f | OH |
| 3307 | CMe | O | Q1b | a bond | Me | a bond | NH | O | NH | T3g | OH |
| 3308 | CMe | O | Q1b | a bond | Me | a bond | NH | O | NH | T3h | OH |
| 3309 | CMe | O | Q1b | a bond | Me | a bond | NH | O | NH | T3i | OH |
| 3310 | CMe | O | Q1b | a bond | Me | a bond | NH | O | NH | T3j | OH |
| 3311 | CMe | O | Q1b | a bond | Me | a bond | NH | O | a bond | T3a | OH |
| 3312 | CMe | O | Q1b | a bond | Me | a bond | NH | O | a bond | T3b | OH |
| 3313 | CMe | O | Q1b | a bond | Me | a bond | NH | O | a bond | T3c | OH |
| 3314 | CMe | O | Q1b | a bond | Me | a bond | NH | O | a bond | T3d | OH |
| 3315 | CMe | O | Q1b | a bond | Me | a bond | NH | O | a bond | T3e | OH |
| 3316 | CMe | O | Q1b | a bond | Me | a bond | NH | O | a bond | T3f | OH |
| 3317 | CMe | O | Q1b | a bond | Me | a bond | NH | O | a bond | T3g | OH |
| 3318 | CMe | O | Q1b | a bond | Me | a bond | NH | O | a bond | T3h | OH |
| 3319 | CMe | O | Q1b | a bond | Me | a bond | NH | O | a bond | T3i | OH |
| 3320 | CMe | O | Q1b | a bond | Me | a bond | NH | O | a bond | T3j | OH |
| 3321 | CMe | O | Q1b | a bond | H | a bond | NH | S | NH | T3a | OH |
| 3322 | CMe | O | Q1b | a bond | H | a bond | NH | S | NH | T3b | OH |
| 3323 | CMe | O | Q1b | a bond | H | a bond | NH | S | NH | T3c | OH |
| 3324 | CMe | O | Q1b | a bond | H | a bond | NH | S | NH | T3d | OH |
| 3325 | CMe | O | Q1b | a bond | H | a bond | NH | S | NH | T3e | OH |

TABLE 2-continued

| No | A | B | R¹ | L¹ | R² | L² | L³ | Y | L⁴ | R³ | X |
|---|---|---|---|---|---|---|---|---|---|---|---|
| 3326 | CMe | O | Q1b | a bond | H | a bond | NH | S | NH | T3f | OH |
| 3327 | CMe | O | Q1b | a bond | H | a bond | NH | S | NH | T3g | OH |
| 3328 | CMe | O | Q1b | a bond | H | a bond | NH | S | NH | T3h | OH |
| 3329 | CMe | O | Q1b | a bond | H | a bond | NH | S | NH | T3i | OH |
| 3330 | CMe | O | Q1b | a bond | H | a bond | NH | S | NH | T3j | OH |
| 3331 | CMe | O | Q1b | a bond | H | a bond | NH | S | a bond | T3a | OH |
| 3332 | CMe | O | Q1b | a bond | H | a bond | NH | S | a bond | T3b | OH |
| 3333 | CMe | O | Q1b | a bond | H | a bond | NH | S | a bond | T3c | OH |
| 3334 | CMe | O | Q1b | a bond | H | a bond | NH | S | a bond | T3d | OH |
| 3335 | CMe | O | Q1b | a bond | H | a bond | NH | S | a bond | T3e | OH |
| 3336 | CMe | O | Q1b | a bond | H | a bond | NH | S | a bond | T3f | OH |
| 3337 | CMe | O | Q1b | a bond | H | a bond | NH | S | a bond | T3g | OH |
| 3338 | CMe | O | Q1b | a bond | H | a bond | NH | S | a bond | T3h | OH |
| 3339 | CMe | O | Q1b | a bond | H | a bond | NH | S | a bond | T3i | OH |
| 3340 | CMe | O | Q1b | a bond | H | a bond | NH | S | a bond | T3j | OH |
| 3341 | CMe | O | Q1b | a bond | H | a bond | NH | O | NH | T3a | OH |
| 3342 | CMe | O | Q1b | a bond | H | a bond | NH | O | NH | T3b | OH |
| 3343 | CMe | O | Q1b | a bond | H | a bond | NH | O | NH | T3c | OH |
| 3344 | CMe | O | Q1b | a bond | H | a bond | NH | O | NH | T3d | OH |
| 3345 | CMe | O | Q1b | a bond | H | a bond | NH | O | NH | T3e | OH |
| 3346 | CMe | O | Q1b | a bond | H | a bond | NH | O | NH | T3f | OH |
| 3347 | CMe | O | Q1b | a bond | H | a bond | NH | O | NH | T3g | OH |
| 3348 | CMe | O | Q1b | a bond | H | a bond | NH | O | NH | T3h | OH |
| 3349 | CMe | O | Q1b | a bond | H | a bond | NH | O | NH | T3i | OH |
| 3350 | CMe | O | Q1b | a bond | H | a bond | NH | O | NH | T3j | OH |
| 3351 | CMe | O | Q1b | a bond | H | a bond | NH | O | a bond | T3a | OH |
| 3352 | CMe | O | Q1b | a bond | H | a bond | NH | O | a bond | T3b | OH |
| 3353 | CMe | O | Q1b | a bond | H | a bond | NH | O | a bond | T3c | OH |
| 3354 | CMe | O | Q1b | a bond | H | a bond | NH | O | a bond | T3d | OH |
| 3355 | CMe | O | Q1b | a bond | H | a bond | NH | O | a bond | T3e | OH |
| 3356 | CMe | O | Q1b | a bond | H | a bond | NH | O | a bond | T3f | OH |
| 3357 | CMe | O | Q1b | a bond | H | a bond | NH | O | a bond | T3g | OH |
| 3358 | CMe | O | Q1b | a bond | H | a bond | NH | O | a bond | T3h | OH |
| 3359 | CMe | O | Q1b | a bond | H | a bond | NH | O | a bond | T3i | OH |
| 3360 | CMe | O | Q1b | a bond | H | a bond | NH | O | a bond | T3j | OH |
| 3361 | CMe | O | Q1c | a bond | Me | a bond | NH | S | NH | T3a | OH |
| 3362 | CMe | O | Q1c | a bond | Me | a bond | NH | S | NH | T3b | OH |
| 3363 | CMe | O | Q1c | a bond | Me | a bond | NH | S | NH | T3c | OH |
| 3364 | CMe | O | Q1c | a bond | Me | a bond | NH | S | NH | T3d | OH |
| 3365 | CMe | O | Q1c | a bond | Me | a bond | NH | S | NH | T3e | OH |
| 3366 | CMe | O | Q1c | a bond | Me | a bond | NH | S | NH | T3f | OH |
| 3367 | CMe | O | Q1c | a bond | Me | a bond | NH | S | NH | T3g | OH |
| 3368 | CMe | O | Q1c | a bond | Me | a bond | NH | S | NH | T3h | OH |
| 3369 | CMe | O | Q1c | a bond | Me | a bond | NH | S | NH | T3i | OH |
| 3370 | CMe | O | Q1c | a bond | Me | a bond | NH | S | NH | T3j | OH |
| 3371 | CMe | O | Q1c | a bond | Me | a bond | NH | S | a bond | T3a | OH |
| 3372 | CMe | O | Q1c | a bond | Me | a bond | NH | S | a bond | T3b | OH |
| 3373 | CMe | O | Q1c | a bond | Me | a bond | NH | S | a bond | T3c | OH |
| 3374 | CMe | O | Q1c | a bond | Me | a bond | NH | S | a bond | T3d | OH |
| 3375 | CMe | O | Q1c | a bond | Me | a bond | NH | S | a bond | T3e | OH |
| 3376 | CMe | O | Q1c | a bond | Me | a bond | NH | S | a bond | T3f | OH |
| 3377 | CMe | O | Q1c | a bond | Me | a bond | NH | S | a bond | T3g | OH |
| 3378 | CMe | O | Q1c | a bond | Me | a bond | NH | S | a bond | T3h | OH |
| 3379 | CMe | O | Q1c | a bond | Me | a bond | NH | S | a bond | T3i | OH |
| 3380 | CMe | O | Q1c | a bond | Me | a bond | NH | S | a bond | T3j | OH |
| 3381 | CMe | O | Q1c | a bond | Me | a bond | NH | O | NH | T3a | OH |
| 3382 | CMe | O | Q1c | a bond | Me | a bond | NH | O | NH | T3b | OH |
| 3383 | CMe | O | Q1c | a bond | Me | a bond | NH | O | NH | T3c | OH |
| 3384 | CMe | O | Q1c | a bond | Me | a bond | NH | O | NH | T3d | OH |
| 3385 | CMe | O | Q1c | a bond | Me | a bond | NH | O | NH | T3e | OH |
| 3386 | CMe | O | Q1c | a bond | Me | a bond | NH | O | NH | T3f | OH |
| 3387 | CMe | O | Q1c | a bond | Me | a bond | NH | O | NH | T3g | OH |
| 3388 | CMe | O | Q1c | a bond | Me | a bond | NH | O | NH | T3h | OH |
| 3389 | CMe | O | Q1c | a bond | Me | a bond | NH | O | NH | T3i | OH |
| 3390 | CMe | O | Q1c | a bond | Me | a bond | NH | O | NH | T3j | OH |
| 3391 | CMe | O | Q1c | a bond | Me | a bond | NH | O | a bond | T3a | OH |
| 3392 | CMe | O | Q1c | a bond | Me | a bond | NH | O | a bond | T3b | OH |
| 3393 | CMe | O | Q1c | a bond | Me | a bond | NH | O | a bond | T3c | OH |
| 3394 | CMe | O | Q1c | a bond | Me | a bond | NH | O | a bond | T3d | OH |
| 3395 | CMe | O | Q1c | a bond | Me | a bond | NH | O | a bond | T3e | OH |
| 3396 | CMe | O | Q1c | a bond | Me | a bond | NH | O | a bond | T3f | OH |
| 3397 | CMe | O | Q1c | a bond | Me | a bond | NH | O | a bond | T3g | OH |
| 3398 | CMe | O | Q1c | a bond | Me | a bond | NH | O | a bond | T3h | OH |
| 3399 | CMe | O | Q1c | a bond | Me | a bond | NH | O | a bond | T3i | OH |
| 3400 | CMe | O | Q1c | a bond | Me | a bond | NH | O | a bond | T3j | OH |
| 3401 | CMe | O | Q1c | a bond | H | a bond | NH | S | NH | T3a | OH |
| 3402 | CMe | O | Q1c | a bond | H | a bond | NH | S | NH | T3b | OH |
| 3403 | CMe | O | Q1c | a bond | H | a bond | NH | S | NH | T3c | OH |

TABLE 2-continued

| No | A | B | R¹ | L¹ | R² | L² | L³ | Y | L⁴ | R³ | X |
|---|---|---|---|---|---|---|---|---|---|---|---|
| 3404 | CMe | O | Q1c | a bond | H | a bond | NH | S | NH | T3d | OH |
| 3405 | CMe | O | Q1c | a bond | H | a bond | NH | S | NH | T3e | OH |
| 3406 | CMe | O | Q1c | a bond | H | a bond | NH | S | NH | T3f | OH |
| 3407 | CMe | O | Q1c | a bond | H | a bond | NH | S | NH | T3g | OH |
| 3408 | CMe | O | Q1c | a bond | H | a bond | NH | S | NH | T3h | OH |
| 3409 | CMe | O | Q1c | a bond | H | a bond | NH | S | NH | T3i | OH |
| 3410 | CMe | O | Q1c | a bond | H | a bond | NH | S | NH | T3j | OH |
| 3411 | CMe | O | Q1c | a bond | H | a bond | NH | S | a bond | T3a | OH |
| 3412 | CMe | O | Q1c | a bond | H | a bond | NH | S | a bond | T3b | OH |
| 3413 | CMe | O | Q1c | a bond | H | a bond | NH | S | a bond | T3c | OH |
| 3414 | CMe | O | Q1c | a bond | H | a bond | NH | S | a bond | T3d | OH |
| 3415 | CMe | O | Q1c | a bond | H | a bond | NH | S | a bond | T3e | OH |
| 3416 | CMe | O | Q1c | a bond | H | a bond | NH | S | a bond | T3f | OH |
| 3417 | CMe | O | Q1c | a bond | H | a bond | NH | S | a bond | T3g | OH |
| 3418 | CMe | O | Q1c | a bond | H | a bond | NH | S | a bond | T3h | OH |
| 3419 | CMe | O | Q1c | a bond | H | a bond | NH | S | a bond | T3i | OH |
| 3420 | CMe | O | Q1c | a bond | H | a bond | NH | S | a bond | T3j | OH |
| 3421 | CMe | O | Q1c | a bond | H | a bond | NH | O | NH | T3a | OH |
| 3422 | CMe | O | Q1c | a bond | H | a bond | NH | O | NH | T3b | OH |
| 3423 | CMe | O | Q1c | a bond | H | a bond | NH | O | NH | T3c | OH |
| 3424 | CMe | O | Q1c | a bond | H | a bond | NH | O | NH | T3d | OH |
| 3425 | CMe | O | Q1c | a bond | H | a bond | NH | O | NH | T3e | OH |
| 3426 | CMe | O | Q1c | a bond | H | a bond | NH | O | NH | T3f | OH |
| 3427 | CMe | O | Q1c | a bond | H | a bond | NH | O | NH | T3g | OH |
| 3428 | CMe | O | Q1c | a bond | H | a bond | NH | O | NH | T3h | OH |
| 3429 | CMe | O | Q1c | a bond | H | a bond | NH | O | NH | T3i | OH |
| 3430 | CMe | O | Q1c | a bond | H | a bond | NH | O | NH | T3j | OH |
| 3431 | CMe | O | Q1c | a bond | H | a bond | NH | O | a bond | T3a | OH |
| 3432 | CMe | O | Q1c | a bond | H | a bond | NH | O | a bond | T3b | OH |
| 3433 | CMe | O | Q1c | a bond | H | a bond | NH | O | a bond | T3c | OH |
| 3434 | CMe | O | Q1c | a bond | H | a bond | NH | O | a bond | T3d | OH |
| 3435 | CMe | O | Q1c | a bond | H | a bond | NH | O | a bond | T3e | OH |
| 3436 | CMe | O | Q1c | a bond | H | a bond | NH | O | a bond | T3f | OH |
| 3437 | CMe | O | Q1c | a bond | H | a bond | NH | O | a bond | T3g | OH |
| 3438 | CMe | O | Q1c | a bond | H | a bond | NH | O | a bond | T3h | OH |
| 3439 | CMe | O | Q1c | a bond | H | a bond | NH | O | a bond | T3i | OH |
| 3440 | CMe | O | Q1c | a bond | H | a bond | NH | O | a bond | T3j | OH |
| 3441 | CMe | O | Q1c | a bond | Me | a bond | NH | S | NH | T3a | OH |
| 3442 | CMe | O | Q1i | a bond | Me | a bond | NH | S | NH | T3b | OH |
| 3443 | CMe | O | Q1i | a bond | Me | a bond | NH | S | NH | T3c | OH |
| 3444 | CMe | O | Q1i | a bond | Me | a bond | NH | S | NH | T3d | OH |
| 3445 | CMe | O | Q1i | a bond | Me | a bond | NH | S | NH | T3e | OH |
| 3446 | CMe | O | Q1i | a bond | Me | a bond | NH | S | NH | T3f | OH |
| 3447 | CMe | O | Q1i | a bond | Me | a bond | NH | S | NH | T3g | OH |
| 3448 | CMe | O | Q1i | a bond | Me | a bond | NH | S | NH | T3h | OH |
| 3449 | CMe | O | Q1i | a bond | Me | a bond | NH | S | NH | T3i | OH |
| 3450 | CMe | O | Q1i | a bond | Me | a bond | NH | S | NH | T3j | OH |
| 3451 | CMe | O | Q1i | a bond | Me | a bond | NH | S | a bond | T3a | OH |
| 3452 | CMe | O | Q1i | a bond | Me | a bond | NH | S | a bond | T3b | OH |
| 3453 | CMe | O | Q1i | a bond | Me | a bond | NH | S | a bond | T3c | OH |
| 3454 | CMe | O | Q1i | a bond | Me | a bond | NH | S | a bond | T3d | OH |
| 3455 | CMe | O | Q1i | a bond | Me | a bond | NH | S | a bond | T3e | OH |
| 3456 | CMe | O | Q1i | a bond | Me | a bond | NH | S | a bond | T3f | OH |
| 3457 | CMe | O | Q1i | a bond | Me | a bond | NH | S | a bond | T3g | OH |
| 3458 | CMe | O | Q1i | a bond | Me | a bond | NH | S | a bond | T3h | OH |
| 3459 | CMe | O | Q1i | a bond | Me | a bond | NH | S | a bond | T3i | OH |
| 3460 | CMe | O | Q1i | a bond | Me | a bond | NH | S | a bond | T3j | OH |
| 3461 | CMe | O | Q1i | a bond | Me | a bond | NH | O | NH | T3a | OH |
| 3462 | CMe | O | Q1i | a bond | Me | a bond | NH | O | NH | T3b | OH |
| 3463 | CMe | O | Q1i | a bond | Me | a bond | NH | O | NH | T3c | OH |
| 3464 | CMe | O | Q1i | a bond | Me | a bond | NH | O | NH | T3d | OH |
| 3465 | CMe | O | Q1i | a bond | Me | a bond | NH | O | NH | T3e | OH |
| 3466 | CMe | O | Q1i | a bond | Me | a bond | NH | O | NH | T3f | OH |
| 3467 | CMe | O | Q1i | a bond | Me | a bond | NH | O | NH | T3g | OH |
| 3468 | CMe | O | Q1i | a bond | Me | a bond | NH | O | NH | T3h | OH |
| 3469 | CMe | O | Q1i | a bond | Me | a bond | NH | O | NH | T3i | OH |
| 3470 | CMe | O | Q1i | a bond | Me | a bond | NH | O | NH | T3j | OH |
| 3471 | CMe | O | Q1i | a bond | Me | a bond | NH | O | a bond | T3a | OH |
| 3472 | CMe | O | Q1i | a bond | Me | a bond | NH | O | a bond | T3b | OH |
| 3473 | CMe | O | Q1i | a bond | Me | a bond | NH | O | a bond | T3c | OH |
| 3474 | CMe | O | Q1i | a bond | Me | a bond | NH | O | a bond | T3d | OH |
| 3475 | CMe | O | Q1i | a bond | Me | a bond | NH | O | a bond | T3e | OH |
| 3476 | CMe | O | Q1i | a bond | Me | a bond | NH | O | a bond | T3f | OH |
| 3477 | CMe | O | Q1i | a bond | Me | a bond | NH | O | a bond | T3g | OH |
| 3478 | CMe | O | Q1i | a bond | Me | a bond | NH | O | a bond | T3h | OH |
| 3479 | CMe | O | Q1i | a bond | Me | a bond | NH | O | a bond | T3i | OH |
| 3480 | CMe | O | Q1i | a bond | Me | a bond | NH | O | a bond | T3j | OH |
| 3481 | CMe | O | Q1i | a bond | H | a bond | NH | S | NH | T3a | OH |

TABLE 2-continued

| No | A | B | R¹ | L¹ | R² | L² | L³ | Y | L⁴ | R³ | X |
|---|---|---|---|---|---|---|---|---|---|---|---|
| 3482 | CMe | O | Q1i | a bond | H | a bond | NH | S | NH | T3b | OH |
| 3483 | CMe | O | Q1i | a bond | H | a bond | NH | S | NH | T3c | OH |
| 3484 | CMe | O | Q1i | a bond | H | a bond | NH | S | NH | T3d | OH |
| 3485 | CMe | O | Q1i | a bond | H | a bond | NH | S | NH | T3e | OH |
| 3486 | CMe | O | Q1i | a bond | H | a bond | NH | S | NH | T3f | OH |
| 3487 | CMe | O | Q1i | a bond | H | a bond | NH | S | NH | T3g | OH |
| 3488 | CMe | O | Q1i | a bond | H | a bond | NH | S | NH | T3h | OH |
| 3489 | CMe | O | Q1i | a bond | H | a bond | NH | S | NH | T3i | OH |
| 3490 | CMe | O | Q1i | a bond | H | a bond | NH | S | NH | T3j | OH |
| 3491 | CMe | O | Q1i | a bond | H | a bond | NH | S | a bond | T3a | OH |
| 3492 | CMe | O | Q1i | a bond | H | a bond | NH | S | a bond | T3b | OH |
| 3493 | CMe | O | Q1i | a bond | H | a bond | NH | S | a bond | T3c | OH |
| 3494 | CMe | O | Q1i | a bond | H | a bond | NH | S | a bond | T3d | OH |
| 3495 | CMe | O | Q1i | a bond | H | a bond | NH | S | a bond | T3e | OH |
| 3496 | CMe | O | Q1i | a bond | H | a bond | NH | S | a bond | T3f | OH |
| 3497 | CMe | O | Q1i | a bond | H | a bond | NH | S | a bond | T3g | OH |
| 3498 | CMe | O | Q1i | a bond | H | a bond | NH | S | a bond | T3h | OH |
| 3499 | CMe | O | Q1i | a bond | H | a bond | NH | S | a bond | T3i | OH |
| 3500 | CMe | O | Q1i | a bond | H | a bond | NH | S | a bond | T3j | OH |
| 3501 | CMe | O | Q1i | a bond | H | a bond | NH | O | NH | T3a | OH |
| 3502 | CMe | O | Q1i | a bond | H | a bond | NH | O | NH | T3b | OH |
| 3503 | CMe | O | Q1i | a bond | H | a bond | NH | O | NH | T3c | OH |
| 3504 | CMe | O | Q1i | a bond | H | a bond | NH | O | NH | T3d | OH |
| 3505 | CMe | O | Q1i | a bond | H | a bond | NH | O | NH | T3e | OH |
| 3506 | CMe | O | Q1i | a bond | H | a bond | NH | O | NH | T3f | OH |
| 3507 | CMe | O | Q1i | a bond | H | a bond | NH | O | NH | T3g | OH |
| 3508 | CMe | O | Q1i | a bond | H | a bond | NH | O | NH | T3h | OH |
| 3509 | CMe | O | Q1i | a bond | H | a bond | NH | O | NH | T3i | OH |
| 3510 | CMe | O | Q1i | a bond | H | a bond | NH | O | NH | T3j | OH |
| 3511 | CMe | O | Q1i | a bond | H | a bond | NH | O | a bond | T3a | OH |
| 3512 | CMe | O | Q1i | a bond | H | a bond | NH | O | a bond | T3b | OH |
| 3513 | CMe | O | Q1i | a bond | H | a bond | NH | O | a bond | T3c | OH |
| 3514 | CMe | O | Q1i | a bond | H | a bond | NH | O | a bond | T3d | OH |
| 3515 | CMe | O | Q1i | a bond | H | a bond | NH | O | a bond | T3e | OH |
| 3516 | CMe | O | Q1i | a bond | H | a bond | NH | O | a bond | T3f | OH |
| 3517 | CMe | O | Q1i | a bond | H | a bond | NH | O | a bond | T3g | OH |
| 3518 | CMe | O | Q1i | a bond | H | a bond | NH | O | a bond | T3h | OH |
| 3519 | CMe | O | Q1i | a bond | H | a bond | NH | O | a bond | T3i | OH |
| 3520 | CMe | O | Q1i | a bond | H | a bond | NH | O | a bond | T3j | OH |
| 3521 | CMe | O | Q1j | a bond | Me | a bond | NH | S | NH | T3a | OH |
| 3522 | CMe | O | Q1j | a bond | Me | a bond | NH | S | NH | T3b | OH |
| 3523 | CMe | O | Q1j | a bond | Me | a bond | NH | S | NH | T3c | OH |
| 3524 | CMe | O | Q1j | a bond | Me | a bond | NH | S | NH | T3d | OH |
| 3525 | CMe | O | Q1j | a bond | Me | a bond | NH | S | NH | T3e | OH |
| 3526 | CMe | O | Q1j | a bond | Me | a bond | NH | S | NH | T3f | OH |
| 3527 | CMe | O | Q1j | a bond | Me | a bond | NH | S | NH | T3g | OH |
| 3528 | CMe | O | Q1j | a bond | Me | a bond | NH | S | NH | T3h | OH |
| 3529 | CMe | O | Q1j | a bond | Me | a bond | NH | S | NH | T3i | OH |
| 3530 | CMe | O | Q1j | a bond | Me | a bond | NH | S | NH | T3j | OH |
| 3531 | CMe | O | Q1j | a bond | Me | a bond | NH | S | a bond | T3a | OH |
| 3532 | CMe | O | Q1j | a bond | Me | a bond | NH | S | a bond | T3b | OH |
| 3533 | CMe | O | Q1j | a bond | Me | a bond | NH | S | a bond | T3c | OH |
| 3534 | CMe | O | Q1j | a bond | Me | a bond | NH | S | a bond | T3d | OH |
| 3535 | CMe | O | Q1j | a bond | Me | a bond | NH | S | a bond | T3e | OH |
| 3536 | CMe | O | Q1j | a bond | Me | a bond | NH | S | a bond | T3f | OH |
| 3537 | CMe | O | Q1j | a bond | Me | a bond | NH | S | a bond | T3g | OH |
| 3538 | CMe | O | Q1j | a bond | Me | a bond | NH | S | a bond | T3h | OH |
| 3539 | CMe | O | Q1j | a bond | Me | a bond | NH | S | a bond | T3i | OH |
| 3540 | CMe | O | Q1j | a bond | Me | a bond | NH | S | a bond | T3j | OH |
| 3541 | CMe | O | Q1j | a bond | Me | a bond | NH | O | NH | T3a | OH |
| 3542 | CMe | O | Q1j | a bond | Me | a bond | NH | O | NH | T3b | OH |
| 3543 | CMe | O | Q1j | a bond | Me | a bond | NH | O | NH | T3c | OH |
| 3544 | CMe | O | Q1j | a bond | Me | a bond | NH | O | NH | T3d | OH |
| 3545 | CMe | O | Q1j | a bond | Me | a bond | NH | O | NH | T3e | OH |
| 3546 | CMe | O | Q1j | a bond | Me | a bond | NH | O | NH | T3f | OH |
| 3547 | CMe | O | Q1j | a bond | Me | a bond | NH | O | NH | T3g | OH |
| 3548 | CMe | O | Q1j | a bond | Me | a bond | NH | O | NH | T3h | OH |
| 3549 | CMe | O | Q1j | a bond | Me | a bond | NH | O | NH | T3i | OH |
| 3550 | CMe | O | Q1j | a bond | Me | a bond | NH | O | NH | T3j | OH |
| 3551 | CMe | O | Q1j | a bond | Me | a bond | NH | O | a bond | T3a | OH |
| 3552 | CMe | O | Q1j | a bond | Me | a bond | NH | O | a bond | T3b | OH |
| 3553 | CMe | O | Q1j | a bond | Me | a bond | NH | O | a bond | T3c | OH |
| 3554 | CMe | O | Q1j | a bond | Me | a bond | NH | O | a bond | T3d | OH |
| 3555 | CMe | O | Q1j | a bond | Me | a bond | NH | O | a bond | T3e | OH |
| 3556 | CMe | O | Q1j | a bond | Me | a bond | NH | O | a bond | T3f | OH |
| 3557 | CMe | O | Q1j | a bond | Me | a bond | NH | O | a bond | T3g | OH |
| 3558 | CMe | O | Q1j | a bond | Me | a bond | NH | O | a bond | T3h | OH |
| 3559 | CMe | O | Q1j | a bond | Me | a bond | NH | O | a bond | T3i | OH |

TABLE 2-continued

| No | A | B | R¹ | L¹ | R² | L² | L³ | Y | L⁴ | R³ | X |
|---|---|---|---|---|---|---|---|---|---|---|---|
| 3560 | CMe | O | Q1j | a bond | Me | a bond | NH | O | a bond | T3j | OH |
| 3561 | CMe | O | Q1j | a bond | H | a bond | NH | S | NH | T3a | OH |
| 3562 | CMe | O | Q1j | a bond | H | a bond | NH | S | NH | T3b | OH |
| 3563 | CMe | O | Q1j | a bond | H | a bond | NH | S | NH | T3c | OH |
| 3564 | CMe | O | Q1j | a bond | H | a bond | NH | S | NH | T3d | OH |
| 3565 | CMe | O | Q1j | a bond | H | a bond | NH | S | NH | T3e | OH |
| 3566 | CMe | O | Q1j | a bond | H | a bond | NH | S | NH | T3f | OH |
| 3567 | CMe | O | Q1j | a bond | H | a bond | NH | S | NH | T3g | OH |
| 3568 | CMe | O | Q1j | a bond | H | a bond | NH | S | NH | T3h | OH |
| 3569 | CMe | O | Q1j | a bond | H | a bond | NH | S | NH | T3i | OH |
| 3570 | CMe | O | Q1j | a bond | H | a bond | NH | S | NH | T3j | OH |
| 3571 | CMe | O | Q1j | a bond | H | a bond | NH | S | a bond | T3a | OH |
| 3572 | CMe | O | Q1j | a bond | H | a bond | NH | S | a bond | T3b | OH |
| 3573 | CMe | O | Q1j | a bond | H | a bond | NH | S | a bond | T3c | OH |
| 3574 | CMe | O | Q1j | a bond | H | a bond | NH | S | a bond | T3d | OH |
| 3575 | CMe | O | Q1j | a bond | H | a bond | NH | S | a bond | T3e | OH |
| 3576 | CMe | O | Q1j | a bond | H | a bond | NH | S | a bond | T3f | OH |
| 3577 | CMe | O | Q1j | a bond | H | a bond | NH | S | a bond | T3g | OH |
| 3578 | CMe | O | Q1j | a bond | H | a bond | NH | S | a bond | T3h | OH |
| 3579 | CMe | O | Q1j | a bond | H | a bond | NH | S | a bond | T3i | OH |
| 3580 | CMe | O | Q1j | a bond | H | a bond | NH | S | a bond | T3j | OH |
| 3581 | CMe | O | Q1j | a bond | H | a bond | NH | O | NH | T3a | OH |
| 3582 | CMe | O | Q1j | a bond | H | a bond | NH | O | NH | T3b | OH |
| 3583 | CMe | O | Q1j | a bond | H | a bond | NH | O | NH | T3c | OH |
| 3584 | CMe | O | Q1j | a bond | H | a bond | NH | O | NH | T3d | OH |
| 3585 | CMe | O | Q1j | a bond | H | a bond | NH | O | NH | T3e | OH |
| 3586 | CMe | O | Q1j | a bond | H | a bond | NH | O | NH | T3f | OH |
| 3587 | CMe | O | Q1j | a bond | H | a bond | NH | O | NH | T3g | OH |
| 3588 | CMe | O | Q1j | a bond | H | a bond | NH | O | NH | T3h | OH |
| 3589 | CMe | O | Q1j | a bond | H | a bond | NH | O | NH | T3i | OH |
| 3590 | CMe | O | Q1j | a bond | H | a bond | NH | O | NH | T3j | OH |
| 3591 | CMe | O | Q1j | a bond | H | a bond | NH | O | a bond | T3a | OH |
| 3592 | CMe | O | Q1j | a bond | H | a bond | NH | O | a bond | T3b | OH |
| 3593 | CMe | O | Q1j | a bond | H | a bond | NH | O | a bond | T3c | OH |
| 3594 | CMe | O | Q1j | a bond | H | a bond | NH | O | a bond | T3d | OH |
| 3595 | CMe | O | Q1j | a bond | H | a bond | NH | O | a bond | T3e | OH |
| 3596 | CMe | O | Q1j | a bond | H | a bond | NH | O | a bond | T3f | OH |
| 3597 | CMe | O | Q1j | a bond | H | a bond | NH | O | a bond | T3g | OH |
| 3598 | CMe | O | Q1j | a bond | H | a bond | NH | O | a bond | T3h | OH |
| 3599 | CMe | O | Q1j | a bond | H | a bond | NH | O | a bond | T3i | OH |
| 3600 | CMe | O | Q1j | a bond | H | a bond | NH | O | a bond | T3j | OH |
| 3601 | N | NMe | Q1i | a bond | Me | a bond | NH | S | NH | Q3e | OH |
| 3602 | N | NMe | Q1i | a bond | Me | a bond | NH | S | a bond | Q3e | OH |
| 3603 | N | NMe | Q1i | a bond | Me | a bond | NH | O | NH | Q3e | OH |
| 3604 | N | NMe | Q1i | a bond | Me | a bond | NH | O | a bond | Q3e | OH |
| 3605 | N | NMe | Q1i | a bond | H | a bond | NH | S | NH | Q3e | OH |
| 3606 | N | NMe | Q1i | a bond | H | a bond | NH | S | a bond | Q3e | OH |
| 3607 | N | NMe | Q1i | a bond | H | a bond | NH | O | NH | Q3e | OH |
| 3608 | N | NMe | Q1i | a bond | H | a bond | NH | O | a bond | Q3e | OH |
| 3609 | N | NMe | Q1j | a bond | Me | a bond | NH | S | NH | Q3e | OH |
| 3610 | N | NMe | Q1j | a bond | Me | a bond | NH | S | a bond | Q3e | OH |
| 3611 | N | NMe | Q1j | a bond | Me | a bond | NH | O | NH | Q3e | OH |
| 3612 | N | MMe | Q1j | a bond | Me | a bond | NH | O | a bond | Q3e | OH |
| 3613 | N | NMe | Q1j | a bond | H | a bond | NH | S | NH | Q3e | OH |
| 3614 | N | NMe | Q1j | a bond | H | a bond | NH | S | a bond | Q3e | OH |
| 3615 | N | NMe | Q1j | a bond | H | a bond | NH | O | NH | Q3e | OH |
| 3616 | N | NMe | Q1j | a bond | H | a bond | NH | O | a bond | Q3e | OH |
| 3617 | N | S | Q1i | a bond | Me | a bond | NH | S | NH | Q3e | OH |
| 3618 | N | S | Q1i | a bond | Me | a bond | NH | S | a bond | Q3e | OH |
| 3619 | N | S | Q1i | a bond | Me | a bond | NH | O | NH | Q3e | OH |
| 3620 | N | S | Q1i | a bond | Me | a bond | NH | O | a bond | Q3e | OH |
| 3621 | N | S | Q1i | a bond | H | a bond | NH | S | NH | Q3e | OH |
| 3622 | N | S | Q1i | a bond | H | a bond | NH | S | a bond | Q3e | OH |
| 3623 | N | S | Q1i | a bond | H | a bond | NH | O | NH | Q3e | OH |
| 3624 | N | S | Q1i | a bond | H | a bond | NH | O | a bond | Q3e | OH |
| 3625 | N | S | Q1j | a bond | Me | a bond | NH | S | NH | Q3e | OH |
| 3626 | N | S | Q1j | a bond | Me | a bond | NH | S | a bond | Q3e | OH |
| 3627 | N | S | Q1j | a bond | Me | a bond | NH | O | NH | Q3e | OH |
| 3628 | N | S | Q1j | a bond | Me | a bond | NH | O | a bond | Q3e | OH |
| 3629 | N | S | Q1j | a bond | H | a bond | NH | S | NH | Q3e | OH |
| 3630 | N | S | Q1j | a bond | H | a bond | NH | S | a bond | Q3e | OH |
| 3631 | N | S | Q1j | a bond | H | a bond | NH | O | NH | Q3e | OH |
| 3632 | N | S | Q1j | a bond | H | a bond | NH | O | a bond | Q3e | OH |
| 3633 | N | O | Q1i | a bond | Me | a bond | NH | S | NH | Q3e | OH |
| 3634 | N | O | Q1i | a bond | Me | a bond | NH | S | a bond | Q3e | OH |
| 3635 | N | O | Q1i | a bond | Me | a bond | NH | O | NH | Q3e | OH |
| 3636 | N | O | Q1i | a bond | Me | a bond | NH | O | a bond | Q3e | OH |
| 3637 | N | O | Q1i | a bond | H | a bond | NH | S | NH | Q3e | OH |

TABLE 2-continued

| No | A | B | R¹ | L¹ | R² | L² | L³ | Y | L⁴ | R³ | X |
|---|---|---|---|---|---|---|---|---|---|---|---|
| 3638 | N | O | Q1i | a bond | H | a bond | NH | S | a bond | Q3e | OH |
| 3639 | N | O | Q1i | a bond | H | a bond | NH | O | NH | Q3e | OH |
| 3640 | N | O | Q1i | a bond | H | a bond | NH | O | a bond | Q3e | OH |
| 3641 | N | O | Q1j | a bond | Me | a bond | NH | S | NH | Q3e | OH |
| 3642 | N | O | Q1j | a bond | Me | a bond | NH | S | a bond | Q3e | OH |
| 3643 | N | O | Q1j | a bond | Me | a bond | NH | O | NH | Q3e | OH |
| 3644 | N | O | Q1j | a bond | Me | a bond | NH | O | a bond | Q3e | OH |
| 3645 | N | O | Q1j | a bond | H | a bond | NH | S | NH | Q3e | OH |
| 3646 | N | O | Q1j | a bond | H | a bond | NH | S | a bond | Q3e | OH |
| 3647 | N | O | Q1j | a bond | H | a bond | NH | O | NH | Q3e | OH |
| 3648 | N | O | Q1j | a bond | H | a bond | NH | O | a bond | Q3e | OH |
| 3649 | CH | NMe | Q1i | a bond | Me | a bond | NH | S | NH | Q3e | OH |
| 3650 | CH | NMe | Q1i | a bond | Me | a bond | NH | S | a bond | Q3e | OH |
| 3651 | CH | NMe | Q1i | a bond | Me | a bond | NH | O | NH | Q3e | OH |
| 3652 | CH | NMe | Q1i | a bond | Me | a bond | NH | O | a bond | Q3e | OH |
| 3653 | CH | NMe | Q1i | a bond | H | a bond | NH | S | NH | Q3e | OH |
| 3654 | CH | NMe | Q1i | a bond | H | a bond | NH | S | a bond | Q3e | OH |
| 3655 | CH | NMe | Q1i | a bond | H | a bond | NH | O | NH | Q3e | OH |
| 3656 | CH | NMe | Q1i | a bond | H | a bond | NH | O | a bond | Q3e | OH |
| 3657 | CH | NMe | Q1j | a bond | Me | a bond | NH | S | NH | Q3e | OH |
| 3658 | CH | NMe | Q1j | a bond | Me | a bond | NH | S | a bond | Q3e | OH |
| 3659 | CH | NMe | Q1j | a bond | Me | a bond | NH | O | NH | Q3e | OH |
| 3660 | CH | NMe | Q1j | a bond | Me | a bond | NH | O | a bond | Q3e | OH |
| 3661 | CH | NMe | Q1j | a bond | H | a bond | NH | S | NH | Q3e | OH |
| 3662 | CH | NMe | Q1j | a bond | H | a bond | NH | S | a bond | Q3e | OH |
| 3663 | CH | NMe | Q1j | a bond | H | a bond | NH | O | NH | Q3e | OH |
| 3664 | CH | NMe | Q1j | a bond | H | a bond | NH | O | a bond | Q3e | OH |
| 3665 | CH | S | Q1i | a bond | Me | a bond | NH | S | NH | Q3e | OH |
| 3666 | CH | S | Q1i | a bond | Me | a bond | NH | S | a bond | Q3e | OH |
| 3667 | CH | S | Q1i | a bond | Me | a bond | NH | O | NH | Q3e | OH |
| 3668 | CH | S | Q1i | a bond | Me | a bond | NH | O | a bond | Q3e | OH |
| 3669 | CH | S | Q1i | a bond | H | a bond | NH | S | NH | Q3e | OH |
| 3670 | CH | S | Q1i | a bond | H | a bond | NH | S | a bond | Q3e | OH |
| 3671 | CH | S | Q1i | a bond | H | a bond | NH | O | NH | Q3e | OH |
| 3672 | CH | S | Q1i | a bond | H | a bond | NH | O | a bond | Q3e | OH |
| 3673 | CH | S | Q1j | a bond | Me | a bond | NH | S | NH | Q3e | OH |
| 3674 | CH | S | Q1j | a bond | Me | a bond | NH | S | a bond | Q3e | OH |
| 3675 | CH | S | Q1j | a bond | Me | a bond | NH | O | NH | Q3e | OH |
| 3676 | CH | S | Q1j | a bond | Me | a bond | NH | O | a bond | Q3e | OH |
| 3677 | CH | S | Q1j | a bond | H | a bond | NH | S | NH | Q3e | OH |
| 3678 | CH | S | Q1j | a bond | H | a bond | NH | S | a bond | Q3e | OH |
| 3679 | CH | S | Q1j | a bond | H | a bond | NH | O | NH | Q3e | OH |
| 3680 | CH | S | Q1j | a bond | H | a bond | NH | O | a bond | Q3e | OH |
| 3681 | CH | O | Q1i | a bond | Me | a bond | NH | S | NH | Q3e | OH |
| 3682 | CH | O | Q1i | a bond | Me | a bond | NH | S | a bond | Q3e | OH |
| 3683 | CH | O | Q1i | a bond | Me | a bond | NH | O | NH | Q3e | OH |
| 3684 | CH | O | Q1i | a bond | Me | a bond | NH | O | a bond | Q3e | OH |
| 3685 | CH | O | Q1i | a bond | H | a bond | NH | S | NH | Q3e | OH |
| 3686 | CH | O | Q1i | a bond | H | a bond | NH | S | a bond | Q3e | OH |
| 3687 | CH | O | Q1i | a bond | H | a bond | NH | O | NH | Q3e | OH |
| 3688 | CH | O | Q1i | a bond | H | a bond | NH | O | a bond | Q3e | OH |
| 3689 | CH | O | Q1j | a bond | Me | a bond | NH | S | NH | Q3e | OH |
| 3690 | CH | O | Q1j | a bond | Me | a bond | NH | S | a bond | Q3e | OH |
| 3691 | CH | O | Q1j | a bond | Me | a bond | NH | O | NH | Q3e | OH |
| 3692 | CH | O | Q1j | a bond | Me | a bond | NH | O | a bond | Q3e | OH |
| 3693 | CH | O | Q1j | a bond | H | a bond | NH | S | NH | Q3e | OH |
| 3694 | CH | O | Q1j | a bond | H | a bond | NH | S | a bond | Q3e | OH |
| 3695 | CH | O | Q1j | a bond | H | a bond | NH | O | NH | Q3e | OH |
| 3696 | CH | O | Q1j | a bond | H | a bond | NH | O | a bond | Q3e | OH |
| 3697 | CMe | NMe | Q1i | a bond | Me | a bond | NH | S | NH | Q3e | OH |
| 3698 | CMe | NMe | Q1i | a bond | Me | a bond | NH | S | a bond | Q3e | OH |
| 3699 | CMe | NMe | Q1i | a bond | Me | a bond | NH | O | NH | Q3e | OH |
| 3700 | CMe | NMe | Q1i | a bond | Me | a bond | NH | O | a bond | Q3e | OH |
| 3701 | CMe | NMe | Q1i | a bond | H | a bond | NH | S | NH | Q3e | OH |
| 3702 | CMe | NMe | Q1i | a bond | H | a bond | NH | S | a bond | Q3e | OH |
| 3703 | CMe | NMe | Q1i | a bond | H | a bond | NH | O | NH | Q3e | OH |
| 3704 | CMe | NMe | Q1i | a bond | H | a bond | NH | O | a bond | Q3e | OH |
| 3705 | CMe | NMe | Q1j | a bond | Me | a bond | NH | S | NH | Q3e | OH |
| 3706 | CMe | NMe | Q1j | a bond | Me | a bond | NH | S | a bond | Q3e | OH |
| 3707 | CMe | NMe | Q1j | a bond | Me | a bond | NH | O | NH | Q3e | OH |
| 3708 | CMe | NMe | Q1j | a bond | Me | a bond | NH | O | a bond | Q3e | OH |
| 3709 | CMe | NMe | Q1j | a bond | H | a bond | NH | S | NH | Q3e | OH |
| 3710 | CMe | NMe | Q1j | a bond | H | a bond | NH | S | a bond | Q3e | OH |
| 3711 | CMe | NMe | Q1j | a bond | H | a bond | NH | O | NH | Q3e | OH |
| 3712 | CMe | NMe | Q1j | a bond | H | a bond | NH | O | a bond | Q3e | OH |
| 3713 | CMe | S | Q1i | a bond | Me | a bond | NH | S | NH | Q3e | OH |
| 3714 | CMe | S | Q1i | a bond | Me | a bond | NH | S | a bond | Q3e | OH |
| 3715 | CMe | S | Q1i | a bond | Me | a bond | NH | O | NH | Q3e | OH |

TABLE 2-continued

| No | A | B | R¹ | L¹ | R² | L² | L³ | Y | L⁴ | R³ | X |
|---|---|---|---|---|---|---|---|---|---|---|---|
| 3716 | CMe | S | Q1i | a bond | Me | a bond | NH | O | a bond | Q3e | OH |
| 3717 | CMe | S | Q1i | a bond | H | a bond | NH | S | NH | Q3e | OH |
| 3718 | CMe | S | Q1i | a bond | H | a bond | NH | S | a bond | Q3e | OH |
| 3719 | CMe | S | Q1i | a bond | H | a bond | NH | O | NH | Q3e | OH |
| 3720 | CMe | S | Q1i | a bond | H | a bond | NH | O | a bond | Q3e | OH |
| 3721 | CMe | S | Q1j | a bond | Me | a bond | NH | S | NH | Q3e | OH |
| 3722 | CMe | S | Q1j | a bond | Me | a bond | NH | S | a bond | Q3e | OH |
| 3723 | CMe | S | Q1j | a bond | Me | a bond | NH | O | NH | Q3e | OH |
| 3724 | CMe | S | Q1j | a bond | Me | a bond | NH | O | a bond | Q3e | OH |
| 3725 | CMe | S | Q1j | a bond | H | a bond | NH | S | NH | Q3e | OH |
| 3726 | CMe | S | Q1j | a bond | H | a bond | NH | S | a bond | Q3e | OH |
| 3727 | CMe | S | Q1j | a bond | H | a bond | NH | O | NH | Q3e | OH |
| 3728 | CMe | S | Q1j | a bond | H | a bond | NH | O | a bond | Q3e | OH |
| 3729 | CMe | O | Q1i | a bond | Me | a bond | NH | S | NH | Q3e | OH |
| 3730 | CMe | O | Q1i | a bond | Me | a bond | NH | S | a bond | Q3e | OH |
| 3731 | CMe | O | Q1i | a bond | Me | a bond | NH | O | NH | Q3e | OH |
| 3732 | CMe | O | Q1i | a bond | Me | a bond | NH | O | a bond | Q3e | OH |
| 3733 | CMe | O | Q1i | a bond | H | a bond | NH | S | NH | Q3e | OH |
| 3734 | CMe | O | Q1i | a bond | H | a bond | NH | S | a bond | Q3e | OH |
| 3735 | CMe | O | Q1i | a bond | H | a bond | NH | O | NH | Q3e | OH |
| 3736 | CMe | O | Q1i | a bond | H | a bond | NH | O | a bond | Q3e | OH |
| 3737 | CMe | O | Q1j | a bond | Me | a bond | NH | S | NH | Q3e | OH |
| 3738 | CMe | O | Q1j | a bond | Me | a bond | NH | S | a bond | Q3e | OH |
| 3739 | CMe | O | Q1j | a bond | Me | a bond | NH | O | NH | Q3e | OH |
| 3740 | CMe | O | Q1j | a bond | Me | a bond | NH | O | a bond | Q3e | OH |
| 3741 | CMe | O | Q1j | a bond | H | a bond | NH | S | NH | Q3e | OH |
| 3742 | CMe | O | Q1j | a bond | H | a bond | NH | S | a bond | Q3e | OH |
| 3743 | CMe | O | Q1j | a bond | H | a bond | NH | O | NH | Q3e | OH |
| 3744 | CMe | O | Q1j | a bond | H | a bond | NH | O | a bond | Q3e | OH |

61) The compounds wherein A, B, R¹, L¹, R², L², L³, Y, L⁴, R³ and X are any of the following combinations in Table 2, tautomers, prodrugs or pharmaceutically acceptable salts of the compounds or solvates thereof (provided that in the case of 61), Q1a, Q1b, Q1c, Q1i, Q1j, T3a, T3b, T3c, T3d, T3e, Q3e, T3f, T3g, T3h, T3i and T3j in Table 2 denote the following substituents).

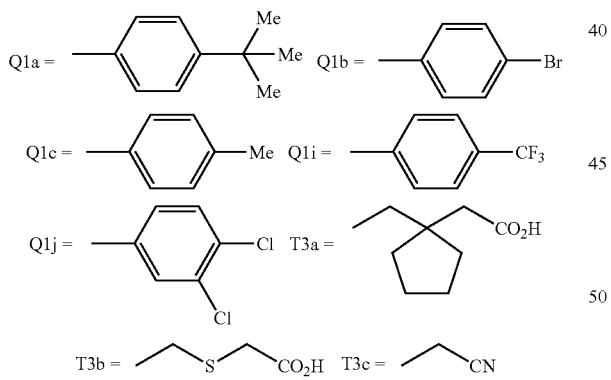

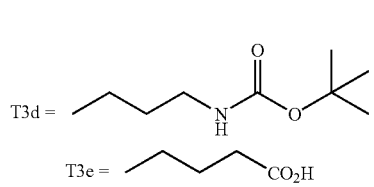

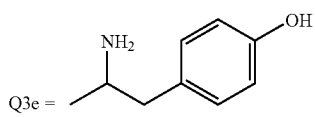

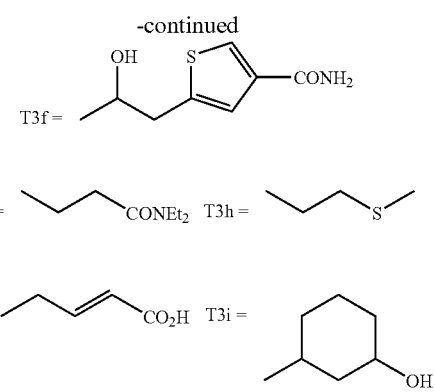

62) The compounds wherein A, B, R¹, L¹, R², L², L³, Y, L⁴, R³ and X are any of the following combinations in Table 3, tautomers, prodrugs or pharmaceutically acceptable salts of the compounds or solvates thereof. The symbols in Table 3 denote the flowing substituents.

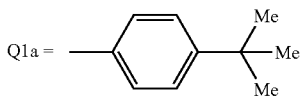

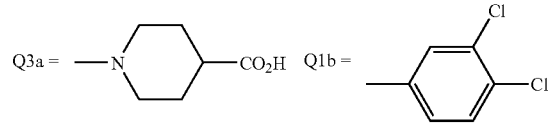

TABLE 3

| No | A | B | R¹ | L¹ | R² | L² | L³ | Y | L⁴ | R³ | X |
|---|---|---|---|---|---|---|---|---|---|---|---|
| 1 | N | NMe | Q1a | NH | Me | a bond | NH | S | NH | Q3a | OH |
| 2 | N | NMe | Q1a | NH | Me | a bond | NH | S | a bond | Q3a | OH |
| 3 | N | NMe | Q1a | NH | Me | a bond | NH | O | NH | Q3a | OH |
| 4 | N | NMe | Q1a | NH | Me | a bond | NH | O | a bond | Q3a | OH |
| 5 | N | NMe | Q1a | NH | H | a bond | NH | S | NH | Q3a | OH |
| 6 | N | NMe | Q1a | NH | H | a bond | NH | S | a bond | Q3a | OH |
| 7 | N | NMe | Q1a | NH | H | a bond | NH | O | NH | Q3a | OH |
| 8 | N | NMe | Q1a | NH | H | a bond | NH | O | a bond | Q3a | OH |
| 9 | N | NMe | Q1b | NH | Me | a bond | NH | S | NH | Q3a | OH |
| 10 | N | NMe | Q1b | NH | Me | a bond | NH | S | a bond | Q3a | OH |
| 11 | N | NMe | Q1b | NH | Me | a bond | NH | O | NH | Q3a | OH |
| 12 | N | NMe | Q1b | NH | Me | a bond | NH | O | a bond | Q3a | OH |
| 13 | N | NMe | Q1b | NH | H | a bond | NH | S | NH | Q3a | OH |
| 14 | N | NMe | Q1b | NH | H | a bond | NH | S | a bond | Q3a | OH |
| 15 | N | NMe | Q1b | NH | H | a bond | NH | O | NH | Q3a | OH |
| 16 | N | NMe | Q1b | NH | H | a bond | NH | O | a bond | Q3a | OH |
| 17 | N | S | Q1a | NH | Me | a bond | NH | S | NH | Q3a | OH |
| 18 | N | S | Q1a | NH | Me | a bond | NH | S | a bond | Q3a | OH |
| 19 | N | S | Q1a | NH | Me | a bond | NH | O | NH | Q3a | OH |
| 20 | N | S | Q1a | NH | Me | a bond | NH | O | a bond | Q3a | OH |
| 21 | N | S | Q1a | NH | H | a bond | NH | S | NH | Q3a | OH |
| 22 | N | S | Q1a | NH | H | a bond | NH | S | a bond | Q3a | OH |
| 23 | N | S | Q1a | NH | H | a bond | NH | O | NH | Q3a | OH |
| 24 | N | S | Q1a | NH | H | a bond | NH | O | a bond | Q3a | OH |
| 25 | N | S | Q1b | NH | Me | a bond | NH | S | NH | Q3a | OH |
| 26 | N | S | Q1b | NH | Me | a bond | NH | S | a bond | Q3a | OH |
| 27 | N | S | Q1b | NH | Me | a bond | NH | O | NH | Q3a | OH |
| 28 | N | S | Q1b | NH | Me | a bond | NH | O | a bond | Q3a | OH |
| 29 | N | S | Q1b | NH | H | a bond | NH | S | NH | Q3a | OH |
| 30 | N | S | Q1b | NH | H | a bond | NH | S | a bond | Q3a | OH |
| 31 | N | S | Q1b | NH | H | a bond | NH | O | NH | Q3a | OH |
| 32 | N | S | Q1b | NH | H | a bond | NH | O | a bond | Q3a | OH |
| 33 | N | O | Q1a | NH | Me | a bond | NH | S | NH | Q3a | OH |
| 34 | N | O | Q1a | NH | Me | a bond | NH | S | a bond | Q3a | OH |
| 35 | N | O | Q1a | NH | Me | a bond | NH | O | NH | Q3a | OH |
| 36 | N | O | Q1a | NH | Me | a bond | NH | O | a bond | Q3a | OH |
| 37 | N | O | Q1a | NH | H | a bond | NH | S | NH | Q3a | OH |
| 38 | N | O | Q1a | NH | H | a bond | NH | S | a bond | Q3a | OH |
| 39 | N | O | Q1a | NH | H | a bond | NH | O | NH | Q3a | OH |
| 40 | N | O | Q1a | NH | H | a bond | NH | O | a bond | Q3a | OH |
| 41 | N | O | Q1b | NH | Me | a bond | NH | S | NH | Q3a | OH |
| 42 | N | O | Q1b | NH | Me | a bond | NH | S | a bond | Q3a | OH |
| 43 | N | O | Q1b | NH | Me | a bond | NH | O | NH | Q3a | OH |
| 44 | N | O | Q1b | NH | Me | a bond | NH | O | a bond | Q3a | OH |
| 45 | N | O | Q1b | NH | H | a bond | NH | S | NH | Q3a | OH |
| 46 | N | O | Q1b | NH | H | a bond | NH | S | a bond | Q3a | OH |
| 47 | N | O | Q1b | NH | H | a bond | NH | O | NH | Q3a | OH |
| 48 | N | O | Q1b | NH | H | a bond | NH | O | a bond | Q3a | OH |
| 49 | CH | NMe | Q1a | NH | Me | a bond | NH | S | NH | Q3a | OH |
| 50 | CH | NMe | Q1a | NH | Me | a bond | NH | S | a bond | Q3a | OH |
| 51 | CH | NMe | Q1a | NH | Me | a bond | NH | O | NH | Q3a | OH |
| 52 | CH | NMe | Q1a | NH | Me | a bond | NH | O | a bond | Q3a | OH |
| 53 | CH | NMe | Q1a | NH | H | a bond | NH | S | NH | Q3a | OH |
| 54 | CH | NMe | Q1a | NH | H | a bond | NH | S | a bond | Q3a | OH |
| 55 | CH | NMe | Q1a | NH | H | a bond | NH | O | NH | Q3a | OH |
| 56 | CH | NMe | Q1a | NH | H | a bond | NH | O | a bond | Q3a | OH |
| 57 | CH | NMe | Q1b | NH | Me | a bond | NH | S | NH | Q3a | OH |
| 58 | CH | NMe | Q1b | NH | Me | a bond | NH | S | a bond | Q3a | OH |
| 59 | CH | NMe | Q1b | NH | Me | a bond | NH | O | NH | Q3a | OH |
| 60 | CH | NMe | Q1b | NH | Me | a bond | NH | O | a bond | Q3a | OH |
| 61 | CH | NMe | Q1b | NH | H | a bond | NH | S | NH | Q3a | OH |
| 62 | CH | NMe | Q1b | NH | H | a bond | NH | S | a bond | Q3a | OH |
| 63 | CH | NMe | Q1b | NH | H | a bond | NH | O | NH | Q3a | OH |
| 64 | CH | NMe | Q1b | NH | H | a bond | NH | O | a bond | Q3a | OH |
| 65 | CH | S | Q1a | NH | Me | a bond | NH | S | NH | Q3a | OH |
| 66 | CH | S | Q1a | NH | Me | a bond | NH | S | a bond | Q3a | OH |
| 67 | CH | S | Q1a | NH | Me | a bond | NH | O | NH | Q3a | OH |
| 68 | CH | S | Q1a | NH | Me | a bond | NH | O | a bond | Q3a | OH |
| 69 | CH | S | Q1a | NH | H | a bond | NH | S | NH | Q3a | OH |
| 70 | CH | S | Q1a | NH | H | a bond | NH | S | a bond | Q3a | OH |
| 71 | CH | S | Q1a | NH | H | a bond | NH | O | NH | Q3a | OH |
| 72 | CH | S | Q1a | NH | H | a bond | NH | O | a bond | Q3a | OH |
| 73 | CH | S | Q1b | NH | Me | a bond | NH | S | NH | Q3a | OH |
| 74 | CH | S | Q1b | NH | Me | a bond | NH | S | a bond | Q3a | OH |
| 75 | CH | S | Q1b | NH | Me | a bond | NH | O | NH | Q3a | OH |
| 76 | CH | S | Q1b | NH | Me | a bond | NH | O | a bond | Q3a | OH |
| 77 | CH | S | Q1b | NH | H | a bond | NH | S | NH | Q3a | OH |
| 78 | CH | S | Q1b | NH | H | a bond | NH | S | a bond | Q3a | OH |

TABLE 3-continued

| No | A | B | R¹ | L¹ | R² | L² | L³ | Y | L⁴ | R³ | X |
|---|---|---|---|---|---|---|---|---|---|---|---|
| 79 | CH | S | Q1b | NH | H | a bond | NH | O | NH | Q3a | OH |
| 80 | CH | S | Q1b | NH | H | a bond | NH | O | a bond | Q3a | OH |
| 81 | CH | O | Q1a | NH | Me | a bond | NH | S | NH | Q3a | OH |
| 82 | CH | O | Q1a | NH | Me | a bond | NH | S | a bond | Q3a | OH |
| 83 | CH | O | Q1a | NH | Me | a bond | NH | O | NH | Q3a | OH |
| 84 | CH | O | Q1a | NH | Me | a bond | NH | O | a bond | Q3a | OH |
| 85 | CH | O | Q1a | NH | H | a bond | NH | S | NH | Q3a | OH |
| 86 | CH | O | Q1a | NH | H | a bond | NH | S | a bond | Q3a | OH |
| 87 | CH | O | Q1a | NH | H | a bond | NH | O | NH | Q3a | OH |
| 88 | CH | O | Q1a | NH | H | a bond | NH | O | a bond | Q3a | OH |
| 89 | CH | O | Q1b | NH | Me | a bond | NH | S | NH | Q3a | OH |
| 90 | CH | O | Q1b | NH | Me | a bond | NH | S | a bond | Q3a | OH |
| 91 | CH | O | Q1b | NH | Me | a bond | NH | O | NH | Q3a | OH |
| 92 | CH | O | Q1b | NH | Me | a bond | NH | O | a bond | Q3a | OH |
| 93 | CH | O | Q1b | NH | H | a bond | NH | S | NH | Q3a | OH |
| 94 | CH | O | Q1b | NH | H | a bond | NH | S | a bond | Q3a | OH |
| 95 | CH | O | Q1b | NH | H | a bond | NH | O | NH | Q3a | OH |
| 96 | CH | O | Q1b | NH | H | a bond | NH | O | a bond | Q3a | OH |
| 97 | CMe | NMe | Q1a | NH | Me | a bond | NH | S | NH | Q3a | OH |
| 98 | CMe | NMe | Q1a | NH | Me | a bond | NH | S | a bond | Q3a | OH |
| 99 | CMe | NMe | Q1a | NH | Me | a bond | NH | O | NH | Q3a | OH |
| 100 | CMe | NMe | Q1a | NH | Me | a bond | NH | O | a bond | Q3a | OH |
| 101 | CMe | NMe | Q1a | NH | H | a bond | NH | S | NH | Q3a | OH |
| 102 | CMe | NMe | Q1a | NH | H | a bond | NH | S | a bond | Q3a | OH |
| 103 | CMe | NMe | Q1a | NH | H | a bond | NH | O | NH | Q3a | OH |
| 104 | CMe | NMe | Q1a | NH | H | a bond | NH | O | a bond | Q3a | OH |
| 105 | CMe | NMe | Q1b | NH | Me | a bond | NH | S | NH | Q3a | OH |
| 106 | CMe | NMe | Q1b | NH | Me | a bond | NH | S | a bond | Q3a | OH |
| 107 | CMe | NMe | Q1b | NH | Me | a bond | NH | O | NH | Q3a | OH |
| 108 | CMe | NMe | Q1b | NH | Me | a bond | NH | O | a bond | Q3a | OH |
| 109 | CMe | NMe | Q1b | NH | H | a bond | NH | S | NH | Q3a | OH |
| 110 | CMe | NMe | Q1b | NH | H | a bond | NH | S | a bond | Q3a | OH |
| 111 | CMe | NMe | Q1b | NH | H | a bond | NH | O | NH | Q3a | OH |
| 112 | CMe | NMe | Q1b | NH | H | a bond | NH | O | a bond | Q3a | OH |
| 113 | CMe | S | Q1a | NH | Me | a bond | NH | S | NH | Q3a | OH |
| 114 | CMe | S | Q1a | NH | Me | a bond | NH | S | a bond | Q3a | OH |
| 115 | CMe | S | Q1a | NH | Me | a bond | NH | O | NH | Q3a | OH |
| 116 | CMe | S | Q1a | NH | Me | a bond | NH | O | a bond | Q3a | OH |
| 117 | CMe | S | Q1a | NH | H | a bond | NH | S | NH | Q3a | OH |
| 118 | CMe | S | Q1a | NH | H | a bond | NH | S | a bond | Q3a | OH |
| 119 | CMe | S | Q1a | NH | H | a bond | NH | O | NH | Q3a | OH |
| 120 | CMe | S | Q1a | NH | H | a bond | NH | O | a bond | Q3a | OH |
| 121 | CMe | S | Q1b | NH | Me | a bond | NH | S | NH | Q3a | OH |
| 122 | CMe | S | Q1b | NH | Me | a bond | NH | S | a bond | Q3a | OH |
| 123 | CMe | S | Q1b | NH | Me | a bond | NH | O | NH | Q3a | OH |
| 124 | CMe | S | Q1b | NH | Me | a bond | NH | O | a bond | Q3a | OH |
| 125 | CMe | S | Q1b | NH | H | a bond | NH | S | NH | Q3a | OH |
| 126 | CMe | S | Q1b | NH | H | a bond | NH | S | a bond | Q3a | OH |
| 127 | CMe | S | Q1b | NH | H | a bond | NH | O | NH | Q3a | OH |
| 128 | CMe | S | Q1b | NH | H | a bond | NH | O | a bond | Q3a | OH |
| 129 | CMe | O | Q1a | NH | Me | a bond | NH | S | NH | Q3a | OH |
| 130 | CMe | O | Q1a | NH | Me | a bond | NH | S | a bond | Q3a | OH |
| 131 | CMe | O | Q1a | NH | Me | a bond | NH | O | NH | Q3a | OH |
| 132 | CMe | O | Q1a | NH | Me | a bond | NH | O | a bond | Q3a | OH |
| 133 | CMe | O | Q1a | NH | H | a bond | NH | S | NH | Q3a | OH |
| 134 | CMe | O | Q1a | NH | H | a bond | NH | S | a bond | Q3a | OH |
| 135 | CMe | O | Q1a | NH | H | a bond | NH | O | NH | Q3a | OH |
| 136 | CMe | O | Q1a | NH | H | a bond | NH | O | a bond | Q3a | OH |
| 137 | CMe | O | Q1b | NH | Me | a bond | NH | S | NH | Q3a | OH |
| 138 | CMe | O | Q1b | NH | Me | a bond | NH | S | a bond | Q3a | OH |
| 139 | CMe | O | Q1b | NH | Me | a bond | NH | O | NH | Q3a | OH |
| 140 | CMe | O | Q1b | NH | Me | a bond | NH | O | a bond | Q3a | OH |
| 141 | CMe | O | Q1b | NH | H | a bond | NH | S | NH | Q3a | OH |
| 142 | CMe | O | Q1b | NH | H | a bond | NH | S | a bond | Q3a | OH |
| 143 | CMe | O | Q1b | NH | H | a bond | NH | O | NH | Q3a | OH |
| 144 | CMe | O | Q1b | NH | H | a bond | NH | O | a bond | Q3a | OH |
| 145 | N | NMe | Q1a | O | Me | a bond | NH | S | NH | Q3a | OH |
| 146 | N | NMe | Q1a | O | Me | a bond | NH | S | a bond | Q3a | OH |
| 147 | N | NMe | Q1a | O | Me | a bond | NH | O | NH | Q3a | OH |
| 148 | N | NMe | Q1a | O | Me | a bond | NH | O | a bond | Q3a | OH |
| 149 | N | NMe | Q1a | O | H | a bond | NH | S | NH | Q3a | OH |
| 150 | N | NMe | Q1a | O | H | a bond | NH | S | a bond | Q3a | OH |
| 151 | N | NMe | Q1a | O | H | a bond | NH | O | NH | Q3a | OH |
| 152 | N | NMe | Q1a | O | H | a bond | NH | O | a bond | Q3a | OH |
| 153 | N | NMe | Q1b | O | Me | a bond | NH | S | NH | Q3a | OH |
| 154 | N | NMe | Q1b | O | Me | a bond | NH | S | a bond | Q3a | OH |
| 155 | N | NMe | Q1b | O | Me | a bond | NH | O | NH | Q3a | OH |
| 156 | N | NMe | Q1b | O | Me | a bond | NH | O | a bond | Q3a | OH |

TABLE 3-continued

| No | A | B | R¹ | L¹ | R² | L² | L³ | Y | L⁴ | R³ | X |
|---|---|---|---|---|---|---|---|---|---|---|---|
| 157 | N | NMe | Q1b | O | H | a bond | NH | S | NH | Q3a | OH |
| 158 | N | NMe | Q1b | O | H | a bond | NH | S | a bond | Q3a | OH |
| 159 | N | NMe | Q1b | O | H | a bond | NH | O | NH | Q3a | OH |
| 160 | N | NMe | Q1b | O | H | a bond | NH | O | a bond | Q3a | OH |
| 161 | N | S | Q1a | O | Me | a bond | NH | S | NH | Q3a | OH |
| 162 | N | S | Q1a | O | Me | a bond | NH | S | a bond | Q3a | OH |
| 163 | N | S | Q1a | O | Me | a bond | NH | O | NH | Q3a | OH |
| 164 | N | S | Q1a | O | Me | a bond | NH | O | a bond | Q3a | OH |
| 165 | N | S | Q1a | O | H | a bond | NH | S | NH | Q3a | OH |
| 166 | N | S | Q1a | O | H | a bond | NH | S | a bond | Q3a | OH |
| 167 | N | S | Q1a | O | H | a bond | NH | O | NH | Q3a | OH |
| 168 | N | S | Q1a | O | H | a bond | NH | O | a bond | Q3a | OH |
| 169 | N | S | Q1b | O | Me | a bond | NH | S | NH | Q3a | OH |
| 170 | N | S | Q1b | O | Me | a bond | NH | S | a bond | Q3a | OH |
| 171 | N | S | Q1b | O | Me | a bond | NH | O | NH | Q3a | OH |
| 172 | N | S | Q1b | O | Me | a bond | NH | O | a bond | Q3a | OH |
| 173 | N | S | Q1b | O | H | a bond | NH | S | NH | Q3a | OH |
| 174 | N | S | Q1b | O | H | a bond | NH | S | a bond | Q3a | OH |
| 175 | N | S | Q1b | O | H | a bond | NH | O | NH | Q3a | OH |
| 176 | N | S | Q1b | O | H | a bond | NH | O | a bond | Q3a | OH |
| 177 | N | O | Q1a | O | Me | a bond | NH | S | NH | Q3a | OH |
| 178 | N | O | Q1a | O | Me | a bond | NH | S | a bond | Q3a | OH |
| 179 | N | O | Q1a | O | Me | a bond | NH | O | NH | Q3a | OH |
| 180 | N | O | Q1a | O | Me | a bond | NH | O | a bond | Q3a | OH |
| 181 | N | O | Q1a | O | H | a bond | NH | S | NH | Q3a | OH |
| 182 | N | O | Q1a | O | H | a bond | NH | S | a bond | Q3a | OH |
| 183 | N | O | Q1a | O | H | a bond | NH | O | NH | Q3a | OH |
| 184 | N | O | Q1a | O | H | a bond | NH | O | a bond | Q3a | OH |
| 185 | N | O | Q1b | O | Me | a bond | NH | S | NH | Q3a | OH |
| 186 | N | O | Q1b | O | Me | a bond | NH | S | a bond | Q3a | OH |
| 187 | N | O | Q1b | O | Me | a bond | NH | O | NH | Q3a | OH |
| 188 | N | O | Q1b | O | Me | a bond | NH | O | a bond | Q3a | OH |
| 189 | N | O | Q1b | O | H | a bond | NH | S | NH | Q3a | OH |
| 190 | N | O | Q1b | O | H | a bond | NH | S | a bond | Q3a | OH |
| 191 | N | O | Q1b | O | H | a bond | NH | O | NH | Q3a | OH |
| 192 | N | O | Q1b | O | H | a bond | NH | O | a bond | Q3a | OH |
| 193 | CH | NMe | Q1a | O | Me | a bond | NH | S | NH | Q3a | OH |
| 194 | CH | NMe | Q1a | O | Me | a bond | NH | S | a bond | Q3a | OH |
| 195 | CH | NMe | Q1a | O | Me | a bond | NH | O | NH | Q3a | OH |
| 196 | CH | NMe | Q1a | O | Me | a bond | NH | O | a bond | Q3a | OH |
| 197 | CH | NMe | Q1a | O | H | a bond | NH | S | NH | Q3a | OH |
| 198 | CH | NMe | Q1a | O | H | a bond | NH | S | a bond | Q3a | OH |
| 199 | CH | NMe | Q1a | O | H | a bond | NH | O | NH | Q3a | OH |
| 200 | CH | NMe | Q1a | O | H | a bond | NH | O | a bond | Q3a | OH |
| 201 | CH | NMe | Q1b | O | Me | a bond | NH | S | NH | Q3a | OH |
| 202 | CH | NMe | Q1b | O | Me | a bond | NH | S | a bond | Q3a | OH |
| 203 | CH | NMe | Q1b | O | Me | a bond | NH | O | NH | Q3a | OH |
| 204 | CH | NMe | Q1b | O | Me | a bond | NH | O | a bond | Q3a | OH |
| 205 | CH | NMe | Q1b | O | H | a bond | NH | S | NH | Q3a | OH |
| 206 | CH | NMe | Q1b | O | H | a bond | NH | S | a bond | Q3a | OH |
| 207 | CH | NMe | Q1b | O | H | a bond | NH | O | NH | Q3a | OH |
| 208 | CH | NMe | Q1b | O | H | a bond | NH | O | a bond | Q3a | OH |
| 209 | CH | S | Q1a | O | Me | a bond | NH | S | NH | Q3a | OH |
| 210 | CH | S | Q1a | O | Me | a bond | NH | S | a bond | Q3a | OH |
| 211 | CH | S | Q1a | O | Me | a bond | NH | O | NH | Q3a | OH |
| 212 | CH | S | Q1a | O | Me | a bond | NH | O | a bond | Q3a | OH |
| 213 | CH | S | Q1a | O | H | a bond | NH | S | NH | Q3a | OH |
| 214 | CH | S | Q1a | O | H | a bond | NH | S | a bond | Q3a | OH |
| 215 | CH | S | Q1a | O | H | a bond | NH | O | NH | Q3a | OH |
| 216 | CH | S | Q1a | O | H | a bond | NH | O | a bond | Q3a | OH |
| 217 | CH | S | Q1b | O | Me | a bond | NH | S | NH | Q3a | OH |
| 218 | CH | S | Q1b | O | Me | a bond | NH | S | a bond | Q3a | OH |
| 219 | CH | S | Q1b | O | Me | a bond | NH | O | NH | Q3a | OH |
| 220 | CH | S | Q1b | O | Me | a bond | NH | O | a bond | Q3a | OH |
| 221 | CH | S | Q1b | O | H | a bond | NH | S | NH | Q3a | OH |
| 222 | CH | S | Q1b | O | H | a bond | NH | S | a bond | Q3a | OH |
| 223 | CH | S | Q1b | O | H | a bond | NH | O | NH | Q3a | OH |
| 224 | CH | S | Q1b | O | H | a bond | NH | O | a bond | Q3a | OH |
| 225 | CH | O | Q1a | O | Me | a bond | NH | S | NH | Q3a | OH |
| 226 | CH | O | Q1a | O | Me | a bond | NH | S | a bond | Q3a | OH |
| 227 | CH | O | Q1a | O | Me | a bond | NH | O | NH | Q3a | OH |
| 228 | CH | O | Q1a | O | Me | a bond | NH | O | a bond | Q3a | OH |
| 229 | CH | O | Q1a | O | H | a bond | NH | S | NH | Q3a | OH |
| 230 | CH | O | Q1a | O | H | a bond | NH | S | a bond | Q3a | OH |
| 231 | CH | O | Q1a | O | H | a bond | NH | O | NH | Q3a | OH |
| 232 | CH | O | Q1a | O | H | a bond | NH | O | a bond | Q3a | OH |
| 233 | CH | O | Q1b | O | Me | a bond | NH | S | NH | Q3a | OH |
| 234 | CH | O | Q1b | O | Me | a bond | NH | S | a bond | Q3a | OH |

TABLE 3-continued

| No | A | B | R¹ | L¹ | R² | L² | L³ | Y | L⁴ | R³ | X |
|---|---|---|---|---|---|---|---|---|---|---|---|
| 235 | CH | O | Q1b | O | Me | a bond | NH | O | NH | Q3a | OH |
| 236 | CH | O | Q1b | O | Me | a bond | NH | O | a bond | Q3a | OH |
| 237 | CH | O | Q1b | O | H | a bond | NH | S | NH | Q3a | OH |
| 238 | CH | O | Q1b | O | H | a bond | NH | S | a bond | Q3a | OH |
| 239 | CH | O | Q1b | O | H | a bond | NH | O | NH | Q3a | OH |
| 240 | CH | O | Q1b | O | H | a bond | NH | O | a bond | Q3a | OH |
| 241 | CMe | NMe | Q1a | O | Me | a bond | NH | S | NH | Q3a | OH |
| 242 | CMe | NMe | Q1a | O | Me | a bond | NH | S | a bond | Q3a | OH |
| 243 | CMe | NMe | Q1a | O | Me | a bond | NH | O | NH | Q3a | OH |
| 244 | CMe | NMe | Q1a | O | Me | a bond | NH | O | a bond | Q3a | OH |
| 245 | CMe | NMe | Q1a | O | H | a bond | NH | S | NH | Q3a | OH |
| 246 | CMe | NMe | Q1a | O | H | a bond | NH | S | a bond | Q3a | OH |
| 247 | CMe | NMe | Q1a | O | H | a bond | NH | O | NH | Q3a | OH |
| 248 | CMe | NMe | Q1a | O | H | a bond | NH | O | a bond | Q3a | OH |
| 249 | CMe | NMe | Q1b | O | Me | a bond | NH | S | NH | Q3a | OH |
| 250 | CMe | NMe | Q1b | O | Me | a bond | NH | S | a bond | Q3a | OH |
| 251 | CMe | NMe | Q1b | O | Me | a bond | NH | O | NH | Q3a | OH |
| 252 | CMe | NMe | Q1b | O | Me | a bond | NH | O | a bond | Q3a | OH |
| 253 | CMe | NMe | Q1b | O | H | a bond | NH | S | NH | Q3a | OH |
| 254 | CMe | NMe | Q1b | O | H | a bond | NH | S | a bond | Q3a | OH |
| 255 | CMe | NMe | Q1b | O | H | a bond | NH | O | NH | Q3a | OH |
| 256 | CMe | NMe | Q1b | O | H | a bond | NH | O | a bond | Q3a | OH |
| 257 | CMe | S | Q1a | O | Me | a bond | NH | S | NH | Q3a | OH |
| 258 | CMe | S | Q1a | O | Me | a bond | NH | S | a bond | Q3a | OH |
| 259 | CMe | S | Q1a | O | Me | a bond | NH | O | NH | Q3a | OH |
| 260 | CMe | S | Q1a | O | Me | a bond | NH | O | a bond | Q3a | OH |
| 261 | CMe | S | Q1a | O | H | a bond | NH | S | NH | Q3a | OH |
| 262 | CMe | S | Q1a | O | H | a bond | NH | S | a bond | Q3a | OH |
| 263 | CMe | S | Q1a | O | H | a bond | NH | O | NH | Q3a | OH |
| 264 | CMe | S | Q1a | O | H | a bond | NH | O | a bond | Q3a | OH |
| 265 | CMe | S | Q1b | O | Me | a bond | NH | S | NH | Q3a | OH |
| 266 | CMe | S | Q1b | O | Me | a bond | NH | S | a bond | Q3a | OH |
| 267 | CMe | S | Q1b | O | Me | a bond | NH | O | NH | Q3a | OH |
| 268 | CMe | S | Q1b | O | Me | a bond | NH | O | a bond | Q3a | OH |
| 269 | CMe | S | Q1b | O | H | a bond | NH | S | NH | Q3a | OH |
| 270 | CMe | S | Q1b | O | H | a bond | NH | S | a bond | Q3a | OH |
| 271 | CMe | S | Q1b | O | H | a bond | NH | O | NH | Q3a | OH |
| 272 | CMe | S | Q1b | O | H | a bond | NH | O | a bond | Q3a | OH |
| 273 | CMe | O | Q1a | O | Me | a bond | NH | S | NH | Q3a | OH |
| 274 | CMe | O | Q1a | O | Me | a bond | NH | S | a bond | Q3a | OH |
| 275 | CMe | O | Q1a | O | Me | a bond | NH | O | NH | Q3a | OH |
| 276 | CMe | O | Q1a | O | Me | a bond | NH | O | a bond | Q3a | OH |
| 277 | CMe | O | Q1a | O | H | a bond | NH | S | NH | Q3a | OH |
| 278 | CMe | O | Q1a | O | H | a bond | NH | S | a bond | Q3a | OH |
| 279 | CMe | O | Q1a | O | H | a bond | NH | O | NH | Q3a | OH |
| 280 | CMe | O | Q1a | O | H | a bond | NH | O | a bond | Q3a | OH |
| 281 | CMe | O | Q1b | O | Me | a bond | NH | S | NH | Q3a | OH |
| 282 | CMe | O | Q1b | O | Me | a bond | NH | S | a bond | Q3a | OH |
| 283 | CMe | O | Q1b | O | Me | a bond | NH | O | NH | Q3a | OH |
| 284 | CMe | O | Q1b | O | Me | a bond | NH | O | a bond | Q3a | OH |
| 285 | CMe | O | Q1b | O | H | a bond | NH | S | NH | Q3a | OH |
| 286 | CMe | O | Q1b | O | H | a bond | NH | S | a bond | Q3a | OH |
| 287 | CMe | O | Q1b | O | H | a bond | NH | O | NH | Q3a | OH |
| 288 | CMe | O | Q1b | O | H | a bond | NH | O | a bond | Q3a | OH |
| 289 | N | NMe | Q1a | CH2 | Me | a bond | NH | S | NH | Q3a | OH |
| 290 | N | NMe | Q1a | CH2 | Me | a bond | NH | S | a bond | Q3a | OH |
| 291 | N | NMe | Q1a | CH2 | Me | a bond | NH | O | NH | Q3a | OH |
| 292 | N | NMe | Q1a | CH2 | Me | a bond | NH | O | a bond | Q3a | OH |
| 293 | N | NMe | Q1a | CH2 | H | a bond | NH | S | NH | Q3a | OH |
| 294 | N | NMe | Q1a | CH2 | H | a bond | NH | S | a bond | Q3a | OH |
| 295 | N | NMe | Q1a | CH2 | H | a bond | NH | O | NH | Q3a | OH |
| 296 | N | NMe | Q1a | CH2 | H | a bond | NH | O | a bond | Q3a | OH |
| 297 | N | NMe | Q1b | CH2 | Me | a bond | NH | S | NH | Q3a | OH |
| 298 | N | NMe | Q1b | CH2 | Me | a bond | NH | S | a bond | Q3a | OH |
| 299 | N | NMe | Q1b | CH2 | Me | a bond | NH | O | NH | Q3a | OH |
| 300 | N | NMe | Q1b | CH2 | Me | a bond | NH | O | a bond | Q3a | OH |
| 301 | N | NMe | Q1b | CH2 | H | a bond | NH | S | NH | Q3a | OH |
| 302 | N | NMe | Q1b | CH2 | H | a bond | NH | S | a bond | Q3a | OH |
| 303 | N | NMe | Q1b | CH2 | H | a bond | NH | O | NH | Q3a | OH |
| 304 | N | NMe | Q1b | CH2 | H | a bond | NH | O | a bond | Q3a | OH |
| 305 | N | S | Q1a | CH2 | Me | a bond | NH | S | NH | Q3a | OH |
| 306 | N | S | Q1a | CH2 | Me | a bond | NH | S | a bond | Q3a | OH |
| 307 | N | S | Q1a | CH2 | Me | a bond | NH | O | NH | Q3a | OH |
| 308 | N | S | Q1a | CH2 | Me | a bond | NH | O | a bond | Q3a | OH |
| 309 | N | S | Q1a | CH2 | H | a bond | NH | S | NH | Q3a | OH |
| 310 | N | S | Q1a | CH2 | H | a bond | NH | S | a bond | Q3a | OH |
| 311 | N | S | Q1a | CH2 | H | a bond | NH | O | NH | Q3a | OH |
| 312 | N | S | Q1a | CH2 | H | a bond | NH | O | a bond | Q3a | OH |

TABLE 3-continued

| No | A | B | R¹ | L¹ | R² | L² | L³ | Y | L⁴ | R³ | X |
|---|---|---|---|---|---|---|---|---|---|---|---|
| 313 | N | S | Q1b | CH2 | Me | a bond | NH | S | NH | Q3a | OH |
| 314 | N | S | Q1b | CH2 | Me | a bond | NH | S | a bond | Q3a | OH |
| 315 | N | S | Q1b | CH2 | Me | a bond | NH | O | NH | Q3a | OH |
| 316 | N | S | Q1b | CH2 | Me | a bond | NH | O | a bond | Q3a | OH |
| 317 | N | S | Q1b | CH2 | H | a bond | NH | S | NH | Q3a | OH |
| 318 | N | S | Q1b | CH2 | H | a bond | NH | S | a bond | Q3a | OH |
| 319 | N | S | Q1b | CH2 | H | a bond | NH | O | NH | Q3a | OH |
| 320 | N | S | Q1b | CH2 | H | a bond | NH | O | a bond | Q3a | OH |
| 321 | N | O | Q1a | CH2 | Me | a bond | NH | S | NH | Q3a | OH |
| 322 | N | O | Q1a | CH2 | Me | a bond | NH | S | a bond | Q3a | OH |
| 323 | N | O | Q1a | CH2 | Me | a bond | NH | O | NH | Q3a | OH |
| 324 | N | O | Q1a | CH2 | Me | a bond | NH | O | a bond | Q3a | OH |
| 325 | N | O | Q1a | CH2 | H | a bond | NH | S | NH | Q3a | OH |
| 326 | N | O | Q1a | CH2 | H | a bond | NH | S | a bond | Q3a | OH |
| 327 | N | O | Q1a | CH2 | H | a bond | NH | O | NH | Q3a | OH |
| 328 | N | O | Q1a | CH2 | H | a bond | NH | O | a bond | Q3a | OH |
| 329 | N | O | Q1b | CH2 | Me | a bond | NH | S | NH | Q3a | OH |
| 330 | N | O | Q1b | CH2 | Me | a bond | NH | S | a bond | Q3a | OH |
| 331 | N | O | Q1b | CH2 | Me | a bond | NH | O | NH | Q3a | OH |
| 332 | N | O | Q1b | CH2 | Me | a bond | NH | O | a bond | Q3a | OH |
| 333 | N | O | Q1b | CH2 | H | a bond | NH | S | NH | Q3a | OH |
| 334 | N | O | Q1b | CH2 | H | a bond | NH | S | a bond | Q3a | OH |
| 335 | N | O | Q1b | CH2 | H | a bond | NH | O | NH | Q3a | OH |
| 336 | N | O | Q1b | CH2 | H | a bond | NH | O | a bond | Q3a | OH |
| 337 | CH | NMe | Q1a | CH2 | Me | a bond | NH | S | NH | Q3a | OH |
| 338 | CH | NMe | Q1a | CH2 | Me | a bond | NH | S | a bond | Q3a | OH |
| 339 | CH | NMe | Q1a | CH2 | Me | a bond | NH | O | NH | Q3a | OH |
| 340 | CH | NMe | Q1a | CH2 | Me | a bond | NH | O | a bond | Q3a | OH |
| 341 | CH | NMe | Q1a | CH2 | H | a bond | NH | S | NH | Q3a | OH |
| 342 | CH | NMe | Q1a | CH2 | H | a bond | NH | S | a bond | Q3a | OH |
| 343 | CH | NMe | Q1a | CH2 | H | a bond | NH | O | NH | Q3a | OH |
| 344 | CH | NMe | Q1a | CH2 | H | a bond | NH | O | a bond | Q3a | OH |
| 345 | CH | NMe | Q1b | CH2 | Me | a bond | NH | S | NH | Q3a | OH |
| 346 | CH | NMe | Q1b | CH2 | Me | a bond | NH | S | a bond | Q3a | OH |
| 347 | CH | NMe | Q1b | CH2 | Me | a bond | NH | O | NH | Q3a | OH |
| 348 | CH | NMe | Q1b | CH2 | Me | a bond | NH | O | a bond | Q3a | OH |
| 349 | CH | NMe | Q1b | CH2 | H | a bond | NH | S | NH | Q3a | OH |
| 350 | CH | NMe | Q1b | CH2 | H | a bond | NH | S | a bond | Q3a | OH |
| 351 | CH | NMe | Q1b | CH2 | H | a bond | NH | O | NH | Q3a | OH |
| 352 | CH | NMe | Q1b | CH2 | H | a bond | NH | O | a bond | Q3a | OH |
| 353 | CH | S | Q1a | CH2 | Me | a bond | NH | S | NH | Q3a | OH |
| 354 | CH | S | Q1a | CH2 | Me | a bond | NH | S | a bond | Q3a | OH |
| 355 | CH | S | Q1a | CH2 | Me | a bond | NH | O | NH | Q3a | OH |
| 356 | CH | S | Q1a | CH2 | Me | a bond | NH | O | a bond | Q3a | OH |
| 357 | CH | S | Q1a | CH2 | H | a bond | NH | S | NH | Q3a | OH |
| 358 | CH | S | Q1a | CH2 | H | a bond | NH | S | a bond | Q3a | OH |
| 359 | CH | S | Q1a | CH2 | H | a bond | NH | O | NH | Q3a | OH |
| 360 | CH | S | Q1a | CH2 | H | a bond | NH | O | a bond | Q3a | OH |
| 361 | CH | S | Q1b | CH2 | Me | a bond | NH | S | NH | Q3a | OH |
| 362 | CH | S | Q1b | CH2 | Me | a bond | NH | S | a bond | Q3a | OH |
| 363 | CH | S | Q1b | CH2 | Me | a bond | NH | O | NH | Q3a | OH |
| 364 | CH | S | Q1b | CH2 | Me | a bond | NH | O | a bond | Q3a | OH |
| 365 | CH | S | Q1b | CH2 | H | a bond | NH | S | NH | Q3a | OH |
| 366 | CH | S | Q1b | CH2 | H | a bond | NH | S | a bond | Q3a | OH |
| 367 | CH | S | Q1b | CH2 | H | a bond | NH | O | NH | Q3a | OH |
| 368 | CH | S | Q1b | CH2 | H | a bond | NH | O | a bond | Q3a | OH |
| 369 | CH | O | Q1a | CH2 | Me | a bond | NH | S | NH | Q3a | OH |
| 370 | CH | O | Q1a | CH2 | Me | a bond | NH | S | a bond | Q3a | OH |
| 371 | CH | O | Q1a | CH2 | Me | a bond | NH | O | NH | Q3a | OH |
| 372 | CH | O | Q1a | CH2 | Me | a bond | NH | O | a bond | Q3a | OH |
| 373 | CH | O | Q1a | CH2 | H | a bond | NH | S | NH | Q3a | OH |
| 374 | CH | O | Q1a | CH2 | H | a bond | NH | S | a bond | Q3a | OH |
| 375 | CH | O | Q1a | CH2 | H | a bond | NH | O | NH | Q3a | OH |
| 376 | CH | O | Q1a | CH2 | H | a bond | NH | O | a bond | Q3a | OH |
| 377 | CH | O | Q1b | CH2 | Me | a bond | NH | S | NH | Q3a | OH |
| 378 | CH | O | Q1b | CH2 | Me | a bond | NH | S | a bond | Q3a | OH |
| 379 | CH | O | Q1b | CH2 | Me | a bond | NH | O | NH | Q3a | OH |
| 380 | CH | O | Q1b | CH2 | Me | a bond | NH | O | a bond | Q3a | OH |
| 381 | CH | O | Q1b | CH2 | H | a bond | NH | S | NH | Q3a | OH |
| 382 | CH | O | Q1b | CH2 | H | a bond | NH | S | a bond | Q3a | OH |
| 383 | CH | O | Q1b | CH2 | H | a bond | NH | O | NH | Q3a | OH |
| 384 | CH | O | Q1b | CH2 | H | a bond | NH | O | a bond | Q3a | OH |
| 385 | CMe | NMe | Q1a | CH2 | Me | a bond | NH | S | NH | Q3a | OH |
| 386 | CMe | NMe | Q1a | CH2 | Me | a bond | NH | S | a bond | Q3a | OH |
| 387 | CMe | NMe | Q1a | CH2 | Me | a bond | NH | O | NH | Q3a | OH |
| 388 | CMe | NMe | Q1a | CH2 | Me | a bond | NH | O | a bond | Q3a | OH |
| 389 | CMe | NMe | Q1a | CH2 | H | a bond | NH | S | NH | Q3a | OH |
| 390 | CMe | NMe | Q1a | CH2 | H | a bond | NH | S | a bond | Q3a | OH |

TABLE 3-continued

| No | A | B | R¹ | L¹ | R² | L² | L³ | Y | L⁴ | R³ | X |
|---|---|---|---|---|---|---|---|---|---|---|---|
| 391 | CMe | NMe | Q1a | CH2 | H | a bond | NH | O | NH | Q3a | OH |
| 392 | CMe | NMe | Q1a | CH2 | H | a bond | NH | O | a bond | Q3a | OH |
| 393 | CMe | NMe | Q1b | CH2 | Me | a bond | NH | S | NH | Q3a | OH |
| 394 | CMe | NMe | Q1b | CH2 | Me | a bond | NH | S | a bond | Q3a | OH |
| 395 | CMe | NMe | Q1b | CH2 | Me | a bond | NH | O | NH | Q3a | OH |
| 396 | CMe | NMe | Q1b | CH2 | Me | a bond | NH | O | a bond | Q3a | OH |
| 397 | CMe | NMe | Q1b | CH2 | H | a bond | NH | S | NH | Q3a | OH |
| 398 | CMe | NMe | Q1b | CH2 | H | a bond | NH | S | a bond | Q3a | OH |
| 399 | CMe | NMe | Q1b | CH2 | H | a bond | NH | O | NH | Q3a | OH |
| 400 | CMe | NMe | Q1b | CH2 | H | a bond | NH | O | a bond | Q3a | OH |
| 401 | CMe | S | Q1a | CH2 | Me | a bond | NH | S | NH | Q3a | OH |
| 402 | CMe | S | Q1a | CH2 | Me | a bond | NH | S | a bond | Q3a | OH |
| 403 | CMe | S | Q1a | CH2 | Me | a bond | NH | O | NH | Q3a | OH |
| 404 | CMe | S | Q1a | CH2 | Me | a bond | NH | O | a bond | Q3a | OH |
| 405 | CMe | S | Q1a | CH2 | H | a bond | NH | S | NH | Q3a | OH |
| 406 | CMe | S | Q1a | CH2 | H | a bond | NH | S | a bond | Q3a | OH |
| 407 | CMe | S | Q1a | CH2 | H | a bond | NH | O | NH | Q3a | OH |
| 408 | CMe | S | Q1a | CH2 | H | a bond | NH | O | a bond | Q3a | OH |
| 409 | CMe | S | Q1b | CH2 | Me | a bond | NH | S | NH | Q3a | OH |
| 410 | CMe | S | Q1b | CH2 | Me | a bond | NH | S | a bond | Q3a | OH |
| 411 | CMe | S | Q1b | CH2 | Me | a bond | NH | O | NH | Q3a | OH |
| 412 | CMe | S | Q1b | CH2 | Me | a bond | NH | O | a bond | Q3a | OH |
| 413 | CMe | S | Q1b | CH2 | H | a bond | NH | S | NH | Q3a | OH |
| 414 | CMe | S | Q1b | CH2 | H | a bond | NH | S | a bond | Q3a | OH |
| 415 | CMe | S | Q1b | CH2 | H | a bond | NH | O | NH | Q3a | OH |
| 416 | CMe | S | Q1b | CH2 | H | a bond | NH | O | a bond | Q3a | OH |
| 417 | CMe | O | Q1a | CH2 | Me | a bond | NH | S | NH | Q3a | OH |
| 418 | CMe | O | Q1a | CH2 | Me | a bond | NH | S | a bond | Q3a | OH |
| 419 | CMe | O | Q1a | CH2 | Me | a bond | NH | O | NH | Q3a | OH |
| 420 | CMe | O | Q1a | CH2 | Me | a bond | NH | O | a bond | Q3a | OH |
| 421 | CMe | O | Q1a | CH2 | H | a bond | NH | S | NH | Q3a | OH |
| 422 | CMe | O | Q1a | CH2 | H | a bond | NH | S | a bond | Q3a | OH |
| 423 | CMe | O | Q1a | CH2 | H | a bond | NH | O | NH | Q3a | OH |
| 424 | CMe | O | Q1a | CH2 | H | a bond | NH | O | a bond | Q3a | OH |
| 425 | CMe | O | Q1b | CH2 | Me | a bond | NH | S | NH | Q3a | OH |
| 426 | CMe | O | Q1b | CH2 | Me | a bond | NH | S | a bond | Q3a | OH |
| 427 | CMe | O | Q1b | CH2 | Me | a bond | NH | O | NH | Q3a | OH |
| 428 | CMe | O | Q1b | CH2 | Me | a bond | NH | O | a bond | Q3a | OH |
| 429 | CMe | O | Q1b | CH2 | H | a bond | NH | S | NH | Q3a | OH |
| 430 | CMe | O | Q1b | CH2 | H | a bond | NH | S | a bond | Q3a | OH |
| 431 | CMe | O | Q1b | CH2 | H | a bond | NH | O | NH | Q3a | OH |
| 432 | CMe | O | Q1b | CH2 | H | a bond | NH | O | a bond | Q3a | OH |
| 433 | N | NMe | Q1a | a bond | Me | a bond | NH | S | CH2 | Q3a | OH |
| 434 | N | NMe | Q1a | a bond | Me | a bond | NH | O | CH2 | Q3a | OH |
| 435 | N | NMe | Q1a | a bond | H | a bond | NH | S | CH2 | Q3a | OH |
| 436 | N | NMe | Q1a | a bond | H | a bond | NH | O | CH2 | Q3a | OH |
| 437 | N | NMe | Q1b | a bond | Me | a bond | NH | S | CH2 | Q3a | OH |
| 438 | N | NMe | Q1b | a bond | Me | a bond | NH | O | CH2 | Q3a | OH |
| 439 | N | NMe | Q1b | a bond | H | a bond | NH | S | CH2 | Q3a | OH |
| 440 | N | NMe | Q1b | a bond | H | a bond | NH | O | CH2 | Q3a | OH |
| 441 | N | S | Q1a | a bond | Me | a bond | NH | S | CH2 | Q3a | OH |
| 442 | N | S | Q1a | a bond | Me | a bond | NH | O | CH2 | Q3a | OH |
| 443 | N | S | Q1a | a bond | H | a bond | NH | S | CH2 | Q3a | OH |
| 444 | N | S | Q1a | a bond | H | a bond | NH | O | CH2 | Q3a | OH |
| 445 | N | S | Q1b | a bond | Me | a bond | NH | S | CH2 | Q3a | OH |
| 446 | N | S | Q1b | a bond | Me | a bond | NH | O | CH2 | Q3a | OH |
| 447 | N | S | Q1b | a bond | H | a bond | NH | S | CH2 | Q3a | OH |
| 448 | N | S | Q1b | a bond | H | a bond | NH | O | CH2 | Q3a | OH |
| 449 | N | O | Q1a | a bond | Me | a bond | NH | S | CH2 | Q3a | OH |
| 450 | N | O | Q1a | a bond | Me | a bond | NH | O | CH2 | Q3a | OH |
| 451 | N | O | Q1a | a bond | H | a bond | NH | S | CH2 | Q3a | OH |
| 452 | N | O | Q1a | a bond | H | a bond | NH | O | CH2 | Q3a | OH |
| 453 | N | O | Q1b | a bond | Me | a bond | NH | S | CH2 | Q3a | OH |
| 454 | N | O | Q1b | a bond | Me | a bond | NH | O | CH2 | Q3a | OH |
| 455 | N | O | Q1b | a bond | H | a bond | NH | S | CH2 | Q3a | OH |
| 456 | N | O | Q1b | a bond | H | a bond | NH | O | CH2 | Q3a | OH |
| 457 | CH | NMe | Q1a | a bond | Me | a bond | NH | S | CH2 | Q3a | OH |
| 458 | CH | NMe | Q1a | a bond | Me | a bond | NH | O | CH2 | Q3a | OH |
| 459 | CH | NMe | Q1a | a bond | H | a bond | NH | S | CH2 | Q3a | OH |
| 460 | CH | NMe | Q1a | a bond | H | a bond | NH | O | CH2 | Q3a | OH |
| 461 | CH | NMe | Q1b | a bond | Me | a bond | NH | S | CH2 | Q3a | OH |
| 462 | CH | NMe | Q1b | a bond | Me | a bond | NH | O | CH2 | Q3a | OH |
| 463 | CH | NMe | Q1b | a bond | H | a bond | NH | S | CH2 | Q3a | OH |
| 464 | CH | NMe | Q1b | a bond | H | a bond | NH | O | CH2 | Q3a | OH |
| 465 | CH | S | Q1a | a bond | Me | a bond | NH | S | CH2 | Q3a | OH |
| 466 | CH | S | Q1a | a bond | Me | a bond | NH | O | CH2 | Q3a | OH |
| 467 | CH | S | Q1a | a bond | H | a bond | NH | S | CH2 | Q3a | OH |
| 468 | CH | S | Q1a | a bond | H | a bond | NH | O | CH2 | Q3a | OH |

TABLE 3-continued

| No | A | B | R¹ | L¹ | R² | L² | L³ | Y | L⁴ | R³ | X |
|---|---|---|---|---|---|---|---|---|---|---|---|
| 469 | CH | S | Q1b | a bond | Me | a bond | NH | S | CH2 | Q3a | OH |
| 470 | CH | S | Q1b | a bond | Me | a bond | NH | O | CH2 | Q3a | OH |
| 471 | CH | S | Q1b | a bond | H | a bond | NH | S | CH2 | Q3a | OH |
| 472 | CH | S | Q1b | a bond | H | a bond | NH | O | CH2 | Q3a | OH |
| 473 | CH | O | Q1a | a bond | Me | a bond | NH | S | CH2 | Q3a | OH |
| 474 | CH | O | Q1a | a bond | Me | a bond | NH | O | CH2 | Q3a | OH |
| 475 | CH | O | Q1a | a bond | H | a bond | NH | S | CH2 | Q3a | OH |
| 476 | CH | O | Q1a | a bond | H | a bond | NH | O | CH2 | Q3a | OH |
| 477 | CH | O | Q1b | a bond | Me | a bond | NH | S | CH2 | Q3a | OH |
| 478 | CH | O | Q1b | a bond | Me | a bond | NH | O | CH2 | Q3a | OH |
| 479 | CH | O | Q1b | a bond | H | a bond | NH | S | CH2 | Q3a | OH |
| 480 | CH | O | Q1b | a bond | H | a bond | NH | O | CH2 | Q3a | OH |
| 481 | CMe | NMe | Q1a | a bond | Me | a bond | NH | S | CH2 | Q3a | OH |
| 482 | CMe | NMe | Q1a | a bond | Me | a bond | NH | O | CH2 | Q3a | OH |
| 483 | CMe | NMe | Q1a | a bond | H | a bond | NH | S | CH2 | Q3a | OH |
| 484 | CMe | NMe | Q1a | a bond | H | a bond | NH | O | CH2 | Q3a | OH |
| 485 | CMe | NMe | Q1b | a bond | Me | a bond | NH | S | CH2 | Q3a | OH |
| 486 | CMe | NMe | Q1b | a bond | Me | a bond | NH | O | CH2 | Q3a | OH |
| 487 | CMe | NMe | Q1b | a bond | H | a bond | NH | S | CH2 | Q3a | OH |
| 488 | CMe | NMe | Q1b | a bond | H | a bond | NH | O | CH2 | Q3a | OH |
| 489 | CMe | S | Q1a | a bond | Me | a bond | NH | S | CH2 | Q3a | OH |
| 490 | CMe | S | Q1a | a bond | Me | a bond | NH | O | CH2 | Q3a | OH |
| 491 | CMe | S | Q1a | a bond | H | a bond | NH | S | CH2 | Q3a | OH |
| 492 | CMe | S | Q1a | a bond | H | a bond | NH | O | CH2 | Q3a | OH |
| 493 | CMe | S | Q1b | a bond | Me | a bond | NH | S | CH2 | Q3a | OH |
| 494 | CMe | S | Q1b | a bond | Me | a bond | NH | O | CH2 | Q3a | OH |
| 495 | CMe | S | Q1b | a bond | H | a bond | NH | S | CH2 | Q3a | OH |
| 496 | CMe | S | Q1b | a bond | H | a bond | NH | O | CH2 | Q3a | OH |
| 497 | CMe | O | Q1a | a bond | Me | a bond | NH | S | CH2 | Q3a | OH |
| 498 | CMe | O | Q1a | a bond | Me | a bond | NH | O | CH2 | Q3a | OH |
| 499 | CMe | O | Q1a | a bond | H | a bond | NH | S | CH2 | Q3a | OH |
| 500 | CMe | O | Q1a | a bond | H | a bond | NH | O | CH2 | Q3a | OH |
| 501 | CMe | O | Q1b | a bond | Me | a bond | NH | S | CH2 | Q3a | OH |
| 502 | CMe | O | Q1b | a bond | Me | a bond | NH | O | CH2 | Q3a | OH |
| 503 | CMe | O | Q1b | a bond | H | a bond | NH | S | CH2 | Q3a | OH |
| 504 | CMe | O | Q1b | a bond | H | a bond | NH | O | CH2 | Q3a | OH |
| 505 | N | NMe | Q1a | a bond | Me | a bond | CH2 | S | a bond | Q3a | OH |
| 506 | N | NMe | Q1a | a bond | Me | a bond | CH2 | S | NH | Q3a | OH |
| 507 | N | NMe | Q1a | a bond | Me | a bond | CH2 | O | a bond | Q3a | OH |
| 508 | N | NMe | Q1a | a bond | Me | a bond | CH2 | O | NH | Q3a | OH |
| 509 | N | NMe | Q1a | a bond | H | a bond | CH2 | S | a bond | Q3a | OH |
| 510 | N | NMe | Q1a | a bond | H | a bond | CH2 | S | NH | Q3a | OH |
| 511 | N | NMe | Q1a | a bond | H | a bond | CH2 | O | a bond | Q3a | OH |
| 512 | N | NMe | Q1a | a bond | H | a bond | CH2 | O | NH | Q3a | OH |
| 513 | N | NMe | Q1b | a bond | Me | a bond | CH2 | S | a bond | Q3a | OH |
| 514 | N | NMe | Q1b | a bond | Me | a bond | CH2 | S | NH | Q3a | OH |
| 515 | N | NMe | Q1b | a bond | Me | a bond | CH2 | O | a bond | Q3a | OH |
| 516 | N | NMe | Q1b | a bond | Me | a bond | CH2 | O | NH | Q3a | OH |
| 517 | N | NMe | Q1b | a bond | H | a bond | CH2 | S | a bond | Q3a | OH |
| 518 | N | NMe | Q1b | a bond | H | a bond | CH2 | S | NH | Q3a | OH |
| 519 | N | NMe | Q1b | a bond | H | a bond | CH2 | O | a bond | Q3a | OH |
| 520 | N | NMe | Q1b | a bond | H | a bond | CH2 | O | NH | Q3a | OH |
| 521 | N | S | Q1a | a bond | Me | a bond | CH2 | S | a bond | Q3a | OH |
| 522 | N | S | Q1a | a bond | Me | a bond | CH2 | S | NH | Q3a | OH |
| 523 | N | S | Q1a | a bond | Me | a bond | CH2 | O | a bond | Q3a | OH |
| 524 | N | S | Q1a | a bond | Me | a bond | CH2 | O | NH | Q3a | OH |
| 525 | N | S | Q1a | a bond | H | a bond | CH2 | S | a bond | Q3a | OH |
| 526 | N | S | Q1a | a bond | H | a bond | CH2 | S | NH | Q3a | OH |
| 527 | N | S | Q1a | a bond | H | a bond | CH2 | O | a bond | Q3a | OH |
| 528 | N | S | Q1a | a bond | H | a bond | CH2 | O | NH | Q3a | OH |
| 529 | N | S | Q1b | a bond | Me | a bond | CH2 | S | a bond | Q3a | OH |
| 530 | N | S | Q1b | a bond | Me | a bond | CH2 | S | NH | Q3a | OH |
| 531 | N | S | Q1b | a bond | Me | a bond | CH2 | O | a bond | Q3a | OH |
| 532 | N | S | Q1b | a bond | Me | a bond | CH2 | O | NH | Q3a | OH |
| 533 | N | S | Q1b | a bond | H | a bond | CH2 | S | a bond | Q3a | OH |
| 534 | N | S | Q1b | a bond | H | a bond | CH2 | S | NH | Q3a | OH |
| 535 | N | S | Q1b | a bond | H | a bond | CH2 | O | a bond | Q3a | OH |
| 536 | N | S | Q1b | a bond | H | a bond | CH2 | O | NH | Q3a | OH |
| 537 | N | O | Q1a | a bond | Me | a bond | CH2 | S | a bond | Q3a | OH |
| 538 | N | O | Q1a | a bond | Me | a bond | CH2 | S | NH | Q3a | OH |
| 539 | N | O | Q1a | a bond | Me | a bond | CH2 | O | a bond | Q3a | OH |
| 540 | N | O | Q1a | a bond | Me | a bond | CH2 | O | NH | Q3a | OH |
| 541 | N | O | Q1a | a bond | H | a bond | CH2 | S | a bond | Q3a | OH |
| 542 | N | O | Q1a | a bond | H | a bond | CH2 | S | NH | Q3a | OH |
| 543 | N | O | Q1a | a bond | H | a bond | CH2 | O | a bond | Q3a | OH |
| 544 | N | O | Q1a | a bond | H | a bond | CH2 | O | NH | Q3a | OH |
| 545 | N | O | Q1b | a bond | Me | a bond | CH2 | S | a bond | Q3a | OH |
| 546 | N | O | Q1b | a bond | Me | a bond | CH2 | S | NH | Q3a | OH |

TABLE 3-continued

| No | A | B | R¹ | L¹ | R² | L² | L³ | Y | L⁴ | R³ | X |
|---|---|---|---|---|---|---|---|---|---|---|---|
| 547 | N | O | Q1b | a bond | Me | a bond | CH2 | O | a bond | Q3a | OH |
| 548 | N | O | Q1b | a bond | Me | a bond | CH2 | O | NH | Q3a | OH |
| 549 | N | O | Q1b | a bond | H | a bond | CH2 | S | a bond | Q3a | OH |
| 550 | N | O | Q1b | a bond | H | a bond | CH2 | S | NH | Q3a | OH |
| 551 | N | O | Q1b | a bond | H | a bond | CH2 | O | a bond | Q3a | OH |
| 552 | N | O | Q1b | a bond | H | a bond | CH2 | O | NH | Q3a | OH |
| 553 | CH | NMe | Q1a | a bond | Me | a bond | CH2 | S | a bond | Q3a | OH |
| 554 | CH | NMe | Q1a | a bond | Me | a bond | CH2 | S | NH | Q3a | OH |
| 555 | CH | NMe | Q1a | a bond | Me | a bond | CH2 | O | a bond | Q3a | OH |
| 556 | CH | NMe | Q1a | a bond | Me | a bond | CH2 | O | NH | Q3a | OH |
| 557 | CH | NMe | Q1a | a bond | H | a bond | CH2 | S | a bond | Q3a | OH |
| 558 | CH | NMe | Q1a | a bond | H | a bond | CH2 | S | NH | Q3a | OH |
| 559 | CH | NMe | Q1a | a bond | H | a bond | CH2 | O | a bond | Q3a | OH |
| 560 | CH | NMe | Q1a | a bond | H | a bond | CH2 | O | NH | Q3a | OH |
| 561 | CH | NMe | Q1b | a bond | Me | a bond | CH2 | S | a bond | Q3a | OH |
| 562 | CH | NMe | Q1b | a bond | Me | a bond | CH2 | S | NH | Q3a | OH |
| 563 | CH | NMe | Q1b | a bond | Me | a bond | CH2 | O | a bond | Q3a | OH |
| 564 | CH | NMe | Q1b | a bond | Me | a bond | CH2 | O | NH | Q3a | OH |
| 565 | CH | NMe | Q1b | a bond | H | a bond | CH2 | S | a bond | Q3a | OH |
| 566 | CH | NMe | Q1b | a bond | H | a bond | CH2 | S | NH | Q3a | OH |
| 567 | CH | NMe | Q1b | a bond | H | a bond | CH2 | O | a bond | Q3a | OH |
| 568 | CH | NMe | Q1b | a bond | H | a bond | CH2 | O | NH | Q3a | OH |
| 569 | CH | S | Q1a | a bond | Me | a bond | CH2 | S | a bond | Q3a | OH |
| 570 | CH | S | Q1a | a bond | Me | a bond | CH2 | S | NH | Q3a | OH |
| 571 | CH | S | Q1a | a bond | Me | a bond | CH2 | O | a bond | Q3a | OH |
| 572 | CH | S | Q1a | a bond | Me | a bond | CH2 | O | NH | Q3a | OH |
| 573 | CH | S | Q1a | a bond | H | a bond | CH2 | S | a bond | Q3a | OH |
| 574 | CH | S | Q1a | a bond | H | a bond | CH2 | S | NH | Q3a | OH |
| 575 | CH | S | Q1a | a bond | H | a bond | CH2 | O | a bond | Q3a | OH |
| 576 | CH | S | Q1a | a bond | H | a bond | CH2 | O | NH | Q3a | OH |
| 577 | CH | S | Q1b | a bond | Me | a bond | CH2 | S | a bond | Q3a | OH |
| 578 | CH | S | Q1b | a bond | Me | a bond | CH2 | S | NH | Q3a | OH |
| 579 | CH | S | Q1b | a bond | Me | a bond | CH2 | O | a bond | Q3a | OH |
| 580 | CH | S | Q1b | a bond | Me | a bond | CH2 | O | NH | Q3a | OH |
| 581 | CH | S | Q1b | a bond | H | a bond | CH2 | S | a bond | Q3a | OH |
| 582 | CH | S | Q1b | a bond | H | a bond | CH2 | S | NH | Q3a | OH |
| 583 | CH | S | Q1b | a bond | H | a bond | CH2 | O | a bond | Q3a | OH |
| 584 | CH | S | Q1b | a bond | H | a bond | CH2 | O | NH | Q3a | OH |
| 585 | CH | O | Q1a | a bond | Me | a bond | CH2 | S | a bond | Q3a | OH |
| 586 | CH | O | Q1a | a bond | Me | a bond | CH2 | S | NH | Q3a | OH |
| 587 | CH | O | Q1a | a bond | Me | a bond | CH2 | O | a bond | Q3a | OH |
| 588 | CH | O | Q1a | a bond | Me | a bond | CH2 | O | NH | Q3a | OH |
| 589 | CH | O | Q1a | a bond | H | a bond | CH2 | S | a bond | Q3a | OH |
| 590 | CH | O | Q1a | a bond | H | a bond | CH2 | S | NH | Q3a | OH |
| 591 | CH | O | Q1a | a bond | H | a bond | CH2 | O | a bond | Q3a | OH |
| 592 | CH | O | Q1a | a bond | H | a bond | CH2 | O | NH | Q3a | OH |
| 593 | CH | O | Q1b | a bond | Me | a bond | CH2 | S | a bond | Q3a | OH |
| 594 | CH | O | Q1b | a bond | Me | a bond | CH2 | S | NH | Q3a | OH |
| 595 | CH | O | Q1b | a bond | Me | a bond | CH2 | O | a bond | Q3a | OH |
| 596 | CH | O | Q1b | a bond | Me | a bond | CH2 | O | NH | Q3a | OH |
| 597 | CH | O | Q1b | a bond | H | a bond | CH2 | S | a bond | Q3a | OH |
| 598 | CH | O | Q1b | a bond | H | a bond | CH2 | S | NH | Q3a | OH |
| 599 | CH | O | Q1b | a bond | H | a bond | CH2 | O | a bond | Q3a | OH |
| 600 | CH | O | Q1b | a bond | H | a bond | CH2 | O | NH | Q3a | OH |
| 601 | CMe | NMe | Q1a | a bond | Me | a bond | CH2 | S | a bond | Q3a | OH |
| 602 | CMe | NMe | Q1a | a bond | Me | a bond | CH2 | S | NH | Q3a | OH |
| 603 | CMe | NMe | Q1a | a bond | Me | a bond | CH2 | O | a bond | Q3a | OH |
| 604 | CMe | NMe | Q1a | a bond | Me | a bond | CH2 | O | NH | Q3a | OH |
| 605 | CMe | NMe | Q1a | a bond | H | a bond | CH2 | S | a bond | Q3a | OH |
| 606 | CMe | NMe | Q1a | a bond | H | a bond | CH2 | S | NH | Q3a | OH |
| 607 | CMe | NMe | Q1a | a bond | H | a bond | CH2 | O | a bond | Q3a | OH |
| 608 | CMe | NMe | Q1a | a bond | H | a bond | CH2 | O | NH | Q3a | OH |
| 609 | CMe | NMe | Q1b | a bond | Me | a bond | CH2 | S | a bond | Q3a | OH |
| 610 | CMe | NMe | Q1b | a bond | Me | a bond | CH2 | S | NH | Q3a | OH |
| 611 | CMe | NMe | Q1b | a bond | Me | a bond | CH2 | O | a bond | Q3a | OH |
| 612 | CMe | NMe | Q1b | a bond | Me | a bond | CH2 | O | NH | Q3a | OH |
| 613 | CMe | NMe | Q1b | a bond | H | a bond | CH2 | S | a bond | Q3a | OH |
| 614 | CMe | NMe | Q1b | a bond | H | a bond | CH2 | S | NH | Q3a | OH |
| 615 | CMe | NMe | Q1b | a bond | H | a bond | CH2 | O | a bond | Q3a | OH |
| 616 | CMe | NMe | Q1b | a bond | H | a bond | CH2 | O | NH | Q3a | OH |
| 617 | CMe | S | Q1a | a bond | Me | a bond | CH2 | S | a bond | Q3a | OH |
| 618 | CMe | S | Q1a | a bond | Me | a bond | CH2 | S | NH | Q3a | OH |
| 619 | CMe | S | Q1a | a bond | Me | a bond | CH2 | O | a bond | Q3a | OH |
| 620 | CMe | S | Q1a | a bond | Me | a bond | CH2 | O | NH | Q3a | OH |
| 621 | CMe | S | Q1a | a bond | H | a bond | CH2 | S | a bond | Q3a | OH |
| 622 | CMe | S | Q1a | a bond | H | a bond | CH2 | S | NH | Q3a | OH |
| 623 | CMe | S | Q1a | a bond | H | a bond | CH2 | O | a bond | Q3a | OH |
| 624 | CMe | S | Q1a | a bond | H | a bond | CH2 | O | NH | Q3a | OH |

TABLE 3-continued

| No | A | B | R¹ | L¹ | R² | L² | L³ | Y | L⁴ | R³ | X |
|---|---|---|---|---|---|---|---|---|---|---|---|
| 625 | CMe | S | Q1b | a bond | Me | a bond | CH2 | S | a bond | Q3a | OH |
| 626 | CMe | S | Q1b | a bond | Me | a bond | CH2 | S | NH | Q3a | OH |
| 627 | CMe | S | Q1b | a bond | Me | a bond | CH2 | O | a bond | Q3a | OH |
| 628 | CMe | S | Q1b | a bond | Me | a bond | CH2 | O | NH | Q3a | OH |
| 629 | CMe | S | Q1b | a bond | H | a bond | CH2 | S | a bond | Q3a | OH |
| 630 | CMe | S | Q1b | a bond | H | a bond | CH2 | S | NH | Q3a | OH |
| 631 | CMe | S | Q1b | a bond | H | a bond | CH2 | O | a bond | Q3a | OH |
| 632 | CMe | S | Q1b | a bond | H | a bond | CH2 | O | NH | Q3a | OH |
| 633 | CMe | O | Q1a | a bond | Me | a bond | CH2 | S | a bond | Q3a | OH |
| 634 | CMe | O | Q1a | a bond | Me | a bond | CH2 | S | NH | Q3a | OH |
| 635 | CMe | O | Q1a | a bond | Me | a bond | CH2 | O | a bond | Q3a | OH |
| 636 | CMe | O | Q1a | a bond | Me | a bond | CH2 | O | NH | Q3a | OH |
| 637 | CMe | O | Q1a | a bond | H | a bond | CH2 | S | a bond | Q3a | OH |
| 638 | CMe | O | Q1a | a bond | H | a bond | CH2 | S | NH | Q3a | OH |
| 639 | CMe | O | Q1a | a bond | H | a bond | CH2 | O | a bond | Q3a | OH |
| 640 | CMe | O | Q1a | a bond | H | a bond | CH2 | O | NH | Q3a | OH |
| 641 | CMe | O | Q1b | a bond | Me | a bond | CH2 | S | a bond | Q3a | OH |
| 642 | CMe | O | Q1b | a bond | Me | a bond | CH2 | S | NH | Q3a | OH |
| 643 | CMe | O | Q1b | a bond | Me | a bond | CH2 | O | a bond | Q3a | OH |
| 644 | CMe | O | Q1b | a bond | Me | a bond | CH2 | O | NH | Q3a | OH |
| 645 | CMe | O | Q1b | a bond | H | a bond | CH2 | S | a bond | Q3a | OH |
| 646 | CMe | O | Q1b | a bond | H | a bond | CH2 | S | NH | Q3a | OH |
| 647 | CMe | O | Q1b | a bond | H | a bond | CH2 | O | a bond | Q3a | OH |
| 648 | CMe | O | Q1b | a bond | H | a bond | CH2 | O | NH | Q3a | OH |
| 649 | CMe | NH | Q1a | NH | Me | a bond | NH | S | NH | Q3a | OH |
| 650 | CMe | NH | Q1a | NH | Me | a bond | NH | S | a bond | Q3a | OH |
| 651 | CMe | NH | Q1a | NH | Me | a bond | NH | O | NH | Q3a | OH |
| 652 | CMe | NH | Q1a | NH | Me | a bond | NH | O | a bond | Q3a | OH |
| 653 | CMe | NH | Q1a | NH | H | a bond | NH | S | NH | Q3a | OH |
| 654 | CMe | NH | Q1a | NH | H | a bond | NH | S | a bond | Q3a | OH |
| 655 | CMe | NH | Q1a | NH | H | a bond | NH | O | NH | Q3a | OH |
| 656 | CMe | NH | Q1a | NH | H | a bond | NH | O | a bond | Q3a | OH |
| 657 | CMe | NH | Q1b | NH | Me | a bond | NH | S | NH | Q3a | OH |
| 658 | CMe | NH | Q1b | NH | Me | a bond | NH | S | a bond | Q3a | OH |
| 659 | CMe | NH | Q1b | NH | Me | a bond | NH | O | NH | Q3a | OH |
| 660 | CMe | NH | Q1b | NH | Me | a bond | NH | O | a bond | Q3a | OH |
| 661 | CMe | NH | Q1b | NH | H | a bond | NH | S | NH | Q3a | OH |
| 662 | CMe | NH | Q1b | NH | H | a bond | NH | S | a bond | Q3a | OH |
| 663 | CMe | NH | Q1b | NH | H | a bond | NH | O | NH | Q3a | OH |
| 664 | CMe | NH | Q1b | NH | H | a bond | NH | O | a bond | Q3a | OH |
| 665 | CMe | NH | Q1a | O | Me | a bond | NH | S | NH | Q3a | OH |
| 666 | CMe | NH | Q1a | O | Me | a bond | NH | S | a bond | Q3a | OH |
| 667 | CMe | NH | Q1a | O | Me | a bond | NH | O | NH | Q3a | OH |
| 668 | CMe | NH | Q1a | O | Me | a bond | NH | O | a bond | Q3a | QH |
| 669 | CMe | NH | Q1a | O | H | a bond | NH | S | NH | Q3a | OH |
| 670 | CMe | NH | Q1a | O | H | a bond | NH | S | a bond | Q3a | OH |
| 671 | CMe | NH | Q1a | O | H | a bond | NH | O | NH | Q3a | OH |
| 672 | CMe | NH | Q1a | O | H | a bond | NH | O | a bond | Q3a | OH |
| 673 | CMe | NH | Q1b | O | Me | a bond | NH | S | NH | Q3a | OH |
| 674 | CMe | NH | Q1b | O | Me | a bond | NH | S | a bond | Q3a | OH |
| 675 | CMe | NH | Q1b | O | Me | a bond | NH | O | NH | Q3a | OH |
| 676 | CMe | NH | Q1b | O | Me | a bond | NH | O | a bond | Q3a | OH |
| 677 | CMe | NH | Q1b | O | H | a bond | NH | S | NH | Q3a | OH |
| 678 | CMe | NH | Q1b | O | H | a bond | NH | S | a bond | Q3a | OH |
| 679 | CMe | NH | Q1b | O | H | a bond | NH | O | NH | Q3a | OH |
| 680 | CMe | NH | Q1b | O | H | a bond | NH | O | a bond | Q3a | OH |
| 681 | CMe | NH | Q1a | CH2 | Me | a bond | NH | S | NH | Q3a | OH |
| 682 | CMe | NH | Q1a | CH2 | Me | a bond | NH | S | a bond | Q3a | OH |
| 683 | CMe | NH | Q1a | CH2 | Me | a bond | NH | O | NH | Q3a | OH |
| 684 | CMe | NH | Q1a | CH2 | Me | a bond | NH | O | a bond | Q3a | OH |
| 685 | CMe | NH | Q1a | CH2 | H | a bond | NH | S | NH | Q3a | OH |
| 686 | CMe | NH | Q1a | CH2 | H | a bond | NH | S | a bond | Q3a | OH |
| 687 | CMe | NH | Q1a | CH2 | H | a bond | NH | O | NH | Q3a | OH |
| 688 | CMe | NH | Q1a | CH2 | H | a bond | NH | O | a bond | Q3a | OH |
| 689 | CMe | NH | Q1b | CH2 | Me | a bond | NH | S | NH | Q3a | OH |
| 690 | CMe | NH | Q1b | CH2 | Me | a bond | NH | S | a bond | Q3a | OH |
| 691 | CMe | NH | Q1b | CH2 | Me | a bond | NH | O | NH | Q3a | OH |
| 692 | CMe | NH | Q1b | CH2 | Me | a bond | NH | O | a bond | Q3a | OH |
| 693 | CMe | NH | Q1b | CH2 | H | a bond | NH | S | NH | Q3a | OH |
| 694 | CMe | NH | Q1b | CH2 | H | a bond | NH | S | a bond | Q3a | OH |
| 695 | CMe | NH | Q1b | CH2 | H | a bond | NH | O | NH | Q3a | OH |
| 696 | CMe | NH | Q1b | CH2 | H | a bond | NH | O | a bond | Q3a | OH |
| 697 | CMe | NH | Q1a | a bond | Me | a bond | NH | S | CH2 | Q3a | OH |
| 698 | CMe | NH | Q1a | a bond | Me | a bond | NH | O | CH2 | Q3a | OH |
| 699 | CMe | NH | Q1a | a bond | H | a bond | NH | S | CH2 | Q3a | OH |
| 700 | CMe | NH | Q1a | a bond | H | a bond | NH | O | CH2 | Q3a | OH |
| 701 | CMe | NH | Q1b | a bond | Me | a bond | NH | S | CH2 | Q3a | OH |
| 702 | CMe | NH | Q1b | a bond | Me | a bond | NH | O | CH2 | Q3a | OH |

TABLE 3-continued

| No | A | B | R¹ | L¹ | R² | L² | L³ | Y | L⁴ | R³ | X |
|---|---|---|---|---|---|---|---|---|---|---|---|
| 703 | CMe | NH | Q1b | a bond | H | a bond | NH | S | CH2 | Q3a | OH |
| 704 | CMe | NH | Q1b | a bond | H | a bond | NH | O | CH2 | Q3a | OH |
| 705 | CMe | NH | Q1a | a bond | Me | a bond | CH2 | S | a bond | Q3a | OH |
| 706 | CMe | NH | Q1a | a bond | Me | a bond | CH2 | S | NH | Q3a | OH |
| 707 | CMe | NH | Q1a | a bond | Me | a bond | CH2 | O | a bond | Q3a | OH |
| 708 | CMe | NH | Q1a | a bond | Me | a bond | CH2 | O | NH | Q3a | OH |
| 709 | CMe | NH | Q1a | a bond | H | a bond | CH2 | S | a bond | Q3a | OH |
| 710 | CMe | NH | Q1a | a bond | H | a bond | CH2 | S | NH | Q3a | OH |
| 711 | CMe | NH | Q1a | a bond | H | a bond | CH2 | O | a bond | Q3a | OH |
| 712 | CMe | NH | Q1a | a bond | H | a bond | CH2 | O | NH | Q3a | OH |
| 713 | CMe | NH | Q1b | a bond | Me | a bond | CH2 | S | a bond | Q3a | OH |
| 714 | CMe | NH | Q1b | a bond | Me | a bond | CH2 | S | NH | Q3a | OH |
| 715 | CMe | NH | Q1b | a bond | Me | a bond | CH2 | O | a bond | Q3a | OH |
| 716 | CMe | NH | Q1b | a bond | Me | a bond | CH2 | O | NH | Q3a | OH |
| 717 | CMe | NH | Q1b | a bond | H | a bond | CH2 | S | a bond | Q3a | OH |
| 718 | CMe | NH | Q1b | a bond | H | a bond | CH2 | S | NH | Q3a | OH |
| 719 | CMe | NH | Q1b | a bond | H | a bond | CH2 | O | a bond | Q3a | OH |
| 720 | CMe | NH | Q1b | a bond | H | a bond | CH2 | O | NH | Q3a | OH |

63) The compounds wherein A, B, R¹, L¹, R², L², L³, Y, L⁴, R³ and X are any of the following combinations in Table 3, tautomers, prodrugs or pharmaceutically acceptable salts of the compounds or solvates thereof (provided that in the case of 63), Q1a, Q1b and Q3a in Table 3 denote the following substituents).

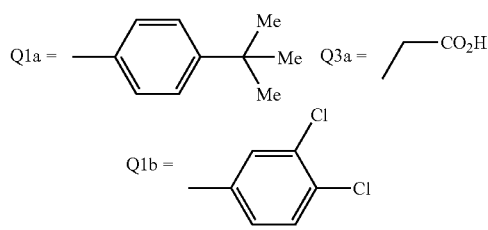

64) The compounds wherein A, B, R¹, L¹, R², L², L³, Y, L⁴, R³ and X are any of the following combinations in Table 2, tautomers, prodrugs or pharmaceutically acceptable salts of the compounds or solvates thereof (provided that in the case of 64), Q1a, Q1b, Q1c, Q1i, Q1j, T3a, T3b, T3c, T3d, T3e, Q3e, T3f, T3g, T3h, T3i and T3j in Table 2 denote the following substituents).

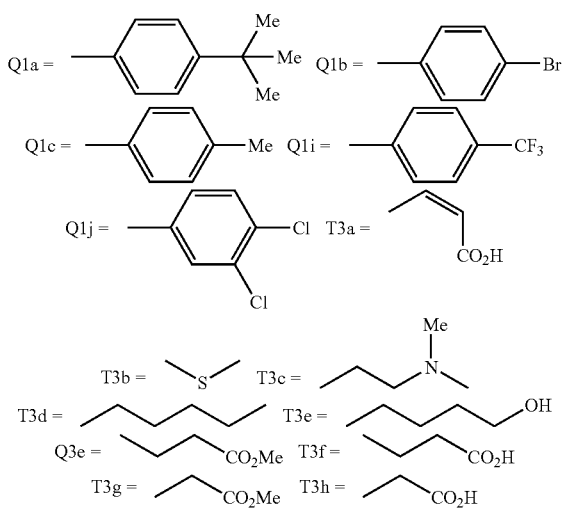

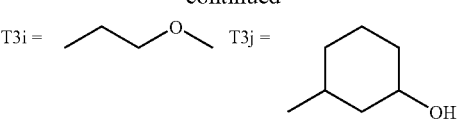

65) The compounds wherein A, B, R¹, L¹, R², L², L³, Y, L⁴, R³ and X are any of the following combinations in Table 1, tautomers, prodrugs or pharmaceutically acceptable salts of the compounds or solvates thereof (provided that in the case of 65), Q1a, Q1b, Q1c, Q1d, Q1e, Q1f, Q1g, Q1h, Q1i, Q1j, Q1k, Q1l, Q1m, Q1n, Q1k', Q1l', Q1m', Q1n', Q3a, Q3b, Q3c, Q3d, Q3e, Q3f, Q3g and Q3h in Table 1 denote the following substituents).

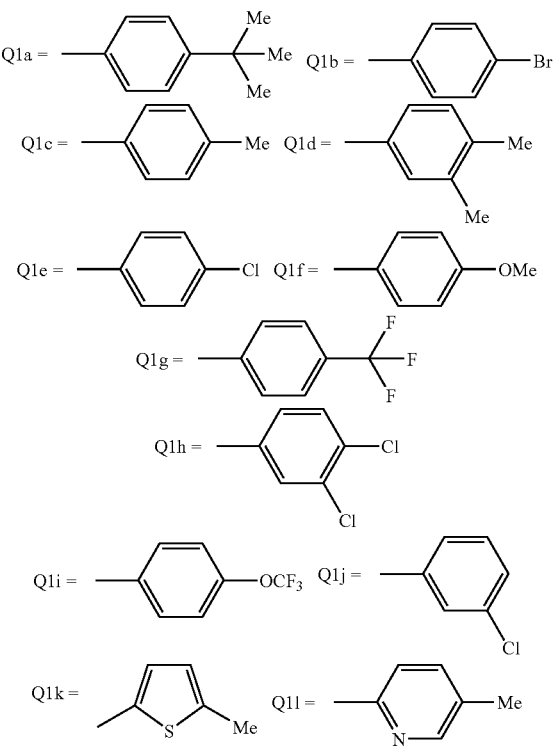

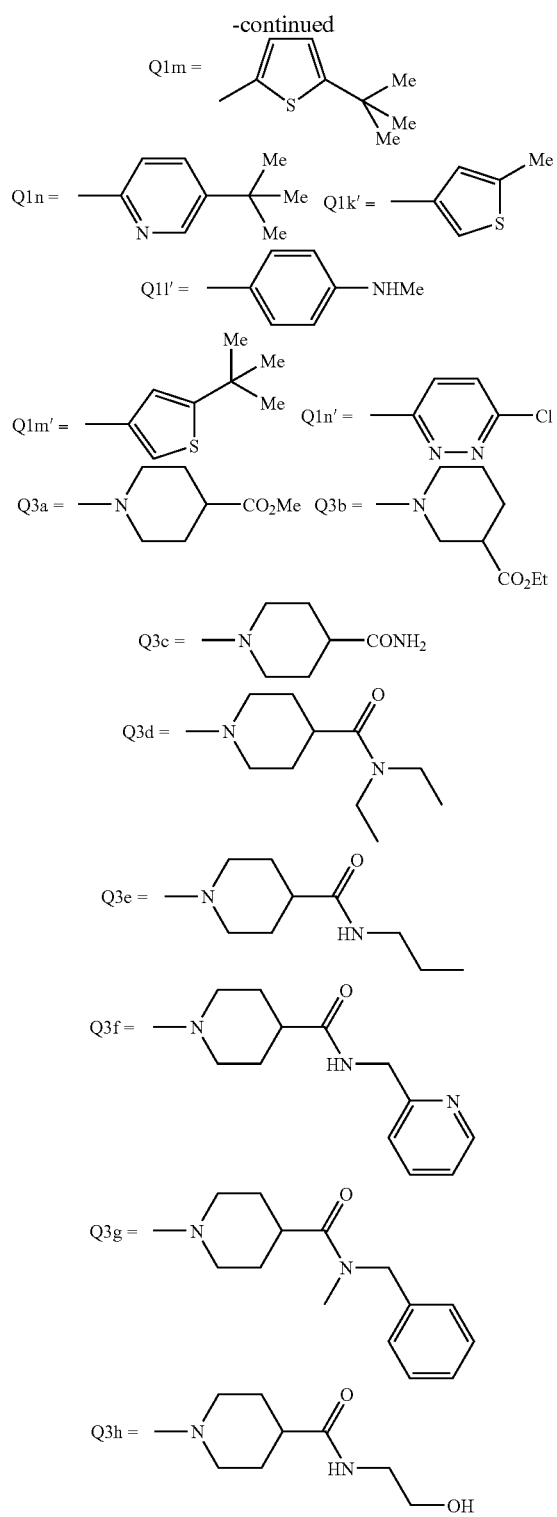
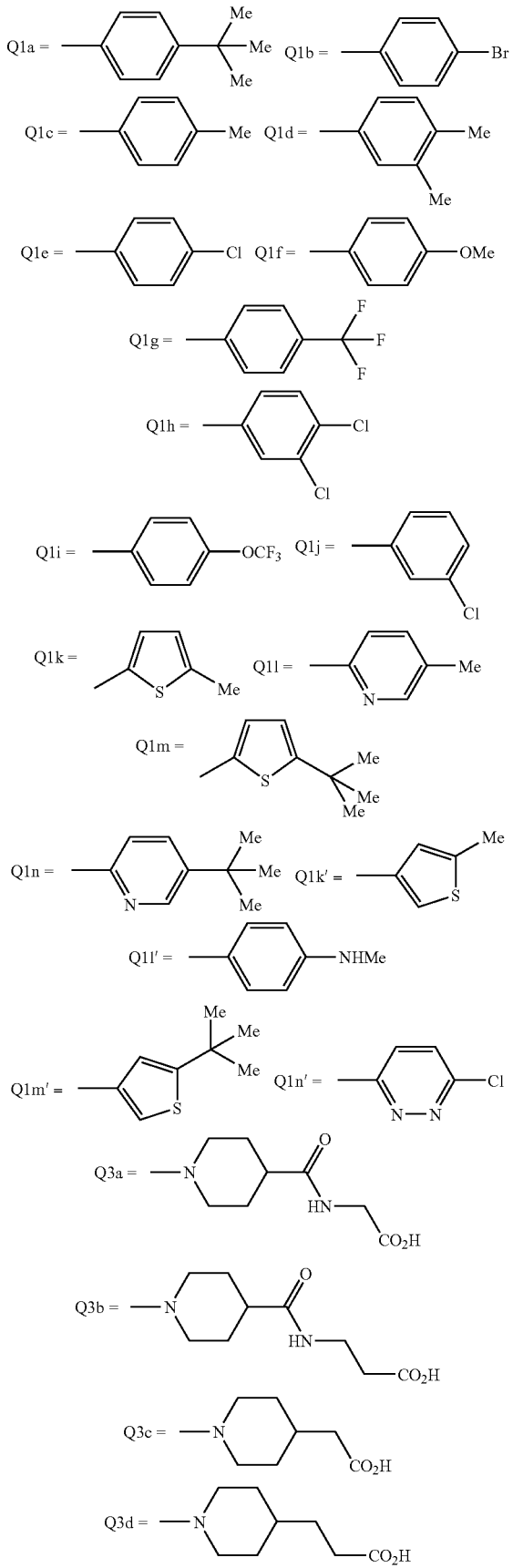
66) The compounds wherein A, B, $R^1$, $L^1$, $R^2$, $L^2$, $L^3$, Y, $L^4$, $R^3$ and X are any of the following combinations in Table 1, tautomers, prodrugs or pharmaceutically acceptable salts of the compounds or solvates thereof (provided that in the case of 66), Q1a, Q1b, Q1c, Q1d, Q1e, Q1f, Q1g, Q1h, Q1i, Q1j, Q1k, Q1l, Q1m, Q1n, Q1k', Q1l', Q1m', Q1n', Q3a, Q3b, Q3c, Q3d, Q3e, Q3f, Q3g and Q3h in Table 1 denote the following substituents).

-continued

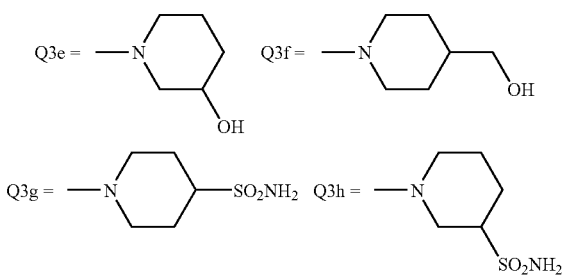

67) The compounds wherein A, B, $R^1$, $L^1$, $R^2$, $L^2$, $L^3$, Y, $L^4$, $R^3$ and X are any of the following combinations in Table 1, tautomers, prodrugs or pharmaceutically acceptable salts of the compounds or solvates thereof (provided that in the case of 67), Q1a, Q1b, Q1c, Q1d, Q1e, Q1f, Q1g, Q1h, Q1i, Q1j, Q1k, Q1l, Q1m, Q1n, Q1k', Q1l', Q1m', Q1n', Q3a, Q3b, Q3c, Q3d, Q3e, Q3f, Q3g and Q3h in Table 1 denote the following substituents).

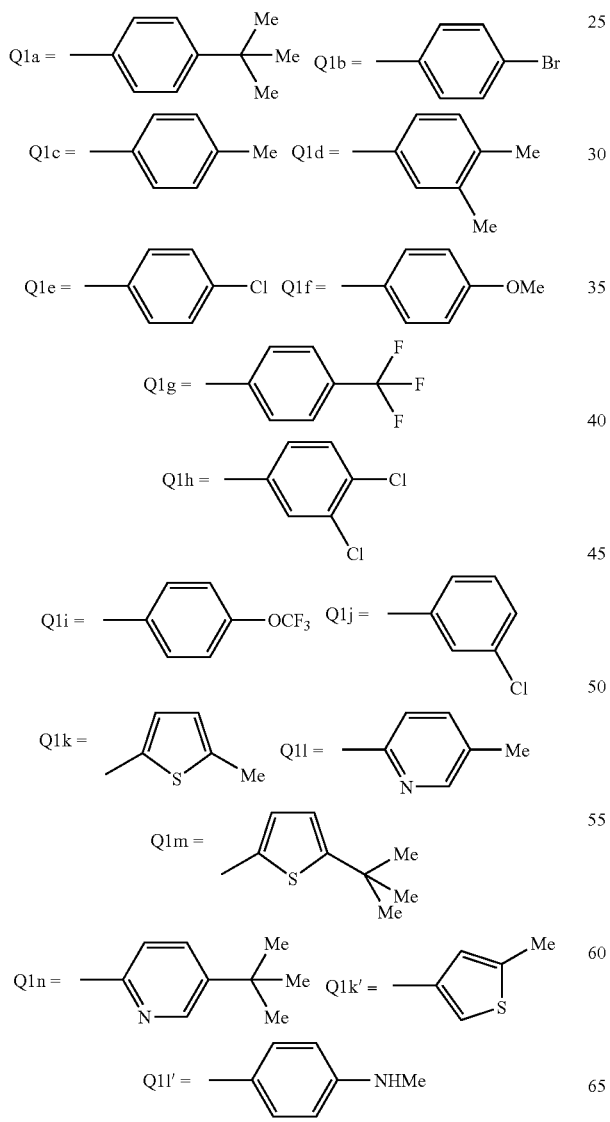

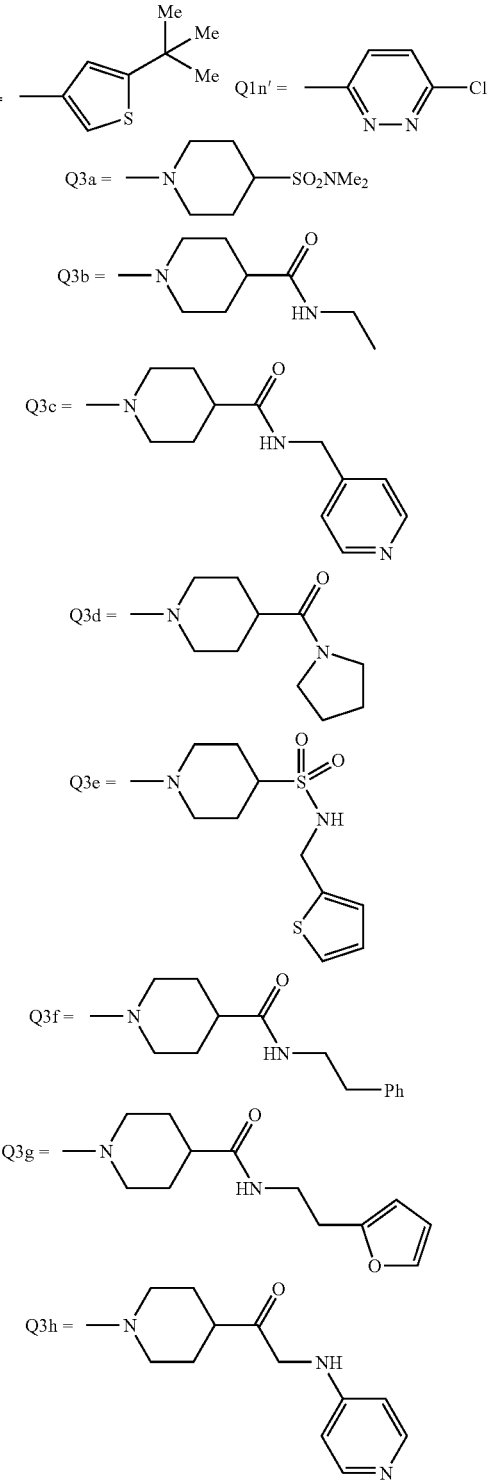

68) The compounds wherein A, B, $R^1$, $L^1$, $R^2$, $L^2$, $L^3$, Y, $L^4$, $R^3$ and X are any of the following combinations in Table 1, tautomers, prodrugs or pharmaceutically acceptable salts of the compounds or solvates thereof (provided that in the case of 68), Q1a, Q1b, Q1c, Q1d, Q1e, Q1f, Q1g, Q1h, Q1i, Q1j, Q1k, Q1l, Q1m, Q1n, Q1k', Q1l', Q1m', Q1n', Q3a, Q3b, Q3c, Q3d, Q3e, Q3f, Q3g and Q3h in Table 1 denote the following substituents).

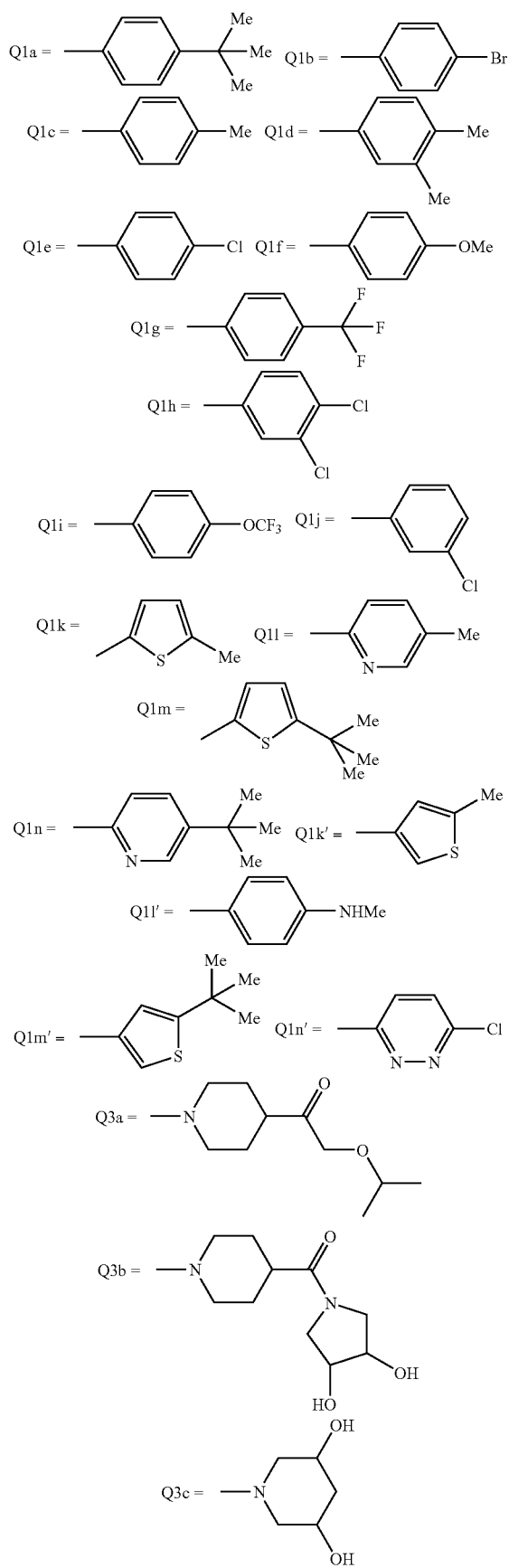
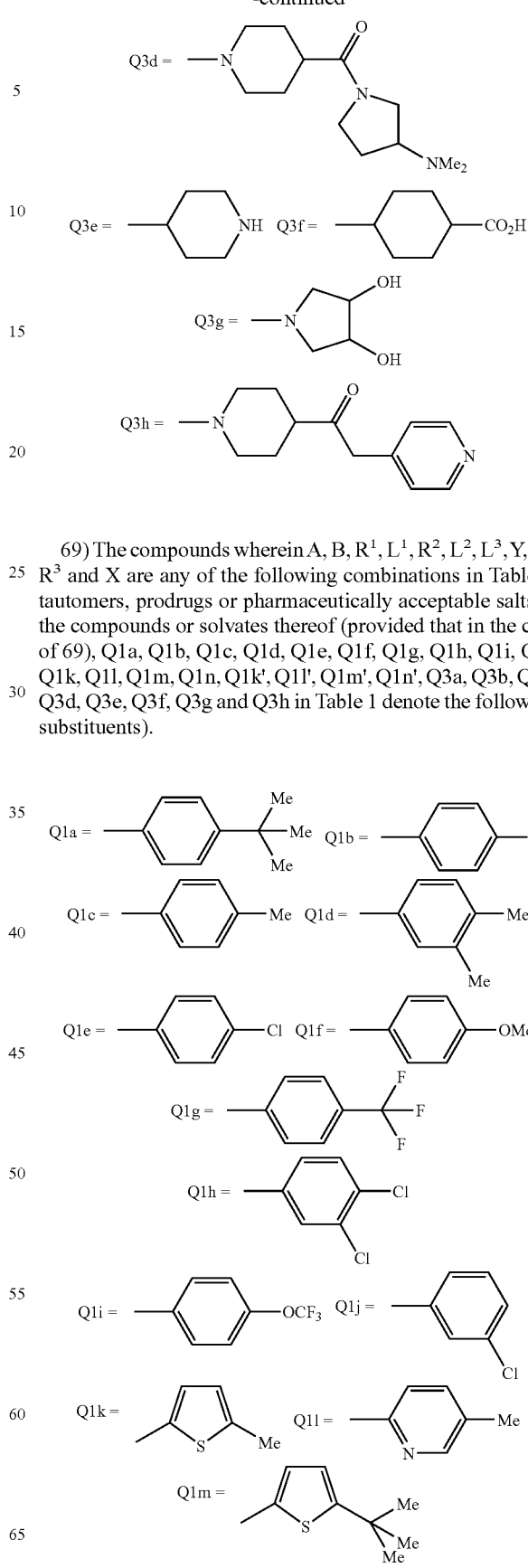
69) The compounds wherein A, B, $R^1$, $L^1$, $R^2$, $L^2$, $L^3$, Y, $L^4$, $R^3$ and X are any of the following combinations in Table 1, tautomers, prodrugs or pharmaceutically acceptable salts of the compounds or solvates thereof (provided that in the case of 69), Q1a, Q1b, Q1c, Q1d, Q1e, Q1f, Q1g, Q1h, Q1i, Q1j, Q1k, Q1l, Q1m, Q1n, Q1k', Q1l', Q1m', Q1n', Q3a, Q3b, Q3c, Q3d, Q3e, Q3f, Q3g and Q3h in Table 1 denote the following substituents).

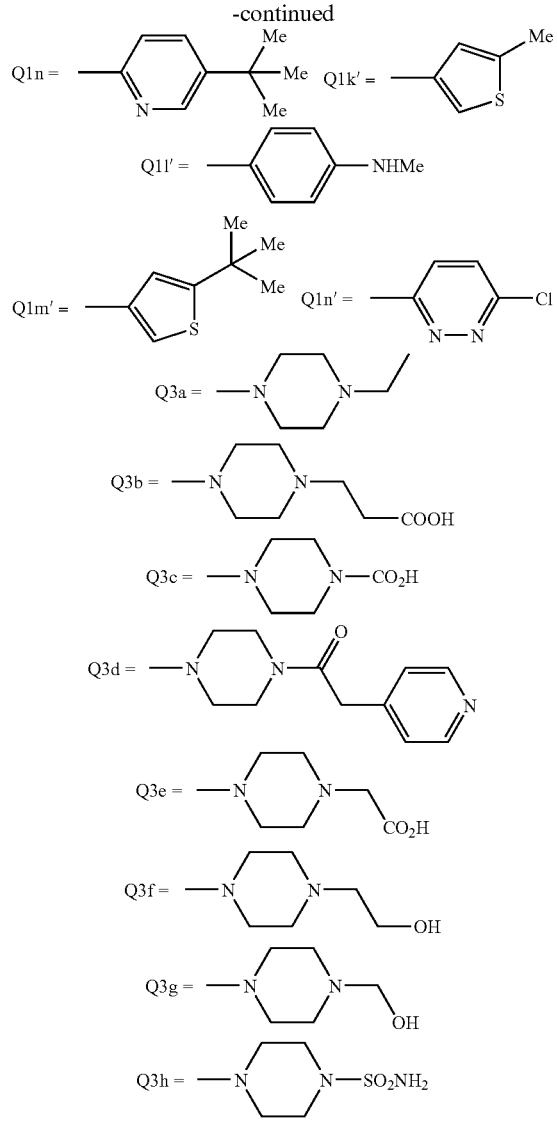
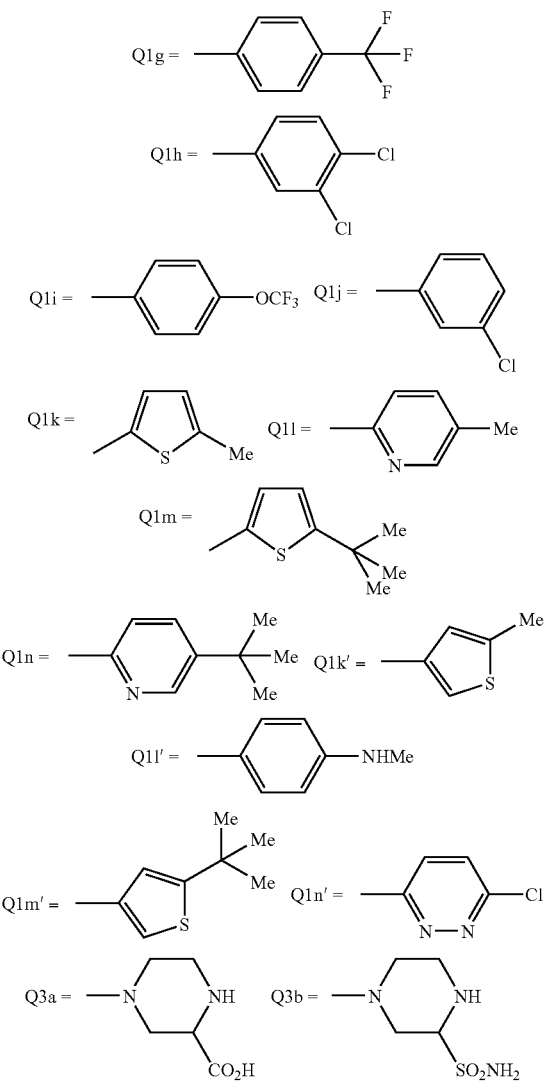
70) The compounds wherein A, B, $R^1$, $L^1$, $R^2$, $L^2$, $L^3$, Y, $L^4$, $R^3$ and X are any of the following combinations in Table 1, tautomers, prodrugs or pharmaceutically acceptable salts of the compounds or solvates thereof (provided that in the case of 70), Q1a, Q1b, Q1c, Q1d, Q1e, Q1f, Q1g, Q1h, Q1i, Q1j, Q1k, Q1l, Q1m, Q1n, Q1k', Q1l', Q1m', Q1n', Q3a, Q3b, Q3c, Q3d, Q3e, Q3f, Q3g and Q3h in Table 1 denote the following substituents).
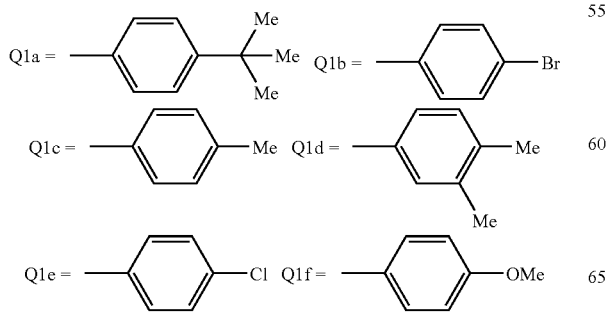

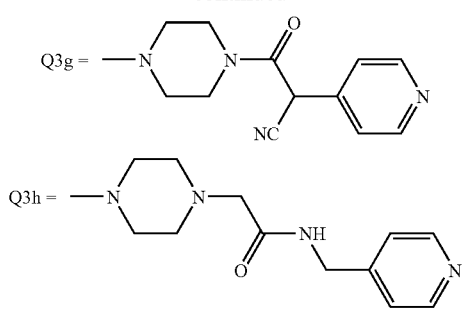

71) The compounds wherein A, B, $R^1$, $L^1$, $R^2$, $L^2$, $L^3$, Y, $L^4$, $R^3$ and X are any of the following combinations in Table 1, tautomers, prodrugs or pharmaceutically acceptable salts of the compounds or solvates thereof (provided that in the case of 71), Q1a, Q1b, Q1c, Q1d, Q1e, Q1f, Q1g, Q1h, Q1i, Q1j, Q1k, Q1l, Q1m, Q1n, Q1k', Q1l', Q1m', Q1n', Q3a, Q3b, Q3c, Q3d, Q3e, Q3f, Q3g and Q3h in Table 1 denote the following substituents).

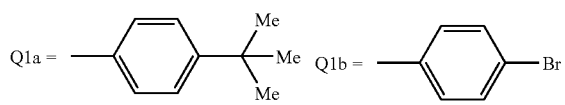
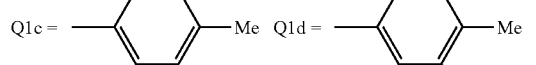
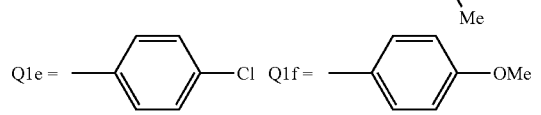
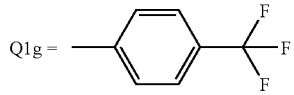
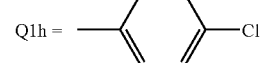
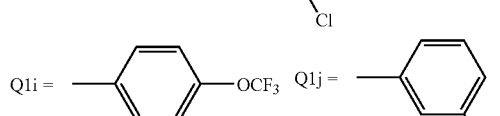
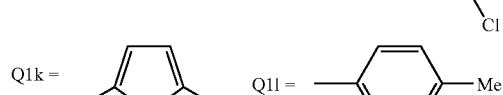
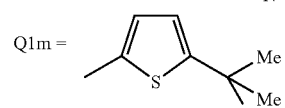
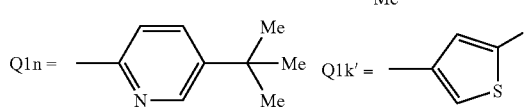
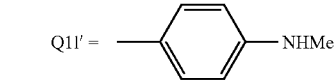

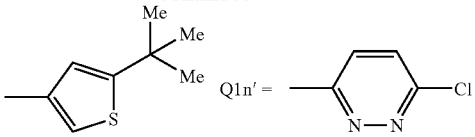
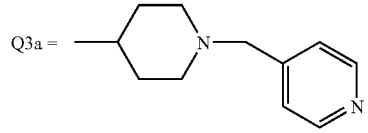
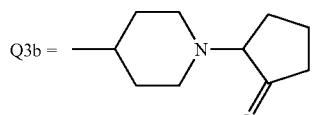
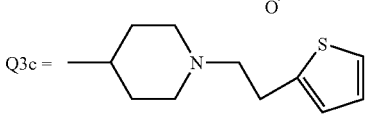
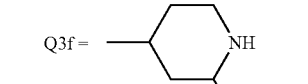
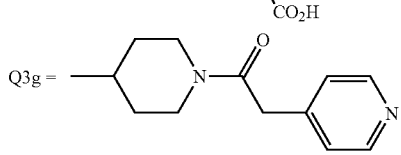
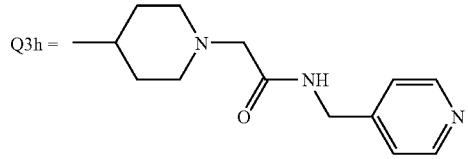

72) The compounds wherein A, B, $R^1$, $L^1$, $R^2$, $L^2$, $L^3$, Y, $L^4$, $R^3$ and X are any of the following combinations in Table 1, tautomers, prodrugs or pharmaceutically acceptable salts of the compounds or solvates thereof (provided that in the case of 72), Q1a, Q1b, Q1c, Q1d, Q1e, Q1f, Q1g, Q1h, Q1i, Q1j, Q1k, Q1l, Q1m, Q1n, Q1k', Q1l', Q1m', Q1n', Q3a, Q3b, Q3c, Q3d, Q3e, Q3f, Q3g and Q3h in Table 1 denote the following substituents).

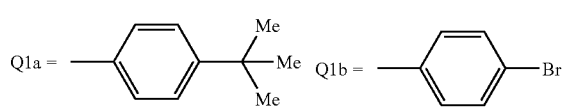
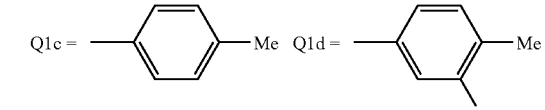
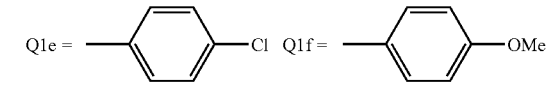

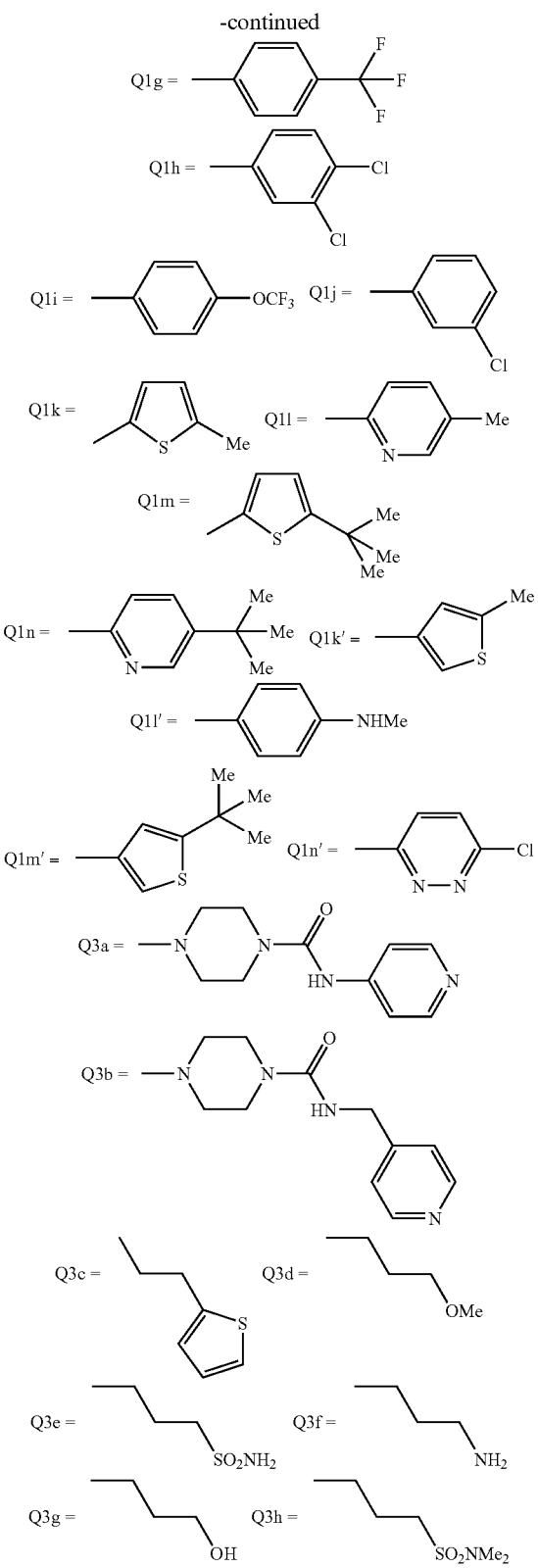
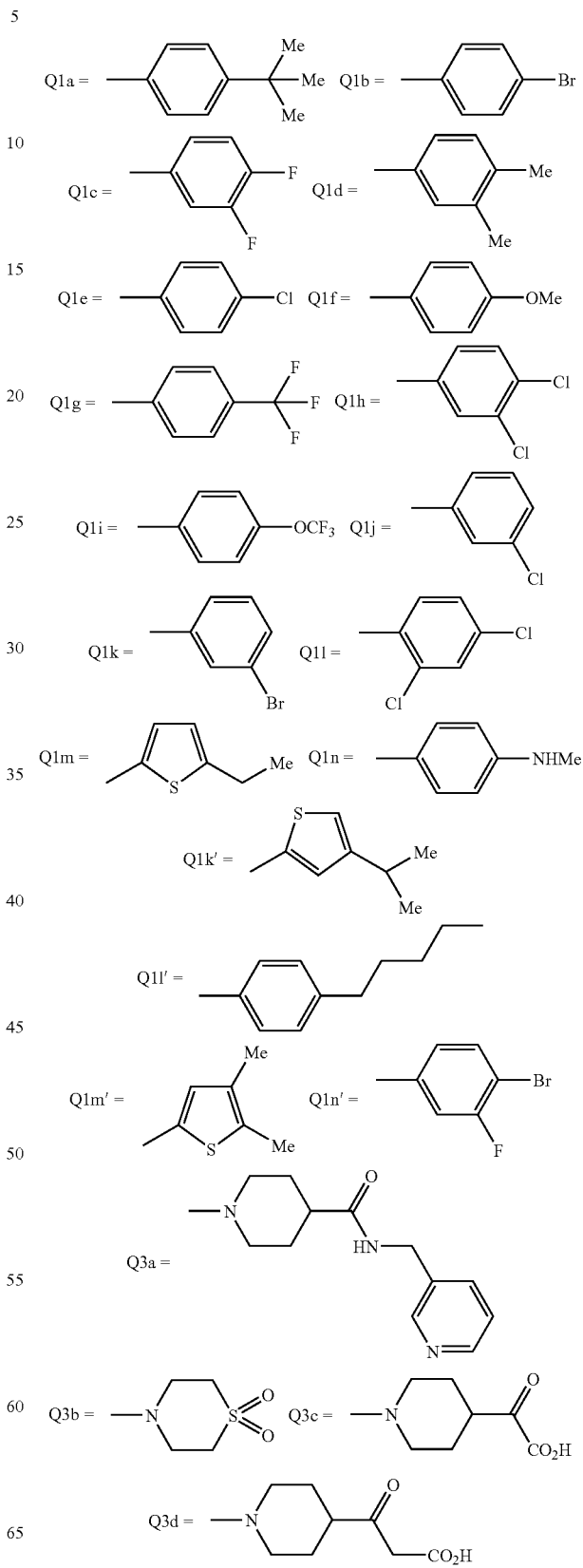
Q1k, Q1l, Q1m, Q1n, Q1k', Q1l', Q1m', Q1n', Q3a, Q3b, Q3c, Q3d, Q3e, Q3f, Q3g and Q3h in Table 1 denote the following substituents).
73) The compounds wherein A, B, R$^1$, L$^1$, R$^2$, L$^2$, L$^3$, Y, L$^4$, R$^3$ and X are any of the following combinations in Table 1, tautomers, prodrugs or pharmaceutically acceptable salts of the compounds or solvates thereof (provided that in the case of 73), Q1a, Q1b, Q1c, Q1d, Q1e, Q1f, Q1g, Q1h, Q1i, Q1j, -continued

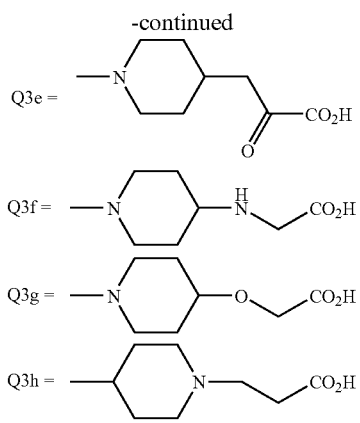

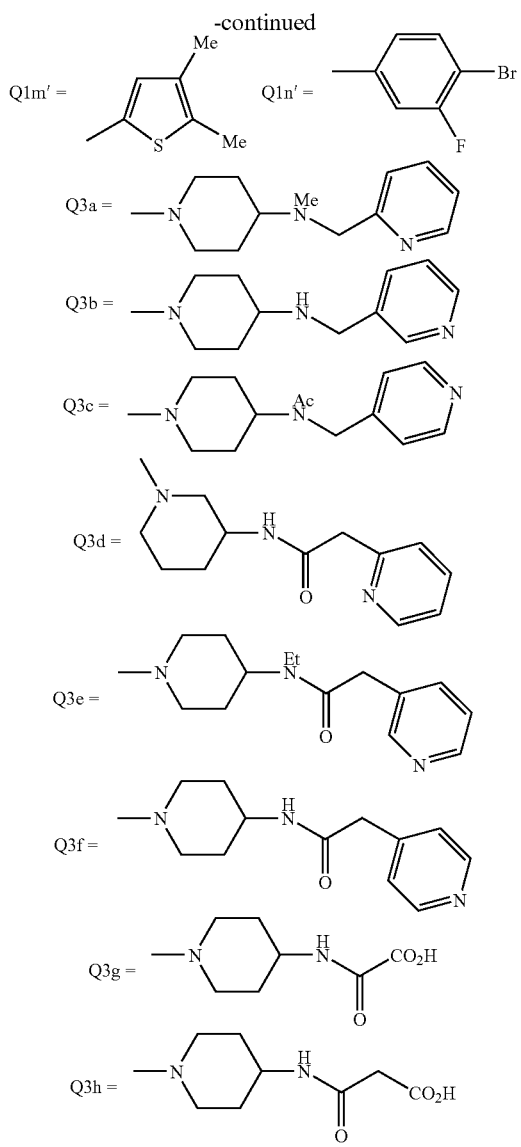

74) The compounds wherein A, B, $R^1$, $L^1$, $R^2$, $L^2$, $L^3$, Y, $L^4$, $R^3$ and X are any of the following combinations in Table 1, tautomers, prodrugs or pharmaceutically acceptable salts of the compounds or solvates thereof (provided that in the case of 74), Q1a, Q1b, Q1c, Q1d, Q1e, Q1f, Q1g, Q1h, Q1i, Q1j, Q1k, Q1l, Q1m, Q1n, Q1k', Q1l', Q1m', Q1n', Q3a, Q3b, Q3c, Q3d, Q3e, Q3f, Q3g and Q3h in Table 1 denote the following substituents).

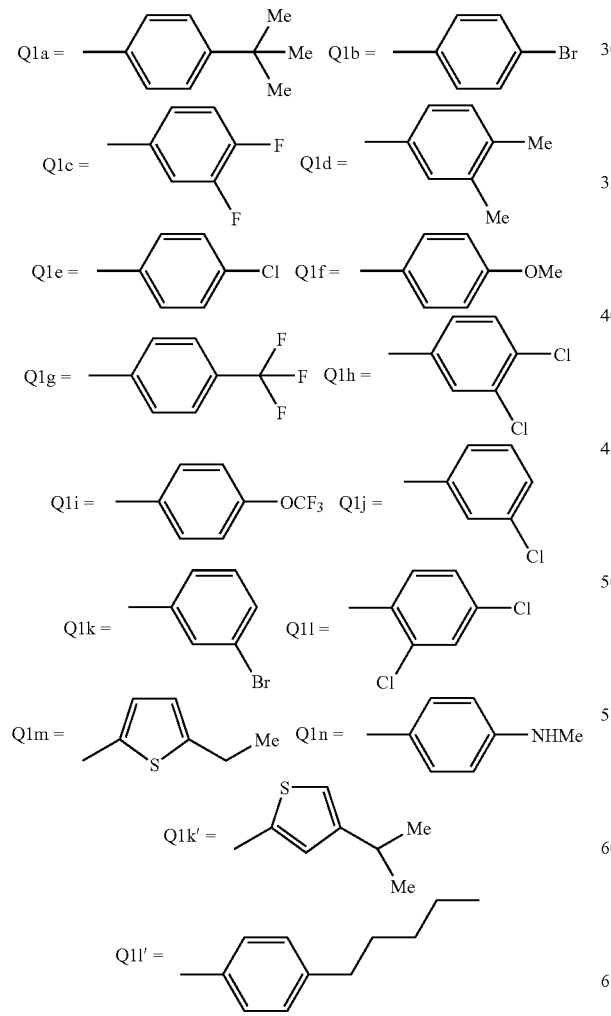

75) The compounds wherein A, B, $R^1$, $L^1$, $R^2$, $L^2$, $L^3$, Y, $L^4$, $R^3$ and X are any of the following combinations in Table 1, tautomers, prodrugs or pharmaceutically acceptable salts of the compounds or solvates thereof (provided that in the case of 75), Q1a, Q1b, Q1c, Q1d, Q1e, Q1f, Q1g, Q1h, Q1i, Q1j, Q1k, Q1l, Q1m, Q1n, Q1k', Q1l', Q1m', Q1n', Q3a, Q3b, Q3c, Q3d, Q3e, Q3f, Q3g and Q3h in Table 1 denote the following substituents).

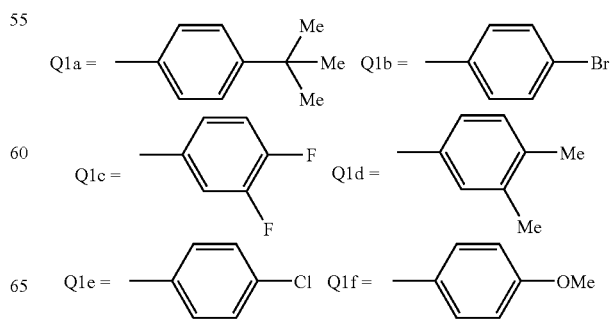

-continued

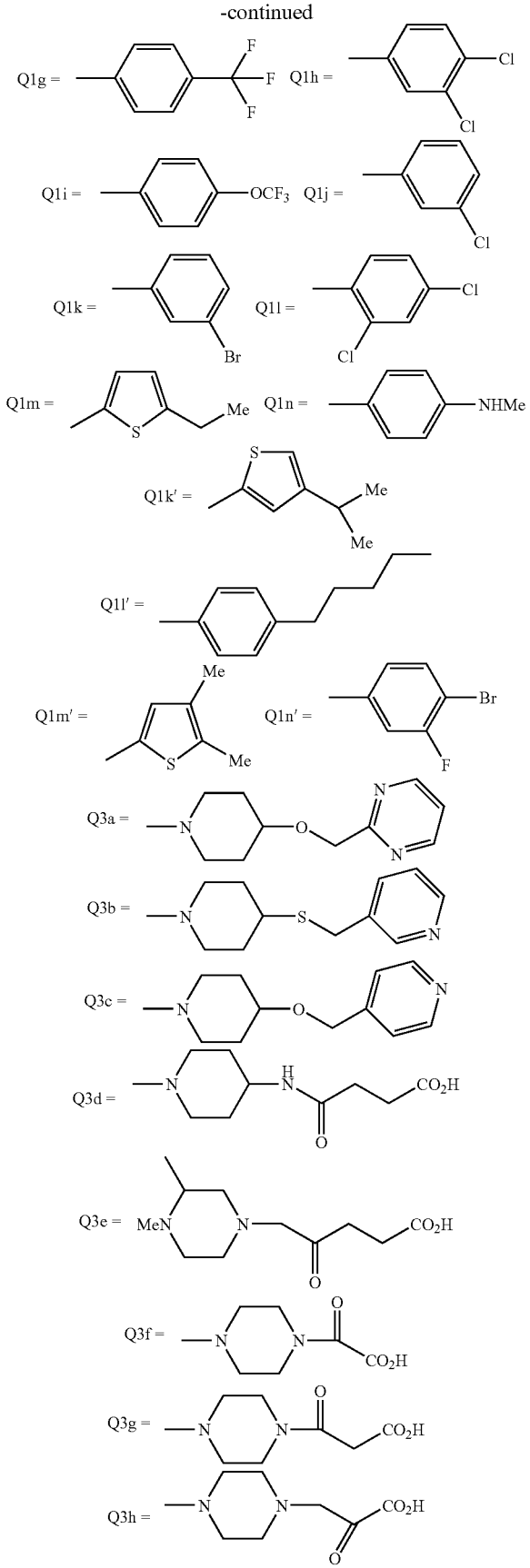

76) The compounds wherein A, B, $R^1$, $L^1$, $R^2$, $L^2$, $L^3$, Y, $L^4$, $R^3$ and X are any of the following combinations in Table 1, tautomers, prodrugs or pharmaceutically acceptable salts of the compounds or solvates thereof (provided that in the case of 76), Q1a, Q1b, Q1c, Q1d, Q1e, Q1f, Q1g, Q1h, Q1i, Q1j, Q1k, Q1l, Q1m, Q1n, Q1k', Q1l', Q1m', Q1n', Q3a, Q3b, Q3c, Q3d, Q3e, Q3f, Q3g and Q3h in Table 1 denote the following substituents).

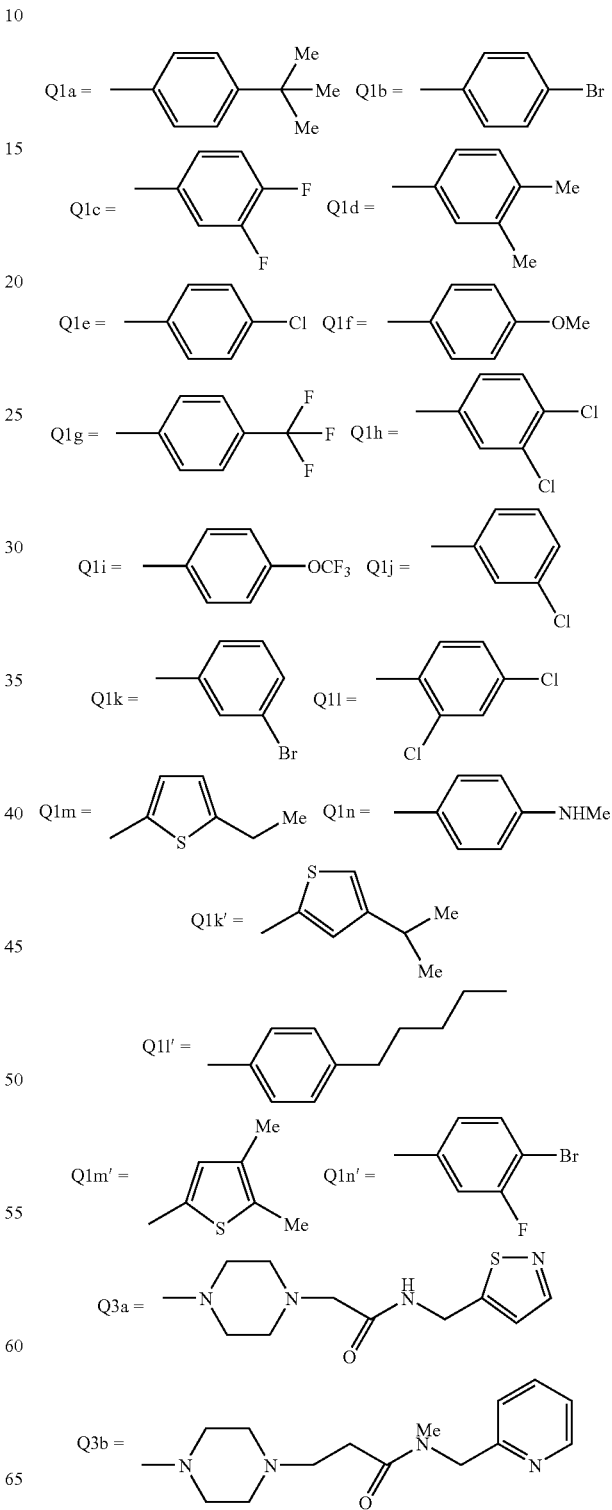

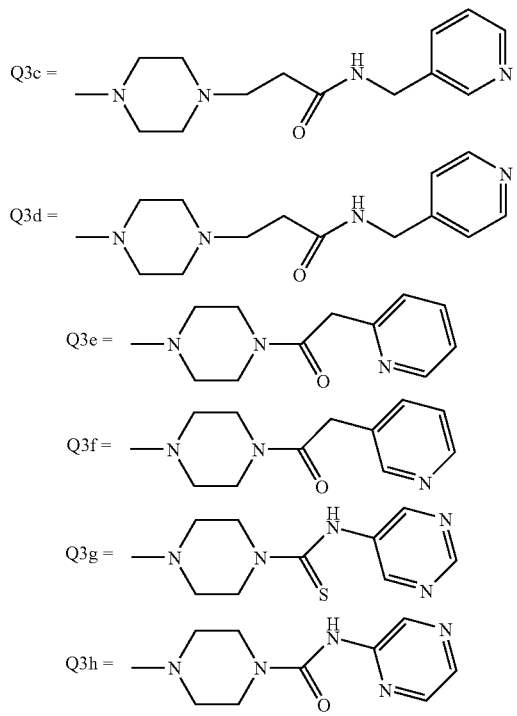
77) The compounds wherein A, B, $R^1$, $L^1$, $R^2$, $L^2$, $L^3$, Y, $L^4$, $R^3$ and X are any of the following combinations in Table 1, tautomers, prodrugs or pharmaceutically acceptable salts of the compounds or solvates thereof (provided that in the case of 77), Q1a, Q1b, Q1c, Q1d, Q1e, Q1f, Q1g, Q1h, Q1i, Q1j, Q1k, Q1l, Q1m, Q1n, Q1k', Q1l', Q1m', Q1n', Q3a, Q3b, Q3c, Q3d, Q3e, Q3f, Q3g and Q3h in Table 1 denote the following substituents).
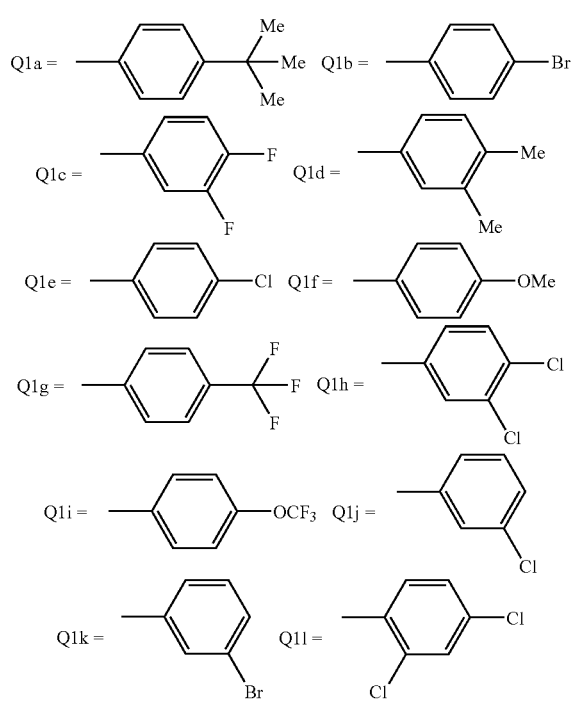
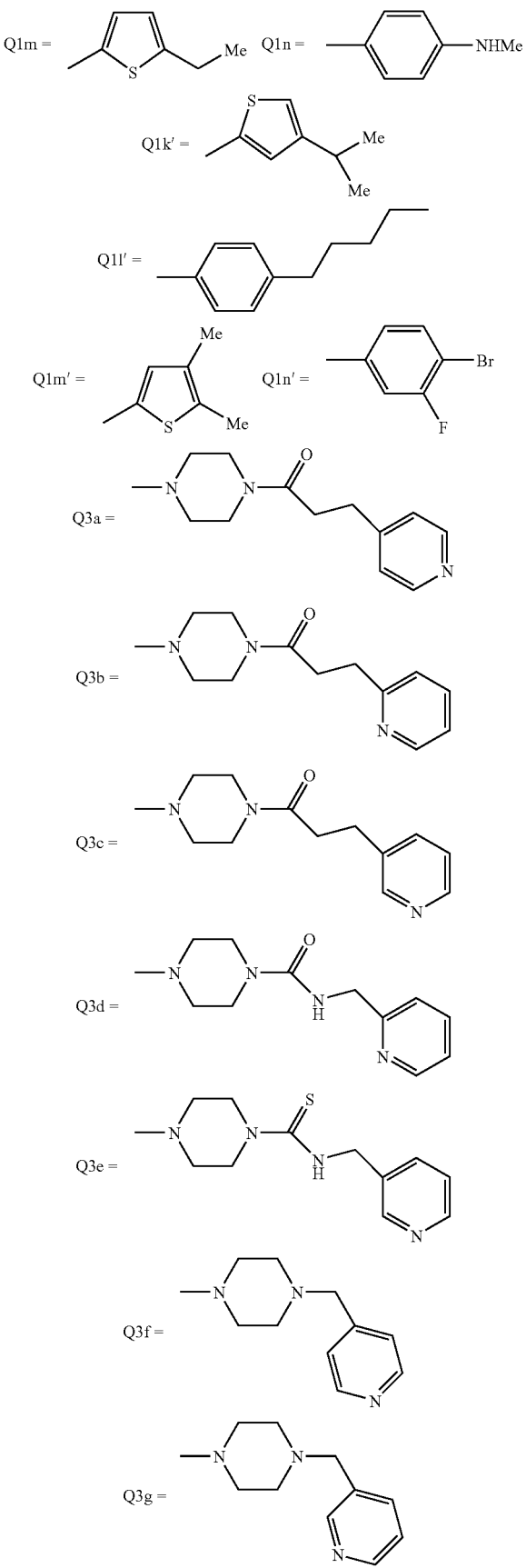

-continued

Q3h = 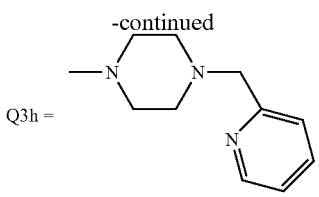

78) The compounds wherein A, B, R¹, L¹, R², L², L³, Y, L⁴, R³ and X are any of the following combinations in Table 1, tautomers, prodrugs or pharmaceutically acceptable salts of the compounds or solvates thereof (provided that in the case of 78), Q1a, Q1b, Q1c, Q1d, Q1e, Q1f, Q1g, Q1h, Q1i, Q1j, Q1k, Q1l, Q1m, Q1n, Q1k'y Q1l', Q1m', Q1n', Q3a, Q3b, Q3c, Q3d, Q3e, Q3f, Q3g and Q3h in Table 1 denote the following substituents).

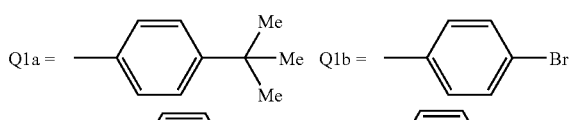

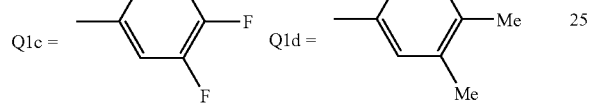

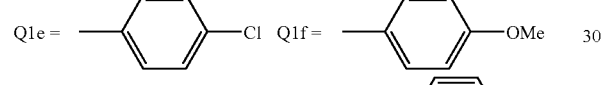

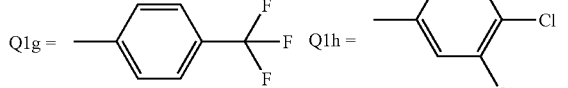

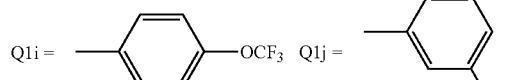

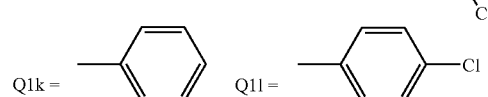

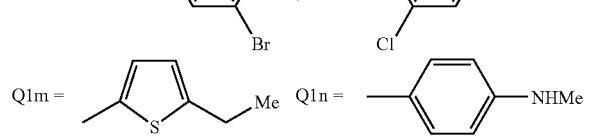

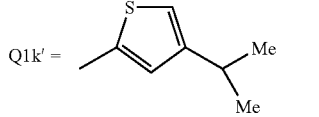

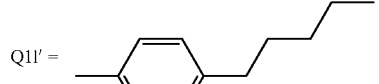

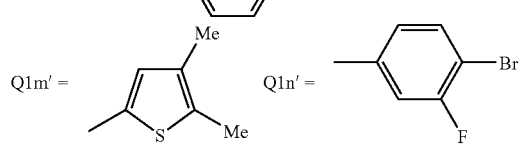

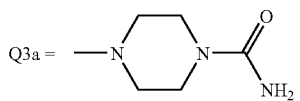

-continued

Q3b = 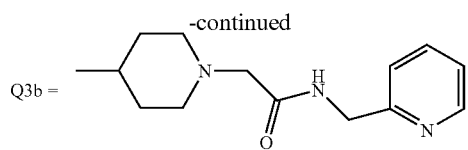

Q3c = 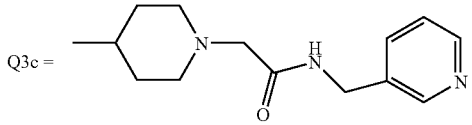

Q3d = 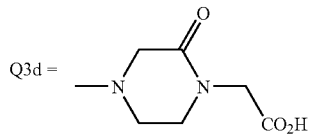

Q3e = 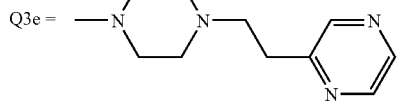

Q3f = 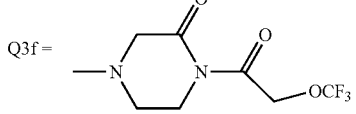

Q3g = 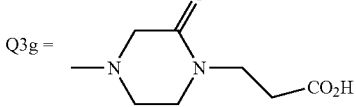

Q3h = 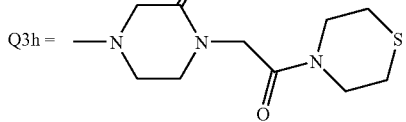

79) The compounds wherein A, B, R¹, L¹, R², L², L³, Y, L⁴, R³ and X are any of the following combinations in Table 1, tautomers, prodrugs or pharmaceutically acceptable salts of the compounds or solvates thereof (provided that in the case of 79), Q1a, Q1b, Q1c, Q1d, Q1e, Q1f, Q1g, Q1h, Q1i, Q1j, Q1k, Q1l, Q1m, Q1n, Q1k', Q1l', Q1m', Q1n', Q3a, Q3b, Q3c, Q3d, Q3e, Q3f, Q3g and Q3h in Table 1 denote the following substituents).

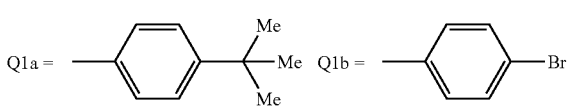

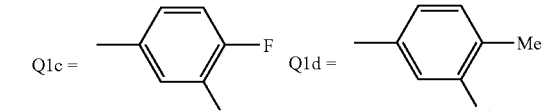

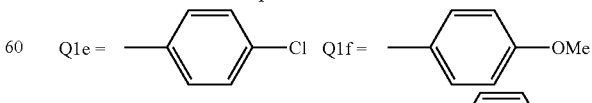

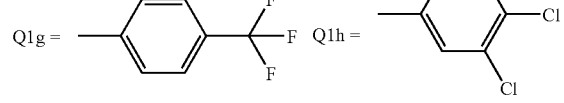

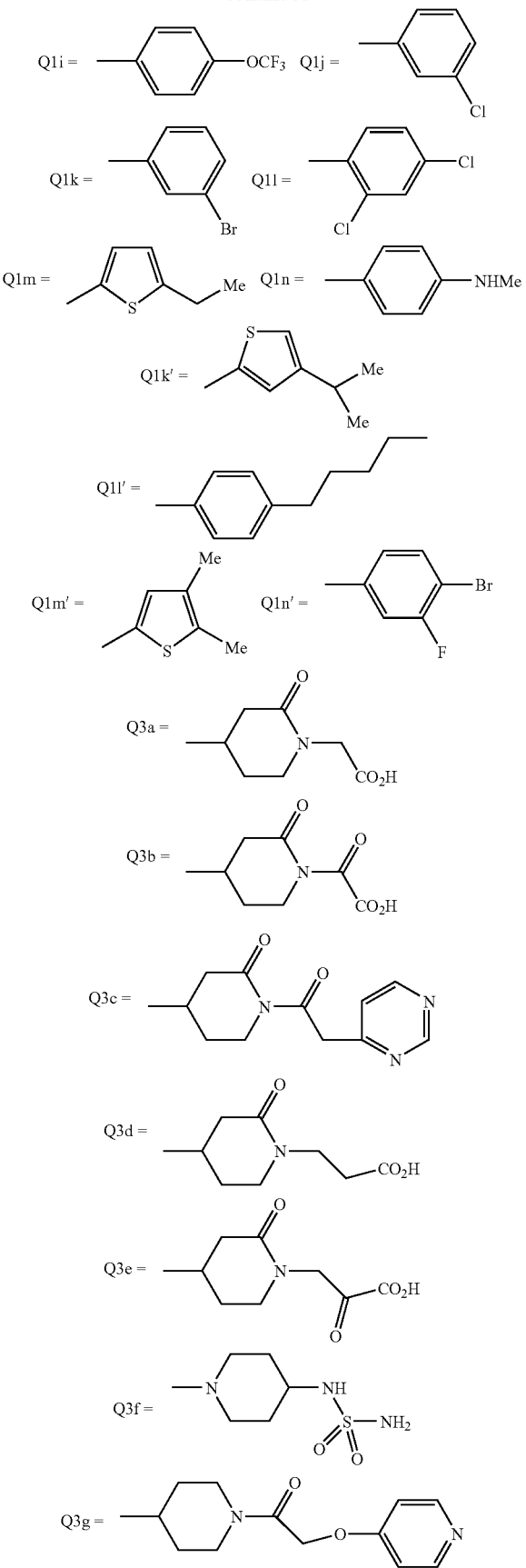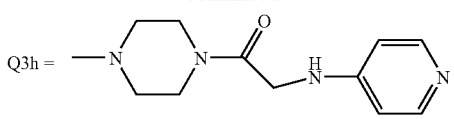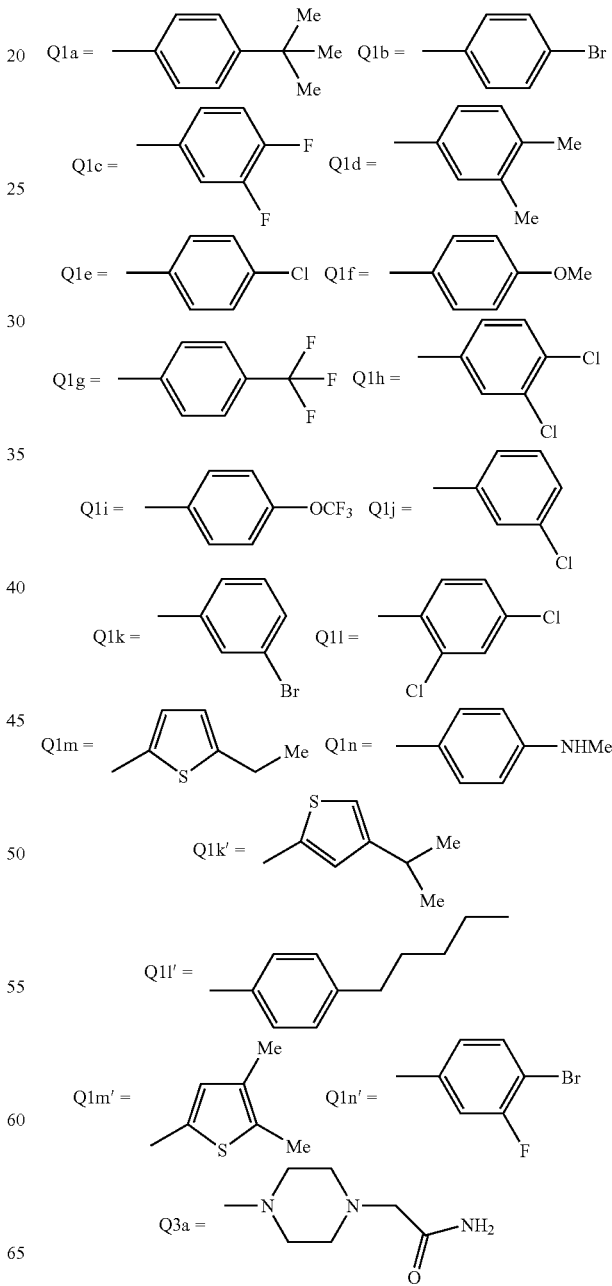
80) The compounds wherein A, B, $R^1$, $L^1$, $R^2$, $L^2$, $L^3$, Y, $L^4$, $R^3$ and X are any of the following combinations in Table 1, tautomers, prodrugs or pharmaceutically acceptable salts of the compounds or solvates thereof (provided that in the case of 80), Q1a, Q1b, Q1c, Q1d, Q1e, Q1f, Q1g, Q1h, Q1i, Q1j, Q1k, Q1l, Q1m, Q1n, Q1k', Q1l', Q1m', Q1n', Q3a, Q3b, Q3c, Q3d, Q3e, Q3f, Q3g and Q3h in Table 1 denote the following substituents).

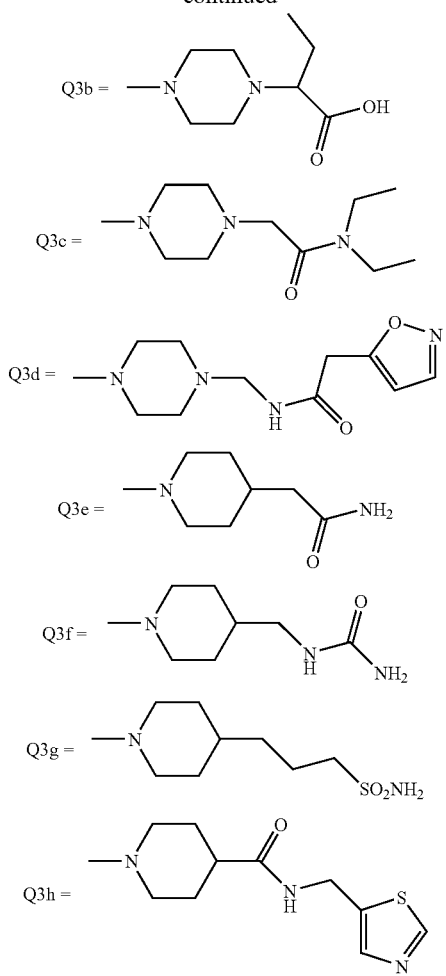
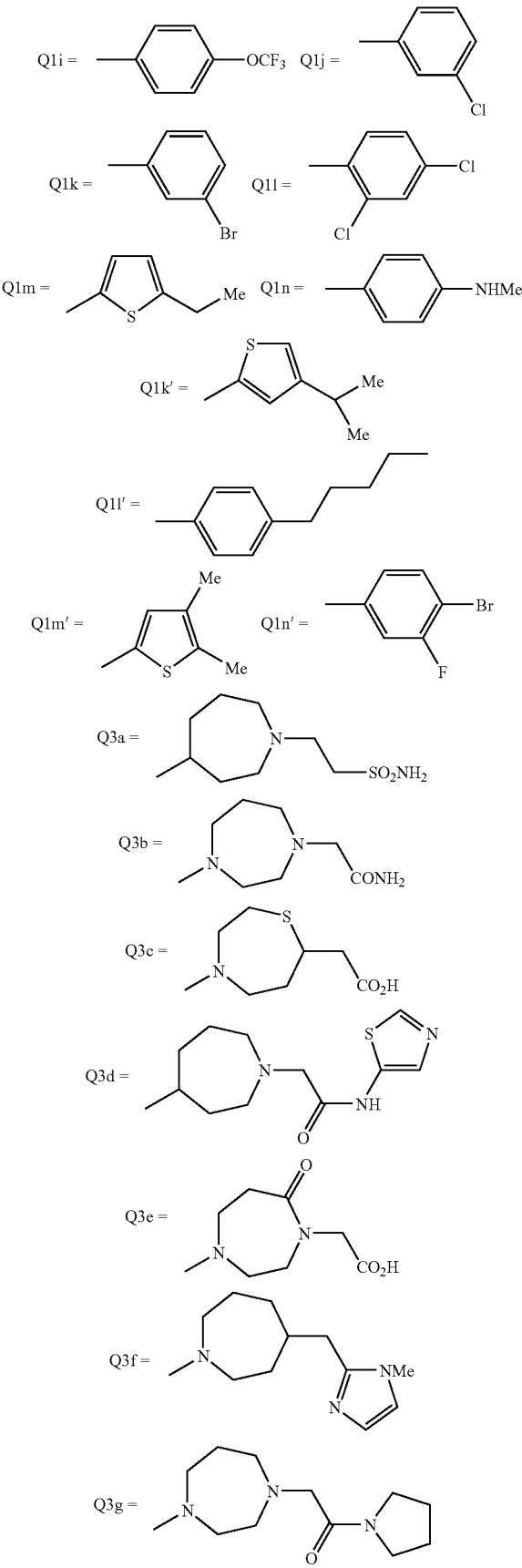
81) The compounds wherein A, B, $R^1$, $L^1$, $R^2$, $L^2$, $L^3$, Y, $L^4$, $R^3$ and X are any of the following combinations in Table 1, tautomers, prodrugs or pharmaceutically acceptable salts of the compounds or solvates thereof (provided that in the case of 81), Q1a, Q1b, Q1c, Q1d, Q1e, Q1f, Q1g, Q1h, Q1i, Q1j, Q1k, Q1l, Q1m, Q1n, Q1k', Q1l', Q1m', Q1n', Q3a, Q3b, Q3c, Q3d, Q3e, Q3f, Q3g and Q3h in Table 1 denote the following substituents).
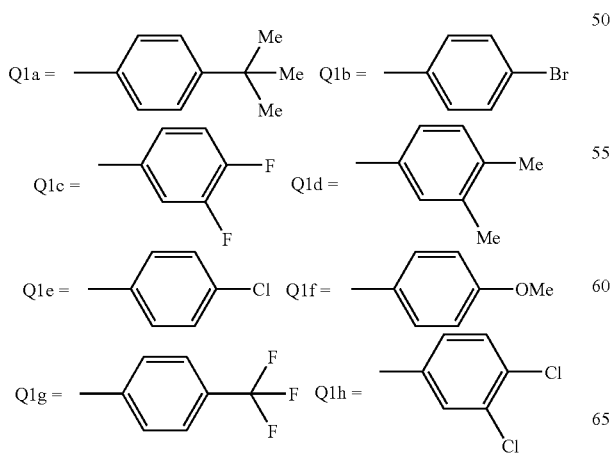

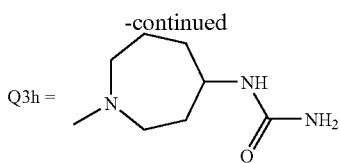

82) The compounds represented by any of 59) to 81) wherein X is converted to SH, tautomers, prodrugs or pharmaceutically acceptable salts of the compounds or solvates thereof.

83) The compounds represented by any of 59) to 81) wherein X is converted to NH₂, tautomers, prodrugs or pharmaceutically acceptable salts of the compounds or solvates thereof.

pharmaceutically acceptable salts of the compounds or solvates thereof, as an active ingredient.

In the present invention, the compounds of the present invention represented by the formula (1) may be present in the form of tautomers or geometrical isomers which undergo endocyclic or exocyclic isomerization, mixtures of tautomers or geometric isomers or mixtures of thereof. When the compounds of the present invention have an asymmetric center, whether or not resulting from an isomerization, the compounds of the present invention may be in the form of resolved optical isomers or in the form of mixtures containing them in certain ratios.

For example, furan compounds, thiophene compounds and pyrrole compounds of the present invention may be present in the form of tetronic acid (4-hydroxy-2(5H)-furanone) analogues, thiotetronic acid (4-hydroxy-2(5H)-thiophenone) analogues and tetraminic acid (4-hydroxy-3-pyrrolin-2-one) analogues as shown below by the formulae (2), (3) and (4), mixtures thereof or mixtures of isomers thereof.

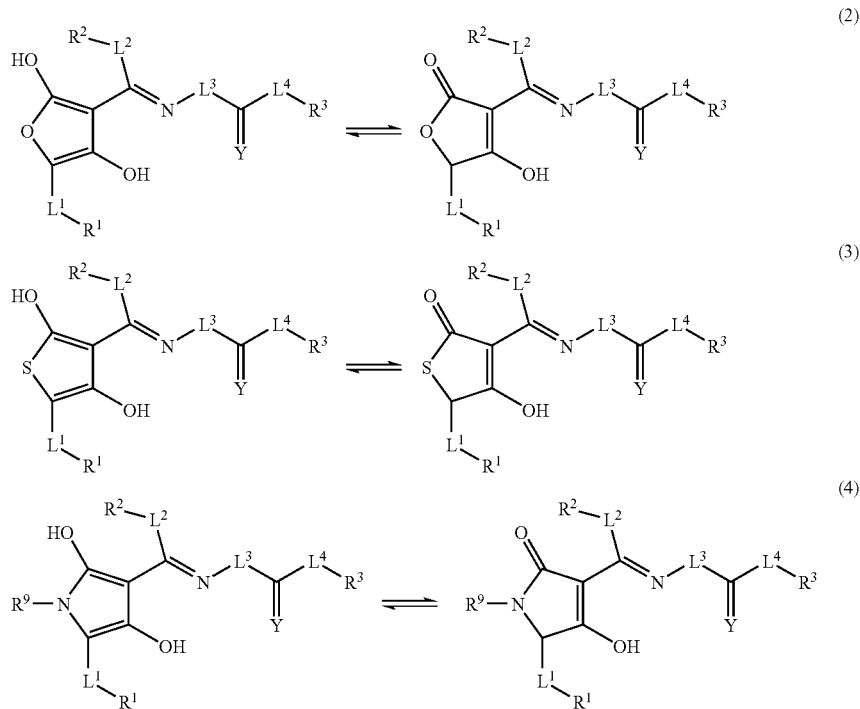

84) The compounds represented by any of 59) to 81) wherein X is converted to OAc, tautomers, prodrugs or pharmaceutically acceptable salts of the compounds or solvates thereof.

85) The thrombopoietin receptor activators represented by any of 1) to 84).

86) Preventive, therapeutic and improving agents for diseases against which activation of the thrombopoietin receptor is effective, which contain the thrombopoietin receptor activators represented by 85) or the formula (1), tautomers, prodrugs or pharmaceutically acceptable salts of the activators or solvates thereof, as an active ingredient.

87) Platelet increasing agents containing the thrombopoietin receptor activators represented by 85) or the formula (1), tautomers, prodrugs or pharmaceutically acceptable salts of the activators or solvates thereof, as an active ingredient.

88) Medicaments containing the compounds represented by any of 1) to 84) or the formula (1), tautomers, prodrugs or The compounds of the present invention represented by the formula (1) or pharmaceutically acceptable salts thereof may be in the form of arbitrary crystals or arbitrary hydrates, depending on the production conditions. The present invention covers these crystals, hydrates and mixtures. They may be in the form of solvates with organic solvents such as acetone, ethanol and tetrahydrofuran, and the present invention covers any of these forms.

The compounds of the present invention represented by the formula (1) may be converted to pharmaceutically acceptable salts or may be liberated from the resulting salts, if necessary. The pharmaceutically acceptable salts of the present invention may be, for example, salts with alkali metals (such as lithium, sodium and potassium), alkaline earth metals (such as magnesium and calcium), ammonium, organic bases and amino acids. They may be salts with inorganic acids (such as hydrochloric acid, hydrobromic acid, phosphoric acid and sulfuric acid) and organic acids (such as acetic acid, citric acid, maleic acid, fumaric acid, benzenesulfonic acid and p-toluenesulfonic acid).

The compounds which serve as prodrugs are derivatives of the present invention having chemically or metabolically degradable groups which give pharmacologically active compounds of the present invention upon solvolysis or under physiological conditions in vivo. Methods for selecting or producing appropriate prodrugs are disclosed, for example, in Design of Prodrug (Elsevier, Amsterdam 1985). In the present invention, when the compound has a hydroxyl group, acyloxy derivatives obtained by reacting the compound with appropriate acyl halides or appropriate acid anhydrides may, for example, be mentioned as prodrugs. Acyloxys particularly preferred as prodrugs include —$OCOC_2H_5$, —$OCO$(t-Bu), —$OCOC_{15}H_{31}$, —$OCO$(m-$CO_2$Na-Ph), —$OCOCH_2CH_2CO_2Na$, —$OCOCH(NH_2)CH_3$, —$OCOCH_2N(CH_3)_2$ and the like. When the compound of the present invention has an amino group, amide derivatives obtained by reacting the compound having an amino group with appropriate acid halides or appropriate mixed acid anhydrides may, for example, be mentioned as prodrugs. Amides particularly preferred as prodrugs include —NHCO$(CH_2)_{20}OCH_3$, —$NHCOCH(NH_2)CH_3$ and the like. When the compound of the present invention has a carboxyl group, carboxylic acid esters with aliphatic alcohols or carboxylic acid esters obtained by the reaction with an alcoholic free hydroxyl group of 1,2- or 1,3-digylcerides may, for example, be mentioned as prodrugs. Particularly preferred prodrugs are methyl esters and ethyl esters.

The preventive, therapeutic and improving agents for diseases against which activation of the thrombopoietin receptor is effective or platelet increasing agents which contain the thrombopoietin receptor activators of the present invention, tautomers, prodrugs or pharmaceutically acceptable salts of the activators or solvates thereof as an active ingredient may usually be administered as oral medicines such as tablets, capsules, powder, granules, pills, and syrup, as rectal medicines, percutaneous medicines or injections. The agents of the present invention may be administered as a single therapeutic agent or as a mixture with other therapeutic agents. Though they may be administered as they are, they are usually administered in the form of medical compositions. These pharmaceutical preparations can be obtained by adding pharmacologically and pharmaceutically acceptable additives by conventional methods. Namely, for oral medicines, ordinary excipients, lubricants, binders, disintegrants, humectants, plasticizers and coating agents may be used. Oral liquid preparations may be in the form of aqueous or oily suspensions, solutions, emulsions, syrups or elixirs or may be supplied as dry syrups to be mixed with water or other appropriate solvents before use. Such liquid preparations may contain ordinary additives such as suspending agents, perfumes, diluents and emulsifiers. In the case of rectal administration, they may be administered as suppositories. Suppositories may use an appropriate substance such as cacao butter, laurin tallow, Macrogol, glycerogelatin, Witepsol, sodium stearate and mixtures thereof as the base and may, if necessary, contain an emulsifier, a suspending agent, a preservative and the like. For injections, pharmaceutical ingredients such as distilled water for injection, physiological saline, 5% glucose solution, propylene glycol and other solvents or solubilizing agents, a pH regulator, an isotonizing agent and a stabilizer may be used to form aqueous dosage forms or dosage forms which need dissolution before use.

The dose of the agents of the present invention for administration to human is usually about from 0.1 to 1000 mg/human/day in the case of oral drugs or rectal administration and about from 0.05 mg to 500 mg/human/day in the case of injections, though it depends on the age and conditions of the patient. The above-mentioned ranges are mere examples, and the dose should be determined from the conditions of the patient.

The present invention is used when the use of compounds which have thrombopoietin receptor affinity and act as thrombopoietin receptor agonists are expected to improve pathological conditions. For example, hematological disorders accompanied by abnormal platelet count may be mentioned. Specifically, it is effective for therapy or prevention of human and mammalian diseases caused by abnormal megakaryopoiesis, especially those accompanied by thrombocytopenia. Examples of such diseases include thrombocytopenia accompanying chemotherapy or radiotherapy of cancer, thrombocytopenia accompanying antiviral therapy for diseases such as hepatitis C, thrombocytopenia caused by bone marrow transplantation, surgery and serious infections, or gastrointestinal bleeding, but such diseases are not restricted to those mentioned. Typical thrombocytopenias such as aplastic anemia, idiopathic thrombocytopenic purpura, myelodysplastic syndrome, hepatic disease, HIV infection and thrombopoietin deficiency are also targets of the agents of the present invention. The present invention may be used as a peripheral stem cell mobilizer, a megakaryoblastic or megakaryocytic leukemia cell differentiation inducer and a platelet increasing agent for platelet donors. In addition, potential applications include therapeutic angiogenesis based on differentiation and proliferation of vascular endothelial cells and endothelial progenitor cells, prevention and therapy of arteriosclerosis, myocardial infarction, unstable angina, peripheral artery occlusive disease, but there is no restriction.

The compounds represented by the formula (1) are prepared by the process represented by the formula (5) illustrated below.

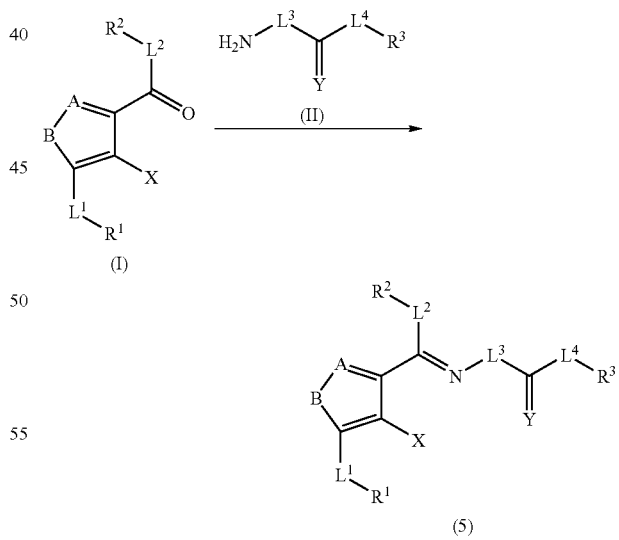

The reaction of the compound (I) with a —$NH_2$ compound (II) in a solvent, if necessary in the presence of a catalyst, under heating with stirring gives a desired compound or its precursor. The precursor may be, if necessary, hydrolyzed, deprotected, reduced or oxidized to a desired compound. The compounds of the present invention usually can be purified by column chromatography, thin layer chromatography, high performance liquid chromatography (HPLC) or high performance liquid chromatography-mass spectrometry (LC-MS) and, if necessary, they may be obtained with high purity by recrystallization or washing with solvents.

For the syntheses of the intermediates (I), syntheses of the following heterocyclic compounds may be referred to.

1) Pyrazole (the formula (6)) J. Chem. Soc. Perkin. TransI, p. 81, (1985)
2) Isothiazole (the formula (7)) Liebigs. Annalen. der. Chemie., 10, 1534-1546 (1979)
3) Isoxazole (the formula (8)) Synthesis, 10, 664-665 (1975)
4) Thiophene (the formula (9)) JP-A-48-026755.
5) Furan (the formula (10)) J. Org. Chem., 21, 1492-1509 (1956) and EP1253146
6) Pyrrole (the formula (11)) J. Heterocyclic Chem., 30, 1253 (1993) and Tetrahedron, 50 (26), 7849-56 (1994)
7) Tetronic acid (4-hydroxy-2(5H)-furanone) analogue (the formula (12)) Synthesis, 7, 564-566 (1988) and Yakugaku Zasshi, 96 (4), 536-543 (1976)
8) Tetraminic acid (4-hydroxy-3-pyrrolin-2-one) analogue (the formula (13)) Synthesis, 2, 190-192 (1987) and Agric. Biol. Chem., 43 (8), 1641-1646 (1979)

(6)

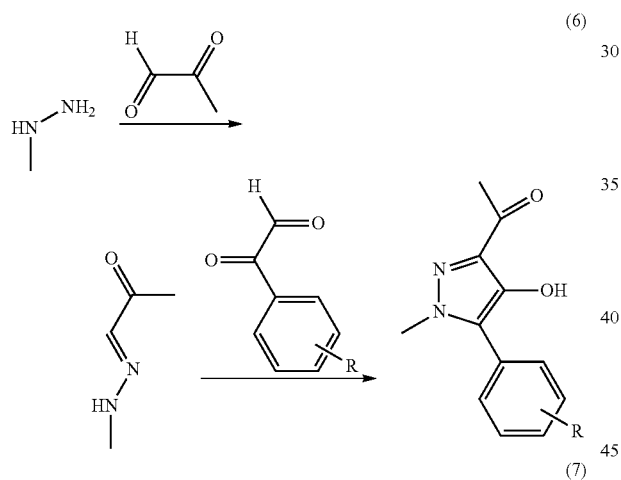

(7)

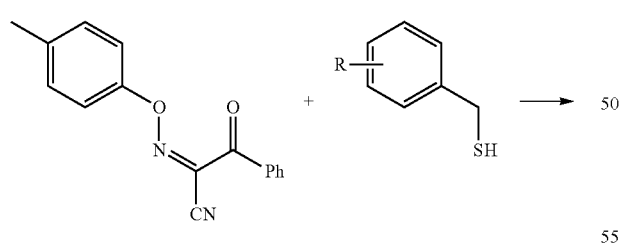

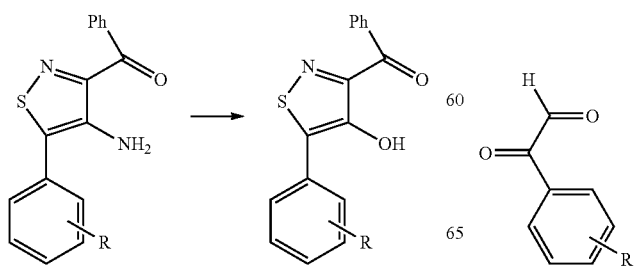

(8)

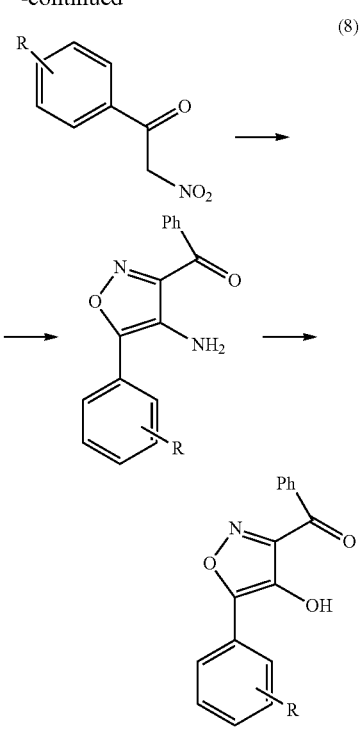

(9)

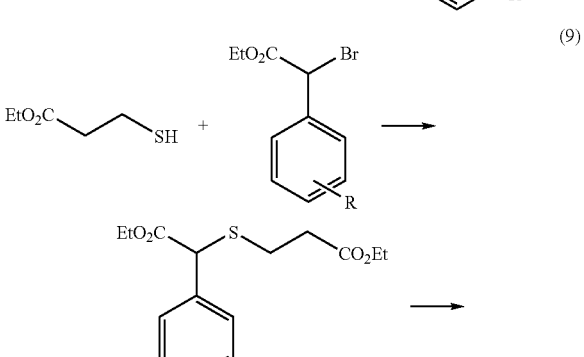

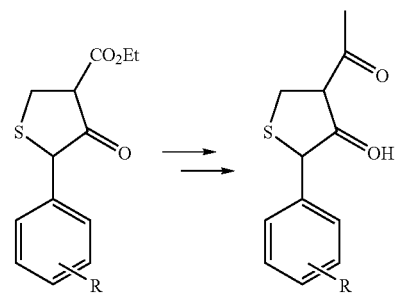

(10)

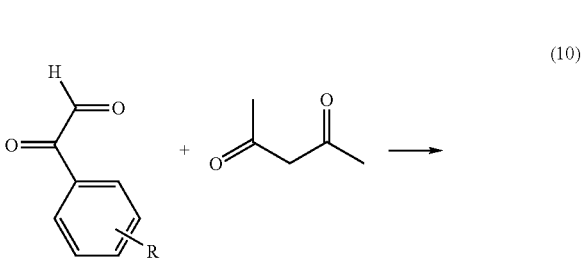

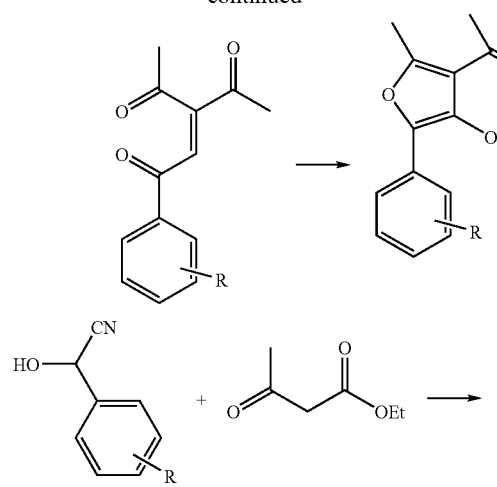
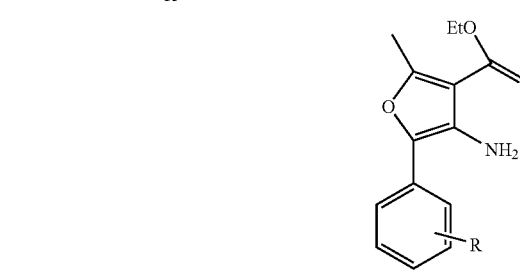
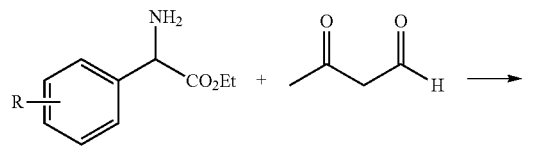
(11)
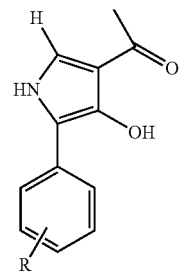
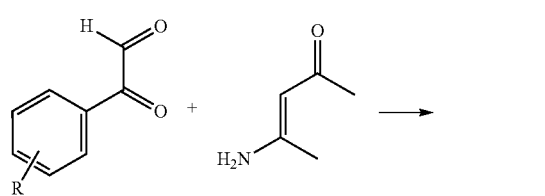
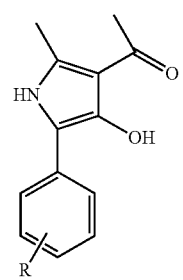
(12)
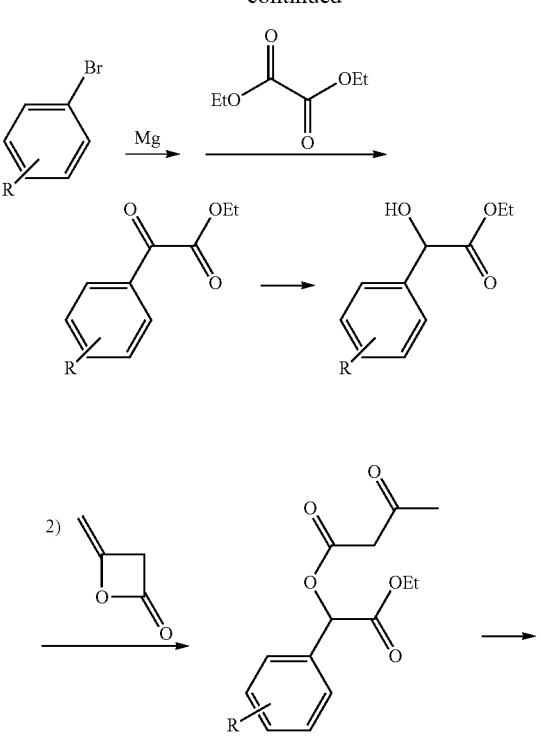
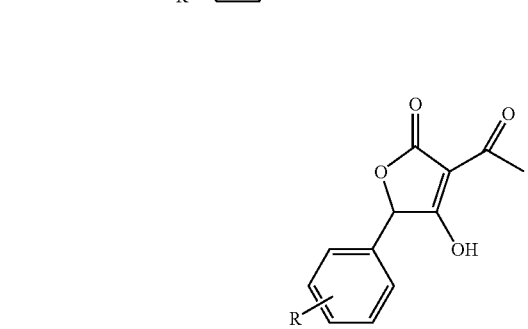
(13)
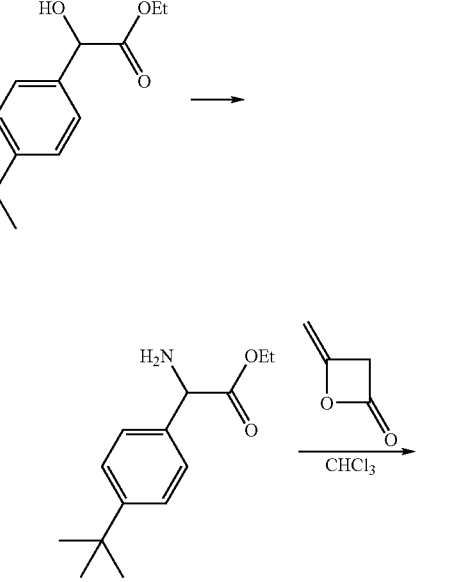

411
-continued

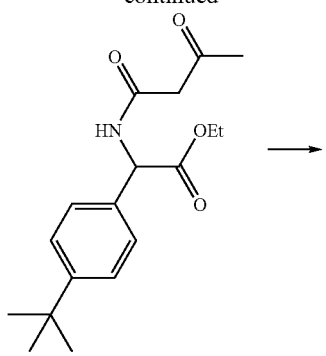

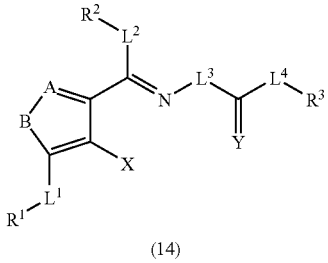

(14)

The compounds represented by the formula (1) wherein $L^3$ is $NR^{19}$, $L^4$ is a bond, and Y is O or S are prepared by the process represented by the formula (15) illustrated below.

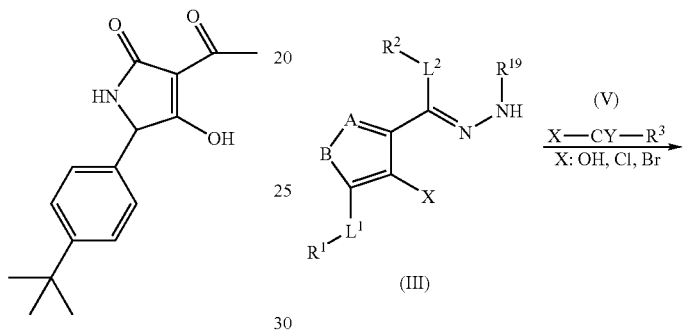

For synthesis of the —$NH_2$ compounds (II), for example, when $L^3$=NH, the following may be referred to.
1) $L^4$=a bond, Y=O Synthetic Commun., 28 (7), 1223-1231 (1998), J. Chem. Soc., 1225 (1948) and J. Chem. Soc., 2831 (1952)
2) $L^4$=NH, Y=O J. Am. Chem. Soc., 46, 2813 (1924) and J. Chem. Soc., 2654 (1952)
3) $L^4$=NH, Y=S Can. J. Chem., 35, 834 (1957)
4) $L^4$=$NR^{22}$ or N-(heterocyclic group formed by $R^{22}$ and $R^3$) J. Org. Chem., 53, 2263 (1988)
5) $L^4$=$CH_2$, Y=O J. Org. Chem., 30, 2487 (1965)
6) $L^4$=O, Y=O Bull. Soc. Chim. Belg., 68, 409, (1959)
7) $L^4$=S, Y=S. J. Med. Chem., 22, 853 (1979)

The compounds represented by the formula (1) wherein $L^3$ is $NR^{19}$, $L^4$ is NH, and Y is O or S are prepared by the process represented by the formula (14) illustrated below.

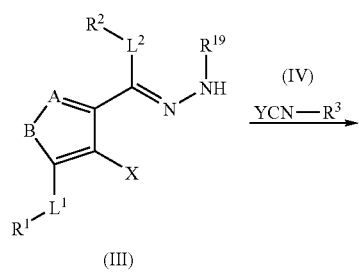

The reaction of the compound (I) with a $NH_2$ compound (IV) in a solvent, if necessary in the presence of a catalyst, under heating with stirring gives the compound (III) as the desired product.

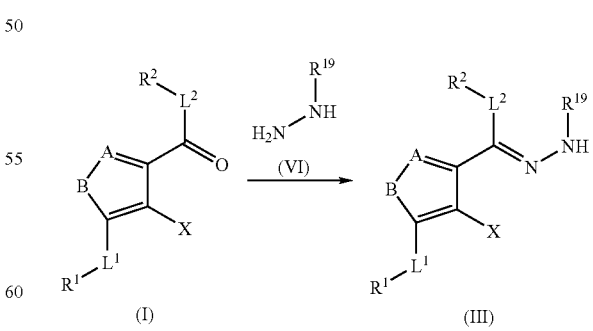

The compounds represented by the formula (1) wherein $L^3$ is $NR^{19}$, $L^4$ is $NR^{22}$ or forms a heterocyclic group together with $R^3$ are prepared by the process represented by the formula (16) illustrated below.

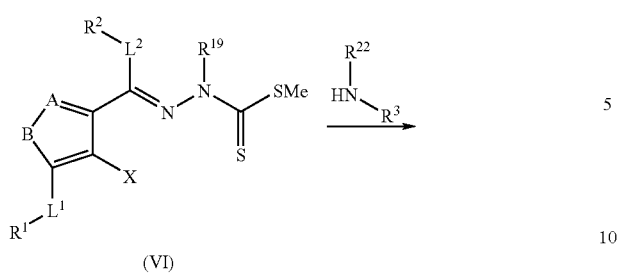

(VI)

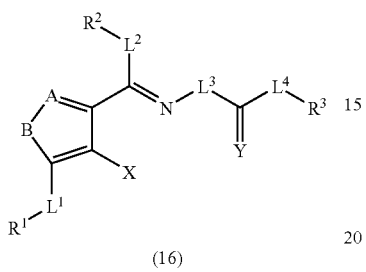

(16)

EXAMPLES

Now, the present invention will be described in further detail with reference to Reference Synthetic Examples, Synthetic Examples, Assay Examples and Formulation Examples. However, it should be understood that the present invention is by no means restricted by these specific Examples.

The $^1$H-NMR analysis was carried out at 300 MHz, and LC/MS was measured under the following conditions.

LC/MS Condition 1
Column: Waters SunFire C18 (3.5 μm, 4.6×30 mm)
Eluent: acetonitrile/0.1% aqueous formic acid (10/90→60/40)
LC/MS conditions 2
Column: Waters SunFire C18 (3.5 μm, 4.6×30 mm)
Eluent: acetonitrile/0.1% aqueous formic acid (10/90→85/15)
LC/MS Conditions 3
Column: Waters SunFire C18 (3.5 μm, 4.6×30 mm)
Eluent: acetonitrile/0.1% aqueous formic acid (20/80→100/0)
LC/MS Conditions 4
Column: Waters Xterra MSC18 (5 μm, 4.6×50 mm)
Eluent: acetonitrile/0.1% aqueous formic acid (10/90→60/40)
LC/MS Conditions 5
Column: Waters Xterra MSC18 (3.5 μm, 2.1×20 mm)
Eluent: acetonitrile/0.2% aqueous formic acid (20/80→90/10)

Reference Synthetic Example 1

Synthesis of 2-(3,4-dichlorophenyl)-4-(1-hydrorazonoethyl)thiophen-3-ol

To a suspension of 2-(3,4-dichlorophenyl)-3-hydroxy-4-methylcarbonylthiophene (300 mg, 1.05 mmol) (prepared by the method disclosed in WO2004/108683) in isopropanol (20 mL) was added hydrazine monohydrate (61 μL, 1.25 mmol). The reaction mixture was refluxed for 1.5 hours, stirred at room temperature for 0.5 hour and at 0° C. for 1 hour. The precipitated solid was collected by filtration and dried by means of a vacuum pump to give the desired product (yield 100%).
Morphology: a pale yellow solid
$^1$H-NMR (DMSO-$d_6$) δ (ppm): 2.10 (s, 3H), 6.63 (br s, 2H), 7.58 (s, 2H), 7.61 (s, 1H), 7.98 (s, 1H), 12.88 (s, 1H).
LC/MS: condition 4, retention time 4.95 (min)
LC/MS (ESI$^+$) m/z; 301, 303 [M+1]$^+$
LC/MS (ESI$^-$) m/z; 299, 301 [M−1]$^-$

Reference Synthetic Example 2

Synthesis of methyl 1-hydrazinothiocarbonylpiperidine-4-carboxylate

To a solution of methyl isonipecotate (1.0 g, 7.0 mmol) in tetrahydrofuran was added thiocarbonyl diimidazole (1.24 g, 6.98 mmol) at room temperature, and the reaction solution was stirred at room temperature for 1.5 hours and then stirred with hydrazine monohydrate (700 mg, 14.0 mmol) for 4 hours. After addition of saturated aqueous sodium chloride, the reaction solution was extracted with ethyl acetate and chloroform, and the extract was dried over anhydrous magnesium sulfate and concentrated to give the desired product (yield 114%).
Morphology: pale yellow solid
LC/MS: condition 5, retention time 0.52 (min)
LC/MS (ESI$^+$) m/z; 218, [M+1]$^+$

Reference Synthetic Example 3

Synthesis of ethyl 1-hydrazinothiocarbonylpiperidine-3-carboxylate

Synthesis was carried out in the same manner as in Reference Synthetic Example 2 by using ethyl nipecotate.

Reference Synthetic Example 4

Synthesis of 1-hydrazinothiocarbonylpiperidine-4-carboxylic acid diethylamide

Synthesis was carried out in the same manner as in Reference Synthetic Example 2 by using isonipecotic acid diethylamide.

Reference Synthetic Example 5

Synthesis of 1-hydrazinothiocarbonylpiperidin-4-ol

A solution of methyl hydrazinecarbothioate (1.0 g, 8.2 mmol) and piperidin-4-ol (1.24 g, 12.3 mmol) in ethanol (7 mL) was refluxed with heating at 90° C. for 2 days. After addition of ethyl acetate, the reaction solution was washed with saturated aqueous sodium chloride, dried over anhydrous magnesium sulfate and concentrated to give the crude desired product. The crude product was used directly for the next reaction.

Reference Synthetic Example 6

Synthesis of 1-hydrazinothiocarbonylpiperidin-3-ol

Synthesis was carried out in the same manner as in Reference Synthetic Example 5 by using piperidin-3-ol.

Reference Synthetic Example 7

Synthesis of
1-hydrazinothiocarbonylpiperidine-4-methanol

Synthesis was carried out in the same manner as in Reference Synthetic Example 5 by using 4-piperidinemethanol.

Reference Synthetic Example 8

Synthesis of methyl
2-[4-(tert-butoxycarbonyl)piperazin-1-yl]acetate

A solution of 1-(tert-butoxycarbonyl)piperazine (1.38 g, 7.41 mmol) in acetonitrile (10 mL) was stirred with triethylamine (2.07 mL, 14.8 mmol) and methyl 2-bromoacetate (1.02 mL, 11.1 mmol) at room temperature for 4 hours and then filtered. The filtrate was concentrated, and after addition of saturated aqueous ammonium chloride, extracted with ethyl acetate. The organic phase was washed with saturated aqueous ammonium chloride and saturated aqueous sodium chloride, dried over anhydrous magnesium sulfate and concentrated to give the desired product (yield 83%).
Morphology: pale yellow liquid
$^1$H-NMR (CDCl$_3$) δ: 1.46 (S, 9H), 2.53 (t, J=5.1 Hz, 4H), 3.24 (S, 2H), 3.49 (t, J=5.1 Hz, 4H), 3.73 (s, 3H)

Reference Synthetic Example 9

Synthesis of ethyl 3-[4-(tert-butoxycarbonyl)piperazin-1-yl]propionate

Synthesis was carried out in the same manner as in Reference Synthetic Example 8 by using ethyl 3-bromopropionate.
Morphology: colorless mixture of solid and liquid
$^1$H-NMR (CDCl$_3$) δ: 1.26 (t, J=7.2 Hz, 3H), 1.46 (s, 9H), 2.41 (t, J=4.8 Hz, 4H), 2.50 (t, J=7.2 Hz, 2H), 2.71 (t, J=7.2 Hz, 2H), 3.42 (t, J=4.8 Hz, 4H), 4.14 (q, J=7.2 Hz, 2H)

Reference Synthetic Example 10

Synthesis of methyl
2-[4-hydrazinothiocarbonylpiperazin-1-yl]acetate

A solution of methyl 2-[4-(tert-butoxycarbonyl)piperazin-1-yl]acetate prepared in Reference Synthetic Example 8 in dioxane (9 mL) was stirred with 4N hydrogen chloride/dioxane solution (3.91 mL, 15.7 mmol) at 80° C. for 1.5 hours. The solution was allowed to cool and filtered. Tetrahydrofuran and triethylamine (0.88 mL, 6.3 mmol) were added to the filter cake, and the procedure in Reference Synthetic Example 2 was followed using the resulting solution. The resulting crude product was used directly for the next reaction.
Morphology: pale yellow solid

Reference Synthetic Example 11

Synthesis of ethyl 3-[4-hydrazinothiocarbonylpiperazin-1-yl]propionate

Synthesis was carried out in the same manner as in Reference Synthetic Example 10 by using ethyl 3-[4-(tert-butoxycarbonyl)piperazin-1-yl]propionate prepared in Reference Synthetic Example 9.
Morphology: pale yellow solid

Synthetic Example 1

Synthesis of methyl 1-{1-[5-(3,4-dichlorophenyl)-4-hydroxythiophen-3-yl]-ethylidene-hydrazinothiocarbonyl}-piperidine-4-carboxylate To a dimethylformamide solution (600 μL) of 2-(3,4-dichlorophenyl)-3-hydroxy-4-methylcarbonylthiophene (30 mg, 0.10 mmol) and methyl 1-hydrazinothiocarbonyl-piperidine-4-carboxylate (46 mg, 0.20 mmol) prepared in Reference Synthetic Example 2, concentrated hydrochloric acid (9 μL, 0.1 mmol) was added at room temperature, and the resulting solution was stirred at room temperature for 8 hours, then mixed with water and extracted with ethyl acetate. The extract was washed with 1 M hydrochloric acid and saturated aqueous sodium chloride, dried over anhydrous magnesium sulfate and concentrated. The resulting residue was purified by silica gel column chromatography (hexane/ethyl acetate=1/1) and recrystallized from chloroform to give the desired product (yield 55%).
Morphology: white solid
$^1$H-NMR (DMSO-d$_6$) δ: 1.55-1.75 (m, 2H), 1.85-1.95 (m, 2H), 2.38 (s, 3H), 2.7-2.8 (m, 1H), 3.15-3.30 (m, 2H), 3.48 (s, 3H), 4.58 (d, J=13.5 Hz, 2H), 7.64 (d, J=8.4 Hz, 1H), 7.71 (d, J=8.4, 2.1 Hz, 1H), 8.00 (s, 1H), 8.03 (d, J=2.1 Hz, 1H), 12.4 (s, 1H)
LC/MS: condition 5, retention time 5.19 (min)
LC/MS (ESI$^+$) m/z; 486, 488 [M+1]$^+$
LC/MS (ESI$^-$) m/z; 484, 486 [M−1]$^-$

Synthetic Example 2

Synthesis of 1-{1-[5-(3,4-dichlorophenyl)-4-hydroxythiophen-3-yl]-ethylidene-hydrazinothiocarbonyl}-piperidine-4-carboxylic acid To a suspension of methyl 1-{1-[5-(3,4-dichlorophenyl)-4-hydroxythiophen-3-yl]-ethylidene-hydrazinocarbonyl}-piperidine-4-carboxylate (10 mg, 0.021 mmol) in methanol (300 μL), 1 M aqueous sodium hydroxide (250 μL) was added at room temperature, and the suspension was stirred at room temperature for 7 hours. After the reaction, 1 M hydrochloric acid (250 μL) was added, and the resulting crystals were collected by filtration as the desired product (yield 71%).
Morphology: gray solid
LC/MS: condition 5, retention time 4.87 (min)
LC/MS (ESI$^+$) m/z; 472, 474 [M+1]$^+$
LC/MS (ESI$^-$) m/z; 470, 472 [M−1]$^-$

Synthetic Example 3

Synthesis of methyl 2-[(2-{1-[5-(3,4-dichlorophenyl)-4-hydroxythiophen-3-yl]-ethylidene}-hydrazinocarbonothioyl)amino]acetate A solution of 2-(3,4-dichlorophenyl)-4-(1-hydrazonoethyl)thiophen-3-ol (30 mg, 0.10 mmol) prepared in Reference Synthetic Example 1 and methyl 2-isothiocyanatoacetate (20 mg, 0.15 mmol) in dimethyl formamide (300 μL) was stirred at room temperature, 40° C. and 50° C. for 2 hours, respectively. After addition of methanol-water, the solution was stirred at room temperature for 0.5 hour, and the resulting crystals were collected by filtration as the desired product (yield 0.72%).
Morphology: white solid
LC/MS: condition 5, retention time 4.95 (min)
LC/MS (ESI$^+$) m/z; 432, 434 [M+1]$^+$
LC/MS (ESI$^-$) m/z; 430, 432 [M−1]$^-$

Synthetic Example 4

Synthesis of 2-[(2-{1-[5-(3,4-dichlorophenyl)-4-hydroxythiophen-3-yl]-etylidene}-hydrazinocarbonothioyl)amino]acetic acid Synthesis was carried out in the same manner as in Synthetic Example 2 using methyl 2-[(2-{1-[5-(3,4-dichlorophenyl)-4-hydroxythiophen-3-yl]-ethylidene}-hydrazinocarbonothioyl)amino]acetate prepared in Synthetic Example 3 (yield 39%).
Morphology: white solid
LC/MS: condition 5, retention time 4.65 (min)
LC/MS (ESI$^+$) m/z; 418, 420 [M+1]$^+$
LC/MS (ESI$^-$) m/z; 416, 418 [M−1]$^-$

Synthetic Example 5

Synthesis of methyl 3-[(2-{1-[5-(3,4-dichlorophenyl)-4-hydroxythiophen-3-yl]-ethylidene}-hydrazinocarbonothioyl)amino]propionate Synthesis was carried out in the same manner as in Synthetic Example 3 by using methyl 3-isothiocyanatopropionate (yield 78%).
Morphology: white solid
LC/MS: condition 5, retention time 5.03 (min)
LC/MS (ESI$^+$) m/z; 446 [M+1]$^+$
LC/MS (ESI$^-$) m/z; 444, 446 [M−1]$^-$

Synthetic Example 6

Synthesis of 3-[(2-{1-[5-(3,4-dichlorophenyl)-4-hydroxythiophen-3-yl]-ethylidene}-hydrazinocarbonothioyl)amino]propionic acid Synthesis was carried out in the same manner as in Synthetic Example 2 by using methyl 3-[(2-{1-[5-(3,4-dichlorophenyl)-4-hydroxythiophen-3-yl]-ethylidene}-hydrazinocarbonothioyl)amino]propionate prepared in Synthetic Example 5 (yield 41%).
Morphology: white solid
LC/MS: condition 5, retention time 4.74 (min)
LC/MS (ESI$^+$) m/z; 432, 434 [M+1]$^+$
LC/MS (ESI$^-$) m/z; 430, 432 [M−1]$^-$

Synthetic Example 7

Synthesis of 1-(2-{1-[5-(3,4-dichlorophenyl)-4-hydroxythiophen-3-yl]-ethylidene}-hydrazinocarbonothioyl)amino-2-methoxyethane Synthesis was carried out in the same manner as in Synthetic Example 3 by using 2-methoxyethyl isothiocyanate (yield 43%).
Morphology: pale yellow solid
LC/MS: condition 5, retention time 5.05 (min)
LC/MS (ESI$^+$) m/z; 418, 420 [M+1]$^+$
LC/MS (ESI$^-$) m/z; 416, 418 [M−1]$^-$

Synthetic Example 8

Synthesis of methyl 1-{1-[5-(4-bromophenyl)-4-hydroxy-thiophen-3-yl]-ethylidene-hydrazinothiocarbonyl}-piperidine-4-carboxylate Synthesis was carried out in the same manner as in Synthetic Example 1 by using 1-[5-(4-bromophenyl)-4-hydroxy-thiophen-3-yl]-ethanone (prepared by the method disclosed in WO2004/108683) and methyl 1-hydrazinothiocarbonyl-piperidine-4-carboxylate prepared in Reference Synthetic Example 2 (yield 64%).
Morphology: pale yellow solid
LC/MS: condition 2, retention time 3.74 (min)
LC/MS (ESI$^+$) m/z; 496, 498 [M+1]$^+$
LC/MS (ESI$^-$) m/z; 494, 496 [M−1]$^-$

Synthetic Example 9

Synthesis of 1-{1-[5-(4-bromophenyl)-4-hydroxy-thiophen-3-yl]-ethylidene-hydrazinothiocarbonyl}-piperidin-4-carboxylic acid Synthesis was carried out in the same manner as in Synthetic Example 2 by using methyl 1-{1-[5-(4-bromophenyl)-4-hydroxy-thiophen-3-yl]-ethylidene-hydrazinothiocarbonyl}-piperidine-4-carboxylate prepared in Synthetic Example 8 (yield 87%).
Morphology: pale yellow solid
LC/MS: condition 2, retention time 3.45 (min)
LC/MS (ESI$^+$) m/z; 482, 484 [M+1]$^+$
LC/MS (ESI$^-$) m/z; 480, 482 [M−1]$^-$

Synthetic Example 10

Synthesis of 1-{1-[4-hydroxy-5-(4-trifluoromethylphenyl)-thiophen-3-yl]-ethylidene-hydrazinothiocarbonyl}-piperidine-4-carboxylic acid Methyl 1-{1-[4-hydroxy-5-(4-trifluoromethylphenyl)-thiophen-3-yl]-ethylidene-hydrazinothiocarbonyl}-piperidine-4-carboxylate Synthesis was carried out in the same manner as in Synthetic Example 1 using 1-[4-hydroxy-5-(4-trifluoromethylphenyl)-thiophen-3-yl]ethanone (prepared by the method disclosed in WO2004/108683) and methyl 1-hydrazinothiocarbonylpiperidine-4-carboxylate prepared in Reference Synthetic Example 2 (yield 36%).
Morphology: pale yellow solid
LC/MS: condition 1, retention time 4.54 (min)
LC/MS (ESI$^+$) m/z; 486 [M+1]$^+$
LC/MS (ESI$^-$) m/z; 484 [M−1]$^-$ 1-{1-[4-Hydroxy-5-(4-trifluoromethylphenyl)-thiophen-3-yl]-ethylidene-hydrazinothiocarbonyl}-piperidine-4-carboxylic acid Synthesis was carried out in the same manner as in Synthetic Example 2 using methyl 1-{1-[4-hydroxy-5-(4-trifluoromethylphenyl)-thiophen-3-yl]-ethylidene-hydrazinothiocarbonyl}-piperidine-4-carboxylate prepared above (yield 58%).
Morphology: white solid
LC/MS: condition 5, retention, time 4.88 (min)
LC/MS (ESI$^+$) m/z; 472 [M+1]$^+$
LC/MS (ESI$^-$) m/z; 470 [M−1]$^-$

Synthetic Example 11

Synthesis of 1-{1-[5-(4-trifluoromethoxyphenyl)-4-hydroxythiophen-3-yl]-ethylidene-hydrazinothiocarbonyl}-piperidine-4-carboxylic acid Methyl 1-{1-[5-(4-trifluoromethoxyphenyl)-4-hydroxythiophen-3-yl]-ethylidene-hydrazinothiocarbonyl}-piperidine-4-carboxylate Synthesis was carried out in the same manner as in Synthetic Example 1 using 1-[5-(4-trifluoromethoxyphenyl)-4-hydroxythiophen-3-yl]ethanone (prepared by the method disclosed in WO2004/108683) and methyl 1-hydrazinothiocarbonylpiperidine-4-carboxylate prepared in Reference Synthetic Example 2 (yield 53%).
Morphology: pale yellow solid
LC/MS: condition 2, retention time 3.75 (min)
LC/MS (ESI$^+$) m/z; 502 [M+1]$^+$
LC/MS (ESI$^-$) m/z; 500 [M−1]$^-$ 1-{1-[5-(4-Trifluoromethoxyphenyl)-4-hydroxythiophen-3-yl]-ethylidene-hydrazinothiocarbonyl}-piperidine-4-carboxylic acid Synthesis was carried out in the same manner as in Synthetic Example 2 using methyl 1-{1-[5-(4-trifluoromethoxyphenyl)-4-hydroxythiophen-3-yl]-ethylidene-hydrazinothiocarbonyl}-piperidine-4-carboxylate prepared above (yield 52%).
Morphology: pale yellow solid
LC/MS: condition 2, retention time 3.49 (min)
LC/MS (ESI$^+$) m/z; 488 [M+1]$^+$
LC/MS (ESI$^-$) m/z; 486 [M−1]$^-$

Synthetic Example 12

Synthesis of 1-{1-[5-(4-chlorophenyl)-4-hydroxy-thiophen-3-yl]-ethilidene-hydrazinothiocarbonyl}-piperidine-4-carboxylic acid Methyl 1-{1-[5-(4-chlorophenyl)-4-hydroxy-thiophen-3-yl]-ethilidene-hydrazinothiocarbonyl}-piperidine-4-carboxylate Synthesis was carried out in the same manner as in Synthetic Example 1 using 1-[5-(4-chlorophenyl)-4-hydroxy-thiophen-3-yl]ethanone (prepared by the method disclosed in WO2004/108683) and methyl 1-hydrazinothiocarbonylpiperidine-4-carboxylate prepared in Reference Synthetic Example 2 (yield 41%).
Morphology: pale yellow solid
LC/MS: condition 1, retention time 4.50 (min)
LC/MS (ESI$^+$) m/z; 452, 454 [M+1]$^+$
LC/MS (ESI$^-$) m/z; 450, 452 [M−1]$^-$ 1-{1-[5-(4-Chlorophenyl)-4-hydroxy-thiophen-3-yl]-ethilidene-hydrazinothiocarbonyl}-piperidine-4-carboxylic acid Synthesis was carried out in the same manner as in Synthetic Example 2 using methyl 1-{1-[5-(4-chlorophenyl)-4-hydroxy-thiophen-3-yl]-ethilidene-hydrazinothiocarbonyl}-piperidine-4-carboxylate prepared above (yield 92%).
Morphology: yellow solid
LC/MS: condition 1, retention time 4.14 (min)
LC/MS (ESI$^+$) m/z; 438, 440 [M+1]$^+$
LC/MS (ESI$^-$) m/z; 436, 438 [M−1]$^-$

Synthetic Example 13

Synthesis of 1-{1-[5-(3,4-dimethylphenyl)-4-hydroxythiophen-3-yl]-ethylidene-hydrazinothiocarbonyl}-piperidine-4-carboxylic acid Methyl 1-{1-[5-(3,4-dimethylphenyl)-4-hydroxy-thiophen-3-yl]-ethylidene-hydrazinothiocarbonyl}-piperidine-4-carboxylate Synthesis was carried out in the same manner as in Synthetic Example 1 using 1-[5-(3,4-dimethylphenyl)-4-hydroxy-thiophen-3-yl]-ethanone (prepared by the method disclosed in WO2004/108683) and methyl 1-hydrazinothiocarbonylpiperidine-4-carboxylate prepared in Reference Synthetic Example 2 (yield 28%).
Morphology: pale yellow solid
LC/MS: condition 2, retention time 3.69 (min)
LC/MS (ESI$^+$) m/z; 446 [M+1]$^+$
LC/MS (ESI$^-$) m/z; 444 [M−1]$^-$ 1-{1-[5-(3,4-Dimethylphenyl)-4-hydroxy-thiophen-3-yl]-ethylidene-hydrazinothiocarbonyl}-piperidine-4-carboxylic acid Synthesis was carried out in the same manner as in Synthetic Example 2 using methyl 1-{1-[5-(3,4-dimethylphenyl)-4-hydroxy-thiophen-3-yl]-ethylidene-hydrazinothiocarbonyl}-piperidine-4-carboxylate prepared above (yield 100%).
Morphology: pale brown solid
LC/MS: condition 2, retention time 3.38 (min)
LC/MS (ESI$^+$) m/z; 431.78 [M+1]$^+$
LC/MS (ESI$^-$) m/z; 429.89 [M−1]$^-$

Synthetic Example 14

Synthesis of 1-{1-[5-(4-t-butylphenyl)-4-hydroxy-thiophen-3-yl]-ethylidene-hydrazinothiocarbonyl}-piperidine-4-carboxylic acid Methyl 1-{1-[5-(4-t-butylphenyl)-4-hydroxy-thiophen-3-yl]-ethylidene-hydrazinothiocarbonyl}-piperidine-4-carboxylate Synthesis was carried out in the same manner as in Synthetic Example 1 using 2-(4-t-butylphenyl)-3-hydroxy-4-methylcarbonylthiophene and methyl 1-hydrazinothiocarbonylpiperidine-4-carboxylate prepared in Reference Synthetic Example 2 (yield 57%).
Morphology: pale brown solid
LC/MS: condition 2, retention time 3.87 (min)
LC/MS (ESI$^+$) m/z; 474 [M+1]$^+$
LC/MS (ESI$^-$) m/z; 472 [M−1]$^-$ 1-{1-[5-(4-t-Butylphenyl)-4-hydroxy-thiophen-3-yl]-ethylidene-hydrazinothiocarbonyl}-piperidine-4-carboxylic acid Synthesis was carried out in the same manner as in Synthetic Example 2 using methyl 1-{1-[5-(4-t-butylphenyl)-4-hydroxy-thiophen-3-yl]-ethylidene-hydrazinothiocarbonyl}-piperidine-4-carboxylate prepared above (yield 89%).
Morphology: dark brown solid
$^1$H-NMR (ppm in DMSO-d$_6$)
δ 1.22 (s, 9H), 1.57-1.61 (m, 2H), 1.88-1.92 (m, 2H), 2.36 (s, 3H), 4.53-4.58 (m, 2H), 7-41 (d, 2H, J=8.5 Hz), 7.67 (d, 2H, J=8.5 Hz), 7.85 (s, 1H), 10.25 (brs, 1H), 11.98 (brs, 1H)

Synthetic Example 15

Synthesis of 1-{1-[5-(3-chlorophenyl)-4-hydroxythiophen-3-yl]-ethylidene-hydrazinothiocarbonyl}-piperidine-4-carboxylic acid

Methyl 1-{1-[5-(3-Chlorophenyl)-4-hydroxythiophen-3-yl]-ethylidene-hydrazinothiocarbonyl}-piperidine-4-carboxylate Synthesis was carried out in the same manner as in Synthetic Example 1 using 1-[5-(3-chlorophenyl)-4-hydroxythiopen-3-yl]ethanone (prepared by the method disclosed in WO2004/108683) and methyl 1-hydrazinothiocarbonylpiperidine-4-carboxylate prepared in Reference Synthetic Example 2 (yield 63%).
Morphology: pale yellow solid
LC/MS: condition 2, retention time 3.67 (min)
LC/MS (ESI$^+$) m/z; 452, 454 [M+1]$^+$
LC/MS (ESI$^-$) m/z; 450, 452 [M−1]$^-$

1-{1-[5-(3-Chlorophenyl)-4-hydroxythiophen-3-yl]-ethylidene-hydrazinothiocarbonyl}-piperidine-4-carboxylic acid Synthesis was carried out in the same manner as in Synthetic Example 2 using methyl 1-{1-[5-(3-chlorophenyl)-4-hydroxythiophen-3-yl]-ethylidene-hydrazinothiocarbonyl}-piperidine-4-carboxylate prepared above (yield 71%).
Morphology: pale yellow solid
LC/MS: condition 2, retention time 3.38 (min)
LC/MS (ESI$^+$) m/z; 438, 440 [M+1]$^+$
LC/MS (ESI$^-$) m/z; 436, 438 [M−1]$^-$

Synthetic Example 16

Synthesis of 1-{1-[4-hydroxy-1-methyl-5-(4-trifluoromethylphenyl)-1H-pyrazol-3-yl]-ethylidene-hydrazinothiocarbonyl}-piperidine-4-carboxylic acid

Methyl 1-{1-[4-hydroxy-1-methyl-5-(4-trifluoromethylphenyl)-1H-pyrazol-3-yl]-ethylidene-hydrazinothiocarbonyl}-piperidine-4-carboxylate Synthesis was carried out in the same manner as in Synthetic Example 1 using 1-[4-hydroxy-1-methyl-5-(4-trifluoromethylphenyl)-1H-pyrazol-3-yl]ethanone (prepared by the method disclosed in WO2004/108683) and methyl 1-hydrazinothiocarbonylpiperidine-4-carboxylate prepared in Reference Synthetic Example 2 (yield 70%).
Morphology: yellow solid
LC/MS: condition 1, retention time 4.12 (min)
LC/MS (ESI$^+$) m/z; 484 [M+1]$^+$
LC/MS (ESI$^-$) m/z; 482 [M−1]$^-$

1-{1-[4-Hydroxy-1-methyl-5-(4-trifluoromethylphenyl)-1H-pyrazol-3-yl]-ethylidene-hydrazinothiocarbonyl}-piperidine-4-carboxylic acid Synthesis was carried out in the same manner as in Synthetic Example 2 using methyl 1-{1-[4-hydroxy-1-methyl-5-(4-trifluoromethylphenyl)-1H-pyrazol-3-yl]-ethylidene-hydrazinothiocarbonyl}-piperidine-4-carboxylate prepared above (yield 85%).
Morphology: pale yellow solid
LC/MS: condition 1, retention time 3.69 (min)
LC/MS (ESI$^+$) m/z; 470 [M+1]$^+$
LC/MS (ESI$^-$) m/z; 468 [M−1]$^-$

Synthetic Example 17

Synthesis of 1-{1-[5-(3,4-dichlorophenyl)-4-hydroxy-1-methyl-1H-pyrazol-3-yl]-ethylidene-hydrazinothiocarbonyl}-piperidine-4-carboxylic acid

Methyl 1-{1-[5-(3,4-dichlorophenyl)-4-hydroxy-1-methyl-1H-pyrazol-3-yl]-ethylidene-hydrazinothiocarbonyl}-piperidine-4-carboxylate Synthesis was carried out in the same manner as in Synthetic Example 1 using 1-[5-(3,4-dichlorophenyl)-4-hydroxy-1-methyl-1H-pyrazol-3-yl]ethanone (prepared by the method disclosed in WO2004/108683) and methyl 1-hydrazinothiocarbonylpiperidine-4-carboxylate prepared in Reference Synthetic Example 2 (yield 61%).
Morphology: pale pink solid
LC/MS: condition 1, retention time 4.30 (min)
LC/MS (ESI$^+$) m/z; 484, 486 [M+1]$^{+LC/MS\ (ESI-)}$) m/z; 482, 484 [M−1]$^-$

1-{1-[5-(3,4-Dichlorophenyl)-4-hydroxy-1-methyl-1H-pyrazol-3-yl]-ethylidene-hydrazinothiocarbonyl}-piperidine-4-carboxylic acid Synthesis was carried out in the same manner as in Synthetic Example 2 using methyl 1-{1-[5-(3,4-dichlorophenyl)-4-hydroxy-1-methyl-1H-pyrazol-3-yl]-ethylidene-hydrazinothiocarbonyl}-piperidine-4-carboxylate prepared above (yield 89%).
Morphology: pale yellow solid
LC/MS: condition 1, retention time 3.79 (min)
LC/MS (ESI$^+$) m/z; 470, 472 [M+1]$^+$
LC/MS (ESI$^-$) m/z; 468, 470 [M−1]$^-$

Synthetic Example 18

Synthesis of 1-{1-[5-(3,4-dichlorophenyl)-4-hydroxythiophen-3-yl]-ethylidene-hydrazinothiocarbonyl}-piperidine-3-carboxylic acid

Ethyl 1-{1-[5-(3,4-dichlorophenyl)-4-hydroxythiophen-3-yl]-ethylidene-hydrazinothiocarbonyl}-piperidine-3-carboxylate Synthesis was carried out in the same manner as in Synthetic Example 1 using ethyl 1-hydrazionothiocarbonylpiperidine-3-carboxylate prepared in Reference Synthetic Example 3 (yield 52%).
Morphology: white solid

1-{1-[5-(3,4-dichlorophenyl)-4-hydroxythiophen-3-yl]-ethylidene-hydrazinothiocarbonyl}-piperidine-3-carboxylic acid Synthesis was carried out in the same manner as in Synthetic Example 2 using ethyl 1-{1-[5-(3,4-dichlorophenyl)-4-hydroxythiophen-3-yl]-ethylidene-hydrazinothiocarbonyl}-piperidine-3-carboxylate prepared above (yield 67%).
Morphology: white solid
LC/MS: condition 5, retention time 4.98 (min)
LC/MS (ESI$^+$) m/z; 472 [M+1]$^+$
LC/MS (ESI$^-$) m/z; 470 [M−1]$^-$

Synthetic Example 19

Synthesis of 1-{1-[5-(3,4-dichlorophenyl)-4-hydroxythiophen-3-yl]-ethylidene-hydrazinothiocarbonyl}-piperidine-4-carboxylic acid diethylamide Synthesis was carried out in the same manner as in Synthetic Example 1 using 1-hydrazionothiocarbonylpiperidine-4-carboxylic acid diethylamide prepared in Reference Synthetic Example 4 (yield 23%).
Morphology: white solid
LC/MS: condition 5, retention time 3.80 (min)
LC/MS (ESI$^+$) m/z; 527 [M+1]$^+$

Synthetic Example 20

Synthesis of 1-{1-[5-(3,4-dichlorophenyl)-4-hydroxythiophen-3-yl]-ethylidene-hydrazinothiocarbonyl}-piperidin-4-ol Synthesis was carried out in the same manner as in Synthetic Example 1 using 1-hydrazinothiocarbonylpiperidin-4-ol prepared in Reference Synthetic Example 5 (yield 21%).
Morphology: white solid
LC/MS: condition 5, retention time 4.88 (min)
LC/MS (ESI$^+$) m/z; 444 [M+1]$^+$
LC/MS (ESI$^-$) m/z; 442 [M−1]$^-$

Synthetic Example 21

Synthesis of 1-{1-[5-(3,4-dichlorophenyl)-4-hydroxythiophen-3-yl]-ethylidene-hydrazinothiocarbonyl}-piperidin-3-ol Synthesis was carried out in the same manner as in Synthetic Example 1 using crude 1-hydrazinothiocarbonylpiperidin-3-ol prepared in Reference Synthetic Example 6 (yield 53%).
Morphology: pale yellow solid
LC/MS: condition 5, retention time 4.92 (min)
LC/MS (ESI$^+$) m/z; 444 [M+1]$^+$
LC/MS (ESI$^-$) m/z; 442 [M−1]$^-$

Synthetic Example 22

Synthesis of 1-{1-[5-(3,4-dichlorophenyl)-4-hydroxythiophen-3-yl]-ethylidene-hydrazinothiocarbonyl}-piperidine-4-methanol Synthesis was carried out in the same manner as in Synthetic Example 1 using crude 1-hydrazinothiocarbonylpiperidine-4-methanol prepared in Reference Synthetic Example 7 (yield 22%).
Morphology: white solid
LC/MS: condition 5, retention time 4.98 (min)
LC/MS (ESI$^+$) m/z; 458 [M+1]$^+$
LC/MS (ESI$^-$) m/z; 456 [M−1]$^-$

Synthetic Example 23

Synthesis of 1-(2-{1-[5-(3,4-dichlorophenyl)-4-hydroxythiophen-3-yl]-ethylidene}-hydrazinocarbonothioyl)amino-3-methoxypropane Synthesis was carried out in the same manner as in Synthetic Example 3 using 3-methoxypropyl isothiocyanate (yield 19%).
Morphology: pale yellow solid
LC/MS: condition 5, retention time 5.22 (min)
LC/MS (ESI$^+$) m/z; 432 [M+1]$^+$
LC/MS (ESI$^-$) m/z; 430 [M−1]$^-$

Synthetic Example 24

Synthesis of 1-{1-[5-(4-bromophenyl)-4-hydroxythiophen-3-yl]-ethylidene-hydrazinothiocarbonyl}-piperidine-4-carboxylic acid 4-picolylamide To 1-{1-[5-(4-bromophenyl)-4-hydroxythiophen-3-yl]-ethylidene-hydrazinothiocarbonyl}-piperidine-4-carboxylic acid (84 mg, 0.17 mmol) prepared in Synthetic Example 9, dimethylformamide (2 mL) and 1-[3-(dimethylamino)propyl]-3-ethylcarbodiimide hydrochloride (66 mg, 0.25 mmol) and HOBt (47 mg, 0.25 mmol) were added, and then dimethylformamide (2.5 mL) and diisopropylethylamine (91 μl, 0.52 mmol) were added. The resulting solution was stirred at room temperature for 1 hour and then stirred with a dimethylformamide solution (1.5 mL) of 4-picolylamine (47 mg, 0.43 mmol) for 24 hours. After addition of water, the reaction mixture was filtered, and the filter cake was dried and washed with isopropyl alcohol repeatedly to give the desired product (yield 34%).
Morphology: pale yellow solid
LC/MS: condition 1, retention time 3.05 (min)
LC/MS (ESI$^+$) m/z; 572, 574 [M+1]$^+$
LC/MS (ESI$^-$) m/z; 570, 572 [M−1]$^-$

Synthetic Example 25

Synthesis of 1-{1-[5-(4-bromophenyl)-4-hydroxythiophen-3-yl]-ethylidene-hydrazinothiocarbonyl}-piperidine-4-carboxylic acid 2-picolylamide Synthesis was carried out in the same manner as in Synthetic Example 24 using 2-picolylamine (yield 22%).
Morphology: pale yellow solid
LC/MS: condition 1, retention time 3.62 (min)
LC/MS (ESI$^+$) m/z; 572, 574 [M+1]$^+$
LC/MS (ESI$^-$) m/z; 570, 572 [M−1]$^-$

Synthetic Example 26

Synthesis of 1-{1-[5-(4-bromophenyl)-4-hydroxythiophen-3-yl]-ethylidene-hydrazinothiocarbonyl}-piperidine-4-carboxylic acid 3-picolylamide Synthesis was carried out in the same manner as in Synthetic Example 24 using 3-picolylamine (yield 4%).
Morphology: yellow solid
LC/MS: condition 1, retention time 3.25 (min)
LC/MS (ESI$^+$) m/z; 572, 574 [M+1]$^+$
LC/MS (ESI$^-$) m/z; 570, 572 [M−1]$^-$

Synthetic Example 27

Synthesis of 2-[4-{1-[5-(3,4-dichlorophenyl)-4-hydroxythiophen-3-yl]-ethylidene-hydrazinothiocarbonyl}-piperazin-1-yl]acetic acid Methyl 2-[4-{1-[5-(3,4-dichlorophenyl)-4-hydroxythiophen-3-yl]-ethylidene-hydrazinothiocarbonyl}-piperazin-1-yl]acetate Methyl 2-[4-hydrazinothiocarbonylpiperazin-1-yl]acetate (356 mg, 1.52 mmol) prepared in Reference Synthetic Example 10 and 2-(3,4-dichlorophenyl)-3-hydroxy-4-methylcarbonylthiophene (147 mg, 0.512 mmol) were stirred with dimethylformamide (4 mL) and concentrated hydrochloric acid (42.6 μL, 1.52 mmol) at room temperature to 60° C. for 5 days. After addition of water, the reaction mixture was filtered, and the filter cake was dried. The filter cake was mixed with chloroform and filtered, and the filtrate was concentrated then mixed with chloroform, isopropyl alcohol and n-hexane and filtered. The filter cake was dried to give the crude desired product (yield 18%). The crude product was used directly for the next reaction.

LC/MS: condition 1, retention time 3.97 (min)
LC/MS (ESI$^+$) m/z; 501, 503 [M+1]$^+$
LC/MS (ESI$^+$ m/z; 499, 501 [M−1]$^−$ Synthesis of 2-[4-{1-[5-(3,4-dichlorophenyl)-4-hydroxythiophen-3-yl]-ethylidene-hydrazinothiocarbonyl}-piperazin-1-yl]acetic acid The procedure in Synthetic Example 2 was followed using methyl 2-[4-{1-[5-(3,4-dichlorophenyl)-4-hydroxythiophen-3-yl]-ethylidene-hydrazinothiocarbonyl}-piperazin-1-yl]acetate to give the crude desired product. The crude product was washed with chloroform to give the desired product (yield 11%).

Morphology: pale yellow solid
LC/MS: condition 1, retention time 3.60 (min)
LC/MS (ESI$^+$) m/z; 487, 489 [M+1]$^+$
LC/MS (ESI$^−$) m/z; 485, 487 [M−1]$^−$ Synthetic Example 28

Synthesis of 2-[4-{1-[5-(4-bromophenyl)-4-hydroxythiophen-3-yl]-ethylidene-hydrazinothiocarbonyl}-piperazin-1-yl]acetic acid Methyl 2-[4-{1-[5-(4-bromophenyl)-4-hydroxythiophen-3-yl]-ethylidene-hydrazinothiocarbonyl}-piperazin-1-yl]acetate The condensation procedure in Synthetic Example 27 was followed using 2-(4-bromophenyl)-3-hydroxy-4-methylcarbonylthiophene to give the crude desired product (yield 57%). The crude product was used directly for the next reaction.

Morphology: pale yellow solid

2-[4-{1-[5-(4-bromophenyl)-4-hydroxythiophen-3-yl]-ethylidene-hydrazinothiocarbonyl}-piperazin-1-yl]acetic acid The hydrolysis procedure in Synthetic Example 27 was followed using methyl 2-[4-{1-[5-(4-bromophenyl)-4-hydroxythiophen-3-yl]-ethylidene-hydrazinothiocarbonyl}-piperazin-1-yl]acetate to give the desired product (yield 43%).

Morphology: pale yellow solid
LC/MS: condition 1, retention time 3.45 (min)
LC/MS (ESI$^+$) m/z; 497, 499 [M+1]$^+$.
LC/MS (ESI$^−$) m/z; 495, 497 [M−1]$^−$ Synthetic Example 29

Synthesis of 3-[4-{1-[5-(4-bromophenyl)-4-hydroxythiophen-3-yl]-ethylidene-hydrazinothiocarbonyl}-piperazin-1-yl]propionic acid Methyl 3-[4-{1-[5-(4-bromophenyl)-4-hydroxythiophen-3-yl]-ethylidene-hydrazinothiocarbonyl}-piperazin-1-yl]propionate The condensation procedure in Synthetic Example 27 was followed using ethyl 3-[4-hydrazinothiocarbonylpiperazin-1-yl]propionate prepared in Reference Synthetic Example 11 to give the crude desired product (yield 13%). The crude product was used directly for the next reaction.

LC/MS: condition 1, retention time 3.05 (min)
LC/MS (ESI$^+$) m/z; 539, 541 [M+1]$^+$
LC/MS (ESI$^−$) m/z; 537, 539 [M−1]$^−$ 3-[4-{1-[5-(4-bromophenyl)-4-hydroxythiophen-3-yl]-ethylidene-hydrazinothiocarbonyl}-piperazin-1-yl]propionic acid The hydrolysis procedure in Synthetic Example 2 was followed using methyl 3-[4-{1-[5-(4-bromophenyl)-4-hydroxythiophen-3-yl]-ethylidene-hydrazinothiocarbonyl}-piperazin-1-yl]propionate and ethanol as the solvent to give the desired product (yield 55%).

Morphology: pale yellow solid
LC/MS: condition 1, retention time 3.07 (min)
LC/MS (ESI$^+$) m/z; 511, 513 [M+1]$^+$
LC/MS (ESI$^−$) m/z; 509, 511 [M−1]$^−$ The structural formulae of the compounds obtained in the Synthetic Examples are given below.

REF. SYN. EX. 1

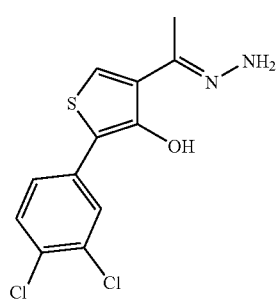

REF. SYN. EX. 2

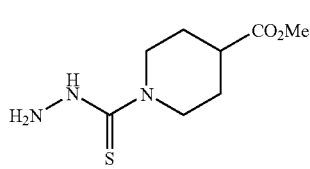

REF. SYN. EX. 3

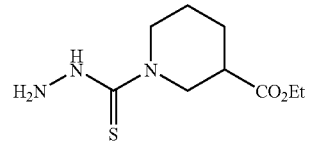

REF. SYN. EX. 4
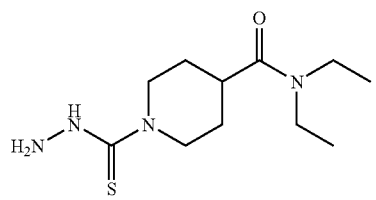
REF. SYN. EX. 5
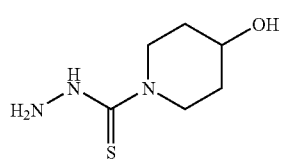
REF. SYN. EX. 6
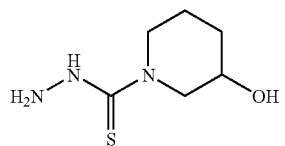
REF. SYN. EX. 7
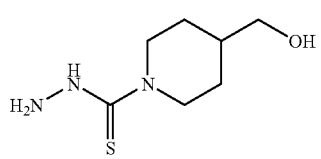
REF. SYN. EX. 8
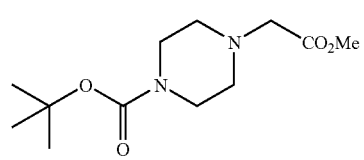
REF. SYN. EX. 9
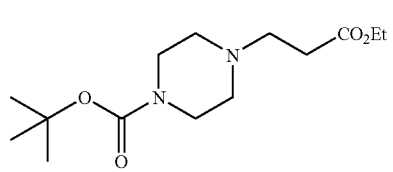
REF. SYN. EX. 10
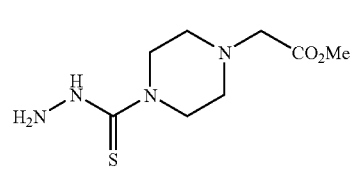
REF. SYN. EX. 11
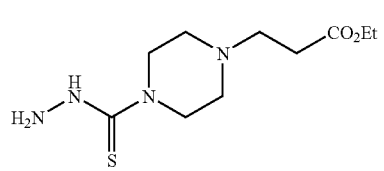
SYN. EX. 1
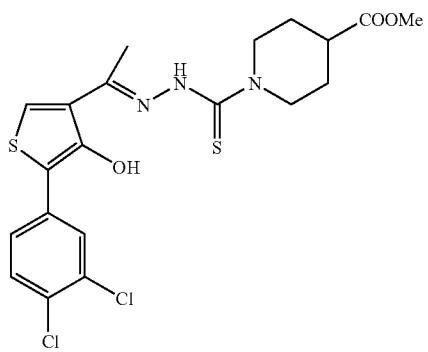
SYN. EX. 2
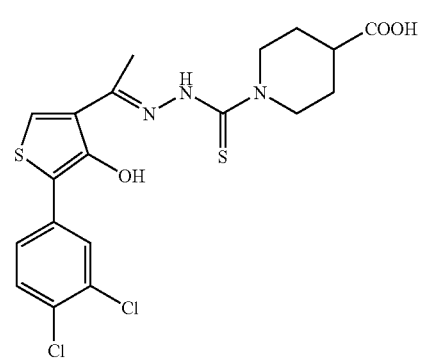
SYN. EX. 3
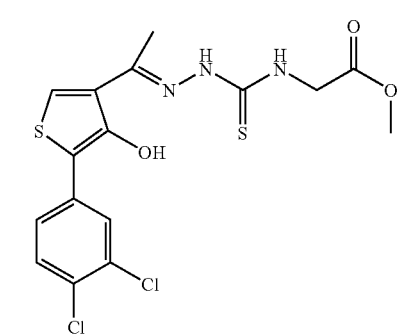
SYN. EX. 4
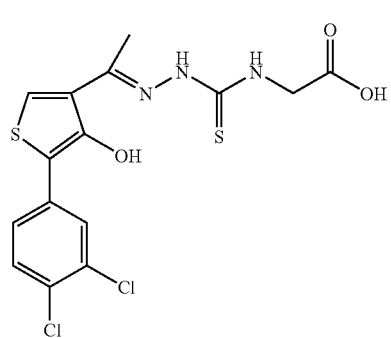

SYN. EX. 5
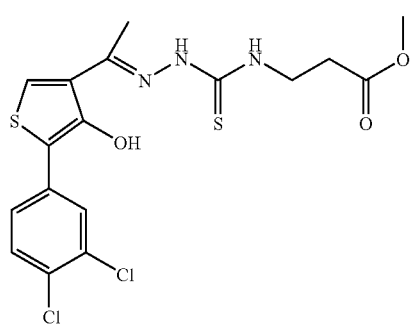
SYN. EX. 6
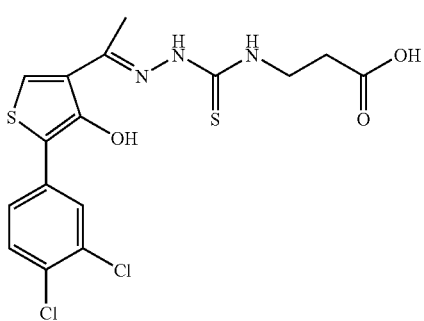
SYN. EX. 7
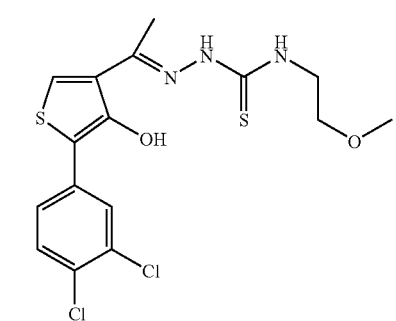
SYN. EX. 8
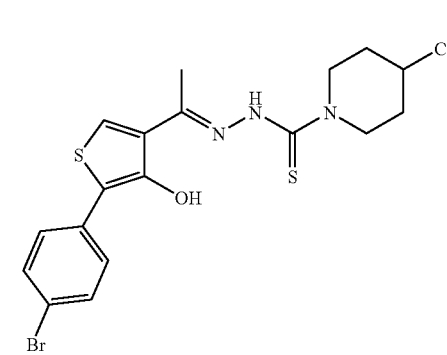
SYN. EX. 9
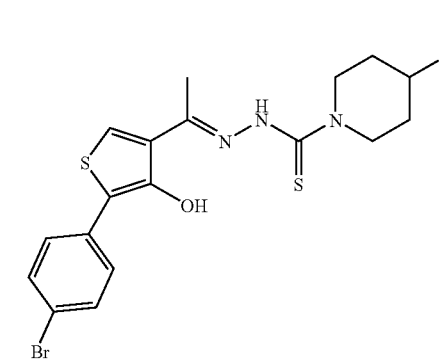
SYN. EX. 10
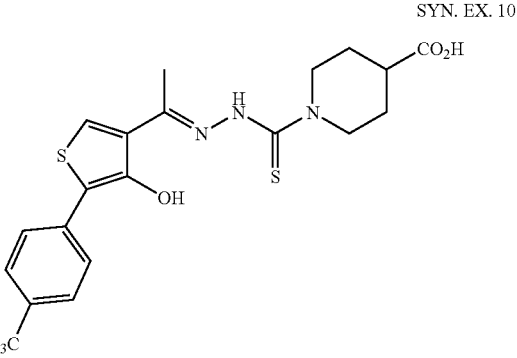
SYN. EX. 11
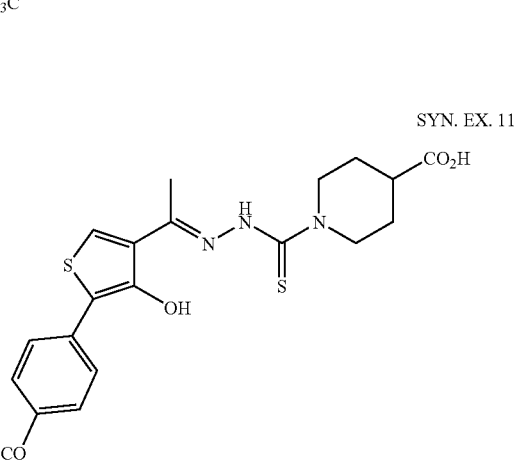
SYN. EX. 12
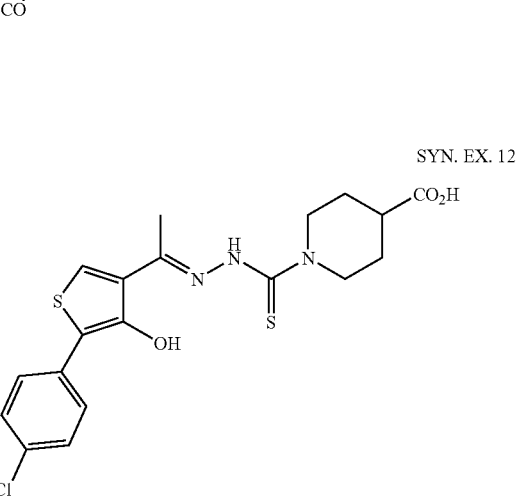
SYN. EX. 13
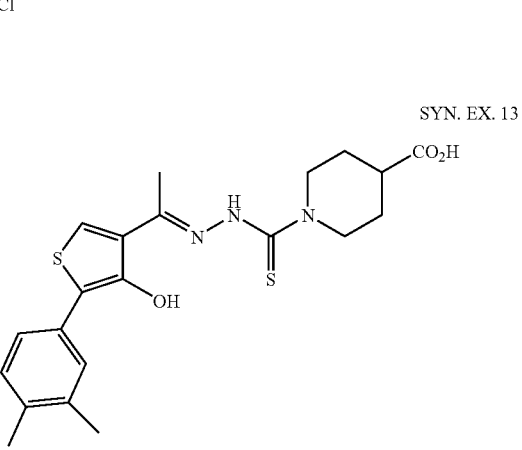

-continued
SYN. EX. 14
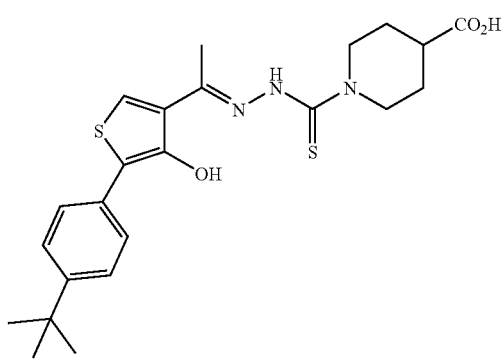
SYN. EX. 15
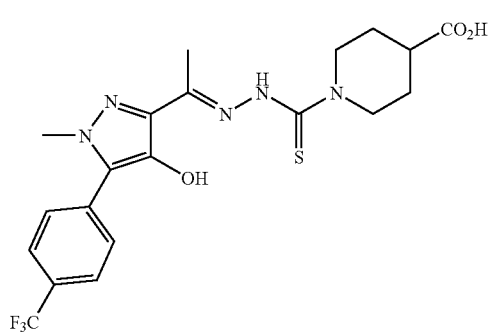
SYN. EX. 16
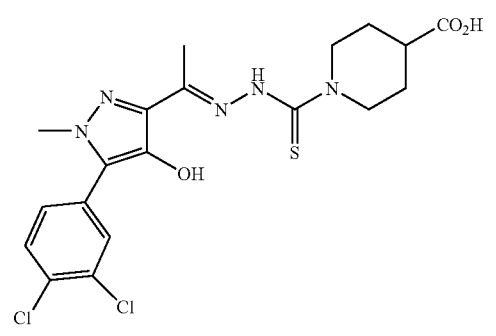
SYN. EX. 17
-continued
SYN. EX. 18
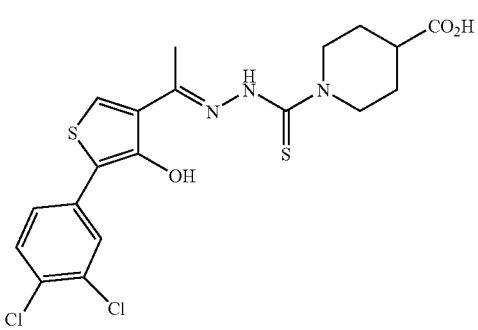
SYN. EX. 19
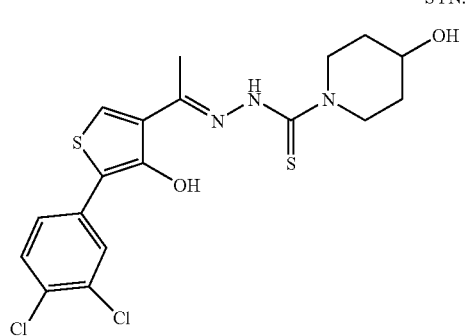
SYN. EX. 20
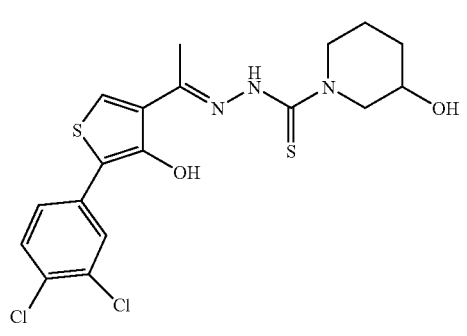
SYN. EX. 21

433
-continued
SYN. EX. 22
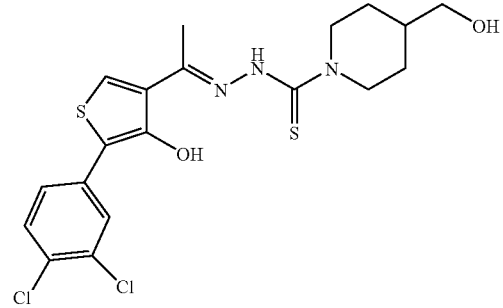
SYN. EX. 23
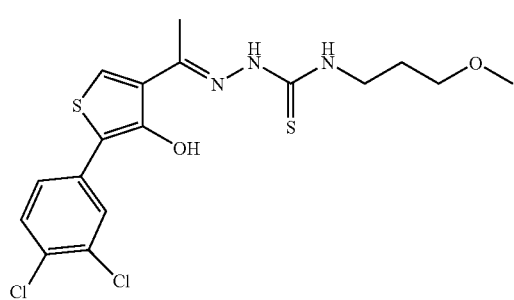
SYN. EX. 24
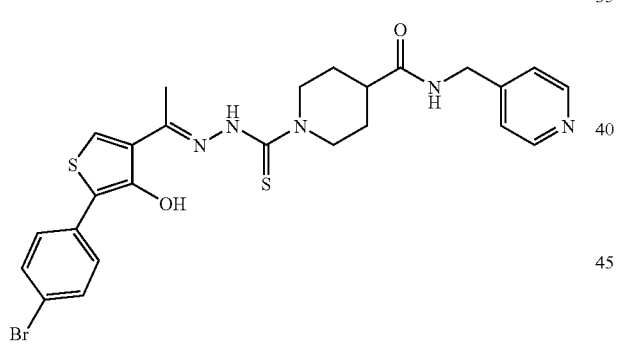
SYN. EX. 25
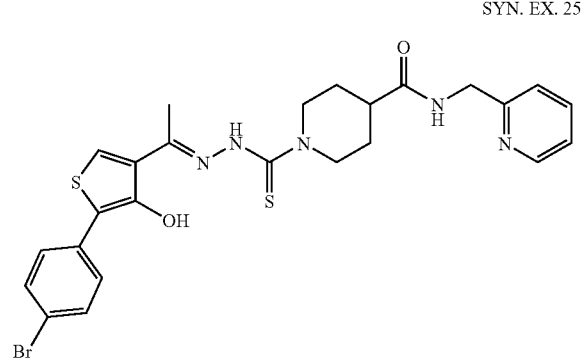
434
-continued
SYN. EX. 26
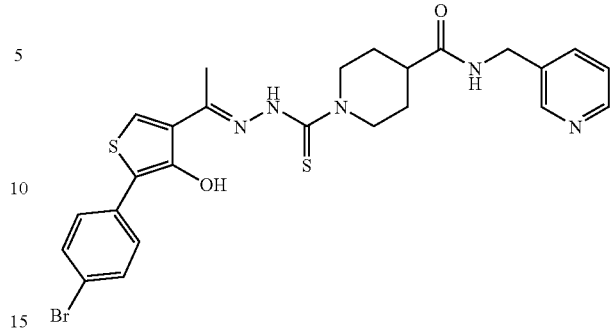
SYN. EX. 27
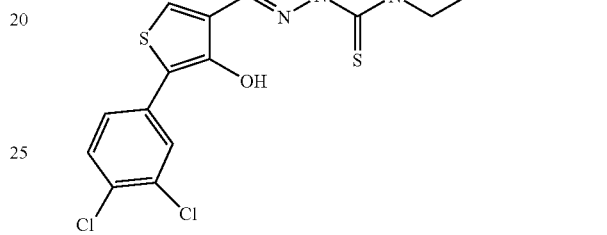
SYN. EX. 28
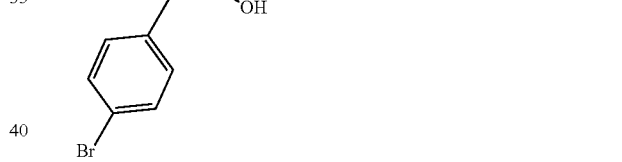
SYN. EX. 29
Assay Example 1
Stimulation of Proliferation of a Thrombopoietin (TPO)-Dependent Cell Line
The reactivity of the compound of Synthetic Example 4 of the present invention with thrombopoietin (TPO) receptor was assayed using a human leukemic cell line, UT7/EPO-mpl.

(1) Cells and Cell Culture

UT7/EPO-mpl is a stable transformed cell line obtained by introducing into human leukemic cell line UT7/EPO a vector that induces expression of human TPO receptor (c-mp1) under control of cytomegalovirus immediate-early promoter by the method of Takatoku et al. (J. Biol. Chem., 272:7259-7263 (1997)). Proliferation of this cell line is stimulated by TPO, while its mother cell line UT7/EPO exhibits no response to TPO. These two cell lines were subcultured in Iscove's modified Dulbecco's medium (IMDM; GIBCO) containing 10% fetal bovine serum (FBS; Thermo Electron or BioWest) using a $CO_2$ incubator (5% $CO_2$, 37° C.).

(2) Cell Proliferation Assay

The subcultured cells described above were washed twice with phosphate buffered saline (PBS) and suspended in IMDM containing 10% FBS at a cell density of $6\times10^4$ cells/ml. The cell suspension was transferred to a 96-well tissue culture plate (CORNING) in 100-µl aliquots. Then either TPO (Pepro Tech EC) or the compound of Synthetic Example 4 dissolved in dimethyl sulfoxide (DMSO) was diluted 83-fold with IMDM containing 10% FBS and added to the aforementioned cell suspension in 20-µl aliquots. The cell suspension was incubated in a $CO_2$ incubator (5% $CO_2$, 37° C.) for 4 days. Cell proliferation was assayed using WST-8 reagent (Kishida Chemical Co., Ltd.) according to instructions by the manufacturer. A 10-µl aliquot of 5 mM WST-8 reagent solution was added to each well of the tissue culture plate, and the plate was incubated at 37° C. for 4 h. The formazan pigment generated was detected by measuring the absorbance at 450 nm with a 96-well microplate reader (Nihon Molecular Devices, Spectramax 190). FIG. 1 shows the results with UT7/EPO-mpl cells, while FIG. 2 shows data obtained with UT7/EPO cells expressing no TPO receptor.

Figure 2:
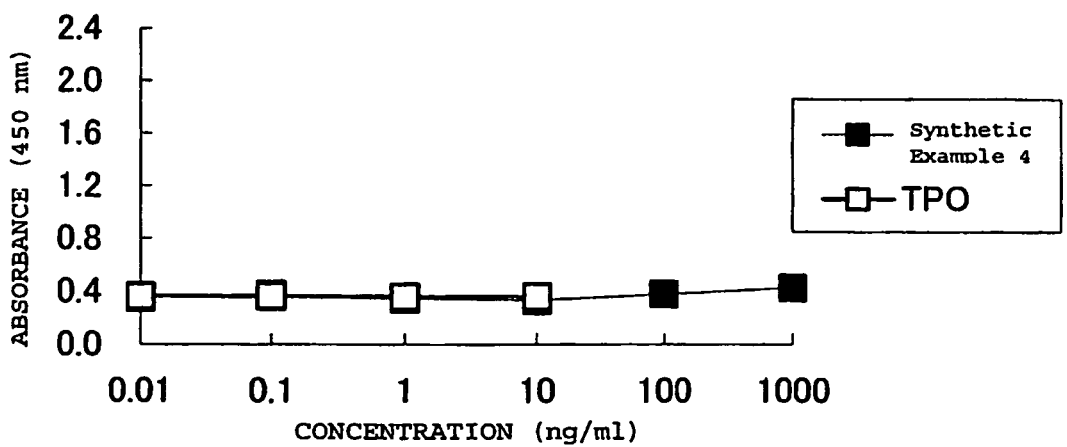
FIG. 2 shows the proliferation of UT7/EPO cells when stimulated by the compound of the present invention (Synthetic Example 4).

FIG. 1 demonstrates that proliferation of TPO-responsive UT7/EPO-mpl cells was stimulated by the compound of Synthetic Example 4 in a concentration-dependent manner, while no effect of this compound on proliferation was observed with UT7/EPO, the mother cell line, as shown in FIG. 2. These results indicate that the compound of Synthetic Example 4 of the present invention acts on the TPO receptor selectively as an activator.

Assay Example 2

The compounds of the following Synthetic Examples were tested according to the method of Assay Example 1 to determine the concentration of each compound that yields a growth rate corresponding to 50% of the growth of human leukemic cell line UT-7/EPO-mpl observed in the presence of 10 ng/ml TPO ($EC_{50}$). The results are summarized in Table 4.

TABLE 4

| SYNTHETIC EXAMPLES NO. | $EC_{50}$ (ng/mL) |
|---|---|
| 1 | 31 |
| 2 | 3.2 |
| 3 | 24 |
| 4 | 5.6 |
| 5 | 30 |
| 6 | 14 |
| 7 | 28 |
| 8 | 25 |
| 9 | 2.3 |
| 10 | 2.7 |
| 11 | 2.9 |
| 12 | 2.1 |
| 13 | 2.6 |

TABLE 4-continued

| SYNTHETIC EXAMPLES NO. | $EC_{50}$ (ng/mL) |
|---|---|
| 14 | 2.6 |
| 15 | 2.6 |
| 16 | 3.8 |
| 17 | 7.8 |
| 18 | 22 |
| 19 | 26 |
| 20 | 3.1 |
| 21 | 23 |
| 22 | 21 |
| 23 | 33 |

Formulation Example 1

A granule preparation containing the following ingredients is prepared.

| Ingredients | |
|---|---|
| Compound represented by the formula (1) | 10 mg |
| Lactose | 700 mg |
| Corn Starch | 274 mg |
| HPC-L | 16 mg |
| | 1000 mg |

A compound represented by the formula (1) and lactose are sifted through a 60-mesh sieve. Corn starch is sifted though a 120-mesh sieve. They are mixed in a V-type blender. The powder mixture is kneaded with a low-viscosity hydroxypropylcellulose (HPC-L) aqueous solution, granulated (extrusion granulation, die size 0.5-1 mm) and dried. The resulting dry granules are sifted through a shaking sieve (12/60 mesh) to obtain a granule preparation.

Formulation Example 2

A powder preparation for capsulation containing the following ingredients is prepared.

| Ingredients | |
|---|---|
| Compound represented by the formula (1) | 10 mg |
| Lactose | 79 mg |
| Corn Starch | 10 mg |
| Magnesium Stearate | 1 mg |
| | 100 mg |

A compound represented by the formula (1) and lactose are sifted through a 60-mesh sieve. Corn starch is sifted though a 120-mesh sieve. They are mixed with magnesium stearate in a V-type blender. The 10% powder is put in hard gelatin capsules No. 5, 100 mg each.

Formulation Example 3

A granule preparation for capsulation containing the following ingredients is prepared.

| Ingredients | |
|---|---|
| Compound represented by the formula (1) | 15 mg |
| Lactose | 90 mg |
| Corn Starch | 42 mg |
| HPC-L | 3 mg |
| | 150 mg |

A compound represented by the formula (1) and lactose are sifted through a 60-mesh sieve. Corn starch is sifted though a 120-mesh sieve. They are mixed in a V-type blender. The powder mixture is kneaded with a low-viscosity hydroxypropylcellulose (HPC-L) aqueous solution, granulated and dried. The resulting dry granules are sifted through a shaking sieve (12/60 mesh). The granules are put in hard capsules No. 4, 150 mg each.

Formulation Example 4

A tablet preparation containing the following ingredients is prepared.

| Ingredients | |
|---|---|
| Compound represented by the formula (1) | 10 mg |
| Lactose | 90 mg |
| Microcrystalline cellulose | 30 mg |
| Magnesium Stearate | 5 mg |
| CMC-Na | 15 mg |
| | 150 mg |

A compound represented by the formula (1), lactose, microcrystalline cellulose and CMC-Na (carboxymethylcellulose sodium salt) are sifted through a 60-mesh sieve and mixed. The powder mixture is mixed with magnesium stearate to give a bulk powder mixture. The powder mixture is compressed directly into 150 mg tablets.

Formulation Example 5

An intravenous preparation is prepared as follows.

| | |
|---|---|
| Compound represented by the formula (1) | 100 mg |
| Saturated Fatty Acid Glyceride | 1000 ml |

Solutions having the above-mentioned composition are usually administered to a patient intravenously at a rate of 1 ml per 1 minute.

INDUSTRIAL APPLICABILITY

The compounds of the present invention which have affinity for thrombopoietin receptor and act as thrombopoietin receptor agonists are useful as preventive, therapeutic and improving agents for diseases against which activation of the thrombopoietin receptor is effective, especially as drugs for hematological disorders accompanied by abnormal platelet count and as drugs for diseases treated or prevented by stimulating differentiation and proliferation of vascular endothelial cells and endothelial progenitor cells, and are useful as medicines.

The invention claimed is:

1. A compound represented by the formula (1)

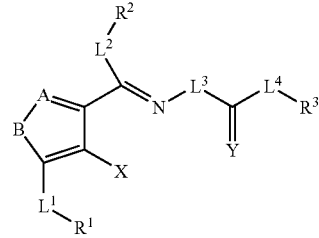

(1)

wherein A is a nitrogen atom or $CR^4$ wherein $R^4$ is a hydrogen atom, a hydroxyl group, a thiol group, an amino group, a formyl group, a halogen atom, a nitro group, a cyano group, a $C_{1-10}$ alkyl group, a $C_{2-6}$ alkenyl group, a $C_{2-6}$ alkynyl group, a $C_{1-10}$ alkylcarbonylamino group, a mono- or di-$C_{1-10}$ alkylamino group, a $C_{1-10}$ alkoxy group, a $C_{2-14}$ aryl group or a $C_{2-14}$ aryloxy group, B is a sulfur atom or $NR^9$ wherein $R^9$ is a $C_{1-10}$ alkyl group, a $C_{2-6}$ alkenyl group, a $C_{2-6}$ alkynyl group, a $C_{1-10}$ alkoxycarbonyl group, a $C_{1-10}$ alkylcarbonyl group a $C_{2-14}$ aryl group or $C_{2-14}$ aryloxy group wherein the $C_{1-10}$ alkyl group, the $C_{2-6}$ alkenyl group, the $C_{2-6}$ alkynyl group, the $C_{1-10}$ alkoxycarbonyl group and the $C_{1-10}$ alkylcarbonyl group may be optionally substituted with one or more substituents selected from the group consisting of a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group, $R^1$ is a $C_{2-14}$ aryl group wherein the $C_{2-14}$ aryl group may be substituted with one or more substituents selected from the group consisting of a halogen atom, a carboxyl group, a nitro group, a formyl group, a cyano group, a hydroxyl group, a protected hydroxyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyl group, a $C_{1-10}$ alkylcarbonyloxy group, and a $C_{1-10}$ alkoxycarbonyl group, wherein the $C_{1-10}$ alkyl group, the $C_{2-6}$ alkenyl group, the $C_{2-6}$ alkynyl group, the $C_{1-10}$ alkoxy group, the $C_{1-10}$ alkylcarbonyl group, the $C_{1-10}$ alkylcarbonyloxy groups and the $C_{1-10}$ alkoxycarbonyl group may be optionally substituted with one or more substituents selected from the group consisting of a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group, $L^1$ is a bond, X is OH, $R^2$ is a hydrogen atom or a $C_{1-10}$ alkyl group, wherein the $C_{1-10}$ alkyl group may be optionally substituted with one or more halogen atoms, $L^2$ is a bond, $L^3$ is NH, Y is an oxygen atom or a sulfur atom, $L^4$ is a bond or NH, and when $L^4$ is a bond, $R^3$ is a $C_{2-9}$ heterocyclic group, wherein the $C_{2-9}$ heterocyclic group may be optionally substituted with one or more substituents independently represented by $W^9(CW^{10}W^{11})_{m11}W^{12}$, $W^9$, $W^{10}$, $W^{11}$, $W^{12}$ and m11 are the same as $W^1$, $W^2$, $W^3$, $W^8$ and m, respectively, $W^1$ is $(CR^{24}R^{25})_n$, an oxygen atom, a sulfur atom or $NR^{36}$, each of $R^{24}$ and $R^{25}$ is independently a hydrogen atom or a $C_{1-6}$ alkyl group or $R^{24}$ and $R^{25}$ mean, together with each other, O=, or S= and n is 0, 1, 2 or 3

$R^{36}$ is a hydrogen atom, a $C_{1-6}$ alkyl group, a formyl group or a $C_{1-6}$ alkylcarbonyl group, each of $W^2$ and $W^3$ is independently a hydrogen atom or a $C_{1-3}$ alkyl group, m is 0, 1, 2 or 3, $W^8$ is a hydroxyl group, a protected hydroxyl group, a thiol group, an amino group, a formyl group, a halogen atom, a nitro group, a cyano group, a $C_{1-10}$ alkyl group, a $C_{2-6}$ alkenyl group, a $C_{2-6}$ alkynyl group, a $C_{2-9}$ heterocyclic group, a $C_{1-10}$ alkoxy group, a $C_{1-10}$ alkylcarbonyloxy group, a $C_{1-10}$ alkylcarbonylamino group, a mono- or di-$C_{1-10}$ alkylamino group, $SO_2R^{28a}$, $SOR^{28a}$, $COR^{28a}$, a tetrazole group or a phosphonic acid group $R^{28a}$ is the same as $R^{28}$ $R^{28}$ is a hydroxyl group, a protected hydroxyl group, a $C_{1-10}$ alkyl group, a $C_{2-6}$ alkenyl group, a $C_{2-6}$ alkynyl group, a $C_{2-9}$ heterocyclic group, a $C_{1-10}$ alkoxy group, a $C_{2-14}$ aryl group, a $C_{2-14}$ aryloxy group or $NR^{29}R^{30}$ each of $R^{29}$ and $R^{30}$ is independently a hydrogen atom, a hydroxyl group, a protected hydroxyl group, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylsulfonyl group, a $C_{1-10}$ alkylcarbonyl group or a $C_{2-14}$ aryl group, wherein the $C_{1-10}$ alkyl group, the $C_{2-6}$ alkenyl group, the $C_{2-6}$ alkynyl group, the $C_{1-10}$ alkoxy group, the $C_{1-10}$ alkylcarbonyloxy group, the $C_{1-10}$ alkoxycarbonyl group, the $C_{1-10}$ alkylsulfonyl group and the $C_{1-10}$ alkylcarbonyl group may be optionally substituted with one or more substituents selected from the group consisting of a carboxyl group, a nitro group, a cyano group, a halogen atom, a $C_{1-10}$ alkoxy group, $C_{1-10}$ a alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group, or $R^{29}$ and $R^{30}$, together with each are —$(CH_2)_{m3}$-G-$(CH_2)_{m4}$—

G is an oxygen atom, a sulfur atom, $CR^{31}R^{32}$ or $NR^{33}$ each of $R^{31}$ and $R^{32}$ is independently a hydrogen atom, a $C_{1-10}$ alkyl group, a $C_{2-14}$ aryl group, a $C_{1-10}$ alkoxy group, a $C_{2-14}$ aryloxy group, a hydroxyl group or a protected hydroxyl group, wherein $R^{33}$ is a hydrogen atom, a hydroxyl group, a formyl group, a $C_{1-10}$ alkyl group, a $C_{2-6}$ alkenyl group, $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylcarbonyl group or a $C_{2-14}$ aryl group, and each of m3 and m4 is independently an integer of from 0 to 5, provided that m3+m4 is 3, 4 or 5 or when $L^4$ is NH, $R^3$ is a $C_{1-10}$ alkyl group, a $C_{2-10}$ alkenyl group, a $C_{2-10}$ alkynyl group, a $C_{2-9}$ heterocyclic group, a $C_{1-10}$ alkoxy group, a $C_{1-10}$ thioalkyl group, a $C_{1-10}$ alkyl carbonyl group, a mono- or di-$C_{1-10}$ alkylamino group, a $C_{1-10}$ alkylcarbonyloxy group, a alkoxycarbonyl group or a $C_{1-10}$ alkylcarbonylamino group wherein the $C_{1-10}$ alkyl group, the $C_{2-10}$ alkenyl group, the $C_{2-10}$ alkynyl group, the $C_{2-9}$ heterocyclic group, the $C_{1-10}$ alkoxy group, the $C_{1-10}$ thioalkyl group, the $C_{1-10}$ alkylcarbonyl group, the mono- or di-$C_{1-10}$ alkylamino group, the $C_{1-10}$ alkylcarbonyloxy group, the $C_{1-10}$ alkoxycarbonyl group and the $C_{1-10}$ alkylcarbonylamino group may be optionally substituted with one or more substituents independently represented by $W^9(CW^{10}W^{11})_{m11}W^{12}$ wherein $W^9$, $W^{10}$, $W^{11}$, $W^{12}$ and m11 are the same as defined above, a tautomer, prodrug or pharmaceutically acceptable salt of the compound thereof.

2. The compound according to claim 1, wherein A is a nitrogen atom or $CR^4$ wherein $R^4$ is a hydrogen atom, B is a sulfur atom or $NR^9$ wherein $R^9$ is a $C_{1-10}$ alkyl group $R^1$ is a phenyl group wherein the phenyl group may be substituted with one or more substituents selected from the group consisting of a halogen atom, a $C_{1-10}$ alkyl group and a $C_{1-10}$ alkoxy group, wherein the $C_{1-10}$ alkyl groups and the $C_{1-10}$ alkoxy groups may be optionally substituted with one or more halogen atoms, $R^2$ is a $C_{1-10}$ alkyl group, Y is a sulfur atom, a tautomer or pharmaceutically acceptable salt of the compound thereof.

3. The compound according to claim 2, wherein A is $CR^4$ wherein $R^4$ is a hydrogen atom, B is a sulfur atom, a tautomer or pharmaceutically acceptable salt of the compound thereof.

4. The compound according to claim 3, wherein $L^4$ is a bond and $R^3$ is a $C_{2-9}$ heterocyclic group wherein the $C_{2-9}$ heterocyclic group may be optionally substituted with one or more substituents independently represented by $W^9(CW^{10}W^{11})_{m11}W^{12}$, $W^9$, $W^{10}$, $W^{11}$, $W^{12}$ and m11 are the same as $W^1$, $W^2$, $W^3$, $W^8$ and m, respectively $W^1$ is $(CR^{24}R^{25})_n$, each of $R^{24}$ and $R^{25}$ is independently a hydrogen atom or a $C_{1-6}$ alkyl, group or $R^{24}$ and $R^{25}$ mean, together with each other, O=, or S=, and n is 0 each of $W^2$ and $W^3$ is independently a hydrogen atom,
m is 0, 1, 2 or 3,
$W^8$ is a hydroxyl group or $COR^{28a}$
$R^{28a}$ is the same as $R^{28}$
$R^{28}$ is a hydroxyl group, a $C_{1-10}$ alkyl group, a $C_{1-10}$ alkoxy group or $NR^{29}R^{30}$
each of $R^{29}$ and $R^{30}$ is independently a hydrogen atom or a $C_{1-10}$ alkyl group,
wherein the $C_{1-10}$ alkyl group may be optionally substituted with a $C_{2-14}$ aryl group;
a tautomer or pharmaceutically acceptable salt of the compound thereof.

5. The compound according to claim 4, wherein $R^2$ is methyl group and
$R^3$ is a piperidinyl group, a piperazinyl group,
wherein the piperidinyl group and the piperazinyl group may be optionally substituted with one or more substituents independently represented by $W^9(CW^{10}W^{11})_{m11}W^{12}$,
$W^9$, $W^{10}$, $W^{11}$, $W^{12}$ and m11 are the same as $W^1$, $W^2$, $W^3$, $W^8$ and m, respectively
$W^1$ is $(CR^{24}R^{25})_n$, each of $R^{24}$ and $R^{25}$ is independently a hydrogen atom or a $C_{1-6}$ alkyl group or $R^{24}$ and $R^{25}$ mean, together with each other, O=, or S=, and n is 0
each of $W^2$ and $W^3$ is independently a hydrogen atom or a $C_{1-3}$ alkyl group,
m is 0, 1, 2 or 3,
$W^8$ is a hydroxyl group or $COR^{28a}$,
$R^{28a}$ is the same as $R^{28}$,
$R^{28}$ is a hydroxyl group, a $C_{1-10}$ alkyl group, a $C_{1-10}$ alkoxy group or $NR^{29}R^{30}$,
each of $R^{29}$ and $R^{30}$ is independently a hydrogen atom or a $C_{1-10}$ alkyl group,
wherein the $C_{1-10}$ alkyl group may be optionally substituted with a pyridiyl group,
a tautomer or pharmaceutically acceptable salt of the compound thereof.

6. The compound according to claim 5, wherein $R^1$ is a 3,4-dichlorophenyl group, a 4-t-butylphenyl group, a 3,4-dimethylphenyl group, a 4-trifluoromethylphenyl group, a 4-chlorophenyl group, a 4-bromophenyl group, a 4-trifluoromethoxyphenyl group or 3-chlorophenyl group and
$R^3$ is a piperidinyl group, or a piperazinyl group,
wherein the piperidinyl group and the piperazinyl group are substituted with a substituent selected from the group consisting of a methoxycarbonyl group, a carboxyl group, a hydroxyl group, a diethylaminocarbonyl group, a pyridylmethylaminocarbonyl group, a hydroxymethyl group, a carboxymethyl group and a carboxyethyl group;
a tautomer or pharmaceutically acceptable salt of the compound thereof.

7. The compound according to claim 6, wherein
$R^3$ is a piperidinyl group,
wherein the piperidinyl group is substituted with a carboxyl group,
a tautomer or pharmaceutically acceptable salt of the compound thereof.

8. The compound according to claim 3, wherein $L^4$ is NH, $R^3$ is a $C_{1-10}$ alkyl group,
wherein the $C_{1-10}$ alkyl group may be optionally substituted with one or more substituents independently represented by —$W^9(CW^{10}W^{11})_{m11}W^{12}$,
a tautomer, or pharmaceutically acceptable salt of the compound thereof.

9. The compound according to claim 8, wherein $R^1$ is a 3,4-dichlorophenyl group,
$R^2$ is methyl group, and
$R^3$ is a carboxymethyl group, a carboxyethyl group, metoxycarbonylmethyl group, metoxycarbonylethyl group, metoxyethyl group, metoxypropyl group,
a tautomer, or pharmaceutically acceptable salt of the compound thereof.

10. The compound according to claim 2, wherein A is a nitrogen atom,
B is $NR^9$
wherein $R^9$ is a $C_{1-10}$, alkyl group
$L^4$ is a bond and
$R^3$ is a $C_{2-9}$ heterocyclic group
wherein the $C_{2-9}$ heterocyclic group may be optionally substituted with one or more substituents independently represented by $W^9(CW^{10}W^{11})_{m11}W^{12}$,
a tautomer or pharmaceutically acceptable salt of the compound thereof.

11. The compound according to claim 10, wherein $R^1$ is a 3,4-dichlorophenyl group,
$R^2$ is methyl group and
$R^3$ is a piperidinyl group
wherein the piperidinyl group is substituted with a carboxyl group,
a tautomer, or pharmaceutically acceptable salt of the compound thereof.

12. The compound according to claim 1 wherein Y is an oxygen atom;
or a tautomer or pharmaceutically acceptable salt of the compound thereof.

13. The compound according to claim 3, wherein
$R^3$ is a $C_{2-9}$ heterocyclic group, which may be optionally substituted with one or more substituents selected from the group consisting of a hydroxyl group, an amino group, a carboxyl group, a phosphonic acid group, a sulfonic acid group, a carbamoyl group, a sulfamoyl group, a tetrazole group, a $C_{1-10}$ alkoxycarbonyl group, a $C_{1-10}$ alkoxy group, a $C_{1-10}$ thioalkyl group, a $C_{1-10}$ alkylcarbonyl group, a $C_{1-10}$ alkylcarbonyloxy group, a $C_{1-10}$ alkylcarbonylamino group and a mono- or di-$C_{1-10}$ alkylamino group;
or a tautomer or pharmaceutically acceptable salt of the compound.

14. The compound according to claim 3, wherein
$R^3$ is a $C_{2-9}$ heterocyclic group, which is substituted with a substituent selected from the group consisting of a hydroxyl group, an amino group, a carboxyl group, a phosphonic acid group, a sulfonic acid group, a carbamoyl group, a sulfamoyl group, a tetrazole group and a $C_{1-10}$ alkoxycarbonyl group; and with a substituent selected from the group consisting of a hydroxyl group, an amino group, a carboxyl group, a phosphonic acid group, a sulfonic acid group, a carbamoyl group, a sulfamoyl group, a tetrazole group, a $C_{1-10}$ alkoxycarbonyl group, a nitro group, a cyano group, a halogen atom, a $C_{1-10}$ alkyl group, a sulfamoyl group substituted with a $C_{1-10}$ alkyl group, a carbamoyl group substituted with a $C_{1-10}$ alkyl group and a $C_{1-10}$ alkylcarbonylamino group;
or a tautomer or pharmaceutically acceptable salt of the compound.

15. The compound according to claim 3, wherein
$R^3$ is a $C_{1-10}$ alkyl group or a $C_{2-10}$ alkenyl group, each of which may be optionally substituted with one or more substituents selected from the group consisting of a $C_{1-10}$ alkyl group, a $C_{2-10}$ alkenyl group, a $C_{1-10}$ alkoxy group, a $C_{1-10}$ thioalkyl group, a $C_{1-10}$ alkylcarbonyl group, a mono- or di-$C_{1-10}$ alkylamino group, a $C_{1-10}$ alkylcarbonyloxy group, a $C_{1-10}$ alkoxycarbonyl group, a $C_{1-10}$ alkylcarbonylamino group, a nitro group, a halogen atom, a hydroxyl groups, an amino group, a carboxyl group, a phosphonic acid group, a sulfonic acid group, a carbamoyl group, a sulfamoyl group, and a tetrazole group;

or a tautomer or pharmaceutically acceptable salt of the compound.

16. The compound according to claim 3, wherein $R^3$ is a $C_{1-10}$ alkyl group or a $C_{2-10}$ alkenyl group, each of which may be optionally substituted with one or more substituents selected from the group consisting of a $C_{1-10}$ alkyl group, a $C_{2-6}$ alkenyl group, a $C_{1-10}$ alkoxy group, a $C_{1-10}$ thioalkyl group, a $C_{1-10}$ alkylcarbonyl group, a mono- or di-$C_{1-10}$ alkylamino group, a $C_{1-10}$ alkylcarbonyloxyl group, a $C_{1-10}$ alkoxycarbonyl group, a $C_{1-10}$ alkylcarbonylamino group, a halogen atom, a nitro group, a hydroxyl group, an amino groups, a carboxyl group, a phosphonic acid group, a sulfonic acid group, a carbamoyl group, a sulfamoyl group, and a tetrazole group;

or a tautomer or pharmaceutically acceptable salt of the compound.

17. The compound according to claim 3, wherein $R^3$ is a $C_{2-9}$ heterocyclic group, which is substituted with one or more substituents selected from the group consisting of a hydroxyl group, an amino group, a halogen atom, a carboxyl group, a sulfonic acid group, a carbamoyl group, a hydroxycarbamoyl group, a sulfamoyl group, a hydroxysulfamoyl group, a thiocarbamoyl group, —CH₂COOH, —OCH₂COOH, —NHCH₂COOH, —CH₂OH, —OCH₂OH, —NHCH₂OH, —CH₂CH₂OH, —(C=O)COOH, —NHSO₂NH₂, a $C_{1-10}$ alkyl group, a $C_{1-10}$ alkylsulfonyl group, a $C_{1-10}$ alkylaminosulfonyl group, a $C_{1-10}$ alkylcarbonyl group, a $C_{1-10}$ alkylaminocarbonyl group, and a $C_{1-10}$ dialkylaminocarbonyl group;

or a tautomer or pharmaceutically acceptable salt of the compound.

18. The compound according to claim 1, which is selected from the group consisting of:
- 1-{1-[5-(3,4-dichlorophenyl)-4-hydroxythiophen-3-yl]-ethylidene-hydrazinothiocarbonyl}-piperidine-4-carboxylic acid;
- 1-{1-[5-(4-bromophenyl)-4-hydroxy-thiophen-3-yl]-ethylidene-hydrazinothiocarbonyl}-piperidin-4-carboxylic acid;
- 1-{1-[4-hydroxy-5-(4-trifluoromethylphenyl)-thiophen-3-yl]-ethylidene-hydrazinothiocarbonyl}-piperidine-4-carboxylic acid;
- 1-{1-[5-(4-trifluoromethoxyphenyl)-4-hydroxythiophen-3-yl]-ethylidene-hydrazinothiocarbonyl}-piperidine-4-carboxylic acid;
- 1-{1-[5-(4-chlorophenyl)-4-hydroxy-thiophen-3-yl]-ethilidene-hydrazinothiocarlbonyl}-piperidine-4-carboxylic acid;
- 1-{1-[5-(3,4-dimethylphenyl)-4-hydroxythiophen-3-yl]-ethylidene-hydrazinothiocarbonyl}-piperidine-4-carboxylic acid;
- 1-{1-[5-(4-t-butylphenyl)-4-hydroxy-thiophen-3-yl]-ethylidene-hydrazinothiocarbonyl}-piperidine-4-carboxylic acid;
- 1-{1-[5-(3-chlorophenyl)-4-hydroxythiophen-3-yl]-ethylidene-hydrazinothiocarbonyl}-piperidine-4-carboxylic acid;

a tautomer thereof; and a pharmaceutically acceptable salt thereof.

19. A composition, comprising at least one compound according to claim 1, a pharmaceutically acceptable salt thereof, a tautomer thereof; and at least one carrier.

20. A method of treating thrombocytopenia in a patient in need thereof, the method comprising administering to the patient an effective amount of at least one compound according to claim 1, a pharmaceutically acceptable salt thereof, a tautomer thereof to treat the thrombocytopenia in the patient.

21. A method of increasing platelets, vascular endothelial cells and/or endothelial progenitor cells in a patient in need thereof, the method comprising administering to the patient an effective amount of at least one compound according to claim 1, a pharmaceutically acceptable salt thereof, a tautomer thereof to increase platelets, vascular endothelial cells and/or endothelial progenitor cells in the patient.

* * * * *